US008575118B2

(12) United States Patent
Guo et al.

(10) Patent No.: US 8,575,118 B2
(45) Date of Patent: Nov. 5, 2013

(54) ANTIVIRAL COMPOUNDS

(75) Inventors: Hongyan Guo, San Mateo, CA (US);
Darryl Kato, San Francisco, CA (US);
Thorsten A. Kirschberg, Redwood City, CA (US); Hongtao Liu, Foster City, CA (US); John O. Link, San Francisco, CA (US); Michael L. Mitchell, Hayward, CA (US); Jay P. Parrish, Redwood City, CA (US); Jianyu Sun, Surrey (CA); James Taylor, San Mateo, CA (US); Elizabeth M. Bacon, Burlingame, CA (US); Eda Canales, San Mateo, CA (US); Aesop Cho, Mountain View, CA (US); Choung U. Kim, San Carlos, CA (US); Jeromy J. Cottell, Redwood City, CA (US); Manoj C. Desai, Pleasant Hill, CA (US); Randall L. Halcomb, Foster City, CA (US); Michael Graupe, Pacifica, CA (US); Evan S. Krygowski, Belmont, CA (US); Scott E. Lazerwith, San Francisco, CA (US); Qi Liu, Union City, CA (US); Richard Mackman, Millbrae, CA (US); Hyung-Jung Pyun, Fremont, CA (US); Joseph H. Saugier, Livermore, CA (US); James Trenkle, Oakland, CA (US); Winston C. Tse, Redwood City, CA (US); Randall W. Vivian, San Mateo, CA (US); Scott D. Schroeder, Foster City, CA (US); William J. Watkins, Saratoga, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/553,517

(22) Filed: Jul. 19, 2012

(65) Prior Publication Data

US 2013/0137877 A1   May 30, 2013

Related U.S. Application Data

(60) Continuation of application No. 13/291,977, filed on Nov. 8, 2011, now Pat. No. 8,273,341, which is a division of application No. 12/779,023, filed on May 12, 2010, now Pat. No. 8,088,368.

(60) Provisional application No. 61/177,972, filed on May 13, 2009, provisional application No. 61/224,745, filed on Jul. 10, 2009, provisional application No. 61/238,760, filed on Sep. 1, 2009.

(51) Int. Cl.
| C07D 401/14 | (2006.01) |
| C07D 403/04 | (2006.01) |
| C07D 403/14 | (2006.01) |
| C07D 409/14 | (2006.01) |
| C07D 417/04 | (2006.01) |
| C07D 417/14 | (2006.01) |
| C07D 495/04 | (2006.01) |
| A61K 31/4184 | (2006.01) |
| A61K 31/501 | (2006.01) |
| A61K 31/439 | (2006.01) |
| A61K 31/7056 | (2006.01) |
| A61K 31/7068 | (2006.01) |
| A61K 31/496 | (2006.01) |
| A61P 31/14 | (2006.01) |

(52) U.S. Cl.
USPC ............... 514/43; 514/252.06; 514/254.06; 514/299; 514/394; 514/49

(58) Field of Classification Search
None
See application file for complete search history.

*Primary Examiner* — Sun Jae Loewe
(74) *Attorney, Agent, or Firm* — Foley & Lardner LLP

(57) ABSTRACT

The invention is related to anti-viral compounds, compositions containing such compounds, and therapeutic methods that include the administration of such compounds, as well as to processes and intermediates useful for preparing such compounds.

4 Claims, No Drawings

ANTIVIRAL COMPOUNDS

CROSS-REFERENCE TO RELATED APPLICATIONS

This application is a continuation of U.S. patent application Ser. No. 13/291,977, filed Nov. 8, 2011, now U.S. Pat. No. 8,273,341, which is a divisional of U.S. patent application Ser. No. 12/779,023, filed May 12, 2010, now U.S. Pat. No. 8,088,368, which claims priority to U.S. Provisional Application Nos. 61/177,972, filed May 13, 2009; 61/224,745, filed Jul. 10, 2009; and 61/238,760, filed Sep. 1, 2009. The entire content of each of these applications is hereby incorporated herein by reference.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

There is a need for new HCV therapeutic agents.

SUMMARY OF THE INVENTION

In one embodiment the invention provides a compound of the invention which is a compound of formula (I):

$$J-Y-J \qquad (I)$$

as described herein, or a pharmaceutically acceptable salt, or prodrug thereof.

The invention also provides isotopically enriched compounds that are compounds of formula I that comprise an enriched isotope at one or more positions in the compound.

The present invention also provides a pharmaceutical composition comprising a compound of the invention and at least one pharmaceutically acceptable carrier.

The present invention also provides a pharmaceutical composition for use in treating disorders associated with HCV.

The present invention also provides a pharmaceutical composition further comprising an interferon or pegylated interferon.

The present invention also provides a pharmaceutical composition further comprising a nucleoside analog.

The present invention also provides for a pharmaceutical composition wherein said nucleoside analogue is selected from ribavirin, viramidine, levovirin, an L-nucleoside, and isatoribine and said interferon is α-interferon or pegylated α-interferon.

The present invention also provides for a method of treating disorders associated with hepatitis C, said method comprising administering to an individual a pharmaceutical composition which comprises a therapeutically effective amount of a compound of the invention.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (preferably for use in inhibiting HCV activity or treating a condition associated with HCV activity), as well as the use of a compound of the invention for the manufacture of a medicament useful for inhibiting HCV or the treatment of a condition associated with HCV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a compound of formula I, or a pharmaceutically acceptable salt or prodrug thereof, for use in the prophylactic or therapeutic treatment of hepatitis C or a hepatitis C associated disorder.

In another aspect the invention provides a method of inhibiting HCV activity in a sample comprising treating the sample with a compound of the invention.

In one embodiment the invention provides a compound having improved inhibitory or pharmacokinetic properties, including enhanced activity against development of viral resistance, improved oral bioavailability, greater potency (for example, in inhibiting HCV activity) or extended effective half-life in vivo. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However, it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "R" or "$A^3$", then it will be understood that the groups may be the same or different, i.e., each group is independently selected.

"Absent"—Some groups are defined such that they can be absent. When a group is absent it becomes a bond connector. The two groups that would otherwise be connected to that absent group are connected to each other through a bond. For example, when W is absent, M is bonded to M.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH(CH₃)CH₂CH₂CH₂CH₃), 3-hexyl (—CH(CH₂CH₃) (CH₂CH₂CH₃)), 2-methyl-2-pentyl (—C(CH₃)₂ CH₂CH₂CH₃), 3-methyl-2-pentyl(—CH(CH₃)CH(CH₃) CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C (CH₃)₂CH(CH₃)₂), 3,3-dimethyl-2-butyl (—CH(CH₃)C (CH₃)₃, and cyclopropylmethyl

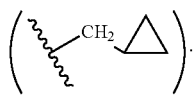

"Alkenyl" is C₂-C₁₈ hydrocarbon containing normal, secondary, tertiary or cyclic carbon atoms with at least one site of unsaturation, i.e. a carbon-carbon, sp² double bond. Examples include, but are not limited to, ethylene or vinyl (—CH═CH₂), allyl (—CH₂CH═CH₂), cyclopentenyl (—C₅H₇), and 5-hexenyl (—CH₂CH₂CH₂CH₂CH═CH₂).

"Alkynyl" is C₂-C₁₈ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "polycarbocycle" refers to a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicyclo[4,5], [5,5], [5,6] or [6,6] ring systems, as well as the following bridged ring systems:

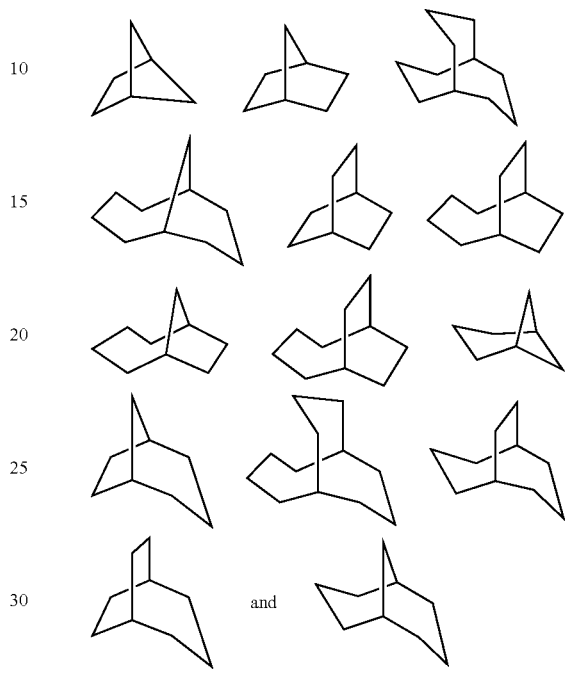

(i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" refers to a polycarbocycle as defined herein, wherein one or more carbon atoms is replaced with a heteroatom (e.g., O, S, S(O), S(O)₂, N⁺(O⁻)R$_x$, or NR$_x$); wherein each R$_x$ is independently H, (C1-10)alkyl, (C2-10)alkenyl, (C2-10)alkynyl, (C1-10)alkanoyl, S(O)₂NR$_n$R$_p$, S(O)₂R$_x$, or (C1-10)alkoxy, wherein each (C1-10) alkyl, (C2-10)alkenyl, (C2-10)alkynyl, (C1-10)alkanoyl, and (C1-10)alkoxy is optionally substituted with one or more halo).

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to: halo (e.g. F, Cl, Br, I), —R, —OR, —SR, —NR₂, —CF₃, —CCl₃, —OCF₃, —CN, —NO₂, —N(R)C(═O)R, —C(═O)R, —OC(═O)R, —C(O)OR, —C(═O)NRR, —S(═O)R, —S(═O)₂OR, —S(═O)₂R, —OS(═O)₂OR, —S(═O)₂NRR, and each R is independently —H, alkyl, aryl, arylalkyl, or heterocycle. Alkylene, alkenylene, and alkynylene groups may also be similarly substituted.

The term "optionally substituted" in reference to a particular moiety of the compound of formula I, (e.g., an optionally substituted aryl group) refers to a moiety having 0, 1, 2, or more substituents.

The symbol "-----" in a ring structure means that a bond is a single or double bond. In a non-limiting example,

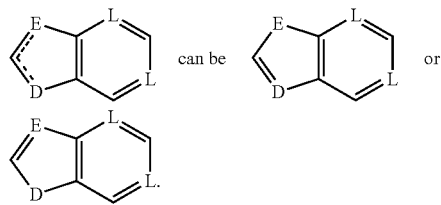

"Haloalkyl" as used herein includes an alkyl group substituted with one or more halogens (e.g. F, Cl, Br, or I). Representative examples of haloalkyl include trifluoromethyl, 2,2, 2-trifluoroethyl, and 2,2,2-trifluoro-1-(trifluoromethyl)ethyl.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

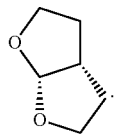

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo[5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "chiral" refers to molecules which have the property of non-superimposability of the minor image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Specific Definitions for Groups $A^o$, $M^o$, $W^o$, $L^o$, $P^o$, $J^o$, $T^o$, $V^o$, $Z^o$, $E^o$, and $R9^o$ For the groups $A^o$, $M^o$, $W^o$, $L^o$, $P^o$, $J^o$, $T^o$, $V^o$, $Z^o$, $E^o$, and $R9^o$ the following definitions apply. These definitions also apply for all other A, M, W, L, P, J, T, B, V, Z, E, and R9 groups unless those groups are otherwise defined herein.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^XR^Y$;

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfanyl," as used herein, refers to an aryl group attached to the parent molecular moiety through a sulfur atom.

The term "arylsulfonyl," as used herein, refers to an aryl group attached to the parent molecular moiety through a sulfonyl group.

The terms "Cap" and "cap" as used herein, refer to the group which is placed on the nitrogen atom of the terminal nitrogen-containing ring. It should be understood that "Cap" or "cap" can refer to the reagent used to append the group to the terminal nitrogen-containing ring or to the fragment in the final product.

The term "carbonyl," as used herein, refers to —C(=O)—.

The term "carboxy," as used herein, refers to —CO$_2$H.

The term "cyano," as used herein, refers to —CN.

The term "cyanoalkyl" as used herein, refers to an alkyl group having at least one —CN substituent.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^X$R$^Y$ wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —NR$^c$R$^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "haloalkylsulfanyl," as used herein, refers to a haloalkyl group attached to the parent molecular moiety through a sulfur atom.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, —(NR$^X$R$^Y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^X$R$^Y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom. $R^a$ and $R^b$ are independently selected from hydrogen, alkenyl, and alkyl.

The term "$(NR^aR^b)$alkyl," as used herein, refers to an alkyl group substituted with one, two, or three —$NR^aR^b$ groups.

The term "$(NR^aR^b)$carbonyl," as used herein, refers to an —$NR^aR^b$ group attached to the parent molecular moiety through a carbonyl group.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "$(NR^cR^d)$alkenyl," as used herein, refers to an alkenyl group substituted with one, two, or three —$NR^cR^d$ groups.

The term "$(NR^cR^d)$alkyl," as used herein, refers to an alkyl group substituted with one, two, or three —$NR^cR^d$ groups. The alkyl part of the $(NR^cR^d)$alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and $(NR^eR^f)$carbonyl; wherein the heterocyclyl is further optionally substituted with one, two, three, four, or five substituents independently selected from alkoxy, alkyl, cyano, halo, haloalkoxy, haloalkyl, and nitro.

The term "$(NR^cR^d)$carbonyl," as used herein, refers to an —$NR^cR^d$ group attached to the parent molecular moiety through a carbonyl group.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl.

The term "$(NR^eR^f)$alkyl," as used herein, refers to an alkyl group substituted with one, two, or three —$NR^eR^f$ groups.

The term "$(NR^eR^f)$alkylcarbonyl," as used herein, refers to an $(NR^eR^f)$alkyl group attached to the parent molecular moiety through a carbonyl group.

The term "$(NR^eR^f)$carbonyl," as used herein, refers to an —$NR^eR^f$ group attached to the parent molecular moiety through a carbonyl group.

The term "$(NR^eR^f)$sulfonyl," as used herein, refers to an —$NR^eR^f$ group attached to the parent molecular moiety through a sulfonyl group.

The term "—$NR^XR^Y$," as used herein, refers to two groups, $R^X$ and $R^Y$, which are attached to the parent molecular moiety through a nitrogen atom. $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl.

The term "$(NR^XR^Y)$alkyl," as used herein, refers to an alkyl group substituted with one, two, or three —$NR^XR^Y$ groups.

The term "oxo," as used herein, refers to =O.

The term "sulfonyl," as used herein, refers to —$SO_2$—.

The term "trialkylsilyl," as used herein, refers to —$SiR_3$, wherein R is alkyl. The R groups may be the same or different The term "trialkylsilylalkyl," as used herein, refers to an alkyl group substituted with one, two, or three trialkylsilyl groups.

The term "trialkylsilylalkoxy," as used herein, refers to a trialkylsilylalkyl group attached to the parent molecular moiety through an oxygen atom.

The term "trialkylsilylalkoxyalkyl," as used herein, refers to an alkyl group substituted with one, two, or three trialkylsilylalkoxy groups.

Prodrugs

The term "prodrug" as used herein refers to any compound that when administered to a biological system generates a compound of the invention that inhibits HCV activity ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C-0 bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

By way of example and not limitation, $R^1$, $R^3$, $R^{41}$, $R^{43}$, and $X^4$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "$R^1$" or "$R^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels. Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV activity it should be kept in mind that the results of enzyme assays may not always correlate with cell culture assays. Thus, a cell based assay should typically be the primary screening tool.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

HCV Combination Therapy

In another embodiment, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-nl (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-790052, BMS-605339, PHX-1766, AS-101, YH-5258, YH5530, YH5531, and ITMN-191, 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, BCX-4678, valopicitabine (NM-283), and MK-0608, 7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), BMS-790052, and A-689, 9) TLR-7 agonists, e.g., imiquimod, 852A, GS-9524, ANA-773, ANA-975, AZD-8848 (DSP-3025), and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831, A-689, and BMS-790052, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating Hepatitis C, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers, e.g., BAS-100 and SPI452, 20) RNAse H inhibitors, e.g., ODN-93 and ODN-112, 21) other anti-HIV agents, e.g., VGV-1, PA-457 (bevirimat); ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV-inhibitory activity of their own.

Methods for determining stability of compounds in surrogate gastrointestinal secretions are known.

Compounds of Formula (I)

In one embodiment the invention provides a compound of formula (I):

$$J-Y-J \quad (I)$$

wherein:
Y is -L-L-, -M-W-M- or $Y^y$;
J is T-P-, -P-T or -$J^m$;
W is a bond or -$W^r$-;
L is -M-A-, -A-M-, or -$L^n$;
T is R9-Z-, -Z-R9, or -$T^p$;
R9 is E-V-, or -V-E, or -$R9^q$;
each A is selected from -$A^s$;
each M is selected from -$M^t$;
each P is selected from -$P^u$;
each Z is selected from -$Z^v$;
each V is selected from -$V^w$;
each E is selected from -$E^x$;
each m is 1
each n is 0, 1, 2, 3, 4, 5, 6, 7, 9, or 10;
each p is 1, 2, 3, 4, 5, 6, 7, or 8;
each q is 0, 1, 2, or 3;
each r is 1, 2, 3, 4, 5, 6, 7, 8, 9, 10, 11, 12, 13, 14, 15, 16, 17, 18, 19, or 20;
each s is 0, 1, 2, 3, 4, 5, 6, 7, 8, 9, 10, 11, 12, 13, 14, 15, 16, 17, 18, or 21;
each t is 0, 1, 2, 3, 4, 5, 6, 7, 8, 9, 10, or 11;
each u is 0, 1, 2, 3, 4, 5, 6, 7, 8, 10, 11, 12, 13, 14, 15, 16, 17, 18, or 19;
each v is 0, 1, 2, 3, 4, 5, or 6;
each w is 0, 1, 2, 3, 4, 5, 6, 7, 8, 9, 10, 11, 12, 13, 14, 15, 16, 17, 18, 19, 20, 21, 22, 23, or 24;
each x is 0, 1, 2, 3, 4, 5, 6, or 7;
each y is 0, 1, or 2;
wherein the sum of m, n, p, q, r, s, t, u, v, w, x, and y is not 0; P is connected to M, L, or $Y^y$; A is connected to A or L; M is connected to P or J; Z is connected to P; V is connected to Z; and when W is a bond M is connected to M;

each $Y^1$ is independently:
a fused nine-ring system with up to thirty-five atoms that may be fully aromatic or partially saturated and contains atoms selected from C, N, O, and S and which ring system is optionally substituted with one or more groups independently selected from H, oxo, $R^{A1}$ and $R^{A3}$;

each $Y^2$ is independently:
a fused five to eight ring system with up to thirty-two atoms that may be fully aromatic or partially saturated and contains atoms selected from C, N, O, and S and which ring system is optionally substituted with one or more groups independently selected from H, oxo, $R^{A1}$ and $R^{A3}$;

each $J^1$ is independently a fused bicyclic saturated, partially unsaturated, or aromatic heterocyclic ring system that is substituted with one or more —N($R^{L7}$)C(=O)O$R^{L7}$, and that is optionally substituted with one or more groups independently selected from oxo, halo, —$R^{L7}$, —O$R^{L7}$, —S$R^{L7}$, —$CF_3$, —$CCl_3$, —$OCF_3$, —CN, —$NO_2$, —N($R^{L7}$)C(=O)$R^{L7}$, —C(=O)$R^{L7}$, —OC(=O)$R^{L7}$, —C(O)O$R^{L7}$, —C(=O)N$R^{L7}$, —S(=O)$R^{L7}$, —S(=O)$_2$O$R^{L7}$, —S(=O)$_2$$R^{L7}$, —O$S^{L7}$, —S(=O)$_2$N$R^{L7}$, alkoxyalkyl, arylalkoxycarbonyl, halo, haloalkyl, hydroxyalkyl, —N$R^a$$R^b$, (N$R^a$$R^b$)alkyl, and (N$R^a$$R^b$)carbonyl;

each $R^{L7}$ is independently —H, alkyl, aryl, arylalkyl, or heterocycle;

$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^0$ is independently:

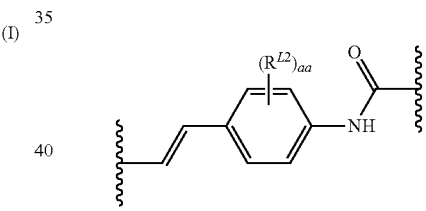

wherein:
each $R^{L2}$ is independently selected from hydrogen, alkenyl, alkoxy, alkyl, halo, and haloalkyl; and
each aa is independently 1, 2, 3, or 4;
each $L^1$ is independently:

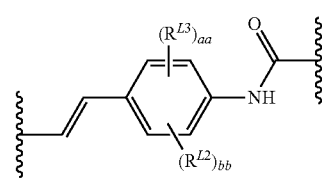

wherein:
each $R^{L2}$ is independently selected from hydrogen, alkenyl, alkoxy, alkyl, halo, and haloalkyl;
each $R^{L3}$ is independently selected from cyano, nitro, SO$R^4$, SO$_2$$R^4$, -alkylSO$_2$$R^4$, haloalkoxy, cyanoalkyl, N$R^4$SO$_2$$R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each R⁴ is independently selected from H, alkyl, haloalkyl, aryl, and arylalkyl;
each bb is 0, 1, 2, 3, or 4; each aa is 1, 2, 3, or 4; and the sum of bb and aa is 1, 2, 3, or 4;
each L² is independently:

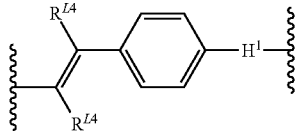

wherein:
the phenyl ring shown in L² is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R$^{L4}$ is independently —H, alkyl, aryl, arylalkyl, or heterocycle;
each R⁴ is independently selected from H, alkyl, haloalkyl, aryl, and arylalkyl;
R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and
each H¹ is a 5 membered saturated, partially unsaturated, or aromatic ring comprising one or more heteroatoms;
each L³ is independently a fused-bicyclic saturated, partially unsaturated, or aromatic heterocyclic ring system that is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R⁴ is independently selected from H, alkyl, haloalkyl, aryl, and arylalkyl; and
R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each L⁴ is independently a fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R⁴ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each L⁵ is independently a —CR═CR-fused bicyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R is independently selected from H or alkyl;
each R⁴ is independently selected from H, alkyl, haloalkyl, aryl, and arylalkyl; and
R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each L⁶ is independently a —CR═CR-fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R is independently selected from H or alkyl;
each R⁴ is independently selected from H, alkyl, haloalkyl, aryl, and arylalkyl; and
R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each L⁷ is independently:

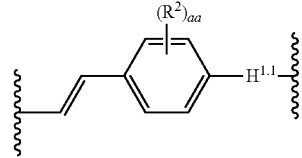

wherein:
each H$^{1.1}$ is independently a fused-bicyclic saturated, partially unsaturated, or aromatic heterocyclic ring system that is optionally substituted with one or more R²;
each R² is independently selected from halo, —R$^{L7}$, —OR$^{L7}$, —SR$^{L7}$—N(R$^{L7}$)₂, —CF₃, —CCl₃, —OCF₃, —CN, —NO₂, —N(R$^{L7}$)C(═O)R$^{L7}$, —C(═O)R$^{L7}$, —OC(═O)R$^{L7}$, —C(O)OR$^{L7}$, —C(═O)NR$^{L7}$, —S(═O)R$^{L7}$, —S(═O)₂OR$^{L7}$, —S(═O)₂R$^{L7}$, —OS$^{L7}$, and —S(═O)₂NR$^{L7}$;
each R$^{L7}$ is independently —H, alkyl, aryl, arylalkyl, or heterocycle; and
each aa is independently 1, 2, 3, or 4;
each L⁹ is independently a fused-tetracyclic saturated, partially unsaturated, or aromatic heterocyclic ring system that is optionally substituted with one or more groups independently selected from oxo, halo, —$R^{L7}$, —$OR^{L7}$, —$SR^{L7}$, —$CF_3$, —$CCl_3$, —$OCF_3$, —CN, —$NO_2$, —$N(R^{L7})C(=O)R^{L7}$, —$C(=O)R^{L7}$, —$OC(=O)R^{L7}$, —$C(=O)R^{L7}$, —$C(=O)NR^{L7}$, —$S(=O)R^{L7}$, —$S(=O)_2OR^{L7}$, —$S(=O)_2R^{L7}$, —$OS(=O)_2OR^{L7}$, —$S(=O)_2NR^{L7}$, alkoxyalkyl, arylalkoxycarbonyl, halo, haloalkyl, hydroxyalkyl, —$NR^aR^b$, $(NR^aR^b)$alkyl, and $(NR^aR^b)$carbonyl;

each $R^{L7}$ is independently —H, alkyl, aryl, arylalkyl, or heterocycle;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^{10}$ is independently a fused-pentacyclic saturated, partially unsaturated, or aromatic heterocyclic ring system that is optionally substituted with one or more groups independently selected from oxo, halo, —$R^{L7}$, —$OR^{L7}$, —$SR^{L7}$, —$CF_3$, —$CCl_3$, —$OCF_3$, —CN, —$NO_2$, —$N(R^{L7})C(=O)R^{L7}$, —$C(=O)R^{L7}$, —$OC(=O)R^{L7}$, —$C(O)OR^{L7}$, —$C(=O)NR^{L7}$, —$S(=O)R^{L7}$, —$S(=O)OR^{L7}$, —$S(=O)_2R^{L7}$, —$OS(=O)_2OR^{L7}$, —$S(=O)_2NR^{L7}$, alkoxyalkyl, arylalkoxycarbonyl, halo, haloalkyl, hydroxyalkyl, —$NR^aR^b$, $(NR^aR^b)$alkyl, and $(NR^aR^b)$carbonyl;

each $R^{L7}$ is independently —H, alkyl, aryl, arylalkyl, or heterocycle;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^{11}$ is independently a six-ring fused saturated, partially unsaturated, or aromatic heterocyclic ring system that is optionally substituted with one or more groups independently selected from oxo, halo, —$R^{L7}$, —$OR^{L7}$, —$SR^{L7}$, —$CF_3$, —$CCl_3$, —$OCF_3$, —CN, —$NO_2$, —$N(R^{L7})C(=O)R^{L7}$, —$C(=O)R^{L7}$, —$OC(=O)R^{L7}$, —$C(O)OR^{L7}$, —$C(=O)NR^{L7}$, —$S(=O)R^{L7}$, —$S(=O)OR^{L7}$, —$S(=O)_2R^{L7}$, —$OS(=O)_2OR^{L7}$, —$S(=O)_2NR^{L7}$, alkoxyalkyl, arylalkoxycarbonyl, halo, haloalkyl, hydroxyalkyl, —$NR^aR^b$, $(NR^aR^b)$alkyl, and $(NR^aR^b)$carbonyl;

each $R^{L7}$ is independently —H, alkyl, aryl, arylalkyl, or heterocycle;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^{90}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, $(NR^cR^d)$alkenyl, $(NR^cR^d)$alkyl, and $(NR^cR^d)$carbonyl;

$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —$C(NCN)NR^XR^Y$, wherein R' is selected from alkyl and unsubstituted phenyl; and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $R^{91}$ is independently —$N(R^{9a})$—$NHC(=O)O$—$R^{9b}$, wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclyl, heterocyclylcarbonylalkyl, hydroxyalkyl, NRRCOalkyl, wherein each R is independently selected from hydrogen and alkyl;

and wherein arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $R^{92}$ is independently —$N(R^{9a})$—$NHC(=O)NR^{9b}_2$; wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO₂alkyl, cycloalkylalkylSO₂alkyl, cyanoalkyl, haloalkyl cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR₂, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; R$^{9b}$ is independently H, alkyl, aryl, haloalkyl, or arylalkyl;

each R$^{93}$ is independently —N(R$^{9a}$)—NHC(=O)R$^{9b}$, wherein each R$^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO₂alkyl, cycloalkylalkylSO₂alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR₂, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, —(NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; R$^{9b}$ is independently H, alkyl, aryl, haloalkyl, or arylalkyl;

each A⁰ is independently:

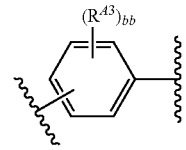

wherein:
each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or
each A⁰ is independently a six-membered heteroaromatic ring containing one, two, or three nitrogen atoms, which ring is optionally substituted with 1, 2, 3, or 4 R$^{43}$ groups;

each A¹ is independently:

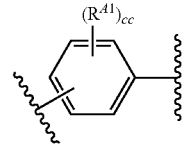

wherein:
each R$^{A1}$ is independently selected from cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each R⁴ is independently selected from H, alkyl, haloalkyl, aryl, and arylalkyl;

each cc is independently 1, 2, 3, or 4
each $A^2$ is independently:

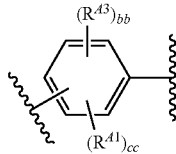

wherein:
each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; each bb is 0, 1, 2, 3, or 4; each cc is 1, 2, 3, or 4; and the sum of bb and cc is 1, 2, 3, or 4;
each $A^3$ is independently a six-membered heteroaromatic ring containing one, two, or three nitrogen atoms, which ring is substituted with one or more $R^{A1}$ groups, and which ring is optionally substituted with one or more $R^{A3}$ groups;
each $A^4$ is independently:

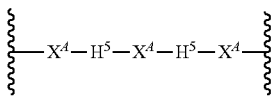

wherein:
each $H^5$ is independently a phenyl ring or a six-membered heteroaromatic ring, which $H^5$ is optionally substituted with one or more groups independently selected from $R^{A1}$ and $R^{A3}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^5$ is independently:

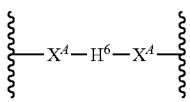

wherein:
each $H^6$ is independently a phenyl ring or a six-membered heteroaromatic ring, which $H^6$ is optionally substituted with one or more groups independently selected from $R^{A1}$ and $R^{A3}$; and each $X^A$ is independently O, NR, SO, $SO_2$, g=O), NRC(=O), C(=O)NR, CR=CR, NRC(=O)NR, allenyl, alkynyl, or absent; provided that at least one $X^A$ is present and each R is independently selected from H or alkyl;
each $A^6$ is independently:

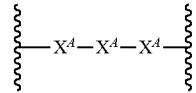

wherein:
each $X^A$ is independently O, NR, SO, $SO_2$, C(=O), NRC(=O), C(=O)NR, CR=CR, allenyl, alkynyl, or absent; provided that at least one $X^A$ is present and each R is independently selected from H or alkyl;
each $A^7$ is independently:

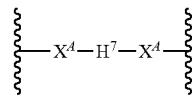

wherein:
each $H^7$ is independently a five-membered heteroaromatic ring, which $H^7$ is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent; and each R is independently selected from H or alkyl;
each $A^8$ is independently:

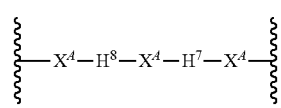

wherein:
each $H^7$ is independently a five-membered heteroaromatic ring, which $H^7$ is optionally substituted with one or more groups independently selected from $R^{A1}$ and $R^{A3}$;
each $H^8$ is independently a phenyl ring, which is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^9$ is independently:

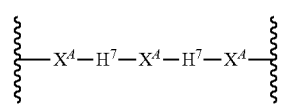

wherein:
each $H^7$ is independently a five-membered heteroaromatic ring, which $H^7$ is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{10}$ is independently:

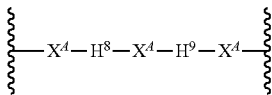

wherein:
each $H^8$ is independently a phenyl ring, which is optionally substituted with one or more groups independently selected from $R^{41}$ and $R^{43}$;
each $H^9$ is independently a six-membered heteroaromatic ring, which is optionally substituted with one or more groups independently selected from $R^{41}$ and $R^{43}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{11}$ is independently:

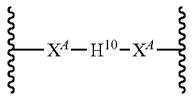

wherein:
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $H^{10}$ is independently a 5-15 carbon unsaturated, partially unsaturated or saturated bicyclic ring system that is optionally fused to an aryl, which $H^{10}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each $R^4$ is independently selected from H, alkyl, haloalkyl, aryl, and arylalkyl each $A^{12}$ is independently:

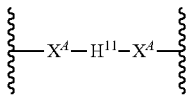

wherein:
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $H^{11}$ is independently a 5-15 carbon unsaturated, partially unsaturated or saturated bicyclic ring system that contains one or more heteroatoms that is optionally fused to an aryl, which $H^{11}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each $R^4$ is independently selected from H, alkyl, haloalkyl, aryl, and arylalkyl; and each $A^{13}$ is independently:

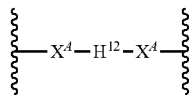

wherein:
each $H^{12}$ is independently a fused aromatic bicyclic carbocycle, which is optionally substituted with one or more groups independently selected from $R^{41}$ and $R^{43}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{14}$ is independently:

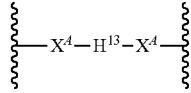

wherein:
each $H^{13}$ is independently a fused aromatic bicyclic heterocycle that comprises at least one heteroatom in the ring system, which ring system is optionally substituted with one or more groups independently selected from $R^{41}$ and $R^{43}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{15}$ is independently:

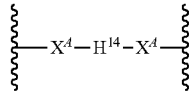

wherein:
each $H^{14}$ is independently a fused unsaturated, partially unsaturated or saturated tricyclic carbocycle which is optionally substituted with one or more groups independently selected from oxo, $R^{41}$ and $R^{43}$; and
each $X^A$ is independently O, NR, SO, SO$_2$, NRC(=O), C(=O)NR, CR=CR, NRC(=O)NR, allenyl, alkynyl, or absent and each R is independently selected from H or alkyl;

each $A^{16}$ is independently:

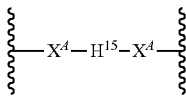

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{17}$ is independently:

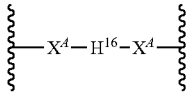

wherein:
each $H^{16}$ is independently a fused bicyclic carbocyclic ring system wherein one ring is aromatic and another ring is partially or fully saturated, which ring system is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{18}$ is independently:

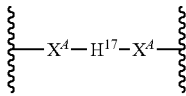

wherein:
each $H^{17}$ is independently a fused bicyclic ring system comprising at least one heteroatom, wherein one ring is aromatic and another ring is partially or fully saturated, which ring system is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and
each R is independently selected from H or alkyl;
each $A^{21}$ is independently:

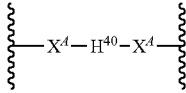

wherein:
each $H^{40}$ is independently an anti-aromatic monocyclic or fused carbocyclic ring system, which carbocyclic ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^1$ is independently —$X^A$—:
wherein:
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^2$ is independently:

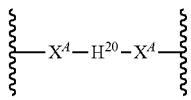

wherein:
each $H^{20}$ is independently a fused aromatic bicyclic carbocycle, which is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^3$ is independently:

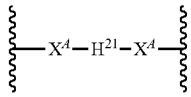

wherein:
each $H^{21}$ is independently a fused bicyclic carbocyclic ring system wherein one ring is aromatic and another ring is partially or fully saturated, which ring system is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^4$ is independently:

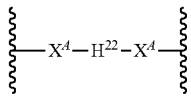

wherein:
each $H^{22}$ is independently a fused aromatic bicyclic heterocycle that comprises at least one heteroatom in the ring system, which ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^5$ is independently:

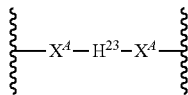

wherein:
each $H^{23}$ is independently a fused bicyclic ring system comprising at least one heteroatom, wherein one ring is aromatic and another ring is partially or fully saturated, which ring system is optionally substituted with one or more groups independently selected from oxo, $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^6$ is independently:

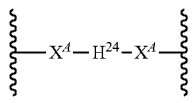

wherein:
each $H^{24}$ is independently a fused unsaturated, partially unsaturated or saturated tricyclic carbocycle, which is optionally substituted with one or more groups independently selected from oxo, $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^7$ is independently:

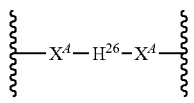

wherein:
each $H^{26}$ is independently a 5-15 carbon unsaturated, partially unsaturated or saturated bicyclic ring system which ring system is optionally substituted with one or more groups independently selected from oxo, $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^8$ is independently:

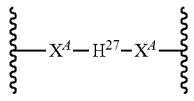

wherein:
each $H^{27}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^9$ is independently:

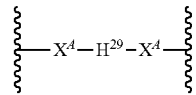

wherein:
each $H^{29}$ is independently a 5-15 carbon unsaturated, partially unsaturated or saturated bicyclic ring system that contains one or more heteroatoms; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;
each $W^{10}$ is independently —$H^{30}$=C=$H^{31}$—
wherein each of —$H^{30}$ and $H^{31}$ is independently a saturated 6-membered heterocyclic ring comprising one or more heteroatoms, which ring is optionally substituted with oxo;
each $W^{11}$ is independently —$H^{32}$=C=$H^{33}$—
wherein each of —$H^{32}$ and $H^{33}$ is independently a saturated 5-membered heterocyclic ring comprising one or more heteroatoms, which ring is optionally substituted with oxo;
each $W^{12}$ is independently an anti-aromatic monocyclic or fused carbocyclic ring system, which carbocyclic ring system is optionally substituted with one or more groups independently selected from $R^{41}$ and $R^{43}$;
each $W^{13}$ is independently a phenyl ring that is optionally substituted with one or more groups independently selected from $R^{41}$ and $R^{43}$;
each $W^{14}$ is independently a 5 or 6 membered heteroaryl ring that is optionally substituted with one or more groups independently selected from $R^{41}$ and $R^{43}$;
each $W^{15}$ is independently a fused unsaturated, partially unsaturated or saturated tetracyclic carbocyclic ring, which ring system is optionally substituted with one or more groups independently selected from oxo, $R^{41}$ and $R^{43}$;
each $W^{16}$ is independently a fused unsaturated, partially unsaturated or saturated tetracyclic heterocycle that comprises at least one heteroatom in the ring system, which ring system is optionally substituted with one or more groups independently selected from oxo, $R^{41}$ and $R^{43}$;
each $W^{17}$ is independently a fused unsaturated, partially unsaturated or saturated pentacyclic carbocyclic ring system, which ring system is optionally substituted with one or more groups independently selected from oxo, $R^{41}$ and $R^{43}$;
each $W^{18}$ is independently a fused unsaturated, partially unsaturated or saturated pentacyclic heterocycle that comprises at least one heteroatom in the ring system, which ring system is optionally substituted with one or more groups independently selected from oxo, $R^{41}$ and $R^{43}$;
each $W^{19}$ is independently a fused unsaturated, partially unsaturated or saturated hexacyclic carbocyclic ring system, which ring system is optionally substituted with one or more groups independently selected from oxo, $R^{41}$ and $R^{43}$;
each $W^{29}$ is independently a fused unsaturated, partially unsaturated or saturated hexacyclic heterocycle that comprises at least one heteroatom in the ring system, which ring system is optionally substituted with one or more groups independently selected from oxo, $R^{41}$ and $R^{43}$;

each M⁰ is independently a five membered heteroaryl group optionally substituted with one or more alkoxycarbonyl, alkyl, arylalkoxycarbonyl, carboxy, haloalkyl, (NR$^a$R$^b$)carbonyl and trialkylsilylalkoxyalkyl;

each M¹ is independently selected from —C(=O)NH—, —C(=O)NH—C(R$^M$)$_2$—, —NHC(=O)—, —C(R$^M$)$_2$NHC(=O)—, —NHC(=O)NR$^M$—, —NHC(=O)O—; wherein each R$^M$ is independently selected from H and alkyl;

each M² is independently a six-membered heteroaromatic ring, which is optionally substituted with one or more groups independently selected from R$^{41}$ and R$^{43}$;

each M³ is independently:

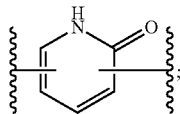

each M⁴ is independently:

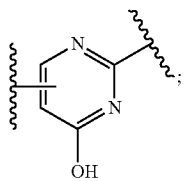

each M⁵ is independently:

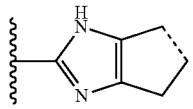

wherein the bond designated with - - - is fused to a ring defined for P;

each M⁶ is independently a bicyclic bridged ring system comprising 5-15 atoms wherein at least one of the atoms is a heteroatom;

each M⁷ is independently a pyrid-di-yl;

each M⁸ is independently partially saturated or a saturated five-membered ring that comprises one or more heteroatoms and that is optionally substituted with one or two oxo;

each M⁹ is independently a fused-bicyclic saturated, partially unsaturated, or aromatic heterocyclic ring system that is optionally substituted with one or more R$^{P11}$;

each M¹⁰ is independently a five membered heteroaryl group substituted with at least one alkoxy, cycloalkyl, cyano, alkylsulfonyl, arylsulfonyl, NR$^h$R$^h$, (NR$^h$R$^h$)sulfonyl, heterocyclylsulfonyl, heteroarylsulfonyl, haloalkoxy, alkoxyalkoxy, haloalkoxyalkyloxy, cycloalkoxyalkoxy, aryloxyalkoxy, heteroaryloxyalkoxy, heterocyclyloxyalkyloxy, (NR$^h$R$^h$) alkoxy, cyanoalkoxy, cycloalkoxy, heterocyclyl, alkoxyalkyl, cycloalkoxyalkyl, (NR$^h$R$^h$)alkyl, wherein each R$^h$ is independently —H, alkyl, alkoxyamino, aryl, arylalkyl, heterocycle, heterocyclyloxy, alkenyl, alkenyloxy, alkynyl, alkoxyalkyl, haloalkyl, cyanoalkyl, haloalkoxyalkyl, and sulfonylalkyl; and wherein the five membered ring is also optionally substituted with one or more alkoxycarbonyl, alkyl, arylalkoxycarbonyl, carboxy, haloalkyl, and (NR$^a$R$^b$)carbonyl;

each M¹¹ is independently a fused-tricyclic saturated, partially unsaturated, or aromatic heterocyclic ring system that is optionally substituted with one or more oxo, halo, —R$^{M7}$, —OR$^{M7}$, —SR$^{M7}$, —N(R$^{M7}$)$_2$, —CF$_3$, —CCl$_3$, —OCF$_3$, —CN, —NO$_2$, —N(R$^{M7}$)C(=O)R$^{M7}$, —C(=O)R$^{M7}$, —OC(=O)R$^{M7}$, —C(O)OR$^{M7}$, —C(=O)NR$^{M7}$, —S(=O)R$^{M7}$, —S(=O)$_2$OR$^{M7}$, —S(=O)$_2$R$^{M7}$, —OS$^{M7}$, or —S(=O)$_2$NR$^{M7}$; each R$^{M7}$ is independently —H, alkyl, aryl, arylalkyl, or heterocycle;

each M¹² is independently a fused-pentacyclic, hexacyclic, or heptacyclic partially unsaturated, or aromatic heterocyclic ring system that is optionally substituted with one or more oxo halo, —R$^{M7}$, —OR$^{M7}$, —SR$^{M7}$, —N(R$^{M7}$)$_2$, —CF$_3$, —CCl$_3$, —OCF$_3$, —CN, —NO$_2$, —N(R$^{M7}$)C(=O)R$^{M7}$, —C(=O)R$^{M7}$, —OC(=O)R$^{M7}$, —C(O)OR$^{M7}$, —C(=O)NR$^{M7}$, —S(=O)R$^{M7}$, —S(=O)$_2$OR$^{M7}$, —S(=O)$_2$R$^{M7}$, —OS(=O)$_2$OR$^{M7}$, or —S(=O)$_2$NR$^{M7}$;

each R$^{M7}$ is independently —H, alkyl, aryl, arylalkyl, or heterocycle;

each P⁰ is independently:

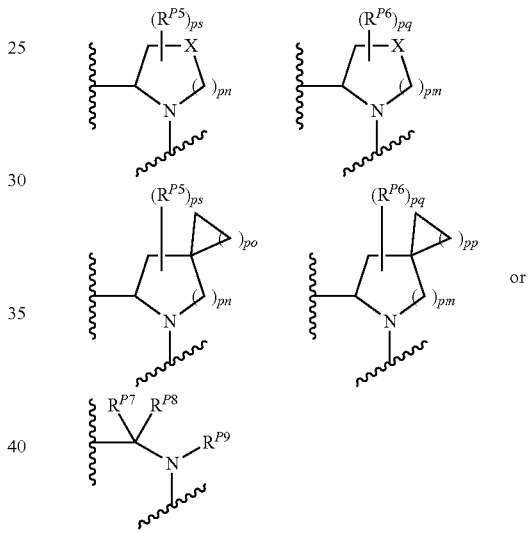

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and $(NR^{Pa}R^{Pb})$alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;

each $P^1$ is independently:

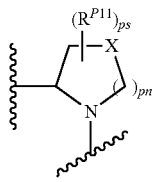

wherein:

X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^ha)$lkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;

pn is 0, 1, or 2;

each $P^2$ is independently:

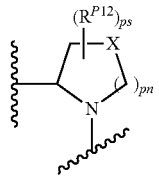

wherein:

each $R^{P12}$ is independently selected from $R^{P5}$, $R^{P11}$, —$C(=O)OR^h$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;

pn is 0, 1, or 2;

each $P^3$ is independently a ring of the formula:

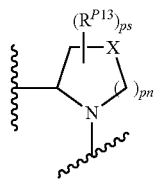

wherein:

the ring is substituted with one or more oxo group;

each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;

pn is 0, 1, or 2;

each P⁴ is independently a ring of the formula:

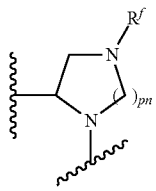

wherein:
the ring is optionally substituted with one or more groups R^{P14} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; and where two groups R^{P14} that are attached to the same carbon when taken together with the carbon to which they are attached can form a 3-6 membered carbocyclic or heterocyclic ring;
pn is 0, 1, or 2;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR^hR^h, —S(=O)$_2$R^h, C(=O)R^h, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁵ is independently a ring of the formula:

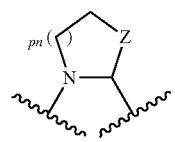

wherein:
the ring is optionally substituted with one or more groups R^{P15} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; and where two groups R^{P15} that are attached to the same carbon when taken together with the carbon to which they are attached can form a 3-6 membered carbocyclic or heterocyclic ring;
pn is 0, 1, or 2;
Z is O, S, S(=O), S(=O)$_2$, or NR^f;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR^hR^h, —S(=O)$_2$R^h, C(=O)R^h, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁶ is independently a ring of the formula:

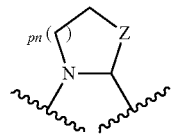

wherein:
the ring is substituted with one or more oxo and is optionally substituted with one or more groups R^{P16} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
Z is O, S, S(=O), S(=O)$_2$, or NR^f;
pn is 0, 1, or 2;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR^hR^h, —S(=O)$_2$R^h, C(=O)R^h, C(=O)OR^h, —C(=O)NR^hR^h; each R^h is independently-H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁷ is a bridged 5-15 membered bicyclic heterocyclic ring that is attached to the remainder of the compound of formula I through one N-link and through one C-link; wherein the ring is optionally substituted with one or more groups independently selected from R^{P6} and R^{P11};
each P⁸ is independently a ring of the formula:

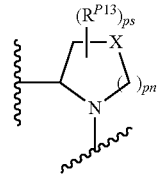

wherein:
ps is 2, 3, 4, 5, or 6;
pn is 0, 1 or 2;
each R^{P13} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

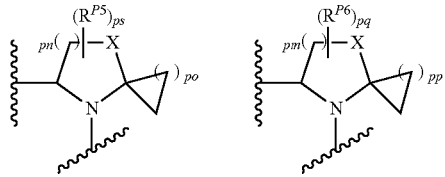

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;

pm and pn are independently 0, 1, or 2;

po and pp are independently 1, 2, or 3;

each $P^{11}$ is independently:

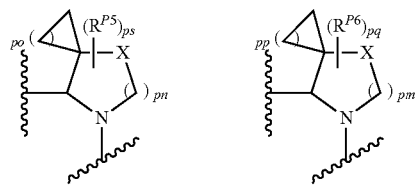

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;

pm and pn are independently 0, 1, or 2;

po and pp are independently 1, 2, or 3;

each $P^{12}$ is independently:

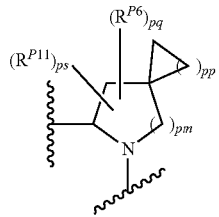

wherein:

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm is independently 0, 1, or 2;

pp is independently 1, 2, or 3;

ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{13}$ is independently:

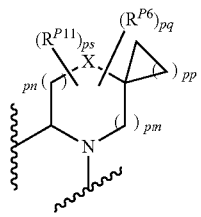

wherein:

X is selected from O, S, S(O), $SO_2$, or $NR^h$;

each $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm and pn are independently 0, 1, or 2 but the sum of pn and pm is greater than zero;

pp are independently 1, 2, or 3;

ps is 1, 2, 3, or 4;

each $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, $-NR^{hh}R$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$, $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{14}$ is independently:

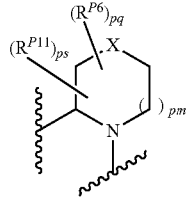

wherein:

the ring is substituted with one or more oxo group;

X is $NR^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm is independently 0, 1, or 2;

ps is 1, 2, 3, or 4;

$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two $R^h$ groups are present then they may come together with the atoms to which they are bound to form a 4-15 membered heterocyclic ring;

each $P^{15}$ is:

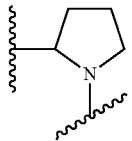 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{16}$ is:

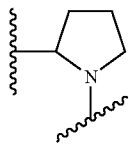

which is substituted with methylene;

each P$^{17}$ is:

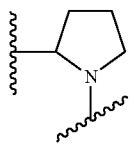 [SMILES: *C1CCCN1*]

which is substituted with one or two groups independently selected from alkenyl, alkynyl, cycloalkyl, cycloalkylalkenyl, and cycloalkylalkynyl;

each P$^{18}$ is:

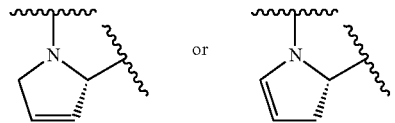 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each P$^{19}$ is:

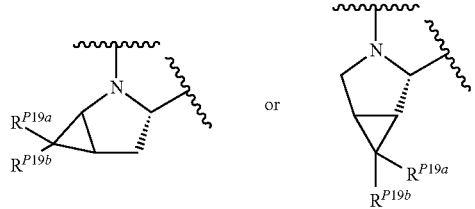

wherein each R$^{P19a}$ is independently selected from H and halo; and each R$^{P19b}$ is independently selected from halo;

each —Z$^0$— is —C(=O)— or —C(=S)—;

each —Z$^1$— is independently a bond, or —C(R$^{Z1}$)$_2$—; wherein each R$^{Z1}$ is independently H, alkyl, haloalkyl, or halo;

each —Z$^2$— is independently saturated or partially unsaturated (C$_3$-C$_8$)cycloalkyl that is optionally substituted with one or more groups independently selected from R$^{A1}$ and R$^{A3}$;

each —Z$^3$— is independently saturated, partially unsaturated, or aromatic 4-8 membered heterocyclic or heteroaryl ring that is optionally substituted with one or more groups independently selected from R$^{A1}$ and R$^{A3}$;

each —Z$^4$— is independently:

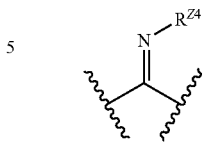

wherein each R$^{Z4}$ is independently H, alkyl, cyano, aryl, or heteroaryl;

each —Z$^5$— is independently:

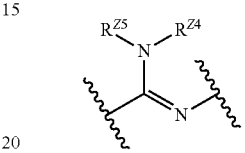

wherein each R$^{Z5}$ is independently H, alkyl, cyano, aryl, or heteroaryl; or two R$^{Z5}$s together with the nitrogen to which they are attached form a 4-8 membered heterocyclic ring that is optionally substituted with one or more oxo and with one or more groups independently selected from R$^{A1}$ and R$^{A3}$;

each —Z$^6$— is independently —C(R$^{Z1}$)— and is double-bonded to a carbocyclic P; wherein R$^{Z1}$ is independently H, alkyl, haloalkyl, or halo;

each E$^0$ is independently —NR$^{Ec}$R$^{Ed}$ wherein

R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E$^1$ is independently —OC(=O)NR$^{Ee}$R$^{Ef}$ wherein each R$^{Ee}$ and R$^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein $R^{Ee}$ and $R^{Ef}$, together with the nitrogen atom to which they are attached, form a heterocycle;

each $E^2$ is independently —$NR^aR^b$, wherein $R^a$ is haloalkyl and $R^b$ is H, alkyl, alkoxycarbonyl or haloalkyl;

each $E^3$ is independently —$NR^{Ec}R^{E3a}$, wherein $R^{E3a}$ is ($C_3$-$C_6$)cycloalkyloxycarbonyl;

each $E^4$ is independently —OC(=O)O$R^{E4a}$, wherein $R^{E4a}$ is cycloalkyl, aryl, or alkyl;

each $E^5$ is independently —$NR^{Ec}S(=O)_2OR^{E5a}$, wherein $R^{E5a}$ is cycloalkyl, aryl or alkyl;

each $E^6$ is independently —$NR^{Ec}S(=O)_2R^{E6a}$, wherein $R^{E6a}$ is cycloalkyl, aryl, or alkyl;

each $E^7$ is independently —$NR^{Ec}OR^{E7a}$, wherein $R^{E7a}$ is cycloalkyl, aryl, alkyl, haloalkyl, cycloalkylalkyl or heteroaryl;

each $V^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —P(O)O$R_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $V^1$ is independently cyanoalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; wherein $R^{Va}$ and $R^{Vb}$ are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^6$ is independently arylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^8$ is independently spirocycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{10}$ is independently fused bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{11}$ is independently fused bicycliccycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{12}$ is independently bridged-bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{13}$ is independently bridged-bicyclic-cycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{14}$ is independently aryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{18}$ is independently heterocyclooxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{20}$ is independently heteroaryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{21}$ is independently heteroarylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{22}$ is independently cycloalkenylalkyl;

each $V^{23}$ is independently arylalkyl, wherein the aryl is substituted with one or more groups independently selected from cycloalkyl, alkenyl, cycloalkylalkyl, cyanoalkyl, cycloalkoxy, hydroxyalkyl, $S(=O)_2NR^XR^Y$, $S(=O)_2NR^XR^Y$, alkylsulfanyl, alkylsulfonyl, haloalkylsulfanyl, haloalkylsulfonyl, alkylsulfonylalkyl, alkylsulfonylalkyl, arylsulfanyl, arylsulfonyl, alkoxyalkoxy, alkynyl, aryloxy, heteroaryloxy, alkylsulfonylamino;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $V^{24}$ is independently heterocycloalkyl, wherein the heterocycle is substituted with one or more groups independently selected from cycloalkyl, alkenyl, cycloalkylalkyl, cyanoalkyl, cycloalkoxy, hydroxyalkoxy, $—C(=O)NR^XR^Y$, $S(=O)_2NR^XR^Y$, alkylsulfanyl, alkylsulfonyl, haloalkylsulfanyl, haloalkylsulfonyl, alkylsulfonylalkyl, alkylsulfonylalkyl, arylsulfanyl, arylsulfonyl, alkoxyalkyoxy, alkynyl, aryloxy, heteroaryloxy, alkylfulfonylamino;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $T^1$ is independently a spiro, branched or fused bicycloalkyl;

each $T^2$ is independently aryl;

each $T^3$ is independently heteroaryl;

each $T^4$ is independently arylalkyl;

each $T^5$ is independently haloalkyl;

each $T^6$ is independently heteroarylalkyl;

each $T^7$ is independently heterocycle; and each $T^8$ is independently heterocycloalkyl.

In another specific embodiment the invention provides a compound of formula (I):

$$J-Y-J \qquad (I)$$

wherein:

Y is -L-L-, -M-W-M- or $Y^y$;

J is T-P-, -P-T or -J$^m$;

W is a bond or -W$^r$-;

L is -M-A-, -A-M-, or -L$^n$;

T is R9-Z-, -Z-R9, or -T$^p$;

R9 is E-V-, or -V-E, or -R9$^q$;

each A is selected from -A$^s$;

each M is selected from -M$^t$;

each P is selected from -P$^u$;

each Z is selected from -Z$^v$;

each V is selected from -V$^w$;

each E is selected from -E$^x$;

each m is 1;

each n is 0, 1, 2, 3, 4, 5, 6, 7, 9, or 10;

each p is 1, 2, 3, 4, 5, 6, 7, or 8;

each q is 0, 1, 2, or 3;

each r is 1, 2, 3, 4, 5, 6, 7, 8, 9, 10, 11, 12, 13, 14, 15, 16, 17, 18, 19, or 20;

each s is 0, 1, 2, 3, 4, 5, 6, 7, 8, 9, 10, 11, 12, 13, 14, 15, 16, 17, 18, or 21;

each t is 0, 1, 2, 3, 4, 5, 6, 7, 8, 9, 10, or 11;

each u is 0, 1, 2, 3, 4, 5, 6, 7, 8, 10, 11, 12, 13, or 14;

each v is 0, 1, 2, 3, 4, 5, or 6;

each w is 0, 1, 2, 3, 4, 5, 6, 7, 8, 9, 10, 11, 12, 13, 14, 15, 16, 17, 18, 19, 20, or 21;

each x is 0 or 1;

each y is 0, 1, or 2;

wherein the sum of m, n, p, q, r, s, t, u, v, w, x, and y is not 0; P is connected to M, L, or $Y^y$; A is connected to A or L; M is connected to P or J; Z is connected to P; V is connected to Z; and when W is a bond M is connected to M;

each Y¹ is independently:
a fused nine-ring system with up to thirty-five atoms that may be fully aromatic or partially saturated and contains atoms selected from C, N, O, and S, and which ring system is optionally substituted with one or more groups independently selected from H, oxo, $R^{41}$ and $R^{43}$;
each Y² is independently:
a fused five to eight ring system with up to thirty-two atoms that may be fully aromatic or partially saturated and contains atoms selected from C, N, O, and S, and which ring system is optionally substituted with one or more groups independently selected from H, oxo, $R^{41}$ and $R^{43}$;
each J¹ is independently a fused bicyclic saturated, partially unsaturated, or aromatic heterocyclic ring system that is substituted with one or more —N($R^{L7}$)C(=O)O$R^{L7}$, and that is optionally substituted with one or more groups independently selected from oxo, halo, —$R^{L7}$, —O$R^{L7}$, —S$R^{L7}$, —CF₃, —CCl₃, —OCF₃, —CN, —NO₂, —N($R^{L7}$)C(=O)$R^{L7}$, —C(=O)$R^{L7}$, —OC(=O)$R^{L7}$, —C(O)O$R^{L7}$, —C(=O)N$R^{L7}$, —S(=O)$R^{L7}$, —S(=O)₂O$R^{L7}$, —S(=O)₂$R^{L7}$, —OS(=O)₂O$R^{L7}$, —S(=O)₂N$R^{L7}$, alkoxyalkyl, arylalkoxycarbonyl, halo, haloalkyl, hydroxyalkyl, —N$R^a R^b$, (N$R^a R^b$)alkyl, and (N$R^a R^b$)carbonyl;
each $R^{L7}$ is independently —H, alkyl, aryl, arylalkyl, or heterocycle;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^0$ is independently:

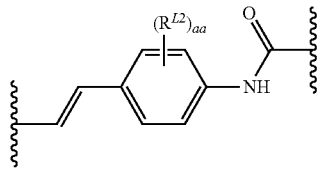

wherein:
each $R^{L2}$ is independently selected from hydrogen, alkenyl, alkoxy, alkyl, halo, and haloalkyl; and
each aa is independently 1, 2, 3, or 4;
each $L^1$ is independently:

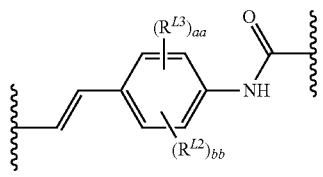

wherein:
each $R^{L2}$ is independently selected from hydrogen, alkenyl, alkoxy, alkyl, halo, and haloalkyl;
each $R^{L3}$ is independently selected from cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each R⁴ is independently selected from H, alkyl, haloalkyl, aryl, and arylalkyl;

each bb is 0, 1, 2, 3, or 4; each aa is 1, 2, 3, or 4; and the sum of bb and aa is 1, 2, 3, or 4;
each $L^2$ is independently:

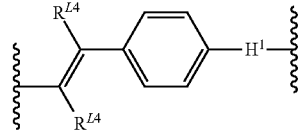

wherein:
the phenyl ring shown in $L^2$ is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, (N$R^a R^b$)alkyl, (N$R^a R^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{L4}$ is independently —H, alkyl, aryl, arylalkyl, or heterocycle;
each R⁴ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and
each H¹ is a 5 membered saturated, partially unsaturated, or aromatic ring comprising one or more heteroatoms;
each $L^3$ is independently a fused-bicyclic saturated, partially unsaturated, or aromatic heterocyclic ring system that is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —N$R^a R^b$, (N$R^a R^b$)alkyl, (N$R^a R^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R⁴ is independently selected from H, alkyl, haloalkyl, aryl, and arylalkyl; and
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^4$ is independently a fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —N$R^a R^b$, (N$R^a R^b$)alkyl, (N$R^a R^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R⁴ is independently selected from H, alkyl, haloalkyl, aryl, and arylalkyl; and
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L⁵ is independently a —CR=CR-fused bicyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R is independently selected from H or alkyl;

each R⁴ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L⁶ is independently a —CR=CR-fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR⁴, SO₂R⁴, -alkylSO₂R⁴, haloalkoxy, cyanoalkyl, NR⁴SO₂R⁴, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R is independently selected from H or alkyl;

each R⁴ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L⁷ is independently:

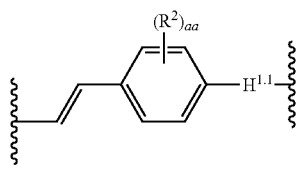

wherein:

each H$^{1.1}$ is independently a fused-bicyclic saturated, partially unsaturated, or aromatic heterocyclic ring system that is optionally substituted with one or more R²;

each R² is independently selected from halo, —R$^{L7}$, —OR$^{L7}$, —SR$^{L7}$, —N(R$^{L7}$)₂, —CF₃, —CCl₃, —OCF₃, —CN, —NO₂, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)₂OR$^{L7}$, —S(=O)₂R$^{L7}$, —OS$^{L7}$, and —S(=O)₂NR$^{L7}$;

each R$^{L7}$ is independently —H, alkyl, aryl, arylalkyl, or heterocycle; and each aa is independently 1, 2, 3, or 4;

each L⁹ is independently a fused-tetracyclic saturated, partially unsaturated, or aromatic heterocyclic ring system that is optionally substituted with one or more groups independently selected from oxo, halo, —R$^{L7}$, —OR$^{L7}$, —SR$^{L7}$, —CF₃, —CCl₃, —OCF₃, —CN, —NO₂, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)₂OR$^{L7}$, —S(=O)₂R$^{L7}$, —OS(=O)₂OR$^{L7}$, —S(=O)₂NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L¹⁰ is independently a fused-pentacyclic saturated, partially unsaturated, or aromatic heterocyclic ring system that is optionally substituted with one or more groups independently selected from oxo, halo, —R$^{L7}$, —OR$^{L7}$, —SR$^{L7}$, —CF₃, —CCl₃, —OCF₃, —CN, —NO₂, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)₂OR$^{L7}$, —S(=O)₂R$^{L7}$, —OS(=O)₂OR$^{L7}$, —S(=O)₂NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L¹¹ is independently a six-ring fused saturated, partially unsaturated, or aromatic heterocyclic ring system that is optionally substituted with one or more groups independently selected from oxo, halo, —R$^{L7}$, —OR$^{L7}$, —SR$^{L7}$, —CF₃, —CCl₃, —OCF₃, —CN, —NO₂, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)₂OR$^{L7}$, —S(=O)₂R$^{L7}$, —OS(=O)₂OR$^{L7}$, —S(=O)₂NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R9⁰ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl;

R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $R^{91}$ is independently —$N(R^{9a})$—$NHC(=O)O$—$R^{9b}$, wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, —$(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $R^{92}$ is independently —$N(R^{9a})$—$NHC(=O)NR^{9b}_2$; wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO2alkyl, cycloalkylalkylSO2alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, -$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, —$(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $R^{93}$ is independently —$N(R^{9a})$—$NHC(=O)R^{9b}$, wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from H or alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, —(NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; R$^{9b}$ is independently H, alkyl, aryl, haloalkyl, or arylalkyl;

each A$^0$ is independently:

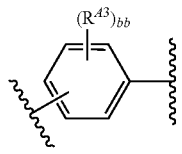

wherein:
each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each A$^0$ is independently a six-membered heteroaromatic ring containing one, two, or three nitrogen atoms, which ring is optionally substituted with 1, 2, 3, or 4 R$^{43}$ groups;

each A$^1$ is independently:

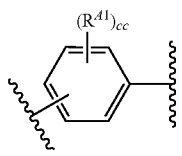

wherein:
each R$^{A1}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each R$^4$ is independently selected from H, alkyl, haloalkyl, aryl, and arylalkyl;

each cc is 1, 2, 3, or 4;

each A$^2$ is independently:

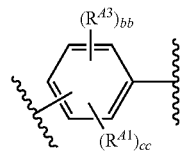

wherein:
each R$^{A1}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R$^4$ is independently selected from H, alkyl, haloalkyl, aryl, and arylalkyl;

R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each A$^3$ is independently a six-membered heteroaromatic ring containing one, two, or three nitrogen atoms, which ring is substituted with one or more R$^{A1}$ groups, and which ring is optionally substituted with one or more R$^{43}$ groups;

each A$^4$ is independently:

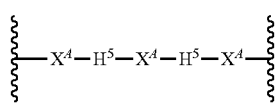

wherein:
each H$^5$ is independently a phenyl ring or a six-membered heteroaromatic ring, which H$^5$ is optionally substituted with one or more groups independently selected from R$^{A1}$ and R$^{43}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^5$ is independently:

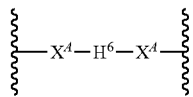

wherein:
each H$^6$ is independently a phenyl ring or a six-membered heteroaromatic ring, which H$^6$ is optionally substituted with one or more groups independently selected from R$^{A1}$ and R$^{43}$; and each X$^A$ is independently O, NR, SO, SO$_2$, C(=O), NRC(=O), C(=O)NR, CR=CR, NRC (=O)NR, allenyl, alkynyl, or absent; provided that at least one $X^A$ is present and each R is independently selected from H or alkyl;
each $A^6$ is independently:

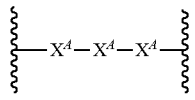

wherein:
each $X^A$ is independently O, NR, SO, SO$_2$, C(=O), NRC(=O), C(=O)NR, CR=CR, allenyl, alkynyl, or absent; provided that at least one $X^A$ is present and each R is independently selected from H or alkyl;
each $A^7$ is independently:

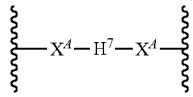

wherein:
each $H^7$ is independently a five-membered heteroaromatic ring, which $H^7$ is optionally substituted with one or more groups independently selected from $R^{A1}$ and $R^{A3}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $A^8$ is independently:

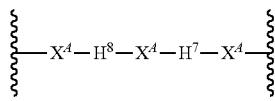

wherein:
each $H^7$ is independently a five-membered heteroaromatic ring, which $H^7$ is optionally substituted with one or more groups independently selected from $R^{A1}$ and $R^{A3}$;
each $H^8$ is independently a phenyl ring, which is optionally substituted with one or more groups independently selected from $R^{A1}$ and $R^{A3}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $A^9$ is independently:

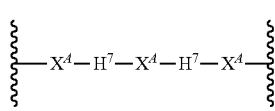

wherein:
each $H^7$ is independently a five-membered heteroaromatic ring, which $H^7$ is optionally substituted with one or more groups independently selected from $R^{A1}$ and $R^{A3}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{10}$ is independently:

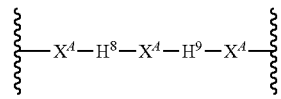

wherein:
each $H^8$ is independently a phenyl ring, which is optionally substituted with one or more groups independently selected from $R^{A1}$ and $R^{A3}$;
each $H^9$ is independently a six-membered heteroaromatic ring, which is optionally substituted with one or more groups independently selected from $R^{A1}$ and $R^{A3}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $A^{11}$ is independently:

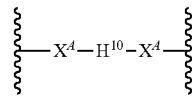

wherein:
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $H^{10}$ is independently a 5-15 carbon unsaturated, partially unsaturated or saturated bicyclic ring system that is optionally fused to an aryl, which $H^{10}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each R$^4$ is independently selected from H, alkyl, haloalkyl, aryl, and arylalkyl;
each $A^{12}$ is independently:

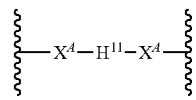

wherein:
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $H^{11}$ is independently a 5-15 carbon unsaturated, partially unsaturated or saturated bicyclic ring system that contains one or more heteroatoms that is optionally fused to an aryl, which $H^{11}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$) carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo) cycloalkyl, heterocycle, (cycloalkyl)alkyl, and (heterocycle)alkyl, wherein each alkyl, heterocycle and cycloalkyl is optionally substituted with one or more halo; and each R$^4$ is independently selected from H, alkyl, haloalkyl, aryl, and arylalkyl; and each A$^{13}$ is independently:

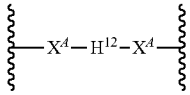

wherein:

each H$^{12}$ is independently a fused aromatic bicyclic carbocycle, which is optionally substituted with one or more groups independently selected from R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{14}$ is independently:

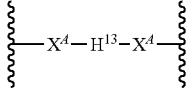

wherein:

each H$^{13}$ is independently a fused aromatic bicyclic heterocycle that comprises at least one heteroatom in the ring system, which ring system is optionally substituted with one or more groups independently selected from R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{15}$ is independently:

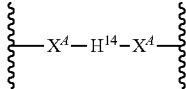

wherein:

each H$^{14}$ is independently a fused unsaturated, partially unsaturated or saturated tricyclic carbocycle which is optionally substituted with one or more groups independently selected from R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{16}$ is independently:

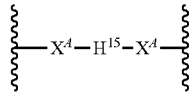

wherein:

each H$^{15}$ is independently a fused unsaturated, partially unsaturated or saturated tricyclic heterocycle that comprises at least one heteroatom in the ring system, which ring system is optionally substituted with one or more groups independently selected from R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{17}$ is independently:

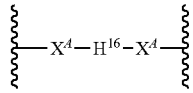

wherein:

each H$^{16}$ is independently a fused bicyclic carbocyclic ring system wherein one ring is aromatic and another ring is partially or fully saturated, which ring system is optionally substituted with one or more groups independently selected from oxo, R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{18}$ is independently:

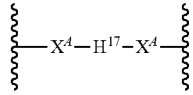

wherein:

each H$^{17}$ is independently a fused bicyclic ring system comprising at least one heteroatom, wherein one ring is aromatic and another ring is partially or fully saturated, which ring system is optionally substituted with one or more groups independently selected from oxo, R$^{A1}$ and R$^{A3}$; and each X$^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^{21}$ is independently:

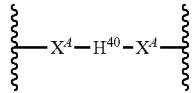

wherein:

each H$^{40}$ is independently an anti-aromatic monocyclic or fused carbocyclic ring system, which carbocyclic ring system is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^1$ is independently —$X^A$—:

wherein:
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^2$ is independently:

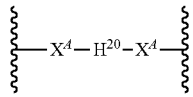

wherein:
each $H^{20}$ is independently is independently a fused aromatic bicyclic carbocycle, which is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^3$ is independently:

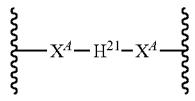

wherein:
each $H^{21}$ is independently a fused bicyclic carbocyclic ring system wherein one ring is aromatic and another ring is partially or fully saturated, which ring system is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^4$ is independently:

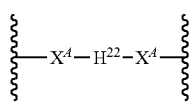

wherein:
each $H^{22}$ is independently a fused aromatic bicyclic heterocycle that comprises at least one heteroatom in the ring system, which ring system is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^5$ is independently:

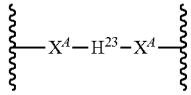

wherein:
each $H^{23}$ is independently a fused bicyclic ring system comprising at least one heteroatom, wherein one ring is aromatic and another ring is partially or fully saturated, which ring system is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^6$ is independently:

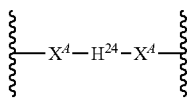

wherein:
each $H^{24}$ is independently a fused unsaturated, partially unsaturated or saturated tricyclic carbocycle, which is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^7$ is independently:

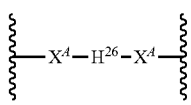

wherein:
each $H^{26}$ is independently a 5-15 carbon unsaturated, partially unsaturated or saturated bicyclic ring system which ring system is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^8$ is independently:

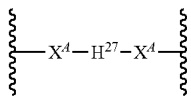

wherein:
each $H^{27}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and each $X^4$ is independently O, NR, SO, SO$_2$, NRC(=O), C(=O)NR, CR=CR, NRC(=O)NR, allenyl, alkynyl, or absent and each R is independently selected from H or alkyl;

each $W^9$ is independently:

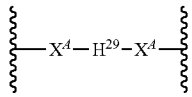

wherein:
each $H^{29}$ is independently a 5-15 carbon unsaturated, partially unsaturated or saturated bicyclic ring system that contains one or more heteroatoms; and
each $X^4$ is independently O, NR, SO, SO$_2$, C(=O), NRC(=O), C(=O)NR, CR=CR, NRC(=O)NR, allenyl, alkynyl, or absent and each R is independently selected from H or alkyl;

each $W^{10}$ is independently —$H^{30}$=C=$H^{31}$—
wherein each of —$H^{30}$ and $H^{31}$ is independently a saturated 6-membered heterocyclic ring comprising one or more heteroatoms, which ring is optionally substituted with oxo;

each $W^{11}$ is independently —$H^{32}$=C=$H^{33}$—
wherein each of —$H^{32}$ and $H^{33}$ is independently a saturated 5-membered heterocyclic ring comprising one or more heteroatoms, which ring is optionally substituted with oxo;

each $W^{12}$ is independently an anti-aromatic monocyclic or fused carbocyclic ring system, which carbocyclic ring system is optionally substituted with one or more groups independently selected from $R^{41}$ and $R^{43}$;

each $W^{13}$ is independently a phenyl ring that is optionally substituted with one or more groups independently selected from $R^{41}$ and $R^{43}$;

each $W^{14}$ is independently a 5 or 6 membered heteroaryl ring that is optionally substituted with one or more groups independently selected from $R^{41}$ and $R^{43}$;

each $W^{15}$ is independently a fused unsaturated, partially unsaturated or saturated tetracyclic carbocyclic ring, which ring system is optionally substituted with one or more groups independently selected from oxo, $R^{41}$ and $R^{43}$;

each $W^{16}$ is independently a fused unsaturated, partially unsaturated or saturated tetracyclic heterocycle that comprises at least one heteroatom in the ring system, which ring system is optionally substituted with one or more groups independently selected from oxo, $R^{41}$ and $R^{43}$;

each $W^{17}$ is independently a fused unsaturated, partially unsaturated or saturated pentacyclic carbocyclic ring system, which ring system is optionally substituted with one or more groups independently selected from oxo, $R^{41}$ and $R^{43}$;

each $W^{18}$ is independently a fused unsaturated, partially unsaturated or saturated pentacyclic heterocycle that comprises at least one heteroatom in the ring system, which ring system is optionally substituted with one or more groups independently selected from oxo, $R^{41}$ and $R^{43}$;

each $W^{19}$ is independently a fused unsaturated, partially unsaturated or saturated hexacyclic carbocyclic ring system, which ring system is optionally substituted with one or more groups independently selected from oxo, $R^{41}$ and $R^{43}$;

each $W^{20}$ is independently a fused unsaturated, partially unsaturated or saturated hexacyclic heterocycle that comprises at least one heteroatom in the ring system, which ring system is optionally substituted with one or more groups independently selected from oxo, $R^{41}$ and $R^{43}$;

each $M^0$ is independently a five membered heteroaryl group optionally substituted with one or more alkoxycarbonyl, alkyl, arylalkoxycarbonyl, carboxy, haloalkyl, (NR$^a$R$^b$)carbonyl and trialkylsilylalkoxyalkyl;

each $M^1$ is independently selected from —C(=O)NH—, —C(=O)NH—C(R$^M$)$_2$—, —NHC(=O)—, —C(R$^M$)$_2$NHC(=O)—, —NHC(=O)NR$^M$—, —NHC(=O)O—; wherein each R$^M$ is independently selected from H and alkyl;

each $M^2$ is independently a six-membered heteroaromatic ring, which is optionally substituted with one or more groups independently selected from $R^{41}$ and $R^{43}$;

each $M^3$ is independently:

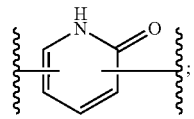

each $M^4$ is independently:

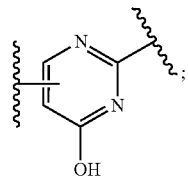

each $M^5$ is independently:

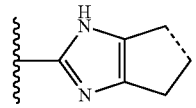

wherein the bond designated with - - - is fused to a ring defined for P;

each $M^6$ is independently a bicyclic bridged ring system comprising 5-15 atoms wherein at least one of the atoms is a heteroatom;

each $M^7$ is independently a pyrid-di-yl;

each $M^8$ is independently partially saturated or a saturated five-membered ring that comprises one or more heteroatoms and that is optionally substituted with one or two oxo;

each $M^9$ is independently a fused-bicyclic saturated, partially unsaturated, or aromatic heterocyclic ring system that is optionally substituted with one or more $R^{P11}$;

each $M^{10}$ is independently a five membered heteroaryl group;

each $M^{11}$ is independently a fused-tricyclic saturated, partially unsaturated, or aromatic heterocyclic ring system that is optionally substituted with one or more oxo, halo, —$R^{M7}$, —OR$^{M7}$, —SR$^{M7}$, —N(R$^{M7}$)$_2$, —CF$_3$, —CCl$_3$, —OCF$_3$, —CN, —NO$_2$, —N(R$^{M7}$)C(=O)R$^{M7}$, —C(=O)R$^{M7}$, —OC(=O)R$^{M7}$, —C(O)OR$^{M7}$, —C(=O)NR$^{M7}$, —S(=O)R$^{M7}$, —S(=O)$_2$OR$^{M7}$, —S(=O)$_2$R$^{M7}$, —OS(=O)$_2$OR$^{M7}$, or —S(=O)$_2$NR$^{M7}$;

each $R^{M7}$ is independently —H, alkyl, aryl, arylalkyl, or heterocycle;

each P⁰ is independently:

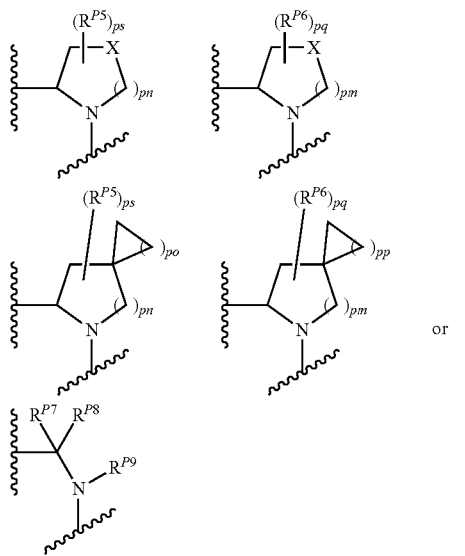

or wherein:
X is selected from O, S, S(O), SO₂, CH₂, CHR$^{P10}$, and C(R$^{P10}$)₂; provided that when pn or pm is 0, X is selected from CH₂, CHR$^{P10}$, and C(R$^{P10}$)₂;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;
R$^{P9}$ is selected from hydrogen and alkyl;
each P¹ is independently:

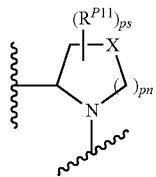

wherein:
X is selected from O, S, S(O), SO₂, CH₂, CHR$^{P10}$, and C(R$^{P10}$)₂; provided that when pn is 0, X is selected from CH₂, CHR$^{P10}$, and C(R$^{P10}$)₂;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
at least one R$^{P11}$ is independently selected from cyano, alkylsulfonyl, arylsulfonyl, (NR$^{h}$R$^{h}$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^{h}$R$^{h}$)alkyloxy, cyanoalkoxy, cyanocycloalkyloxy, cycloalkyloxy, oxo, heterocyclyl, —NR$^{hh}$R$^{h}$, (NR$^{hh}$R$^{h}$)alkyl, (NR$^{hh}$R$^{h}$)carbonyl, wherein each R$^{h}$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^{h}$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^{h}$R$^{h}$)sulfonyl, heteroarylsulfonyl, —S(═O)₂R$^{h}$, —C(═O)R$^{h}$, —C(═O)NR$^{h}$R$^{h}$; and the remaining R$^{P11}$ are independently selected from R$^{P5}$, cyano, alkylsulfonyl, arylsulfonyl, (NR$^{h}$R$^{h}$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^{h}$R$^{h}$)alkyloxy, cyanoalkoxy, cyanocycloalkyloxy, cycloalkyloxy, oxo, heterocyclyl; wherein each R$^{h}$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^{h}$ groups are present then they may come together with the atoms to which they are bound to form a 4-15 membered heterocyclic ring;
ps is 1, 2, 3, or 4;
pn is 0, 1, or 2;
each P² is independently:

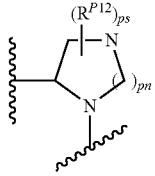

wherein:
each R$^{P12}$ is independently selected from R$^{P5}$, R$^{P11}$, —C(O)OR$^{h}$, cyano, alkylsulfonyl, arylsulfonyl, (NR$^{h}$R$^{h}$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^{h}$R$^{h}$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 1, 2, 3, or 4;
pn is 0, 1, or 2;
each P$^3$ is independently a ring of the formula:

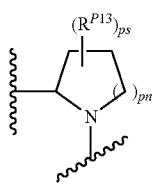

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 0, 1, 2, 3, or 4;
pn is 0, 1, or 2;
each P$^4$ is independently a ring of the formula:

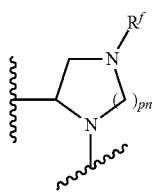

wherein:
the ring is optionally substituted with one or more groups R$^{P14}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P14}$ that are attached to the same carbon when taken together with the carbon to which they are attached can form a 3-6 membered carbocyclic or heterocyclic ring;
pn is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(═O)$_2$NR$^h$R$^h$, —S(═O)$_2$R$^h$, C(═O)R$^h$, C(═O)OR$^h$, —C(═O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^5$ is independently a ring of the formula:

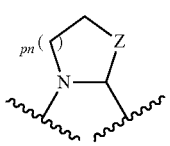

wherein:
the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;
pn is 0, 1, or 2;
Z is O, S, S(═O), S(═O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(═O)$_2$NR$^h$R$^h$, —S(═O)$_2$R$^h$, C(═O)R$^h$, C(═O)OR$^h$, —C(═O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^6$ is independently a ring of the formula:

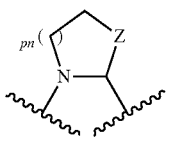

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

Z is O, S, S(=O), S(=O)$_2$, or NR$^f$;
pn is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;

each P$^8$ is independently a ring of the formula:

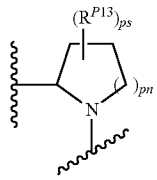

wherein:
ps is 2, 3, 4, 5, or 6;
pn is 0, 1, or 2;
each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;

each P$^{10}$ is independently:

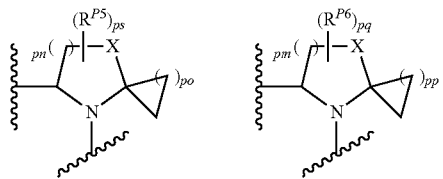

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each P$^{11}$ is independently:

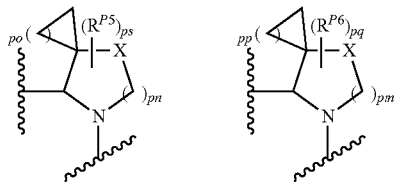

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each P$^{12}$ is independently:

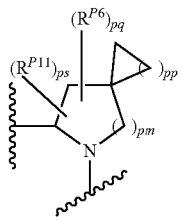

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl, —NR^{hh}R^h, (NR^{hh}R^h)alkyl, (NR^{hh}R^h)carbonyl, wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R^h groups are present then they may come together with the atoms to which they are bound to form a 4-15 membered heterocyclic ring; wherein each R^{hh} is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, NR^hR^hsulfonyl, heteroarylsulfonyl, —S(=O)_2R^h, —C(=O)R^h, —C(=O)NR^hR^h; and the remaining R^{P11} are independently selected from R^{P5}, cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl; wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R^h groups are present then they may come together with the atoms to which they are bound to form a 4-15 membered heterocyclic ring;

each P^{13} is independently:

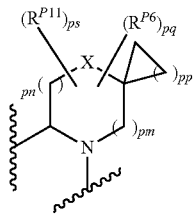

wherein:
X is selected from O, S, S(O), SO_2, or NR^h;
each R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm and pn are independently 0, 1, or 2 but the sum of pn and pm is greater than zero;
pp are independently 1, 2, or 3;
ps is 1, 2, 3, or 4;
each R^{P11} is independently selected from cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl, —NR^{hh}R^h, (NR^{hh}R^h)alkyl, (NR^{hh}R^h)carbonyl, wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R^h groups are present then they may come together with the atoms to which they are bound to form a 4-15 membered heterocyclic ring; wherein each R^{hh} is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR^hR^h)sulfonyl, heteroarylsulfonyl, —S(=O)_2R^h, —C(=O)R^h, —C(=O)NR^hR^h, R^{P5}, cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl; wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R^h groups are present then they may come together with the atoms to which they are bound to form a 4-15 membered heterocyclic ring;

each P^{14} is independently:

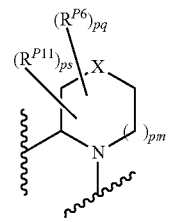

wherein:
the ring is substituted with one or more oxo group;
X is NR^f;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)_2NR^hR^h, —S(=O)_2R^h, C(=O)R^h, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
ps is 1, 2, 3, or 4;
R^{P11} is independently selected from cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl; wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two $R^h$ groups are present then they may come together with the atoms to which they are bound to form a 4-15 membered heterocyclic ring;

each —$Z^0$— is —C(=O)— or —C(=S)—;
each —$Z^1$— is independently a bond, or —C($R^{Z1}$)$_2$—; wherein each $R^{Z1}$ is independently H, alkyl, haloalkyl, or halo;
each —$Z^2$— is independently saturated or partially unsaturated ($C_3$-$C_8$)cycloalkyl that is optionally substituted with one or more groups independently selected from $R^{A1}$ and $R^{A3}$;
each —$Z^3$— is independently saturated, partially unsaturated, or aromatic 4-8 membered heterocyclic or heteroaryl ring that is optionally substituted with one or more groups independently selected from $R^{A1}$ and $R^{A3}$;
each —$Z^4$— is independently:

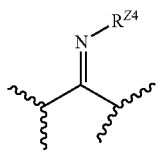

wherein each $R^{Z4}$ is independently H, alkyl, cyano, aryl, or heteroaryl;
each —$Z^5$— is independently:

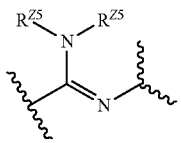

wherein each $R^{Z5}$ is independently H, alkyl, cyano, aryl, or heteroaryl; or two $R^{Z5}$s together with the nitrogen to which they are attached form a 4-8 membered heterocyclic ring that is optionally substituted with one or more oxo and with one or more groups independently selected from $R^{A1}$ and $R^{A3}$;
each —$Z^6$— is independently —C($R^{Z1}$)— and is double-bonded to a carbocyclic P; wherein $R^{Z1}$ is independently H, alkyl, haloalkyl, or halo;
each $E^0$ is independently —$NR^{Ec}R^{Ed}$ wherein
$R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently —OC(=O)$NR^{Ee}R^{Ef}$ wherein each $R^{Ee}$ and $R^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein $R^{Ee}$ and $R^{Ef}$, together with the nitrogen atom to which they are attached, form a heterocycle;

each $V^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —($NR^XR^Y$)alkyl, oxo, and —P(O)$OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $V^1$ is independently cyanoalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^6$ is independently arylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^8$ is independently spirocycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{10}$ is independently fused bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{11}$ is independently fused bicycliccycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{12}$ is independently bridged-bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{13}$ is independently bridged-bicyclic-cycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{14}$ is independently aryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{18}$ is independently heterocyclooxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{20}$ is independently heteroaryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{21}$ is independently heteroarylalkylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $T^1$ is independently a spiro, branched or fused bicycloalkyl;

each $T^2$ is independently aryl;

each $T^3$ is independently heteroaryl;

each T⁴ is independently arylalkyl;
each T⁵ is independently haloalkyl;
each T⁶ is independently heteroarylalkyl;
each T⁷ is independently heterocycle; and
each T⁸ is independently heterocyclealkyl.

In another specific embodiment the invention provides a compound of formula (I) which comprises $M^0$-W-$M^0$, $M^0$-W-$M^9$, $M^9$-W-$M^0$, or $M^9$-W-$M^9$, $M^{10}$-W-$M^0$, $M^0$-W-$M^{10}$, $M^{10}$-W-$M^9$, $M^9$-W-$M^{10}$, or $M^{10}$-W-$M^{10}$.

In another specific embodiment the invention provides a compound of formula (I) wherein W is $W^2$.

In another specific embodiment the invention provides a compound of formula (I) wherein W is $W^8$.

In another specific embodiment the invention provides a compound of formula (I) wherein W is $W^{15}$.

In another specific embodiment the invention provides a compound of formula (I) wherein W is $W^{16}$.

In another specific embodiment the invention provides a compound of formula (I) wherein W is $W^{18}$.

In another specific embodiment the invention provides a compound of formula (I) which comprises $M^0$-A-A-$M^0$, $M^0$-A-A-$M^9$, $M^9$-A-A-$M^0$, or $M^9$-A-A-$M^9$, $M^{10}$-A-A-$M^0$, $M^0$-A-A-$M^{10}$, $M^{10}$-A-A-$M^9$, $M^9$-A-A-$M^{10}$, or $M^{10}$-A-A-$M^{10}$.

In another specific embodiment the invention provides a compound of formula (I) wherein -A-A- is -$A^0$-$A^0$-.

In another specific embodiment the invention provides a compound of formula (I) wherein -A-A- is -$A^0$-$A^5$-.

In another specific embodiment the invention provides a compound of formula (I) wherein -A-A- is -$A^0$-$A^{13}$-.

In another specific embodiment the invention provides a compound of formula (I) wherein -A-A- is -$A^{13}$-$A^{13}$-.

In another specific embodiment the invention provides a compound of formula (I) wherein -A-A- is -$A^0$-$A^{11}$-.

In another specific embodiment the invention provides a compound of formula (I) wherein -A-A- is -$A^{13}$-$A^6$-.

In another specific embodiment the invention provides a compound of formula (I) wherein W is $W^6$.

In another specific embodiment the invention provides a compound of formula (I) wherein each $X^4$ is absent where it is allowed to be absent.

In another specific embodiment the invention provides a compound of formula (I) wherein one or two $X^4$ are present and $X^4$ is alkynyl.

In another specific embodiment the invention provides a compound of formula (I) wherein one or two $X^4$ are present and $X^4$ is alkenyl.

In another specific embodiment the invention provides a compound of formula (I) wherein $W^6$ is selected from:

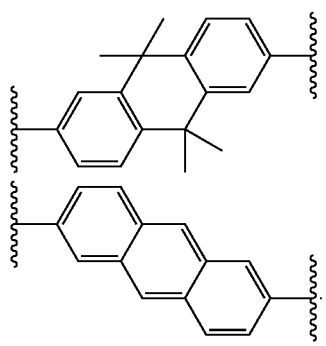

In another specific embodiment the invention provides a compound of formula (I) wherein $W^6$ is selected from:

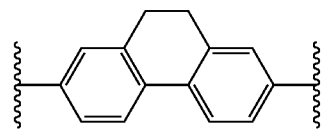

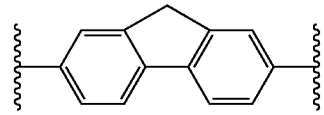
and

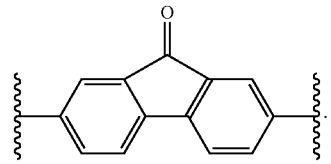

In another specific embodiment the invention provides a compound of formula (I) wherein W is $W^8$.

In another specific embodiment the invention provides a compound of formula (I) wherein $W^8$ is selected from:

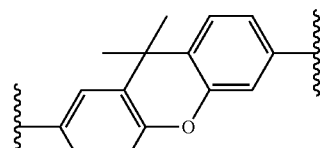

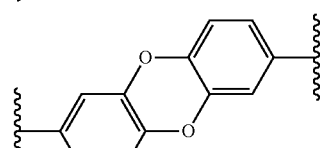

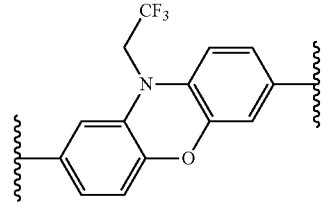

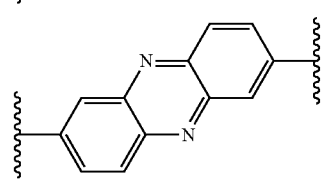

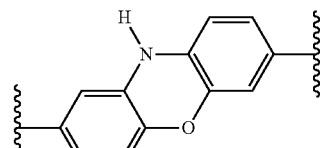

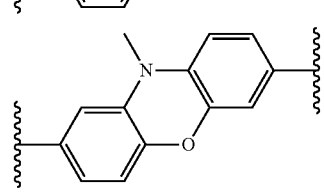

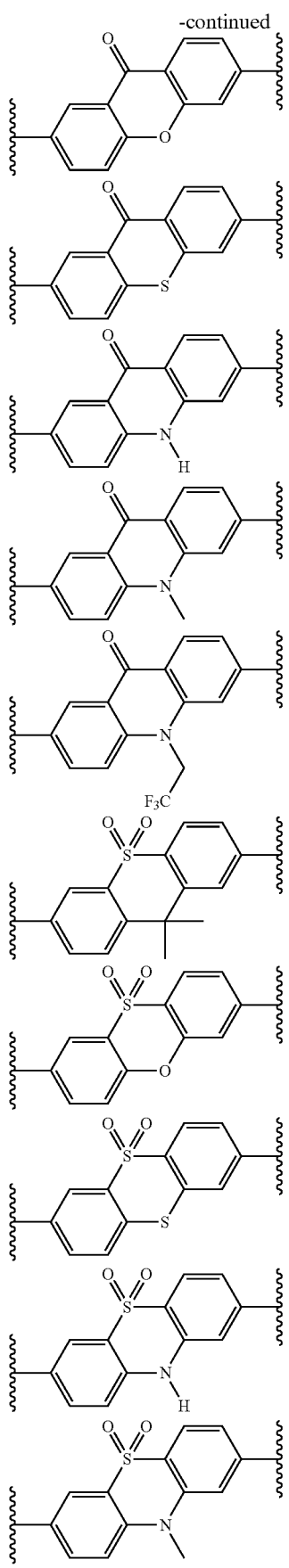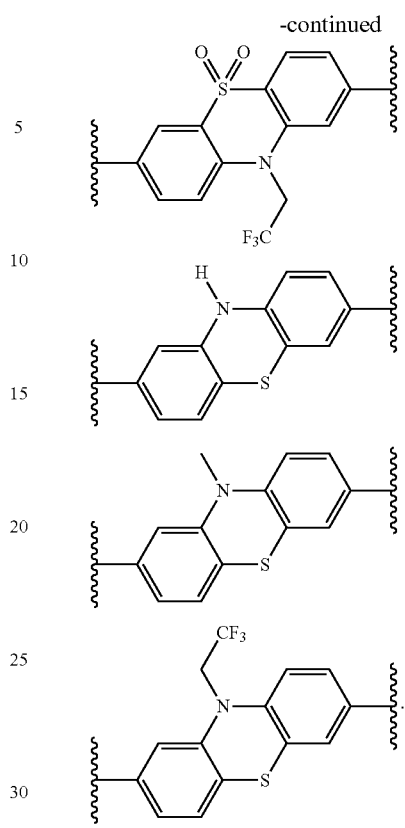
In another specific embodiment the invention provides a compound of formula (I) wherein $W^8$ is selected from:
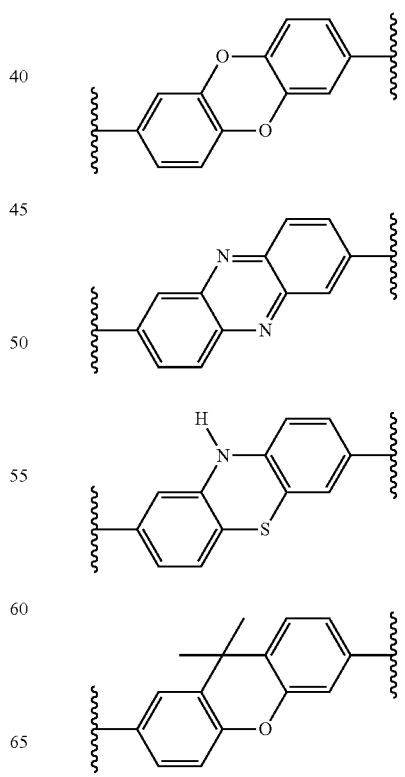
and -continued
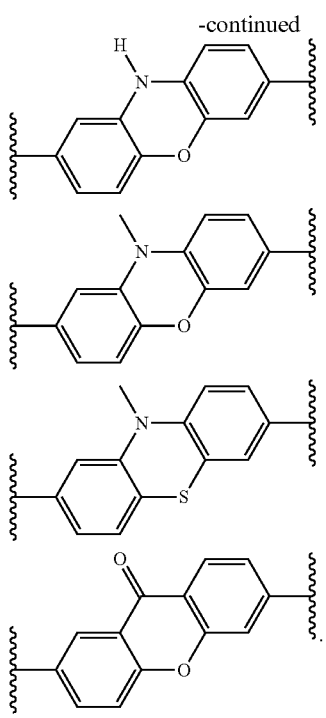
In another specific embodiment the invention provides a compound of formula (I) $W^8$ is selected from:
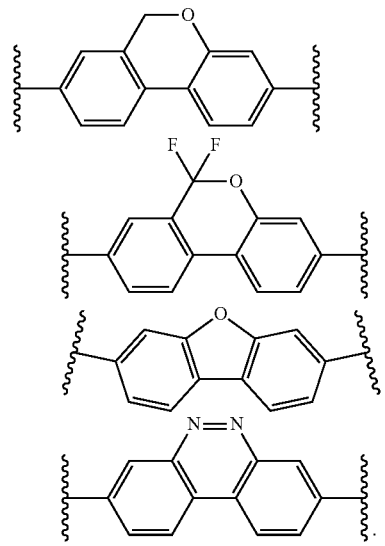
and
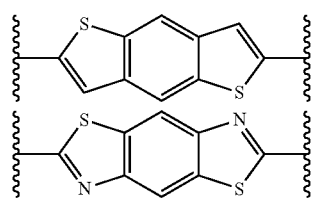
and
-continued
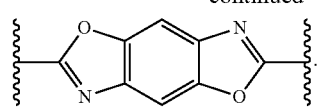
In another specific embodiment the invention provides a compound of formula (I) wherein $W^8$ is selected from:
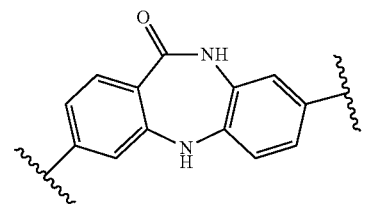
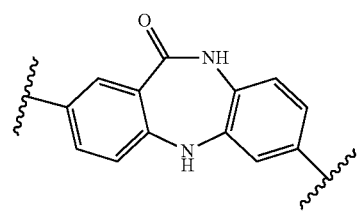
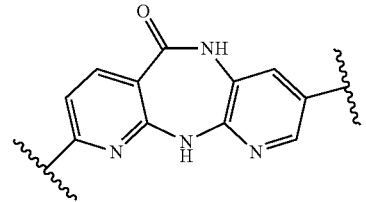
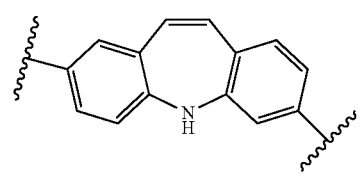
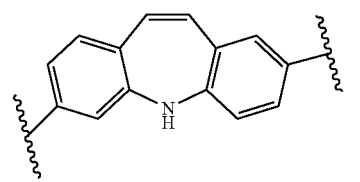
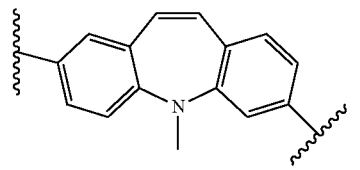
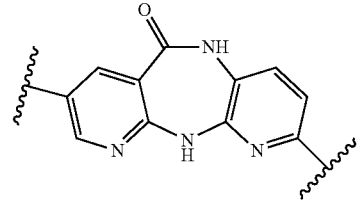
and -continued

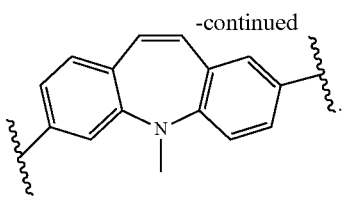

In another specific embodiment the invention provides a compound of formula (I) wherein W is $W^8$ that is unsubstituted.

In another specific embodiment the invention provides a compound of formula (I) wherein $W^{12}$ is:

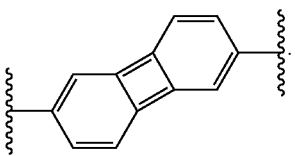 [SMILES: *c1ccc2c(c1)=c1ccc(*)cc1=2]

In another specific embodiment the invention provides a compound of formula (I) wherein W is $W^{15}$ or $W^{16}$.

In another specific embodiment the invention provides a compound of formula (I) wherein W is a ring system of formula:

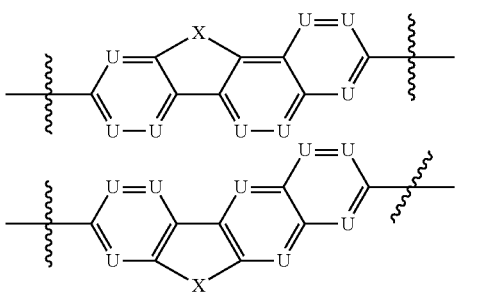

wherein:
U is CH or N; and
X is —CH$_2$—, —C(=O)—, —CH$_2$CH$_2$—, —CH$_2$CH$_2$CH$_2$—, or —CH=CH—;
wherein the ring system is optionally substituted with one or more $R^{41}$ or $R^{43}$.

In another specific embodiment the invention provides a compound of formula (I) wherein W is a ring system of formula:

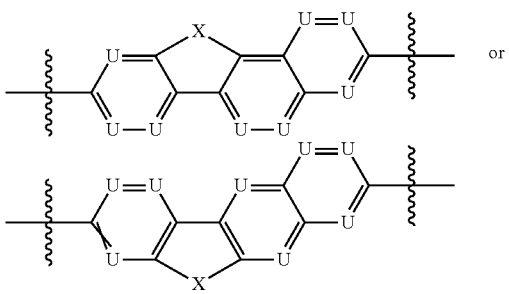

wherein:
U is CH or N; and
X is —OCH$_2$—, —CH$_2$O—, —CH$_2$OCH$_2$—, or CF$_2$;
wherein the ring system is optionally substituted with one or more $R^{41}$ or $R^{43}$.

In another specific embodiment the invention provides a compound of formula (I) wherein W is $W^{15}$.

In another specific embodiment the invention provides a compound of formula (I) wherein W is selected from:

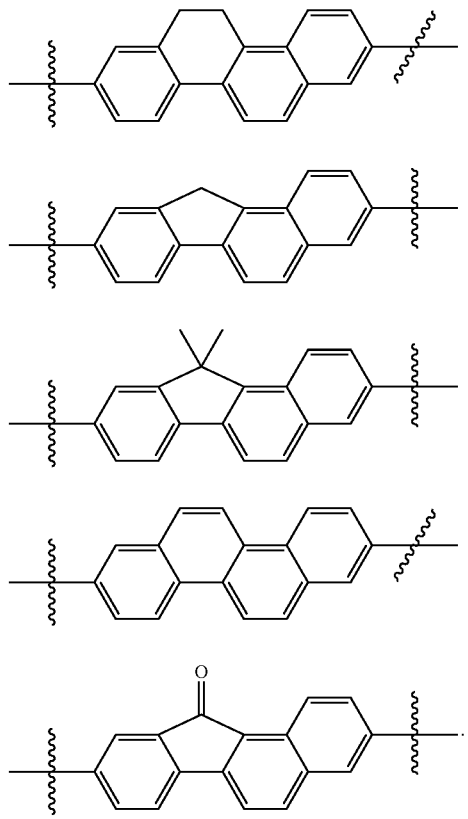

and

In another specific embodiment the invention provides a compound of formula (I) wherein W is selected from:

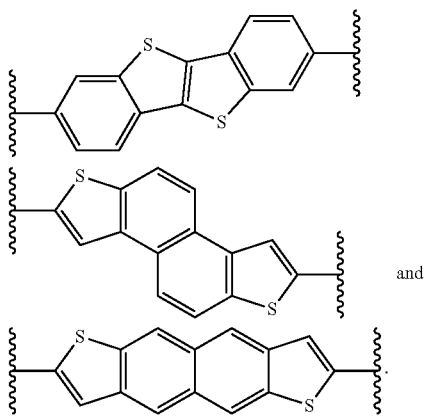

and

In another specific embodiment the invention provides a compound of formula (I) wherein W is selected from:

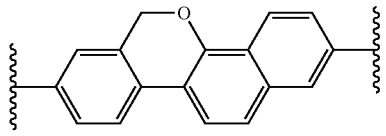

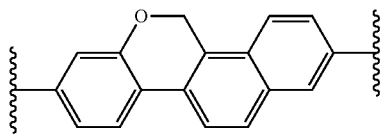

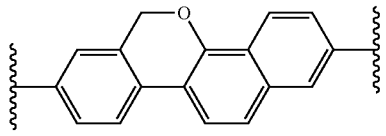 and

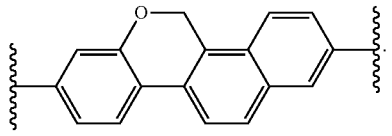

In another specific embodiment the invention provides a compound of formula (I) wherein W is $W^{18}$.

In another specific embodiment the invention provides a compound of formula (I) wherein W is selected from:

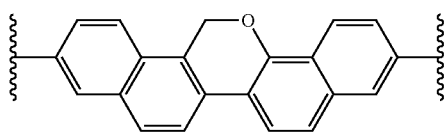

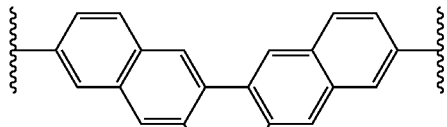 and

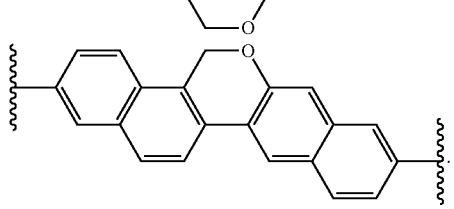

In another specific embodiment of the invention W is

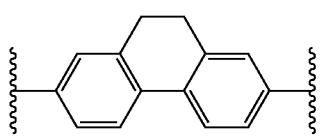

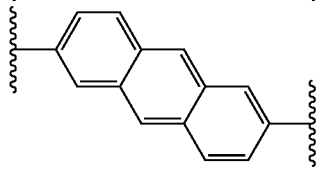

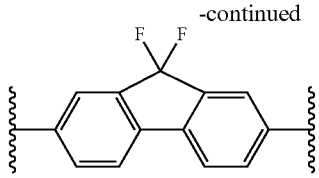 or

In another specific embodiment of the invention W is

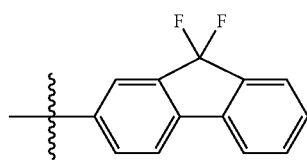 or

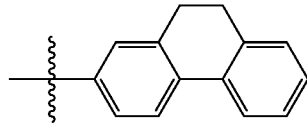

In another specific embodiment of the invention W is

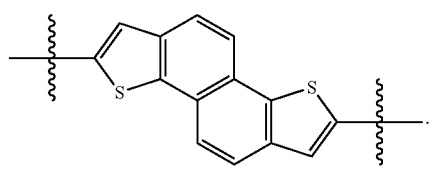

In another specific embodiment the invention provides a compound of formula (I) wherein one A is $A^0$ and one A is $A^5$, wherein one $X^A$ in the $A^5$ is absent and the other $X^A$ in the $A^5$ is alkynyl.

In another specific embodiment the invention provides a compound of formula (I) wherein -$A^0$-$A^5$- has the following structure:

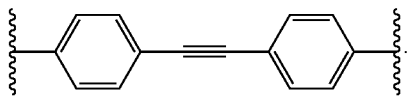

In another specific embodiment the invention provides a compound of formula (I) wherein one A is $A^0$ and one A is $A^{13}$, wherein both $X^A$ in the $A^{13}$ are absent.

In another specific embodiment the invention provides a compound of formula (I) wherein -$A^0$-$A^{13}$- has the following structure:

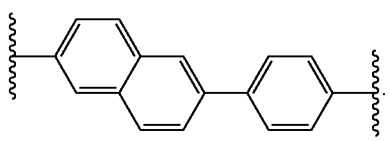 [SMILES: *c1ccc(-c2ccc3cc(*)ccc3c2)cc1]

In another specific embodiment the invention provides a compound of formula (I) that comprises $A^{13}$-$A^{13}$, wherein all $X^4$ in both $A^{13}$ are absent.

In another specific embodiment the invention provides a compound of formula (I) wherein -$A^{13}$-$A^{13}$- has the following structure:

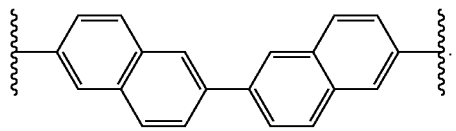 [SMILES: *c1ccc2cc(-c3ccc4cc(*)ccc4c3)ccc2c1]

In another specific embodiment the invention provides a compound of formula (I) that comprises $A^0$-$A^{11}$ wherein all $X^4$ in both the $A^0$ and the $A^{11}$, are absent or alkynyl.

In another specific embodiment the invention provides a compound of formula (I) wherein -$A^0$-$A^{11}$- has the following structure:

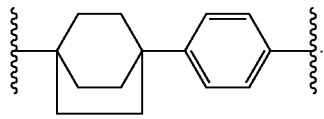

In another specific embodiment the invention provides a compound of formula (I) that comprises one $A^{13}$ and one $A^6$ wherein all $X^4$ in the $A^{13}$ are bonds.

In another specific embodiment the invention provides a compound of formula (I) wherein -$A^{13}$-$A^6$- has the following structure:

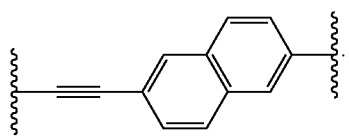

In another specific embodiment the invention provides a compound of formula (I) wherein W is $W^2$ and within the $W^2$ one $X^4$ is absent and one $X^4$ is RC=CR and each R is independently selected from H or alkyl.

In another specific embodiment the invention provides a compound of formula (I) wherein $W^2$ has the following structure:

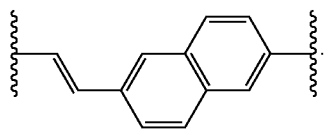 [SMILES: */C=C/c1ccc2cc(*)ccc2c1]

In another specific embodiment the invention provides a compound of formula (I) wherein W is $W^2$ and within the $W^2$ one $X^4$ is absent and one $X^4$ is selected from absent, alkynyl, or RC=CR and each R is independently selected from H or alkyl; and M is selected from $M^0$ or $M^9$.

In another specific embodiment the invention provides a compound of formula (I) wherein $M^0$ is imidazolyl and $M^9$ is benzimidazolyl.

In another specific embodiment the invention provides a compound of formula (I) that comprises a group $M^9$-$W^2$-$M^9$.

In another specific embodiment the invention provides a compound of formula (I) wherein the group $M^9$-$W^2$-$M^9$ has the following structure:

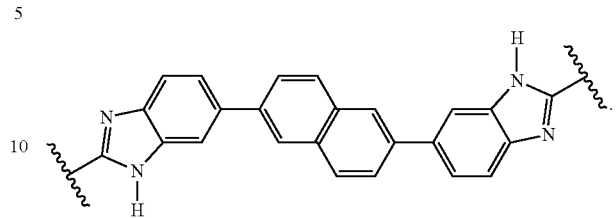

In another specific embodiment the invention provides a compound of formula (I) wherein A is $A^0$ and L is $L^2$.

In another specific embodiment the invention provides a compound of formula (I) wherein $A^0$-$L^2$ has the following structure:

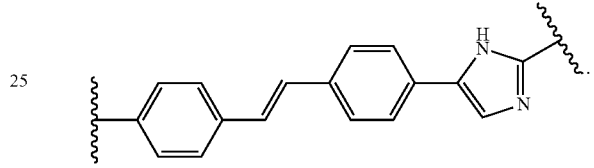

In another specific embodiment the invention provides a compound of formula (I) that comprises two $A^0$ and one M is $M^9$.

In another specific embodiment the invention provides a compound of formula (I) that comprises two $A^0$ and one M is $M^0$ and another M is $M^9$. In another specific embodiment the invention provides a compound of formula (I) wherein $A^0$-$A^0$-$M^9$ has the following structure:

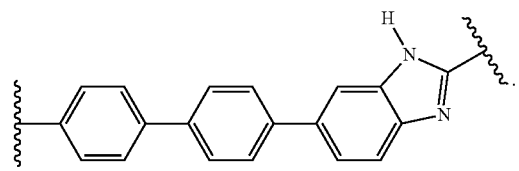 [SMILES: *c1ccc(-c2ccc(-c3ccc4nc(*)[nH]c4c3)cc2)cc1]

In another specific embodiment the invention provides a compound of formula (I) that comprises $M^0$-$A^0$-$A^0$-$M^9$. In another specific embodiment the invention provides a compound of formula (I) wherein $M^0$-$A^0$-$A^0$-$M^9$ has the following structure:

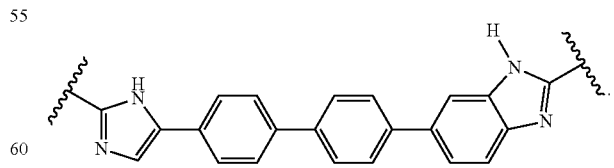

In another specific embodiment the invention provides a compound of formula (I) that comprises $A^0$-$A^7$-$M^9$. In another specific embodiment the invention provides a compound of formula (I) wherein $A^0$-$A^7$-$M^9$ has the following structure:

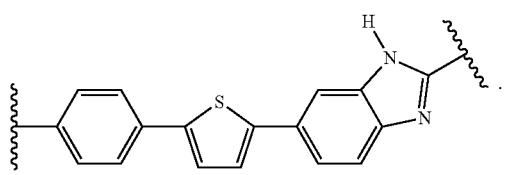 [SMILES: *c1ccc(-c2ccc(-c3ccc4nc(*)[nH]c4c3)s2)cc1]

In another specific embodiment the invention provides a compound of formula (I) that comprises one or two M and each M is $M^0$.

In another specific embodiment the invention provides a compound of formula (I) that comprises one or two M and each M is imidazolyl.

In another specific embodiment the invention provides a compound of formula (I) that comprises one or two M and each M is $M^9$.

In another specific embodiment the invention provides a compound of formula (I) that comprises one or two M and each M is benzimidazolyl.

In another specific embodiment the invention provides a compound of formula (I) that comprises two M wherein one M is $M^0$ and one M is $M^9$.

In another specific embodiment the invention provides a compound of formula (I) that comprises two M wherein one M is imidazolyl and one M is benzimidazolyl.

In another specific embodiment of the invention $M^0$ is:

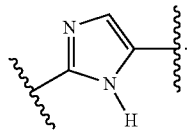 [SMILES: *c1cnc(*)[nH]1]

In another specific embodiment of the invention $M^9$ is:

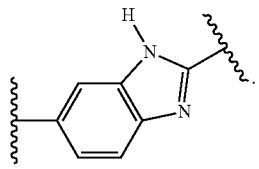

In another specific embodiment of the invention M is $M^{11}$ and is:

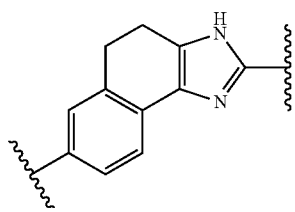

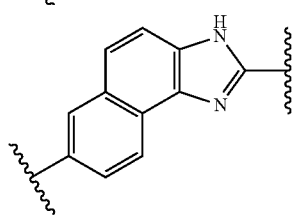

or

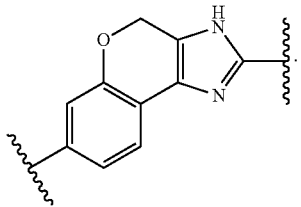

In another specific embodiment the invention provides a compound of formula (I) that comprises one or two L wherein each L is $L^3$.

In another specific embodiment the invention provides a compound of formula (I) that comprises one or two L wherein each L is benzimidazolyl.

In another specific embodiment the invention provides a compound of formula (I) wherein W is a ring system of formula:

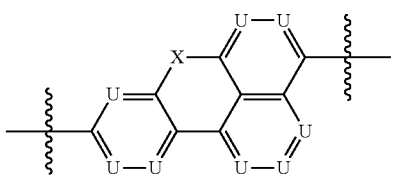

wherein:

U is CH or N; and

X is —$CH_2$—, —C(=O)—, —$CH_2CH_2$—, —$CH_2CH_2CH_2$—, or —CH=CH—;

wherein the ring system is optionally substituted with one or more $R^{41}$ or $R^{43}$.

In another specific embodiment the invention provides a compound of formula (I) wherein W is selected from:

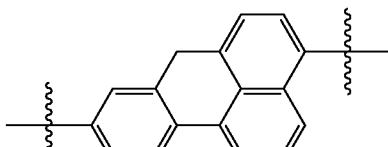

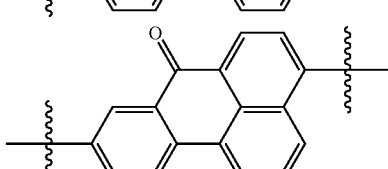

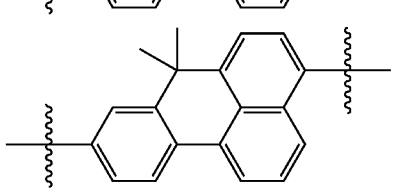

and

-continued

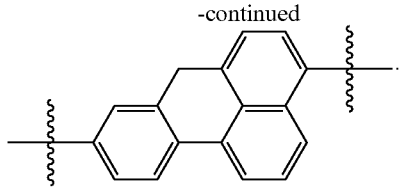

In another specific embodiment the invention provides a compound of formula (I) wherein A-A is selected from:

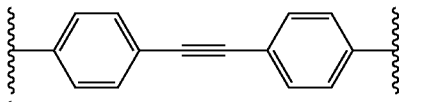


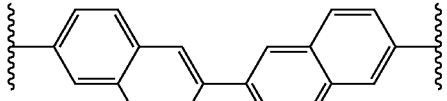

and

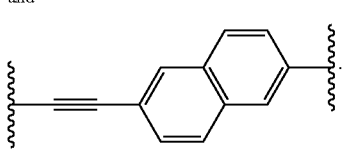

In another specific embodiment the invention provides a compound of formula (I) wherein M-W-M is:

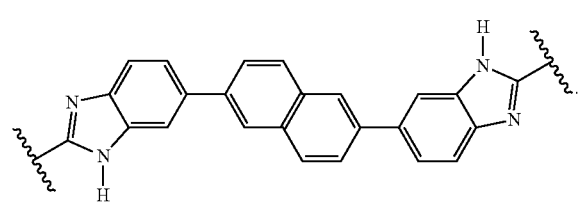 [SMILES: *c1nc2ccc(-c3ccc4cc(-c5ccc6nc(*)[nH]c6c5)ccc4c3)cc2[nH]1]

In another specific embodiment the invention provides a compound of formula (I) wherein -A-L- is selected from:

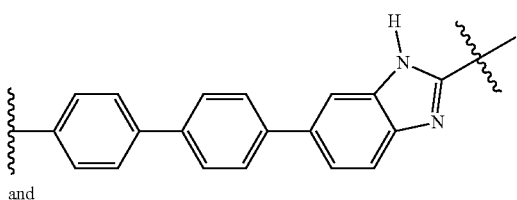

and

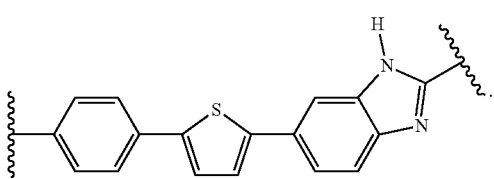

In another specific embodiment the invention provides a compound of formula (I) that has the formula E-V-Z-P-M-A-L-P-Z-V-E.

In another specific embodiment the invention provides a compound of formula (I) that has the formula E-V-Z-P-M-A-L″-P-Z-V-E.

In another specific embodiment the invention provides a compound of formula (I) wherein W is selected from:

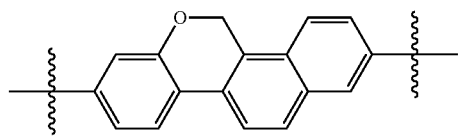

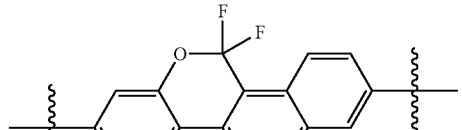

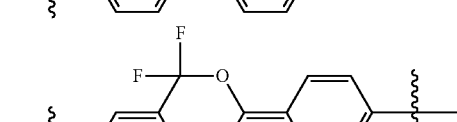

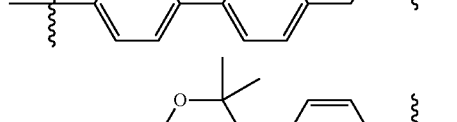

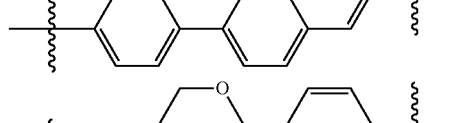

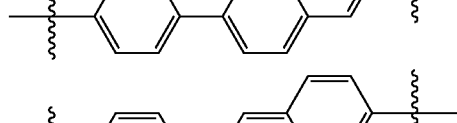

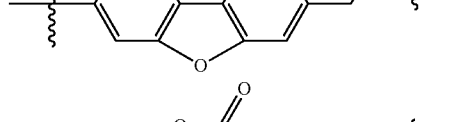

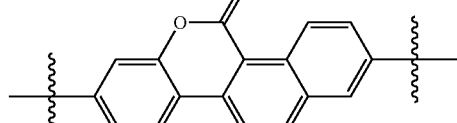

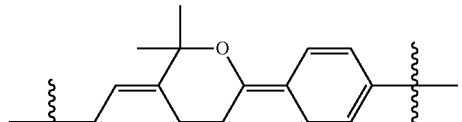

-continued

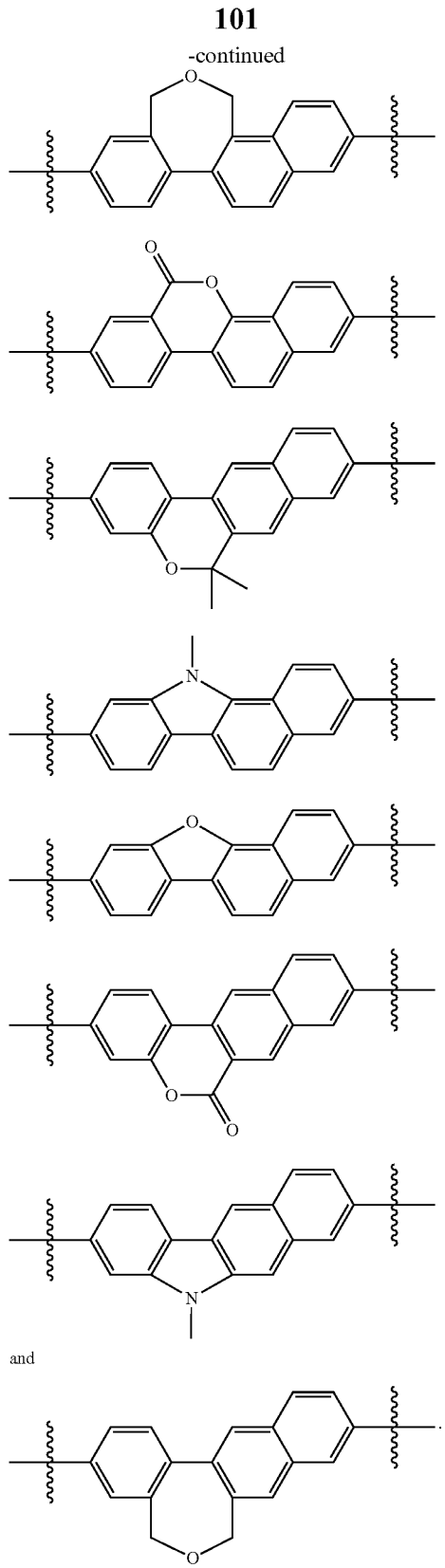

In another specific embodiment the invention provides a compound of formula (I) wherein W is $W^{17}$.

In another specific embodiment the invention provides a compound of formula (I) wherein W is selected from:

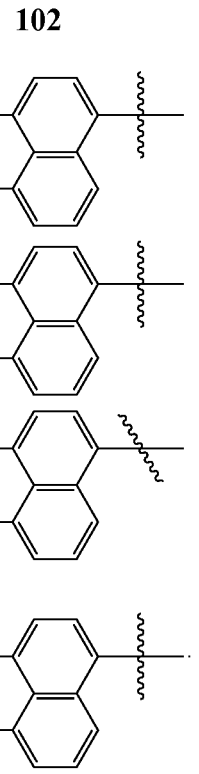

and

In another specific embodiment the invention provides a compound of formula (I) that has the formula J-M-W-M-J.

In another specific embodiment the invention provides a compound of formula (I) that has the formula E-V-Z-P-M-W-M-P-Z-V-E.

In another specific embodiment the invention provides a compound of formula (I) that has the formula E-V-Z-P-M-A-A-M-P-Z-V-E.

In another specific embodiment the invention provides a compound of formula (I) that has the formula E-V-Z-P-M-A-L-P-Z-V-E.

In another specific embodiment the invention provides a compound of formula (I) that has the formula E-V-Z-P-M-A-L"-P-Z-V-E.

In another specific embodiment the invention provides a compound of formula (I) wherein -M-W-M- is selected from $M^0$-W-$M^0$, $M^0$-W-$M^9$, $M^9$-W-$M^0$, and $M^9$-W-$M^9$.

In another specific embodiment the invention provides a compound of formula (I) wherein -M-W-M- is selected from $M^{10}$-W-$M^0$, $M^0$-W-$M^{10}$, $M^{10}$-W-$M^9$, $M^9$-W-$M^{10}$, and $M^{10}$-W-$M^{10}$.

In another specific embodiment the invention provides a compound of formula (I) wherein -M-A-A-M- is selected from $M^0$-A-A-$M^0$, $M^0$-A-A-$M^9$, $M^9$-A-A-$M^0$, and $M^9$-A-A-$M^9$.

In another specific embodiment the invention provides a compound of formula (I), wherein -M-W-M- is selected from $M^{10}$-A-A-$M^0$, $M^0$-A-A-$M^{10}$, $M^{10}$-A-A-$M^9$, $M^9$-A-A-$M^{10}$, and $M^{10}$-A-A-$M^{10}$.

In another specific embodiment the invention provides a compound of formula (I) wherein each E is $E^0$.

In another specific embodiment the invention provides a compound of formula (I) wherein each E is —NHC(=O) Oalkyl.

In another specific embodiment the invention provides a compound of formula (I) wherein each E is methoxycarbonylamino.

In another specific embodiment the invention provides a compound of formula (I) wherein each V is V⁰.

In another specific embodiment the invention provides a compound of formula (I) wherein each V is alkyl.

In another specific embodiment the invention provides a compound of formula (I) wherein each V is isopropyl.

In another specific embodiment the invention provides a compound of formula (I) wherein each V is V².

In another specific embodiment the invention provides a compound of formula (I) wherein each V is haloalkyl.

In another specific embodiment the invention provides a compound of formula (I) wherein each Z is Z⁰.

In another specific embodiment the invention provides a compound of formula (I) wherein each Z is —C(=O)—.

In another specific embodiment the invention provides a compound of formula (I) wherein each M is independently a 5-membered heteroaryl ring.

In another specific embodiment the invention provides a compound of formula (I) wherein each M is 2,4-imidazoldiyl.

In another specific embodiment the invention provides a compound of formula (I) wherein -M-A-L- is selected from:

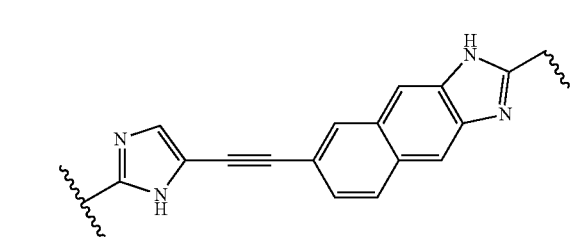

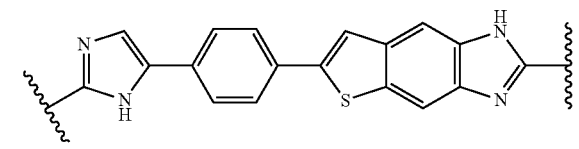

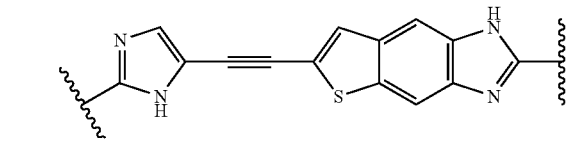

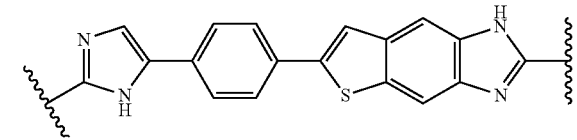

and

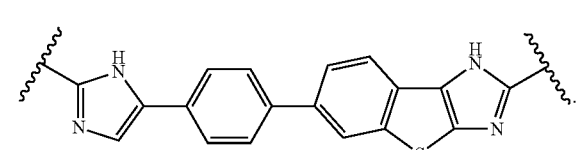

In another specific embodiment the invention provides a compound of formula (I) wherein M is M⁶.

In another specific embodiment the invention provides a compound of formula (I) wherein M is selected from:

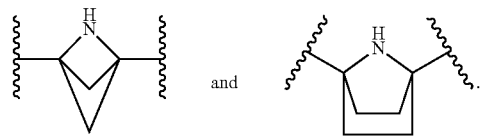 [SMILES: *C12CC(*)(C1)N2 ; *C12CCC(*)(CC1)N2]

In another specific embodiment the invention provides a compound of formula (I) wherein M is M⁷.

In another specific embodiment the invention provides a compound of formula (I) wherein M is:

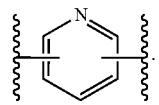

In another specific embodiment the invention provides a compound of formula (I) wherein M is M⁸.

In another specific embodiment the invention provides a compound of formula (I) wherein M is:

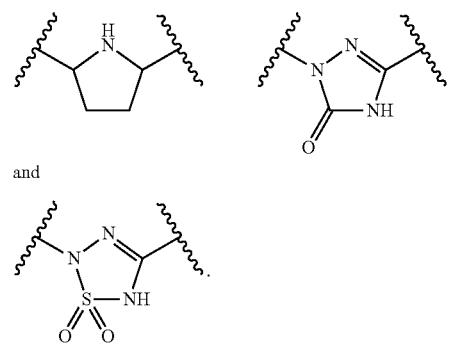

In another specific embodiment the invention provides a compound of formula (I) wherein P is P⁰.

In another specific embodiment the invention provides a compound of formula (I) wherein P is

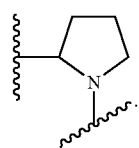

In another specific embodiment the invention provides a compound of formula (I) wherein P is:

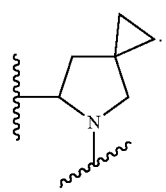 [SMILES: *C1CC2(CC2)CN1*]

In another specific embodiment the invention provides a compound of formula (I) wherein P is

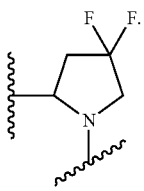 [SMILES: *C1CC(F)(F)CN1*]

In another specific embodiment the invention provides a compound of formula (I) wherein P is $P^1$.

In another specific embodiment the invention provides a compound of formula (I) wherein P is $P^2$.

In another specific embodiment the invention provides a compound of formula (I) wherein P is $P^2$; and pn is 1.

In another specific embodiment the invention provides a compound of formula (I) wherein P is $P^2$; pn is 1; and $R^{P12}$ is independently selected from alkylsulfonyl, arylsulfonyl, heterocyclylsulfonyl, heteroarylsulfonyl, —C(=O)$R^h$, —C(=O)N$R^h R^h$; —C(=O)O$R^h$, and haloalkyl.

In another specific embodiment the invention provides a compound of formula (I) wherein P is $P^3$; pn is 1 and ps is zero.

In another specific embodiment the invention provides a compound of formula (I) wherein P is $P^5$.

In another specific embodiment the invention provides a compound of formula (I) wherein P is $P^5$; pn is 1; and Z is O, S, S(=O), S(=O)$_2$, or N$R^f$.

In another specific embodiment the invention provides a compound of formula (I) wherein P is $P^5$; pn is 1; and Z is O, or S.

In another specific embodiment the invention provides a compound of formula (I) wherein P is $P^6$.

In another specific embodiment the invention provides a compound of formula (I) wherein P is $P^6$; pn is 1; and Z is O, S, S(=O), S(=O)$_2$, or N$R^f$.

In another specific embodiment the invention provides a compound of formula (I) wherein P is $P^7$ wherein $P^7$ is a [2.2.1] or a [2.2.2] ring system.

In another specific embodiment the invention provides a compound of formula (I) wherein P is $P^7$ wherein $P^7$ is a [2.2.1] ring system.

In another specific embodiment the invention provides a compound of formula (I) wherein P is

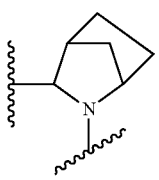 [SMILES: *C1C2CCC(C2)N1*]

optionally substituted with one or more groups independently selected from $R^{P6}$ and $R^{P11}$.

In another specific embodiment the invention provides a compound of formula (I) wherein P is

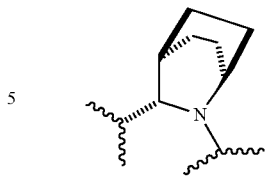

optionally substituted with one or more groups independently selected from $R^{P6}$ and $R^{P11}$.

In another specific embodiment the invention provides a compound of formula (I) wherein P is

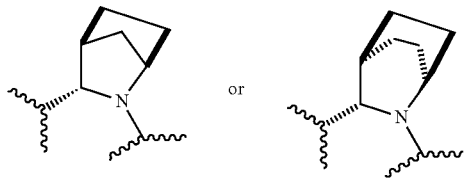 [SMILES: *[C@@H]1[C@H]2CC[C@H](C2)N1* ; *[C@@H]1[C@H]2CC[C@H](CC2)N1*]

optionally substituted with one or more groups independently selected from $R^{P6}$ and $R^{P11}$.

In another specific embodiment the invention provides a compound of formula (I) wherein P is $P^8$.

In another specific embodiment the invention provides a compound of formula (I) wherein P is $P^8$; and pn is 1.

In another specific embodiment the invention provides a compound of formula (I) wherein P is $P^8$; pn is 1; and ps is 2.

In another specific embodiment the invention provides a compound of formula (I) wherein P is $P^{10}$.

In another specific embodiment the invention provides a compound of formula (I) wherein P is $P^{10}$; pn is 1; and X is O, S, S(=O), S(=O)$_2$, CHR$^{P10}$, or CH(R$^{P10}$)$_2$.

In another specific embodiment the invention provides a compound of formula (I) wherein P is $P^{10}$; pn is 1; po is 1; and X is O, S, S(=O), S(=O)$_2$, CHR$^{P10}$, or CH(R$^{P10}$)$_2$.

In another specific embodiment the invention provides a compound of formula (I) wherein P is $P^{10}$; pn is 1; po is 1; ps is 0; and X is O, S, S(=O), S(=O)$_2$, CHR$^{P10}$, or CH(R$^{P10}$)$_2$.

In another specific embodiment the invention provides a compound of formula (I) wherein P is $P^{11}$.

In another specific embodiment the invention provides a compound of formula (I) wherein P is $P^{111}$; pn is 1; po is 1; ps is 0; and X is O, S, S(=O), S(=O)$_2$, CHR$^{P10}$, or CH(R$^{P10}$)$_2$.

In another specific embodiment the invention provides a compound of formula (I) wherein P is $P^{12}$.

In another specific embodiment the invention provides a compound of formula (I) wherein P is $P^{12}$; pm is 1; and pp is 1.

In another specific embodiment the invention provides a compound of formula (I) wherein P is $P^{13}$.

In another specific embodiment the invention provides a compound of formula (I) wherein P is $P^{13}$; pm is 1; pn is 0; ps is 0; pp is 1; pq is 0; and X is O, S, or S(=O)$_2$.

In another specific embodiment the invention provides a compound of formula (I) wherein P is $P^{14}$.

In another specific embodiment the invention provides a compound of formula (I) wherein P is $P^{14}$; pm is 0; and pq is 0.

In another specific embodiment the invention provides a compound of formula (I) wherein P is selected from:

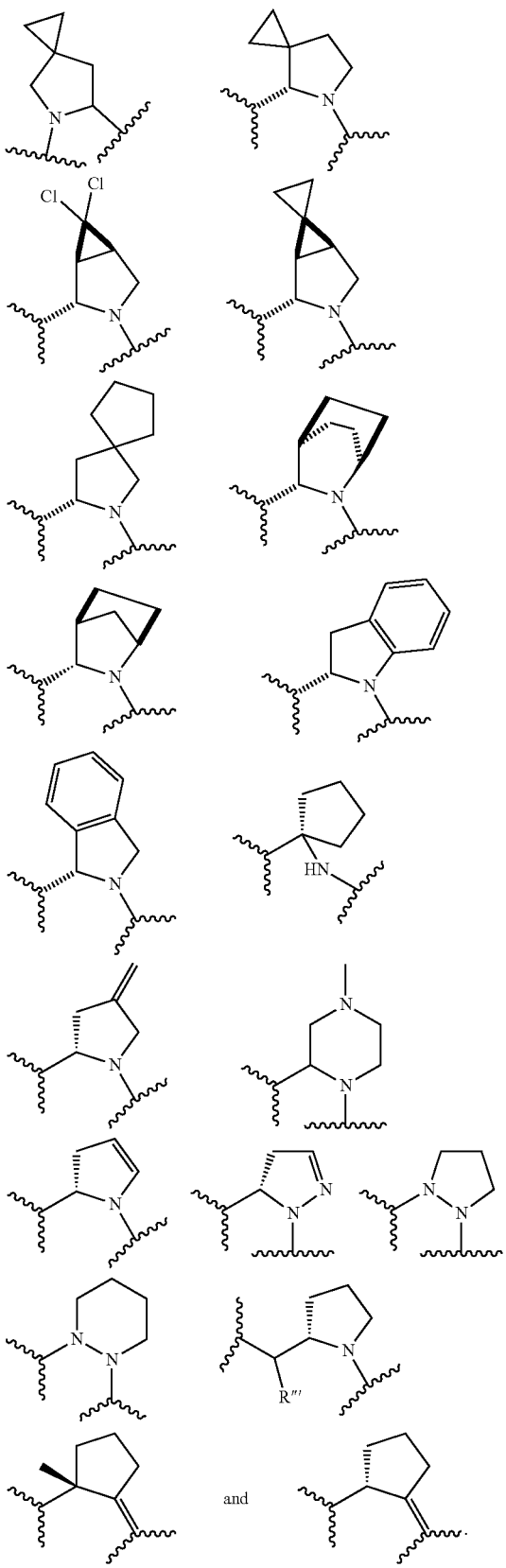

In another specific embodiment the invention provides a compound of formula (I) having a formula selected from:

T-P-Y-P-T; T-P-Y-J; J-Y-J; T-P-Y-P-Z-R9; R9-Z-P-Y-P-Z-R9; J-Y-P-Z-R9; T-P-Y-P-Z-V-E; E-V-Z-P-Y-P-Z-V-E; J-Y-P-Z-V-E; T-P-L-L-P-T; T-P-L-L-J; J-L-L-J; T-P-L-L-P-Z-R9; R9-Z-P-L-L-P-Z-R9; J-L-L-P-Z-R9; T-P-L-L-P-Z-V-E; E-V-Z-P-L-L-P-Z-V-E; J-L-L-P-Z-V-E; T-P-M-A-L-P-T; T-P-M-A-L-J; J-M-A-L-J; T-P-M-A-L-P-Z-R9; R9-Z-P-M-A-L-P-Z-R9; J-M-A-L-P-Z-R9; L-P-M-A-L-P-Z-V-E; E-V-Z-P-M-A-L-P-Z-V-E; J-M-A-L-P-Z-V-E; T-B-A-L-P-T; T-B-A-L-J; T-B-A-L-P-Z-R9; R9-Z-B-A-L-P-Z-R9; T-B-A-L-P-Z-V-E; E-V-Z-B-A-L-P-Z-V-E; T-P-M-A-A-M-P-T; T-P-M-A-A-M-J; J-M-A-A-M-J; T-P-M-A-A-M-P-Z-R9; R9-Z-P-M-A-A-M-P-Z-R9; J-M-A-A-M-P-Z-R9; T-P-M-A-A-M-P-Z-V-E; E-V-Z-P-M-A-A-M-P-Z-V-E; J-M-A-A-M-P-Z-V-E; T-B-A-A-M-P-T; T-B-A-A-M-J; T-B-A-A-M-P-Z-R9; R9-Z-B-A-A-M-P-Z-R9; T-B-A-A-M-P-Z-V-E; E-V-Z-B-A-A-M-P-Z-V-E; T-P-M-A-A-B-T; T-P-M-A-A-B-Z-R9; R9-Z-P-M-A-A-B-Z-R9 J-M-A-A-B-Z-R9; T-P-M-A-A-B-Z-V-E; E-V-Z-P-M-A-A-B-Z-V-E; J-M-A-A-B-Z-V-E; T-B-A-A-B-T; T-B-A-A-B-Z-R9; R9-Z-B-A-A-B-Z-R9; T-B-A-A-B-Z-V-E; E-V-Z-B-A-A-B-Z-V-E; T-P-M-W-M-P-T; T-P-M-W-M-J; J-M-W-M-J; T-P-M-W-M-P-Z-R9; R9-Z-P-M-W-M-P-Z-R9; J-M-W-M-P-Z-R9; T-P-M-W-M-P-Z-V-E; E-V-Z-P-M-W-M-P-Z-V-E; J-M-W-M-P-Z-V-E; T-B-W-M-P-T; T-B-W-M-J; T-B-W-M-P-Z-R9; R9-Z-B-W-M-P-Z-R9; T-B-W-M-P-Z-V-E; E-V-Z-B-W-M-P-Z-V-E; T-P-M-W-B-T; T-P-M-W-B-Z-R9; R9-Z-P-M-W-B-Z-R9; J-M-W-B-Z-R9; T-P-M-W-B-Z-V-E; E-V-Z-P-M-W-B-Z-V-E J-M-W-B-Z-V-E; T-B-W-B-T; T-B-W-B-Z-R9; R9-Z-B-W-B-Z-R9; T-B-W-B-Z-V-E; E-V-Z-B-W-B-Z-V-E; T-P-M-M-P-T; T-P-M-M-J; J-M-M-J; T-P-M-M-P-Z-R9; R9-Z-P-M-M-P-Z-R9; J-M-M-P-Z-R9; T-P-M-M-P-Z-V-E; E-V-Z-P-M-M-P-Z-V-E; J-M-M-P-Z-V-E; T-B-M-P-T; T-B-M-J; T-B-M-P-Z-R9; R9-Z-B-M-P-Z-R9; T-B-M-P-Z-V-E; E-V-Z-B-M-P-Z-V-E; T-P-M-B-T; T-P-M-B-Z-R9; R9-Z-P-M-B-Z-R9; J-M-B-Z-R9; T-P-M-B-Z-V-E; E-V-Z-P-M-B-Z-V-E; J-M-B-Z-V-E; T-B-B-T; T-B-B-Z-R9; R9-Z-B-B-Z-R9; and T-B-B-Z-V-E; E-V-Z-B-B-Z-V-E; or a pharmaceutically acceptable salt thereof.

In another specific embodiment the invention provides a compound of formula (I) having a formula selected from:
T-P-Y-P-T; T-P-Y-J; J-Y-J; T-P-Y-P-Z-R9; R9-Z-P-Y-P-Z-R9; J-Y-P-Z-R9; T-P-Y-P-Z-V-E; E-V-Z-P-Y-P-Z-V-E; J-Y-P-Z-V-E; R9-Z-P-Y-P-Z-V-E; T-P-L-L-P-T; T-P-L-L-J; J-L-L-J; T-P-L-L-P-Z-R9; R9-Z-P-L-L-P-Z-R9; J-L-L-P-Z-R9; T-P-L-L-P-Z-V-E; E-V-Z-P-L-L-P-Z-V-E; J-L-L-P-Z-V-E; R9-Z-P-L-L-P-Z-V-E; T-P-M-A-L-P-T; T-P-M-A-L-J; J-M-A-L-J; T-P-M-A-L-P-Z-R9; R9-Z-P-M-A-L-P-Z-R9; J-M-A-L-P-Z-R9; T-P-M-A-L-P-Z-V-E; E-V-Z-P-M-A-L-P-Z-V-E; J-M-A-L-P-Z-V-E; J-M-A-L-P-T; R9-Z-P-M-A-L-J; R9-Z-P-M-A-L-P-T; R9-Z-P-M-A-L-P-Z-V-E; E-V-Z-P-M-A-L-J; E-V-Z-P-M-A-L-P-T; E-V-Z-P-M-A-L-P-Z-R9; T-P-M-A-A-M-P-T; T-P-M-A-A-M-J; J-M-A-A-M-J; T-P-M-A-A-M-P-Z-R9; R9-Z-P-M-A-A-M-P-Z-R9; J-M-A-A-M-P-Z-R9; T-P-M-A-A-M-P-Z-V-E; E-V-Z-P-M-A-A-M-P-Z-V-E; J-M-A-A-M-P-Z-V-E; R9-Z-P-M-A-A-M-P-Z-V-E; T-P-M-W-M-P-T; T-P-M-W-M-J; J-M-W-M-J; T-P-M-W-M-P-Z-R9; R9-Z-P-M-W-M-P-Z-R9; J-M-W-M-P-Z-R9; T-P-M-W-M-P-Z-V-E; E-V-Z-P-M-W-M-P-Z-V-E; J-M-W-M-P-Z-V-E; R9-Z-P-M-W-M-P-Z-V-E; T-P-M-M-P-T; T-P-M-M-J; J-M-M-J; T-P-M-M-P-Z-R9; R9-Z-P-M-M-P-Z-R9; J-M-M-P-Z-R9; T-P-M-M-P-Z-V-E; E-V-Z-P-M-M-P-Z-V-E; J-M-M-P-Z-V-E; R9-Z-P-M-M-P-Z-V-E; or a pharmaceutically acceptable salt thereof.

In another specific embodiment the invention provides a compound of formula (I) having a formula selected from:
$T^p$-$P^u$-$Y^y$-$P^u$-$T^p$; $T^p$-$P^u$-$Y^y$-$J^m$; $J^m$-$Y^y$-$J^m$; $T^p$-$P^u$-$Y^y$-$P^u$-$Z^v$-$R9^q$; $R9^q$-$Z^o$-$P^u$-$Y^y$-$P^u$-$Z^v$-$R9^q$; $J^m$-$Y^y$-$P^u$-$Z^v$-$R9^q$; $T^p$-$P^u$-

$Y^y-P^u-Z^v-V^w-E^x$; $E^x-V^w-Z^v-P^u-Y^y-P^u-Z^v-V^w-E^x$; $J^m-Y^y-P^u-Z^v-V^w-E^x$; $R9^q-Z^v-P^u-Y^y-P^u-Z^v-V^w-Ex$; $T^p-P^u-L^n-L^n-P^u-T^p$; $T^p-P^u-L^n-L^n-J^m$; $J^m-L^n-L^n-J^m$; $T^p-P^u-L^n-L^n-P^u-Z^v-R9^q$; $R9^q-Z^v-P^u-L^n-L^n-P^u-Z^v-R9^q$; $J^m-L^n-L^n-P^u-Z^v-R9^q$; $T^p-P^u-L^n-L^n-P^u-Z^v-V^w-E^x$; $E^x-V^w-Z^v-P^u-L^n-L^n-P^u-Z^v-V^w-E^x$; $J^m-L^n-L^n-P^u-Z^v-V^w-E^x$; $R9^q-Z^v-P^u-L^n-L^n-P^u-Z^v-V^w-E^x$; $T^p-P^u-M^t-A^s-L^n-P^u-T^p$; $T^p-P^u-M^t-A^s-L^n-J^m$; $J^m-M^t-A^s-L^n-J^m$; $T^p-P^u-M^t-A^s-L^n-P^u-Z^v-R9^q$; $R9^q-Z^v-P^u-M^t-A^s-L^n-P^u-Z^v-R9^q$; $J^m-M^t-A^s-L^n-P^u-Z^v-R9^q$; $T^p-P^u-M^t-A^s-L^n-P^u-Z^v-V^w-E^x$; $E^x-V^w-Z^v-P^u-M^t-A^s-L^n-P^u-Z^v-V^w-E^x$; $J^m-M^t-A^s-L^n-P^u-Z^v-V^w-E^x$; $J^m-M^t-A^s-L^n-P^u-T^p$; $R9^q-Z^v-P^u-M^t-A^s-L^n-J^m$; $R9^q-Z^v-P^u-M^t-A^s-L^n-P^u-T^p$; $R9^q-Z^v-P^u-M^t-A^s-L^n-P^u-Z^v-V^w-E^x$; $E^x-V^w-Z^v-P^u-M^t-A^s-L^n-J^m$; $E^x-V^w-Z^v-P^u-M^t-A^s-L^n-P^u-T^p$; $E^x-V^w-Z^v-P^u-M^t-A^s-L^n-P^u-Z^v-R9^q$; $T^p-P^u-M^t-A^s-A^s-M^t-P^u-T^p$; $T^p-P^u-M^t-A^s-A^s-M^t-J^m$; $J^m-M^t-A^s-A^s-M^t-J^m$; $T-P^u-M^t-A^s-A^s-M^t-P^u-Z^v-R9^q$; $R9^q-Z^v-P^u-M^t-A^s-A^s-M^t-P^u-Z^v-R9^q$; $J^m-M^t-A^s-A^s-M^t-P^u-Z^v-R9^q$; $T^p-P^u-M^t-A^s-A^s-M^t-P^u-Z^v-V^w-E^x$; $E^x-V^w-Z^v-P^u-M^t-A^s-A^s-M^t-P^u-Z^v-V^w-E^x$; $J^m-M^t-A^s-A^s-M^t-P^u-Z^v-V^w-E^x$; $R9^q-Z^v-P^u-M^t-A^s-A^s-M^t-P^u-Z^v-V^w-E^x$; $T^p-P^u-M^t-W^r-M^t-P^u-T^p$; $T^p-P^u-M^t-W^r-M^t-J^m$; $J^m-M^t-W^r-M^t-J^m$; $T^p-P^u-M^t-W^r-M^t-P^u-Z^v-R9^q$; $R9^q-Z^v-P^u-M^t-W^r-M^t-P^u-Z^v-R9^q$; $J^m-M^t-W^r-M^t-P^u-Z^v-R9^q$; $T^p-P^u-M^t-W^r-M^t-P-Z^v-V^w-E^x$; $E^x-V^w-Z^v-V^w-P^u-M^t-W^r-M^t-P^u-Z^v-V^w-E^x$; $J^m-M^t-W^r-M^t-P^u-Z^v-V^w-E^x$; $R9^q-Z^v-P^u-M^t-W^r-M^t-P^u-Z^v-V^w-E^x$; $T^p-P^u-M^t-M^t-P^u-T^p$; $T^p-P^u-M^t-M^t-J^m$; $J^m-M^t-M^t-J^m$; $T^p-P^u-M^t-M^t-P^u-Z^v-R9^q$; $R9^q-Z^v-P^u-M^t-M^t-P^u-Z^v-R9^q$; $J^m-M^t-M^t-P^u-Z^v-R9^q$; $T^p-P^u-M^t-M^t-P^u-Z^v-V^w-E^x$; $E^X-V^w-Z^v-P^u-M^t-M^t-P^u-Z^v-V^w-E^x$; $J^m-M^t-M^t-M^t-P^u-Z^v-V^w-E^x$; $R9^q-Z^v-P^u-M^t-M^t-P^u-Z^v-V^w-E^x$ or a pharmaceutically acceptable salt thereof.

In another specific embodiment of the invention s is 0, 1, 2, 3, 4, 5, 6, 7, 8, 9, 10, 13, 14, 15, 16, 17, 18, 19, 20, or 21.

In another specific embodiment of the invention r is 1, 2, 3, 4, 5, 6, 8, 13, 14, 15, 16, 17, 18, 19, or 20.

In another specific embodiment the invention provides a compound which is a prodrug or a pharmaceutically acceptable salt of a compound of formula (I).

In one specific embodiment the invention provides a compound of formula (I) wherein W is not a group of the following formula:

wherein:

each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is independently 0, 1, 2, or 3; and $R^{A4}$ and $R^{A4'}$, together with the atoms to which they are attached, form a five- to eight-membered unsaturated ring optionally containing one or two heteroatoms independently selected from nitrogen, oxygen, and sulfur; wherein the five- to eight-membered unsaturated ring is optionally substituted with one, two or three substituents independently selected from $R^{A3}$, oxo and a spirocycle.

In one specific embodiment the invention, the sum of m, n, p, q, s, t, u, v, w, x, and y is not 0 when W is a group of the following formula:

wherein:

each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is independently 0, 1, 2, or 3; and $R^{A4}$ and $R^{A4'}$, together with the atoms to which they are attached, form a five- to eight-membered unsaturated ring optionally containing one or two heteroatoms independently selected from nitrogen, oxygen, and sulfur; wherein the five- to eight-membered unsaturated ring is optionally substituted with one, two or three substituents independently selected from $R^{A3}$, oxo and a spirocycle.

In one embodiment when M comprises an imidazole ring it is connected to P through the 2-position.

In one embodiment when M or L comprises a benzimidazole it is connected to P through the 2-position.

Compounds of Formula (Ia)

In one embodiment of the invention, the compound of formula (I) is a compound of formula (Ia):

E-V-Z-P-M-W-M-P-Z-V-E (Ia)

wherein:

W is a bond or $-W^r$—;

each M is selected from $-M^t$;

each P is selected from $-P^u$;

each Z is selected from $-Z^v$;

each V is selected from $-V^w$;

each E is selected from $-E^x$;

each r is 1, 2, 3, 4, 5, 6, 7, 8, 9, 10, 11, 12, 13, 14, 15, 16, 17, 18, 19, or 20;

each t is 0, 1, 2, 3, 4, 5, 6, 7, 8, 9, 10, or 11;

each u is 0, 1, 2, 3, 4, 5, 6, 7, 8, 10, 11, 12, 13, or 14;

each v is 0, 1, 2, 3, 4, 5, or 6;

each w is 0, 1, 2, 3, 4, 5, 6, 7, 8, 9, 10, 11, 12, 13, 14, 15, 16, 17, 18, 19, 20 or 21;

each x is 0 or 1;

wherein the sum of r, t, u, v, w, and x is not 0;

each $W^1$ is independently —$X^A$—:

wherein:

each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each W² is independently:


wherein:
each H²⁰ is independently is independently a fused aromatic bicyclic carbocycle, which is optionally substituted with one or more groups independently selected from $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W³ is independently:

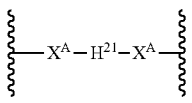

wherein:
each H²¹ is independently a fused bicyclic carbocyclic ring system wherein one ring is aromatic and another ring is partially or fully saturated, which ring system is optionally substituted with one or more groups independently selected from oxo, $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁴ is independently:

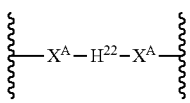

wherein:
each H²² is independently a fused aromatic bicyclic heterocycle that comprises at least one heteroatom in the ring system, which ring system is optionally substituted with one or more groups independently selected from $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁵ is independently:

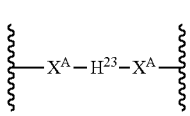

wherein:
each H²³ is independently a fused bicyclic ring system comprising at least one heteroatom, wherein one ring is aromatic and another ring is partially or fully saturated, which ring system is optionally substituted with one or more groups independently selected from oxo, $R^{41}$ and $R^{43}$; and each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁶ is independently:

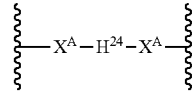

wherein:
each H²⁴ is independently a fused unsaturated, partially unsaturated or saturated tricyclic carbocycle, which is optionally substituted with one or more groups independently selected from $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁷ is independently:

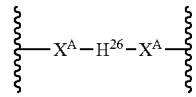

wherein:
each H²⁶ is independently a 5-15 carbon unsaturated, partially unsaturated or saturated bicyclic ring system which ring system is optionally substituted with one or more groups independently selected from oxo, $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁸ is independently:

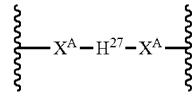

wherein:
each H²⁷ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
each $X^A$ is independently O, NR, SO, SO₂, C(=O), NRC(=O), C(=O)NR, CR=CR, NRC(=O)NR, allenyl, alkynyl, or absent and each R is independently selected from H or alkyl;
each W⁹ is independently:

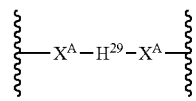

wherein:
each H²⁹ is independently a 5-15 carbon unsaturated, partially unsaturated or saturated bicyclic ring system that contains one or more heteroatoms; and
each X^A is independently O, NR, SO, SO₂, C(=O), NRC (=O), C(=O)NR, CR=CR, NRC(=O)NR, allenyl, alkynyl, or absent and each R is independently selected from H or alkyl;
each W¹⁰ is independently —H³⁰=C=H³¹—
wherein each of —H³⁰ and H³¹ is independently a saturated 6-membered heterocyclic ring comprising one or more heteroatoms, which ring is optionally substituted with oxo;
each W¹¹ is independently —H³²=C=H³³—
wherein each of —H³² and H³³ is independently a saturated 5-membered heterocyclic ring comprising one or more heteroatoms, which ring is optionally substituted with oxo;
each W¹² is independently an anti-aromatic monocyclic or fused carbocyclic ring system, which carbocyclic ring system is optionally substituted with one or more groups independently selected from $R^{A1}$ and $R^{A3}$;
each W¹³ is independently an phenyl ring that is optionally substituted with one or more groups independently selected from $R^{A1}$ and $R^{A3}$;
each W¹⁴ is independently a 5 or 6 membered heteroaryl ring that is optionally substituted with one or more groups independently selected from $R^{A1}$ and $R^{A3}$;
each W¹⁵ is independently a fused unsaturated, partially unsaturated or saturated tetracyclic carbocyclic ring, which ring system is optionally substituted with one or more groups independently selected from oxo, $R^{A1}$ and $R^{A3}$;
each W¹⁶ is independently a fused unsaturated, partially unsaturated or saturated tetracyclic heterocycle that comprises at least one heteroatom in the ring system, which ring system is optionally substituted with one or more groups independently selected from oxo, $R^{A1}$ and $R^{A3}$;
each W¹⁷ is independently a fused unsaturated, partially unsaturated or saturated pentacyclic carbocyclic ring system, which ring system is optionally substituted with one or more groups independently selected from oxo, $R^{A1}$ and $R^{A3}$;
each W¹⁸ is independently a fused unsaturated, partially unsaturated or saturated pentacyclic heterocycle that comprises at least one heteroatom in the ring system, which ring system is optionally substituted with one or more groups independently selected from oxo, $R^{A1}$ and $R^{A3}$;
each W¹⁹ is independently a fused unsaturated, partially unsaturated or saturated hexacyclic carbocyclic ring system, which ring system is optionally substituted with one or more groups independently selected from oxo, $R^{A1}$ and $R^{A3}$;
each W²⁰ is independently a fused unsaturated, partially unsaturated or saturated hexacyclic heterocycle that comprises at least one heteroatom in the ring system, which ring system is optionally substituted with one or more groups independently selected from oxo, $R^{A1}$ and $R^{A3}$;
each M⁰ is independently a five membered heteroaryl group optionally substituted with one or more alkoxycarbonyl, alkyl, arylalkoxycarbonyl, carboxy, haloalkyl, $(NR^aR^b)$carbonyl and trialkylsilylalkoxyalkyl;
each M¹ is independently selected from —C(=O)NH—, —C(=O)NH—C(R^M)₂—, —NHC(=O)—, —C(R^M)₂NHC (=O)—, —NHC(=O)NR^M—, —NHC(=O)O—; wherein each R^M is independently selected from H and alkyl;
each M² is independently a six-membered heteroaromatic ring, which is optionally substituted with one or more groups independently selected from $R^{A1}$ and $R^{A3}$;

each M³ is independently:

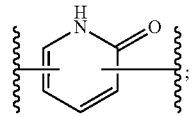

each M⁴ is independently:

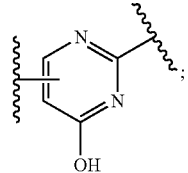

each M⁵ is independently:

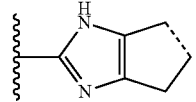

wherein the bond designated with - - - is fused to a ring defined for P;
each M⁶ is independently a bicyclic bridged ring system comprising 5-15 atoms wherein at least one of the atoms is a heteroatom;
each M⁷ is independently a pyrid-di-yl;
each M⁸ is independently partially saturated or a saturated five-membered ring that comprises one or more heteroatoms and that is optionally substituted with one or two oxo;
each M⁹ is independently a fused-bicyclic saturated, partially unsaturated, or aromatic heterocyclic ring system that is optionally substituted with one or more $R^{P11}$;
each M¹⁰ is independently a five membered heteroaryl group;
each M¹¹ is independently a fused-tricyclic saturated, partially unsaturated, or aromatic heterocyclic ring system that is optionally substituted with one or more oxo halo, —R^M7, —OR^M7, —SR^M7, —N(R^M7)₂, —CF₃, —CCl₃, —OCF₃, —CN, —NO₂, —N(R^M7)C(=O)R^M7, —C(=O)R^M7, —OC (=O)R^M7, —C(O)OR^M7, —C(O)NR^M7, —S(=O)R^M7, —S(=O)₂OR^M7, —S(=O)₂R^M7, —OS^M7, or —S(=O)₂NR^M7;
each R^M7 is independently —H, alkyl, aryl, arylalkyl, or heterocycle;
each P⁰ is independently:

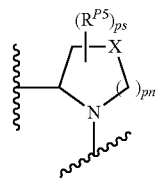 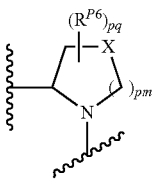

115

-continued

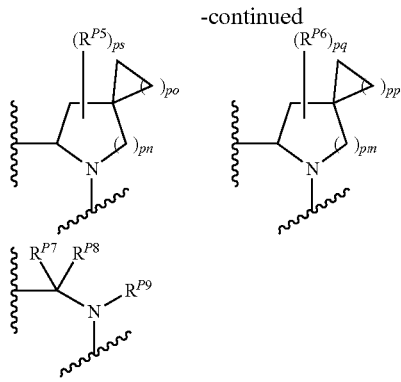

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{P'}$ is selected from hydrogen and alkyl;
R$^{P9}$ is selected from hydrogen and alkyl;
each P$^1$ is independently:

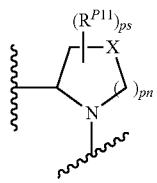

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

116 at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 1, 2, 3, or 4;
pn is 0, 1, or 2;
each P$^2$ is independently:

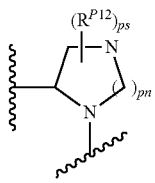

wherein:
each R$^{P12}$ is independently selected from R$^{P5}$, R$^{P11}$, —C(=O)OR$^h$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 1, 2, 3, or 4;

pn is 0, 1, or 2;
each $P^3$ is independently a ring of the formula:

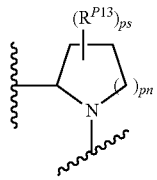

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^4$ is independently a ring of the formula:

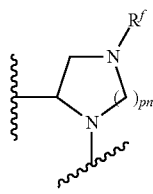

wherein:
the ring is optionally substituted with one or more groups $R^{P14}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P14}$ that are attached to the same carbon when taken together with the carbon to which they are attached can form a 3-6 membered carbocyclic or heterocyclic ring;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^5$ is independently a ring of the formula:

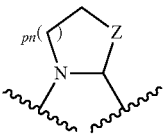

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
pn is 0, 1, or 2;
Z is O, S, $S(=O)$, $S(=O)_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

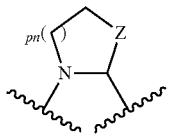

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
Z is O, S, $S(=O)$, $S(=O)_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$.

each $P^8$ is independently a ring of the formula:

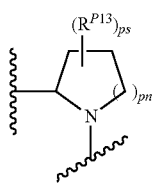

wherein:
ps is 2, 3, 4, 5, or 6;
each $R^{P13}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

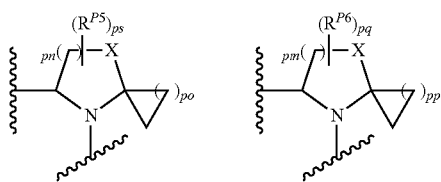

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;

each $P^{11}$ is independently:

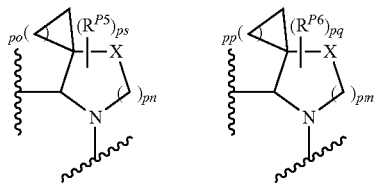

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;

each $P^{12}$ is independently:

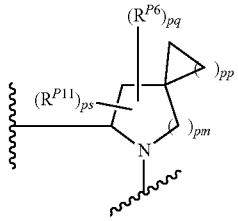

wherein:
each $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl, wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —S(=O)$_2R^h$, —C(=O)$R^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{13}$ is independently:

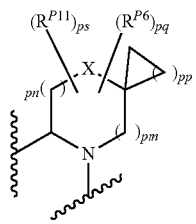

wherein:

X is selected from O, S, S(O), SO$_2$, or NR$^h$;

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm and pn are independently 0, 1, or 2 but the sum of pn and pm is greater than zero;

pp are independently 1, 2, or 3;

ps is 1, 2, 3, or 4;

each $R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2R^h$, —C(=O)$R^h$, —C(=O)NR$^h$R$^h$, $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{14}$ is independently:

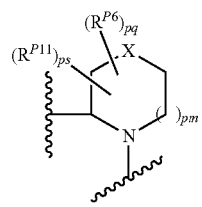

wherein:

the ring is substituted with one or more oxo group;

X is NR$^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2R^h$, C(=O)$R^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm is independently 0, 1, or 2;

ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two $R^h$ groups are present then they may come together with the atoms to which they are bound to form a 4-15 membered heterocyclic ring;

each —Z$^0$— is —C(=O)— or —C(=S)—;

each —Z¹— is independently a bond, or —C(R$^{Z1}$)$_2$—; wherein each R$^{Z1}$ is independently H, alkyl, haloalkyl, or halo;

each —Z²— is independently saturated or partially unsaturated (C$_3$-C$_8$)cycloalkyl that is optionally substituted with one or more groups independently selected from R$^{A1}$ and R$^{A3}$;

each —Z³— is independently saturated, partially unsaturated, or aromatic 4-8 membered heterocyclic or heteroaryl ring that is optionally substituted with one or more groups independently selected from R$^{A1}$ and R$^{A3}$;

each —Z⁴— is independently:

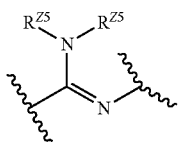

wherein each R$^{Z4}$ is independently H, alkyl, cyano, aryl, or heteroaryl;

each —Z⁵— is independently:

wherein each R$^{Z5}$ is independently H, alkyl, cyano, aryl, or heteroaryl; or two R$^{Z5}$s together with the nitrogen to which they are attached form a 4-8 membered heterocyclic ring that is optionally substituted with one or more oxo and with one or more groups independently selected from R$^{A1}$ and R$^{A3}$;

each —Z⁶— is independently —C(R$^{Z1}$)— and is double-bonded to P; wherein R$^{Z1}$ is independently H, alkyl, haloalkyl, or halo;

each E⁰ is independently —NR$^{Ec}$R$^{Ed}$ wherein

R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E¹ is independently —OC(=O)NR$^{Ee}$R$^{Ef}$ wherein each R$^{Ee}$ and R$^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein R$^{Ee}$ and R$^{Ef}$, together with the nitrogen atom to which they are attached, form a heterocycle;

each V⁰ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each V¹ is independently cyanoalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^6$ is independently arylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^8$ is independently spirocycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{10}$ is independently fused bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{11}$ is independently fused bicycliccycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{12}$ is independently bridged-bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{13}$ is independently bridged-bicyclic-cycloalkylalkyl,] which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{14}$ is independently aryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{18}$ is independently heterocyclooxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

each $V^{20}$ is independently heteroaryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl; and each $V^{21}$ is independently heteroarylalkylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O-$; $R^{Va}$ and $R^{Vb}$ are each independently selected from hydrogen, alkenyl, and alkyl;

or a pharmaceutically acceptable salt, or prodrug thereof.

In another specific embodiment of the invention r is 1, 2, 3, 4, 5, 6, 8, 13, 14, 15, 16, 17, 18, 19, or 20.

In another specific embodiment of the invention W is $W^2$.

In another specific embodiment the invention W is $W^4$.

In another specific embodiment of the invention W is $W^8$.

In another specific embodiment of the invention W is $W^6$.

In another specific embodiment of the invention W is $W^{15}$.

In another specific embodiment of the invention W is $W^{16}$.

In another specific embodiment of the invention $W^{16}$ is selected from:

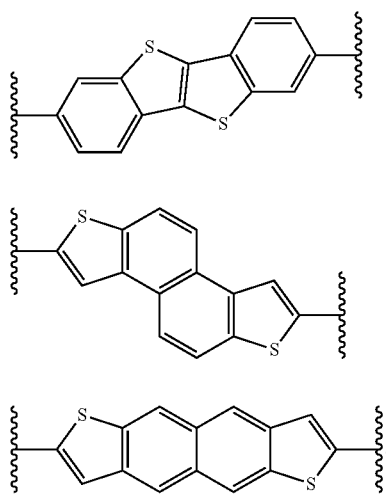
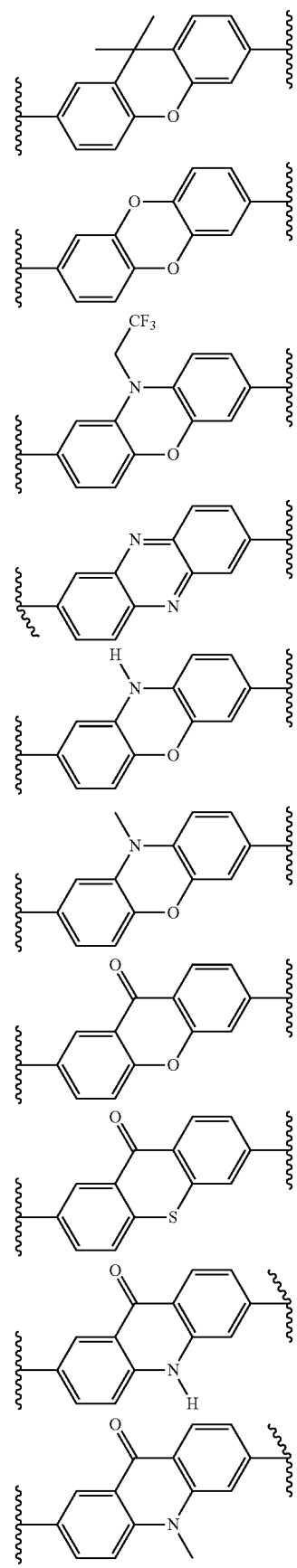
In another specific embodiment of the invention W is $W^{17}$.
In another specific embodiment of the invention W is $W^{18}$.
In another specific embodiment of the invention $W^6$ is selected from:
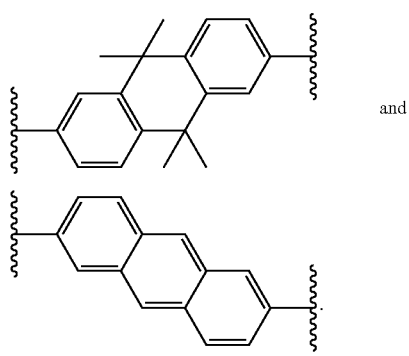
and
In another specific embodiment of the invention $W^6$ is selected from:
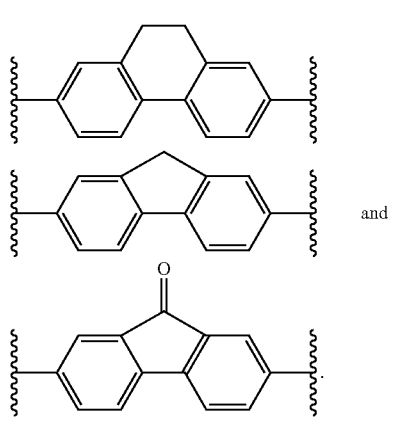
and
In another specific embodiment of the invention $W^8$ is selected from:

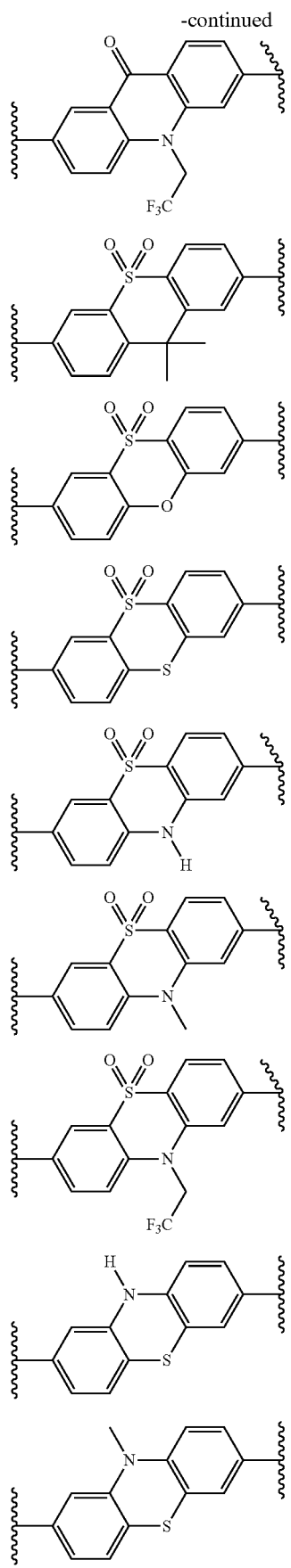
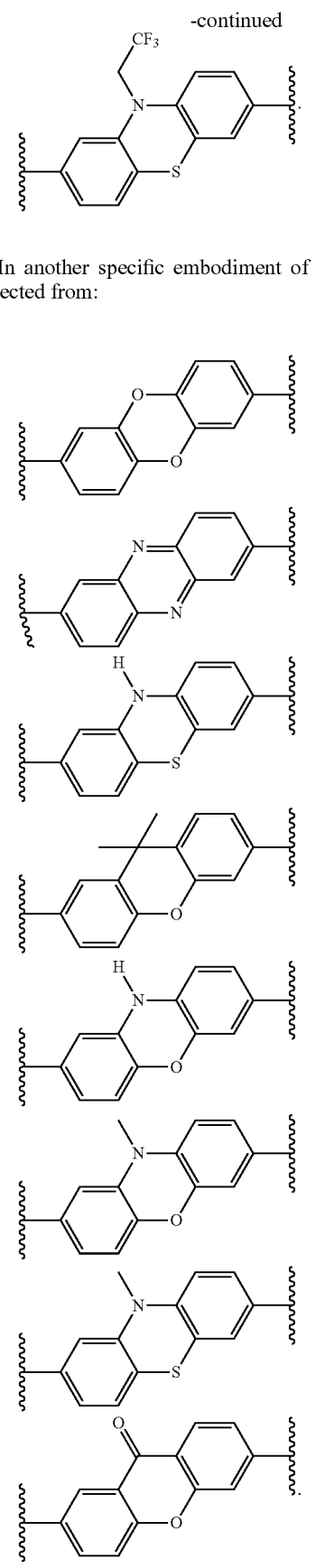
In another specific embodiment of the invention $W^8$ is selected from:

In another specific embodiment of the invention $W^8$ is selected from:

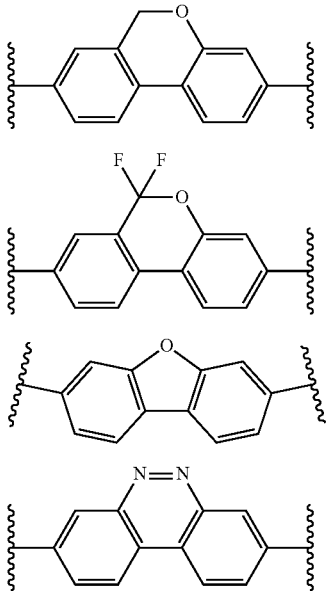

and

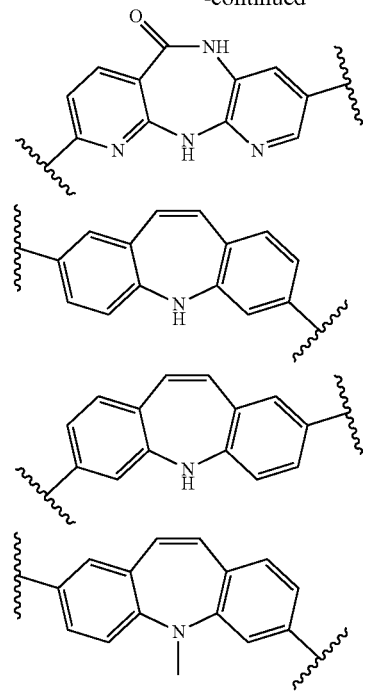

In another specific embodiment of the invention $W^8$ is selected from:

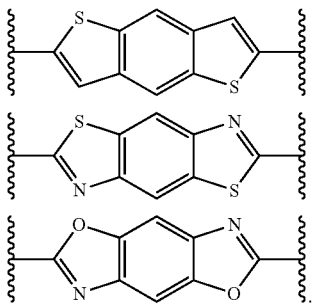

and

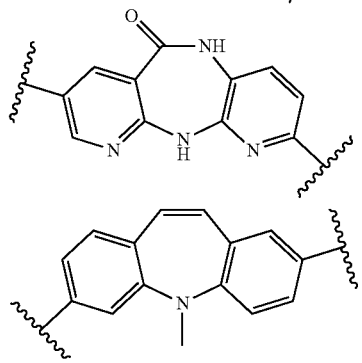

In another specific embodiment of the invention $W^8$ is selected from:

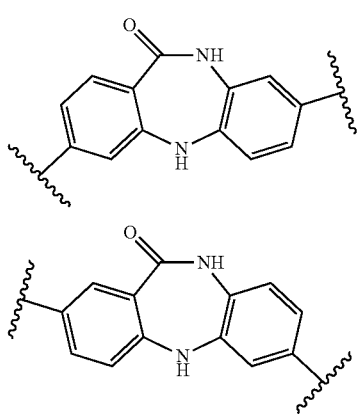

In another specific embodiment of the invention W is $W^8$ that is unsubstituted.

In another specific embodiment of the invention $W^{12}$ is:

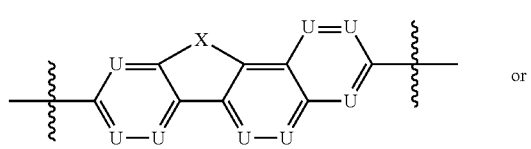

In another specific embodiment of the invention W is $W^{15}$ or $W^{16}$.

In another specific embodiment of the invention W is a ring system of formula:

-continued

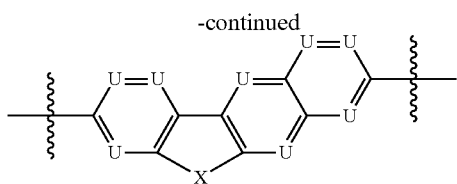

wherein:
U is CH or N; and
X is —CH$_2$—, —C(=O)—, —CH$_2$CH$_2$—, —CH$_2$CH$_2$CH$_2$—, or —CH=CH—;
wherein the ring system is optionally substituted with one or more R$^{41}$ or R$^{43}$.

In another specific embodiment of the invention W is selected from:

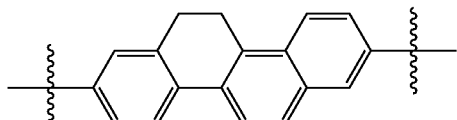

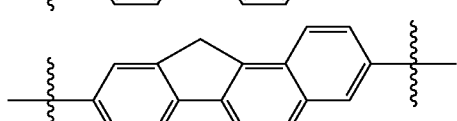

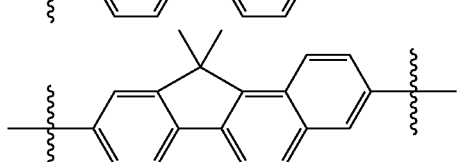

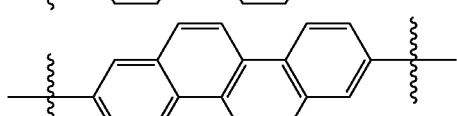

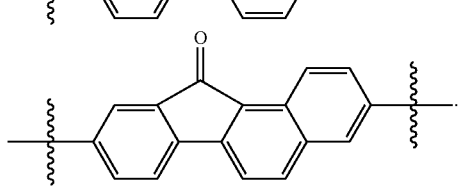

In another specific embodiment of the invention W is selected from:

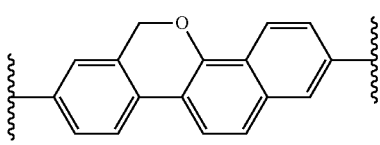

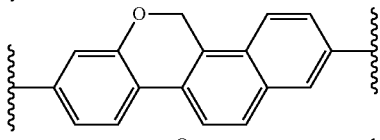

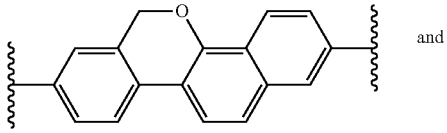

and

-continued

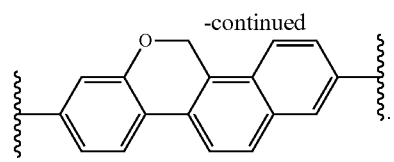

In another specific embodiment of the invention W is selected from:

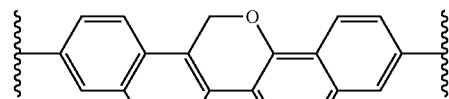

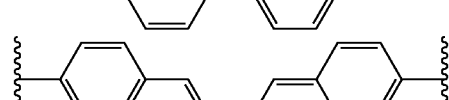

and

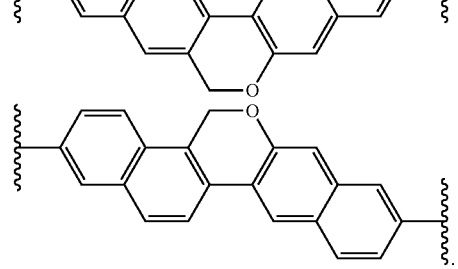

In another specific embodiment of the invention W is W$^2$ and within the W$^2$ one X$^A$ is absent and one X$^A$ is RC=CR and each R is independently selected from H or alkyl.

In another specific embodiment of the invention W$^2$ has the following structure:

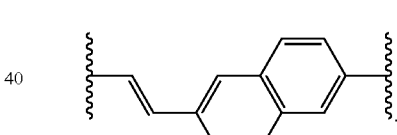

In another specific embodiment of the invention W is W$^2$ and within the W$^2$ one X$^A$ is absent and one X$^A$ is selected from absent, alkynyl, or RC=CR and each R is independently selected from H or alkyl; and M is selected from M$^0$ or M$^9$.

In another specific embodiment of the invention W is a ring system of formula:

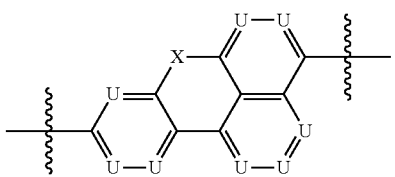

wherein:
U is CH or N; and
X is —CH$_2$—, —C(=O)—, —CH$_2$CH$_2$—, —CH$_2$CH$_2$CH$_2$—, or —CH=CH—;
wherein the ring system is optionally substituted with one or more R$^{41}$ or R$^{43}$.

In another specific embodiment of the invention W is selected from:
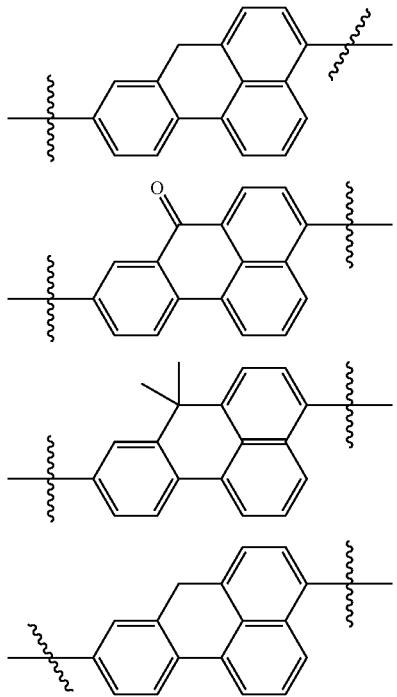
and
In another specific embodiment of the invention W is selected from:
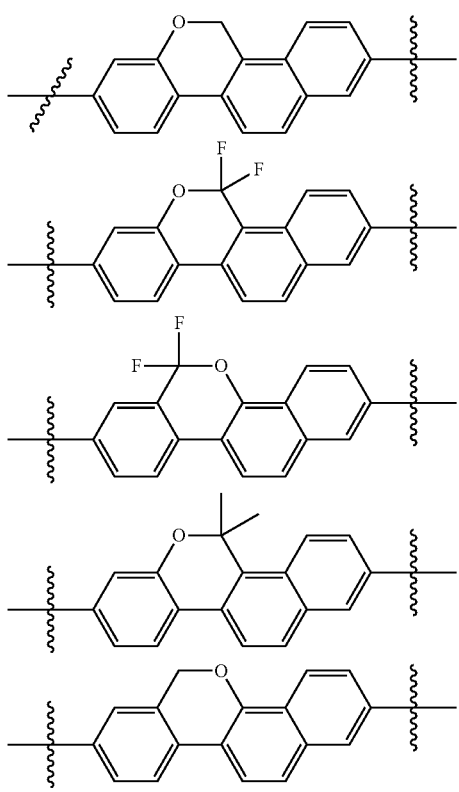
-continued
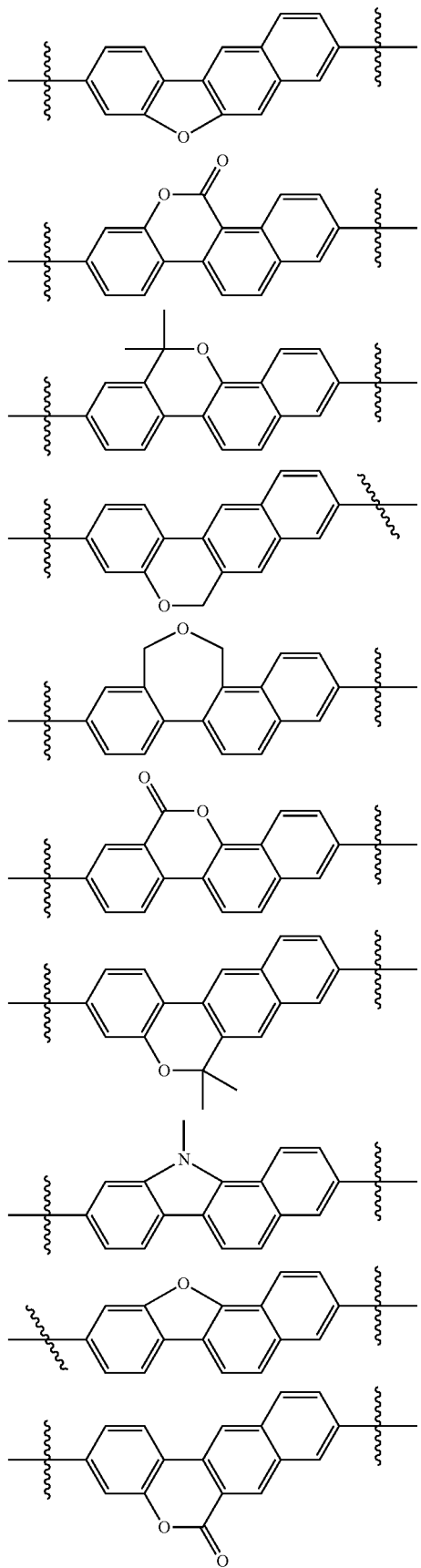

-continued
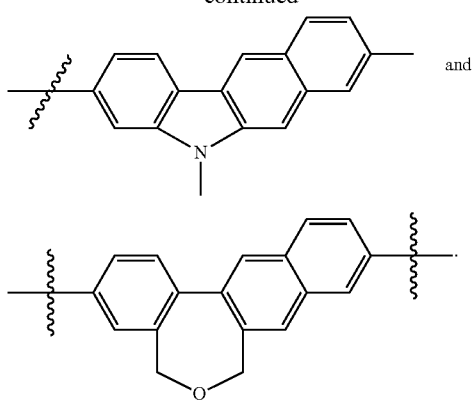 and
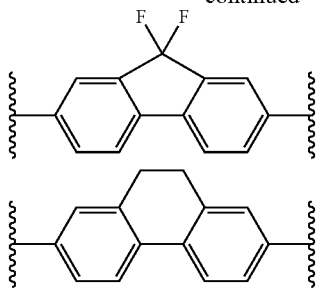 or
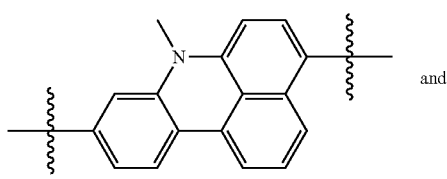
In another specific embodiment of the invention W is selected from:
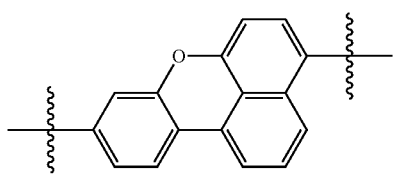
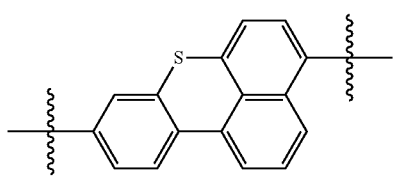
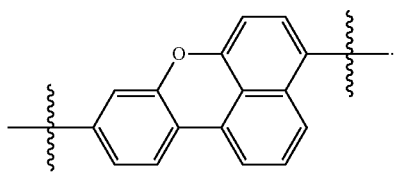 and
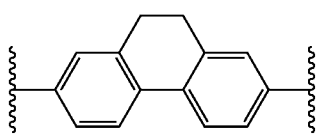
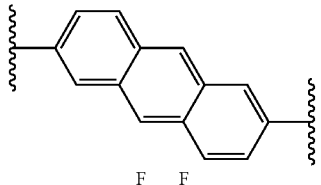
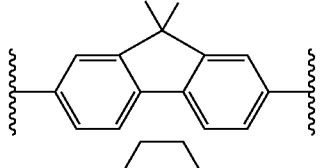 or
In another specific embodiment of the invention W is
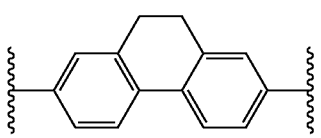
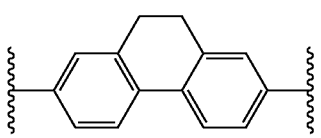
In another specific embodiment of the invention W is
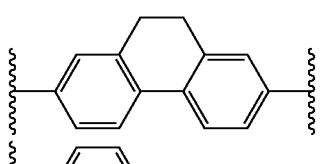
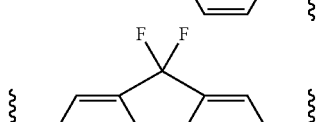 or
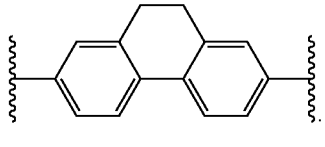.
In another specific embodiment of the invention W is In another specific embodiment of the invention W is

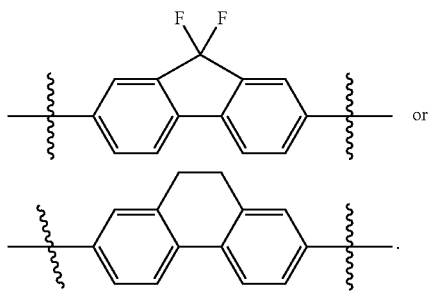

or

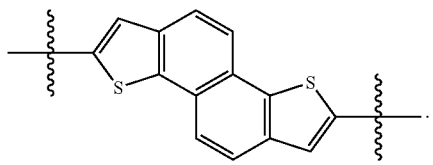 [SMILES: *c1cc2ccc3c(ccc4cc(*)sc43)c2s1 ; "."]

In another specific embodiment of the invention W is

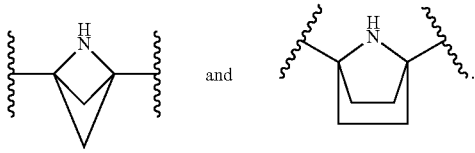 [SMILES: *C12CC(*)(C1)N2 ; "and" ; *C12CCC(*)(CC1)N2 ; "."]

In another specific embodiment of the invention each $X^A$ within W is absent.

In another specific embodiment of the invention t is 0, 9, 10, or 11.

In another specific embodiment of the invention $M^0$ is imidazolyl and $M^9$ is benzimidazolyl.

In another specific embodiment of the invention the compound of formula (Ia) comprises a group $M^9\text{-}W^2\text{-}M^9$.

In another specific embodiment of the invention M is $M^0$.

In another specific embodiment of the invention M is imidazolyl.

In another specific embodiment of the invention M is $M^9$.

In another specific embodiment of the invention each M is benzimidazolyl.

In another specific embodiment of the invention one M is $M^0$ and one M is $M^9$.

In another specific embodiment of the invention one M is imidazolyl and one M is benzimidazolyl.

In another specific embodiment of the invention each M is independently a 5-membered heteroaryl ring.

In another specific embodiment of the invention each M is 2,4-imidazoldiyl.

In another specific embodiment of the invention M is $M^6$.

In another specific embodiment of the invention M is selected from:

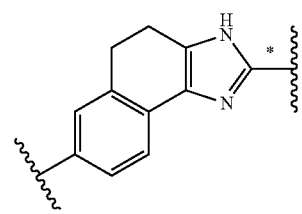

In another specific embodiment of the invention M is $M^7$.

In another specific embodiment of the invention M is:

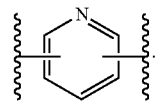

In another specific embodiment of the invention M is $M^8$.
In another specific embodiment of the invention M is:

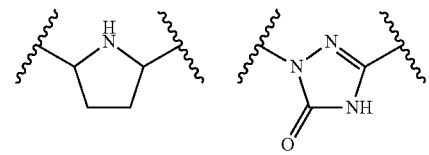
and

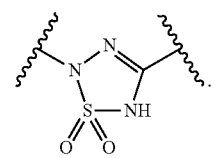

In another specific embodiment of the invention $M^0$ is:

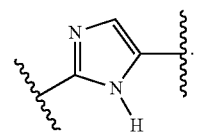 [SMILES: *c1cnc(*)[nH]1 ; "."]

In another specific embodiment of the invention $M^9$ is:

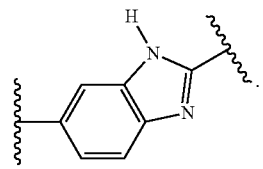 [SMILES: *c1ccc2nc(*)[nH]c2c1 ; "."]

In another specific embodiment of the invention M is $M^{11}$ and is:

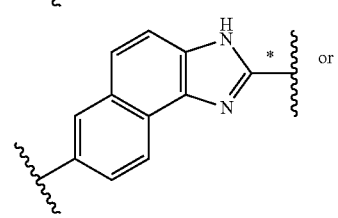

or

-continued

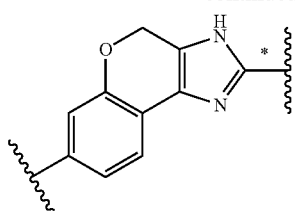

wherein * designates the site of connection to P.

In another specific embodiment of the invention the compound of formula (Ia) is a compound of formula (Ia1): E-V-Z-P-$M^0$-$W^6$-$M^9$-P-Z-V-E (Ia1).

In another specific embodiment of the invention the compound of formula (Ia) is a compound of formula (Ia2): $E^9$-$V^0$-$Z^0$-P-$M^0$-$W^6$-$M^9$-P-$Z^0$-$V^0$-$E^0$ (Ia2)

In another specific embodiment of the invention the compound of formula (Ia) is a compound of formula (Ia3): E-V-Z-$P^0$-$M^0$-$W^6$-$M^9$-$P^7$-Z-V-E (Ia3).

In another specific embodiment of the invention the compound of formula (Ia) is a compound of formula (Ia4): $E^0$-$V^0$-$Z^0$-$P^0$-$M^0$-$W^6$-$M^9$-$P^7$-$Z^0$-$V^0$-$E^0$ (Ia4).

In another specific embodiment of the invention the compound of formula (Ia) is a compound of formula (Ia5):

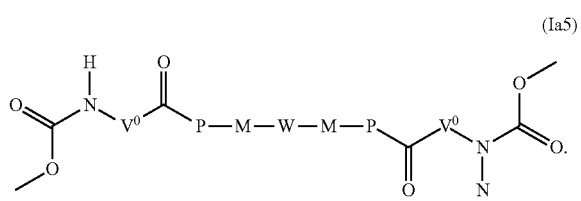

(Ia5)

In another specific embodiment of the invention the compound of formula (Ia) is a compound of formula (Ia6):

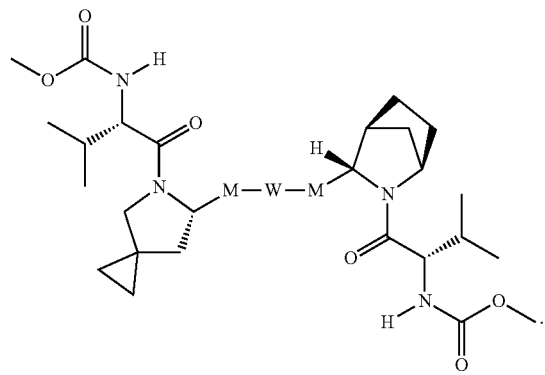

(Ia6)

In another specific embodiment of the invention the compound of formula (Ia) is a compound of formula (Ia7):

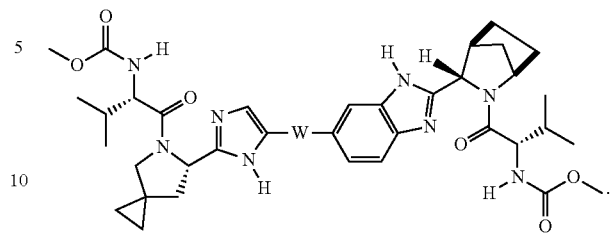

(Ia7)

In another specific embodiment the invention provides a compound of formula (Ia5), (Ia6) or (Ia7), wherein W is $W^2$.

In another specific embodiment the invention provides a compound of formula (Ia5), (Ia6) or (Ia7), wherein W is $W^6$.

In another specific embodiment the invention provides a compound of formula (Ia5), (Ia6) or (Ia7), wherein W is $W^8$.

In another specific embodiment the invention provides a compound of formula (Ia5), (Ia6) or (Ia7), wherein W is $W^{16}$.

In another specific embodiment the invention provides a compound of formula (Ia5), (Ia6) or (Ia7), wherein $W^{16}$ is selected from:

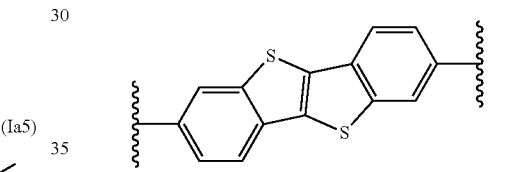

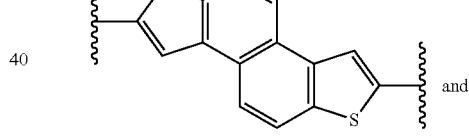

and

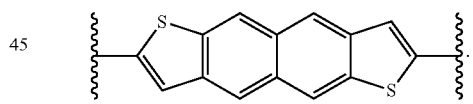

In another specific embodiment of the invention the compound of formula (Ia) is a compound of formula (Ia9):

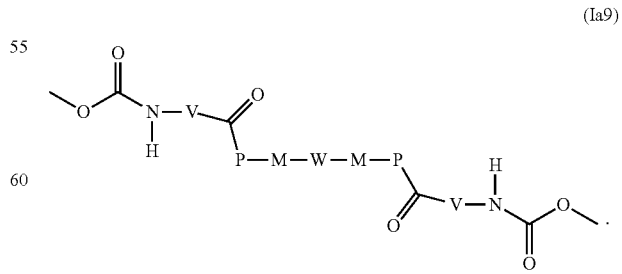

(Ia9)

In another specific embodiment of the invention the compound of formula (Ia) is a compound of formula (Ia10):

(Ia10)

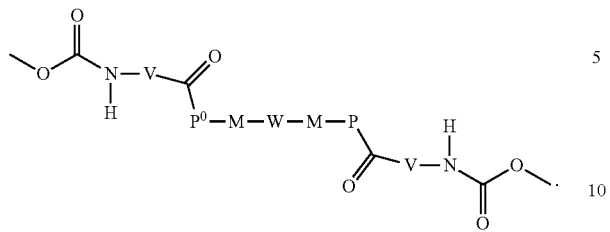

In another specific embodiment of the invention the compound of formula (Ia) is a compound of formula (Ia11):

(Ia11)


In another specific embodiment of the invention the compound of formula (Ia) is a compound of formula (Ia12):

(Ia12)

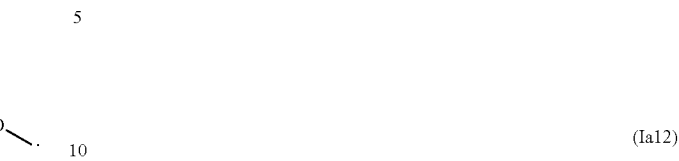

In another specific embodiment of the invention the compound of formula (Ia) is a compound of formula (Ia13):

(Ia13)

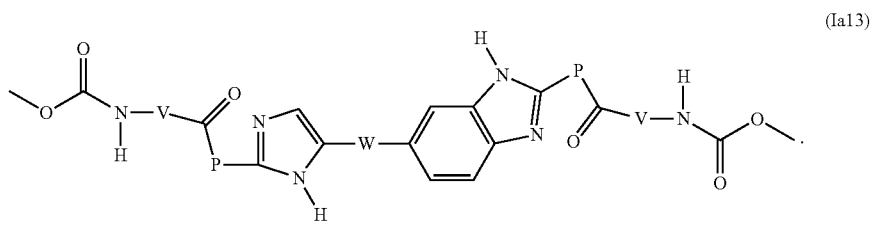

In another specific embodiment of the invention the compound of formula (Ia) is a compound of formula (Ia14):

(Ia14)

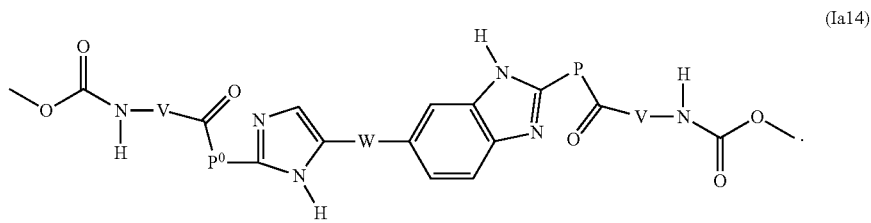

In another specific embodiment of the invention the compound of formula (Ia) is a compound of formula (Ia15):

(Ia15)

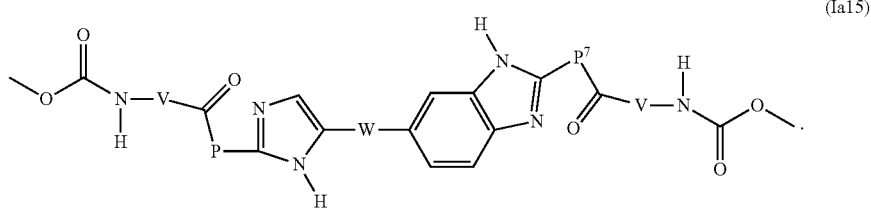

In another specific embodiment of the invention the compound of formula (Ia) is a compound of formula (Ia16):

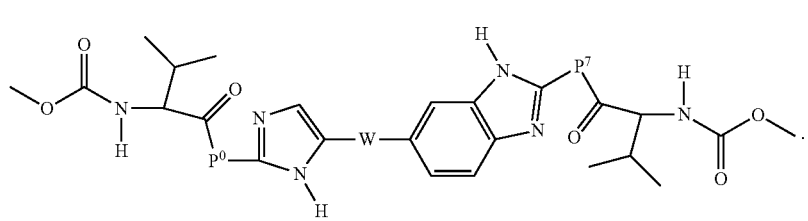

(Ia16)

In one embodiment of the invention, the compound of formula (Ia) is a compound of formula (Ia8):

$$E^x\text{-}V^w\text{-}Z^v\text{-}P^u\text{-}M^t\text{-}W^r\text{-}M^{t1}\text{-}P^{u1}\text{-}Z^{v1}\text{-}V^{w1}\text{-}E^{x1}$$ (Ia8)

wherein:

r is 2, 4, 6, 8, or 16; t is 0 or 10; u is 0, 1, 3, 5, 7, 8, 10, or 11; v is 0; w is 0, 1, 2, 3, 4, or 5; x is 0; t1 is 9; u1 is 0, 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein: r is 6; t is 0 or 10; u is 0, 1, 3, 5, 7, 8, 10, or 11; v is 0; w is 0, 1, 2, 3, 4, or 5; x is 0; t1 is 9; u1 is 0, 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein $E^0$ is:

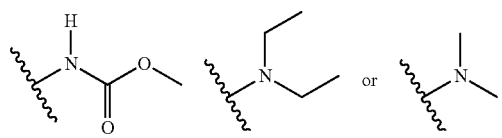

In one embodiment of the invention, the compound of formula (Ia) is a compound of formula (Ia8) wherein $M^0$ is:

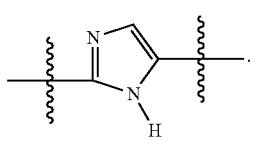 [SMILES: *c1cnc(*)[nH]1]

In one embodiment of the invention, the compound of formula (Ia) is a compound of formula (Ia8) wherein $M^9$ is:

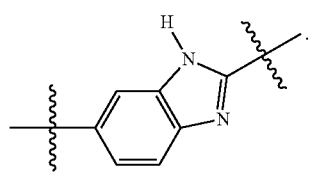 [SMILES: *c1ccc2nc(*)[nH]c2c1]

In one embodiment of the invention, the compound of formula (Ia) is a compound of formula (Ia8) wherein r is 6 and $W^6$ is:

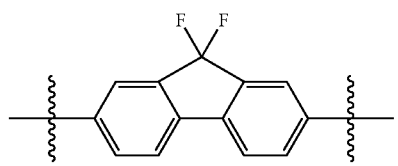

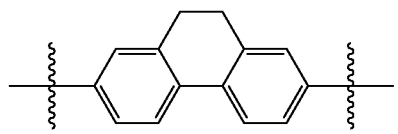

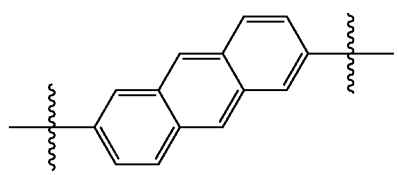

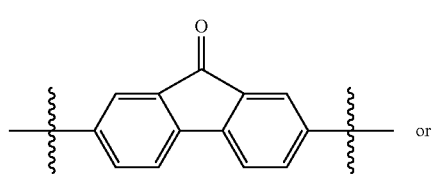

or

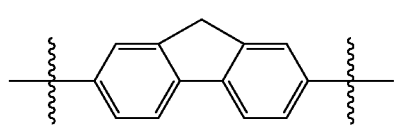

In one embodiment of the invention, the compound of formula (Ia) which is selected from:

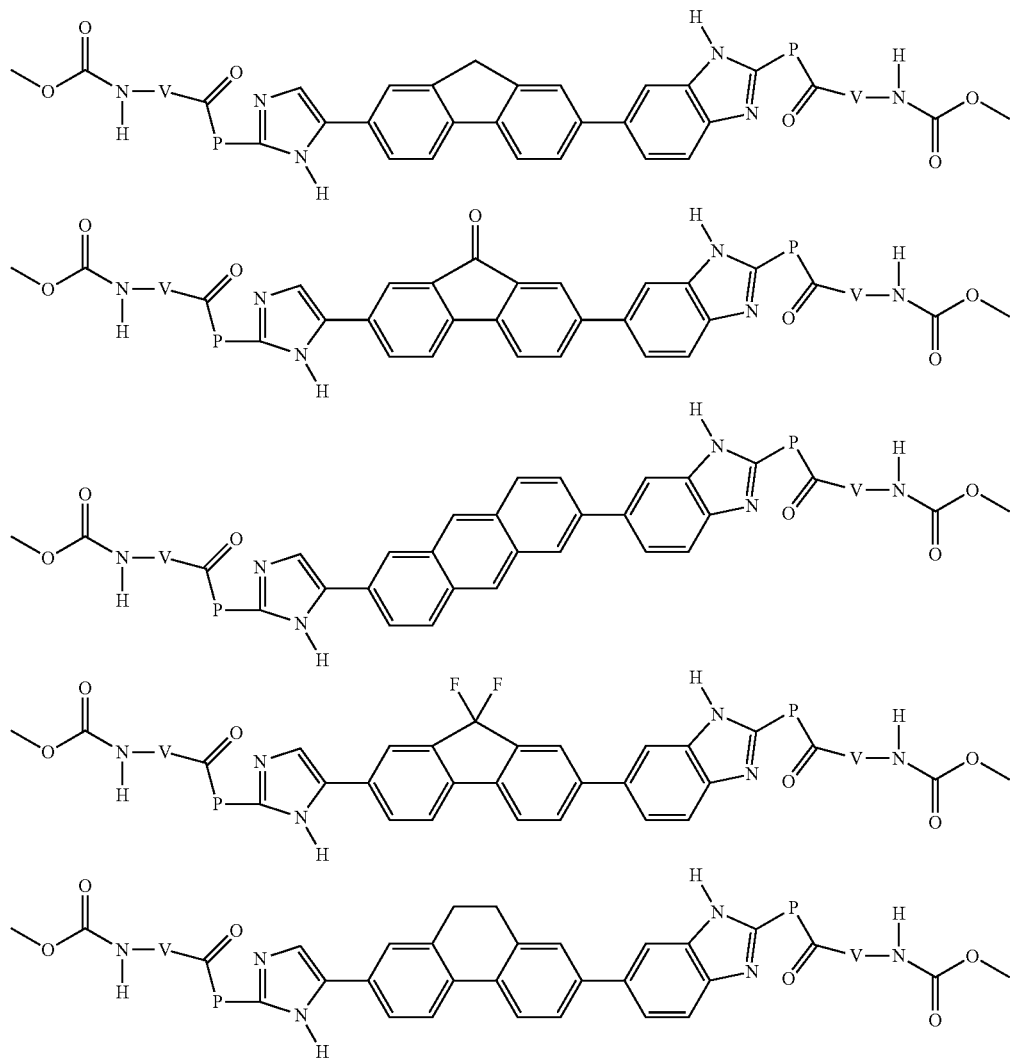

In one embodiment of the invention, the compound of formula (Ia) is a compound of formula (Ia8) wherein r is 2 and $W^2$ is:

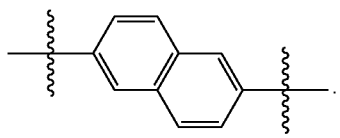

In one embodiment of the invention, the compound of formula (Ia) is a compound of formula (Ia8) wherein r is 4 and $W^4$ is:

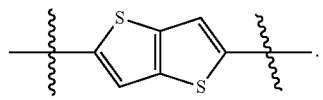

In one embodiment of the invention, the compound of formula (Ia) is a compound of formula (Ia8) which is:

In one embodiment of the invention, the compound of formula (Ia) is a compound of formula (Ia8) which is:

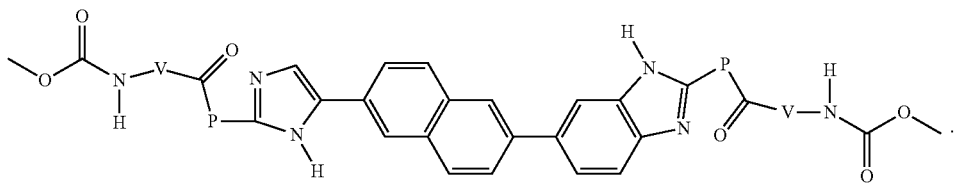

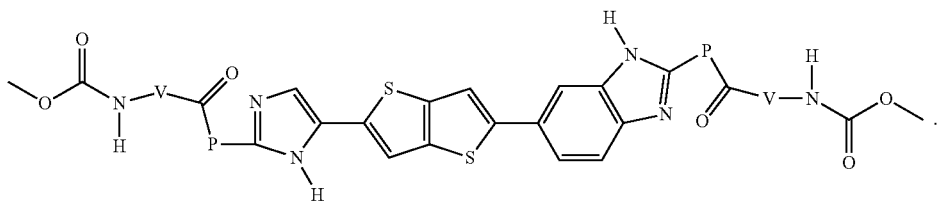
In one embodiment of the invention, the compound of formula (Ia) is a compound of formula (Ia8) wherein r is 8 and W⁸ is:
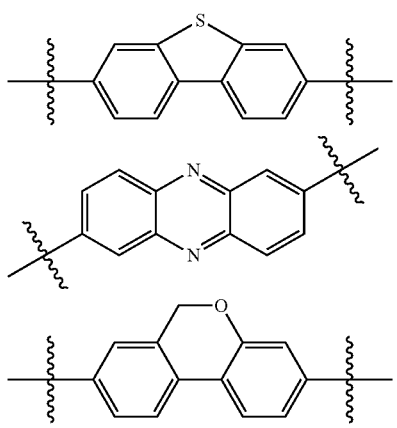
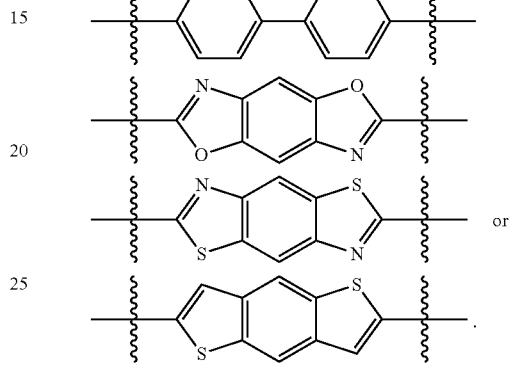
In one embodiment of the invention, the compound of formula (Ia) is a compound of formula (Ia8) which is selected from:
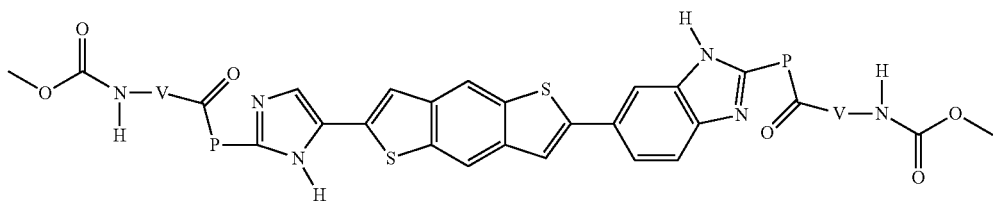
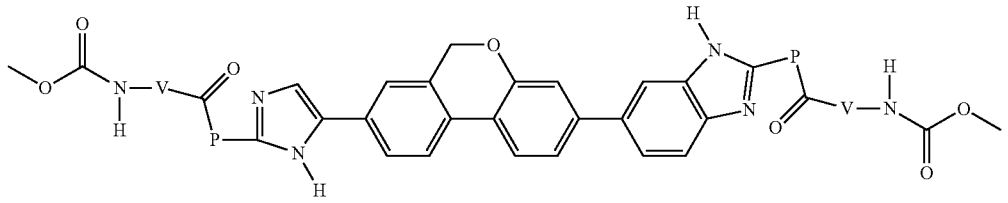
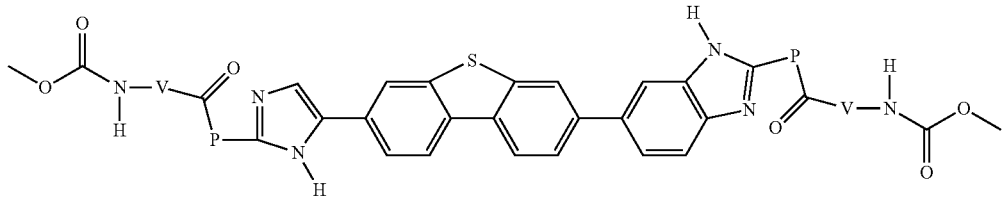
and
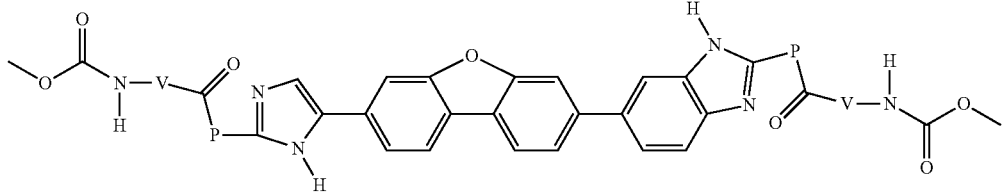

In one embodiment of the invention, the compound of formula (Ia) is a compound of formula (Ia8) wherein r is 16 and $W^{16}$ is:

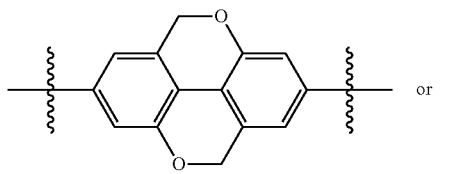

or

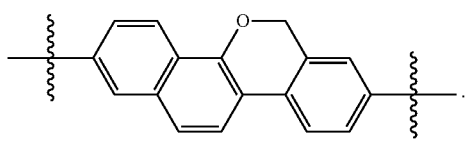

In one embodiment of the invention, the compound of formula (Ia) is a compound of formula (Ia8) which is selected from:

In one embodiment of the invention, the compound of formula (Ia) is a compound of formula (Ia8) wherein: r is 6, or 8; t is 0 or 10; u is 0, 1, 3, 5, 7, 8, 10, or 11; v is 0; w is 0, 1, 2, 3, 4, or 5; x is 0; t1 is 9; u1 is 0, 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein: r is 6, or 8; t is 0 or 10; u is 0, 1, 3, 5, 7, 8, 10, or 11; v is 0; w is 1, 2, 3, 4, or 5; x is 0; t1 is 9; u1 is 0, 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein: r is 6, or 8; t is 0 or 10; u is 0, 1, 3, 5, 7, 8, 10, or 11; v is 0; w is 0, 1, 2, 3, 4, or 5; x is 0; t1 is 9; u1 is 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein: r is 6, or 8; t is 0 or 10; u is 0, 1, 3, 5, 7, 8, 10, or 11; v is 0; w is 1, 2, 3, 4, or 5; x is 0; t1 is 9; u1 is 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) which is selected from:

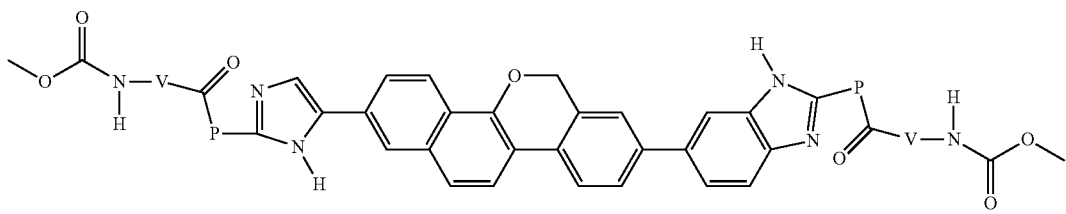

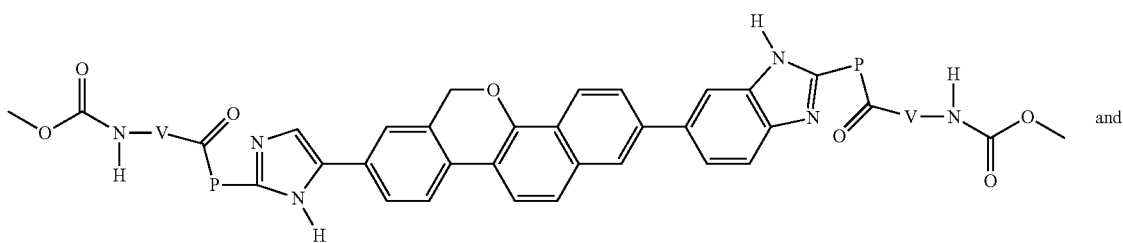 and

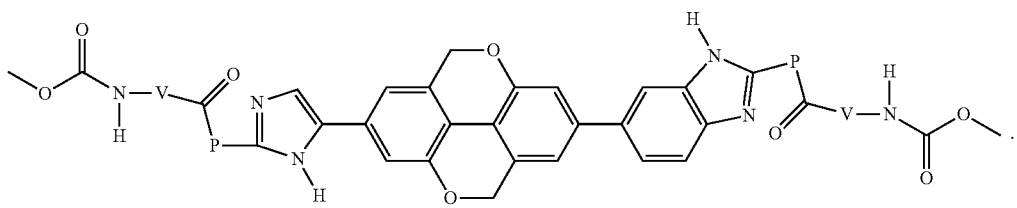

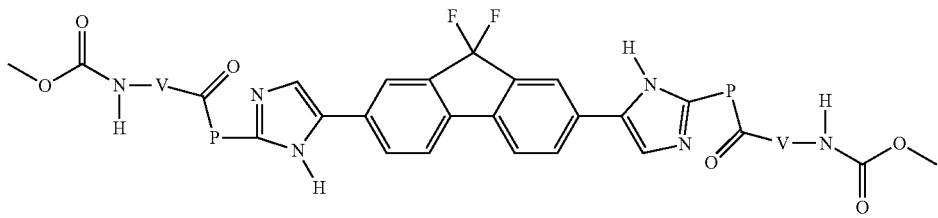
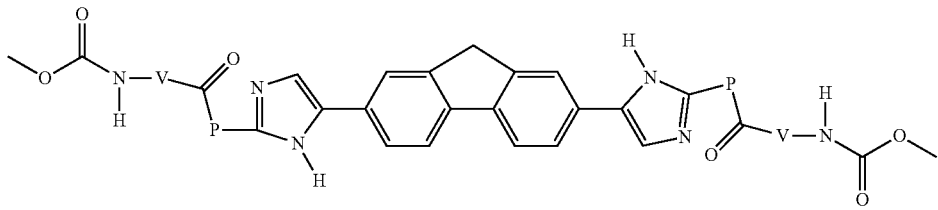
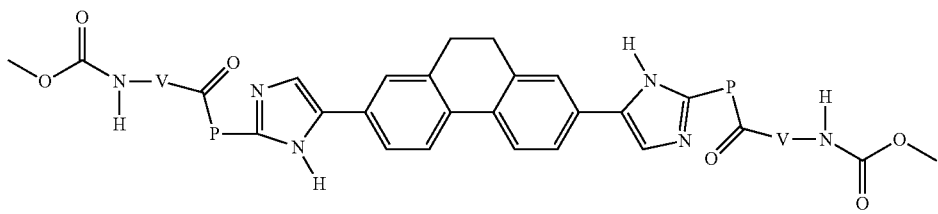
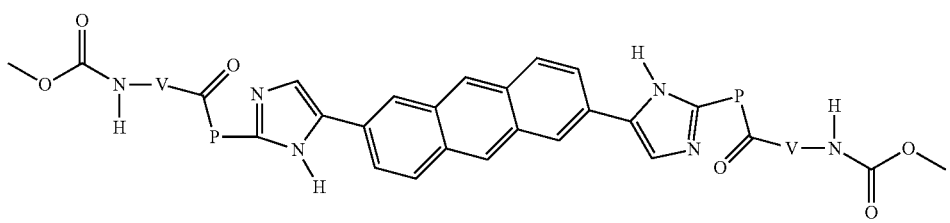
and
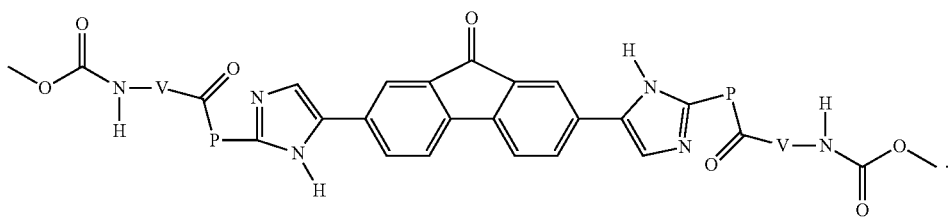
In one embodiment of the invention, the compound of formula (Ia) is a compound of formula (Ia8) which is selected from:
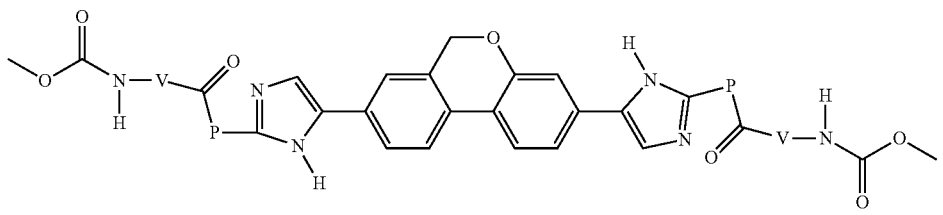
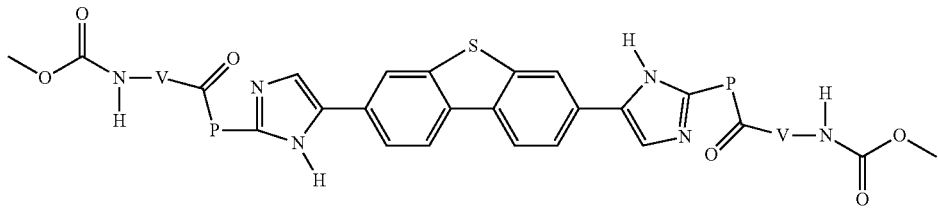

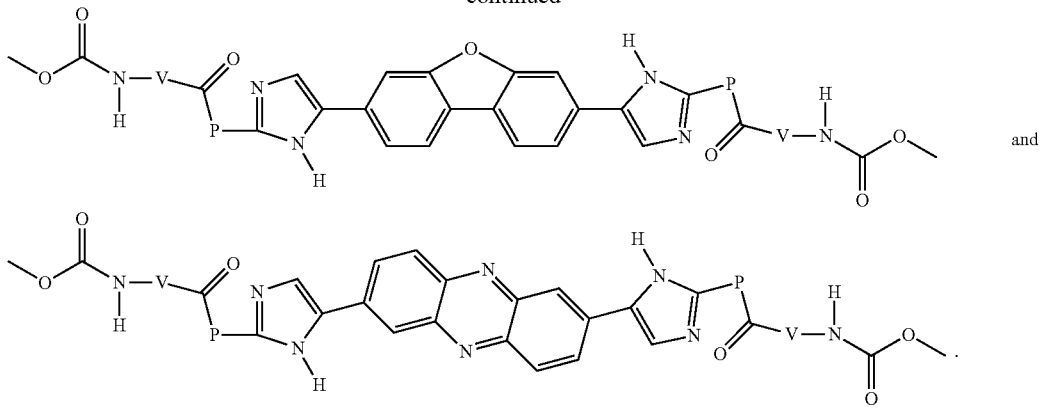

and

In one embodiment of the invention, the compound of formula (Ia) is a compound of formula (Ia8) wherein: r is 6, or 8; t is 0 or 10; u is 0, 1, 3, 5, 7, 8, 10, or 11; v is 0; w is 0, 1, 2, 3, 4, or 5; x is 0; t1 is 0 or 10; u1 is 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) which has the formula:

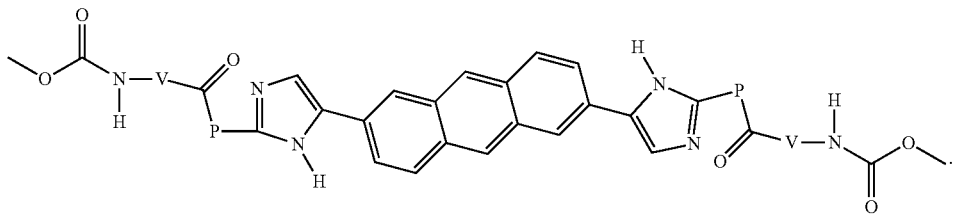

In one embodiment of the invention, the compound of formula (Ia) is a compound of formula (Ia8) which is selected from:

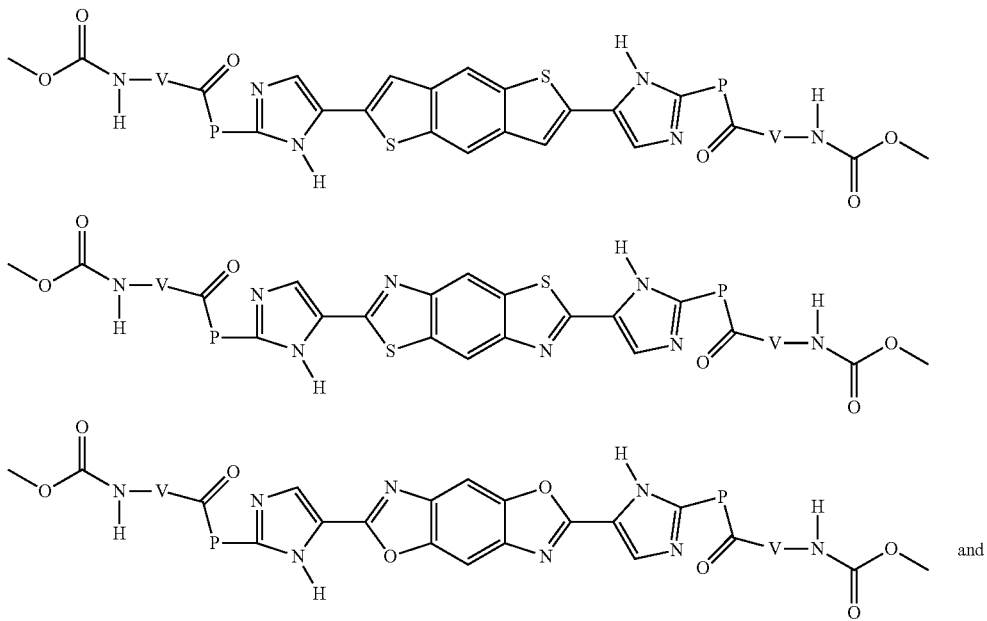

and

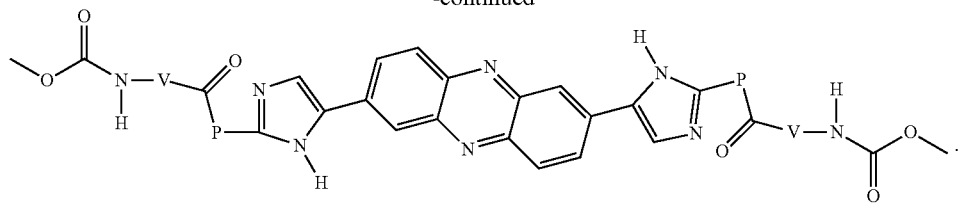

In one embodiment of the invention, the compound of formula (Ia) is a compound of formula (Ia8) wherein: r is 16 or 18; t is 0 or 10; u is 0, 1, 3, 5, 7, 8, 10, or 11; v is 0; w is 0, 1, 2, 3, 4, or 5; x is 0; t1 is 0 or 10; u1 is 0, 1, 3, 5, 7, 8, 10, or 11; v1 is 0; w1 is 0, 1, 2, 3, 4, or 5; and x1 is 0.

In one embodiment of the invention, the compound of formula (Ia) is a compound of formula (Ia8) wherein r is 16 and $W^{16}$ is:

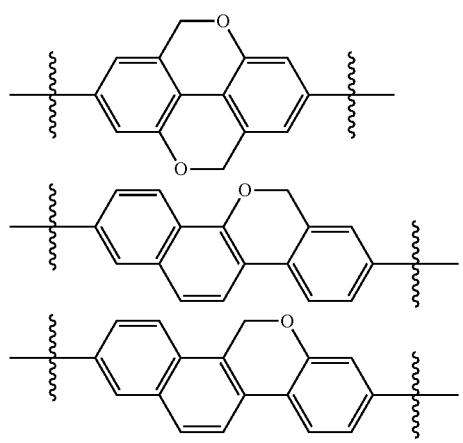

-continued

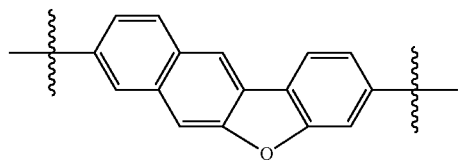

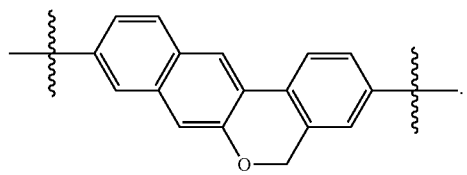 or

In one embodiment of the invention, the compound of formula (Ia) is a compound of formula (Ia8) which is selected from:

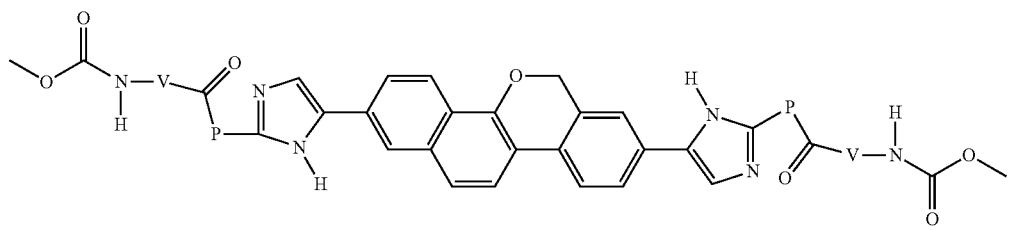

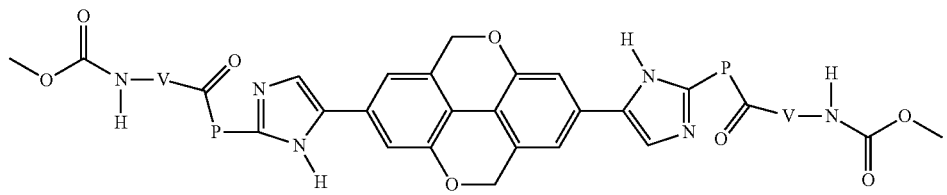

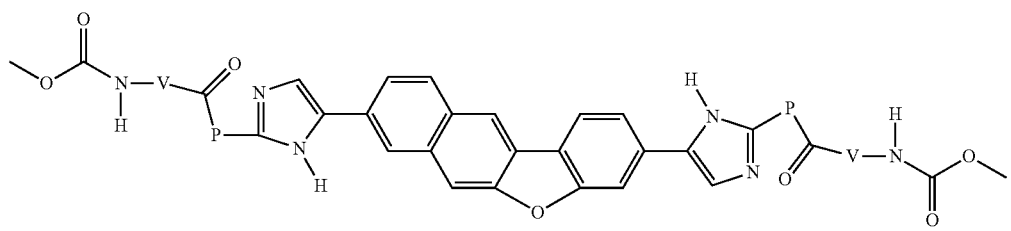

-continued

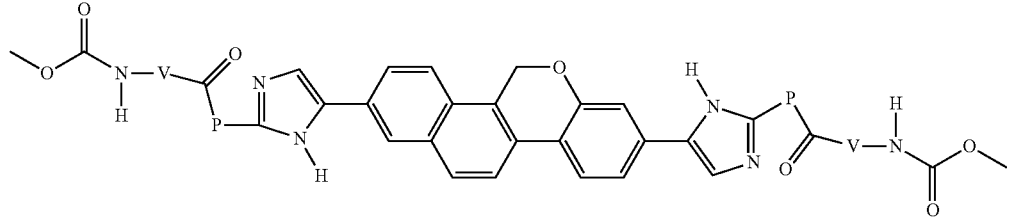

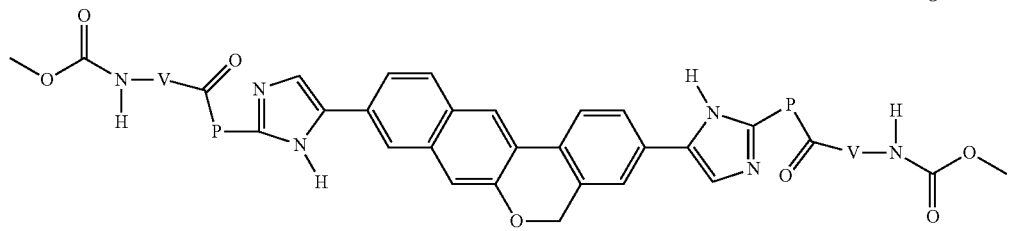

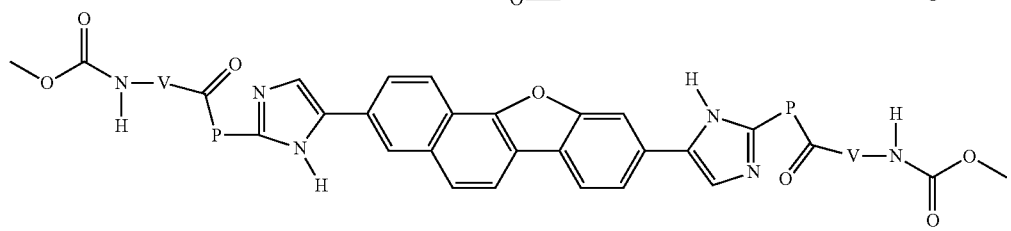

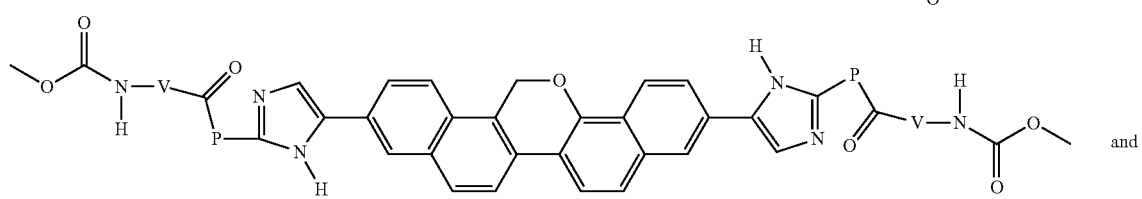

and

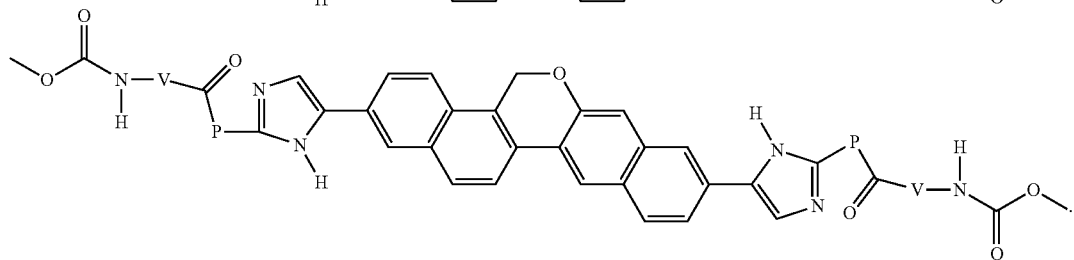

In one embodiment of the invention, the compound of formula (Ia) is a compound of formula (Ia8) wherein r is 18 and $W^{18}$ is:

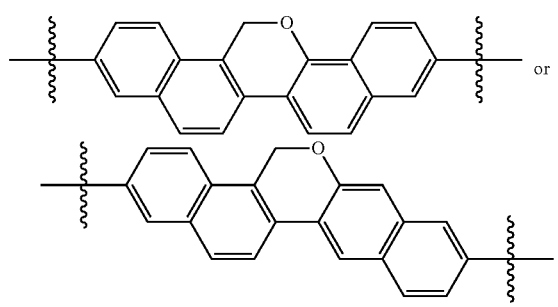

In one embodiment of the invention, the compound of formula (Ia) is a compound of formula (Ia17):

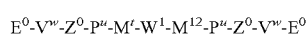      (Ia17)

wherein:
each u is independently 0, 1, 3, 5, 7, 8, 10, or 11;
each w is independently 0, 1, 2, 3, 4, or 5;
t is 0, 9, 10, or 11;
$W^1$ is a bond;
$M^{12}$ is a fused unsaturated, partially unsaturated or saturated hexacyclic heterocycle that comprises at least one heteroatom in the ring system, which ring system is optionally substituted with one or more groups independently selected from oxo, $R^{A1}$ and $R^{A3}$;
each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^4$ is independently selected from H, alkyl, haloalkyl, aryl, and arylalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

In one embodiment the invention provides a compound of formula (Ia17) wherein $M^{12}$ is:

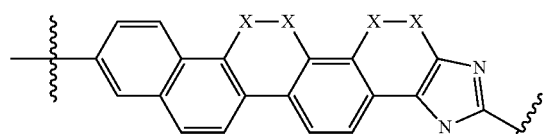

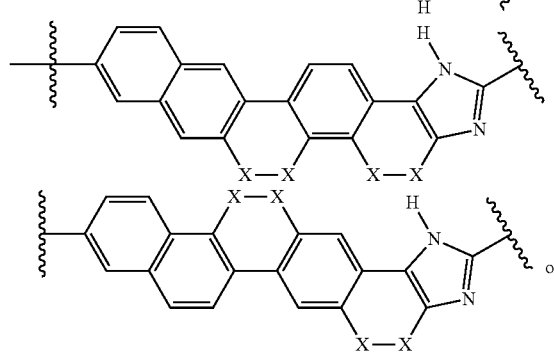

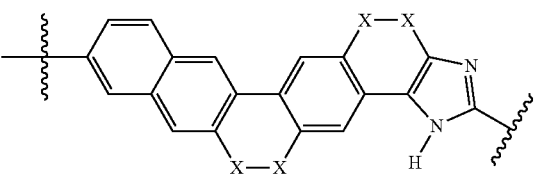

wherein X—X is selected from O, $CH_2$, CH=CH, $CH_2$—$CH_2$, $CH_2$—O, O—$CH_2$, $CH_2$—$CH_2$—$CH_2$, and $CH_2$—O—$CH_2$.

In one embodiment the invention provides a compound of formula (Ia17) wherein $M^0$ is:

In one embodiment the invention provides a compound of formula (Ia17) which is selected from:

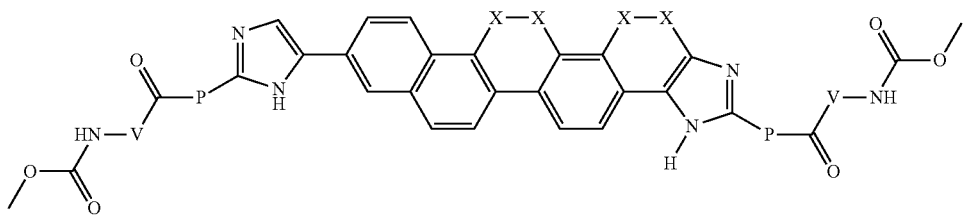

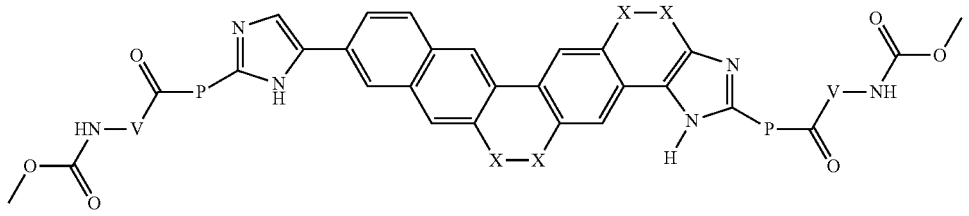

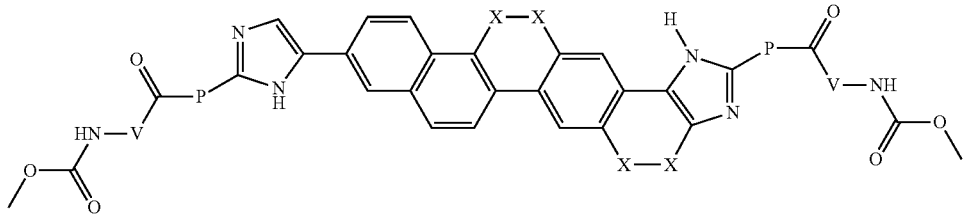

and

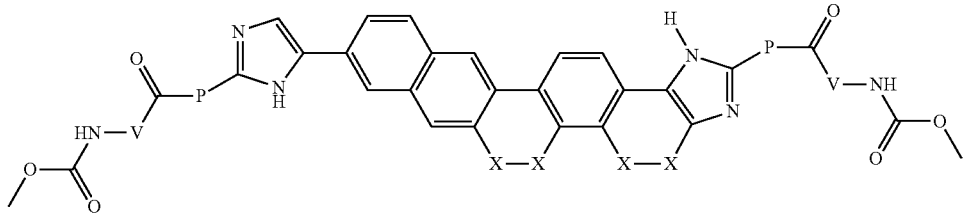

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.
In one embodiment the invention provides a compound of formula (Ia17) wherein M$^9$ is:
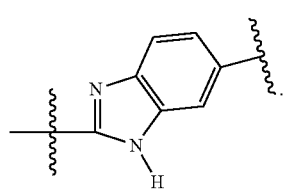 [SMILES: *c1ccc2nc(*)[nH]c2c1]
In one embodiment the invention provides a compound of formula (Ia17) which is selected from:
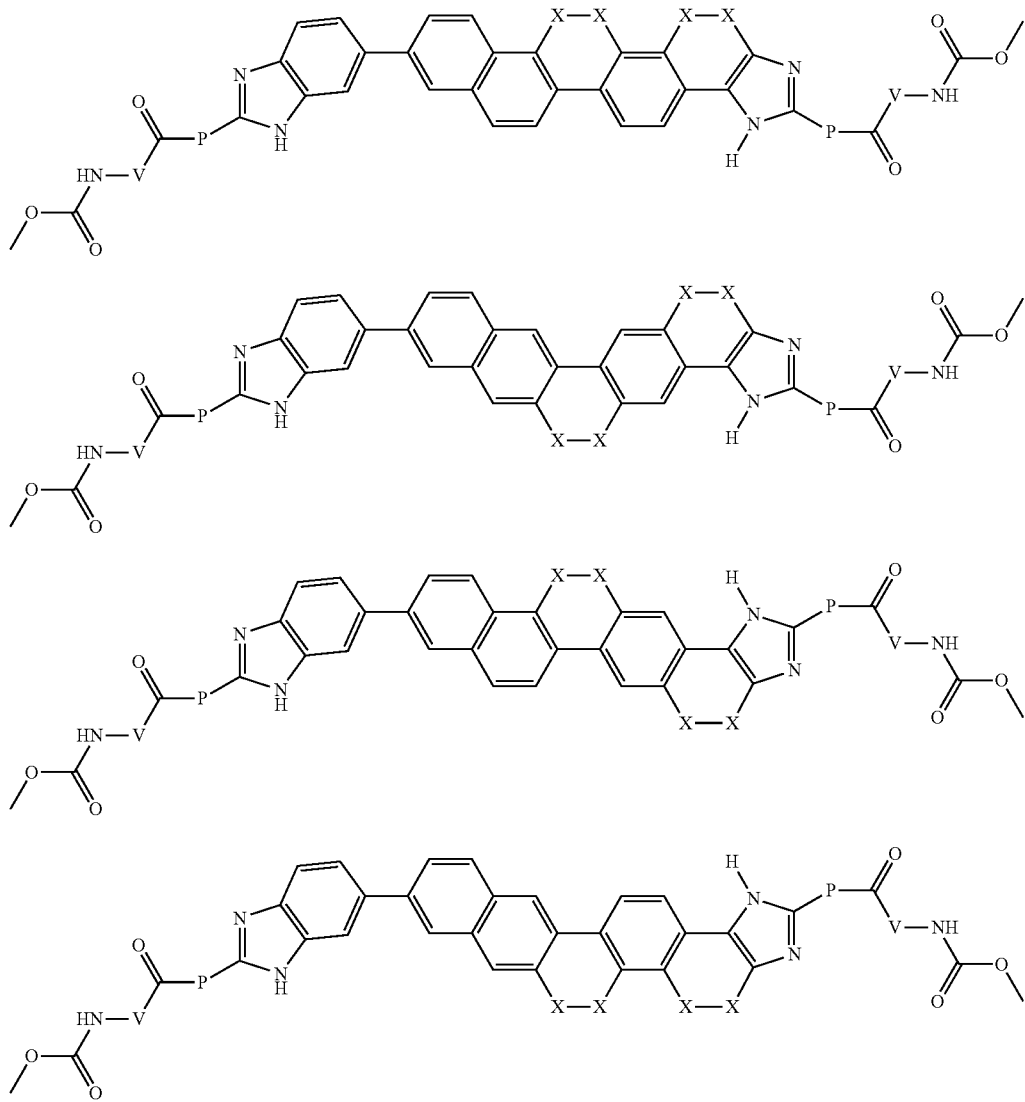

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ia17) wherein M$^{11}$ is:

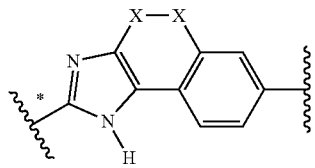

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; and wherein * designates the site of connection to P.

In one embodiment of the invention, the compound of formula (Ia) is selected from:

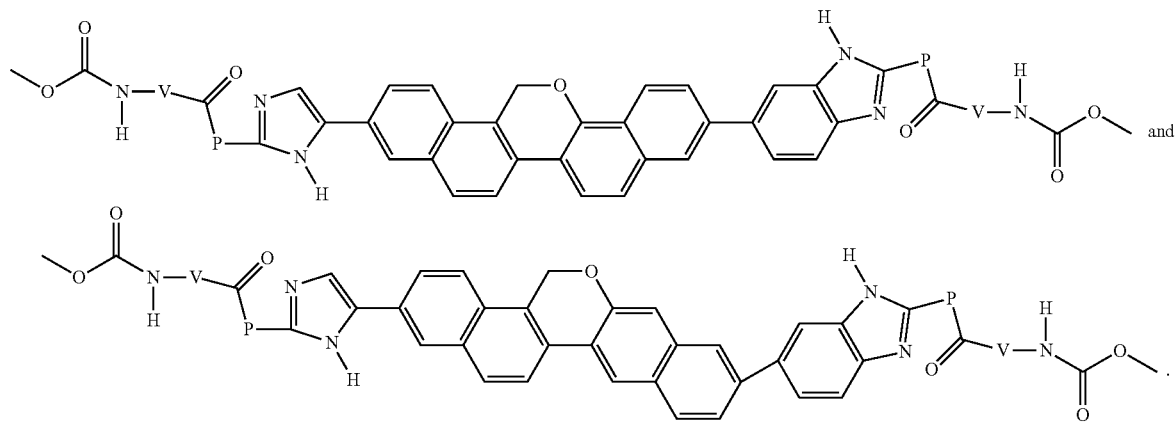

In one embodiment the invention provides a compound of formula (Ia18):

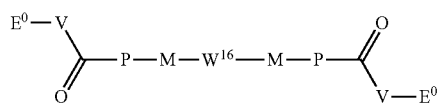
(Ia18)

wherein:

each P is independently selected from:

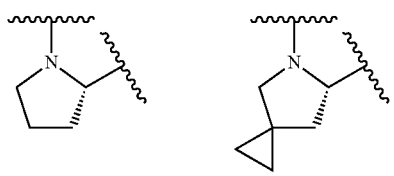

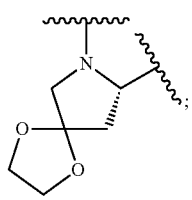

each M is independently M$^0$, M$^9$, or M$^{10}$; and W$^{16}$ is selected from:

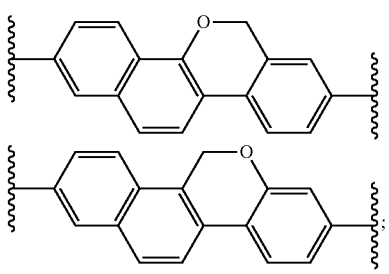

or a pharmaceutically acceptable salts or prodrug thereof.

In one embodiment the invention provides a compound of formula (Ia19):

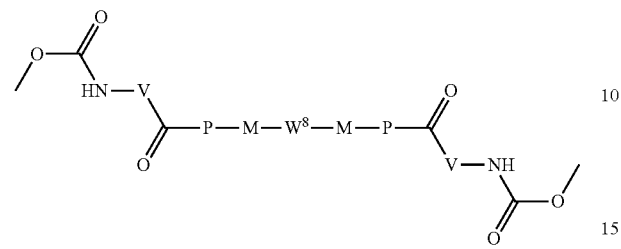
(Ia19)

wherein:

each P is independently selected from:

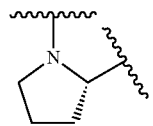 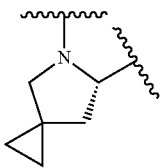

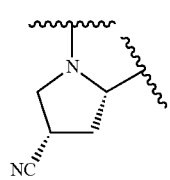 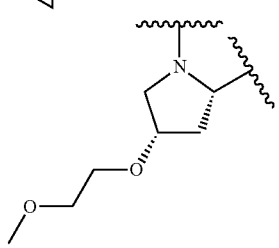

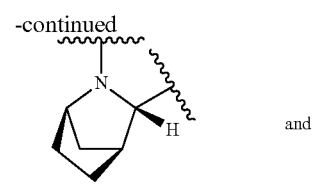

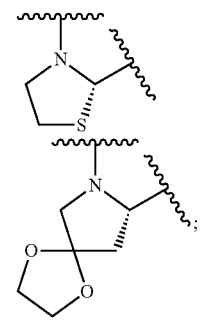

each M is independently $M^0$, $M^9$, or $M^{10}$; and $W^8$ is selected from:

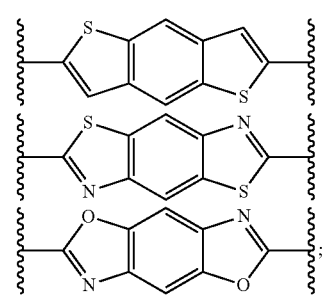

or a pharmaceutically acceptable salts or prodrug thereof.

In one embodiment the invention provides a compound of formula (Ia18) or (Ia19) wherein each $E^0$ is methoxycarbonylamino.

In another specific embodiment of the invention the compound of formula (Ia) is:

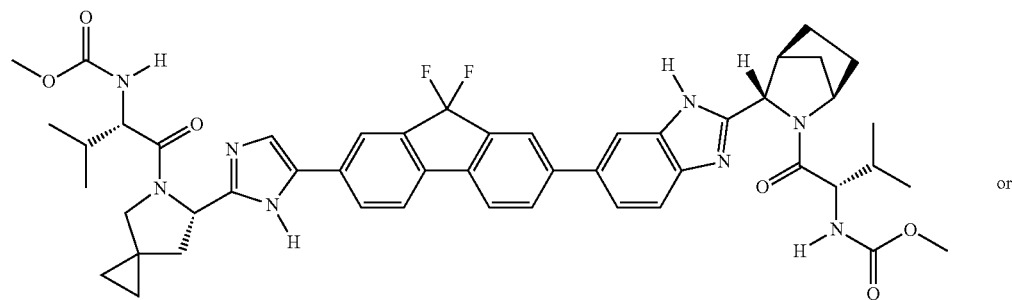
or

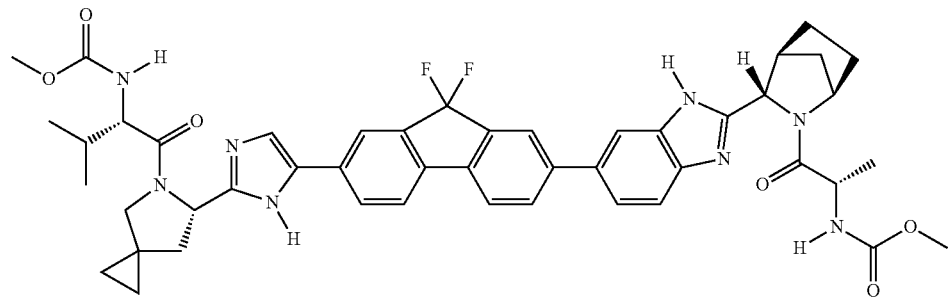

or a pharmaceutically acceptable salt, or prodrug thereof.

In another specific embodiment of the invention the compound of formula (Ia) is:

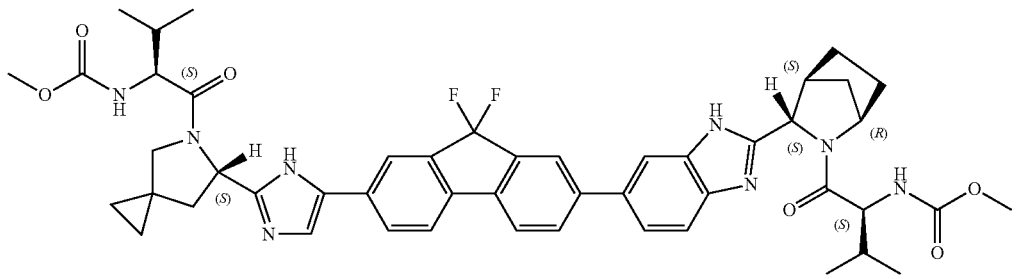

or a pharmaceutically acceptable salt, or prodrug thereof.

In another specific embodiment of the invention the compound of formula (Ia) is a compound of formula: R9-Z-P-M-W-M-P-Z-R9.

In another specific embodiment of the invention the compound of formula (Ia) is a compound of formula: R9-Z-P-M$^O$-W$^6$-M$^9$-P-Z-R9.

In another specific embodiment of the invention the compound of formula (Ia) is a compound of formula: R9-Z-P$^O$-M$^O$-W$^6$-M$^9$-P$^7$-Z-R9.

In another specific embodiment the invention provides a compound of formula (Ia) wherein the sum of t, u, v, w, and x is not 0.

In another specific embodiment the invention provides a compound of formula (Ia) wherein at least two of r, t, u, v, w, and x are other than 0.

In another specific embodiment the invention provides a compound of formula (Ia) wherein at least three of r, t, u, v, w, and x are other than 0.

In another specific embodiment the invention provides a compound of formula (Ia) wherein at least four of r, t, u, v, w, and x are other than 0.

In another specific embodiment the invention provides a compound of formula (Ia) wherein at least five of r, t, u, v, w, and x are other than 0.

In another specific embodiment the invention provides a compound of formula (Ia) wherein at least two of r, t, u, v, w or x are not zero and at least one t is selected from 0, 1, 2, 3, 4, 5, 6, 7, 8, 10, and 11.

In another specific embodiment the invention provides a compound of formula (Ia) wherein at least two of r, t, u, v, w and x are not zero and at least two of the non-zero groups are not the same letter (for example, one w and two u's can be non zero, but just having two u's being non-zero and the remaining r, t, v, w, and x values all zero is not acceptable).

In another specific embodiment the invention provides a compound of formula (Ia) wherein at least three of r, t, u, v, w or x are not zero and at least two of the non-zero groups are not the same letter.

In another specific embodiment the invention provides a compound of formula (Ia) wherein at least three of r, t, u, v, w or x are not zero and at least three of the non-zero groups are not the same letter.

In another specific embodiment the invention provides a compound of formula (Ia) wherein at least four of r, t, u, v, w or x are not zero and at least two of the non-zero groups are not the same letter.

In another specific embodiment the invention provides a compound of formula (Ia) wherein at least four of r, t, u, v, w or x are not zero and at least three of the non-zero groups are not the same letter.

In another specific embodiment the invention provides a compound of formula (Ia) wherein at least four of r, t, u, v, w or x are not zero and at least four of the non-zero groups are not the same letter.

In another specific embodiment the invention provides a compound of formula (Ia) wherein the sum of t, u, v, w or x is not zero.

In another specific embodiment the invention provides a compound of formula (Ia) wherein the sum of r, u, v, w or x is not zero.

In another specific embodiment the invention provides a compound of formula (Ia) wherein r is 2, 3, 4, 5, 6, 7, 8, 9, 10, 11, and at least one t is not zero.

In another specific embodiment the invention provides a compound of formula (Ia) wherein at least one u is not zero.

In another specific embodiment the invention provides a compound of formula (Ia) wherein r, and at least one t and at least one u are all not zero.

In another specific embodiment the invention provides a compound of formula (Ia) wherein at least two of u, w and t are not zero.

In another specific embodiment the invention provides a compound of formula (Ia) wherein at least two of r, u, and w are not zero.

In another specific embodiment the invention provides a compound of formula (Ia) wherein at least two of r, u, and w are not zero and at least two of the non-zero groups are not the same letter.

In another specific embodiment the invention provides a compound of formula (Ia) wherein at least r and both u are not zero.

In another specific embodiment the invention provides a compound of formula (Ia) wherein at least two of u, v, w and x are not zero and at least two of the non-zero groups are not the same letter.

In another specific embodiment the invention provides a compound of formula (Ia) wherein at least one of u and or w is not zero.

In another specific embodiment the invention provides a compound of formula (Ia) wherein at least two of u and or w are not zero.

In another specific embodiment the invention provides a compound of formula (Ia) wherein at least one u is not zero, and at least one w is not zero.

In another specific embodiment the invention provides a compound of formula (Ia) wherein at least two u are not zero.

In another specific embodiment the invention provides a compound of formula (Ia) wherein at least one w is not zero.

In another specific embodiment the invention provides a compound of formula (Ia) wherein at least two w are not zero.

In another specific embodiment the invention provides a compound of formula (Ia) wherein both u are not zero, and at least one w is not zero.

In another specific embodiment the invention provides a compound of formula (Ia) wherein both t are 9 and r is 2, 3, 4, 5, 6, 7, 8, 9, 10, 11, 12, 15, 16, 17, 18, 19, or 20.

In another specific embodiment the invention provides a compound of formula (Ia) wherein r is 1, 13, or 14; one t is 0, 1, 2, 3, 4, 5, 6, 7, 8, 9, 10, or 11; and the other t is 0, 1, 2, 3, 4, 5, 6, 7, 8, 10, or 11.

In another specific embodiment the invention provides a compound of formula (Ia) wherein one t is 0; the other t is 11; and r is 1, 2, 3, 4, 5, 6, 7, 8, 9, 10, 11, 12, 14, 15, 16, 17, 18, 19, or 20.

In another specific embodiment the invention provides a compound of formula (Ia) wherein r is 13; one t is 0; and the other t is 0, 1, 2, 3, 4, 5, 6, 7, 8, 9, or 10.

In another specific embodiment the invention provides a compound of formula (Ia) wherein r is 13; one t is 11; and the other t is 1, 2, 3, 4, 5, 6, 7, 8, 9, 10, or 11.

In another specific embodiment the invention provides a compound of formula (Ia) wherein both t are 11; and W is not a bond, or r is 2, 3, 4, 5, 6, 7, 8, 9, 10, 11, 12, 13, 14, 15, 16, 17, 18, 19, or 20.

In another specific embodiment the invention provides a compound of formula (Ia) wherein, when W is a bond or $W^1$ is absent, then one t is 0, 1, 2, 3, 4, 5, 6, 7, 8, 9, 10, or 11 and the other t is 0, 1, 2, 3, 4, 5, 6, 7, 8, 9, or 10.

In another specific embodiment the invention provides a compound of formula (Ia) wherein when W is $W^r$ and r is 6 or 8 then at least one t is not 0.

In another specific embodiment the invention provides a compound of formula (Ia) wherein when both t are 0, then r is 1, 2, 3, 4, 5, 7, 9, 10, 11, 12, 13, 14, 15, 16, 17, 18, 19, or 20.

In another specific embodiment the invention provides a compound of formula (Ia) wherein at least one of t, u, v, w or x are not zero.

In another specific embodiment the invention provides a compound of formula (Ia) wherein at least one of u, v, w or x are not zero.

In another specific embodiment the invention provides a compound of formula (Ia) wherein at least two of r, t, u, w or x are not zero.

In another specific embodiment the invention provides a compound of formula (Ia) wherein at least three of r, t, u, v, w or x are not zero.

In another specific embodiment the invention provides a compound of formula (Ia) wherein at least four of r, t, u, v, w or x are not zero.

In another specific embodiment the invention provides a compound of formula (Ia) wherein at least two of r, t, u, w or x are not zero and at least one t is selected from 0, 1, 2, 3, 4, 5, 6, 7, 8, 10, 11.

In another specific embodiment the invention provides a compound of formula (Ia) wherein at least two of r, t, u, w or x are not zero and at least two of the non-zero groups are not in the same letter.

In another specific embodiment the invention provides a compound of formula (Ia) wherein at least three of r, t, u, v, w or x are not zero and at least two of the non-zero groups are not in the same letter.

In another specific embodiment the invention provides a compound of formula (Ia) wherein at least three of r, t, u, v, w or x are not zero and at least three of the non-zero groups are not in the same letter.

In another specific embodiment the invention provides a compound of formula (Ia) wherein at least four of r, t, u, v, w or x are not zero and at least two of the non-zero groups are not in the same letter.

In another specific embodiment the invention provides a compound of formula (Ia) wherein the sum of t, u, v, w or x is not zero.

In another specific embodiment the invention provides a compound of formula (Ia) wherein the sum of r, u, v, w or x is not zero.

In another specific embodiment the invention provides a compound of formula (Ia) wherein r is 2, 3, 4, 5, 6, 7, 8, 9, 10, 11 and at least one t is not zero.

In another specific embodiment the invention provides a compound of formula (Ia) wherein at least one u is not zero.

In another specific embodiment the invention provides a compound of formula (Ia) wherein r, and at least one t, and at least one u are all not zero.

In another specific embodiment the invention provides a compound of formula (Ia) wherein at least two of u, w and t are not zero.

In another specific embodiment the invention provides a compound of formula (Ia) wherein at least two of r, u, and w are not zero.

In another specific embodiment the invention provides a compound of formula (Ia) wherein at least two of r, u, and w are not zero and at least two of the non-zero groups are not the same letter.

In another specific embodiment the invention provides a compound of formula (Ia) wherein at least r and both u are not zero.

In another specific embodiment the invention provides a compound of formula (Ia) wherein at least two of u, w or x are not zero and at least two of the non-zero groups are not the same letter.

In another specific embodiment the invention provides a compound of formula (Ia) wherein the sum of u, v, w and x is not zero.

In another specific embodiment the invention provides a compound of formula (Ia) wherein at least one of u, or w are not zero.

In another specific embodiment the invention provides a compound of formula (Ia) wherein at least two of u, or w are not zero.

In another specific embodiment the invention provides a compound of formula (Ia) wherein at least one u is not zero, and at least one w is not zero.

In another specific embodiment the invention provides a compound of formula (Ia) wherein both u are not zero, and at least one w is not zero.

In another specific embodiment the invention provides a compound of formula (Ia) wherein at least one u is not zero.

In another specific embodiment the invention provides a compound of formula (Ia) wherein both of u are not zero.

In another specific embodiment the invention provides a compound of formula (Ia) wherein at least one of w is not zero.

In another specific embodiment the invention provides a compound of formula (Ia) wherein both w are not zero.

In another specific embodiment the invention provides a compound of the following formula (Ia35): $E^x\text{-}V^w\text{-}Z^v\text{-}P^0\text{-}M^9\text{-}W^r\text{-}M^9\text{-}P^u\text{-}Z^v\text{-}V^w\text{-}E^x$ (Ia35) wherein r is 1, 13, or 14.

In another specific embodiment the invention provides a compound of formula (Ia) wherein for a compound of formula (Ia35) at least one of u, w or x are not zero.

In another specific embodiment of the invention for a compound of formula (Ia35) at least two of u, v, w or x are not zero.

In another specific embodiment of the invention for a compound of formula (Ia35) at least three of u, v, w or x are not zero.

In another specific embodiment of the invention for a compound of formula (Ia35) at least four of u, v, w or x are not zero.

In another specific embodiment of the invention for a compound of formula (Ia35) at least two u, v, w or x are not zero and at least two of the non-zero groups are not the same letter.

In another specific embodiment of the invention for a compound of formula (Ia35) at least three of u, v, w or x are not zero and at least two of the non-zero groups are not in the same letter.

In another specific embodiment of the invention for a compound of formula (Ia35) at least three of u, v, w or x are not zero and at least three of the non-zero groups are not in the same letter.

In another specific embodiment of the invention for a compound of formula (Ia35) at least four of u, v, w or x are not zero and at least two of the non-zero groups are not in the same letter.

In another specific embodiment of the invention for a compound of formula (Ia35) the sum of u, v, w and x is not zero.

In another specific embodiment of the invention for a compound of formula (Ia35) at least one of u, or w are not zero.

In another specific embodiment of the invention for a compound of formula (Ia35) at least two of u, or w are not zero.

In another specific embodiment of the invention for a compound of formula (Ia35) at least one u is not zero, and at least one w is not zero.

In another specific embodiment of the invention for a compound of formula (Ia35) both u are not zero, and at least one w is not zero.

In another specific embodiment of the invention for a compound of formula (Ia35) at least one u is not zero.

In another specific embodiment of the invention for a compound of formula (Ia35) both of u are not zero.

In another specific embodiment of the invention for a compound of formula (Ia35) at least one of w is not zero.

In another specific embodiment of the invention for a compound of formula (Ia35) both w are not zero.

In another specific embodiment the invention provides a compound of the following formula (Ia36): $W^x$-$V^w$-$Z^v$-$P^u$-$M^0$-$W^{13}$-$M^{11}$-$P^u$-$Z^v$-$V^w$-$E^x$ (Ia36).

In another specific embodiment of the invention for a compound of formula (Ia36) at least one of u, w or x are not zero.

In another specific embodiment of the invention for a compound of formula (Ia36) at least two of u, v, w or x are not zero.

In another specific embodiment of the invention for a compound of formula (Ia36) at least three of u, v, w or x are not zero.

In another specific embodiment of the invention for a compound of formula (Ia36) at least four of u, v, w or x are not zero.

In another specific embodiment of the invention for a compound of formula (Ia36) at least two u, v, w or x are not zero and at least two of the non-zero groups are not the same letter.

In another specific embodiment of the invention for a compound of formula (Ia36) at least three of u, v, w or x are not zero and at least two of the non-zero groups are not in the same letter.

In another specific embodiment of the invention for a compound of formula (Ia36) at least three of u, v, w or x are not zero and at least three of the non-zero groups are not in the same letter.

In another specific embodiment of the invention for a compound of formula (Ia36) at least four of u, v, w or x are not zero and at least two of the non-zero groups are not in the same letter.

In another specific embodiment of the invention for a compound of formula (Ia36) the sum of u, v, w and x is not zero.

In another specific embodiment of the invention for a compound of formula (Ia36) at least one of u or w are not zero.

In another specific embodiment of the invention for a compound of formula (Ia36) at least two of u or w are not zero.

In another specific embodiment of the invention for a compound of formula (Ia36) at least one u is not zero, and at least one w is not zero.

In another specific embodiment of the invention for a compound of formula (Ia36) both u are not zero, and at least one w is not zero.

In another specific embodiment of the invention for a compound of formula (Ia36) at least one u is not zero.

In another specific embodiment of the invention for a compound of formula (Ia36) both of u are not zero.

In another specific embodiment of the invention for a compound of formula (Ia36) at least one of w is not zero.

In another specific embodiment of the invention for a compound of formula (Ia36) both w are not zero.

In another specific embodiment the invention provides a compound of the following formula (Ia37): $E^x$-$V^w$-$Z^v$-$P^u$-$M^{11}$-$M^{11}$-$P^u$-$Z^v$-$V^w$-$E^x$ (Ia37).

In another specific embodiment of the invention for a compound of formula (Ia37) at least one of u, w or x are not zero.

In another specific embodiment of the invention for a compound of formula (Ia37) at least two of u, v, w or x are not zero.

In another specific embodiment of the invention for a compound of formula (Ia37) at least three of u, v, w or x are not zero.

In another specific embodiment of the invention for a compound of formula (Ia37) at least four of u, v, w or x are not zero.

In another specific embodiment of the invention for a compound of formula (Ia37) at least two u, v, w or x are not zero and at least two of the non-zero groups are not the same letter.

In another specific embodiment of the invention for a compound of formula (Ia37) at least three of u, v, w or x are not zero and at least two of the non-zero groups are not in the same letter.

In another specific embodiment of the invention for a compound of formula (Ia37) at least three of u, v, w or x are not zero and at least three of the non-zero groups are not in the same letter.

In another specific embodiment of the invention for a compound of formula (Ia37) at least four of u, v, w or x are not zero and at least two of the non-zero groups are not in the same letter.

In another specific embodiment of the invention for a compound of formula (Ia37) the sum of u, v, w and x is not zero.

In another specific embodiment of the invention for a compound of formula (Ia37) at least one of u, or w are not zero.

In another specific embodiment of the invention for a compound of formula (Ia37) at least two of u, or w are not zero.

In another specific embodiment of the invention for a compound of formula (Ia37) at least one u is not zero, and at least one w is not zero.

In another specific embodiment of the invention for a compound of formula (Ia37) both u are not zero, and at least one w is not zero.

In another specific embodiment of the invention for a compound of formula (Ia37) at least one u is not zero.

In another specific embodiment of the invention for a compound of formula (Ia37) both of u are not zero.

In another specific embodiment of the invention for a compound of formula (Ia37) at least one of w is not zero.

In another specific embodiment of the invention for a compound of formula (Ia37) both w are not zero.

In another specific embodiment the invention provides a compound of the following formula (Ia38): $E^x$-$V^w$-$Z^v$-$P^u$-$Z^v$-$V^w$-$E^x$ (Ia38) wherein r is 6 or 8.

In another specific embodiment of the invention for a compound of formula (Ia38) at least one of u, w or x are not zero.

In another specific embodiment of the invention for a compound of formula (Ia38) at least two of u, v, w or x are not zero.

In another specific embodiment of the invention for a compound of formula (Ia38) at least three of u, v, w or x are not zero.

In another specific embodiment of the invention for a compound of formula (Ia38) at least four of u, v, w or x are not zero.

In another specific embodiment of the invention for a compound of formula (Ia38) at least two u, v, w or x are not zero and at least two of the non-zero groups are not the same letter.

In another specific embodiment of the invention for a compound of formula (Ia38) at least three of u, v, w or x are not zero and at least two of the non-zero groups are not in the same letter.

In another specific embodiment of the invention for a compound of formula (Ia38) at least three of u, v, w or x are not zero and at least three of the non-zero groups are not in the same letter.

In another specific embodiment of the invention for a compound of formula (Ia38) at least four of u, v, w or x are not zero and at least two of the non-zero groups are not in the same letter.

In another specific embodiment of the invention for a compound of formula (Ia38) the sum of u, v, w and x is not zero.

In another specific embodiment of the invention for a compound of formula (Ia38) at least one of u, or w are not zero.

In another specific embodiment of the invention for a compound of formula (Ia38) at least two of u or w are not zero.

In another specific embodiment of the invention for a compound of formula (Ia38) at least one u is not zero, and at least one w is not zero.

In another specific embodiment of the invention for a compound of formula (Ia38) both u are not zero, and at least one w is not zero.

In another specific embodiment of the invention for a compound of formula (Ia38) at least one u is not zero.

In another specific embodiment of the invention for a compound of formula (Ia38) both of u are not zero.

In another specific embodiment of the invention for a compound of formula (Ia38) at least one of w is not zero.

In another specific embodiment of the invention for a compound of formula (Ia38) both w are not zero.

Compounds of Formula (Ib)

In one embodiment of the invention, the compound of formula (I) is a compound of formula (Ib):

$$E-V-Z-P-M-A-L-P-Z-V-E \quad (Ib)$$

wherein:
L is -$L^n$;
each A is selected from -$A^s$;
each M is selected from -$M^t$;
each P is selected from —$P^a$;
each Z is selected from -$Z^v$;
each V is selected from -$V^w$;
each E is selected from -$E^x$;
each n is 0, 1, 2, 3, 4, 5, 6, 7, 9, or 10;
each s is 0, 1, 2, 3, 4, 5, 6, 7, 8, 9, 10, 11, 12, 13, 14, 15, 16, 17, 18 or 21;
each t is 0, 1, 2, 3, 4, 5, 6, 7, 8, 9, 10, or 11;
each u is 0, 1, 2, 3, 4, 5, 6, 7, 8, 10, 11, 12, 13, or 14;
each v is 0, 1, 2, 3, 4, 5, or 6;
each w is 0, 1, 2, 3, 4, 5, 6, 7, 8, 9, 10, 11, 12, 13, 14, 15, 16, 17, 18, 19, 20 or 21;
each x is 0 or 1;
wherein the sum of n, s, t, u, v, w, and x is not 0;
each $L^0$ is independently:

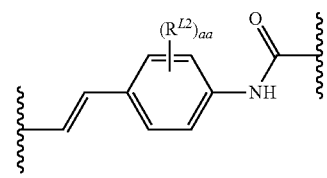

wherein:
each $R^{L2}$ is independently selected from hydrogen, alkenyl, alkoxy, alkyl, halo, and haloalkyl; and
each aa is independently 1, 2, 3, or 4;
each $L^1$ is independently:

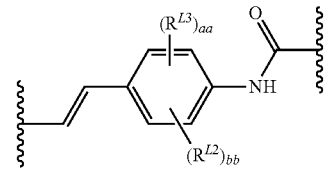

wherein:
each $R^{L2}$ is independently selected from hydrogen, alkenyl, alkoxy, alkyl, halo, and haloalkyl;
each $R^{L3}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each bb is 0, 1, 2, 3, or 4; each aa is 1, 2, 3, or 4; and the sum of bb and aa is 1, 2, 3, or 4;
each $L^2$ is independently:

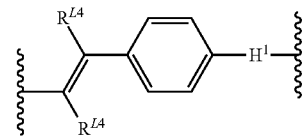

wherein:
the phenyl ring shown in $L^2$ is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{L4}$ is independently —H, alkyl, aryl, arylalkyl, or heterocycle;

each $R^4$ is independently selected from H, alkyl, haloalkyl, aryl, and arylalkyl;

$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each $H^1$ is a 5 membered saturated, partially unsaturated, or aromatic ring comprising one or more heteroatoms;

each $L^3$ is independently a fused-bicyclic saturated, partially unsaturated, or aromatic heterocyclic ring system that is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^4$ is independently selected from H, alkyl, haloalkyl, aryl, and arylalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^4$ is independently a fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^4$ is independently selected from H, alkyl, haloalkyl, aryl, and arylalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^5$ is independently a —CR=CR-fused bicyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^4$ is independently selected from H, alkyl, haloalkyl, aryl, and arylalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^6$ is independently a —CR=CR-fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^4$ is independently selected from H, alkyl, haloalkyl, aryl, and arylalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^7$ is independently:

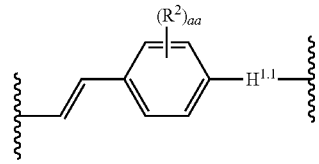

wherein:
each $H^{1.1}$ is independently a fused-bicyclic saturated, partially unsaturated, or aromatic heterocyclic ring system that is optionally substituted with one or more $R^2$;

each $R^2$ is independently selected from halo, —$R^{L7}$, —$OR^{L7}$, —$SR^{L7}$, —$N(R^{L7})_2$, —$CF_3$, —$CCl_3$, —$OCF_3$, —CN, —$NO_2$, —$N(R^{L7})C(=O)R^{L7}$, —$C(=O)R^{L7}$, —$OC(=O)R^{L7}$, —$C(O)OR^{L7}$, —$C(=O)NR^{L7}$, —$S(=O)R^{L7}$, —$S(=O)_2OR^{L7}$, —$S(=O)_2R^{L7}$, —$OS(=O)_2OR^{L7}$, and —$S(=O)_2NR^{L7}$;

each $R^{L7}$ is independently —H, alkyl, aryl, arylalkyl, or heterocycle; and each aa is independently 1, 2, 3, or 4;

each $L^9$ is independently a fused-tetracyclic saturated, partially unsaturated, or aromatic heterocyclic ring system that is optionally substituted with one or more groups independently selected from oxo, halo, —$R^{L7}$, —$OR^{L7}$, —$SR^{L7}$, —$CF_3$, —$CCl_3$, —$OCF_3$, —CN, —$NO_2$, —$N(R^{L7})C(=O)R^{L7}$, —$C(=O)R^{L7}$, —$OC(=O)R^{L7}$, —$C(O)OR^{L7}$, —$C(=O)NR^{L7}$, —$S(=O)R^{L7}$, —$S(=O)_2OR^{L7}$, —$S(=O)_2R^{L7}$, $OS(=O)_2OR^{L7}$, —$S(=O)_2NR^{L7}$, alkoxyalkyl, arylalkoxycarbonyl, halo, haloalkyl, hydroxyalkyl, —$NR^aR^b$, ($NR^aR^b$)alkyl, and ($NR^aR^b$)carbonyl;

each $R^{L7}$ is independently —H, alkyl, aryl, arylalkyl, or heterocycle;

$R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $L^{10}$ is independently a fused-pentacyclic saturated, partially unsaturated, or aromatic heterocyclic ring system that is optionally substituted with one or more groups independently selected from oxo, halo, —$R^{L7}$, —$OR^{L7}$, —$SR^{L7}$, —$CF_3$, —$CCl_3$, —$OCF_3$, —CN, —$NO_2$, —$N(R^{L7})C(=O)R^{L7}$, —$C(=O)R^{L7}$, —$OC^{L7}$, —$C(O)OR^{L7}$, —$C(=O)NR^{L7}$, —S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^{11}$ is independently a six-ring fused saturated, partially unsaturated, or aromatic heterocyclic ring system that is optionally substituted with one or more groups independently selected from oxo, halo, —R$^{L7}$, —OR$^{L7}$, —SR$^{L7}$, —CF$_3$, —CCl$_3$, —OCF$_3$, —CN, —NO$_2$, —N(R$^{L7}$)C(=O)R$^{L7}$, —C(=O)R$^{L7}$, —OC(=O)R$^{L7}$, —C(=O)NR$^{L7}$—S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each A$^0$ is independently:

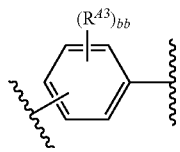

wherein:
each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each A$^0$ is independently a six-membered heteroaromatic ring containing one, two, or three nitrogen atoms, which ring is optionally substituted with 1, 2, 3, or 4 R$^{43}$ groups;

each A$^1$ is independently:

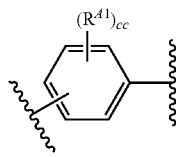

wherein:
each R$^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each R$^4$ is independently selected from H, alkyl, haloalkyl, aryl, and arylalkyl;

each cc is independently 1, 2, 3, or 4 each A$^2$ is independently:

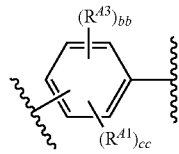

wherein:
each R$^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R$^4$ is independently selected from H, alkyl, haloalkyl, aryl, and arylalkyl;

R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each A$^3$ is independently a six-membered heteroaromatic ring containing one, two, or three nitrogen atoms, which ring is substituted with one or more R$^{41}$ groups, and which ring is optionally substituted with one or more R$^{43}$ groups;

each A$^4$ is independently:

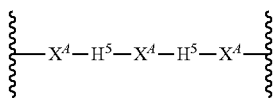

wherein:
each H$^5$ is independently a phenyl ring or a six-membered heteroaromatic ring, which H$^5$ is optionally substituted with one or more groups independently selected from R$^{41}$ and R$^{43}$; and each X$^4$ is independently O, NR, SO, SO$_2$, C(=O), NRC(=O), C(=O)NR, CR=CR, NRC(=O)NR, allenyl, alkynyl, or absent and each R is independently selected from H or alkyl;

each A$^5$ is independently:

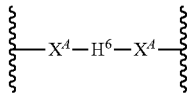

wherein:
each $H^6$ is independently a phenyl ring or a six-membered heteroaromatic ring, which $H^6$ is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent; provided that at least one $X^A$ is present and each R is independently selected from H or alkyl;
each $A^6$ is independently:

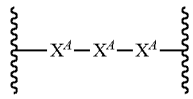

wherein:
each $X^A$ is independently O, NR, SO, $SO_2$, C(=O), NRC(=O), C(=O)NR, CR=CR, allenyl, alkynyl, or absent; provided that at least one $X^A$ is present and each R is independently selected from H or alkyl;
each $A^7$ is independently:

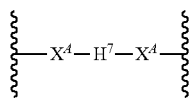

wherein:
each $H^7$ is independently a five-membered heteroaromatic ring, which $H^7$ is optionally substituted with one or more groups independently selected from $R^{41}$ and $R^{43}$; and
each $X^A$ is independently O, NR, SO, $SO_2$, NRC(=O), C(=O)NR, CR=CR, NRC(=O)NR, allenyl, alkynyl, or absent and each R is independently selected from H or alkyl;
each $A^8$ is independently:

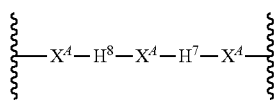

wherein:
each $H^7$ is independently a five-membered heteroaromatic ring, which $H^7$ is optionally substituted with one or more groups independently selected from $R^{41}$ and $R^{43}$;
each $H^8$ is independently a phenyl ring, which is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^9$ is independently:

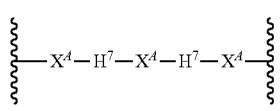

wherein:
each $H^7$ is independently a five-membered heteroaromatic ring, which $H^7$ is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{10}$ is independently:

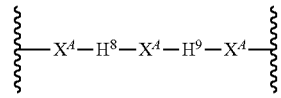

wherein:
each $H^8$ is independently a phenyl ring, which is optionally substituted with one or more groups independently selected from $R^{41}$ and $R^{43}$;
each $H^9$ is independently a six-membered heteroaromatic ring, which is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{11}$ is independently:

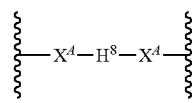

wherein:
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $H^{10}$ is independently a 5-15 carbon unsaturated, partially unsaturated or saturated bicyclic ring system that is optionally fused to an aryl, which $H^{10}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each $R^4$ is independently selected from H, alkyl, haloalkyl, aryl, and arylalkyl
each $A^{12}$ is independently:

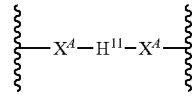

wherein:
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each H$^{11}$ is independently a 5-15 carbon unsaturated, partially unsaturated or saturated bicyclic ring system that contains one or more heteroatoms that is optionally fused to an aryl, which H$^{11}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and each R$^4$ is independently selected from H, alkyl, haloalkyl, aryl, and arylalkyl; and each A$^{13}$ is independently:

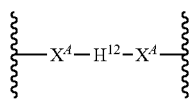

wherein:
each H$^{12}$ is independently a fused aromatic bicyclic carbocycle, which is optionally substituted with one or more groups independently selected from R$^1$ and R$^3$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{14}$ is independently:

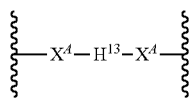

wherein:
each H$^{13}$ is independently a fused aromatic bicyclic heterocycle that comprises at least one heteroatom in the ring system, which ring system is optionally substituted with one or more groups independently selected from R$^{A1}$ and R$^{A3}$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{15}$ is independently:

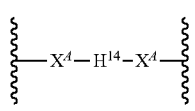

wherein:
each H$^{14}$ is independently a fused unsaturated, partially unsaturated or saturated tricyclic carbocycle which is optionally substituted with one or more groups independently selected from R$^{A1}$ and R$^{A3}$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{16}$ is independently:

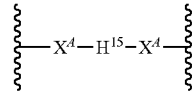

wherein:
each H$^{15}$ is independently a fused unsaturated, partially unsaturated or saturated tricyclic heterocycle that comprises at least one heteroatom in the ring system, which ring system is optionally substituted with one or more groups independently selected from R$^{A1}$ and R$^{A3}$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{17}$ is independently:

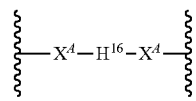

wherein:
each H$^{16}$ is independently a fused bicyclic carbocyclic ring system wherein one ring is aromatic and another ring is partially or fully saturated, which ring system is optionally substituted with one or more groups independently selected from oxo, R$^{A1}$ and R$^{A3}$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{18}$ is independently:

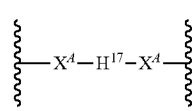

wherein:
each H$^{17}$ is independently a fused bicyclic ring system comprising at least one heteroatom, wherein one ring is aromatic and another ring is partially or fully saturated, which ring system is optionally substituted with one or more groups independently selected from oxo, R$^{A1}$ and R$^{A3}$; and each X$^A$ is independently O, NR, SO, SO$_2$, C(═O), NRC(═O), C(═O)NR, CR═CR, NRC(═O)NR, allenyl, alkynyl, or absent and each R is independently selected from H or alkyl;

each A$^{21}$ is independently:

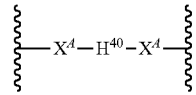

wherein:
each H$^{40}$ is independently an anti-aromatic monocyclic or fused carbocyclic ring system, which carbocyclic ring system is optionally substituted with one or more groups independently selected from $R^{A1}$ and $R^{A3}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $M^0$ is independently a five membered heteroaryl group optionally substituted with one or more alkoxycarbonyl, alkyl, arylalkoxycarbonyl, carboxy, haloalkyl, $(NR^aR^b)$carbonyl and trialkylsilylalkoxyalkyl;

each $M^1$ is independently selected from —C(=O)NH—, —C(=O)NH—C(R$^M$)$_2$—, —NHC(=O)—, —C(R$^M$)$_2$NHC(=O)—, —NHC(=O)NR$^M$—, —NHC(=O)O—; wherein each $R^M$ is independently selected from H and alkyl;

each $M^2$ is independently a six-membered heteroaromatic ring, which is optionally substituted with one or more groups independently selected from $R^{A1}$ and $R^{A3}$;

each $M^3$ is independently:

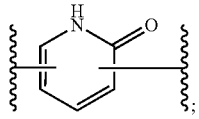

each $M^4$ is independently:

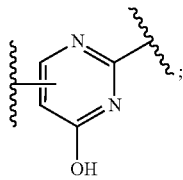

each $M^5$ is independently:

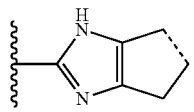

wherein the bond designated with - - - is fused to a ring defined for P;

each $M^6$ is independently a bicyclic bridged ring system comprising 5-15 atoms wherein at least one of the atoms is a heteroatom;

each $M^7$ is independently a pyrid-di-yl;

each $M^8$ is independently partially saturated or a saturated five-membered ring that comprises one or more heteroatoms and that is optionally substituted with one or two oxo;

each $M^9$ is independently a fused-bicyclic saturated, partially unsaturated, or aromatic heterocyclic ring system that is optionally substituted with one or more $R^{P11}$;

each $M^{10}$ is independently a five membered heteroaryl group;

each $M^{11}$ is independently a fused-tricyclic saturated, partially unsaturated, or aromatic heterocyclic ring system that is optionally substituted with one or more oxo halo, —$R^{M7}$, —$OR^{M7}$, —$SR^{M7}$, —$N(R^{M7})_2$, —$CF_3$, —$CCl_3$, —$OCF_3$, —CN, —$NO_2$, —$N(R^{M7})C(=O)R^{M7}$, —C(=O)$R^{M7}$, —OC(=O)$R^{M7}$, —C(O)O$R^{M7}$, —C(=O)NR$^{M7}$, —S(=O)$R^{M7}$, —S(=O)$_2$O$R^{M7}$, —S(=O)$_2$R$^{M7}$, —OS(=O)$_2$OR$^{M7}$, or —S(=O)$_2$NR$^{M7}$;

each $R^{M7}$ is independently —H, alkyl, aryl, arylalkyl, or heterocycle;

each $P^0$ is independently:

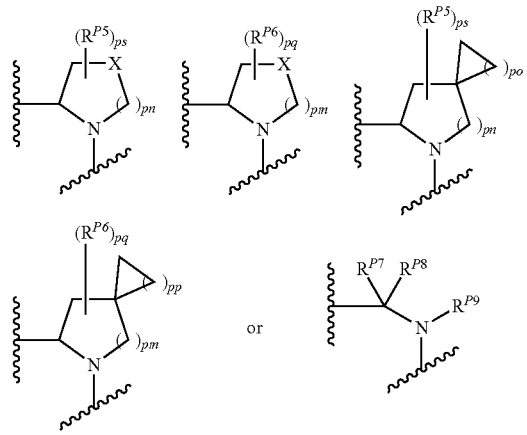

wherein:
X is selected from O, S, S(O), $SO_2$, $CH_2$, CHR$^{P10}$, and C(R$^{P10}$)$_2$; provided that when pn or pm is 0, X is selected from $CH_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

$R^{P9}$ is selected from hydrogen and alkyl;

each $P^1$ is independently:

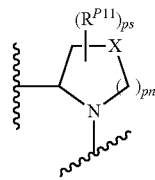

wherein:
X is selected from O, S, S(O), $SO_2$, $CH_2$, CHR$^{P10}$, and C(R$^{P10}$)$_2$; provided that when pn is 0, X is selected from $CH_2$, CHR$^{P10}$, and C(R$^{P10}$)$_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

at least one $R^{P10}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;

each $P^2$ is independently:

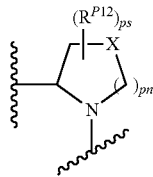

wherein:
each $R^{P12}$ is independently selected from $R^{P5}$, $R^{P11}$, —$C(=O)OR^h$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;

each $P^3$ is independently a ring of the formula:

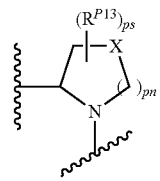

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;

each $P^4$ is independently a ring of the formula:

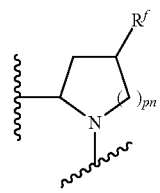

wherein:
the ring is optionally substituted with one or more groups $R^{P14}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P14}$ that are attached to the same carbon when taken together with the carbon to which they are attached can form a 3-6 membered carbocyclic or heterocyclic ring;

pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^5$ is independently a ring of the formula:

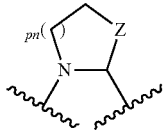

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2$$R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

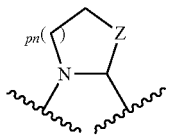

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2$$R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

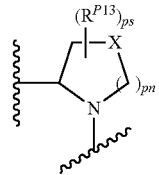

wherein:
ps is 2, 3, 4, 5, or 6;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

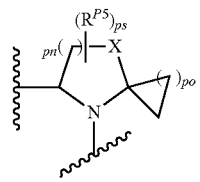 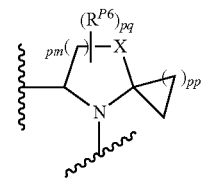

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;

po and pp are independently 1, 2, or 3;
each P¹¹ is independently:

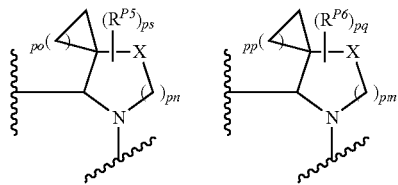

wherein:
X is selected from O, S, S(O), SO₂, CH₂, CHR$^{P10}$, and C(R$^{P10}$)₂; provided that when pn or pm is 0, X is selected from CH₂, CHR$^{P10}$, and C(R$^{P10}$)₂;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each P¹² is independently:

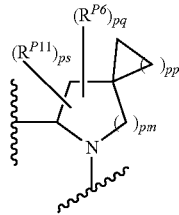

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)₂R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl;
wherein each R$^h$ is independently —H, alkyl, alkoxyamino, aryl, arylalkyl, heterocycle, heterocyclyoxy, alkenyl, alkenyloxy; alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
each P¹³ is independently:

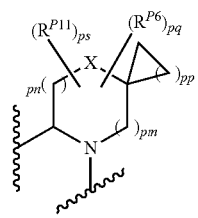

wherein:
X is selected from O, S, S(O), SO₂, or NR$^h$;
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm and pn are independently 0, 1, or 2 but the sum of pn and pm is greater than zero;
pp are independently 1, 2, or 3;
ps is 1, 2, 3, or 4;
each R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)₂R$^h$, —C(=O)R$^h$, —C(=O)NR$^h$R$^h$, R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
each P$^{14}$ is independently:

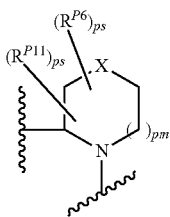

wherein:
the ring is substituted with one or more oxo group;
X is NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two R$^h$ groups are present then they may come together with the atoms to which they are bound to form a 4-15 membered heterocyclic ring;
each —Z$^0$— is —C(=O)— or —C(=S)—;

each —Z$^1$— is independently a bond, or —C(R$^{Z1}$)$_2$—; wherein each R$^{Z1}$ is independently H, alkyl, haloalkyl, or halo;
each —Z$^2$— is independently saturated or partially unsaturated (C$_3$-C$_8$)cycloalkyl that is optionally substituted with one or more groups independently selected from R$^{A1}$ and R$^{A3}$;
each —Z$^3$— is independently saturated, partially unsaturated, or aromatic 4-8 membered heterocyclic or heteroaryl ring that is optionally substituted with one or more groups independently selected from R$^{A1}$ and R$^{A3}$;
each —Z$^4$— is independently:

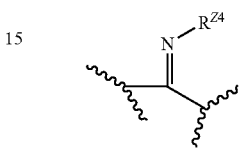

wherein each R$^{Z4}$ is independently H, alkyl, cyano, aryl, or heteroaryl;
each —Z$^5$— is independently:

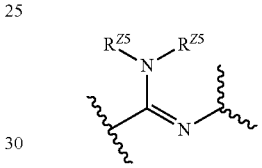

wherein each R$^{Z5}$ is independently H, alkyl, cyano, aryl, or heteroaryl; or two R$^{Z5}$s together with the nitrogen to which they are attached form a 4-8 membered heterocyclic ring that is optionally substituted with one or more oxo and with one or more groups independently selected from R$^{A1}$ and R$^{A3}$;
each —Z$^6$— is independently —C(R$^{Z1}$)— and is double-bonded to P; wherein R$^{Z1}$ is independently H, alkyl, haloalkyl, or halo;
each E$^0$ is independently —NR$^{Ec}$R$^{Ed}$ wherein
R$^E$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;
each E$^1$ is independently —OC(=O)NR$^{Ee}$R$^{Ef}$ wherein each R$^{Ee}$ and R$^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein $R^{Ee}$ and $R^{Ef}$, together with the nitrogen atom to which they are attached, form a heterocycle;

each $V^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —P(O)$OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $V^1$ is independently cyanoalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and NRaRbC(=O)O—; Ra and Rb are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^6$ is independently arylsulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^8$ is independently spirocycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^{10}$ is independently fused bicicliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^{11}$ is independently fused bicicliccycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^{12}$ is independently bridged-bicicliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^{13}$ is independently bridged-bicyclic-cycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{14}$ is independently aryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{18}$ is independently heterocyclooxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

each $V^{20}$ is independently heteroaryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl; and each $V^{21}$ is independently heteroarylalkylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O$—; $R^{Va}$ and $R^{Vb}$ are each independently selected from hydrogen, alkenyl, and alkyl;

or a pharmaceutically acceptable salt, or prodrug thereof.

In another specific embodiment of the invention L is $L^3$.

In another specific embodiment of the invention L is benzimidazolyl.

In another specific embodiment of the invention -A-L- is selected from:

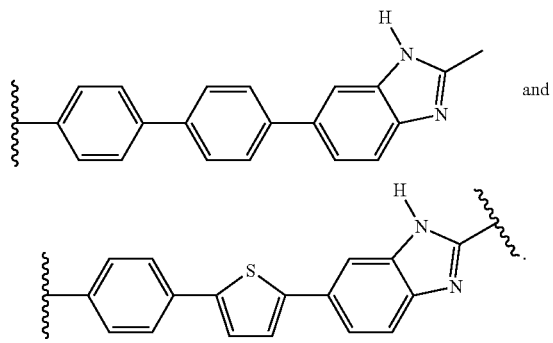

In another specific embodiment of the invention -M-A-L- is selected from:

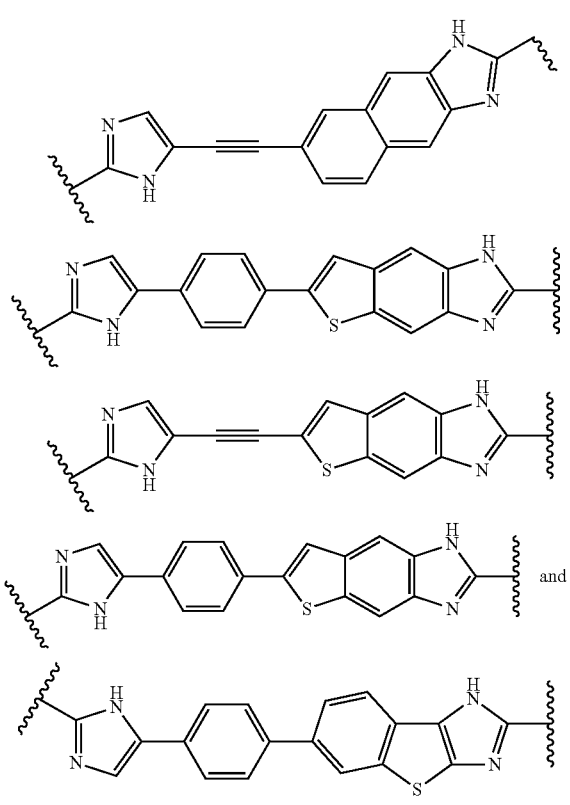

optionally substituted with one or more groups independently selected from $R^{P6}$ and $R^{P11}$.

In another specific embodiment of the invention the compound of formula (Ib) is a compound of formula (Ib1): $E^0$-$V^0$-$Z^0$-P-M-$A^{15}$-L-P-$Z^0$-$V^0$-$E^0$ (Ib1).

In another specific embodiment of the invention the compound of formula (Ib) is a compound of formula (Ib2): $E^0$-$V^0$-$Z^0$-P-M-$A^{15}$-$L^3$-P-$Z^0$-$V^0$-$E^0$ (Ib2).

In another specific embodiment of the invention the compound of formula (Ib) is a compound of formula (Ib3): $E^0$-$V^0$-$Z^0$-P-$M^0$-$A^{15}$-$L^3$-P-$Z^0$-$V^0$-$E^0$ (Ib3).

In another specific embodiment of the invention the compound of formula (Ib) is a compound of formula (Ib4): $E^0$-$V^0$-$Z^0$-P-M-$A^{16}$-L-P-$Z^0$-$V^0$-$E^0$ (Ib4).

In another specific embodiment of the invention the compound of formula (Ib) is a compound of formula (Ib5): $E^0$-$V^0$-$Z^0$-P-M-$A^{16}$-$L^3$-P-$Z^0$-$V^0$-$E^0$ (Ib5).

In another specific embodiment of the invention the compound of formula (Ib) is a compound of formula (Ib6): $E^0$-$V^0$-$Z^0$-P-$M^0$-$A^{16}$-$L^3$-P-$Z^0$-$V^0$-$E^0$ (Ib6).

In another specific embodiment of the invention the compound of formula (Ib) is a compound of formula (Ib7): $E^0$-$V^0$-$Z^0$-P-$M^9$-$A^{16}$-$L^3$-P-$Z^0$-$V^0$-$E^0$ (Ib7).

In another specific embodiment of the invention the compound of formula (Ib) is:

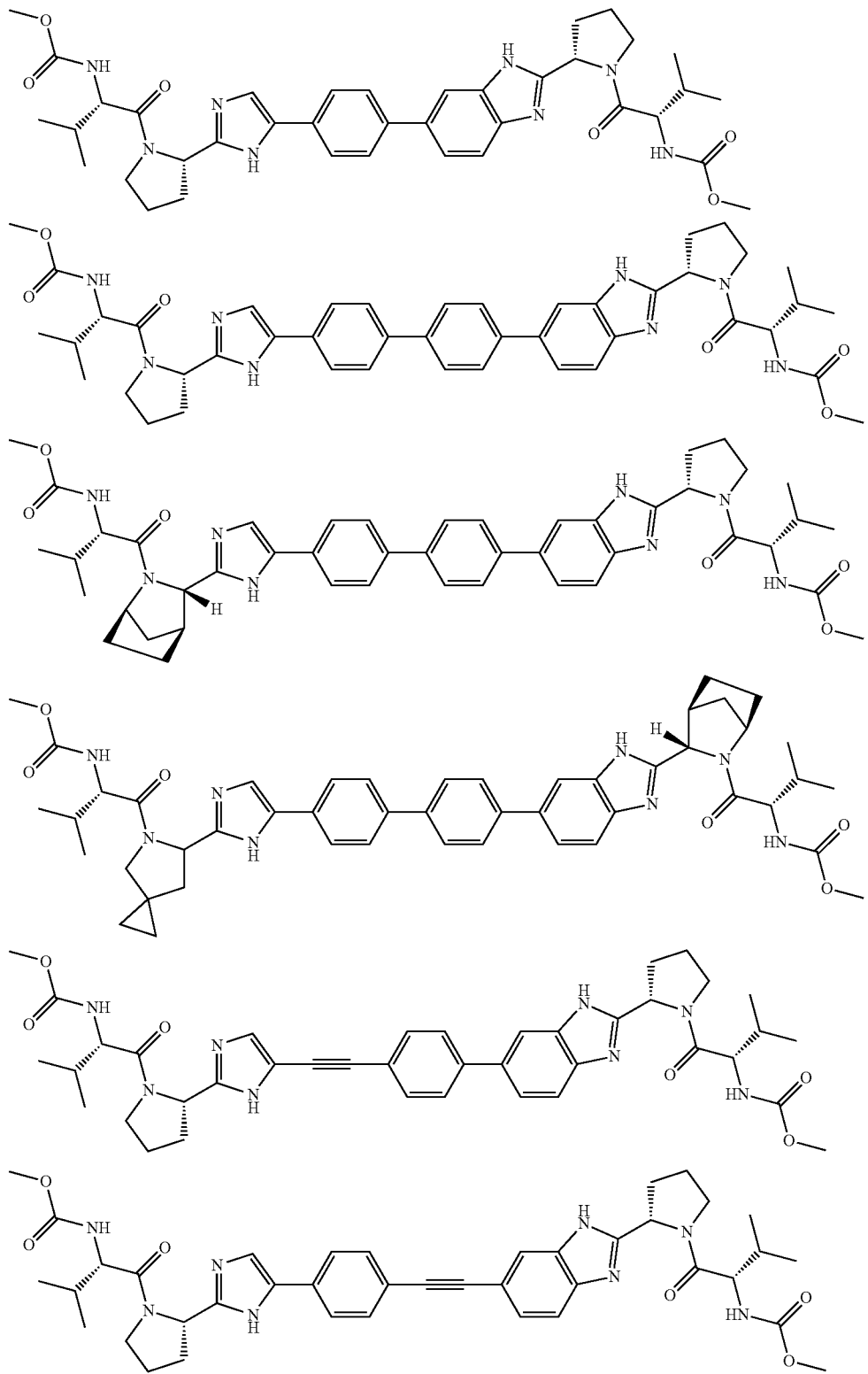

-continued
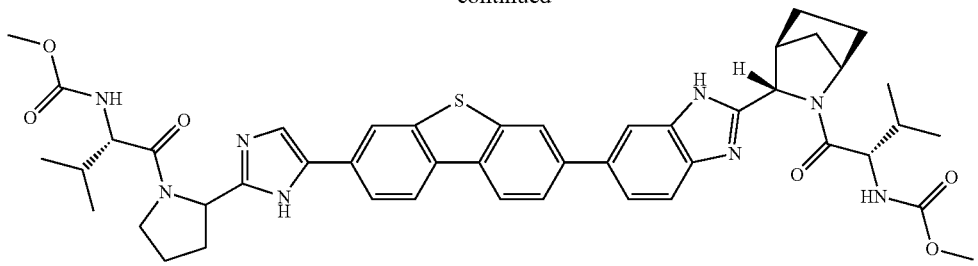
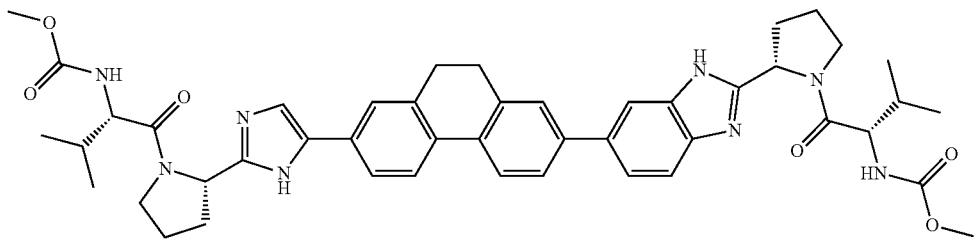
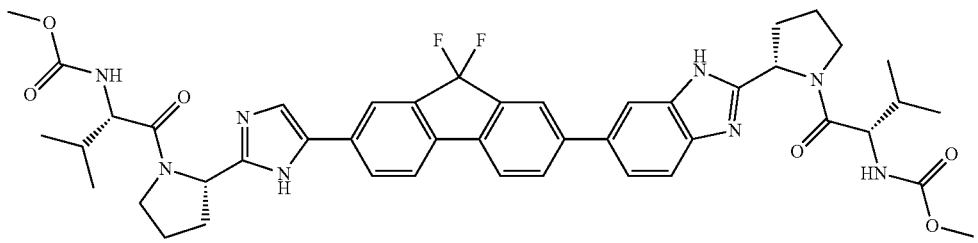
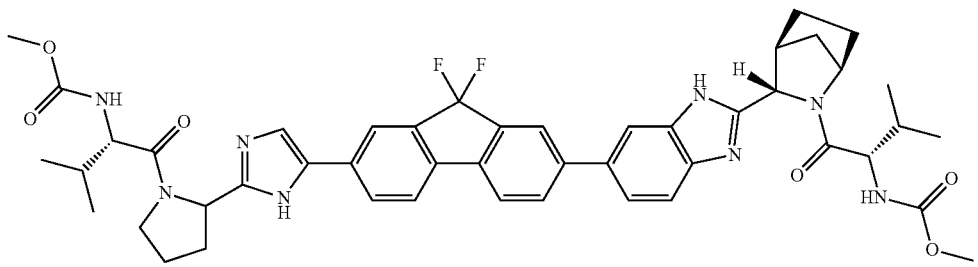
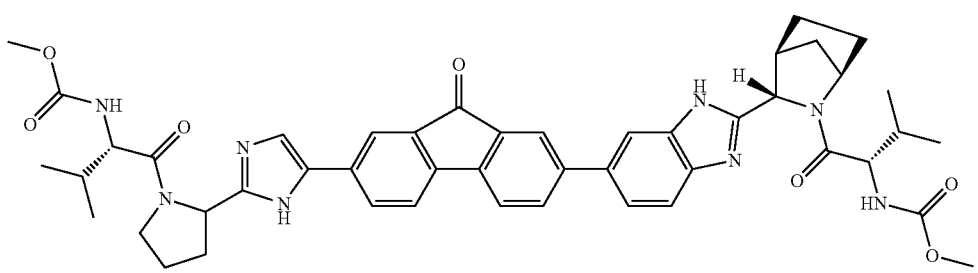
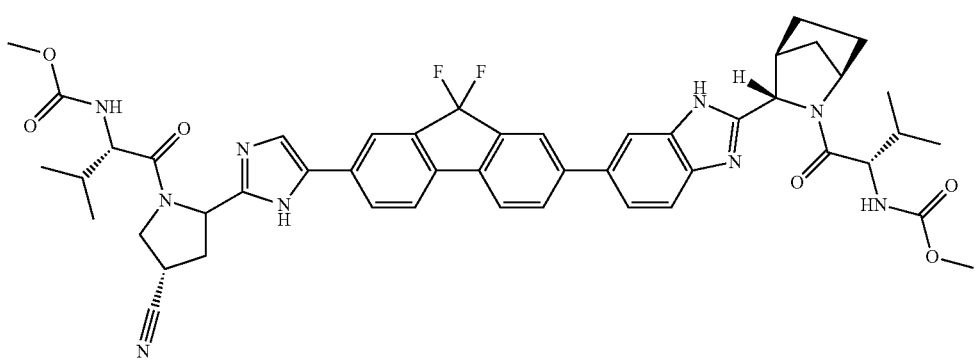

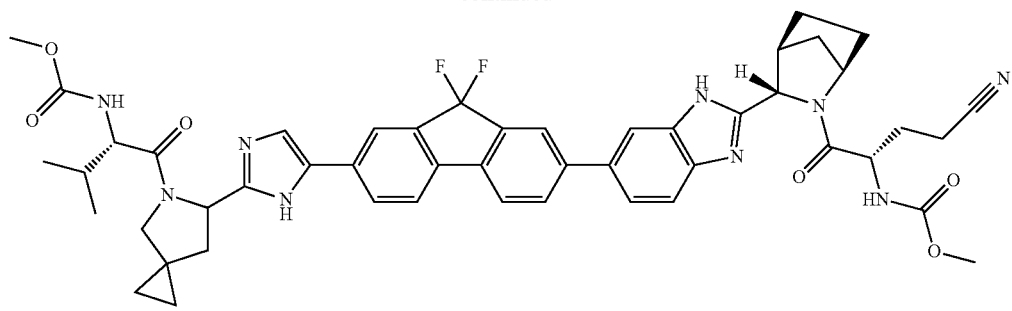
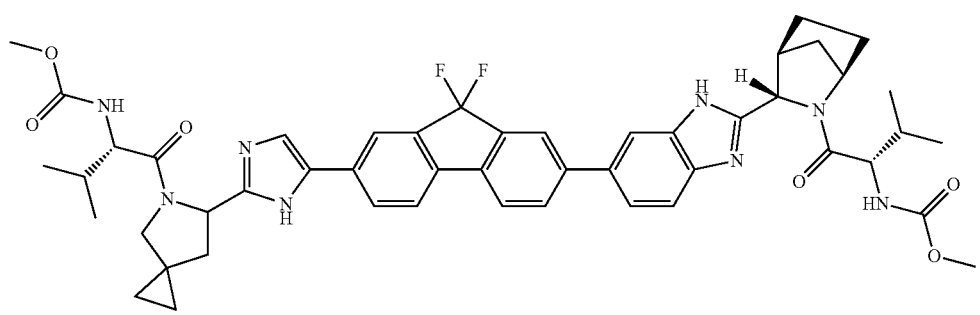
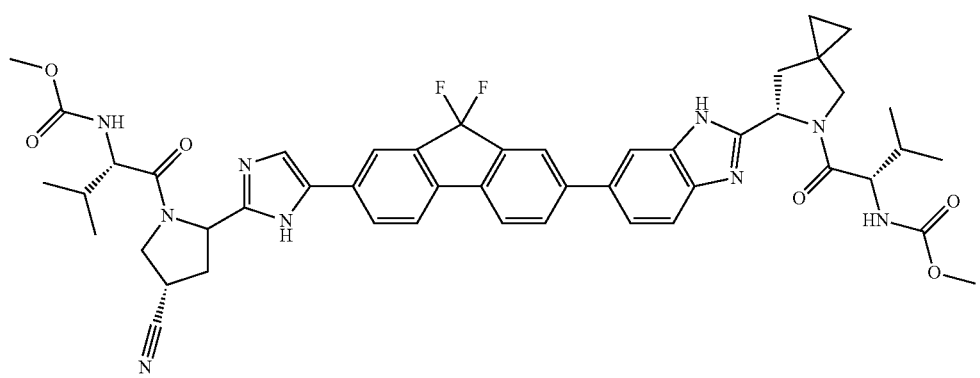
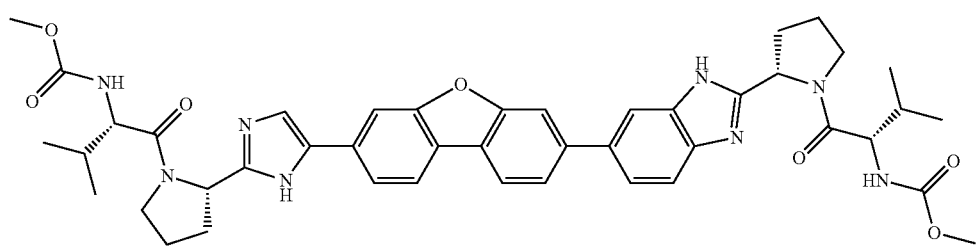
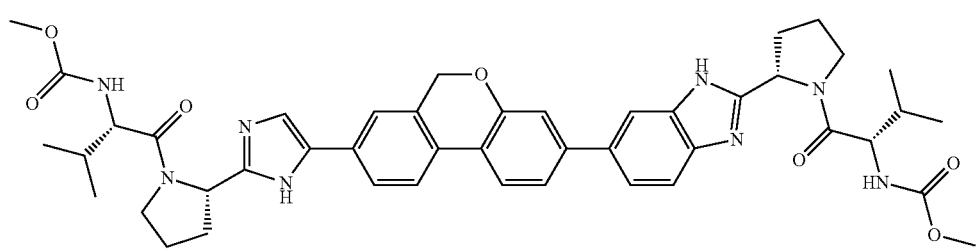

-continued

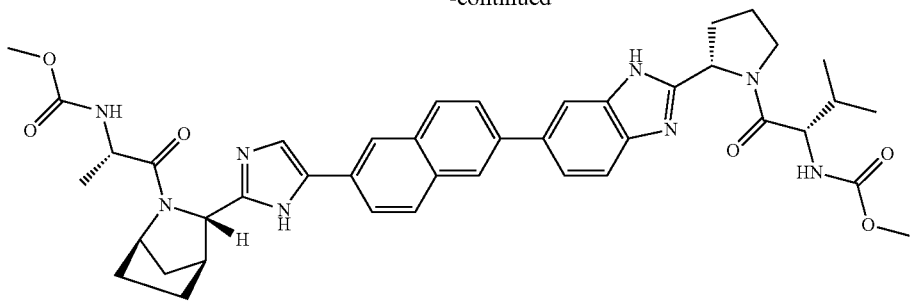

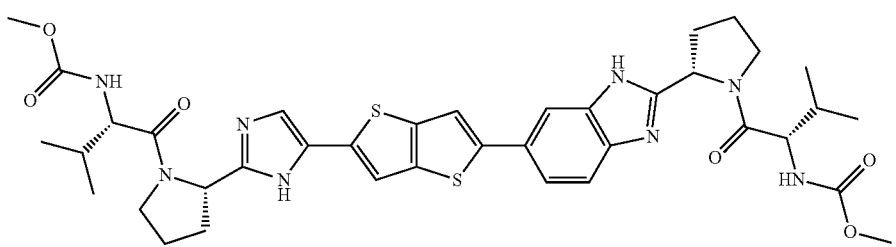

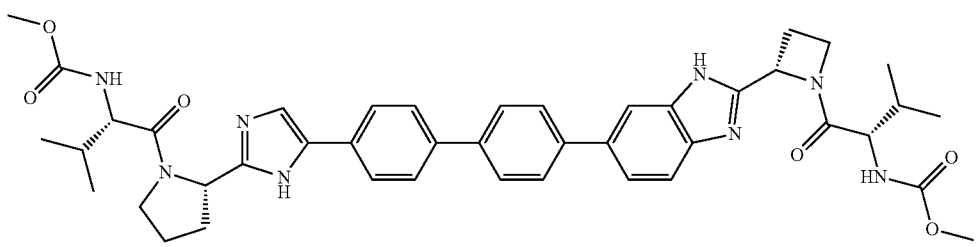

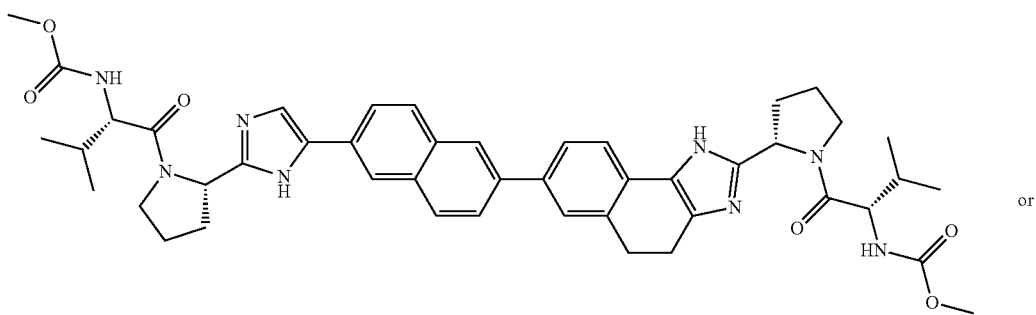

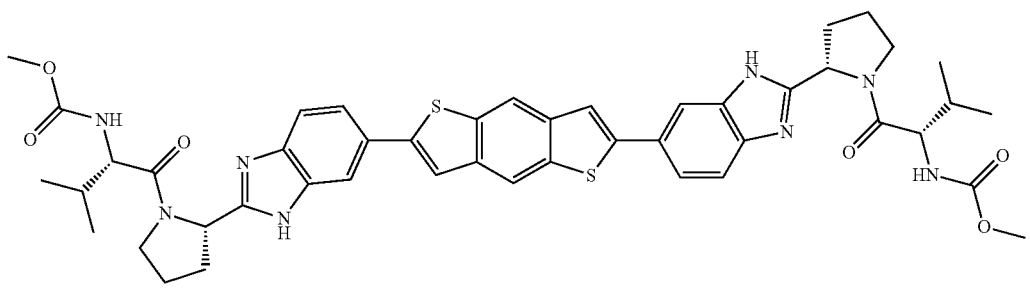

or a pharmaceutically acceptable salt, or prodrug thereof.

In another specific embodiment of the invention the compound of formula (Ib) is a compound of formula (Ib60):
$E^0$-V-$Z^0$-P-M-$A^{15}$-L-P-$Z^0$-V-$E^0$ (Ib60).

In another specific embodiment of the invention the compound of formula (Ib) is a compound of formula (Ib61):
$E^0$-V-$Z^0$-P-M-$A^{16}$-L-P-$Z^0$-V-$E^0$ (Ib61).

In another specific embodiment the invention provides a compound of formula (Ib35):

(Ib35)

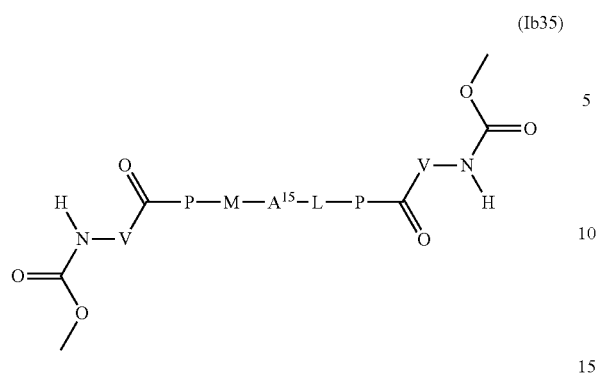

wherein:
V is alkyl;
L is benzimidazolyl;
M is a 5-membered heteroaryl ring;
$A^{15}$ is:

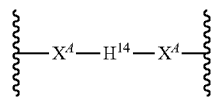

each $H^{14}$ is independently a fused unsaturated, partially unsaturated or saturated tricyclic carbocycle which is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, alkenyl, alkynyl, or absent and each R is independently selected from H or alkyl;

each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^4$ is independently selected from H, alkyl, haloalkyl, aryl, and arylalkyl; and each P is independently selected from:

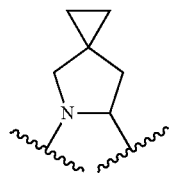 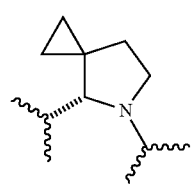

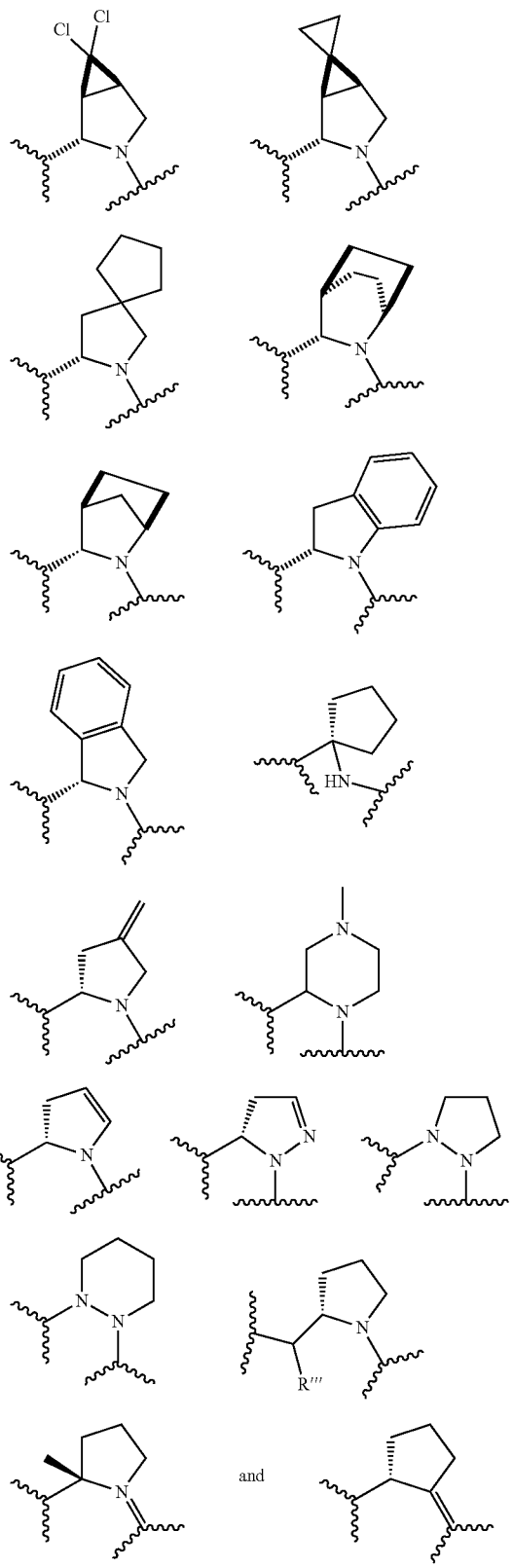

or a pharmaceutically acceptable salt, or prodrug thereof.

In another specific embodiment the invention provides a compound of formula (Ib36):

(Ib36)

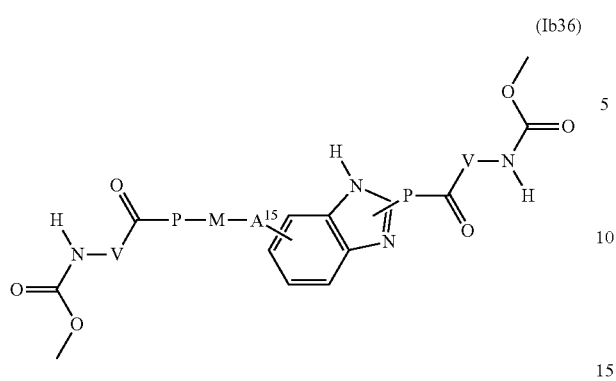

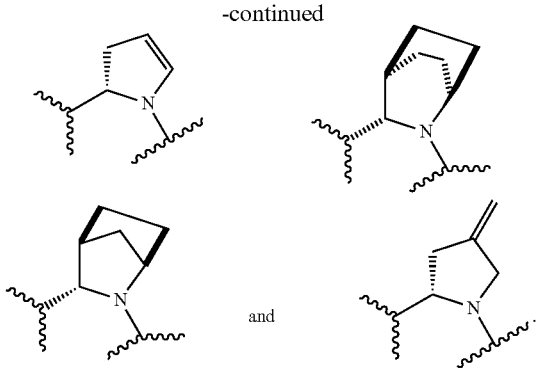

or a pharmaceutically acceptable salt, or prodrug thereof.

In another specific embodiment the invention provides a compound of formula (Ib37):

In another specific embodiment the invention provides a compound of formula (Ib35), (Ib36), or (Ib37): wherein P is:

(Ib37)

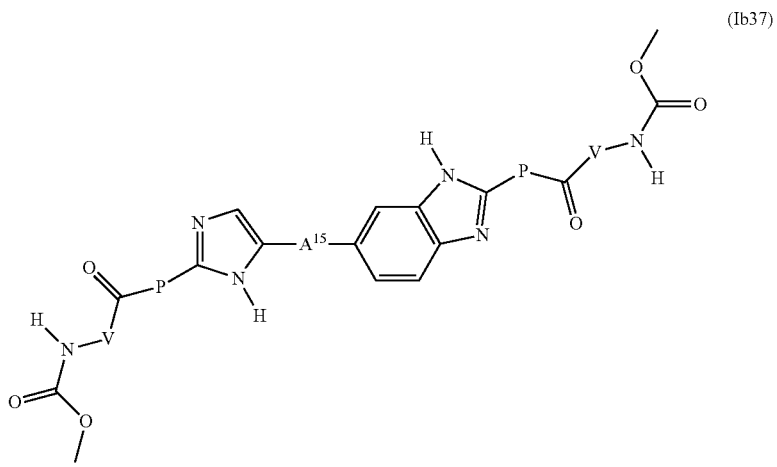

or a pharmaceutically acceptable salt, or prodrug thereof.

In another specific embodiment the invention provides a compound of formula (Ib35), (Ib36), or (Ib37) wherein P is selected from:

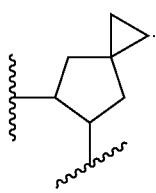 [SMILES: *C1CC2(CC2)CC1*]

In another specific embodiment the invention provides a compound of formula (Ib35), (Ib36), or (Ib37): wherein P is:

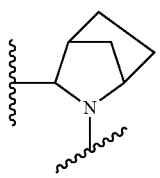 [SMILES: *C1C2CCC(C2)N1*]

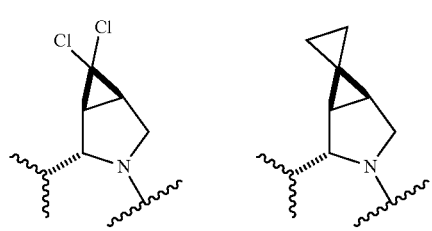

optionally substituted with one or more groups independently selected from $R^{P6}$ and $R^{P11}$;

each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; $R^{Pa}$ and $R^{Pb}$ are each independently H, alkyl, aryl, or arylalkyl; or $R^{Pa}$ and $R^{Pb}$ taken together with the atom to which they are attached form a heterocycle;

each $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, and —$S(=O)_2R^h$, —$C(=O)R^h$, —$C(=O)NR^hR^h$.

In another specific embodiment the invention provides a compound of formula (Ib38):

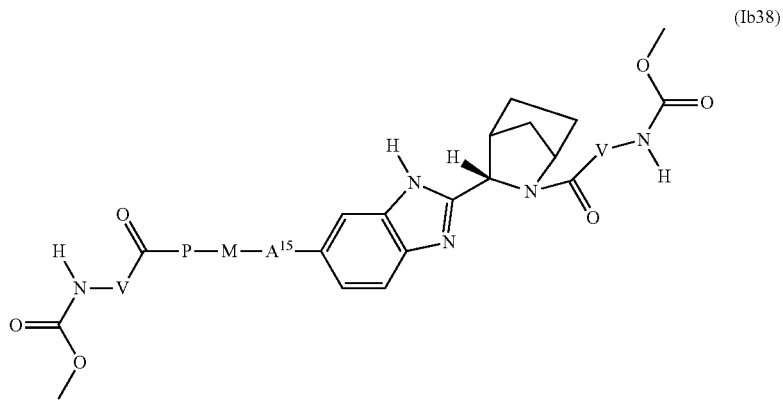

(Ib38)

or a pharmaceutically acceptable salt, or prodrug thereof.

In another specific embodiment the invention provides a compound of formula (Ib39):

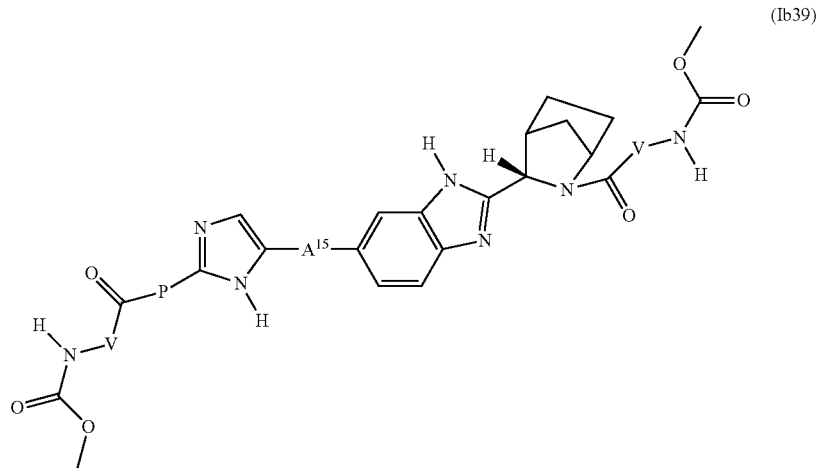

(Ib39)

or a pharmaceutically acceptable salt, or prodrug thereof.

In another specific embodiment the invention provides a compound of formula (Ib40):

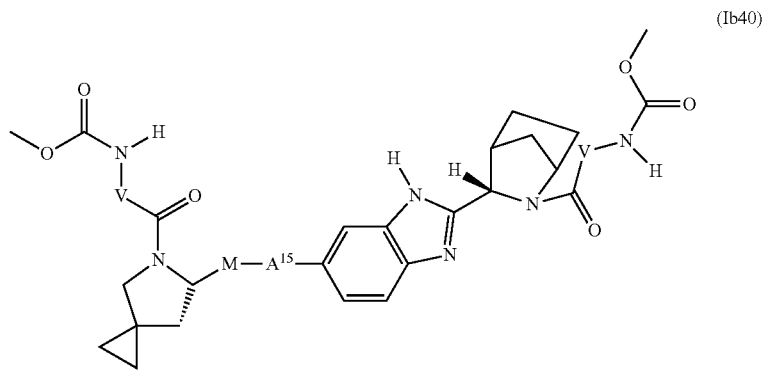

(Ib40)

or a pharmaceutically acceptable salt, or prodrug thereof.

In another specific embodiment the invention provides a compound of formula (Ib41):

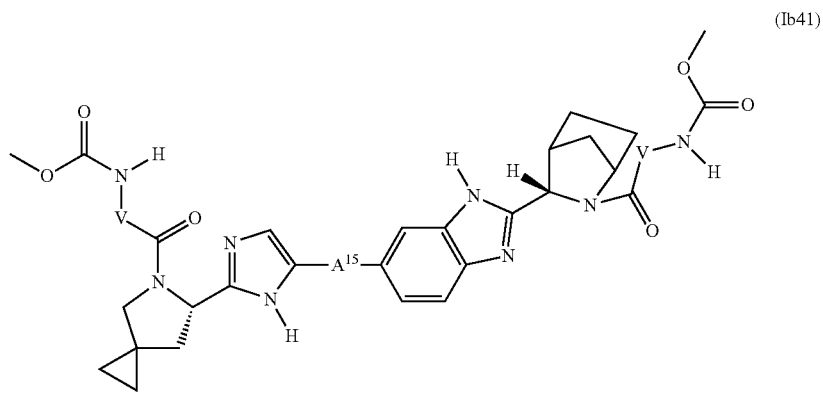

(Ib41)

or a pharmaceutically acceptable salt, or prodrug thereof.

In another specific embodiment the invention provides a compound of formula (Ib42):

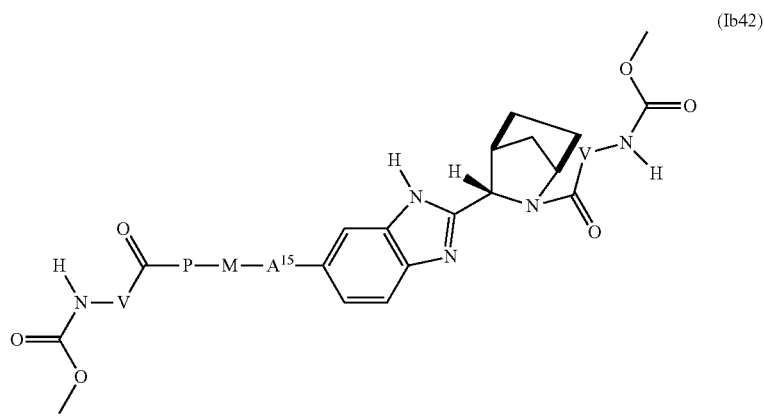

(Ib42)

or a pharmaceutically acceptable salt, or prodrug thereof.

In another specific embodiment the invention provides a compound of formula (Ib43):

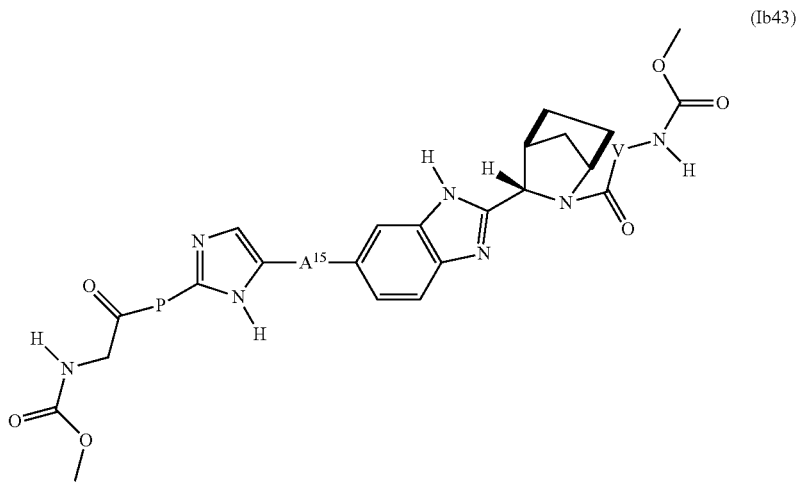

or a pharmaceutically acceptable salt, or prodrug thereof.

In another specific embodiment the invention provides a compound of formula (Ib44):

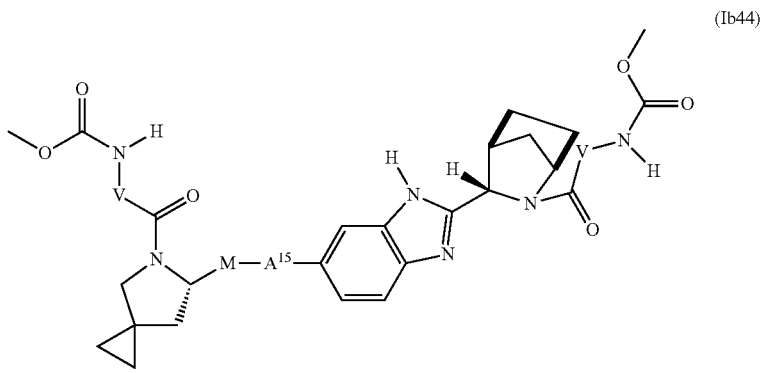

or a pharmaceutically acceptable salt, or prodrug thereof.

In another specific embodiment the invention provides a compound of formula (Ib45):

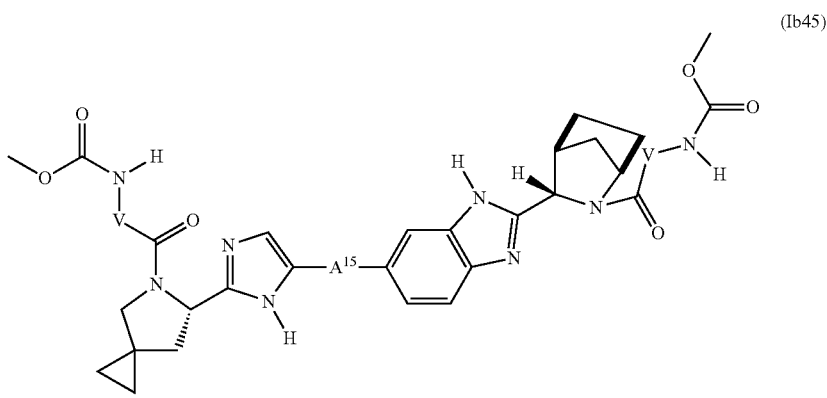

or a pharmaceutically acceptable salt, or prodrug thereof.

In another specific embodiment the invention provides a compound of formula (Ib35), (Ib36), (Ib37), (Ib38), (Ib39), (Ib40), (Ib41), (Ib42), (Ib43), (Ib44), or (Ib45) wherein each $X^A$ that is allowed to be absent is absent.

In another specific embodiment the invention provides a compound of formula (Ib35), (Ib36), (Ib37), (Ib38), (Ib39), (Ib40), (Ib41), (Ib42), (Ib43), (Ib44), or (Ib45) wherein $A^{15}$ is selected from:

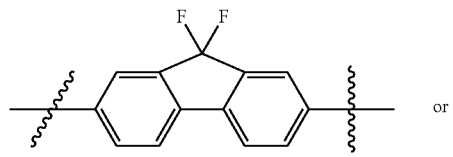

or

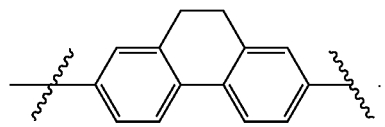

In another specific embodiment the invention provides a compound of formula (Ib35), (Ib36), (Ib37), (Ib38), (Ib39), (Ib40), (Ib41), (Ib42), (Ib43), (Ib44), or (Ib45) wherein $A^{15}$ is selected from:

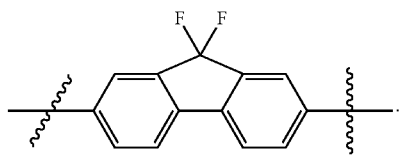

In another specific embodiment the invention provides a compound of formula (Ib35), (Ib36), (Ib37), (Ib38), (Ib39), (Ib40), (Ib41), (Ib42), (Ib43), (Ib44), or (Ib45) wherein each V is:

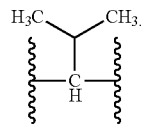

In another specific embodiment the invention provides a compound which is:

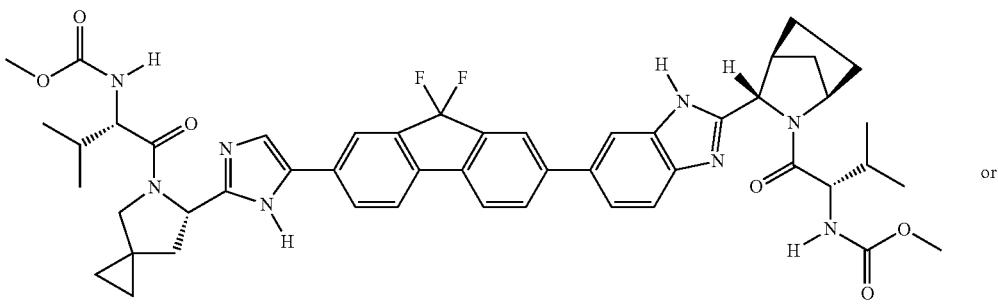

or

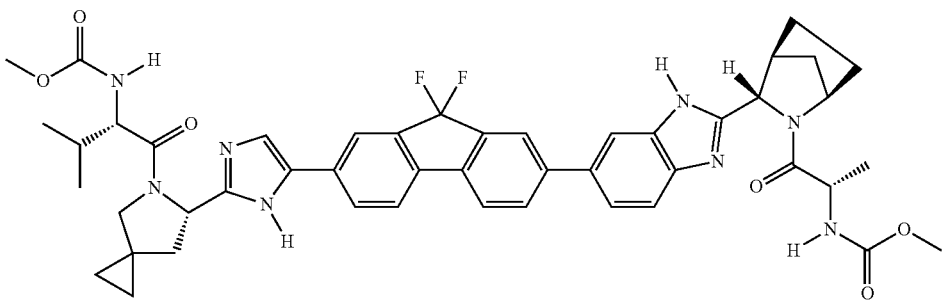

or a pharmaceutically acceptable salt, or prodrug thereof.

In another specific embodiment of the invention the compound of formula (Ib) is a compound of formula (Ib8)

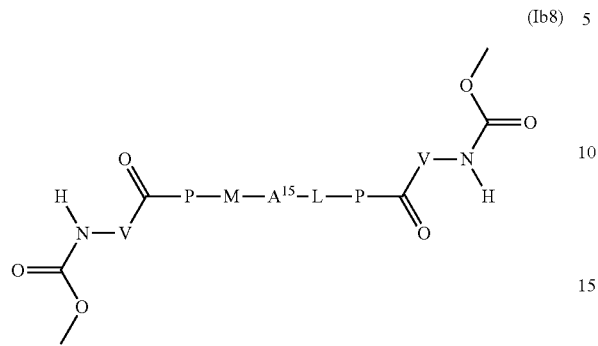
(Ib8)

wherein:
V is alkyl;
L is benzimidazolyl;
M is a 5-membered heteroaryl ring;
$A^{15}$ is:

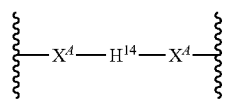

each $H^{14}$ is independently a fused unsaturated, partially unsaturated or saturated tricyclic carbocycle which is optionally substituted with one or more groups independently selected from $R^{A1}$ and $R^{A3}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^4$ is independently selected from H, alkyl, haloalkyl, aryl, and arylalkyl; and P is selected from:

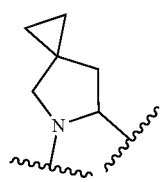 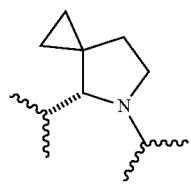

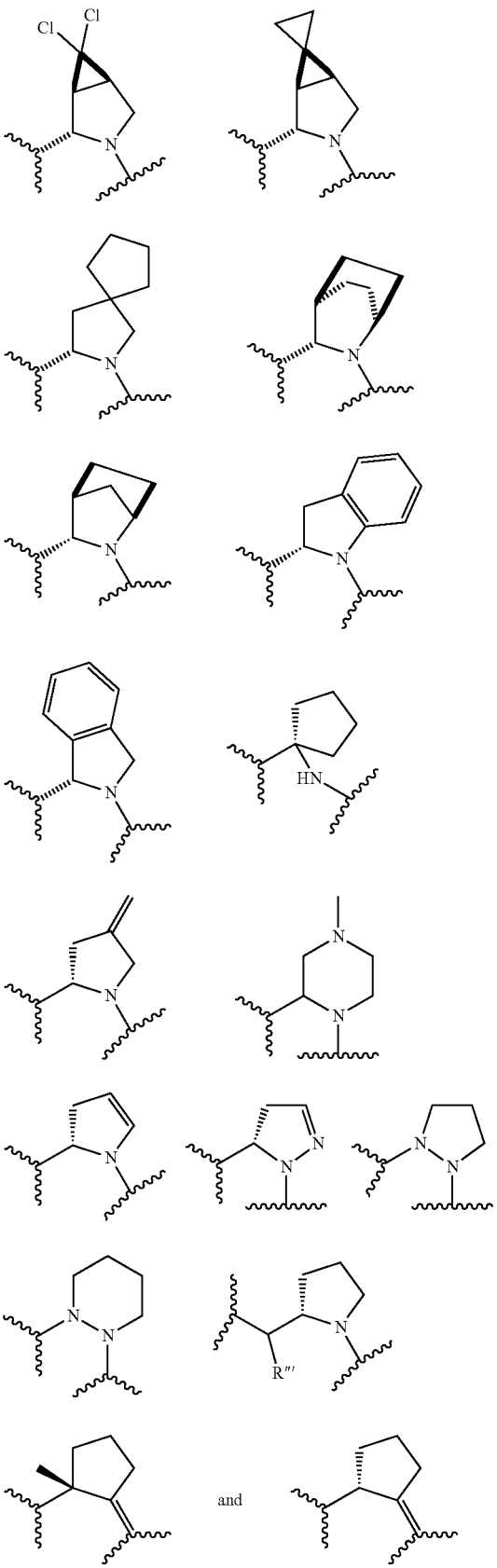

or a pharmaceutically acceptable salt, or prodrug thereof.

In another specific embodiment of the invention the compound of formula (Ib) is a compound of formula (Ib9):

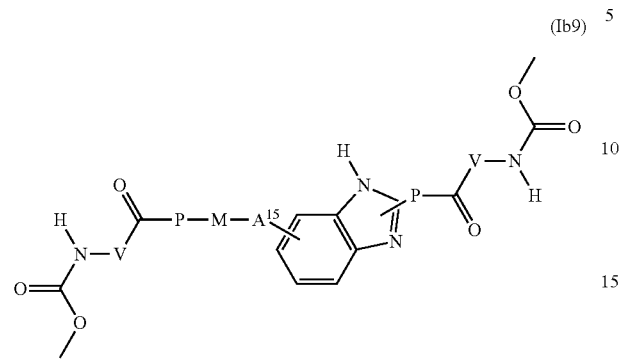

or a pharmaceutically acceptable salt, or prodrug thereof.

In another specific embodiment of the invention the compound of formula (Ib) is a compound of formula (Ib10):

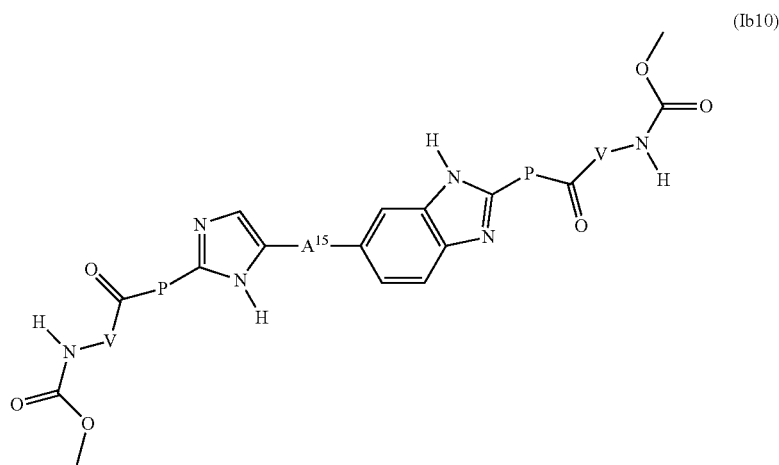

or a pharmaceutically acceptable salt, or prodrug thereof.

In another specific embodiment of the invention the compound of formula (Ib) is a compound of formula (Ib11):

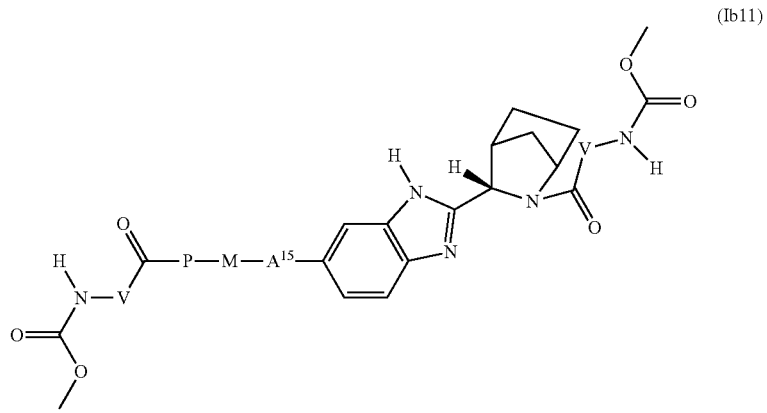

or a pharmaceutically acceptable salt, or prodrug thereof.

In another specific embodiment of the invention the compound of formula (Ib) is a compound of formula (Ib12):

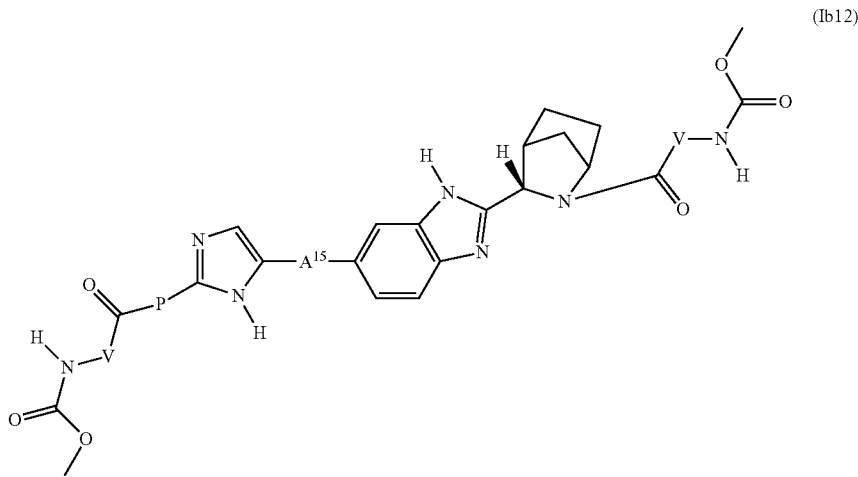

or a pharmaceutically acceptable salt, or prodrug thereof.

In another specific embodiment of the invention the compound of formula (Ib) is a compound of formula (Ib13):

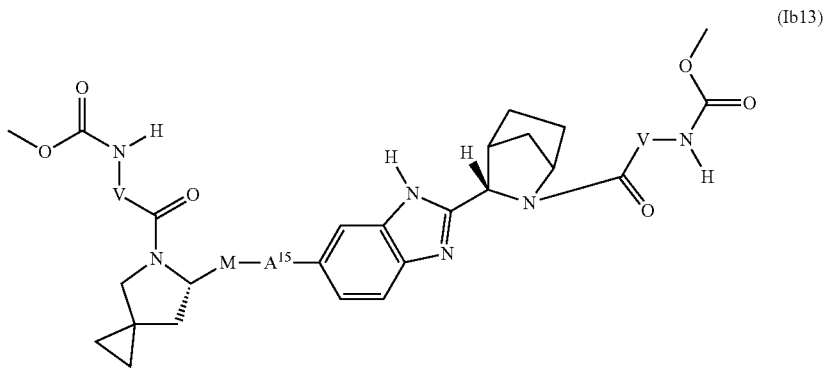

or a pharmaceutically acceptable salt, or prodrug thereof.

In another specific embodiment of the invention the compound of formula (Ib) is a compound of formula (Ib14):

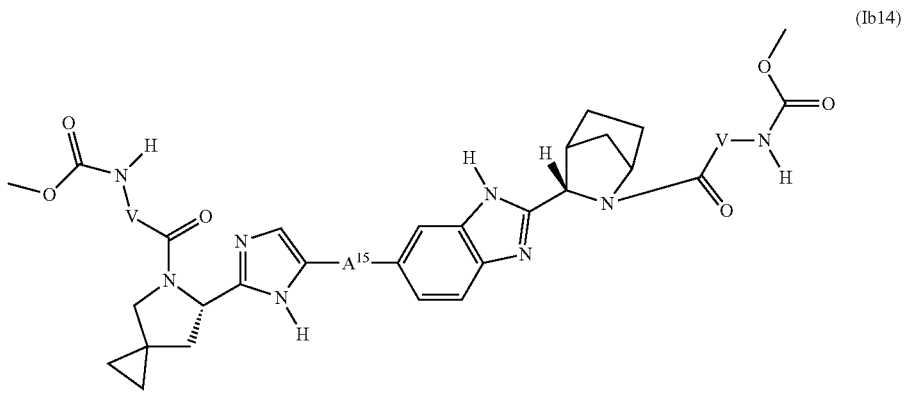

or a pharmaceutically acceptable salt, or prodrug thereof.

In another specific embodiment of the invention the compound of formula (Ib) is a compound of formula (Ib15):

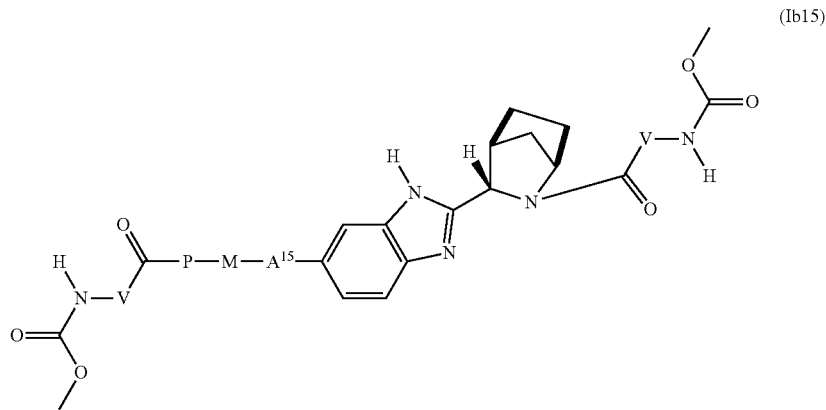

or a pharmaceutically acceptable salt, or prodrug thereof.

In another specific embodiment of the invention the compound of formula (Ib) is a compound of formula (Ib16):

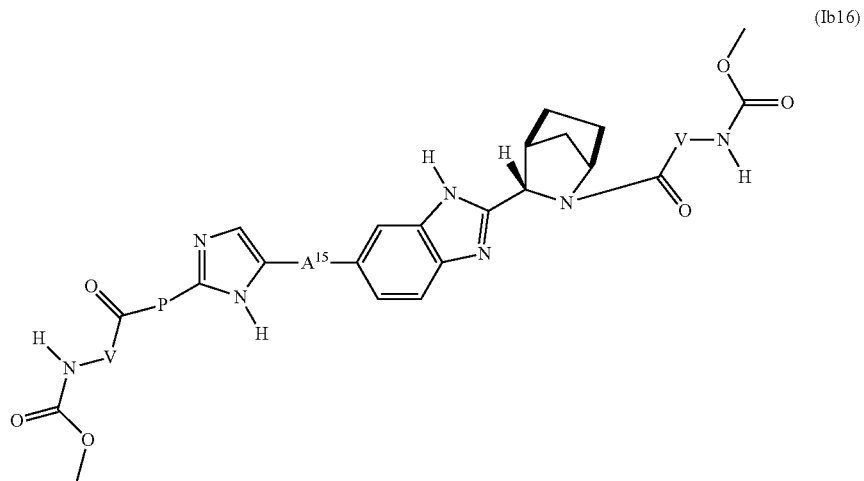

or a pharmaceutically acceptable salt, or prodrug thereof.

In another specific embodiment of the invention the compound of formula (Ib) is a compound of formula (Ib17):

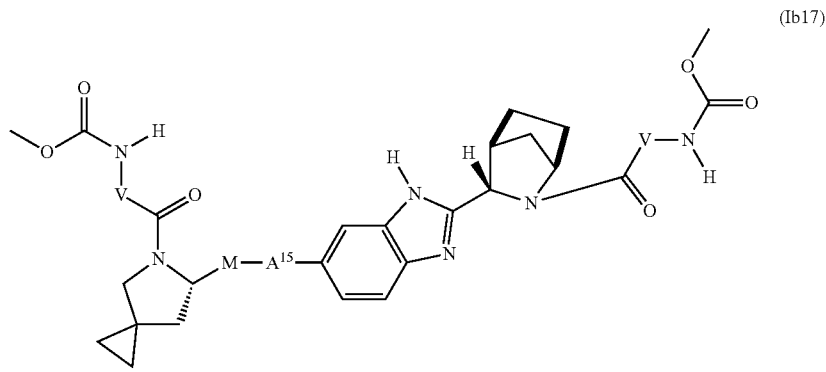

or a pharmaceutically acceptable salt, or prodrug thereof.

In another specific embodiment of the invention the compound of formula (Ib) is a compound of formula (Ib18):

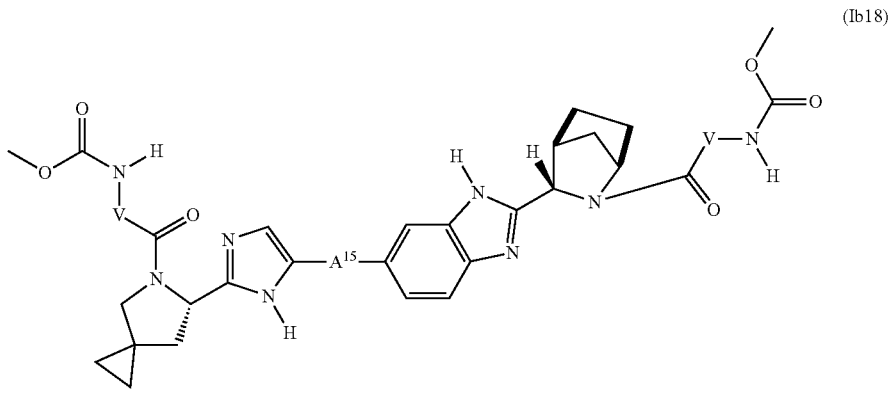

or a pharmaceutically acceptable salt, or prodrug thereof.

In another specific embodiment the invention provides a compound of formula (Ib) wherein P is

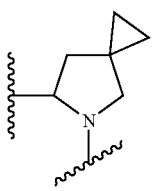

In another specific embodiment the invention provides a compound of formula (Ib) wherein P is

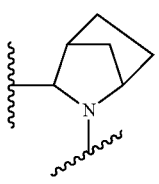

optionally substituted with one or more groups independently selected from $R^{P6}$ and $R^{P11}$;

each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; $R^{Pa}$ and $R^{Pb}$ are each independently H, alkyl, aryl, or arylalkyl; or $R^{Pa}$ and $R^{Pb}$ taken together with the atom to which they are attached form a heterocycle;

each $R^{11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, and —$S(=O)_2R^h$, —$C(=O)R^h$, —$C(=O)NR^hR^h$.

In another specific embodiment the invention provides a compound of formula (Ib) wherein each $X^A$ that is allowed to be absent is absent.

In another specific embodiment the invention provides a compound of formula (Ib) wherein $A^{15}$ is selected from:

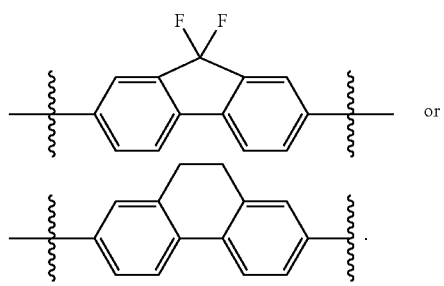

In another specific embodiment the invention provides a compound of formula (Ib) wherein each V is:

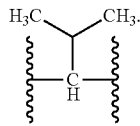

In one embodiment of the invention, the compound of formula (I) is a compound of formula (Ib19):

$$E^0\text{-}V^w\text{-}Z^0\text{-}P^u\text{-}M^0\text{-}A^s\text{-}L^9\text{-}P^u\text{-}Z^0\text{-}V^w\text{-}E^0 \quad \text{(Ib19)}$$

wherein:

each u is independently 0, 1, 3, 5, 7, 8, 10, or 11; each w is independently 0, 1, 2, 3, 4, or 5; and each s is 0, 6, 13, or 14.

In one embodiment the invention provides a compound of formula (Ib19) wherein $L^9$ is:

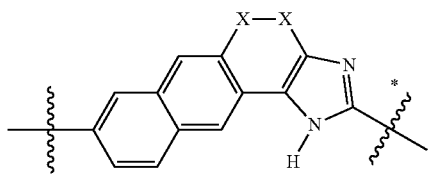

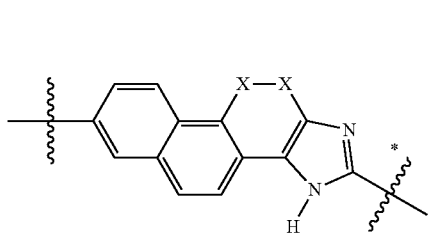

wherein X—X is selected from O, $CH_2$, CH=CH, $CH_2$—$CH_2$, $CH_2$—O, O—$CH_2$, $CH_2$—$CH_2$—$CH_2$, and $CH_2$—O—$CH_2$; wherein * designates the site of connection to P.

In one embodiment the invention provides a compound of formula (Ib19) wherein $M^0$ is:

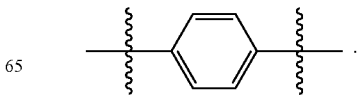

In one embodiment the invention provides a compound of formula (Ib19) which is:

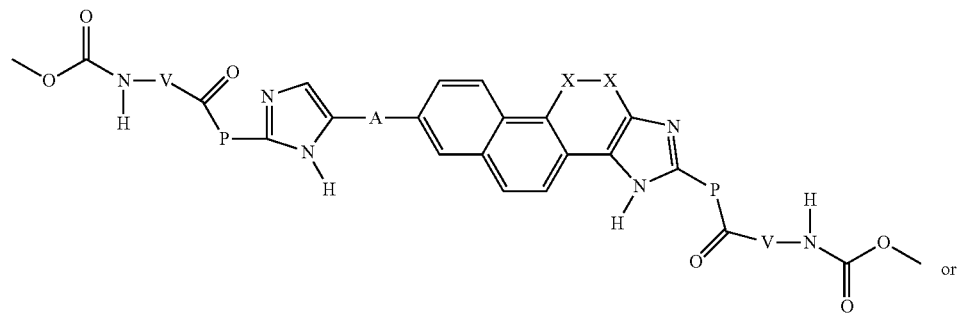

or

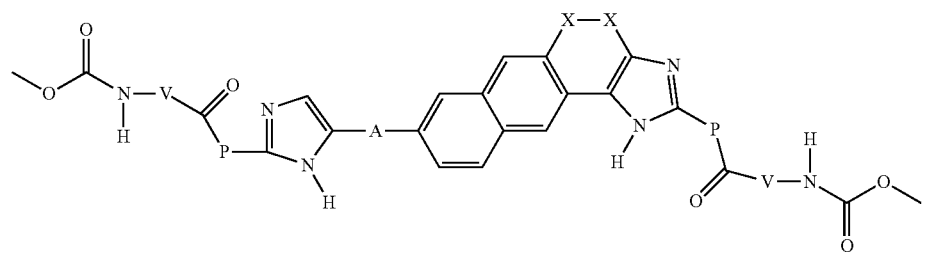

or a pharmaceutically acceptable salt, or prodrug thereof.

In one embodiment the invention provides a compound of formula (Ib19) wherein $A^0$ is:

In one embodiment the invention provides a compound of formula (Ib19) which is:
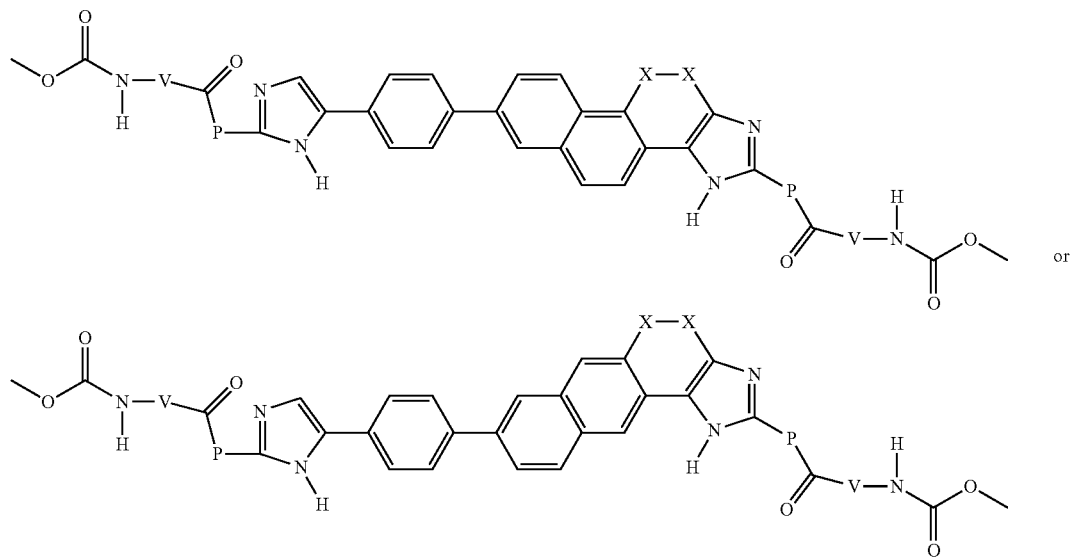
or a pharmaceutically acceptable salt, or prodrug thereof.
In one embodiment the invention provides a compound of formula (Ib19) wherein $A^6$ is:
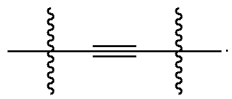 [SMILES: *C#C*]
In one embodiment the invention provides a compound of formula (Ib19) which is:
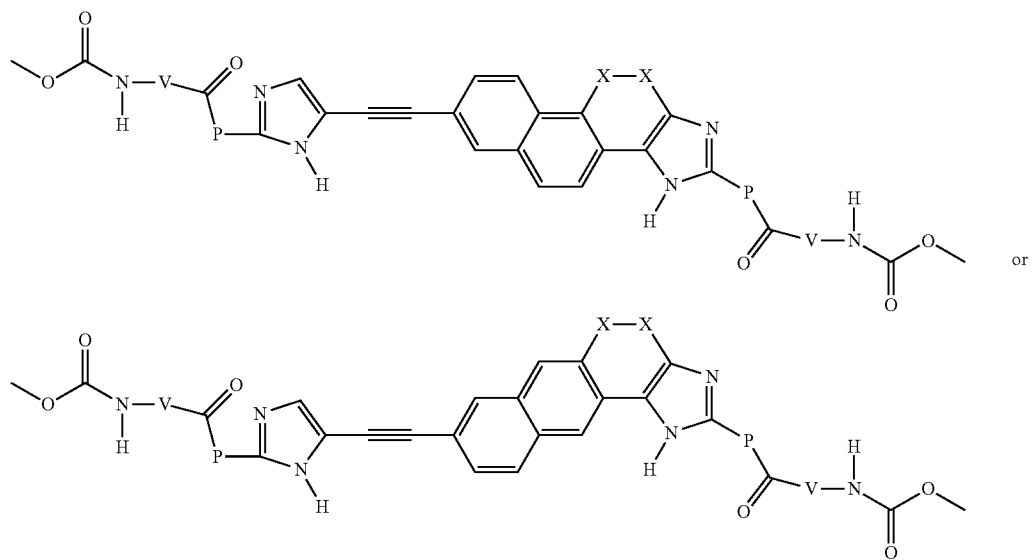
or a pharmaceutically acceptable salt, or prodrug thereof.

In one embodiment the invention provides a compound of formula (Ib19) wherein $A^{13}$ is:

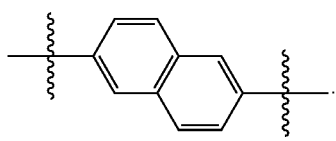 [SMILES: *c1ccc2cc(*)ccc2c1]

In one embodiment the invention provides a compound of formula (Ib19) which is:

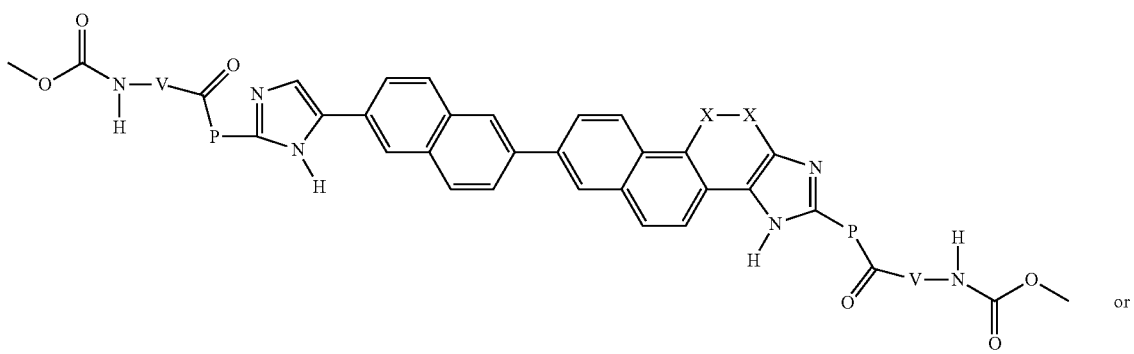

or

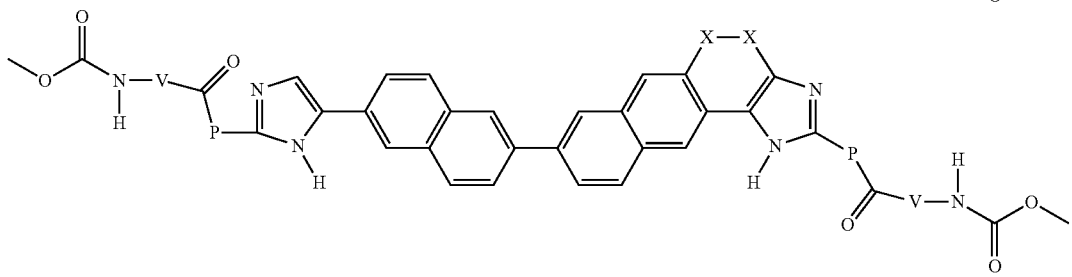

or a pharmaceutically acceptable salt, or prodrug thereof.

In one embodiment the invention provides a compound of formula (Ib19) wherein $A^{14}$ is:

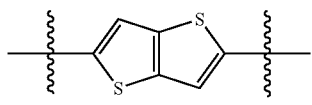

or

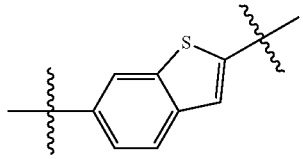

-continued

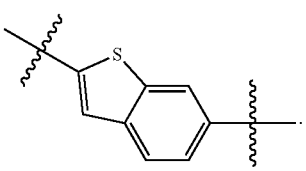

In one embodiment the invention provides a compound of formula (Ib19) which is:

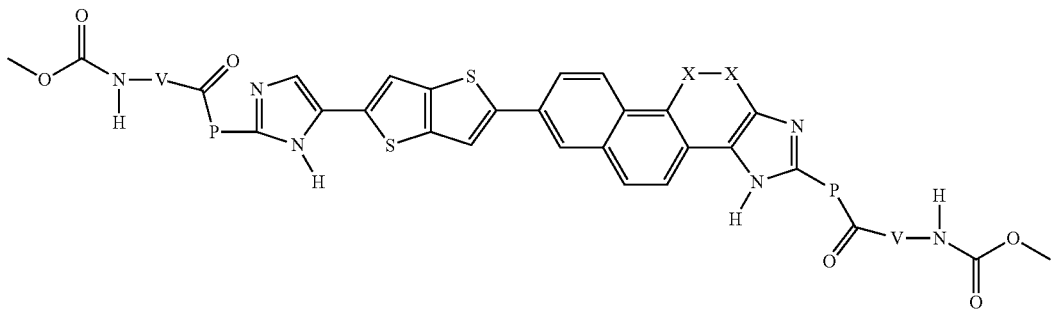

-continued

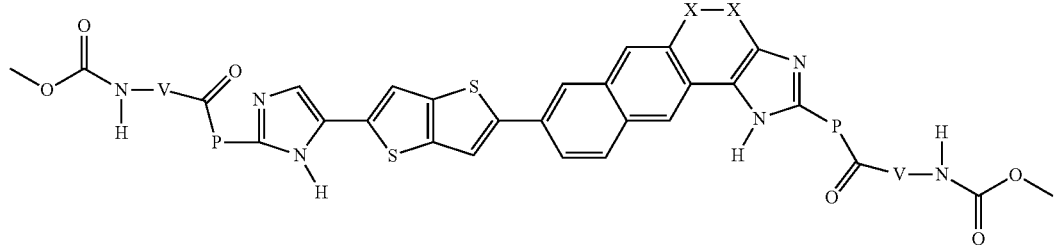

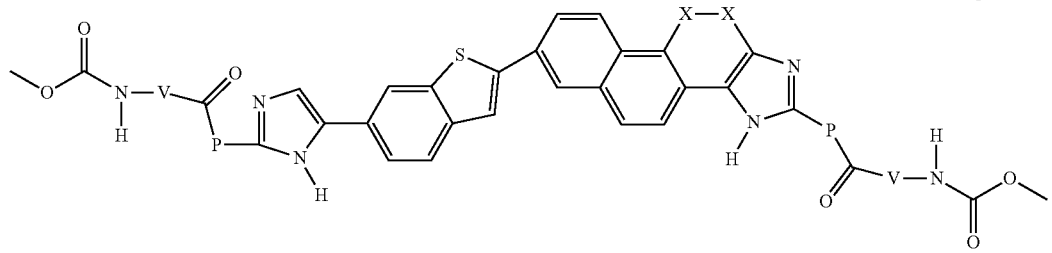

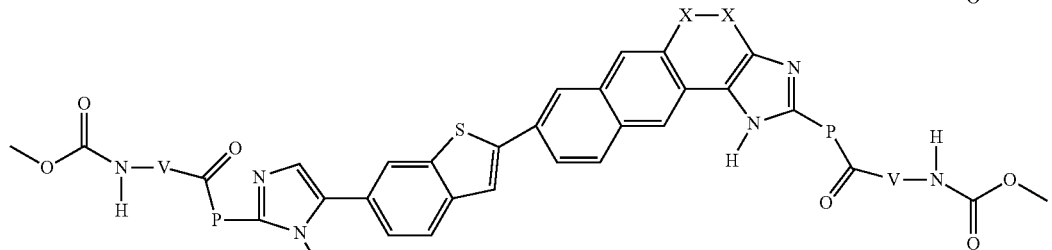

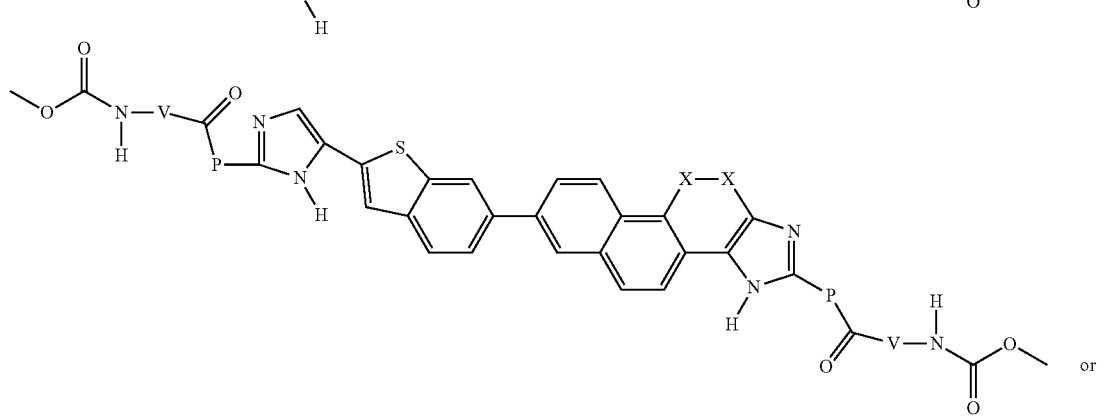

or

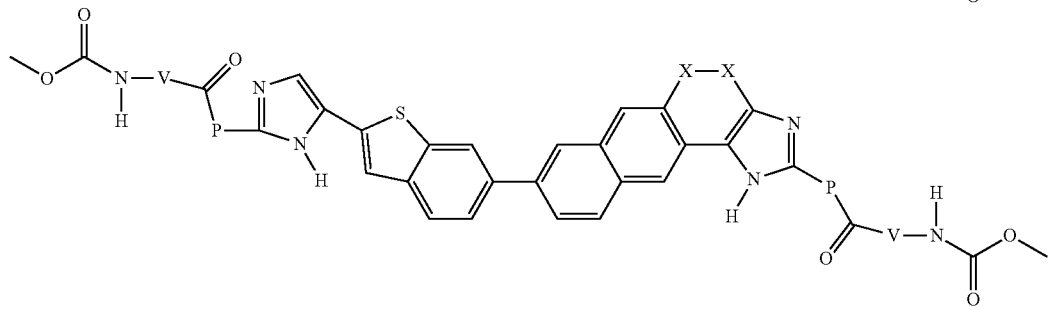

or a pharmaceutically acceptable salt, or prodrug thereof.

In one embodiment of the invention, the compound of formula (I) is a compound of formula (Ib20):

$$E^0\text{-}V^w\text{-}Z^0\text{-}P^u\text{-}M^0\text{-}A^0\text{-}L^4\text{-}P^u\text{-}Z^0\text{-}V^w\text{-}E^0 \quad \text{(Ib20)}$$

wherein:

each u is independently 0, 1, 3, 5, 7, 8, 10, or 11; and each w is independently 0, 1, 2, 3, 4, or 5.

In one embodiment of the invention, the compound of formula (I) is a compound of formula (Ib21):

$$E^0\text{-}V^w\text{-}Z^0\text{-}P^{u1}\text{-}M^0\text{-}A^0\text{-}L^4\text{-}P^2\text{-}Z^0\text{-}V^w\text{-}E^0 \quad \text{(Ib21)}$$

wherein:

each u1 is 1, 3, 5, 7, 8, 10, or 11; u2 is 0, 1, 3, 5, 7, 8, 10, or 11; and each w is independently 0, 1, 2, 3, 4, or 5.

In one embodiment of the invention, the compound of formula (I) is a compound of formula (Ib22):

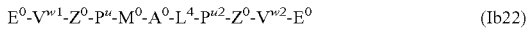 (Ib22)

wherein:

each u is independently 0, 1, 3, 5, 7, 8, 10, or 11; each u2 is independently 0, 1, 3, 5, 7, 8, 10, or 11; w1 is independently 0, 1, 2, 3, 4, or 5; and each w2 is independently 1, 2, 3, 4, or 5.

In one embodiment of the invention, the compound of formula (I) is a compound of formula (Ib23):

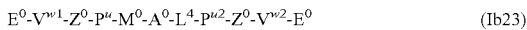 (Ib23)

wherein:

each u is independently 0, 1, 3, 5, 7, 8, 10, or 11; each u2 is independently 0, 1, 3, 5, 7, 8, 10, or 11; w1 is independently 1, 2, 3, 4, or 5; and each w2 is independently 0, 1, 2, 3, 4, or 5.

In one embodiment the invention provides a compound of formula (Ib20)-(Ib23) wherein $M^0$ is:

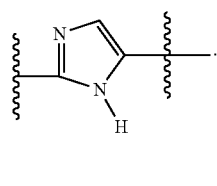 [SMILES: *c1cnc(*)[nH]1]

In one embodiment the invention provides a compound of formula (Ib20)-(Ib23) wherein $A^0$ is:

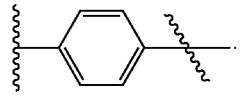

In one embodiment the invention provides a compound of formula (Ib20)-(Ib23) wherein $L^4$ is:

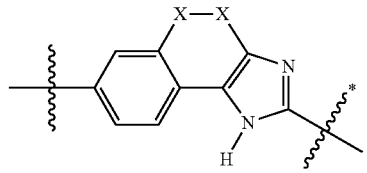

wherein X—X is selected from O, $CH_2$, CH=CH, $CH_2$—$CH_2$, $CH_2$—O, o—$CH_2$, $CH_2$—$CH_2$—$CH_2$, and $CH_2$—O—$CH_2$; and wherein * designates the site of connection to P.

In one embodiment of the invention, the compound of formula (I) is a compound of formula (Ib24):

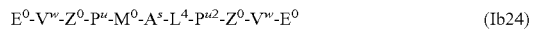 (Ib24)

wherein:

each u is independently 0, 1, 3, 5, 7, 8, 10, or 11; each u2 is independently 0, 1, 3, 5, 7, 8, 10, or 11; each w is independently 0, 1, 2, 3, 4, or 5; and s is 5, 6, 13, 14, 15, or 16.

In one embodiment the invention provides a compound of formula (Ib24) wherein s is 16 and $A^{16}$ is:

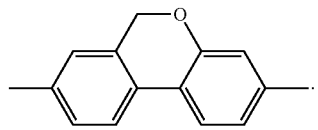

In one embodiment the invention provides a compound of formula:

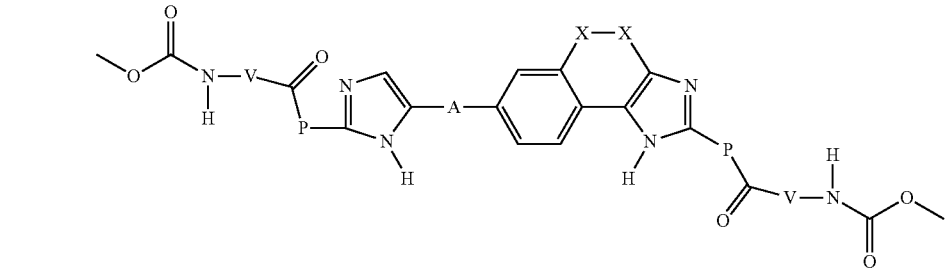

wherein X—X is selected from O, $CH_2$, CH=CH, $CH_2$—$CH_2$, $CH_2$—O, O—$CH_2$, $CH_2$—$CH_2$—$CH_2$, and $CH_2$—O—$CH_2$; and A is $A^0$; or a pharmaceutically acceptable salt, or prodrug thereof.

In one embodiment the invention provides a compound of formula:

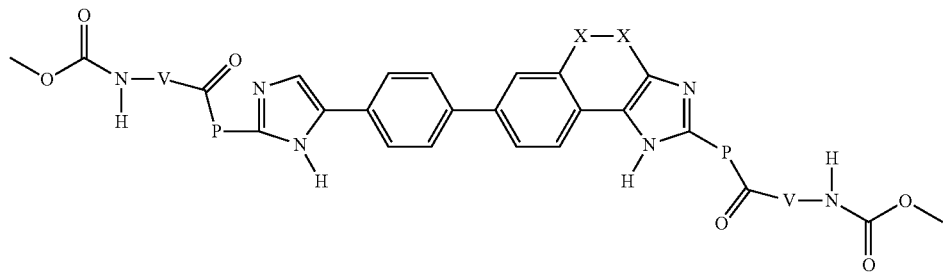

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ib24) wherein s is 6 and A$^6$ is:

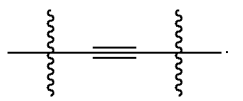

In one embodiment the invention provides a compound of formula (Ib25):

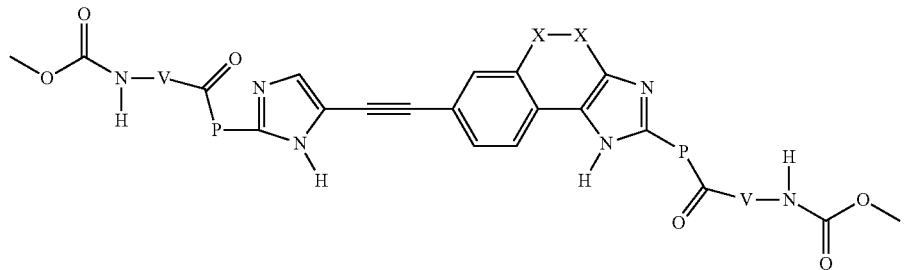

(Ib25)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ib24) wherein s is 5 and A$^5$ is:

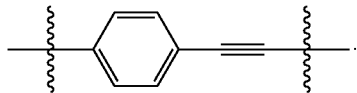

In one embodiment the invention provides a compound of formula (Ib26):

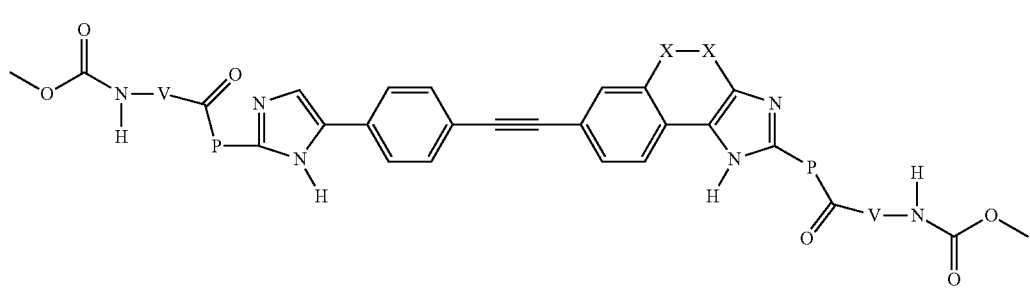

(Ib26)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ib24) wherein s is 13 and A$^{13}$ is:

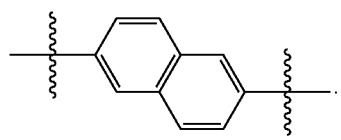 [SMILES: *c1ccc2cc(*)ccc2c1]

In one embodiment the invention provides a compound of formula (Ib27):

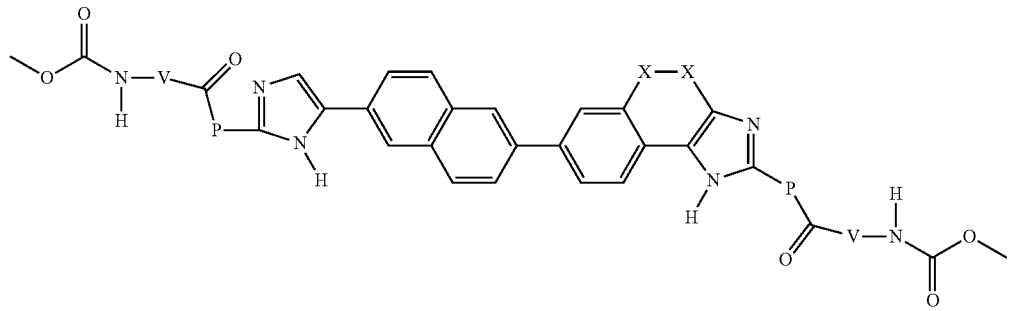

(Ib27)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ib24) wherein s is 14 and A$^{14}$ is:

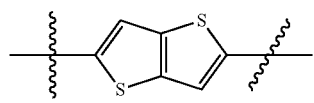

-continued

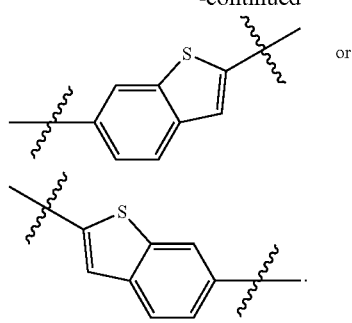

or

In one embodiment the invention provides a compound of formula:

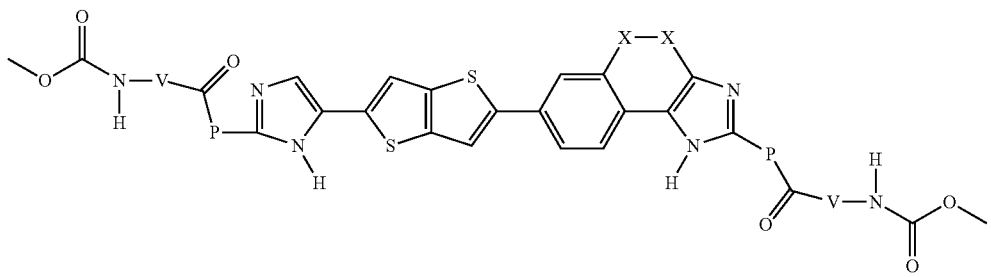
(Ib29)
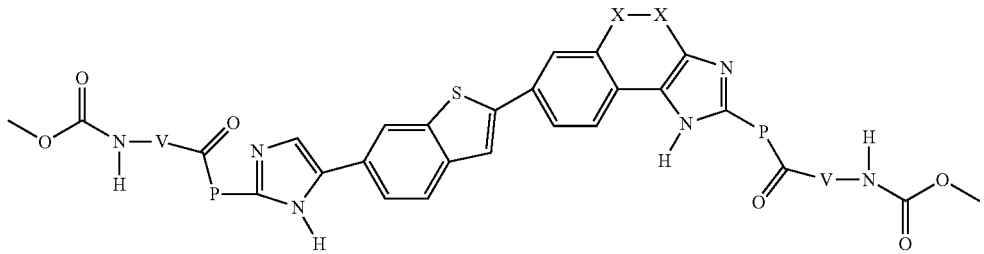
(Ib30)
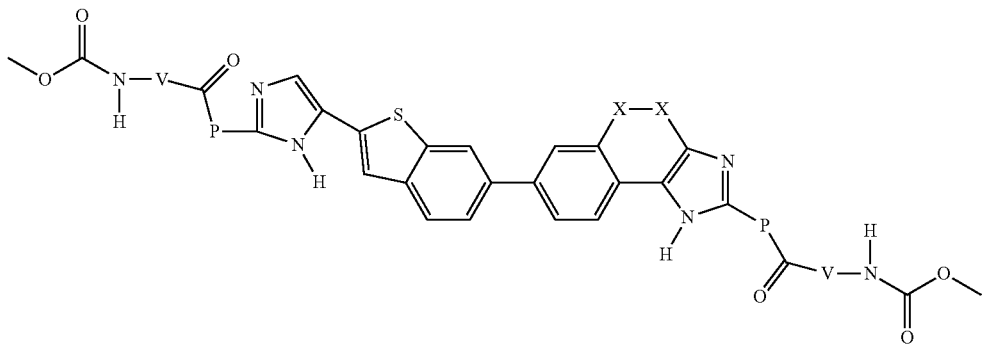
(Ib31)
wherein X—X is selected from O, CH$_2$, CH═CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.
In one embodiment the invention provides a compound of formula (Ib24) wherein s is 15 and A$^{15}$ is:
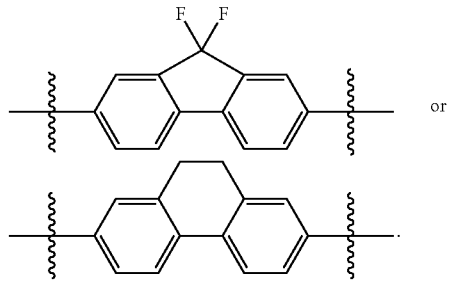
In one embodiment the invention provides a compound of formula:
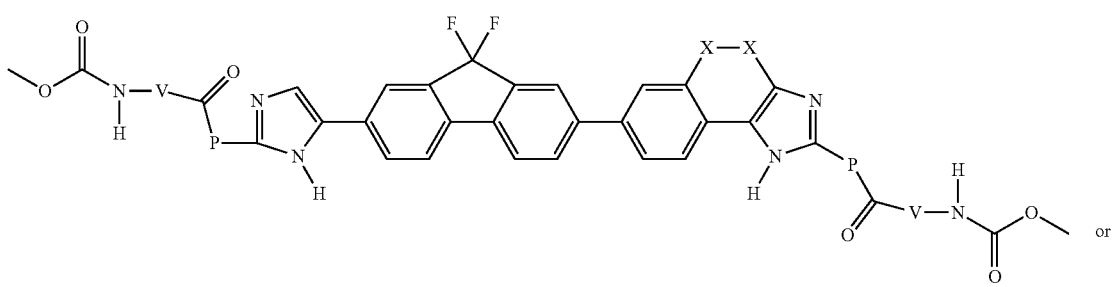
(Ib32)
or

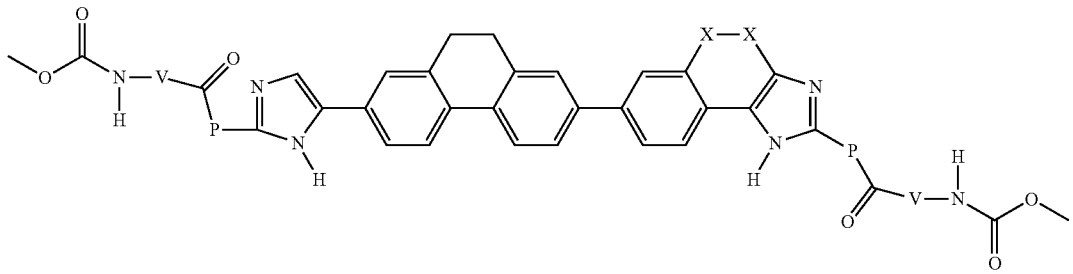

(Ib33)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Ib34):

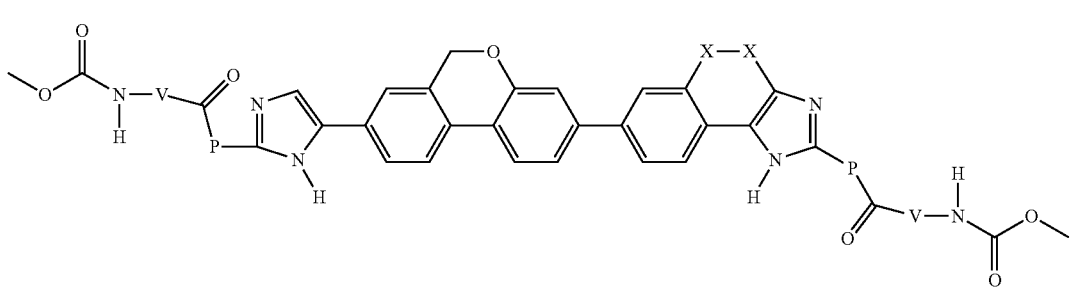

(Ib34)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In another specific embodiment of the invention the compound of formula (Ib) is a compound of formula: R9-Z-P-M-A$^{15}$-L-P-Z-R9.

In another specific embodiment of the invention the compound of formula (Ib) is a compound of formula: R$^9$-Z-P-M-A$^{15}$-L$^3$-P-Z-R9.

In another specific embodiment of the invention the compound of formula (Ib) is a compound of formula: R9-Z-P-M$^o$-A$^{15}$-L$^3$-P-Z-R9.

In another specific embodiment of the invention the compound of formula (Ib) is a compound of formula: R9-Z-P-M-A$^{16}$-L-P-Z-R9.

In another specific embodiment of the invention the compound of formula (Ib) is a compound of formula: R9-Z-P-M-A$^{16}$-L$^3$-P-Z-R9.

In another specific embodiment of the invention the compound of formula (Ib) is a compound of formula: R9-Z-P-M$^o$-A$^{16}$-L$^3$-P-Z-R9.

In another specific embodiment of the invention the compound of formula (Ib) is a compound of formula: R9-Z-P-M$^9$-A$^{16}$-L$^3$-P-Z-R9.

In another specific embodiment the invention provides a compound of the following formula (Ib50): E$^x$-V$^w$-Z$^v$-P$^u$-M$^t$-A$^s$-L$^n$-P$^u$-Z$^v$-V$^w$-E$^x$ (Ib50) wherein the sum of t, s, n, u, v, w and x is not zero.

In another specific embodiment the invention provides a compound of formula (Ib50) wherein at least two of n, s, t, u, v, w or x are not zero.

In another specific embodiment the invention provides a compound of formula (Ib50) wherein at least three of n, s, t, u, v, w or x are not zero.

In another specific embodiment the invention provides a compound of formula (Ib50) wherein at least two of n, s, t, u, v, w or x are not zero and at least two of the non-zero groups are not the same letter.

In another specific embodiment the invention provides a compound of formula (Ib50) wherein at least three of n, s, t, u, v, w or x are not zero and at least two of the non-zero groups are not the same letter.

In another specific embodiment the invention provides a compound of formula (Ib50) wherein at least three of n, s, t, u, v, w or x are not zero and at least three of the non-zero groups are not the same letter.

In another specific embodiment the invention provides a compound of formula (Ib50) wherein at least four of n, s, t, u, v, w or x are not zero.

In another specific embodiment the invention provides a compound of formula (Ib50) wherein at least four of n, s, t, u, v, w or x are not zero and at least two of the non-zero groups are not the same letter.

In another specific embodiment the invention provides a compound of formula (Ib50) wherein at least four of n, s, t, u, v, w or x are not zero and at least three of the non-zero groups are not the same letter.

In another specific embodiment the invention provides a compound of formula (Ib50) wherein at least four of n, s, t, u, v, w or x are not zero and at least four of the non-zero groups are not the same letter.

In another specific embodiment the invention provides a compound of formula (Ib50) wherein the sum of n, t, u, v, w or x is not zero.

In another specific embodiment the invention provides a compound of formula (Ib50) wherein the sum of s, u, v, w or x is not zero.

In another specific embodiment the invention provides a compound of formula (Ib50) wherein at least one u is not zero.

In another specific embodiment the invention provides a compound of formula (Ib50) wherein s, and at least one t, and at least one u are all not zero.

In another specific embodiment the invention provides a compound of formula (Ib50) wherein at least two of u, w and t are not zero.

In another specific embodiment the invention provides a compound of formula (Ib50) wherein at least two of s, u, and w are not zero.

In another specific embodiment the invention provides a compound of formula (Ib50) wherein at least two of s, u, and w are not zero and at least two of the non-zero groups are not the same letter.

In another specific embodiment the invention provides a compound of formula (Ib50) wherein at least s and both u are not zero.

In another specific embodiment the invention provides a compound of formula (Ib50) wherein at least two of u, v, w or x are not zero and at least two of the non-zero groups are not the same letter In another specific embodiment the invention provides a compound of formula (Ib50) wherein at least one of u, or w is not zero.

In another specific embodiment the invention provides a compound of formula (Ib50) wherein at least two of u, or w are not zero.

In another specific embodiment the invention provides a compound of formula (Ib50) wherein at least one u is not zero, and at least one w is not zero.

In another specific embodiment the invention provides a compound of formula (Ib50) wherein at least two of u are not zero.

In another specific embodiment the invention provides a compound of formula (Ib50) wherein at least one of w is not zero.

In another specific embodiment the invention provides a compound of formula (Ib50) wherein at least two of w are not zero.

In another specific embodiment the invention provides a compound of formula (Ib50) wherein both u are not zero, and at least one w is not zero.

In another specific embodiment the invention provides a compound of the formula (Ib50) wherein t is 0 or 10; n is 0, 1, 2, 3, 4, 5, 6, 7, 8, 9, or 10; and s is 0, 1, 2, 3, 4, 5, 6, 7, 8, 9, 10, 11, 12, 13, 14, 15, 16, 17, 18, or 21.

In another specific embodiment the invention provides a compound of the formula (Ib50) wherein t is 0 or 10; n is 0, 1, 2, 4, 5, 6, 7, 8, 9, or 10; and s is 0, 1, 2, 3, 4, 5, 6, 7, 8, 9, 10, 11, 12, 13, 14, 15, 16, 17, 18, 21.

In another specific embodiment the invention provides a compound of the formula (Ib50) wherein t is 9; n is 3; and s is 3, 4, 8, 9, 10, 11, 12, 13, 14, 15, 16, 17, 18, or 21.

In another specific embodiment the invention provides a compound of the formula (Ib50) wherein t is 0, 1, 2, 4, 5, 6, 7, 8, 9, 10, or 11; n is 0, 1, 2, 3, 4, 5, 6, 7, 8, 9, or 10; and s is 1, 2, 3, 4, 5, 6, 7, 8, 9, 10, 11, 12, 13, 14, 15, 16, 17, 18, 21.

In another specific embodiment the invention provides a compound of the formula (Ib50) wherein t is 0; n is 0, 1, 2, 3, 5, 6, 7, 8, 9, or 10; and s is 0, 1, 2, 3, 4, 5, 6, 7, 8, 9, 10, 11, 12, 13, 14, 15, 16, 17, or 20.

In another specific embodiment the invention provides a compound of the formula (Ib50) wherein t is 1, 2, 4, 5, 6, 7, 8, 9, 10, or 11; n is 4; and s is 0, 1, 2, 3, 4, 5, 6, 7, 8, 9, 10, 11, 12, 13, 14, 15, 16, 17, 18, or 21.

In another specific embodiment the invention provides a compound of the formula (Ib50) wherein at least one of u, v, w or x are not zero.

In another specific embodiment the invention provides a compound of the formula (Ib50) wherein at least two of n, s, t, u, v, w or x are not zero.

In another specific embodiment the invention provides a compound of the formula (Ib50) wherein at least three of n, s, t, u, v, w or x are not zero.

In another specific embodiment the invention provides a compound of the formula (Ib50) wherein at least two of n, s, t, u, v, w or x are not zero and at least two of the non-zero groups are not the same letter.

In another specific embodiment the invention provides a compound of the formula (Ib50) wherein at least three of n, s, t, u, v, w or x are not zero and at least two of the non-zero groups are not the same letter.

In another specific embodiment the invention provides a compound of the formula (Ib50) wherein at least three of n, s, t, u, v, w or x are not zero and at least three of the non-zero groups are not the same letter.

In another specific embodiment the invention provides a compound of the formula (Ib50) wherein at least four of n, s, t, u, v, w or x are not zero.

In another specific embodiment the invention provides a compound of the formula (Ib50) wherein at least four of n, s, t, u, v, w or x are not zero and at least two of the non-zero groups are not the same letter.

In another specific embodiment the invention provides a compound of the formula (Ib50) wherein at least four of n, s, t, u, v, w or x are not zero and at least three of the non-zero groups are not the same letter.

In another specific embodiment the invention provides a compound of the formula (Ib50) wherein at least four of n, s, t, u, v, w or x are not zero and at least four of the non-zero groups are not the same letter.

In another specific embodiment the invention provides a compound of the formula (Ib50) wherein the sum of n, t, u, v, w or x is not zero.

In another specific embodiment the invention provides a compound of the formula (Ib50) wherein the sum of s, u, v, w or x is not zero.

In another specific embodiment the invention provides a compound of the formula (Ib50) wherein at least one u is not zero.

In another specific embodiment the invention provides a compound of the formula (Ib50) wherein s, and at least one t, and at least one u are all not zero.

In another specific embodiment the invention provides a compound of the formula (Ib50) wherein at least two of u, w and t are not zero.

In another specific embodiment the invention provides a compound of the formula (Ib50) wherein at least two of s, u, and w are not zero.

In another specific embodiment the invention provides a compound of the formula (Ib50) wherein at least two of s, u, and w are not zero and at least two of the non-zero groups are not the same letter.

In another specific embodiment the invention provides a compound of the formula (Ib50) wherein at least s and both u are not zero.

In another specific embodiment the invention provides a compound of the formula (Ib50) wherein at least two of u, v, w or x are not zero and at least two of the non-zero groups are not the same letter.

In another specific embodiment the invention provides a compound of the formula (Ib50) wherein at least one of u, or w is not zero.

In another specific embodiment the invention provides a compound of the formula (Ib50) wherein at least two of u, or w are not zero.

In another specific embodiment the invention provides a compound of the formula (Ib50) wherein at least one u is not zero, and at least one w is not zero.

In another specific embodiment the invention provides a compound of the formula (Ib50) wherein at least two of u are not zero.

In another specific embodiment the invention provides a compound of the formula (Ib50) wherein at least one of w is not zero.

In another specific embodiment the invention provides a compound of the formula (Ib50) wherein at least two of w are not zero.

In another specific embodiment the invention provides a compound of the formula (Ib50) wherein both u are not zero, and at least one w is not zero.

In another specific embodiment the invention provides a compound of the following formula (Ib51): $E^x$-$V^w$-$Z^v$-$P^u$-$M^q$-$A^s$-$L^3$-$P^u$-$Z^v$-$V^w$-$E^x$ (Ib51) wherein s is 0, 1, 2, 5, 6, or 7.

In another specific embodiment the invention provides a compound of the formula (Ib51) wherein at least one of u, v, w or x are not zero.

In another specific embodiment the invention provides a compound of the formula (Ib51) wherein at least two of u, v, w or x are not zero.

In another specific embodiment the invention provides a compound of the formula (Ib51) wherein at least three of u, v, w or x are not zero.

In another specific embodiment the invention provides a compound of the formula (Ib51) wherein at least four of u, v, w or x are not zero.

In another specific embodiment the invention provides a compound of the formula (Ib51) wherein at least two u, v, w or x are not zero and at least two of the non-zero groups are not the same letter.

In another specific embodiment the invention provides a compound of the formula (Ib51) wherein at least three of u, v, w or x are not zero and at least two of the non-zero groups are not the same letter.

In another specific embodiment the invention provides a compound of the formula (Ib51) wherein at least three of u, v, w or x are not zero and at least three of the non-zero groups are not the same letter.

In another specific embodiment the invention provides a compound of the formula (Ib51) wherein at least four of u, v, w or x are not zero and at least two of the non-zero groups are not the same letter.

In another specific embodiment the invention provides a compound of the formula (Ib51) wherein the sum of u, v, w and x is not zero.

In another specific embodiment the invention provides a compound of the formula (Ib51) wherein at least one of u, or w are not zero.

In another specific embodiment the invention provides a compound of the formula (Ib51) wherein at least two of u, or w are not zero.

In another specific embodiment the invention provides a compound of the formula (Ib51) wherein at least one u is not zero, and at least one w is not zero.

In another specific embodiment the invention provides a compound of the formula (Ib51) wherein both u are not zero, and at least one w is not zero.

In another specific embodiment the invention provides a compound of the formula (Ib51) wherein at least one u is not zero.

In another specific embodiment the invention provides a compound of the formula (Ib51) wherein both of u are not zero.

In another specific embodiment the invention provides a compound of the formula (Ib51) wherein at least one of w is not zero.

In another specific embodiment the invention provides a compound of the formula (Ib51) wherein both w are not zero.

In another specific embodiment the invention provides a compound of the following formula (Ib52): $E^x$-$V^w$-$Z^v$-$P^u$-$M^o$-$A^o$-$L^4$-$P^u$-$Z^v$-$V^w$-$E^x$ (Ib52).

In another specific embodiment the invention provides a compound of the formula (Ib52) wherein at least one of u, v, w or x are not zero.

In another specific embodiment the invention provides a compound of the formula (Ib52) wherein at least two of u, v, w or x are not zero.

In another specific embodiment the invention provides a compound of the formula (Ib52) wherein at least three of u, v, w or x are not zero.

In another specific embodiment the invention provides a compound of the formula (Ib52) wherein at least four of u, v, w or x are not zero.

In another specific embodiment the invention provides a compound of the formula (Ib52) wherein at least two u, v, w or x are not zero and at least two of the non-zero groups are not the same letter.

In another specific embodiment the invention provides a compound of the formula (Ib52) wherein at least three of u, v, w or x are not zero and at least two of the non-zero groups are not the same letter.

In another specific embodiment the invention provides a compound of the formula (Ib52) wherein at least three of u, v, w or x are not zero and at least three of the non-zero groups are not the same letter.

In another specific embodiment the invention provides a compound of the formula (Ib52) wherein at least four of u, v, w or x are not zero and at least two of the non-zero groups are not the same letter.

In another specific embodiment the invention provides a compound of the formula (Ib52) wherein the sum of u, v, w and x is not zero.

In another specific embodiment the invention provides a compound of the formula (Ib52) wherein at least one of u, or w are not zero.

In another specific embodiment the invention provides a compound of the formula (Ib52) wherein at least two of u, or w are not zero.

In another specific embodiment the invention provides a compound of the formula (Ib52) wherein at least one u is not zero, and at least one w is not zero.

In another specific embodiment the invention provides a compound of formula (Ib52) wherein both u are not zero, and at least one w is not zero.

In another specific embodiment the invention provides a compound of the formula (Ib52) wherein at least one u is not zero.

In another specific embodiment the invention provides a compound of the formula (Ib52) wherein both of u are not zero.

In another specific embodiment the invention provides a compound of the formula (Ib52) wherein at least one of w is not zero.

In another specific embodiment the invention provides a compound of the formula (Ib52) wherein both w are not zero.

Compounds of formula (Ic)

In one embodiment of the invention, the compound of formula (I) is a compound of formula (Ic):

E-V-Z-P-M-A-A-M-P-Z-V-E     (Ic)

wherein:
each A is selected from -$A^s$;
each M is selected from -$M^t$;
each P is selected from -$P^u$;
each Z is selected from -$Z^v$;
each V is selected from -$V^w$;
each E is selected from -$E^x$;
each s is 0, 1, 2, 3, 4, 5, 6, 7, 8, 9, 10, 11, 12, 13, 14, 15, 16, 17, 18, 19, 20, or 21;
each t is 0, 1, 2, 3, 4, 5, 6, 7, 8, 9, 10, or 11;
each u is 0, 1, 2, 3, 4, 5, 6, 7, 8, 10, 11, 12, 13, or 14;
each v is 0, 1, 2, 3, 4, 5, or 6;
each w is 0, 1, 2, 3, 4, 5, 6, 7, 8, 9, 10, 11, 12, 13, 14, 15, 16, 17, 18, 19, 20 or 21;
each x is 0 or 1;
wherein the sum of s, t, u, v, w, and x is not 0;
each $A^0$ is independently:

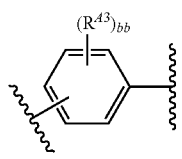

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or
each $A^0$ is independently a six-membered heteroaromatic ring containing one, two, or three nitrogen atoms, which ring is optionally substituted with 1, 2, 3, or 4 $R^{43}$ groups;
each $A^1$ is independently:

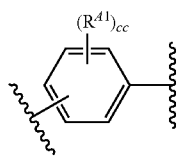

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each cc is independently 1, 2, 3, or 4;

each $A^2$ is independently:

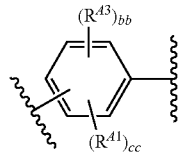

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each bb is 0, 1, 2, 3, or 4; each cc is 1, 2, 3, or 4; and the sum of bb and cc is 1, 2, 3, or 4;
each $A^3$ is independently a six-membered heteroaromatic ring containing one, two, or three nitrogen atoms, which ring is substituted with one or more $R^{41}$ groups, and which ring is optionally substituted with one or more $R^{43}$ groups;
each $A^4$ is independently:

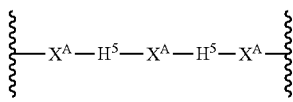

wherein:
each $H^5$ is independently a phenyl ring or a six-membered heteroaromatic ring, which $H^5$ is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent
each $A^5$ is independently:

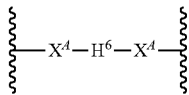

wherein:
each $H^6$ is independently a phenyl ring or a six-membered heteroaromatic ring, which $H^6$ is optionally substituted with one or more groups independently selected from $R^{41}$ and $R^{43}$; and each $X^A$ is independently O, NR, SO, SO$_2$, C(=O), NRC(=O), C(=O)NR, CR=CR, NRC(=O)NR, allenyl, alkynyl, or absent; provided that at least one X$^A$ is present;

each A$^6$ is independently:

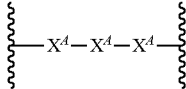

wherein:
each X$^A$ is independently O, NR, SO, SO$_2$, C(=O), NRC(=O), C(=O)NR, CR=CR, allenyl, alkynyl, or absent; provided that at least one X$^A$ is present;

each A$^7$ is independently:

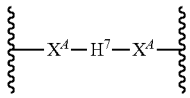

wherein:
each H$^7$ is independently a five-membered heteroaromatic ring, which H$^7$ is optionally substituted with one or more groups independently selected from R$^{41}$ and R$^{43}$; and
each X$^A$ is independently O, NR, SO, SO$_2$, C(=O), NRC(=O), C(=O)NR, CR=CR, NRC(=O)NR, allenyl, alkynyl, or absent;

each A$^8$ is independently:

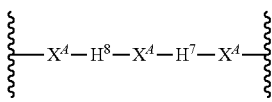

wherein:
each H$^7$ is independently a five-membered heteroaromatic ring, which H$^7$ is optionally substituted with one or more groups independently selected from R$^{41}$ and R$^{43}$;
each H$^8$ is independently a phenyl ring, which is optionally substituted with one or more groups independently selected from R$^{41}$ and R$^{43}$; and
each X$^A$ is independently O, NR, SO, SO$_2$, C(=O), NRC(=O), C(=O)NR, CR=CR, NRC(=O)NR, allenyl, alkynyl, or absent;

each A$^9$ is independently:

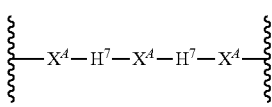

wherein:
each H$^7$ is independently a five-membered heteroaromatic ring, which H$^7$ is optionally substituted with one or more groups independently selected from R$^{41}$ and R$^{43}$; and
each X$^A$ is independently O, NR, SO, SO$_2$, C(=O), NRC(=O), C(=O)NR, CR=CR, NRC(=O)NR, allenyl, alkynyl, or absent;

each A$^{10}$ is independently:

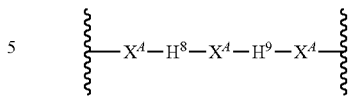

wherein:
each H$^8$ is independently a phenyl ring, which is optionally substituted with one or more groups independently selected from R$^{41}$ and R$^{43}$;
each H$^9$ is independently a six-membered heteroaromatic ring, which is optionally substituted with one or more groups independently selected from R$^{41}$ and R$^{43}$; and
each X$^A$ is independently O, NR, SO, SO$_2$, C(=O), NRC(=O), C(=O)NR, CR=CR, NRC(=O)NR, allenyl, alkynyl, or absent each A$^H$ is independently:

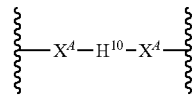

wherein:
each X$^A$ is independently O, NR, SO, SO$_2$, C(=O), NRC(=O), C(=O)NR, CR=CR, NRC(=O)NR, allenyl, alkynyl, or absent;
each H$^{10}$ is independently a 5-15 carbon unsaturated, partially unsaturated or saturated bicyclic ring system that is optionally fused to an aryl, which H$^{10}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each R$^4$ is independently selected from H, alkyl, haloalkyl, aryl, and arylalkyl each A$^{12}$ is independently:

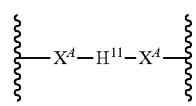

wherein:
each X$^A$ is independently O, NR, SO, SO$_2$, C(=O), NRC(=O), C(=O)NR, CR=CR, NRC(=O)NR, allenyl, alkynyl, or absent;
each H$^{11}$ is independently a 5-15 carbon unsaturated, partially unsaturated or saturated bicyclic ring system that contains one or more heteroatoms that is optionally fused to an aryl, which H$^{11}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
each $R^4$ is independently selected from H, alkyl, haloalkyl, aryl, and arylalkyl; and
each $A^{13}$ is independently:

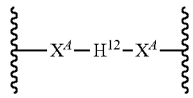

wherein:
each $H^{12}$ is independently a fused aromatic bicyclic carbocycle, which is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{14}$ is independently:

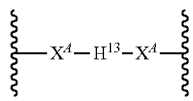

wherein:
each $H^{13}$ is independently a fused aromatic bicyclic heterocycle that comprises at least one heteroatom in the ring system, which ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{15}$ is independently:

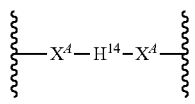

wherein:
each $H^{14}$ is independently a fused unsaturated, partially unsaturated or saturated tricyclic carbocycle which is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{16}$ is independently:

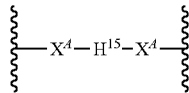

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{17}$ is independently:

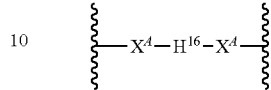

wherein:
each $H^{16}$ is independently a fused bicyclic carbocyclic ring system wherein one ring is aromatic and another ring is partially or fully saturated, which ring system is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{18}$ is independently:

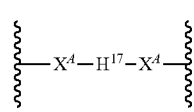

wherein:
each $H^{17}$ is independently a fused bicyclic ring system comprising at least one heteroatom, wherein one ring is aromatic and another ring is partially or fully saturated, which ring system is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $A^{21}$ is independently:

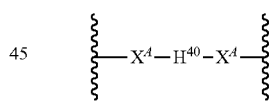

wherein:
each $H^{40}$ is independently an anti-aromatic monocyclic or fused carbocyclic ring system, which carbocyclic ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent;
each $M^0$ is independently a five membered heteroaryl group optionally substituted with one or more alkoxycarbonyl, alkyl, arylalkoxycarbonyl, carboxy, haloalkyl, $(NR^aR^b)$carbonyl and trialkylsilylalkoxyalkyl;
each $M^1$ is independently selected from —C(=O)NH—, —C(=O)NH—C($R^M$)$_2$—, —NHC(=O)—, —C($R^M$)$_2$NHC(=O)—, —NHC(=O)N$R^M$—, —NHC(=O)O—; wherein each $R^M$ is independently selected from H and alkyl;
each $M^2$ is independently a six-membered heteroaromatic ring, which is optionally substituted with one or more groups independently selected from $R^{A1}$ and $R^{A3}$;

each M³ is independently:

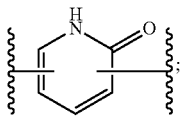

each M⁴ is independently:

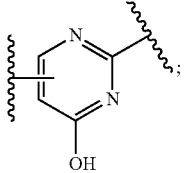

each M⁵ is independently:

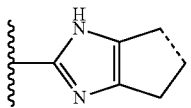

wherein the bond designated with - - - is fused to a ring defined for P;

each M⁶ is independently a bicyclic bridged ring system comprising 5-15 atoms wherein at least one of the atoms is a heteroatom;

each M⁷ is independently a pyrid-di-yl;

each M⁸ is independently partially saturated or a saturated five-membered ring that comprises one or more heteroatoms and that is optionally substituted with one or two oxo;

each M⁹ is independently a fused-bicyclic saturated, partially unsaturated, or aromatic heterocyclic ring system that is optionally substituted with one or more $R^{P11}$;

each M¹⁰ is independently a five membered heteroaryl group;

each M¹¹ is independently a fused-tricyclic saturated, partially unsaturated, or aromatic heterocyclic ring system that is optionally substituted with one or more oxo halo, —$R^{M7}$, —$OR^{M7}$, —$SR^{M7}$, —$N(R^{M7})_2$, —$CF_3$, —$CCl_3$, —$OCF_3$, —CN, —$NO_2$, —$N(R^{M7})C(=O)R^{M7}$, —$C(=O)R^{M7}$, —OC(=O)$R^{M7}$, —C(O)O$R^{M7}$, —$C(=O)NR^{M7}$, —$S(=O)R^{M7}$, —$S(=O)_2OR^{M7}$, —$S(=O)_2R^{M7}$, —$OS(=O)_2OR^{M7}$, or —$S(=O)_2NR^{M7}$;

each $R^{M7}$ is independently —H, alkyl, aryl, arylalkyl, or heterocycle;

each P⁰ is independently:

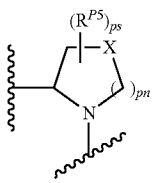 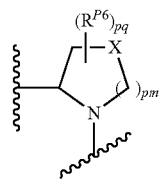

-continued

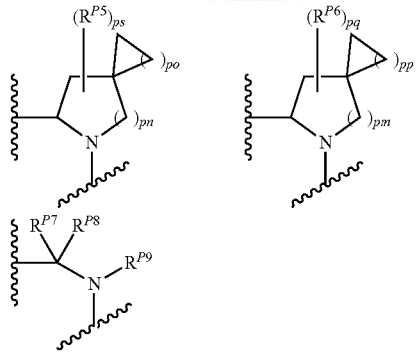

wherein:
X is selected from O, S, S(O), SO₂, CH₂, CHR$^{P10}$, and C(R$^{P10}$)₂; provided that when pn or pm is 0, X is selected from CH₂, CHR$^{P10}$, and C(R$^{P10}$)₂;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;

each P¹ is independently:

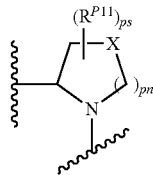

wherein:
X is selected from O, S, S(O), SO₂, CH₂, CHR$^{P10}$, and C(R$^{P10}$)₂; provided that when pn is 0, X is selected from CH₂, CHR$^{P10}$, and C(R$^{P10}$)₂;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl, wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^2$ is independently:

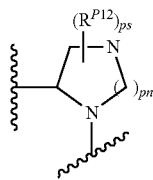

wherein:
each $R^{P12}$ is independently selected from $R^{P5}$, $R^{P11}$, $-C(=O)OR^h$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

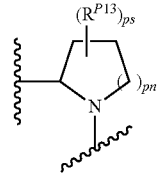

wherein:
the ring is substituted with one or more oxo groups;
each $R^{P10}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;
each $P^4$ is independently a ring of the formula:

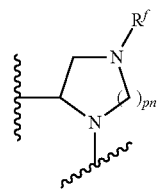

wherein:
the ring is optionally substituted with one or more groups $R^{P14}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P14}$ that are attached to the same carbon when taken together with the carbon to which they are attached can form a 3-6 membered carbocyclic or heterocyclic ring;
pn is 0, 1, or 2;
each $R^f$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^5$ is independently a ring of the formula:

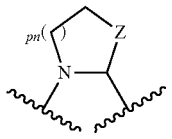

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;

pn is 0, 1, or 2;

Z is O, S, S(=O), S(=O)$_2$, or $NR^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2R^h$, C(=O)$R^h$, C(=O)$OR^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

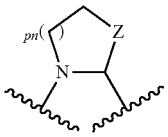

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

Z is O, S, S(=O), S(=O)$_2$, or $NR^f$;

pn is 0, 1, or 2;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2R^h$, C(=O)$R^h$, C(=O)$OR^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

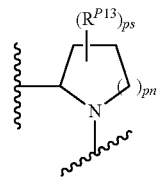

wherein:
ps is 2, 3, 4, 5, or 6;
pn is 0, 1 or t;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

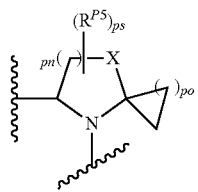 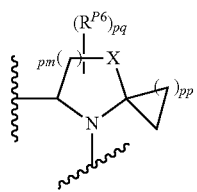

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;

each P¹¹ is independently:

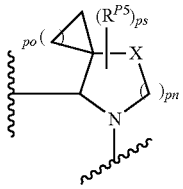 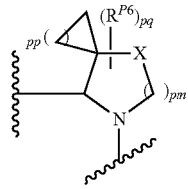

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each P¹² is independently:

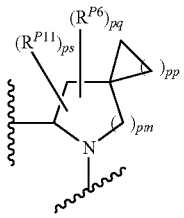

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
each P¹³ is independently:

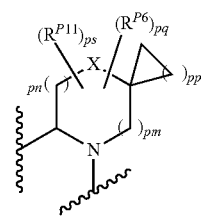

wherein:
X is selected from O, S, S(O), SO$_2$, or NR$^h$;
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm and pn are independently 0, 1, or 2 but the sum of pn and pm is greater than zero;
pp are independently 1, 2, or 3;
ps is 1, 2, 3, or 4;
each R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$(NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$, R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{14}$ is independently:

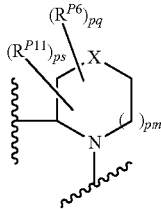

wherein:

the ring is substituted with one or more oxo group;

X is NR$^f$;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq is independently 0, 1, 2, 3, or 4;

pm is independently 0, 1, or 2;

ps is 1, 2, 3, or 4;

R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, NR$^h$R$^h$alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two R$^h$ groups are present then they may come together with the atoms to which they are bound to form a 4-15 membered heterocyclic ring;

each -Z$^0$— is —C(=O)— or —C(=S)—;

each —Z$^1$— is independently a bond, or —C(R$^{Z1}$)$_2$—; wherein each R$^{Z1}$ is independently H, alkyl, haloalkyl, or halo;

each —Z$^2$— is independently saturated or partially unsaturated (C$_3$-C$_8$)cycloalkyl that is optionally substituted with one or more groups independently selected from R$^{A1}$ and R$^{A3}$;

each —Z$^3$— is independently saturated, partially unsaturated, or aromatic 4-8 membered heterocyclic or heteroaryl ring that is optionally substituted with one or more groups independently selected from R$^{A1}$ and R$^{A3}$;

each —Z$^4$— is independently:

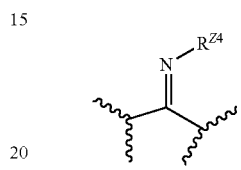

wherein each R$^{Z4}$ is independently H, alkyl, cyano, aryl, or heteroaryl;

each —Z$^5$— is independently:

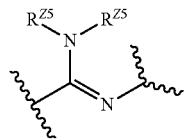

wherein each R$^{Z5}$ is independently H, alkyl, cyano, aryl, or heteroaryl; or two R$^{Z5}$s together with the nitrogen to which they are attached form a 4-8 membered heterocyclic ring that is optionally substituted with one or more oxo and with one or more groups independently selected from R$^{A1}$ and R$^{A3}$;

each —Z$^6$— is independently —C(R$^{Z1}$)— and is double-bonded to P; wherein R$^{Z1}$ is independently H, alkyl, haloalkyl, or halo;

each E$^0$ is independently —NR$^{Ee}$R$^{Ed}$ wherein

R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently —OC(=O)NR$^{Ee}$R$^{Ef}$ wherein each R$^{Ee}$ and R$^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein R$^{Ee}$ and R$^{Ef}$, together with the nitrogen atom to which they are attached, form a heterocycle;

each $V^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and wherein arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $V^1$ is independently cyanoalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and NRaRbC(=O)O—; Ra and Rb are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^6$ is independently arylsulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^8$ is independently spirocycloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^{10}$ is independently fused bicycliccycloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^{11}$ is independently fused bicycliccycloalkylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each $V^{12}$ is independently bridged-bicycliccycloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{13}$ is independently bridged-bicyclic-cycloalkylalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{14}$ is independently aryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{18}$ is independently heterocyclooxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl;

each $V^{20}$ is independently heteroaryloxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl; and each $V^{21}$ is independently heteroarylalkylalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}C(=O)O—$; $R^{Va}$ and $R^{Vb}$ are each independently selected from hydrogen, alkenyl, and alkyl.

In another specific embodiment of the invention the compound of formula (Ic) comprises: $M^0$-A-A-$M^0$, $M^0$-A-A-$M^9$, $M^9$-A-A-$M^0$, or $M^9$-A-A-$M^9$, $M^{10}$-A-A-$M^0$, $M^0$-A-A-$M^{10}$, $M^{10}$-A-A-$M^9$, $M^9$-A-A-$M^{10}$, or $M^{10}$-A-A-$M^{10}$.

In another specific embodiment of the invention -A-A- is -$A^0$-$A^5$-.

In another specific embodiment of the invention -A-A- is -$A^0$-$A^{13}$-.

In another specific embodiment of the invention -A-A- is -$A^{13}$-$A^{13}$-.

In another specific embodiment of the invention -A-A- is -$A^0$-$A^{11}$-.

In another specific embodiment of the invention -A-A- is -$A^{13}$-$A^6$-.

In another specific embodiment of the invention one A is $A^0$ and one A is $A^5$, wherein one $X^A$ in the $A^5$ is absent and the other $X^A$ in the $A^5$ is alkynyl.

In another specific embodiment of the invention -$A^0$-$A^5$- has the following structure:

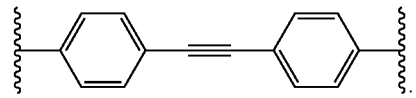

In another specific embodiment of the invention one A is $A^0$ and one A is $A^{13}$, wherein both $X^A$ in the $A^{13}$ are absent.

In another specific embodiment of the invention -$A^0$-$A^{13}$- has the following structure:

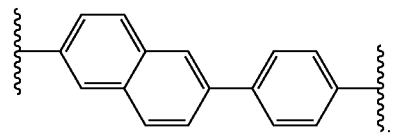

In another specific embodiment of the invention A-A is $A^{13}$-$A^{13}$, wherein all $X^A$ in both $A^{13}$ are absent.

In another specific embodiment of the invention -$A^{13}$-$A^{13}$- has the following structure:

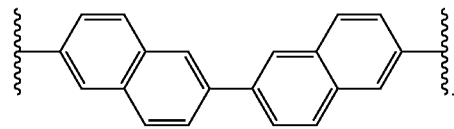

In another specific embodiment of the invention A-A- is $A^0$-$A^{11}$ wherein all $X^A$ in both the $A^0$ and the $A^{11}$, are absent or alkynyl.

In another specific embodiment of the invention -$A^0$-$A^{11}$- has the following structure:

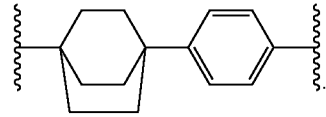 [SMILES: *c1ccc(C23CCC(*)(CC2)CC3)cc1]

In another specific embodiment of the invention the compound of formula (Ic) comprises one $A^{13}$ and one $A^6$ wherein all $X^A$ in the $A^{13}$ are absent.

In another specific embodiment of the invention -A$^{13}$-A$^6$- has the following structure:

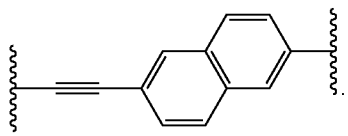 [SMILES: *C#Cc1ccc2cc(*)ccc2c1]

In another specific embodiment of the invention M$^0$ is imidazolyl and M$^9$ is benzimidazolyl.

In another specific embodiment of the invention the compound of formula (Ic) comprises two A$^0$ and one M is M$^9$.

In another specific embodiment of the invention the compound of formula (Ic) comprises two A$^0$ and one M is M$^0$ and another M is M$^9$.

In another specific embodiment of the invention the compound of formula (Ic) comprises A$^0$-A$^0$-M$^9$ which has the following structure:

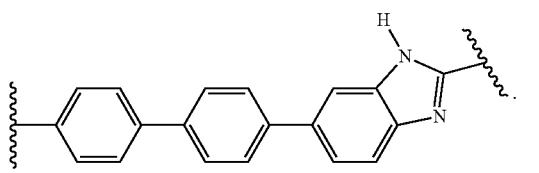 [SMILES: *c1ccc(-c2ccc(-c3ccc4nc(*)[nH]c4c3)cc2)cc1]

In another specific embodiment of the invention the compound of formula (Ic) comprises M$^0$-A$^0$-A$^0$-M$^9$.

In another specific embodiment of the invention M$^0$-A$^0$-A$^0$-M$^9$ has the following structure:

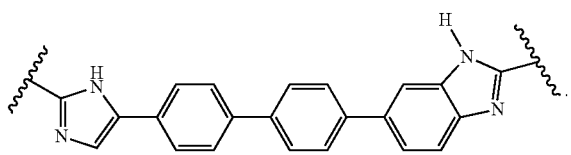 [SMILES: *c1ncc(-c2ccc(-c3ccc(-c4ccc5nc(*)[nH]c5c4)cc3)cc2)[nH]1]

In another specific embodiment of the invention the compound of formula (Ic) comprises A$^0$-A$^7$-M$^9$.

In another specific embodiment of the invention A$^0$-A$^7$-M$^9$ has the following structure:

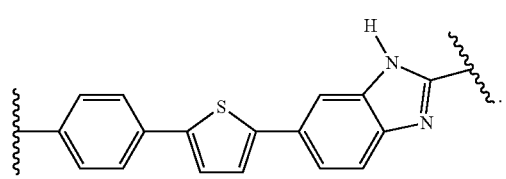 [SMILES: *c1ccc(-c2ccc(-c3ccc4nc(*)[nH]c4c3)s2)cc1]

In another specific embodiment of the invention the compound of formula (Ic) comprises one or two M and each M is M$^0$.

In another specific embodiment of the invention the compound of formula (Ic) comprises one or two M and each M is imidazolyl.

In another specific embodiment of the invention the compound of formula (Ic) comprises one or two M and each M is M$^9$.

In another specific embodiment of the invention the compound of formula (Ic) comprises one or two M and each M is benzimidazolyl.

In another specific embodiment of the invention the compound of formula (Ic) comprises two M wherein one M is M$^0$ and one M is M$^9$.

In another specific embodiment of the invention the compound of formula (Ic) comprises two M wherein one M is imidazolyl and one M is benzimidazolyl.

In another specific embodiment of the invention A-A is selected from:

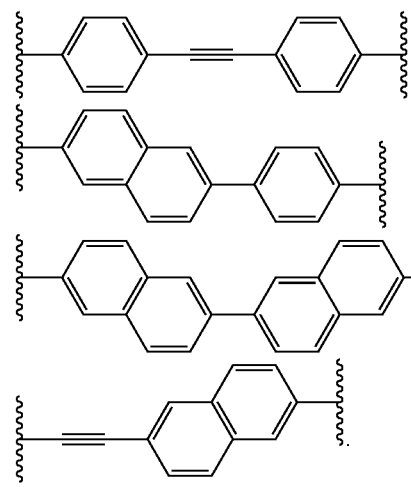

and

In another specific embodiment of the invention -M-A-A-M- is selected from M$^0$-A-A-M$^0$, M$^0$-A-A-M$^9$, M$^9$-A-A-M$^0$, and M$^9$-A-A-M$^9$.

In another specific embodiment of the invention the compound of formula (Ic) M-A-A-M is selected from M$^{10}$-A-A-M$^0$, M$^0$-A-A-M$^{10}$, M$^{10}$-A-A-M$^9$, M$^9$-A-A-M$^{10}$, and M$^{10}$-A-A-M$^{10}$.

In another specific embodiment of the invention each M is independently a 5-membered heteroaryl ring.

In another specific embodiment of the invention each M is 2,4-imidazoldiyl.

In another specific embodiment of the invention M is M$^6$.

In another specific embodiment of the invention M is selected from:

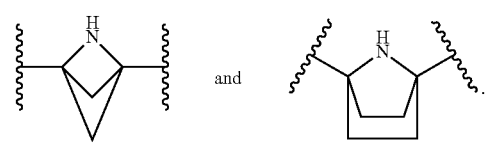 [SMILES: *C12CC(*)(C1)N2 ; *C12CCC(*)(CC1)N2]

In another specific embodiment of the invention M is M$^7$.

In another specific embodiment of the invention M is:

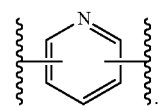

In another specific embodiment of the invention M is M$^8$.

In another specific embodiment of the invention M is selected from the group consisting of:

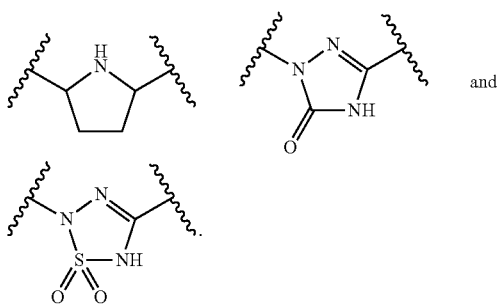

In another specific embodiment of the invention $M^0$ is:

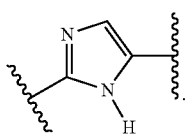

In another specific embodiment of the invention M is $M^9$ which is:

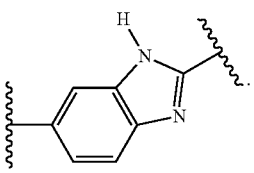

In another specific embodiment of the invention the sum of s, t, u, v, w, and x is not 0;

In another specific embodiment of the invention at least two of s, t, u, v, w, and x are other than 0.

In another specific embodiment of the invention at least three of s, t, u, v, w, and x are other than 0.

In another specific embodiment of the invention at least four of s, t, u, v, w, and x are other than 0.

In another specific embodiment of the invention at least five of s, t, u, v, w, and x are other than 0.

In another specific embodiment of the invention the compound of formula (Ic) is a compound of formula (Ic1): $E^0$-$V^0$-$Z^0$-P-M-$Z^{13}$-$A^6$-M-P-$Z^0$-$V^0$-$E^0$ (Ic1) or a pharmaceutically acceptable salt, or prodrug thereof.

In another specific embodiment of the invention the compound of formula (Ic) is a compound of formula (Ic2): $E^0$-$V^0$-$Z^0$-P-$M^9$-$A^{13}$-$A^6$-M-P-$Z^0$-$V^0$-$E^0$ (Ic2) or a pharmaceutically acceptable salt, or prodrug thereof.

In another specific embodiment of the invention the compound of formula (Ic) is a compound of formula (Ic3): $E^0$-$V^0$-$Z^0$-P-$M^{10}$-$A^{13}$-$A^6$-M-P-$Z^0$-$V^0$-$E^0$ (Ic3) or a pharmaceutically acceptable salt, or prodrug thereof.

In another specific embodiment of the invention the compound of formula (Ic) is a compound of formula (Ic4): $E^0$-$V^0$-$Z^0$-P-$M^{11}$-$A^{13}$-$A^6$-M-P-$Z^0$-$V^0$-$E^0$ (Ic4) or a pharmaceutically acceptable salt, or prodrug thereof.

In another specific embodiment of the invention the compound of formula (Ic) is a compound of formula (Ic5): $E^0$-$V^0$-$Z^0$-P-$M^0$-$A^{13}$-$A^0$-M-P-$Z^0$-$V^0$-$E^0$ (Ic5) or a pharmaceutically acceptable salt, or prodrug thereof.

In another specific embodiment of the invention the compound of formula (Ic) is a compound of formula (Ic6): $E^0$-$V^0$-$Z^0$-P-$M^9$-$A^{13}$-$A^0$-M-P-$Z^0$-$V^0$-$E^0$ (Ic6) or a pharmaceutically acceptable salt, or prodrug thereof.

In another specific embodiment of the invention the compound of formula (Ic) is a compound of formula (Ic7): $E^0$-$V^0$-$Z^0$-P-$M^{10}$-$A^{13}$-$A^0$-M-P-$Z^0$-$V^0$-$E^0$ (Ic7) or a pharmaceutically acceptable salt, or prodrug thereof.

In another specific embodiment of the invention the compound of formula (Ic) is a compound of formula (Ic8): $E^0$-$V^0$-$Z^0$-P-$M^{11}$-$A^{13}$-$A^0$-M-P-$Z^0$-$V^0$-$E^0$ (Ic8) or a pharmaceutically acceptable salt, or prodrug thereof.

In another specific embodiment of the invention $A''$-$A^0$ is:

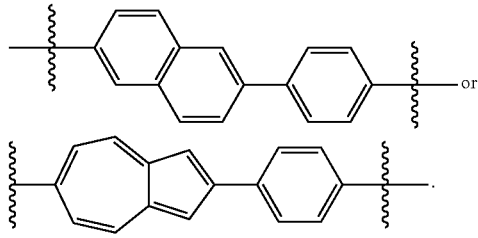

In another specific embodiment of the invention the compound of formula (Ic) is:

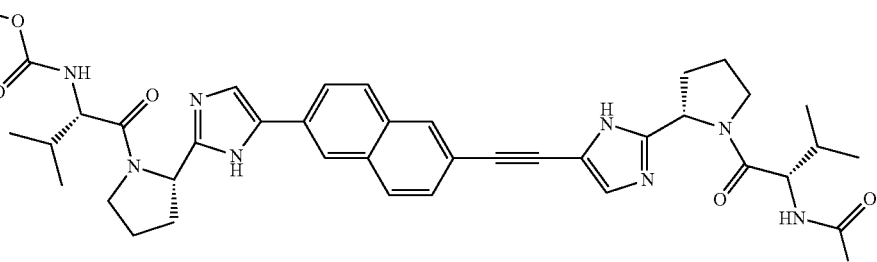

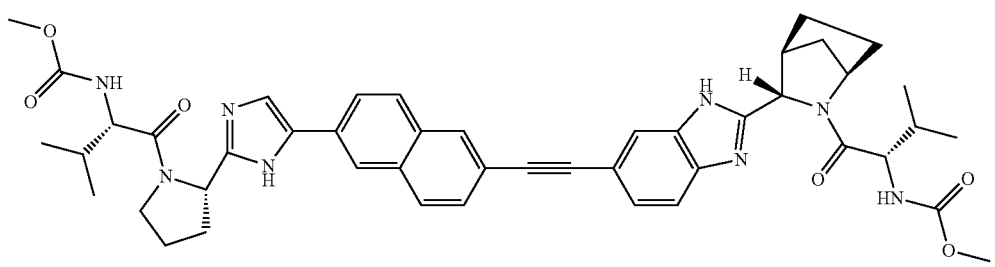

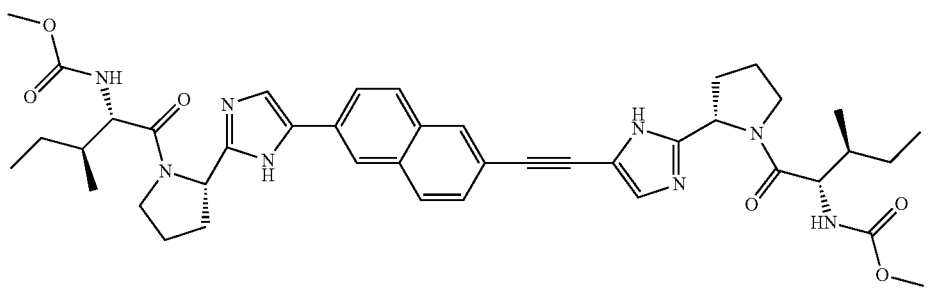
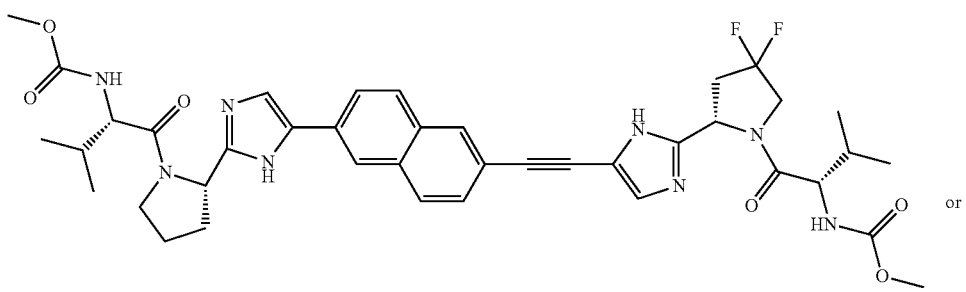
or
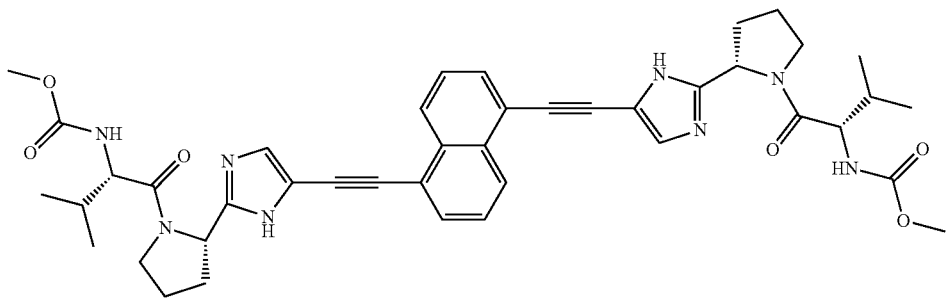
or a pharmaceutically acceptable salt, or prodrug thereof.
In another specific embodiment of the invention the compound of formula (Ic) is:
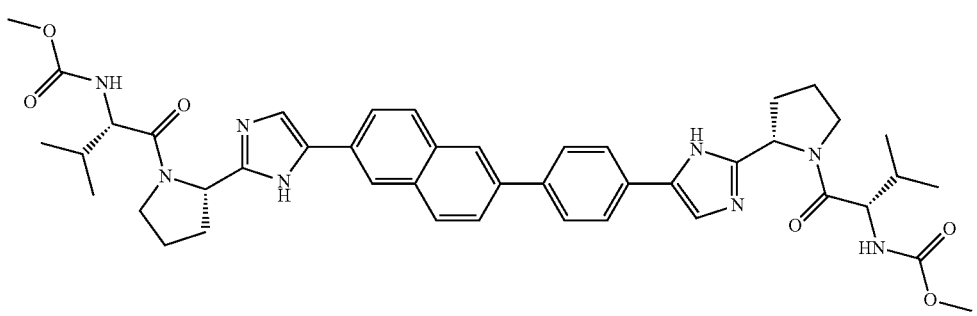

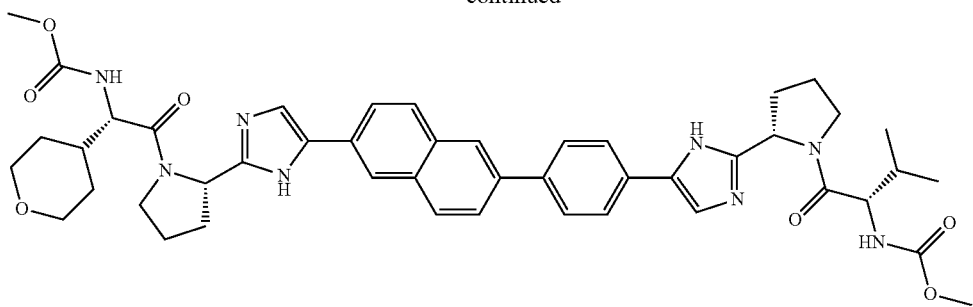
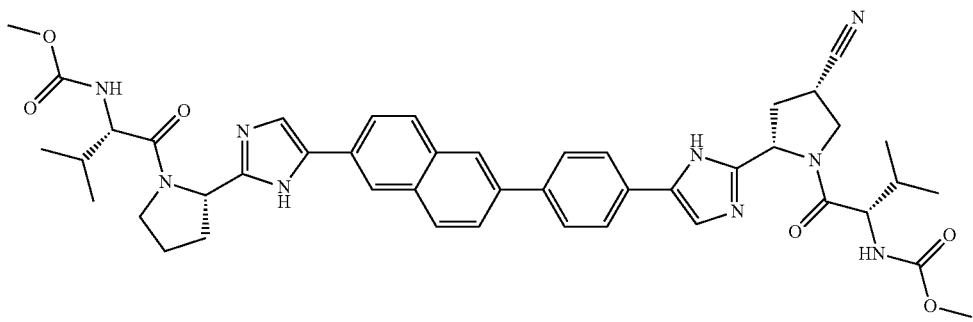
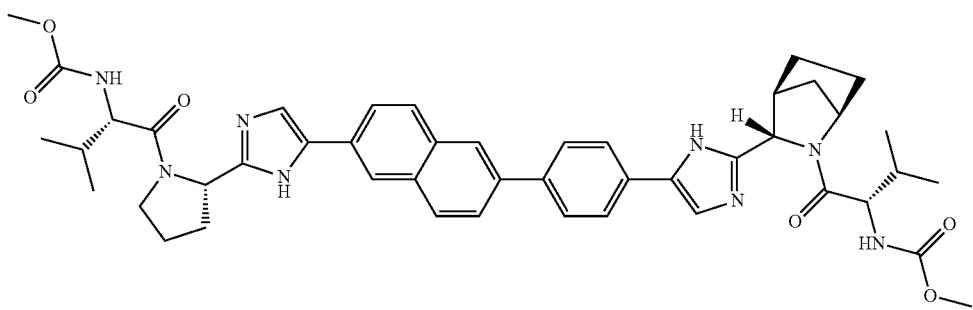
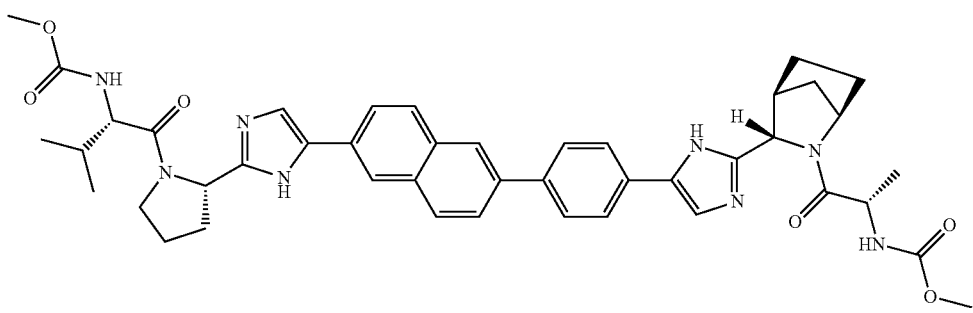
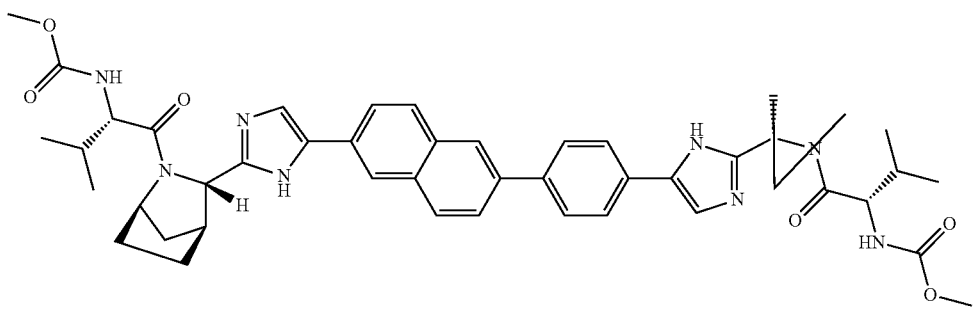

-continued
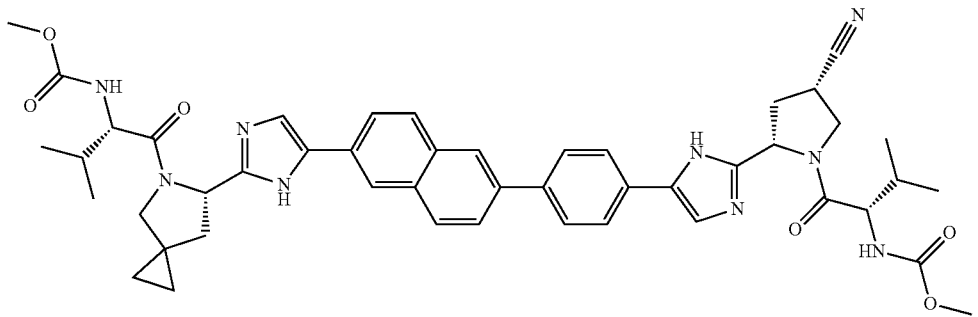
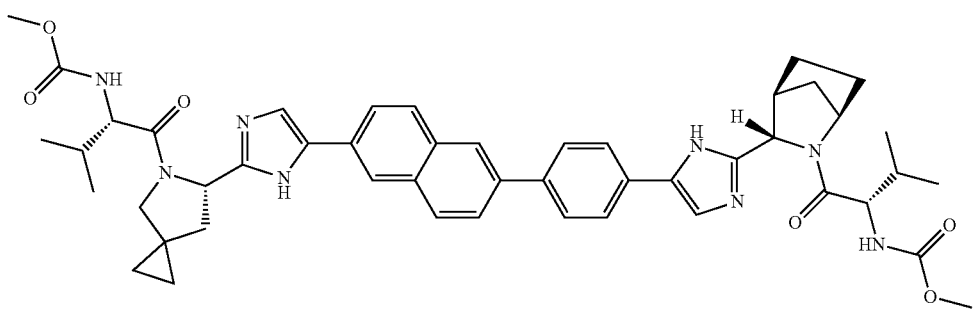
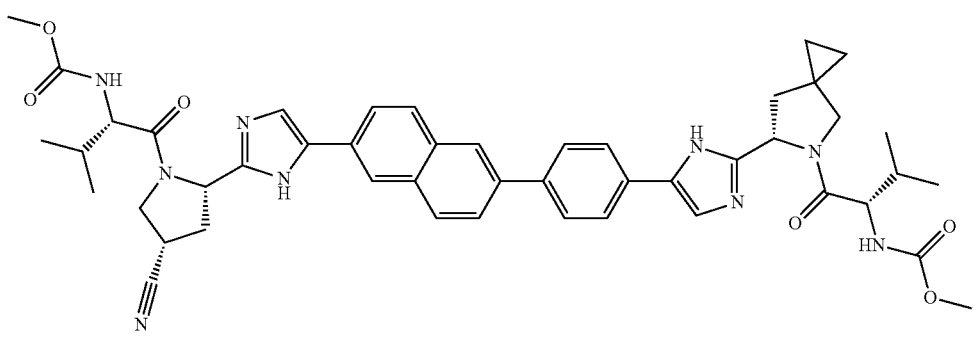
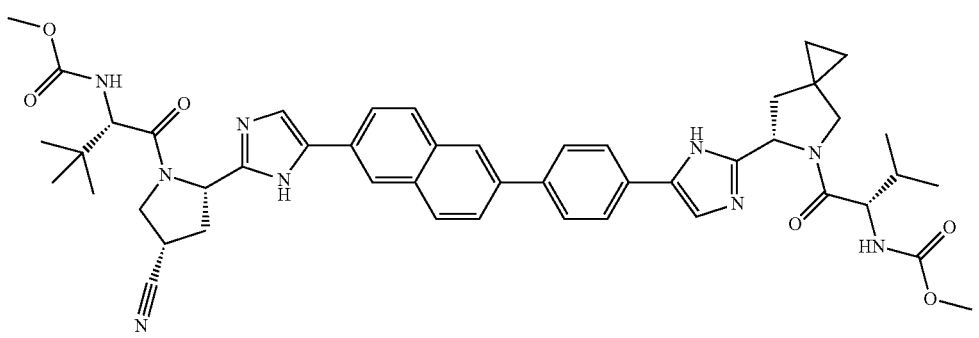
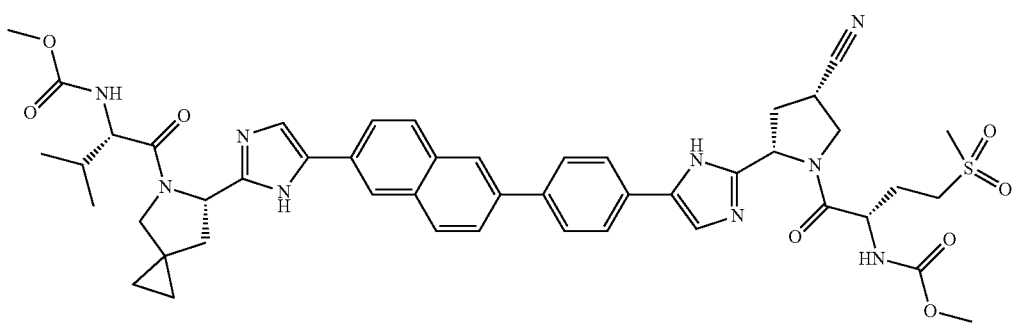

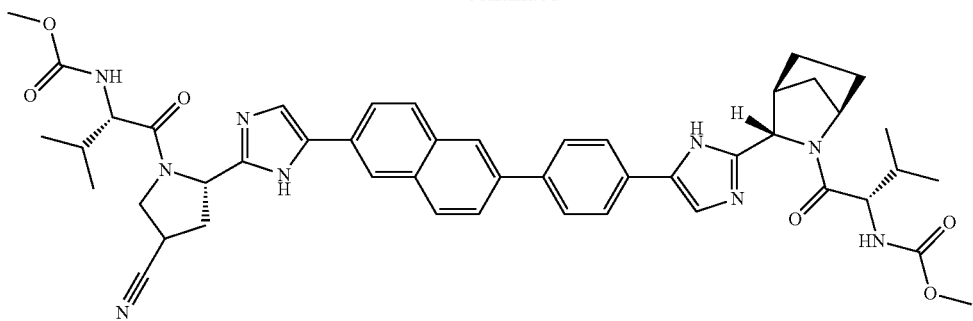
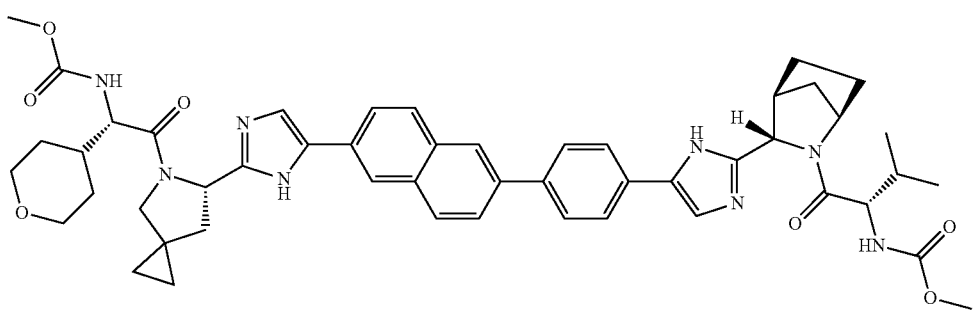
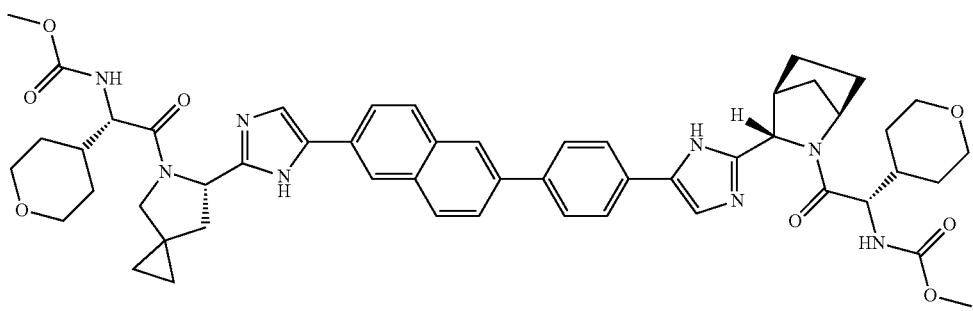
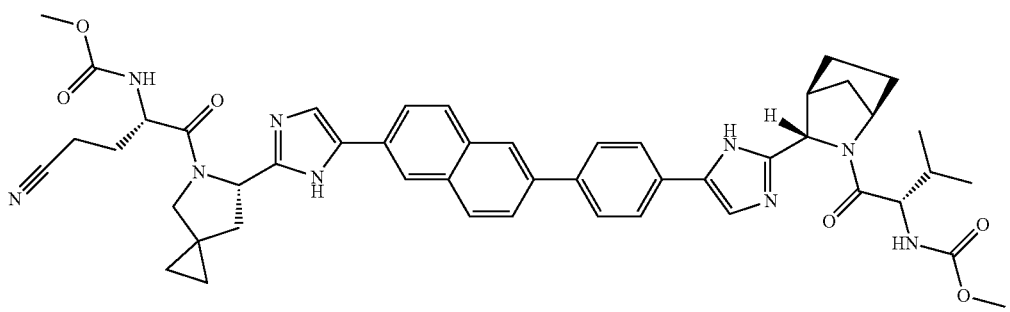
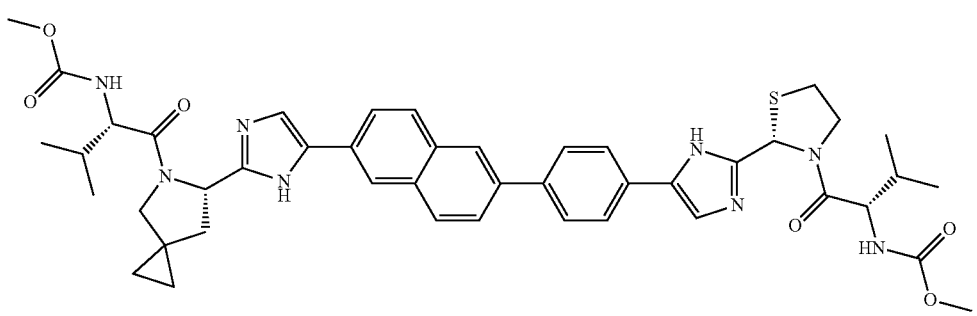

-continued
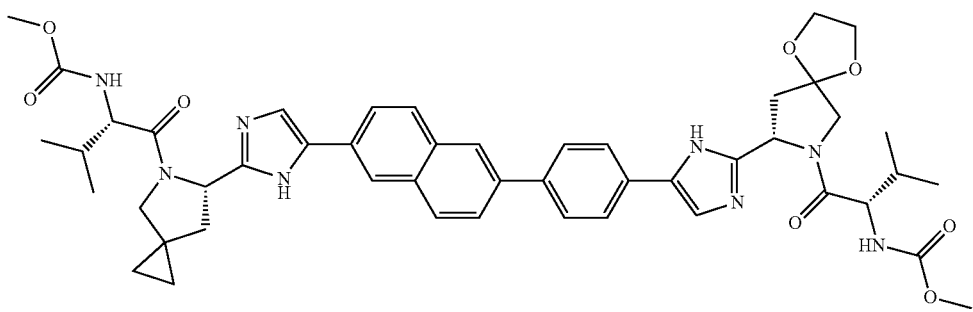
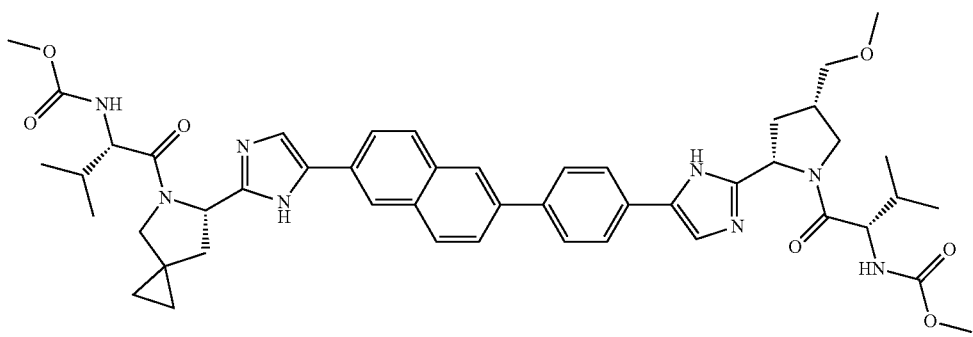
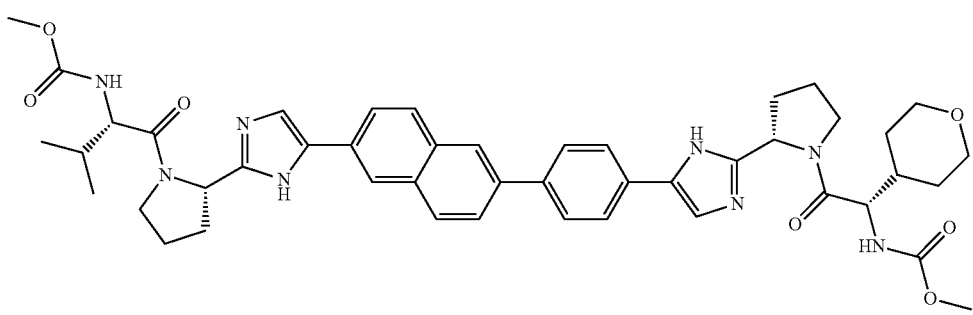
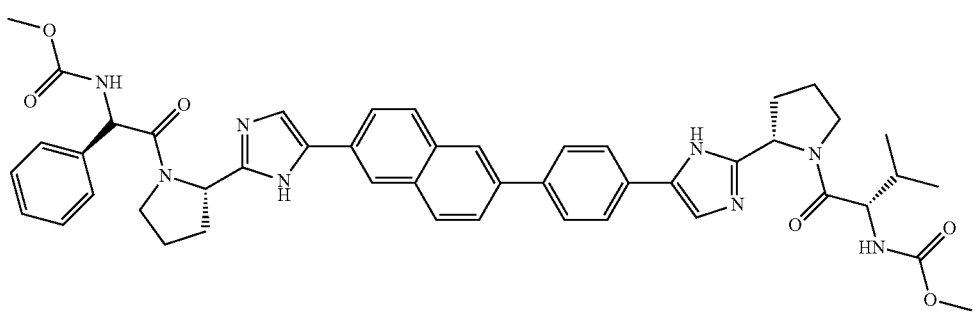
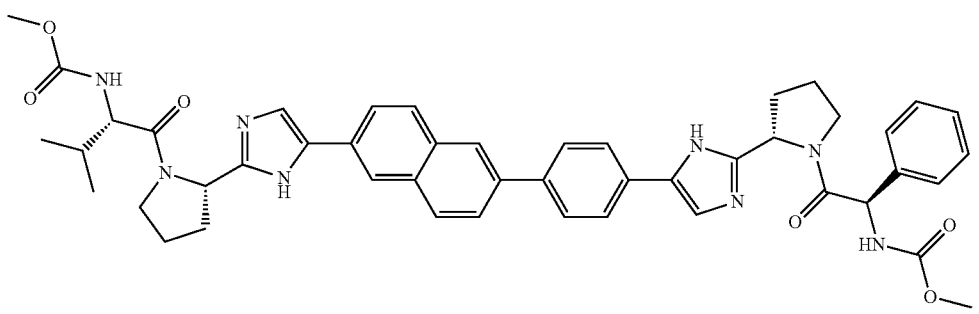

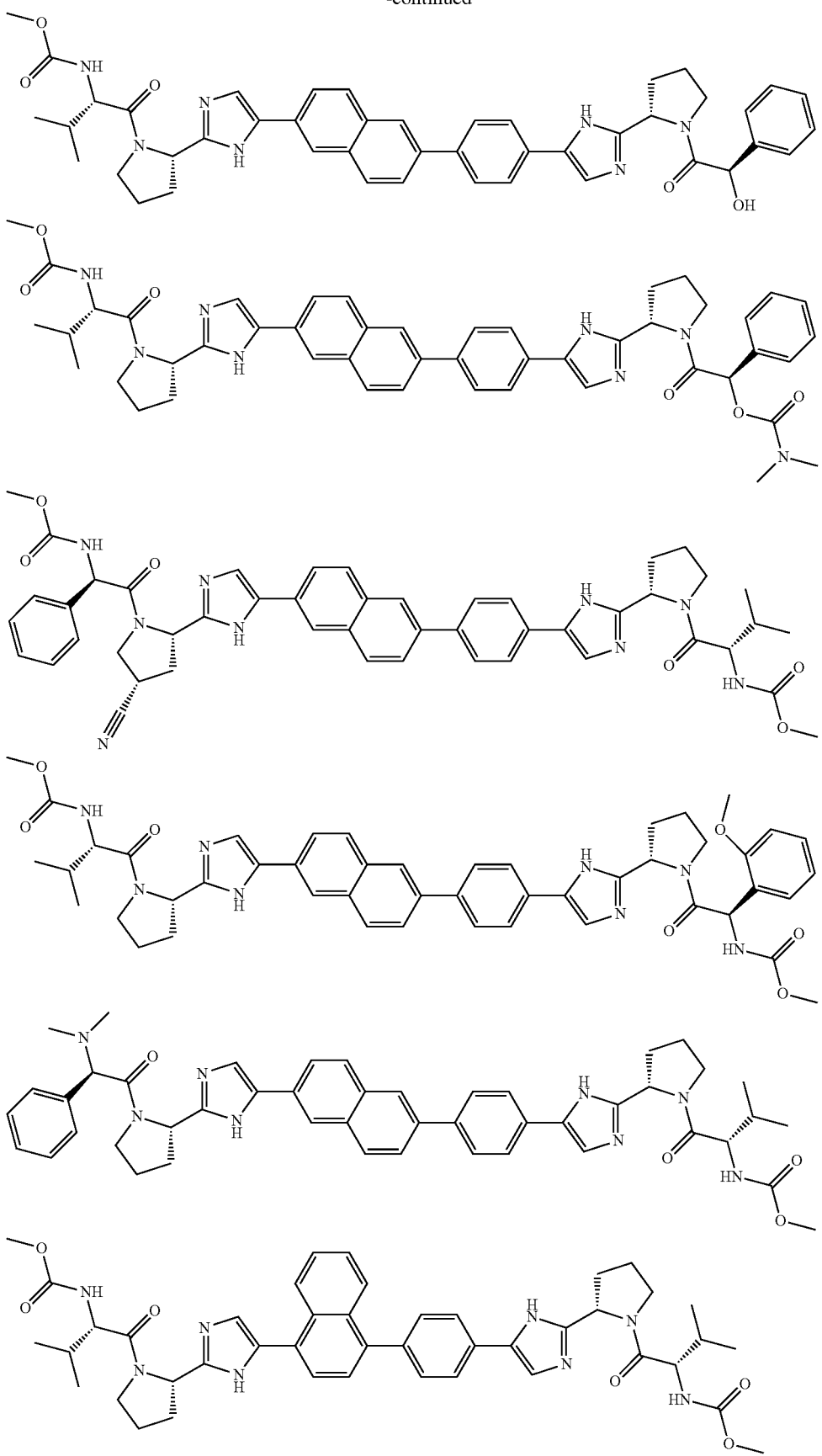

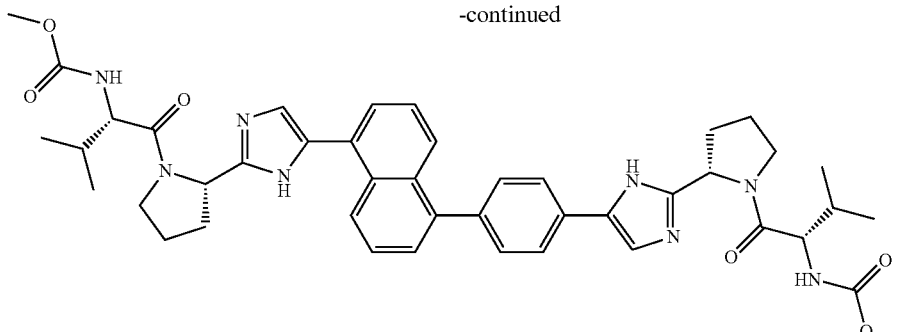

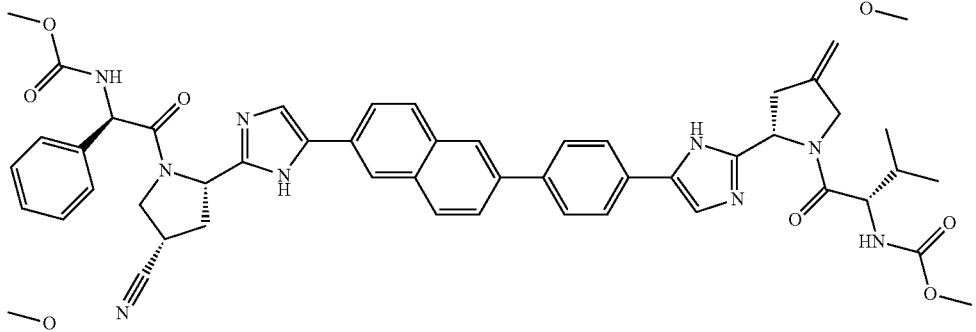

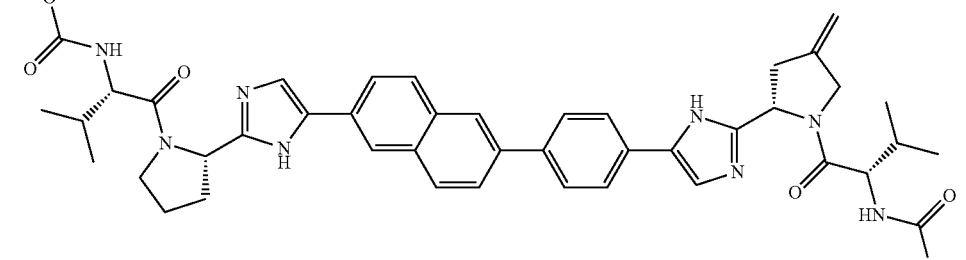

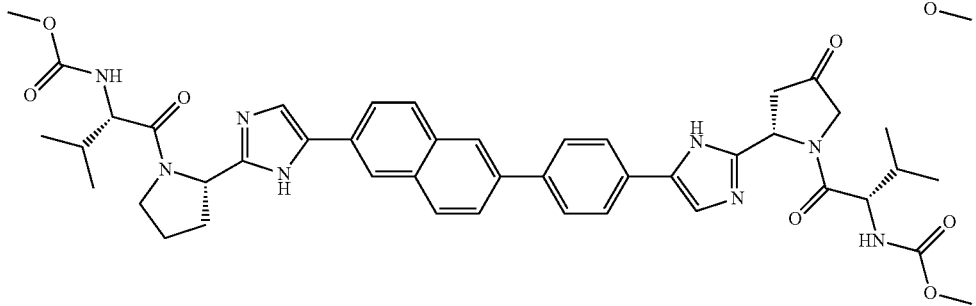

or a pharmaceutically acceptable salt, or prodrug thereof.

In another specific embodiment of the invention the compound of formula (Ic) is a compound of formula (Ic9):

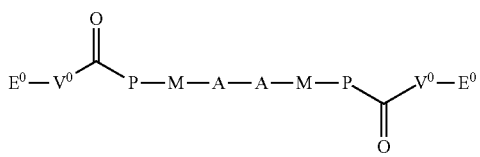

(Ic9)

or a pharmaceutically acceptable salt, or prodrug thereof.

In another specific embodiment of the invention the compound of formula (Ic) is a compound of formula (Ic10):

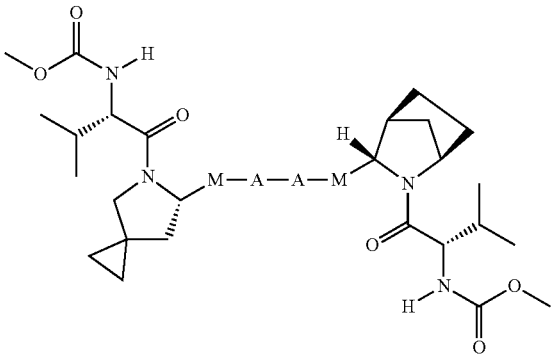

(Ic10)

or a pharmaceutically acceptable salt, or prodrug thereof.

In another specific embodiment of the invention the compound of formula (Ic) is a compound of formula (Ic11):

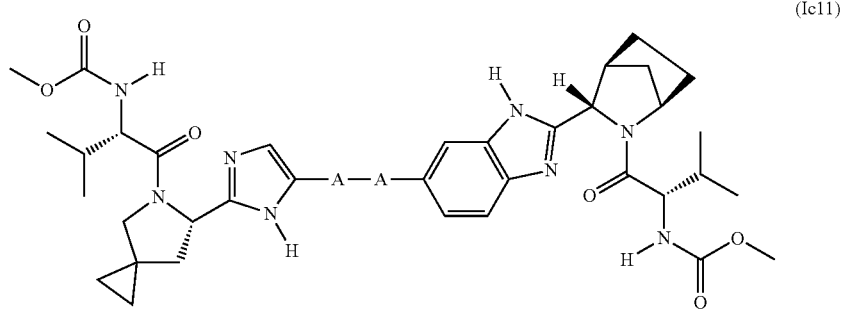

(Ic11)

or a pharmaceutically acceptable salt, or prodrug thereof.

In another specific embodiment of the invention the compound of formula (Ic) is a compound of formula (Ic9), (Ic10), or (Ic11) wherein -A-A- is -$A^{13}$-$A^6$-.

In another specific embodiment of the invention the compound of formula (Ic) is a compound of formula (Ic9), (Ic10), or (Ic11) wherein -A-A- is -$A^{13}$-$A^0$-.

In one embodiment of the invention, the compound of formula (I) is a compound of formula (Ic12):

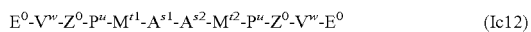

(Ic12)

or a pharmaceutically acceptable salt, or prodrug thereof, wherein:

each u is independently 0, 1, 3, 5, 7, 8, 10, or 11; each w is independently 0, 1, 2, 3, 4, or 5; each t1 is 0 or 10; each t2 is 0 or 10; each s1 is 4, 5, 6, 13, 14, 15, or 16; and each s2 is 0, 4, or 13.

In one embodiment the invention provides a compound of formula (Ic12) wherein $M^0$ is:

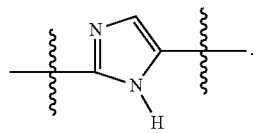 [SMILES: *c1cnc(*)[nH]1]

In one embodiment the invention provides a compound of formula (Ic13)

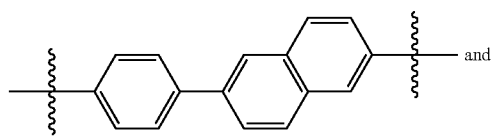

(Ic13)

or a pharmaceutically acceptable salt, or prodrug thereof.

In one embodiment the invention provides a compound of formula (Ic13) wherein A-A is $A^0$-$A^{13}$ and is selected from:

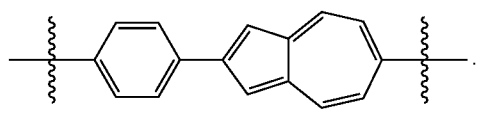

and

In one embodiment the invention provides a compound of formula (Ic14)

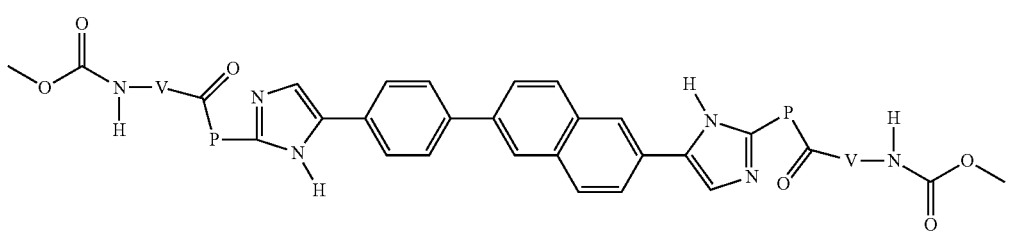

(Ic14)

or a pharmaceutically acceptable salt, or prodrug thereof.

In one embodiment the invention provides a compound of formula (Ic12) which is:

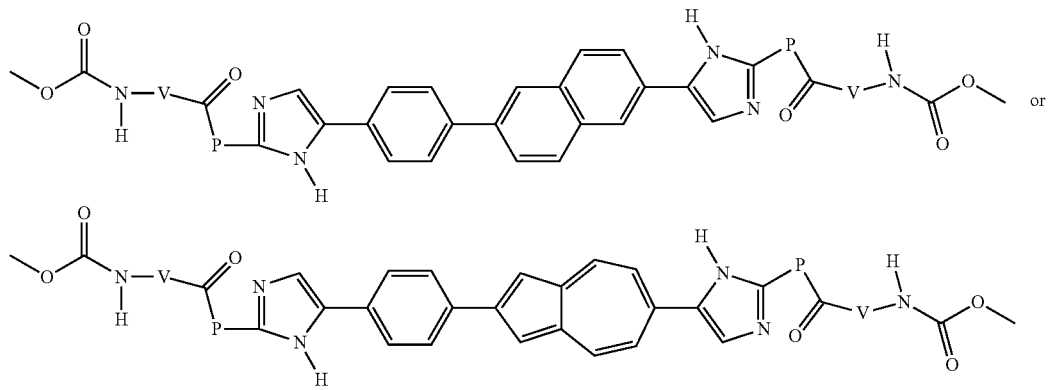

or or a pharmaceutically acceptable salt, or prodrug thereof.

In one embodiment the invention provides a compound of formula (Ic12) which is:

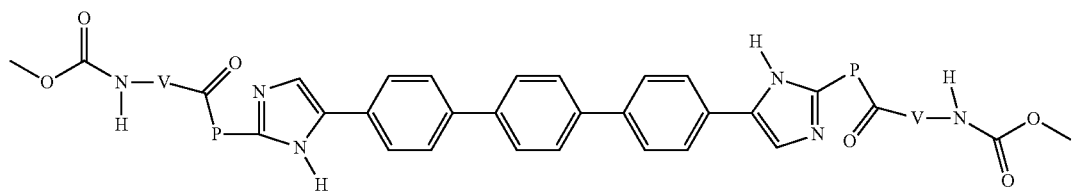

or a pharmaceutically acceptable salt, or prodrug thereof.

In one embodiment the invention provides a compound of formula (Ic13) wherein A-A is $A^0$-$A^4$ and is:

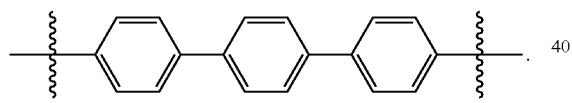

In one embodiment the invention provides a compound of formula (Ic12) which is:

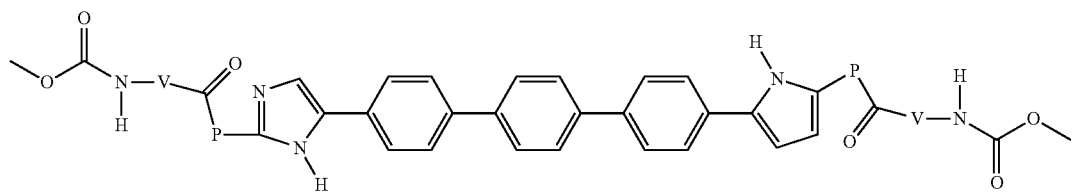

or a pharmaceutically acceptable salt, or prodrug thereof.

In one embodiment the invention provides a compound of formula (Ic13) wherein A-A is $A^0$-$A^{14}$ and is:

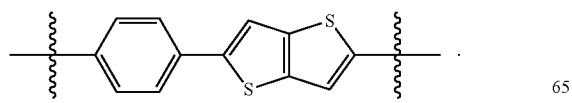

In one embodiment the invention provides a compound of formula (Ic12) which is:

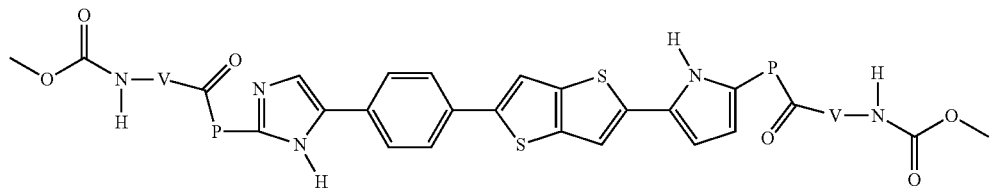

or a pharmaceutically acceptable salt, or prodrug thereof.

In one embodiment the invention provides a compound of formula (Ic13) wherein A-A is $A^{13}$-$A^{14}$ and is:

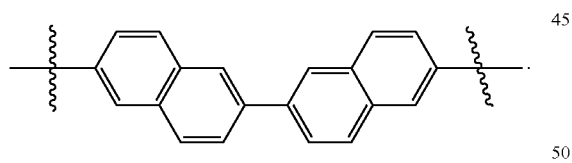

In one embodiment the invention provides a compound of formula (Ic13) wherein A-A is $A^{15}$-$A^6$ and is:

In one embodiment the invention provides a compound of formula (Ic12) which is:

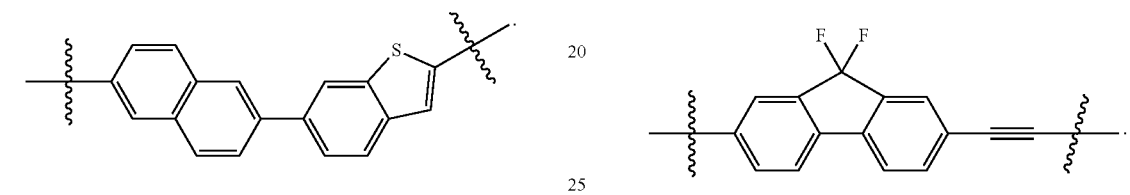

or a pharmaceutically acceptable salt, or prodrug thereof.

In one embodiment the invention provides a compound of formula (Ic13) wherein A-A is $A^{13}$-$A^{13}$ and is:

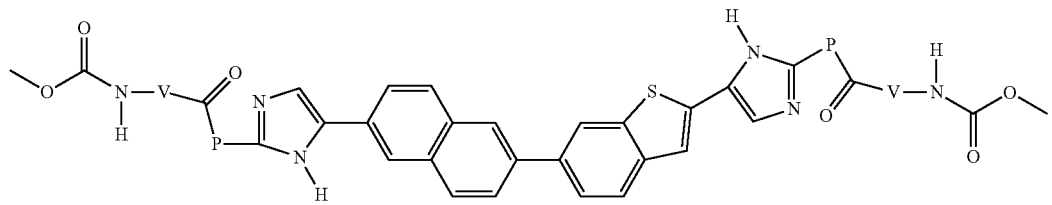

In one embodiment the invention provides a compound of formula (Ic12) which is:

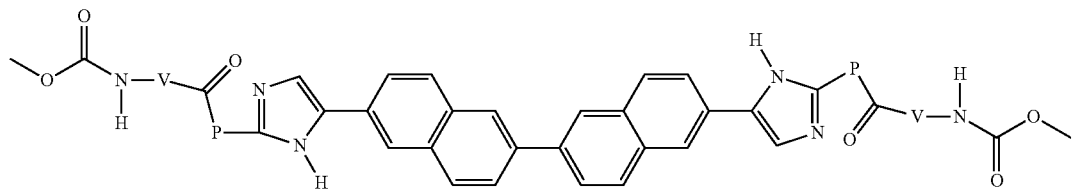

or a pharmaceutically acceptable salt, or prodrug thereof.

In one embodiment the invention provides a compound of formula (Ic12) which is:

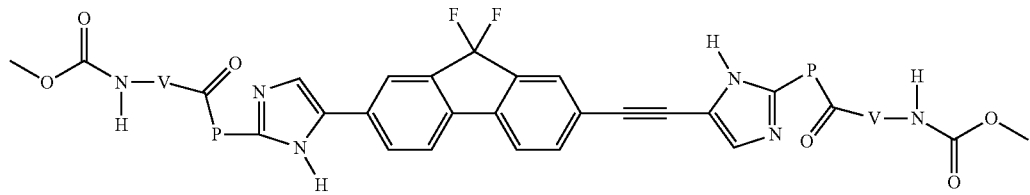

or a pharmaceutically acceptable salt, or prodrug thereof.

In one embodiment the invention provides a compound of formula (Ic13) wherein A-A is $A^{14}$-$A^6$ and is:

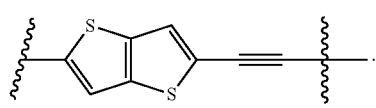 [SMILES: *C#Cc1cc2sc(*)cc2s1 ; "."]

In one embodiment the invention provides a compound of formula (Ic12) which is:

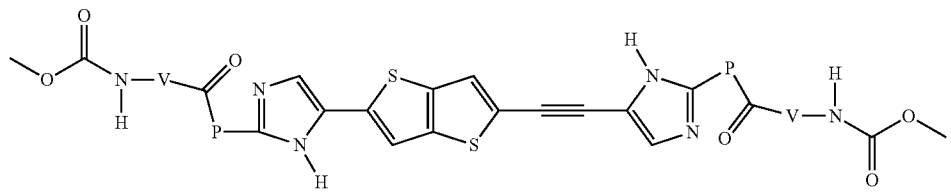

or a pharmaceutically acceptable salt, or prodrug thereof.

In one embodiment the invention provides a compound of formula (Ic13) wherein A-A is $A^{13}$-$A^6$ and is:

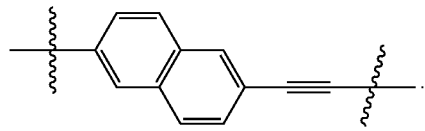

In one embodiment the invention provides a compound of formula (Ic12) which is:

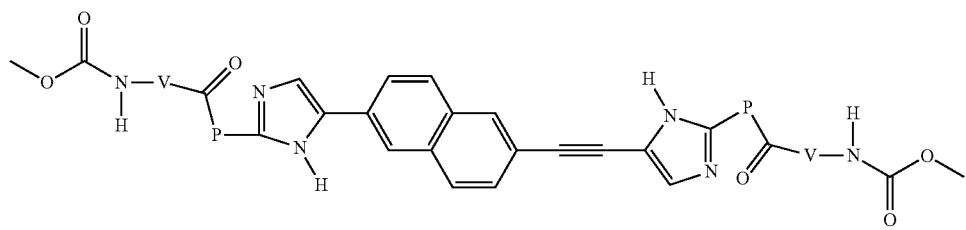

or a pharmaceutically acceptable salt, or prodrug thereof.

In one embodiment the invention provides a compound of formula (Ic13) wherein A-A is $A^{16}$-$A^6$ and is:

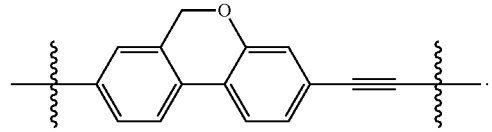 [SMILES: *C#Cc1ccc2c(c1)OCc1cc(*)ccc1-2 ; "."]

In one embodiment the invention provides a compound of formula (Ic12) which is:

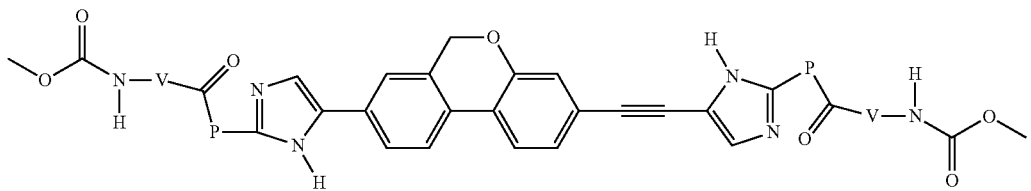

or a pharmaceutically acceptable salt, or prodrug thereof.

In one embodiment the invention provides a compound of formula (Ic13) wherein A-A is $A^0$-$A^5$ and is:

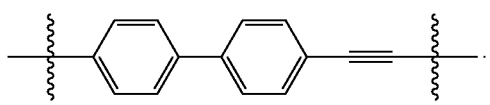

In one embodiment the invention provides a compound of formula (Ic12) which is:

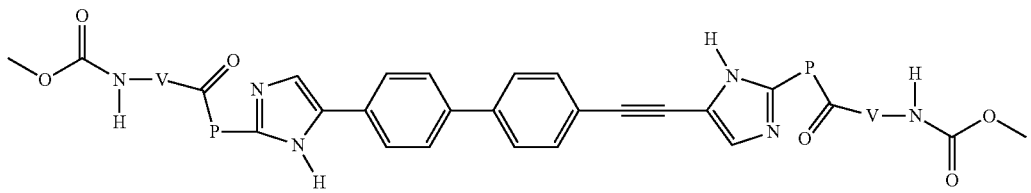

or a pharmaceutically acceptable salt, or prodrug thereof.

In one embodiment the invention provides a compound of formula (Ic13) wherein A-A is $A^0$-$A^5$ and is:

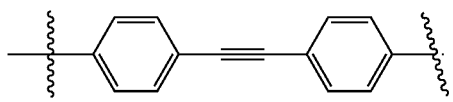 [SMILES: *c1ccc(C#Cc2ccc(*)cc2)cc1 ; "."]

In one embodiment the invention provides a compound of formula (Ic12) which is:

In one embodiment of the invention, the compound of formula (I) is a compound of formula (Ic15):

$$E^0\text{-}V^w\text{-}Z^0\text{-}P^u\text{-}M^{t1}\text{-}A^{s1}\text{-}A^{s2}\text{-}M^{t2}\text{-}P^u\text{-}Z^0\text{-}V^w\text{-}E^0 \qquad (Ic15)$$

or a pharmaceutically acceptable salt, or prodrug thereof, wherein:

each u is independently 0, 1, 3, 5, 7, 8, 10, or 11; each w is independently 0, 1, 2, 3, 4, or 5; each t1 is 0, 10, or 13; t2 is 9; s1 is 4, 5, 6, 13, 14, 15, or 16; and s2 is 0, 4, or 13.

In one embodiment of the invention, the compound of formula (I) is a compound of formula (Ic16):

$$E^0\text{-}V^w\text{-}Z^0\text{-}P^u\text{-}M^{t1}\text{-}A^{s1}\text{-}A^{s2}\text{-}M^{t2}\text{-}P^u\text{-}Z^0\text{-}V^w\text{-}E^0 \qquad (Ic16)$$

or a pharmaceutically acceptable salt, or prodrug thereof, wherein:

each u is independently 0, 1, 3, 5, 7, 8, 10, or 11; each w is independently 0, 1, 2, 3, 4, or 5; each t1 is 9; t2 is 0, 10, or 13; s1 is 4, 5, 6, 13, 14, 15, or 16; and s2 is 0, 4, or 13.

In one embodiment the invention provides a compound of formula (Ic15) or (Ic16) wherein $M^0$ is:

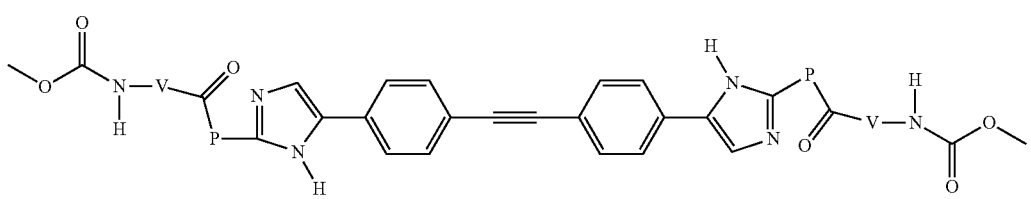

or a pharmaceutically acceptable salt, or prodrug thereof.

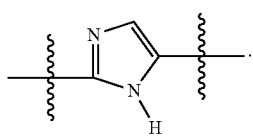 [SMILES: *c1cnc(*)[nH]1]

In one embodiment the invention provides a compound of formula (Ic15) or (Ic16) wherein $M^9$ is:

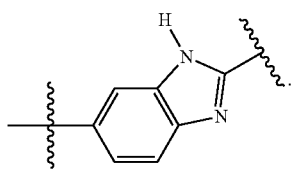 [SMILES: *c1ccc2nc(*)[nH]c2c1]

In one embodiment the invention provides a compound of formula (Ic15) or (Ic16) wherein A-A is $A^0$-$A^{13}$ and is:

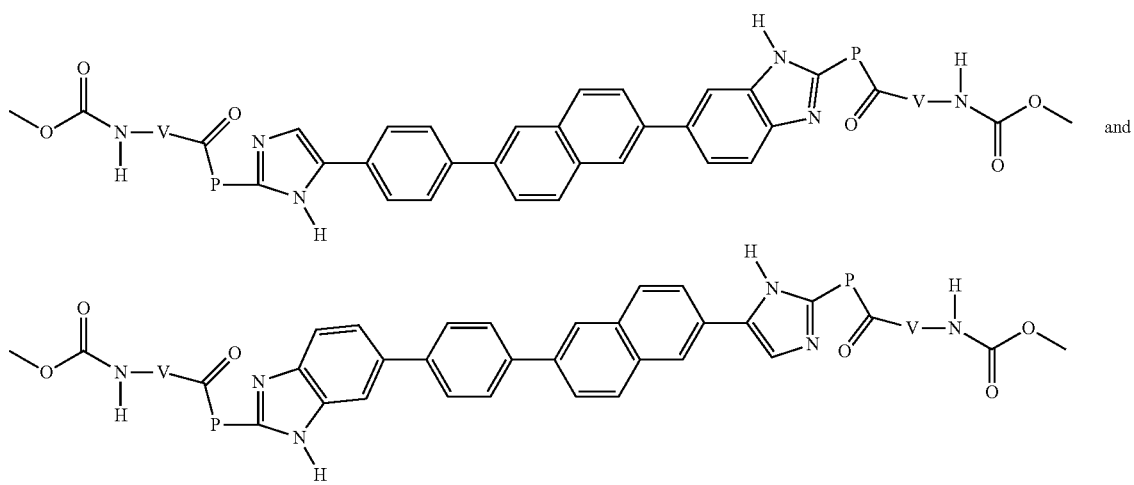

In one embodiment the invention provides a compound of formula (Ic15) or (Ic16) which is selected from:

and pharmaceutically acceptable salts and prodrugs thereof.

In one embodiment the invention provides a compound of formula (Ic15) or (Ic16) wherein A-A is $A^0$-$A^{13}$ and is:

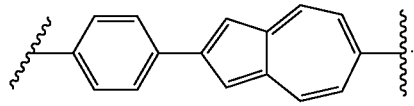 [SMILES: *c1ccc(-c2cc3ccc(*)ccc-3c2)cc1]

In one embodiment the invention provides a compound of formula (Ic15) or (Ic16) which is selected from:

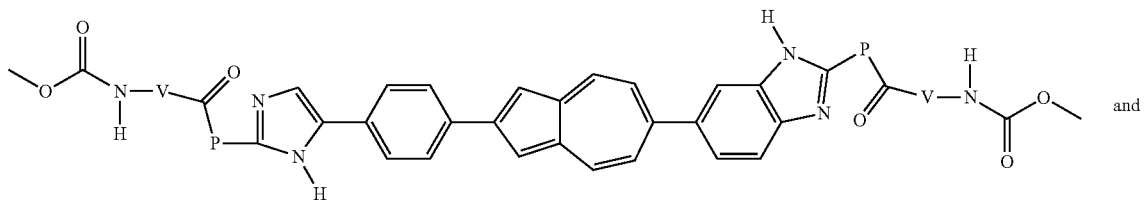

and

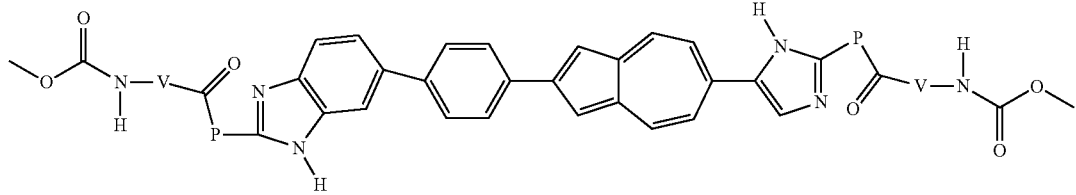

and pharmaceutically acceptable salts and prodrugs thereof.

In one embodiment the invention provides a compound of formula (Ic15) or (Ic16) wherein A-A is $A^0$-$A^4$ and is:

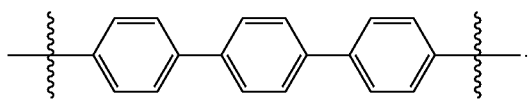

In one embodiment the invention provides a compound of formula (Ic15) or (Ic16):

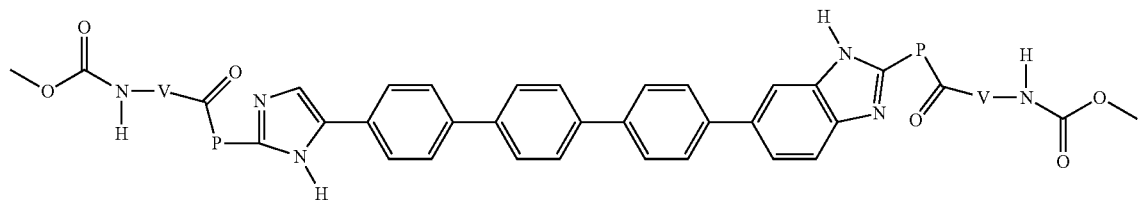

or a pharmaceutically acceptable salt or prodrug thereof.

In one embodiment the invention provides a compound of formula (Ic15) or (Ic16) wherein A-A is $A^0$-$A^4$ and is:

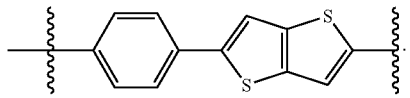 [SMILES: *c1ccc(-c2cc3sc(*)cc3s2)cc1]

In one embodiment the invention provides a compound of formula (Ic15) or (Ic16) which is selected from:

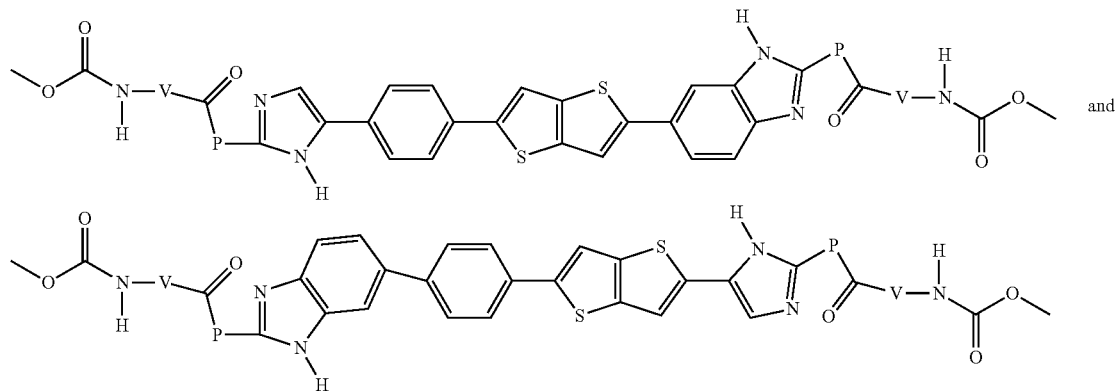

and pharmaceutically acceptable salts and prodrugs thereof.

In one embodiment the invention provides a compound of formula (Ic15) or (Ic16) wherein A-A is $A^{13}$-$A^{14}$ and is:

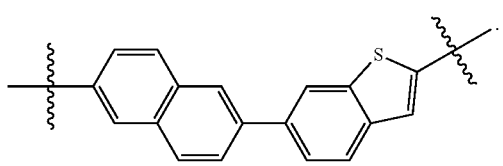

In one embodiment the invention provides a compound of formula (Ic15) or (Ic16) which is selected from:

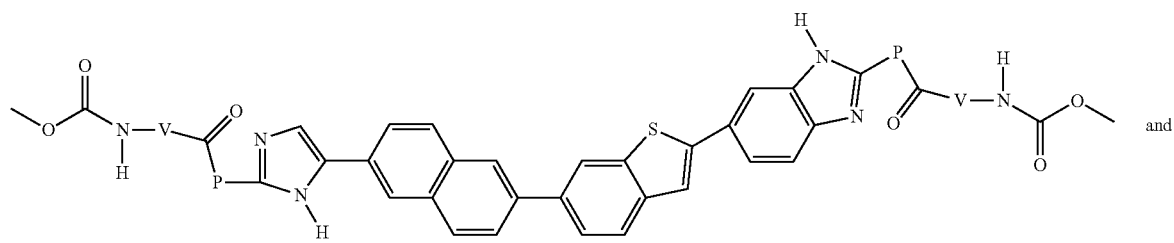

and

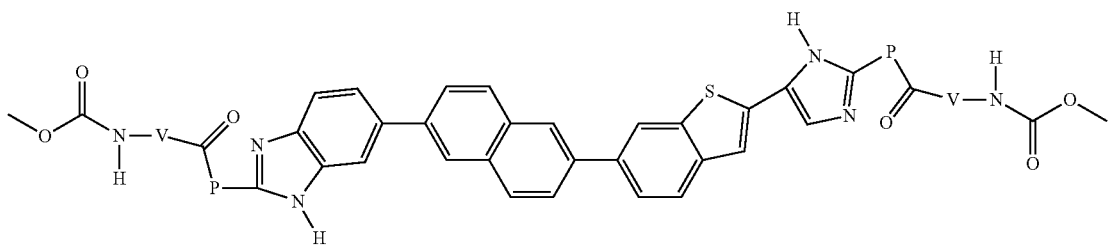

and pharmaceutically acceptable salts and prodrugs thereof.

In one embodiment the invention provides a compound of formula (Ic15) or (Ic16) wherein A-A is $A^{13}$-$A^{13}$ and is:

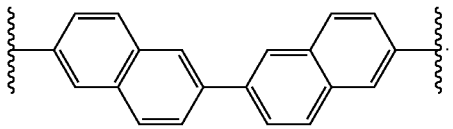 [SMILES: *c1ccc2cc(-c3ccc4cc(*)ccc4c3)ccc2c1]

In one embodiment the invention provides a compound of formula (Ic15) or (Ic16):

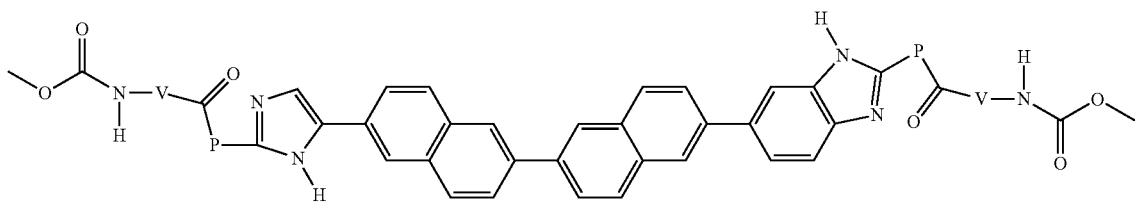

or a pharmaceutically acceptable salt or prodrug thereof.

In one embodiment the invention provides a compound of formula (Ic15) or (Ic16) wherein A-A is $A^{15}$-$A^6$ and is:

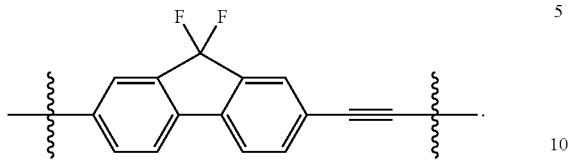

In one embodiment the invention provides a compound of formula (Ic15) or (Ic16) which is selected from:

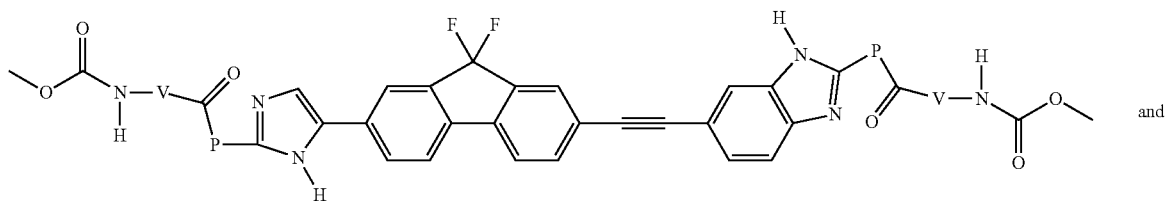

and

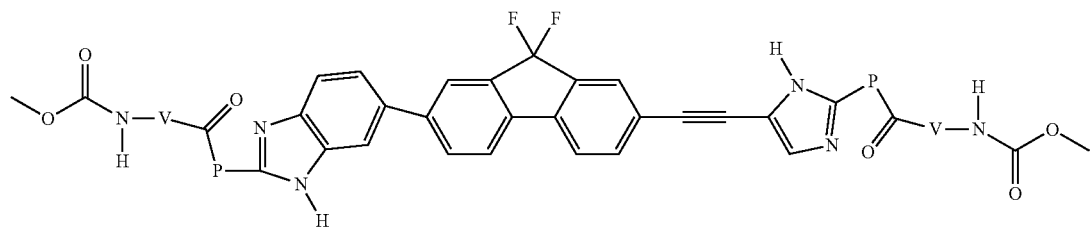

and pharmaceutically acceptable salts and prodrugs thereof.

In one embodiment the invention provides a compound of formula (Ic15) or (Ic16) wherein A-A is $A^0$-$A^5$ and is:

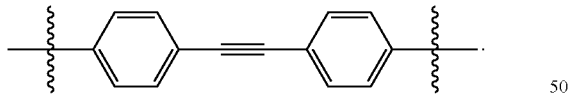

In one embodiment the invention provides a compound of formula (Ic15) or (Ic16):

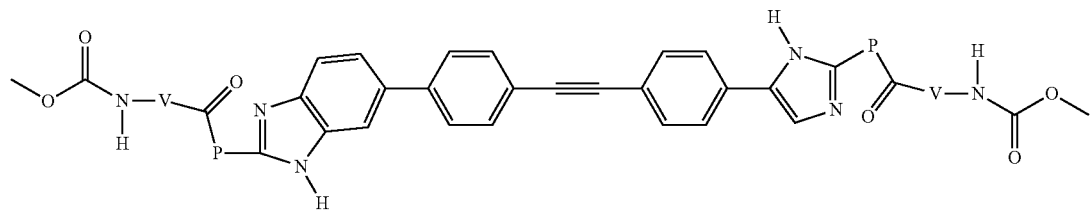

or a pharmaceutically acceptable salt or prodrug thereof.

In one embodiment the invention provides a compound of formula (Ic15) or (Ic16) wherein A-A is $A^0$-$A^5$ and is:

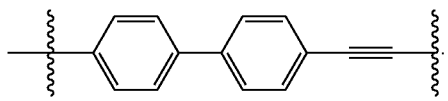 [SMILES: *C#Cc1ccc(-c2ccc(*)cc2)cc1]

In one embodiment the invention provides a compound of formula (Ic15) or (Ic16) which is selected from:

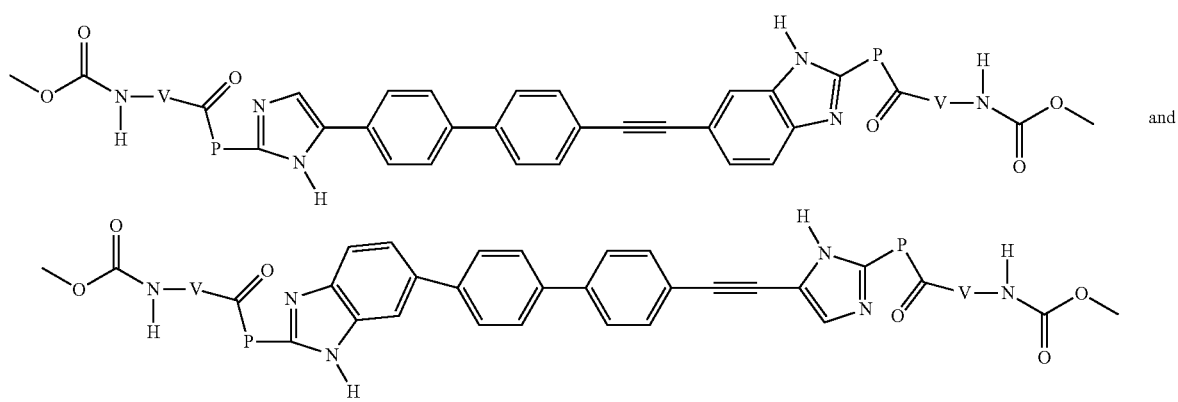

and pharmaceutically acceptable salts and prodrugs thereof.

In one embodiment the invention provides a compound of formula (Ic15) or (Ic16) wherein A-A is $A^{14}$-$A^6$ and is:

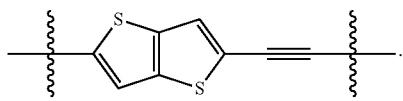

In one embodiment the invention provides a compound of formula (Ic15) or (Ic16) which is selected from:

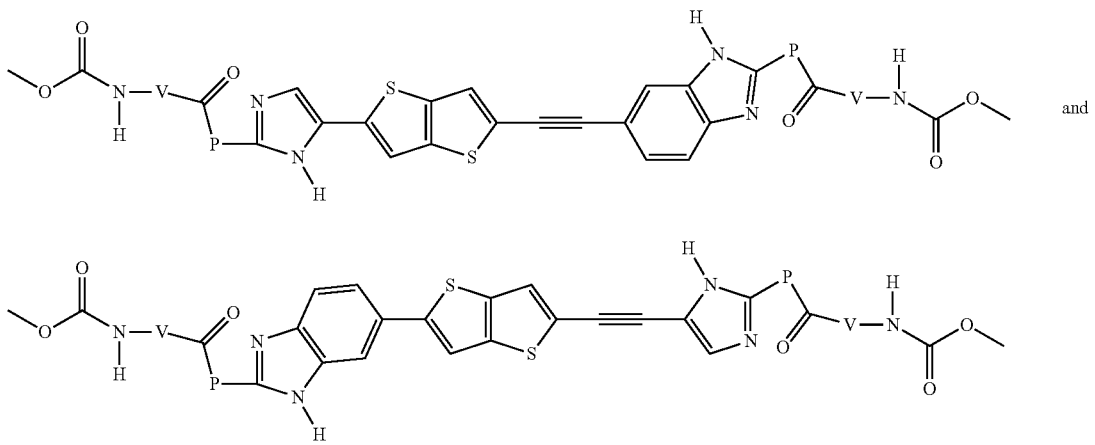

and pharmaceutically acceptable salts and prodrugs thereof.

In one embodiment the invention provides a compound of formula (Ic15) or (Ic16) wherein A-A is $A^{13}$-$A^6$ and is:

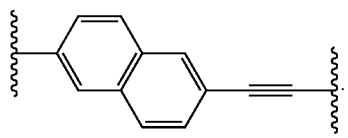 [SMILES: *C#Cc1ccc2cc(*)ccc2c1]

In one embodiment the invention provides a compound of formula (Ic15) or (Ic16) which is selected from:

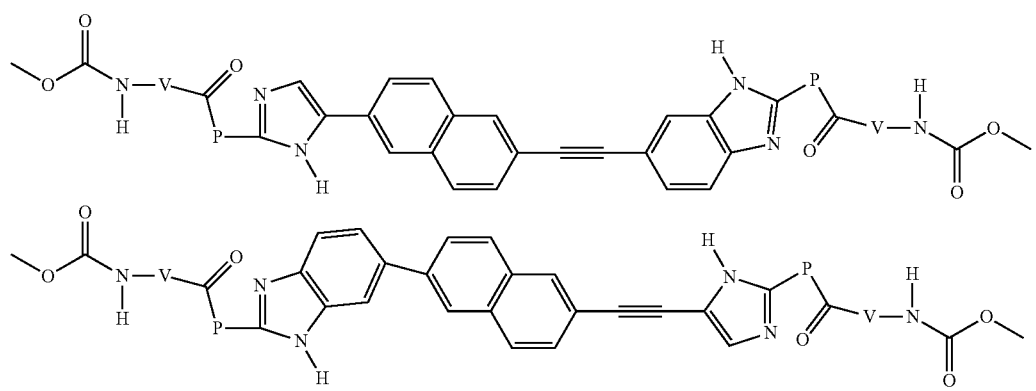

and and pharmaceutically acceptable salts and prodrugs thereof.

In one embodiment the invention provides a compound of formula (Ic15) or (Ic16) wherein A-A is $A^{16}$-$A^6$ and is:

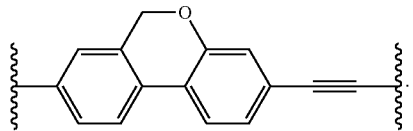 [SMILES: *C#Cc1ccc2c(c1)OCc1cc(*)ccc1-2]

In one embodiment the invention provides a compound of formula (Ic15) or (Ic16) which is selected from:

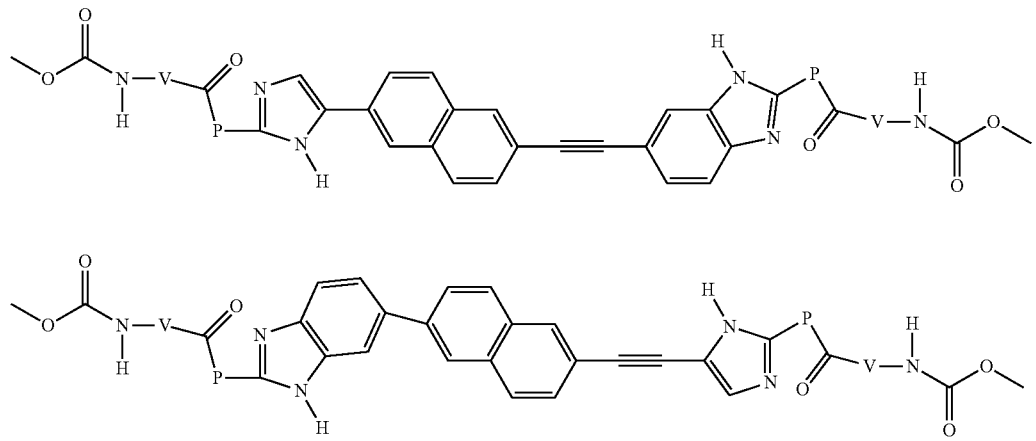

and and pharmaceutically acceptable salts and prodrugs thereof.

In one embodiment the invention provides a compound of formula (Ic17) or (Ic18)

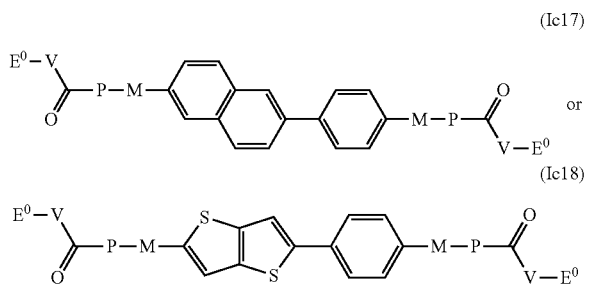

wherein:
each P is independently selected from:

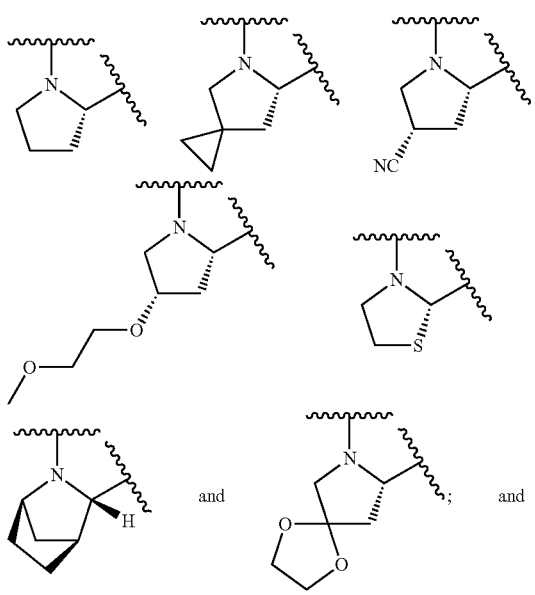

each M is independently $M^0$, $M^9$, or $M^{10}$;
or a pharmaceutically acceptable salts or prodrug thereof.

In one embodiment the invention provides a compound of formula (Ic17) or (Ic18) wherein each $E^0$ is methoxycarbonylamino.

In one embodiment the invention provides a compound of formula (Ic17) or (Ic18) wherein at least one $E^0$ is —$NR^{Ec}R^{Ed}$ wherein $R^{Ec}$ is H, alkyl or cycloalkyl and $R^{Ed}$ is heterocycle.

In another specific embodiment the invention provides a compound of the following formula (Ic30): $E^x$-$V^w$-$Z^v$-$P^u$-$M^t$-$A^s$-$A^s$-$M^t$-$P^u$-$Z^v$-$V^w$-$E^x$ (Ic30) wherein at least two of s, t, u, v, w or x are not zero.

In another specific embodiment the invention provides a compound of formula (Ic30) wherein at least one of u, v, w or x is not zero.

In another specific embodiment the invention provides a compound of formula (Ic30) wherein at least one t is 0 or 10.

In another specific embodiment the invention provides a compound of formula (Ic30) wherein both t are 9; one s is 0; and one s is 0, 1, 2, 3, 4, 5, 7, 8, 9, 10, 11, 12, 13, 14, 15, 16, 17, 18, 19, 20, or 21.

In another specific embodiment the invention provides a compound of formula (Ic30) wherein both t are 9; one s is 1, 2, 3, 4, 5, 7, 8, 9, 10, 11, 12, 13, 14, 15, 16, 17, 18, 19, 20, or 21; and one s is 0, 1, 2, 3, 4, 5, 6, 7, 8, 9, 10, 11, 12, 13, 14, 15, 16, 17, 18, 19, 20, or 21.

In another specific embodiment the invention provides a compound of formula (Ic30) wherein at least two of s, t, u, v, w or x are not zero and at least one t is selected from 0, 1, 2, 3, 4, 5, 6, 7, 8, 10, 11

In another specific embodiment the invention provides a compound of formula (Ic30) wherein at least three of s, t, u, v, w or x are not zero.

In another specific embodiment the invention provides a compound of formula (Ic30) wherein at least two of s, t, u, v, w or x are not zero and at least two of the non-zero groups are not the same letter.

In another specific embodiment the invention provides a compound of formula (Ic30) wherein at least three of s, t, u, v, w or x are not zero and at least two of the non-zero groups are not the same letter.

In another specific embodiment the invention provides a compound of formula (Ic30) wherein at least three of s, t, u, v, w or x are not zero and at least three of the non-zero groups are not the same letter.

In another specific embodiment the invention provides a compound of formula (Ic30) wherein at least four of s, t, u, v, w or x are not zero.

In another specific embodiment the invention provides a compound of formula (Ic30) wherein at least four of s, t, u, v, w or x are not zero and at least two of the non-zero groups are not the same letter.

In another specific embodiment the invention provides a compound of formula (Ic30) wherein at least four of s, t, u, v, w or x are not zero and at least three of the non-zero groups are not the same letter.

In another specific embodiment the invention provides a compound of formula (Ic30) wherein at least four of s, t, u, v, w or x are not zero and at least four of the non-zero groups are not the same letter.

In another specific embodiment the invention provides a compound of formula (Ic30) wherein the sum of t, u, v, w or x is not zero.

In another specific embodiment the invention provides a compound of formula (Ic30) wherein the sum of s, u, v, w or x is not zero.

In another specific embodiment the invention provides a compound of formula (Ic30) wherein at least one u is not zero.

In another specific embodiment the invention provides a compound of formula (Ic30) wherein s, and at least one t, and at least one u are all not zero.

In another specific embodiment the invention provides a compound of formula (Ic30) wherein at least two of u, w and t are not zero.

In another specific embodiment the invention provides a compound of formula (Ic30) wherein at least two of s, u, and w are not zero.

In another specific embodiment the invention provides a compound of formula (Ic30) wherein at least two of s, u, and w are not zero and at least two of the non-zero groups are not the same letter.

In another specific embodiment the invention provides a compound of formula (Ic30) wherein at least s and both u are not zero.

In another specific embodiment the invention provides a compound of formula (Ic30) wherein at least two of u, v, w or x are not zero and at least two of the non-zero groups are not the same letter.

In another specific embodiment the invention provides a compound of formula (Ic30) wherein at least one of u, or w is not zero.

In another specific embodiment the invention provides a compound of formula (Ic30) wherein at least two of u or w are not zero.

In another specific embodiment the invention provides a compound of formula (Ic30) wherein at least one u is not zero, and at least one w is not zero.

In another specific embodiment the invention provides a compound of formula (Ic30) wherein at least two of u are not zero.

In another specific embodiment the invention provides a compound of formula (Ic30) wherein at least one of w is not zero.

In another specific embodiment the invention provides a compound of formula (Ic30) wherein at least two of w are not zero.

In another specific embodiment the invention provides a compound of formula (Ic30) wherein both u are not zero, and at least one w is not zero.

In another specific embodiment the invention provides a compound of formula (Ic30) wherein both t are 9; one s is 0; and one s is 0, 1, 2, 3, 4, 5, 7, 8, 9, 10, 11, 12, 13, 14, 15, 16, 17, 18, 19, 20, or 21.

In another specific embodiment the invention provides a compound of formula (Ic30) wherein both t are 9; one s is 1, 2, 3, 4, 5, 7, 8, 9, 10, 11, 12, 13, 14, 15, 16, 17, 18, 19, 20, or 21; and one s is 0, 1, 2, 3, 4, 5, 6, 7, 8, 9, 10, 11, 12, 13, 14, 15, 16, 17, 18, 19, 20, or 21.

In another specific embodiment the invention provides a compound of the following formula (Ic31): $E^x$-$V^v$-$Z^v$-$P^u$-$M^9$-$A^s$-$A^s$-$M^9$-$P^u$-$Z^v$-$V^w$-$E^x$ (Ic31) wherein one s is 0 or 6 and one s is 6.

In another specific embodiment the invention provides a compound of formula (Ic31) wherein at least one of u, v, w or x are not zero.

In another specific embodiment the invention provides a compound of formula (Ic31) wherein at least two of u, v, w or x are not zero.

In another specific embodiment the invention provides a compound of formula (Ic31) wherein at least three of u, v, w or x are not zero.

In another specific embodiment the invention provides a compound of formula (Ic31) wherein at least four of u, v, w or x are not zero.

In another specific embodiment the invention provides a compound of formula (Ic31) wherein at least two u, v, w or x are not zero and at least two of the non-zero groups are not the same letter.

In another specific embodiment the invention provides a compound of formula (Ic31) wherein at least three of u, v, w or x are not zero and at least two of the non-zero groups are not the same letter.

In another specific embodiment the invention provides a compound of formula (Ic31) wherein at least three of u, v, w or x are not zero and at least three of the non-zero groups are not the same letter.

In another specific embodiment the invention provides a compound of formula (Ic31) wherein at least four of u, v, w or x are not zero and at least two of the non-zero groups are not the same letter.

In another specific embodiment the invention provides a compound of formula (Ic31) wherein the sum of u, v, w and x is not zero.

In another specific embodiment the invention provides a compound of formula (Ic31) wherein at least one of u or w are not zero.

In another specific embodiment the invention provides a compound of formula (Ic31) wherein at least two of u or w are not zero.

In another specific embodiment the invention provides a compound of formula (Ic31) wherein at least one u is not zero, and at least one w is not zero.

In another specific embodiment the invention provides a compound of formula (Ic31) wherein both u are not zero, and at least one w is not zero.

In another specific embodiment the invention provides a compound of formula (Ic31) wherein at least one u is not zero.

In another specific embodiment the invention provides a compound of formula (Ic31) wherein both of u are not zero.

In another specific embodiment the invention provides a compound of formula (Ic31) wherein at least one of w is not zero.

In another specific embodiment the invention provides a compound of formula (Ic31) wherein both w are not zero.

Compounds of Formula (Id)

In one embodiment of the invention, the compound of formula (I) is a compound of formula (Id):

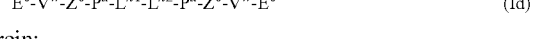

$$E^0\text{-}V^w\text{-}Z^0\text{-}P^u\text{-}L^{n1}\text{-}L^{n2}\text{-}P^u\text{-}Z^0\text{-}V^w\text{-}E^0 \qquad (Id)$$

wherein:
n1 is 3, 4, or 9;
n2 is 9;
each u is 0, 1, 3, 5, 7, 8, 10, or 11;
each w is 0, 1, 2, 3, 4, or 5;
each $L^3$ is independently a fused-bicyclic saturated, partially unsaturated, or aromatic heterocyclic ring system that is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^4$ is independently selected from H, alkyl, haloalkyl, aryl, and arylalkyl; and
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^4$ is independently a fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, ($NR^aR^b$)carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^4$ is independently selected from H, alkyl, haloalkyl, aryl, and arylalkyl; and
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^9$ is independently a fused-tetracyclic saturated, partially unsaturated, or aromatic heterocyclic ring system that is optionally substituted with one or more groups independently selected from oxo, halo, —R$^{L7}$, —OR$^{L7}$, —SR$^{L7}$, —CF$_3$, —CCl$_3$, —OCF$_3$, —CN, —NO$_2$, —N(R$^{L3}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each P$^0$ is independently:

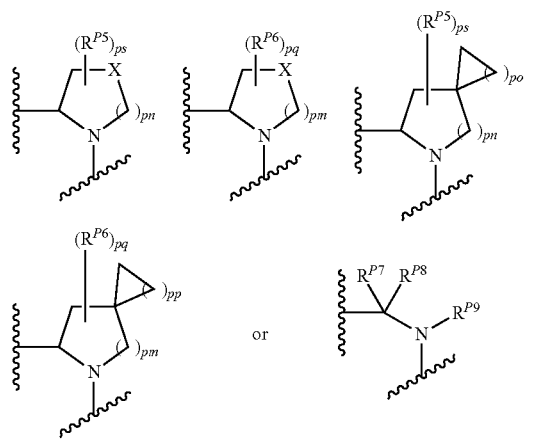

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

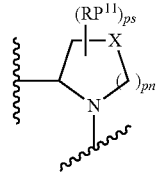

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 1, 2, 3, or 4;
pn is 0, 1, or 2;

each $P^3$ is independently a ring of the formula:

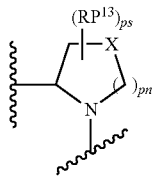

wherein:
the ring is substituted with one or more oxo groups;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

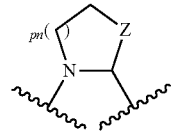

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{15}$ that are attached to the same carbon when taken together with the carbon to which they are attached can form a 3-6 membered carbocyclic or heterocyclic ring;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each $P^8$ is independently a ring of the formula:

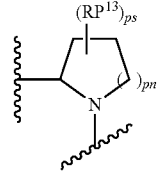

wherein:
ps is 2, 3, 4, 5, or 6;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
each $P^{10}$ is independently:

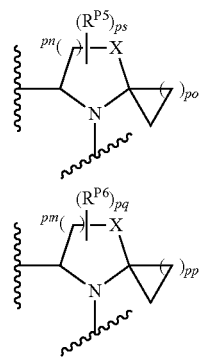

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;

each P¹¹ is independently:

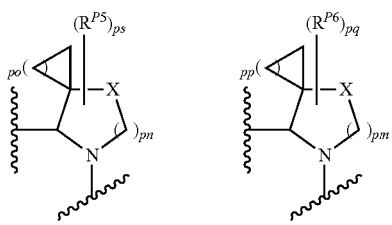

wherein:
X is selected from O, S, S(O), SO₂, CH₂, CHR^{P10}, and C(R^{P10})₂; provided that when pn or pm is 0, X is selected from CH₂, CHR^{P10}, and C(R^{P10})₂;
each R^{P10} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
each R^{P5} and R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each —Z⁰— is —C(=O)— or —C(=S)—;
each E⁰ is independently —NR^{Ec}R^{Ed} wherein
R^{Ec} and R^{Ed} are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR^eR^f)alkyl, (NR^eR^f)alkylcarbonyl, (NR^eR^f)carbonyl, (NR^eR^f)sulfonyl, —C(NCN)OR', and —C(NCN)NR^XR^Y, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR^eR^f group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;
each V⁰ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl;
and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;
and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR^XR^Y, -(NR^XR^Y)alkyl, oxo, and —P(O)OR₂, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;
and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR^XR^Y, (NR^XR^Y)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;
each V¹ is independently cyanoalkyl, which is optionally substituted with one or more groups independently selected from cycloalkyl, alkoxy, haloalkoxy, cycloalkenyl, heterocycle, heteroaryl, hydroxy, and NR^{Va}R^{Vb}C(=O)O—; R^{Va} and R^{Vb} are each independently selected from hydrogen, alkenyl, and alkyl;
each V² is independently haloalkyl, which is optionally substituted with one or more groups independently selected from cycloalkyl, alkoxy, haloalkoxy, cycloalkenyl, heterocycle, heteroaryl, hydroxy, and NR^{Va}R^{Vb}C(=O)O—; R^{Va} and R^{Vb} are each independently selected from hydrogen, alkenyl, and alkyl;
each V³ is independently alkyl, which is substituted with one or more oxo, and which is optionally substituted with one or more groups independently selected from cycloalkyl, halo, aryl, alkenyl, and cyano; and
each V⁴ is independently haloalkoxyalkyl, which is optionally substituted with one or more groups independently selected from cycloalkyl, alkoxy, haloalkoxy, cycloalkenyl, heterocycle, heteroaryl, hydroxy, and NR^aR^bC(=O)O—; R^a and R^b are each independently selected from hydrogen, alkenyl, and alkyl; and
each V⁵ is independently alkylsulfonylalkyl, which is optionally substituted with one or more groups independently selected from cycloalkyl, alkoxy, haloalkoxy, cycloalkenyl, heterocycle, heteroaryl, hydroxy, and NR^{Va}R^{Vb}C(=O)O—; R^{Va} and R^{Vb} are each independently selected from hydrogen, alkenyl, and alkyl.

In one embodiment the invention provides a compound of formula (Id) wherein each L is benzimidazolyl.

In one embodiment the invention provides a compound of formula (Id1) or (Id2) which is selected from:

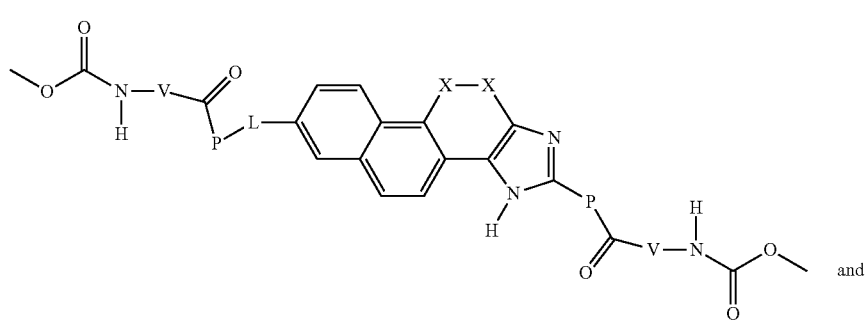

(Id1)

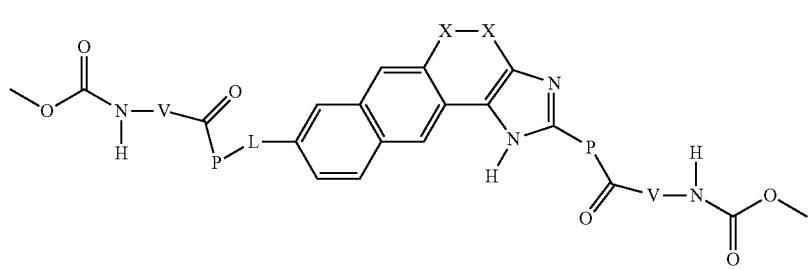

(Id2)

and wherein X—X is selected from O, CH₂, CH═CH, CH₂—CH₂, CH₂—O, O—CH₂, CH₂—CH₂—CH₂, and CH₂—O—CH₂; or a pharmaceutically acceptable salt, or prodrug thereof.

In one embodiment the invention provides a compound of formula (Id) wherein L⁹ is:

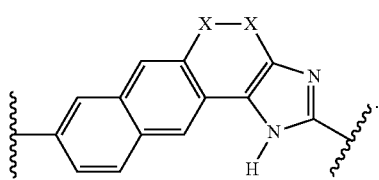

In one embodiment the invention provides a compound of formula (Id) wherein L⁹ is:

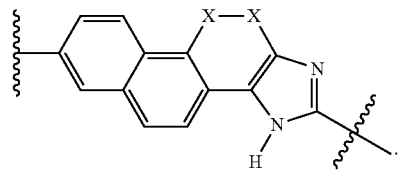

In one embodiment the invention provides a compound of formula (Id3) or (Id4) which is selected from:

(Id3)

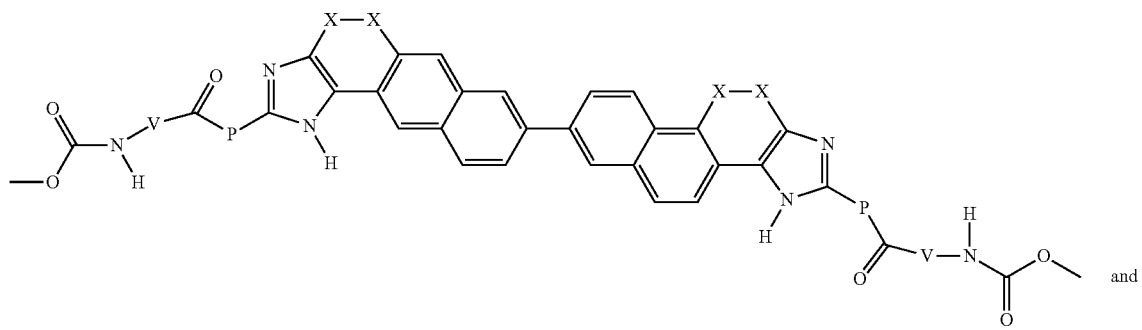

and (Id4)

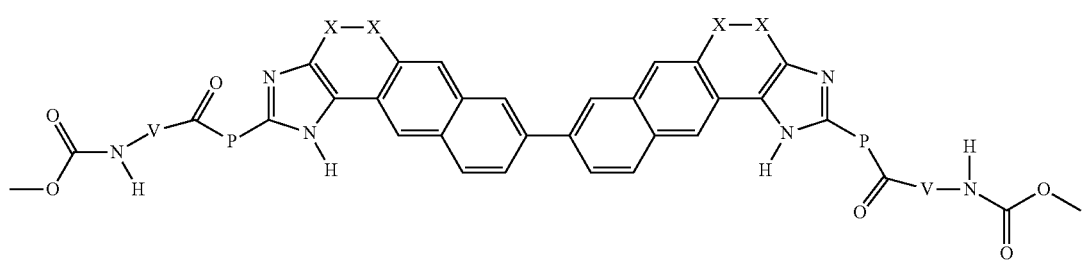

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Id) wherein L$^3$ is:

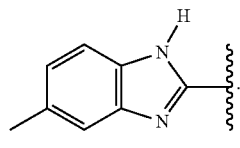 [SMILES: *c1nc2cc(C)ccc2[nH]1]

In one embodiment the invention provides a compound of formula (Id5) or (Id6) which is selected from:

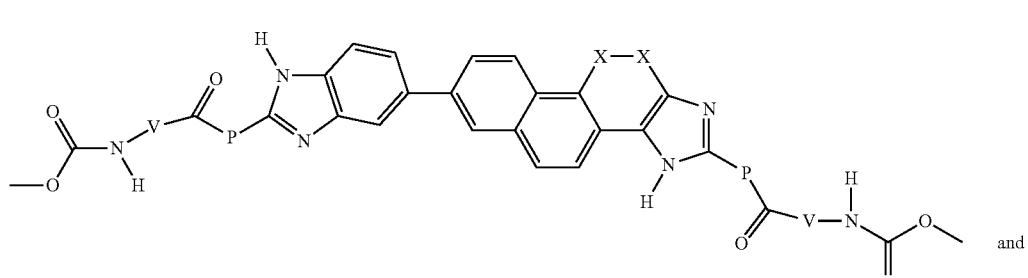

(Id5)

and

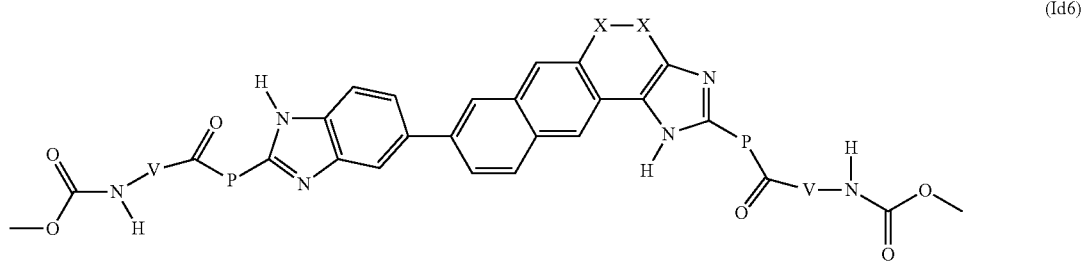

(Id6)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In one embodiment the invention provides a compound of formula (Id) wherein L$^4$ is:

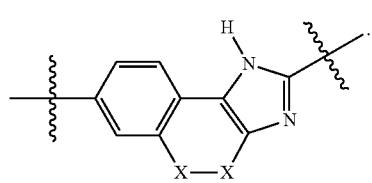

In one embodiment the invention provides a compound of formula (Id5) or (Id6) which is selected from:

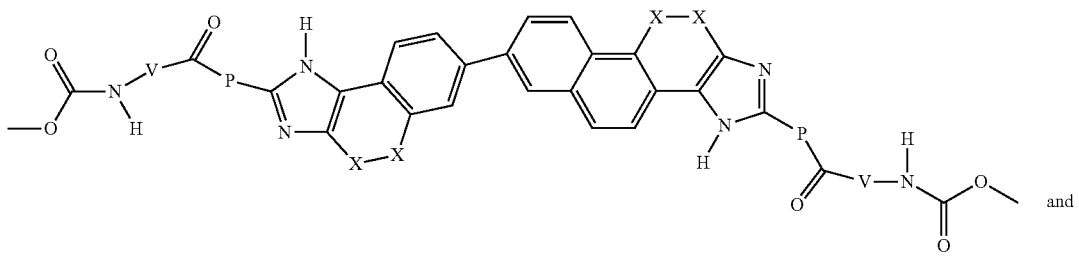
(Id7)

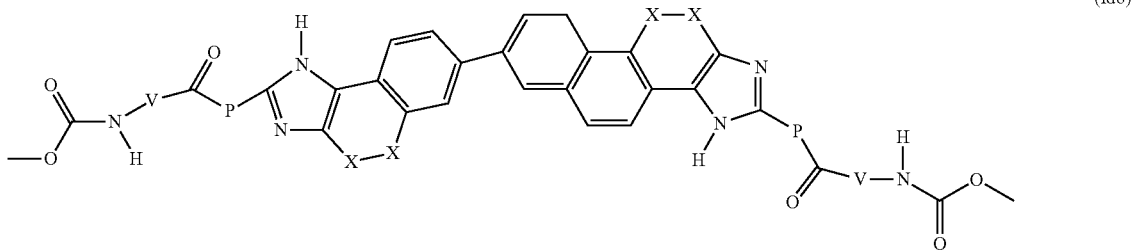
(Id8)

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

In another specific embodiment the invention provides a compound of the following formula (Id30): E$^x$-V$^w$-Z$^v$-P$^u$-L$^n$-L$^n$-P$^u$-Z$^v$-V$^w$-E$^x$ (Id30); wherein at least one of u, v, w or x are not zero.

In another specific embodiment the invention provides a compound of formula (Id30) wherein one n is 0, 1, 2, 4, 5, 6, 7, 8, 9, or 10; and one n is 1, 2, 3, 5, 6, 7, 8, 9, or 10.

In another specific embodiment the invention provides a compound of formula (Id30) wherein at least two of n, u, v, w or x are not zero.

In another specific embodiment the invention provides a compound of formula (Id30) wherein at least two of n, u, v, w or x are not zero and at least one n is selected from 0, 1, 2, 4, 5, 6, 7, 8, and 10

In another specific embodiment the invention provides a compound of formula (Id30) wherein at least two of n, u, v, w or x are not zero and at least one n is selected from 0, 1, 2, 3, 5, 6, 7, 8, and 10
Wherein at least three of n, u, v, w or x are not zero.

In another specific embodiment the invention provides a compound of formula (Id30) wherein at least two of n, u, v, w or x are not zero and at least two of the non-zero groups are not the same letter.

In another specific embodiment the invention provides a compound of formula (Id30) wherein at least three of n, u, v, w or x are not zero and at least two of the non-zero groups are not the same letter.

In another specific embodiment the invention provides a compound of formula (Id30) wherein at least three of n, u, v, w or x are not zero and at least three of the non-zero groups are not the same letter.

In another specific embodiment the invention provides a compound of formula (Id30) wherein at least four of n, u, v, w or x are not zero.

In another specific embodiment the invention provides a compound of formula (Id30) wherein at least four of n, u, v, w or x are not zero and at least two of the non-zero groups are not the same letter.

In another specific embodiment the invention provides a compound of formula (Id30) wherein at least four of n, u, v, w or x are not zero and at least three of the non-zero groups are not the same letter.

In another specific embodiment the invention provides a compound of formula (Id30) wherein at least four of n, u, v, w or x are not zero and at least four of the non-zero groups are not the same letter.

In another specific embodiment the invention provides a compound of formula (Id30) wherein the sum of n, u, v, w or x is not zero.

In another specific embodiment the invention provides a compound of formula (Id30) wherein the sum of u, v, w or x is not zero.

In another specific embodiment the invention provides a compound of formula (Id30) wherein at least one u is not zero.

In another specific embodiment the invention provides a compound of formula (Id30) wherein at least one n, and at least one u are all not zero.

In another specific embodiment the invention provides a compound of formula (Id30) wherein at least two of u, w and n are not zero.

In another specific embodiment the invention provides a compound of formula (Id30) wherein at least two of u, and w are not zero.

In another specific embodiment the invention provides a compound of formula (Id30) wherein at least two of u, and w are not zero and at least two of the non-zero groups are not the same letter.

In another specific embodiment the invention provides a compound of formula (Id30) wherein at least w and both u are not zero.

In another specific embodiment the invention provides a compound of formula (Id30) wherein at least two of u, v, w or x are not zero and at least two of the non-zero groups are not the same letter.

In another specific embodiment the invention provides a compound of formula (Id30) wherein at least one of u, or w is not zero.

In another specific embodiment the invention provides a compound of formula (Id30) wherein at least two of u, or w are not zero.

In another specific embodiment the invention provides a compound of formula (Id30) wherein at least one u is not zero, and at least one w is not zero.

In another specific embodiment the invention provides a compound of formula (Id30) wherein at least two of u are not zero.

In another specific embodiment the invention provides a compound of formula (Id30) wherein at least one of w is not zero.

In another specific embodiment the invention provides a compound of formula (Id30) wherein at least two of w are not zero.

In another specific embodiment the invention provides a compound of formula (Id30) wherein both u are not zero, and at least one w is not zero.

In another specific embodiment the invention provides a compound of the following formula (Id31): $E^x\text{-}V^w\text{-}Z^v\text{-}P^u\text{-}L^3\text{-}L^3\text{-}P^u\text{-}Z^v\text{-}V^w\text{-}E^x$ (Id31).

In another specific embodiment the invention provides a compound of formula (Id31) wherein at least one of u, v, w or x are not zero.

In another specific embodiment the invention provides a compound of formula (Id31) wherein at least two of u, v, w or x are not zero.

In another specific embodiment the invention provides a compound of formula (Id31) wherein at least three of u, v, w or x are not zero.

In another specific embodiment the invention provides a compound of formula (Id31) wherein at least four of u, v, w or x are not zero.

In another specific embodiment the invention provides a compound of formula (Id31) wherein at least two u, v, w or x are not zero and at least two of the non-zero groups are not the same letter.

In another specific embodiment the invention provides a compound of formula (Id31) wherein at least three of u, v, w or x are not zero and at least two of the non-zero groups are not the same letter.

In another specific embodiment the invention provides a compound of formula (Id31) wherein at least three of u, v, w or x are not zero and at least three of the non-zero groups are not the same letter.

In another specific embodiment the invention provides a compound of formula (Id31) wherein at least four of u, v, w or x are not zero and at least two of the non-zero groups are not the same letter.

In another specific embodiment the invention provides a compound of formula (Id31) wherein the sum of u, v, w and x is not zero.

In another specific embodiment the invention provides a compound of formula (Id31) wherein at least one of u, or w are not zero.

In another specific embodiment the invention provides a compound of formula (Id31) wherein at least two of u, or w are not zero.

In another specific embodiment the invention provides a compound of formula (Id31) wherein at least one u is not zero, and at least one w is not zero.

In another specific embodiment the invention provides a compound of formula (Id31) wherein both u are not zero, and at least one w is not zero.

In another specific embodiment the invention provides a compound of formula (Id31) wherein at least one u is not zero.

In another specific embodiment the invention provides a compound of formula (Id31) wherein both of u are not zero.

In another specific embodiment the invention provides a compound of formula (Id31) wherein at least one of w is not zero.

In another specific embodiment the invention provides a compound of formula (Id31) wherein both w are not zero.

In another specific embodiment the invention provides a compound of the following formula (Id32): $E^x\text{-}V^w\text{-}Z^v\text{-}P^u\text{-}L^4\text{-}L^4\text{-}P^u\text{-}Z^v\text{-}V^w\text{-}E^x$ (Id32).

In another specific embodiment the invention provides a compound of formula (Id32) wherein at least one of u, v, w or x are not zero.

In another specific embodiment the invention provides a compound of formula (Id32) wherein at least two of u, v, w or x are not zero.

In another specific embodiment the invention provides a compound of formula (Id32) wherein at least three of u, v, w or x are not zero.

In another specific embodiment the invention provides a compound of formula (Id32) wherein at least four of u, v, w or x are not zero.

In another specific embodiment the invention provides a compound of formula (Id32) wherein at least two u, v, w or x are not zero and at least two of the non-zero groups are not the same letter.

In another specific embodiment the invention provides a compound of formula (Id32) wherein at least three of u, v, w or x are not zero and at least two of the non-zero groups are not the same letter.

In another specific embodiment the invention provides a compound of formula (Id32) wherein at least three of u, v, w or x are not zero and at least three of the non-zero groups are not the same letter.

In another specific embodiment the invention provides a compound of formula (Id32) wherein at least four of u, v, w or x are not zero and at least two of the non-zero groups are not the same letter.

In another specific embodiment the invention provides a compound of formula (Id32) wherein the sum of u, v, w and x is not zero.

In another specific embodiment the invention provides a compound of formula (Id32) wherein at least one of u, or w are not zero.

In another specific embodiment the invention provides a compound of formula (Id32) wherein at least two of u, or w are not zero.

In another specific embodiment the invention provides a compound of formula (Id32) wherein at least one u is not zero, and at least one w is not zero.

In another specific embodiment the invention provides a compound of formula (Id32) wherein both u are not zero, and at least one w is not zero.

In another specific embodiment the invention provides a compound of formula (Id32) wherein at least one u is not zero.

In another specific embodiment the invention provides a compound of formula (Id32) wherein both of u are not zero.

In another specific embodiment the invention provides a compound of formula (Id32) wherein at least one of w is not zero.

In another specific embodiment the invention provides a compound of formula (Id32) wherein both w are not zero.

Compounds of Formula (Ie)

In one embodiment of the invention, the compound of formula (I) is a compound of formula (Ie):

$$E^0\text{-}V^w\text{-}Z^0\text{-}P^u\text{-}Y^2\text{-}P^u\text{-}Z^0\text{-}V^w\text{-}E^0 \qquad (Ie)$$

wherein:
  each u is 0, 1, 3, 5, 7, 8, 10, or 11;
  each w is 0, 1, 2, 3, 4, or 5;
each $Y^2$ is independently:
a fused five to eight ring system with up to thirty-two atoms that may be fully aromatic or partially saturated and contains atoms selected from C, N, O, S, $SO_2$, SO and which ring system is optionally substituted with one or more groups independently selected from H, oxo, $R^{A1}$ and $R^{A3}$;
  each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
  each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
  each $R^4$ is independently selected from H, alkyl, haloalkyl, aryl, and arylalkyl;
  $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $P^0$ is independently:

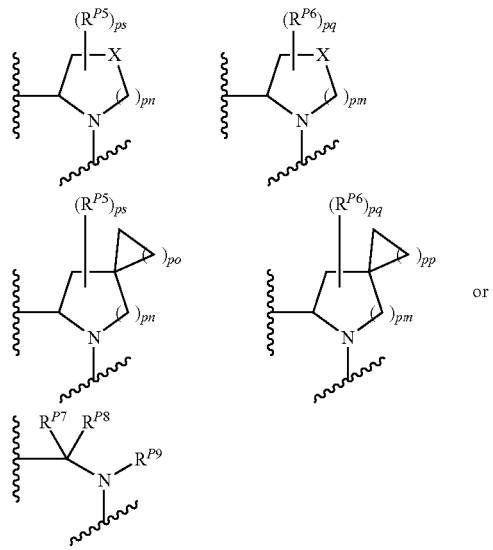

wherein:
  X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
  each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
  each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; $R^{Pa}$ and $R^{Pb}$ are each independently H, alkyl, aryl, or arylalkyl; or $R^{Pa}$ and $R^{Pb}$ taken together with the atom to which they are attached form a heterocycle;
  pq and ps are independently 0, 1, 2, 3, or 4;
  pm and pn are independently 0, 1, or 2;
  po and pp are independently 1, 2, or 3;
  $R^{P7}$ and $R^{P8}$ are each independently selected from hydrogen, alkenyl, alkoxyalkyl, alkyl, haloalkyl, and $(NR^{Pa}R^{Pb})$alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;
  $R^{P9}$ is selected from hydrogen and alkyl;
each $P^1$ is independently:

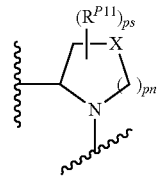

wherein:
  X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;
  each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
  at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

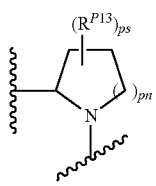

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;
each $P^5$ is independently a ring of the formula:

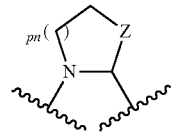

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

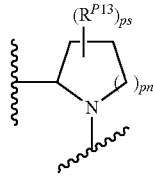

wherein:
ps is 2, 3, 4, 5, or 6;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

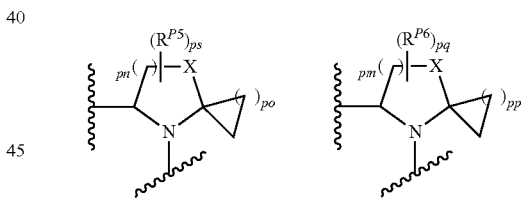

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;

each $P^{11}$ is independently:

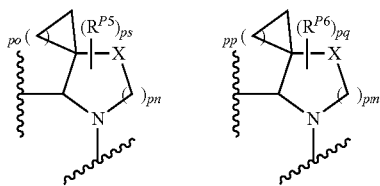

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;
each —Z$^O$— is —C(=O)— or —C(=S)—;
each E$^0$ is independently —NR$^{Ec}$R$^{Ed}$ wherein
R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each V$^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each V$^1$ is independently cyanoalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^2$ is independently haloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^3$ is independently alkyl, which is substituted with one or more oxo, and which is optionally substituted with one or more groups independently selected from cycloalkyl, halo, aryl, alkenyl, and cyano;

each V$^4$ is independently haloalkoxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl; and each V$^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

In one embodiment the invention provides a compound of formula (Ie) wherein Y$^2$ is:

335
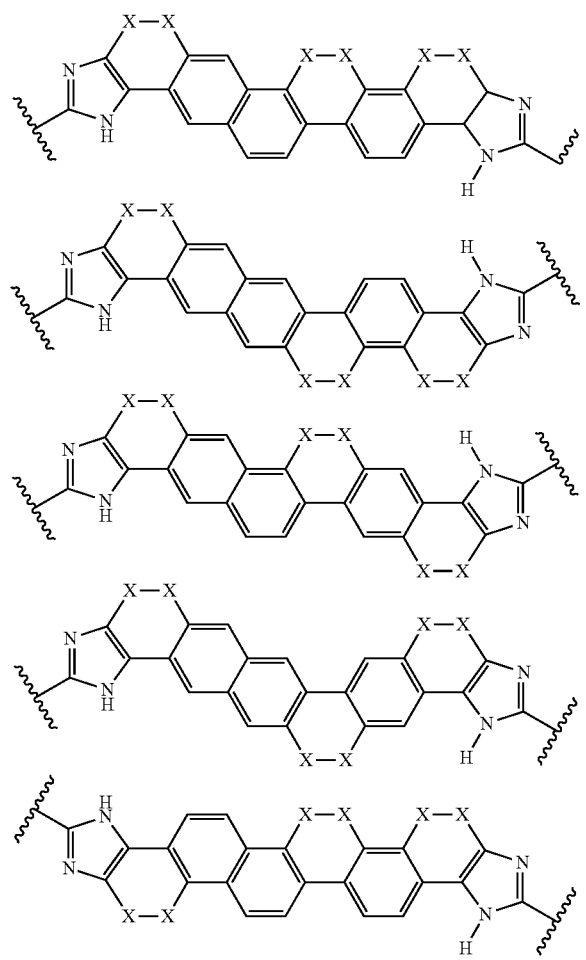
336
-continued
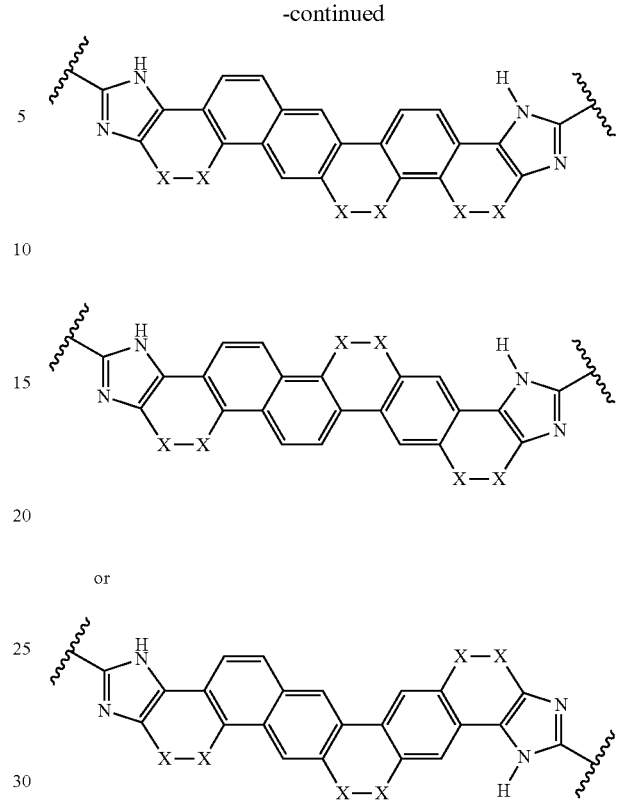
wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$.
In one embodiment the invention provides a compound of formula (Ie) which is selected from:
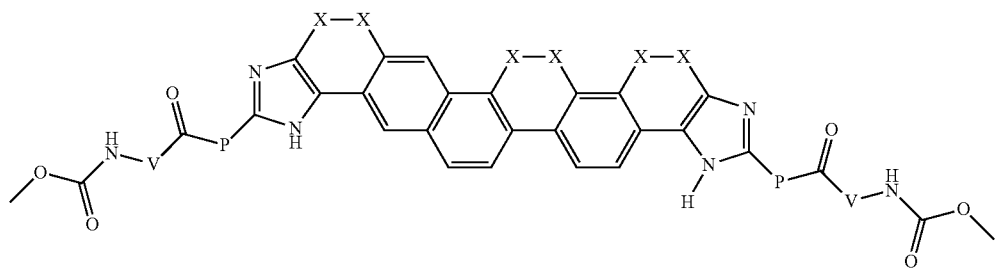
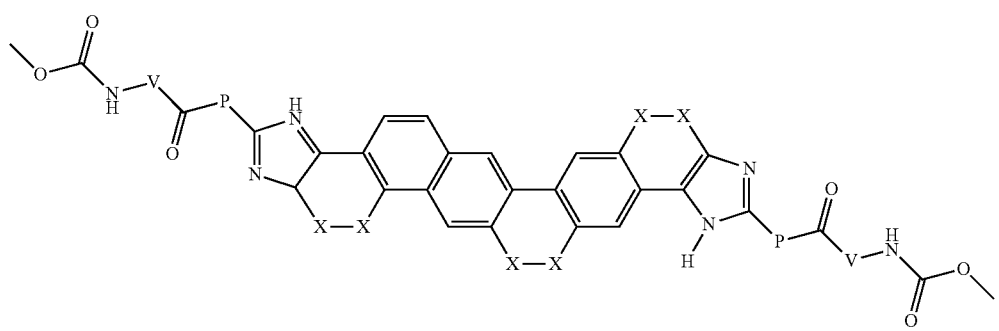

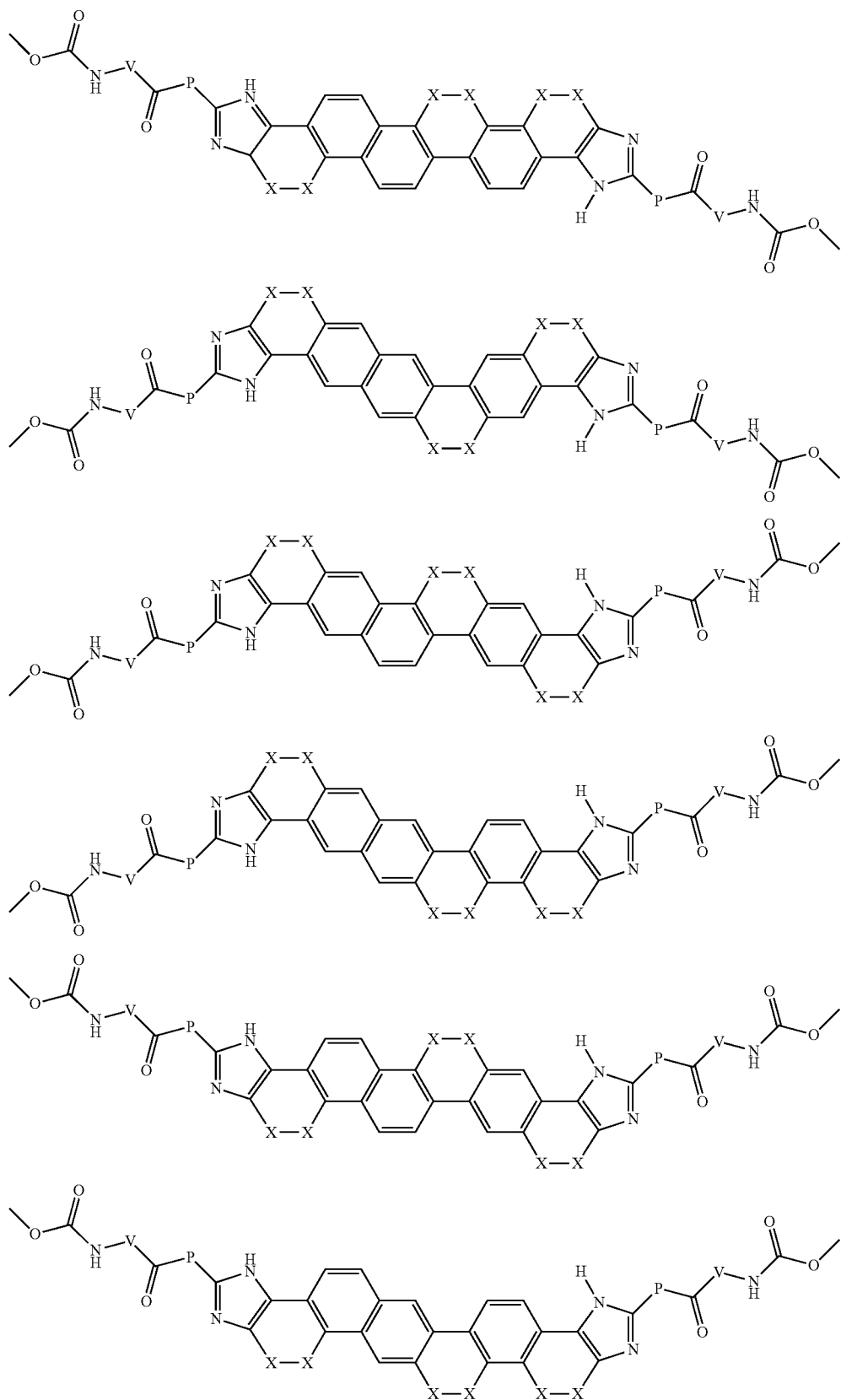

wherein X—X is selected from O, CH$_2$, CH=CH, CH$_2$—CH$_2$, CH$_2$—O, O—CH$_2$, CH$_2$—CH$_2$—CH$_2$, and CH$_2$—O—CH$_2$; or a pharmaceutically acceptable salt, or prodrug thereof.

Specific values for E, P, V, and Z

In another specific embodiment of the invention each E is E$^o$.

In another specific embodiment of the invention each E is —NHC(=O)Oalkyl.

In another specific embodiment of the invention E$^o$ is methoxycarbonylamino.

In one embodiment the invention E$^o$ is —NH2, alkylamino or dialkylamino.

In one embodiment the invention E$^o$ is cycloalkylamino or cycloalkyl(alkyl)amino, or dicycloalkylamino.

In one embodiment the invention E$^o$ is heterocyclyl.

In one embodiment the invention E$^o$ is heterocyclylamino where the amino is optionally substituted with alkyl.

In one embodiment the invention provides a compound of formula (I) wherein at least one E$^o$ is —NR$^{Ec}$R$^{Ed}$ wherein R$^{Ec}$ is H and R$^{Ed}$ is methoxycarbonyl.

In one embodiment the invention provides a compound of formula (I) wherein at least one E$^o$ is —NR$^{Ec}$R$^{Ed}$ wherein R$^{Ec}$ is H or alkyl and R$^{Ed}$ is H or alkyl.

In one embodiment the invention provides a compound of formula (I) wherein at least one E$^o$ is —NR$^{Ec}$R$^{Ed}$ wherein R$^{Ec}$ is H, alkyl or cycloalkyl and R$^{Ed}$ is cycloalkyl.

In one embodiment the invention provides a compound of formula (I) wherein at least one E$^o$ is an N-linked heterocyclyl.

In one embodiment the invention provides a compound of formula (I) wherein at least one E$^o$ is —NR$^{Ec}$R$^{Ed}$ wherein R$^{Ec}$ is H, alkyl, or cycloalkyl; and R$^{Ed}$ is heterocycle.

In another specific embodiment of the invention P is selected from:

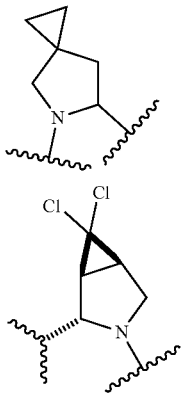
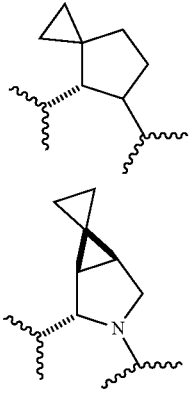
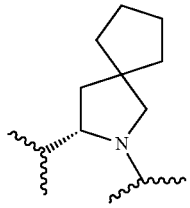
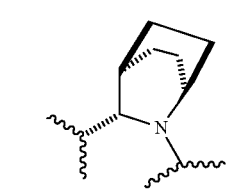

-continued

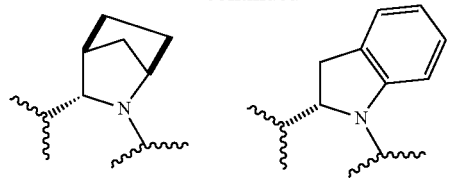
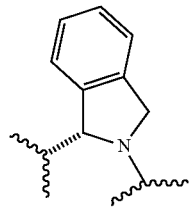
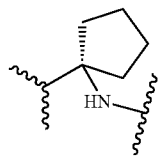
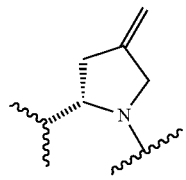
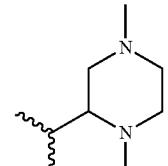
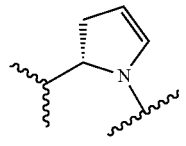
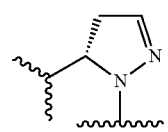
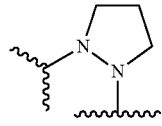
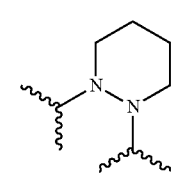
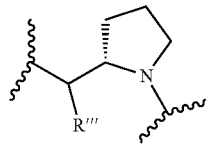
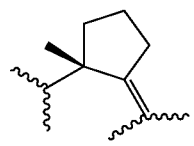
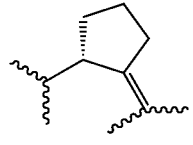
and
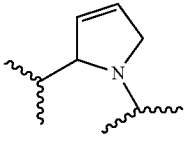

wherein R'" is hydrogen or methyl.

In another specific embodiment of the invention P is selected from

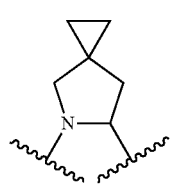
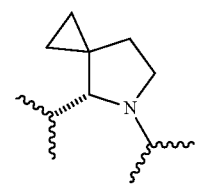

-continued
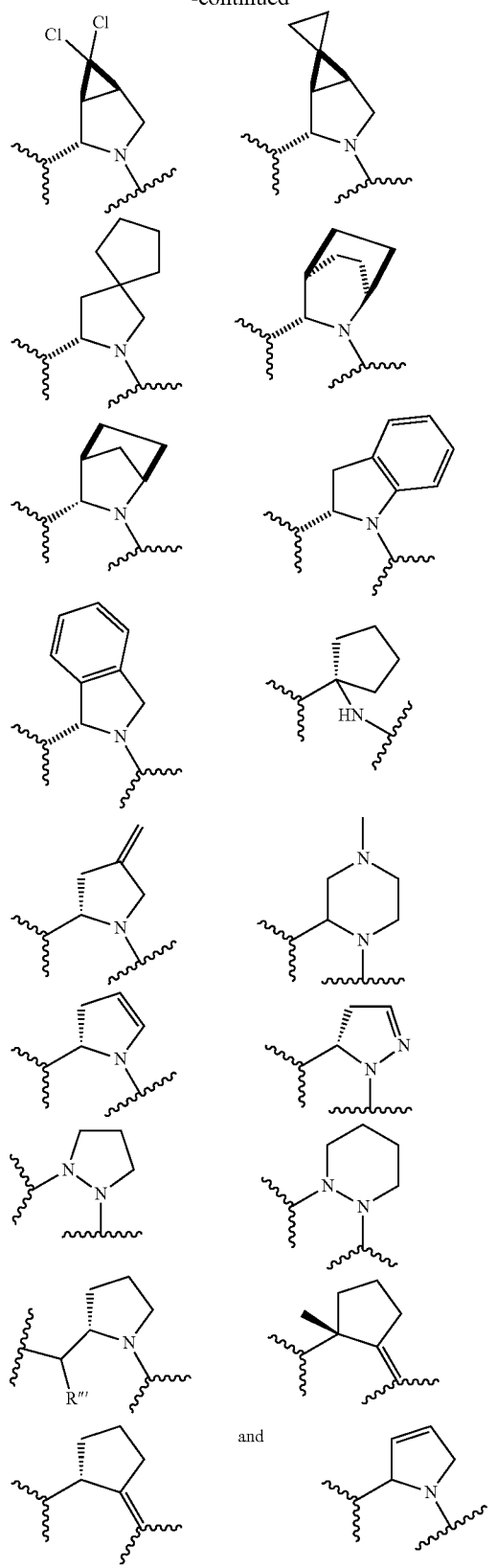
and another P is P⁰.
In another specific embodiment of the invention P is selected from
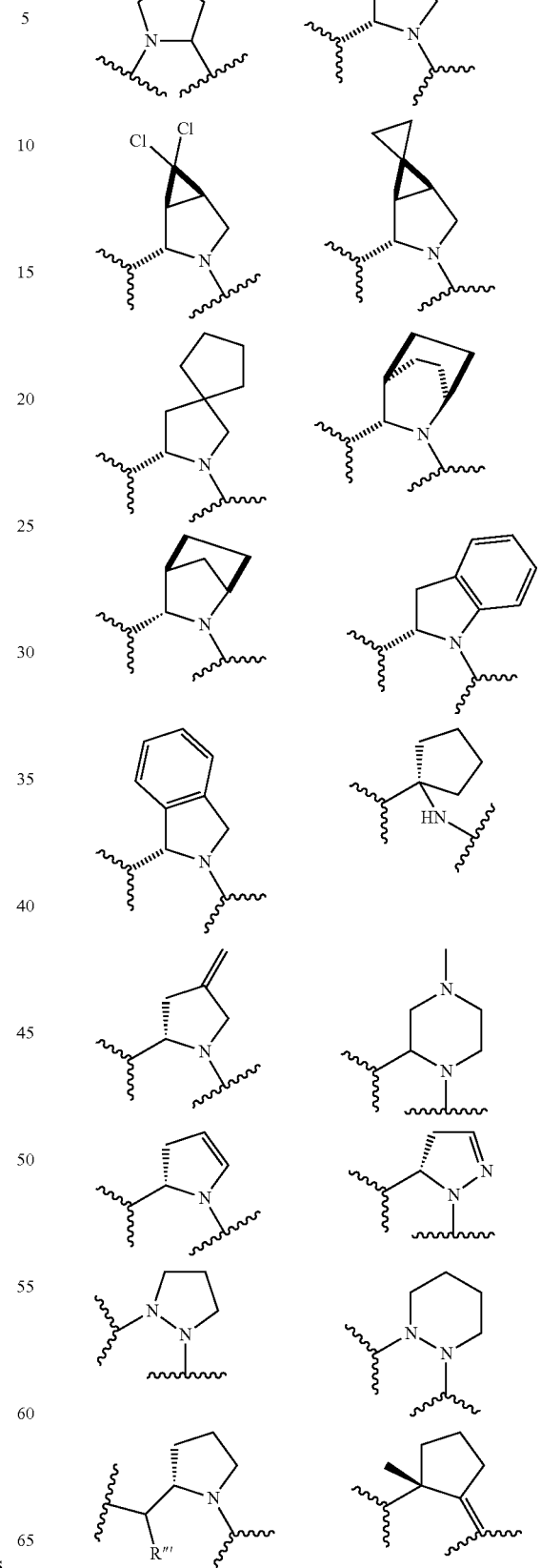

-continued

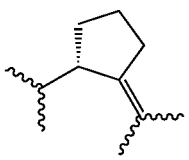

and wherein R''' is hydrogen or methyl; and another P is P⁰.

In another specific embodiment of the invention P is selected from:

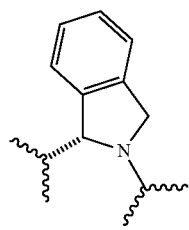 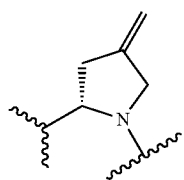

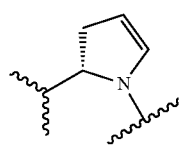 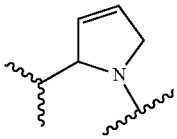

and 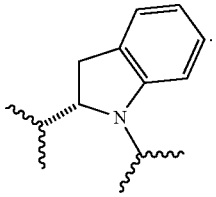

In another specific embodiment of the invention at least one P is $P^7$ and is:

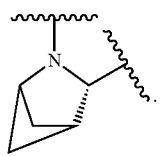 [SMILES: *[C@@H]1C2CC(C2)N1*]

In another specific embodiment of the invention at least one P is $P^8$ and is:

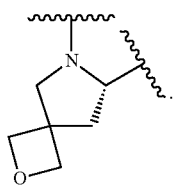 [SMILES: *[C@@H]1CC2(COC2)CN1*]

In another specific embodiment of the invention P is $P^{10}$ and is:

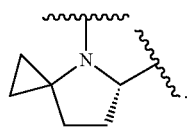 [SMILES: *[C@@H]1CCC2(CC2)N1*]

In another specific embodiment of the invention P is $P^{11}$ and is:

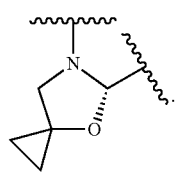 [SMILES: *[C@@H]1OC2(CC2)CN1*]

In another specific embodiment of the invention each P is independently selected from:

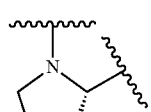 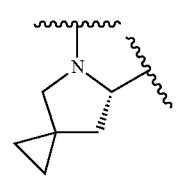

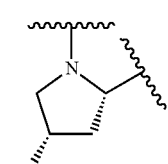 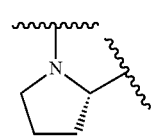

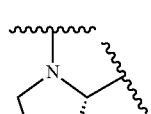 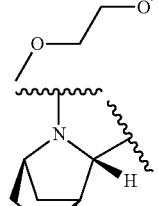

and 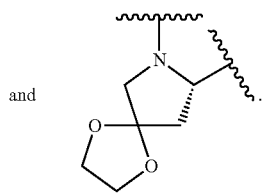

In another specific embodiment of the invention $P^0$ is

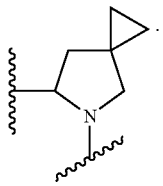 [SMILES: *C1CC2(CC2)CN1*]

In another specific embodiment of the invention $P^7$ is a [2.2.1] or a [2.2.2] ring system.

In another specific embodiment of the invention P⁷ is

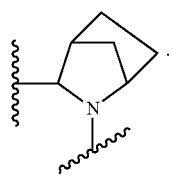 [SMILES: *C1C2CCC(C2)N1*]

optionally substituted with one or more groups independently selected from $R^{P6}$ and $R^{P11}$.

In another specific embodiment of the invention P is selected from:

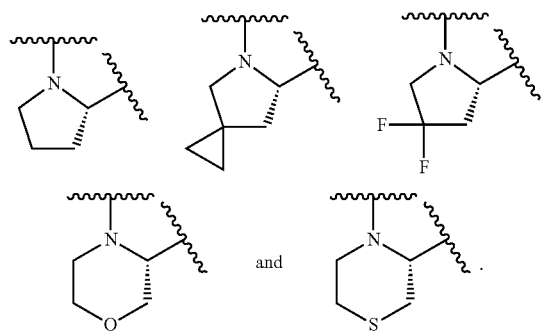

and

In another specific embodiment of the invention P is selected from:

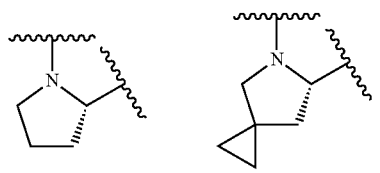

and

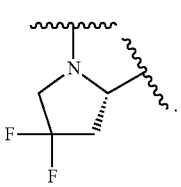

In another specific embodiment of the invention P is selected from:

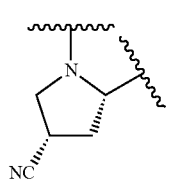 and 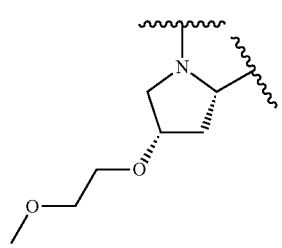

In another specific embodiment of the invention P is:

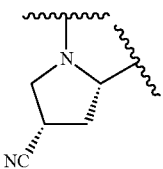

In another specific embodiment of the invention P is:

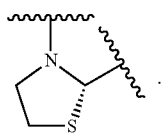 [SMILES: *[C@@H]1SCCN1*]

In another specific embodiment of the invention P is:

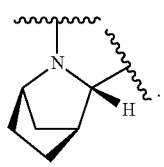 [SMILES: *[C@@H]1[C@H]2CC[C@H](C2)N1*]

In another specific embodiment of the invention P is:

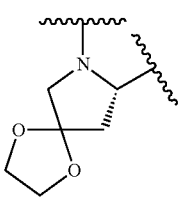

In another specific embodiment of the invention P is selected from:

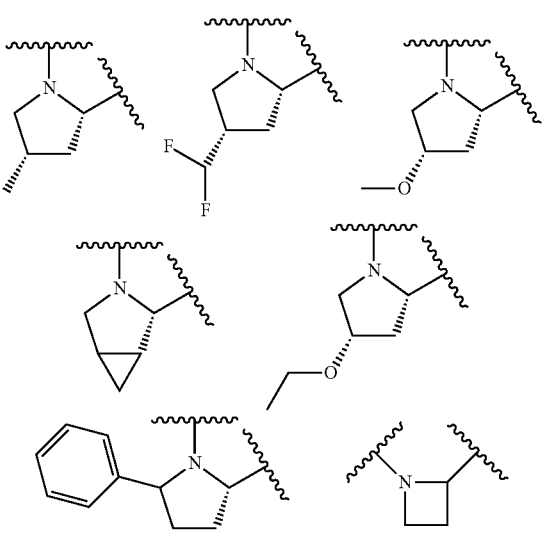

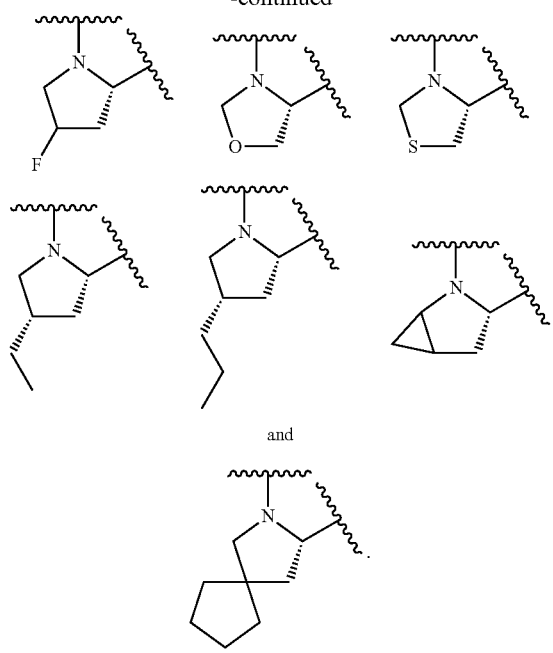
In another specific embodiment of the invention P is selected from:
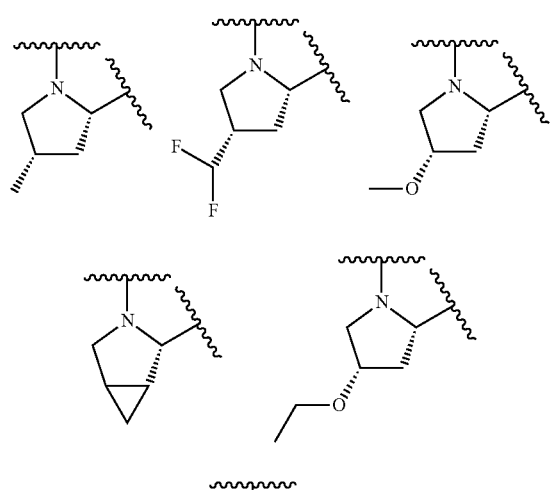
In another specific embodiment of the invention P is selected from:
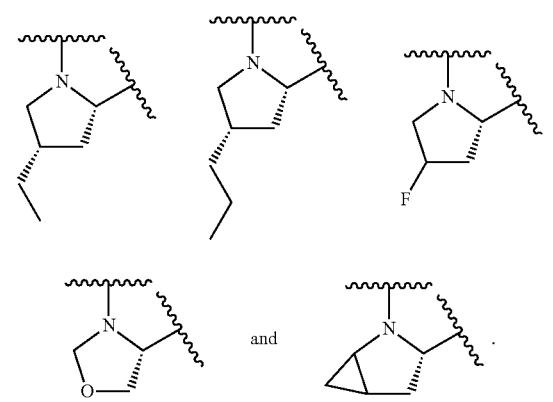
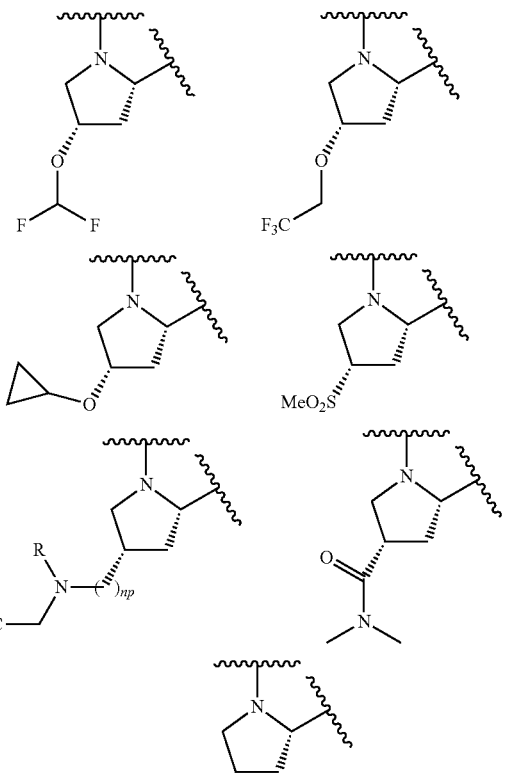
wherein R is hydrogen or methyl and np is 0 or 1.
In another specific embodiment of the invention P is selected from:
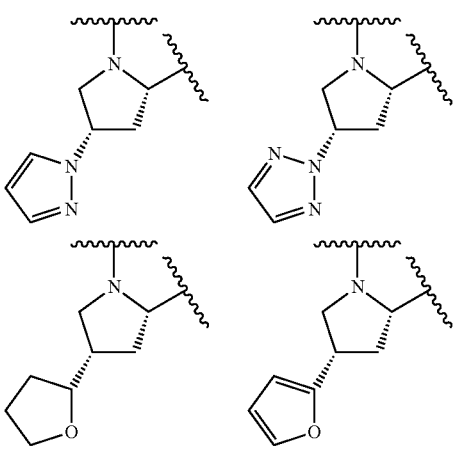

-continued

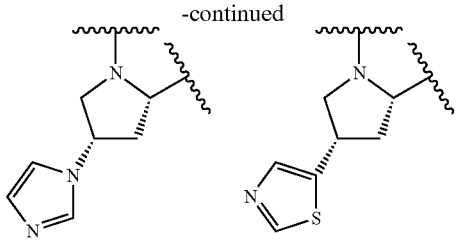

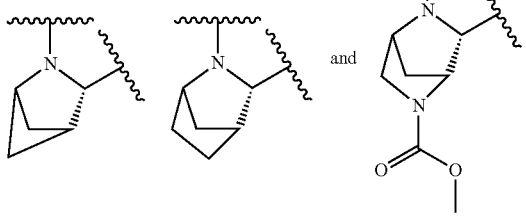

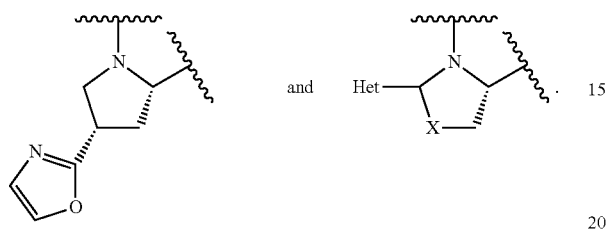

wherein X is O or S; and Het is a heterocycle.

In another specific embodiment of the invention P is selected from:

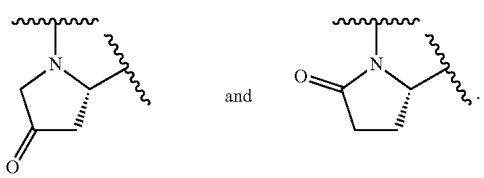 [SMILES: *[C@@H]1CC(=O)CN1* ; *[C@@H]1CCC(=O)N1*]

In another specific embodiment of the invention P is selected from:

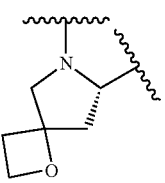

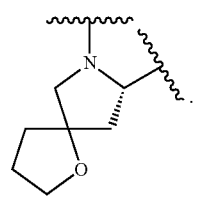

In another specific embodiment of the invention P is:

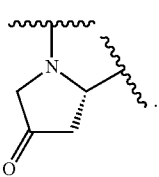 [SMILES: *[C@@H]1CC(=O)CN1*]

In another specific embodiment of the invention P is selected from:

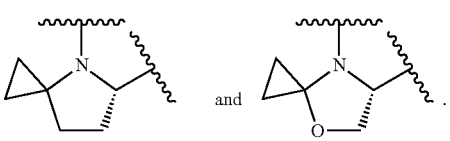

In another specific embodiment of the invention P is selected from:

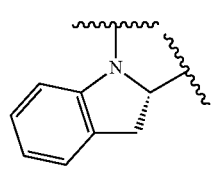

In another specific embodiment of the invention P is selected from:

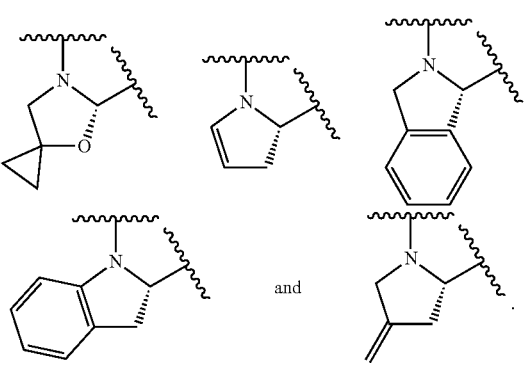

In another specific embodiment of the invention P is selected from:

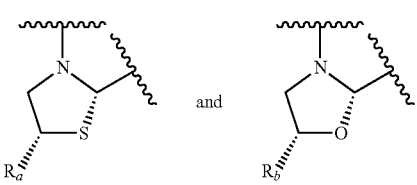

wherein $R_a$ is hydrogen or methyl and $R_b$ is methyl, or ethyl.

In another specific embodiment of the invention P is selected from:

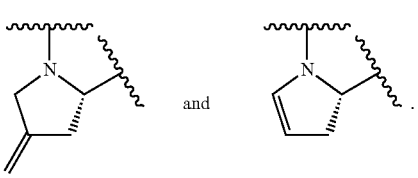

In another specific embodiment of the invention P is selected from:

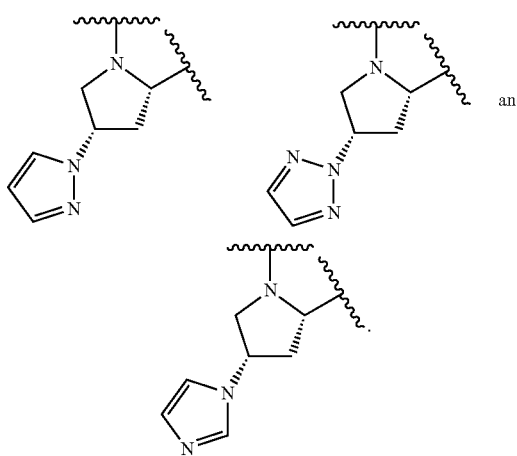

In another specific embodiment of the invention P is selected from:

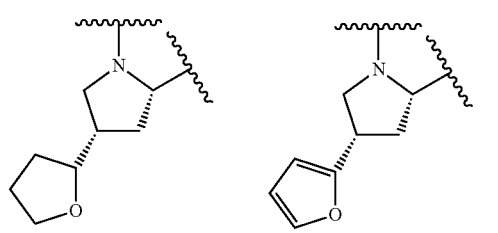

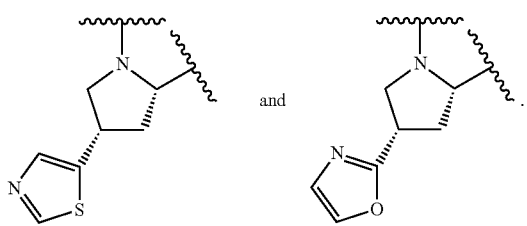

In another specific embodiment of the invention P is selected from:

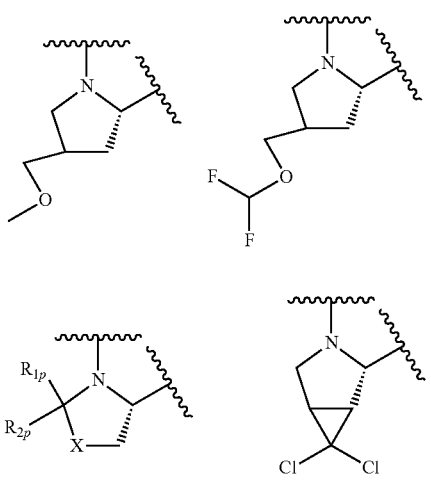

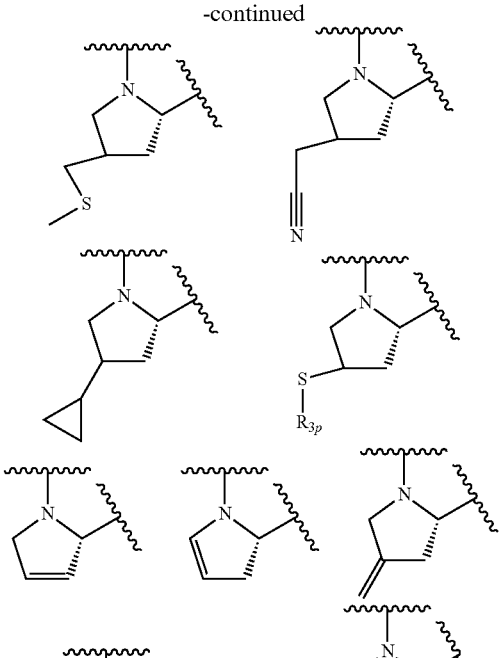

wherein X is O or S; $R_{1p}$ and $R_{2p}$ are carbon linked and when taken together form a 4-6 membered heterocycle; $R_{3p}$ is alkyl or cycloalkyl; and $R_{4p}$ is hydrogen, methyl, or cyclopropyl.

In another specific embodiment of the invention P is $P^O$ and is selected from:

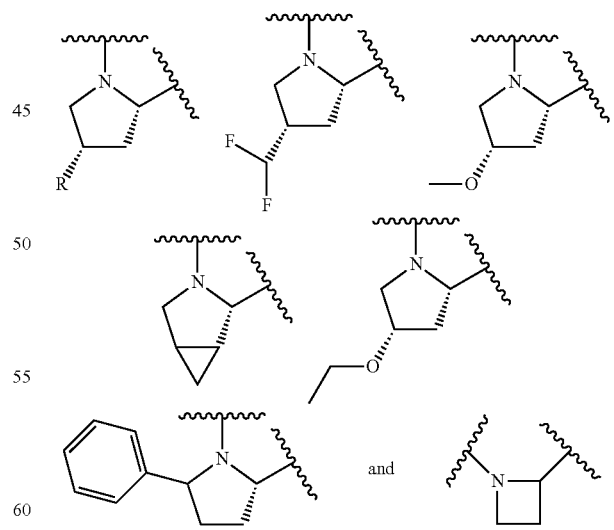

wherein R is alkyl.

In another specific embodiment of the invention when P is a divalent group that is linked through a nitrogen of P and through a carbon of P, it is the nitrogen of P that is connected to Z.

In another specific embodiment of the invention each V is V⁰.

In another specific embodiment of the invention each V is alkyl.

In another specific embodiment of the invention each V is isopropyl.

In another specific embodiment of the invention each V is isobutyl.

In another specific embodiment of the invention each V is V².

In another specific embodiment of the invention each V is haloalkyl.

In another specific embodiment of the invention each V is independently selected from V⁰, V¹, V², V³, V⁴, and V⁵.

In another specific embodiment of the invention at least one V is selected from:

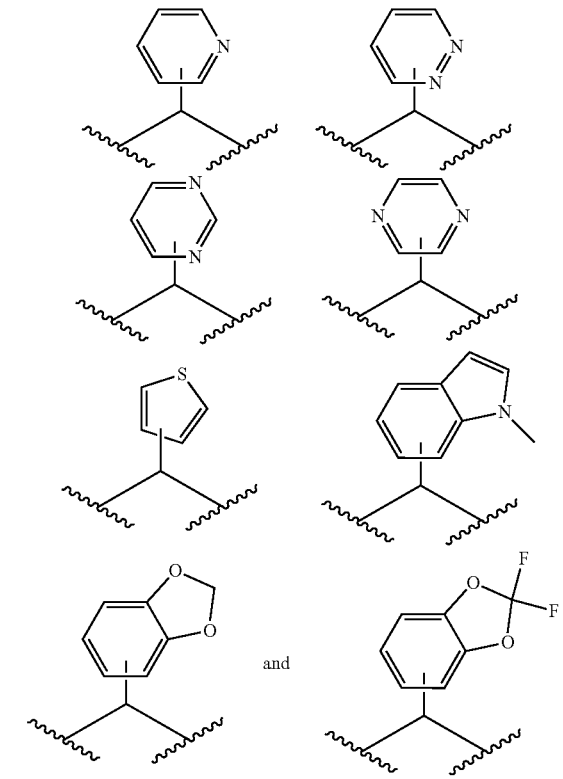

In another specific embodiment of the invention at least one V is selected from:

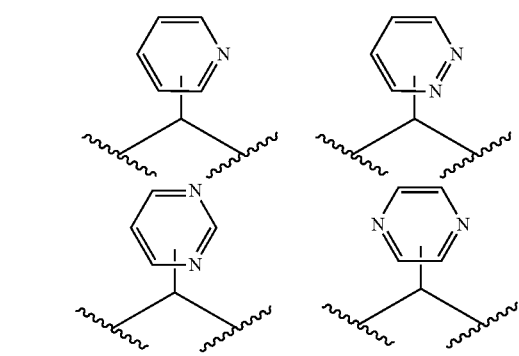

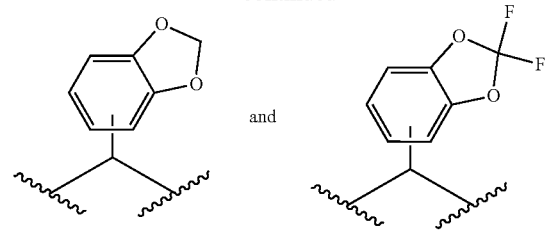

In another specific embodiment of the invention at least one V is selected from:

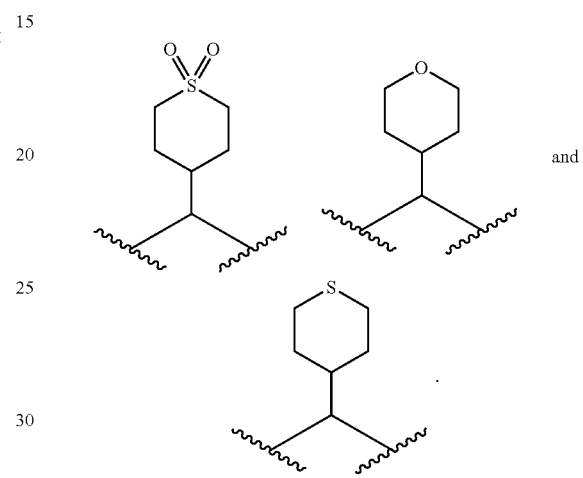

In another specific embodiment of the invention at least one V is selected from:

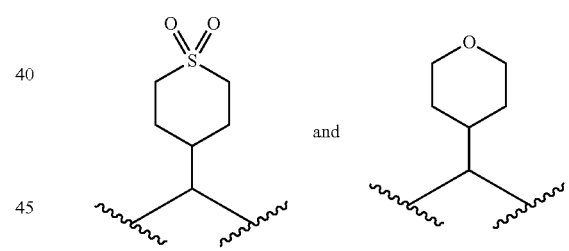

In another specific embodiment of the invention at least one V is selected from:

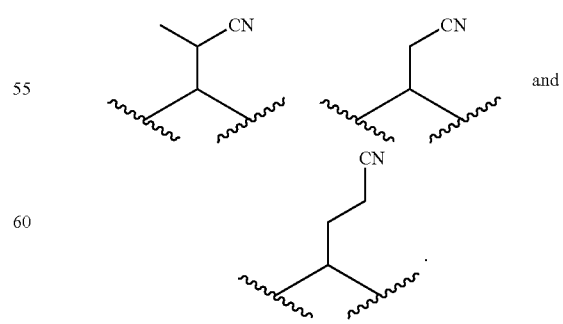

In another specific embodiment of the invention at least one V is selected from:

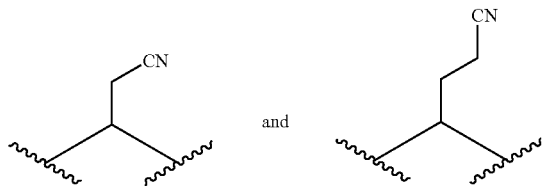and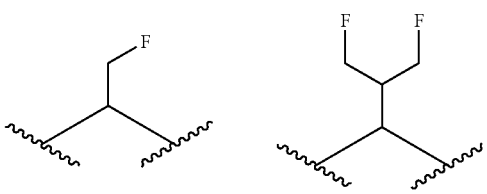.

In another specific embodiment of the invention at least one V is selected from:

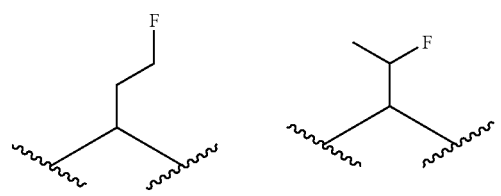

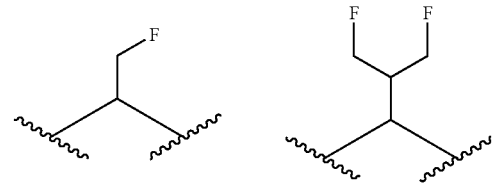

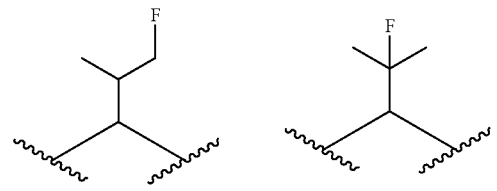

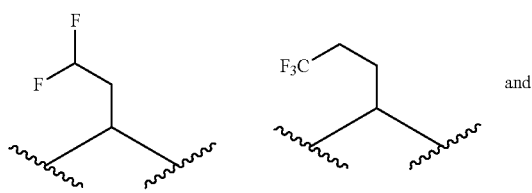and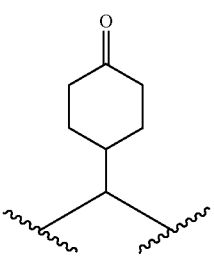

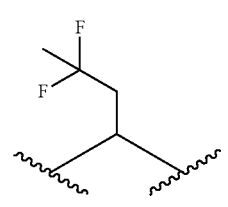.

In another specific embodiment of the invention at least one V is selected from:

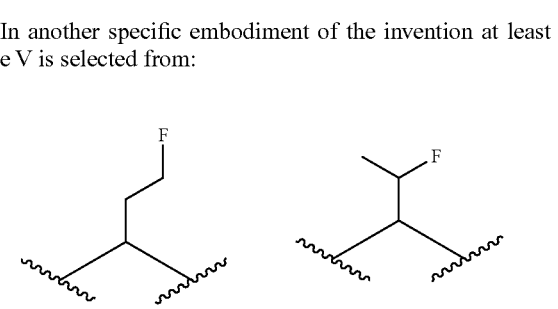

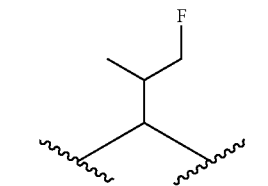

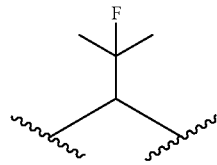and

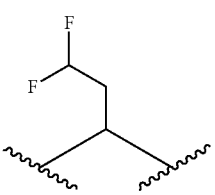.

In another specific embodiment of the invention at least one V is selected from:

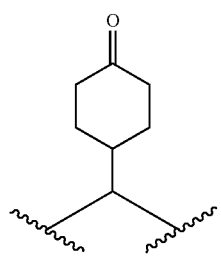and (ketone structure) .

In another specific embodiment of the invention at least one V is:

(cyclohexanone structure)

In another specific embodiment of the invention at least one V is selected from:

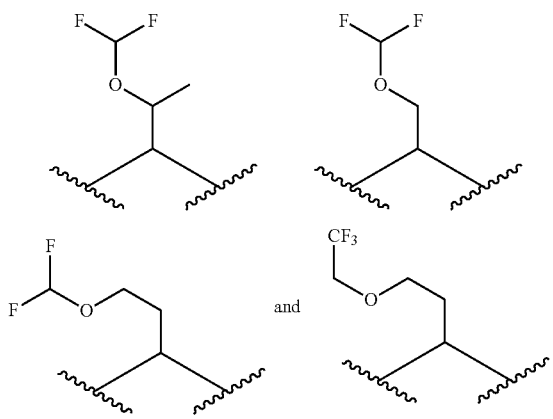

In another specific embodiment of the invention at least one V is selected from:

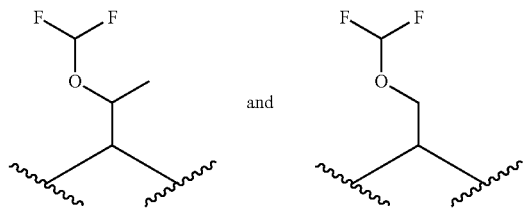

In another specific embodiment of the invention at least one V is selected from:

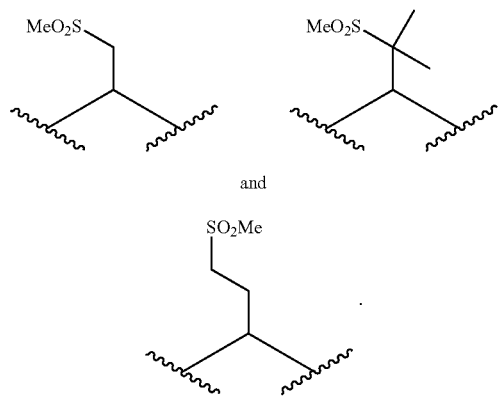

In another specific embodiment of the invention at least one V is:

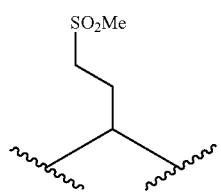

In another specific embodiment of the invention each V is:

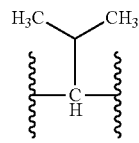

In another specific embodiment of the invention each $V^2$ is independently haloalkyl, which is optionally substituted with one or more groups independently selected from cycloalkyl, alkoxy, haloalkoxy, cycloalkenyl, hydroxy, and $NR^{Va}R^{Vb}C(=O)O—$; $R^{Va}$ and $R^{Vb}$ are each independently selected from hydrogen, alkenyl, and alkyl; and each $V^4$ is independently haloalkoxyalkyl, which is optionally substituted with one or more groups independently selected from cycloalkyl, alkoxy, haloalkoxy, cycloalkenyl, hydroxy, and $NR^{Va}R^{Vb}C(=O)O—$; $R^{Va}$ and $R^{Vb}$ are each independently selected from hydrogen, alkenyl, and alkyl.

In another specific embodiment of the invention each $V^0$ is independently arylalkyl or heterocyclylalkyl, wherein arylalkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, $—NR^XR^Y$, $—(NR^XR^Y)alkyl$, oxo, and $—P(O)OR_2$, wherein each R is independently selected from hydrogen and alkyl; and wherein the alkyl part of the heterocyclylalkyl is further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, $—NR^XR^Y$, $—(NR^XR^Y)alkyl$, and oxo.

In another specific embodiment the invention each V is isobutyl.

In another specific embodiment the invention at least one V is isobutyl.

In another specific embodiment the invention at least one V is phenylmethyl where the Z and E groups are each connected to the methyl group (i.e. —CH(Ph)—).

In another specific embodiment the invention at least one V is $V^0$ and at least one $V^0$ is phenylmethyl where the Z and E groups are each connected to the methyl group and the phenyl can be substituted as described in the description for the $V^0$ aryl group.

In another specific embodiment the invention at least one $V^0$ is arylmethyl where the Z and E groups are each connected to the methyl group and the aryl can be substituted as described in the description for the $V^0$ aryl group.

In another specific embodiment the invention at least one V is $V^0$ and at least one $V^0$ is heterocyclylmethyl where the Z and E groups are each connected to the methyl group.

In another specific embodiment the invention at least one V is $V^0$ and at least one $V^0$ is heterocyclylmethyl where the Z and E groups are each connected to the methyl group and the heterocyclyl group can be substituted as described in the description for the $V^0$ heterocyclyl group.

In another specific embodiment the invention each $V^2$ is independently haloalkyl, which is optionally substituted with one or more groups independently selected from cycloalkyl, alkoxy, haloalkoxy, cycloalkenyl, hydroxy, and $NR^{Va}R^{Vb}C(=O)O-$; $R^{Va}$ and $R^{Vb}$ are each independently selected from hydrogen, alkenyl, and alkyl.

In another specific embodiment the invention each $V^4$ is independently haloalkoxyalkyl, which is optionally substituted with one or more groups independently selected from cycloalkyl, alkoxy, haloalkoxy, cycloalkenyl, hydroxy, and $NR^{Va}R^{Vb}C(=O)O-$; wherein $R^{Va}$ and $R^{Vb}$ are each independently selected from hydrogen, alkenyl, and alkyl.

In another specific embodiment of the invention each Z is $Z^o$.

In another specific embodiment of the invention each Z is $-C(=O)-$.

For the compounds of formula (I) described herein, including the compounds of formulae (Ia), (Ib), (Ic), (Id), and (Ie), any of the above specific values or embodiments for the variables E, P, V, and Z, can be applied. Thus, the invention also includes specific embodiments wherein one or more of the specific values or embodiments for J, T, P, W, L, M, A, R9, E, P, V, and Z described herein are combined with one of formulae (Ia), (Ib), (Ic), (Id), and (Ie), to provide a sub-set of compounds that represents a specific embodiment of the invention.

For example, by selecting a compound of formula (Ia9) above, along with specific values for P, M, W, and V identified herein, one can identify a specific embodiment the invention which is a compound of formula (Ia9):

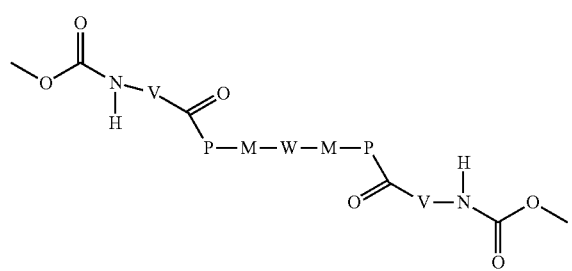

(Ia9)

wherein:
W is

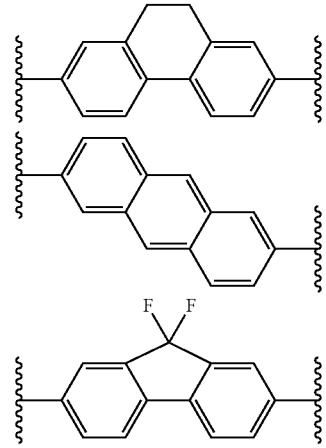

-continued

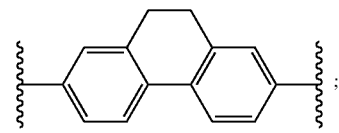

or one M is imidazolyl and one M is benzimidazolyl;
one P is $P^7$ and is:

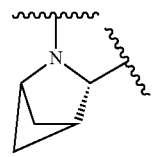 [SMILES: *[C@@H]1C2CC(C2)N1*]

one P is $P^8$ and is:

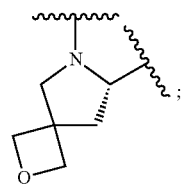 [SMILES: *[C@@H]1CC2(COC2)CN1*]

one V is selected from:

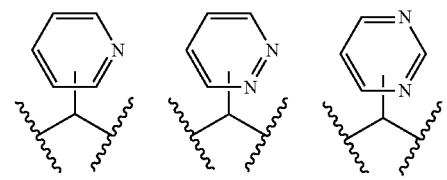

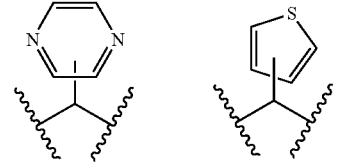

and

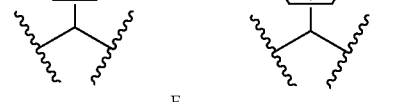

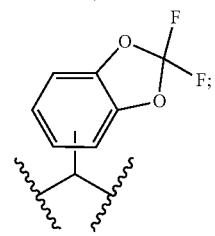

and one V is:

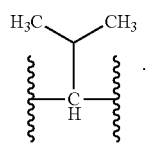

Synthetic Intermediates

The invention also provides synthetic processes and novel synthetic intermediates disclosed herein. For example, the invention provides the following specific intermediate compounds that are useful for preparing compounds of formula (I):

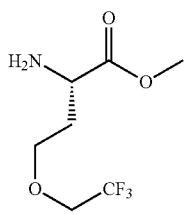

2-Amino-4-(2,2,2-trifluoro-ethoxy)-butyric acid methyl ester

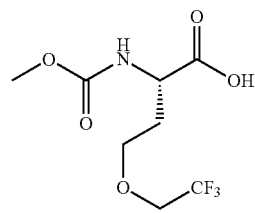

2-Methoxycarbonylamino-4-(2,2,2-trifluoro-ethoxy)-butyric acid

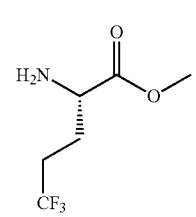

2-Amino-5,5,5-trifluoro-pentanoic acid methyl ester

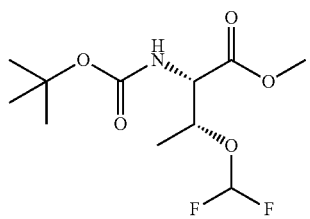

2-tert-Butoxycarbonylamino-3-difluoromethoxy-butyric acid methyl ester

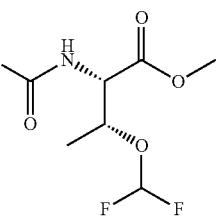

3-Difluoromethoxy-2-methoxycarbonylamino-butyric acid methyl ester

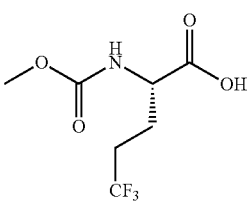

5,5,5-Trifluoro-2-methoxy-carbonylamino-pentanoic acid

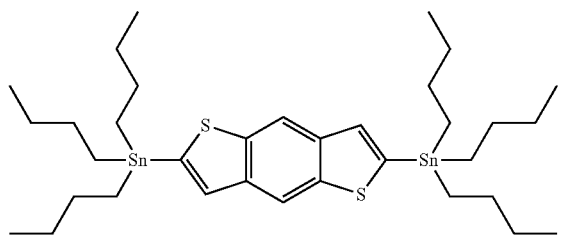

2,6-bis(tri-n-butylstannyl)-benzo[1,2-b:4,5-b']dithiophene

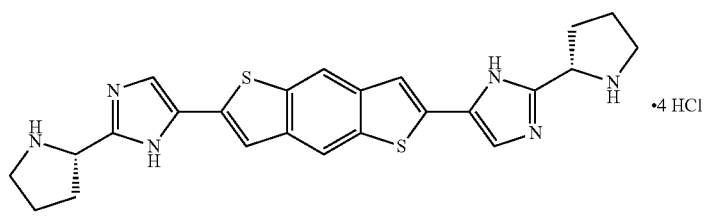

2-[5-(6-{2-[pyrrolidin-2-yl]-3H-imidazol-4-yl}-benzo[1,2-b:4,5-b']dithiophene-2-yl)-1H-imidazol-2-yl]-pyrrolidine tetrahydrochloride The invention provides all such combinations as specific embodiments of the invention.

-continued

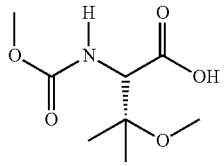

(s)-3-Methyoxy-2-
methoxycarbonylamino-
3-methyl-butyric acid

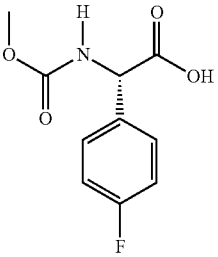

(R)-(4-Flouro-phenyl)-
methoxycarbonylamino-
acetic acid

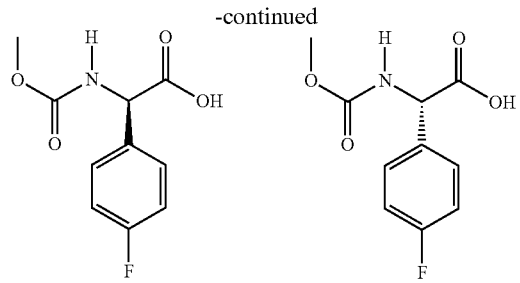

(S)-(4-Flouro-phenyl)-
methoxycarbonylamino-
acetic acid

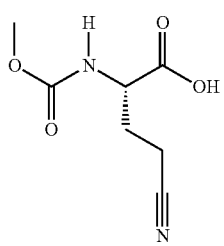

(S)-4-Cyano-2-
methoxycarbonyl-
aminobutyric acid

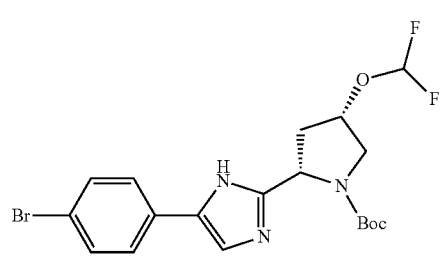

2-[5-(4-Bromo-phenyl)-1H-imidazol-2-yl]-
4-difluoromethoxy-pyrrolidine-1-carboxylic acid tert-butyl ester

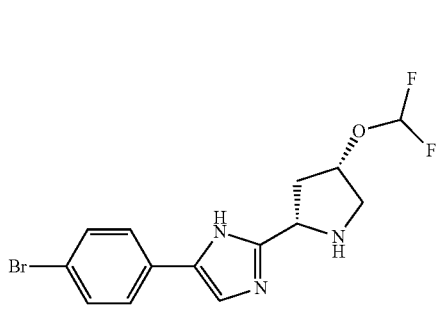

5-(4-Bromo-phenyl)-2-(4-difluoromethoxy-
pyrrolidin-2-yl)-1H-imidazole

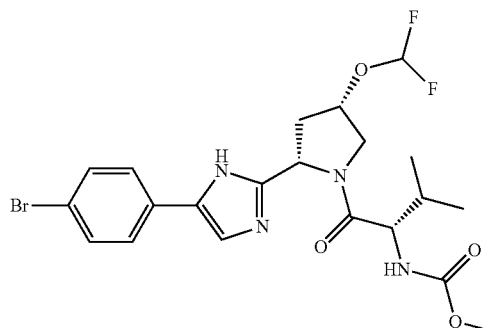

(1-{2-[5-(4-Bromo-phenyl)-1H-imidazole-2-yl]-
4-difluoromethoxy-pyrrolidine-1-carbonyl}-2-
methyl-propyl)-carbamic acid methyl ester

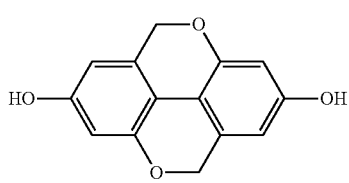

5,10-Dihydro-chromeno
[5,4,3-cde]chromene-2,7-diol

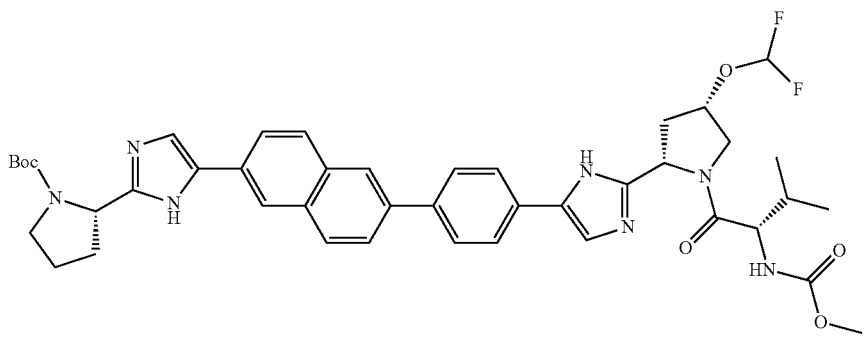

2-{5-[6-(4-{2-[4-Difluoromethoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester

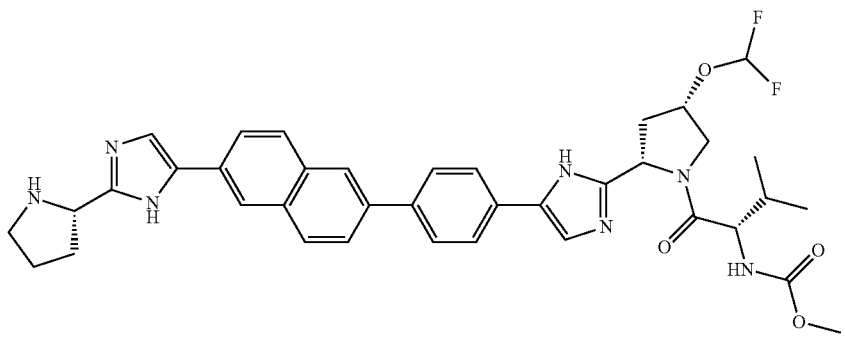

{1-[4-Difluoromethoxy-2-(5-{4-[6-(2-pyrrolidin-2-yl-3H-imidazol-4-yl)-naphthalen-2-yl]-phenyl}-1H-imidazol-2-yl)-pyrrolidine-1-carbonyl]-carbonyl]-2-methyl-propyl}-carbamic acid methyl ester

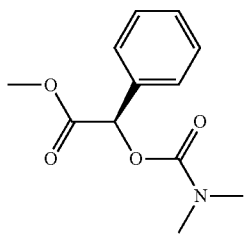

Dimethylcarbamoyloxy-phenyl-acetic acid methyl ester

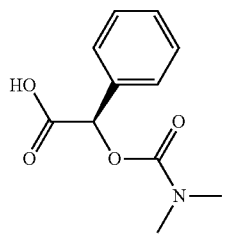

Dimethylcarbamoyloxy-phenyl-acetic acid

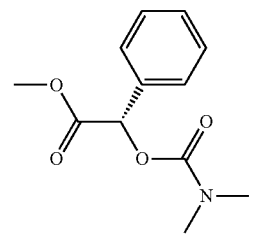

Dimethylcarbamoyloxy-phenyl-acetic acid methyl ester

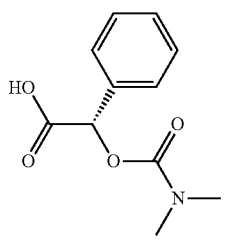

Dimethylcarbamoyloxy-phenyl-acetic acid

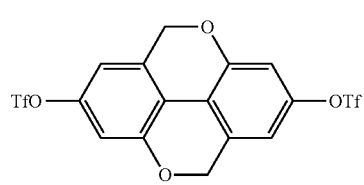

Trifluoro-methanesulfonic acid 7-trifluoro methanesulfonyloxy-5,10-dihydro-chromeno[5,4,3-cde]chromen-2-yl-ester -continued

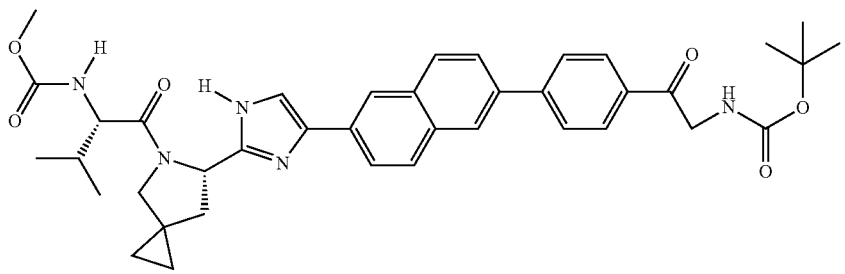

{1-[6-(4-{6-[4-(2-tert-Butoxycarbonylamino-acetyl)-phenyl]-naphthalen-2-yl}-1H-imidazol-2-yl)-5-aza-spiro[2.4]heptane-5-carbonyl]-2-methyl-propyl}-carbamic acid methyl ester

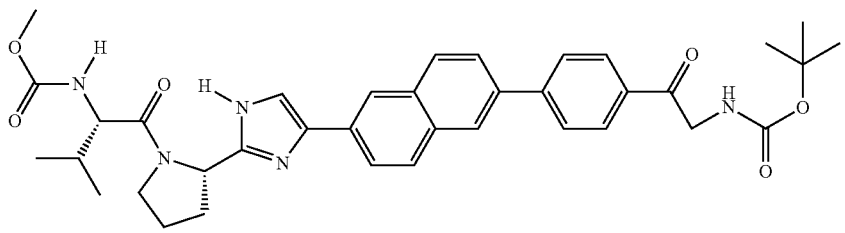

{1-[2-(4-{6-[4-(2-tert-Butoxycarbonylamino-acetyl)-phenyl]-naphthalen-2-yl}-1H-imidazol-2-yl)-pyrrolidine-1-carbonyl]-2-methyl-propyl}-carbamic acid methyl ester

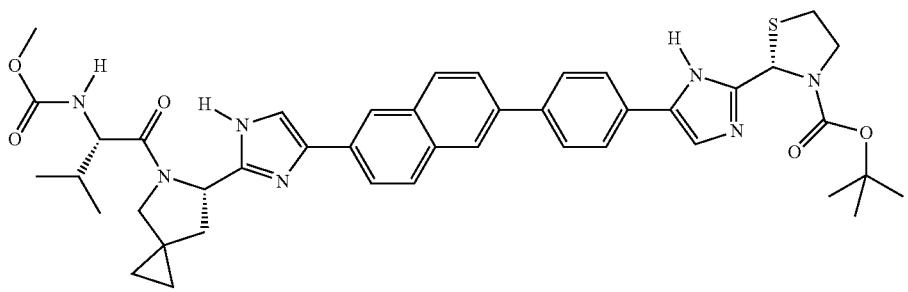

2-{5-[4-(6-{2-[5-(2-Methoxycarbonylamino-3-methyl-butyryl)-5-aza-spiro[2.4]hept-6-yl]-1H-imidazol-2-yl)-thiazolidine-3-carboxylic acid tert-butyl ester

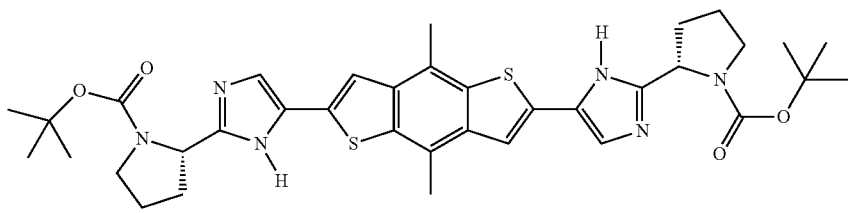

1-{2-[5-(6-{2-[1-carbamic acid tert. buty ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert.butyl ester

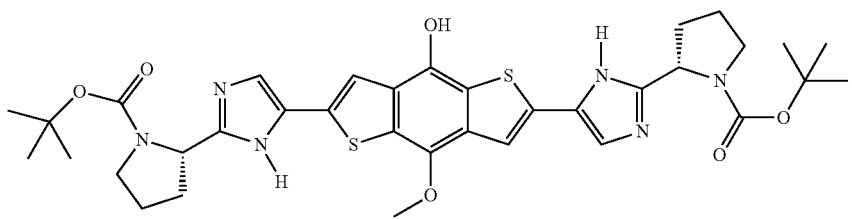

1-{2-[5-(6-{2-[1-carbamic acid tert. buty ester-pyrrolidin-2-yl]-3H-imidazol-4-yl}-4,8-dimethoxy-1,5-dithia-s-indacen-2-yl)-1H-imidazol-2-yl]-pyrrolidine-1-carbamic acid tert.butyl ester -continued

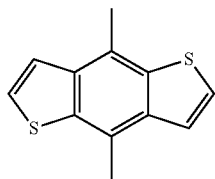

4,8-Dimethyl-1,5-dithia-s-indacene

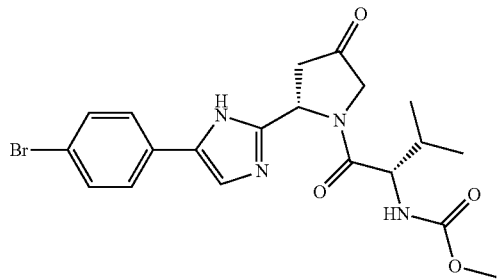

(1-{2-[5-(4-Bromo-phenyl)-1H-imidazol-2-yl]-4-oxo-pyrrolidine-1-carbonyl}-2-methyl-propyl)-carbamic acid methyl ester

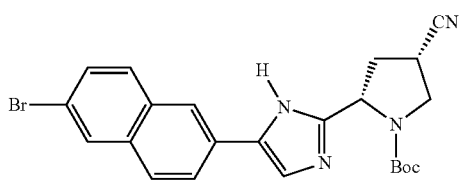

2-[5-(6-Bromo-naphthalen-2-yl)-1H-imidazol-2-yl]-4-cyano-pyrrolidine-1-carboxylic acid tert-butyl ester

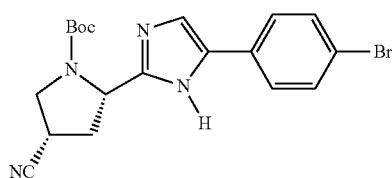

2-[5-(4-Bromo-phenyl)-1H-imidazol-2-yl]-4-cyano-pyrrolidine-1-carboxylic acid tert-butyl ester

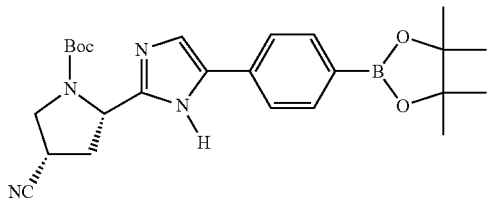

4-Cyano-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester

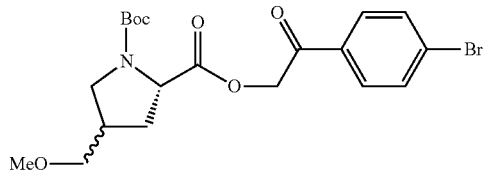

4-Methoxymethyl-pyrrolidine-1,2-dicarboxylic acid 2-[2-(4-bromo-phenyl)-2-oxo-ethyl] ester 1-tert-butyl ester

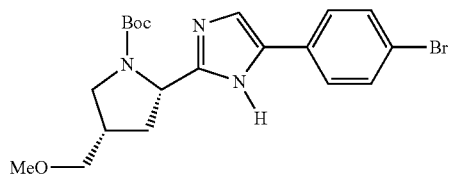

2-[5-(4-Bromo-phenyl)-1H-imidazol-2-yl]-4-methoxymethyl-pyrrolidine-1-carboxylic acid tert-butyl ester

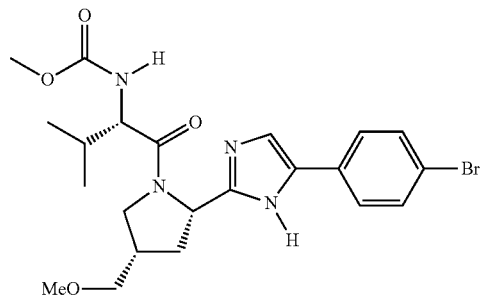

(1-{2-[5-(4-Bromo-phenyl)-1H-imidazol-2-yl]-4-methoxymethyl-pyrrolidine-1-carbonyl}-2-methyl-propyl)-carbamic acid methyl ester

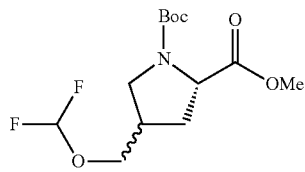

4-Difluoromethoxymethyl-pyrrolidine-1,2-dicarboxylic acid 1-tert-butyl ester 2-methyl ester

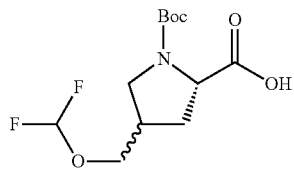

4-Difluoromethoxymethyl-pyrrolidine-1,2-dicarboxylic acid 1-tert-butyl ester

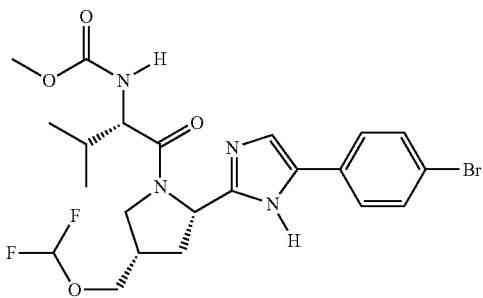

(1-{2-[5-(4-Bromo-phenyl)-1H-imidazol-2-yl]-4-difluoromethoxymethyl-pyrrolidine-1-carbonyl}-2-methyl-propyl)-carbamic acid methyl ester

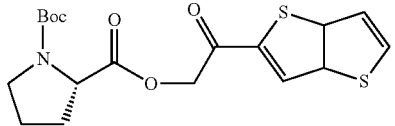

Pyrrolidine-1,2-dicarboxylic acid 1-tert-butyl ester 2-[2-(3a,6a-dihydro-thieno[3,2-b]thiophen-2-yl)-2-oxo-ethyl]ester

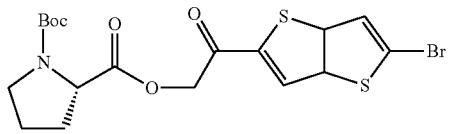

Pyrrolidine-1,2-dicarboxylic acid 2-[2-(5-bromo-3a,6a-dihydro-thieno[3,2-b]thiophen-2-yl)-2-oxo-ethyl]ester 1-tert-butyl ester

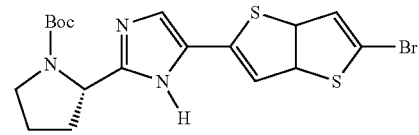

2-[5-(5-Bromo-3a,6a-dihydro-thieno[3,2-b]thiophen-2-yl)-1H-imidazol-2-yl]-pyrrolidine-1-carboxylic acid tert-butyl ester

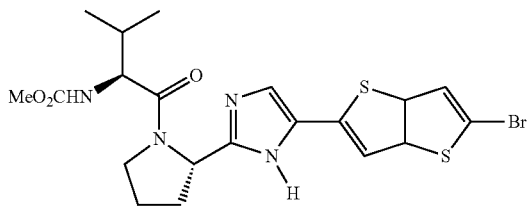

(1-{2-[5-(5-Bromo-3a,6a-dihydro-thieno[3,2-b]thiophen-2-yl)-1H-imidazol-2-yl]-pyrrolidine-1-carbonyl}-2-methyl-propyl-carbamic acid methyl ester

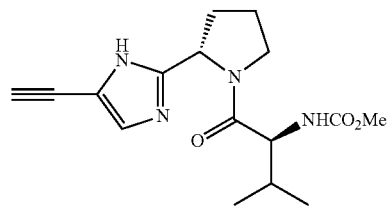

{1-[2-(5-Ethynyl-1H-imidazol-2-yl)-pyrrolidine-1-carbonyl]-2-methyl-propyl}-carbamic acid methyl ester

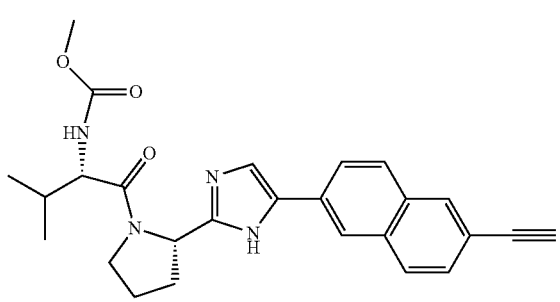

(1-{2-[5-(6-Ethynyl-naphthalen-2-yl)-1H-imidazol-2-yl]-pyrrolidine-1-carbonyl}-2-methyl-propyl)-carbamic acid methyl ester

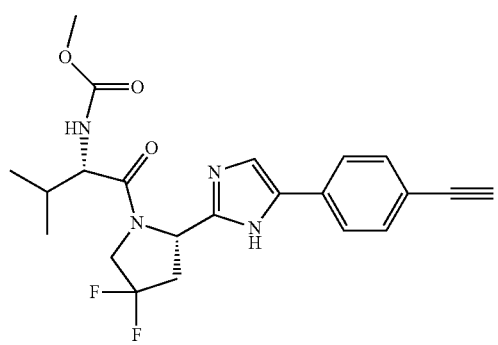

(1-{2-[5-(4-Ethynyl-phenyl)-1H-imidazol-2-yl]-4,4-difluoro-pyrrolidine-1-carbonyl}-2-methyl-propyl)-carbamic acid methyl ester

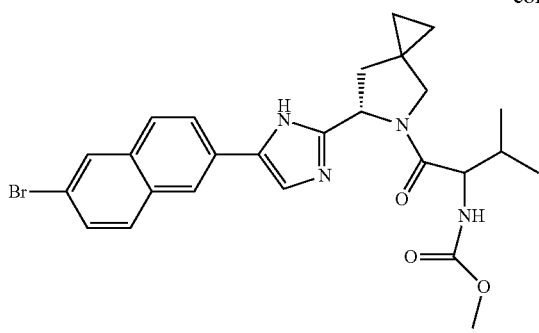

(1-{6-[5-(6-Bromo-naphthalen-2-yl)-1H-imidazol-2-yl]-5-aza-spiro
[2.4]heptane-5-carbonyl}-2-methyl-propyl)-carbamic acid methyl ester

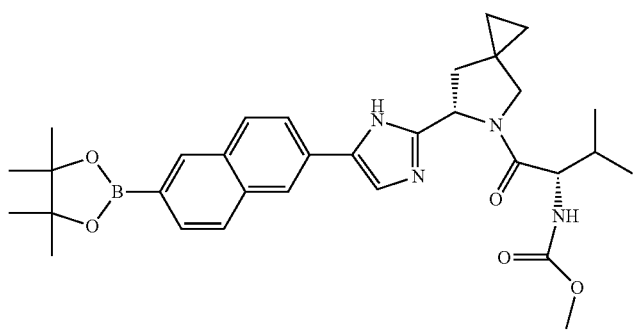

[2-Methyl-1-(6-{5-[6-(4,4,5,5-tetramethyl-[1,3,2]dioxaborolan-2-yl)-naphthalen-2-yl]-
1H-imidazol-2-yl}-5-aza-spiro[2.4]heptane-5-carbonyl)propyl]-carbamic acid methyl ester

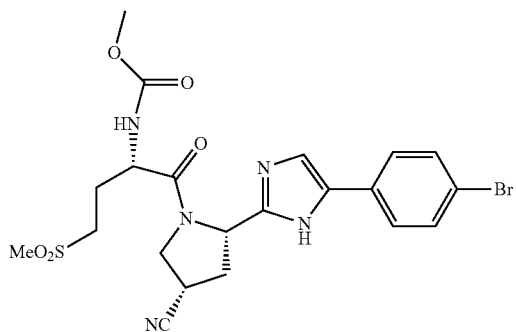

(1-{2-[5-(4-Bromo-phenyl)-1H-imidazol-2-yl]-4-cyano-pyrrolidine-
1-carbonyl}-3-methanesulfonyl-propyl)-carbamic acid methyl ester

2-Bromo-9,9-difluoro-7-iodo-9H-flourene

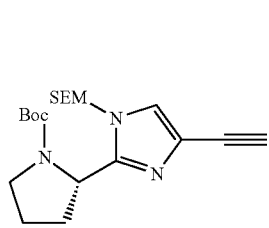

2-[4-Ethynyl-1-(2-trimethylsilanyl-ethoxymethyl)-1H-
imidazol-2-yl]-pyrrolidine-1-carboxylic acid tert-butyl ester

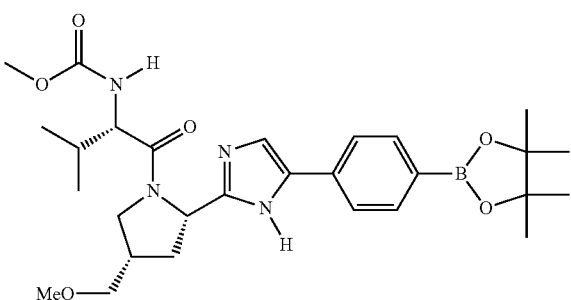

[1-(4-Methoxymethyl-2-{5-[4-(4,4,5,5-tetramethyl-[1,3,2]
dioxaborolan-2-yl)-phenyl]-1H-imidazol-2-yl}-pyrrolidine-
1-carbonyl)-2-methyl-propyl]-carbamic acid methyl ester -continued

375

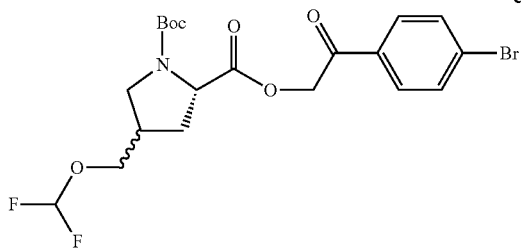

4-Difluoromethyoxymethyl-pyrrolidine-1,2-dicarboxylic
acid 2-[2-(4-bromo-phenyl)-2-oxo-ethyl] ester 1-tert-butyl ester

376

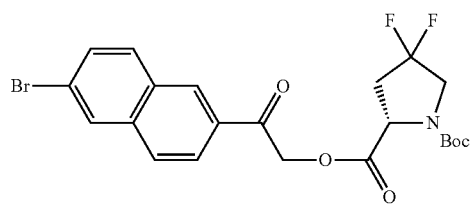

4,4-Difluoro-pyrrolidine-1,2-dicarboxylic acid 2-[2-
(6-bromo-naphthalen-2-yl)-2-oxo-ethyl] ester 1-tert butyl ester

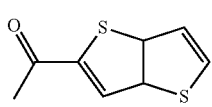

1-(3a,6a-Dihydro-thieno
[3,2-b]thiophen-2-yl)-ethanone

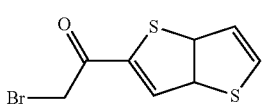

2-Bromo-1-(3a,6a-dihydro-thieno
[3,2-b]thiophen-2-yl)-ethanone

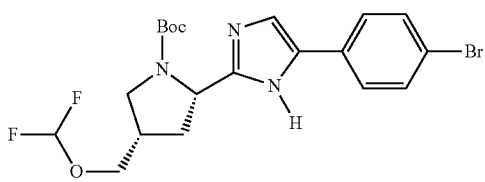

2-[5-(4-Bromo-phenyl)-1H-imidazol-2-yl]-
4-difluoromethoxymethyl-pyrrolidine-1-
carboxylic acid tert-butyl ester

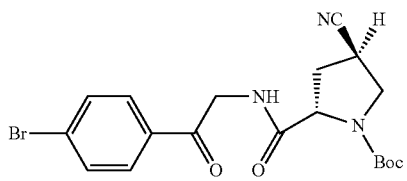

2-[2-(4-Bromo-phenyl)-2-oxo-ethylcarbamoyl]-
4-cyano-pyrrolidine-1-carboxylic acid tert-butyl ester

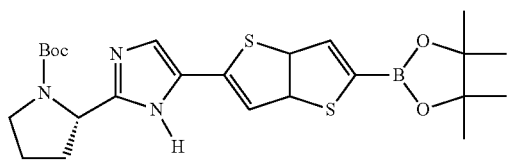

2-{5-[5-(4,4,5,5-Tetramethyl-[1,3,2]dioxaborolan-2-yl)-
3a,6a-dihydro-thieno[3,2-b]thiophen-2-yl]-1H-imidazol-
2-yl}-pyrrolidine-1-carboxylic acid tert-butyl ester

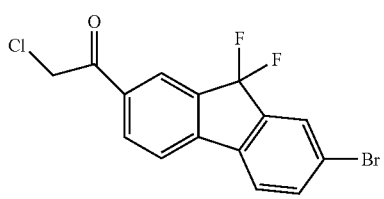

1-(7-Bromo-9,9-difluoro-9H-fluoren-
2-yl)-2-chloro-ethanone

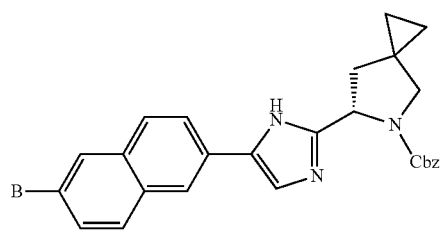

6-[5-(6-Bromo-naphthalen-2-yl)-1H-imidazol-2-yl]-
5-aza-spiro[2.4]heptane-5-carboxylic acid benzyl ester

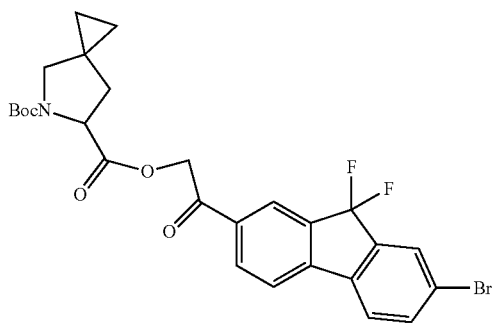

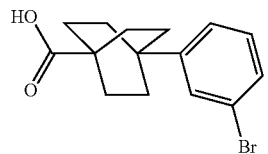

377 378
-continued
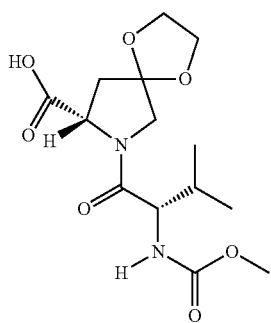
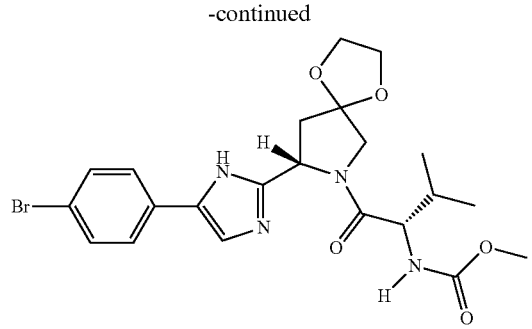
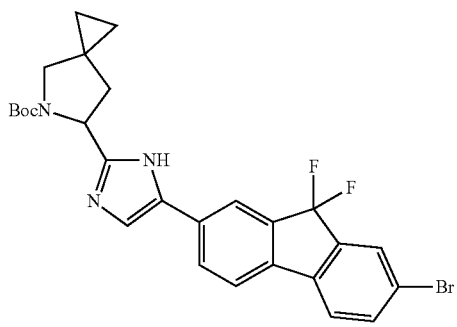
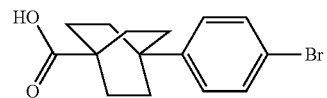
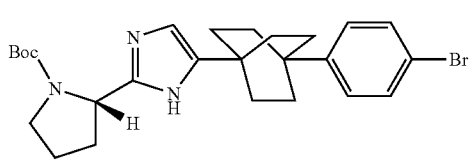
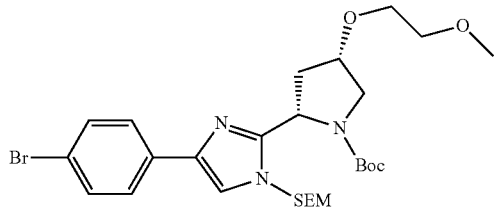
2-[4-(4-Bromo-phenyl)-1-(2-trimethylsilanyl-
ethoxymethyl)-1H-imidazol-2-yl]-4-(2-methoxy-
ethoxy)-pyrrolidine-1-carboxylic acid tert-butyl ester
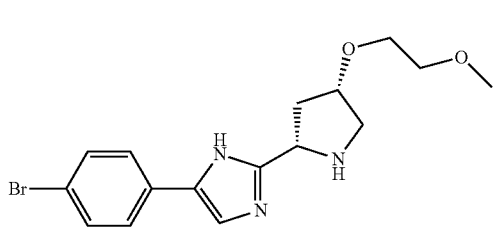
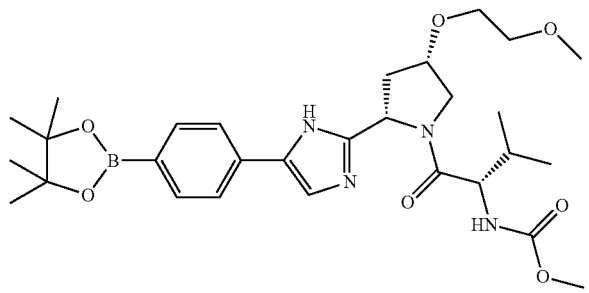
5-(4-Bromo-phenyl)-2-[4-(2-methoxy-ethoxy)-
pyrrolidin-2-yl]-1H-imidazole
[1-(4-(2-Methoxy-ethoxy)-2-{5-[4-(4,4,5,5-tetramethyl-1,3,2]dioxaborolan-2-yl)-
phenyl]-1H-imidazol-2-yl}-pyrrolidine-1-carbonyl)-2-
methyl-propyl]-carbamic acid methyl ester -continued

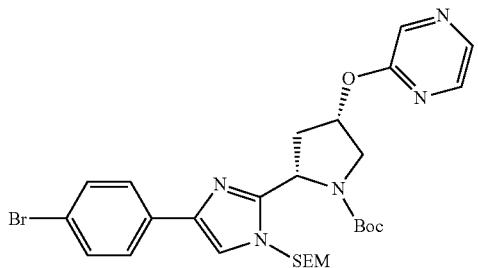

2-[4-(4-Bromo-phenyl)-1-(2-trimethylsilanyl-ethoxymethyl)-1H-imidazol-2-yl]-4-(pyrazin-2-yloxy)-pyrrolidine-1-carboxylic acid tert-butyl ester

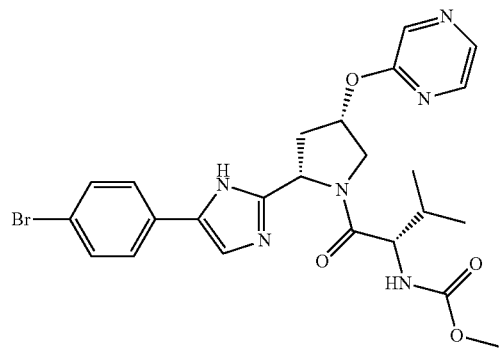

{-1-[2-[5-(4-Bromo-phenyl)-1H-imidazol-2-yl]-4-(pyrazin-2-yloxy)-pyrrolidine-1-carbonyl]-2-methyl-propyl}-carbamic acid methyl ester

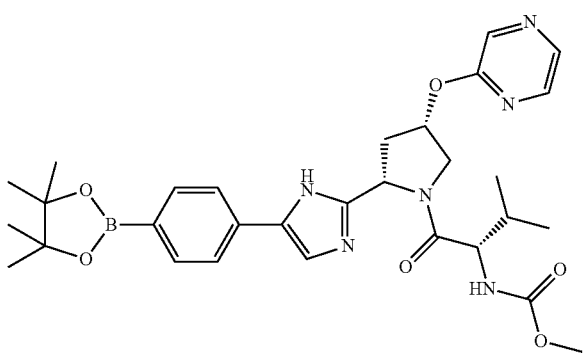

[2-Methyl-1-(4-(pyrazin-2-yloxy)-2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester

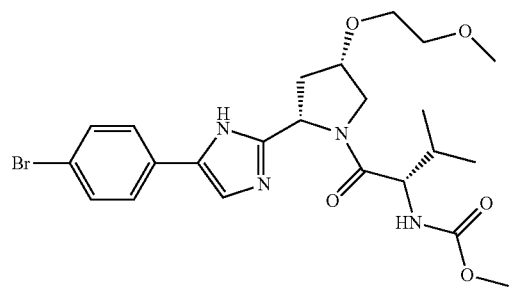

{1-[2-[5-(4-Bromo-phenyl)-1H-imidazol-2-yl]-40-(2-methoxy-ethoxy)-pyrrolidine-1-carbonyl]-2-methyl-propyl}-carbamic acid methyl ester

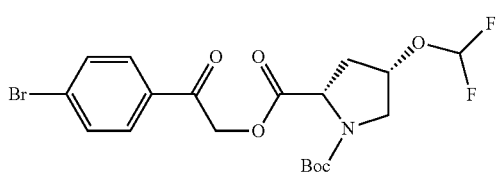

4-Difluoromethoxy-pyrrolidine-1,2-dicarboxylic acid 2-[2-(4-bromo-phenyl)-2-oxo-ethyl] ester 1-tert-butyl ester

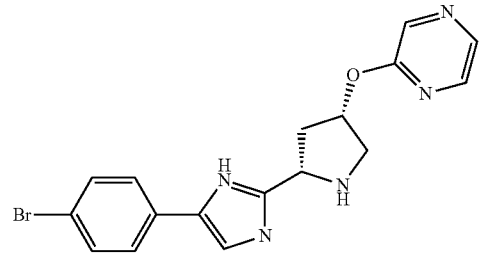

2-{5-[5-(4-Bromo-phenyl)-1H-imidazol-2-yl]-pyrrolidin-3-yloxy}-pyrazine

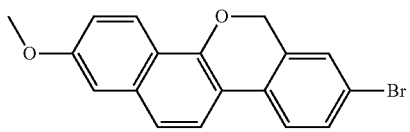

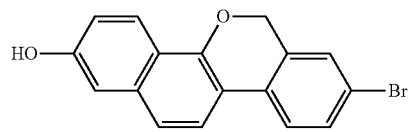

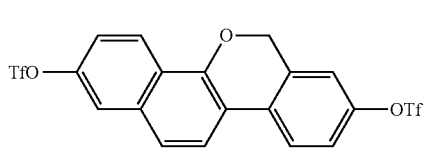

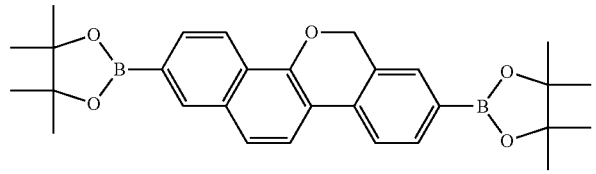

381
-continued
382
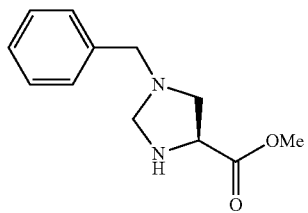
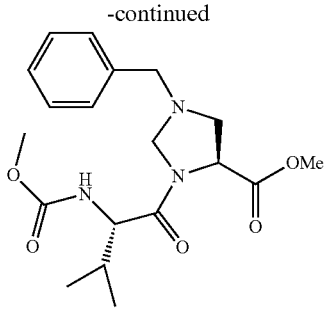
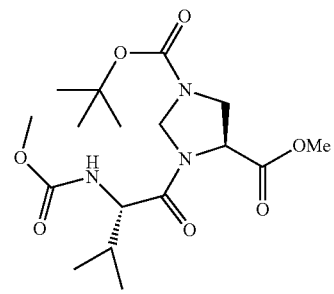
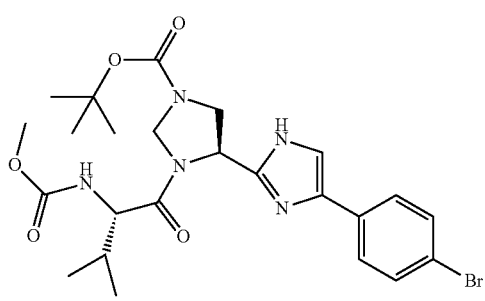
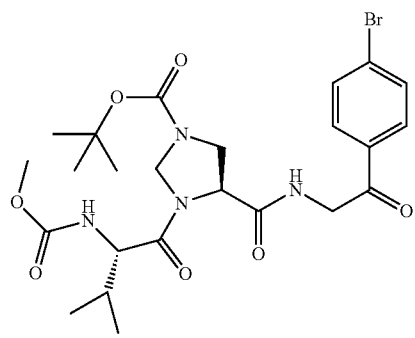
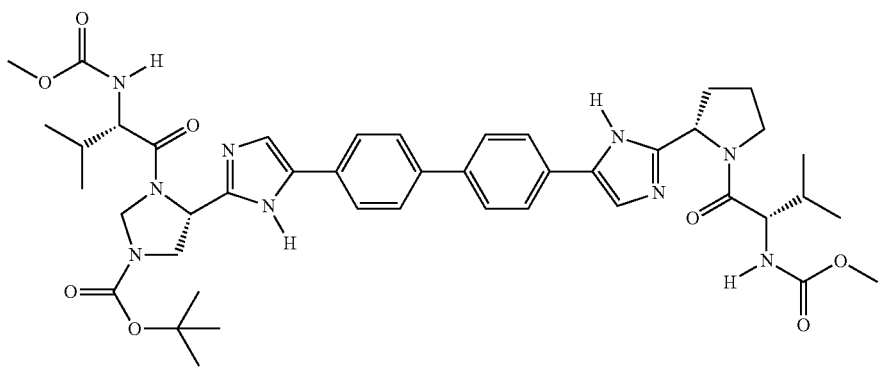
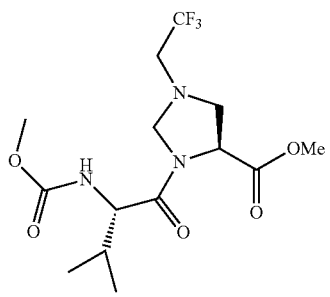
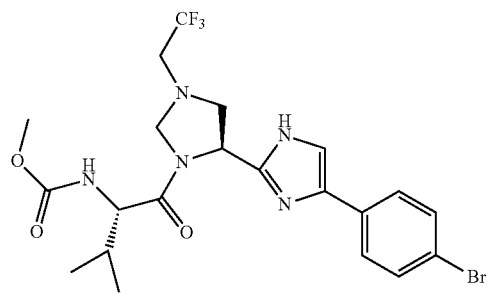
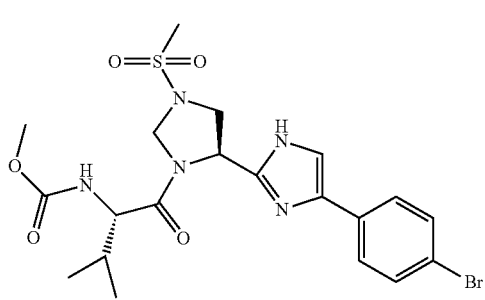
and
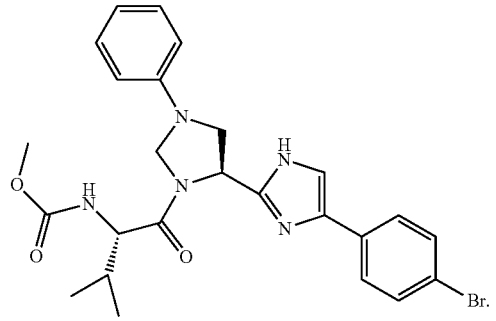

Exemplary Methods of Making the Compounds of the Invention

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing). Other methods suitable for preparing compounds of the invention are described in International Patent Application Publication Number WO 2006/020276.

A number of exemplary methods for the preparation of the compositions of the invention are provided in the schemes and examples below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the Examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113, 3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3)

separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. In the exemplary methods described herein, the fragment E-V- can also be written as R9-. Subsequently, the fragment E-V-Z- or R9-Z- can be written as T-. The fragments E-V-Z-P, R9-Z-P-, or T-P- can all be written as J-.

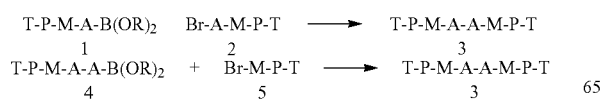

Scheme 1: Representative synthesis of T-P-M-A-A-M-P-T

T-P-M-A-B(OR)₂   Br-A-M-P-T   ⟶   T-P-M-A-A-M-P-T
1                2                3
T-P-M-A-A-B(OR)₂ + Br-M-P-T   ⟶   T-P-M-A-A-M-P-T
4                5                3

Scheme 1 shows a general synthesis of the T-P-M-A-A-M-P-T molecule of the invention, wherein transition metal-mediated cross-coupling reaction is utilized to construct the A-A bond and/or A-M bond. For illustrative purposes, the Suzuki reaction is employed to couple a Br-M-P-T and an (RO)₂B-A-A-M-P-T intermediate or a Br-A-M-P-T and a (RO)₂B-A-M-P-T intermediate. Boronic ester 1 (or 4) is coupled with an appropriate coupling partner (e.g. arylbromide 2 or 5) using a palladium catalyst, such as Pd(PPh₃)₄, to afford 3. Palladium mediated cross-coupling reactions that enable the A-A bond formation, but employ alternative coupling partners and reagents, include for example the Negishi, Kumada, Sonagashira and Stille reactions.

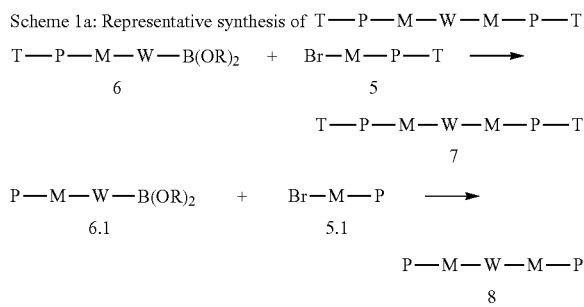

Scheme 1a: Representative synthesis of T—P—M—W—M—P—T

T—P—M—W—B(OR)₂  +  Br—M—P—T   ⟶
6                    5
                                  T—P—M—W—M—P—T
                                          7

P—M—W—B(OR)₂  +  Br—M—P   ⟶
6.1               5.1
                                  P—M—W—M—P
                                       8

Scheme 1a shows a general synthesis of the T-P-M-W-M-P-T molecule and the P-M-W-M-P molecule of the invention, wherein transition metal-mediated cross-coupling reaction is utilized to construct the W-M bond. For illustrative purposes, the Suzuki reaction is employed to couple a Br-M-P-T and a (RO)₂B-W-M-P-T intermediate or a Br-M-P-PG to a (RO)₂B-W-M-P-PG intermediate. Boronic ester 6 (or 6.1) is coupled with an appropriate coupling partner (e.g. arylbromide 5 or 5.1) using a palladium catalyst, such as Pd(PPh₃)₄, to afford 7 and 8. Palladium mediated cross-coupling reactions that enable the A-A bond formation, but employ alternative coupling partners and reagents, include for example the Negishi, Kumada, Sonagashira and Stille reactions.

Scheme 2: Representative synthesis of A—M—P—T

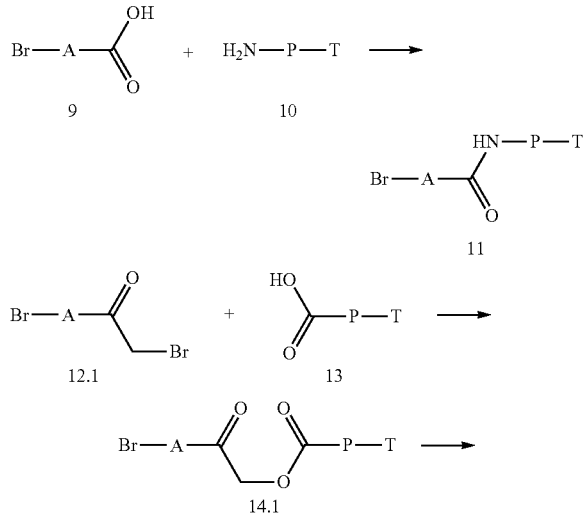

387

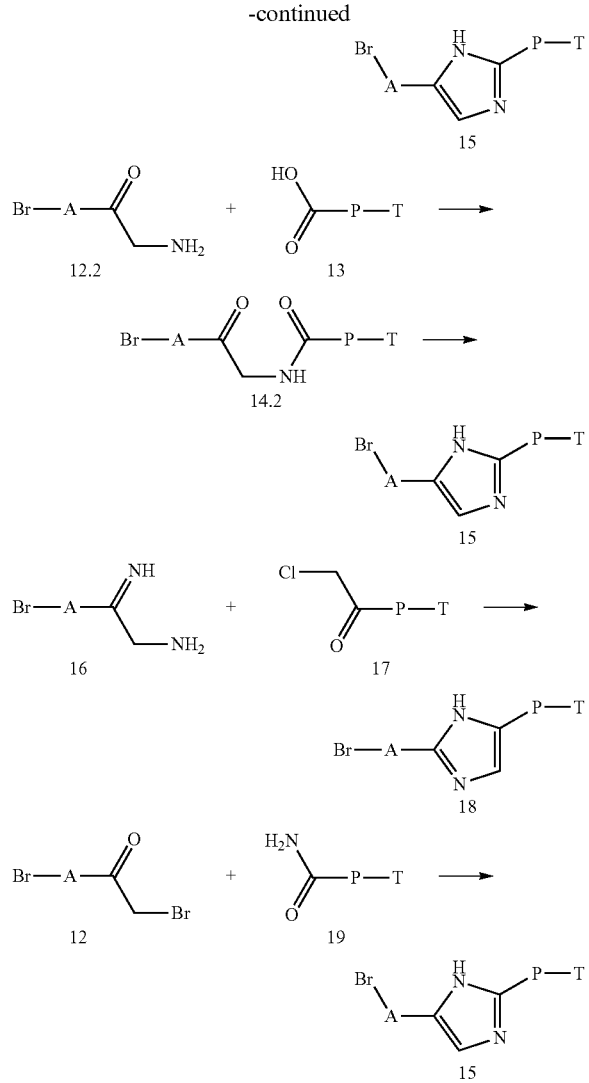

Scheme 2 shows a general synthesis of an A-M-P-T molecule of the invention wherein, for illustrative purposes, M is an amide or an imidazole. Coupling of amine 10 with acid 9 is accomplished using a peptide coupling reagent (e.g. HATU) to afford amide containing 11. The acid 13 is coupled with an α-haloketone, such as α-bromoketone 12.1, under basic conditions (e.g. Et₃N) to afford 14.1. Alternatively, the acid 13 is coupled with an α-aminoketone 12.2, under amide formation conditions (e.g. EDC, Et₃N) to afford 14.2. Reaction of 14.1 or 14.2 with an amine or amine salt (e.g. ammonium acetate) affords the imidazole containing molecule Br-A-M-P-T.

The benzamidine 16 is coupled with an α-haloketone such as α-chloroketone 17 under basic conditions such as $K_2CO_3$ to afford the imidazole containing molecule Br-A-M-P-T 18. A-M-P-T 15 can be prepared analogously.

Scheme 3: Representative synthesis of A—M—P—T

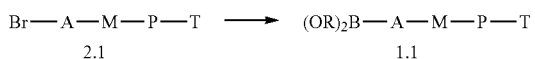

388

Scheme 3 shows a general synthesis of an A-M-P-T molecule of the invention wherein borate or boronic acid 1.1 can be synthesized from bromide 2.1.

Scheme 4: Representative synthesis of A—M—P—Z—R9

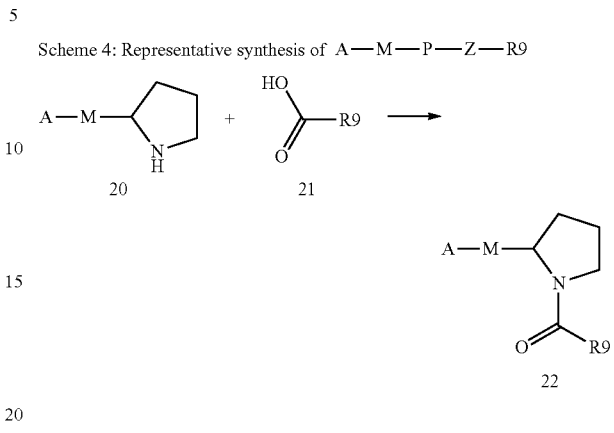

Scheme 4 shows a general synthesis of an A-M-P-Z-R9 fragment of the invention wherein, for illustrative purposes, P=pyrrolidine and Z=carbonyl. Coupling of amine 20 with acid 21 is accomplished using a peptide coupling reagent (e.g. HATU) to afford 22.

Scheme 5: Representative synthesis of L—P

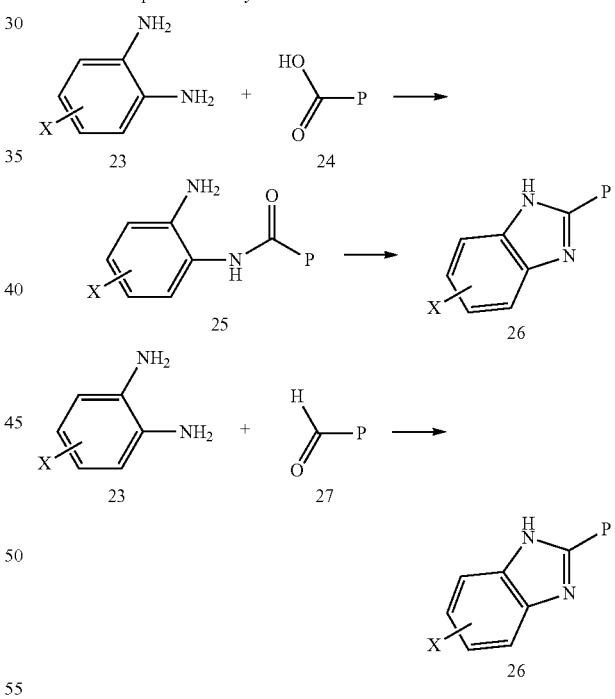

Scheme 5 shows a general synthesis of an L-P molecule of the invention wherein, for illustrative purposes, L=benzimidazole. The acid 24 is coupled with 23 using a peptide coupling reagent such as HATU to afford 25. Heating in solvent (such as refluxing ethanol) affords L-P fragment 26.

Alternatively, the L-P fragment 26 is obtained by reaction of diamine (such as 23) and carbonyl compound (such as aldehyde 27) in a solvent under heating conditions (e.g. ethanol under microwave irradiation).

Scheme 6: Representative synthesis of P—M—A—A—M—P fragment

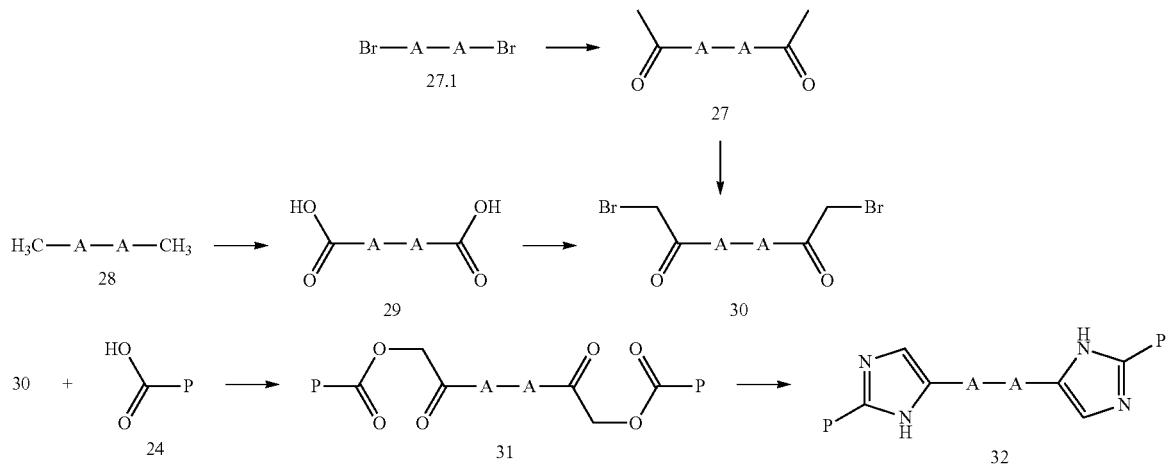

Scheme 6 shows a general synthesis of P-M-A-A-M-P molecule of the invention wherein, for illustrative purposes, M=imidazole. For example, the diketone 27 is converted to 30 using bromine. Compound 27 can be commercially available or can be prepared from dibromide 27.1 through coupling with a vinyltin reagent such as tributyl(ethoxyvinyl)stannane with palladium. Coupling of 30 with acid 24 under basic conditions such as diisopropylethylamine affords diester 31. Imidazole formation is accomplished by treatment of 31 with ammonium acetate to provide the imidazole containing molecule P-M-A-A-M-P.

Alternatively, bromide 30 can be synthesized from 28. The methyl compound 28 can be converted to the corresponding diacid 29 using potassium permanganate as oxidant.

Conversion of 29 to 30 can be accomplished by a multi-step reaction, first treatment of 29 with oxalyl chloride, then by trimethylsilyl diazomethane, then with hydrobromic acid to afford compound 30.

poses, P=pyrrolidine and Z=carbonyl. Coupling of amine 33 with acid 34 is accomplished using a peptide coupling reagent, such as HATU, to afford 35.

Scheme 8: Representative synthesis of P—M—W—M—P

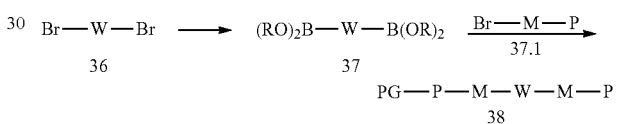

Scheme 8 shows a general synthesis of P-M-W-M-P molecule of the invention wherein, for illustrative purposes, W=polycyclic. Conversion of 36 to 37 was accomplished using transition metal-mediated reactions. Diboronic ester or acid 37 is coupled with a suitable reaction partner, such as bromide 37.1 using Suzuki coupling conditions to afford 38.

Scheme 7: Representative synthesis of
E—V—P—M—A—A—M—P—V—E

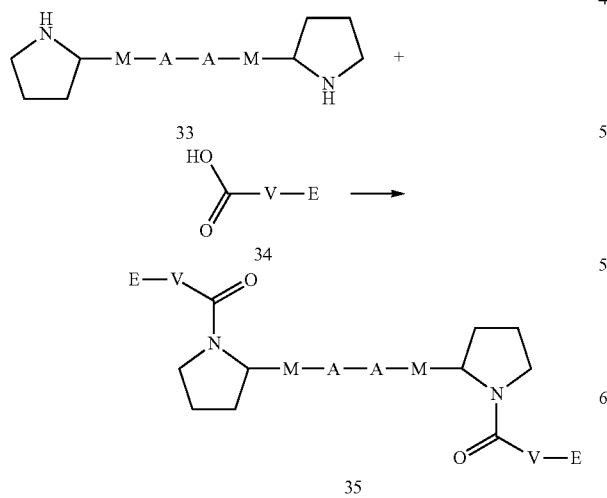

Scheme 9: Representative synthesis of
E—V—P—M—W—M—P—V—E

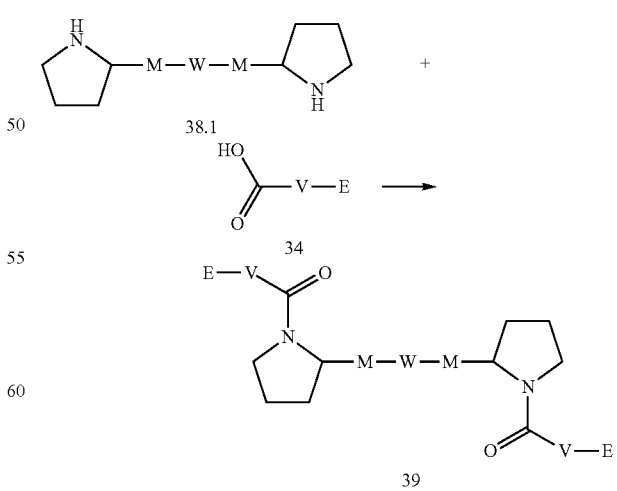

Scheme 7 shows a general synthesis of an E-V-P-M-A-A-M-P-V-E molecule of the invention wherein, for illustrative pur- Scheme 9 shows a general synthesis of an E-V-P-M-W-M-P-V-E molecule of the invention wherein, for illustrative purposes, P=pyrrolidine and Z=carbonyl. Coupling of amine 38.1 with acid 34 is accomplished using a peptide coupling reagent, such as HATU, to afford 39.

Scheme 9a: Representative synthesis of P—M—W—M—P

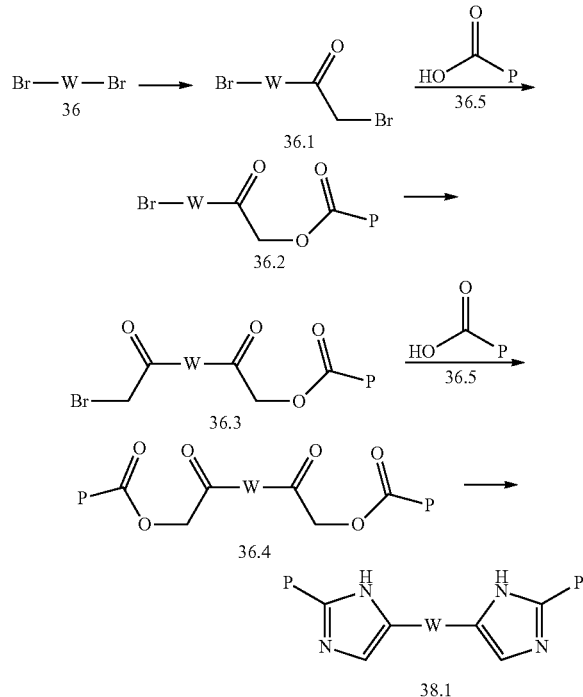

Scheme 9a shows a general synthesis of a P-M-W-M-P molecule of the invention wherein, for illustrative purposes, M=imidazole, W=polycyclic. The compound 36 was coupled with a vinyltin reagent such as tributyl(ethoxyvinyl)stannane with palladium, followed by bromination and hydrolysis with NBS and water, to give bromoketone 36.1. The reaction between bromide 36.1 and a carboxylic acid (36.5) under basic condition generated ester 36.2. Following the same reaction sequence, compound 36.2 was converted to diester 36.4. Conversion of 36.4 to 38.1 was accomplished with ammonia reagents such as ammonium acetate at elevated temperature.

Scheme 10: Representative synthesis of M—P

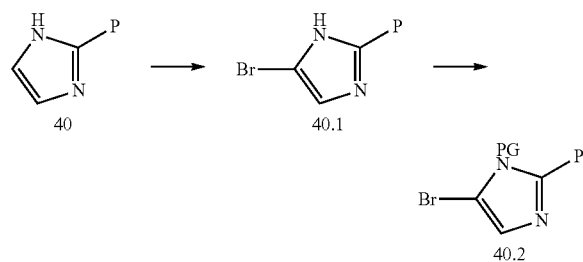

Scheme 10 shows a general synthesis of an M-P molecule of the invention wherein, for illustrative purposes, PG is a protecting group. Imidazole 40 can be halogenated, for example, under the action of N-bromosuccinimide to provide bromoimidazole 40.1. Bromoimidazole 40.1 can be protected using standard conditions to give 40.2, such as SEM-Cl and sodium hydride when PG=SEM.

Scheme 11: Representative synthesis of P—M—A—A—M—P

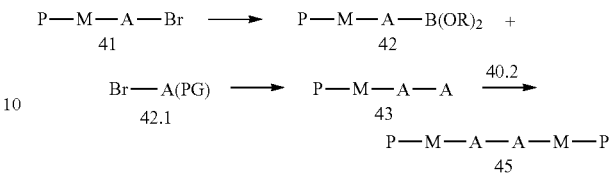

Scheme 11 shows a general synthesis of a P-M-A-A-M-P molecule of the invention wherein, for illustrative purposes, M=imidazole. Boronic ester 42, which can be prepared from bromide 41, is coupled with a suitably protected appropriate coupling partner (e.g. arylbromide 42.1, optionally protected with PG) using a palladium catalyst, such as Pd(PPh$_3$)$_4$, to afford 43. Palladium mediated cross-coupling reactions that enable the A-A bond formation, but employ alternative coupling partners and reagents, include for example the Negishi, Kumada and Stille reactions. If optionally protected, removal of the protecting group (PG) (for example, catalytic hydrogenation of a benzyl ether) provides the deprotected compound 43. Coupling of 43 with suitably protected imidazole 40.2 (for example, PG=SEM ether) using a metal catalyst (e.g. Cue gives protected P-M-A-A-M-P (45). Deprotection (for example deprotection of a SEM ether using an acid such as TFA) provides the imidazole containing fragment P-M-A-A-M-P 45.

Scheme 12: Representative synthesis of P—M—W—M—P

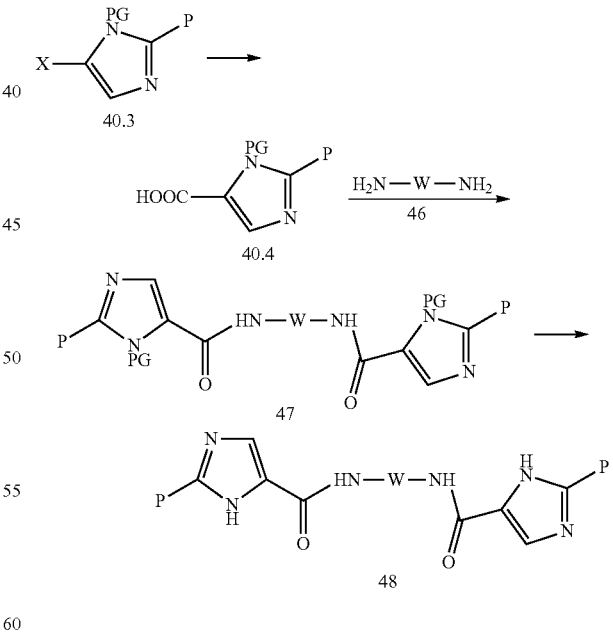

Scheme 12 shows a general synthesis of a P-M-W-M-P molecule of the invention wherein, for illustrative purposes, X=halogen or triflate, M=imidazole, and W is 46, PG=protecting group. Haloimdiazole 40.3, such as a bromoimidazole, is subjected to a metal-halogen exchange reaction, such as BuLi in THF, and then treated with a CO$_2$ source, such as solid CO$_2$, to give 40.4. Coupling of 40.4 and 46 using peptide coupling conditions, such as HATU, gives 47. PG deprotection, such as TFA deprotection of a SEM group, gives the compound P-M-W-M-P 48.

Scheme 13: Representative synthesis of P—M—A—A—M—P

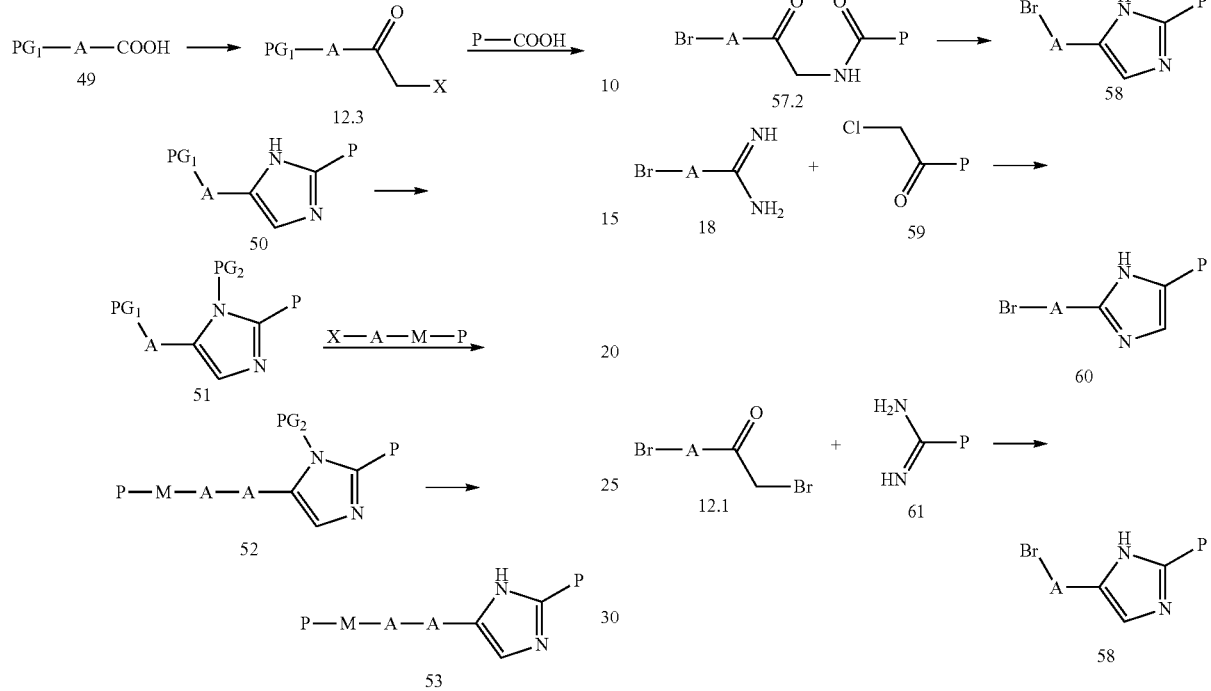

Scheme 13 shows a general synthesis of a P-M-A-A-M-P molecule of the invention wherein, for illustrative purposes, X=halogen, amine or triflate, M=imidazole, $PG_1$ and $PG_2$=protecting groups. The protected acid 49 (PG1 is a suitable protecting group, such as Cbz) is converted to α-halomethyl ketone 12.3., which is then transformed to $PG_1$-A-M-P 50 using the analogous conditions for converting 12.1 and 12.2 to 15. The imidazole is subjected to protection, with SEM for instance, to afford 51, which is deprotected, with $H_2$ and Pd to remove a Cbz for example, followed by coupling with fragment X-A-M-P, using standard Pd coupling conditions for example, to afford 52. PG deprotection, such as TFA deprotection of a SEM group, gives the compound P-M-A-A-M-P 53.

Scheme 14: Representative synthesis of A—M—P

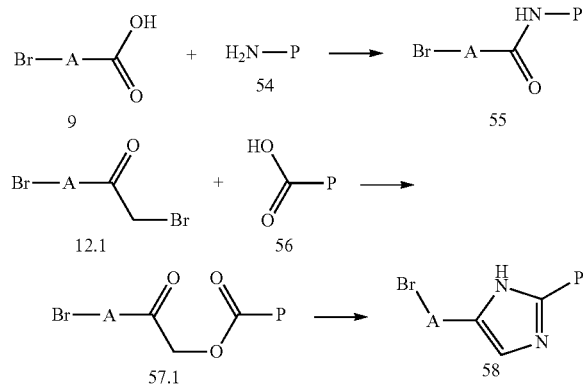

Scheme 14 shows a general synthesis of an A-M-P molecule of the invention wherein, for illustrative purposes, M is an amide bond, or an imidazole. Coupling of amine 54 with acid 9 is accomplished using a peptide coupling reagent (e.g. HATU) to afford amide containing 55. The acid 56 is coupled with an α-haloketone, such as α-bromoketone 12.1, under basic conditions (e.g. $Et_3N$) to afford 57.1. Alternatively, the acid 56 is coupled with an α-aminoketone 12.2, under amide formation conditions (e.g. EDC, $Et_3N$) to afford 57.2. Reaction of 57.1 and 57.2 with an amine or amine salt (e.g. ammonium acetate) affords the imidazole containing molecule A-M-P.

The benzamidine 18 is coupled with an α-haloketone such as α-chloroketone 59 under basic conditions such as $K_2CO_3$ to afford the imidazole containing molecule A-M-P 60. A-M-P 58 can be prepared analogously.

Scheme 15: Representative synthesis of P——M—A—A—M—P

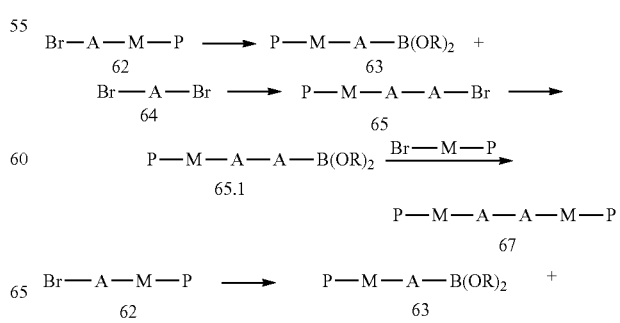

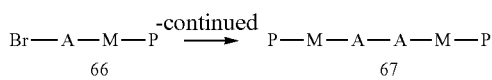

Scheme 15 shows a general synthesis of a P-M-A-A-M-P molecule of the invention. Boronic acid or its ester 63, can be prepared from bromide 62 using a palladium catalyst (e.g. Pd(PPh$_3$)$_4$) and a boron reagent (bis(pinacolato)diboron, for example), is coupled with an excess of appropriate coupling partner (e.g. a di-halo-aromatic or di-halo-heteroaromatic moiety 64) using a palladium catalyst, such as Pd(PPh$_3$)$_4$, to afford bromide 65, which then is converted to boronic acid or ester 65.1. Palladium mediated cross-coupling reactions that enable the A-A bond formation, but employ alternative coupling partners and reagents, include for example the Negishi, Kumada and Stille reactions. Suzuki coupling of 65.1 with halo-imidazole such as bromo-imidazole using a palladium catalyst (such as Pd(PPh$_3$)$_4$) gives P-M-A-A-M-P fragment 67.

Alternatively, Suzuki coupling of 63 with halo-A-M-P fragment using a palladium catalyst (such as Pd(PPh$_3$)$_4$) gives P-M-A-A-M-P fragment 67.

Scheme 16: Representative synthesis of
R9—P—L—A—M—P—R9 and
R9—P—L—L—P—R9

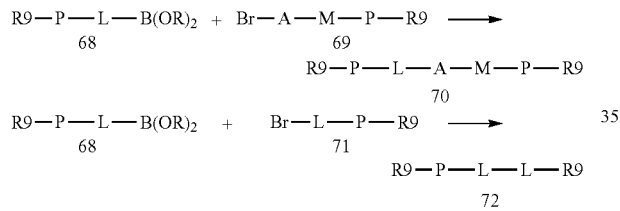

Scheme 16 shows a general synthesis of an R9-P-L-A-M-P-R9 molecule and a R9-P-L-L-P-R9 molecule of the invention wherein a transition metal-mediated cross-coupling reaction is utilized to construct the A-A bond. For illustrative purposes, the Suzuki reaction is employed to couple (RO)$_2$B-L-P-R9 and Br-A-M-P-R9. Boronic ester 68 is coupled with an appropriate coupling partner (e.g. arylbromide 69) using a palladium catalyst (such as Pd(PPh$_3$)$_4$) to afford 70. Similarly, R9-P-L-L-P-R972 is prepared by coupling compounds 68 and 71.

Scheme 17: Representative sythesis of P—T

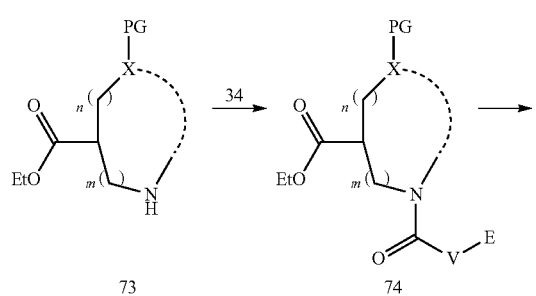

Scheme 17 shows a general synthesis of a P-T molecule of the invention wherein, for illustrative purposes, P=either an acyclic or cyclic amino ester (such as ethyl ester), optionally protected with PG if necessary, Z=carbonyl, X=carbon or heteroatom, and m and n=0-5, independently. Coupling of amine 73 with acid 34 is accomplished using a peptide coupling reagent, such as HATU, to afford 75, which after removal of ethyl group provides the P-T compound.

Scheme 18: Representative synthesis of P

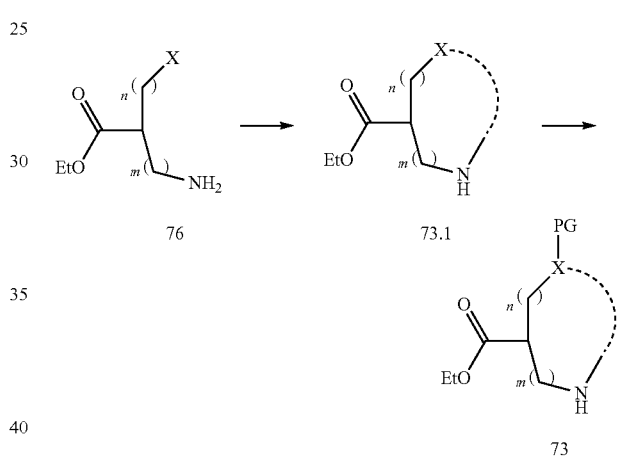

Scheme 18 shows a general synthesis of a P molecule of the invention wherein X=carbon or heteroatom and m and n=0-5, independently. For illustrative purposes, P is substituted with an ethoxylcarbonyl group. Commercially available amino ester such an ethyl ester is converted to substituted or cyclized amino ester 73.1, through for example, reductive amination or Mitsunobu reaction. Compound 73.1 can be protected to provide compound 73 if necessary.

Scheme 19: Representative Synthesis of E—V

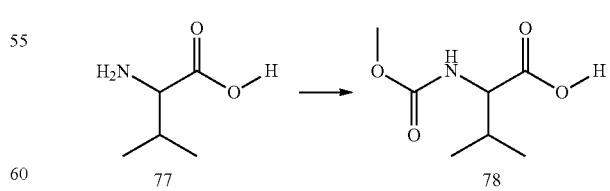

Scheme 19 shows a general synthesis of an E-V molecule of the invention wherein, for illustrative purposes, V is isobutyl and E is methoxycarbonylamino. Amino acid 77 can be converted to the corresponding carbamate 78, such as a methyl carbamate by reaction with methyl chloroformate under basic conditions (sodium bicarbonate).

Scheme 20: Synthesis of the E—V—Z—P—M—A

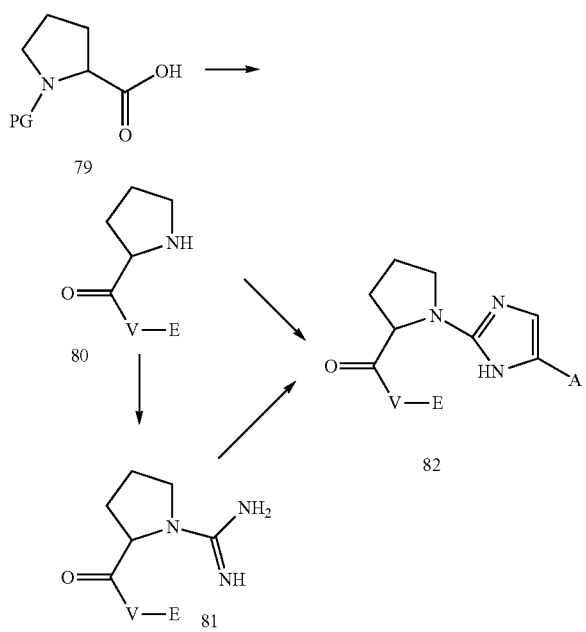

Scheme 20 shows the synthesis of a E-V-Z-P-M-A molecule of the invention wherein, for illustrative purposes, M is imidazole, P is pyrrolidine, and Z is carbonyl. An amino acid derivative can be reacted with an N-protected proline derivative via reaction conditions employing a coupling reagent, such as HATU, deprotection of the resulting coupling product, for example in the case of tert-butoxy carbonyl, the treatment with a proton source such as HCl yielded compound 80. The conversion of 80 to E-V-Z-P-M-A (82) can be obtained under reaction conditions of nucleophilic aromatic substitution, for example the displacement of methyl sulfonate under basic conditions and elevated temperatures.

Alternatively, for illustrative purposes, the amino acid derivative 80 can be converted to a guanidinium containing compound 81, via a reaction with a guanidylation reagent. The E-V-Z-P-M-A compound 82 can be obtained via reaction with a 1,2 di-electrophile such as an α-halogenated carbonyl group under basic conditions.

Scheme 21: Representative synthesis of P—M—W—M—P

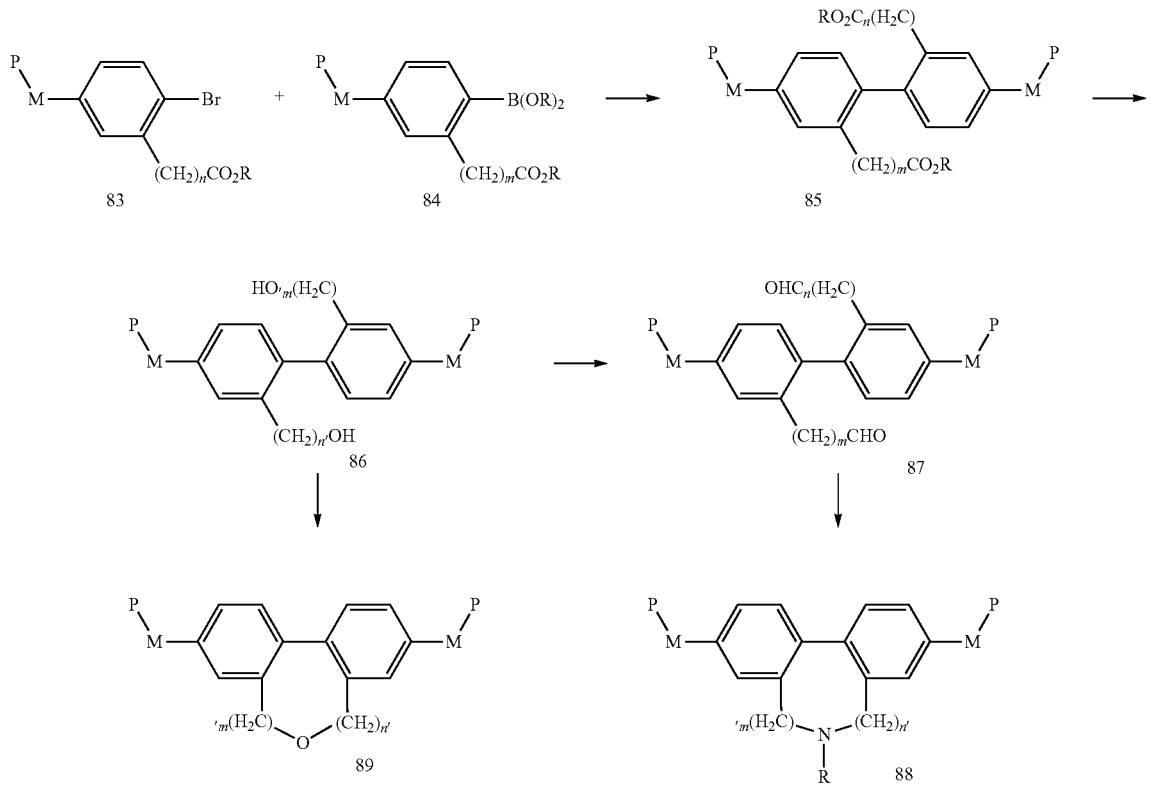

m, n, m', n' = 0, 1, 2, etc

Scheme 21 shows a general synthesis of a P-M-W-M-P molecule of the invention wherein. Boronic ester 84 is coupled with an appropriate coupling partner (e.g. arylbromide 83) using a palladium catalyst, such as Pd(PPh$_3$)$_4$, to afford 85. Carboxylate 85 is reduced with reagents such as DIBAL-H to afford diol 86. The treatment of diol 86 with acids such as H$_3$PO$_4$ at elevated temperature generates P-M-W-M-P compound 89. Alternatively, diol 86 can be oxidized with reagents such as pyridine-sulfur trioxide to form dialdehyde 87, which react with amines in the presence of reducing reagents such as NaBH(OAc)$_3$ to provide P-M-W-M-P compound 88.

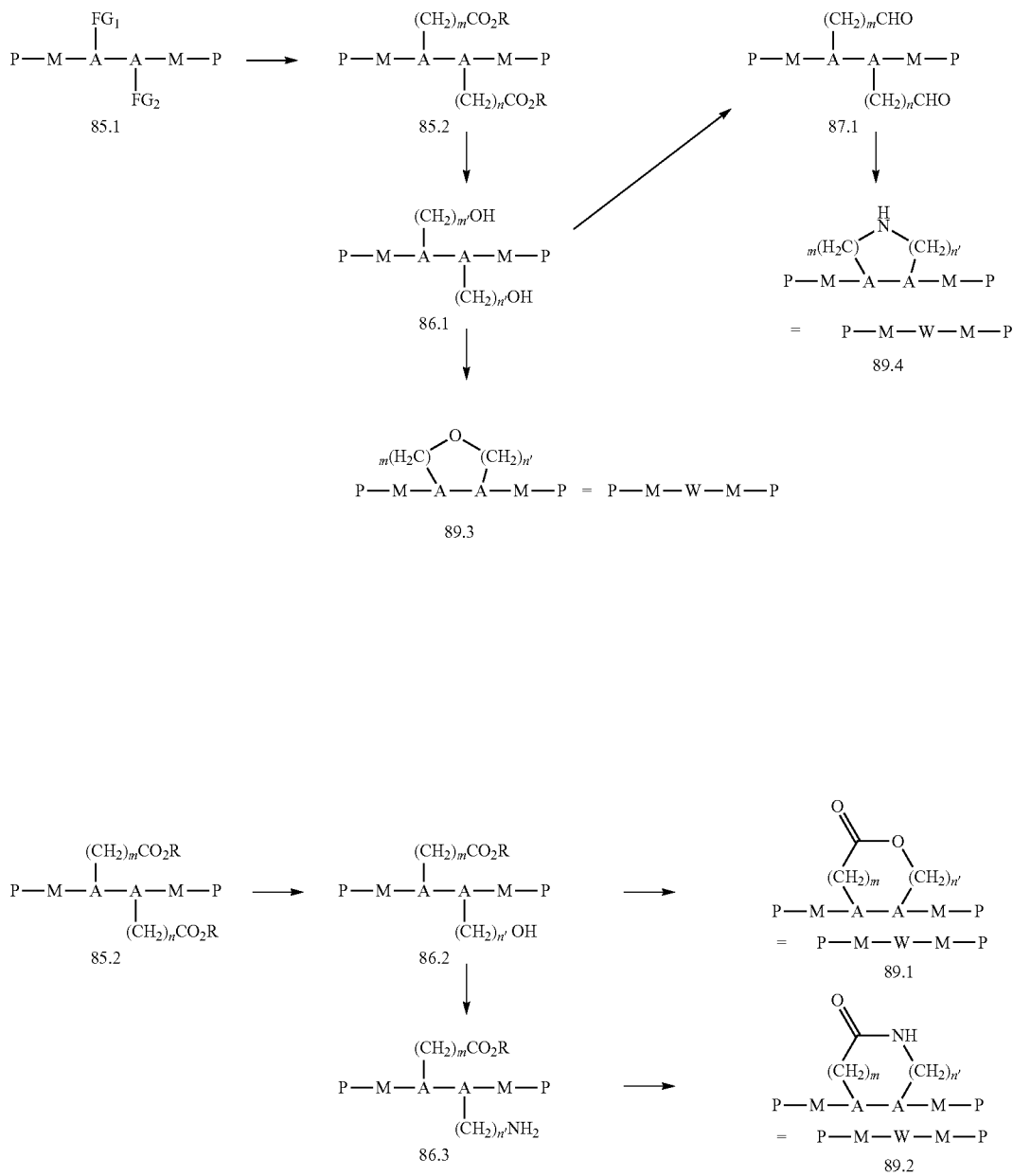

Scheme 21a shows a general synthesis of a P-M-W-M-P molecule of the invention. For illustrative purposes, $FG_1$ and $FG_2$ can be converted to esters attached to an A group. Carboxylate 85.2 is reduced with reagents, such as DIBAL-H, to afford diol 86.1. The treatment of diol 86.1 with acids, such as $H_3PO_4$, at elevated temperature generates P-M-W-M-P compound 89.3. Alternatively, diol 86.1 can be oxidized with reagents such as pyridine-sulfur trioxide to form dialdehyde 87.1, which reacts with amines in the presence of reducing reagents such as $NaBH(OAc)_3$ to provide P-M-W-M-P compound 89.4. The carboxylate 85.2 is selectively reduced to provide hydroxyl ester 86.2, which can be cyclized to form P-M-W-M-P compound 89.1. Compound 86.1 is converted to amine ester 86.3, for example through azide formation and reduction with hydrogenation. Compound 86.3 can be cyclized to form P-M-W-M-P compound 89.2.

Scheme 22: Construction of a R9—Z—P—M—A

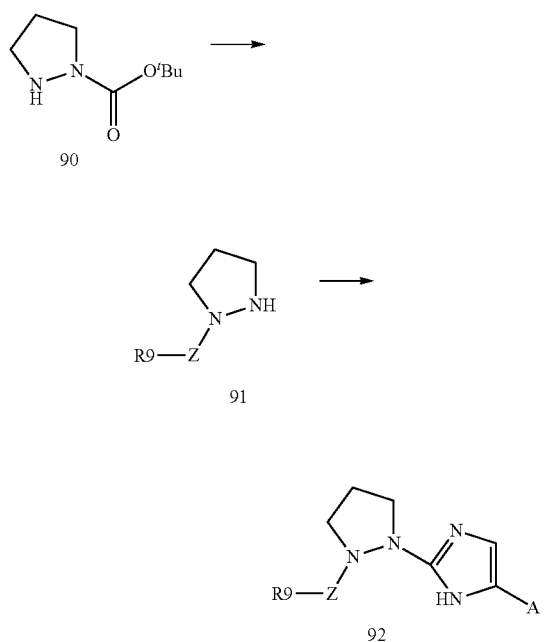

Scheme 22 shows the general synthesis of a R9-Z-P-M-A molecule, for illustrative purposes starting with tert-butoxy carbonyl derivative 90 (J. Am. Chem. Soc. 2003, 1221). Compound 90 can be acylated with substituent T wherein Z is carbonyl, via reaction conditions employing a coupling reagent such as HATU. Removal of the protecting group, for example in the case of tert-butoxycarbonyl by the treatment with a proton source such as HCl, yields compound 91. A compound like 91 can be obtained under reaction conditions of nucleophilic aromatic substitution, for example the displacement of methyl sulfonate under basic conditions and elevated temperatures to provide the R9-Z-P-M-A compound 92. Alternatively, 91 can be converted into a guanidinium derivative. When suitably substituted, cyclization provides the R9-Z-P-M-A compound 92.

Scheme 23: Representative synthesis of
T—P—M—A—A—M—P—T

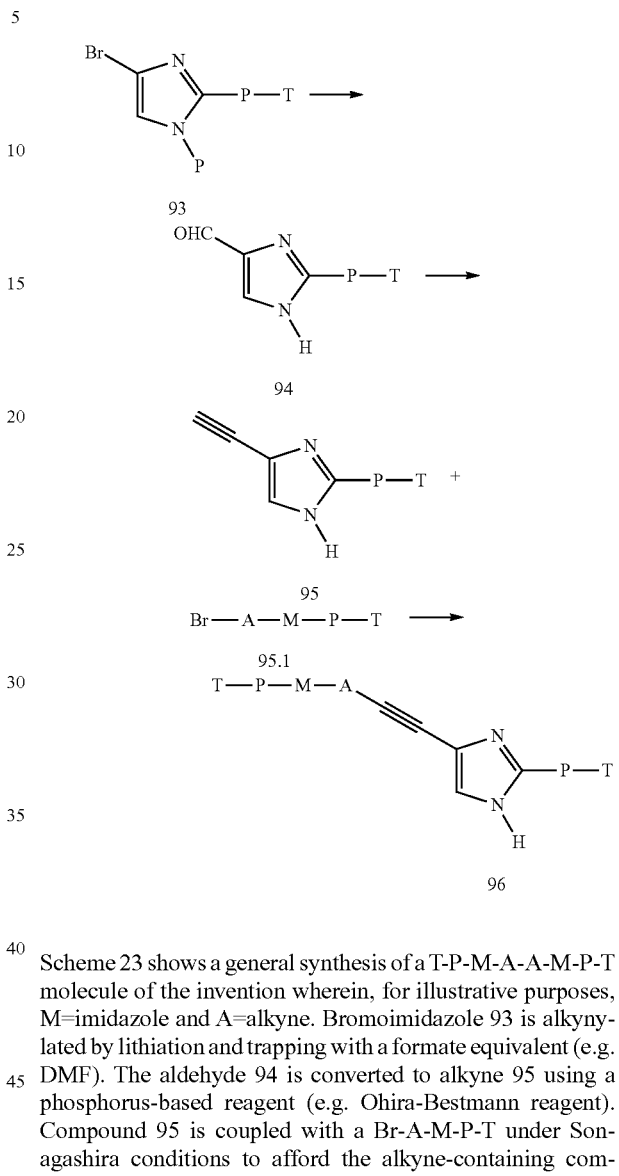

Scheme 23 shows a general synthesis of a T-P-M-A-A-M-P-T molecule of the invention wherein, for illustrative purposes, M=imidazole and A=alkyne. Bromoimidazole 93 is alkynylated by lithiation and trapping with a formate equivalent (e.g. DMF). The aldehyde 94 is converted to alkyne 95 using a phosphorus-based reagent (e.g. Ohira-Bestmann reagent). Compound 95 is coupled with a Br-A-M-P-T under Sonagashira conditions to afford the alkyne-containing compound 96.

Scheme 24: Representative Synthesis of R9 Fragment

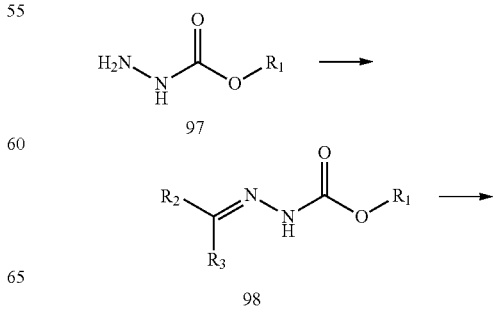

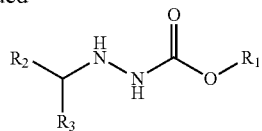

99

Scheme 24 shows a general synthesis of an R9 molecule of the invention. Reaction of hydrazine carboxylate 97 with a ketone or aldehyde, such as acetone, under acidic conditions (e.g. AcOH) affords the imine 98. Reaction of 98 under reducing conditions, such as PtO₂ and hydrogen gas, affords the substituted hydrazinecarboxylate 99.

Scheme 25: Representative synthesis of
E—V—Z—P—M—A—A—M—P—Z—V—E

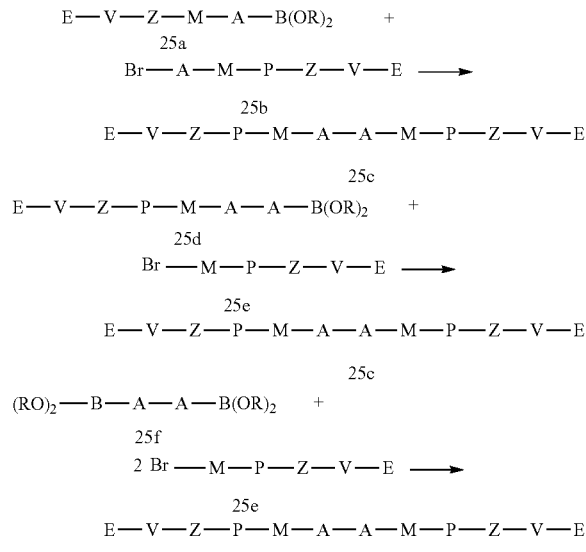

Scheme 25 shows a general synthesis of the E-V-Z-P-M-A-A-M-P-Z-V-E molecule of the invention, wherein a transition metal-mediated cross-coupling reaction is utilized to construct the A-A bond and/or A-M bond. For illustrative purposes, the Suzuki reaction is employed to couple Br-M-P-Z-V-E and (RO)₂B-A-A-M-P-Z-V-E or (RO)₂B-A-M-P-Z-V-E and Br-A-M-P-Z-V-E. Boronic ester 25a (or 25d) is coupled with an appropriate coupling partner (e.g. arylbromide 25b or 25e) using a palladium catalyst, such as Pd(PPh₃)₄, to afford 25c. Formation of multiple A-M bonds can be conducted in a similar manner. For example, the Suzuki reaction can also be employed to couple (RO)₂B-A-A-B(OR)₂ (25f) and two equivalents of Br-M-P-Z-V-E. For each transition metal-mediated cross-coupling reaction the roles of the nucleophile and electrophile can be reversed to provide the same coupling product. Palladium mediated cross-coupling reactions that enable the A-A and/or A-M bond formation, but employ alternative coupling partners and reagents, include for example the Negishi, Kumada, Sonagashira and Stille reactions.

Scheme 26: Representative synthesis of
E—V—Z—P—M—A—A—M—P—Z—V—E

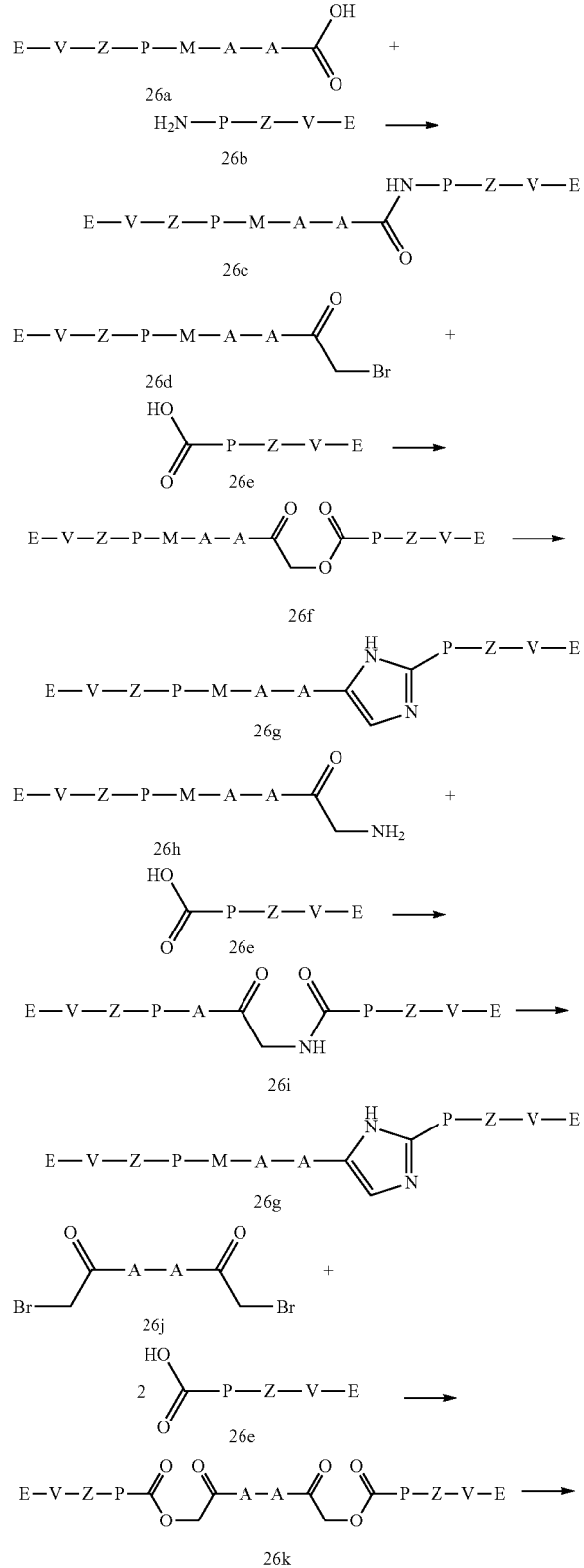

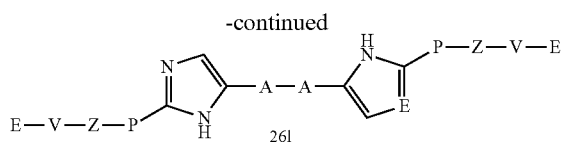

261

Scheme 26 shows a general synthesis of an E-V-Z-P-M-A-A-M-P-Z-V-E molecule of the invention wherein, for illustrative purposes, M is an amide, or an imidazole. Coupling of acid 26a with amine 26b is accomplished using a peptide coupling reagent (e.g. HATU) to afford the amide product 26c.

The formation of an imidazole is accomplished by coupling the acid 26d with an α-haloketone, such as α-bromoketone 26e, under basic conditions (e.g. Et₃N) to afford 26f. Alternatively, the acid 26d is coupled with an α-aminoketone 26h, under amide formation conditions (e.g. EDC, Et₃N) to afford 26i. Reaction of 26f or 26i with an amine or amine salt (e.g. ammonium acetate) affords the imidazole containing molecule 26g. The formation of multiple imidazoles is performed in the same manner, starting with a bis-α-haloketone such as α-bromoketone 26j, to provide molecule 26l.

Scheme 27: Representative synthesis of
E—V—Z—P—M—A—A—M—P—Z—V—E

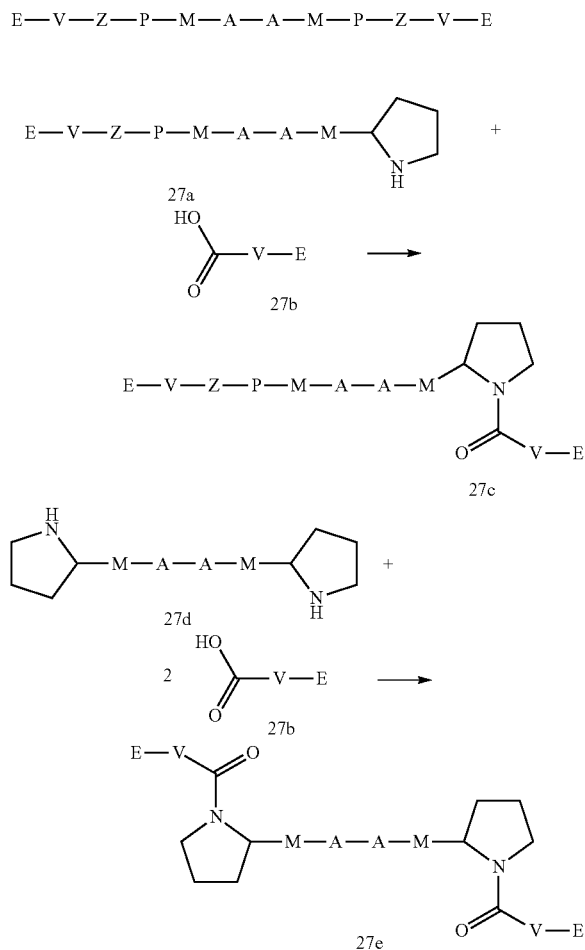

Scheme 27 shows a general synthesis of an E-V-Z-P-M-A-A-M-P-Z-V-E molecule of the invention wherein, for illustrative purposes, P is pyrrolidine and Z is a carbonyl. Coupling of amine 27a with acid 27b is accomplished using a peptide coupling reagent (e.g. HATU) to afford 27c. Alternatively, amine 27d is coupled with two equivalents of 27b under similar conditions to provide 27e.

Scheme 28: Representative synthesis of
E—V—Z—P—M—A—A—M—P—Z—V—E

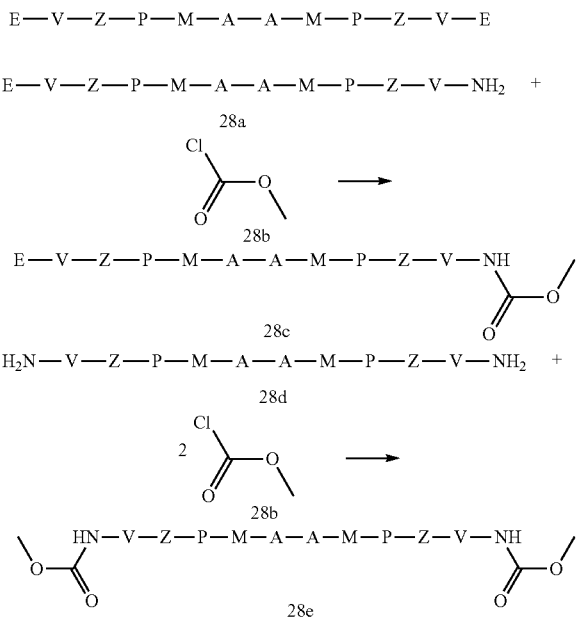

Scheme 28 shows a general synthesis of an E-V-Z-P-M-A-A-M-P-Z-V-E molecule of the invention wherein, for illustrative purposes, E is methoxycarbonylamino. The treatment of either 28a or 28d with one or two equivalents respectively of 28b under basic conditions (e.g. sodium bicarbonate) provides the molecule 28c or 28e.

Scheme 29: Representative synthesis of
E—V—Z—P—M—W—M—P—Z—V—E

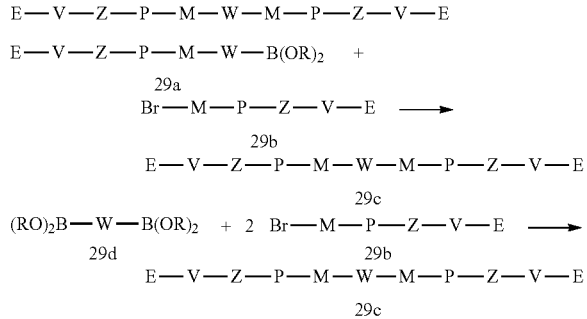

Scheme 29 shows a general synthesis of the E-V-Z-P-M-W-M-P-Z-V-E molecule of the invention, wherein transition metal-mediated cross-coupling reaction is utilized to construct the W-M bond. For illustrative purposes, the Suzuki reaction is employed to couple Br-M-P-Z-V-E to a (RO)₂B-W-M-P-Z-V-E or (RO)₂B-W-B(OR)₂ molecule. Boronic ester 29a (or 29d) is coupled with an appropriate coupling partner (e.g. arylbromide 29b) using a palladium catalyst, such as Pd(PPh₃)₄, to afford 29c. For each transition metal-mediated cross-coupling reaction the roles of the nucleophile and electrophile can be reversed to provide the same coupling product. Palladium mediated cross-coupling reactions that enable the M-W bond formation, but employ alternative coupling partners and reagents, include for example the Negishi, Kumada, Sonagashira and Stille reactions.

Scheme 30: Representative synthesis of
E—V—Z—P—M—W—M—P—Z—V—E

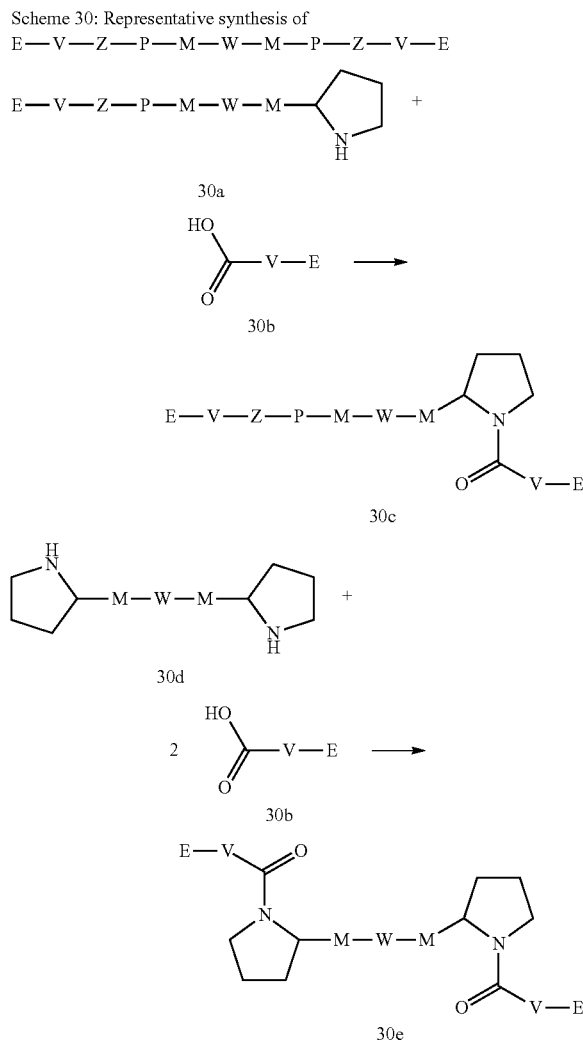

Scheme 30 shows a general synthesis of an E-V-Z-P-M-W-M-P-Z-V-E molecule of the invention wherein, for illustrative purposes, P is pyrrolidine and Z is a carbonyl. Coupling of amine 30a with acid 30b is accomplished using a peptide coupling reagent (e.g. HATU) to afford 30c. Alternatively, amine 30d is coupled with two equivalents of 30b under similar conditions to provide 30e.

Scheme 31: Representative synthesis of
E—V—Z—P—M—W—M—P—Z—V—E

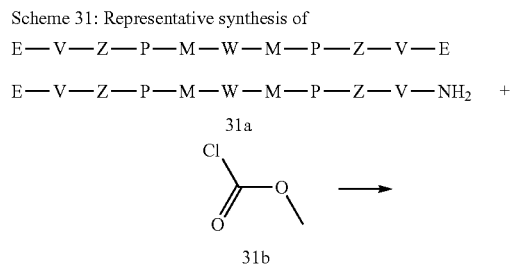

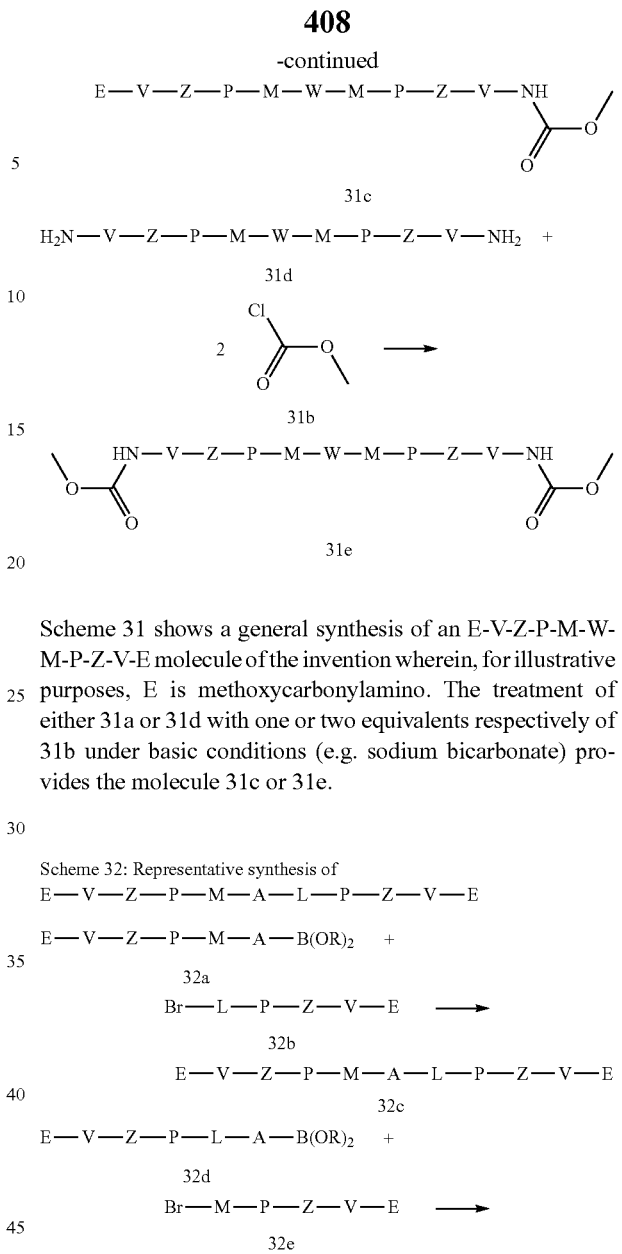

Scheme 31 shows a general synthesis of an E-V-Z-P-M-W-M-P-Z-V-E molecule of the invention wherein, for illustrative purposes, E is methoxycarbonylamino. The treatment of either 31a or 31d with one or two equivalents respectively of 31b under basic conditions (e.g. sodium bicarbonate) provides the molecule 31c or 31e.

Scheme 32: Representative synthesis of
E—V—Z—P—M—A—L—P—Z—V—E

E—V—Z—P—M—A—B(OR)$_2$     +
32a
Br—L—P—Z—V—E     →
32b
E—V—Z—P—M—A—L—P—Z—V—E
32c
E—V—Z—P—L—A—B(OR)$_2$     +
32d
Br—M—P—Z—V—E     →
32e
E—V—Z—P—M—A—L—P—Z—V—E
32c

Scheme 32 shows a general synthesis of the E-V-Z-P-M-A-L-P-Z-V-E molecule of the invention, wherein transition metal-mediated cross-coupling reaction is utilized to construct the M-A or A-L bond. For illustrative purposes, the Suzuki reaction is employed to couple a boronic ester to an arylbromide. Boronic ester 32a (or 32d) is coupled with an appropriate coupling partner (e.g. arylbromide 32b or 32e) using a palladium catalyst, such as Pd(PPh$_3$)$_4$, to afford 32c. For each transition metal-mediated cross-coupling reaction the roles of the nucleophile and electrophile can be reversed to provide the same coupling product. Palladium mediated cross-coupling reactions that enable either the M-A or A-L bond formation, but employ alternative coupling partners and reagents, include for example the Negishi, Kumada, Sonagashira and Stille reactions.

Scheme 33: Representative synthesis of E—V—Z—P—M—A—L—P—Z—V—E
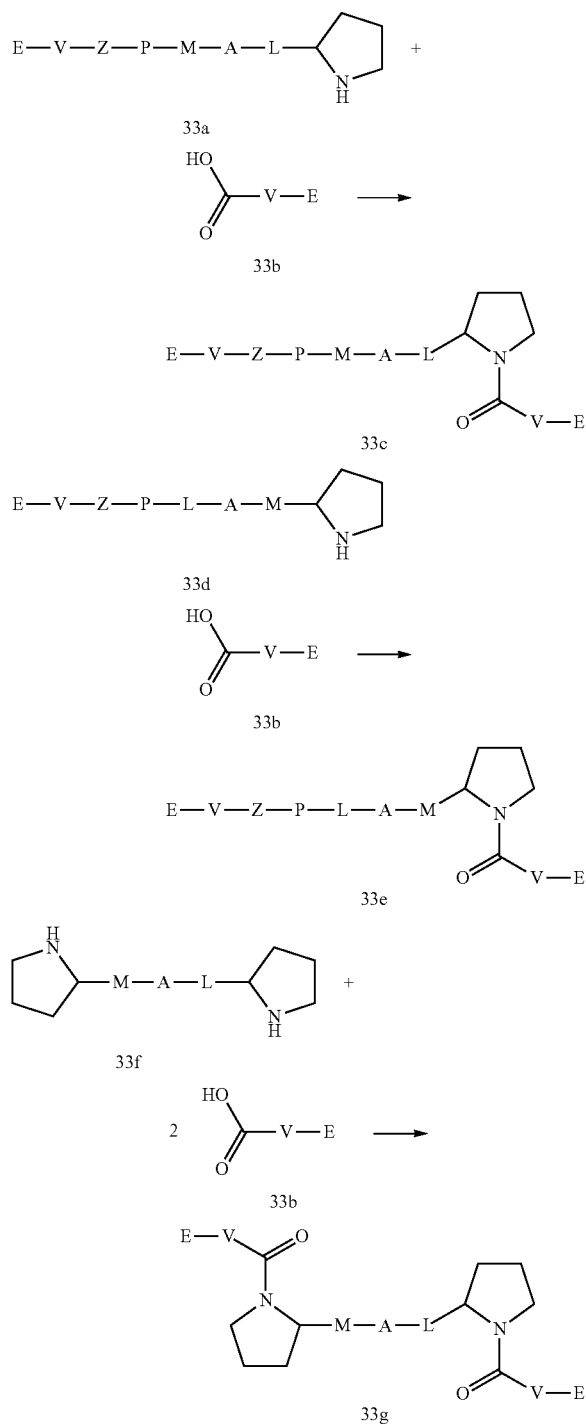
33a

33b

33c

33d

33b

33e

33f

33b

33g

Scheme 33 shows a general synthesis of an E-V-Z-P-M-A-L-P-Z-V-E molecule of the invention wherein, for illustrative purposes, P is pyrrolidine and Z is a carbonyl. Coupling of amine 33a or 33d with acid 33b is accomplished using a peptide coupling reagent (e.g. HATU) to afford 33c or 33e, respectively. Alternatively, amine 33f is coupled with two equivalents of 33b under similar conditions to provide 33g.

Scheme 34: Representative synthesis of E—V—Z—P—M—A—L—P—Z—V—E

34a

34b

34c

34d

34b

34e

34f

34b

34g

Scheme 34 shows a general synthesis of an E-V-Z-P-M-A-L-P-Z-V-E molecule of the invention wherein, for illustrative purposes, E is methoxycarbonylamino. The treatment of either 34a or 34d with 34b under basic conditions (e.g. sodium bicarbonate) provides the molecule 34c or 34e. Correspondingly, the treatment of 34f with two equivalents of 34b provides 34g under similar conditions.

Scheme 35: Representative synthesis of E—V—Z—P—L—L—P—Z—V—E

E—V—Z—P—L—B(OR)$_2$ +

35a

Br—L—P—Z—V—E

35b

E—V—Z—P—L—L—P—Z—V—E

35c

Scheme 35 shows a general synthesis of the E-V-Z-P-L-L-P-Z-V-E molecule of the invention, wherein transition metal-mediated cross-coupling reaction is utilized to construct the L-L bond. For illustrative purposes, the Suzuki reaction is employed to couple a boronic ester to an arylbromide. Boronic ester 35a is coupled with an appropriate coupling partner (e.g. arylbromide 35b) using a palladium catalyst, such as Pd(PPh$_3$)$_4$, to afford 35c. For each transition metal-mediated cross-coupling reaction the roles of the nucleophile and electrophile can be reversed to provide the same coupling product. Palladium mediated cross-coupling reactions that enable either the L-L bond formation, but employ alternative coupling partners and reagents, include for example the Negishi, Kumada, Sonagashira and Stille reactions.

Scheme 36: Representative synthesis of
E—V—Z—P—L—L—P—Z—V—E

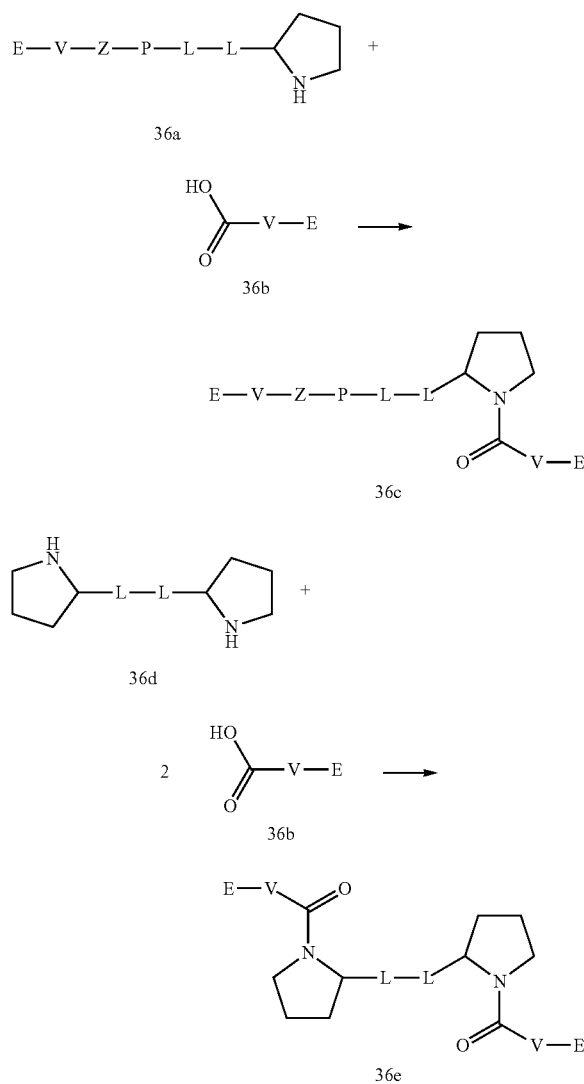

Scheme 36 shows a general synthesis of an E-V-Z-P-L-L-P-Z-V-E molecule of the invention wherein, for illustrative purposes, P is pyrrolidine and Z is a carbonyl. Coupling of amine 36a with acid 36b is accomplished using a peptide coupling reagent (e.g. HATU) to afford 36c. Alternatively, amine 36d is coupled with two equivalents of 36b under similar conditions to provide 36e.

Scheme 37: Representative synthesis of
E—V—Z—P—L—L—P—Z—V—E

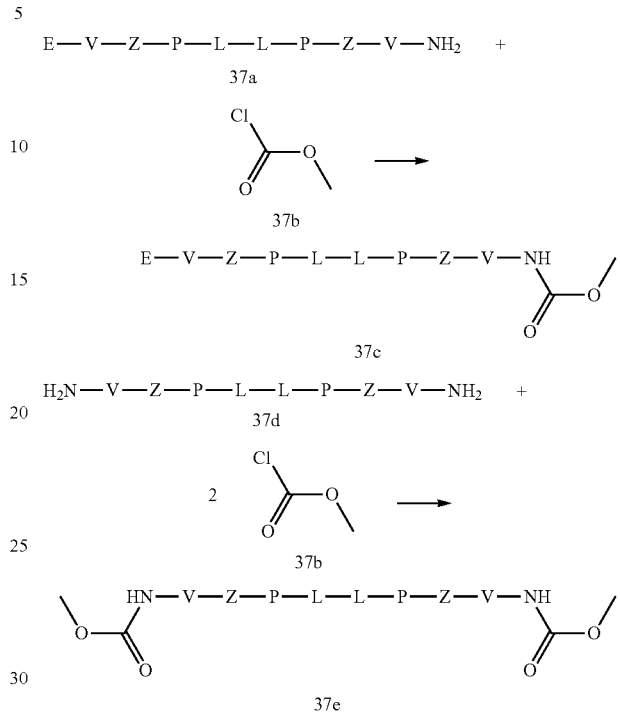

Scheme 37 shows a general synthesis of an E-V-Z-P-L-L-P-Z-V-E molecule of the invention wherein, for illustrative purposes, E is methoxycarbonylamino. The treatment of either 37a or 37d with 37b under basic conditions (e.g. sodium bicarbonate) provides the molecule 37c or 37e.

Scheme 38: Representative synthesis of R—A—M—P—R$^1$

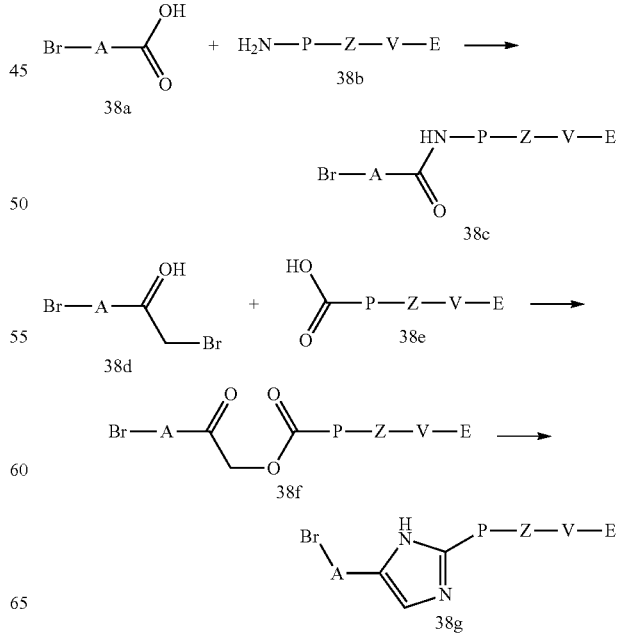

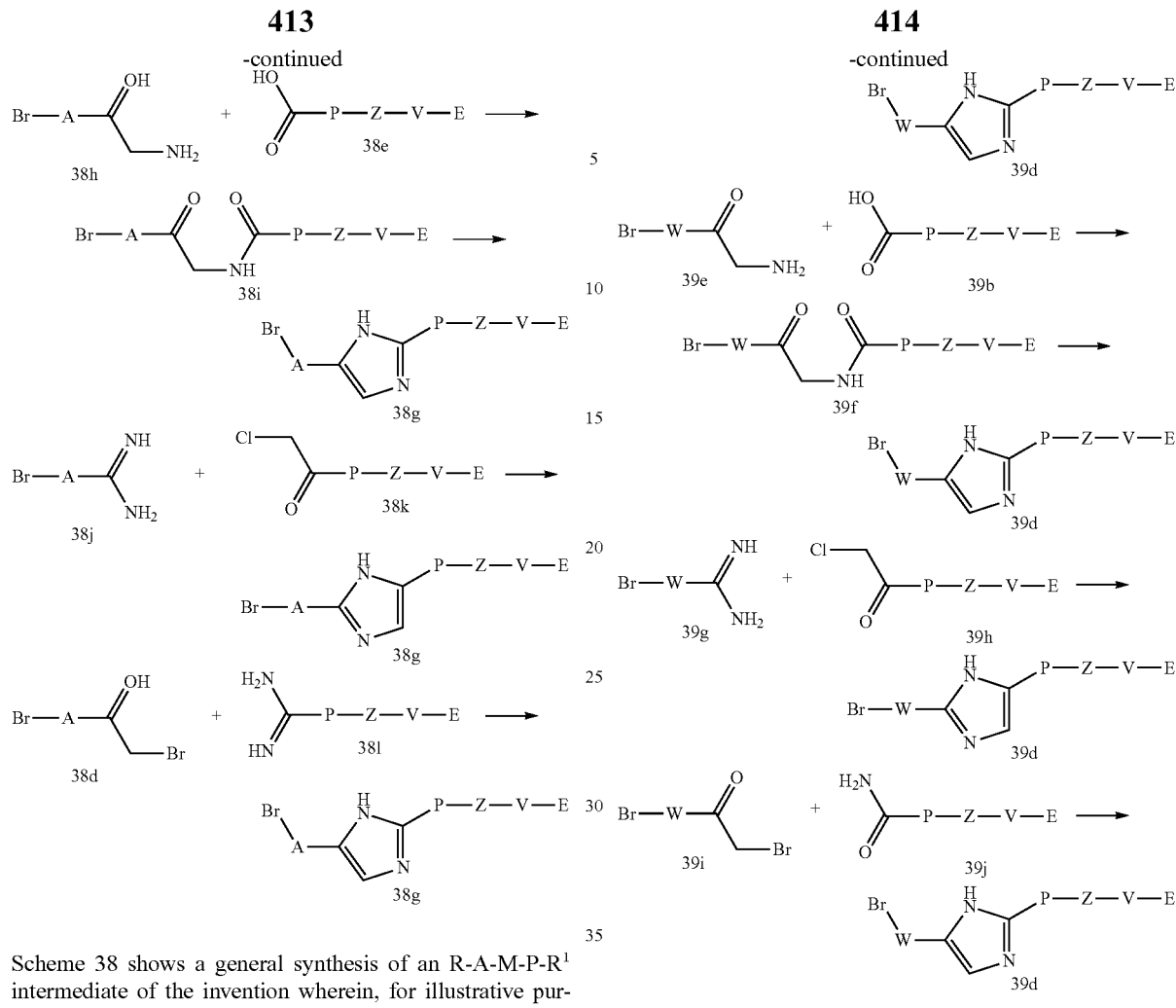

Scheme 38 shows a general synthesis of an R-A-M-P-R$^1$ intermediate of the invention wherein, for illustrative purposes, M is an amide or an imidazole, R is a generic group that is depicted as Br, and R$^1$ is a generic group that is depicted as -Z-V-E. Coupling of amine 38b with acid 38a is accomplished using a peptide coupling reagent (e.g. HATU) to afford amide containing 38c. The acid 38e is coupled with an α-haloketone, such as α-bromoketone 38d, under basic conditions (e.g. Et$_3$N) to afford 38f. Alternatively, the acid 38e is coupled with an α-aminoketone 38h, under amide formation conditions (e.g. EDC, Et$_3$N) to afford 38i. Reaction of 38f or 38i with an amine or amine salt (e.g. ammonium acetate) affords the imidazole containing intermediate Br-A-M-P-Z-V-E (38g).

The benzamidine 38j is coupled with an α-haloketone such as α-chloroketone 38k under basic conditions such as K$_2$CO$_3$ to afford 38g. The Br-A-M-P-Z-V-E intermediate can be prepared analogously from the coupling of 38d and 38l.

Scheme 39 shows a general synthesis of an R-W-M-P-R$^1$ intermediate of the invention wherein, for illustrative purposes, M is an amide or an imidazole, R is a generic group that is depicted as Br, and R$^1$ is a generic group that is depicted as -Z-V-E. The acid 39b is coupled with an α-haloketone, such as α-bromoketone 39a, under basic conditions (e.g. Et$_3$N) to afford 39c. Alternatively, the acid 39b is coupled with an α-aminoketone 39e, under amide formation conditions (e.g. EDC, Et$_3$N) to afford 39f. Reaction of 39c or 39f with an amine or amine salt (e.g. ammonium acetate) affords the imidazole containing intermediate Br-A-M-P-Z-V-E (39d).

The benzamidine 39g is coupled with an α-haloketone such as α-chloroketone 39h under basic conditions such as K$_2$CO$_3$ to afford 39d. The Br-A-M-P-Z-V-E intermediate can be prepared analogously from the coupling of 39i and 39j.

Scheme 39: Representation synthesis of R—W—M—P—R$^1$

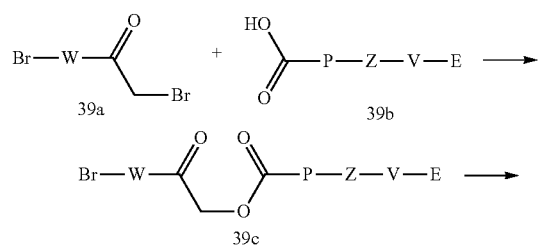

Scheme 40: Representative synthesis of R—A—R$^1$

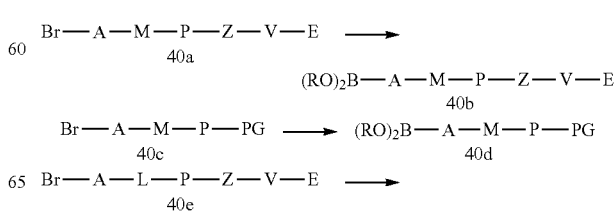

-continued

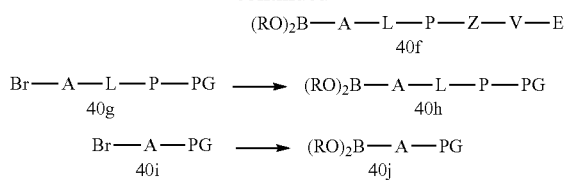
40f
40g
40h
40i
40j

Scheme 40 shows a general synthesis of an R-A-R¹ intermediate of the invention wherein, for illustrative purposes, R is a generic group that is depicted as a boronic ester and R¹ is a generic group that is depicted as -M-P-Z-V-E, -M-P-PG, -L-P-Z-V-E, -L-P-PG, or a protecting group. A transition metal-mediated cross-coupling reaction is utilized to install the boronic ester on an A group. Treatment of the corresponding arylbromide with a palladium catalyst, such as PdCl₂(dppf), and a boron source such as bis(pinacolato)diborane provides the boronic ester 40b, 40d, 40f, 40h, or 40j.

Scheme 41: Representative synthesis of R—W—R¹

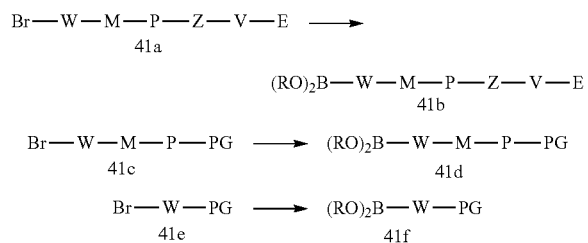
41a
41b
41c
41d
41e
41f

Scheme 41 shows a general synthesis of an R-W-R¹ intermediate of the invention wherein, for illustrative purposes, R is a generic group that is depicted as a boronic ester and R¹ is a generic group that is depicted as -M-P-Z-V-E, -M-P-PG, or a protecting group. A transition metal-mediated cross-coupling reaction is utilized to install the boronic ester on a W group. Treatment of the corresponding arylbromide with a palladium catalyst, such as PdCl₂(dppf), and a boron source such as bis(pinacolato)diborane provides the boronic ester 41b, 41d, or 41f.

Scheme 42: Representative synthesis of R—M—R¹

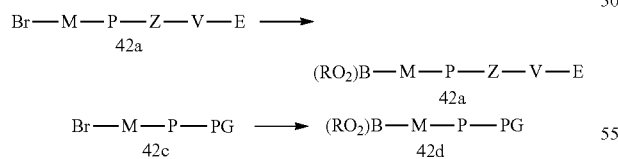
42a
42a
42c
42d

Scheme 42 shows a general synthesis of an R-M-R¹ intermediate of the invention wherein, for illustrative purposes, R is a generic group that is depicted as a boronic ester and R¹ is a generic group that is depicted as -P-Z-V-E or -P-PG. A transition metal-mediated cross-coupling reaction is utilized to install the boronic ester on an M group. Treatment of the corresponding arylbromide with a palladium catalyst, such as PdCl₂(dppf), and a boron source such as bis(pinacolato)diborane provides the boronic ester 42b or 42d.

Scheme 43: Representative synthesis of R—L—R¹

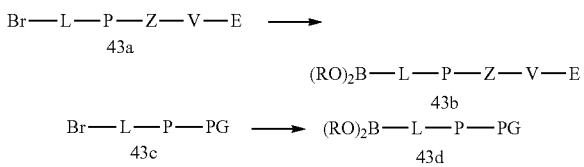
43a
43b
43c
43d

Scheme 43 shows a general synthesis of an R-L-R¹ intermediate of the invention wherein, for illustrative purposes, R is a generic group that is depicted as a boronic ester and R¹ is a generic group that is depicted as -P-Z-V-E or -P-PG. A transition metal-mediated cross-coupling reaction is utilized to install the boronic ester on an L group. Treatment of the corresponding arylbromide with a palladium catalyst, such as PdCl₂(dppf), and a boron source such as bis(pinacolato)diborane provides the boronic ester 43b or 43d.

Scheme 44: Representative synthesis of R-A-M-P-Z-V-E

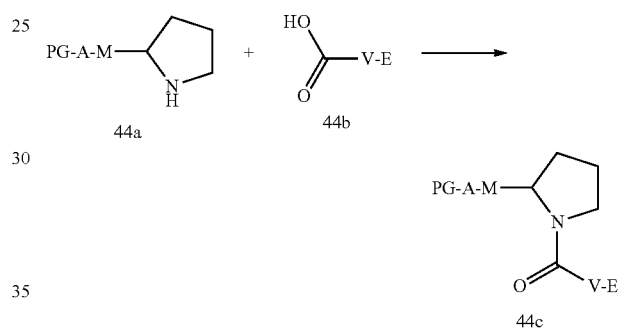
44a    44b
44c
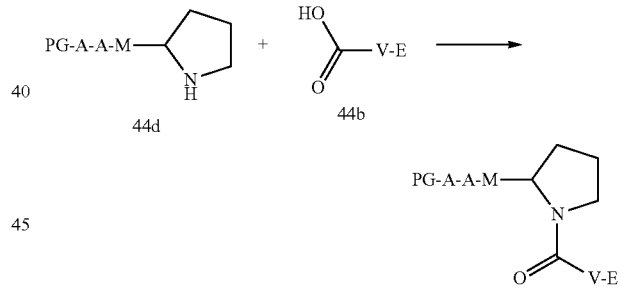
44d    44b
44e
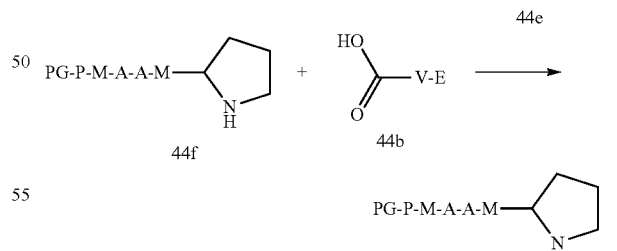
44f    44b
44g
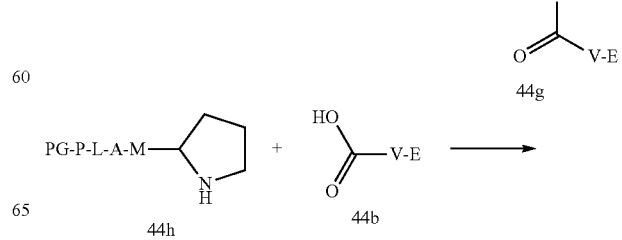
44h    44b

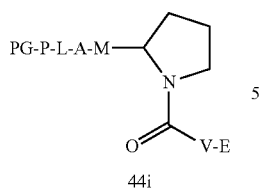

Scheme 44 shows a general synthesis of an R-A-M-P-Z-V-E intermediate of the invention wherein, for illustrative purposes, P is pyrrolidine, Z is carbonyl, and R is a generic group that is depicted as either -A-PG, -A-M-P-PG, -L-P-PG, or a protecting group. Coupling of amine 44a, 44d, 44f, or 44h with acid 44b is accomplished using a peptide coupling reagent (e.g. HATU) to afford 44c, 44e, 44g, or 44i, respectively.

Scheme 45: Representative synthesis of R-W-M-P-Z-V-E

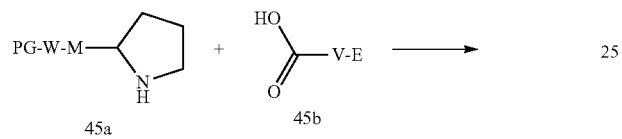

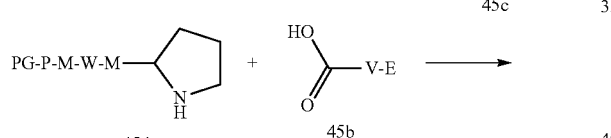

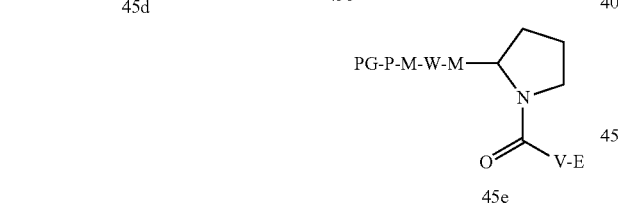

Scheme 45 shows a general synthesis of an R-W-M-P-Z-V-E intermediate of the invention wherein, for illustrative purposes, P is pyrrolidine, Z is carbonyl, and R is a generic group that is depicted as either -M-P-PG or a protecting group. Coupling of amine 45a or 45d with acid 45b is accomplished using a peptide coupling reagent (e.g. HATU) to afford 45c or 45e, respectively.

Scheme 46: Representative synthesis of R-A-L-P-Z-V-E

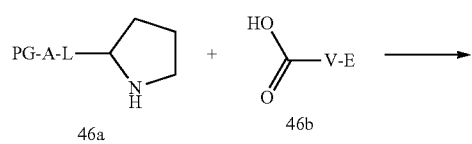

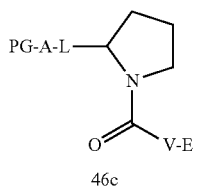

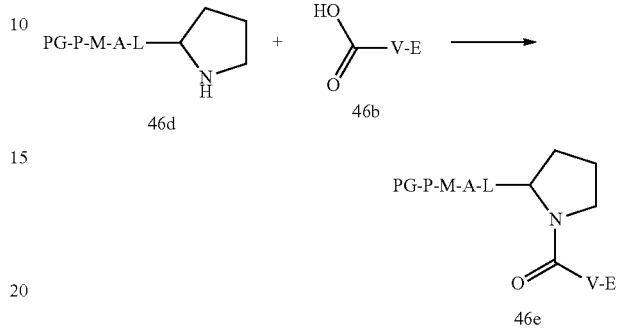

Scheme 46 shows a general synthesis of an R-A-L-P-Z-V-E intermediate of the invention wherein, for illustrative purposes, P is pyrrolidine, Z is carbonyl, and R is a generic group that is depicted as either -M-P-PG or a protecting group. Coupling of amine 46a or 46d with acid 46b is accomplished using a peptide coupling reagent (e.g. HATU) to afford 46c or 46e, respectively.

Scheme 47: Representative synthesis of R-L-P-Z-V-E and R-M-P-Z-V-E

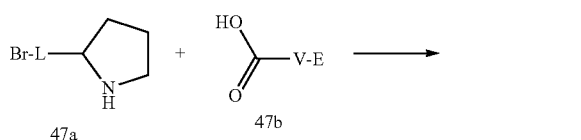

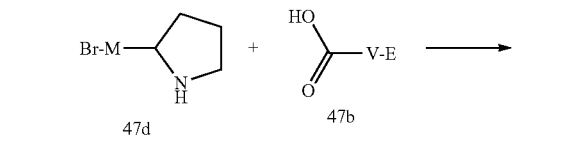

Scheme 47 shows a general synthesis of an R-L-P-Z-V-E or R-M-P-Z-V-E intermediate of the invention wherein, for illustrative purposes, P is pyrrolidine, Z is carbonyl, and R is a generic group that is depicted as Br. Coupling of amine 47a or 47d with acid 47b is accomplished using a peptide coupling reagent (e.g. HATU) to afford 47c or 47e, respectively.

Scheme 48: Representative synthesis of R-A-M-P-Z-V-E
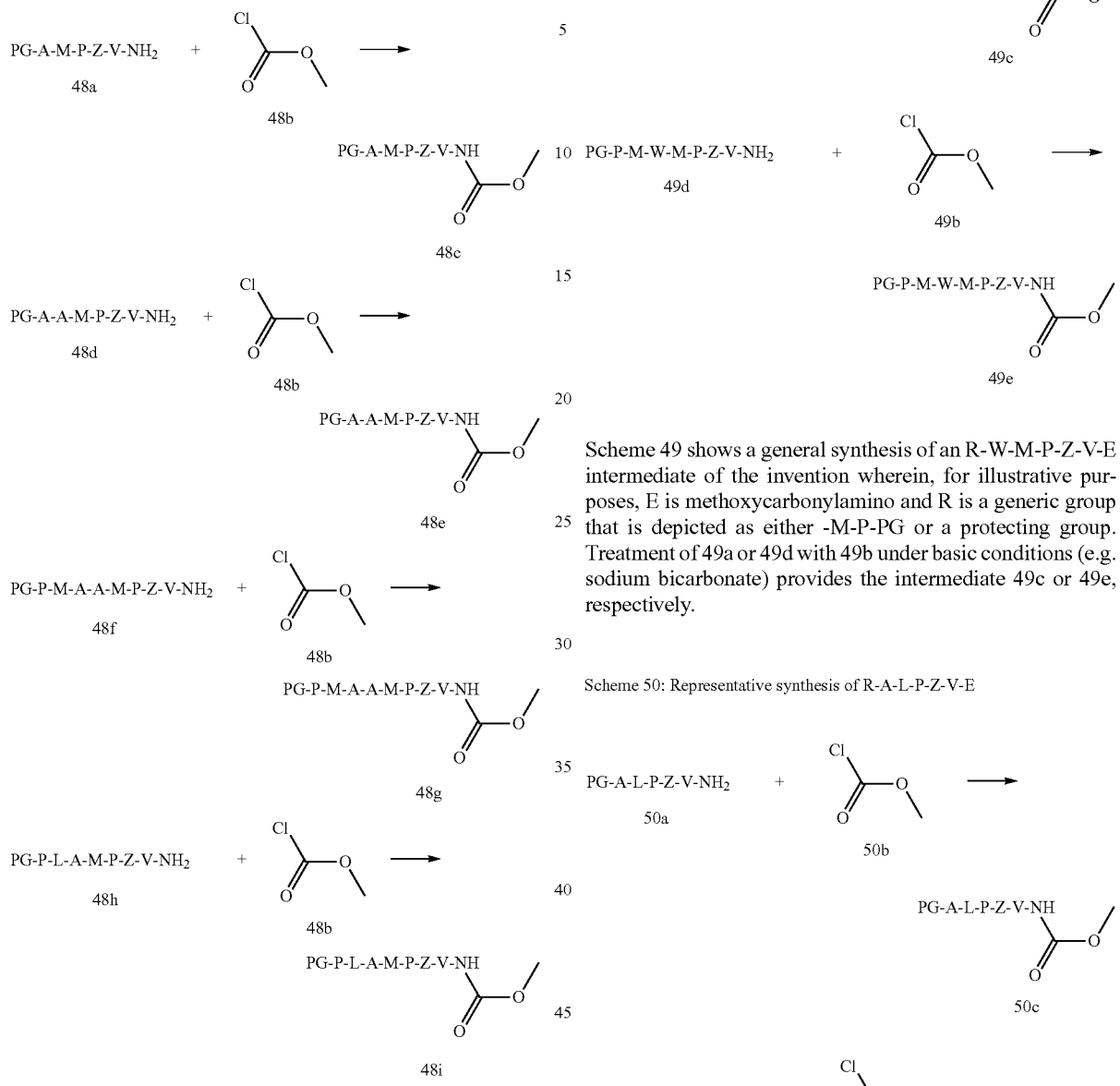

48a 48b 48c 48d 48b 48e 48f 48b 48g 48h 48b 48i

Scheme 48 shows a general synthesis of an R-A-M-P-Z-V-E intermediate of the invention wherein, for illustrative purposes, E is methoxycarbonylamino and R is a generic group that is depicted as a either -A-PG, -A-M-P-PG, -L-P-PG, or a protecting group. Treatment of 48a, 48d, 48f, or 48h with 48b under basic conditions (e.g. sodium bicarbonate) provides the intermediate 48c, 48e, 48g, or 48i, respectively.

Scheme 49: Representative synthesis of R-W-M-P-Z-V-E 49a 49b

-continued

49c 49d 49b 49e

Scheme 49 shows a general synthesis of an R-W-M-P-Z-V-E intermediate of the invention wherein, for illustrative purposes, E is methoxycarbonylamino and R is a generic group that is depicted as either -M-P-PG or a protecting group. Treatment of 49a or 49d with 49b under basic conditions (e.g. sodium bicarbonate) provides the intermediate 49c or 49e, respectively.

Scheme 50: Representative synthesis of R-A-L-P-Z-V-E 50a 50b 50c 50d 50b 50e

Scheme 50 shows a general synthesis of an R-A-L-P-Z-V-E intermediate of the invention wherein, for illustrative purposes, E is methoxycarbonylamino and R is a generic group that is depicted as a either -M-P-PG or a protecting group. Treatment of 50a or 50d with 50b under basic conditions (e.g. sodium bicarbonate) provides the intermediate 50c or 50e, respectively.

Scheme 51: Representative synthesis of R-A-L-P-Z-V-E

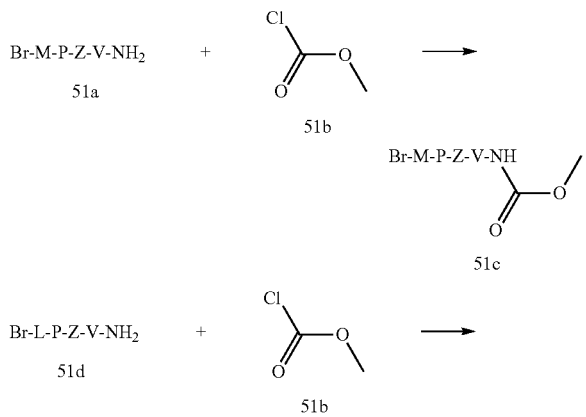

Scheme 51 shows a general synthesis of an R-L-P-Z-V-E or R-M-P-Z-V-E intermediate of the invention wherein, for illustrative purposes, E is methoxycarbonylamino and R is a generic group that is depicted as a Br. Treatment of 51a or 51d with 51b under basic conditions (e.g. sodium bicarbonate) provides the intermediate 51c or 51e, respectively.

Scheme 51a: Representative synthesis of R-P-Z-V-E

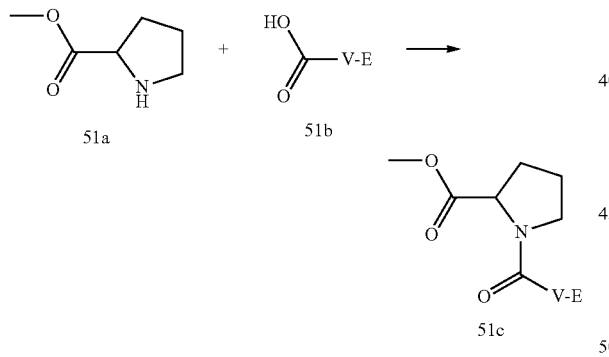

Scheme 51a shows a general synthesis of an R-P-Z-V-E intermediate of the invention wherein, for illustrative purposes, P is pyrrolidine, Z is carbonyl, and R is a generic group that is depicted as a methoxycarbonyl. Coupling of amine 51a with acid 51b is accomplished using a peptide coupling reagent (e.g. HATU) to afford 51c.

Scheme 52: Representative synthesis of R-Z-V-E

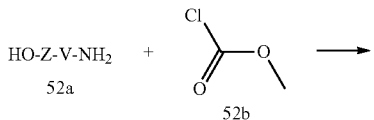

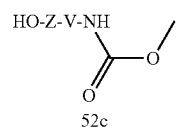

Scheme 52 shows a general synthesis of an R-Z-V-E intermediate of the invention wherein, for illustrative purposes, E is methoxycarbonylamino and R is a generic group that is depicted as a hydroxyl. Treatment of 52a under basic conditions (e.g. sodium bicarbonate) with 52b provides the intermediate 52c.

Scheme 53: Representative synthesis of R-L-P-R$^1$

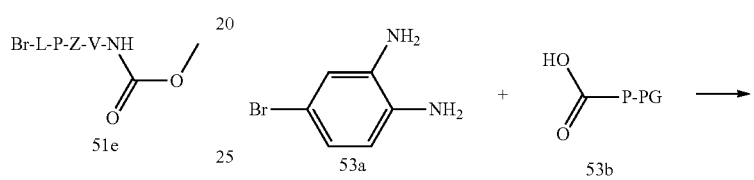

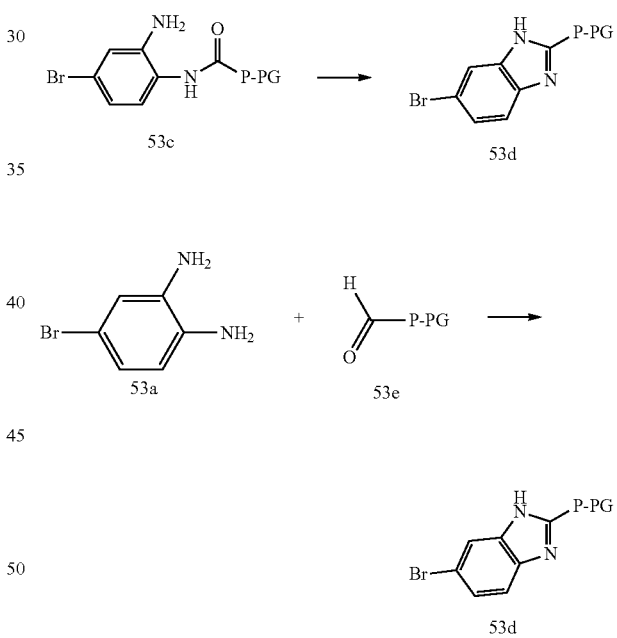

Scheme 53 shows a general synthesis of an R-L-P-R$^1$ intermediate of the invention wherein, for illustrative purposes, L is benzimidazole, R is a generic group that is depicted as a bromide, and R$^1$ is a protecting group. The acid 53b is coupled with 53a using a peptide coupling reagent such as HATU to afford 53c. Heating in solvent (such as refluxing ethanol) affords the R-L-P-R$^1$ intermediate 53d.

Alternatively, the R-L-P-R$^1$ intermediate 53d is obtained by reaction of a diamine (such as 53a) and carbonyl compound (such as aldehyde 53e) in a solvent under heating conditions (e.g. ethanol under microwave irradiation).

Scheme 54: Representative synthesis of R-M-P-R[1]

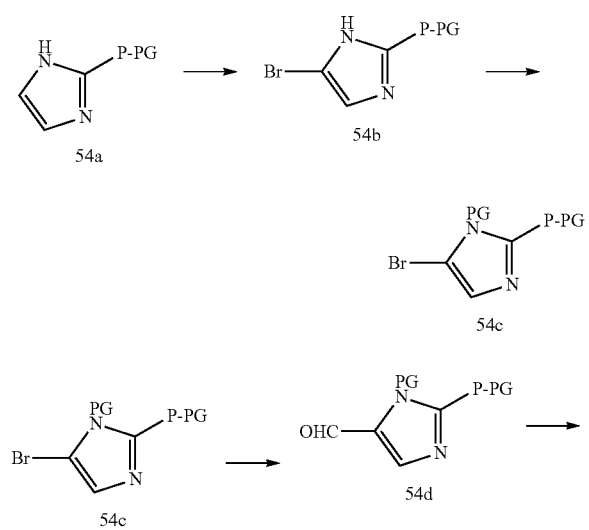
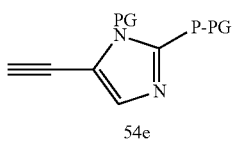

Scheme 54 shows a general synthesis of an R-M-P-R[1] intermediate of the invention wherein, for illustrative purposes, M is imidazole, R is a generic group that is depicted as a bromide, aldehyde, or alkyne and R[1] is a protecting group. Imidazole 54a can be halogenated, for example, under the action of N-bromosuccinimide to provide bromoimidazole 54b.

Bromoimidazole 54b can be protected using standard conditions to give 54c, such as SEM-Cl and sodium hydride when PG=SEM. The bromoimidazole 54b can be further elaborated, for example, to the corresponding aldehyde or alkyne. Lithiation of 54c and condensation with a formate equivalent (e.g. DMF) provides the aldehyde 54d. The aldehyde 54d is converted to alkyne 54e using a phosphorus-based reagent (e.g. Ohira-Bestmann reagent).

Scheme 55: Representative synthesis of R-P-M-A-A-M-P-R

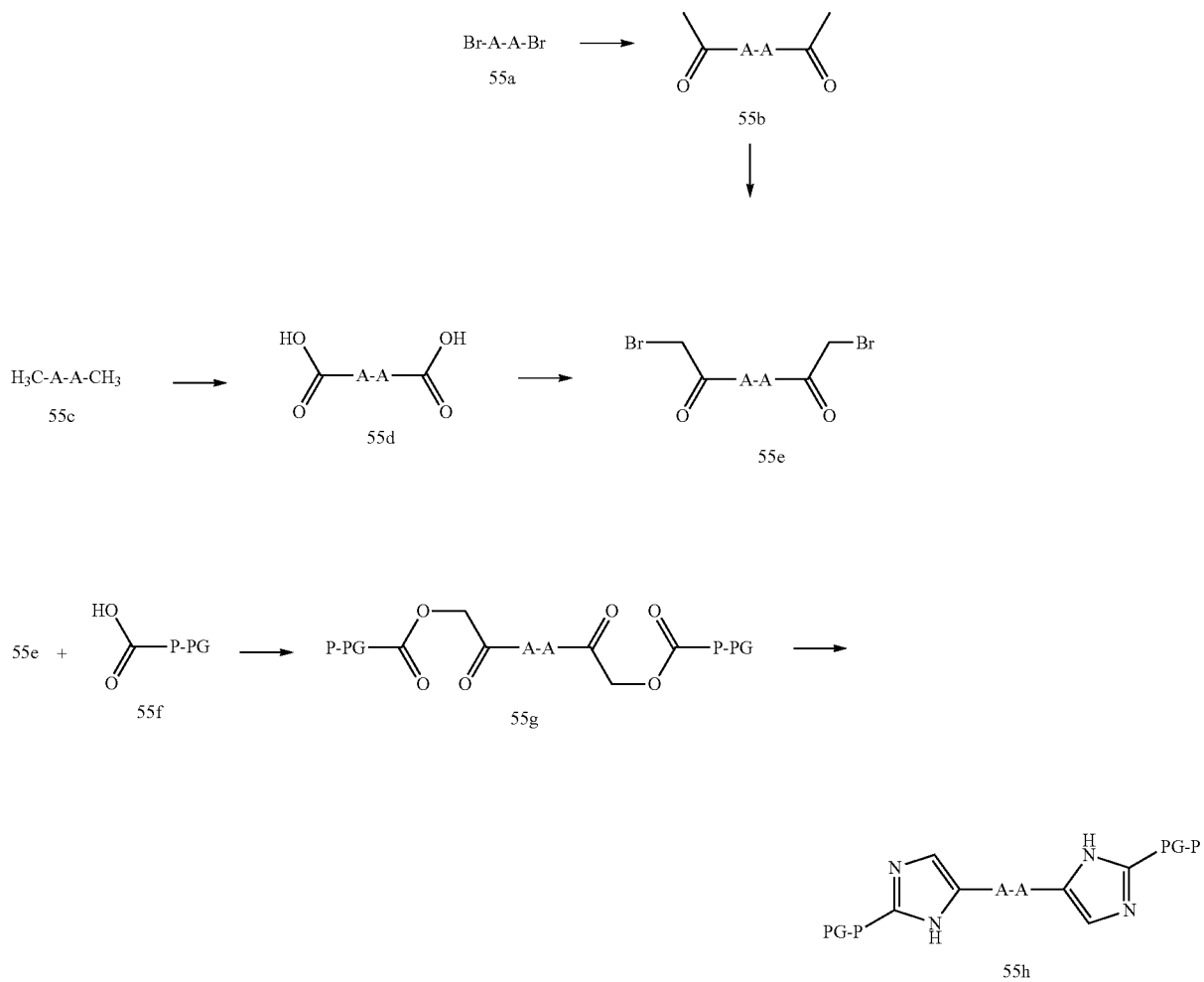

Scheme 55 shows a general synthesis of an R-P-M-A-A-M-P-R intermediate of the invention wherein, for illustrative purposes, M is imidazole and R is a generic group that is depicted as a protecting group. For example, the diketone 55b is converted to 55e using bromine. Compound 55b can be commercially available or can be prepared from the corresponding dibromide 55a through coupling with a vinyltin reagent such as tributyl(ethoxyvinyl)stannane in the presence of a palladium catalyst. Coupling of 55e with acid 55f under basic conditions such as diisopropylethylamine affords diester 55g. Imidazole formation is accomplished by treatment of 55g with ammonium acetate to provide the imidazole containing intermediate R-P-M-A-A-M-P-R (55h).

Alternatively, bromide 55e can be synthesized from 55c. The dimethyl compound 55c can be converted to the corresponding diacid 55d using potassium permanganate as oxidant.

Conversion of 55d to 55e can be accomplished by a multi-step homologation. For example, the treatment of 55d with oxalyl chloride, followed by trimethylsilyl diazomethane and then hydrobromic acid can afford compound 55e.

Scheme 56: Representative synthesis of R-P-M-W-M-P-R

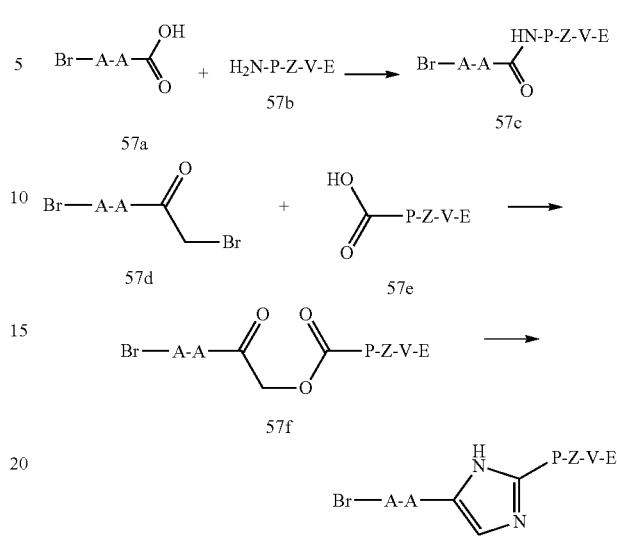

Scheme 57: Representative synthesis of R-A-A-M-P-R¹

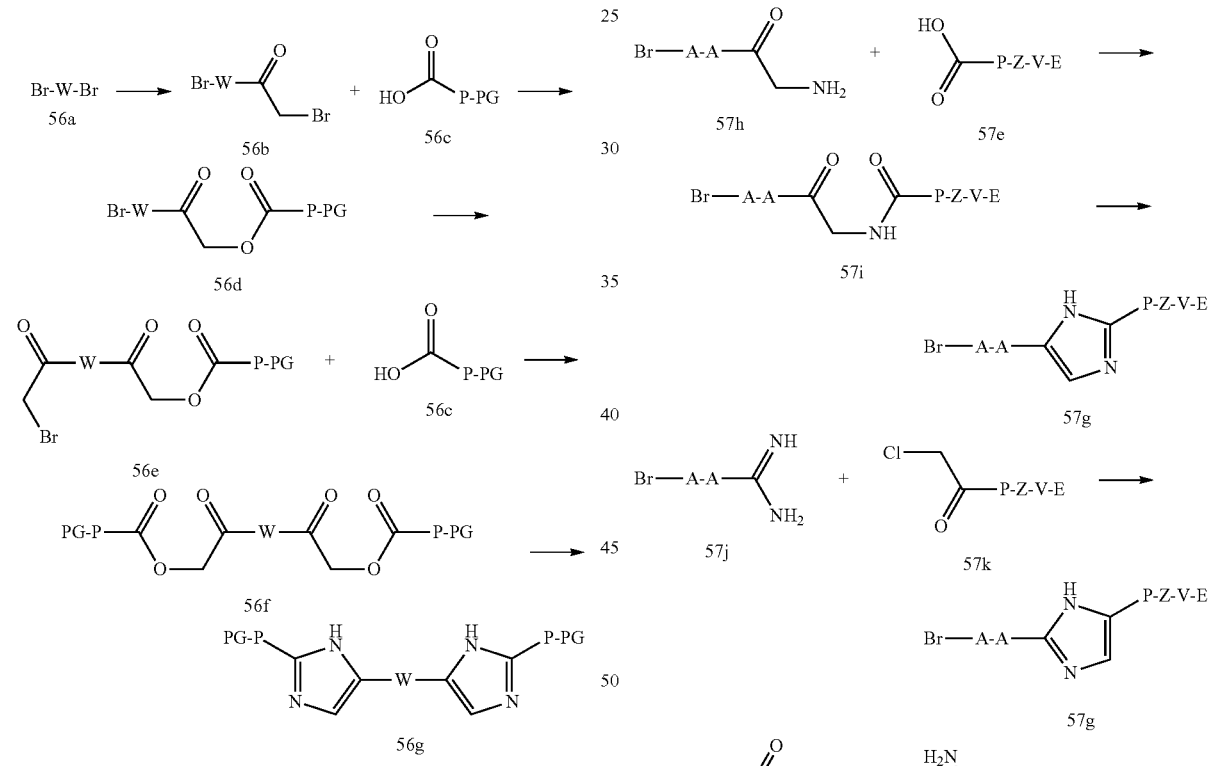

Scheme 56 shows a general synthesis of an R-P-M-W-M-P-R intermediate of the invention wherein, for illustrative purposes, M is imidazole and R is a generic group that is depicted as a protecting group. The compound 56a is coupled with vinyltin reagent such as tributyl(ethoxyvinyl)stannane in the presence of a palladium catalyst, followed by bromination and hydrolysis with NBS and water, to give the bromoketone 56b. The reaction between bromide 56b and a carboxylic acid under basic condition generates the ester 56d. Following the same reaction sequence, compound 56d can be elaborated to the diester 56f. Conversion of 56f to 56g is accomplished with ammonia reagents such as ammonium acetate at elevated temperature.

Scheme 57 shows a general synthesis of an R-A-A-M-P-R¹ intermediate of the invention wherein, for illustrative purposes, M is an amide or an imidazole, R is a generic group that is depicted as Br, and R¹ is a generic group that is depicted as -Z-V-E. Coupling of amine 57b with acid 57a is accomplished using a peptide coupling reagent (e.g. HATU) to afford amide containing 57c.

The acid 57e is coupled with an α-haloketone, such as α-bromoketone 57d, under basic conditions (e.g. Et₃N) to afford 57f. Alternatively, the acid 57e is coupled with an α-aminoketone 57h, under amide formation conditions (e.g. EDC, Et₃N) to afford 57i. Reaction of 57f or 57i with an amine or amine salt (e.g. ammonium acetate) affords the imidazole containing intermediate Br-A-M-P-Z-V-E (57g). Coupling of 57j and 57k and, in the alternative, coupling of 57d and 57l under appropriate conditions can also be used in preparation of intermediate Br-A-M-P-Z-V-E (57g).

Scheme 58: Representative synthesis of R-A-A-M-P-R¹

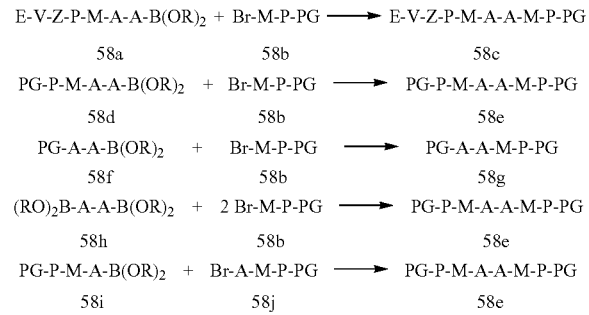

Scheme 58 shows a general synthesis of the R-A-A-M-P-R¹ molecule of the invention, wherein a transition metal-mediated cross-coupling reaction is utilized to construct the A-A bond or A-M bond. For illustrative purposes, the Suzuki reaction is employed to couple two corresponding intermediates, R is a generic group that is depicted as -M-P-Z-V-E, -M-P-PG, or a protecting group, and R¹ is a generic group that is depicted as a protecting group. Boronic ester 58a, 58d, 58f or 58i is coupled with an appropriate coupling partner (e.g. arylbromide 58b or 58j) using a palladium catalyst, such as Pd(PPh₃)₄, to afford 58c, 58e, or 58g. Formation of multiple A-M bonds can be conducted in a similar manner. For example, the Suzuki reaction can also be employed to couple (RO)₂B-A-A-B(OR)₂ (58h) and two equivalents of Br-M-P-PG. For each transition metal-mediated cross-coupling reaction the roles of the nucleophile and electrophile can be reversed to provide the same coupling product. Palladium mediated cross-coupling reactions that enable the A-A and/or A-M bond formation, but employ alternative coupling partners and reagents, include for example the Negishi, Kumada, Sonagashira and Stille reactions.

Scheme 59: Representative synthesis of R-W-M-P-R¹

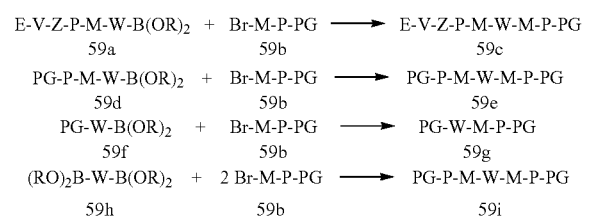

Scheme 59 shows a general synthesis of the R-W-M-P-R¹ molecule of the invention, wherein a transition metal-mediated cross-coupling reaction is utilized to construct the W-M bond. For illustrative purposes, the Suzuki reaction is employed to couple two corresponding intermediates, R is a generic group that is depicted as -M-P-Z-V-E, -M-P-PG, or a protecting group, and R¹ is a generic group that is depicted as a protecting group. Boronic ester 59a, 59d, or 59f is coupled with an appropriate coupling partner (e.g. arylbromide 59b) using a palladium catalyst, such as Pd(PPh₃)₄, to afford 59c, 59e, or 59g. Formation of multiple W-M bonds can be conducted in a similar manner. For example, the Suzuki reaction can also be employed to couple (RO)₂B-W-B(OR)₂ (59h) and two equivalents of Br-M-P-PG. For each transition metal-mediated cross-coupling reaction the roles of the nucleophile and electrophile can be reversed to provide the same coupling product. Palladium mediated cross-coupling reactions that enable the W-M bond formation, but employ alternative coupling partners and reagents, include for example the Negishi, Kumada, Sonagashira and Stille reactions.

Scheme 60: Representative sythesis of R-A-L-P-R¹

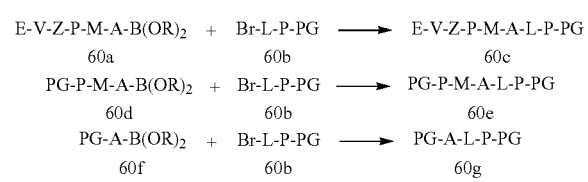

Scheme 60 shows a general synthesis of the R-A-L-P-R¹ molecule of the invention, wherein a transition metal-mediated cross-coupling reaction is utilized to construct the A-L bond. For illustrative purposes, the Suzuki reaction is employed to couple two corresponding intermediates, R is a generic group that is depicted as -M-P-Z-V-E, -M-P-PG, or a protecting group, and R¹ is a generic group that is depicted as a protecting group. Boronic ester 60a, 60d, or 60f is coupled with an appropriate coupling partner (e.g. arylbromide 60b) using a palladium catalyst, such as Pd(PPh₃)₄, to afford 60c, 60e, or 60g. For each transition metal-mediated cross-coupling reaction the roles of the nucleophile and electrophile can be reversed to provide the same coupling product. Palladium mediated cross-coupling reactions that enable the A-L bond formation, but employ alternative coupling partners and reagents, include for example the Negishi, Kumada, Sonagashira and Stille reactions.

Scheme 61: Representative sythesis of R-A-M-P-R¹

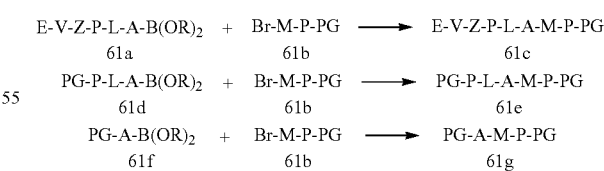

Scheme 61 shows a general synthesis of the R-A-M-P-R¹ molecule of the invention, wherein a transition metal-mediated cross-coupling reaction is utilized to construct the A-M bond. For illustrative purposes, the Suzuki reaction is employed to couple two corresponding intermediates, R is a generic group that is depicted as -L-P-Z-V-E, -L-P-PG, or a protecting group, and R¹ is a generic group that is depicted as a protecting group. Boronic ester 61a, 61d, or 61f is coupled with an appropriate coupling partner (e.g. arylbromide 61b) using a palladium catalyst, such as Pd(PPh$_3$)$_4$, to afford 61c, 61e, or 61g. For each transition metal-mediated cross-coupling reaction the roles of the nucleophile and electrophile can be reversed to provide the same coupling product. Palladium mediated cross-coupling reactions that enable the A-M bond formation, but employ alternative coupling partners and reagents, include for example the Negishi, Kumada, Sonagashira and Stille reactions.

Scheme 62: Representative synthesis of R-P-H

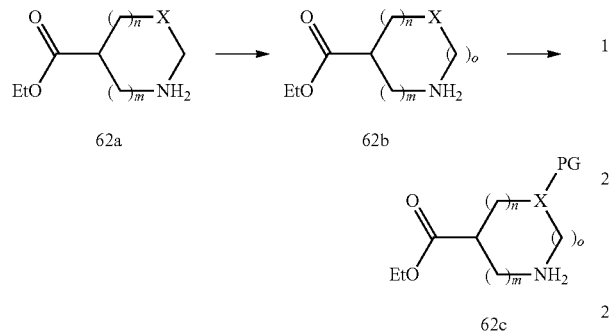

Scheme 62 shows a general synthesis of a R-P-H molecule of the invention wherein, for illustrative purposes, R is a generic group that is depicted as ethoxycarbonyl and P is a carbocyclic or heterocyclic ring (e.g. X is carbon or heteroatom) and m, n, and o are 0-3, independently. The amino ester 62a is converted to the substituted or cyclized amino ester 62b through for example a reductive amination or Mitsunobu reaction. Compound 62b can be protected to provide compound 62c if necessary.

Scheme 63: Representative sythesis of R-P-M-W-M-P-R

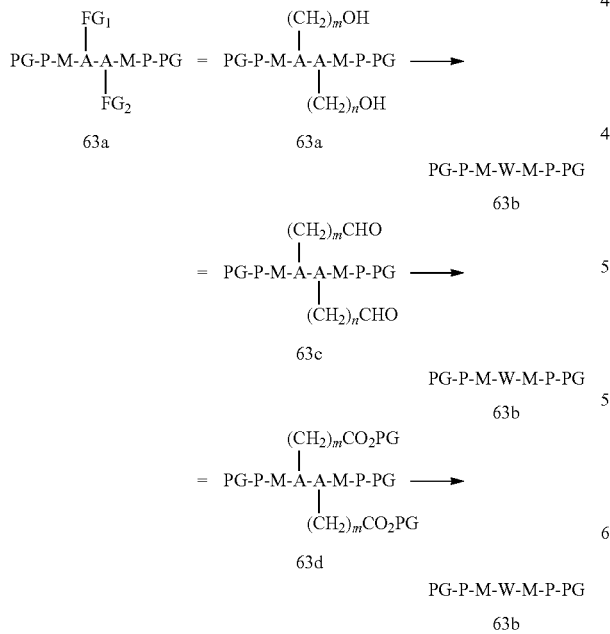

Scheme 63 shows a general synthesis of a R-P-M-W-M-P-R intermediate of the invention wherein, for illustrative purposes, R is a generic group that is depicted as a protecting group and A is functionalized with a group depicted as either hydroxyalkyl, aminoalkyl, carbonylalkyl, or alkoxycarbonylalkyl. The cyclization of 63a, 63c, and 63d can be performed through several functional group transformations which include, but are not limited to, Mitsunobu reaction, reductive amination, and lactamization.

Scheme 64: Representative Sythesis of H-V-E

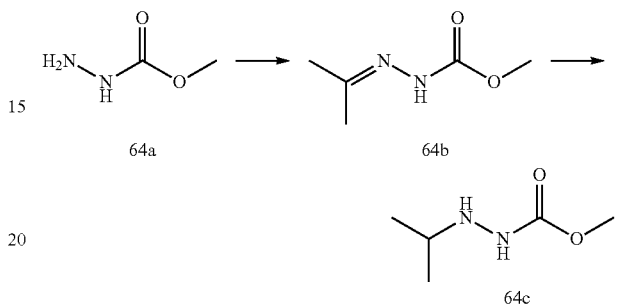

Scheme 64 shows a general synthesis of a H-V-E intermediate of the invention wherein, for illustrative purposes E is methoxycarbonylamino and V is isopropylamino. The reaction of hydrazine carboxylate 64a with a ketone or aldehyde, such as acetone, under acidic conditions (e.g. AcOH) affords the imine 64b. Reaction of 64b under reducing conditions, such as PtO$_2$ and hydrogen gas, affords the substituted hydrazinecarboxylate 64c.

The invention will now be illustrated by the following non-limiting Examples.

EXAMPLES

Example AA

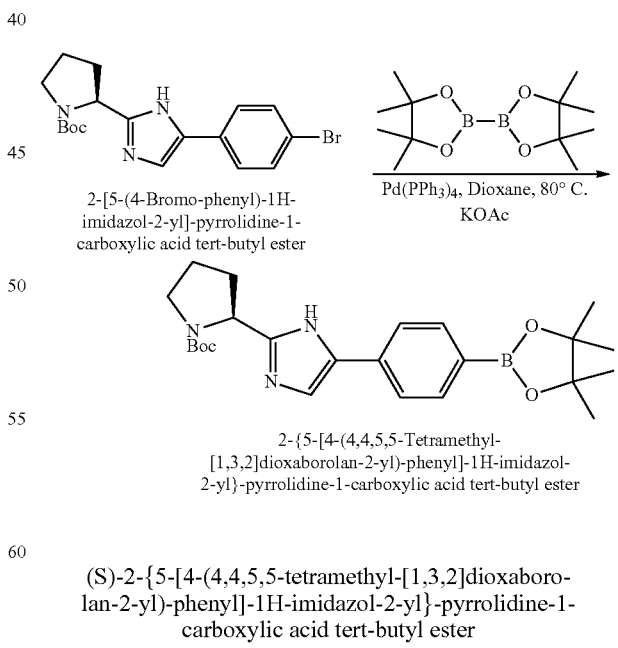

(S)-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester 1,4-Dioxane (300 mL) was added to a mixture of (S)-2-[5-(4-bromo-phenyl)-1H-imidazol-2-yl]-pyrrolidine-1-carboxylic acid tert-butyl ester (21.1 g, 53.7 mmol), bis(pinacolato)diboron (27.3 g, 107.5 mmol), tetrakis (triphenylphosphine)palladium (0) (3.10 g, 2.68 mmol), and potassium acetate (15.02 g, 153.0 mmol), and heated at 80° C. for 16 hours. The mixture was cooled and the resulting solid was filtered. The majority of the 1,4-dioxane was removed from the filtrate under reduced pressure and resulting residue was taken up in ethyl acetate (300 mL) The organic phase was washed with saturated sodium bicarbonate (2×150 mL), brine (100 mL) and dried over sodium sulfate. After filtration the solvent was removed from the filtrate under reduced pressure. The resulting oil was subjected to silica gel chromatography using a 330 g ISCO column and effluent of 20-100% ethyl acetate and hexanes. The fractions containing product were combined and the solvent was removed under reduced pressure to provide (S)-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (18 g, 76%) and light yellow solid.

Example AB

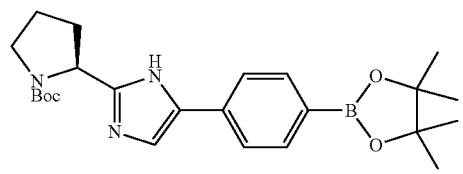

2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester HCl/Dioxane
DCM

2-Pyrrolidin-2-yl-5-[4,4,5,5-tetramethyl-[1,3,2]dioxaborolan-2-yl)-phenyl]-1H-imidazole (S)-2-Pyrrolidin-2-yl-5-[4-(4,4,5,5-tetramethyl-[1,3,2]dioxaborolan-2-yl)-phenyl]-1H-imidazole hydrochloride A solution of hydrogen chloride in 1,4-dioxane (4 N, 75 mL) was added to a solution of (S)-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (7.0 g, 15.9 mmol) in dichloromethane (50 mL). Gas evolution was observed. After 30 minutes, a solid formed. After 1.5 hours, the resulting solid was isolated by filtration with diethyl ether washing. Any residual solvent was removed under reduced pressure to provide (S)-2-pyrrolidin-2-yl-5-[4-(4,4,5,5-tetramethyl-[1,3,2]dioxaborolan-2-yl)-phenyl]-1H-imidazole hydrochloride (5.6 g, 95%) as an off-white solid.

Example AC

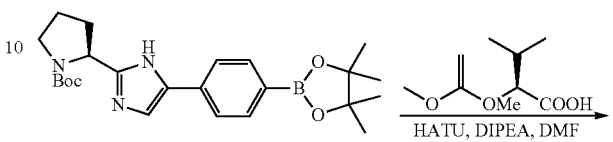

2-Pyrrolidin-2-yl-5-[4,4,5,5-tetramethyl-[1,3,2]dioxaborolan-2-yl)-phenyl]-1H-imidazole

HATU, DIPEA, DMF

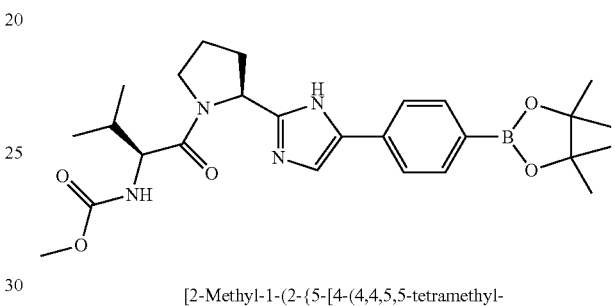

[2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (S,S)-[2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester Diisopropylethylamine (7.63 mL, 43.8 mmol) was added to a suspension of (S)-2-pyrrolidin-2-yl-5-[4-(4,4,5,5-tetramethyl-[1,3,2]dioxaborolan-2-yl)-phenyl]-1H-imidazole hydrochloride (7.33 g, 19.5 mmol), O-(7-azabenzotriazol-1-yl)-N,N,N',N'-tetramethyluronium hexafluorophosphate (7.6 g, 19.9 mmol) and (S) 2-methoxycarbonylamino-3-methylbutyric acid (3.59 g, 20.5 mmol) in dimethylformamide (75 mL). All solids dissolved. After 30 min the reaction mixture was diluted with ethyl acetate (300 mL) and was washed with ½ saturated sodium chloride (1×300 mL), half saturated sodium bicarbonate (2×150 mL) and brine (1×100 mL). The organic phase was dried with sodium sulfate, filtered and the solvent was removed under reduced pressure. The resulting tan foam was subjected to silica gel chromatography with eluate of 20-100% ethyl acetate and hexanes, to provide (S,S)-[2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (6.6 g, 68%) as a white foam: 1H (DMSO-d6): δ=11.81 (br s, 1H), 7.72 (m, 2H), 7.61 (m, 2H), 7.51 (br s, 1H), 7.27 (d, J=8.4 Hz, 1H), 5.05 (m, 1H), 4.04 (m, 2H), 3.78 (m, 2H), 3.52 (s, 3H), 2.11 (m, 2H), 1.93 (m, 2H), 1.28 (s, 12H), 0.85 (dd, $J_1$=6.6 Hz, $J_2$=11.4 Hz, 6H).

Example AD

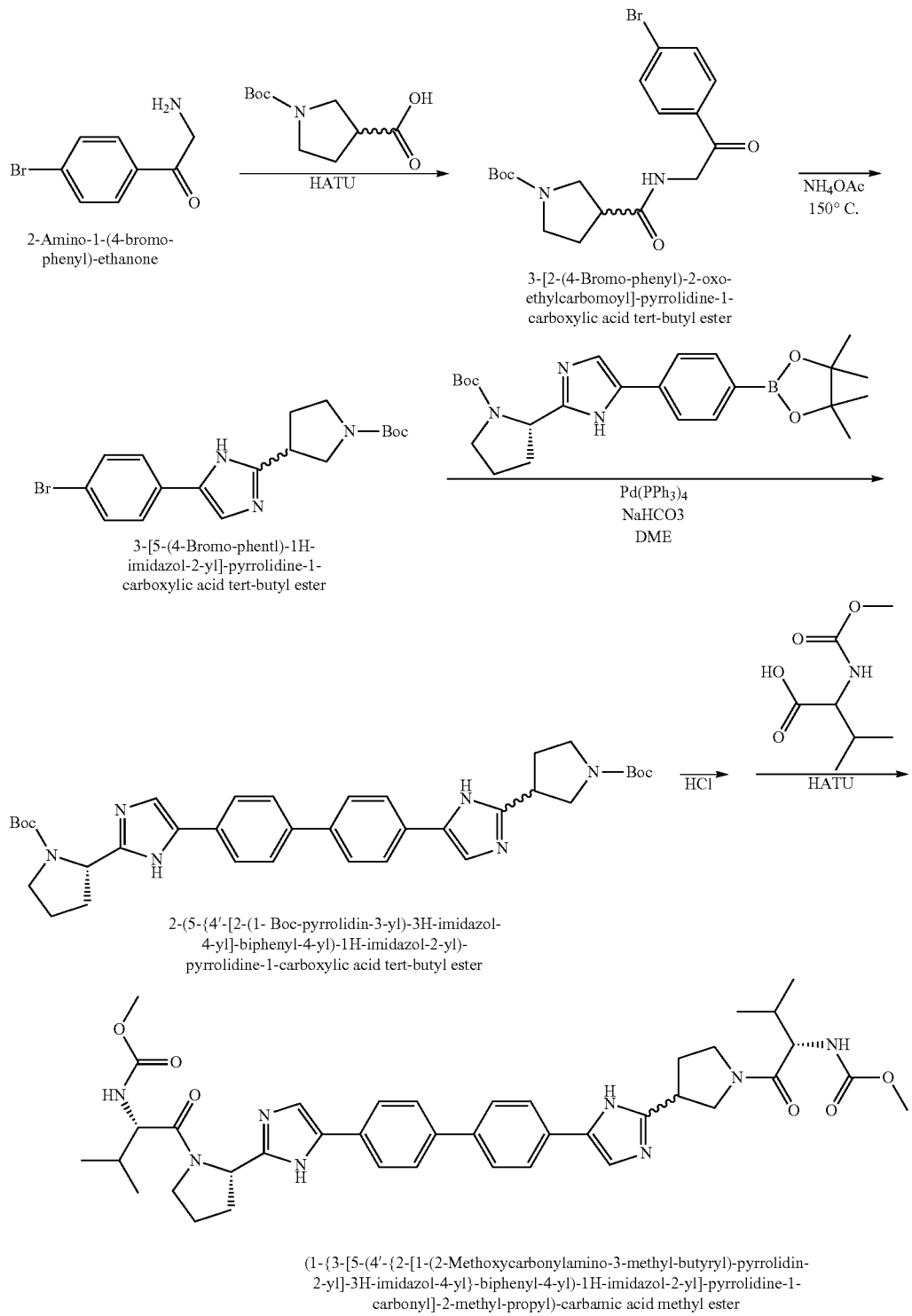

3-[2-(4-Bromo-phenyl)-2-oxo-ethylcarbamoyl]-pyrrolidine-1-carboxylic acid tert-butyl ester N,N-diisopropylethylamine (5.3 mL, 30.6 mmol) was added dropwise to a mixture of pyrrolidine-1,3-dicarboxylic acid 1-tert-butyl ester (2.2 g, 10.1 mmol), HATU (4.0 g, 10.5 mmol), the HCl salt of 2-amino-1-(4-bromophenyl)ethanone (2.4 g, 9.6 mmol), and DMF (40 mL), and stirred at ambient condition for 1 hour. Most of the volatile component was removed in vacuo, and the resulting residue was dissolved in ethyl acetate (150 mL), washed with water and brine, dried over Na$_2$SO$_4$, filtered and concentrated in vacuo. The obtained residue was purified by flash chromatography to provide the desired product as a white foam-like solid (3.5 g, 90%). m/z 432.9, 434.9 (M+Na)$^+$.

3-[5-(4-Bromo-phenyl)-1H-imidazol-2-yl]-pyrrolidine-1-carboxylic acid tert-butyl ester A mixture of 3-[2-(4-bromo-phenyl)-2-oxo-ethylcarbamoyl]-pyrrolidine-1-carboxylic acid tert-butyl ester (1.5 g, 3.6 mmol) and ammonium acetate (1.4 g, 18.2 mmol) in xylene (15 mL) was heated in a sealed tube at 140° C. for 2 hours. The volatile component was removed in vacuo, and the residue was dissolved in ethyl acetate (150 mL), washed with NaHCO$_3$ solution, water and brine, dried over Na$_2$SO$_4$, filtered and concentrated in vacuo. The obtained residue was purified by flash chromatography to provide the desired product as a white solid (795 mg, 56%). m/z 391.8, 393.8 (M+H)$^+$.

2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester Pd(Ph$_3$)$_4$ (54 mg, 0.046 mmol) was added to a mixture 3-[5-(4-bromo-phenyl)-1H-imidazol-2-yl]-pyrrolidine-1-carboxylic acid tert-butyl ester (378 mg, 0.97 mmol), 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (408 mg, 0.93 mmol), NaHCO$_3$ (273 mg, 3.26 mmol) in 1,2-dimethoxyethane (8 mL) and water (2 mL). The reaction mixture was flushed with nitrogen, heated at 80° C. for 6 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product as a white solid (370 mg, 64%). m/z 625.1 (M+H)$^+$.

(1-{3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester To a solution of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester (200 mg, 0.232 mmol) in methanol (5 mL) was added 4.0 M solution of HCl in dioxane (1 mL, excess). The mixture was stirred for 3 hours at 50° C. and concentrated under reduced pressure. The residue was treated with ether to remove excess HCl. The obtained white solid was dissolved in DMF (5 mL). To the solution was added 2-methoxycarbonylamino-3-methyl-butyric acid (123 mg, 0.71 mmol), HATU (285 mg, 0.75 mmol) and N,N-diisopropylethylamine (0.14 mL, 0.77 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by flash chromatography to provide the desired product as a white solid (100 mg, 42%). $^1$H-NMR (300 MHz, CD$_3$OD) δ 8.00-7.80 (m, 10H), 5.26 (t, 1H), 4.40-3.42 (m, 15H), 2.65-2.00 (m, 8H), 1.50-0.93 (m, 12H); m/z 739.3 (M+H)$^+$.

Example AE

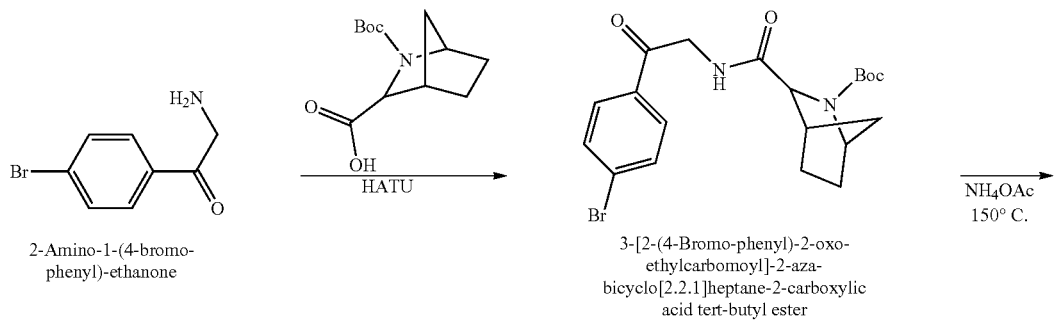

2-Amino-1-(4-bromo-phenyl)-ethanone

3-[2-(4-Bromo-phenyl)-2-oxo-ethylcarbomoyl]-2-aza-bicyclo[2.2.1]heptane-2-carboxylic acid tert-butyl ester

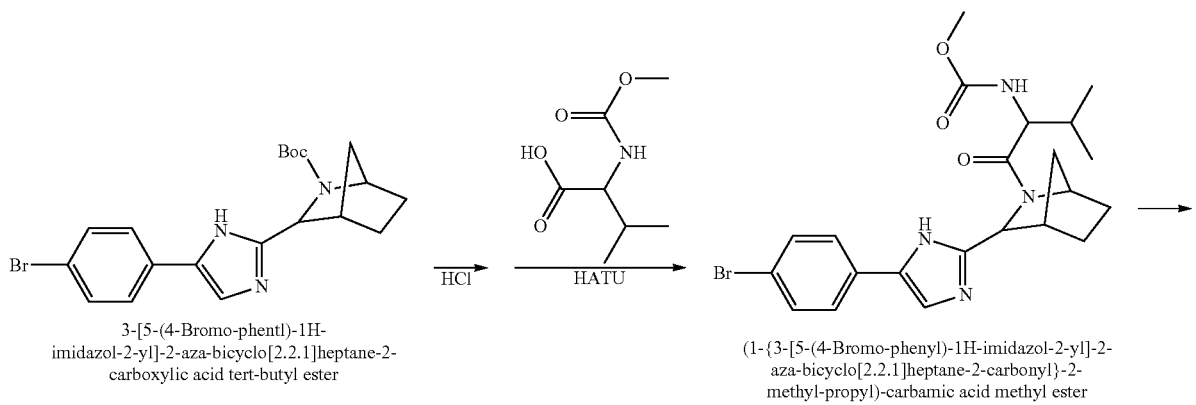

3-[5-(4-Bromo-phentl)-1H-imidazol-2-yl]-2-aza-bicyclo[2.2.1]heptane-2-carboxylic acid tert-butyl ester (1-{3-[5-(4-Bromo-phenyl)-1H-imidazol-2-yl]-2-aza-bicyclo[2.2.1]heptane-2-carbonyl}-2-methyl-propyl)-carbamic acid methyl ester -continued

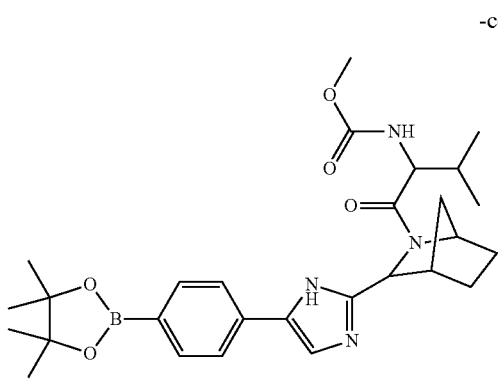

[2-Methyl-1-(3-{5-[4-(4,4,5,5-tetramethyl-[1,3,2]dioxaborolan-2-yl)-phenyl-1H-imidazol-2-yl}-2-aza-bicycli[2.2.1]heptane-2-carbonyl)-propyl]-carbamic acid methyl ester

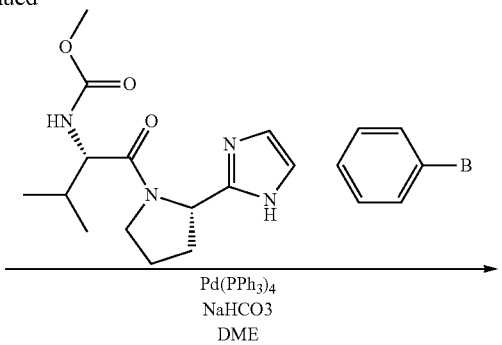

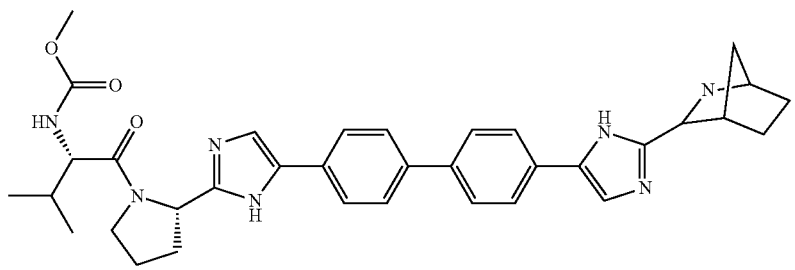

(1-{3-[5-(4'-{2-[1-(2-Methoxycarbonylamino-3-methyl-butyryl)-2-aza-bicyclo[2.2.1]hept-3-yl]-3H--imidazol-4-yl}-biphenyl-4-yl)-1H-imidazol-2-yl]-pyrrolidine-1-carbonyl]-2-methyl-propyl)-carbamic acid methyl ester

3-[2-(4-Bromo-phenyl)-2-oxo-ethylcarbamoyl]-2-aza-bicyclo[2.2.1]heptane-2-carboxylic acid tert-butyl ester Following the procedure used to prepare compound 3-[2-(4-bromo-phenyl)-2-oxo-ethylcarbamoyl]-pyrrolidine-1-carboxylic acid tert-butyl ester, except that 2-aza-bicyclo[2.2.1]heptane-2,3-dicarboxylic acid 2-tert-butyl ester was used instead of pyrrolidine-1,3-dicarboxylic acid 1-tert-butyl ester.

3-[5-(4-Bromo-phenyl)-1H-imidazol-2-yl]-2-aza-bicyclo[2.2.1]heptane-2-carboxylic acid tert-butyl ester Following the procedure used to prepare compound 3-[5-(4-bromo-phenyl)-1H-imidazol-2-yl]-pyrrolidine-1-carboxylic acid tert-butyl ester, except that 3-[2-(4-bromo-phenyl)-2-oxo-ethylcarbamoyl]-2-aza-bicyclo[2.2.1]heptane-2-carboxylic acid tert-butyl ester was used instead of 3-[2-(4-bromo-phenyl)-2-oxo-ethylcarbamoyl]-pyrrolidine-1-carboxylic acid tert-butyl ester.

(1-{3-[5-(4-Bromo-phenyl)-1H-imidazol-2-yl]-2-aza-bicyclo[2.2.1]heptane-2-carbonyl}-2-methyl-propyl)-carbamic acid methyl ester To a solution of 3-[5-(4-bromo-phenyl)-1H-imidazol-2-yl]-2-aza-bicyclo[2.2.1]heptane-2-carboxylic acid tert-butyl ester (1.0 g, 2.4 mmol) in methanol (20 mL) was added 4.0 M solution of HCl in dioxane (4.0 mL, excess). The mixture was stirred for 3 hours at 50° C. and concentrated under reduced pressure. The residue was treated with ether to remove excess HCl. The obtained white solid was dissolved in DMF (20 mL). To the solution was added 2-methoxycarbonylamino-3-methyl-butyric acid (0.46 g, 2.6 mmol), HATU (1.0 g, 2.6 mmol) and N,N-diisopropylethylamine (2.5 mL, 14.4 mmol). The mixture was stirred at ambient for 2 hours, and then the volatile component was removed in vacuo. The residue was dissolved in ethyl acetate (200 mL), washed with 1 N NaOH solution, water and brine, dried over MgSO$_4$, filtered and concentrated in vacuo. The obtained residue was purified by flash chromatography to provide the desired product as a white solid (1.0 g, 89%). m/z 475.1, 477.1 (M+H)$^+$.

[2-Methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester Pd(PPh$_3$)$_4$ (73 mg, 0.06 mmol) was added to a sealed tube containing a mixture of (1-{3-[5-(4-bromo-phenyl)-1H-imidazol-2-yl]-2-aza-bicyclo[2.2.1]heptane-2-carbonyl}-2-methyl-propyl)-carbamic acid methyl ester (600 mg, 1.27 mmol), bis(pinacolato)diboron (675 mg, 2.66 mmol), potassium acetate (324 mg, 3.3 mmol) and 1,4-dioxane (15 mL). The reaction mixture was flushed with nitrogen, heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product as a white solid (440 mg, 66%). m/z 523.2 (M+H)$^+$.

439

(1-{2-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-pyrrolidine-1-carbonyl}-2-methyl-propyl)-carbamic acid methyl ester Following the procedure used to prepare compound 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester, except that [2-methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester and (1-{2-[5-(4-bromo-phenyl)-1H-imidazol-2-yl]-pyrrolidine-1-carbonyl}-2-methyl-propyl)-carbamic acid methyl ester were used instead of 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester and 3-[5-(4-bromo-phenyl)-1H-imidazol-2-yl]-pyrrolidine-1-carboxylic acid tert-butyl ester. $^1$H-NMR (300 MHz, CD$_3$OD) δ 7.90-7.70 (m, 10H), 7.20-7.10 (m, 1H), 5.24 (t, 1H), 4.63 (s, 1H), 4.40-3.80 (m, 4H), 3.68 (s, 3H), 3.66 (s, 3H), 2.60-1.60 (m, 13H), 1.05-0.90 (m, 12H); m/z 765.2 (M+H)$^+$.

440

(1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[2.2.1]heptane-2-carbonyl}-2-methyl-propyl)-carbamic acid methyl ester Following the procedure used to prepare compound 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester, except that [2-methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester and (1-{3-[5-(4-bromo-phenyl)-1H-imidazol-2-yl]-2-aza-bicyclo[2.2.1]heptane-2-carbonyl}-2-methyl-propyl)-carbamic acid methyl ester were used instead of 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester and 3-[5-(4-bromo-phenyl)-1H-imidazol-2-yl]-pyrrolidine-1-carboxylic acid tert-butyl ester. $^1$H-NMR (300 MHz, CD$_3$OD) δ 7.90-7.20 (m, 10H), 4.83-4.25 (m, 5H), 3.90-3.40 (m, 6H), 2.90-2.70 (m, 2H), 2.40-2.10 (m, 3H), 2.10-1.40 (m, 11H), 1.10-0.90 (m, 12H); m/z 791.3 (M+H)$^+$.

Example AF

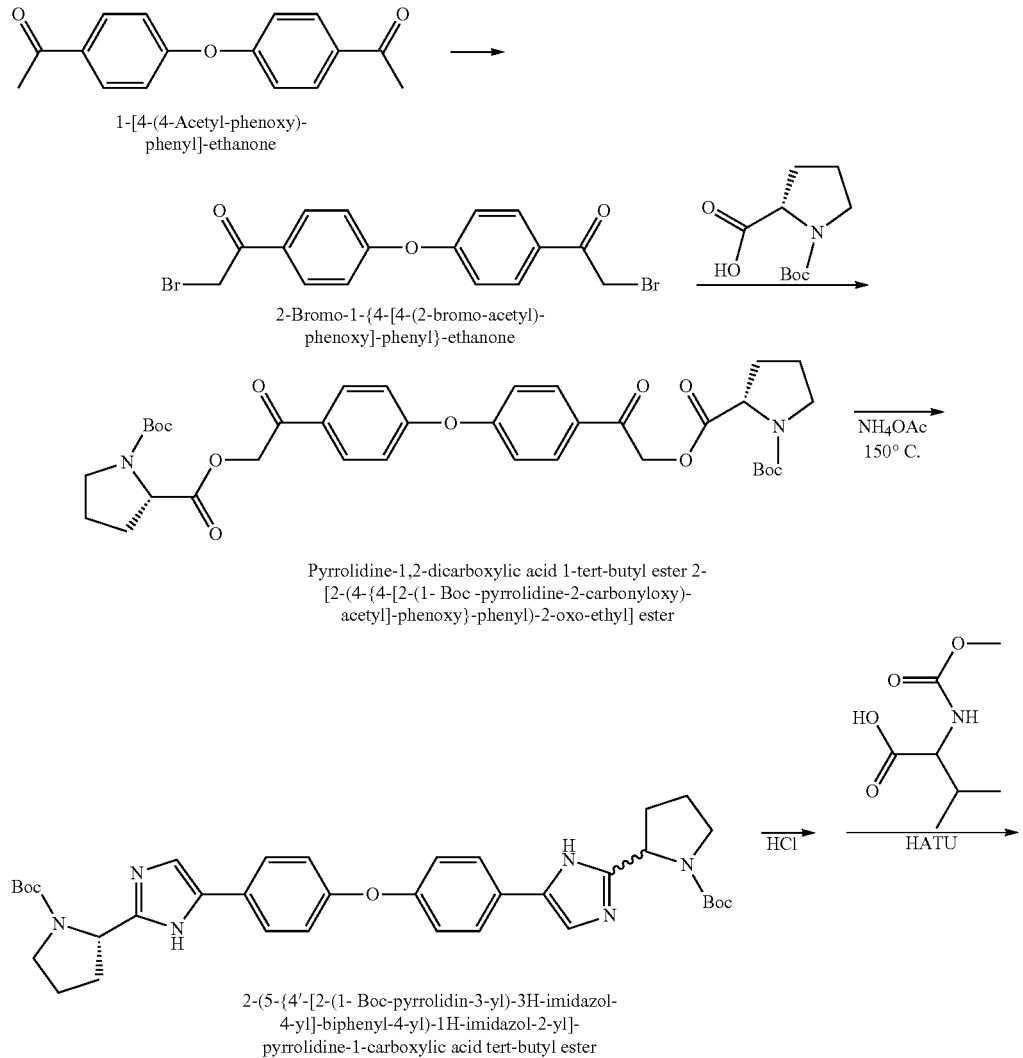

1-[4-(4-Acetyl-phenoxy)-phenyl]-ethanone

2-Bromo-1-{4-[4-(2-bromo-acetyl)-phenoxy]-phenyl}-ethanone

Pyrrolidine-1,2-dicarboxylic acid 1-tert-butyl ester 2-[2-(4-{4-[2-(1-Boc-pyrrolidine-2-carbonyloxy)-acetyl]-phenoxy}-phenyl)-2-oxo-ethyl] ester 2-(5-{4'-[2-(1-Boc-pyrrolidin-3-yl)-3H-imidazol-4-yl-biphenyl-4-yl)-1H-imidazol-2-yl]-pyrrolidine-1-carboxylic acid tert-butyl ester

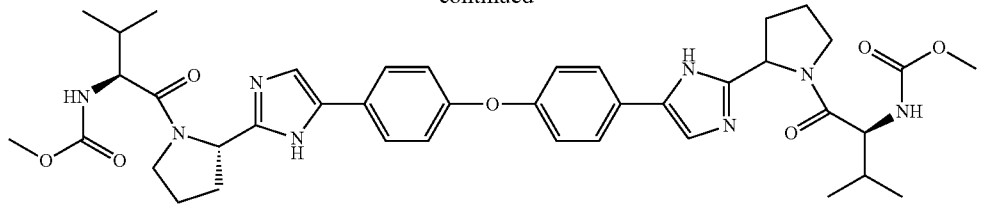

(1-(2-{5-[4-(4-{2-[1-(2-Methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl]-2-methyl-propyl)-carbamic acid methyl ester

2-Bromo-1-{4-[4-(2-bromo-acetyl)-phenoxy]-phenyl}-ethanone

Bromine (2.02 mL, 39.3 mmol) in dichloromethane (25 mL) was added slowly to a stirred solution of 4-acetylphenyl ether (5.0 g, 19.7 mmol) in dichloromethane (65 mL) at 30° C. The mixture was stirred at ambient for 16 hours, and then the volatile component was removed in vacuo. The residue was recrystallized from ethanol (40 mL) to get a yellow crystal like product (2.3 g, 29%).

Pyrrolidine-1,2-dicarboxylic acid 1-tert-butyl ester 2-[2-(4-{4-[2-(1-Boc-pyrrolidine-2-carbonyloxy)-acetyl]-phenoxy}-phenyl)-2-oxo-ethyl]ester To a stirred mixture of 2-bromo-1-{4-[4-(2-bromo-acetyl)-phenoxy]-phenyl}-ethanone (2.0 g, 4.9 mmol) and pyrrolidine-1,2-dicarboxylic acid 1-tert-butyl ester (2.2 g, 10.2 mmol) in acetonitrile (20 mL) was added DIPEA (1.76 mL, 10.1 mmol). The slurry was stirred for 3 hours at ambient temperature. The mixture was diluted with ethyl acetate (150 mL), washed with water and brine, dried over MgSO$_4$, filtered and concentrated in vacuo. The obtained residue was purified by flash chromatography to provide the desired product as a white solid (2.2 g, 65%). m/z 703.1 (M+Na)$^+$.

2-[5-(4-{4-[2-(1-Boc-pyrrolidin-2-yl)-3H-imidazol-4-yl]-phenoxy}-phenyl)-1H-imidazol-2-yl]-pyrrolidine-1-carboxylic acid tert-butyl ester A mixture of pyrrolidine-1,2-dicarboxylic acid 1-tert-butyl ester 2-[2-(4-{4-[2-(1-Boc-pyrrolidine-2-carbonyloxy)-acetyl]-phenoxy}-phenyl)-2-oxo-ethyl]ester (250 mg, 0.37 mmol) and ammonium acetate (570 mg, 7.3 mmol) in xylene (8 mL) was heated in microwave machine at 140° C. for 80 minutes. The volatile component was removed in vacuo, and the residue was dissolved in ethyl acetate (100 mL), washed with NaHCO$_3$ solution, water and brine, dried over MgSO$_4$, filtered and concentrated in vacuo. The obtained residue was purified by flash chromatography to provide the desired product as a white solid (62 mg, 26%). m/z 641.1 (M+H)$^+$.

[1-(2-{5-[4-(4-{2-[1-(2-Methoxycarbonylamino-3-methyl-butyryl)-pyrrolidin-2-yl]-3H-imidazol-4-yl}-phenoxy)-phenyl]-1H-imidazol-2-yl}-pyrrolidine-1-carbonyl)-2-methyl-propyl]-carbamic acid methyl ester Following the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-[5-(4-{4-[2-(1-Boc-pyrrolidin-2-yl)-3H-imidazol-4-yl}-phenoxy]-phenyl)-1H-imidazol-2-yl]-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. $^1$H-NMR (300 MHz, CD$_3$OD) δ 7.80-7.60 (m, 4H), 7.30-7.20 (m, 2H), 7.10-0.95 (m, 4H), 5.16 (t, 1H), 4.30-3.50 (m, 12H), 2.40-1.90 (m, 10H), 1.10-0.90 (m, 12H); m/z 755.2 (M+H)$^+$.

Example AG

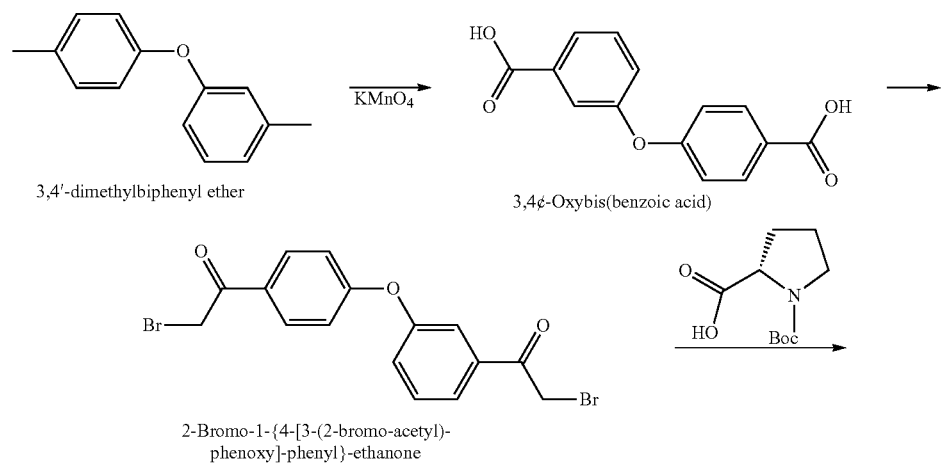

3,4'-dimethylbiphenyl ether 3,4¢-Oxybis(benzoic acid)

2-Bromo-1-{4-[3-(2-bromo-acetyl)-phenoxy]-phenyl}-ethanone

-continued

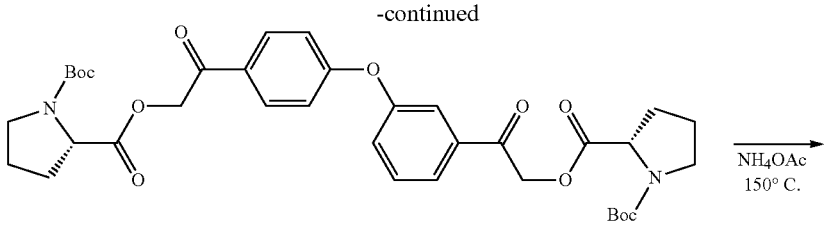

Pyrrolidine-1,2-dicarboxylic acid 1-tert-butyl ester 2-[2-(4-{3-[2-(1-Boc-pyrrolidine-2-carbonyloxy)-acetyl]-phenoxy}-phenyl)-2-oxo-ethyl] ester

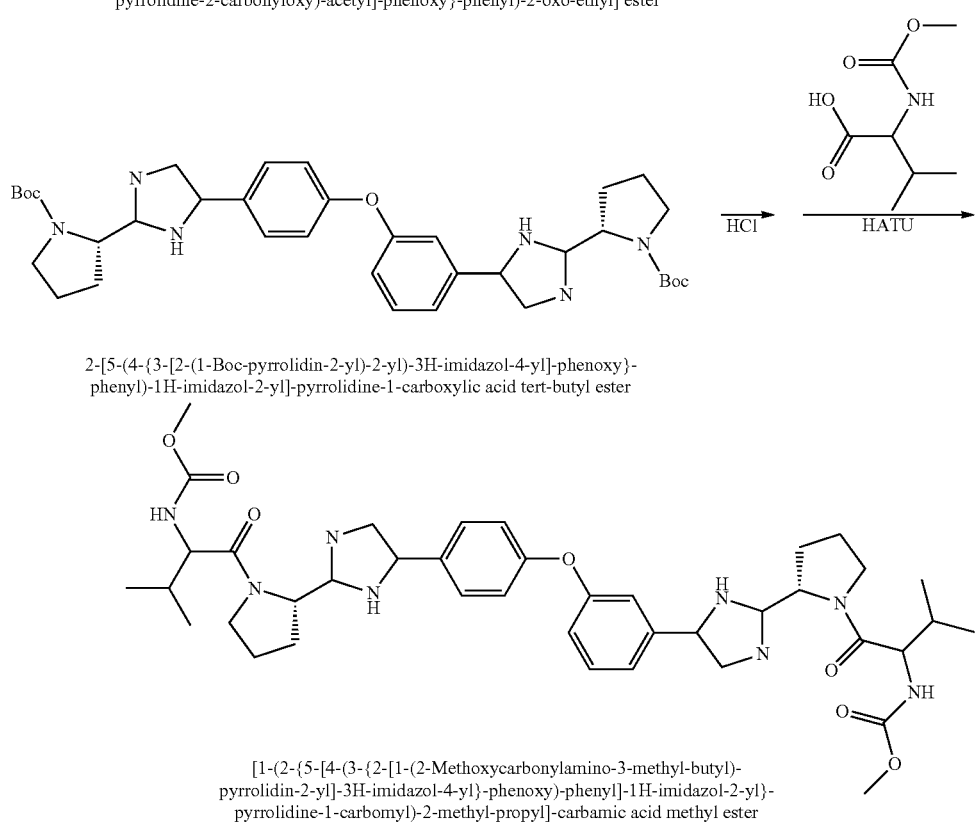

2-[5-(4-{3-[2-(1-Boc-pyrrolidin-2-yl)-2-yl]-3H-imidazol-4-yl]-phenoxy}-phenyl)-1H-imidazol-2-yl]-pyrrolidine-1-carboxylic acid tert-butyl ester

[1-(2-{5-[4-(3-{2-[1-(2-Methoxycarbonylamino-3-methyl-butyl)-pyrrolidin-2-yl]-3H-imidazol-4-yl}-phenoxy)-phenyl]-1H-imidazol-2-yl}-pyrrolidine-1-carbomyl)-2-methyl-propyl]-carbamic acid methyl ester

3,4'-Oxybis(benzoic acid)

A mixture of 3,4'-dimethylbiphenyl ether (1.7 g, 8.6 mmol) and potassium permanganate (6.0 g, 38 mmol) in water (200 mL) was refluxed for 6 hours. The hot solution was filtered, cooled, and extracted with chloroform. The aqueous layer was acidified by 2 N HCl. The precipitate was filtered off and washed with water to give a white solid (0.55 g, 25%). m/z 257.1 (M−H)⁻.

2-Bromo-1-{4-[3-(2-bromo-acetyl)-phenoxy]-phenyl}-ethanone

A mixture of 3,4'-oxybis(benzoic acid) (0.55 g, 2.1 mmol)) and oxalyl chloride (10.6 mL, 21.3 mmol) in dichloromethane (40 mL) containing DMF (4 drops) was stirred at ambient temperature for 4 hours, then concentrated and co-evaporated with toluene (3×) and dried under high vacuum. The resulting residue was suspended in dichloromethane (15 mL) at 0° C. and treated with 2.0 M trimethylsilyldiazomethane in ether (3.2 mL, 6.4 mmol) over 15 minutes to give a brown mixture. Reaction mixture was warmed to ambient temperature overnight and then concentrated. The resulting brown solid was suspended in ethyl acetate (15 mL) and cooled to 0° C. HBr in acetic acid (1.2 mL, 33% W, 6.4 mmol) was added over 5 minutes and reaction mixture was warmed to ambient temperature over 1 hour. Solid sodium bicarbonate (0.3 g) was added and stirred for 30 minutes. Water was added giving a biphasic mixture with a brown precipitate. The solid was removed by filtration and filtrate was extracted with dichloromethane, dried over MgSO₄ and concentrated. The residue was purified by flash column chromatography to give a brown solid (0.47 g).

Pyrrolidine-1,2-dicarboxylic acid 1-tert-butyl ester 2-[2-(4-{3-[2-(1-Boc-pyrrolidine-2-carbonyloxy)-acetyl]-phenoxy}-phenyl)-2-oxo-ethyl]ester Following the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-bromo-1-{4-[3-(2-bromo-acetyl)-phenoxy]-phenyl}-ethanone was used instead of 2-bromo-1-{4-[4-(2-bromo-acetyl)-phenoxy]-phenyl}-ethanone. m/z 703.1 (M+Na)⁺.

2-[5-(4-{3-[2-(1-Boc-pyrrolidin-2-yl)-3H-imidazol-4-yl]-phenoxy}-phenyl)-1H-imidazol-2-yl]-pyrrolidine-1-carboxylic acid tert-butyl ester Following the procedure used to prepare compound 2-[5-(4-{4-[2-(1-Boc-pyrrolidin-2-yl)-3H-imidazol-4-yl]-phenoxy}-phenyl)-1H-imidazol-2-yl]-pyrrolidine-1-carboxylic acid tert-butyl ester, except that pyrrolidine-1,2-dicarboxylic acid 1-tert-butyl ester 2-[2-(4-{3-[2-(1-Boc-pyrrolidine-2-carbonyloxy)-acetyl]-phenoxy}-phenyl)-2-oxo-ethyl]ester was used instead of pyrrolidine-1,2-dicarboxylic acid 1-tert-butyl ester 2-[2-(4-{4-[2-(1-Boc-pyrrolidine-2-carbonyloxy)-acetyl]-phenoxy}-phenyl)-2-oxo-ethyl]ester. m/z 641.0 (M+H)+.

[1-(2-{5-[4-(3-{2-[1-(2-Methoxycarbonylamino-3-methyl-butyryl)-pyrrolidin-2-yl]-3H-imidazol-4-yl}-phenoxy)-phenyl]-1H-imidazol-2-yl}-pyrrolidine-1-carbonyl)-2-methyl-propyl]-carbamic acid methyl ester Following the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-[5-(4-{3-[2-(1-Boc-pyrrolidin-2-yl)-3H-imidazol-4-yl]-phenoxy}-phenyl)-1H-imidazol-2-yl]-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. 1H-NMR (300 MHz, CD3OD) δ 7.80-7.10 (m, 10H), 5.30-5.15 (m, 2H), 4.30-4.20 (m, 2H), 4.18-4.05 (m, 2H), 3.95-3.80 (m, 2H), 3.70-3.60 (m, 6H), 2.65-2.45 (m, 2H), 2.40-2.00 (m, 8H), 1.05-0.85 (m, 12H); m/z 755.3 (M+H)+.

Example AH

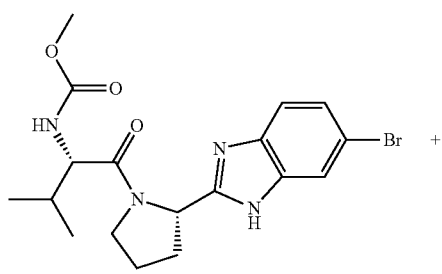

{1-[2-(6-Bromo-1H-benzoimidazol-2-yl)-pyrrolidine-1-carbonyl]-2-methyl-propyl}-carbamic acid methyl ester

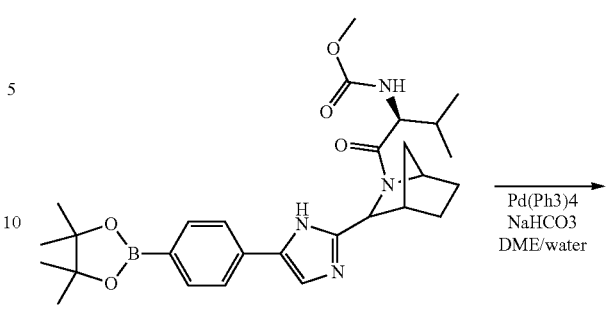

[2-Methyl-1-(3-{5-[4-(4,4,5,5-tetramethyl-[1,3,4]dioxaborolan-2-yl)-phenyl]-1H-imidazol-2-yl}-2-aza-bicyclo[2.2.1]heptane-2-carbonyl)-propyl]-carbamic acid methyl ester

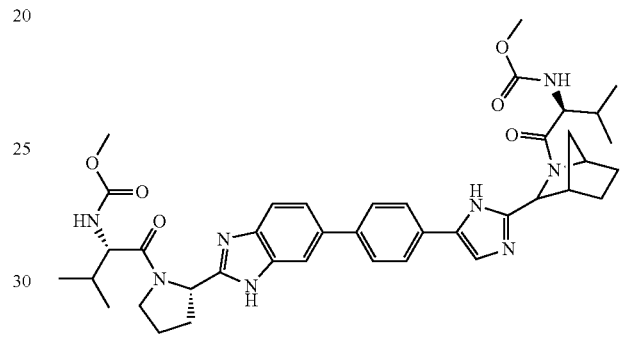

(1-{2-[6-(4-{2-[2-(2-Methoxycarbonylamino-3-methyl-butyryl)-2-aza-bicyclo[2.2.1]hept-3-yl]-3H-imidazol-4-yl}-phenyl)-1H-benzoimidazol-2-yl]-pyrrolidine-1-carbonyl}-2-methyl-propyl)-carbamic acid methyl ester

(1-{2-[6-(4-{2-[2-(2-Methoxycarbonylamino-3-methyl-butyryl)-2-aza-bicyclo[2.2.1]hept-3-yl]-3H-imidazol-4-yl}-phenyl)-1H-benzoimidazol-2-yl]-pyrrolidine-1-carbonyl}-2-methyl-propyl)-carbamic acid methyl ester Following the procedure used to prepare compound 2-(5-{4'-[2-(1-Boc-pyrrolidin-3-yl)-3H-imidazol-4-yl}-biphenyl-4-yl]-11'-imidazol-2-yl)-pyrrolidine-1-carboxylic acid tert-butyl ester, except that [2-methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester and {1-[2-(6-bromo-1H-benzoimidazol-2-yl)-pyrrolidine-1-carbonyl]-propyl}-carbamic acid methyl ester were used instead of 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester and 3-[5-(4-bromo-phenyl)-1H-imidazol-2-yl]-pyrrolidine-1-carboxylic acid tert-butyl ester. 1H-NMR (300 MHz, CD3OD) δ 8.10-7.80 (m, 7H), 5.42-5.30 (m, 1H), 4.65 (s, 1H), 4.40-4.25 (m, 2H), 4.20-3.90 (m, 2H, 3.80-3.60 (m, 6H), 3.00-2.80 (m, 1H), 2.70-2.55 (m, 1H), 2.50-1.60 (m, 12H), 1.10-0.80 (m, 12H); m/z 739.3 (M+H)+.

Example AI
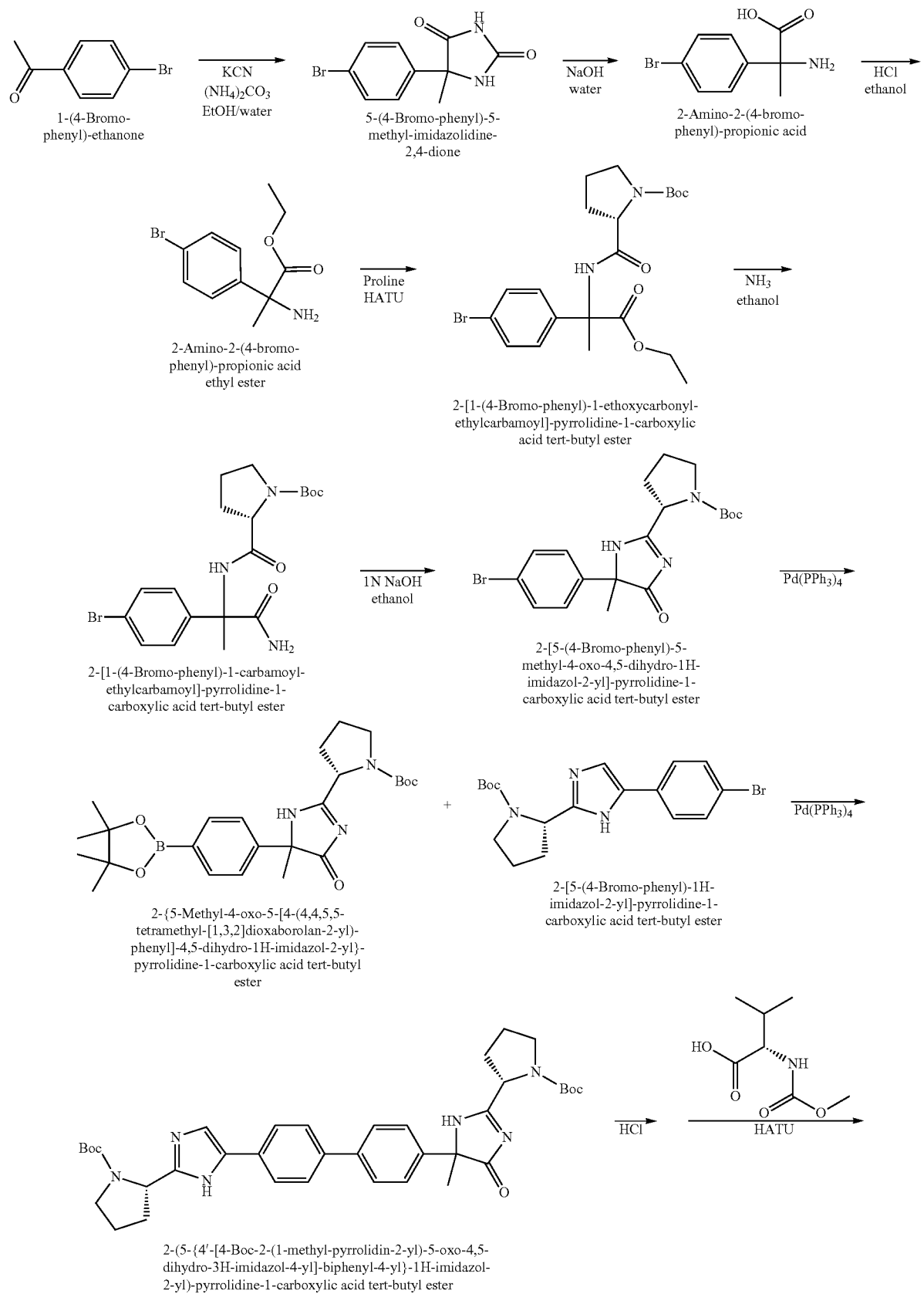

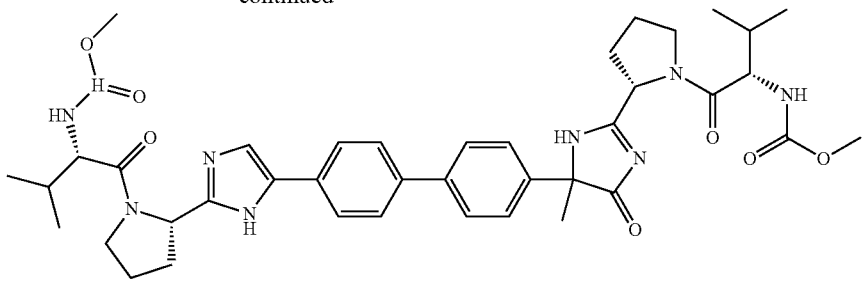

(1-{2-[5-(4'-{2-[1-(2-Methoxycarbonylamino-3-methyl-butyryl)-pyrrolidin-2-yl]-4-methyl-5-oxo-4,5-dihydro-3H-imidazol-4-yl}-biphenyl-4-yl)-1H-imidazol-2-yl]-pyrrolidine-1-carbonyl}-2-methyl-propyl)-carbamic acid methyl ester

5-(4-Bromo-phenyl)-5-methyl-imidazolidine-2,4-dione

A mixture of 4-bromo acetophenone (8.0 g, 40.2 mmol), ammonium carbonate (40 g, 402 mmol) and potassium cyanide (3.4 g, 52.3 mmol) in a mixed solvent of ethanol (90 mL) and water (90 mL) was stirred at 55° C. for 5 hours, then 12 hours at ambient. The solution was adjusted to pH=6 with 6 N HCl carefully and subsequently stirred at room temperature for 2 hours. The precipitate was filtered off, washed with water. The collected white solid was dried under vacuum to give the product (9.2 g, 85%). m/z 267.1, 269.1 (M−H)⁻.

2-Amino-2-(4-bromo-phenyl)-propionic acid

A mixture of 5-(4-bromo-phenyl)-5-methyl-imidazolidine-2,4-dione (4.0 g, 14.9 mmol) and 3 N NaOH (50 mL) was heated in a sealed tube at 145° C. for two days, then diluted with water (100 mL) The solution was adjusted to pH=4 with 6 N HCl carefully and subsequently stirred at room temperature for 2 hours. The precipitate was filtered off, washed with water. The collected white solid was dried under vacuum to give the product (2.5 g, 65%). m/z 243.7, 245.7 (M+H)⁺.

2-Amino-2-(4-bromo-phenyl)-propionic acid ethyl ester

To a solution of 2-amino-2-(4-bromo-phenyl)-propionic acid (1.0 g, 4.1 mmol) in ethanol (20 mL) was bubbled through HCl gas for five minutes. The mixture was stirred at ambient for 24 hours, then refluxed for 18 hours. The volatile component was removed in vacuo, and the residue was dissolved in ethyl acetate (150 mL), washed with NaHCO₃ solution, water and brine, dried over MgSO₄, filtered and concentrated in vacuo. The obtained residue was purified by flash chromatography to provide the desired product (800 mg, 72%). m/z 271.7, 273.7 (M+H)⁺.

2-[1-(4-Bromo-phenyl)-1-ethoxycarbonyl-ethylcarbamoyl]-pyrrolidine-1-carboxylic acid tert-butyl ester N,N-diisopropylethylamine (4.1 mL, 23.6 mmol) was added dropwise to a mixture of pyrrolidine-1,3-dicarboxylic acid 1-tert-butyl ester (0.7 g, 3.2 mmol), HATU (1.2 g, 3.2 mmol) and 2-amino-2-(4-bromo-phenyl)-propionic acid ethyl ester (0.8 g, 2.9 mmol) in DMF (20 mL), and stirred at ambient condition for 3 hours. Most of the volatile component was removed in vacuo, and the resulting residue was dissolved in ethyl acetate (150 mL), washed with water and brine, dried over Na₂SO₄, filtered and concentrated in vacuo. The obtained residue was purified by flash chromatography to provide the desired product as a colorless oil (0.8 g, 58%). m/z 490.9, 492.9 (M+Na)⁺.

2-[1-(4-Bromo-phenyl)-1-carbamoyl-ethylcarbamoyl]-pyrrolidine-1-carboxylic acid tert-butyl ester To a stirred solution of 2-[1-(4-bromo-phenyl)-1-ethoxycarbonyl-ethylcarbamoyl]-pyrrolidine-1-carboxylic acid tert-butyl ester (280 mg, 0.6 mmol) in ethanol (8 mL) was bubbled through NH₃ gas for 5 minutes at −78° C. The solution was stirred at ambient for 3 days in a sealed tube. Most of the volatile component was removed in vacuo, and the resulting residue was dissolved in ethyl acetate (150 mL), washed with water and brine, dried over Na₂SO₄, filtered and concentrated in vacuo. The obtained residue was purified by flash chromatography to provide the desired product as a colorless oil (169 mg, 64%). m/z 439.8, 441.8 (M+H)⁺.

2-[5-(4-Bromo-phenyl)-5-methyl-4-oxo-4,5-dihydro-4H-imidazol-2-yl]-pyrrolidine-1-carboxylic acid tert-butyl ester To a stirred solution of 2-[1-(4-bromo-phenyl)-1-carbamoyl-ethylcarbamoyl]-pyrrolidine-1-carboxylic acid tert-butyl ester (160 mg, 0.36 mmol) in ethanol (10 mL) was added 1 N NaOH (5 mL), and stirred at ambient condition for 3 hours. Most of the volatile component was removed in vacuo, and the resulting residue was dissolved in ethyl acetate (100 mL), washed with water and brine, dried over Na₂SO₄, filtered and concentrated in vacuo. The obtained residue was purified by flash chromatography to provide the desired product as a white solid (120 mg, 79%). m/z 421.8, 423.8 (M+H)⁺.

2-{5-Methyl-4-oxo-5-[4-(4,4,5,5-tetramethyl-[1,3,2]dioxaborolan-2-yl)-phenyl]-4,5-dihydro-1H-imidazol-2-yl}-pyrrolidine-4-carboxylic acid tert-butyl ester Pd(PPh₃)₄ (31 mg, 0.03 mmol) was added to a sealed tube containing a mixture of 2-[5-(4-bromo-phenyl)-5-methyl-4-oxo-4,5-dihydro-1H-imidazol-2-yl]-pyrrolidine-1-carboxylic acid tert-butyl ester (113 mg, 0.27 mmol), bis(pinacolato) diboron (144 mg, 0.57 mmol), potassium acetate (66 mg, 0.68 mmol) and 1,4-dioxane (3 mL). The reaction mixture was flushed with nitrogen, heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product as a colorless oil (100 mg, 79%). m/z 470.0 (M+H)$^+$.

2-(5-{4'-[4-Boc-2-(1-methyl-pyrrolidin-2-yl)-5-oxo-4,5-dihydro-3H-imidazol-4-yl]-biphenyl-4-yl}-1H-imidazol-2-yl)-pyrrolidine-1-carboxylic acid tert-butyl ester Following the procedure used to prepare compound 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester, except that 2-{5-methyl-4-oxo-5-[4-(4,4,5,5-tetramethyl-[1,3,2]dioxaborolan-2-yl)-phenyl]-4,5-dihydro-1H-imidazol-2-yl}-pyrrolidine-1-carboxylic acid tert-butyl ester was used instead of 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester. m/z 655.1 (M+H)$^+$.

(1-{2-[5-(4'-{2-[1-(2-Methoxycarbonylamino-3-methyl-butyryl)-pyrrolidin-2-yl]-4-methyl-5-oxo-4,5-dihydro-3H-imidazol-4-yl}-biphenyl-4-yl)-1H-imidazol-2-yl]-pyrrolidine-1-carbonyl}-2-methyl-propyl)-carbamic acid methyl ester Following the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-(5-{4'-[4-Boc-2-(1-methyl-pyrrolidin-2-yl)-5-oxo-4,5-dihydro-3H-imidazol-4-yl]-biphenyl-4-yl}-1H-imidazol-2-yl)-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. $^1$H-NMR (300 MHz, CD$_3$OD) δ 7.90-7.50 (m, 9H), 5.25 (t, 1H), 4.23 (d, 2H), 4.18-3.75 (m, 4H), 3.75-3.30 (m, 6H), 2.65-2.40 (m, 2H), 2.40-1.70 (m, 12H), 1.10-0.80 (m, 12H); m/z 769.2 (M+H)$^+$.

Example AJ

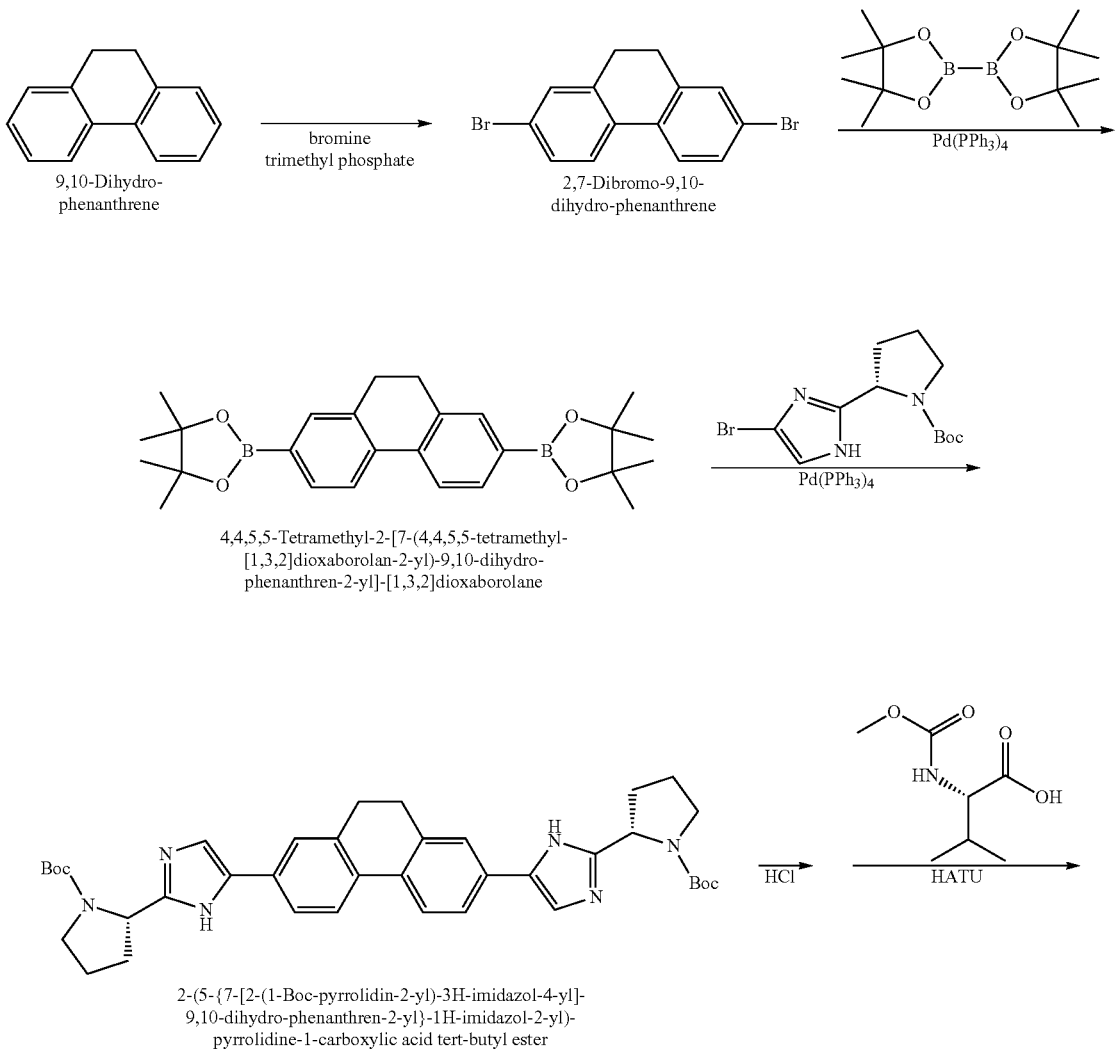

9,10-Dihydro-phenanthrene 2,7-Dibromo-9,10-dihydro-phenanthrene 4,4,5,5-Tetramethyl-2-[7-(4,4,5,5-tetramethyl-[1,3,2]dioxaborolan-2-yl)-9,10-dihydro-phenanthren-2-yl]-[1,3,2]dioxaborolane 2-(5-{7-[2-(1-Boc-pyrrolidin-2-yl)-3H-imidazol-4-yl]-9,10-dihydro-phenanthren-2-yl}-1H-imidazol-2-yl)-pyrrolidine-1-carboxylic acid tert-butyl ester

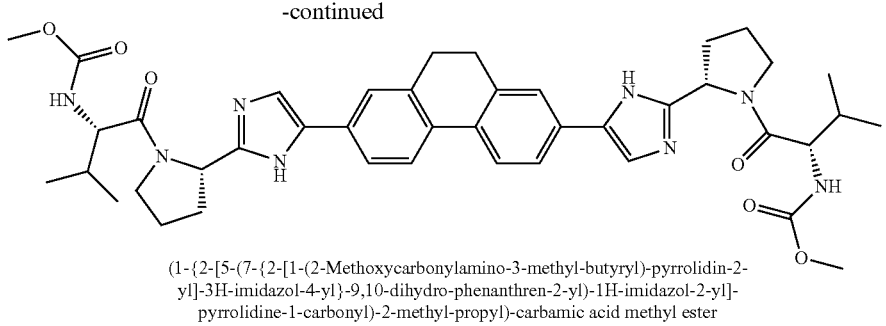

(1-{2-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-pyrrolidine-1-carbonyl)-2-methyl-propyl)-carbamic acid methyl ester 2,7-Dibromo-9,10-dihydro-phenanthrene To a stirred solution of 9,10-dihydrophenanthrend (10 g, 55.5 mmol) in trimethylphosphate (60 mL) was added a solution of bromine (6.13 mL, 119.3 mmol) in trimethylphosphate (40 mL) slowly. After addition, the mixture was stirred at ambient for 18 hours, the volatile component was removed in vacuo. The residue was recrystallized from chloroform to give a white crystal (9.45 g, 51%).

4,4,5,5-Tetramethyl-2-[7-(4,4,5,5-tetramethyl-[1,3,2] dioxaborolan-2-yl)-9,10-dihydro-phenanthren-2-yl]-[1,3,2]dioxaborolane $Pd(PPh_3)_4$ (24 mg, 0.03 mmol) was added to a sealed tube containing a mixture of 2,7-dibromo-9,10-dihydro-phenanthrene (1.0 g, 3.0 mmol), bis(pinacolato)diboron (3.8 g, 14.9 mmol), potassium acetate (1.5 g, 14.9 mmol) and 1,4-dioxane (30 mL). The reaction mixture was flushed with nitrogen, heated at 80° C. for 16 hours, and then the volatile component was removed in vacuo. The residue was dissolved in ethyl acetate (300 mL), washed with water and brine, dried over $Na_2SO_4$, filtered and concentrated in vacuo. The obtained residue was purified by flash chromatography to provide the desired product as a white solid (1.2 g, 93%). m/z 432.8 (M+H)$^+$.

2-(5-{7-[2-(1-Boc-pyrrolidin-2-yl)-3H-imidazol-4-yl]-9,10-dihydro-phenanthren-2-yl}-1H-imidazol-2-yl)-pyrrolidine-1-carboxylic acid tert-butyl ester $Pd(PPh_3)_4$ (31 mg, 0.03 mmol) was added to a mixture 4,4,5,5-tetramethyl-2-[7-(4,4,5,5-tetramethyl-[1,3,2]dioxaborolan-2-yl)-9,10-dihydro-phenanthren-2-yl]-[1,3,2]dioxaborolane (115 mg, 0.27 mmol), 2-(4-bromo-1H-imidazol-2-yl)-pyrrolidine-1-carboxylic acid tert-butyl ester (173 mg, 0.55 mmol), $NaHCO_3$ (159 mg, 1.9 mmol) in 1,2-dimethoxyethane (5 mL) and water (1 mL). The reaction mixture was flushed with nitrogen, heated at 80° C. for 6 hours, and then the volatile component was removed in vacuo. The residue was dissolved in ethyl acetate (100 mL), washed with $NaHCO_3$ solution, water and brine, dried over $Na_2SO_4$, filtered and concentrated in vacuo. The obtained residue was purified by flash chromatography to provide the desired product as a white solid (42 mg, 24%). m/z 651.0 (M+H)$^+$.

(1-{2-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-pyrrolidine-1-carbonyl}-2-methyl-propyl)-carbamic acid methyl ester Followed the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-(5-{7-[2-(1-Boc-pyrrolidin-2-yl)-3H-imidazol-4-yl]-9,10-dihydro-phenanthren-2-yl}-1H-imidazol-2-yl)-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. $^1$H-NMR (300 MHz, CD$_3$OD) δ 7.99 (d, 2H), 7.88 (s, 2H), 7.80-7.65 (m, 4H), 5.30-5.20 (m, 2H), 4.24 (d, 2H), 4.20-4.05 (m, 2H), 3.95-3.80 (m, 2H), 3.75-3.60 (m, 6H), 3.00 (s, H), 2.65-2.50 (m, 2H), 2.40-2.00 (m, 8H), 1.05-0.80 (m, 12H); m/z 765.3 (M+H)$^+$.

Example AK

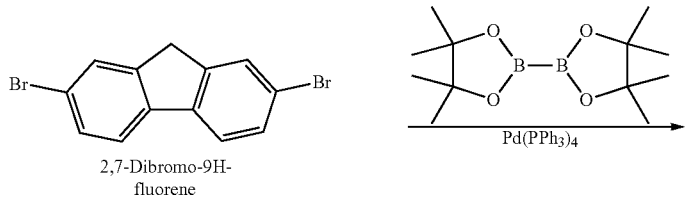

2,7-Dibromo-9H-fluorene

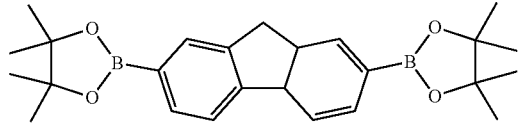
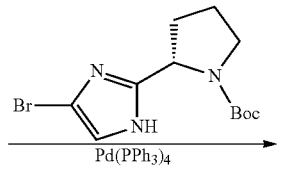

4,4,5,5-Tetramethyl-2-[7-(4,4,5,5-tetramethyl-[1,3,2]dioxaborolan-2-yl)-9H-fluoren-2-yl]-[1,3,2]dioxaborolane

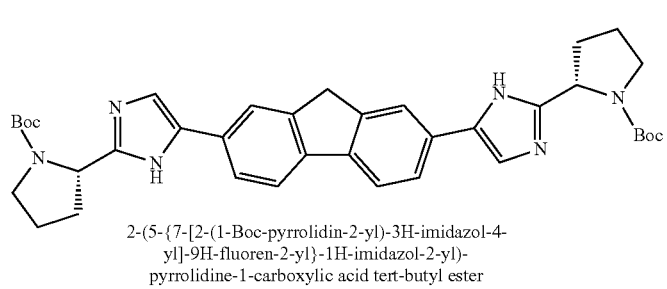
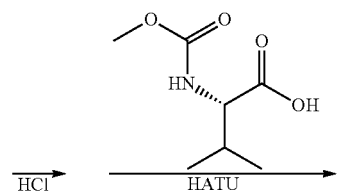

2-(5-{7-[2-(1-Boc-pyrrolidin-2-yl)-3H-imidazol-4-yl]-9H-fluoren-2-yl}-1H-imidazol-2-yl)-pyrrolidine-1-carboxylic acid tert-butyl ester

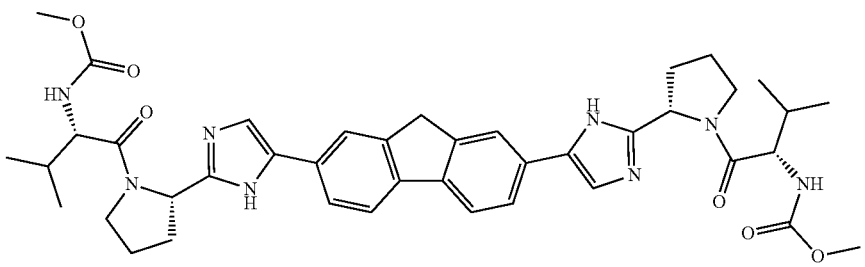

(1-{2-[5-(7-{2-[1-(2-Methoxycarbonylamino-3-methyl-butyryl)-pyrrolidin-2-yl]-3H-imidazol-4-yl}-9H-fluoren-2-yl)-1H-imidazol-2-yl]-pyrrolidine-1-carbonyl}-2-methyl-propyl)-carbamic acid methyl ester

4,4,5,5-Tetramethyl-2-[7-(4,4,5,5-tetramethyl-[1,3,2] dioxaborolan-2-yl)-9H-fluoren-2-yl]-[1,3,2]dioxaborolane Followed the procedure used to prepare 4,4,5,5-tetramethyl-2-[7-(4,4,5,5-tetramethyl-[1,3,2]dioxaborolan-2-yl)-9,10-dihydro-phenanthren-2-yl]-[1,3,2]dioxaborolane, except that 2,7-dibromofluorene was used instead of 2,7-dibromo-9,10-dihydro-phenanthrene. $^1$H-NMR (300 MHz, CDCl$_3$) δ 8.01 (s, 2H), 7.84 (s, 4H), 3.90 (s, 2H), 1.38 (s, 24H).

2-(5-{7-[2-(1-Boc-pyrrolidin-2-yl)-3H-imidazol-4-yl]-9H-fluoren-2-yl}-1H-imidazol-2-yl)-pyrrolidine-1-carboxylic acid tert-butyl ester Followed the procedure used to prepare compound 2-(5-{7-[2-(1-Boc-pyrrolidin-2-yl)-3H-imidazol-4-yl]-9,10-dihydro-phenanthren-2-yl}-1H-imidazol-2-yl)-pyrrolidine-1-carboxylic acid tert-butyl ester, except that 4,4,5,5-tetramethyl-2-[7-(4,4,5,5-tetramethyl-[1,3,2]dioxaborolan-2-yl)-9H-fluoren-2-yl]-[1,3,2]dioxaborolane was used instead of 4,4,5,5-tetramethyl-2-[7-(4,4,5,5-tetramethyl-[1,3,2]dioxaborolan-2-yl)-9,10-dihydro-phenanthren-2-yl]-[1,3,2]dioxaborolane. m/z 637.1 (M+H)$^+$.

(1-{2-[5-(7-{2-[1-(2-Methoxycarbonylamino-3-methyl-butyryl)-pyrrolidin-2-yl]-3H-imidazol-4-yl}-9H-fluoren-2-yl)-1H-imidazol-2-yl]-pyrrolidine-1-carbonyl}-2-methyl-propyl)-carbamic acid methyl ester Followed the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-(5-{7-[2-(1-Boc-pyrrolidin-2-yl)-3H-imidazol-4-yl]-9H-fluoren-2-yl}-1H-imidazol-2-yl)-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. $^1$H-NMR (300 MHz, CD$_3$OD) δ 8.03 (d, 2H), 7.96 (s, 2H), 7.88 (s, 2H), 7.77 (d, 2H), 5.26 (t, 2H), 4.24 (d, 2H), 4.20-4.05 (m, 4H), 3.95-3.80 (m, 2H), 3.75-3.60 (m, 6H), 2.65-2.50 (m, 2H), 2.40-2.00 (m, 8H), 1.05-0.90 (m, 12H); m/z 751.3 (M+H)$^+$.

Example AL

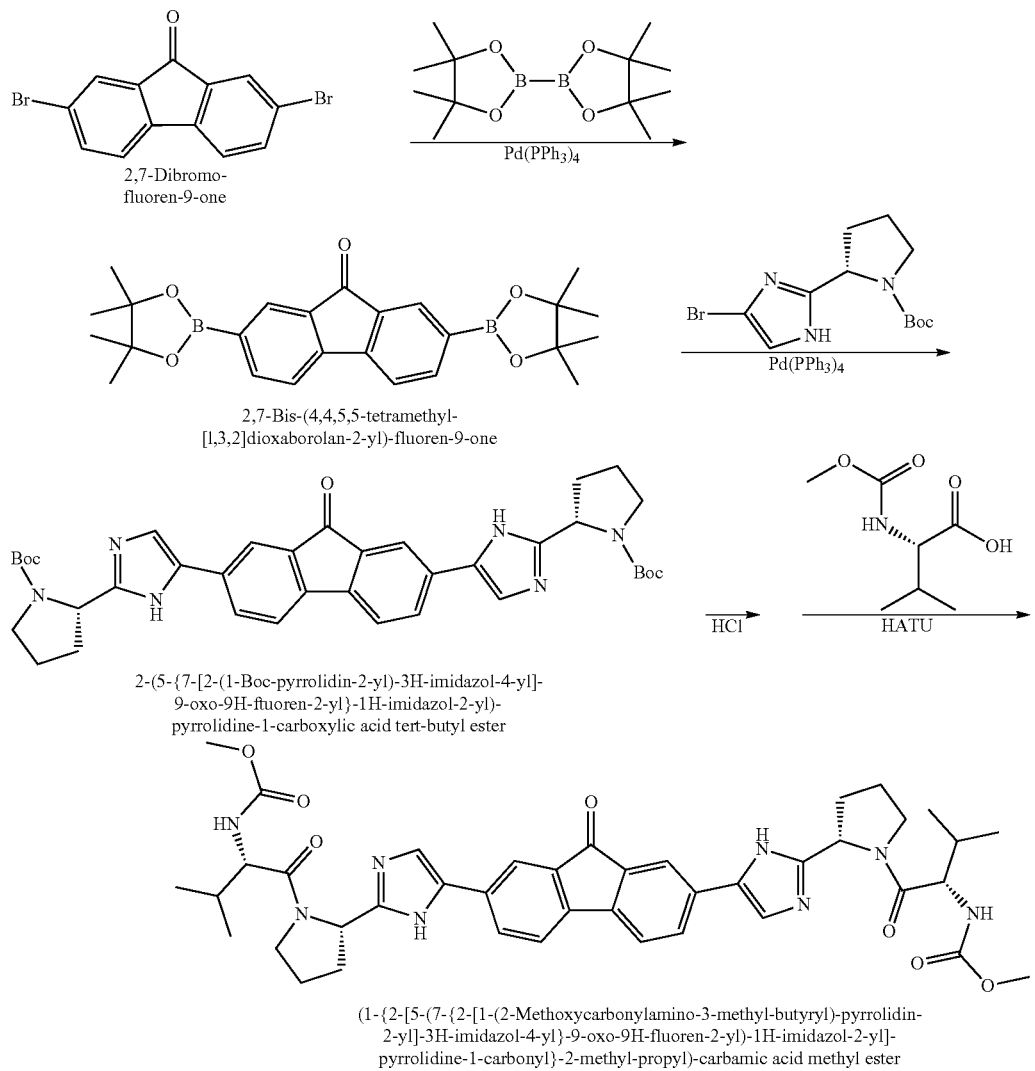

(1-{2-[5-(7-{2-[1-(2-Methoxycarbonylamino-3-methyl-butyryl)-pyrrolidin-2-yl]-3H-imidazol-4-yl}-9-oxo-9H-fluoren-2-yl)-1H-imidazol-2-yl]-pyrrolidine-1-carbonyl}-2-methyl-propyl)-carbamic acid methyl ester

2,7-Bis-(4,4,5,5-tetramethyl-[1,3,2]dioxaborolan-2-yl)-fluoren-9-one

Followed the procedure used to prepare 4,4,5,5-tetramethyl-2-[7-(4,4,5,5-tetramethyl-[1,3,2]dioxaborolan-2-yl)-9,10-dihydro-phenanthren-2-yl]-[1,3,2]dioxaborolane, except that 2,7-dibromo-9-fluorenone was used instead of 2,7-dibromo-9,10-dihydro-phenanthrene.

2-(5-{7-[2-(1-Boc-pyrrolidin-2-yl)-3H-imidazol-4-yl]-9-oxo-9H-fluoren-2-yl}-1H-imidazol-2-yl)-pyrrolidine-1-carboxylic acid tert-butyl ester Followed the procedure used to prepare compound 2-(5-{7-[2-(1-Boc-pyrrolidin-2-yl)-3H-imidazol-4-yl]-9,10-dihydro-phenanthren-2-yl}-1H-imidazol-2-yl)-pyrrolidine-1-carboxylic acid tert-butyl ester, except that 2,7-bis-(4,4,5,5-tetramethyl-[1,3,2]dioxaborolan-2-yl)-fluoren-9-one was used instead of 4,4,5,5-tetramethyl-2-[7-(4,4,5,5-tetramethyl-[1,3,2]dioxaborolan-2-yl)-9,10-dihydro-phenanthren-2-yl]-[1,3,2]dioxaborolane. m/z 650.9 (M+H)$^+$.

(1-{2-[5-(7-{2-[1-(2-Methoxycarbonylamino-3-methyl-butyryl)-pyrrolidin-2-yl]-3H-imidazol-4-yl}-9-oxo-9H-fluoren-2-yl)-1H-imidazol-2-yl]-pyrrolidine-1-carbonyl}-2-methyl-propyl)-carbamic acid methyl ester Followed the procedure used to prepare compound (1-{3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester, except that 2-(5-{7-[2-(1-Boc-pyrrolidin-2-yl)-3H-imidazol-4-yl]-9-oxo-9H-fluoren-2-yl}-1H-imidazol-2-yl)-pyrrolidine-1-carboxylic acid tert-butyl ester was used instead of 2-(5-{4'-[2-(1-Boc-pyrrolidin-3-yl)-3H-imidazol-4-yl]-biphenyl-4-yl}-1H-imidazol-2-yl)-pyrrolidine-1-carboxylic acid tert-butyl ester. $^1$H-NMR (300 MHz, CD$_3$OD) δ 8.05-7.85 (m, 8H), 5.22 (t, 2H), 4.23 (d, 2H), 4.20-4.05 (m, 2H), 3.95-3.80 (m, 2H), 3.67 (s, 6H), 2.65-2.50 (m, 2H), 2.40-2.00 (m, 8H), 1.05-0.90 (m, 12H); m/z 765.3 (M+H)$^+$.

Example AM

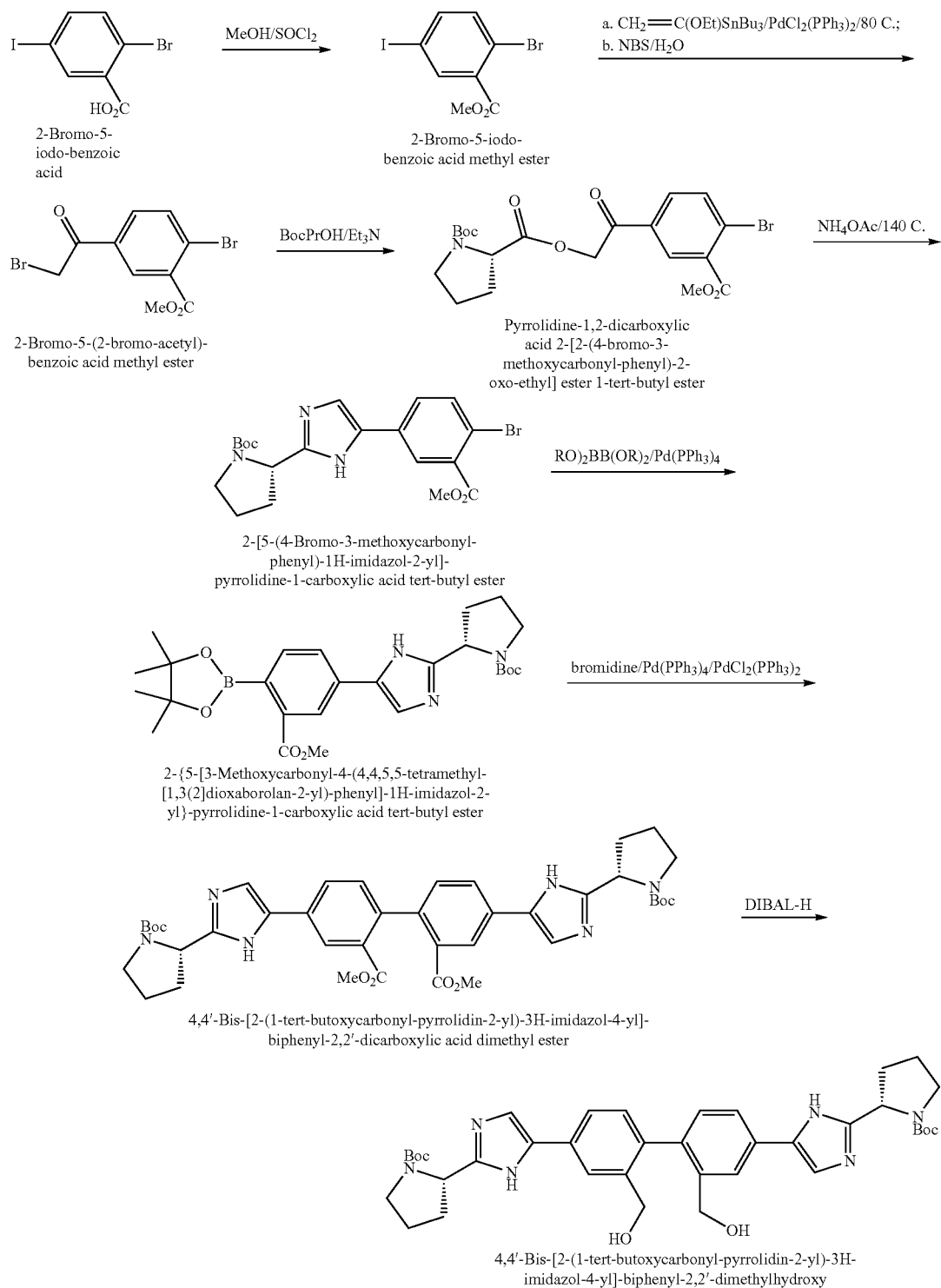

2-Bromo-5-iodo-benzoic acid methyl ester

To the solution of 2-bromo-5-iodo-benzoic acid (10 g, 31 mmol) in methanol (100 ml) was added thionyl chloride (5 ml, 68 mmol). The mixture was heated at 55° C. for 12 hours. The solvent and reagent were removed under reduced pressure and the mixture was diluted with EtOAc. The organic solution was washed with saturated sodium bicarbonate, water, and brine, and was dried with sodium sulfate. Concentration gave 2-bromo-5-iodo-benzoic acid methyl ester (10.5 g).

2-Bromo-5-(2-bromo-acetyl)-benzoic acid methyl ester

To the solution of 2-bromo-5-iodo-benzoic acid methyl ester (4.33 g, 12.7 mmol) and tributyl(ethoxyvinyl)stannane (4.79 g, 13.3 mmol) in dioxane (56 ml) was added PdCl$_2$(PPh$_3$)$_2$ (322 mg). The mixture was heated at 80° C. for 17 hours and was cooled to 0° C. Water (19 ml) was added, followed by slow addition of NBS (2.33 g, 12.9 mmol) over 10 minutes period. The mixture was stirred at 0° C. for additional 40 minutes, and the solvent was removed under reduced pressure. The mixture was diluted with EtOAc, and was washed with water and brine and dried with sodium sulfate. Concentration and purification by flash column chromatography (hexane/EtOAc=2/1) gave 2-bromo-5-(2-bromo-acetyl)-benzoic acid methyl ester (3.48 g).

Pyrrolidine-1,2-dicarboxylic acid 2-[2-(4-bromo-3-methoxycarbonyl-phenyl)-2-oxo-ethyl]ester 1-tert-butyl ester To the solution of (s)Boc-PrOH (2.5 g, 11.6 mmol) and triethylamine (1.55 ml, 11.1 mmol) in acetonitrile (34 ml) was added a solution of 2-bromo-5-(2-bromo-acetyl)-benzoic acid methyl ester (3.48 g, 10.4 mmol) in acetonitrile (17 ml). The mixture was stirred for 10 hours, and the solvent was evaporated. The mixture was diluted with EtOAc, and washed with water and brine, and was dried with sodium sulfate. Purification by flash column chromatography (hexane/EtOAc=1/1.5) gave pyrrolidine-1,2-dicarboxylic acid 2-[2-(4-bromo-3-methoxycarbonyl-phenyl)-2-oxo-ethyl]ester 1-tert-butyl ester (3.9 g): m/z: 491.9 (M+Na)$^+$.

2-[5-(4-Bromo-3-methoxycarbonyl-phenyl)-1H-imidazol-2-yl]-pyrrolidine-1-carboxylic acid tert-butyl ester The mixture of pyrrolidine-1,2-dicarboxylic acid 2-[2-(4-bromo-3-methoxycarbonyl-phenyl)-2-oxo-ethyl]ester 1-tert-butyl ester (460 mg, 1 mmol) and ammonium acetate (860 mg, 11 mmol) in xylenes (5 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (EtOAc) gave 2-[5-(4-bromo-3-methoxycarbonyl-phenyl)-1H-imidazol-2-yl]-pyrrolidine-1-carboxylic acid tert-butyl ester (320 mg). m/z: 449.8 (M+H)$^+$, 448.1 (M−H)$^-$.

2-{5-[3-Methoxycarbonyl-4-(4,4,5,5-tetramethyl-[1,3,2]dioxaborolan-2-yl)-phenyl]-1H-imidazol-2-yl}-pyrrolidine-1-carboxylic acid tert-butyl ester To the solution of 2-[5-(4-bromo-3-methoxycarbonyl-phenyl)-1H-imidazol-2-yl]-pyrrolidine-1-carboxylic acid tert-butyl ester (200 mg, 0.44 mmol) and bis(pinacolato)diboron (225 mg, 0.89 mmol) in 1,4-dioxane (3.4 ml) and DMF (2 ml) was added potassium acetate (110 g, 1.1 mmol), followed by Pd(PPh$_3$)$_4$ (20 mg) and PdCl$_2$(dppf)CH$_2$Cl$_2$ (20 mg). The mixture was heated at 80° C. for 12 hours. The mixture was diluted with EtOAc, and was washed with water and brine, and was dried with sodium sulfate. Concentration and purification by flash column chromatography (EtOAc) gave 2-{5-[3-Methoxycarbonyl-4-(4,4,5,5-tetramethyl-[1,3,2]dioxaborolan-2-yl)-phenyl]-1H-imidazol-2-yl}-pyrrolidine-1-carboxylic acid tert-butyl ester (168 mg). m/z: 498.0 (M+H)$^+$.

4,4'-Bis-[2-(1-tert-butoxycarbonyl-pyrrolidin-2-yl)-3H-imidazol-4-yl]-biphenyl-2,2'-dicarboxylic acid dimethyl ester To the solution of 2-[5-(4-bromo-3-methoxycarbonyl-phenyl)-1H-imidazol-2-yl]-pyrrolidine-1-carboxylic acid tert-butyl ester (158 mg, 0.35 mmol) and 2-{5-[3-Methoxycarbonyl-4-(4,4,5,5-tetramethyl-[1,3,2]dioxaborolan-2-yl)-phenyl]-1H-imidazol-2-yl}-pyrrolidine-1-carboxylic acid tert-butyl ester (166 mg, 0.33 mmol) in 1,2-dimethoxyether (3 ml) and water (1 ml) was added sodium bicarbonate (91 mg, 1.1 mmol), followed by Pd(PPh$_3$)$_4$ (15 mg) and PdCl$_2$(dppf)CH$_2$Cl$_2$ (15 mg). The mixture was heated at 80° C. for 7 hours. The mixture was diluted with EtOAc, and was washed with water and brine, and was dried with sodium sulfate. Concentration and purification by flash column chromatography (EtOAc) gave 4,4'-Bis-[2-(1-tert-butoxycarbonyl-pyrrolidin-2-yl)-3H-imidazol-4-yl]-biphenyl-2,2'-dicarboxylic acid dimethyl ester (85 mg). m/z: 741.0 (M+H)$^+$, 370.9 (M+2H)$^+$/2.

4,4'-Bis-[2-(1-tert-butoxycarbonyl-pyrrolidin-2-yl)-3H-imidazol-4-yl]-biphenyl-2,2'-dimethylhydroxy To the solution of 4,4'-Bis-[2-(1-tert-butoxycarbonyl-pyrrolidin-2-yl)-3H-imidazol-4-yl]-biphenyl-2,2'-dicarboxylic acid dimethyl ester (85 mg, 0.11 mmol) in THF (2 ml) at −78° C. was added DIBAL-H THF solution (1.4 ml, 1.4 mmol). The mixture was warmed to 25° C. and stirred for 5 hours. The mixture was cooled to 0° C. and quenched with 2.0 N NaOH solution until PH=11. The mixture was extracted with EtOAc. The organic phase was washed with water and brine, and was dried with sodium sulfate. Concentration and purification by flash column chromatography (DCM/MeOH) gave 4,4'-bis-[2-(1-tert-butoxycarbonyl-pyrrolidin-2-yl)-3H-imidazol-4-yl]-biphenyl-2,2'-dimethylhydroxy (54 mg). m/z: 685.1 (M+H)$^+$, 343.0 (M+2H)$^+$/2.

Example AN

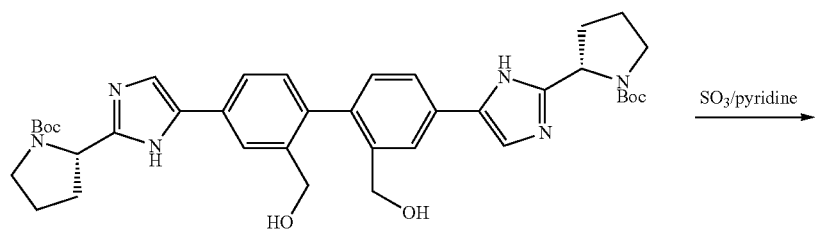

4,4'-Bis-[2-(1-tert-butoxycarbonyl-pyrrolidin-2-yl)-3H-imidazol-4-yl]-biphenyl-2,2'-dimethylhydroxy -continued

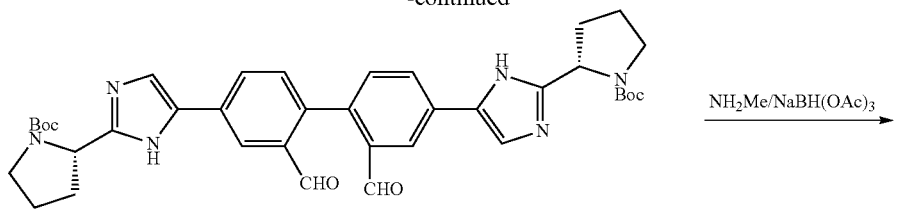

4,4'-Bis-[2-(1-tert-butoxycarbonyl-pyrrolidin-2-yl)-
3H-imidazol-4-yl]-biphenyl-2,2'-dicarboaldehyde NH$_2$Me/NaBH(OAc)$_3$

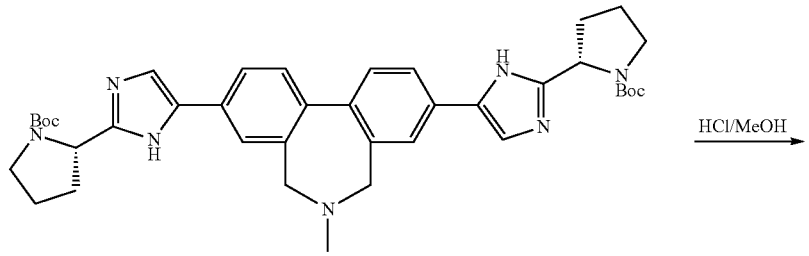

3,9- bis-[2-(1-tert-butoxycarbonyl-pyrrolidin-2-yl)-3H-
imidazol-4-yl] -6-methyl-6,7-dihydro-5H-dibenzo[c,e]azepine HCl/MeOH

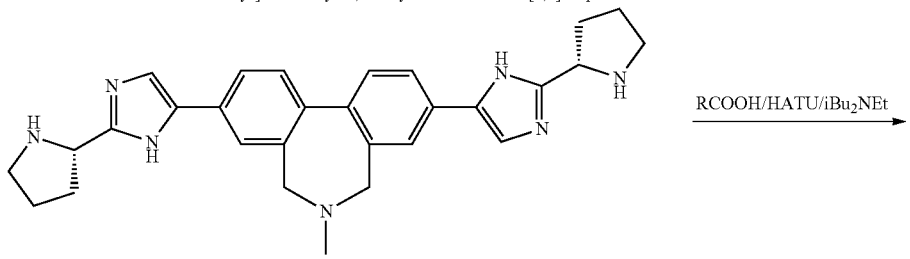

6-Methyl-3,9-bis-(2-pyrrolidin-2-yl-3H-imidazol-4-yl)-6,7-
dihydro-5H-dibenzo[c,e]azepine RCOOH/HATU/iBu$_2$NEt

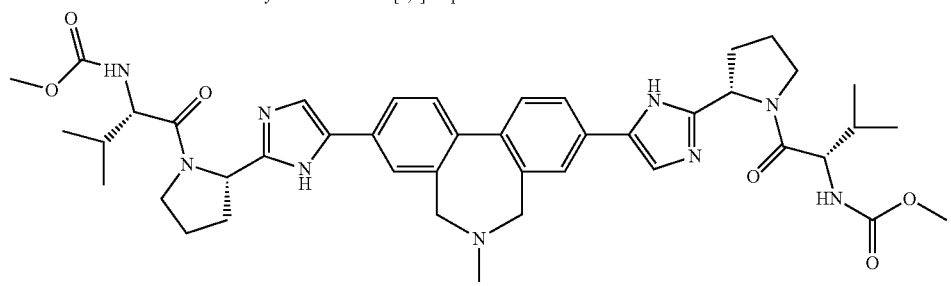

(1-{2-[5-(9-{2-[1-(2-Methoxycarbonylamino-3-methyl-butyryl)-pyrrolidin-
2-yl]-3H-imidazol-4-yl}-6-methyl-6,7-dihydro-5H-dibenzo[c,e]azepin-3-yl)-1H-
imidazol-2-yl]-pyrrolidine-1-carbonyl}-2-methyl-propyl)-carbamic acid methyl ester

4,4'-Bis-[2-(1-tert-butoxycarbonyl-pyrrolidin-2-yl)-3H-imidazol-4-yl]-biphenyl-2,2'-dicarboaldehyde To the solution of 4,4'-Bis-[2-(1-tert-butoxycarbonyl-pyrrolidin-2-yl)-3H-imidazol-4-yl]-biphenyl-2,2'-dimethylhydroxy (54 mg, 0.08 mmol) in DMSO (1.2 ml) was added triethylamine (0.14 ml). The mixture was stirred for 5 minutes, and pyridine-sulfur trioxide (170 mg) was added. The mixture was stirred for 90 minutes and was quenched with ice-water. The stirring was continued for additional 30 minutes and the mixture was extracted with EtOAc. The organic phase was washed with water and brine, and was dried with sodium sulfate. Concentration gave 4,4'-bis-[2-(1-tert-butoxycarbonyl-pyrrolidin-2-yl)-3H-imidazol-4-yl]-biphenyl-2,2'-dicarboaldehyde (40 mg). m/z: 681.0 (M+H)$^+$.

3,9-Bis-[2-(1-tert-butoxycarbonyl-pyrrolidin-2-yl)-3H-imidazol-4-yl]-6-methyl-6,7-dihydro-5H-dibenzo[c,e]azepine To the solution of 4,4'-bis-[2-(1-tert-butoxycarbonyl-pyrrolidin-2-yl)-3H-imidazol-4-yl]-biphenyl-2,2'-dicarboaldehyde (40 mg, 0.06 mmol) in MeOH/THF (2.5 ml/0.5 ml) was added methylamine methanol solution (29 μl, 0.06 mmol), followed by acetic acid (14 μl, 0.23 mmol) and NaBH(OAc)$_3$ (50 mg, 0.23 mmol). The mixture was stirred for 12 hours and was quenched with water. The mixture was extracted with EtOAc. The organic phase was washed with 1.0 N sodium hydroxide solution, water, and brine, and was dried with sodium sulfate. Concentration and purification by flash column chromatography (DCM/MeOH) gave compound 3,9- bis-[2-(1-tert-butoxycarbonyl-pyrrolidin-2-yl)-3H-imidazol-4-yl]-6-methyl-6,7-dihydro-5H-dibenzo[c,e]azepine (24 mg). m/z: 680.3 (M+H)$^+$.

3,9-Bis-[2-(pyrrolidin-2-yl)-3H-imidazol-4-yl]-6-methyl-6,7-dihydro-5H-dibenzo[c,e]azepine To the solution of 3,9-bis-[2-(1-tert-butoxycarbonyl-pyrrolidin-2-yl)-3H-imidazol-4-yl]-6-methyl-6,7-dihydro-5H-dibenzo[c,e]azepine (24 mg) in DCM/MeOH (1.6 ml/0.75 ml) was added hydrochloric acid in dioxane (0.44 ml, 1.7 mmol). The mixture was heated at 50° C. for 3 hours and the solvents were evaporated under reduced pressure. The mixture was diluted with water and acetonitrile, and was freezer-dried to give 3,9-bis-[2-(pyrrolidin-2-yl)-3H-imidazol-4-yl]-6-methyl-6,7-dihydro-5H-dibenzo[c,e]azepine as brown powder (25 mg). m/z: 480.1 (M+H)$^+$.

1-{2-[5-(9-{2-[1-(2-Methoxycarbonylamino-3-methyl-butyryl)-pyrrolidin-2-yl]-3H-imidazol-4-yl}-6-methyl-6,7-dihydro-5H-dibenzo[c,e]azepin-3-yl)-1H-imidazol-2-yl]-pyrrolidine-1-carbonyl}-2-methyl-propyl)-carbamic acid methyl ester To the solution of 3,9-bis-[2-(pyrrolidin-2-yl)-3H-imidazol-4-yl]-6-methyl-6,7-dihydro-5H-dibenzo[c,e]azepine (25 mg, 0.035 mmol) and MeOCO-Val-OH (13 mg, 0.074 mmol) in DMF (1.2 ml) was added HATU (28 mg, 0.074 mmol), followed by diisopropylethylamine (61 µl, 0.35 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{2-[5-(9-{2-[1-(2-methoxycarbonylamino-3-methyl-butyryl)-pyrrolidin-2-yl]-3H-imidazol-4-yl}-6-methyl-6,7-dihydro-5H-dibenzo[c,e]azepin-3-yl)-1H-imidazol-2-yl]-pyrrolidine-1-carbonyl}-2-methyl-propyl)-carbamic acid methyl ester (24 mg). m/z: 794.3 (M+H)$^+$, 397.8 (M+2H)$^+$/2. $^1$H NMR (CD$_3$OD, 300 MHz) δ 8.0-7.9 (8H, m), 5.27 (2H, m), 4.3-4.2 (2H, m), 4.2-3.8 (8H, m), 3.66 (6H, s), 3.08 (3H, s), 2.7-2.5 (2H, m), 2.4-1.9 (8H, m), 0.94-0.90 (12H, m).

Example AO

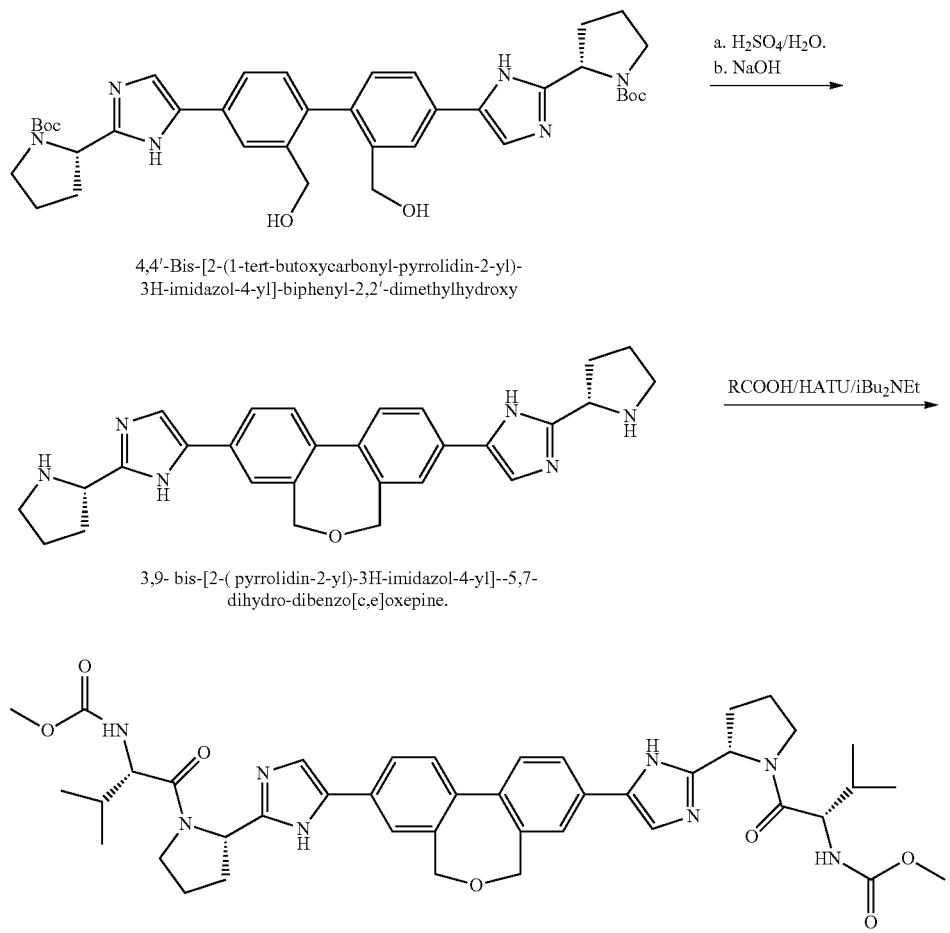

4,4'-Bis-[2-(1-tert-butoxycarbonyl-pyrrolidin-2-yl)-3H-imidazol-4-yl]-biphenyl-2,2'-dimethylhydroxy 3,9- bis-[2-( pyrrolidin-2-yl)-3H-imidazol-4-yl]--5,7-dihydro-dibenzo[c,e]oxepine.

(1-{2-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepine-3-yl)-1H-imidazol-2-yl]-pyrrolidine-1-carbonyl}-2-methyl-propyl)-carbamic acid methyl ester

3,9-Bis-[2-(pyrrolidin-2-yl)-3H-imidazol-4-yl]-5,7-dihydrodibenzo[c,e]oxepine To the suspension of 4,4'-bis-[2-(1-tert-butoxycarbonyl-pyrrolidin-2-yl)-3H-imidazol-4-yl]-biphenyl-2,2'-dimethyl-hydroxy (8 mg, 0.011 mmol) in water (1.5 ml) was added sulfuric acid (1.5 ml). The mixture was heated at 60° C. for 14 hours. The mixture was cooled to 0° C., and 2 N sodium hydroxide solution was added until pH=7. The mixture was freezer-dried to give 3,9-bis-[2-(pyrrolidin-2-yl)-3H-imidazol-4-yl]-5,7-dihydro-dibenzo[c,e]oxepine. m/z: 467.1 (M+H)$^+$.

(1-{2-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-pyrrolidine-1-carbonyl}-2-methyl-propyl)-carbamic acid methyl ester To the solution of 3,9-bis-[2-(pyrrolidin-2-yl)-3H-imidazol-4-yl]-5,7-dihydro-dibenzo[c,e]oxepine (0.011 mmol) and MeOCO-Val-OH (4 mg, 0.023 mmol) in DMF (5 ml) was added HATU (9 mg, 0.023 mmol), followed by diisopropylethylamine (38 µl, 0.22 mmol). The mixture was stirred for 60 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{2-[5-(9-{2-[1-(2-methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-pyrrolidine-1-carbonyl}-2-methyl-propyl)-carbamic acid methyl ester (1.5 mg). m/z: 781.2 (M+1), 391.2 (M+2)/2; $^1$H NMR (CD$_3$OD, 300 MHz) δ 7.9-7.8 (8H, m), 5.27 (2H, m), 4.44 (4H, s), 4.22 (2H, m), 4.17-4.05 (2H, m), 3.95-3.83 (2H, m), 5.67 (6H, s), 2.65-2.50 (2H, m), 2.35-1.95 (8H, m), 0.99-0.89 (12H, m).

Example AP

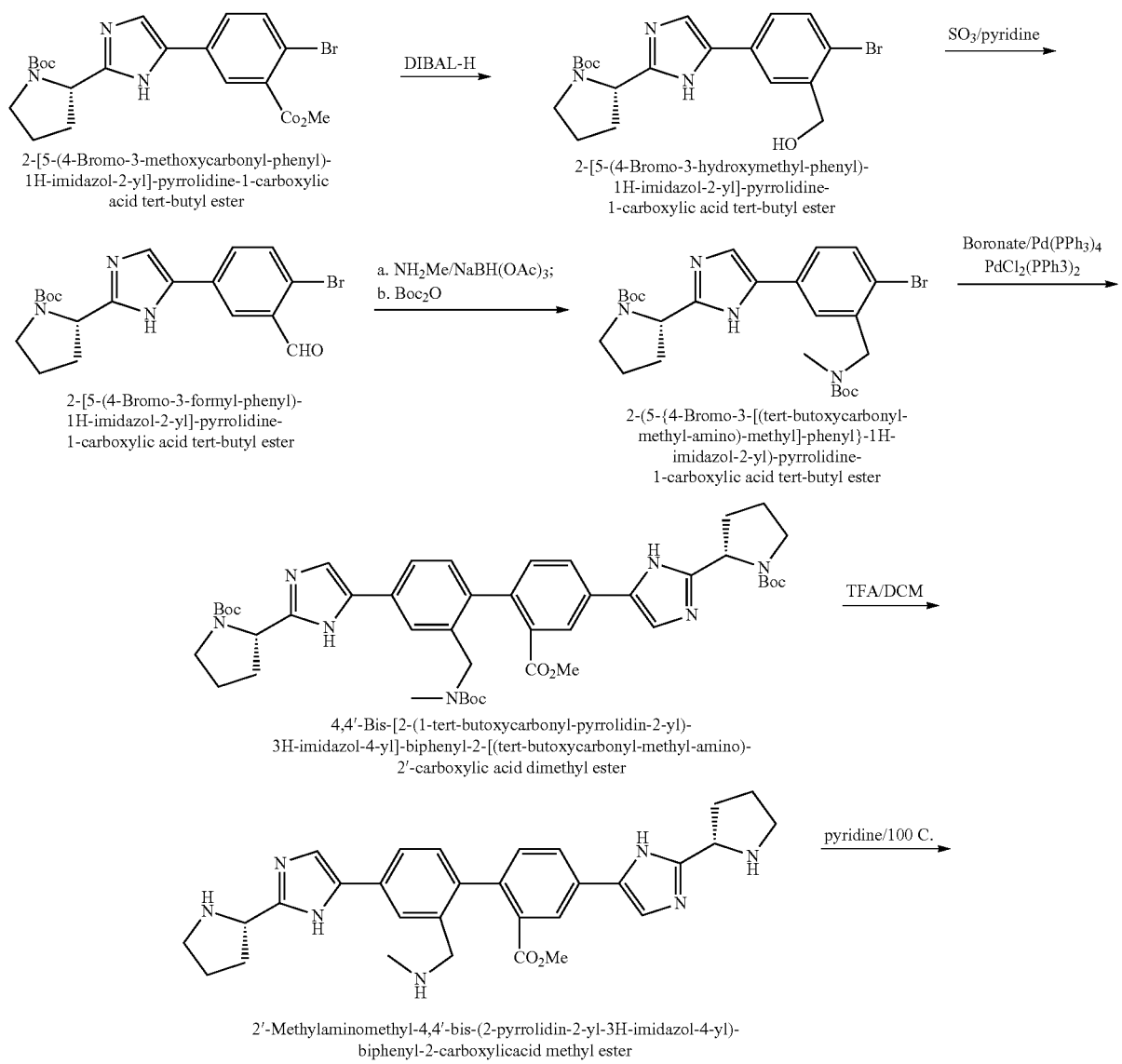

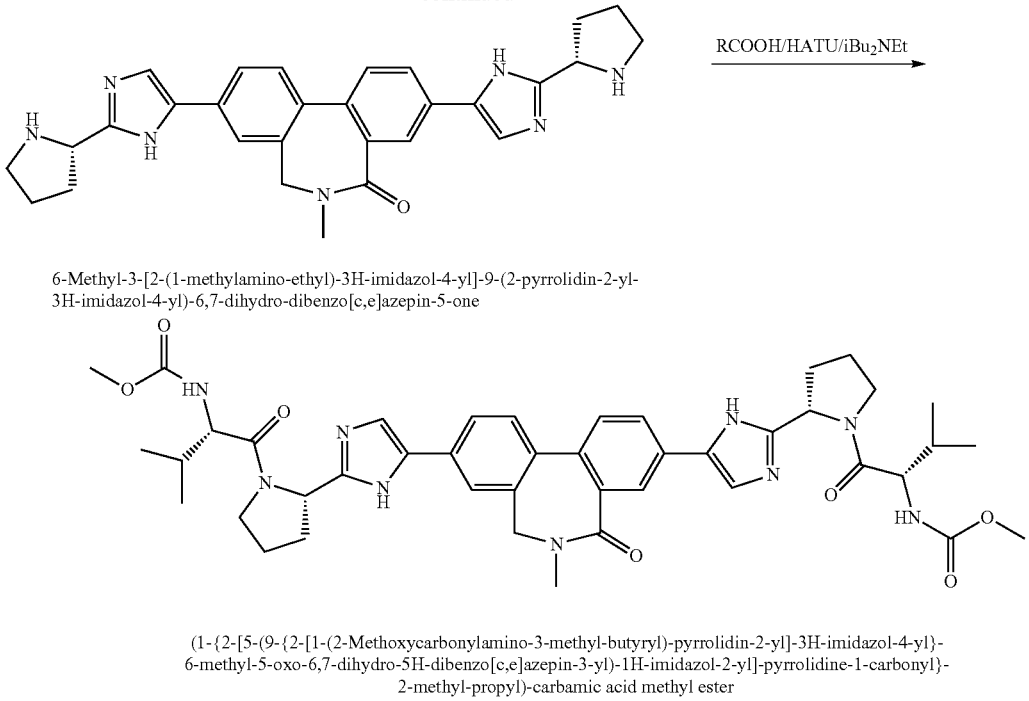

6-Methyl-3-[2-(1-methylamino-ethyl)-3H-imidazol-4-yl]-9-(2-pyrrolidin-2-yl-
3H-imidazol-4-yl)-6,7-dihydro-dibenzo[c,e]azepin-5-one (1-{2-[5-(9-{2-[1-(2-Methoxycarbonylamino-3-methyl-butyryl)-pyrrolidin-2-yl]-3H-imidazol-4-yl}-
6-methyl-5-oxo-6,7-dihydro-5H-dibenzo[c,e]azepin-3-yl)-1H-imidazol-2-yl]-pyrrolidine-1-carbonyl}-
2-methyl-propyl)-carbamic acid methyl ester

2-[5-(4-Bromo-3-hydroxymethyl-phenyl)-1H-imidazol-2-yl]-pyrrolidine-1-carboxylic acid tert-butyl ester To the solution of 2-[5-(4-Bromo-3-methoxycarbonyl-phenyl)-1H-imidazol-2-yl]-pyrrolidine-1-carboxylic acid tert-butyl ester (200 mg, 0.44 mmol) in THF (4 ml) at −78° C. was added DIBAL-H THF solution (3.33 ml, 3.33 mmol). The mixture was warmed to 25° C. and stirred for 5 hours. The mixture was cooled to 0° C. and quenched with 2.0 N NaOH solution until PH=11. The mixture was extracted with EtOAc. The organic phase was washed with water and brine, and was dried with sodium sulfate. Concentration gave 2-[5-(4-bromo-3-hydroxymethyl-phenyl)-1H-imidazol-2-yl]-pyrrolidine-1-carboxylic acid tert-butyl ester (196 mg). m/z: 421.9 (M+H)$^+$, 420.2 (M−H)$^-$.

2-[5-(4-Bromo-3-formyl-phenyl)-1H-imidazol-2-yl]-pyrrolidine-1-carboxylic acid tert-butyl ester To the solution of 2-[5-(4-bromo-3-hydroxymethyl-phenyl)-1H-imidazol-2-yl]-pyrrolidine-1-carboxylic acid tert-butyl ester (196 mg, 0.46 mmol) in DMSO (3.5 ml) was added triethylamine (0.40 ml). The mixture was stirred for 30 minutes, and pyridine-sulfur trioxide (500 mg) was added. The mixture was stirred for 2 hours and was quenched with ice-water. The stirring was continued for additional 30 minutes and the mixture was extracted with EtOAc.

The organic phase was washed with water and brine, and was dried with sodium sulfate. Concentration gave 2-[5-(4-Bromo-3-formyl-phenyl)-1H-imidazol-2-yl]-pyrrolidine-1-carboxylic acid tert-butyl ester (180 mg).

2-(5-[4-Bromo-3-[(tert-butoxycarbonyl-methyl-amino)-methyl]-phenyl]-1H-imidazol-2-yl)-pyrrolidine-1-carboxylic acid tert-butyl ester To the solution of 2-[5-(4-bromo-3-formyl-phenyl)-1H-imidazol-2-yl]-pyrrolidine-1-carboxylic acid tert-butyl ester (180 mg, 0.46 mmol) in MeOH/THF (2.5 ml/2.5 ml) was added methylamine methanol solution (0.69 ml, 1.38 mmol), followed by acetic acid (110 µl, 1.84 mmol) and NaBH(OAc)$_3$ (975 mg, 4.6 mmol). The mixture was stirred for 12 hours and was quenched with 1 N sodium hydroxide solution. The mixture was extracted with EtOAc. The organic phase was washed with water and brine, and was dried with sodium sulfate. Concentration gave the intermediate (171 mg). To the solution of the above intermediate (171 mg, 0.39 mmol) in DCM (4 ml) was added di-tert-butyl dicarbonate (86 mg, 0.39 mmol), followed by diisopropylethylamine (135 6l, 0.78 mmol). The mixture was stirred for 12 hours, and the solvent and reagent was evaporated. Purification by flash column chromatography (hexanes/EtOAc) gave 2-(5-{4-bromo-3-[(tert-butoxycarbonyl-methyl-amino)-methyl]-phenyl}-1H-imidazol-2-yl)-pyrrolidine-1-carboxylic acid tert-butyl ester (142 mg). m/z: 535 (M+H)$^+$.

4,4'-Bis-[2-(1-tert-butoxycarbonyl-pyrrolidin-2-yl)-3H-imidazol-4-yl]-biphenyl-2-[(tert-butoxycarbonyl-methyl-amino)-2'-carboxylic acid dimethyl ester To the solution of 2-(5-{4-bromo-3-[(tert-butoxycarbonyl-methyl-amino)-methyl]-phenyl}-1H-imidazol-2-yl)-pyrrolidine-1-carboxylic acid tert-butyl ester (142 mg, 0.27 mmol) and 2-{5-[3-Methoxycarbonyl-4-(4,4,5,5-tetramethyl-[1,3,2]dioxaborolan-2-yl)-phenyl]-1H-imidazol-2-yl}-pyrrolidine-1-carboxylic acid tert-butyl ester (125 mg, 0.25 mmol) in 1,2-dimethoxyether (2.3 ml) and water (0.7 ml) was added sodium bicarbonate (63 mg, 0.75 mmol), followed by Pd(PPh$_3$)$_4$ (12 mg) and PdCl$_2$(dppf)CH$_2$Cl$_2$ (12 mg). The mixture was heated at 80° C. for 20 hours. The mixture was diluted with EtOAc, and was washed with water and brine, and was dried with sodium sulfate. Concentration and purification by flash column chromatography (hexanes/EtOAc) gave 4,4'-bis-[2-(1-tert-butoxycarbonyl-pyrrolidin-2-yl)-3H- imidazol-4-yl]-biphenyl-2-[(tert-butoxycarbonyl-methyl-amino)-2'-carboxylic acid dimethyl ester (82 mg). m/z: 826 (M+H)+, 413.6 (M+2H)+/2.

2'-Methylaminomethyl-4,4'-bis-(2-pyrrolidin-2-yl-3H-imidazol-4-yl)-biphenyl-2-carboxylic acid methyl ester To the solution of 4,4'-bis-[2-(1-tert-butoxycarbonyl-pyrrolidin-2-yl)-3H-imidazol-4-yl]-biphenyl-2-[(tert-butoxycarbonyl-methyl-amino)-2'-carboxylic acid dimethyl ester (77 mg, 0.09 mmol) in DCM (3 ml) was added trifluoroacetic acid (3 ml). The mixture was stirred for 2 hours, and the solvent and reagent were removed under reduced pressure. The mixture was diluted with acetonitrile and water, was freezer-dried to give 2'-methylaminomethyl-4,4'-bis-(2-pyrrolidin-2-yl-3H-imidazol-4-yl)-biphenyl-2-carboxylic acid methyl ester as white powder (90 mg). m/z: 526.1 (M+H)+.

6-Methyl-3,9-bis-(2-pyrrolidin-2-yl-3H-imidazol-4-yl)-6,7-dihydro-dibenzo[c,e]azepin-5-one To the solution of 2'-methylaminomethyl-4,4'-bis-(2-pyrrolidin-2-yl-3H-imidazol-4-yl)-biphenyl-2-carboxylic acid methyl ester (90 mg) in pyridine (5 ml) was added diisopropylethylamine (1 ml). The mixture was heated at 100° C. for 2 hours. The solvents were evaporated. The mixture was diluted with acetonitrile and water, was freezer-dried to give 6-Methyl-3,9-bis-(2-pyrrolidin-2-yl-3H-imidazol-4-yl)-6,7-dihydro-dibenzo[c,e]azepin-5-one as brown powder. m/z: 494.1 (M+H)+.

(1-{2-[5-(9-{2-[1-(2-Methoxycarbonylamino-3-methyl-butyryl)-pyrrolidin-2-yl]-3H-imidazol-4-yl}-6-methyl-5-oxo-6,7-dihydro-5H-dibenzo[c,e]azepin-3-yl)-1H-imidazol-2-yl]-pyrrolidine-1-carbonyl}-2-methyl-propyl)-carbamic acid methyl ester To the solution of 6-methyl-3,9-bis-(2-pyrrolidin-2-yl-3H-imidazol-4-yl)-6,7-dihydro-dibenzo[c,e]azepin-5-one (0.09 mmol) and MeOCO-Val-OH (33 mg, 0.19 mmol) in DMF (3 ml) was added HATU (71 mg, 0.19 mmol), followed by diisopropylethylamine (323 µl, 1.86 mmol). The mixture was stirred for 60 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{2-[5-(9-{2-[1-(2-Methoxycarbonylamino-3-methyl-butyryl)-pyrrolidin-2-yl]-3H-imidazol-4-yl}-6-methyl-5-oxo-6,7-dihydro-5H-dibenzo[c,e]azepin-3-yl)-1H-imidazol-2-yl]-pyrrolidine-1-carbonyl}-2-methyl-propyl)-carbamic acid methyl ester (16 mg). m/z: 808.2 (M+1), 404.8 (M+2)/2, 806.3 (M−1). $^1$H NMR (CD$_3$OD, 300 MHz) δ 8.1-7.8 (8H, m), 5.4-5.2 (2H, m), 4.6-4.2 (4H, m), 4.2-4.0 (2H, m), 3.95-3.80 (2H, m), 3.64 (6H, m), 3.25 (3H, s), 2.65-2.45 (2H, m), 2.35-2.0 (8H, m), 1.05-0.9 (12H, m).

Example AQ

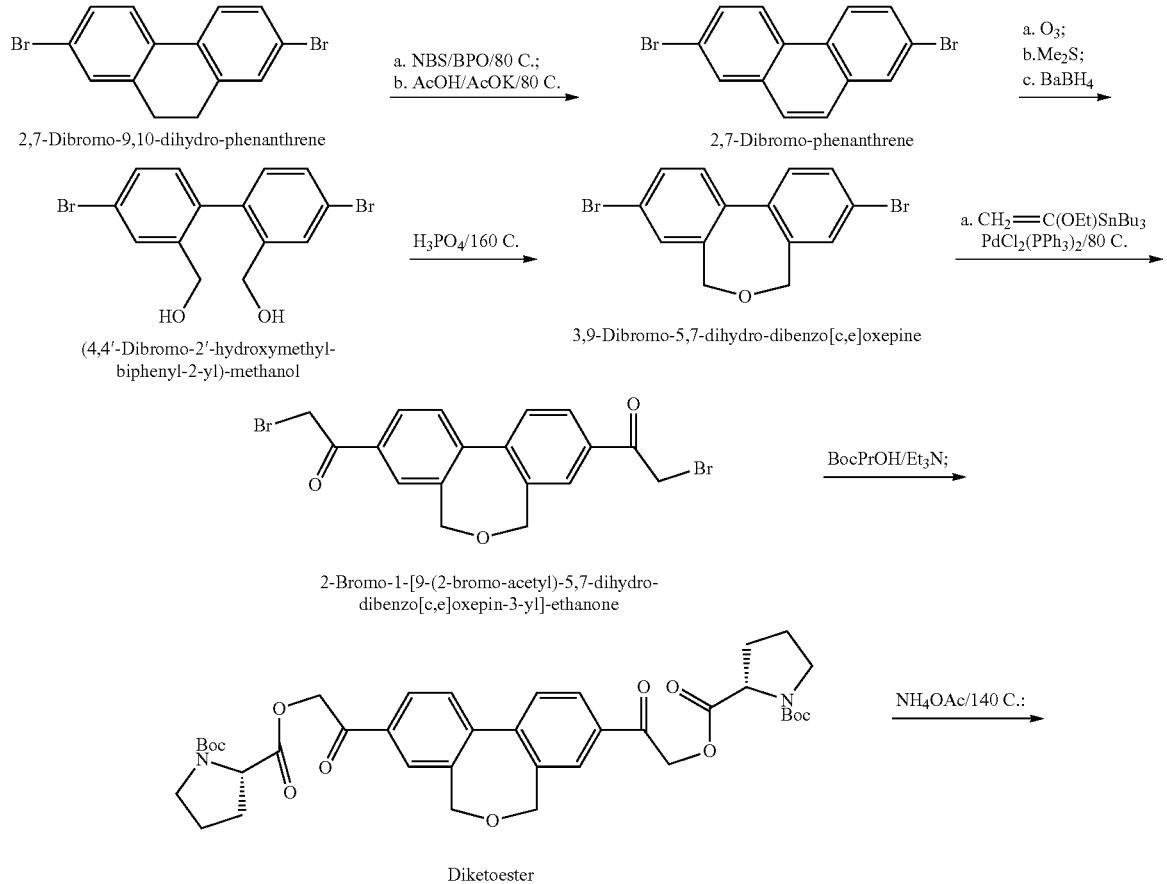

-continued

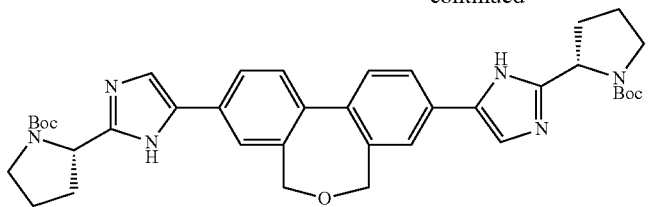

3,9-Bis-[2-(1-tert-butoxycarbonyl-pyrrolidin-2-yl)-3H-imidazol-4-yl]-5,7-dihydro-dibenzo[c,e]oxepine a. TFA/DCM;
b. RCOOH/HATU/iBu₂NEt

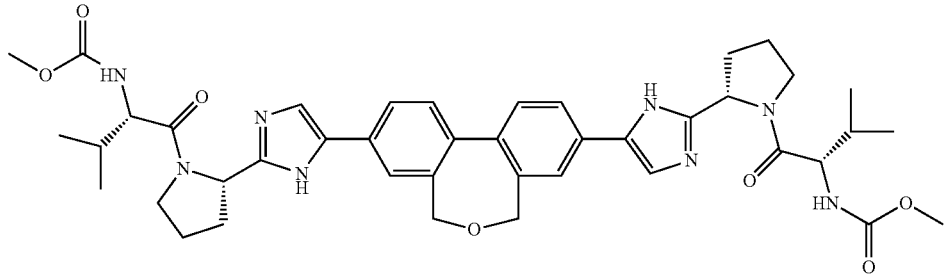

(1-{2-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-pyrrolidine-1-carbonyl}-2-methyl-propyl)-carbamic acid methyl ester

2,7-Dibromo-phenanthrene

The mixture of 2,7-dibromo-9,10-dihydro-phenanthrene (2.4 g, 7.1 mmol), NBS (1.4 g, 7.8 mmol), and benzoyl peroxide (0.2 g) in carbon tetrachloride (300 ml) was refluxed for 2 hours. Potassium acetate (3.6 g) and acetic acid (3.2 ml) were added, and the refluxing was continued for additional 2 hours. The mixture was cooled and diluted with EtOAc. The organic phase was washed with water, saturated sodium bicarbonate, and brine, and was dried with sodium sulfate. Concentration gave 2,7-dibromo-phenanthrene (2.3 g).

(4,4'-Dibromo-2'-hydroxymethyl-biphenyl-2-yl)-methanol

The solution of 2,7-dibromo-phenanthrene (3.8 g) in DCM/MeOH (120 ml/1 ml) was cooled to −78° C., and it became a suspension. Ozone was bubbled thorough for 20 minutes, and the mixture became blue. Oxygen was bubbled for 5 minutes and dimethyl sulfide (3 ml) was added. The mixture was warmed to 25° C. and stirred for 12 hours. Concentration and purification by flash column chromatography (hexanes/EtOAc) gave 4,4'-dibromo-biphenyl-2,2'-dicarbaldehyde (600 mg). To the solution of 4,4'-dibromo-biphenyl-2,2'-dicarbaldehyde (600 mg, 1.7 mmol) in THF/MeOH (10 ml/10 ml) at 0° C. was added sodium borohydride (320 mg, 8.2 mmol). The mixture was warmed to 25° C. and stirred for 12 hours. The mixture was quenched with water, and extracted with EtOAc. The organic phase was washed with water and brine, and was dried with sodium sulfate. Concentration gave (4,4'-dibromo-2'-hydroxymethyl-biphenyl-2-yl)-methanol (550 mg).

3,9-Dibromo-5,7-dihydro-dibenzo[c,e]oxepine

The suspension of (4,4'-dibromo-2'-hydroxymethyl-biphenyl-2-yl)-methanol (460 mg) in phosphoric acid (25 ml) was heated at 160° C. for 4 hours. The mixture was cooled and diluted with water (100 ml), and was extracted with EtOAC. The organic phase was washed with water, saturated sodium bicarbonate, and brine, and was dried with sodium sulfate. Concentration yielded 3,9-dibromo-5,7-dihydro-dibenzo[c,e]oxepine (416 mg).

2-Bromo-1-[9-(2-bromo-acetyl)-5,7-dihydro-dibenzo[c,e]oxepin-3-yl]-ethanone

To the solution of 3,9-dibromo-5,7-dihydro-dibenzo[c,e]oxepine (416 mg, 1.2 mmol) and tributyl(ethoxyvinyl)stannane (878 μl, 2.6 mmol) in dioxane (6 ml) was added PdCl₂(PPh₃)₂ (30 mg). The mixture was heated at 80° C. for 16 hours and was cooled to 0° C. Water (2 ml) was added, followed by slow addition of NBS (464 mg, 2.6 mmol) over 5 minutes period. The mixture was stirred at 0° C. for additional 40 minutes, and the solvent was removed under reduced pressure. The mixture was diluted with EtOAc, and was washed with water and brine and dried with sodium sulfate. Concentration and purification by flash column chromatography (hexane/EtOAc) gave 2-bromo-1-[9-(2-bromo-acetyl)-5,7-dihydro-dibenzo[c,e]oxepin-3-yl]-ethanone (160 mg).

Diketoester

To the solution of (S)-Boc-Pro-OH (275 mg, 1.28 mmol) and triethylamine (154 μl, 1.11 mmol) in acetonitrile (3.4 ml) was added a solution of 2-bromo-1-[9-(2-bromo-acetyl)-5,7-dihydro-dibenzo[c,e]oxepin-3-yl]-ethanone (160 mg, 0.37 mmol) in DMF (6 ml). The mixture was stirred for 10 hours, and the solvent was evaporated. The mixture was diluted with EtOAc, and washed with water and brine, and was dried with sodium sulfate. Concentration gave the intermediate diketoester. m/z: 729.1 (M+Na)⁺.

3,9-Bis-[2-(1-tert-butoxycarbonyl-pyrrolidin-2-yl)-3H-imidazol-4-yl]-5,7-dihydro-dibenzo[c,e]oxepine The mixture of above diketoester (0.37 mmol) and ammonium acetate (860 mg, 11 mmol) in xylene (5 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (DCM/EtOAc) gave 3,9-bis-[2-(1-tert-butoxycarbonyl-pyrrolidin-2-yl)-3H-imidazol-4-yl]-5,7-dihydro-dibenzo[c,e]oxepine (195 mg). m/z: 667.1 (M+H)+.

(1-{2-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-pyrrolidine-1-carbonyl}-2-methyl-propyl)-carbamic acid methyl ester To the solution of 3,9-bis-[2-(1-tert-butoxycarbonyl-pyrrolidin-2-yl)-3H-imidazol-4-yl]-5,7-dihydro-dibenzo[c,e]oxepine (190 mg) in DCM (3 ml) was added TFA (1.5 ml). The mixture was stirred for 60 minutes, and the solvent and reagent were removed under reduced pressure. The mixture was diluted with acetonitrile and water, and was freezer-dried to give dipyrrolidine. To the solution of dipyrrolidine (0.29 mmol) and (S—)-Moc-Val-OH (100 mg, 0.57 mmol) in DMF (8 ml) was added HATU (227 mg, 0.60 mmol), followed by diisopropylethylamine (0.5 ml, 2.9 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{2-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-pyrrolidine-1-carbonyl}-2-methyl-propyl)-carbamic acid methyl ester (142 mg). m/z: 781.3 (M+1), 779.3 (M−1), 391.3 (M+2)/2. $^1$H NMR (CD$_3$OD, 300 MHz) δ 7.9-7.8 (8H, m), 5.27 (2H, m), 4.44 (4H, s), 4.22 (2H, m), 4.17-4.05 (2H, m), 3.95-3.83 (2H, m), 5.67 (6H, s), 2.65-2.50 (2H, m), 2.35-1.95 (8H, m), 0.99-0.89 (12H, m).

Example AR

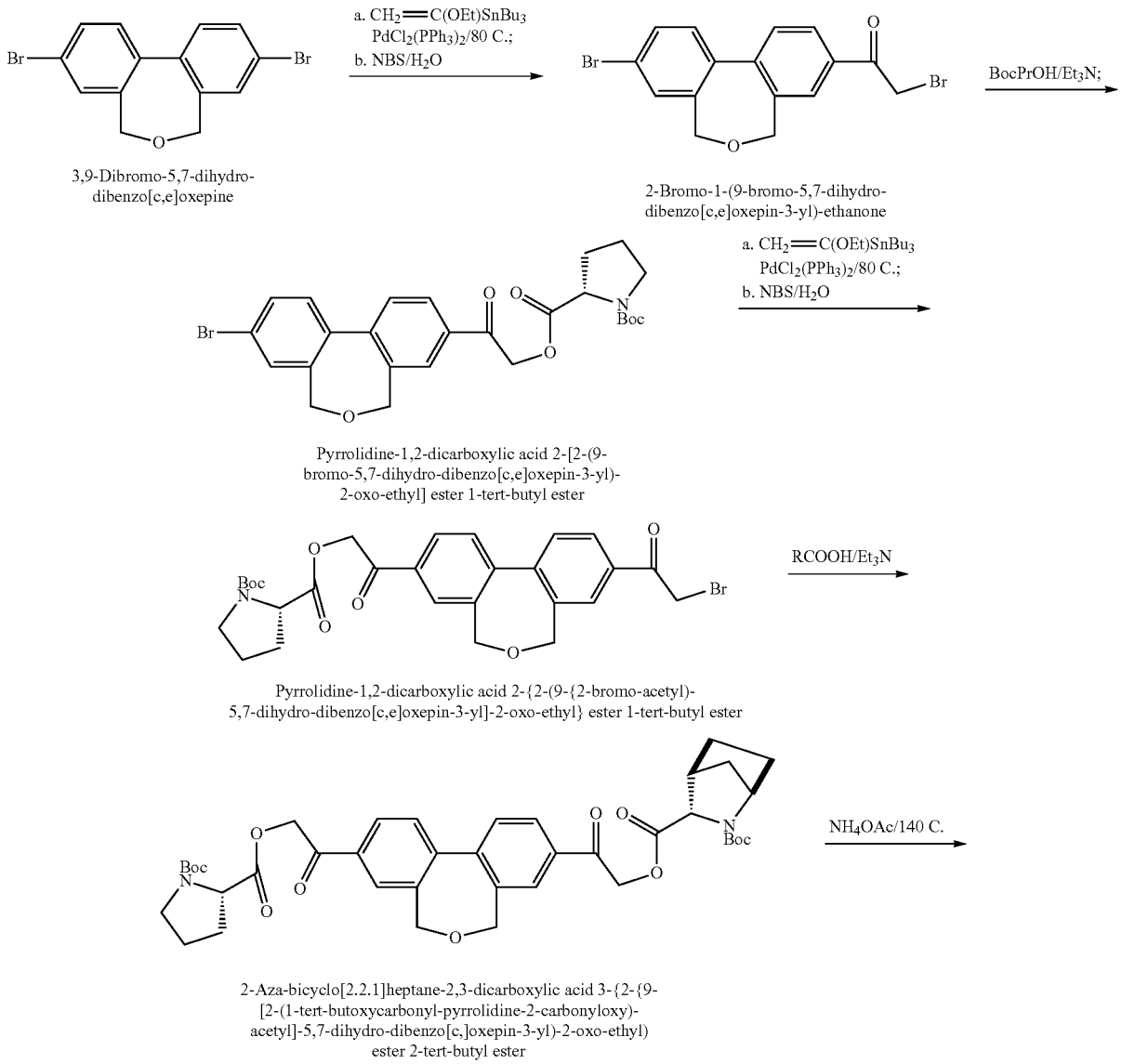

-continued

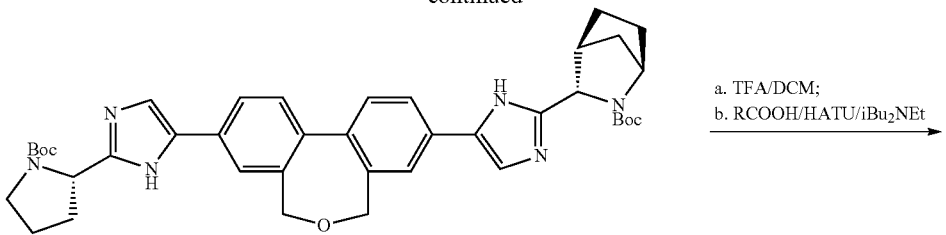

3-(5-{9-{2-(1-tert-Butoxycarbonyl-pyrrolidin-2-yl)-3H-
imidazol-4-yl]-5,7-dihydro-dibenzo[c,e]oxepin-3-yl}-1H-imidazol-
2-yl)-2-aza-bicyclo[2.2.1]heptane-2-carboxylic acid tert-butyl ester a. TFA/DCM;
b. RCOOH/HATU/iBu$_2$NEt

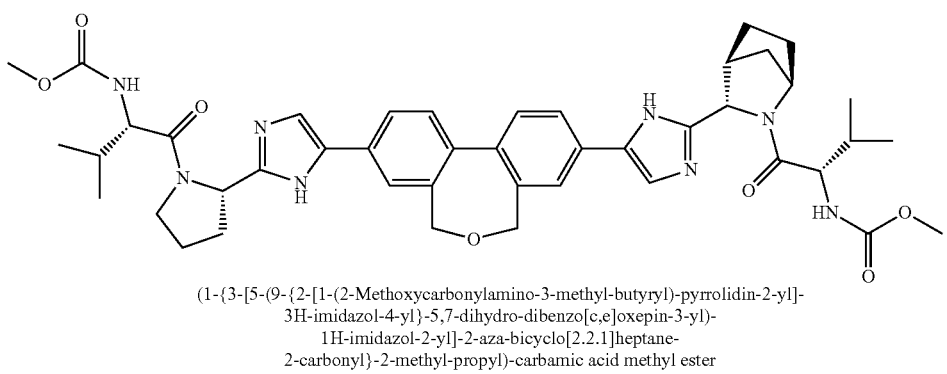

(1-{3-[5-(9-{2-[1-(2-Methoxycarbonylamino-3-methyl-butyryl)-pyrrolidin-2-yl]-
3H-imidazol-4-yl}-5,7-dihydro-dibenzo[c,e]oxepin-3-yl)-
1H-imidazol-2-yl]-2-aza-bicyclo[2.2.1]heptane-
2-carbonyl}-2-methyl-propyl)-carbamic acid methyl ester

2-Bromo-1-(9-bromo-5,7-dihydro-dibenzo[c,e]oxepin-3-yl)-ethanone

To the solution of 3,9-dibromo-5,7-dihydro-dibenzo[c,e]oxepine (416 mg, 1.2 mmol) and tributyl(ethoxyvinyl)stannane (878 μl, 2.6 mmol) in dioxane (6 ml) was added PdCl$_2$(PPh$_3$)$_2$ (30 mg). The mixture was heated at 80° C. for 16 hours and was cooled to 0° C. Water (2 ml) was added, followed by slow addition of NBS (464 mg, 2.6 mmol) over 5 minutes period. The mixture was stirred at 0° C. for additional 40 minutes, and the solvent was removed under reduced pressure. The mixture was diluted with EtOAc, and was washed with water and brine and dried with sodium sulfate. Concentration and purification by flash column chromatography (hexane/EtOAc) gave 2-bromo-1-(9-bromo-5,7-dihydro-dibenzo[c,e]oxepin-3-yl)-ethanone (120 mg). Pyrrolidine-1,2-dicarboxylic acid 2-[2-(9-bromo-5,7-dihydro-dibenzo[c,e]oxepin-3-yl)-2-oxo-ethyl]ester 1-tert-butyl ester: To the solution of (S)-Boc-Pro-OH (118 mg, 0.55 mmol) and triethylamine (65 μl, 0.46 mmol) in acetonitrile (2 ml) was added a solution of 2-bromo-1-(9-bromo-5,7-dihydro-dibenzo[c,e]oxepin-3-yl)-ethanone (120 mg, 0.31 mmol) in DMF (4 ml). The mixture was stirred for 10 hours, and the solvent was evaporated. The mixture was diluted with EtOAc, and washed with water and brine, and was dried with sodium sulfate. Concentration gave pyrrolidine-1,2-dicarboxylic acid 24-[2-(9-bromo-5,7-dihydro-dibenzo[c,e]oxepin-3-yl)-2-oxo-ethyl]ester 1-tert-butyl ester (160 mg). m/z: 553.8 (M+Na)$^+$.

Pyrrolidine-1,2-dicarboxylic acid 2-{2-[9-(2-bromo-acetyl)-5,7-dihydro-dibenzo[c,e]oxepin-3-yl]-2-oxo-ethyl}ester 1-tert-butyl ester To the solution of pyrrolidine-1,2-dicarboxylic acid 2-[2-(9-bromo-5,7-dihydro-dibenzo[c,e]oxepin-3-yl)-2-oxo-ethyl]ester 1-tert-butyl ester (160 mg, 0.30) and tributyl (ethoxyvinyl)stannane (112 μl, 0.33 mmol) in dioxane (2 ml) was added PdCl$_2$(PPh$_3$)$_2$ (8 mg). The mixture was heated at 80° C. for 16 hours and was cooled to 0° C. Water (0.7 ml) was added, followed by slow addition of NBS (59, 0.33 mmol) over 5 minutes period. The mixture was stirred at 0° C. for additional 40 minutes, and the solvent was removed under reduced pressure. The mixture was diluted with EtOAc, and was washed with water and brine and dried with sodium sulfate. Concentration and purification by flash column chromatography (hexane/EtOAc) gave pyrrolidine-1,2-dicarboxylic acid 2-{2-[9-(2-bromo-acetyl)-5,7-dihydro-dibenzo[c,e]oxepin-3-yl]-2-oxo-ethyl}ester 1-tert-butyl ester (156 mg). m/z: 593.9 (M+Na)$^+$.

2-Aza-bicyclo[2.2.1]heptane-2,3-dicarboxylic acid 3-(2-{9-[2-(1-tert-butoxycarbonyl-pyrrolidine-2-carbonyloxy)-acetyl]-5,7-dihydro-dibenzo[c,e]oxepin-3-yl}-2-oxo-ethyl) ester 2-tert-butyl ester To the solution of 2-Aza-bicyclo[2.2.1]heptane-2,3-dicarboxylic acid 2-tert-butyl ester (100 mg, 0.42 mmol) and triethylamine (50 μl, 0.36 mmol) in acetonitrile (2 ml) was added a solution of pyrrolidine-1,2-dicarboxylic acid 2-{2-[9-(2-bromo-acetyl)-5,7-dihydro-dibenzo[c,e]oxepin-3-yl]-2-oxo-ethyl}ester 1-tert-butyl ester (136 mg, 0.24 mmol) in DMF (4 ml). The mixture was stirred for 10 hours, and the solvent was evaporated. The mixture was diluted with EtOAc, and washed with water and brine, and was dried with sodium sulfate. Concentration gave 2-aza-bicyclo[2.2.1]heptane-2,3-dicarboxylic acid 3-(2-{9-[2-(1-tert-butoxycarbonyl-pyrrolidine-2-carbonyloxy)-acetyl]-5,7-dihydro-dibenzo[c,e]oxepin-3-yl}-2-oxo-ethyl)ester 2-tert-butyl ester (142 mg). m/z: 731.3 (M–H)$^-$, 755.2 (M+Na)$^+$.

3-(5-{9-[2-(1-tert-Butoxycarbonyl-pyrrolidin-2-yl)-3H-imidazol-4-yl]-5,7-dihydro-dibenzo[c,e]oxepin-3-yl}-1H-imidazol-2-yl)-2-aza-bicyclo[2.2.1]heptane-2-carboxylic acid tert-butyl ester The mixture of 2-aza-bicyclo[2.2.1]heptane-2,3-dicarboxylic acid 3-(2-{9-[2-(1-tert-butoxycarbonyl-pyrrolidine-2-carbonyloxy)-acetyl]-5,7-dihydro-dibenzo[c,e]oxepin-3-yl}-2-oxo-ethyl)ester 2-tert-butyl ester (142 mg, 0.19 mmol) and ammonium acetate (860 mg, 11 mmol) in xylene (5 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (DCM/EtOAc) gave 3-(5-{9-[2-(1-tert-Butoxycarbonyl-pyrrolidin-2-yl)-3H-imidazol-4-yl]-5,7-dihydro-dibenzo[c,e]oxepin-3-yl}-1H-imidazol-2-yl)-2-aza-bicyclo[2.2.1]heptane-2-carboxylic acid tert-butyl ester (86 mg). m/z: 693.1 (M+H)$^+$.

(1-{3-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-2-aza-bicyclo[2.2.1]heptane-2-carbonyl}-2-methyl-propyl)-carbamic acid methyl ester To the solution of 3-(5-{9-[2-(1-tert-Butoxycarbonyl-pyrrolidin-2-yl)-3H-imidazol-4-yl]-5,7-dihydro-dibenzo[c,e]oxepin-3-yl}-1H-imidazol-2-yl)-2-aza-bicyclo[2.2.1]heptane-2-carboxylic acid tert-butyl ester (86 mg) in DCM (3 ml) was added TFA (1.5 ml). The mixture was stirred for 60 minutes, and the solvent and reagent were removed under reduced pressure. The mixture was diluted with acetonitrile and water, and was freezer-dried to give brown powder. To the solution of above powder (0.12 mmol) and (S)-Moc-Val-OH (44 mg, 0.25 mmol) in DMF (4 ml) was added HATU (99 mg, 0.26 mmol), followed by diisopropylethylamine (0.22 ml, 1.2 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{3-[5-(9-{2-[1-(2-Methoxycarbonylamino-3-methyl-butyryl)-pyrrolidin-2-yl]-3H-imidazol-4-yl}-5,7-dihydro-dibenzo[c,e]oxepin-3-yl)-1H-imidazol-2-yl]-2-aza-bicyclo[2.2.1]heptane-2-carbonyl}-2-methyl-propyl)-carbamic acid methyl ester (84 mg). m/z: 807.4 (M+1), 805.3 (M−1), 404.4 (M+2)/2. $^1$H NMR (CD$_3$OD, 300 MHz) δ 8.0-7.8 (8H, m), 5.26 (2H, m), 4.66 (1H, m), 4.44 (4H, m), 4.35 (1H, m), 4.25 (1H, m), 4.15 (1H, m), 3.89 (1H, m), 3.67 (6H, m), 2.85 (2H, m), 2.60 (2H, m), 2.3-1.4 (9H, m), 1.05-0.85 (12H, m).

Example AS

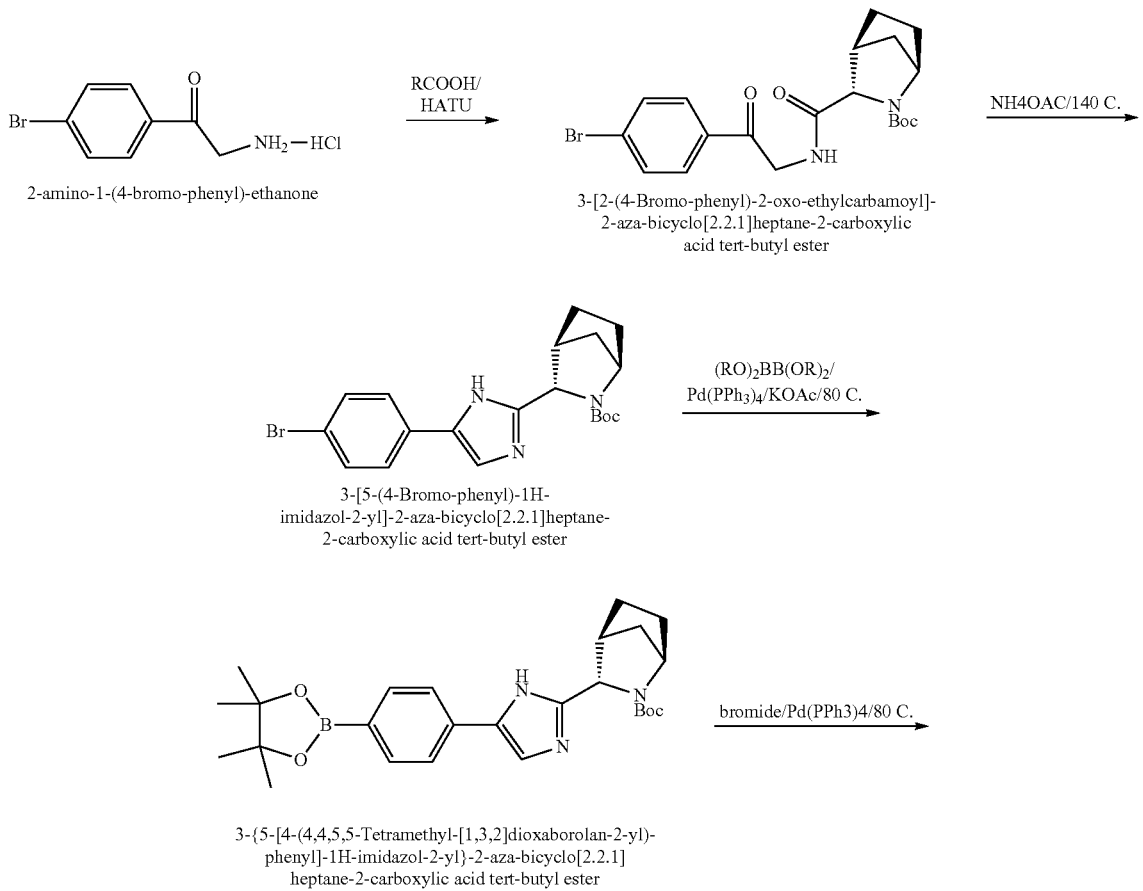

2-amino-1-(4-bromo-phenyl)-ethanone

3-[2-(4-Bromo-phenyl)-2-oxo-ethylcarbamoyl]-2-aza-bicyclo[2.2.1]heptane-2-carboxylic acid tert-butyl ester 3-[5-(4-Bromo-phenyl)-1H-imidazol-2-yl]-2-aza-bicyclo[2.2.1]heptane-2-carboxylic acid tert-butyl ester 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester

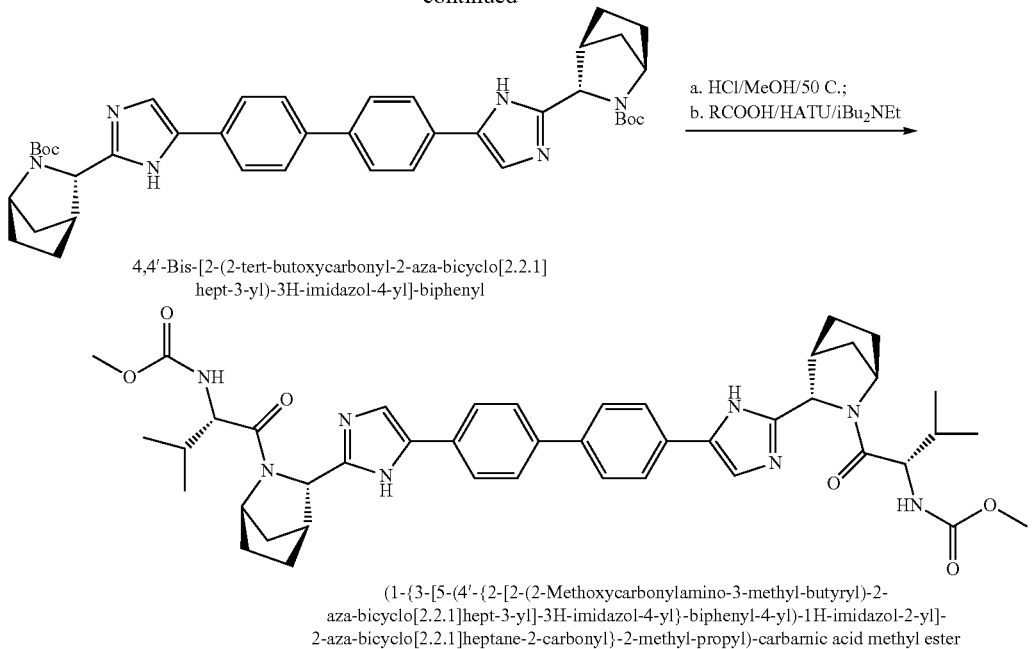

4,4'-Bis-[2-(2-tert-butoxycarbonyl-2-aza-bicyclo[2.2.1]hept-3-yl)-3H-imidazol-4-yl]-biphenyl (1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[2.2.1]heptane-2-carbonyl}-2-methyl-propyl)-carbamic acid methyl ester

3-[2-(4-Bromo-phenyl)-2-oxo-ethylcarbamoyl]-2-aza-bicyclo[2.2.1]heptane-2-carboxylic acid tert-butyl ester To the solution of 2-amino-1-(4-bromo-phenyl)-ethanone (HCl salt, 1.0 g, 4 mmol) and 2-aza-bicyclo[2.2.1]heptane-2,3-dicarboxylic acid 2-tert-butyl ester (0.98 g, 4 mmol) in DMF (13 ml) was added HATU (1.64 g, 4.3 mmol), followed by slow addition of diisopropylethylamine (2.2 ml, 12.7 mmol). The mixture was stirred for 4 hours and was diluted with EtOAc. The organic phase was washed with 1 N NaOH solution, water, and brine, and was dried with sodium sulfate. Concentration and purification by flash column chromatography (hexane/EtOAc) gave 3-[2-(4-bromo-phenyl)-2-oxo-ethylcarbamoyl]-2-aza-bicyclo[2.2.1]heptane-2-carboxylic acid tert-butyl ester (1.7 g). m/z: 460.9 (M+Na)$^+$.

3-[5-(4-Bromo-phenyl)-1H-imidazol-2-yl]-2-aza-bicyclo[2.2.1]heptane-2-carboxylic acid tert-butyl ester The mixture of 3-[2-(4-bromo-phenyl)-2-oxo-ethylcarbamoyl]-2-aza-bicyclo[2.2.1]heptane-2-carboxylic acid tert-butyl ester (1.7 g, 4 mmol), acetic acid (24 µl), and ammonium acetate (1.54 g, 20 mmol) in xylene (20 ml) was heated at 140° C. for 20 hours. The mixture was quenched with saturated sodium carbonate solution, and extracted with EtOAc. The organic phase was washed with water and brine, and was dried with sodium sulfate. Concentration and purification by flash column chromatography (hexanes/EtOAc) gave 3-[5-(4-bromo-phenyl)-1H-imidazol-2-yl]-2-aza-bicyclo[2.2.1]heptane-2-carboxylic acid tert-butyl ester (1.21 g). m/z: 417.9 (M+H)$^+$.

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester To the solution of 3-[5-(4-Bromo-phenyl)-1H-imidazol-2-yl]-2-aza-bicyclo[2.2.1]heptane-2-carboxylic acid tert-butyl ester (667 mg, 1.6 mmol) and bis(pinacolato)diboron (813 mg, 3.2 mmol) in 1,4-dioxane (12.5 ml) was added potassium acetate (401 mg, 4.1 mmol), followed by Pd(PPh$_3$)$_4$ (78 mg). The mixture was heated at 80° C. for 12 hours. The mixture was diluted with EtOAc, and was washed with water and brine, and was dried with sodium sulfate. Concentration and purification by flash column chromatography (hexanes/EtOAc) gave 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (560 mg). m/z: 466.1 (M+H)$^+$.

4,4'-Bis-[2-(2-tert-butoxycarbonyl-2-aza-bicyclo[2.2.1]hept-3-yl)-3H-imidazol-4-yl]-biphenyl To the solution of 3-{5-[4-(4,4,5,5-tetramethyl-[1,3,2]dioxaborolan-2-yl)-phenyl]-1H-imidazol-2-yl}-2-aza-bicyclo[2.2.1]heptane-2-carboxylic acid tert-butyl ester (560 mg, 1.22 mmol) and 3-[5-(4-bromo-phenyl)-1H-imidazol-2-yl]-2-aza-bicyclo[2.2.1]heptane-2-carboxylic acid tert-butyl ester (535 mg, 1.28 mmol) in 1,2-dimethoxyether (11 ml) and water (3.5 ml) was added sodium bicarbonate (343 mg, 4 mmol), followed by Pd(PPh$_3$)$_4$ (55 mg). The mixture was heated at 80° C. for 7 hours. The mixture was diluted with EtOAc, and was washed with water and brine, and was dried with sodium sulfate. Concentration and purification by flash column chromatography (DCM/MeOH) gave 4,4'-bis-[2-(2-tert-butoxycarbonyl-2-aza-bicyclo[2.2.1]hept-3-yl)-3H-imidazol-4-yl]-biphenyl (50 mg). m/z: 677.2 (M+H)$^+$.

(1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[2.2.1]heptane-2-carbonyl}-2-methyl-propyl)-carbamic acid methyl ester To the solution of 4,4'-Bis-[2-(2-tert-butoxycarbonyl-2-aza-bicyclo[2.2.1]hept-3-yl)-3H-imidazol-4-yl]-biphenyl (50 mg, 0.07 mmol) in MeOH (2 ml) was added hydrochloric acid (0.24 ml, 1.48 mmol) The mixture was heated at 50° C. for 5 hours, and the solvent and reagent were removed under reduced pressure. The mixture was diluted with acetonitrile and water, and was freezer-dried to give brown powder. m/z: 477.2 (M+1), 239.1 (M+2)/2. To the solution of above powder (29 mg, 0.047 mmol) and MeOCO-Val-OH (20 mg, 0.0.113 mmol) in DMF (1.5 ml) was added HATU (40 mg, 0.10 mmol), followed by diisopropylethylamine (50 ml, 0.28 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/C $H_3$CN/0.1% TFA/$H_2$O) gave (1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[2.2.1]heptane-2-carbonyl}-2-methyl-propyl)-carbamic acid methyl ester (15 mg). m/z: 791.2 (M+1), 396.5 (M+2)/2. $^1$H NMR (CD$_3$OD, 300 MHz) δ 7.92-7.82 (10H, m), 4.82 (2H, m), 4.32 (2H, m), 4.05 (2H, m), 3.65 (6H, m), 2.85 (2H, m), 2.3-1.6 (14H, m), 1.05-0.85 (12H, m).

Example AT

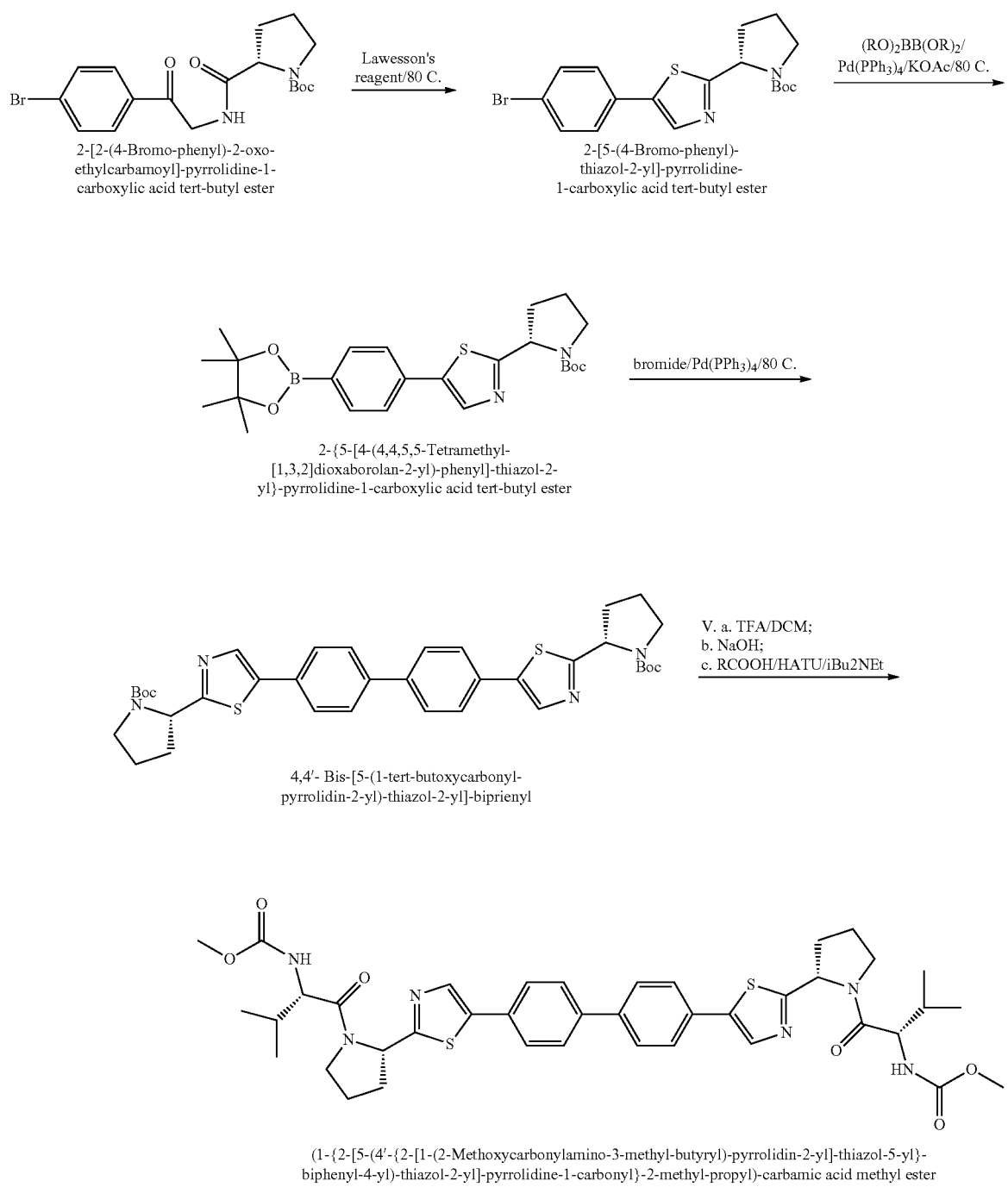

2-[5-(4-Bromo-phenyl)-thiazol-2-yl]-pyrrolidine-1-carboxylic acid tert-butyl ester The mixture of 2-[2-(4-Bromo-phenyl)-2-oxo-ethylcarbamoyl]-pyrrolidine-1-carboxylic acid tert-butyl ester (1.0 g, 2.44 mmol) and Lawesson's reagent (1.23 g, 3.0 mmol) in THF (16 ml) was heated at 80° C. for 4 hours. The solvent was removed under reduced pressure and the mixture was diluted with EtOAc. The organic phase was washed with saturated sodium bicarbonate, water, and brine, and was dried with sodium sulfate. Concentration and purification by flash column chromatography (hexanes/EtOAc) gave 2-[5-(4-Bromo-phenyl)-thiazol-2-yl]-pyrrolidine-1-carboxylic acid tert-butyl ester (655 mg). m/z: 410.7 (M+H)$^+$.

2-{5-[4-(4,4,5,5-Tetramethyl-[1,3,2]dioxaborolan-2-yl)-phenyl]-thiazol-2-yl}-pyrrolidine-1-carboxylic acid tert-butyl ester To the solution of 2-[5-(4-Bromo-phenyl)-thiazol-2-yl]-pyrrolidine-1-carboxylic acid tert-butyl ester (380 mg, 0.93 mmol) and bis(pinacolato)diboron (500 mg, 2.0 mmol) in 1,4-dioxane (7 ml) was added potassium acetate (240 mg, 2.1 mmol), followed by Pd(PPh$_3$)$_4$ (46 mg). The mixture was heated at 80° C. for 20 hours. The mixture was diluted with EtOAc, and was washed with water and brine, and was dried with sodium sulfate. Concentration and purification by flash column chromatography (hexanes/EtOAc) gave 2-{5-[4-(4,4,5,5-Tetramethyl-[1,3,2]dioxaborolan-2-yl)-phenyl]-thiazol-2-yl}-pyrrolidine-1-carboxylic acid tert-butyl ester (400 mg). m/z: 479.0 (M+Na)$^+$.

4,4'-Bis-[5-(1-tert-butoxycarbonyl-pyrrolidin-2-yl)-thiazol-2-yl]-biphenyl

To the solution of 2-{5-[4-(4,4,5,5-Tetramethyl-[1,3,2]dioxaborolan-2-yl)-phenyl]-thiazol-2-yl}-pyrrolidine-1-carboxylic acid tert-butyl ester (242 mg, 0.53 mmol) and 2-[5-(4-Bromo-phenyl)-thiazol-2-yl]-pyrrolidine-1-carboxylic acid tert-butyl ester (224 mg, 0.55 mmol) in 1,2-dimethoxy-ether (4.7 ml) and water (1.5 ml) was added sodium bicarbonate (150 mg, 1.8 mmol), followed by Pd(PPh$_3$)$_4$ (24 mg). The mixture was heated at 80° C. for 7 hours. The mixture was diluted with EtOAc, and was washed with water and brine, and was dried with sodium sulfate. Concentration and purification by flash column chromatography (DCM/MeOH) gave 4,4'-bis-[5-(1-tert-butoxycarbonyl-pyrrolidin-2-yl)-thiazol-2-yl]-biphenyl (270 mg).

(1-{2-[5-(4'-{2-[1-(2-Methoxycarbonylamino-3-methyl-butyryl)-pyrrolidin-2-yl]-thiazol-5-yl}-biphenyl-4-yl)-thiazol-2-yl]-pyrrolidine-1-carbonyl}-2-methyl-propyl)-carbamic acid methyl ester To the solution of 4,4'-Bis-[5-(1-tert-butoxycarbonyl-pyrrolidin-2-yl)-thiazol-2-yl]-biphenyl (270 mg) in DCM (4 ml) was added TFA (2 ml) The mixture was stirred for 4 hours, and the solvent and reagent were removed under reduced pressure. The mixture was diluted DCM, and 1.0 N sodium hydroxide solution was added until pH 11. The organic phase was separated and dried with sodium sulfate. Concentration gave a white solid (182 mg). To the solution of above powder (46 mg, 0.1 mmol) and MeOCO-Val-OH (42 mg, 0.24 mmol) in DMF (3 ml) was added HATU (84 mg, 0.22 mmol), followed by diisopropylethylamine (100 µl, 0.6 mmol). The mixture was stirred for 90 minutes and was diluted with EtOAc. The organic phase was washed with 1 N NaOH solution, water, and brine, and was dried with sodium sulfate. Concentration and purification by flash column chromatography (DCM/EtOAc) gave (1-{2-[5-(4'-{2-[1-(2-Methoxycarbonylamino-3-methyl-butyryl)-pyrrolidin-2-yl]-thiazol-5-yl}-biphenyl-4-yl)-thiazol-2-yl]-pyrrolidine-1-carbonyl]-2-methyl-propyl)-carbamic acid methyl ester (57 mg). m/z: 773.3 (M+1). $^1$H NMR (DMSO-d6, 300 MHz) δ 8.14 (2H, s), 7.8-7.6 (8H, m), 7.37 (2H, d, J=8.6 Hz), 5.32 (2H, m), 4.11 (2H, m), 3.80 (4H, m), 3.51 (6H, s), 2.3-1.9 (10H, m), 0.90 (12H, m).

Example AU

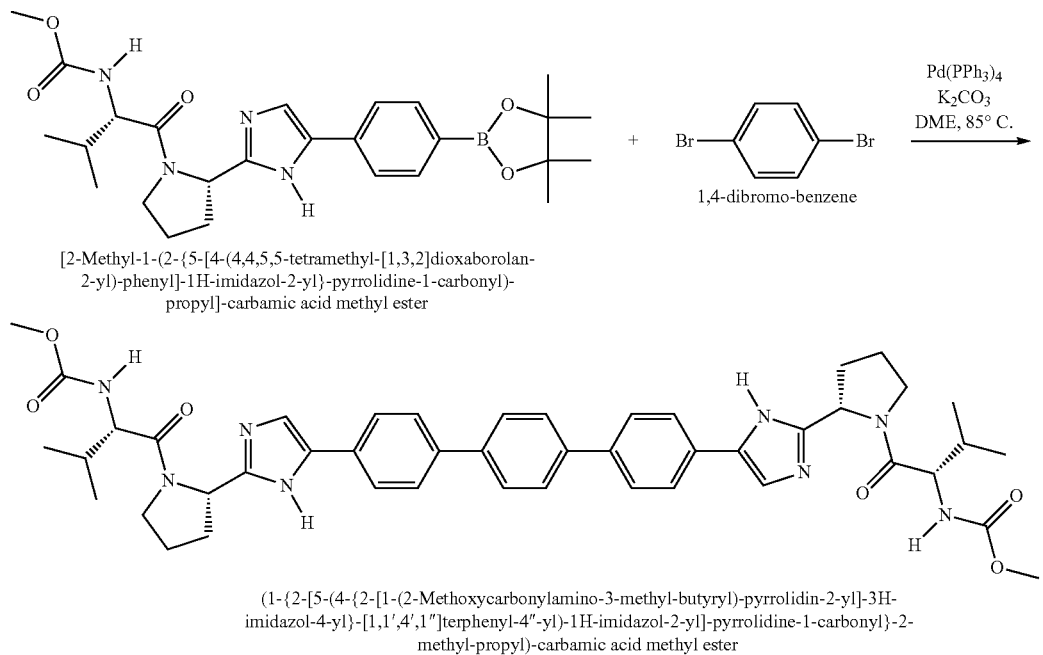

[2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (1-{2-[5-(4-{2-[1-(2-Methoxycarbonylamino-3-methyl-butyryl)-pyrrolidin-2-yl]-3H-imidazol-4-yl}-[1,1',4',1'']terphenyl-4''-yl)-1H-imidazol-2-yl]-pyrrolidine-1-carbonyl}-2-methyl-propyl)-carbamic acid methyl ester (1-{2-[5-(4-{2-[1-(2-Methoxycarbonylamino-3-methyl-butyryl)-pyrrolidin-2-yl]-3H-imidazol-4-yl}-[1,1';4',1"]terphenyl-4"-yl)-1H-imidazol-2-yl]-pyrrolidine-1-carbonyl}-2-methyl-propyl)-carbamic acid methyl ester A solution of [2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (300 mg, 0.60 mmol), 1,4-dibromo-benzene (95 mg, 0.40 mmol) and aqueous $K_2CO_3$ (800 µl of a 2M solution) in dimethoxyethane (4 mL) was degassed with $N_2$ gas for 20 minutes. To the degassed solution was added $Pd(PPh_3)_4$ and the reaction was heated to 85° C. overnight. After cooling to room temperature, the reaction was quenched with acetic acid, filtered, and then concentrated. The crude product was purified by reverse phase preparative HPLC (10-85% MeCN—$H_2O$; 0.1% formic acid modifier) to afford both the monosubstituted product (1-{2-[5-(4'-bromo-biphenyl-4-yl)-1H-imidazol-2-yl]-pyrrolidine-1-carbonyl}-2-methyl-propyl)-carbamic acid methyl ester (111 mg, 0.21 mmol, 53% yield) and the desired bis substituted product (1-{2-[5-(4-{2-[1-(2-methoxycarbonylamino-3-methyl-butyryl)-pyrrolidin-2-yl]-3H-imidazol-4-yl}-[1,1';4',1"]terphenyl-4"-yl)-1H-imidazol-2-yl]-pyrrolidine-1-carbonyl}-2-methyl-propyl)-carbamic acid methyl ester (24 mg, 0.074 mmol, 19% yield): $^1$H-NMR: 400 MHz, (DMSO-$d_6$) δ: 11.79 (s, 2H), 7.85-7.62 (m, 12H), 7.53 (s, 2H), 7.29 (d, 2H), 5.02 (m, 2H), 4.07 (t, 2H), 3.82 (m, 4H), 3.54 (s, 6H), 2.15-1.90 (m, 10H), 0.91 (d, 6H), 0.86 (d, 6H). LCMS-ESI$^+$: calc'd for $C_{46}H_{55}N_8O_6$: 815.4 (M+H)$^+$; Found: 815.7 (M+H)$^+$.

Example AV

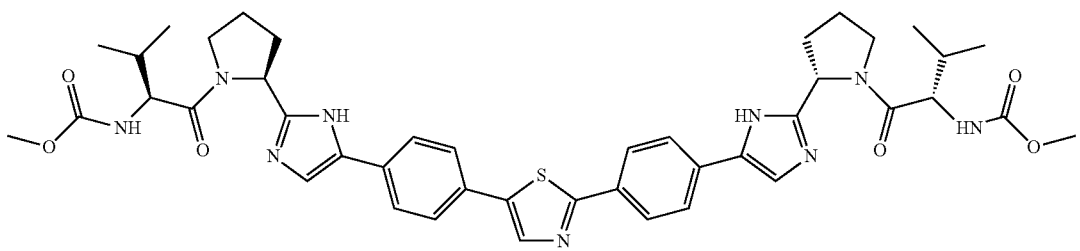

{1-[2-(5-{4-[5-(4-{2-[1-(2-Methoxycarbonylamino-3-methyl-butyryl)-pyrrolidin-2-yl]-3H-imidazol-4-yl}-phenyl)-thiazol-2-yl]-phenyl}-1H-imidazol-2-yl)-pyrrolidine-1-carbonyl]-2-methyl-propyl}-carbamic acid methyl ester {1-[2-(5-{4-[5-(4-{2-[1-(2-Methoxycarbonylamino-3-methyl-butyryl)-pyrrolidin-2-yl]-3H-imidazol-4-yl}-phenyl)-thiazol-2-yl]-phenyl}-1H-imidazol-2-yl)-pyrrolidine-1-carbonyl]-2-methyl-propyl}-carbamic acid methyl ester Title compound was prepared following the method detailed for (1-{2-[5-(4-{2-[1-(2-methoxycarbonylamino-3-methyl-butyryl)-pyrrolidin-2-yl]-3H-imidazol-4-yl}-[1,1';4',1"]terphenyl-4"-yl)-1H-imidazol-2-yl]-pyrrolidine-1-carbonyl}-2-methyl-propyl)-carbamic acid methyl ester, substituting 2,5-dibromo-thiazole for 2,6-dibromobenzene: $^1$H (DMSO-d6): δ=8.09 (s, 2H), 7.85 (m, 8H), 7.71 (s, 2H), 7.33 (d, J=11.2 Hz, 2H), 5.13 (t, J=8.8 Hz, 2H), 4.11 (t, J=10.4 Hz, 2H), 3.84 (m, 2H), 3.53 (s, 6H), 2.38 (m, 2H), 2.15 (m, 3H), 2.03 (m, 6H), 0.82 (m 12H). $C_{43}H_{51}N_9O_6S$ calculated 821.4 observed [M+H]$^+$ 822.6; rt=1.61 min Example AW

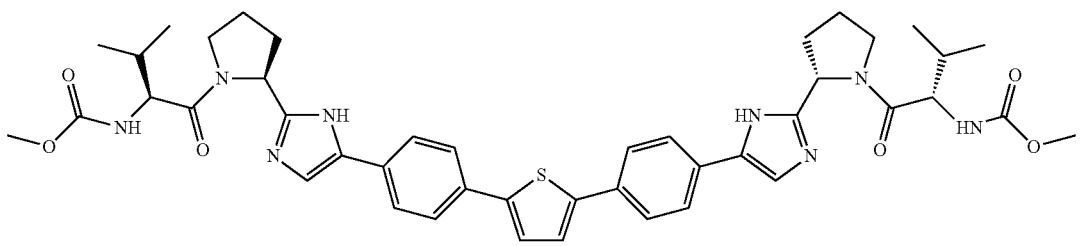

{1-[2-(5-{4-[5-(4-{2-[1-(2-Methoxycarbonylamino-3-methyl-butyryl)-pyrrolidin-2-yl]-3H-imidazol-4-yl}-phenyl)-thiophen-2-yl]-phenyl}-1H-imidazol-2-yl)-pyrrolidine-1-carbonyl]-2-methyl-propyl}-carbamic acid methyl ester

489

{1-[2-(5-{4-[5-(4-{2-[1-(2-Methoxycarbonylamino-3-methyl-butyryl)-pyrrolidin-2-yl]-3H-imidazol-4-yl}-phenyl)-thiophen-2-yl]-phenyl}-1H-imidazol-2-yl)-pyrrolidine-1-carbonyl]-2-methyl-propyl}-carbamic acid methyl ester

Title compound was prepared following the method detailed for (1-{2-[5-(4-{2-[1-(2-methoxycarbonylamino-3-methyl-butyryl)-pyrrolidin-2-yl]-3H-imidazol-4-yl]-[1,1';4',1"]terphenyl-4"-yl)-1H-imidazol-2-yl]-pyrrolidine-1-carbonyl}-2-methyl-propyl)-carbamic acid methyl ester, substituting 2,5-dibromo-thiophene for 2,6-dibromobenzene: $^1$H (DMSO-d6): δ=8.47 (s, 2H), 8.09 (m, 4H), 7.89 (m, 6H), 7.33 (d J=10.4 Hz, 2H), 5.12 (t, J=10.0 ZH, 2H), 4.10 (t, J=11.2 Hz, 2H), 3.82 (m, 2H), 3.61 (m, 4H), 2.37 (m, 2H), 2.10 (m, 9H), 0.822 (m, 12H). $C_{44}H_{52}N_8O_6S$ calculated 820.4 observed $[M+1]^+$ 821.8; rt=1.66 min

Example AX

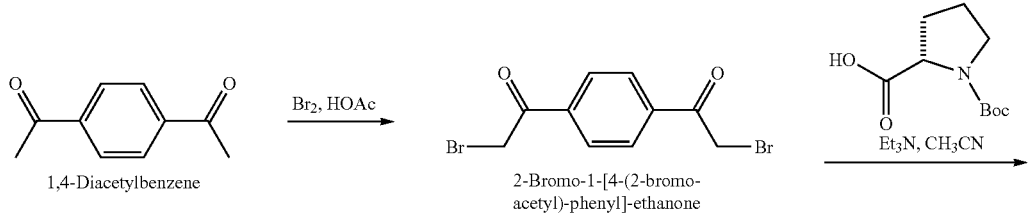

1,4-Diacetylbenzene → 2-Bromo-1-[4-(2-bromo-acetyl)-phenyl]-ethanone

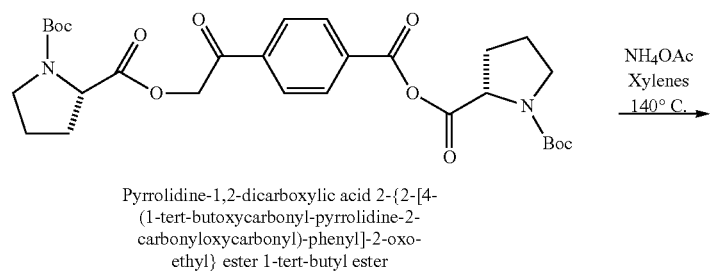

Pyrrolidine-1,2-dicarboxylic acid 2-{2-[4-(1-tert-butoxycarbonyl-pyrrolidine-2-carbonyloxycarbonyl)-phenyl]-2-oxo-ethyl} ester 1-tert-butyl ester

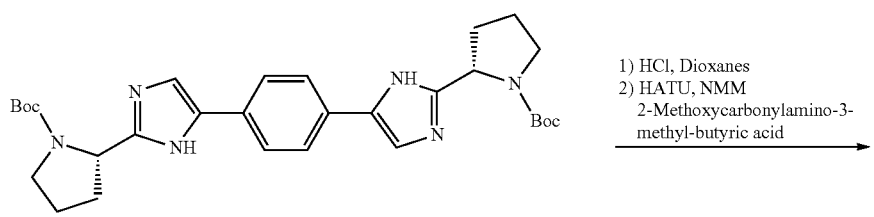

1-[2-(5-{4-[2-(1-tert-Butoxycarbonyl-pyrrolidin-2-yl)-3H-imidazol-4-yl]-phenyl}-1H-imidazol-2-yl)-pyrrolidin-1-yl]-ethanone 1) HCl, Dioxanes
2) HATU, NMM
   2-Methoxycarbonylamino-3-methyl-butyric acid

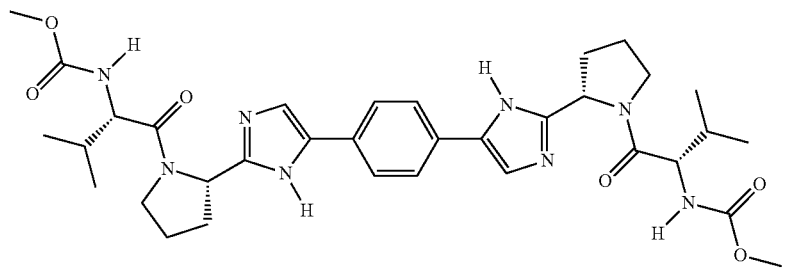

(1-{2-[5-(4-{2-[1-(2-Methoxycarbonylamino-3-methyl-butyryl)-pyrrolidin-2-yl]-3H-imidazol-4-yl}-phenyl)-1H-imidazol-2-yl]-pyrrolidine-1-carbonyl}-2-methyl-propyl)-carbamic acid methyl ester

2-Bromo-1-[4-(2-bromo-acetyl)-phenyl]-ethanone

To a solution of $Br_2$ (1.27 mL, 24.66 mmol) in HOAc (12 mL) was added 1,4-diacetylbenzene (2.00 g, 12.33 mmol). After stirring for 2 h, the reaction was diluted with water and the precipitate collected by filtration. The crude product was then recrystallized from toluene to afford 2-bromo-1-[4-(2-bromo-acetyl)-phenyl]-ethanone (2.87 g, 8.97 mmol, 73% yield). $^1$H-NMR: 400 MHz, (DMSO-$d_6$) δ: 8.13 (s, 4H), 5.01 (s, 4H).

Pyrrolidine-1,2-dicarboxylic acid 2-{2-[4-(1-tert-butoxycarbonyl-pyrrolidine-2-carbonyloxycarbonyl)-phenyl]-2-oxo-ethyl}ester 1-tert-butyl ester A suspension of 2-bromo-1-[4-(2-bromo-acetyl)-phenyl]-ethanone (2.87 g, 8.97 mmol) in $CH_3CN$ (15 mL) was added dropwise to a solution of pyrrolidine-1,2-dicarboxylic acid 1-tert-butyl ester (3.85 g, 17.9 mmol) and triethylamine (2.49 mL, 17.9 mmol) in $CH_3CN$ (30 mL). The reaction was stirred for 4 hours then concentrated and purified by silica gel chromatography (20-60% EtOAc-hexanes gradient) to afford pyrrolidine-1,2-dicarboxylic acid 2-{2-[4-(1-tert-butoxycarbonyl-pyrrolidine-2-carbonyloxycarbonyl)-phenyl]-2-oxo-ethyl}ester 1-tert-butyl ester (4.91 g, 8.34 mmol, 93% yield). $^1$H-NMR: 400 MHz, (DMSO-$d_6$) δ: 8.11 (s, 4H), 5.69-5.50 (m, 4H), 4.37-4.32 (m, 2H), 3.42-3.29 (m, 6H), 2.34-2.24 (m, 2H), 2.14-2.10 (m, 2H), 1.92-1.82 (m, 4H), 1.40 (s, 9H), 1.37 (s, 9H).

1-[2-(5-{4-[2-(1-tert-Butoxycarbonyl-pyrrolidin-2-yl)-3H-imidazol-4-yl]-phenyl}-1H-imidazol-2-yl)-pyrrolidin-1-yl]-ethanone A solution of pyrrolidine-1,2-dicarboxylic acid 2-{2-[4-(1-tert-butoxycarbonyl-pyrrolidine-2-carbonyloxycarbonyl)-phenyl]-2-oxo-ethyl}ester 1-tert-butyl ester (4.91 g, 8.35 mmol) and ammonium acetate (6.44 g, 8.36 mmol) in xylenes (42 mL) was heated to 140° C. overnight in a sealed pressure flask. After cooling to room temperature, the reaction was diluted with EtOAc and washed with saturated $NaHCO_3$ and brine. The organic layer was dried over $Na_2SO_4$ then concentrated. The crude material was purified by silica gel chromatography (3-10% MeOH—$CH_2Cl_2$ gradient) to afford 1-[2-(5-{4-[2-(1-tert-butoxycarbonyl-pyrrolidin-2-yl)-3H-imidazol-4-yl]-phenyl}-1H-imidazol-2-yl)-pyrrolidin-1-yl]ethanone (1.58 g, 2.87 mmol, 34% yield). LCMS-ESI$^+$: calc'd for $C_{30}H_{41}N_6O_4$: 549.3 (M+H$^+$); Found: 549.3 (M+H$^+$).

(1-{2-[(5-(4-{2-[1-(2-Methoxycarbonylamino-3-methyl-butyryl)-pyrrolidin-2-yl]-3H-imidazol-4-yl}-phenyl)-1H-imidazol-2-yl]-pyrrolidine-1-carbonyl}-2-methyl-propyl)-carbamic acid methyl ester To 1-[2-(5-{4-[2-(1-tert-butoxycarbonyl-pyrrolidin-2-yl)-3H-imidazol-4-yl]-phenyl}-1H-imidazol-2-yl)-pyrrolidin-1-yl]-ethanone (500 mg, 0.91 mmol) in dioxanes (5 mL) was added 4N HCl in dioxanes (3 mL). The suspension was stirred for 2 hours then concentrated to afford the HCl salt of the crude amine (530 mg). To a portion of the crude amine (200 mg, 0.41 mmol) in DMF (2 mL) was added N-methylmorpholine (270 μl, 2.44 mmol). After all material dissolved, 2-methoxycarbonylamino-3-methyl-butyric acid (144 mg, 0.82 mmol) and HATU (312 mg, 0.82 mmol) were added. After stirring for 1 hour the reaction was quenched with AcOH then purified by reverse phase preparative HPLC (10-85% MeCN—$H_2O$; 0.1% formic acid modifier) to afford (1-{2-[5-(4-{2-[1-(2-Methoxycarbonylamino-3-methyl-butyryl)-pyrrolidin-2-yl]-3H-imidazol-4-yl}-phenyl)-1H-imidazol-2-yl]-pyrrolidine-1-carbonyl}-2-methyl-propyl)-carbamic acid methyl ester (56 mg, 0.085 mmol, 21% yield). $^1$H-NMR: 400 MHz, (DMSO-$d_6$) δ: 11.68 (s, 2H), 7.62 (m, 4H), 7.41 (s, 2H), 7.27 (d, 2H), 5.07-5.05 (m, 2H), 4.06 (t, 2H), 3.80 (m, 4H), 3.54 (s, 6H), 2.13 (m, 4H), 1.95 (m, 6H), 0.90 (d, 6H), 0.85 (d, 6H). LCMS-ESI$^+$: calc'd for $C_{34}H_{47}N_8O_6$: 663.4 (M+H$^+$); Found: 663.1 (M+H$^+$).

Example AY

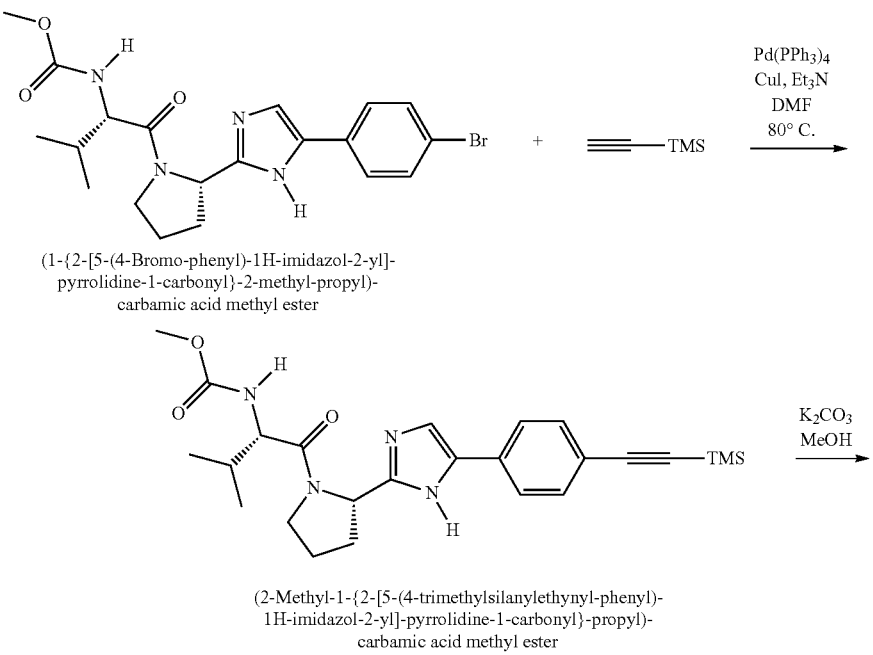

(1-{2-[5-(4-Bromo-phenyl)-1H-imidazol-2-yl]-pyrrolidine-1-carbonyl}-2-methyl-propyl)-carbamic acid methyl ester (2-Methyl-1-{2-[5-(4-trimethylsilanylethynyl-phenyl)-1H-imidazol-2-yl]-pyrrolidine-1-carbonyl}-propyl)-carbamic acid methyl ester

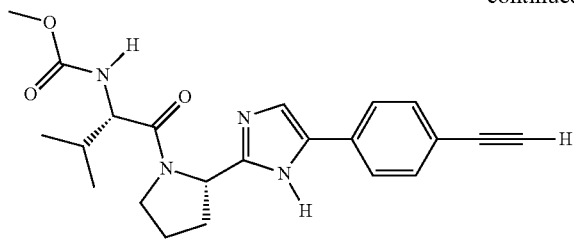

(1-{2-[5-(4-Ethynyl-phenyl)-1H-imidazol-2-yl]-pyrrolidine-1-carbonyl}-2-methyl-propyl)-carbamic acid methyl ester Pd(PPh₃)₄, CuI, Et₃N,
(1-{2-[5-(4-Bromo-phenyl)-1H-imidazol-2-yl]-pyrrolidine-1-carbonyl}-2-methyl-propyl)-carbamic acid methyl ester
DMF, 80° C.

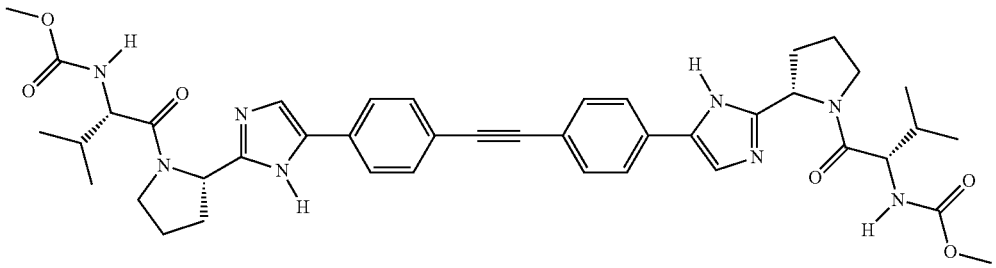

[1-(2-{5-(4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester

(2-Methyl-1-{2-[5-(4-trimethylsilanylethynyl-phenyl)-1H-imidazol-2-yl]-pyrrolidine-1-carbonyl}-propyl)-carbamic acid methyl ester A solution of (1-{2-[5-(4-bromo-phenyl)-1H-imidazol-2-yl]-pyrrolidine-1-carbonyl}-2-methyl-propyl)-carbamic acid methyl ester (5.00 g, 11.1 mmol), TMS-acetylene (7.90 mL, 55.5 mmol) and triethylamine (4.64 mL, 33.3 mmol) in DMF (56 mL) was degassed with $N_2$ gas for 20 minutes. To the degassed solution was added Pd(PPh₃)₄ (1.28 g, 1.11 mmol) and CuI (106 mg, 0.56 mmol). The pressure flask was sealed then heated at 80° C. overnight. After cooling to room temperature, the reaction was concentrated then diluted with EtOAc and washed with water. The aqueous phase was back-extracted two times then the organic phases were combined and dried over $Na_2SO_4$. After concentration, the crude material was purified by silica gel chromatography (10-80% EtOAc-hexanes gradient) to afford (2-methyl-1-{2-[5-(4-trimethylsilanylethynyl-phenyl)-1H-imidazol-2-yl]-pyrrolidine-1-carbonyl}-propyl)-carbamic acid methyl ester (3.08 g, 6.60 mmol, 59% yield). LCMS-ESI⁺: calc'd for $C_{25}H_{35}N_4O_3Si$: 467.3 (M+H⁺); Found: 467.1 (M+H⁺).

(1-{2-[5-(4-Ethynyl-phenyl)-1H-imidazol-2-yl]-pyrrolidine-1-carbonyl}-2-methyl-propyl)-carbamic acid methyl ester To (2-methyl-1-{2-[5-(4-trimethylsilanylethynyl-phenyl)-1H-imidazol-2-yl]-pyrrolidine-1-carbonyl}-propyl)-carbamic acid methyl ester (3.08 g, 6.60 mmol) in MeOH was added $K_2CO_3$ (1.82 g, 13.2 mmol). After stirring for 5 h, the reaction was filtered then concentrated. The residue was diluted with EtOAc then washed with $H_2O$. The aqueous phase was back-extracted with EtOAc two times then the organic phases were combined, washed with brine, dried over $Na_2SO_4$, and concentrated. The crude material was purified by silica gel chromatography (5-10% MeOH—$CH_2Cl_2$ gradient) to afford (1-{2-[5-(4-ethynyl-phenyl)-1H-imidazol-2-yl]-pyrrolidine-1-carbonyl}-2-methyl-propyl)-carbamic acid methyl ester (2.62 g, 6.6 mmol, quantitative yield). LCMS-ESI⁺: calc'd for $C_{22}H_{27}N_4O_3$: 395.2 (M+H⁺); Found: 395.2 (M+H⁺).

[1-(2-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester A solution of (1-{2-[5-(4-bromo-phenyl)-1H-imidazol-2-yl]-pyrrolidine-1-carbonyl}-2-methyl-propyl)-carbamic acid methyl ester (947 mg, 2.11 mmol), (1-{2-[5-(4-ethynyl-phenyl)-1H-imidazol-2-yl]-pyrrolidine-1-carbonyl}-2-methyl-propyl)-carbamic acid methyl ester (1.00 g, 2.53 mmol), and triethylamine (882 µl, 6.33 mmol) in DMF (13 mL) was degassed with $N_2$ gas for 20 minutes. To the degassed solution was added Pd(PPh₃)₄ (244 mg, 0.21 mmol) and CuI (40 mg, 0.21 mmol). The pressure flask was sealed then heated at 80° C. overnight. After cooling to room temperature, the reaction was concentrated then diluted with EtOAc and washed with water. The aqueous phase was back-extracted two times then the organic phases were combined and dried over $Na_2SO_4$. After concentration, the crude material was purified by silica gel chromatography (0-20% MeOH-EtOAc gradient) then reverse phase preparative HPLC (10-85% MeCN—$H_2O$; 0.1% formic acid modifier) to afford [1-(2-{5-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester (600 mg, 1.00 mmol, 47% yield). ¹H-NMR: 400 MHz, (DMSO-d₆) δ: 11.84 (s, 2H), 7.75 (d, 4H), (7.56 (s, 2H), 7.47 (d, 4H), 7.28 (d, 2H), 5.06 (m, 2H), 4.06-4.04 (m, 2H), 3.80 (m, 4H), 3.54 (s, 6H), 2.14 (m, 4H) 2.00-1.90 (m, 6H), 0.89 (d, 6H), 0.84 (d, 6H). LCMS-ESI⁺: calc'd for $C_{42}H_{51}N_8O_6$: 763.4 (M+H⁺); Found: 763.4 (M+H⁺).

Example AZ

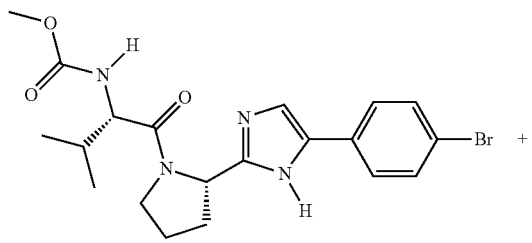

(1-{2-[5-(4-Bromo-phenyl)-1H-imidazol-2-yl]-
pyrrolidine-1-1carbonly}-2-methyl-propyl)-
carbamic acid methyl ester

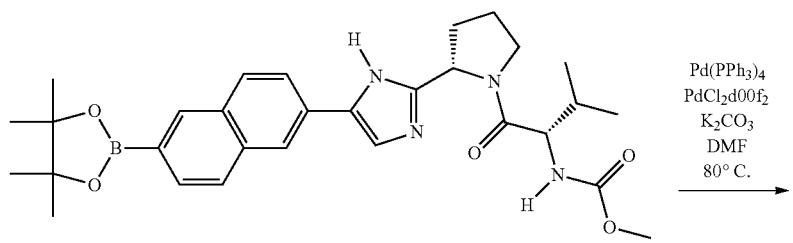

[2-Methyl-1-(2-{5-[6-(4,4,5,5-tetramethyl-
[1,3,2]dioxaborolan-2-yl)-naphthalen-2-yl]-1H-imidazol-2-yl}-
pyrrolidine-1-carbonly)-propyl]-carbamic aid methyl ester

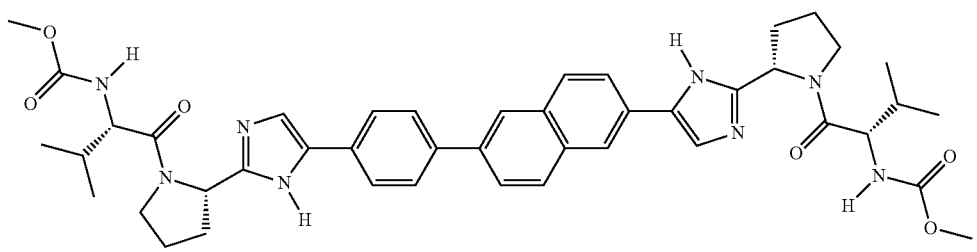

[1-(2-{5-[6-(4-{2-[1-(2-Methoxycarbonlyamino-3-methyl-butyryl)-pyrrolidin-2-yl]-3H-
imidazol-4-yl}-phenyl)-napthalen-2-yl]-1H-imidazol-2-yl}-pyrrolidine-1-carbonly)-2-
methyl-propyl]-carbamic acid methyl ester

[1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester A solution of (1-{2-[5-(4-bromo-phenyl)-1H-imidazol-2-yl]-pyrrolidine-1-carbonyl}-2-methyl-propyl)-carbamic acid methyl ester (244 mg, 0.54 mmol), [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (270 mg, 0.49 mmol) and aqueous $K_2CO_3$ (490 µl of a 2M solution, 0.98 mmol) in toluene (3 mL) and DMF (1 mL) was degassed with $N_2$ gas for 20 minutes. To the degassed solution was added $Pd(PPh_3)_4$ (31 mg, 0.027 mmol) and $PdCl_2(dppf)$ (20 mg, 0.027 mmol) then the reaction was heated to 80° C. overnight. After cooling to room temperature, the reaction was quenched with acetic acid, filtered, and then concentrated. The crude product was purified by reverse phase preparative HPLC (10-85% MeCN—$H_2O$; 0.1% formic acid modifier) to afford [1-(2-{5-[6-(4-{2-[1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (149 mg, 0.19 mmol, 35% yield). $^1$H-NMR: 400 MHz, (DMSO-$d_6$) δ: 11.82 (s, 1H), 11.79 (s, 1H), 8.21-8.16 (m, 2H), 7.92-7.79 (m, 8H), 7.62 (s, 1H), 7.54 (s, 1H), 7.31-7.29 (m, 2H), 5.10 (m, 2H), 4.09-4.07 (m, 2H), 3.82 (m, 4H), 3.54 (s, 6H), 2.20-1.85 (m, 10H), 0.95-0.86 (m, 12H). LCMS-ESI$^+$: calc'd for $C_{44}H_{53}N_8O_6$: 789.4 (M+H$^+$); Found: 789.2 (M+H$^+$).

Example AA1

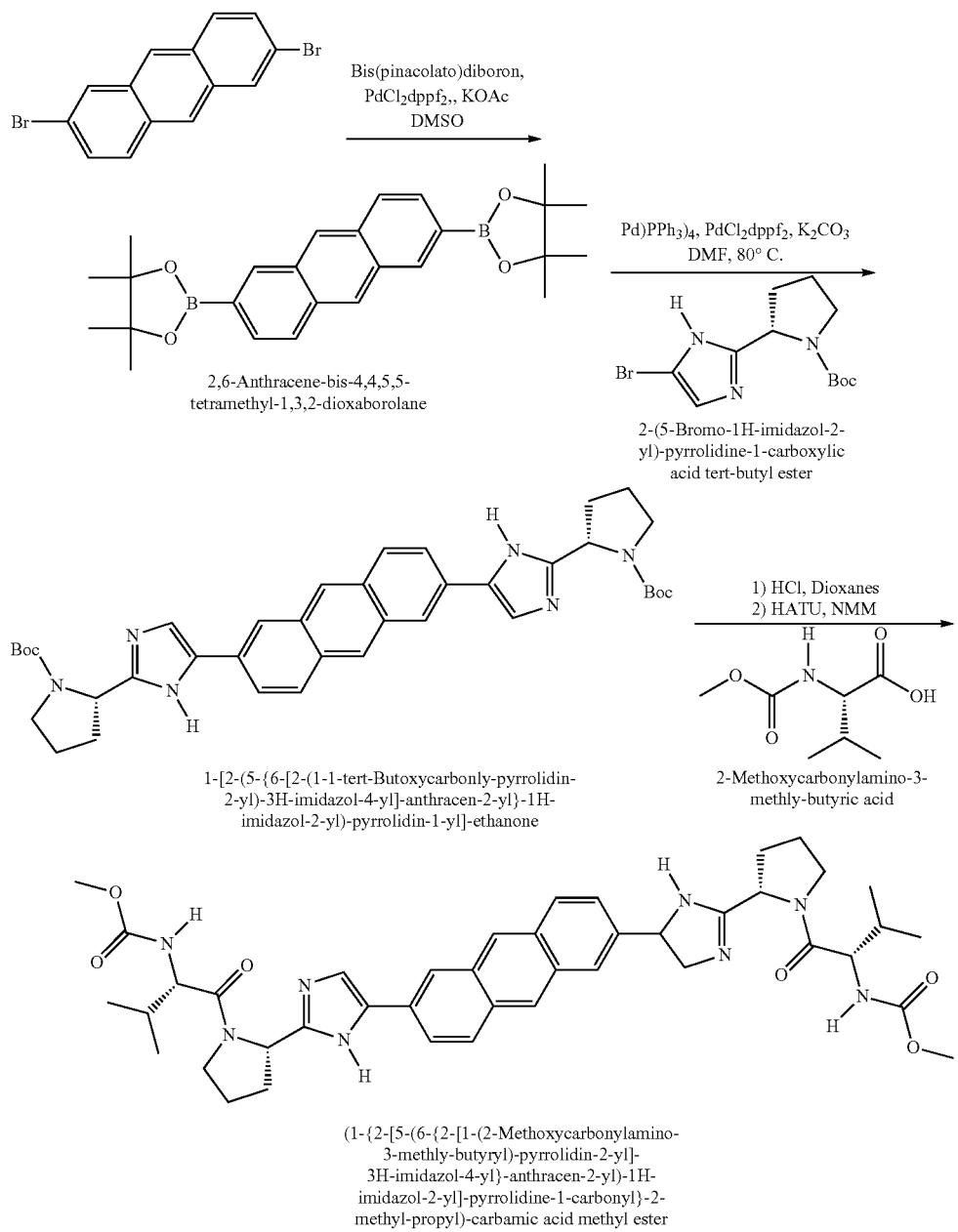

2,6-Anthracene-bis-4,4,5,5-tetramethyl-1,3,2-dioxaborolane

A mixture of 2,6-dibromoanthracene (500 mg, 1.49 mmol), bis(pinacolato)diboron (756 mg, 2.98 mmol) and KOAc (585 mg, 5.96 mmol) in DMSO (10 mL) was degassed with $N_2$ gas for 20 minutes. To the degassed solution was added $PdCl_2(dppf)$ (55 mg, 0.075 mmol) then the reaction was heated to 80° C. overnight. After cooling to room temperature, the reaction was poured into $H_2O$ and extracted with $CH_2Cl_2$. The organic phase was collected then washed with $H_2O$ and brine. After drying over $Na_2SO_4$, the organic phase was concentrated then purified by silica gel chromatography (30-100% $CH_2Cl_2$-hexanes gradient) to afford 2,6-anthracene-bis-4,4,5,5-tetramethyl-1,3,2-dioxaborolane (241 mg, 0.56 mmol, 38% yield). $^1$H-NMR: 400 MHz, (DMSO-$d_6$) δ: 8.57 (s, 2H), 8.46 (s, 2H), 8.00 (d, 2H), 7.79 (d, 2H).

1-[2-(5-{6-[2-(1-1-tert-Butoxycarbonyl-pyrrolidin-2-yl)-3H-imidazol-4-yl]-anthracen-2-yl}-1H-imidazol-2-yl)-pyrrolidin-1-yl]-ethanone A solution of 2,6-anthracene-bis-4,4,5,5-tetramethyl-1,3,2-dioxaborolane (241 mg, 0.56 mmol), 2-(5-bromo-1H-imidazol-2-yl)-pyrrolidine-1-carboxylic acid tert-butyl ester (531 mg, 1.68 mmol) and aq $K_2CO_3$ (1.12 mL of a 2M solution, 2.24 mmol) in toluene (6 mL) and DMF (1 mL) was degassed with $N_2$ gas for 20 minutes. To the degassed solution was added Pd(PPh$_3$)$_4$ (32 mg, 0.028 mmol) and PdCl$_2$(dppf) (21 mg, 0.028 mmol) then the reaction was heated to 80° C. overnight. After cooling to room temperature, the reaction was concentrated. The crude material was diluted with EtOAc then washed with saturated NaHCO$_3$. The aqueous phase was back-extracted two times then the organic layers were combined, dried over Na$_2$SO$_4$, and concentrated. The crude product was purified by reverse phase preparative HPLC (20-80% MeCN—H$_2$O; 0.1% formic acid modifier) to afford 1-[2-(5-{6-[2-(1-1-tert-butoxycarbonyl-pyrrolidin-2-yl)-3H-imidazol-4-yl]-anthracen-2-yl}-1H-imidazol-2-yl)-pyrrolidin-1-yl]-ethanone (117 mg, 0.18 mmol, 32% yield). LCMS-ESI$^+$: calc'd for C$_{38}$H$_{45}$N$_6$O$_4$: 649.4 (M+H$^+$); Found: 648.9 (M+H$^+$).

(1-{2-[5-(6-{2-[1-(2-Methoxycarbonylamino-3-methyl-butyryl)-pyrrolidin-2-yl]-3H-imidazol-4-yl}-anthracen-2-yl)-1H-imidazol-2-yl]-pyrrolidine-1-carbonyl}-2-methyl-propyl)-carbamic acid methyl ester To 1-[2-(5-{6-[2-(1-1-tert-butoxycarbonyl-pyrrolidin-2-yl)-3H-imidazol-4-yl]-anthracen-2-yl}-1H-imidazol-2-yl)-pyrrolidin-1-yl]-ethanone (117 mg, 0.18 mmol) in dioxanes (5 mL) was added 4N HCl in dioxanes (180 µl, 0.72 mmol). The suspension overnight then concentrated to afford the HCl salt of the crude amine. To the amine in DMF (3 mL) was added N-methylmorpholine (119 µl, 1.08 mmol). After all the material dissolved, 2-methoxycarbonylamino-3-methyl-butyric acid (76 mg, 0.43 mmol) and HATU (151 mg, 0.40 mmol) were added. After stirring overnight the reaction was quenched with AcOH then purified by reverse phase preparative HPLC (15-70% MeCN—H$_2$O; 0.1% formic acid modifier) to afford (1-{2-[5-(6-{2-[1-(2-methoxycarbonylamino-3-methyl-butyryl)-pyrrolidin-2-yl]-3H-imidazol-4-yl}-anthracen-2-yl)-1H-imidazol-2-yl]-pyrrolidine-1-carbonyl}-2-methyl-propyl)-carbamic acid methyl ester (46 mg, 0.098 mmol, 54% yield). $^1$H-NMR: 400 MHz, (DMSO-d$_6$) δ: 11.84 (s, 2H), 8.38 (s, 2H), 8.31 (s, 2H), 8.00 (d, 2H), 7.86 (d, 2H), 7.62 (s, 2H), 7.30 (d, 2H), 5.12 (m, 2H), 4.10 (m, 2H), 3.84 (m, 4H), 3.55 (s, 6H), 2.18-1.95 (m, 10H), 0.96 (d, 6H), 0.88 (d, 6H). LCMS-ESI$^+$: calc'd for C$_{42}$H$_{51}$N$_8$O$_6$: 763.4 (M+H$^+$); Found: 763.1 (M+H$^+$).

Example AB1

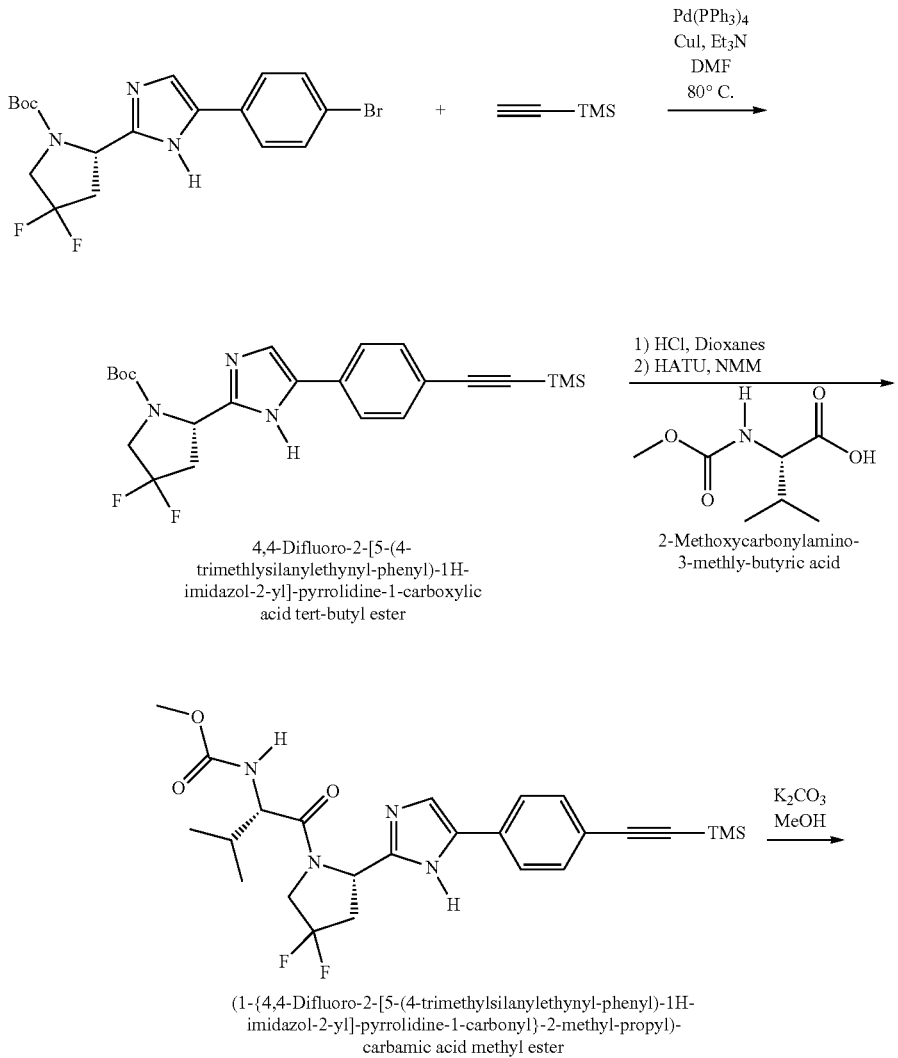

4,4-Difluoro-2-[5-(4-trimethlysilanylethynyl-phenyl)-1H-imidazol-2-yl]-pyrrolidine-1-carboxylic acid tert-butyl ester 2-Methoxycarbonylamino-3-methly-butyric acid (1-{4,4-Difluoro-2-[5-(4-trimethylsilanylethynyl-phenyl)-1H-imidazol-2-yl]-pyrrolidine-1-carbonyl}-2-methyl-propyl)-carbamic acid methyl ester -continued

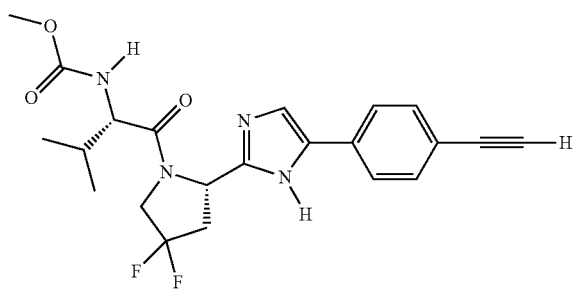

(1-{2-[5-(4-Ethynyl-phenyl)-1H-imidazol-2-yl]-4,4-difluoro-
pyrrolidine-1-carbonyl}-2-methyl-propyl)-carbamic acid
methyl ester Pd(PPh₃)₄, CuI, Et₃N,
(1-{2-[5-(4-Bromo-phenyl)-1H-
imidazol-2-yl]-pyrrolidine-1-carbonyl}-
2-methyl-propyl)pcarbamic acid
methyl ester
DMF, 80° C.

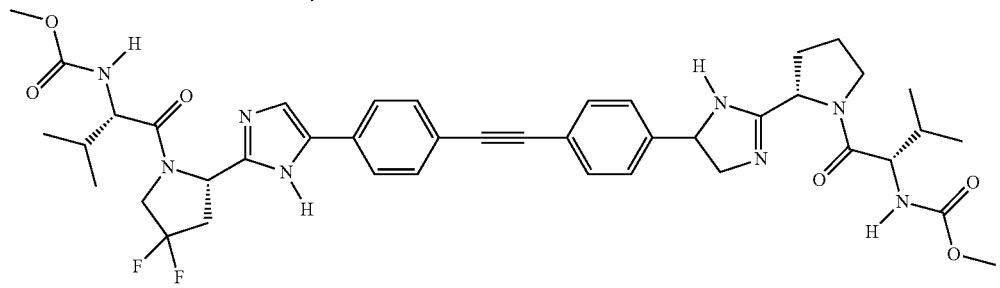

[1-(2-{5-[4-(4-{2-[4,4-Difluoro-1-(2-methoxycarbonylamino-3-methyl-butyryl)-pyrrolidin-2-yl]-
3H-imidazol-4-yl}-phenylethynyl)-phenyl]-1H-imidazol-2-yl}-pyrrolidine-1-carbonyl)-2-
methyl-propyl]-carbamic acid methyl ester

4,4-Difluoro-2-[5-(4-trimethylsilanylethynyl-phenyl)-1H-imidazol-2-yl]-pyrrolidine-1-carboxylic acid tert-butyl ester A solution of 2-[5-(4-bromo-phenyl)-1H-imidazol-2-yl]-4,4-difluoro-pyrrolidine-1-carboxylic acid tert-butyl ester (700 mg, 1.56 mmol), TMS-acetylene (1.11 mL, 7.79 mmol) and triethylamine (1.1 mL, 7.8 mmol) in DMF (8 mL) was degassed with $N_2$ gas for 20 minutes. To the degassed solution was added Pd(PPh₃)₄ (180 mg, 0.16 mmol) and CuI (14.8 mg, 0.078 mmol). The pressure flask was sealed then heated at 80° C. overnight. After cooling to room temperature, the reaction was concentrated then diluted with EtOAc and washed with water. The aqueous phase was back-extracted two times then the organic phases were combined and dried over $Na_2SO_4$. After concentration, the crude material was purified by silica gel chromatography (10-50% EtOAc-hexanes gradient) to afford 4,4-difluoro-2-[5-(4-trimethylsilanylethynyl-phenyl)-1H-imidazol-2-yl]-pyrrolidine-1-carboxylic acid tert-butyl ester (547 g, 1.23 mmol, 79% yield). LCMS-ESI⁺: calc'd for $C_{23}H_{30}F_2N_3O_2Si$: 446.2 (M+H⁺); Found: 445.8 (M+H⁺).

(1-{4,4-Difluoro-2-[5-(4-trimethylsilanylethynyl-phenyl)-1H-imidazol-2-yl]-pyrrolidine-1-carbonyl}-2-methyl-propyl)-carbamic acid methyl ester To 4,4-difluoro-2-[5-(4-trimethylsilanylethynyl-phenyl)-1H-imidazol-2-yl]-pyrrolidine-1-carboxylic acid tert-butyl ester (547 mg, 1.23 mmol) in dioxanes (6 mL) was added 4N HCl in dioxanes (1.65 mL, 6.6 mmol). The suspension was stirred overnight then concentrated to afford the HCl salt of the crude amine. To the amine in DMF (5 mL) was added N-methylmorpholine (406 µl, 3.69 mmol). After all the material dissolved, 2-methoxycarbonylamino-3-methyl-butyric acid (236 mg, 1.35 mmol) and HATU (513 mg, 1.35 mmol) were added. After stirring for 2 hours the reaction was concentrated then diluted with EtOAc and washed with $H_2O$. The aqueous phase was back-extracted two times then the organic layers were combined, dried over $Na_2SO_4$, and concentrated. The crude product was purified by silica gel chromatography (20-60% EtOAc-hexanes gradient) to afford (1-{4,4-difluoro-2-[5-(4-trimethylsilanylethynyl-phenyl)-1H-imidazol-2-yl]-pyrrolidine-1-carbonyl}-2-methyl-propyl)-carbamic acid methyl ester (412 mg, 0.82 mmol, 67% yield). LCMS-ESI⁺: calc'd for $C_{25}H_{33}F_2N_4O_3Si$: 503.2 (M+H⁺); Found: 503.2 (M+H⁺).

(1-{2-[5-(4-Ethynyl-phenyl)-1H-imidazol-2-yl]-4,4-difluoro-pyrrolidine-1-carbonyl}-2-methyl-propyl)-carbamic acid methyl ester To (1-{4,4-difluoro-2-[5-(4-trimethylsilanylethynyl-phenyl)-1H-imidazol-2-yl]-pyrrolidine-1-carbonyl}-2-methyl-propyl)-carbamic acid methyl ester (412 mg, 0.82 mmol) in MeOH (8 mL) was added $K_2CO_3$ (227 mg, 1.64 mmol). After stirring for 5 h, the reaction was filtered then concentrated. The residue was diluted with EtOAc then washed with $H_2O$. The aqueous phase was back-extracted with EtOAc two times then the organic phases were combined, washed with brine, dried over $Na_2SO_4$, and concentrated. The crude material was purified by silica gel chromatography (20-80% EtOAc-hexanes gradient) to afford (1-{2-[5-(4-ethynyl-phenyl)-1H-imidazol-2-yl]-pyrrolidine-1-carbonyl}-2-methyl-propyl)-carbamic acid methyl ester (371 mg, 0.82 mmol, quantitative yield). LCMS-ESI⁺: calc'd for $C_{22}H_{25}F_2N_4O_3$: 431.2 (M+H⁺); Found: 431.1 (M+H⁺).

[1-(2-{5-[4-(4-{2-[4,4-Difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester A solution of (1-{2-[5-(4-bromo-phenyl)-1H-imidazol-2-yl]-pyrrolidine-1-carbonyl}-2-methyl-propyl)-carbamic acid methyl ester (400 mg, 0.89 mmol), (1-{2-[5-(4-ethynyl-phenyl)-1H-imidazol-2-yl]-pyrrolidine-1-carbonyl}-2-methyl-propyl)-carbamic acid methyl ester (371 mg, 0.89 mmol), and triethylamine (372 µl, 2.67 mmol) in DMF (8 mL) was degassed with $N_2$ gas for 20 minutes. To the degassed solution was added Pd(PPh$_3$)$_4$ (103 mg, 0.089 mmol) and CuI (17 mg, 0.089 mmol). The pressure flask was sealed then heated at 80° C. overnight. After cooling to room temperature, the reaction was quenched with AcOH then purified by reverse phase preparative HPLC (10-70% MeCN—H$_2$O; 0.1% formic acid modifier) then silica gel chromatography (0-10% MeOH-EtOAc gradient) to afford [1-(2-{5-[4-(4-{2-[4,4-difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester (231 mg, 0.29 mmol, 33% yield). $^1$H-NMR: 400 MHz, (DMSO-d$_6$) δ: 12.04 (s, 1H), 11.84 (s, 1H), 7.78-7.76 (m, 4H), 7.61 (s, 1H), 7.56 (s, 1H), 7.50-7.48 (m, 6H), 7.28 (d, 2H), 5.29 (t, 1H), 5.07 (m, 1H), 4.52 (m, 1H), 4.24-4.14 (m, 1H), 4.06 (t, 1H), 3.93 (t, 1H), 3.80 (m, 2H), 3.55 (s, 3H), 3.54 (s, 3H), 2.93 (m, 1H), 2.77 (m, 1H), 2.14-1.88 (m, 6H), 0.90-0.84 (m, 12H). LCMS-ESI$^+$: calc'd for $C_{42}H_{49}N_8O_6$: 799.4 (M+H$^+$); Found: 799.0 (M+H$^+$).

Example AC1

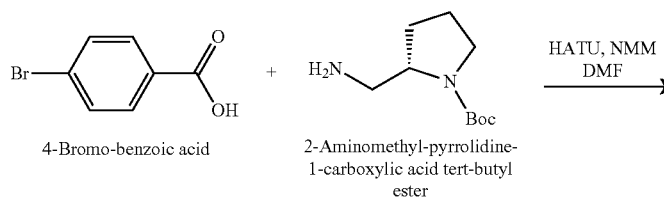

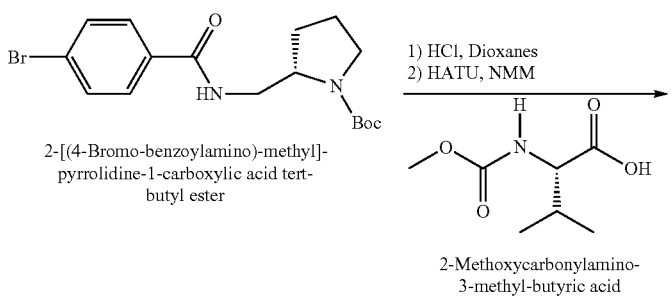

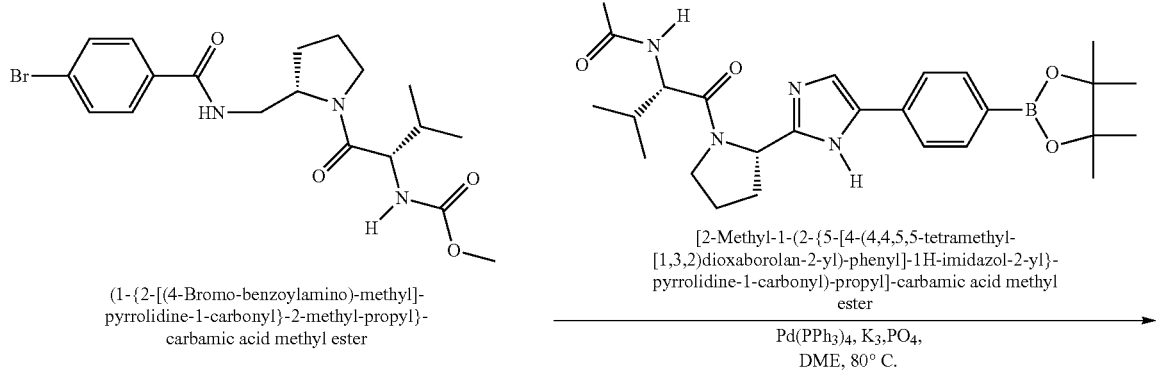

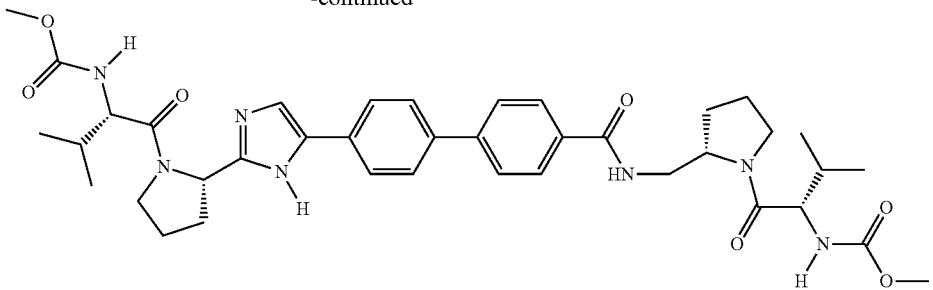

[1-(2-{[(4'-{2-[1-2-Methoxycarbonylamino-3-methyl-butyryl)-pyrrolidin-2-yl]-3H-imidazol-4-yl}-biphenyl-4-carbonyl)-amino]-methyl}-pyrrolidine-1-carbonyl)-2-methyl-propyl]-carbamic acid methyl ester

2-[(4-Bromo-benzoylamino)-methyl]-pyrrolidine-1-carboxylic acid tert-butyl ester To 2-aminomethyl-pyrrolidine-1-carboxylic acid tert-butyl ester (1.00 g, 4.97 mmol) and 4-bromo-benzoic acid (996 mg, 4.97 mmol) in DMF (25 mL) was added N-methylmorpholine (655 µl, 5.96 mmol) and HATU (1.89 g, 4.97 mmol). After stirring for 3 hours the reaction was concentrated then diluted with EtOAc and washed with 1N HCl, saturated NaHCO₃, and brine. The organic phase was then dried over Na₂SO₄ and concentrated. The crude material was purified by silica gel chromatography (20-50% EtOAc-hexanes gradient) to afford 2-[(4-bromo-benzoylamino)-methyl]-pyrrolidine-1-carboxylic acid tert-butyl ester (1.91 g, 4.97 mmol, quantitative yield). LCMS-ESI⁺: calc'd for $C_{17}H_{24}BrN_2O_3$: 383.1 (M+H⁺); Found: 383.6 (M+H⁺).

(1-{2-[(4-Bromo-benzoylamino)-methyl]-pyrrolidine-1-carbonyl}-2-methyl-propyl)-carbamic acid methyl ester To 2-[(4-bromo-benzoylamino)-methyl]pyrrolidine-1-carboxylic acid tert-butyl ester (1.00 g, 2.61 mmol) in dioxanes (15 mL) was added 4N HCl in dioxanes (5 mL, 20 mmol). The solution was stirred overnight then concentrated to afford the HCl salt of the crude amine. To the amine in DMF (13 mL) was added N-methylmorpholine (574 µl, 5.22 mmol), 2-methoxycarbonylamino-3-methyl-butyric acid (457 mg, 2.61) and HATU (992 mg, 2.61 mmol). After stirring for 2 hours the reaction was concentrated then diluted with EtOAc and washed with 1N HCl, saturated NaHCO₃, and brine. The crude product was purified by silica gel chromatography (100% EtOAc) to afford (1-{2-[(4-bromo-benzoylamino)-methyl]-pyrrolidine-1-carbonyl}-2-methyl-propyl)-carbamic acid methyl ester (950 mg, 2.18 mmol, 84% yield). LCMS-ESI⁺: calc'd for $C_{19}H_{27}BrN_3O_4$: 440.1 (M+H⁺); Found: 440.2 (M+H⁺).

[1-(2-{[(4'-{2-[1-(2-methoxycarbonylamino-3-methyl-butyryl)-pyrrolidin-2-yl]-3H-imidazol-4-yl}-biphenyl-4-carbonyl)-amino]-methyl}-pyrrolidine-1-carbonyl)-2-methyl-propyl]-carbamic acid methyl ester A solution of (1-{2-[(4-bromo-benzoylamino)-methyl]-pyrrolidine-1-carbonyl}-2-methyl-propyl)-carbamic acid methyl ester (104 mg, 0.24 mmol), [2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (117 mg, 0.24 mmol) and aq K₃PO₄ (480 µl of a 2M solution, 0.96 mmol) in DME (3 mL) was degassed with N₂ gas for 20 minutes. To the degassed solution was added Pd(PPh₃)₄ (13.9 mg, 0.012 mmol) then the reaction was heated to 80° C. overnight. After cooling to room temperature, the reaction was concentrated and purified by reverse phase preparative HPLC (15-60% MeCN—H₂O; 0.1% formic acid modifier) to afford [1-(2-{[(4'-{2-[1-(2-methoxycarbonylamino-3-methyl-butyryl)-pyrrolidin-2-yl]-3H-imidazol-4-yl}-biphenyl-4-carbonyl)-amino]-methyl}-pyrrolidine-1-carbonyl)-2-methyl-propyl]-carbamic acid methyl ester (26 mg, 0.036 mmol, 15% yield). ¹H-NMR: 400 MHz, (DMSO-d₆) δ: 11.8 (s, 1H), 8.61 (m, 1H), 7.94-7.73 (m, 9H), 7.34 (d, 1H), 7.29 (d, 1H), 5.08 (m, 1H), 4.23 (t, 1H), 4.30 (m, 1H), 4.07 (t, 1H), 4.01 (t, 1H), 4.07-4.01 (m, 1H), 3.18 (m, 2H), 3.73-3.70 (m, 1H), 3.61 (m, 1H), 3.63 (s, 3H), 3.61 (s, 3H), 2.16-1.81 (m, 10H), 0.90-0.84 (m, 12H). LCMS-ESI⁺: calc'd for $C_{39}H_{52}N_7O_7$: 730.4 (M+H⁺); Found: 730.1 (M+H⁺).

Example AD1

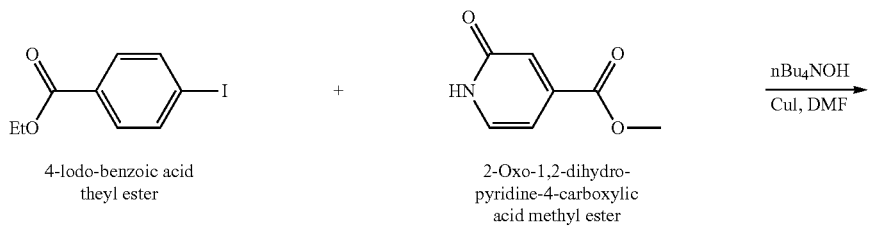

4-Iodo-benzoic acid theyl ester

2-Oxo-1,2-dihydro-pyridine-4-carboxylic acid methyl ester

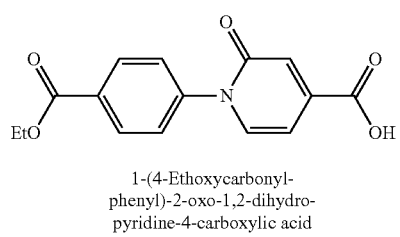

1-(4-Ethoxycarbonyl-phenyl)-2-oxo-1,2-dihydro-pyridine-4-carboxylic acid

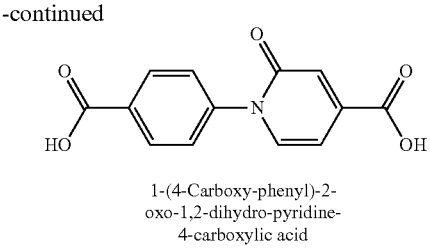

1-(4-Carboxy-phenyl)-2-oxo-1,2-dihydro-pyridine-4-carboxylic acid

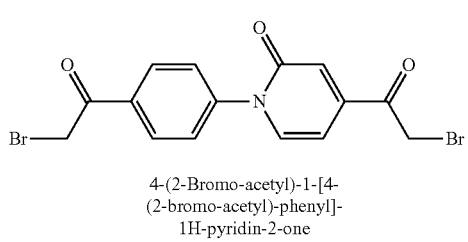

4-(2-Bromo-acetyl)-1-[4-(2-bromo-acetyl)-phenyl]-1H-pyridin-2-one

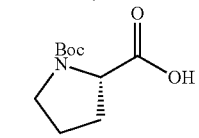

Pyrrolidine-1,2-dicarboxylic acid 1-tert-butyl ester

1. DIPEA, ACN
2. NH₄OAc
   Tolune, 100 C.

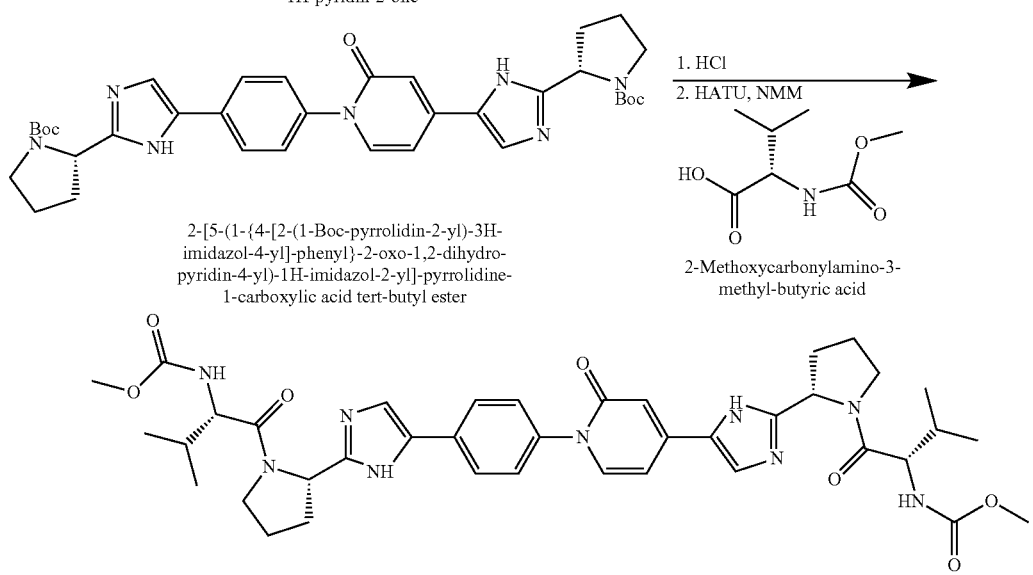

2-[5-(1-{4-[2-(1-Boc-pyrrolidin-2-yl)-3H-imidazol-4-yl]-phenyl}-2-oxo-1,2-dihydro-pyridin-4-yl)-1H-imidazol-2-yl]-pyrrolidine-1-carboxylic acid tert-butyl ester 1. HCl
2. HATU, NMM 2-Methoxycarbonylamino-3-methyl-butyric acid

[1-(2-{5-[1-(4-{2-[1-(2-Methoxycarbonylamino-3-methyl-butyryl)-pyrrolidin-2-yl]-3H-imidazol-4-yl}-phenyl)-2-oxo-1,2-dihydro-pyridin-4-yl]-1H-imidazol-2-yl}-pyrrolidine-1-carbonyl)-2-methyl-propyl]-carbamic acid methyl ester

1-(4-Ethoxycarbonyl-phenyl)-2-oxo-1,2-dihydro-pyridine-4-carboxylic acid

A mixture of 2-oxo-1,2-dihydro-pyridine-4-carboxylic acid methyl ester (2.00 g), 1.0M tetrabutylammonium hydroxide in H₂O (13 ml) and toluene (50 mL) was stirred for 2 hours at ambient temperature. Mixture was concentrated and co-evaporated with toluene (3×100 mL) and dried under high vacuum. To the residue was added 4-Iodo-benzoic acid ethyl ester (2.40 g) and co-evaporated with toluene (2×20 mL). Copper iodide (0.829 g) and DMF (10 mL) were added and reaction mixture heated at 95° C. for 18 hours, protected from light. To the cooled reaction mixture was added 3N ammonium hydroxide and extracted with dichloromethane (4×). Organic layer was dried (MgSO₄), concentrated and purified by flash column chromatography (silica gel, 0 to 5% methanol/dichloromethane+1% triethylamine) to give 1-(4-Ethoxycarbonyl-phenyl)-2-oxo-1,2-dihydro-pyridine-4-carboxylic acid (1.155 g) as the triethylammonium salt: LCMS-ESI⁻: calc'd for $C_{15}H_{12}NO_5$: 286.27 (M–H⁺); Found: 286.1 (M–H⁺).

1-(4-Carboxy-phenyl)-2-oxo-1,2-dihydro-pyridine-4-carboxylic acid

To a solution of 1-(4-Ethoxycarbonyl-phenyl)-2-oxo-1,2-dihydro-pyridine-4-carboxylic acid (1.155 g) in THF (20 mL) at 0° C. was added 5 M sodium hydroxide (1.19 mL) and mixture stirred overnight at ambient temperature. Reaction mixture was acidified to pH 1 with concentrated HCl, producing a precipitate. The solid was collected by filtration, washed with H₂O and dried under high vacuum to give 1-(4-Carboxy-phenyl)-2-oxo-1,2-dihydro-pyridine-4-carboxylic acid (0.7196 g). LCMS-ESI⁻: calc'd for $C_{13}H_8NO_5$: 258.2 (M–H⁺); Found: 258.1 (M–H⁺).

4-(2-Bromo-acetyl)-1-[4-(2-bromo-acetyl)-phenyl]-1H-pyridin-2-one

A mixture of 1-(4-Carboxy-phenyl)-2-oxo-1,2-dihydro-pyridine-4-carboxylic acid (0.696 g) and oxalyl chloride (2.34 mL) in dichloromethane (20 mL) containing DMF (4 drops) was stirred at ambient temperature for 4 hours, then concentrated and co-evaporated with toluene (3×) and dried under high vacuum. The resulting residue was suspended in dichloromethane (10 mL) at 0° C. and treated with 2.0 M trimethylsilyldiazomethane in ether (4.0 mL) over 15 minutes to give a brown mixture. Reaction mixture was warmed to ambient temperature overnight and then concentrated. The resulting brown solid was suspended in ethyl acetate (10 mL) and cooled to 0° C. 5.7 M HBr in acetic acid was added over 5 minutes and reaction mixture was warmed to ambient temperature over 1 hour. Solid sodium bicarbonate (0.3 g) was added and stirred for 30 minutes. H$_2$O was added giving a biphasic mixture with a brown precipitate. The solid was removed by filtration and filtrate was extracted with dichloromethane (2×), dried (MgSO$_4$) and concentrated. The residue was purified by flash column chromatography (silica gel, 30 to 80% ethyl acetate/hexanes) to give 4-(2-Bromo-acetyl)-1-[4-(2-bromo-acetyl)-phenyl]-1H-pyridin-2-one (0.555 g). LCMS-ESI$^+$: calc'd for C$_{15}$H$_{12}$Br$_2$NO$_3$: 414.06 (M+H$^+$); Found: 411.9, 413.9, 415.8 (M+H$^+$).

2-[5-(1-{4-[2-(1-Boc-pyrrolidin-2-yl)-3H-imidazol-4-yl]phenyl}-2-oxo-1,2-dihydro-pyridin-4-yl)-1H-imidazol-2-yl]-pyrrolidine-1-carboxylic acid tert-butyl ester A mixture of 4-(2-Bromo-acetyl)-1-[4-(2-bromo-acetyl)-phenyl]-1H-pyridin-2-one (0.555 g) Pyrrolidine-1,2-dicarboxylic acid 1-tert-butyl ester (0.6 g) and diisopropylethylamine (0.48 mL) in acetonitrile (10.8 mL) was stirred for 2 hours at ambient temperature. Reaction mixture was diluted with ethyl acetate, washed with brine and back-extracted with ethyl acetate. The combined organic layer was washed with diluted brine (2×), dried (MgSO$_4$) and concentrated to give a brown oil (1.034 g). LCMS-ESI$^-$: calc'd for C$_{35}$H$_{42}$N$_3$O$_{11}$: 680.73 (M−H$^+$); Found: 680.3 (M−H$^+$). Residue was dissolved in toluene (5.5 mL) and ammonium acetate (2.066 g) was added. The reaction mixture was stirred at 100° C. for 2 hours and then concentrated. The residue was partitioned between dichloromethane and dilute sodium bicarbonate solution. The aqueous layer was extracted with dichloromethane containing methanol (3×) and the combined organic layer was dried (MgSO$_4$), concentrated and purified by flash column chromatography (silica gel, 0 to 15% methanol/dichloromethane) to give 2-[5-(1-{4-[2-(1-Boc-pyrrolidin-2-yl)-3H-imidazol-4-yl]-phenyl}-2-oxo-1,2-dihydro-pyridin-4-yl)-1H-imidazol-2-yl]-pyrrolidine-1-carboxylic acid tert-butyl ester (0.098 g). LCMS-ESI$^+$: calc'd for C$_{35}$H$_{44}$N$_7$O$_5$: 642.76 (M+H$^+$); Found: 642.1 (M+H$^+$).

[1-(2-{5-[1-(4-{2-[1-(2-Methoxycarbonylamino-3-methyl-butyryl)-pyrrolidin-2-yl]-3H-imidazol-4-yl}-phenyl)-2-oxo-1,2-dihydro-pyridin-4-yl]-1H-imidazol-2-yl}-pyrrolidine-1-carbonyl)-2-methyl-propyl]-carbamic acid methyl ester 2-[5-(1-{4-[2-(1-Boc-pyrrolidin-2-yl)-3H-imidazol-4-yl]-phenyl}-2-oxo-1,2-dihydro-pyridin-4-yl)-1H-imidazol-2-yl]-pyrrolidine-1-carboxylic acid tert-butyl ester (0.098 g) in dichloromethane (6.0 mL) was treated with 4N HCl in dioxane (2.0 mL) for 90 minutes at ambient temperature. Reaction mixture was concentrated and dried overnight under vacuum. Residue was dissolved in DMF (2.0 mL) and to this solution was added 2-Methoxycarbonylamino-3-methyl-butyric acid (0.055 g), 4-methylmorpholine (0.099 mL), followed by HATU (0.116 g). Reaction mixture was stirred for 90 minutes at ambient temperature and then concentrated. Residue was dissolved in dichloromethane and washed with dilute sodium bicarbonate solution. Aqueous layer back-extracted with dichloromethane and combined organic layer dried (MgSO$_4$), concentrated and purified by preparative reverse phase HPLC (Gemini, 5 to 100% ACN/H2O+0.1% TFA). Product was lyophilized to give [1-(2-{5-[1-(4-{2-[1-(2-Methoxycarbonylamino-3-methyl-butyryl)-pyrrolidin-2-yl]-3H-imidazol-4-yl}-phenyl)-2-oxo-1,2-dihydro-pyridin-4-yl]-1H-imidazol-2-yl}-pyrrolidine-1-carbonyl)-2-methyl-propyl]-carbamic acid methyl ester as the bis-TFA salt (0.037 g): $^1$H-NMR: 300 MHz, (DMSO-d$_6$) δ: 8.14 (s, 2H), 7.88 (d, J=8.4, 2H), 7.79 (d, J=7.2, 1H), 7.63 (d, J=8.4, 2H), 7.35-7.30 (m, 2H), 6.88 (s, H), 6.74 (d, J=8.4, 1H), 5.13-5.10 (m, 2H), 3.90-3.80 (m, 8H), 3.53 (s, 6H), 2.40-2.01 (m, 10H), 0.83-0.75 (m, 12H); LCMS-ESI$^+$: calc'd for C$_{39}$H$_{50}$N$_9$O$_7$: 756.86 (M+H$^+$); Found: 756.3 (M+H$^+$).

Example AE1

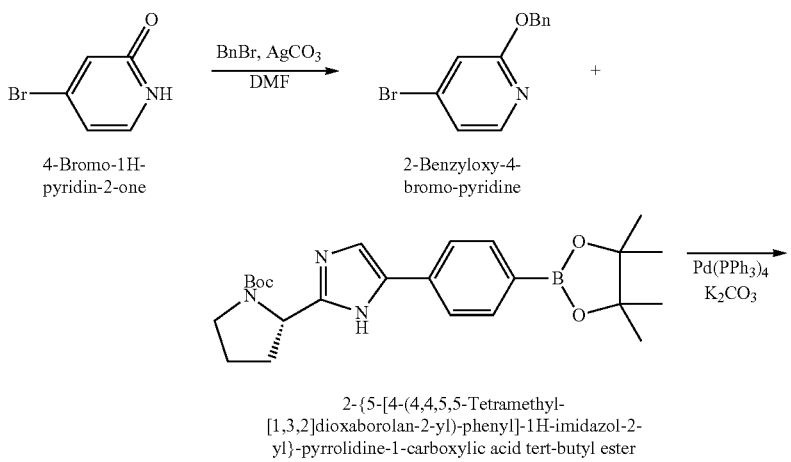

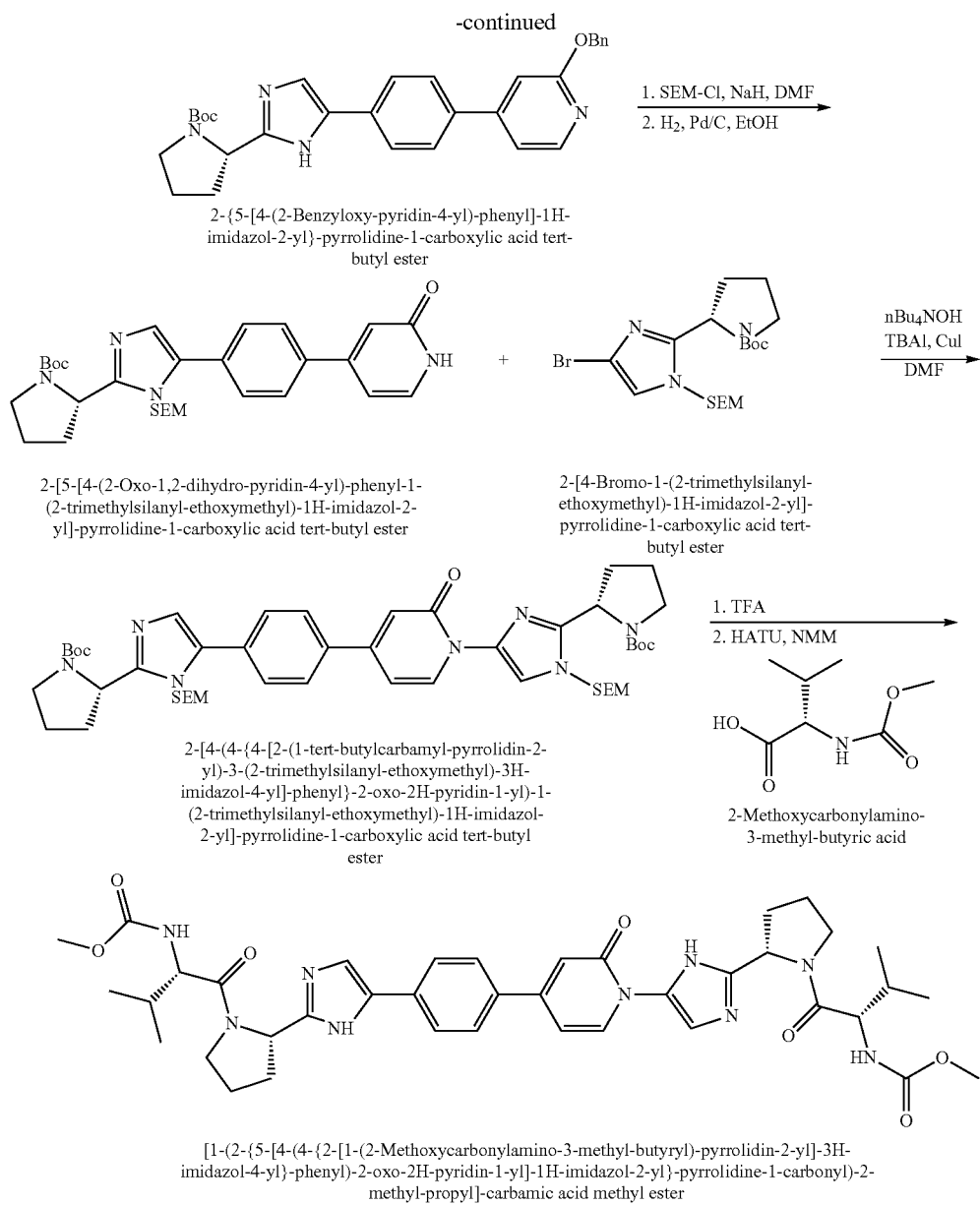

2-Benzyloxy-4-bromo-pyridine

A mixture of 4-Bromo-1H-pyridin-2-one (0.613 g), silver carbonate (0.63 g) and benzyl bromide (0.50 mL) in benzene (10 mL) was heated at 50° C. for 24 hours, protected from light. Reaction mixture stirred ambient temperature for 16 hours. Reaction mixture was filtered through a pad of CELITE, which was washed ethyl acetate. The filtrate was concentrated and purified by flash column chromatography (silica gel, 0 to 10% ethyl acetate/hexanes) to give 2-Benzyloxy-4-bromo-pyridine (0.6043 g): LCMS-ESI$^+$: calc'd for $C_{12}H_{11}BrNO$: 265.12 (M+H$^+$); Found: 263.8, 265.8 (M+H$^+$).

2-{5-[4-(2-Benzyloxy-pyridin-4-yl)-phenyl]-1H-imidazol-2-yl}-pyrrolidine-1-carboxylic acid tert-butyl ester A mixture of 2-Benzyloxy-4-bromo-pyridine (0.292 g), 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.533 g, prepared according to WO2008021927 A2) and Pd(PPh$_3$)$_4$ (0.064 g) in aq. K$_2$CO$_3$ solution/dimethoxyethane (1.82 mL/5.0 mL) was heated at 80-90° C. for 8 hours. Reaction mixture was cooled, diluted with ethyl acetate, washed with brine, dried (MgSO$_4$) and concentrated. The residue was purified by flash column chromatography (silica gel, 20 to 80% ethyl acetate/hexanes) to give 2-{5-[4-(2-Benzyloxy-pyridin-4-yl)-phenyl]-1H-imidazol-2-yl}-pyrrolidine-1-carboxylic acid tert-butyl ester (0.530 g): LCMS-ESI$^+$: calc'd for $C_{30}H_{33}N_4O_3$: 497.6 (M+H$^+$); Found: 497.0 (M+H$^+$).

2-[5-[4-(2-oxo-1,2-dihydro-pyridin-4-yl)-phenyl]-1-(2-trimethylsilanyl-ethoxymethyl)-1H-imidazol-2-yl]-pyrrolidine-1-carboxylic acid tert-butyl ester To a solution of 2-{5-[4-(2-Benzyloxy-pyridin-4-yl)-phenyl]-1H-imidazol-2-yl}-pyrrolidine-1-carboxylic acid tert-butyl ester (0.530 g) in DMF (5.0 mL) at 0° C. was added 60% sodium hydride (0.047 g). After stirring for 5 minutes, 2-(trimethylsilyl)ethoxylmethyl chloride was added and reaction mixture stirred for 2 hours. Saturated ammonium chloride was added and mixture was extracted with ethyl acetate (2×). Organic layer was washed with 5% lithium chloride solution (2×), brine and dried (MgSO$_4$). Concentrated and purified by flash column chromatography (silica gel, 20 to 80% ethyl acetate/hexanes) to give 2-[5-[4-(2-Benzyloxy-pyridin-4-yl)-phenyl]-1-(2-trimethylsilanyl-ethoxymethyl)-1H-imidazol-2-yl]-pyrrolidine-1-carboxylic acid tert-butyl ester (0.495 g). LCMS-ESI$^+$: calc'd for C$_{36}$H$_{47}$N$_4$O$_4$Si: 627.87 (M+H$^+$); Found: 627.1 (M+H$^+$). A mixture of 2-[5-[4-(2-Benzyloxy-pyridin-4-yl)-phenyl]-1-(2-trimethylsilanyl-ethoxymethyl)-1H-imidazol-2-yl]-pyrrolidine-1-carboxylic acid tert-butyl ester (0.495 g) and 10% Pd/C (0.023 g) in ethanol (5.5 mL) was stirred under hydrogen atmosphere for 1 hour. Reaction mixture was filtered through a pad of Celite, which was washed with methanol. The filtrate was concentrated and purified by flash column chromatography (silica gel, 0 to 10% methanol/ethyl acetate) to give 2-[5-[4-(2-oxo-1,2-dihydro-pyridin-4-yl)-phenyl]-1-(2-trimethylsilanyl-ethoxymethyl)-1H-imidazol-2-yl]-pyrrolidine-1-carboxylic acid tert-butyl ester (0.3027 g): LCMS-ESI$^+$: calc'd for C$_{29}$H$_{41}$N$_4$O$_4$Si: 537.47 (M+H$^+$); Found: 537.0 (M+H$^+$).

2-[4-(4-{4-[2-(1-tert-butylcarbamyl-pyrrolidin-2-yl)-3-(2-trimethylsilanyl-ethoxymethyl)-3H-imidazol-4-yl]-phenyl}-2-oxo-2H-pyridin-1-yl)-1-(2-trimethylsilanyl-ethoxymethyl)-1H-imidazol-2-yl]-pyrrolidine-1-carboxylic acid tert-butyl ester To a solution of 2-[5-[4-(2-Oxo-1,2-dihydro-pyridin-4-yl)-phenyl]-1-(2-trimethylsilanyl-ethoxymethyl)-1H-imidazol-2-yl]-pyrrolidine-1-carboxylic acid tert-butyl ester (0.3027 g) in ethanol (5.0 mL) was added tetrabutylammonium hydroxide (0.375 mL of 1.5 M solution) and reaction mixture stirred for 1 hour., then concentrated to give a colorless oil. Residue was lyophilized from acetonitrile to give a yellow residue. To this residue was added 2-[4-Bromo-1-(2-trimethylsilanyl-ethoxymethyl)-1H-imidazol-2-yl]-pyrrolidine-1-carboxylic acid tert-butyl ester (0.301 g, prepared by reacting 2-(4-Bromo-1H-imidazol-2-yl)-pyrrolidine-1-carboxylic acid tert-butyl ester (prepared according to WO2008021927 A2) with 2-(trimethylsilyl)ethoxylmethyl chloride using sodium hydride in DMF) and mixture co-evaporated with toluene (15 mL). DMF (1.0 mL) and copper (I) iodide (0.035 g) were added and the reaction mixture was stirred at 95° C. for 24 hour, protected from light. To the reaction mixture was added tetrabutylammonium iodide (50 mg) and reaction continued for 2 days. Added more 2-[4-Bromo-1-(2-trimethylsilanyl-ethoxymethyl)-1H-imidazol-2-yl]-pyrrolidine-1-carboxylic acid tert-butyl ester (0.35 g) and copper(I) iodide (0.050 g) and reaction continued for 24 hours. Reaction mixture was cooled and diluted with ethyl acetate and washed with 3N ammonium hydroxide. The aqueous layer was back-extracted with ethyl acetate (2×). The combined organic layer was washed with 3N ammonium hydroxide, H$_2$O, brine and dried (MgSO$_4$) then concentrated and purified by flash column chromatography (silica gel, 0 to 10% isopropanol/hexane) to give impure product that was repurified by preparative reverse phase HPLC (Gemini, 25 to 100% ACN/H$_2$O+0.1% TFA). Product was lyophilized to give 2-[4-(4-{4-[2-(1-tert-butylcarbamyl-pyrrolidin-2-yl)-3-(2-trimethylsilanyl-ethoxymethyl)-3H-imidazol-4-yl]-phenyl}-2-oxo-2H-pyridin-1-yl)-1-(2-trimethylsilanyl-ethoxymethyl)-1H-imidazol-2-yl]-pyrrolidine-1-carboxylic acid tert-butyl ester (0.042 g): LCMS-ESI$^+$: calc'd for C$_{47}$H$_{72}$N$_7$O$_7$Si$_2$: 903.28 (M+H$^+$); Found: 902.2, 903.2 (M+H$^+$).

[1-(2-{5-[4-(4-{2-[1-(2-Methoxycarbonylamino-3-methyl-butyryl)-pyrrolidin-2-yl]-3H-imidazol-4-yl}-phenyl)-2-oxo-2H-pyridin-1-yl]-1H-imidazol-2-yl}-pyrrolidine-1-carbonyl)-2-methyl-propyl]-carbamic acid methyl ester 2-[4-(4-{4-[2-(1-tert-butylcarbamyl-pyrrolidin-2-yl)-3-(2-trimethyl silanyl-ethoxymethyl)-3H-imidazol-4-yl]-phenyl}-2-oxo-2H-pyridin-1-yl)-1-(2-trimethylsilanyl-ethoxymethyl)-1H-imidazol-2-yl]-pyrrolidine-1-carboxylic acid tert-butyl ester (0.042 g) in dichloromethane (1.0 mL) was treated with trifluoroacetic acid (0.3 mL) for 7 hours at ambient temperature. Reaction mixture was concentrated and dried for 1 hour under vacuum. Residue was dissolved in DMF (0.7 mL) and to this solution was added 2-Methoxycarbonylamino-3-methyl-butyric acid (0.013 g), 4-methylmorpholine (0.024 mL), followed by HATU (0.028 g). Reaction mixture was stirred for 45 minutes at ambient temperature and then more 4-methylmorpholine (0.024 mL) was added. Reaction continued for 30 minutes, diluted with ethyl acetate and washed with dilute sodium bicarbonate solution, brine and dried (MgSO$_4$), concentrated and purified by preparative reverse phase HPLC (Gemini, 5 to 100% ACN/H$_2$O+0.1% TFA). Product was lyophilized to give [1-(2-{5-[4-(4-{2-[1-(2-Methoxycarbonylamino-3-methyl-butyryl)-pyrrolidin-2-yl]-3H-imidazol-4-yl}-phenyl)-2-oxo-2H-pyridin-1-yl]-1H-imidazol-2-yl}-pyrrolidine-1-carbonyl)-2-methyl-propyl]-carbamic acid methyl ester as the bis-TFA salt (0.077 mg): $^1$H-NMR: 300 MHz, (CD$_3$OD) δ: 8.48 (d, J=7.2, 1H), 7.96-7.80 (m, 6H), 7.64 (s, 1H), 6.92-6.85 (m, 2H), 5.29-5.17 (m, 2H), 4.26-3.88 (m, 8H), 3.66 (s, 6H), 2.60-2.01 (m, 12H), 0.83-0.75 (m, 12H); LCMS-ESI$^+$: calc'd for C$_{39}$H$_{50}$N$_9$O$_7$: 756.86 (M+H$^+$); Found: 756.3 (M+H$^+$).

Example AF1

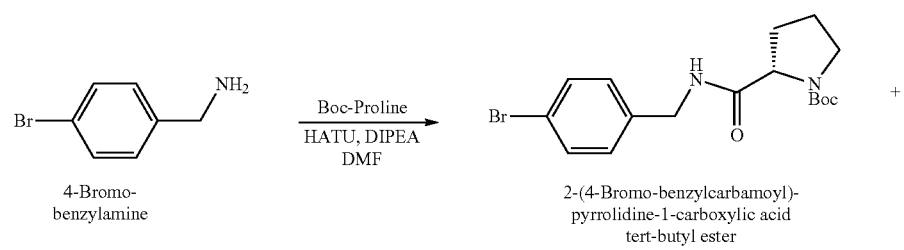

4-Bromo-benzylamine 2-(4-Bromo-benzylcarbamoyl)-pyrrolidine-1-carboxylic acid tert-butyl ester

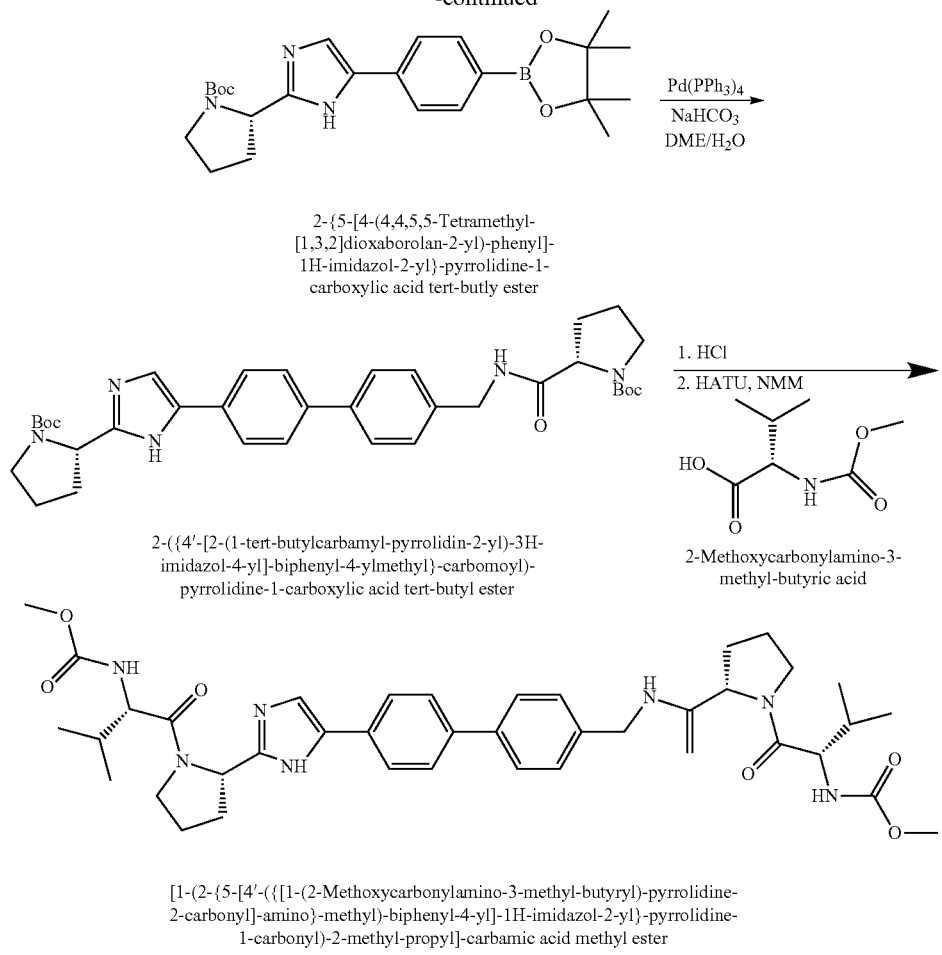

2-(4-Bromo-benzylcarbamoyl)-pyrrolidine-1-carboxylic acid tert-butyl ester

To a mixture of 4-Bromo-benzylamine (2.00 g), Boc-L-proline (2.01 g), and 4-methylmorpholine (3.26 mL) in DMF (40 mL) was added HATU (3.48 g). Reaction mixture was stirred for 45 minutes, then concentrated, diluted with dichloromethane and washed with 10:1 $H_2O$/saturated sodium bicarbonate solution. The aqueous layer was back-extracted with dichloromethane and the combined organic layers were dried ($MgSO_4$), concentrated and purified by flash column chromatography (silica gel, 50 to 100% ethyl acetate/hexanes) to give 2-(4-Bromo-benzylcarbamoyl)-pyrrolidine-1-carboxylic acid tert-butyl ester (3.38 g): LCMS-ESI$^+$: calc'd for $C_{17}H_{24}BrN_2NaO_3$: 405.29 (M+Na$^+$); Found: 405.0 (M+Na$^+$).

2-({4'-[2-(1-tert-butylcarbamyl-pyrrolidin-2-yl)-3H-imidazol-4-yl]-biphenyl-4-yl methyl}-carbamoyl)-pyrrolidine-1-carboxylic acid tert-butyl ester A mixture of 2-(4-Bromo-benzylcarbamoyl)-pyrrolidine-1-carboxylic acid tert-butyl ester (0.257 g), 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.309 g, prepared according to WO2008021927 A2), $NaHCO_3$ (0.186 g) and $Pd(PPh_3)_4$ (0.064 g) in $H_2O$ (2.0 mL)/dimethoxyethane (6.0 mL) was heated at 80° C. for 16 hours. Reaction mixture was cooled and concentrated. Residue was dissolved in dichloromethane, washed with $H_2O$. Aqueous layer was back-extracted with dichloromethane and combined organic layer was dried ($MgSO_4$), concentrated and purified by flash column chromatography (silica gel, 50 to 100% ethyl acetate/hexanes) to give 2-({4'-[2-(1-tert-butylcarbamyl-pyrrolidin-2-yl)-3H-imidazol-4-yl]-biphenyl-4-ylmethyl}-carbamoyl)-pyrrolidine-1-carboxylic acid tert-butyl ester (0.280 g): LCMS-ESI$^+$: calc'd for $C_{35}H_{46}N_5O_5$: 616.76 (M+H$^+$); Found: 616.1 (M+H$^+$).

[1-(2-{5-[4'-({[1-(2-Methoxycarbonylamino-3-methyl-butyryl)-pyrrolidine-2-carbonyl]-amino}-methyl)-biphenyl-4-yl]-1H-imidazol-2-yl}-pyrrolidine-1-carbonyl)-2-methyl-propyl]-carbamic acid methyl ester 2-({4'-[2-(1-tert-butylcarbamyl-pyrrolidin-2-yl)-3H-imidazol-4-yl]-biphenyl-4-ylmethyl}-carbamoyl)-pyrrolidine-1-carboxylic acid tert-butyl ester (0.280 g) in dichloromethane (5.0 mL) was treated with 4N HCl in dioxane (3.0 mL) for 2 hours at ambient temperature. Reaction mixture was concentrated and dried overnight under vacuum to give a yellow powder (0.2548 g). Yellow powder (0.129 g) was dissolved in DMF (2.0 mL) and to this solution was added 2-Methoxycarbonylamino-3-methyl-butyric acid (0.090 g), 4-methylmorpholine (0.136 mL), followed by HATU (0.192 g). Reaction mixture was stirred for 90 minutes at ambient temperature and then concentrated. Residue was dissolved in dichloromethane and washed with dilute sodium bicarbonate solution. The aqueous layer was back-extracted with dichloromethane and the combined organic layers were dried (MgSO₄), concentrated and purified by preparative reverse phase HPLC (Gemini, 5 to 100% ACN/H$_2$O+0.1% TFA). Product was lyophilized to give [1-(2-{5-[4'-({[1-(2-Methoxycarbonylamino-3-methyl-butyryl)-pyrrolidine-2-carbonyl]-amino}-methyl)-biphenyl-4-yl]-1H-imidazol-2-yl}-pyrrolidine-1-carbonyl)-2-methyl-propyl]-carbamic acid methyl ester as the bis-TFA salt (0.089 mg).

$^1$H-NMR: 300 MHz, (DMSO-d$_6$) δ: 8.40-8.37 (m, 1H), 8.02 (s, 1H), 7.83 (d, J=8.4, 2H), 7.72 (d, J=8.1, 2H), 7.63 (d, J=8.4, 2H), 7.37-7.29 (m, 3H), 4.90-4.87 (m, 1H), 4.35-4.28 (m, 3H), 4.03-3.95 (m, 4H), 3.90-3.80 (m, 3H), 3.53 (s, 6H), 2.30-1.80 (m, 10H), 0.90 (d, J=6.9, 3H), 0.86 (d, J=6.3, 3H), 0.78 (d, J=6.6, 3H), 0.68 (d, J=6.9, 3H).

LCMS-ESI⁻: calc'd for C$_{39}$H$_{50}$N$_7$O$_7$: 728.86 (M−H⁺); Found: 728.2 (M−H⁺).

Example AG1

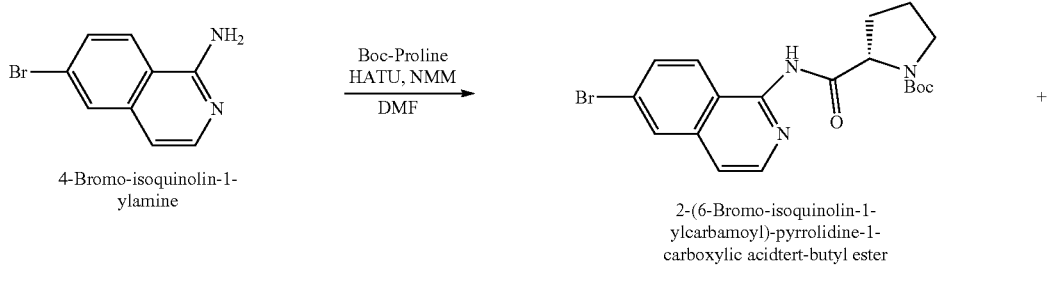

4-Bromo-isoquinolin-1-ylamine 2-(6-Bromo-isoquinolin-1-ylcarbamoyl)-pyrrolidine-1-carboxylic acidtert-butyl ester

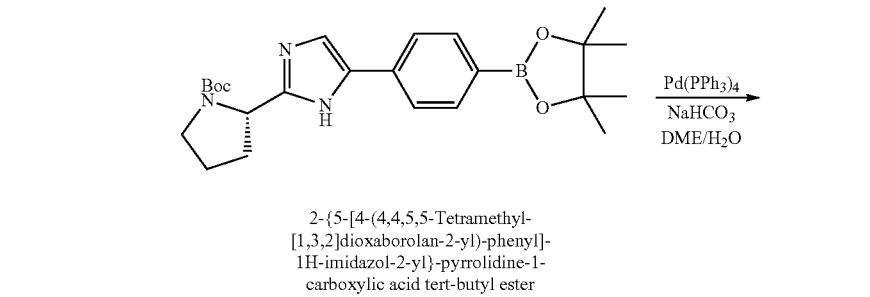

2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester

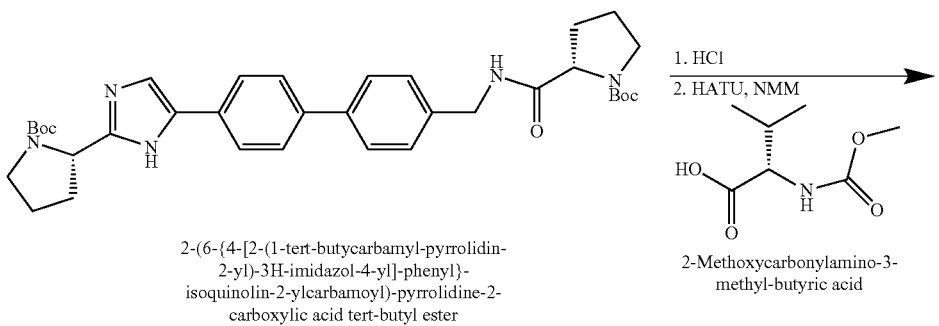

2-(6-{4-[2-(1-tert-butycarbamyl-pyrrolidin-2-yl)-3H-imidazol-4-yl]-phenyl}-isoquinolin-2-ylcarbamoyl)-pyrrolidine-2-carboxylic acid tert-butyl ester 2-Methoxycarbonylamino-3-methyl-butyric acid

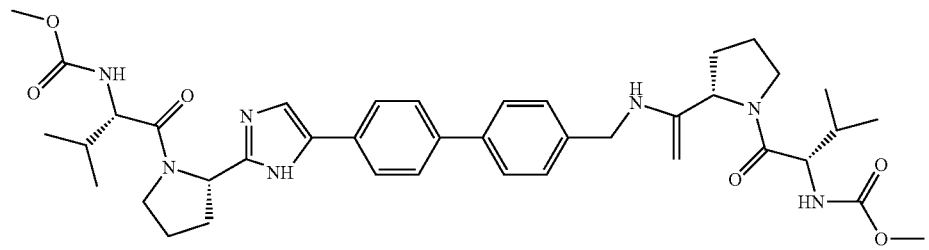

[1-(2-{5-[4'-{[1-(2-Methoxycarbonylamino-3-methyl-butyryl)-pyrrolidine-2-carbonyl]-amino}-isoquinolin-6-yl)-phenyl]-1H-imidazol-2-yl}-pyrrolidine-2-carbonyl)-2-methyl-propyl]-carbamic acid methyl ester

2-(6-Bromo-isoquinolin-1-yl carbamoyl)-pyrrolidine-1-carboxylic acid tert-butyl ester To a mixture of 6-Bromo-isoquinolin-1-ylamine (0.80 g), Boc-L-proline (0.803 g), and 4-methylmorpholine (0.83 mL) in DMF (10 mL) was added HATU (1.39 g). Reaction mixture was stirred for 6 hours. Additional Boc-L-proline (0.803 g), 4-methylmorpholine (0.83 mL) and HATU (1.39 g) were added and reaction stirred overnight at ambient temperature and then concentrated. The residue was dissolved in ethyl acetate and washed with 10:1 H$_2$O/saturated sodium bicarbonate solution, 5% lithium chloride solution, brine and dried (MgSO$_4$), concentrated and purified by flash column chromatography (silica gel, 20 to 70% ethyl acetate/hexanes) to give 2-(6-Bromo-isoquinolin-1-yl carbamoyl)-pyrrolidine-1-carboxylic acid tert-butyl ester (1.74 g): LCMS-ESI$^+$: calc'd for C$_{19}$H$_{23}$BrN$_3$O$_3$: 421.31 (M+H$^+$); Found: 419.8, 421.8 (M+H$^+$).

2-(6-{4-[2-(1-tert-butylcarbamyl-pyrrolidin-2-yl)-3H-imidazol-4-yl]-phenyl}-isoquinolin-1-yl carbamoyl)-pyrrolidine-1-carboxylic acid tert-butyl ester A mixture 2-(6-Bromo-carbamoyl)-pyrrolidine-1-carboxylic acid tert-butyl ester (0.426 g), 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.405 g, prepared according to WO2008021927 A2), and Pd(PPh$_3$)$_4$ (0.053 g) in 2M aq. K$_2$CO$_3$ (1.4 mL)/dimethoxyethane (3.0 mL) was heated at 90° C. for 16 hours. Reaction mixture was cooled and diluted with ethyl acetate, washed with brine, dried (MgSO$_4$), concentrated and purified by flash column chromatography (silica gel, 50 to 100% ethyl acetate/hexanes) to give 2-(6-{4-[2-(1-tert-butylcarbamyl-pyrrolidin-2-yl)-3H-imidazol-4-yl]-phenyl}-isoquinolin-1-ylcarbamoyl)-pyrrolidine-1-carboxylic acid tert-butyl ester (0.272 g): LCMS-ESI$^+$: calc'd for C$_{37}$H$_{45}$N$_6$O$_5$: 653.78 (M+H$^+$); Found: 653.1 (M+H$^+$).

[1-(2-{5-[4-(1-{[1-(2-Methoxycarbonylamino-3-methyl-butyryl)-pyrrolidine-2-carbonyl]-amino}-isoquinolin-6-yl)-phenyl]-1H-imidazol-2-yl}-pyrrolidine-1-carbonyl)-2-methyl-propyl]-carbamic acid methyl ester 2-(6-{4-[2-(1-tert-butylcarbamyl-pyrrolidin-2-yl)-3H-imidazol-4-yl]-phenyl}-isoquinolin-1-yl carbamoyl)-pyrrolidine-1-carboxylic acid tert-butyl ester (0.272 g) in dichloromethane (5.0 mL) was treated with 4N HCl in dioxane (5.0 mL) for 2 hours at ambient temperature. Reaction mixture was concentrated and suspended in ethyl ether. The solid was collected by filtration, washed with ethyl ether and dried overnight under vacuum to give a yellow powder (0.2279 g). Yellow powder (0.1005 g) was dissolved in DMF (1.5 mL) and to this solution was added 2-Methoxycarbonylamino-3-methyl-butyric acid (0.061 g), 4-methylmorpholine (0.092 mL), followed by HATU (0.130 g). Reaction mixture was stirred for 1 hour at ambient temperature and then diluted with ethyl acetate and washed with dilute sodium bicarbonate solution, brine and dried (MgSO$_4$). Organic layer was concentrated and purified by preparative reverse phase HPLC (Gemini, 5 to 100% ACN/H$_2$O+0.1% TFA). Product was lyophilized to give [1-(2-{5-[4-(1-{[1-(2-Methoxycarbonylamino-3-methyl-butyryl)-pyrrolidine-2-carbonyl]-amino}-isoquinolin-6-yl)-phenyl]-1H-imidazol-2-yl}-pyrrolidine-1-carbonyl)-2-methyl-propyl]-carbamic acid methyl ester as the bis-TFA salt (0.093 mg).

$^1$H-NMR: 300 MHz, (DMSO-d$_6$) δ: 8.36 (s, 1H), 8.30-8.15 (m, 2H), 8.13 (s, 1H), 8.05-7.95 (m, 3H), 7.88 (d, J=8.7, 2H), 7.70 (d, J=8.4, 1H), 7.32 (d, J=8.7, 1H), 7.29 (d, J=8.7, 1H), 5.10-5.05 (m, 1H), 4.70-4.65 (m, 1H), 4.10-3.908 (m, 3H), 4.03-3.95 (m, 4H), 3.90-3.80 (m, 3H), 3.49 (s, 6H), 2.39-1.80 (m, 10H), 0.90-0.70 (m, 12H): LCMS-ESI$^-$: calc'd for C$_{41}$H$_{51}$N$_8$O$_7$: 767.89 (M+H$^+$); Found: 767.2 (M+H$^+$).

Example AH1

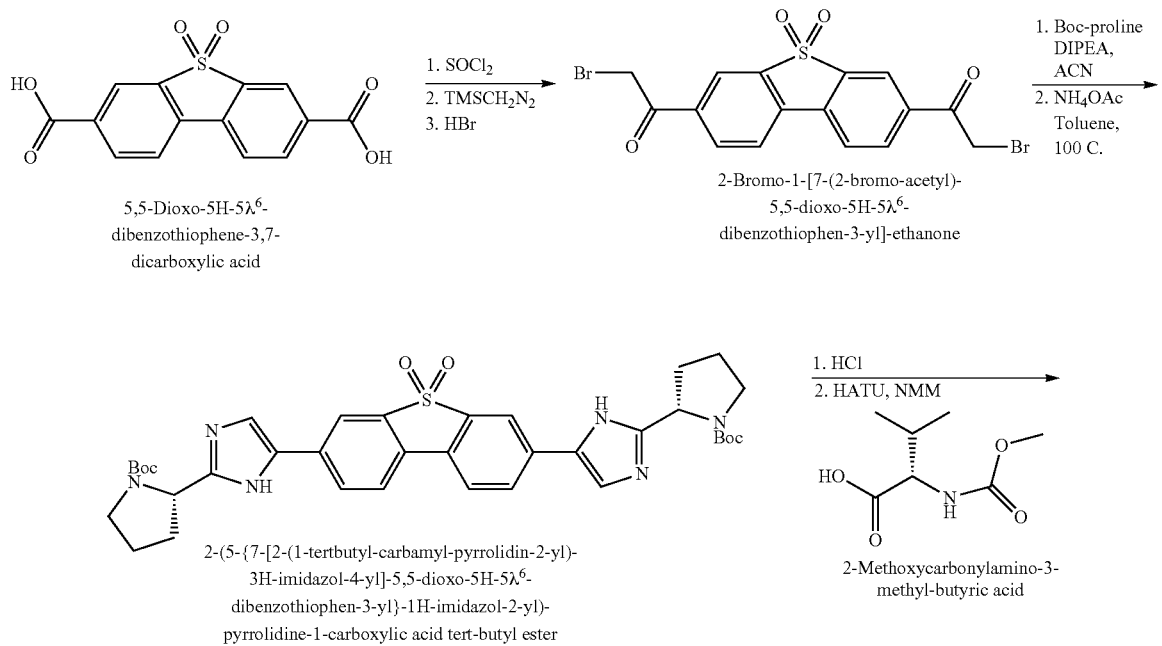

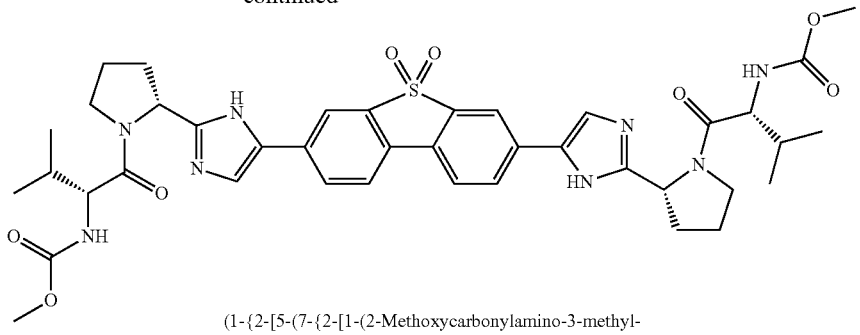

(1-{2-[5-(7-{2-[1-(2-Methoxycarbonylamino-3-methyl-butyryl)-pyrrolidin-2-yl]-3H-imidazol-4-yl}-5,5-dioxo-5H-5λ⁶-dibenzothiophen-3-yl)-1H-imidazol-2-yl]-pyrrolidine-1-carbonyl}-2-methyl-propyl)-carbamic acid methyl ester

2-Bromo-1-[7-(2-bromo-acetyl)-5,5-dioxo-5H-5λ⁶-dibenzothiophen-3-yl]-ethanone A mixture of 5,5-Dioxo-5H-5λ⁶-dibenzothiophene-3,7-dicarboxylic acid (10.85 g, prepared according to OL' Khouk et. Al. Russian J. Org. Chem. 2006, 42(8) 1164-1168) and oxalyl chloride (31.11 mL) in dichloromethane (250 mL) containing DMF (0.2 mL) was stirred at ambient temperature for 6 hours. A small amount of solid material was removed by filtration and the filtrate was concentrated to give a brown solid.

This brown solid was suspended in dichloromethane and cooled to 0° C. To this mixture was added 2.0M (trimethylsilyl)diazomethane in hexane (52.5 mL) and warmed to ambient temperature over 16 hours. Reaction mixture was concentrated providing a brown residue. The resulting brown residue was suspended in ethyl acetate (200 mL) and cooled to 0° C. 5.7M Hydrobromic acid in acetic acid (15.3 mL) was added slowly and stirred for 1 hour at 0° C., then 1 hour at ambient temperature. The reaction mixture was quenched with solid sodium bicarbonate and stirred for 30 minutes Saturated sodium bicarbonate solution was added, giving a brown precipitate. The solid was collected, washed with H₂O, ethyl acetate and dried under vacuum to give 2-Bromo-1-[7-(2-bromo-acetyl)-5,5-dioxo-5H-5λ⁶-dibenzothiophen-3-yl]-ethanone as a brown solid (25 g): LCMS-ESI⁻: calc'd for $C_{16}H_{11}Br_2O_4S$: 459.12 (M+H⁺); Found: no product mass observed.

2-(5-{7-[2-(1-tertbutyl-carbamyl-pyrrolidin-2-yl)-3H-imidazol-4-yl]-5,5-dioxo-5H-5λ⁶-dibenzothiophen-3-yl}-1H-imidazol-2-yl)-pyrrolidine-1-carboxylic acid tert-butyl ester A mixture of 2-Bromo-1-[7-(2-bromo-acetyl)-5,5-dioxo-5H-5λ⁶-dibenzothiophen-3-yl]-ethanone (25 g), Boc-L-proline (15.82 g) and diisopropylethylamine (12.6 mL) in acetonitrile (300 mL) was stirred for 3 hours at ambient temperature. Reaction mixture was concentrated and residue dissolved in ethyl acetate, washed with brine and back-extracted with ethyl acetate (3×). The combined organic layer was washed with brine, dried (MgSO₄) and purified by flash column chromatography (silica gel, 20 to 800% ethyl acetate/hexanes) to give yellow foam (10 g). LCMS-ESI⁻: calc'd for $C_{36}H_{41}N_2O_{12}S$: 725.79 (M−H⁺); Found: 725.1 (M−H⁺). A mixture of the yellow foam (7 g) and ammonium acetate (3.72 g) in xylenes (20 mL) was stirred at 120° C. for 3.5 hours and then cooled. Diluted with ethyl acetate and washed with dilute sodium bicarbonate solution. The aqueous layer was extracted with ethyl acetate (3×), then dichloromethane containing methanol (3×). The combined organic layer was dried (MgSO₄), concentrated and purified by flash column chromatography (silica gel, 0 to 5% methanol/ethyl acetate) to give 2-(5-{7-[2-(1-tert-butyl-carbamyl-pyrrolidin-2-yl)-3H-imidazol-4-yl]-5,5-dioxo-5H-5λ⁶-dibenzothiophen-3-yl}-1H-imidazol-2-yl)-pyrrolidine-1-carboxylic acid tert-butyl ester (4.56 g): LCMS-ESI⁺: calc'd for $C_{36}H_{43}N_6O_6S$: 687.82 (M+H⁺); Found: 687.0 (M+H⁺).

(1-{2-[5-(7-{2-[1-(2-Methoxycarbonylamino-3-methyl-butyryl)-pyrrolidin-2-yl]-3H-imidazol-4-yl}-5,5-dioxo-5H-5λ⁶-dibenzothiophen-3-yl)-1H-imidazol-2-yl]-pyrrolidine-1-carbonyl}-2-methyl-propyl)-carbamic acid methyl ester 2-(5-{7-[2-(1-tertbutyl-carbamyl-pyrrolidin-2-yl)-3H-imidazol-4-yl]-5,5-dioxo-5H-5λ⁶-dibenzothiophen-3-yl}-1H-imidazol-2-yl)-pyrrolidine-1-carboxylic acid tert-butyl ester (4.56 g) in dichloromethane (50 mL) was treated with 4N HCl in dioxane (50 mL) for 3 hours at ambient temperature. Reaction mixture was concentrated, triturated with ethyl ether and the orange solid dried overnight under vacuum. A portion of this orange solid (0.15 g) was dissolved in DMF (2.5 mL) and to this solution was added 2-Methoxycarbonylamino-3-methyl-butyric acid (0.187 g), 4-methylmorpholine (0.13 mL), followed by HATU (0.184 g). Reaction mixture was stirred for 1 hour at ambient temperature and then diluted with ethyl acetate, washed with dilute sodium bicarbonate solution, 5% lithium chloride solution, brine dried (MgSO₄). Concentration and purification by preparative reverse phase HPLC (Gemini, 5 to 100% ACN/H₂O+0.1% TFA) and lyophilization gave (1-{2-[5-(7-{2-[1-(2-Methoxycarbonylamino-3-methyl-butyryl)-pyrrolidin-2-yl]-3H-imidazol-4-yl}-5,5-dioxo-5H-5λ⁶-dibenzothiophen-3-yl)-1H-imidazol-2-yl]-pyrrolidine-1-carbonyl}-2-methyl-propyl)-carbamic acid methyl ester as the bis-TFA salt (0.150 mg): ¹H-NMR: 300 MHz, (DMSO-d₆) δ: 8.40-8.14 (m, 8H), 7.33 (d, J=8.1, 2H), 5.13-5.10 (m, 2H), 4.13-4.07 (m, 2H), 3.90-3.80 (m, 4H), 3.53 (s, 6H), 2.34-1.98 (m, 10H), 0.85 (d, J=6.6, 6H), 0.81 (d, J=6.6, 6H).

LCMS-ESI⁺: calc'd for $C_{40}H_{49}N_8O_8S$: 801.92 (M+H⁺); Found: 801.2 (M+H⁺).

Example AI1

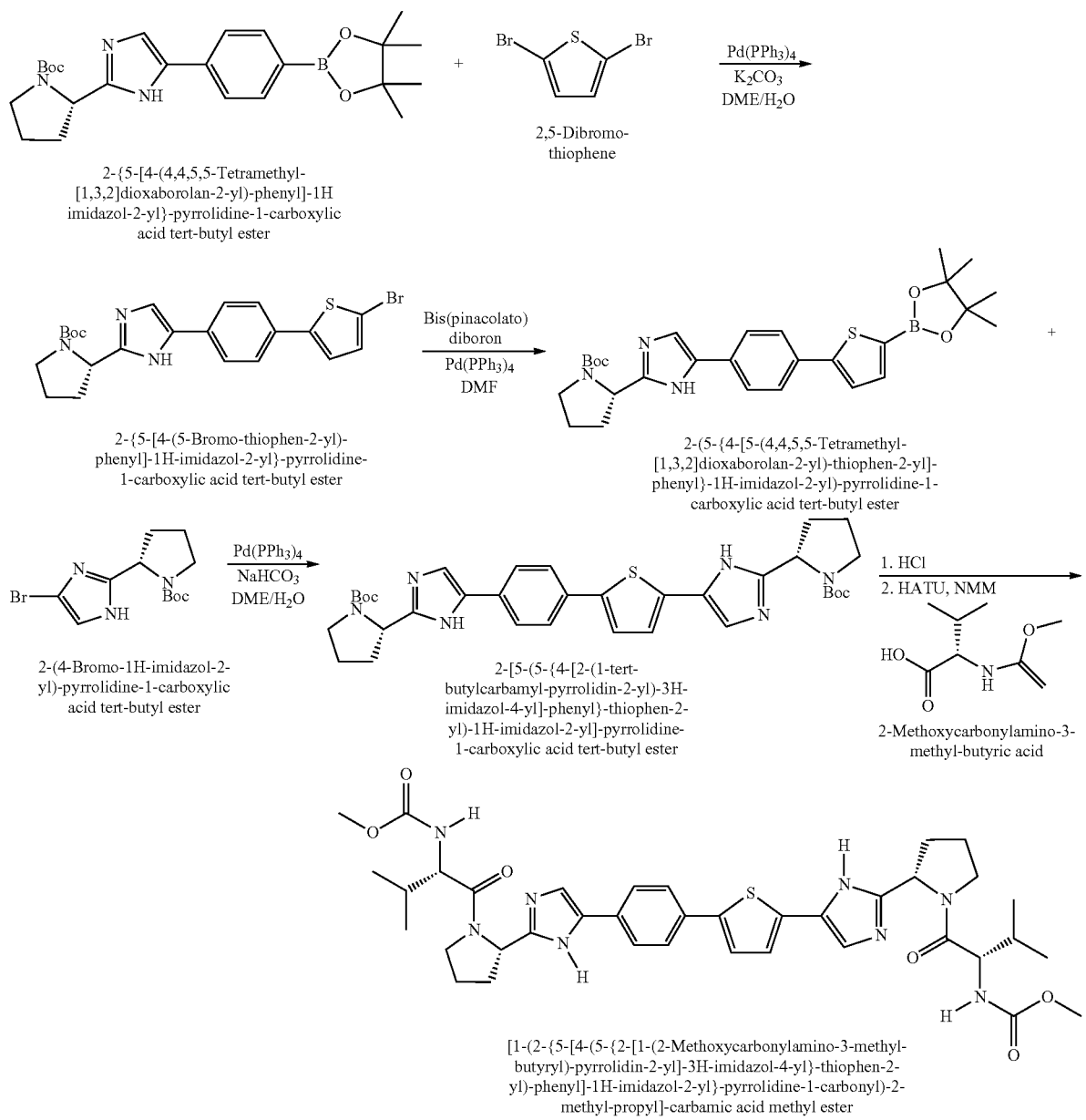

2-{5-[4-(5-Bromo-thiophen-2-yl)-phenyl]-1H-imidazol-2-yl}-pyrrolidine-1-carboxylic acid tert-butyl ester A mixture of 2,5-Dibromo-thiophene (4.93 g), 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.896 g, prepared according to WO2008021927 A2), and Pd(PPh$_3$)$_4$ (0.118 g) in 2M K$_2$CO$_3$ (3.06 mL)/dimethoxyethane (6.12 mL) was heated at 90° C. for 8 hours. Reaction mixture was cooled, diluted with ethyl acetate and washed with brine, dried (MgSO$_4$), concentrated and purified by flash column chromatography (silica gel, 0 to 100% ethyl acetate/hexanes) to give 2-{5-[4-(5-Bromo-thiophen-2-yl)-phenyl]-1H-imidazol-2-yl}-pyrrolidine-1-carboxylic acid tert-butyl ester (0.955 g): LCMS-ESI$^+$: calc'd for C$_{22}$H$_{25}$BrN$_3$O$_2$S: 475.42 (M+H$^+$); Found: 473.8, 475.9 (M+H$^+$).

2-(5-{4-[5-(4,4,5,5-Tetramethyl-[1,3,2]dioxaborolan-2-yl)-thiophen-2-yl]-phenyl}-1H-imidazol-2-yl)-pyrrolidine-1-carboxylic acid tert-butyl ester A mixture of 2-{5-[4-(5-Bromo-thiophen-2-yl)-phenyl]-1H-imidazol-2-yl}-pyrrolidine-1-carboxylic acid tert-butyl ester (0.4807 g), bis(pinacolato)diboron (0.54 g), Pd(PPh$_3$)$_4$ (0.058) and potassium acetate (0.257 g) in 1,4-dioxane was heated at 90° C. for 16 hours. Reaction mixture was cooled to ambient temperatures and diluted with ethyl acetate. Organic layer was washed with brine, dried (MgSO$_4$), concentrated and purified by flash column chromatography (silica gel, 20 to 80% ethyl acetate/hexanes) to give 2-(5-{4-[5-(4,4,5,5-Tetramethyl-[1,3,2]dioxaborolan-2-yl)-thiophen-2-yl]-phenyl}-1H-imidazol-2-yl)-pyrrolidine-1-carboxylic acid tert-butyl ester (0.3752 g) as a brown foam: LCMS-ESI+: calc'd for $C_{28}H_{37}BN_3O_4S$: 522.48 (M+H+); Found: 521.9 (M+H+).

2-[5-(5-{4-[2-(1-tert-butylcarbamyl-pyrrolidin-2-yl)-3H-imidazol-4-yl]-phenyl}-thiophen-2-yl)-1H-imidazol-2-yl]-pyrrolidine-1-carboxylic acid tert-butyl ester A mixture of 2-(5-{4-[5-(4,4,5,5-Tetramethyl-[1,3,2]dioxaborolan-2-yl)-thiophen-2-yl]-phenyl}-1H-imidazol-2-yl)-pyrrolidine-1-carboxylic acid tert-butyl ester (0.1050 g), 2-(4-Bromo-1H-imidazol-2-yl)-pyrrolidine-1-carboxylic acid tert-butyl ester (0.070 g, prepared according to WO2008021927 A2) and Pd(PPh3)4 (0.012 g) in 2.0M sodium bicarbonate solution (0.33 mL) and dimethoxyethane (0.66 mL) was stirred under microwave irradiation at 120° C. for 20 minutes. Reaction mixture was diluted with ethyl acetate, washed with brine, dried (MgSO4), concentrated and purified by flash column chromatography (silica gel, 50 to 100% ethyl acetate/hexanes) to give 2-[5-(5-{4-[2-(1-tert-butylcarbamyl-pyrrolidin-2-yl)-3H-imidazol-4-yl]-phenyl}-thiophen-2-yl)-1H-imidazol-2-yl]-pyrrolidine-1-carboxylic acid tert-butyl ester (0.069 g) as a brown foam: LCMS-ESI+: calc'd for $C_{34}H_{43}N_6O_4S$: 631.80 (M+H+); Found: 631.0 (M+H+).

[1-(2-{5-[4-(5-{2-[1-(2-Methoxycarbonylamino-3-methyl-butyryl)-pyrrolidin-2-yl]-3H-imidazol-4-yl}-thiophen-2-yl)-phenyl]-1H-imidazol-2-yl}-pyrrolidine-1-carbonyl)-2-methyl-propyl]-carbamic acid methyl ester 2-[5-(5-{4-[2-(1-tert-butylcarbamyl-pyrrolidin-2-yl)-3H-imidazol-4-yl]-phenyl}-thiophen-2-yl)-1H-imidazol-2-yl]-pyrrolidine-1-carboxylic acid tert-butyl ester (0.069 g) in dichloromethane (3.0 mL) was treated with 4N HCl in dioxane (3.0 mL) for 30 minutes at ambient temperature. Reaction mixture was concentrated and dried overnight under vacuum to give a reddish-brown solid (0.084 g). Residue was dissolved in DMF (1.0 mL) and to this solution was added 2-Methoxycarbonylamino-3-methyl-butyric acid (0.053 g), 4-methylmorpholine (0.083 mL), followed by HATU (0.113 g). Reaction mixture was stirred for 1 hour at ambient temperature then diluted with ethyl acetate, washed with dilute sodium bicarbonate solution, 5% lithium chloride solution, brine, then dried (MgSO4). Concentration and purification by preparative reverse phase HPLC (Gemini, 5 to 100% ACN/H2O+0.1% TFA) and lyophilization gave [1-(2-{5-[4-(5-{2-[1-(2-Methoxycarbonylamino-3-methyl-butyryl)-pyrrolidin-2-yl]-3H-imidazol-4-yl}-thiophen-2-yl)-phenyl]-1H-imidazol-2-yl}-pyrrolidine-1-carbonyl)-2-methyl-propyl]-carbamic acid methyl ester as the bis-TFA salt (0.040 mg).

1H-NMR: 300 MHz, (DMSO-d6) δ: 8.09 (s, 1H), 7.81 (br s, 4H), 7.65-7.60 (m, 1H), 7.45-7.40 (m, 1H), 7.402-7.30 (m, 21H), 5.20-5.00 (m, 2H), 4.10 (q, J=6.9, 3H), 3.90-3.80 (m, 3H), 3.53 (s, 6H), 2.40-1.90 (m, 10H), 0.90-0.76 (m, 12H): LCMS-ESI-: calc'd for $C_{38}H_{49}N_8O_6S$: 745.90 (M+H+); Found: 745.2 (M+H+).

Example AJ1

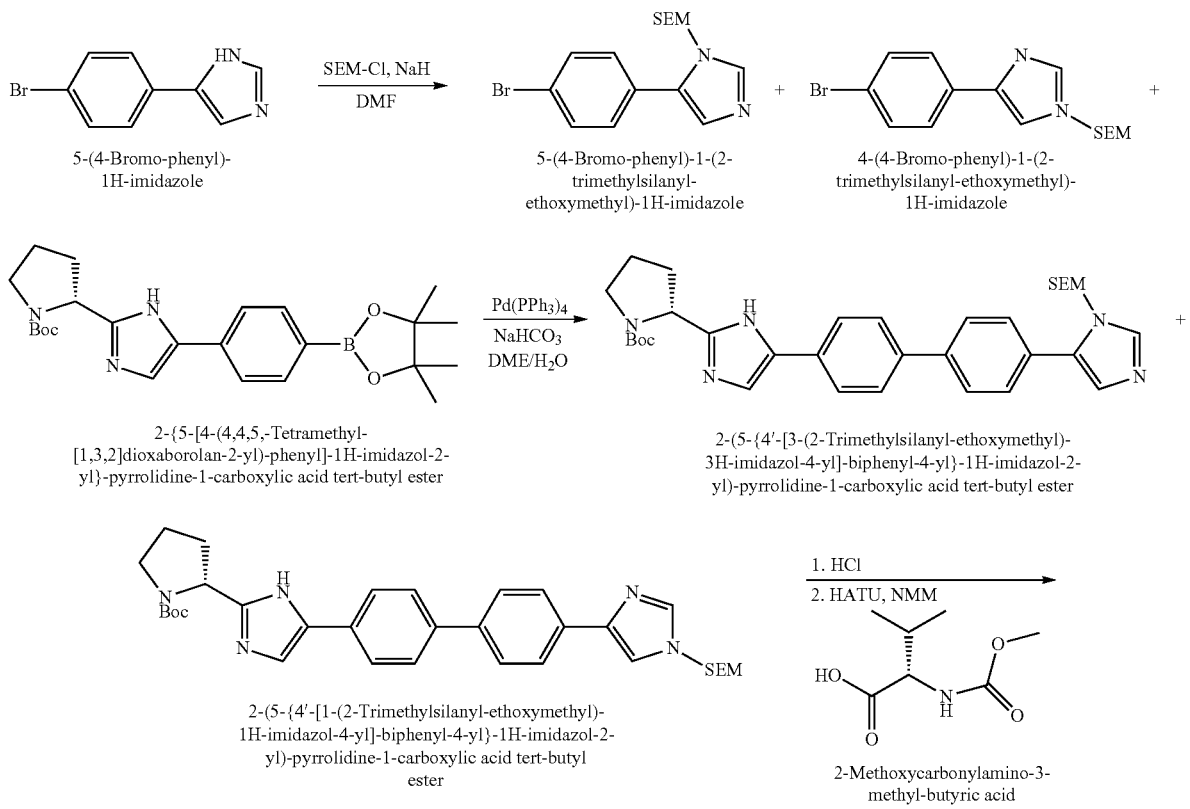

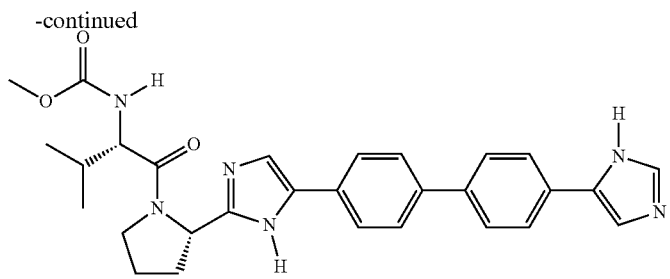

[1-(2-{5-[4'-(3H-Imidazol-4-yl)-
biphenyl-4-yl]-1H-imidazol-2-yl}-
pyrrolidine-1-carbonyl)-2-methyl-
propyl]-carbamic acid methyl ester

5-(4-Bromo-phenyl)-1-(2-trimethylsilanyl-ethoxymethyl)-1H-imidazole and 4-(4-Bromo-phenyl)-1-(2-trimethylsilanyl-ethoxymethyl)-1H-imidazole To a solution of 5-(4-Bromo-phenyl)-1H-imidazole (0.997 g) in DMF (15.0 mL) at 0° C. was added 60% sodium hydride (0.197 g). After stirring for 5 minutes, 2-(trimethylsilyl) ethoxylmethyl chloride (1.18 mL) was added and reaction mixture stirred for 2 hours. Reaction mixture was concentrated, dissolved in ethyl acetate. Organic layer was washed with 5% lithium chloride solution (2×), brine and dried (MgSO$_4$). Concentrated and purified by flash column chromatography (silica gel, ethyl acetate/hexanes) to give a 1:1 mixture of 5-(4-Bromo-phenyl)-1-(2-trimethylsilanyl-ethoxymethyl)-1H-imidazole and 4-(4-Bromo-phenyl)-1-(2-trimethylsilanyl-ethoxymethyl)-1H-imidazole (0.89 g): LCMS-ESI$^+$: calc'd for C$_{15}$H$_{22}$BrN$_2$OSi: 354.33 (M+H$^+$); Found: no product mass observed.

2-(5-{4'-[3-(2-Trimethylsilanyl-ethoxymethyl)-3H-imidazol-4-yl]-biphenyl-4-yl}-1H-imidazol-2-yl)-pyrrolidine-1-carboxylic acid tert-butyl ester and 2-(5-{4'-[1-(2-Trimethylsilanyl-ethoxymethyl)-1H-imidazol-4-yl]-biphenyl-4-yl}-1H-imidazol-2-yl)-pyrrolidine-1-carboxylic acid tert-butyl ester A mixture of 1:1 mixture of 5-(4-Bromo-phenyl)-1-(2-trimethylsilanyl-ethoxymethyl)-1H-imidazole and 4-(4-Bromo-phenyl)-1-(2-trimethylsilanyl-ethoxymethyl)-1H-imidazole (0.145 g), 2-{5-[4-(4,4,5,5-Tetramethyl-[1,3,2] dioxaborolan-2-yl)-phenyl]-1H-imidazol-2-yl}-pyrrolidine-1-carboxylic acid tert-butyl ester (0.150 g, prepared according to WO2008021927 A2) and Pd(PPh$_3$)$_4$ (0.020 g) in aq. K$_2$CO$_3$ solution (0.51 mL)/dimethoxyethane (1.5 mL) was heated at 80° C. for 18 hours. Reaction mixture was cooled, diluted with ethyl acetate, washed with brine, dried (MgSO$_4$) and concentrated. The residue was purified by flash column chromatography (silica gel, 50 to 100% ethyl acetate/hexanes) to give a 1:1 mixture 2-(5-{4'-[3-(2-Trimethylsilanyl-ethoxymethyl)-3H-imidazol-4-yl]-biphenyl-4-yl}-1H-imidazol-2-yl)-pyrrolidine-1-carboxylic acid tert-butyl ester and 2-(5-{4'-[1-(2-Trimethylsilanyl-ethoxymethyl)-1H-imidazol-4-yl]-biphenyl-4-yl}-1H-imidazol-2-yl)-pyrrolidine-1-carboxylic acid tert-butyl ester (0.0998 g): LCMS-ESI$^+$: calc'd for C$_{33}$H$_{44}$N$_5$O$_3$Si: 586.82 (M+H$^+$); Found: 586.0 (M+H$^+$).

[1-(2-{5-[4'-(3H-Imidazol-4-yl)-biphenyl-4-yl]-1H-imidazol-2-yl}-pyrrolidine-1-carbonyl)-2-methyl-propyl]-carbamic acid methyl ester A 1:1 mixture 2-(5-{4'-[3-(2-Trimethylsilanyl-ethoxymethyl)-3H-imidazol-4-yl]-biphenyl-4-yl}-1H-imidazol-2-yl)-pyrrolidine-1-carboxylic acid tert-butyl ester and 2-(5-{4'-[1-(2-Trimethylsilanyl-ethoxymethyl)-1H-imidazol-4-yl]-biphenyl-4-yl}-1H-imidazol-2-yl)-pyrrolidine-1-carboxylic acid tert-butyl ester (0.0998 g) in dichloromethane (3.0 mL) was treated with trifluoroacetic acid (3.0 mL) for 18 hours at ambient temperature. Reaction mixture was concentrated, co-evaporated with acetonitrile and purified by preparative reverse phase HPLC (Gemini, 5 to 100% ACN/H$_2$O+ 0.1% TFA) and concentrated to give a yellow film (0.087 g). Residue was dissolved in DMF (1.0 mL) and to this solution was added 2-Methoxycarbonylamino-3-methyl-butyric acid (0.023 g), 4-methylmorpholine (0.055 mL), followed by HATU (0.049 g). Reaction mixture was stirred for 1 hour at ambient temperature, diluted with ethyl acetate and washed with dilute sodium bicarbonate solution, brine and dried (MgSO$_4$), concentrated and purified by preparative reverse phase HPLC (Gemini, 5 to 100% ACN/H$_2$O+0.1% TFA). Product was lyophilized to give [1-(2-{5-[4'-(3H-Imidazol-4-yl)-biphenyl-4-yl]-1H-imidazol-2-yl}-pyrrolidine-1-carbonyl)-2-methyl-propyl]-carbamic acid methyl ester as the bis-TFA salt (0.016 mg): $^1$H-NMR: 300 MHz, (DMSO-d$_6$) δ: 9.10 (s, 1H), 8.20 (s, 1H), 8.05 (br s, 1H), 7.93-7.80 (m, 8H), 7.32 (d, J=7.8, 1H), 5.20-5.12 (m, 1H), 4.15-4.05 (m, 1H), 3.85-3.80 (m, 3H), 3.54 (s, 3H), 2.40-1.85 (m, 6H), 0.83 (d, J=7.2, 3H), 0.80 (d, J=6.9, 3H): LCMS-ESI$^+$: calc'd for C$_{29}$H$_{33}$N$_6$O$_3$: 513.61 (M+H$^+$); Found: 513.1 (M+H$^+$).

Examples AK1 and AL1

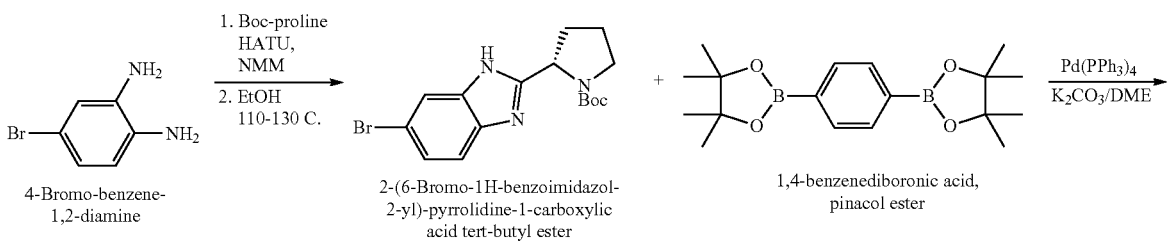

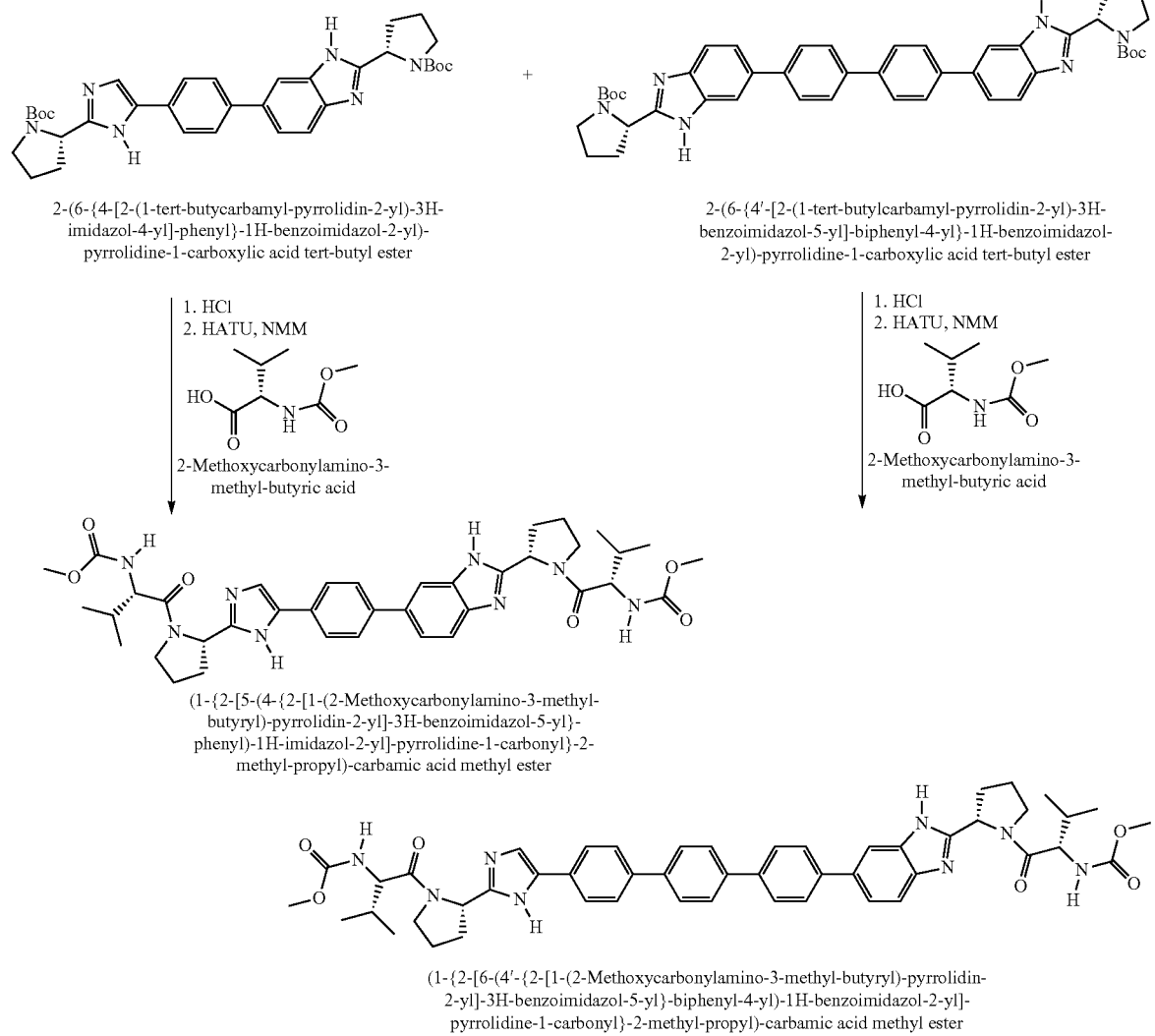

2-(6-Bromo-1H-benzoimidazol-2-yl)-pyrrolidine-1-carboxylic acid tert-butyl ester To a mixture of 4-Bromo-benzene-1,2-diamine (5.0 g), Boc-L-proline (6.0 g), and 4-methylmorpholine (5.88 mL) in DMF (100 mL) was added HATU (10.7 g). Reaction mixture was stirred for 16 hours and then concentrated. Residue was dissolved in ethyl acetate and washed with 5% lithium chloride solution (2×), brine and dried (MgSO4), concentrated and purified by flash column chromatography (silica gel, 30 to 60% ethyl acetate/hexanes) to a dark brown foam. Brown foam was dissolved in ethanol (100 mL) and heated in a sealed tube at 110-130° C. for 2 days. Reaction mixture was cooled and concentrated. Residue was dissolved in ethyl acetate and extracted with 1N HCl (3×). Aqueous layer was basified with 50% NaOH solution to pH 10 and extracted with ethyl acetate (2×). The organic layer was dried (MgSO$_4$), concentrated and purified by flash column chromatography (silica gel, 0 to 10% isopropanol/hexanes) to give 2-(6-Bromo-1H-benzoimidazol-2-yl)-pyrrolidine-1-carboxylic acid tert-butyl ester (6.5 g) as an off-white foam: LCMS-ESI$^+$: calc'd for $C_{16}H_{21}BrN_3O_2$: 367.26 (M+H$^+$); Found: 365.8, 367.8 (M+H$^+$).

2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester A mixture 2-(6-Bromo-1H-benzoimidazol-2-yl)-pyrrolidine-1-carboxylic acid tert-butyl ester (0.257 g), 1,4-benzenediboronic acid, pinacol ester (1.158 g), Pd(PPh$_3$)$_4$ (0.041 g) and potassium carbonate (0.485 g) in H$_2$O (2.0 mL)/dimethoxyethane (5.0 mL) was heated in microwave at 120° C. for 30 minutes. Reaction mixture was cooled and diluted with ethyl acetate, washed with brine, dried (MgSO$_4$), concentrated and purified by flash column chromatography (silica gel, 20 to 70% ethyl acetate/hexanes) to give 2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester (0.187 g): LCMS-ESI$^+$: calc'd for C$_{28}$H$_{37}$BN$_3$O$_4$: 490.42 (M+H$^+$); Found: 490.0 (M+H$^+$).

2-(6-{4-[2-(1-tert-butylcarbamyl-pyrrolidin-2-yl)-3H-imidazol-4-yl]-phenyl}-1H-benzoimidazol-2-yl)-pyrrolidine-1-carboxylic acid tert-butyl ester A mixture of 2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester (0.116 g), 2-(5-Bromo-1H-imidazol-2-yl)-pyrrolidine-1-carboxylic acid tert-butyl ester (0.112 g, prepared according to WO2008021927 A2) and Pd(PPh$_3$)$_4$ (0.014 g) in 2.0M potassium carbonate solution (0.35 mL) and dimethoxyethane (1.0 mL) was heated at 90° C. for 6 hours. Additional Pd(PPh$_3$)$_4$ (0.014 g) was added and reaction continued for 12 hours. Reaction mixture was cooled, diluted with ethyl acetate, washed with H$_2$O, brine, dried (MgSO$_4$), concentrated and purified by flash column chromatography (silica gel, 1 to 30% isopropanol/hexanes) and preparative reverse phase HPLC (Gemini, 5 to 100% ACN/H$_2$O+0.1% TFA) to give 2-(6-{4-[2-(1-tert-butylcarbamyl-pyrrolidin-2-yl)-3H-imidazol-4-yl]-phenyl}-1H-benzoimidazol-2-yl)-pyrrolidine-1-carboxylic acid tert-butyl ester (0.035 g) as a bis-TFA salt: LCMS-ESI$^+$: calc'd for C$_{34}$H$_{43}$N$_6$O$_4$: 599.74 (M+H$^+$); Found: 599.1 (M+H$^+$). A reaction side-product was also isolated and determined to be 2-(6-{4'-[2-(1-tert-butylcarbamyl-pyrrolidin-2-yl)-3H-benzoimidazol-5-yl]-biphenyl-4-yl}-1H-benzoimidazol-2-yl)-pyrrolidine-1-carboxylic acid tert-butyl ester (0.013 g) as the bis-TFA salt: LCMS-ESI$^+$: calc'd for C$_{44}$H$_{49}$N$_6$O$_4$: 725.89. (M+H$^+$); Found: 725.1 (M+H$^+$).

(1-{2-[5-(4-{2-[1-(2-Methoxycarbonylamino-3-methyl-butyryl)-pyrrolidin-2-yl]-3H-benzoimidazol-5-yl}-phenyl)-1H-imidazol-2-yl]-pyrrolidine-1-carbonyl}-2-methyl-propyl)-carbamic acid methyl ester 2-(6-{4-[2-(1-tert-butylcarbamyl-pyrrolidin-2-yl)-3H-imidazol-4-yl]-phenyl}-1H-benzoimidazol-2-yl)-pyrrolidine-1-carboxylic acid tert-butyl ester (0.035 g) in dichloromethane (1.0 mL) was treated with 4N HCl in dioxane (1.0 mL) for 1 hour at ambient temperature. Reaction mixture was concentrated and dried under vacuum. The residue was dissolved in DMF (1.0 mL) and to this solution was added 2-Methoxycarbonylamino-3-methyl-butyric acid (0.0155 g), 4-methylmorpholine (0.023 mL), followed by HATU (0.033 g). Reaction mixture was stirred for 1 hour at ambient temperature and then diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give (1-{2-[5-(4-{2-[1-(2-Methoxycarbonylamino-3-methyl-butyryl)-pyrrolidin-2-yl]-3H-benzoimidazol-5-yl}-phenyl)-1H-imidazol-2-yl]-pyrrolidine-1-carbonyl}-2-methyl-propyl)-carbamic acid methyl ester as the bis-TFA salt (0.0226 g).

$^1$H-NMR: 300 MHz, (CD$_3$OD) δ: 7.98 (s, 1H), 7.90-7.70 (m, 8H), 5.32 (t, J=6.9, 1H), 5.21 (t, J=6.9, 1H), 4.22 (dd, J=10.8, 6.9, 2H), 4.10-3.80 (m, 4H), 3.61 (s, 6H), 2.65-1.80 (m, 10H), 0.950-0.80 (m, 12H): LCMS-ESI$^-$: calc'd for C$_{38}$H$_{49}$N$_8$O$_6$: 713.84 (M+H$^+$); Found: 713.3 (M+H$^+$).

Example AL1

(1-{2-[6-(4'-{2-[1-(2-Methoxycarbonylamino-3-methyl-butyryl)-pyrrolidin-2-yl]-3H-benzoimidazol-5-yl}-biphenyl-4-yl)-1H-benzoimidazol-2-yl]-pyrrolidine-1-carbonyl}-2-methyl-propyl)-carbamic acid methyl ester 2-(6-{4'-[2-(1-tert-butylcarbamyl-pyrrolidin-2-yl)-3H-benzoimidazol-5-yl]-biphenyl-4-yl}-1H-benzoimidazol-2-yl)-pyrrolidine-1-carboxylic acid tert-butyl ester (0.013 g) in dichloromethane (1.0 mL) was treated with 4N HCl in dioxane (1.0 mL) for 1 hour at ambient temperature. Reaction mixture was concentrated and dried under vacuum. The residue was dissolved in DMF (1.0 mL) and to this solution was added 2-Methoxycarbonylamino-3-methyl-butyric acid (0.0155 g), 4-methylmorpholine (0.023 mL), followed by HATU (0.033 g). After stirring for 1 hour at ambient temperature, additional 2-Methoxycarbonylamino-3-methyl-butyric acid (0.0155 g), HATU (0.033 g) were added followed by 4-methylmorpholine (0.023 mL). After stirring for 30 minutes, reaction mixture was diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give (1-{2-[6-(4'-{2-[1-(2-Methoxycarbonylamino-3-methyl-butyryl)-pyrrolidin-2-yl]-3H-benzoimidazol-5-yl}-biphenyl-4-yl)-1H-benzoimidazol-2-yl]-pyrrolidine-1-carbonyl}-2-methyl-propyl)-carbamic acid methyl ester as the bis-TFA salt (0.0106 g). $^1$H-NMR: 300 MHz, (CD$_3$OD) δ: 8.00 (s, 2H), 7.90-7.70 (m, 14H), 5.40-5.35 (m, 2H), 4.28 (d, J=7.2, 2H), 4.15-3.85 (m, 5H), 3.67 (s, 6H), 2.65-2.06 (m, 10H), 0.95 (d, J=6.6, 6H), 0.88 (d, J=6.6, 6H): LCMS-ESI$^-$: calc'd for C$_{48}$H$_{55}$N$_8$O$_6$: 839.99 (M+H$^+$); Found: 839.4 (M+H$^+$).

Example AM1

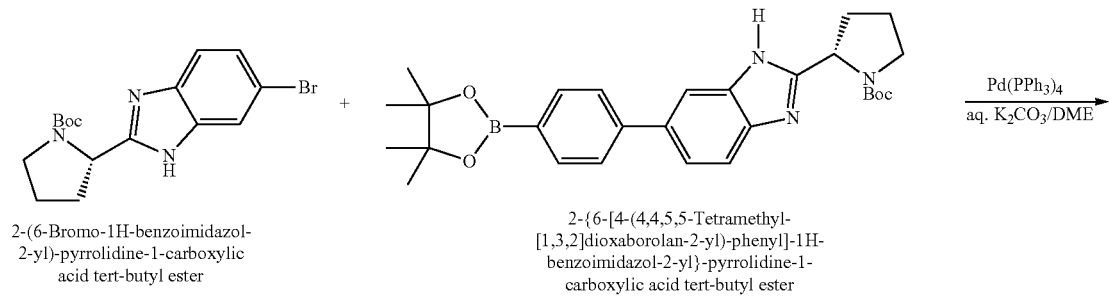

2-(6-Bromo-1H-benzoimidazol-2-yl)-pyrrolidine-1-carboxylic acid tert-butyl ester 2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester

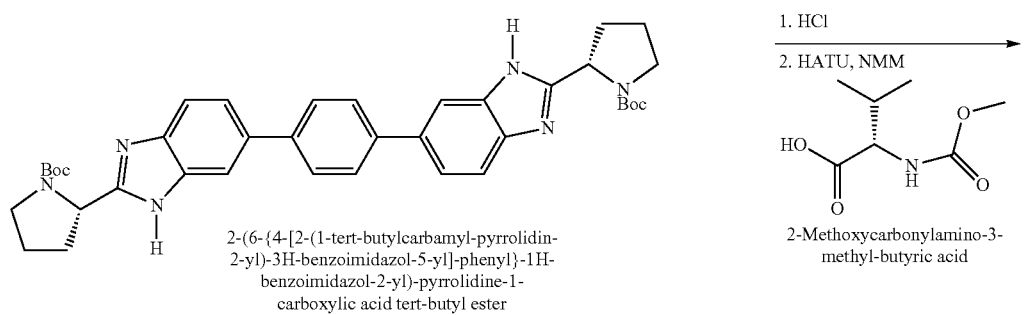

2-(6-{4-[2-(1-tert-butylcarbamyl-pyrrolidin-2-yl)-3H-benzoimidazol-5-yl]-phenyl}-1H-benzoimidazol-2-yl)-pyrrolidine-1-carboxylic acid tert-butyl ester 2-Methoxycarbonylamino-3-methyl-butyric acid

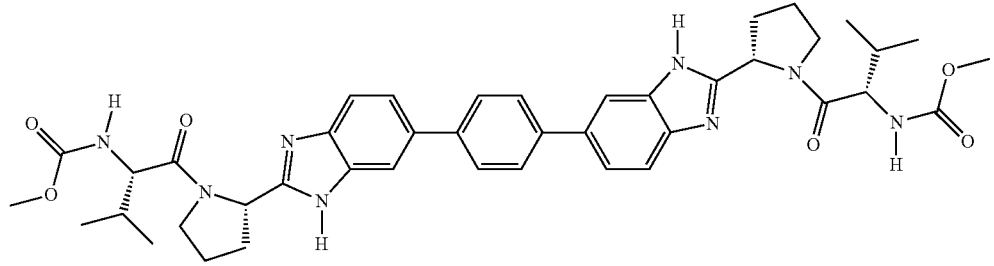

(1-{2-[6-(4-{2-[1-(2-Methoxycarbonylamino-3-methyl-butyryl)-pyrrolidin-2-yl]-3H-benzoimidazol-5-yl}-phenyl)-1H-benzoimidazol-2-yl]-pyrrolidine-1-carbonyl}-2-methyl-propyl)-carbamic acid methyl ester 2-(6-{4-[2-(1-tert-butylcarbamyl-pyrrolidin-2-yl)-3H-benzoimidazol-5-yl]-phenyl}-1H-benzoimidazol-2-yl)-pyrrolidine-1-carboxylic acid tert-butyl ester A mixture of 2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester (0.058 g), 2-(6-Bromo-1H-benzoimidazol-2-yl)-pyrrolidine-1-carboxylic acid tert-butyl ester (0.052 g) and Pd(PPh3)$_4$ (0.0069 g) in 2.0M potassium carbonate solution (0.18 mL) and dimethoxyethane (0.36 mL) was heated in microwave at 110° C. for 30 minutes, then at 120° C. for 60 minutes. Additional Pd(PPh$_3$)$_4$ (0.069 g) was added and reaction was heated conventionally at 90° C. for 12 hours. Reaction mixture was cooled, diluted with ethyl acetate, washed with brine, dried (MgSO$_4$), concentrated and purified by flash column chromatography (silica gel, 1 to 20% isopropanol/hexanes) and preparative reverse phase HPLC (Gemini, 5 to 100% ACN/H$_2$O+ 0.1% TFA) to give 2-(6-{4-[2-(1-tert-butylcarbamyl-pyrrolidin-2-yl)-3H-benzoimidazol-5-yl]-phenyl}-1H-benzoimidazol-2-yl)-pyrrolidine-1-carboxylic acid tert-butyl ester (0.0315 g) as a bis-TFA salt: LCMS-ESI$^+$: calc'd for C$_{38}$H$_{45}$N$_6$O$_4$: 649.79 (M+H$^+$); Found: 649.1 (M+H$^+$).

(1-{2-[6-(4-{2-[1-(2-Methoxycarbonylamino-3-methyl-butyryl)-pyrrolidin-2-yl]-3H-benzoimidazol-5-yl}-phenyl)-1H-benzoimidazol-2-yl]-pyrrolidine-1-carbonyl}-2-methyl-propyl)-carbamic acid methyl ester A solution of 2-(6-{4-[2-(1-tert-butylcarbamyl-pyrrolidin-2-yl)-3H-benzoimidazol-5-yl]-phenyl}-1H-benzoimidazol- 2-yl)-pyrrolidine-1-carboxylic acid tert-butyl ester (0.0315 g) in dichloromethane (2.0 mL) was treated with 4N HCl in dioxane (1.0 mL) for 1 hour at ambient temperature. Reaction mixture was concentrated and dried under vacuum. The residue was dissolved in DMF (1.0 mL) and to this solution was added 2-Methoxycarbonylamino-3-methyl-butyric acid (0.0128 g), 4-methylmorpholine (0.023 mL), followed by HATU (0.027 g). Reaction mixture was stirred for 1 hour at ambient temperature and additional 4-methylmorpholine (0.023 mL) was added. After stirring for 30 minutes, reaction mixture was diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give (1-{2-[6-(4-{2-[1-(2-Methoxycarbonylamino-3-methyl-butyryl)-pyrrolidin-2-yl]-3H-benzoimidazol-5-yl}-phenyl)-1H-benzoimidazol-2-yl]-pyrrolidine-1-carbonyl}-2-methyl-propyl)-carbamic acid methyl ester as the bis-TFA salt (0.0263 g). $^1$H-NMR: 300 MHz, (CD$_3$OD) δ: 8.00 (s, 2H), 7.90-7.70 (m, 8H), 5.40-5.35 (m, 2H), 4.28 (d, J=7.2, 2H), 4.15-3.85 (m, 4H), 3.67 (s, 6H), 2.65-2.06 (m, 10H), 0.95 (d, J=6.6, 6H), 0.88 (d, J=6.6, 6H): LCMS-ESI$^-$: calc'd for C$_{42}$H$_{57}$N$_8$O$_6$: 763.90 (M+H$^+$); Found: 763.3 (M+H$^+$).

Example AN1

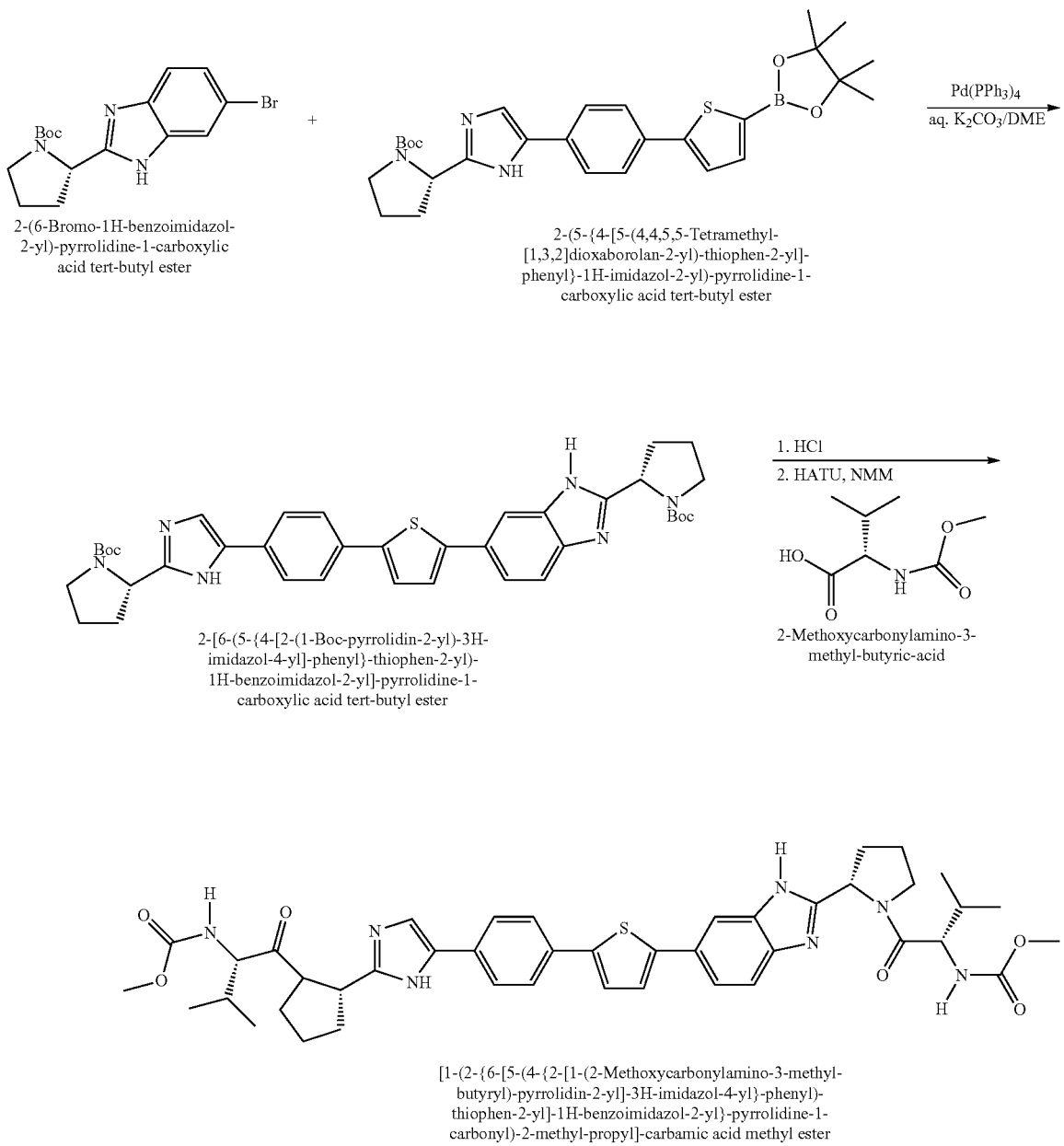

2-[6-(5-{4-[2-(1-Boc-pyrrolidin-2-yl)-3H-imidazol-4-yl]-phenyl}-thiophen-2-yl)-1H-benzoimidazol-2-yl]-pyrrolidine-1-carboxylic acid tert-butyl ester A mixture of 2-(5-{4-[5-(4,4,5,5-Tetramethyl-[1,3,2]dioxaborolan-2-yl)-thiophen-2-yl]-phenyl}-1H-imidazol-2-yl)-pyrrolidine-1-carboxylic acid tert-butyl ester (0.110 g), 2-(6-Bromo-1H-benzoimidazol-2-yl)-pyrrolidine-1-carboxylic acid tert-butyl ester (0.115 g) and Pd(PPh$_3$)$_4$ (0.012 g) in 2.0M potassium carbonate solution (0.32 mL) and dimethoxyethane (0.64 mL) was heated in microwave at 110° C. for 30 minutes. Reaction mixture was cooled, diluted with ethyl acetate, washed with brine, dried (MgSO$_4$), concentrated and purified by flash column chromatography (silica gel, 50 to 100% ethyl acetate/hexanes) and preparative reverse phase HPLC (Gemini, 5 to 100% ACN/H$_2$O+0.1% TFA) to give 2-[6-(5-{4-[2-(1-Formyl-pyrrolidin-2-yl)-3H-imidazol-4-yl]-phenyl}-thiophen-2-yl)-1H-benzoimidazol-2-yl]-pyrrolidine-1-carboxylic acid tert-butyl ester (0.085 g) as a bis-TFA salt: LCMS-ESI$^+$: calc'd for C$_{38}$H$_{45}$N$_6$O$_4$S: 681.86 (M+H$^+$); Found: 681.0 (M+H$^+$).

[1-(2-{6-[5-(4-{2-[1-(2-Methoxycarbonylamino-3-methyl-butyryl)-pyrrolidin-2-yl]-3H-imidazol-4-yl}-phenyl)-thiophen-2-yl]-1H-benzoimidazol-2-yl}-pyrrolidine-1-carbonyl)-2-methyl-propyl]-carbamic acid methyl ester A solution of 2-[6-(5-{4-[2-(1-Formyl-pyrrolidin-2-yl)-3H-imidazol-4-yl]-phenyl}-thiophen-2-yl)-1H-benzoimidazol-2-yl]-pyrrolidine-1-carboxylic acid tert-butyl ester (0.085 g) in dichloromethane (2.0 mL) was treated with 4N HCl in dioxane (2.0 mL) for 1.5 hour at ambient temperature. Reaction mixture was concentrated and dried under vacuum. The residue was dissolved in DMF (1.0 mL) and to this solution was added 2-Methoxycarbonylamino-3-methyl-butyric acid (0.033 g), 4-methylmorpholine (0.060 mL), followed by HATU (0.070 g). Reaction mixture was stirred for 45 minutes at ambient temperature and reaction mixture was diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give [1-(2-{6-[5-(4-{2-[1-(2-Methoxycarbonylamino-3-methyl-butyryl)-pyrrolidin-2-yl]-3H-imidazol-4-yl}-phenyl)-thiophen-2-yl]-1H-benzoimidazol-2-yl}-pyrrolidine-1-carbonyl)-2-methyl-propyl]-carbamic acid methyl ester as the bis-TFA salt (0.048 mg): $^1$H-NMR: 300 MHz, (DMSO-d$_6$) δ: 8.09 (br s, 1H), 7.90-7.75 (m, 8H), 7.70-7.55 (m, 4H), 7.34 (d, J=8.1, 2H), 5.25-5.10 (m, 2H), 4.20-4.15 (m, 4H), 4.15-3.85 (m, 4H), 3.54 (s, 6H), 2.50-1.85 (m, 10H), 0.87-0.75 (m, 12H): LCMS-ESI$^-$: calc'd for C$_{42}$H$_{51}$N$_8$O$_6$S: 795.96 (M+H$^+$); Found: 795.2 (M+H$^+$).

Example AO1

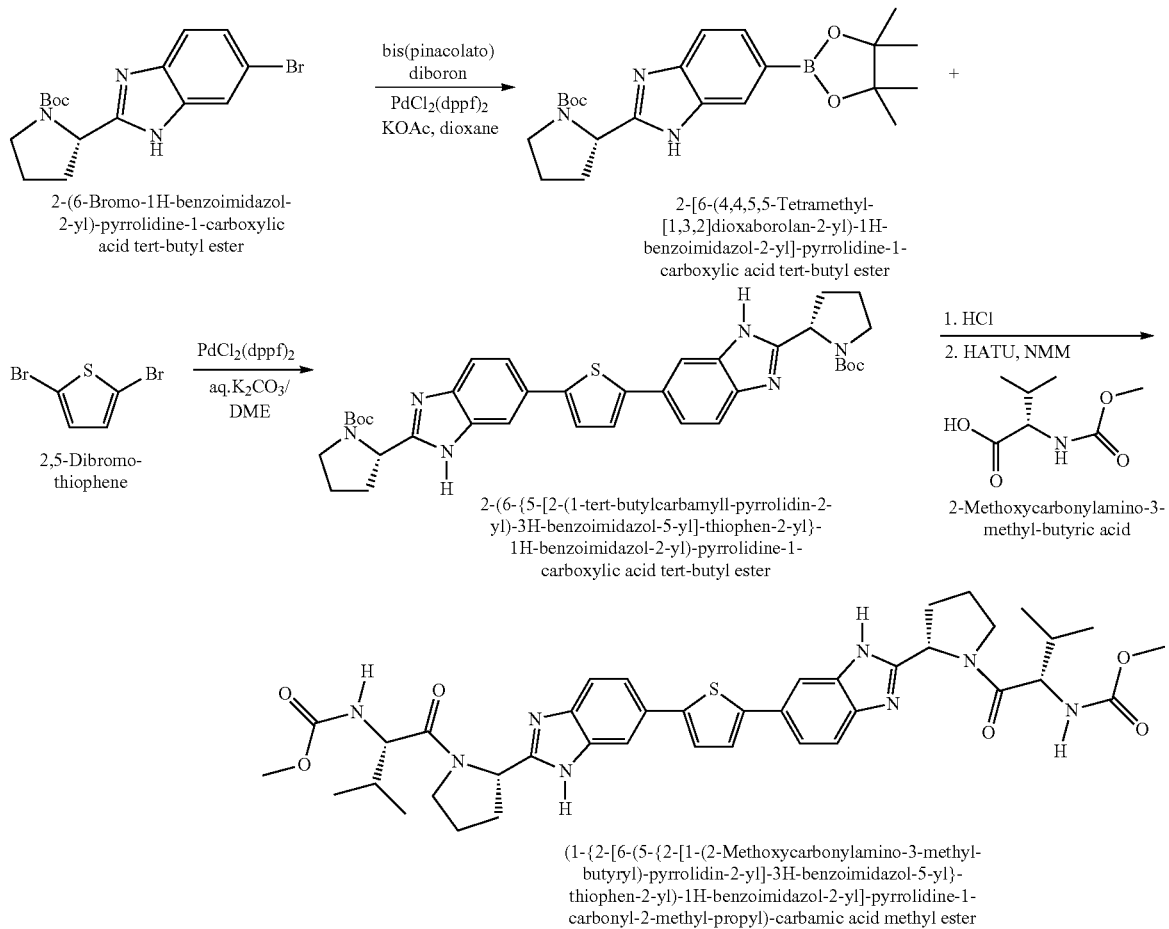

(1-{2-[6-(5-{2-[1-(2-Methoxycarbonylamino-3-methyl-butyryl)-pyrrolidin-2-yl]-3H-benzoimidazol-5-yl}-thiophen-2-yl)-1H-benzoimidazol-2-yl]-pyrrolidine-1-carbonyl-2-methyl-propyl)-carbamic acid methyl ester

2-[6-(4,4,5,5-Tetramethyl-[1,3,2]dioxaborolan-2-yl)-1H-benzoimidazol-2-yl]-pyrrolidine-1-carboxylic acid tert-butyl ester A mixture of 2-(6-Bromo-1H-benzoimidazol-2-yl)-pyrrolidine-1-carboxylic acid tert-butyl ester (0.450 g), bis(pinacolato)diboron (0.655 g), PdCl$_2$(dppf) (0.050 g) and potassium acetate (0.314 g) in 1,4-dioxane was heated at 90° C. for 16 hours. Reaction mixture was cooled to ambient temperatures and diluted with ethyl acetate. The organic layer was washed with brine, dried (MgSO$_4$), concentrated and purified by flash column chromatography (silica gel, 30 to 70% ethyl acetate/hexanes) to give 2-[6-(4,4,5,5-. Tetramethyl-[1,3,2]dioxaborolan-2-yl)-1H-benzoimidazol-2-yl]-pyrrolidine-1-carboxylic acid tert-butyl ester (0.452 g) as an off-white foam: LCMS-ESI$^+$: calc'd for C$_{22}$H$_{33}$BN$_3$O$_4$: 414.32 (M+H$^+$); Found: 414.0 (M+H$^+$).

2-(6-{5-[2-(1-tert-butylcarbamyl-pyrrolidin-2-yl)-3H-benzoimidazol-5-yl]-thiophen-2-yl}-1H-benzoimidazol-2-yl)-pyrrolidine-1-carboxylic acid tert-butyl ester A mixture of 2-[6-(4,4,5,5-Tetramethyl-[1,3,2]dioxaborolan-2-yl)-1H-benzoimidazol-2-yl]-pyrrolidine-1-carboxylic acid tert-butyl ester (0.149 g), 2,5-Dibromo-thiophene (0.035 g) and PdCl$_2$(dppf)$_2$ (0.006 g) in 2.0M potassium carbonate solution (0.36 mL) and dimethoxyethane (1.0 mL) was heated at 90° C. for 18 hours. Additional 2M potassium carbonate solution (0.36 mL) and PdCl$_2$(dppf) (0.006 g) was added and reaction was continued for 48 hours. Reaction mixture was cooled, diluted with ethyl acetate, washed with brine, dried (MgSO$_4$), concentrated and purified using preparative reverse phase HPLC (Gemini, 5 to 100% ACN/H$_2$O+ 0.1% TFA) to give 2-(6-{5-[2-(1-tert-butylcarbamyl-pyrrolidin-2-yl)-3H-benzoimidazol-5-yl]-thiophen-2-yl}-1H-benzoimidazol-2-yl)-pyrrolidine-1-carboxylic acid tert-butyl ester (0.0475 g) as a bis-TFA salt: LCMS-ESI$^+$: calc'd for C$_{36}$H$_{43}$N$_6$O$_4$S: 655.82 (M+H$^+$); Found: 655.0 (M+H$^+$).

(1-{2-[6-(5-{2-[1-(2-Methoxycarbonylamino-3-methyl-butyryl)-pyrrolidin-2-yl]-3H-benzoimidazol-5-yl}-thiophen-2-yl)-1H-benzoimidazol-2-yl]-pyrrolidine-1-carbonyl}-2-methyl-propyl)-carbamic acid methyl ester A solution of 2-(6-{5-[2-(1-tert-butylcarbamyl-pyrrolidin-2-yl)-3H-benzoimidazol-5-yl]-thiophen-2-yl}-1H-benzoimidazol-2-yl)-pyrrolidine-1-carboxylic acid tert-butyl ester (0.0475 g) in dichloromethane (1.0 mL) was treated with 4N HCl in dioxane (1.0 mL) for 1.5 hour at ambient temperature. Reaction mixture was concentrated and dried under vacuum. The residue was dissolved in DMF (1.0 mL) and to this solution was added 2-Methoxycarbonylamino-3-methyl-butyric acid (0.0196 g), 4-methylmorpholine (0.035 mL), followed by HATU (0.042 g). Reaction mixture was stirred for 1 hour at ambient temperature and additional 4-methylmorpholine (0.023 mL) was added. After stirring for 30 minutes, reaction mixture was diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give (1-{2-[6-(5-{2-[1-(2-Methoxycarbonylamino-3-methyl-butyryl)-pyrrolidin-2-yl]-3H-benzoimidazol-5-yl}-thiophen-2-yl)-1H-benzoimidazol-2-yl]-pyrrolidine-1-carbonyl}-2-methyl-propyl)-carbamic acid methyl ester as the bis-TFA salt (0.0296 g): $^1$H-NMR: 300 MHz, (DMSO-d$_6$) δ: 7.91 (s, 2H), 7.71 (s, 4H), 7.61 (s, 2H), 7.35 (d, J=9.0, 2H), 5.25-5.15 (m, 2H), 4.15-4.00 (m, 4H), 3.95-3.75 (m, 4H), 3.54 (s, 6H), 2.25-1.85 (m, 10H), 0.83 (d, J=6.6, 6H), 0.79 (d, J=6.9, 6H); LCMS-ESI$^-$: calc'd for C$_{40}$H$_{49}$N$_8$O$_6$S: 769.92 (M+H$^+$); Found: 769.2 (M+H$^+$).

Example AP1

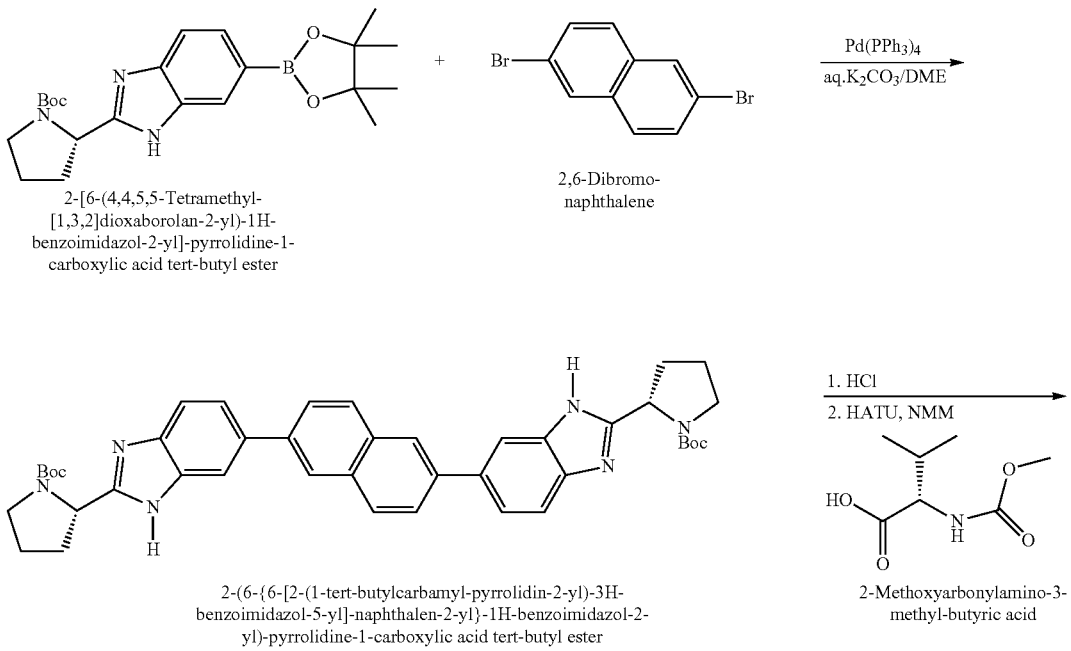

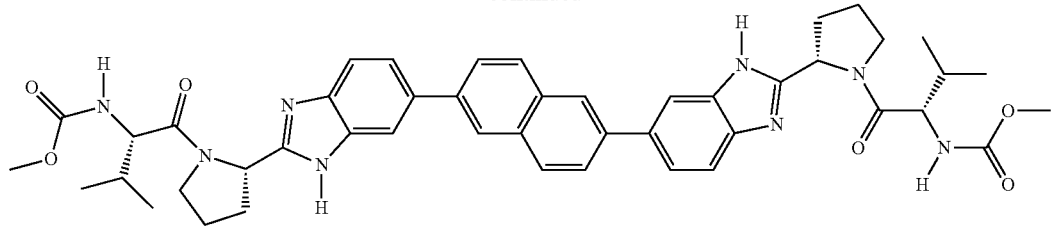

(1-{2-[6-(6-{2-[1-(2-Methoxycarbonylamino-3-methyl-butyryl)-pyrrolidin-2-yl]-3H-benzoimidazol-5-yl}-naphthalen-2-yl)-1H-benzoimidazol-2-yl]-pyrrolidine-1-carbonyl}-2-methyl-propyl)-carbamic acid methyl ester 2-(6-{6-[2-(1-tert-butylcarbamyl-pyrrolidin-2-yl)-3H-benzoimidazol-5-yl]-naphthalen-2-yl}-1H-benzoimidazol-2-yl)-pyrrolidine-1-carboxylic acid tert-butyl ester A mixture of 2-[6-(4,4,5,5-Tetramethyl-[1,3,2]dioxaborolan-2-yl)-1H-benzoimidazol-2-yl]-pyrrolidine-1-carboxylic acid tert-butyl ester (0.170 g), 2,6-Dibromo-naphthalene (0.047 g) and Pd(PPh$_3$)$_4$ (0.0095 g) in 2.0M potassium carbonate solution (0.41 mL) and dimethoxyethane (0.8 mL) was heated in microwave at 110° C. for 40 minutes. Reaction mixture was cooled, diluted with ethyl acetate, washed with brine, dried (MgSO$_4$), concentrated and purified by flash column chromatography (silica gel, 50 to 100% ethyl acetate/hexanes) to give 2-(6-{6-[2-(1-tert-butylcarbamyl-pyrrolidin-2-yl)-3H-benzoimidazol-5-yl]-naphthalen-2-yl}-1H-benzoimidazol-2-yl)-pyrrolidine-1-carboxylic acid tert-butyl ester (0.0961 g) as a yellow film: LCMS-ESI$^+$: calc'd for C$_{42}$H$_{47}$N$_6$O$_4$: 699.85 (M+H$^+$); Found: 699.1 (M+H$^+$).

(1-{2-[6-(6-{2-[1-(2-Methoxycarbonylamino-3-methyl-butyryl)-pyrrolidin-2-yl]-3H-benzoimidazol-5-yl}-naphthalen-2-yl)-1H-benzoimidazol-2-yl]-pyrrolidine-1-carbonyl}-2-methyl-propyl)-carbamic acid methyl ester A solution of 2-(6-{6-[2-(1-tert-butylcarbamyl-pyrrolidin-2-yl)-3H-benzoimidazol-5-yl]-naphthalen-2-yl}-1H-benzoimidazol-2-yl)-pyrrolidine-1-carboxylic acid tert-butyl ester (0.0961 g) in dichloromethane (2.0 mL) was treated with 4N HCl in dioxane (1.0 mL) for 1 hour at ambient temperature. Reaction mixture was concentrated and dried under vacuum. The residue was dissolved in DMF (1.1 mL) and to this solution was added 2-Methoxycarbonylamino-3-methyl-butyric acid (0.0501 g), 4-methylmorpholine (0.091 mL), followed by HATU (0.107 g). Reaction mixture was stirred for 1 hour at ambient temperature, diluted with ethyl acetate and washed with dilute sodium bicarbonate solution, 5% lithium chloride solution, brine and dried (MgSO$_4$). Organic layer was concentrated and purified by preparative reverse phase HPLC (Gemini, 5 to 100% ACN/H$_2$O+0.1% TFA). Product was lyophilized to give (1-{2-[6-(6-{2-[1-(2-Methoxycarbonylamino-3-methyl-butyryl)-pyrrolidin-2-yl]-3H-benzoimidazol-5-yl}-naphthalen-2-yl)-1H-benzoimidazol-2-yl]-pyrrolidine-1-carbonyl}-2-methyl-propyl)-carbamic acid methyl ester as the bis-TFA salt (0.035 mg): $^1$H-NMR: 300 MHz, (DMSO-d$_6$) δ: 8.33 (s, 2H), 8.18-8.01 (m, 4H), 7.95-7.80 (m, 5H), 7.35 (d, J=8.70, 2H), 5.25-5.15 (m, 2H), 4.20-4.00 (m, 4H), 3.95-3.75 (m, 4H), 3.55 (s, 6H), 2.55-1.90 (m, 10H), 0.84 (d, J=6.6, 6H), 0.79 (d, J=6.9, 6H); LCMS-ESI$^-$: calc'd for C$_{46}$H$_{53}$N$_8$O$_6$: 813.96 (M+H$^+$); Found: 813.3 (M+H$^+$).

Example AQ1

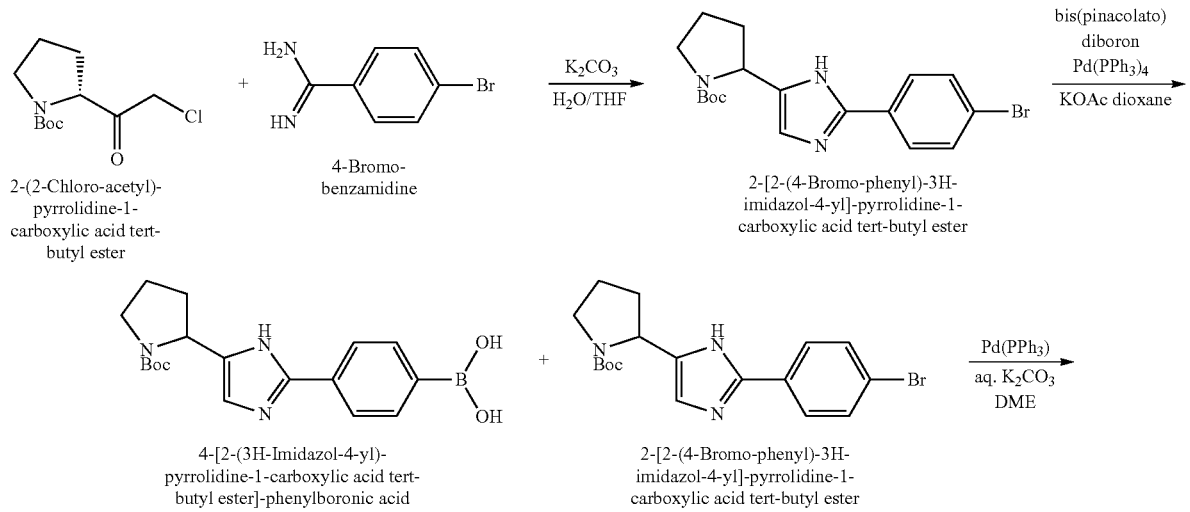

-continued

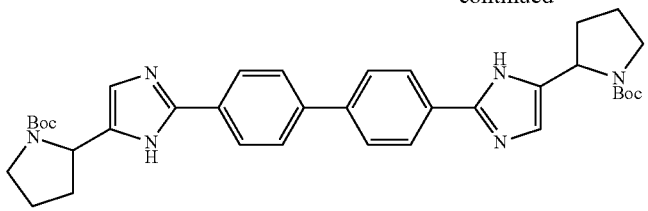

2-(2-{4'-[5-(1-tert-butyl-carbamyl-pyrrolidin-2-yl)-
1H-imidazol-2-yl]-biphenyl-4-yl}-3H-imidazol-4-
yl)-pyrrolidine-1-carboxylic acid tert-butyl ester 1. HCl
2. HATU, NMM

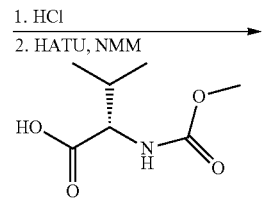

2-Methoxycarbonylamino-3-
methyl-butyric acid

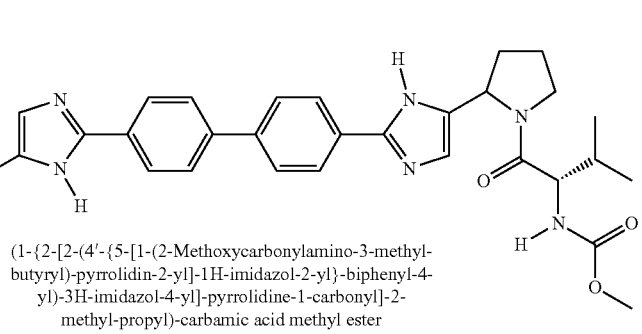

(1-{2-[2-(4'-{5-[1-(2-Methoxycarbonylamino-3-methyl-
butyryl)-pyrrolidin-2-yl]-1H-imidazol-2-yl}-biphenyl-4-
yl)-3H-imidazol-4-yl]-pyrrolidine-1-carbonyl]-2-
methyl-propyl)-carbamic acid methyl ester 2-[2-(4-Bromo-phenyl)-3H-imidazol-4-yl]-pyrroli-
dine-1-carboxylic acid tert-butyl ester A mixture of 4-Bromo-benzamidine (0.202 g) and potassium carbonate (0.237 g) in $H_2O$ (0.286 mL) and THF (1.1 mL) was heated to 65° C. 2-(2-Chloro-acetyl)-pyrrolidine-1-carboxylic acid tert-butyl ester (0.106 g) in THF (0.7 mL) was added over 1 hour and reaction mixture heated at 65° C. for 18 hours. Reaction mixture was concentrated to ~0.5 mL and extracted with ethyl acetate. Organic layer was washed with $H_2O$, brine and dried ($MgSO_4$), concentrated and purified by flash column chromatography (silica gel, 20 to 100% ethyl acetate/hexanes) to give 2-[2-(4-Bromo-phenyl)-3H-imidazol-4-yl]-pyrrolidine-1-carboxylic acid tert-butyl ester (0.075 g) as an orange film: LCMS-ESI$^-$: calc'd for $C_{18}H_{23}BrN_3O_2$: 393.30 (M+H$^+$); Found: 391.8, 393.83 (M+H$^+$).

4-[2-(3H-Imidazol-4-yl)-pyrrolidine-1-carboxylic
acid tert-butyl ester]-phenylboronic acid A mixture of 2-[2-(4-Bromo-phenyl)-3H-imidazol-4-yl]-pyrrolidine-1-carboxylic acid tert-butyl ester (0.075 g), bis(pinacolato)diboron (0.102 g), Pd(PPh$_3$)$_4$ (0.011 g) and potassium acetate (0.049 g) in 1,4-dioxane (1.5 mL) was heated at 100° C. for 16 hours. More Pd(PPh$_3$)$_4$ (0.011 g) was added and the reaction was continued for 24 hours. Reaction mixture was cooled to ambient temperatures and diluted with ethyl acetate. Organic layer was washed with brine, dried (MgSO$_4$), concentrated and purified by purified by preparative reverse phase HPLC (Gemini, 5 to 100% ACN/H$_2$O+ 0.1% TFA). Product was lyophilized to give 4-[2-(3H-Imidazol-4-yl)-pyrrolidine-1-carboxylic acid tert-butyl ester]-phenylboronic acid (0.027 g) as a white powder: LCMS-ESI$^+$: calc'd for $C_{18}H_{25}BN_3O_4$: 357.21 (M+H$^+$); Found: 357.9 (M+H$^+$).

2-(2-{4'-[5-(1-tert-butyl-carbamyl-pyrrolidin-2-yl)-
1H-imidazol-2-yl]-biphenyl-4-yl}-3H-imidazol-4-
yl)-pyrrolidine-1-carboxylic acid tert-butyl ester A mixture of 4-[2-(3H-Imidazol-4-yl)-pyrrolidine-1-carboxylic acid tert-butyl ester]-phenylboronic acid (0.0098 g), 2-[2-(4-Bromo-phenyl)-3H-imidazol-4-yl]-pyrrolidine-1-carboxylic acid tert-butyl ester (0.0118 g) and Pd(PPh$_3$)$_4$ (0.0012 g) in 2.0M potassium carbonate solution (0.031 mL) and dimethoxyethane (0.8 mL) was heated at 90° C. for 18 hours. PdCl$_2$(dppf) (0.003 g) was added and reaction mixture was heated at 100° C. for 18 hours. Reaction mixture was cooled, diluted with ethyl acetate, washed with brine, dried (MgSO$_4$), concentrated and purified using preparative reverse phase HPLC (Gemini, 5 to 100% ACN/H$_2$O+0.1% TFA). Product was lyophilized to give 2-(2-{4'-[5-(1-tert-butyl-carbamyl-pyrrolidin-2-yl)-1H-imidazol-2-yl]-biphenyl-4-yl}-3H-imidazol-4-yl)-pyrrolidine-1-carboxylic acid tert-butyl ester (0.0018 g) as a white powder: LCMS-ESI$^+$: calc'd for $C_{36}H_{45}N_6O_4$: 624.77 (M+H$^+$); Found: 625.0 (M+H$^+$).

(1-{2-[2-(4'-{5-[1-(2-Methoxycarbonylamino-3-
methyl-butyryl)-pyrrolidin-2-yl]-1H-imidazol-2-yl}-
biphenyl-4-yl)-3H-imidazol-4-yl]-pyrrolidine-1-
carbonyl}-2-methyl-propyl)-carbamic acid methyl
ester A solution of 2-(2-{4'-[5-(1-tert-butyl-carbamyl-pyrrolidin-2-yl)-1H-imidazol-2-yl]-biphenyl-4-yl}-3H-imidazol-4-yl)-pyrrolidine-1-carboxylic acid tert-butyl ester (0.0018 g) in dichloromethane (0.5 mL) was treated with 4N HCl in dioxane (0.5 mL) for 1 hour at ambient temperature. Reaction mixture was concentrated and dried under vacuum. The residue was dissolved in DMF (0.4 mL) and to this solution was added 2-methoxycarbonylamino-3-methyl-butyric acid (0.0008 g), 4-methylmorpholine (0.0024 mL), followed by HATU (0.0016 g). Reaction mixture was stirred for 1.5 hour at ambient temperature, then purified by preparative reverse phase HPLC (Gemini, 5 to 100% ACN/H$_2$O+0.1% TFA). Product was lyophilized to give (1-{2-[2-(4'-{5-[1-(2-Methoxycarbonylamino-3-methyl-butyryl)-pyrrolidin-2-yl]-1H-imidazol-2-yl}-biphenyl-4-yl)-3H-imidazol-4-yl]-pyrrolidine-1-carbonyl}-2-methyl-propyl)-carbamic acid methyl ester as a mixture of diastereomers of the bis-TFA salt (0.0017 g): $^1$H-NMR: 300 MHz, (CD$_3$OD) δ: 8.10-7.95 (m, 8H), 7.55-7.40 (m, 2H), 5.25-5.15 (m, 2H), 4.20-3.65 (m, 6H), 3.62 (s, 6H), 2.40-1.90 (m, 10H), 1.05-0.85 (m, 12H); LCMS-ESI⁻: calc'd for $C_{40}H_{51}N_8O_6$: 739.88 (M+H⁺); Found: 739.3 (M+H⁺).

Example AR1

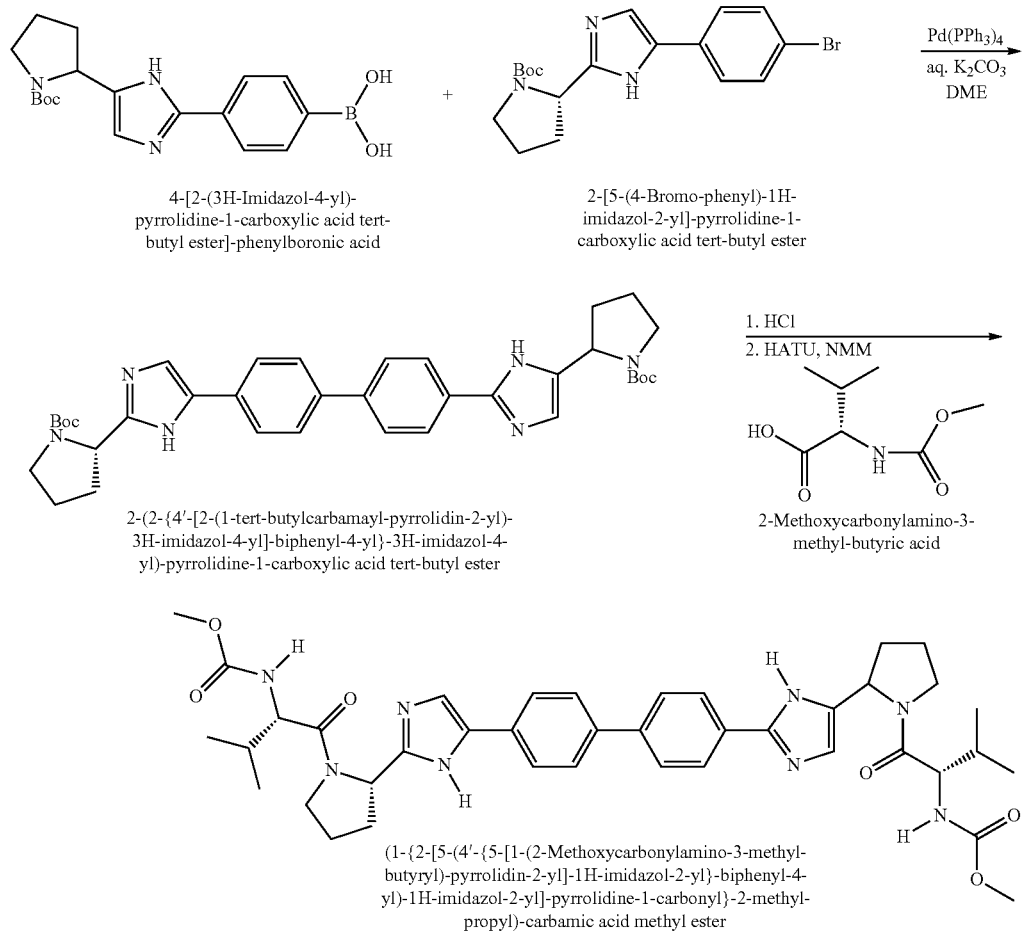

2-(2-{4'-[2-(1-tert-butylcarbamyl-pyrrolidin-2-yl)-3H-imidazol-4-yl]-biphenyl-4-yl}-3H-imidazol-4-yl)-pyrrolidine-1-carboxylic acid tert-butyl ester A mixture of 4-[2-(3H-Imidazol-4-yl)-pyrrolidine-1-carboxylic acid tert-butyl ester]-phenylboronic acid (0.0177 g), 2-[5-(4-Bromo-phenyl)-1H-imidazol-2-yl]-pyrrolidine-1-carboxylic acid tert-butyl ester (0.0148 g) and Pd(PPh₃)₄ (0.0022 g), PdCl₂(dppf) (0.0016 g) in 2.0M potassium carbonate solution (0.056 mL) and dimethoxyethane (0.8 mL) was heated at 90° C. for 18 hours. Reaction mixture was cooled, diluted with ethyl acetate, washed with brine, dried (MgSO₄), concentrated and purified using preparative reverse phase HPLC (Gemini, 5 to 100% ACN/H2O+0.1% TFA). Product was lyophilized to give 2-(2-{4'-[2-(1-tert-butylcarbamyl-pyrrolidin-2-yl)-3H-imidazol-4-yl]-biphenyl-4-yl}-3H-imidazol-4-yl)-pyrrolidine-1-carboxylic acid tert-butyl ester (0.0066 g) as a white powder: LCMS-ESI⁺: calc'd for $C_{36}H_{45}N_6O_4$: 624.77 (M+H⁺); Found: 625.0 (M+H⁺).

(1-{2-[5-(4'-{5-[1-(2-Methoxycarbonylamino-3-methyl-butyryl)-pyrrolidin-2-yl]-1H-imidazol-2-yl}-biphenyl-4-yl)-1H-imidazol-2-yl]-pyrrolidine-1-carbonyl}-2-methyl-propyl)-carbamic acid methyl ester A solution of 2-(2-{4'-[2-(1-tert-butylcarbamyl-pyrrolidin-2-yl)-3H-imidazol-4-yl]-biphenyl-4-yl}-3H-imidazol-4-yl)-pyrrolidine-1-carboxylic acid tert-butyl ester (0.0066 g) in dichloromethane (0.5 mL) was treated with 4N HCl in dioxane (0.5 mL) for 1 hour at ambient temperature. Reaction mixture was concentrated and dried under vacuum. The residue was dissolved in DMF (0.4 mL) and to this solution was added 2-Methoxycarbonylamino-3-methyl-butyric acid (0.0028 g), 4-methylmorpholine (0.012 mL), followed by HATU (0.006 g). Reaction mixture was stirred for 2 hours at ambient temperature, then purified by preparative reverse phase HPLC (Gemini, 5 to 100% ACN/H₂O+0.1% TFA). Product was lyophilized to give (1-{2-[5-(4'-{5-[1-(2-Methoxycarbonylamino-3-methyl-butyryl)-pyrrolidin-2-yl]-1H-imidazol-2-yl}-biphenyl-4-yl)-1H-imidazol-2-yl]-pyrrolidine-1-carbonyl}-2-methyl-propyl)-carbamic acid methyl ester as a mixture of diastereomers of the bis-TFA salt (0.0081 g): $^1$H-NMR: 300 MHz, (CD$_3$OD) δ: 8.05-7.80 (m, 9H), 7.55-7.40 (m, 1H), 5.25-5.15 (m, 2H), 4.20-3.65 (m, 6H), 3.62 (s, 6H), 2.55-1.95 (m, 10H), 1.05-0.85 (m, 12H); LCMS-ESI$^-$: calc'd for C$_{40}$H$_{51}$N$_8$O$_6$: 739.88 (M+H$^+$); Found: 739.3 (M+H$^+$).

Example AS1

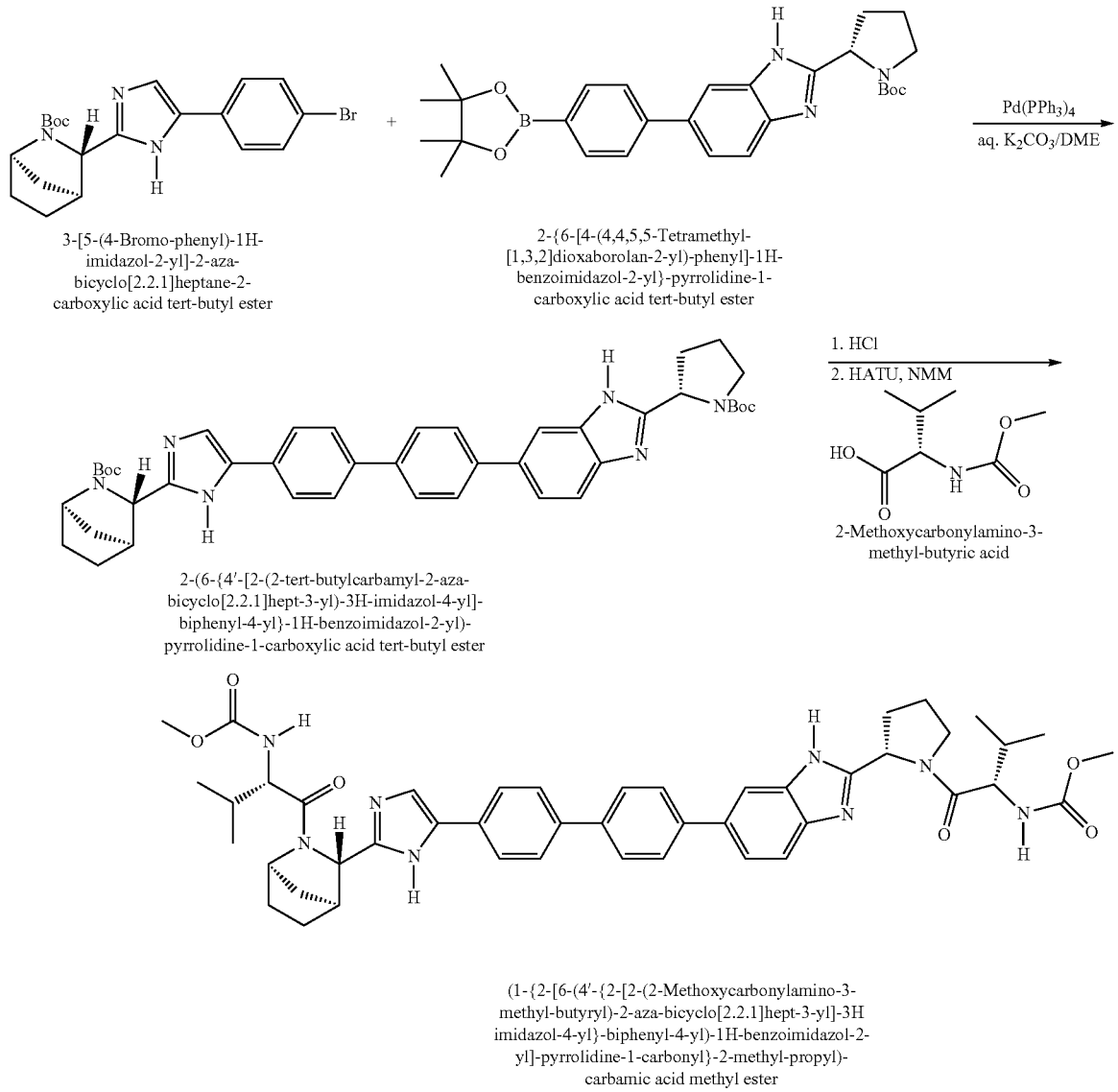

(1-{2-[6-(4'-{2-[2-(2-Methoxycarbonylamino-3-methyl-butyryl)-2-aza-bicyclo[2.2.1]hept-3-yl]-3H imidazol-4-yl}-biphenyl-4-yl)-1H-benzoimidazol-2-yl]-pyrrolidine-1-carbonyl}-2-methyl-propyl)-carbamic acid methyl ester 2-(6-{4'-[2-(2-tert-butylcarbamyl-2-aza-bicyclo [2.2.1]hept-3-yl)-3H-imidazol-4-yl]-biphenyl-4-yl}-1H-benzoimidazol-2-yl)-pyrrolidine-1-carboxylic acid tert-butyl ester A mixture of 2-{6-[4-(4,4,5,5-Tetramethyl-[1,3,2]dioxaborolan-2-yl)-phenyl]-1H-benzoimidazol-2-yl}-pyrrolidine-1-carboxylic acid tert-butyl ester (0.142 g), 3-[5-(4-Bromo-phenyl)-1H-imidazol-2-yl]-2-aza-bicyclo[2.2.1] heptane-2-carboxylic acid tert-butyl ester (0.1013 g) and Pd(PPh$_3$)$_4$ (0.014 g) in 2.0M potassium carbonate solution (0.036 mL) and dimethoxyethane (0.8 mL) was heated in microwave at 110° C. for 30 minutes. Reaction mixture was diluted with ethyl acetate, washed with brine, dried (MgSO$_4$), concentrated and purified using preparative reverse phase HPLC (Gemini, 5 to 100% ACN/H$_2$O+0.1% TFA). Product was lyophilized to give 2-(6-{4'-[2-(2-tert-butylcarbamyl-2-aza-bicyclo[2.2.1]hept-3-yl)-3H-imidazol-4-yl]-biphenyl-4-yl}-1H-benzoimidazol-2-yl)-pyrrolidine-1-carboxylic acid tert-butyl ester (0.128 g) as a white powder: LCMS-ESI$^+$: calc'd for C$_{42}$H$_{49}$N$_6$O$_4$: 701.87 (M+H$^+$); Found: 701.1 (M+H$^+$).

(1-{2-[6-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-benzoimidazol-2-yl]-pyrrolidine-1-carbonyl}-2-methyl-propyl)-carbamic acid methyl ester A solution of 2-(6-{4'-[2-(2-tert-butylcarbamyl-2-aza-bicyclo[2.2.1]hept-3-yl]-3H-imidazol-4-yl]-biphenyl-4-yl}-1H-benzoimidazol-2-yl)-pyrrolidine-1-carboxylic acid tert-butyl ester (0.128 g) in dichloromethane (2.0 mL) was treated with 4N HCl in dioxane (1.0 mL) for 1 hour at ambient temperature. Reaction mixture was concentrated and dried under vacuum. The residue was dissolved in DMF (2.0 mL) and to this solution was added 2-Methoxycarbonylamino-3-methyl-butyric acid (0.050 g), 4-methylmorpholine (0.090 mL), followed by HATU (0.106 g). Reaction mixture was stirred for 1 hour at ambient temperature. Additional 4-methylmorpholine (0.090 mL) was added and reaction mixture stirred for 1 hour. Reaction mixture was diluted with ethyl acetate, washed with dilute sodium bicarbonate solution, 5% lithium chloride solution, brine and dried ($MgSO_4$), then concentrated and purified by preparative reverse phase HPLC (Gemini, 5 to 100% $ACN/H_2O$+0.1% TFA). Product was lyophilized to (1-{2-[6-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-benzoimidazol-2-yl]-pyrrolidine-1-carbonyl}-2-methyl-propyl)-carbamic acid methyl ester as the bis-TFA salt (0.080 g): $^1$H-NMR: 300 MHz, ($CD_3OD$) δ: 8.05-7.70 (m, 13H), 7.35-7.25 (m, 2H), 5.25-5.15 (m, 1H), 4.67 (s, 1H), 4.43 (s, 1H), 4.20-4.00 (m, 2H), 3.85-3.75 (m, 4H), 3.51 (s, 3H), 3.49 (s, 3H), 2.50-1.45 (m, 14H), 0.95-0.75 (m, 12H); LCMS-ESI$^-$: calc'd for $C_{46}H_{55}N_8O_6$: 815.97 (M+H$^+$); Found: 815.3 (M+H$^+$).

Example AT1

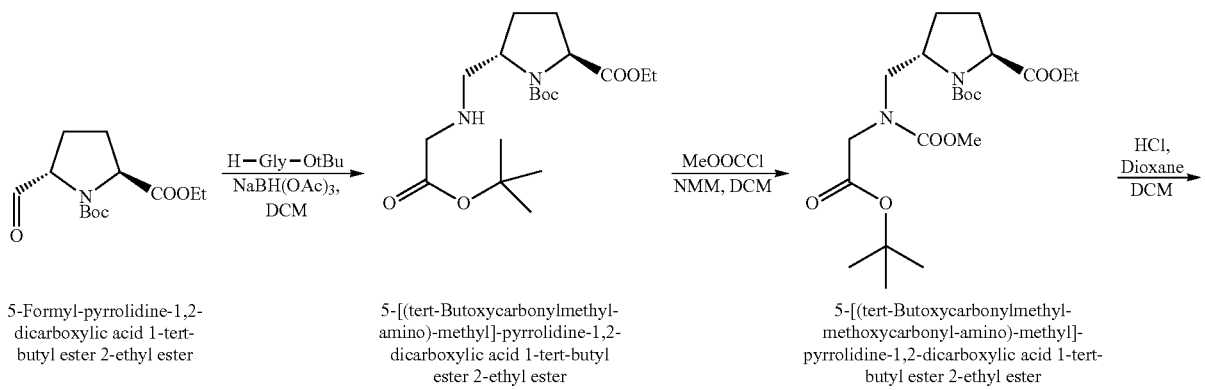

5-Formyl-pyrrolidine-1,2-dicarboxylic acid 1-tert-butyl ester 2-ethyl ester

5-[(tert-Butoxycarbonylmethyl-amino)-methyl]-pyrrolidine-1,2-dicarboxylic acid 1-tert-butyl ester 2-ethyl ester 5-[(tert-Butoxycarbonylmethyl-methoxycarbonyl-amino)-methyl]-pyrrolidine-1,2-dicarboxylic acid 1-tert-butyl ester 2-ethyl ester

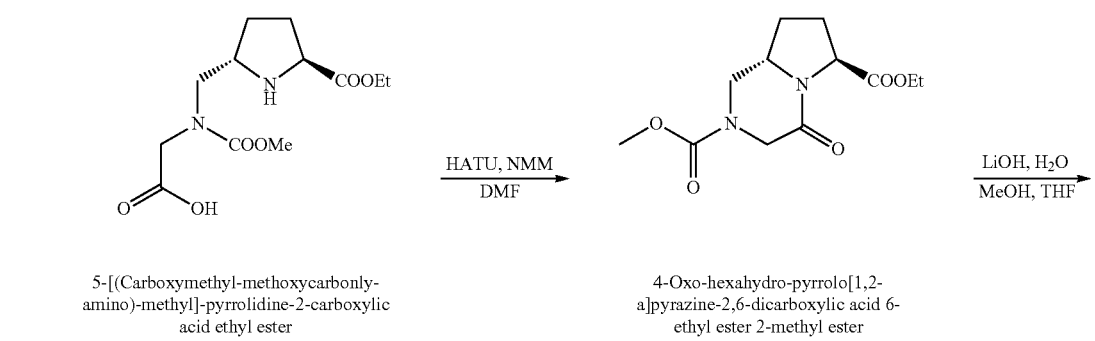

5-[(Carboxymethyl-methoxycarbonly-amino)-methyl]-pyrrolidine-2-carboxylic acid ethyl ester 4-Oxo-hexahydro-pyrrolo[1,2-a]pyrazine-2,6-dicarboxylic acid 6-ethyl ester 2-methyl ester

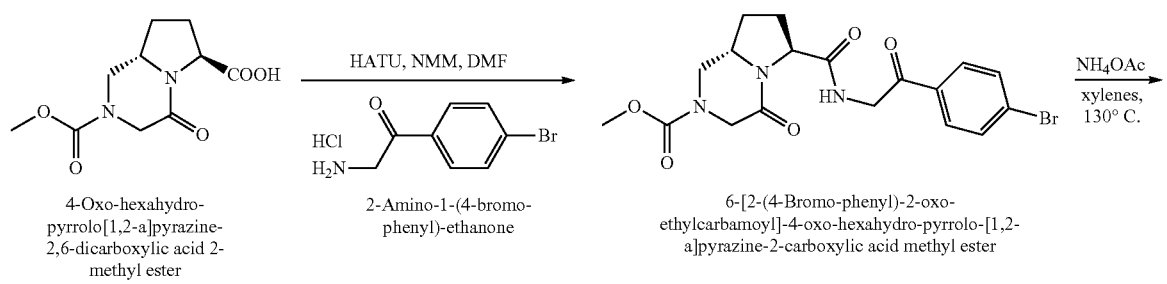

4-Oxo-hexahydro-pyrrolo[1,2-a]pyrazine-2,6-dicarboxylic acid 2-methyl ester

2-Amino-1-(4-bromo-phenyl)-ethanone

6-[2-(4-Bromo-phenyl)-2-oxo-ethylcarbamoyl]-4-oxo-hexahydro-pyrrolo-[1,2-a]pyrazine-2-carboxylic acid methyl ester

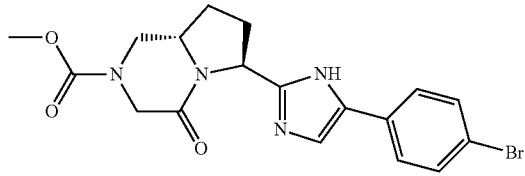

6-[5-(4-Bromo-phenyl)-1H-imidazol-2-yl]-4-oxo-hexahydro-pyrrolo[1,2-a]pyrazine-2-carboxylic acid methyl ester

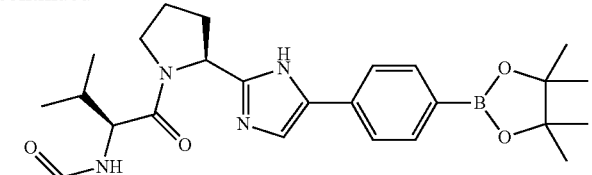

Pd(PPh$_3$)$_4$, K$_2$CO$_3$, DME, H$_2$O, MW 120° C.

[2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester

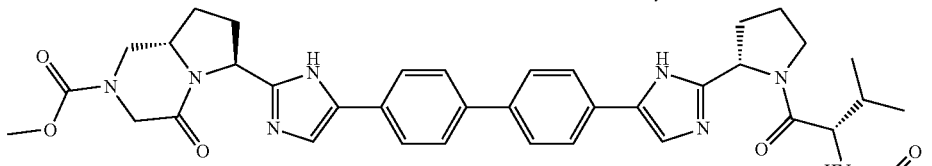

6-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-4-oxo-hexahydro-pyrrolo[1,2-a]pyrazine-2-carboxylic acid methyl ester

5-Formyl-pyrrolidine-1,2-dicarboxylic acid 1-tert-butyl ester 2-ethyl ester

5-Formyl-pyrrolidine-1,2-dicarboxylic acid 1-tert-butyl ester 2-ethyl ester was prepared according to: *J. Org. Chem.* 1995, 60, 5011-5015.

5-[(tert-Butoxycarbonylmethyl-amino)-methyl]-pyrrolidine-1,2-dicarboxylic acid 1-tert-butyl ester 2-ethyl ester Sodium triacetoxyborohydride (2.08 g, 9.86 mmol) was added to a solution of 5-formyl-pyrrolidine-1,2-dicarboxylic acid 1-tert-butyl ester 2-ethyl ester (891 mg, 3.29 mmol) and glycine t-butyl ester (1.65 g, 9.86 mmol) in dichloromethane (20 mL) over 2 minutes—a small amount of gas evolution was observed. After 1 hour the reaction was quenched with saturated ammonium chloride (5 mL). The mixture was extracted with ethyl acetate (3×25 mL). The combined organic phases were dried over sodium sulfate, filtered and the solvent was removed under reduced pressure. The resulting residue was purified by flash chromatography with methanol and dichloromethane as the eluant at a gradient of 0-10%. The fractions containing product were combined and the solvent was removed under reduced pressure to provide 5-[(tert-butoxycarbonylmethyl-amino)-methyl]-pyrrolidine-1,2-dicarboxylic acid 1-tert-butyl ester 2-ethyl ester (601 mg, 1.55 mmol, 47%). C$_{19}$H$_{34}$N$_2$O$_6$ calculated 386.2, observed [M+1]$^+$ 387.2; rt=1.61 min.

5-[(tert-Butoxycarbonylmethyl-methoxycarbonyl-amino)-methyl]-pyrrolidine-1,2-dicarboxylic acid 1-tert-butyl ester 2-ethyl ester Methyl chloroformate (0.065 mL, 0.85 mmol) was added to a solution of 5-[(tert-butoxycarbonylmethyl-amino)-methyl]-pyrrolidine-1,2-dicarboxylic acid 1-tert-butyl ester 2-ethyl ester (300 mg, 0.77 mmol) and 4-methylmorpholine (0.12 mL, 1.2 mmol) in dichloromethane (10 mL) at 0° C. After 15 minutes the mixture was diluted with dichloromethane (30 mL) and washed with water (15 mL), saturated ammonium chloride (15 mL) and saturated sodium chloride (15 mL). The organic phase was dried over sodium sulfate and the solvent was removed under reduced pressure to provide 5-[(tert-butoxycarbonylmethyl-methoxycarbonyl-amino)-methyl]-pyrrolidine-1,2-dicarboxylic acid 1-tert-butyl ester 2-ethyl ester (304 mg, 0.68 mmol, 88%). C$_{21}$H$_{36}$N$_2$O$_8$ calculated 444.3, observed [M+1]$^+$ 445.3; rt=2.58 min.

5-[(Carboxymethyl-methoxycarbonyl-amino)-methyl]-pyrrolidine-2-carboxylic acid ethyl ester 5-[(tert-Butoxycarbonylmethyl-methoxycarbonyl-amino)-methyl]-pyrrolidine-1,2-dicarboxylic acid 1-tert-butyl ester 2-ethyl ester (304 mg, 0.68 mmol) was added to a solution of hydrogen chloride in dioxane (4N, 15 mL). After 16 hours the solvent was removed under reduced pressure and the resulting residue was azeotroped with toluene to provide 5-[(carboxymethyl-methoxycarbonyl-amino)-methyl]-pyrrolidine-2-carboxylic acid ethyl ester (224 mg)—assumed 100% yield.

4-Oxo-hexahydro-pyrrolo[1,2-a]pyrazine-2,6-dicarboxylic acid 6-ethyl ester 2-methyl ester HATU (390 mg, 1.03 mmol) was added to solution of 5-[(carboxymethyl-methoxycarbonyl-amino)-methyl]-pyrrolidine-2-carboxylic acid ethyl ester (187 mg, 0.68 mmol) and 4-methylmorpholine (375 µL, 3.4 mmol) in dimethylformamide (30 mL). After 50 minutes the solvent was removed under reduced pressure and the resulting residue was taken up in ethyl acetate (20 mL) which was washed with half saturated sodium chloride (2×10 mL), saturated sodium bicarbonate (2×10 mL) and dried over sodium sulfate. The aqueous phase also contained product. The water was removed under reduced pressure and the residue was azeotroped with toluene and then stirred with ethyl acetate (50 mL). The mixture was filtered and combined with the organic extracts.

The solvent was removed under reduced pressure and the resulting residue was subjected to flash chromatography with eluent of (10% methanol in ethyl acetate) and hexane. The product-containing fractions were combined and the solvent was removed under reduced pressure to provide 4-oxo-hexahydro-pyrrolo[1,2-a]pyrazine-2,6-dicarboxylic acid 6-ethyl ester 2-methyl ester (141 mg, 0.52 mmol, 76%). $C_{12}H_{18}N_2O_5$ calculated 270.1, observed $[M+1]^+$ 271.1; rt=1.54 min.

The Following (Ester Hydrolysis) Constitutes an Example of Method 801

4-Oxo-hexahydro-pyrrolo[1,2-a]pyrazine-2,6-dicarboxylic acid 2-methyl ester

A solution of lithium hydroxide monohydrate (16.8 mg, 0.38 mmol) in water (0.5 mL) was added to a solution of 4-oxo-hexahydro-pyrrolo[1,2-a]pyrazine-2,6-dicarboxylic acid 6-ethyl ester 2-methyl ester (86 mg, 0.32 mmol) in methanol (1 mL) and tetrahydrofuran (1 mL). After 2 hours, an aqueous solution of hydrogen chloride (1N, 0.41 mL, 0.41 mmol) was added and the organic solvents were removed under reduced pressure. The resulting aqueous solution was lyophilized for 16 hours to give 4-oxo-hexahydro-pyrrolo[1,2-a]pyrazine-2,6-dicarboxylic acid 2-methyl ester. A yield of 100% was assumed for the subsequent step. $C_{10}H_{14}N_2O_5$ calculated 242.1, observed $[M+1]^+$ 242.9, $[M+1]^-$ 241.1; rt=1.54 min.

The Following Three Steps (Amide Formation, Imidazole Cyclization and Suzuki Coupling) Constitute an Example of Method 802

6-[2-(4-Bromo-phenyl)-2-oxo-ethylcarbamoyl]-4-oxo-hexahydro-pyrrolo[1,2-a]pyrazine-2-carboxylic acid methyl ester A solution of 4-oxo-hexahydro-pyrrolo[1,2-a]pyrazine-2,6-dicarboxylic acid 2-methyl ester (81 mg, 0.33 mmol), HATU (152 mg, 0.40 mmol), and 4-methyl morpholine (146 µL, 1.33 mmol) in dimethylformamide (4 mL) was stirred at ambient temperature for 5 minutes. 2-Amino-1-(4-bromo-phenyl)-ethanone hydrochloride (91 mg, 0.37 mmol) was added to the reaction mixture. After 1 hour the solvent was removed under reduced pressure and the resulting residue was taken up in ethyl acetate (10 mL). The resulting mixture contained a solid and was filtered. The solvent was removed under reduced pressure from the filtrate. The resulting residue was subjected to flash chromatography with eluent of (10% methanol in ethyl acetate) and hexane. The product-containing fractions were combined and the solvent was removed under reduced pressure to provide 6-[2-(4-bromo-phenyl)-2-oxo-ethylcarbamoyl]-4-oxo-hexahydro-pyrrolo[1,2-a]pyrazine-2-carboxylic acid methyl ester (110 mg, 0.25 mmol, 75%). $C_{18}H_{20}BrN_3O_5$ calculated 437.1 observed $[M+1]^+$ 438.1; rt=1.82 min.

6-[5-(4-Bromo-phenyl)-1H-imidazol-2-yl]-4-oxo-hexahydro-pyrrolo[1,2-a]pyrazine-2-carboxylic acid methyl ester A mixture of 6-[2-(4-bromo-phenyl)-2-oxo-ethylcarbamoyl]-4-oxo-hexahydro-pyrrolo[1,2-a]pyrazine-2-carboxylic acid methyl ester (110 mg, 0.25 mmol), ammonium acetate (193 mg, 2.5 mmol) and xylenes (8 mL) was heated to 130° C. After 1 hour the mixture was cooled and the xylenes were removed under reduced pressure. Dichloromethane was added to the resulting residue and the mixture was filtered. The solvent was removed under reduced pressure from the filtrate and the resulting residue was subjected to flash chromatography with eluent of (10% methanol in ethyl acetate) and hexane. The product-containing fractions were combined and the solvent was removed under reduced pressure to provide 6-[5-(4-bromo-phenyl)-1H-imidazol-2-yl]-4-oxo-hexahydro-pyrrolo[1,2-a]pyrazine-2-carboxylic acid methyl ester (65 mg, 0.15 mmol, 60%). $C_{18}H_0BrN_4O_3$ calculated 418.1 observed $[M+1]^+$ 419.1; rt=1.50 min.

6-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-4-oxo-hexahydro-pyrrolo[1,2-a]pyrazine-2-carboxylic acid methyl ester A mixture of 6-[5-(4-bromo-phenyl)-1H-imidazol-2-yl]-4-oxo-hexahydro-pyrrolo[1,2-a]pyrazine-2-carboxylic acid methyl ester (65 mg, 0.15 mmol), [2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (77 mg, 0.15 mmol), tetrakis(triphenylphosphine)palladium(0) (18 mg, 0.015 mmol), potassium carbonate (42.8 mg, 0.31 mmol), 1,2-dimethoxyethane (4 mL) and water (1 mL) was heated in a microwave reactor at 120° C. for 20 minutes. The mixture was cooled and all volatiles were removed under reduced pressure. The resulting residue was taken up in dimethylformamide (2 mL) and subjected to reverse phase chromatography with an eluent of 0.1% TFA in water and 0.1% TFA in acetonitrile. The product-containing fractions were combined and the solvent was removed by lyophilization to provide 6-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-4-oxo-hexahydro-pyrrolo[1,2-a]pyrazine-2-carboxylic acid methyl ester (16.8 mg, 0.024 mmol, 15%). $C_{38}H_{44}BrN_8O_6$ calculated 708.3 observed $[M+1]^+$ 709.4; rt=1.39 min. $^1H$ (DMSO-d6): δ=8.10 (s, 2H), 7.89 (m, 7H), 7.33 (d, J=9 Hz, 1H), 5.03 (t, J=7.8 Hz, 1H), 5.12 (m, 1H), 4.30 (m, 1H), 4.23 (m, 1H), 4.11 (t, J=8.1 Hz, 1H), 3.99 (m, 2H), 3.83 (m, 1H), 3.67 (s, 3H), 3.54 (m, 3H), 2.90 (m, 1H), 2.41 (m, 1H), 2.18 (m, 2H), 2.01 (m, 4H), 1.67 (m, 1H), 0.82 (m, 6H).

Example AU1

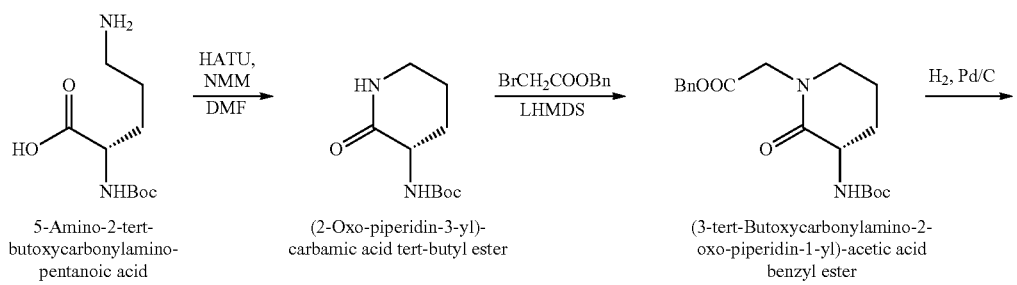

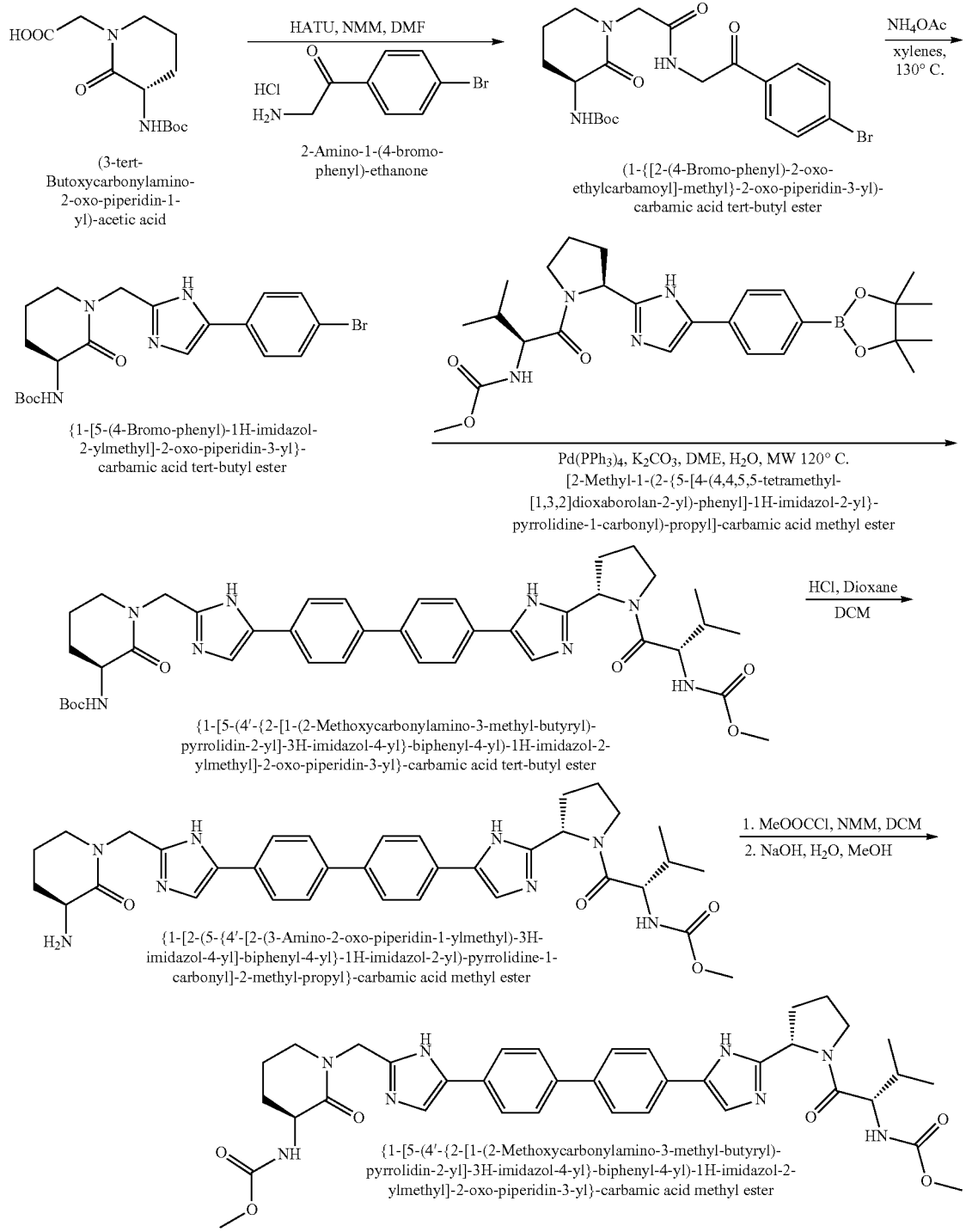

(2-Oxo-piperidin-3-yl)-carbamic acid tert-butyl ester

4-Methylmorpholine (4.73 mL, 43.0 mmol) was added to a suspension of R-5-amino-2-tert-butoxycarbonylamino-pentanoic acid (5 g, 21.5 mmol) and HATU (9 g, 23.6 mmol) in dimethylformamide (100 mL). After 2 hours the solvent was removed under reduced pressure. Saturated sodium bicarbonate (100 mL) was added to the residue and the resulting mixture was extracted with dichloromethane (3×75 mL). The combined organic extracts were washed with saturated sodium chloride (50 mL), dried over sodium sulfate and filtered. The solvent was removed under reduced pressure and the residue was subjected to flash chromatography with eluent of (10% methanol in ethyl acetate) and hexane. The product-containing fractions were combined and the solvent was removed under reduced pressure to provide (R)-(2-oxo-piperidin-3-yl)-carbamic acid tert-butyl ester (3 g, 14.0 mmol, 66%). $C_{10}H_{18}N_2O_3$ calculated 214.1 observed $[M+1]^+$ 215.2; rt=1.73 min.

R-(3-tert-Butoxycarbonylamino-2-oxo-piperidin-1-yl)-acetic acid benzyl ester A solution of lithium bis(trimethylsilyl)amide (1.0 M, 16.8 mL, 16.8 mmol) in tetrahydrofuran was added dropwise to a solution of R-2-oxo-piperidin-3-yl)-carbamic acid tert-butyl ester (3 g, 14.0 mmol) in tetrahydrofuran in a dry flask under an atmosphere of nitrogen. After 30 minutes bromo-acetic acid benzyl ester (2.41 mL, 15.4 mmol) was added dropwise. After an additional 30 minutes the mixture was quenched with saturated ammonium chloride (30 mL). The aqueous phase was extracted with ethyl acetate (3×50 mL) The combined organic phases were washed with saturated sodium chloride (50 mL) and dried over sodium sulfate. The mixture was filtered and the solvent was removed under reduced pressure. The residue was subjected to flash chromatography with eluent of ethyl acetate and hexane. The product-containing fractions were combined and the solvent was removed under reduced pressure to provide (R)-(3-tert-butoxycarbonylamino-2-oxo-piperidin-1-yl)-acetic acid benzyl ester (2.31 g, 6.37 mmol, 45%). $C_{19}H_{26}N_2O_5$ calculated 362.2 observed [M+1]$^+$ 363.1; rt=2.40 min.

The Following (Benzyl Ester Cleavage) Constitutes and Example of Method 803

(R)-(3-tert-Butoxycarbonylamino-2-oxo-piperidin-1-yl)-acetic acid

Palladium on carbon (10%, 500 mg) was added to a solution of (R)-(3-tert-butoxycarbonylamino-2-oxo-piperidin-1-yl)-acetic acid benzyl ester (2.31 g, 6.37 mmol) in ethanol (50 mL) The atmosphere was replaced with hydrogen and maintained with a balloon filled with hydrogen and the above mixture was vigorously stirred. After 16 hours the hydrogen was removed and CELITE was added to the mixture with stirring and then the mixture was filtered though a pad of CELITE. The solvent was removed under reduced pressure and the resulting residue was azeotroped with toluene to provide (R)-(3-tert-butoxycarbonylamino-2-oxo-piperidin-1-yl)-acetic acid (1.65 g, 6.06 mmol, 95%). $C_{12}H_{20}N_2O_5$ calculated 272.3 observed [M+1]$^+$ 271.2; rt=1.80 min.

(R)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl methyl]-2-oxo-piperidin-3-yl}-carbamic acid tert-butyl ester (R)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl methyl]-2-oxo-piperidin-3-yl}-carbamic acid tert-butyl ester was prepared by Method 802 substituting (3-tert-butoxycarbonylamino-2-oxo-piperidin-1-yl)-acetic acid for 4-oxo-hexahydro-pyrrolo[1,2-a]pyrazine-2,6-dicarboxylic acid 2-methyl ester. $C_{40}H_{50}N_8O_6$ calculated 738.4 observed [M+1]$^+$ 739.5; rt=1.83 min; $^1$H (DMSO-d6): δ=11.82 (s, 1H), 7.79 (m, 4H), 7.64 (m, 4H), 7.47 (s, 1H), 7.25 (d, J=8.4 Hz, 1H), 6.95 (d, J=8 Hz, 1H), 5.05 (m, 1H), 4.62 (d, J=15.6 Hz, 1H), 4.43 (d, J=15.2 Hz, 1H), 4.03 (m, 2H), 3.77 (m, 1H), 3.50 (s, 2H), 3.1 (m, 1H), 3.28 (s, 3H), 2.11 (m, 2H), 1.93 (m, 4H), 1.74 (m, 3H), 1.37 (s, 9H), 0.850 (m, 6H).

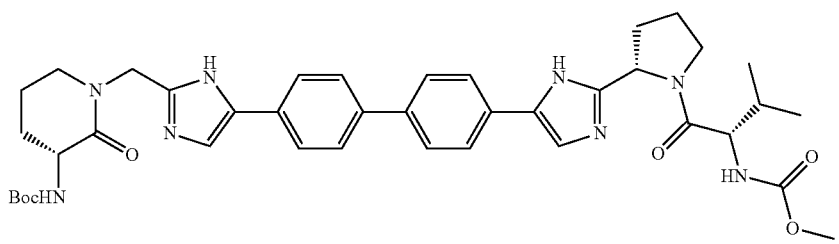

{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester

(S)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl methyl]-2-oxo-piperidin-3-yl}-carbamic acid tert-butyl ester (S)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl methyl]-2-oxo-piperidin-3-yl}-carbamic acid tert-butyl ester was prepared following the method described above. $C_{40}H_{50}N_8O_6$ calculated 738.4 observed [M+1]$^+$ 739.5; rt=1.80 min. $^1$H (DMSO-d6): δ=8.09 (s, 1H), 7.90 (m, 8H), 7.30 (d, J=8.4 Hz, 1H), 6.97 (d, J=8.4 Hz, 1H), 5.10 (t, J=7.2 Hz, 1H), 7.85 (d, J=16.4 Hz, 1H), 4.56 (d, J=15.6 Hz, 1H), 4.09 (t, J=8.0 Hz, 1H), 3.99 (m, 2H), 3.82 (m, 2H), 3.51 (s, 2H), 3.43 (t, J=5.6 Hz, 1H), 2.20 (m, 1H), 2.14-1.86 (series m, 9H), 1.34 (s, 9H), 0.810 (m, 6H).

The Following (Boc Deportation) Constitutes an Example of Method 804

(R)-{1-[2-(5-{4'-[2-(3-Amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester A solution of hydrogen chloride (4N, 8 mL) in dioxane was added to a solution of (R)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester (175 mg, 0.24 mmol) in dichloromethane (2 mL). After 1 hour the solvent was removed under reduced pressure. The resulting residue was placed on a high vacuum for 1 hour to provide (R)-{1-

[2-(5-{4'-[2-(3-amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester. The yield was assumed to be 100% percent. A sample suitable for analysis was obtained by subjection to reverse phase chromatography with an eluent of 0.1% TFA in water and 0.1% TFA in acetonitrile. The product-containing fractions were combined and the solvent was removed by lyophilization. $C_{35}H_{42}N_8O_4$ calculated 638.3 observed $[M+1]^+$ 639.4; rt=1.41 min. $^1$H (DMSO-d6): δ=8.33 (m, 1H), 8.12 (m, 1H), 7.99 (m, 1H), 7.92 (m, 6H), 7.26 (d, J=8.4 Hz, 1H), 5.13 (t, J=8.0 Hz, 1H), 4.83 (m, 2H), 4.09 (t J=8.0 Hz, 1H), 4.09-3.82 (series m, 6H), 2.36 (m, 2H), 2.14 (m, 2H), 1.96 (m, 4H), 0.76 (m, 6H).

The Following Two Steps (Carbamate Formation and Imidazole Deprotection) Constitute an Example of Method 805

(R)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl methyl]-2-oxo-piperidin-3-yl}-carbamic acid methyl ester 4-Methylmorpholine (71 μl, 0.64 mmol) was added to a suspension of (R)-{1-[2-(5-{4'-[2-(3-amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester (137 mg, 0.21 mmol) in dichloromethane (5 mL). Methyl chloroformate (16.5 μl, 0.21

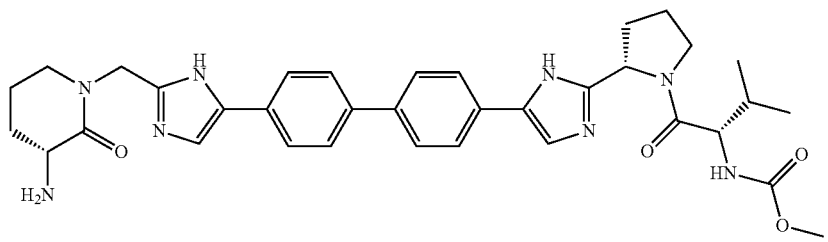

{1-[2-(5-{4'-[2-(3-Amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester (S)-{1-[2-(5-{4'-[2-(3-Amino-2-oxo-piperidin-1-yl methyl)-3H-imidazol-4-yl]-biphenyl-4-yl}-1H-imidazol-2-yl)-pyrrolidine-1-carbonyl]-2-methyl-propyl}-carbamic acid methyl ester (S)-{1-[2-(5-{4'-[2-(3-Amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester was prepared following the method used for the (R)-isomer with the appropriate substitution described above. $C_{35}H_{42}N_8O_4$ calculated 638.3 observed $[M+1]^+$ 639.5; rt=1.39 min $^1$H (DMSO-d6): δ=8.32 (m, 2H), 7.91 (m, 8H), 7.27 (d, J=8.8 Hz, 1H), 5.13 (t, J=7.2 Hz, 1H), 4.79 (m, 3H), 4.09 (t, J=7.2 Hz, 1H), 3.89 (m, 4H), 3.51 (s, 3H), 3.45 (m, 1H), 3.40 (m, 1H), 2.35 (m, 2H), 2.32 (m, 3H), 1.95 (m, 6H), 0.78 (m, 6H).

mmol) was added to the resulting solution. After 20 minutes the solvent was removed under reduced pressure. The residue was taken up in tetrahydrofuran (4 mL) and methanol (2 mL) and an aqueous solution of sodium hydroxide (2 N, 1 mL) was added. After 2 hours the organic solvents were removed under reduced pressure and the aqueous phase was decanted. The residue was taken up in dimethylformamide (2 mL) and subjected to reverse phase chromatography with an eluent of 0.1% TFA in water and 0.1% TFA in acetonitrile. The product-containing fractions were combined and the solvent was removed by lyophilization to provide (R)-{1-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid methyl ester (46.7 mg, 0.67 mmol, 32%). $C_{37}H_{44}N_8O_6$ calculated 696.3 observed $[M+1]^+$ 697.4; rt=1.58 min. $^1$H (DMSO-d6): δ=8.05 (s, 1H), 7.87 (m, 8H) 7.30 (m, 1H), 5.10 (t, J=7.2 Hz, 1H), 4.85 (d, J=15.6 Hz, 1H), 4.53 (d, J=16.0 Hz, 1H), 4.08 (m, 2H), 3.81 (m, 2H), 3.51 (s, 3H), 3.50 (s, 3H), 2.14 (m, 1H), 2.05-1.78 (series m, 8H), 0.78 (m, 6H).

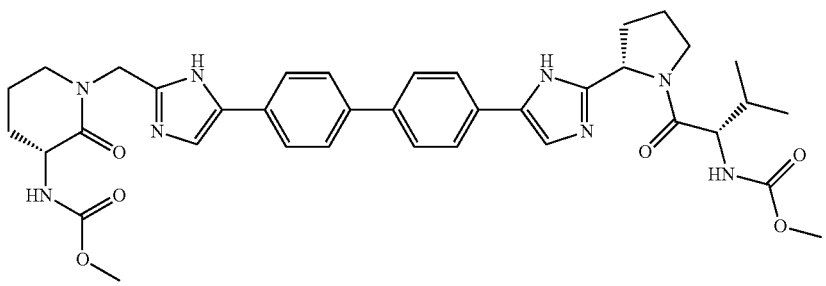

{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid methyl ester (S)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid methyl ester (S)-{1-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid methyl ester was prepared following the method described above for the (R) isomer with the appropriate substitution. $C_{37}H_{44}N_8O_6$ calculated 696.3 observed [M+1]$^+$ 697.4; rt=1.54 min. $^1$H (DMSO-d6): δ=8.03 (m, 1H), 7.86 (m, 8H), 7.03 (m, 1H), 5.10 (t, J=6.4 Hz, 1H), 4.84 (d, J=16.8 Hz, 1H), 4.52 (d, J=16.4 Hz, 1H), 4.08 (m, 2H), 3.80 (m, 3H), 3.51 (s, 3H), 3005 (s, 3H), 2.29 (m, 1H), 2.14-1.78 (series m, 9H), 0.78 (m, 6H).

Example AV1

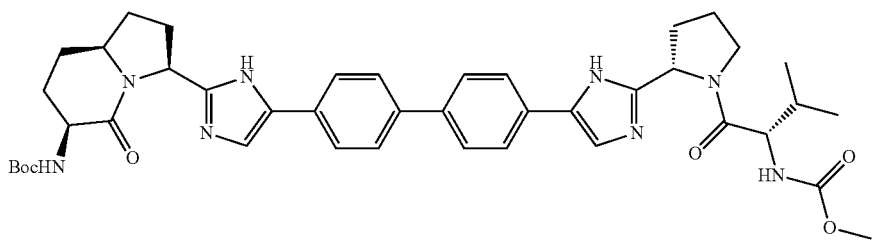

{3-[5-(4'-{2-[1-(2-Methoxycarbonylamino-3-methyl-butyryl)-pyrrolidin-2-yl]-3H-imidazol-4-yl}-biphenyl-4-yl)-1H-imdazol-2-yl]-5-oxo-octahydro-indolizin-6-yl}-carbamic acid tert-butyl ester {3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid tert-butyl ester {3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid tert-butyl ester was prepared following method 802 substituting 6-tert-butoxycarbonylamino-5-oxo-octahydro-indolizine-3-carboxylic acid for 4-oxo-hexahydro-pyrrolo[1,2-a]pyrazine-2,6-dicarboxylic acid 2-methyl ester. $C_{42}H_{52}N_8O_6$ calculated 764.4 observed [M+1]$^+$ 765.5; rt=1.86 min. $^1$H (DMSO-d6): δ=7.89 (m, 8H), 7.33 (d, J=11.2 Hz, 1H), 6.88 (m, 1H), 5.12 (m, 2H), 4.09 (m, 2H), 3.84 (m, 2H), 3.60-3.45 (series m, 4H), 3.53 (s, 3H), 2.34 (m, 2H), 2.10 (m 8H), 1.79 (m, 3H), 1.37 (s, 9H), 0.81 (dd, J=8.8 Hz, J=17.2 Hz, 6H).

Example AW1

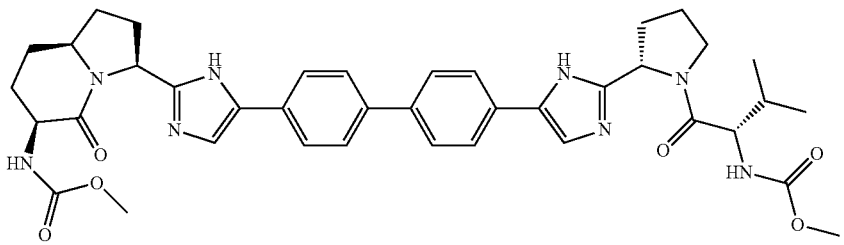

{3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid methyl ester {3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid methyl ester {3-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid methyl ester was prepared following method 804 followed by method 805, substituting {3-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-5-oxo-octahydro-indolizin-6-yl}-carbamic acid tert-butyl ester for {1-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester in method 804, and substituting {1-[2-(5-{4'-[2-(6-Amino-5-oxo-octahydro-indolizin-3-yl)-3H-imidazol-4-yl]-biphenyl-4-yl}-1H-imidazol-2-yl)-pyrrolidine-1-carbonyl]-2-methyl-propyl}-carbamic acid methyl ester for {1-[2-(5-{4'-[2-(3-amino-2-oxo-piperidin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester in method 805. $C_{39}H_{46}N_8O_6$ calculated 722.4 observed $[M+1]^+$ 723.4; rt=1.62 min. $^1$H (DMSO-d6): δ=8.10 (m, 1H), 7.90 (m, 8H), 7.31 (m, 2H), 5.12 (m, 2H), 4.11 (m, 2H), 3.84 (m 2H), 3.74 (m, 1H), 3.53 (s, 6H), 2.38 (m, 2H), 2.14 (m, 3H), 2.05 (m, 5H), 1.82 (m 3H), 0.81 (dd, J=8.8 Hz, J=17.6 Hz, 6H).

Example AX1

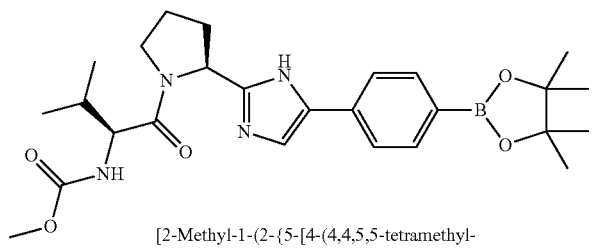 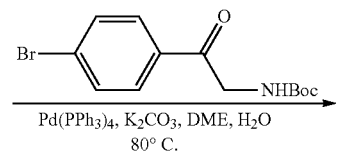

[2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester

[2-(4-Bromo-phenyl)-2-oxo-ethyl]-carbamic acid tert-butyl ester

Pd(PPh3)4, K2CO3, DME, H2O
80° C.

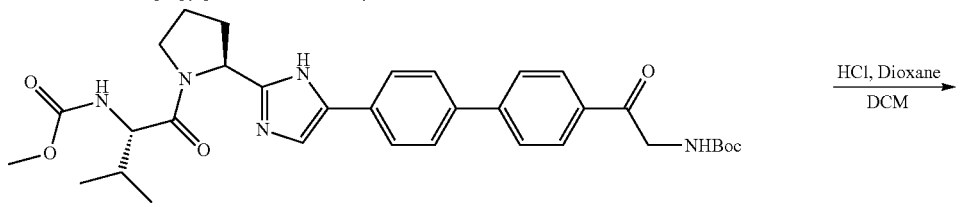

[1-(2-{5-[4'-(2-tert-Butoxycarbonylamino-acetyl)-biphenyl-4-yl]-1H-imidazol-2-yl}-pyrrolidine-1-carbonyl)-2-methyl-propyl]-carbamic acid methyl ester HCl, Dioxane
DCM

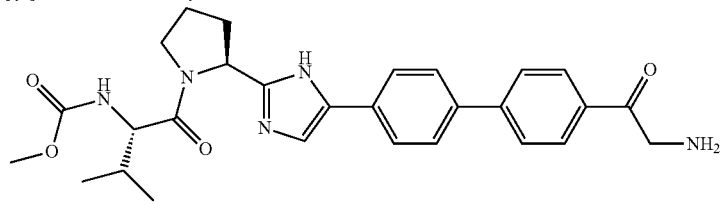

[1-(2-{5-[4'-(2-Amino-acetyl)-biphenyl-4-yl]-1H-imidazol-2-yl}-pyrrolidine-1-carbonyl)-2-methyl-propyl]-carbamic acid methyl ester

[1-(2-{5-[4'-(2-tert-Butoxycarbonylamino-acetyl)-biphenyl-4-yl]-1H-imidazol-2-yl}-pyrrolidine-1-carbonyl)-2-methyl-propyl]-carbamic acid methyl ester A mixture of [2-(4-Bromo-phenyl)-2-oxo-ethyl]-carbamic acid tert-butyl ester (1 g, 3.2 mmol), [2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (1.57 g, 3.2 mmol), tetrakis(triphenylphosphine)palladium(0) (183 mg, 0.15 mmol), potassium carbonate (878 mg, 6.5 mmol), 1,2-dimethoxyethane (25 mL) and water (2.5 mL) was stirred at 80° C. for 16 hours. The mixture was cooled and all volatiles were removed under reduced pressure. The resulting residue was taken up in dichloromethane (100 mL) and washed with water (25 mL) and saturated sodium chloride (25 mL). The organic phase was dried over sodium sulfate and filtered. The solvent was removed under reduced pressure and the residue was subjected to flash chromatography with eluent of (10% methanol in ethyl acetate) and hexane. The product-containing fractions were combined and the solvent was removed under reduced pressure to provide [1-(2-{5-[4'-(2-tert-butoxycarbonylamino-acetyl)-biphenyl-4-yl]-1H-imidazol-2-yl}-pyrrolidine-1-carbonyl)-2-methyl-propyl]-carbamic acid methyl ester (869 mg, 1.4 mmol, 44%).

$C_{33}H_{41}N_5O_6$ calculated 603.3 observed $[M+1]^+$ 604.3; rt=2.01 min. $^1H$ (DMSO-d6): δ=11.82 (s, 1H), 8.03 (m, 2H), 7.84 (m 4H), 7.72 (m, 2H), 7.56 (d, J=1.8 Hz, 1H), 7.29 (d, J=8.7 Hz, 1H), 7.08 (m, 1H), 5.08 (m, 1H), 4.46 (d, J=5.7 Hz, 2H), 4.03 (m, 1H), 3.80 (m, 2H), 3.53 (s, 3H), 2.14 (m, 2H), 1.95 (m, 2H), 0.86 (dd, J=6.9 Hz, J=15.9 Hz, 6H).

[1-(2-{5-[4'-(2-Amino-acetyl)-biphenyl-4-yl]-1H-imidazol-2-yl}-pyrrolidine-1-carbonyl)-2-methyl-propyl]-carbamic acid methyl ester

[1-(2-{5-[4'-(2-Amino-acetyl)-biphenyl-4-yl]-1H-imidazol-2-yl}-pyrrolidine-1-carbonyl)-2-methyl-propyl]-carbamic acid methyl ester was prepared using method 804 substituting [1-(2-{5-[4'-(2-tert-butoxycarbonylamino-acetyl)-biphenyl-4-yl]-1H-imidazol-2-yl}-pyrrolidine-1-carbonyl)-2-methyl-propyl]-carbamic acid methyl ester for {1-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester. $C_{28}H_{33}N_5O_4$ calculated 503.3 observed $[M+1]^+$ 504.2; rt=1.42 min.

Example AY1

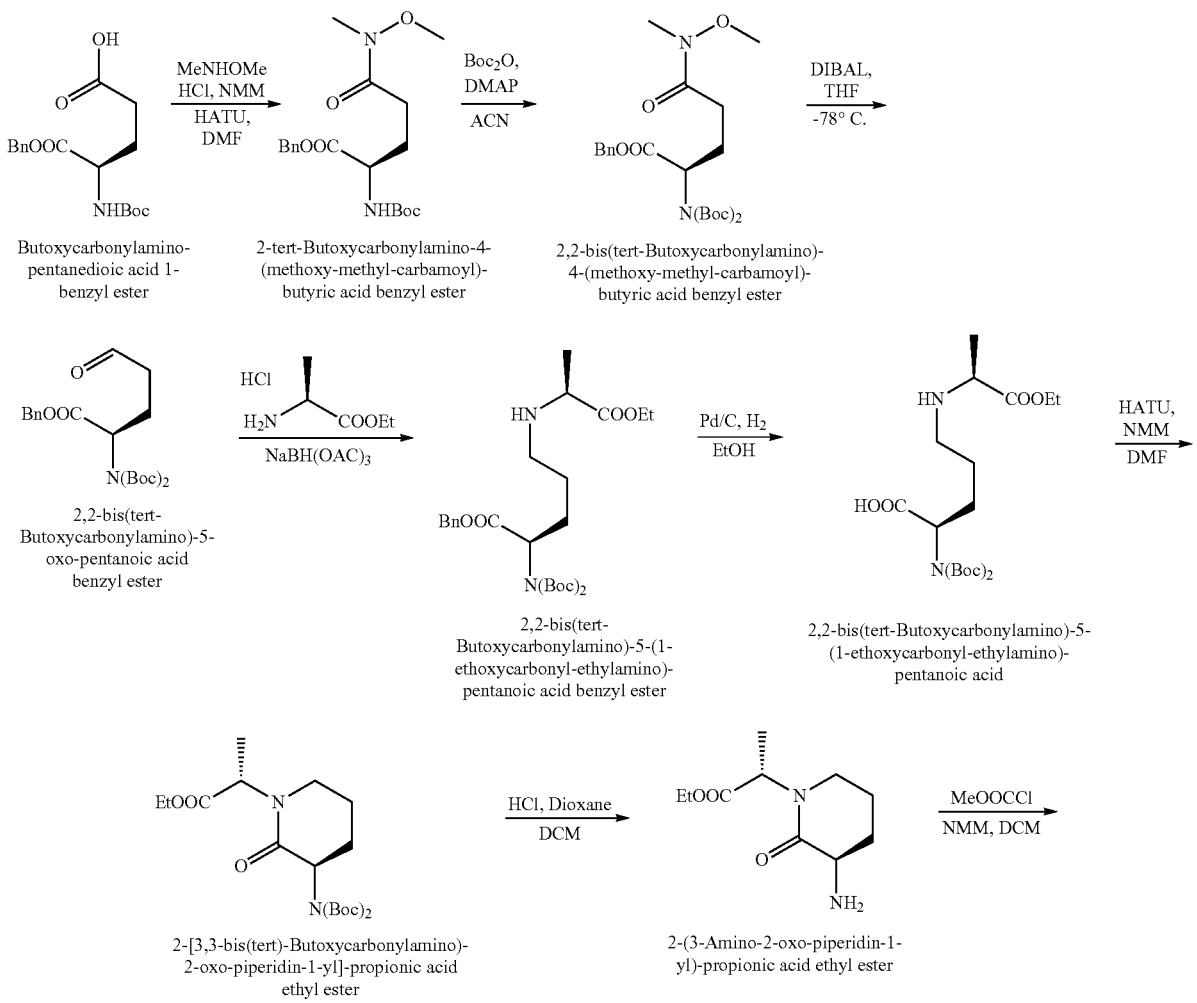

-continued

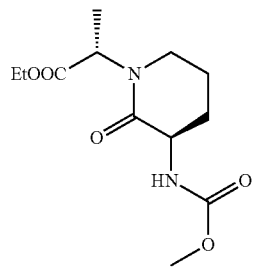

2-(3-Methoxycarbonylamino-2-
oxo-piperidin-1-yl)-propionic
acid ethyl ester

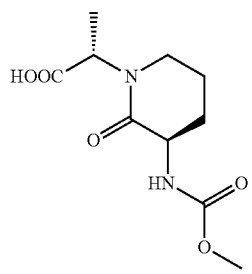

2-(3-Methoxycarbonylamino-
2-oxo-piperidin-1-yl)-
propionic acid

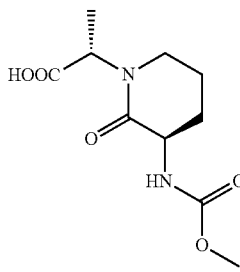

2-(3-Methoxycarbonylamino-
2-oxo-piperidin-1-yl)-
propionic acid

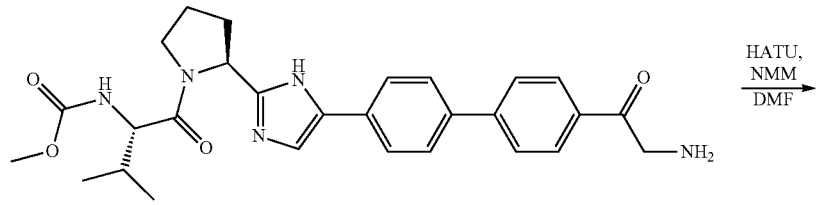

[1-(2-{5-[4'-(2-Amino-acetyl)-biphenyl-4-yl]-1H-
imidazol-2-yl}-pyrrolidine-1-carbonyl-2-methyl-propyl]-
carbamic acid methyl ester

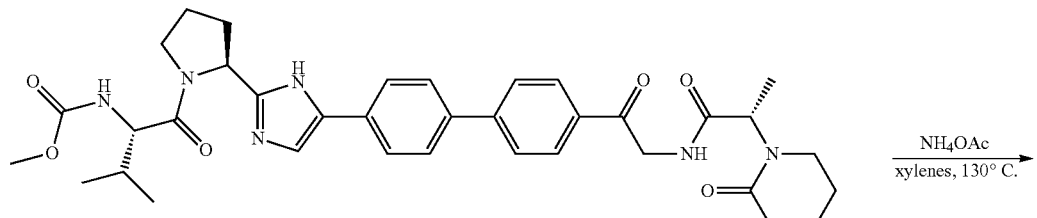

(1-{1-[2-(4'-{2-[1-(2-Methoxycarbonylamino-
3-methyl-butyryl)-pyrrolidin-2-yl]-3H-
imidazol-4-yl}-biphenyl-4-yl)-2-oxo-
ethylcarbamoyl]-ethyl}-2-oxo-piperidin-3-yl)-
carbamic acid methyl ester

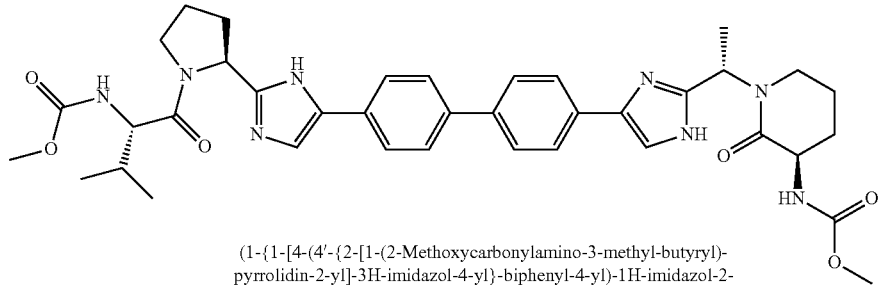

(1-{1-[4-(4'-{2-[1-(2-Methoxycarbonylamino-3-methyl-butyryl)-
pyrrolidin-2-yl]-3H-imidazol-4-yl}-biphenyl-4-yl)-1H-imidazol-2-
yl]-ethyl}-2-oxo-piperidin-3-yl)-carbamic acid methyl ester

2-tert-Butoxycarbonylamino-4-(methoxy-methyl-carbamoyl)-butyric acid benzyl ester 4-Methylmorpholine (9.77 mL, 88.9 mmol) was added to a suspension of 2-tert-butoxycarbonylamino-pentanedioic acid 1-benzyl ester (6 g, 17.7 mmol), and HATU (8.11 g, 21.3 mmol) in dimethylformamide (20 mL). After 5 minutes N,O-dimethylhydroxylamine hydrochloride (2.60 g, 26.7 mmol), was added to the solution. After 1 hour the solvent was removed under reduced pressure. The residue was taken up in ethyl acetate (150 mL), and washed with water (100 mL), aqueous hydrogen chloride (0.5 N, 2×100 mL), saturated sodium bicarbonate (100 mL), and saturated sodium chloride (100 mL). The organic phase was dried over sodium sulfate, filtered and the solvent was removed under reduced pressure. The residue was subjected to flash chromatography with eluent of ethyl acetate and hexane. The product-containing fractions were combined and the solvent was removed under reduced pressure to yield 2-tert-butoxycarbonylamino-4-(methoxy-methyl-carbamoyl)-butyric acid benzyl ester (6.8 g, 17.8 mmol, 99%). $C_{19}H_{28}N_2O_6$ calculated 380.2 observed $[M+1]^+$ 381.2; rt=2.48 min.

2,2-bis(tert-Butoxycarbonylamino)-4-(methoxy-methyl-carbamoyl)-butyric acid benzyl ester Di-tert-butyl dicarbonate (4.20 g, 19.6 mmol) was added to a solution of 2-tert-butoxycarbonylamino-4-(methoxy-methyl-carbamoyl)-butyric acid benzyl ester (6.8 g, 17.8 mmol) and dimethylamino pyridine (436 mg, 3.5 mmol) in acetonitrile (40 mL). After 16 hours starting material remained and di-tert-Butyl dicarbonate (4.20 g, 19.6 mmol) was added again. After 6 days the solvent was removed under reduced pressure. The residue was taken up in ethyl acetate (250 mL), washed with water (2×100 mL) and saturated ammonium chloride (100 mL), dried over sodium sulfate and filtered. The solvent was removed under reduced pressure. The residue was subjected to flash chromatography with eluent of ethyl acetate and hexane. The product-containing fractions were combined and the solvent was removed under reduced pressure to yield 2,2-bis(tert-butoxycarbonylamino)-4-(methoxy-methyl-carbamoyl)-butyric acid benzyl ester (8.2 g, 17.0 mmol, 95%). $C_{24}H_{36}N_2O_6$ calculated 480.3 observed $[M+1]^+$ 481.1; rt=2.83 min.

2,2-bis(tert-Butoxycarbonylamino)-5-oxo-pentanoic acid benzyl ester

A solution of DIBAL (1.0 M, 14.7 mL, 14.7 mmol) in hexane was added dropwise to a solution of 2,2-bis(tert-butoxycarbonylamino)-4-(methoxy-methyl-carbamoyl)-butyric acid benzyl ester (4 g, 10.5 mmol) under an atmosphere of nitrogen at −78° C. After 2 hours the mixture was quenched with saturated ammonium chloride (30 mL) and allowed to warm to room temperature. Water (20 mL) was added, and the mixture was extracted with diethyl ether (3×50 mL). The combined organic phases were left to stand at room temperature for 15 minutes. The resulting thick gel was filtered through a pad of CELITE. The filtrate was dried over sodium sulfate, filtered and the solvent was removed under reduced pressure to provide 2,2-bis(tert-butoxycarbonylamino)-5-oxo-pentanoic acid benzyl ester (3.34 g, 7.9 mmol, 75%). This was used immediately in the next step.

2,2-bis(tert-Butoxycarbonylamino)-5-(1-ethoxycarbonyl-ethylamino)-pentanoic acid benzyl ester Sodium triacetoxyborohydride (5 g, 23.5 mmol) was added to a solution of 2,2-bis(tert-butoxycarbonylamino)-5-oxo-pentanoic acid benzyl ester (3.34 g, 7.9 mmol) and alanine ethyl ester hydrochloride (3.62 g, 23.5 mmol) in dichloromethane (30 mL). After 1 hour saturated ammonium chloride (10 mL) was added and the mixture was stirred for 5 minutes. The aqueous phase was extracted with dichloromethane (2×15 mL), and the combined organic phases were dried over sodium sulfate, filtered and the solvent was removed under reduced pressure. The resulting residue was subjected to flash chromatography with eluent of (10% methanol in ethyl acetate) and hexane. The product-containing fractions were combined and the solvent was removed under reduced pressure to provide 2,2-bis(tert-butoxycarbonylamino)-5-(1-ethoxycarbonyl-ethylamino)-pentanoic acid benzyl ester (1.7 g, 3.3 mmol, 41%). $C_{27}H_{42}N_2O_8$ calculated 522.3 observed $[M+1]^+$ 523.3; rt=2.08 min.

2,2-bis(tert-Butoxycarbonylamino)-5-(1-ethoxycarbonyl-ethylamino)-pentanoic acid 2,2-bis(tert-Butoxycarbonylamino)-5-(1-ethoxycarbonyl-ethylamino)-pentanoic acid was prepared using method 803, substituting 2,2-bis(tert-butoxycarbonylamino)-5-(1-ethoxycarbonyl-ethylamino)-pentanoic acid benzyl ester for (3-tert-butoxycarbonylamino-2-oxo-piperidin-1-yl)-acetic acid benzyl ester. $C_{20}H_{36}N_2O_8$ calculated 432.3 observed $[M+1]^+$ 433.1; rt=1.73 min.

2-[3,3-bis(tert-Butoxycarbonylamino)-2-oxo-piperidin-1-yl]-propionic acid ethyl ester HATU (1.72 g, 4.5 mmol) was added to a solution of 2,2-bis(tert-butoxycarbonylamino)-5-(1-ethoxycarbonyl-ethylamino)-pentanoic acid (1.31 g, 3.0 mmol) and 4-methylmorpholine in dimethylformamide (50 mL). After 30 minutes the solvent was removed under reduced pressure and the residue was subjected to flash chromatography with eluent of ethyl acetate and hexane. The product-containing fractions were combined and the solvent was removed under reduced pressure to provide 2-[3,3-bis(tert-butoxycarbonylamino)-2-oxo-piperidin-1-yl]-propionic acid ethyl ester (1.11 g, 2.6 mmol, 86%). $C_{20}H_{34}N_2O_7$ calculated 414.2 observed $[M+1]^+$ 415.2; rt=2.77 min.

2-(3-Amino-2-oxo-piperidin-1-yl)-propionic acid ethyl ester 2-(3-Amino-2-oxo-piperidin-1-yl)-propionic acid ethyl ester was prepared using method 804 substituting 2-[3,3-bis(tert-butoxycarbonylamino)-2-oxo-piperidin-1-yl]-propionic acid ethyl ester for {1-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester. $C_{10}H_{18}N_2O_3$ calculated 214.2 observed $[M+1]^+$ 215.2; rt=1.21 min.

The Following (Carbamate Formation) Constitutes an Example of Method 806

2-(3-Methoxycarbonylamino-2-oxo-piperidin-1-yl)-propionic acid ethyl ester

Methyl chloroformate (192 μL, 2.5 mmol) was added to a solution of 2-(3-amino-2-oxo-piperidin-1-yl)-propionic acid ethyl ester (353 mg, 1.6 mmol) and 4-methylmorpholine (907 μL, 8.24 mmol) in dichloromethane (10 mL). After 15 minutes the mixture was diluted with dichloromethane (20 mL) and washed with water (10 mL), and aqueous hydrogen chloride (0.5 N, 10 mL). The organic phase was dried over sodium sulfate and filtered. The solvent was removed under reduced pressure to provide 2-(3-methoxycarbonylamino-2-oxo-piperidin-1-yl)-propionic acid ethyl ester (332 mg, 1.2 mmol, 75%). $C_{12}H_{20}N_2O_5$ calculated 272.1 observed $[M+1]^+$ 273.0; rt=1.82 min.

2-(3-Methoxycarbonylamino-2-oxo-piperidin-1-yl)-propionic acid 2-(3-Methoxycarbonylamino-2-oxo-piperidin-1-yl)-propionic acid was prepared by method 801 substituting 2-(3-methoxycarbonylamino-2-oxo-piperidin-1-yl)-propionic acid ethyl ester for 4-oxo-hexahydro-pyrrolo[1,2-a]pyrazine-2,6-dicarboxylic acid 6-ethyl ester 2-methyl ester. $C_{10}H_{16}N_2O_5$ calculated 244.1 observed $[M+1]^+$ 245.1; rt=1.53 min.

(1-{1-[2-(4'-{2-[1-(2-Methoxycarbonylamino-3-methyl-butyryl)-pyrrolidin-2-yl]-3H-imidazol-4-yl}-biphenyl-4-yl)-2-oxo-ethylcarbamoyl]-ethyl}-2-oxo-piperidin-3-yl)-carbamic acid methyl ester A solution of 2-(3-methoxycarbonylamino-2-oxo-piperidin-1-yl)-propionic acid (48.5 mg, 0.20 mmol), HATU (91 mg, 0.24 mmol), and 4-methylmorpholine (109 μL, 0.99 mmol) in dimethylformamide (5 mL) was stirred at ambient temperature for 5 minutes. [1-(2-{5-[4'-(2-Amino-acetyl)-biphenyl-4-yl]-1H-imidazol-2-yl}-pyrrolidine-1-carbonyl)-2-methyl-propyl]-carbamic acid methyl ester (100 mg, 0.20 mmol) was added to the reaction mixture. After 40 minutes the solvent was removed under reduced pressure and the resulting residue was taken up in ethyl acetate (10 mL). The resulting mixture contained a solid and was subjected to flash chromatography with eluent of (10% methanol in ethyl acetate) and hexane followed by 30% methanol in DCM. The product-containing fractions were combined and the solvent was removed under reduced pressure to provide (1-{1-[2-(4'-{2-[1-(2-methoxycarbonylamino-3-methyl-butyryl)-pyrrolidin-2-yl]-3H-imidazol-4-yl}-biphenyl-4-yl)-2-oxo-ethylcarbamoyl]-ethyl}-2-oxo-piperidin-3-yl)-carbamic acid methyl ester (149 mg, 0.20 mmol, 99%). $C_{38}H_{47}N_7O_8$ calculated 729.4 observed $[M+1]^+$ 730.6; rt=1.78 min.

(1-{1-[4-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-ethyl}-2-oxo-piperidin-3-yl)-carbamic acid methyl ester A mixture of ammonium acetate (157 mg, 2.0 mmol), (1-{1-[2-(4'-{2-[1-(2-methoxycarbonylamino-3-methyl-butyryl)-pyrrolidin-2-yl]-3H-imidazol-4-yl}-biphenyl-4-yl)-2-oxo-ethylcarbamoyl]-ethyl}-2-oxo-piperidin-3-yl)-carbamic acid methyl ester (149 mg, 0.20 mmol) and xylenes (20 mL) was heated at 130° C. for 1 hour. The solvent was removed under reduced pressure. The residue was taken up in dichloromethane (15 mL) and filtered. The solvent was removed under reduced pressure. The residue was taken up in dimethylformamide (2 mL) and subjected to reverse phase chromatography with an eluent of 0.1% TFA in water and 0.1% TFA in acetonitrile. The product-containing fractions were combined and the solvent was removed by lyophilization to provide (1-{1-[4-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-ethyl}-2-oxo-piperidin-3-yl)-carbamic acid methyl ester (20.5 mg, 0.029 mmol, 15%). $C_{38}H_{46}N_8O_6$ calculated 710.4 observed $[M+1]^+$ 711.4; rt=1.59 min.

$^1$H (DMSO-d6): δ=8.10 (m, 1H), 7.88 (m, 8H), 7.33 (d, J=8.7 Hz, 2H), 5.33 (m, 1H), 5.12 (t, J=6.9 Hz, 1H), 4.11 (t, J=9.0 Hz, 1H), 3.97 (m, 1H), 3.54 (s, 3H), 3.26 (m, 2H), 2.37 (m, 1H), 2.26-1.74 (series m, 8H), 1.63 (d, J=6.3 Hz, 3H), 0.81 (dd, J=6.9 Hz, J=13.2 Hz, 6H).

Example AZ1

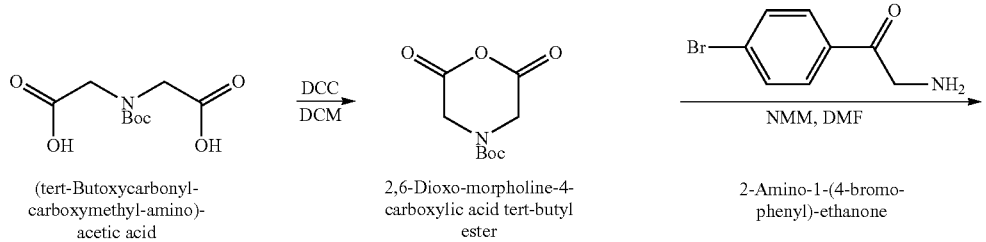

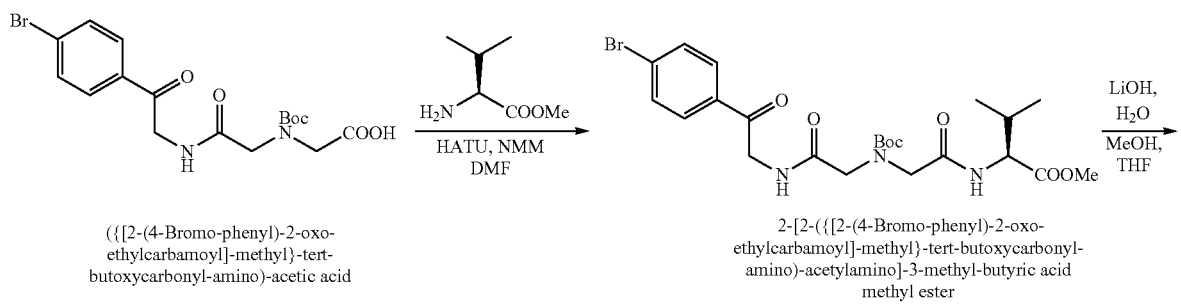

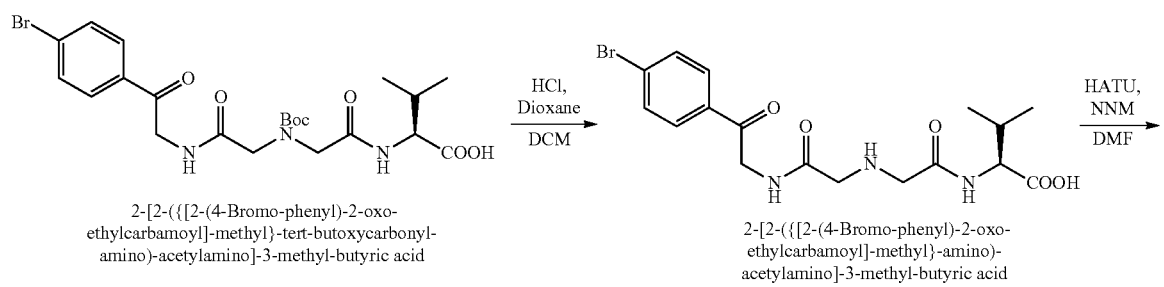

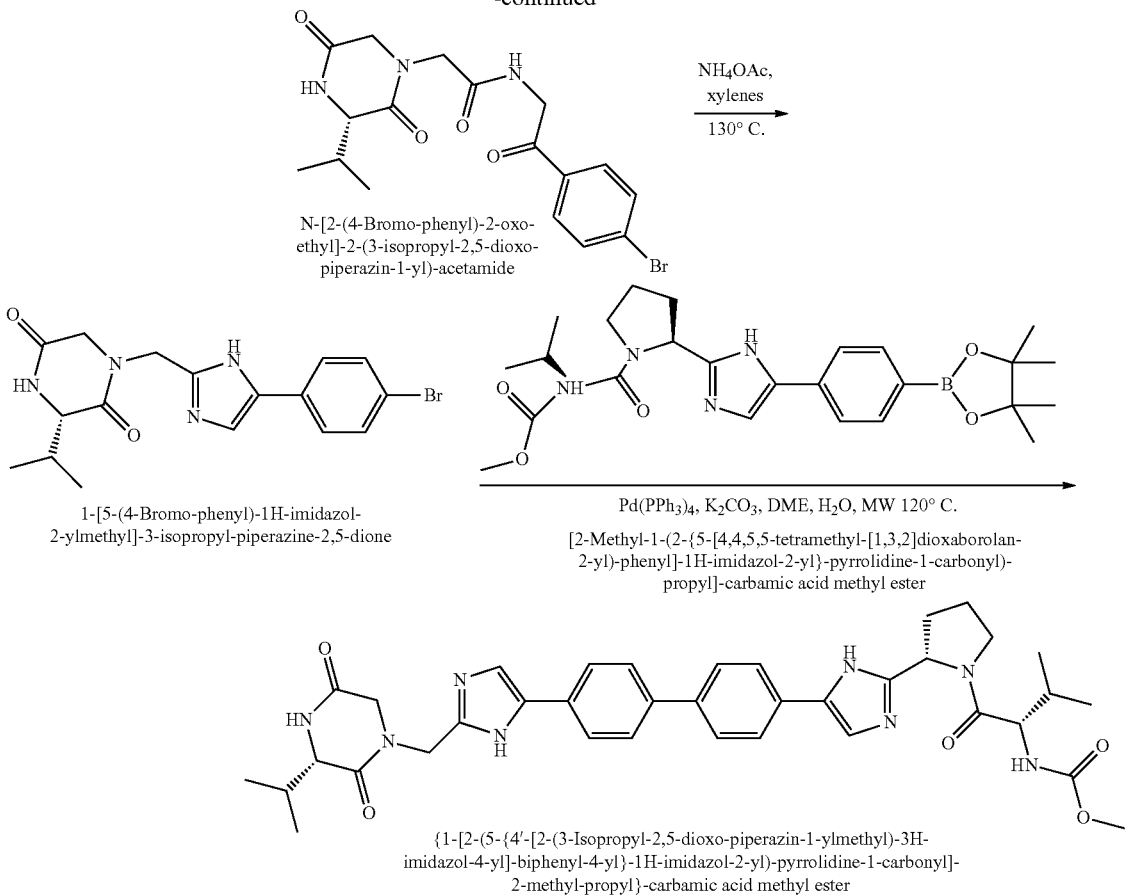

2,6-Dioxo-morpholine-4-carboxylic acid tert-butyl ester

A suspension of (tert-butoxycarbonyl-carboxymethyl-amino)-acetic acid (5 g, 21.4 mmol) and DCC (4.85 g, 23.6 mmol) in dichloromethane was stirred for 16 hours. The mixture was filtered and the solvent was removed from the filtrate to provide 2,6-dioxo-morpholine-4-carboxylic acid tert-butyl ester (4.86 g, 21.0 mmol, 99%).

({[2-(4-Bromo-phenyl)-2-oxo-ethylcarbamoyl]-methyl}-tert-butoxycarbonyl-amino)-acetic acid 2,6-Dioxo-morpholine-4-carboxylic acid tert-butyl ester (2.5 g, 11.6 mmol) was added to a solution of 2-amino-1-(4-bromo-phenyl)-ethanone hydrochloride (3.05 g, 12.2 mmol) and 4-methylmorpholine (1.92 mL, 17.4 mmol) in dimethylformamide (15 mL). After 30 min the solvent was removed under reduced pressure. The residue was taken up in ethyl acetate (100 mL) and washed with water (50 mL), aqueous hydrogen chloride (0.5 N, 2×50 mL), and saturated sodium bicarbonate (2×50 mL). The basic extracts were neutralized and extracted with ethyl acetate (2×75 mL). The combined organic phases from the second extraction were dried over sodium sulfate, and filtered. The solvent was removed under reduced pressure to provide ({[2-(4-bromo-phenyl)-2-oxo-ethylcarbamoyl]-methyl}-tert-butoxycarbonyl-amino)-acetic acid (4 g, 9.3 mmol, 80%). $C_{17}H_{21}BrN_2O_6$ calculated 428.0 observed $[M+1]^+$ 431.1; rt=2.36 min.

2-[2-({[2-(4-Bromo-phenyl)-2-oxo-ethylcarbamoyl]-methyl}-tert-butoxycarbonyl-amino)-acetylamino]-3-methyl-butyric acid methyl ester 4-Methylmorpholine (4.1 mL, 37.3 mmol) was added to a suspension of ({[2-(4-bromo-phenyl)-2-oxo-ethylcarbamoyl]-methyl}-tert-butoxycarbonyl-amino)-acetic acid (4 g, 9.3 mmol), and HATU (4.61 g, 12.1 mmol) in dimethylformamide (25 mL). After 5 minutes d-valine methyl ester hydrochloride (1.56 g, 9.3 mmol), was added to the solution. After 1 hour the solvent was removed under reduced pressure. The residue was taken up in ethyl acetate (150 mL), and washed with water (100 mL), aqueous hydrogen chloride (0.5 N, 2×100 mL), saturated sodium bicarbonate (100 mL), and saturated sodium chloride (100 mL). The organic phase was dried over sodium sulfate, filtered and the solvent was removed under reduced pressure. The residue was subjected to flash chromatography with eluent of (10% methanol in ethyl acetate) and hexane. The product-containing fractions were combined and the solvent was removed under reduced pressure to yield 2-[2-({[2-(4-bromo-phenyl)-2-oxo-ethylcarbamoyl]-methyl}-tert-butoxycarbonyl-amino)-acetylamino]-3-methyl-butyric acid methyl ester (4.37 g, 8.1 mmol, 87%). $C_{23}H_{32}BrN_3O_7$ calculated 541.1 observed $[M+1]^+$ 431.1; rt=2.65 min.

2-[2-({[2-(4-Bromo-phenyl)-2-oxo-ethylcarbamoyl]-methyl}-tert-butoxycarbonyl-amino)-acetylamino]-3-methyl-butyric acid 2-[2-({[2-(4-Bromo-phenyl)-2-oxo-ethylcarbamoyl]-methyl}-tert-butoxycarbonyl-amino)-acetylamino]-3-methylbutyric acid was prepared using method 801 substituting 2-[2-({[2-(4-bromo-phenyl)-2-oxo-ethylcarbamoyl]-methyl}-ten-butoxycarbonyl-amino)-acetylamino]-3-methyl-butyric acid methyl ester for 4-oxo-hexahydro-pyrrolo[1,2-a]pyrazine-2,6-dicarboxylic acid 6-ethyl ester 2-methyl ester. $C_{22}H_{30}BrN_3O_7$ calculated 527.1 observed $[M+1]^+$ 528.1; rt=2.39 min.

2-[2-({[2-(4-Bromo-phenyl)-2-oxo-ethylcarbamoyl]-methyl}-amino)-acetylamino]-3-methyl-butyric acid 2-[2-({[2-(4-Bromo-phenyl)-2-oxo-ethylcarbamoyl]-methyl}-amino)-acetylamino]-3-methyl-butyric acid was prepared using method 804 substituting 2-[2-({[2-(4-bromo-phenyl)-2-oxo-ethylcarbamoyl]-methyl}-tert-butoxycarbonyl-amino)-acetylamino]-3-methyl-butyric acid for 1-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-ylmethyl]-2-oxo-piperidin-3-yl}-carbamic acid tert-butyl ester. $C_{17}H_{22}BrN_3O_5$ calculated 427.1 observed $[M+1]^+$ 428.0; rt=2.39 min.

N-[2-(4-Bromo-phenyl)-2-oxo-ethyl]-2-(3-isopropyl-2,5-dioxo-piperazin-1-yl)-acetamide HATU (3.70 g, 9.7 mmol) was added to a solution of 2-[2-({[2-(4-bromo-phenyl)-2-oxo-ethylcarbamoyl]-methyl}-amino)-acetylamino]-3-methyl-butyric acid (2.78 g, 6.5 mmol), and 4-methylmorpholine (3.57 mL, 32.5 mmol) in DMF (100 mL). After 30 min the solvent was removed under reduced pressure. The residue was taken up in dichloromethane (150 mL) and washed with water (50 mL), aqueous hydrogen chloride (0.5 N, 2×50 mL), saturated sodium bicarbonate (50 mL) and dried over sodium sulfate. The mixture was filtered and the solvent was removed under reduced pressure. The residue was subjected to flash chromatography with eluent of (10% methanol in ethyl acetate) and hexane. The product-containing fractions were combined and the solvent was removed under reduced pressure to yield N-[2-(4-bromo-phenyl)-2-oxo-ethyl]-2-(3-isopropyl-2,5-dioxo-piperazin-1-yl)-acetamide (1.56 g, 3.8 mmol, 60%). $C_{17}H_{20}BrN_3O_4$ calculated 409.1 observed $[M+1]^+$ 410.1; rt=2.00 min.

{1-[2-(5-{4'-[2-(3-Isopropyl-2,5-dioxo-piperazin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester {1-[2-(5-{4'-[2-(3-Isopropyl-2,5-dioxo-piperazin-1-ylmethyl)-3H-imidazol-4-yl]-biphenyl-4-yl}-1H-imidazol-2-yl)-pyrrolidine-1-carbonyl]-2-methyl-propyl}-carbamic acid methyl ester was prepared using the imidazole cyclization from method 802, substituting N-[2-(4-bromo-phenyl)-2-oxo-ethyl]-2-(3-isopropyl-2,5-dioxo-piperazin-1-yl)-acetamide for 6-[2-(4-bromo-phenyl)-2-oxo-ethylcarbamoyl]-4-oxo-hexahydro-pyrrolo[1,2-a]pyrazine-2-carboxylic acid methyl ester and using [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester in the coupling reaction. $C_{37}H_{44}N_8O_5$ calculated 680.3 observed $[M+1]^+$ 681.4; rt=1.57 min. $^1H$ (DMSO-d6): δ=8.39 (d, J=3.0 Hz, 1H), 8.11 (m, 1H), 8.04 (m, 1H), 7.88 (m, 5H), 7.33 (d, J=8.7 Hz, 1H), 8.13 (m, 1H), 4.79 (m, 1H), 4.65 (d, J=15.9 Hz, 1H), 4.26-4.02 (m, 2H), 3.83 (m, 2H), 3.73 (m, 1H), 3.54 (s, 3H), 2.38 (m, 1H), 2.14 (m, 2H), 2.05 (m, 2H), 8.40 (m, 8H).

The Following 3 Steps (Sonogashira Coupling, SEM Protection, Boc Deprotection) Constitute an Example of Method 807

Example BA

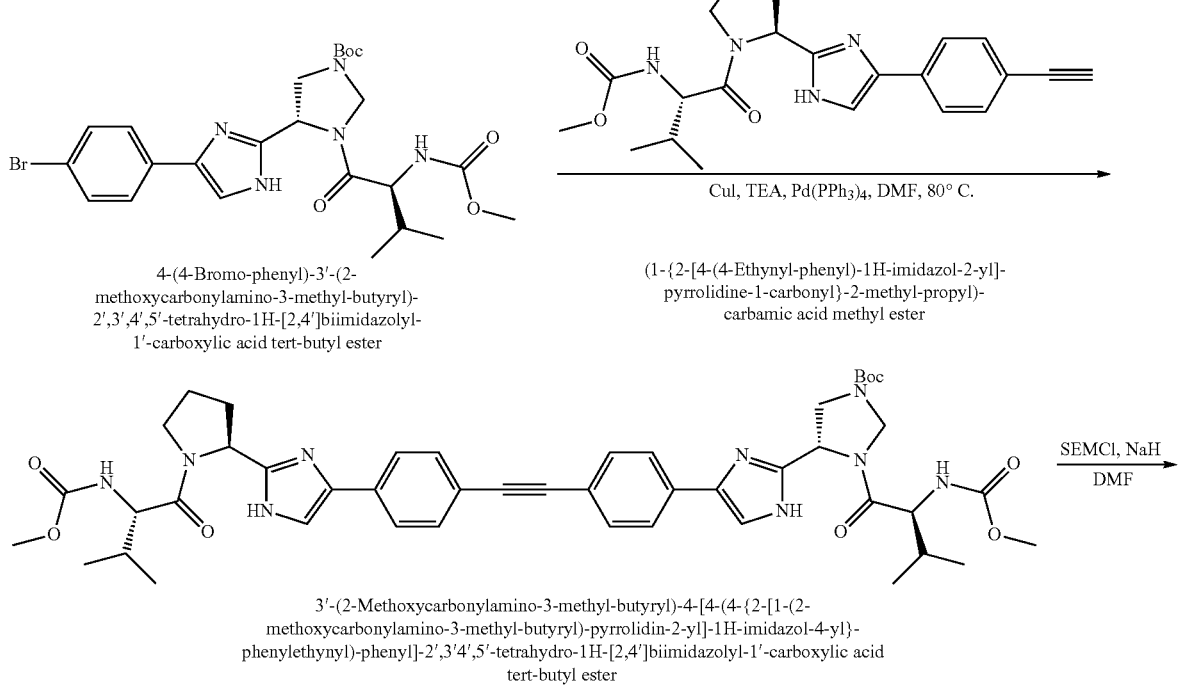

4-(4-Bromo-phenyl)-3'-(2-methoxycarbonylamino-3-methyl-butyryl)-2',3',4',5'-tetrahydro-1H-[2,4']biimidazolyl-1'-carboxylic acid tert-butyl ester (1-{2-[4-(4-Ethynyl-phenyl)-1H-imidazol-2-yl]-pyrrolidine-1-carbonyl}-2-methyl-propyl)-carbamic acid methyl ester 3'-(2-Methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenylethynyl)-phenyl]-2',3'4',5'-tetrahydro-1H-[2,4']biimidazolyl-1'-carboxylic acid tert-butyl ester -continued

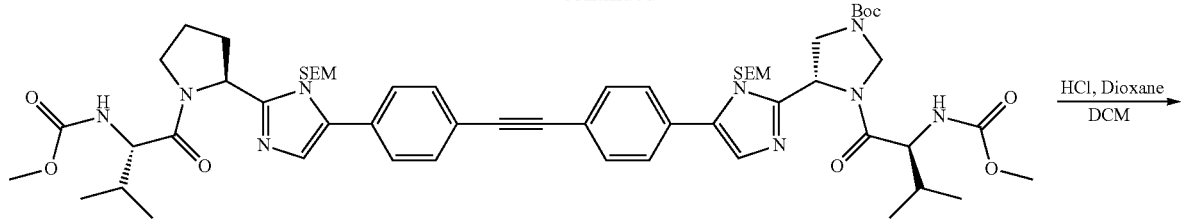

3'-(2-Methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4'-5'-tetrahydro-1H-[2,4']biimidazolyl-1'-carboxylic acid tert-butyl ester

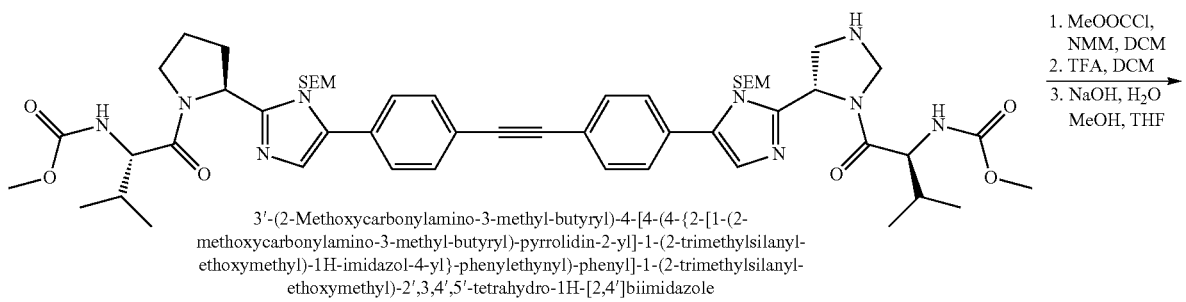

3'-(2-Methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3,4',5'-tetrahydro-1H-[2,4']biimidazole

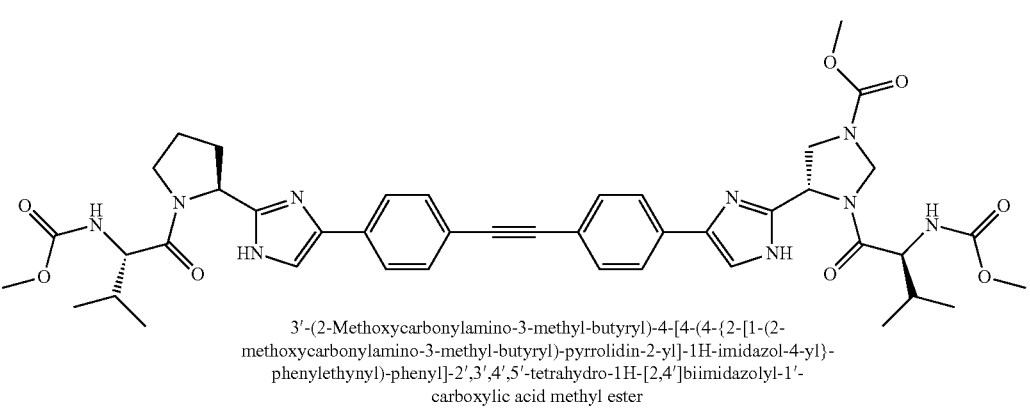

3'-(2-Methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenylethynyl)-phenyl]-2',3',4',5'-tetrahydro-1H-[2,4']biimidazolyl-1'-carboxylic acid methyl ester

3'(2-Methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenylethynyl)-phenyl]-2',3',4',5'-tetrahydro-1H-[2,4]biimidazolyl-1'-carboxylic acid tert-butyl ester A mixture of 4-(4-bromo-phenyl)-3'-(2-methoxycarbonylamino-3-methyl-butyryl)-2',3',4',5'-tetrahydro-1H-[2,4]biimidazolyl-1'-carboxylic acid tert-butyl ester (686 mg, 1.74 mmol), (1-{2-[4-(4-ethynyl-phenyl)-1H-imidazol-2-yl]-pyrrolidine-1-carbonyl}-2-methyl-propyl)-carbamic acid methyl ester (800 mg, 1.45 mmol), copper(I) iodide (28 mg, 0.14 mmol), tetrakis(triphenylphosphine)palladium(0) (167 mg, 0.14 mmol), triethylamine (2.0 mL, 14.5 mmol) and degassed dimethylformamide (10 mL) was stirred at 80° C. for 1 hour. (1-{2-[4-(4-Ethynyl-phenyl)-1H-imidazol-2-yl]-pyrrolidine-1-carbonyl}-2-methyl-propyl)-carbamic acid methyl ester (200 mg, 0.57 mmol) was added. After 1 hour the solvent was removed under reduced pressure. The residue was taken up in dichloromethane (50 mL) and washed with water (10 mL), saturated ammonium chloride (2×10 mL), dried over sodium sulfate and filtered. The solvent was removed under reduced pressure. The residue was subjected to flash chromatography with eluent of (10% methanol in ethyl acetate) and hexane. The product-containing fractions were combined and the solvent was removed under reduced pressure to yield 3'-(2-methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenylethynyl)-phenyl]-2',3',4',5'-tetrahydro-1H-[2,4']biimidazolyl-P-carboxylic acid tert-butyl ester (439 mg, 0.50 mmol, 35%). $C_{46}H_{57}N_9O_8$ calculated 863.4 observed $[M+1]^+$ 864.5; rt=1.91 min. $^1H$ (DMSO-d6): δ=8.07 (m, 1H), 7.76 (m, 4H), 7.68 (m, H), 7.56 (d, J=7.6 Hz, 2H), 7.30 (d, J=8.8 Hz, 1H), 5.37 (m, 1H), 5.21 (m, 1H), 5.08 (m, 2H), 4.80 (m, 1H), 4.07 (t, J=7.2 Hz, 2H), 3.81 (m, 2H), 3.52 (s, 3H), 3.51 (s, 3H), 2.33 (m, 2H), 2.08 (m, 1H), 1.97 (m, 4H), 1.39 (s, 9H), 1.34 (m, 2H), 0.81 (m, 12H).

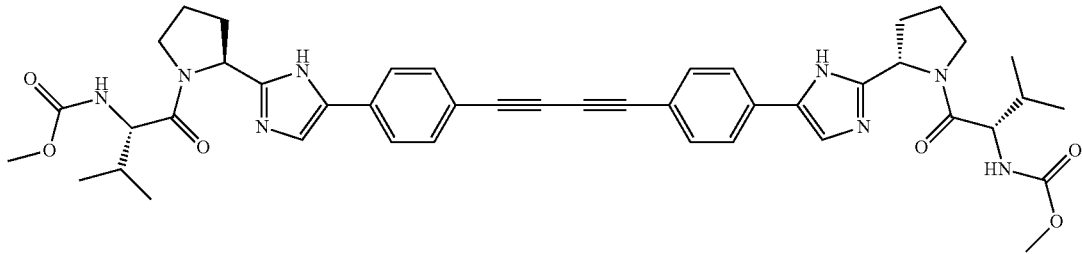

{1-[2-(5-{4-[4-{2-[1-(2-Methoxycarbonylamino-3-methyl-butyryl)-pyrrolidin-2-yl]-3H-imidazol-4-yl}-phenyl)-buta-1,3-diynyl]-phenyl}-1H-imidazol-2-yl)-pyrrolidine-1-carbonyl]-2-methyl-propyl}-carbamic acid methyl ester {1-[2-(5-{4-[4-(4-{2-[(1-(2-Methoxycarbonylamino-3-methyl-butyryl)-pyrrolidin-2-yl]-3H-imidazol-4-yl}-phenyl)-buta-1,3-diynyl]-phenyl}-1H-imidazol-2-yl)-pyrrolidine-1-carbonyl]-2-methyl-propyl}-carbamic acid methyl ester {1-[2-(5-{4-[4-(4-{2-[1-(2-Methoxycarbonylamino-3-methyl-butyryl)-pyrrolidin-2-yl]-3H-imidazol-4-yl}-phenyl)-buta-1,3-diynyl]-phenyl}-1H-imidazol-2-yl)-pyrrolidine-1-carbonyl]-2-methyl-propyl}-carbamic acid methyl ester was also isolated in the flash chromatography. The fractions containing this product were combined and the solvent was removed under reduced pressure. The resulting residue was taken up in dimethylformamide (2 mL) and subjected to reverse phase chromatography with an eluent of 0.1% TFA in water and 0.1% TFA in acetonitrile. The product-containing fractions were combined and the solvent was removed by lyophilization to provide {1-[2-(5-{4-[4-(4-{2-[1-(2-methoxycarbonylamino-3-methyl-butyryl)-pyrrolidin-2-yl]-3H-imidazol-4-yl}-phenyl)-buta-1,3-diynyl]-phenyl}-1H-imidazol-2-yl)-pyrrolidine-1-carbonyl]-2-methyl-propyl}-carbamic acid methyl ester (83.2 mg, 0.10 mmol). $C_{44}H_{50}N_8O_6$ calculated 786.4 observed [M+1]$^+$ 787.6; rt=2.59 min $^1$H (DMSO-d6): δ=8.06 (s, 2H), 7.79 (m, 4H), 7.72 (m, 4H), 7.28 (d, J=8.8 Hz, 2H), 5.08 (t, J=7.2 Hz, 2H), 4.07 (t, J=8.0 Hz, 2H), 3.80 (m, 4H), 3.51 (s, 6H), 2.32 (m, 2H), 2.11 (m, 2H), 1.99 (m 6H), 0.84 (m, 1H), 0.78 (dd, J=6.8 Hz, J=17.6 Hz, 12H).

3'-(2-Methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4']biimidazolyl-1'-carboxylic acid tert-butyl ester Sodium hydride (60% in mineral oil, 27 mg, 0.55 mmol) was added to a solution of 3'-(2-methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenylethynyl)-phenyl]-2',3',4',5'-tetrahydro-1H-[2,4']biimidazolyl-1'-carboxylic acid tert-butyl ester (248 mg, 0.23 mmol) in dimethylformamide (8 mL) under an atmosphere of nitrogen at 0° C. After 15 minutes 2-(trimethylsilyl)ethoxymethyl chloride (107.5 μL, 0.48 mmol) was added and the reaction was allowed to warm to ambient temperature. After 2 hours the solvent was removed under reduced pressure. The residue was taken up in dichloromethane (50 mL) washed with water (20 mL), and dried over sodium sulfate and filtered. The solvent was removed under reduced pressure. The residue was subjected to flash chromatography with eluent of (10% methanol in ethyl acetate) and hexane. The product-containing fractions were combined and the solvent was removed under reduced pressure to yield 3'-(2-methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4]biimidazolyl-1'-carboxylic acid tert-butyl ester (410 mg, 0.36 mmol). $C_{58}H_{85}N_9O_{10}Si_2$ calculated 1123.6 observed [M+1]$^+$ 1124.7; rt=3.10 min.

3'(2-Methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4']biimidazole 3'-(2-Methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4']biimidazole was prepared using method 804 substituting 3'-(2-methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4]biimidazolyl-1'-carboxylic acid tert-butyl ester for {1-[5-(4'-{2-[1-(2-Methoxycarbonylamino-3-methyl-butyryl)-pyrrolidin-2-yl]-

3H-imidazol-4-yl}-biphenyl-4-yl)-1H-imidazol-2-ylm-ethyl]-2-oxo-piperidin-3-yl}-carbamic acid tert-butyl ester. $C_{53}H_{77}N_9O_8Si_2$ calculated 1023.5 observed $[M+1]^+$ 1024.7; rt=2.81 min.

The Following Step Constitutes an Example of Method 808

3'(2-Methoxycarbonylamino-3-methyl-butyryl)-4-[4-(4-{2-[1-(2-methoxycarbonylamino-3-methyl-butyryl)-pyrrolidin-2-yl]-1H-imidazol-4-yl}-phenyl-ethynyl)-phenyl]-2',3',4',5'-tetrahydro-1H-[2,4'] biimidazolyl-1'-carboxylic acid methyl ester Methyl chloroformate (15 µL, 0.19 mmol) was added to a solution of 3'-(2-methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4]biimidazole (97 mg, 0.09 mmol), and 4-methylmorpholine (40 µL, 0.36 mmol) in dichloromethane (3 mL) After 30 minutes the solvent was removed under reduced pressure and azeotroped with toluene. The residue was taken up in dichloromethane (5 mL) and trifluoroacetic acid (5 mL) was added. After 16 hours the volatiles were removed under reduced pressure and the residue was taken up in tetrahydrofuran (4 mL) and methanol (2 mL). An aqueous solution of sodium hydroxide (2 N, 1 mL) was added. After 30 min the organic solvents were removed under reduced pressure and the resulting precipitate was isolated by filtration. The solid was taken up in dimethylformamide (2 mL) and subjected to reverse phase chromatography with an eluent of 0.1% TFA in water and 0.1% TFA in acetonitrile. The product-containing fractions were combined and the solvent was removed by lyophilization to provide 3'-(2-methoxycarbonylamino-3-methyl-butyryl)-4-(4-{2-[1-(2-methoxycarbonylamino-3-methyl-butyryl)-pyrrolidin-2-yl]-1H-imidazol-4-yl}-phenylethynyl)-phenyl]-2',3',4',5'-tetrahydro-1H-[2,4'] biimidazolyl-1'-carboxylic acid methyl ester (14.1 mg, 0.017 mmol, 10%).

$C_{43}H_{51}N_9O_8$ calculated 821.4 observed $[M+1]^+$ 822.8; rt=1.72 min. $^1$H (DMSO-d6): δ=8.07 (m, 1H), 7.77 (m, 7H), 7.67 (m, 2H), 7.57 (m, 3H), 7.29 (d, J=8.4 Hz, 1H), 5.41 (m, 1H), 5.27 (d, J=5.6 Hz, 1H), 5.15 (d, J=5.6 Hz, 1H), 5.08 (t, J=7.6 Hz, 2H), 4.07 (t, J=13.2 Hz, 2H), 3.83 (m, 2H), 3.76 (m, 2H), 3.64 (s, 3H), 3.58 (m, 1H), 3.52 (s, 3H), 3.51 (s, 3H), 2.33 (m, 2H), 2.13 (m, 1H), 2.03 (m, 5H), 1.90 (m, 2H), 0.805 (m, 18H).

Example BB

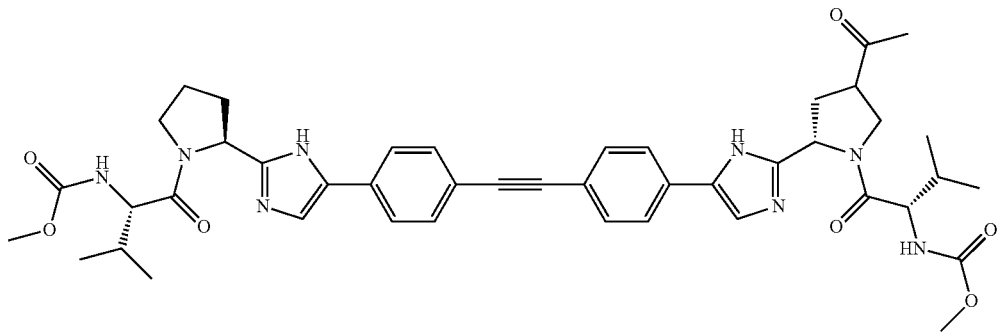

(1-{2-[5-(4-{4-[1'Acetyl-3'-(2-methoxycarbonylamino-3-methyl-butyryl)-2', 3', 4', 5',-tetrahydro-3H- 1'H-[2,4']biimidazolyl-4-yl]-phenylethynyl}-phenyl)-1H-imidazol-2-yl]-pyrrolidine-1-carbonyl}-2-methyl-propyl)-carbamic acid methyl ester (1-{2-[5-(4-{4-[1'-Acetyl-3'-(2-methoxycarbonylamino-3-methyl-butyryl)-2',3',4',5'-tetrahydro-3H,1'H-[2,4]biimidazolyl-4-yl]-phenylethynyl}-phenyl)-1H-imidazol-2-yl]-pyrrolidine-1-carbonyl}-2-methyl-propyl)-carbamic acid methyl ester was prepared following method 808 in Example BA substituting acetic anhydride for methyl chloroformate in the first step of the synthesis. $C_{43}H_{51}N_9O_7$ calculated 805.4 observed $[M+1]^+$ 806.5; rt=1.65 min; $^1$H (DMSO-d6): δ=8.06 (m, 1H), 776 (m, 6H), 7.68 (m, 3H), 7.56 (d, J=7.6 Hz, 3H), 7.29 (d, J=9.2 Hz, 1H), 5.47 (m, 1H), 5.38 (m, 1H), 5.27 (m, 1H), 5.18 (m, 1H), 5.08 (t, J=6.8 Hz, 2H), 4.17 (m, 1H), 4.07 (t, J=8.0 Hz, 2H), 3.93 (m, 2H), 3.84 (m, 4H), 3.52 (s, 3H), 3.51 (s, 6H), 3.37 (m, 1H), 2.34 (m, 2H), 2.13 (m, 1H), 1.99 (m, 12H), 0.81 (m, 18H).

Example BC

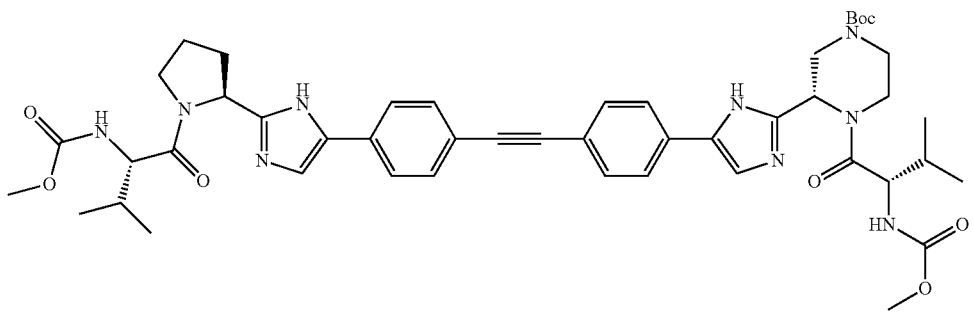

4-(2-Methoxycarbonylamino-3-methyl-butyryl)-3-{5-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid tert-butyl ester 4-(2-Methoxycarbonylamino-3-methyl-butyryl)-3-{5-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid tert-butyl ester was prepared following step one of method 807, substituting (1-{2-[4-(4-bromo-phenyl)-1H-imidazol-2-yl]-piperazine-1-carbonyl}-2-methyl-propyl)-carbamic acid methyl ester for 4-(4-bromo-phenyl)-3'-(2-methoxycarbonylamino-3-methyl-butyryl)-2',3',4',5'-tetrahydro-1H-[2,4']biimidazolyl-1'-carboxylic acid tert-butyl ester in the first step of Example BA. $C_{47}H_{59}N_9O_8$ calculated 877.5 observed $[M+1]^+$ 878.5; rt=1.65 min $^1$H (DMSO-d6): δ=8.08 (m, 1H), 7.78 (m, 4H), 7.68 (m, 2H), 7.54 (m, 2H), 7.29 (d, J=9.2 Hz, 2H), 5.54 (m, 1H), 5.08 (t, J=6.0 Hz, 1H), 4.32 (m, 2H), 4.07 (t, J=8.0 Hz, 2H), 3.81 (m, 4H), 3.52 (s, 3H), 3.51 (s, 3H), 3.41 (m, 1H), 2.34 (m, 1H), 2.14 (m, 1H), 2.00 (m, 4H), 1.28 (3, 3H), 1.17 (br s, 3H), 0.80 (m, 12H).

Example BD

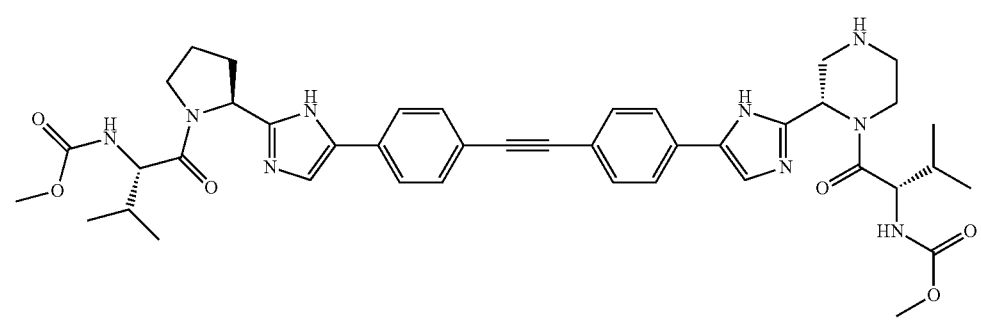

[1-(2-{5-[4-(4-{2-[1-(2-Methoxycarbonylamino-3-methyl-butyryl)-piperazin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester

[1-(2-{5-[4-(4-{2-[1-(2-Methoxycarbonylamino-3-methyl-butyryl)-piperazin-2-yl]-3H-imidazol-4-yl}-phenyl-ethynyl)-phenyl]-1H-imidazol-2-yl}-pyrrolidine-1-carbonyl)-2-methyl-propyl]-carbamic acid methyl ester was prepared following method 807 substituting (1-{2-[4-(4-bromo-phenyl)-1H-imidazol-2-yl]-piperazine-1-carbonyl}-2-methyl-propyl)-carbamic acid methyl ester for 4-(4-bromo-phenyl)-3'-(2-methoxycarbonylamino-3-methyl-butyryl)-2',3',4',5'-tetrahydro-1H-[2,4]biimidazolyl-1'-carboxylic acid tert-butyl ester. Followed by method 808, substituting [1-(2-{5-[4-(4-{2-[1-(2-methoxycarbonylamino-3-methyl-butyryl)-piperazin-2-yl]-1-(2-trimethylsilanyl-ethoxymethyl)-3H-imidazol-4-yl}-phenylethynyl)-phenyl]-1-(2-trimethylsilanyl-ethoxymethyl)-1H-imidazol-2-yl}-pyrrolidine-1-carbonyl)-2-methyl-propyl]-carbamic acid methyl ester for 3'-(2-methoxycarbonylamino-3-methyl-butyryl)-4-[4-(4-{2-[1-(2-methoxycarbonylamino-3-methyl-butyryl)-pyrrolidin-2-yl]-1-(2-trimethylsilanyl-ethoxymethyl)-1H-imidazol-4-yl}-phenylethynyl)-phenyl]-1-(2-trimethylsilanyl-ethoxymethyl)-2',3',4',5'-tetrahydro-1H-[2,4]biimidazole and leaving out methyl chloroformate. $C_{42}H_{51}N_9O_6$ calculated 777.4 observed [M+1]+778.4; rt=1.58 min.

$^1$H (DMSO-d6): δ=9.30 (m, 1H), 7.9 (m, 2H), 7.75 (m, 3H), 7.63 (m, 2H), 7.52 (m 2H), 7.28 (d, J=8.0 Hz, 1H), 5.96 (1H), 5.07 (m, 1H), 4.49 (m, 1H), 4.28 (m, 2H), 4.06 (m, 2H), 3.80 (m, 4H), 3.56 (m, 1H), 3.53 (s, 3H), 3.51 (s, 3H), 3.27 (m, 2.12 (m, 1H), 1.96 (m, 4H), 0.95 (m, 1H), 0.81 (m, 12H).

Example BE

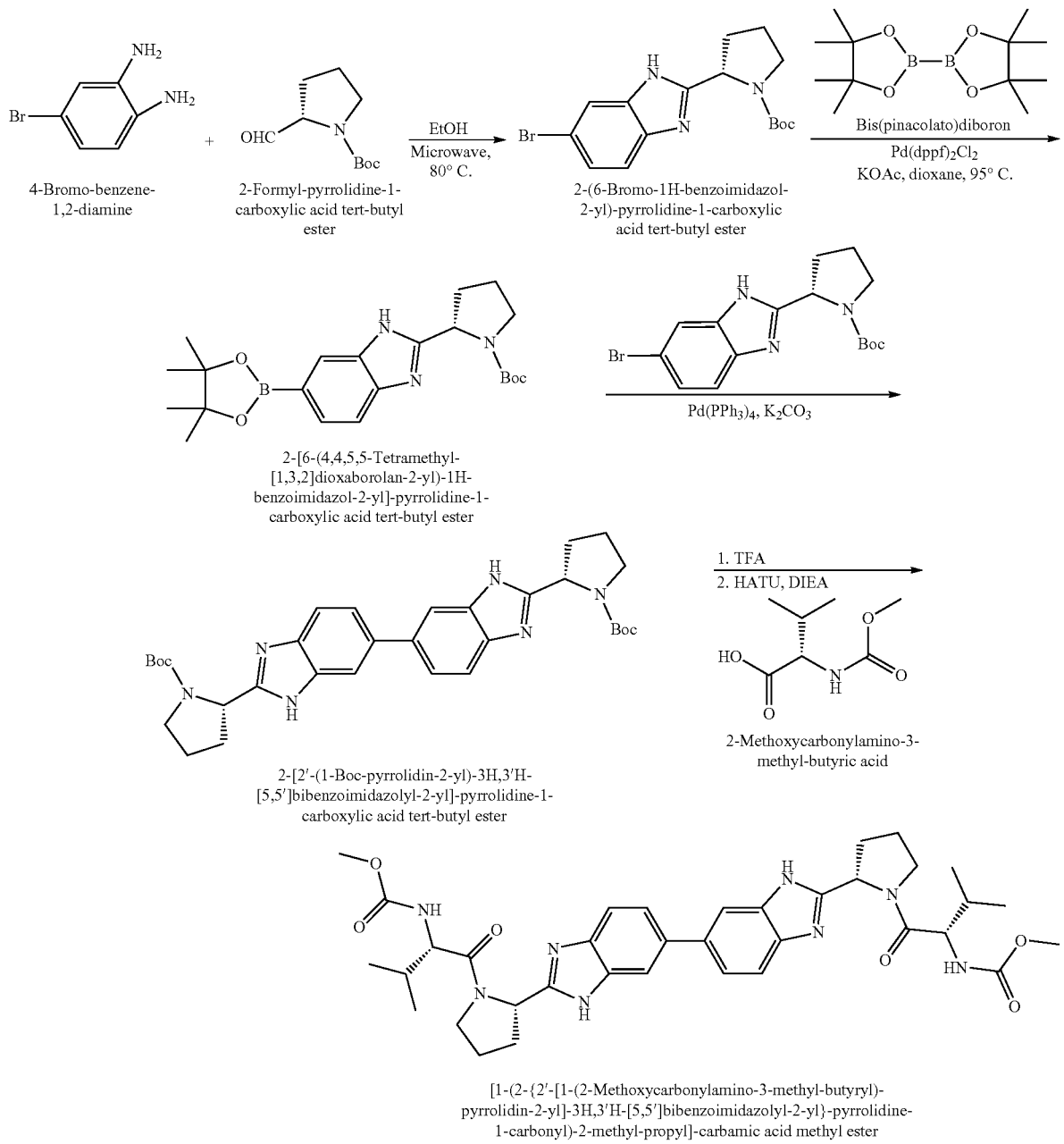

[1-(2-{2'-[1-(2-Methoxycarbonylamino-3-methyl-butyryl)-pyrrolidin-2-yl]-3H,3'H-[5,5']bibenzoimidazolyl-2-yl}-pyrrolidine-1-carbonyl)-2-methyl-propyl]-carbamic acid methyl ester

2-(6-bromo-1H-benzoimidazol-2-yl)-pyrrolidine-1-carboxylic acid tert-butyl ester A mixture of 4-bromo-benzene-1,2-diamine (2.4 g) and 2-formyl-pyrrolidine-1-carboxylic acid tert-butyl ester (2.55 g) in ethanol (5 mL) was heated in microwave at 80° C. for 1 hour. Mixture was concentrated and purified by flash column chromatography (silica gel, 20 to 80% ethyl acetate/hexane) to give 2-(6-bromo-1H-benzoimidazol-2-yl)-pyrrolidine-1-carboxylic acid tert-butyl ester (2.6 g, yield 55%). LCMS-ESI⁻: calc'd for $C_{16}H_{20}BrN_3O_2$: 366.25; Found: 365.8 (M+H⁺).

2-[6-(4,4,5,5-tetramethyl-[1,3,2]dioxaborolan-2-yl)-1H-benzoimidazol-2-yl]-pyrrolidine-1-carboxylic acid tert-butyl ester A mixture of 2-(6-bromo-1H-benzoimidazol-2-yl)-pyrrolidine-1-carboxylic acid tert-butyl ester (890 mg, 2.43 mmol), bis(pinacolato)diboron (1.36 g, 5.35 mmol), [1,1'-bis(diphenylphosphino)ferrocene]dichloropalladium(II)(99 mg, 0.12 mmol) and potassium acetate (620 mg, 6.32 mmol) in 15 mL dioxane was heated to 95° C. for 4 hour. The reaction mixture was cooled and dissolved in ethyl acetate and washed with saturated sodium bicarbonate solution. The organic layer dried (MgSO4), concentrated and purified by flash column chromatography (silica gel, 20 to 80% ethyl acetate/hexane) to give 2-[6-(4,4,5,5-tetramethyl-[1,3,2]dioxaborolan-2-yl)-1H-benzoimidazol-2-yl]-pyrrolidine-1-carboxylic acid tert-butyl ester (588 mg, yield 59%). LCMS-ESI⁻: calc'd for $C_{32}H_{20}BN_3O_4$: 413.32; Found: 414.0 (M+H⁺).

2-[2'-(1-Boc-pyrrolidin-2-yl)-3H,3'H-[5,5]bibenzoimidazolyl-2-yl]-pyrrolidine-1-carboxylic acid tert-butyl ester A mixture of 2-(6-bromo-1H-benzoimidazol-2-yl)-pyrrolidine-1-carboxylic acid tert-butyl ester (64 mg, 0.174 mmol), 2-[6-(4,4,5,5-tetramethyl-[1,3,2]dioxaborolan-2-yl)-1H-benzoimidazol-2-yl]-pyrrolidine-1-carboxylic acid tert-butyl ester (72 mg, 0.174 mmol), tetrakis(triphenylphosphine)palladium (30 mg, 0.026 mmol) and potassium carbonate (48 mg, 0.35 mmol) in 2 ml 1,2-dimethoxyethane and 1 mL water was heated to 110° C. in microwave for 15 minutes. The reaction mixture was cooled and dissolved in ethyl acetate and washed with 5% lithium chloride aqueous solution. The organic layer dried (MgSO4), concentrated and purified by flash column chromatography (silica gel, 0 to 10% methanol/ethyl acetate) to give 2-[2'-(1-Boc-pyrrolidin-2-yl)-3H,3'H-[5,5]bibenzoimidazolyl-2-yl]-pyrrolidine-1-carboxylic acid tert-butyl ester (15 mg, yield 15%). LCMS-ESI⁻: calc'd for $C_{32}H_{40}N_6O_4$: 572.70; Found: 573.1 (M+H⁺).

[1-(2-{2'-[1-(2-Methoxycarbonylamino-3-methyl-butyryl)-pyrrolidin-2-yl]-3H,3'H-[5,5]bibenzoimidazolyl-2-yl}-pyrrolidine-1-carbonyl)-2-methyl-propyl]-carbamic acid methyl ester Trifluoroacetic acid (0.5 mL) was added to (2-[2'-(1-Boc-pyrrolidin-2-yl)-3H,3'H-[5,5]bibenzoimidazolyl-2-yl]-pyrrolidine-1-carboxylic acid tert-butyl ester (15 mg, 0.0262 mmol) and the reaction mixture was stirred at room temperature for 2 hours. The reaction mixture was concentrated and dried overnight under vacuum. The residue was dissolved in DMF (1.5 mL) and to this solution was added 2-Methoxycarbonylamino-3-methyl-butyric acid (10 mg, 0.058 mmol), diisopropylethylamine (27 µL), followed by HATU (20 mg). Reaction mixture was stirred at 0° C. for 60 minutes. The reaction mixture was dissolved in ethyl acetate and washed with dilute sodium bicarbonate solution. The organic layer was dried (MgSO4), concentrated and purified by preparative reverse phase HPLC (GEMINI, 5 to 100% ACN/H₂O+0.1% TFA). Product was lyophilized to give [1-(2-{2'-[1-(2-Methoxycarbonylamino-3-methyl-butyryl)-pyrrolidin-2-yl]-3H,3'H-[5,5]bibenzoimidazolyl-2-yl}-pyrrolidine-1-carbonyl)-2-methyl-propyl]-carbamic acid methyl ester as the bis-TFA salt (8.1 mg).

¹H-NMR: 300 MHz, (CD₃OD-d₄) δ: 8.02 (s, 2H), 7.88 (m, 4H), 5.38 (m, 2H), 4.27 (d, 2H), 4.12 (m, 2H), 3.96 (m, 2H), 3.62 (s, 6H), 2.62 (m, 2H), 2.40-2.20 (m, 6H), 2.08 (m, 2H), 0.95-0.85 (m, 12H); LCMS-ESI⁺: calc'd for $C_{36}H_{46}N_8O_6$: 686.80; Found: 687.3 (M+H⁺).

Example BF

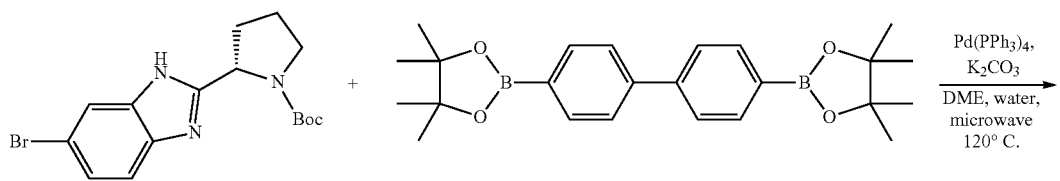

2-(6-Bromo-1H-benxoimidazol-2-yl)-pyrrolidine-1-carboxylic acid tert-butyl ester 4,4'-bipheynidiboronic acid dipinacol ester

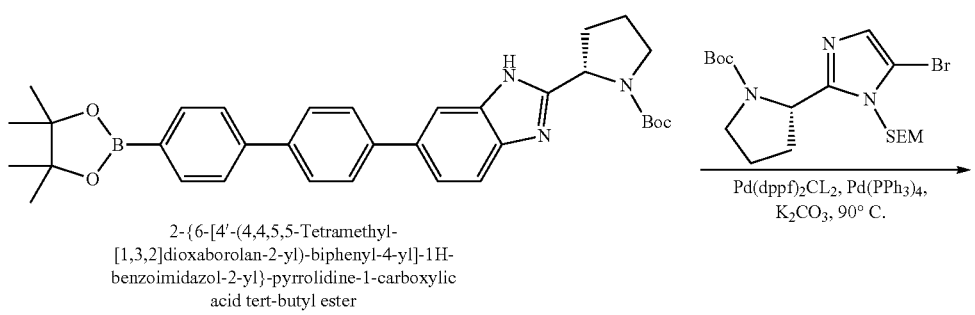

2-{6-[4'-(4,4,5,5-Tetramethyl-[1,3,2]dioxaborolan-2-yl)-biphenyl-4-yl]-1H-benzoimidazol-2-yl}-pyrrolidine-1-carboxylic acid tert-butyl ester 2-[5-Bromo-1-(2-trimethylsilanyl-ethoxymethyl)-1H-imidazol-2-yl}-pyrrolidine-1-carboxylic acid tert-butyl ester

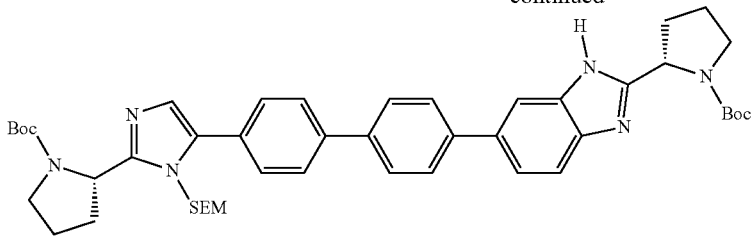
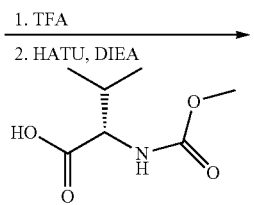

2-(6-{4'-[2-(1-Boc-pyrrolidin-2-yl)-3-(2-trimethylsilanyl-ethoxymethyl)-3H-imidazol-4-yl]-biphenyl-4-yl}-1H-benzoimidazol-2-yl)-pyrrolidine-1-carboxylic acid tert-butyl ester 2-Methoxycarbonylamino-3-methyl-butyric acid

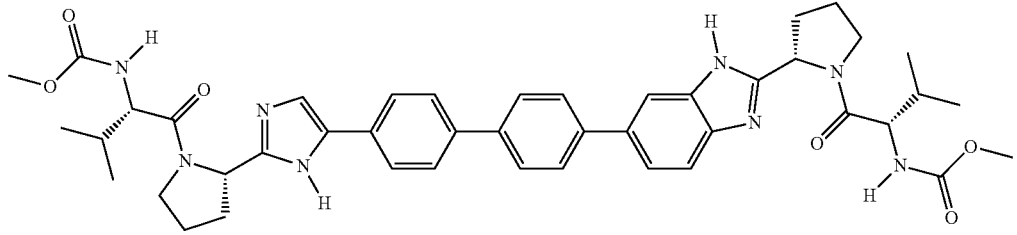

(1-{2-[5-(4'-{2-[1-(2-Methoxycarbonylamino-3-methyl-butyryl)-pyrrolidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester

2-{6-[4'-(4,4,5,5-tetramethyl-[1,3,2]dioxaborolan-2-yl)-biphenyl-4-yl]-1H-benzoimidazol-2-yl}-pyrrolidine-1-carboxylic acid tert-butyl ester A mixture of 2-(6-bromo-1H-benzoimidazol-2-yl)-pyrrolidine-1-carboxylic acid tert-butyl ester (230 mg, 0.628 mmol), 4,4'-bipheynldiboronic acid dipinacol ester (1.28 g, 3.14 mmol), tetrakis(triphenylphosphine)palladium (73 mg, 0.063 mmol) and potassium carbonate (521 mg, 3.77 mmol) in 10 ml 1,2-dimethoxyethane and 5 mL water was heated to 120° C. in microwave for 40 minutes. The reaction mixture was cooled and dissolved in ethyl acetate and washed with 5% lithium chloride aqueous solution. The organic layer was dried (MgSO4), concentrated and purified by flash column chromatography (silica gel, 20 to 100% ethyl acetate/hexane) to give 2-{6-[4'-(4,4,5,5-tetramethyl-[1,3,2]dioxaborolan-2-yl)-biphenyl-4-yl]-1H-benzoimidazol-2-yl}-pyrrolidine-1-carboxylic acid tert-butyl ester (15 mg, yield 15%). LCMS-ESI$^-$: calc'd for $C_{34}H_{40}BN_3O_4$: 65.51; Found: 566.1 (M+H$^+$).

2-(6-{4'-[2-(1-Boc-pyrrolidin-2-yl)-3-(2-trimethylsilanyl-ethoxymethyl)-3H-imidazol-4-yl]-biphenyl-4-yl}-1H-benzoimidazol-2-yl)-pyrrolidine-1-carboxylic acid tert-butyl ester A mixture of 2-{6-[4'-(4,4,5,5-tetramethyl-[1,3,2]dioxaborolan-2-yl)-biphenyl-4-yl]-1H-benzoimidazol-2-yl}-pyrrolidine-1-carboxylic acid tert-butyl ester (147 mg, 0.26 mmol), 2-[5-bromo-1-(2-trimethylsilanyl-ethoxymethyl)-1H-imidazol-2-yl]-pyrrolidine-1-carboxylic acid tert-butyl ester (116 mg, 0.26 mmol), tetrakis(triphenylphosphine)palladium (30 mg, 0.026 mmol), Pd(dppf)Cl$_2$ (21 mg, 0.026 mmol) and potassium carbonate (72 mg, 0.52 mmol) in 3 ml 1,2-dimethoxyethane and 1 mL water was heated to 90° C. for 2.5 hours. The reaction mixture was cooled and dissolved in ethyl acetate and washed with 5% lithium chloride aqueous solution. The organic layer was dried (MgSO4), concentrated and purified by preparative reverse phase HPLC (GEMINI, 5 to 100% ACN/H$_2$O+0.1% TFA). Product was lyophilized to give 2-(6-{4'-[2-(1-Boc-pyrrolidin-2-yl)-3-(2-trimethylsilanyl-ethoxymethyl)-3H-imidazol-4-yl]-biphenyl-4-yl}-1H-benzoimidazol-2-yl)-pyrrolidine-1-carboxylic acid tert-butyl ester (52 mg, yield 25%); LCMS-ESI$^+$: calc'd for $C_{46}H_{60}N_6O_5Si$: 805.09; Found: 805.1 (M+H$^+$).

(1-{2-[5-(4'-{2-[1-(2-methoxycarbonylamino-3-methyl-butyryl)-pyrrolidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester Trifluoroacetic acid (2 mL) was added to 2-(6-{4'-[2-(1-Boc-pyrrolidin-2-yl)-3-(2-trimethylsilanyl-ethoxymethyl)-3H-imidazol-4-yl]-biphenyl-4-yl}-1H-benzoimidazol-2-yl)-pyrrolidine-1-carboxylic acid tert-butyl ester (52 mg, 0.056 mmol) and the reaction mixture was stirred at room temperature for 4 hours. The reaction mixture was concentrated and dried overnight under vacuum. The residue was dissolved in DMF (1.5 mL) and to this solution was added 2-methoxycarbonylamino-3-methyl-butyric acid (20 mg), diisopropylethylamine (59 µL), followed by HATU (43 mg). Reaction mixture was stirred at 0° C. for 30 minutes. The reaction mixture was dissolved in ethyl acetate and washed with dilute sodium bicarbonate solution. The organic layer was dried (MgSO$_4$), concentrated and purified by preparative reverse phase HPLC (GEMINI, 5 to 100% ACN/H$_2$O+0.1% TFA). Product was lyophilized to give (1-{2-[5-(4'-{2-[1-(2-methoxycarbonylamino-3-methyl-butyryl)-pyrrolidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester as the bis-TFA salt (4.8 mg).

$^1$H-NMR: 300 MHz, (CD$_3$OD-d$_4$) δ: 8.0 (s, 1H), 7.92-7.82 (m, 11H), 5.38 (t, 1H), 5.24 (t, 1H), 4.27 (dd, 2H), 4.16 (m,

2H), 3.96 (m, 2H), 3.63 (s, 6H), 2.62 (m, 2H), 2.40-2.18 (m, 6H), 2.08 (m, 2H), 0.95-0.85 (m, 12H); LCMS-ESI$^+$: calc'd for $C_{44}H_{52}N_8O_6$: 788.93; Found: 789.3 (M+H$^+$).

Example BG

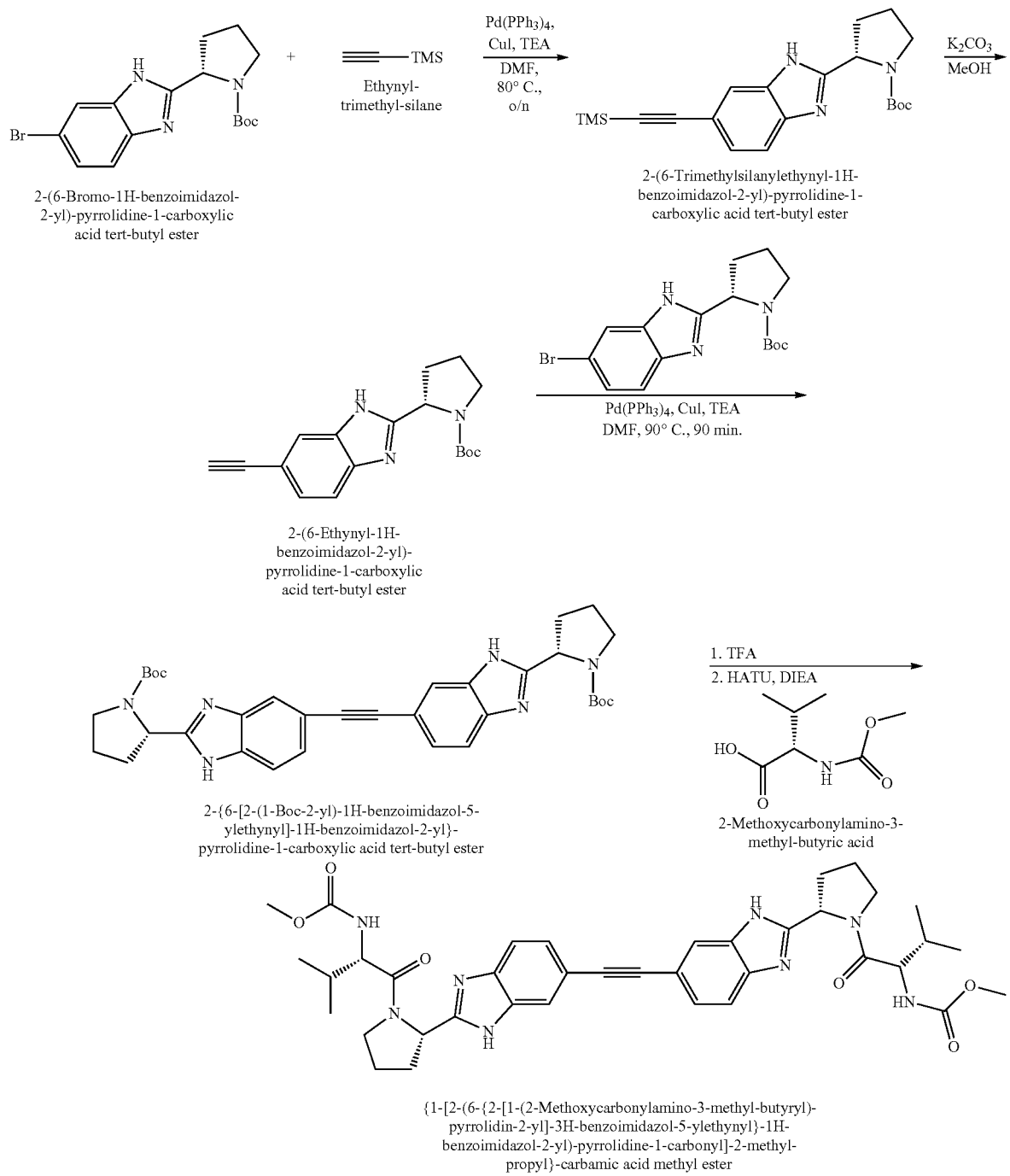

{1-[2-(6-{2-[1-(2-Methoxycarbonylamino-3-methyl-butyryl)-pyrrolidin-2-yl]-3H-benzoimidazol-5-ylethynyl}-1H-benzoimidazol-2-yl)-pyrrolidine-1-carbonyl]-2-methyl-propyl}-carbamic acid methyl ester 2-(6-trimethylsilanylethynyl-1H-benzoimidazol-2-yl)-pyrrolidine-1-carboxylic acid tert-butyl ester A mixture of 2-(6-bromo-1H-benzoimidazol-2-yl)-pyrrolidine-1-carboxylic acid tert-butyl ester (309 mg, 0.84 mmol), ethynyl-trimethyl-silane (1.2 mL, 8.4 mmol), tetrakis(triphenylphosphine)palladium (97 mg, 0.08 mmol), copper(I) iodide (32 mg, 0.16 mmol) and triethylamine (0.7 mL, 5.04 mmol) in 5 ml DMF was heated to 80° C. for 8 hours. The reaction mixture was cooled and dissolved in ethyl acetate and washed with 5% lithium chloride aqueous solution. The organic layer was dried (MgSO$_4$), concentrated and purified by flash column chromatography (silica gel, 20 to 100% ethyl acetate/hexane) to give 2-(6-trimethylsilanylethynyl-1H-benzoimidazol-2-yl)-pyrrolidine-1-carboxylic acid tert-butyl ester (200 mg, yield 62%). LCMS-ESI$^-$: calc'd for $C_{21}H_{29}N_3O_2Si$: 383.56; Found: 384.1 (M+H$^+$).

2-(6-ethynyl-1H-benzoimidazol-2-yl)-pyrrolidine-1-carboxylic acid tert-butyl ester Potassium carbonate (144 mg) was added to 2-(6-trimethylsilanylethynyl-1H-benzoimidazol-2-yl)-pyrrolidine-1-carboxylic acid tert-butyl ester (200 mg, 0.52 mmol) in 6 ml methanol. The reaction was stirred at room temperature for 2 hours. The reaction mixture was concentrated and purified by flash column chromatography (silica gel, 20 to 100% ethyl acetate/hexane) to give 2-(6-ethynyl-1H-benzoimidazol-2-yl)-pyrrolidine-1-carboxylic acid tert-butyl ester (121 mg, yield 75%). LCMS-ESI$^-$: calc'd for $C_{18}H_{21}N_3O_2$: 311.38; Found: 311.8 (M+H$^+$).

2-{6-[2-(1-Boc-2-yl)-1H-benzoimidazol-5-ylethynyl]-1H-benzoimidazol-2-yl}-pyrrolidine-1-carboxylic acid tert-butyl ester A mixture of 2-(6-bromo-1H-benzoimidazol-2-yl)-pyrrolidine-1-carboxylic acid tert-butyl ester (91 mg, 0.24 mmol), 2-(6-ethynyl-1H-benzoimidazol-2-yl)-pyrrolidine-1-carboxylic acid tert-butyl ester (77 mg, 0.24 mmol), tetrakis(triphenylphosphine)palladium (14 mg), copper(I) iodide (5 mg) and triethylamine (138 IA) in 2 ml DMF was heated to 90° C. for 2 hours. The reaction mixture was cooled and dissolved in ethyl acetate and washed with 5% lithium chloride aqueous solution. The organic layer was dried (MgSO$_4$), concentrated and purified by flash column chromatography (silica gel, 0-10% IPA/DCM:acetone (3:2) mixture) to give 2-{6-[2-(1-Boc-2-yl)-1H-benzoimidazol-5-ylethynyl]-1H-benzoimidazol-2-yl}-pyrrolidine-1-carboxylic acid tert-butyl ester (5.4 mg). LCMS-ESI$^-$: calc'd for $C_{34}H_{40}N_6O_4$: 596.72; Found: 597.0 (M+H$^+$).

{1-[2-(6-{2-[1-(2-methoxycarbonylamino-3-methyl-butyryl)-pyrrolidin-2-yl]-3,1-benzoimidazol-5-yl-ethynyl}-1H-benzoimidazol-2-yl)-pyrrolidine-1-carbonyl]-2-methyl-propyl}-carbamic acid methyl ester Trifluoroacetic acid (1 mL) was added to 2-{6-[2-(1-Boc-2-yl)-1H-benzoimidazol-5-ylethynyl]-1H-benzoimidazol-2-yl}-pyrrolidine-1-carboxylic acid tert-butyl ester (5.4 mg, 0.0065 mmol) and the reaction mixture was stirred at room temperature for 4 hours. The reaction mixture was concentrated and dried overnight under vacuum. The residue was dissolved in DMF (1 mL) and to this solution was added 2-methoxycarbonylamino-3-methyl-butyric acid (2.6 mg), diisopropylethylamine (9 µL), followed by HATU (5.5 mg). Reaction mixture was stirred at 0° C. for 30 minutes. The reaction mixture was dissolved in ethyl acetate and washed with dilute sodium bicarbonate solution. The organic layer was dried (MgSO$_4$), concentrated and purified by preparative reverse phase HPLC (GEMINI, 5 to 100% ACN/H$_2$O+0.1% TFA). Product was lyophilized to give {1-[2-(6-{2-[1-(2-methoxycarbonylamino-3-methyl-butyryl)-pyrrolidin-2-yl]-3H-benzoimidazol-5-ylethynyl}-1H-benzoimidazol-2-yl)-pyrrolidine-1-carbonyl]-2-methyl-propyl}-carbamic acid methyl ester as the bis-TFA salt (0.9 mg).

$^1$H-NMR: 300 MHz, (CD$_3$OD-d$_4$) δ: 7.82 (s, 2H), 7.68-7.60 (m, 4H), 5.32 (m, 2H), 4.27 (dd, 2H), 4.11 (m, 2H), 3.96 (m, 2H), 3.63 (s, 6H), 2.58 (m, 2H), 2.40-2.12 (m, 6H), 2.08 (m, 2H), 0.95-0.85 (m, 12H); LCMS-ESI$^+$: calc'd for $C_{38}H_{46}N_8O_6$: 710.82; Found: 711.2 (M+H$^+$).

Example BH

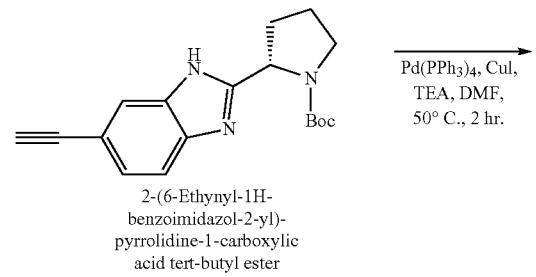

2-(6-Ethynyl-1H-benzoimidazol-2-yl)-pyrrolidine-1-carboxylic acid tert-butyl ester

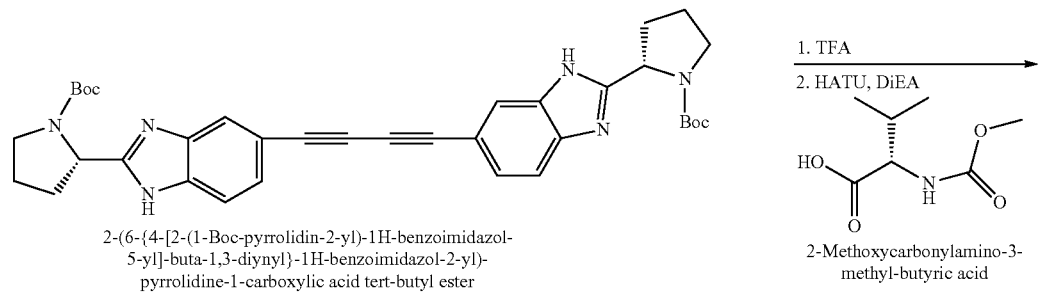

2-(6-{4-[2-(1-Boc-pyrrolidin-2-yl)-1H-benzoimidazol-5-yl]-buta-1,3-diynyl}-1H-benzoimidazol-2-yl)-pyrrolidine-1-carboxylic acid tert-butyl ester 2-Methoxycarbonylamino-3-methyl-butyric acid

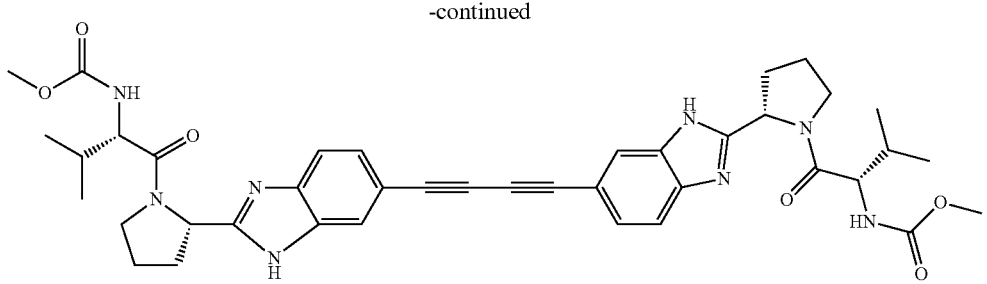

(1-{2-[6-(4-{2-[1-(2-Methoxycarbonylamino-3-methyl-butyryl)-pyrrolidin-2-yl]-3H-benzoimidazol-5-yl}-buta-1,3-diynyl)-1H-benzoimidazol-2-yl]-pyrrolidine-1-carbonyl}-2-methyl-propyl)-carbamic acid methyl ester 2-(6-{4-[2-(1-Boc-pyrrolidin-2-yl)-1H-benzoimidazol-5-yl]-buta-1,3-diynyl}-1H-benzoimidazol-2-yl)-pyrrolidine-1-carboxylic acid tert-butyl ester A mixture of 2-(6-ethynyl-1H-benzoimidazol-2-yl)-pyrrolidine-1-carboxylic acid tert-butyl ester (88 mg), tetrakis(triphenylphosphine)palladium (16 mg), copper(I) iodide (3 mg) and triethylamine (120 μL) in 1.5 ml DMF was heated to 50° C. for 2 hours. The reaction mixture was cooled and dissolved in ethyl acetate and washed with 5% lithium chloride aqueous solution. The organic layer was dried (MgSO$_4$), concentrated and purified by preparative reverse phase HPLC (GEMINI, 5 to 100% ACN/H$_2$O+0.1% TFA) to give 2-(6-{4-[2-(1-Boc-pyrrolidin-2-yl)-1H-benzoimidazol-5-yl]-buta-1,3-diynyl}-1H-benzoimidazol-2-yl)-pyrrolidine-1-carboxylic acid tert-butyl ester (12 mg). LCMS-ESI$^-$: calc'd for C$_{36}$H$_{40}$N$_6$O$_4$: 620.74; Found: 621.0 (M+H$^+$).

(1-{2-[6-(4-{2-[1-(2-Methoxycarbonylamino-3-methyl-butyryl)-pyrrolidin-2-yl]-3H-benzoimidazol-5-yl}-buta-1,3-diynyl)-1H-benzoimidazol-2-yl]-pyrrolidine-1-carbonyl}-2-methyl-propyl)-carbamic acid methyl ester Trifluoroacetic acid (1 mL) was added to 2-(6-{4-[2-(1-Boc-pyrrolidin-2-yl)-1H-benzoimidazol-5-yl]-buta-1,3-diynyl}-1H-benzoimidazol-2-yl)-pyrrolidine-1-carboxylic acid tert-butyl ester (12 mg) and the reaction mixture was stirred at room temperature for 3 hours. The reaction mixture was concentrated and dried overnight under vacuum. The residue was dissolved in DMF (1 mL) and to this solution was added 2-methoxycarbonylamino-3-methyl-butyric acid (5.5 mg), diisopropylethylamine (13 μL), followed by HATU (12 mg). Reaction mixture was stirred at 0° C. for 30 minutes. The reaction mixture was dissolved in ethyl acetate and washed with dilute sodium bicarbonate solution. The organic layer was dried (MgSO4), concentrated and purified by preparative reverse phase HPLC (GEMINI, 5 to 100% ACN/H$_2$O+0.1% TFA). Product was lyophilized to give (1-{2-[6-(4-{2-[1-(2-Methoxycarbonylamino-3-methyl-butyryl)-pyrrolidin-2-yl]-3H-benzoimidazol-5-yl}-buta-1,3-diynyl)-1H-benzoimidazol-2-yl]-pyrrolidine-1-carbonyl}-2-methyl-propyl)-carbamic acid methyl ester as the bis-TFA salt (4 mg).

$^1$H-NMR: 300 MHz, (CD$_3$OD-d$_4$) δ: 7.82 (s, 2H), 7.72-7.62 (m, 4H), 5.32 (m, 2H), 4.27 (d, 2H), 4.11 (m, 2H), 3.90 (m, 2H), 3.63 (s, 6H), 2.54 (m, 2H), 2.38-2.12 (m, 6H), 2.06 (m, 2H), 0.95-0.85 (m, 12H); LCMS-ESI$^+$: calc'd for C$_{40}$H$_{46}$N$_8$O$_6$: 734.84; Found: 735.2 (M+H$^+$).

Example BI

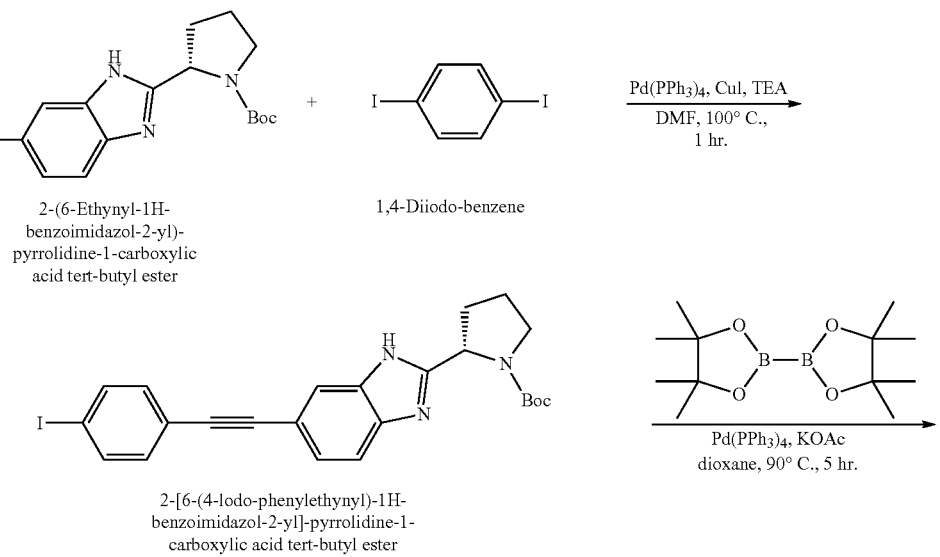

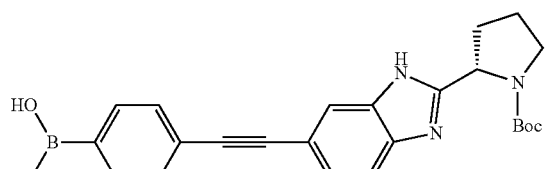

2-{6-boronic acid)-phenylethynyl]-1H-benzoimidazol-2-yl}-pyrrolidine-1-carboxylic acid tert-butyl ester

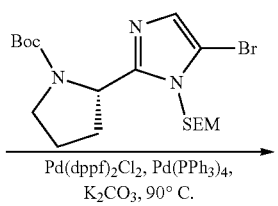

2-[5-Bromo-1-(2-trimethylsilanyl-ethoxymethyl)-1H-imidazol-2-yl]-pyrrolidine-1-carboxylic acid tert-butyl ester Pd(dppf)$_2$Cl$_2$, Pd(PPh$_3$)$_4$,
K$_2$CO$_3$, 90° C.

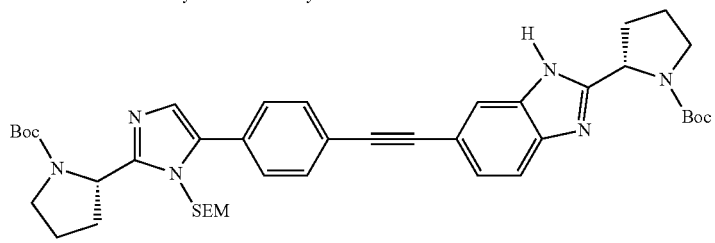

2-(6-{4-[2-(1-Boc-pyrrolidin-2-yl)-3-(2-trimethylsilanyl-ethoxymethyl)-3H-imidazol-4-yl]-phenylethynyl}-1H-benzoimidazol-2-yl)-pyrrolidine-1-carboxylic acid tert-butyl ester

1. TFA
2. HATU, DIEA

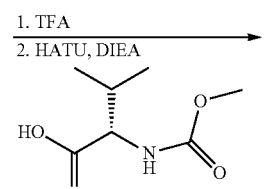

2-Methoxycarbonylamino-3-methyl-butyric acid

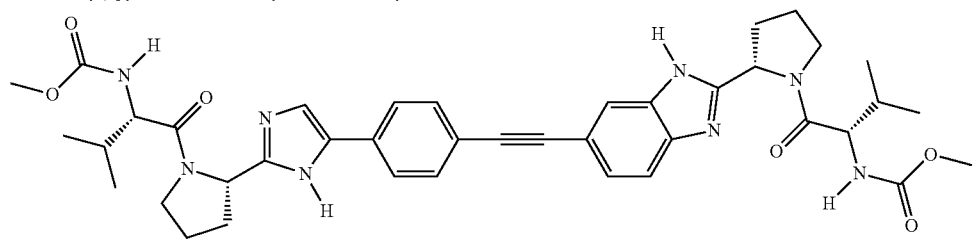

(1-{2-[5-(4-{2-[1-(2-Methoxycarbonylamino-3-methyl-butyryl)-pyrrolidin-2-yl]-3H-benzoimidazol-5-ylethynyl}-phenyl)-1H-imidazol-2-yl]-pyrrolidine-1-carbonyl}-2-methyl-propyl)-carbamic acid methyl ester 2-[6-(4-Iodo-phenylethynyl)-1H-benzoimidazol-2-yl]-pyrrolidine-1-carboxylic acid tert-butyl ester A mixture of 2-(6-ethynyl-1H-benzoimidazol-2-yl)-pyrrolidine-1-carboxylic acid tert-butyl ester (100 mg, 0.321 mmol), 1,4-Diiodo-benzene (529 mg, 1.61 mmol), tetrakis(triphenylphosphine)palladium (37 mg, 0.03 mmol), copper (I) iodide (12 mg, 0.06 mmol) and triethylamine (0.135 mL, 0.96 mmol) in 2 ml DMF was heated to 100° C. in the microwave for 1 hour. The reaction mixture was cooled and dissolved in ethyl acetate and washed with 5% lithium chloride aqueous solution. The organic layer was dried (MgSO$_4$), concentrated and purified by flash column chromatography (silica gel, 20 to 100% ethyl acetate/hexane) to give 2-[6-(4-Iodo-phenylethynyl)-1H-benzoimidazol-2-yl]-pyrrolidine-1-carboxylic acid tert-butyl ester (123 mg, yield 75%). LCMS-ESI$^-$: calc'd for C$_{24}$H$_{24}$IN$_3$O$_2$: 513.37; Found: 531.8 (M+H$^+$).

2-{6-[4-boronic acid-phenylethynyl]-1H-benzoimidazol-2-yl}-pyrrolidine-1-carboxylic acid tert-butyl ester A mixture of 2-[6-(4-Iodo-phenylethynyl)-1H-benzoimidazol-2-yl]-pyrrolidine-1-carboxylic acid tert-butyl ester (123 mg, 0.24 mmol), bis(pinacolato)diboron (122 mg, 0.48 mmol), tetrakis(triphenylphosphine)palladium (52 mg, 0.02 mmol) and potassium acetate (52 mg, 0.53 mmol) in 3 ml 1,4-dioxane was heated to 90° C. for 5 hours. The reaction mixture was cooled and dissolved in ethyl acetate and washed with 5% lithium chloride aqueous solution. The organic layer was dried (MgSO4), concentrated and purified by flash column chromatography (silica gel, 20 to 100% ethyl acetate/hexane) and followed by preparative reverse phase HPLC (GEMINI, 5 to 100% ACN/H$_2$O+0.1% TFA) to give the corresponding boronic acid of 2-{6-[4-(4,4,5,5-Tetramethyl-[1,3,2]dioxaborolan-2-yl)-phenylethynyl]-1H-benzoimidazol-2-yl}-pyrrolidine-1-carboxylic acid tert-butyl ester (15 mg). LCMS-ESI$^-$: calc'd for C$_{24}$H$_{26}$BN$_3$O$_4$: 431.29; Found: 431.9 (M+H$^+$).

2-(6-{4-[2-(1-Boc-pyrrolidin-2-yl)-3-(2-trimethylsilanyl-ethoxymethyl)-3H-imidazol-4-yl]-phenylethynyl}-1H-benzoimidazol-2-yl)-pyrrolidine-1-carboxylic acid tert-butyl ester A mixture of 2-{6-[4-boronic acid-phenylethynyl]-1H-benzoimidazol-2-yl}-pyrrolidine-1-carboxylic acid tert-butyl ester (11 mg, 0.025), 2-[5-Bromo-1-(2-trimethylsilanyl-ethoxymethyl)-1H-imidazol-2-yl]-pyrrolidine-1-carboxylic acid tert-butyl ester (34 mg, 0.076 mmol), tetrakis(triphenylphosphine)palladium (1.5 mg), Pd(dppf)Cl$_2$ (1 mg) and potassium carbonate (3.5 mg) in 1 ml DME and 0.3 mL water was heated to 90° C. for 30 minutes. The reaction mixture was cooled and dissolved in ethyl acetate and washed with 5% lithium chloride aqueous solution. The organic layer was dried (MgSO$_4$), concentrated and purified by preparative reverse phase HPLC (GEMINI, 5 to 100% ACN/H$_2$O+0.1% TFA) to give 2-(6-{4-[2-(1-Boc-pyrrolidin-2-yl)-3-(2-trimethylsilanyl-ethoxymethyl)-3H-imidazol-4-yl]-phenylethynyl}-1H-benzoimidazol-2-yl)-pyrrolidine-1-carboxylic acid tert-butyl ester (4 mg, yield 21%). LCMS-ESI$^-$: calc'd for C$_{43}$H$_{60}$N$_6$O$_5$Si; 753.02; Found: 751.4 (M−H$^+$).

(1-{2-[5-(4-{2-[1-(2-Methoxycarbonylamino-3-methyl-butyryl)-pyrrolidin-2-yl]-3H-benzoimidazol-5-ylethynyl}-phenyl)-1H-imidazol-2-yl]-pyrrolidine-1-carbonyl}-2-methyl-propyl)-carbamic acid methyl ester Trifluoroacetic acid (1 mL) was added to 2-(6-{4-[2-(1-Boc-pyrrolidin-2-yl)-3-(2-trimethylsilanyl-ethoxymethyl)-3H-imidazol-4-yl]-phenylethynyl}-1H-benzoimidazol-2-yl)-pyrrolidine-1-carboxylic acid tert-butyl ester (4 mg) and the reaction mixture was stirred at room temperature for 5 hours. The reaction mixture was concentrated and dried overnight under vacuum. The residue was dissolved in DMF (1 mL) and to this solution was added 2-methoxycarbonylamino-3-methyl-butyric acid (2 mg), diisopropylethylamine (6 µL), followed by HATU (4 mg). Reaction mixture was stirred at 0° C. for 30 minutes. The reaction mixture was dissolved in ethyl acetate and washed with dilute sodium bicarbonate solution. The organic layer was dried (MgSO$_4$), concentrated and purified by preparative reverse phase HPLC (GEMINI, 5 to 100% ACN/H$_2$O+0.1% TFA). Product was lyophilized to give (1-{2-[5-(4-{2-[1-(2-Methoxycarbonylamino-3-methyl-butyryl)-pyrrolidin-2-yl]-3H-benzoimidazol-5-ylethynyl}-phenyl)-1H-imidazol-2-yl]-pyrrolidine-1-carbonyl}-2-methyl-propyl)-carbamic acid methyl ester as the bis-TFA salt (2.8 mg); $^1$H-NMR: 300 MHz, (CD$_3$OD-d$_4$) δ: 7.86 (s, 1H), 7.82 (s, 1H), 7.78-7.60 (m, 5H), 5.32 (m, 2H), 4.27 (dd, 2H), 4.11 (m, 2H), 3.96 (m, 2H), 3.63 (s, 6H), 2.58 (m, 2H), 2.40-2.12 (m, 6H), 2.08 (m, 2H), 0.95-0.85 (m, 12H); LCMS-ESI$^+$: calc'd for C$_{40}$H$_{46}$N$_8$O$_6$: 736.86; Found: 737.3 (M+H$^+$).

Example BJ

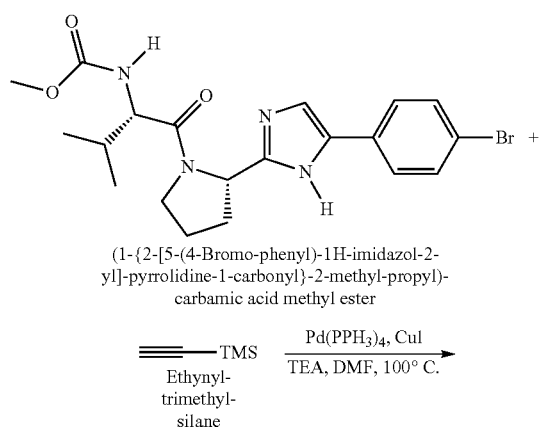

(1-{2-[5-(4-Bromo-phenyl)-1H-imidazol-2-yl]-pyrrolidine-1-carbonyl}-2-methyl-propyl)-carbamic acid methyl ester

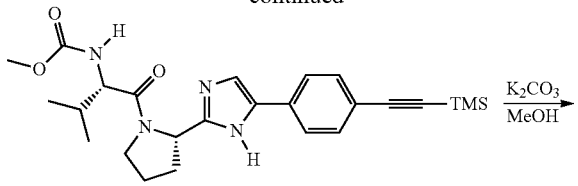

(2-Methyl-1-(2-[5-(4-trimethylsilanylethynyl-phenyl)-1H-imidazol-2-yl]-pyrrolidine-1-carbonyl}-propyl)-carbamic acid methyl ester

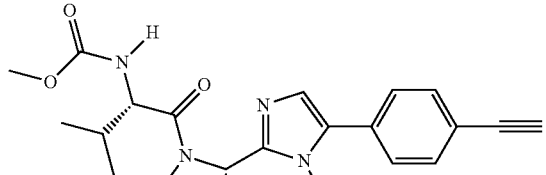

(1-{2-[5-(4-Ethynyl-phenyl)-1H-imidazol-2-yl]-pyrrolidine-1-carbonyl}-2-methyl-propyl)-carbamic acid methyl ester

(2-Methyl-1-{2-[5-(4-trimethylsilanylethynyl-phenyl)-1H-imidazol-2-yl]-pyrrolidine-1-carbonyl}-propyl)-carbamic acid methyl ester A mixture of (1-{2-[5-(4-Bromo-phenyl)-1H-imidazol-2-yl]-pyrrolidine-1-carbonyl}-2-methyl-propyl)-carbamic acid methyl ester (364 mg, 0.81 mmol), Ethynyl-trimethylsilane (0.68 mL, 4.9 mmol), Copper(I) iodide (154 mg, 0.81 mmol), tetrakis(triphenylphosphine)palladium (94 mg, 0.08 mmol) and triethylamine (0.67 mL, 4.9 mmol) in 5 ml DMF was heated to 70° C. overnight. The reaction mixture was cooled and dissolved in ethyl acetate and washed with 5% lithium chloride aqueous solution. The organic layer was dried (MgSO$_4$), concentrated and purified by flash column chromatography (silica gel, 20 to 100% ethyl acetate/hexane) and followed by preparative reverse phase HPLC (GEMINI, 5 to 100% ACN/H$_2$O+0.1% TFA) to give (2-Methyl-1-{2-[5-(4-trimethylsilanylethynyl-phenyl)-1H-imidazol-2-yl]-pyrrolidine-1-carbonyl}-propyl)-carbamic acid methyl ester (324 mg). LCMS-ESI$^-$: calc'd for C$_{25}$H$_{34}$BN$_4$O$_3$Si: 466.65; Found: 467.1 (M+H$^+$).

(1-{2-[5-(4-Ethynyl-phenyl)-1H-imidazol-2-yl]-pyrrolidine-1-carbonyl}-2-methyl-propyl)-carbamic acid methyl ester Potassium carbonate (192 mg) was added to (2-Methyl-1-{2-[5-(4-trimethylsilanylethynyl-phenyl)-1H-imidazol-2-yl]-pyrrolidine-1-carbonyl}-propyl)-carbamic acid methyl ester (324 mg) in 7 mL MeOH solution. The reaction mixture was stirred at room temperature overnight. The reaction mixture was concentrated down and purified by flash column chromatography (silica gel, 20 to 100% ethyl acetate/hexane) to give (1-{2-[5-(4-Ethynyl-phenyl)-1H-imidazol-2-yl]-pyrrolidine-1-carbonyl}-2-methyl-propyl)-carbamic acid methyl ester (234 mg).

$^1$H-NMR: 300 MHz, (CD$_3$OD-d$_4$) δ: 7.84 (s, 1H), 7.84 (d, 2H), 6.98 (d, 2H), 5.22 (t, 1H), 4.21 (d, 1H), 4.11 (m, 1H), 3.86 (m, 1H), 3.63 (s, 3H), 2.55 (m, 1H), 2.31-2.02 (m, 4H), 0.95-0.85 (m, 6H); LCMS-ESI⁺: calc'd for $C_{22}H_{26}N_4O_3$: 394.47; Found: 395.1 (M+H⁺).

Example BK

{1-[2-(6-Ethynyl-1H-benzoimidazol-2-yl)-pyrrolidine-1-carbonyl]-2-methyl-propyl}-carbamic acid methyl ester Trifluoroacetic acid (1 mL) was added to 2-(6-Ethynyl-1H-benzoimidazol-2-yl)-pyrrolidine-1-carboxylic acid tert-butyl ester (20 mg) and the reaction mixture was stirred at room temperature for 1 hour. The reaction mixture was concentrated and dried overnight under vacuum. The residue was dissolved in DMF (1 mL) and to this solution was added 2-methoxycarbonylamino-3-methyl-butyric acid (12 mg), diisopropylethylamine (67 µL), followed by HATU (24 mg). Reaction mixture was stirred at 0° C. for 30 minutes. The reaction mixture was dissolved in ethyl acetate and washed with dilute sodium bicarbonate solution. The organic layer was dried (MgSO₄), concentrated and purified by preparative reverse phase HPLC (GEMINI, 5 to 100% ACN/H₂O+0.1% TFA). Product was lyophilized to give {1-[2-(6-Ethynyl-1H-benzoimidazol-2-yl)-pyrrolidine-1-carbonyl]-2-methyl-propyl}-carbamic acid methyl ester as the mono TFA salt (23 mg): ¹H-NMR: 300 MHz, (CD₃OD-d₄) δ: 7.82 (s, 1H), 7.72 (d, 1H), 7.62 (d, 1H), 5.32 (t, 1H), 4.24 (d, 1H), 4.11 (m, 1H), 3.90 (m, 1H), 3.63 (s, 4H), 2.58 (m, 1H), 2.38-2.12 (m, 3H), 2.04 (m, 1H), 0.95-0.85 (m, 6H); LCMS-ESI⁺: calc'd for $C_{22}H_{26}N_4O_3$: 368.43; Found: 369.0 (M+H⁺).

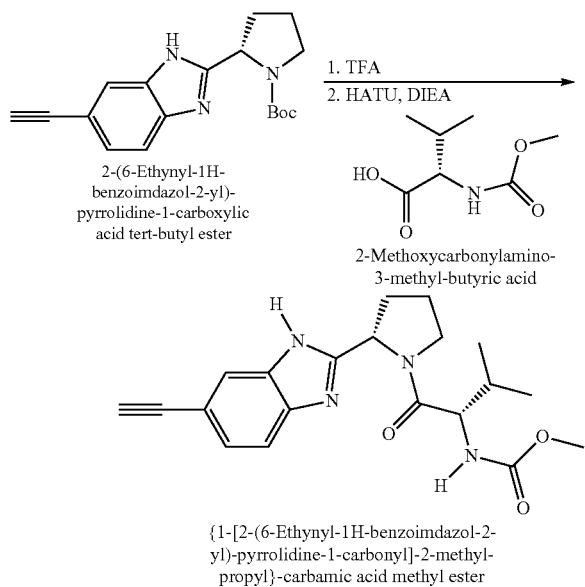

Example BL

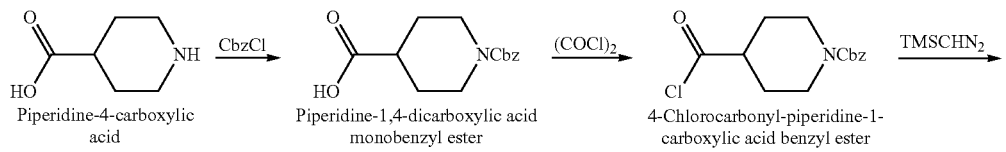

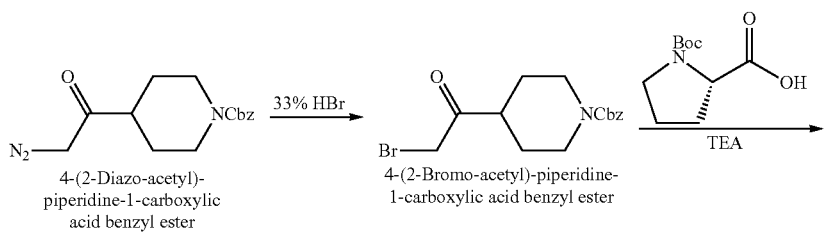

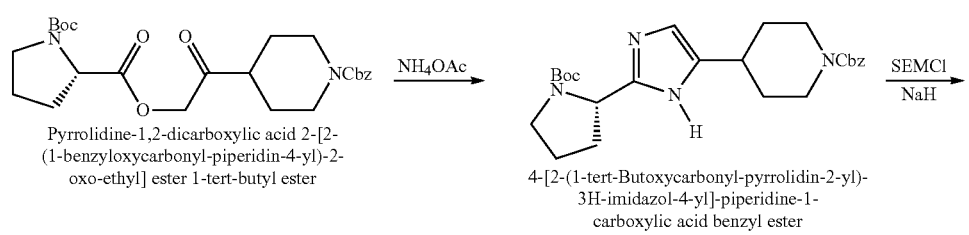

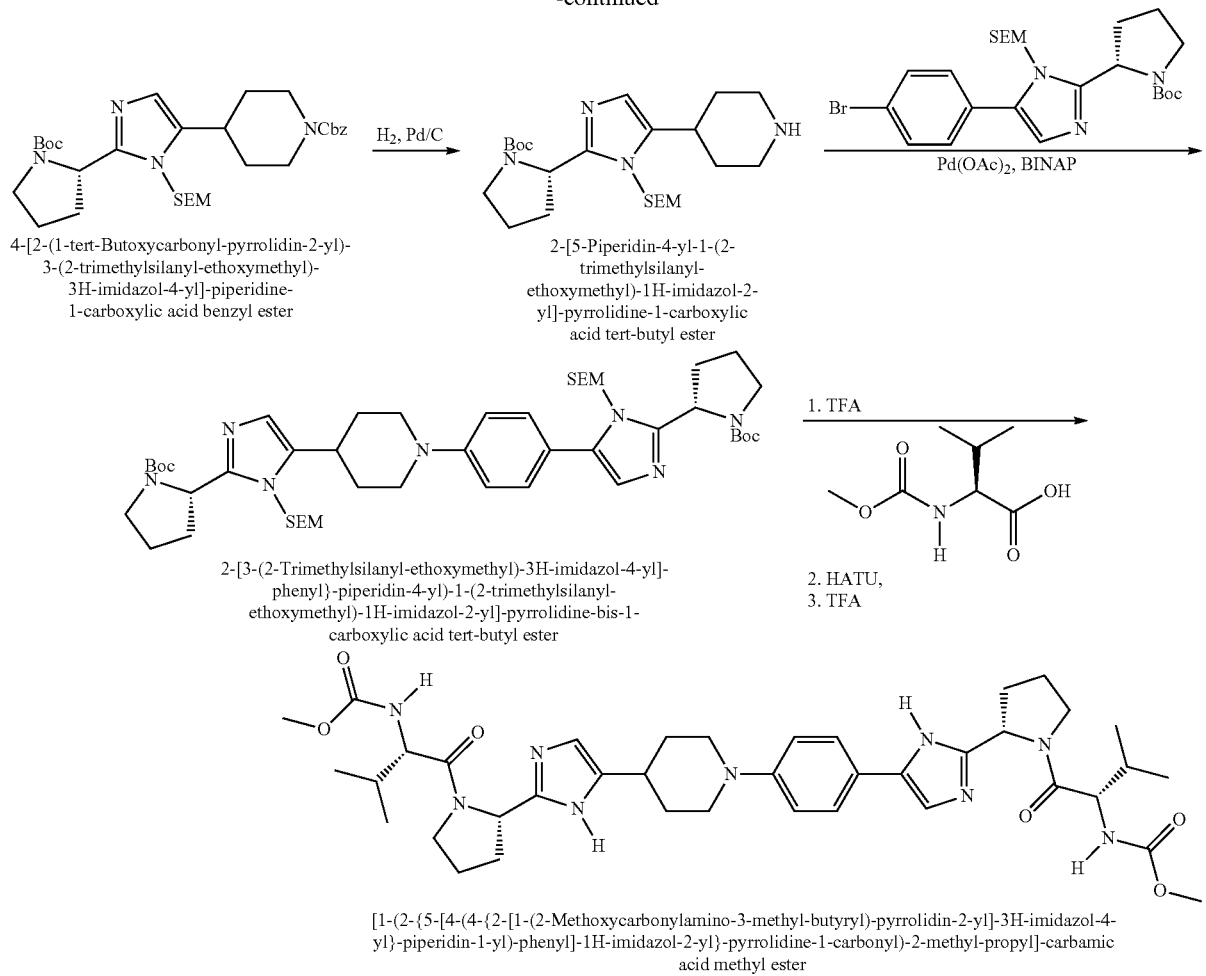

Piperidine-1,4-dicarboxylic acid monobenzyl ester

Piperidine-4-carboxylic acid (64.8 g, 0.5 mol) in $H_2O$ (50 mL) was treated with NaOH (44.0 g, 1.1 mol). The reaction mixture was cooled to 0° C. and treated with CbzCl (93.8 g, 0.55 mol). The reaction mixture was stirred at ambient temperature for 4 hours and the mixture was extracted with $Et_2O$ (3 150 mL) The aqueous phase was acidified with 6 N HCl (140 mL) and extracted with EtOAc (3 200 mL). The solution was dried over $MgSO_4$, filtered, and concentrated to afford crude piperidine-1,4-dicarboxylic acid monobenzyl ester (120 g), which was used without further purification: MS (ESI) m/z 262 [M−H]$^+$.

4-Chlorocarbonyl-piperidine-1-carboxylic acid benzyl ester

Piperidine-1,4-dicarboxylic acid monobenzyl ester (40.2 g, 0.15 mol) in dichloromethane (300 mL) was treated with oxalyl chloride (100 g, 0.79 mol). The reaction mixture was stirred at ambient temperature for 4 hours and the mixture was concentrated to afford crude 4-chlorocarbonyl-piperidine-1-carboxylic acid benzyl ester (43 g), which was used without further purification.

4-(2-Diazo-acetyl)-piperidine-1-carboxylic acid benzyl ester

4-Chlorocarbonyl-piperidine-1-carboxylic acid benzyl ester (43 g, 0.15 mol) in dichloromethane (300 mL) was treated with (trimethylsilyl)diazomethane (2.0 M in hexanes, 150 mL, 0.31 mol) over 15 min. The reaction mixture was stirred at ambient temperature for 18 hours and the mixture was concentrated to afford crude 4-(2-diazo-acetyl)-piperidine-1-carboxylic acid benzyl ester (44 g), which was used without further purification.

4-(2-Bromo-acetyl)-piperidine-1-carboxylic acid benzyl ester 4-(2-Diazo-acetyl)-piperidine-1-carboxylic acid benzyl ester (44 g, 0.15 mol) in EtOAc (300 mL) was cooled to 0° C. The solution was treated with 33% HBr/HOAc (75 mL, 0.42 mol) over 15 min and stirred at ambient temperature for 2 hours. The mixture was slowly treated with saturated $NaHCO_3$ solution (300 mL) until pH was neutral or slightly basic and filtered. The solution was dried over $MgSO_4$ and subjected to a 330 g $SiO_2$ COMBIFLASH column (0-100% EtOAc-hexanes gradient) to afford 4-(2-bromo-acetyl)-piperidine-1-carboxylic acid benzyl ester (38.1 g, 81%): MS (ESI) m/z 341 [M+H]$^+$.

Pyrrolidine-1,2-dicarboxylic acid 2-[2-(1-benzyloxycarbonyl-piperidin-4-yl)-2-oxo-ethyl]ester 1-tert-butyl ester (S)-Proline (13 g, 61 mmol) in MeCN (250 mL) was treated with triethylamine (8.5 mL, 61 mmol). 4-(2-Bromoacetyl)-piperidine-1-carboxylic acid benzyl ester (19 g, 56 mmol) in MeCN (50 mL) was added dropwise over 15 min and the reaction was stirred for 2 hours. The mixture was concentrated and suspended in dicholormethane (100 mL) and washed with H$_2$O (50 mL). The solution was dried over MgSO$_4$ and subjected to a 330 g SiO$_2$ COMBIFLASH column (0-100% EtOAc-hexanes gradient) to afford pyrrolidine-1,2-dicarboxylic acid 2-[2-(1-benzyloxycarbonyl-piperidin-4-yl)-2-oxo-ethyl]ester 1-tert-butyl ester (20 g, 75%): MS (ESI) m/z 497 [M+Na]$^+$.

4-[2-(1-tert-Butoxycarbonyl-pyrrolidin-2-yl)-3H-imidazol-4-yl]-piperidine-1-carboxylic acid benzyl ester Pyrrolidine-1,2-dicarboxylic acid 2-[2-(1-benzyloxycarbonyl-piperidin-4-yl)-2-oxo-ethyl]ester 1-tert-butyl ester (20 g, 42 mmol) in xylenes (100 mL) was treated with ammonium acetate (16 g, 210 mmol). The reaction was stirred at 130° C. in a sealed tube for 3 hours. The mixture was concentrated and suspended in dicholormethane (100 mL) and washed with saturated NaHCO$_3$ (50 mL). The solution was dried over MgSO$_4$ and subjected to a 330 g SiO$_2$ COMBIFLASH column (0-100% EtOAc-hexanes followed by 0-20% MeOH-EtOAc gradient) to afford 4-[2-(1-tert-butoxycarbonyl-pyrrolidin-2-yl)-3H-imidazol-4-yl]-piperidine-1-carboxylic acid benzyl ester (6.8 g, 36%): MS (ESI) m/z 455 [M+H]$^+$.

4-[2-(1-tert-Butoxycarbonyl-pyrrolidin-2-yl)-3-(2-trimethylsilanyl-ethoxymethyl)-3H-imidazol-4-yl]-piperidine-1-carboxylic acid benzyl ester 4-[2-(1-tert-Butoxycarbonyl-pyrrolidin-2-yl)-3H-imidazol-4-yl]-piperidine-1-carboxylic acid benzyl ester (6.8 g, 14.9 mmol) in DMF (115 mL) was treated with NaH (60% dispersion in mineral oil, 655 mg, 16.4 mmol) in one portion. After 5 min, the mixture was treated with SEMCl (2.75 mL, 15.7 mmol) in 0.1 mL portions over 10 min. The reaction was stirred for 3 hours and diluted with saturated NH$_4$Cl solution (50 mL) and EtOAc (100 mL). The organic layer was washed with H$_2$O (3 50 mL) and brine (50 mL). The solution was dried over MgSO$_4$ and subjected to a 120 g SiO$_2$ COMBIFLASH column (0-100% EtOAc-hexanes followed by 0-20% MeOH-EtOAc gradient) to afford 4-[2-(1-tert-butoxycarbonyl-pyrrolidin-2-yl)-3-(2-trimethylsilanyl-ethoxymethyl)-3H-imidazol-4-yl]-piperidine-1-carboxylic acid benzyl ester (2.8 g, 32%): MS (ESI) m/z 585 [M+H]$^+$.

2-[5-Piperidin-4-yl-1-(2-trimethylsilanyl-ethoxymethyl)-1H-imidazol-2-yl]-pyrrolidine-1-carboxylic acid tert-butyl ester 4-[2-(1-tert-Butoxycarbonyl-pyrrolidin-2-yl)-3-(2-trimethylsilanyl-ethoxymethyl)-3H-imidazol-4-yl]-piperidine-1-carboxylic acid benzyl ester (2.8 g, 6.1 mmol) in EtOH (60 mL) was treated with 20% PdOH/C (600 mg) and placed under an atmosphere of H$_2$. The reaction was stirred for 18 hours and filtered through a CELITE plug to afford crude 2-[5-piperidin-4-yl-1-(2-trimethylsilanyl-ethoxymethyl)-1H-imidazol-2-yl]-pyrrolidine-1-carboxylic acid tert-butyl ester (2.0 g), which was used without further purification: MS (ESI) m/z 451 [M+H]$^+$.

2-[3-(2-Trimethylsilanyl-ethoxymethyl)-3H-imidazol-4-yl]-phenyl}-piperidin-4-yl)-1-(2-trimethylsilanyl-ethoxymethyl)-1H-imidazol-2-yl]-pyrrolidine-bis-1-carboxylic acid tert-butyl ester 2-[5-Piperidin-4-yl-1-(2-trimethylsilanyl-ethoxymethyl)-1H-imidazol-2-yl]-pyrrolidine-1-carboxylic acid tert-butyl ester (170 mg, 0.37 mmol) and 4-Bromophenyl-1-SEM-imidazol-2-yl-pyrrolidine-1-Boc (164 mg, 0.31 mmol, prepared according to WO 2008/021927) in toluene (3.5 mL) were treated with Pd(OAc)$_2$ (1.4 mg, 0.0064 mmol, via 10% solution in toluene), BINAP (19 mg, 0.031 mmol), and NaOtBu (42 mg, 0.44 mmol). The mixture was stirred in a sealed tube at 110° C. for 36 hours. The solution was concentrated, diluted with EtOAc (50 mL), and washed with saturated NaHCO$_3$ (20 mL), H$_2$O (20 mL), and brine (20 mL). The solution was dried over MgSO$_4$ and subjected to a 40 g SiO$_2$ COMBIFLASH column (0-100% EtOAc-hexanes followed by 0-20% MeOH-EtOAc gradient) to afford 2-[3-(2-trimethylsilanyl-ethoxymethyl)-3H-imidazol-4-yl]-phenyl}-piperidin-4-yl)-1-(2-trimethylsilanyl-ethoxymethyl)-1H-imidazol-2-yl]-pyrrolidine-bis-1-carboxylic acid tert-butyl ester (35 mg, 13%): MS (ESI) m/z 892 [M+H]$^+$.

[1-(2-{5-[4-(4-{2-[1-(2-Methoxycarbonylamino-3-methyl-butyryl)-pyrrolidin-2-yl]-3H-imidazol-4-yl}-piperidin-1-yl)-phenyl]-1H-imidazol-2-yl}-pyrrolidine-1-carbonyl)-2-methyl-propyl]-carbamic acid methyl ester 2-[3-(2-Trimethylsilanyl-ethoxymethyl)-3H-imidazol-4-yl]-phenyl}-piperidin-4-yl)-1-(2-trimethylsilanyl-ethoxymethyl)-1H-imidazol-2-yl]-pyrrolidine-bis-1-carboxylic acid tert-butyl ester (35 mg, 0.04 mmol) in dichloromethane (1.0 mL) was treated with trifluoroacetic acid (0.2 mL) and the mixture was stirred for 1 hours. The solution was concentrated and the residue was suspended in DMF (1.0 mL) and treated with (S)-Moc-Val-OH (15 mg, 0.086 mmol), HATU (32 mg, 0.085 mmol), and N-methyl morpholine (0.034 mL, 0.31 mmol). The mixture was stirred for 2 hours then diluted with EtOAc (25 mL), and washed with saturated NaHCO$_3$ (3 10 mL), H$_2$O (10 mL), and brine (10 mL). The solution was dried over MgSO$_4$ and suspended in trifluoroacetic acid (1.0 mL) and stirred in a screw-cap vial at 40° C. for 1 hour. The solution was concentrated and subjected to a reverse phase HPLC column (5-95% MeCN—H$_2$O; 0.1% TFA modifier) to afford [1-(2-{5-[4-(4-{2-[1-(2-methoxycarbonylamino-3-methyl-butyryl)-pyrrolidin-2-yl]-3H-imidazol-4-yl}-piperidin-1-yl)-phenyl]-1H-imidazol-2-yl}-pyrrolidine-1-carbonyl)-2-methyl-propyl]-carbamic acid methyl ester (9.5 mg, 33%) as a white solid (TFA salt): $^1$H NMR (CD$_3$OD, 300 MHz) 7.64 (s, 1H), 7.57 (d, J=9.0 Hz, 2H), 7.29 (s, 1H), 7.11 (d, J=9.0 Hz, 2H), 5.18 (m, 2H), 4.21 (m, 2H), 4.08 (m, 2H), 3.96 (m, 2H), 3.84 (m, 2H), 3.65, (s, 3H), 3.64 (s, 3H), 2.96 (m, 3H), 2.51 (m, 2H), 2.20 (m, 2H), 2.13 (m, 7H), 1.82 (m, 2H), 0.91 (m, 12H); MS (ESI) m/z 746 [M+H]$^+$.

Example BM

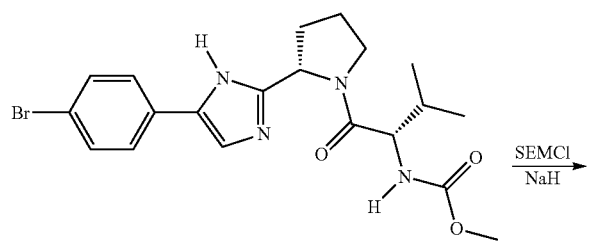

(1-{2-[5-(4-Bromo-phenyl)-1H-imidazol-2-yl]-pyrrolidine-1-carbonyl}-2-methyl-propyl)-carbamic acid methyl ester

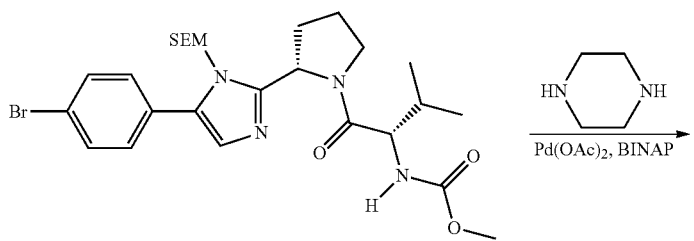

(1-{2-[5-(4-Bromo-phenyl)-1-(2-trimethylsilanyl-ethoxymethyl)-1H-imidazol-2-yl]-pyrrolidine-1-carbonyl}-2-methyl-propyl)-carbamic acid methyl ester

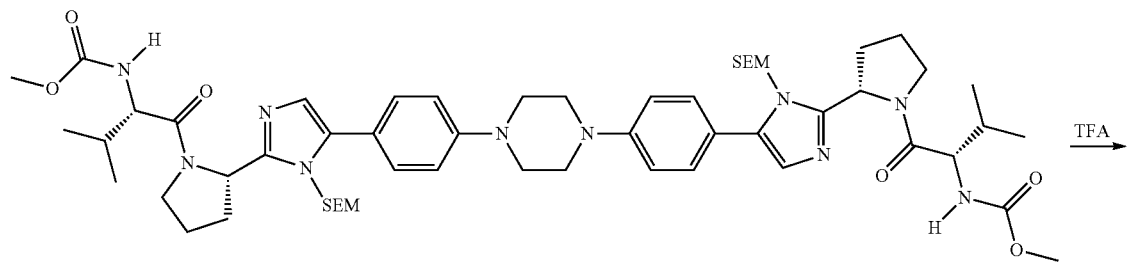

{1-{2-(5-{4-[4-(4-{2-[1-(2-Methoxycarbonylamino-3-methyl-butyryl)-pyrrolidin-2-yl]-(2-trimethylsilanyl-ethoxymethyl)-3H-imidazol-4-yl}-phenyl)-piperazin-1-yl]-phenyl}-1-(2-trimethylsilanyl-ethoxymethyl)-1H-imidazol-2-yl)-pyrrolidine-1-carbonyl]-2-methyl-propyl}-carbamic acid methyl ester

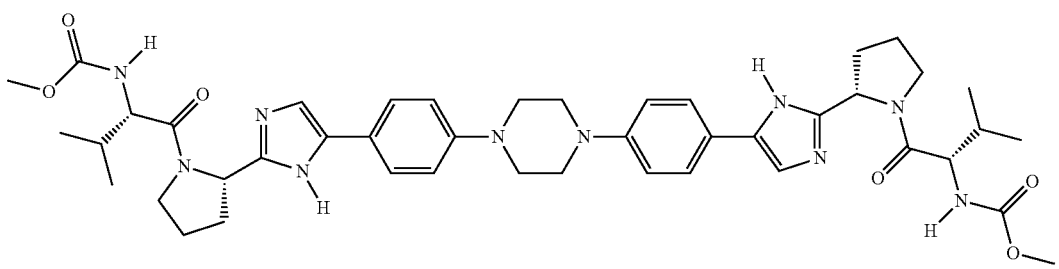

{1-[2-(5-{4-[4-(4-{2-[1-(2-Methoxycarbonylamino-3-methyl-butyryl)-pyrrolidin-2-yl]-3H-imidazol-4-yl}-phenyl)-piperazin-1-yl]-phenyl}-1H-imidazol-2-yl)-pyrrolidine-1-carbonyl]-2-methyl-propyl}-carbamic acid methyl ester (1-{2-[5-(4-Bromo-phenyl)-1-(2-trimethylsilanyl-ethoxymethyl)-1H-imidazol-2-yl]-pyrrolidine-1-carbonyl}-2-methyl-propyl)-carbamic acid methyl ester (1-{2-[5-(4-Bromo-phenyl)-1H-imidazol-2-yl]-pyrrolidine-1-carbonyl}-2-methyl-propyl)-carbamic acid methyl ester (2.6 g, 5.8 mmol) in DMF (60 mL) was treated with NaH (60% dispersion in mineral oil, 256 mg, 6.4 mmol) in one portion. After 5 min, the mixture was treated with SEMCl (1.08 mL, 6.1 mmol) in 0.1 mL portions over 10 min. The reaction was stirred for 2 hours and diluted with saturated NH$_4$Cl solution (50 mL) and EtOAc (100 mL). The organic layer was washed with H$_2$O (3 50 mL) and brine (50 mL). The solution was dried over MgSO$_4$ and subjected to a 120 g SiO$_2$ COMBIFLASH column (0-100% EtOAc-hexanes gradient) to afford (1-{2-[5-(4-bromo-phenyl)-1-(2-trimethylsilanyl-ethoxymethyl)-1H-imidazol-2-yl]-pyrrolidine-1-carbonyl}-2-methyl-propyl)-carbamic acid methyl ester (2.4 g, 71%).

{1-[2-(5-{4-[4-(4-{2-[1-(2-Methoxycarbonylamino-3-methyl-butyryl)-pyrrolidin-2-yl]-(2-trimethylsilanyl-ethoxymethyl)-3H-imidazol-4-yl}-phenyl)-piperazin-1-yl]-phenyl}-1-(2-trimethylsilanyl-ethoxymethyl)-1H-imidazol-2-yl)-pyrrolidine-1-carbonyl]-2-methyl-propyl}-carbamic acid methyl ester (1-{2-[5-(4-Bromo-phenyl)-1-(2-trimethylsilanyl-ethoxymethyl)-1H-imidazol-2-yl]-pyrrolidine-1-carbonyl}-2-methyl-propyl)-carbamic acid methyl ester (222 mg, 0.38 mmol) and piperazine (17 mg, 0.19 mmol) in toluene (3.5 mL) were treated with Pd(OAc)$_2$ (2.1 mg, 0.0096 mmol, via 10% solution in toluene), BINAP (12 mg, 0.019 mmol), and NaOtBu (64 mg, 0.67 mmol). The mixture was stirred in a sealed tube at 120° C. for 4 hours. The solution was concentrated, diluted with EtOAc (50 mL), and washed with saturated NaHCO$_3$ (20 mL), H$_2$O (20 mL), and brine (20 mL). The solution was dried over MgSO$_4$ and subjected to a reverse phase HPLC column (5-95% MeCN—H$_2$O; 0.1% TFA modifier) to afford {1-[2-(5-{4-[4-(4-{2-[1-(2-methoxycarbonylamino-3-methyl-butyryl)-pyrrolidin-2-yl]-(2-trimethylsilanyl-ethoxymethyl)-3H-imidazol-4-yl}-phenyl)-piperazin-1-yl]-phenyl}-1-(2-trimethylsilanyl-ethoxymethyl)-1H-imidazol-2-yl)-pyrrolidine-1-carbonyl]-2-methyl-propyl}-carbamic acid methyl ester (8 mg, 4%): MS (ESI) m/z 1105 [M+Na]$^+$.

{1-[2-(5-{4-[4-(4-{2-[1-(2-Methoxycarbonylamino-3-methyl-butyryl)-pyrrolidin-2-yl]-3H-imidazol-4-yl}-phenyl)-piperazin-1-yl]-phenyl}-1H-imidazol-2-yl)-pyrrolidine-1-carbonyl]-2-methyl-propyl}-carbamic acid methyl ester {1-[2-(5-{4-[4-(4-{2-[1-(2-Methoxycarbonylamino-3-methyl-butyryl)-pyrrolidin-2-yl]-(2-trimethylsilanyl-ethoxymethyl)-3H-imidazol-4-yl}-phenyl)-piperazin-1-yl]-phenyl}-1-(2-trimethylsilanyl-ethoxymethyl)-1H-imidazol-2-yl)-pyrrolidine-1-carbonyl]-2-methyl-propyl}-carbamic acid methyl ester (8 mg, 0.007 mmol) in trifluoroacetic acid (1.0 mL) was stirred in a screw-cap vial at 40° C. for 1 hours. The solution was concentrated and subjected to a reverse phase HPLC column (5-95% MeCN—H$_2$O; 0.1% TFA modifier) to afford {1-[2-(5-{4-[4-(4-{2-[1-(2-methoxycarbonylamino-3-methyl-butyryl)-pyrrolidin-2-yl]-3H-imidazol-4-yl}-phenyl)-piperazin-1-yl]-phenyl}-1H-imidazol-2-yl)-pyrrolidine-1-carbonyl]-2-methyl-propyl}-carbamic acid methyl ester (1.9 mg, 32%) as a white solid (TFA salt): $^1$H NMR (CD$_3$OD, 300 MHz) 7.66 (s, 2H), 7.60 (d, J=8.7 Hz, 4H), 7.13 (d, J=8.7 Hz, 4H), 5.21 (app t, J=8.1 Hz, 2H), 4.22 (d, J=7.2 Hz, 2H), 4.09 (m, 2H), 3.85 (m, 2H), 3.66 (s, 6H), 3.31 (m, 5H), 2.52 (m, 2H), 2.16 (m, 8H), 0.91 (m, 12H); MS (ESI) m/z 824 [M+H]$^+$.

Example BN

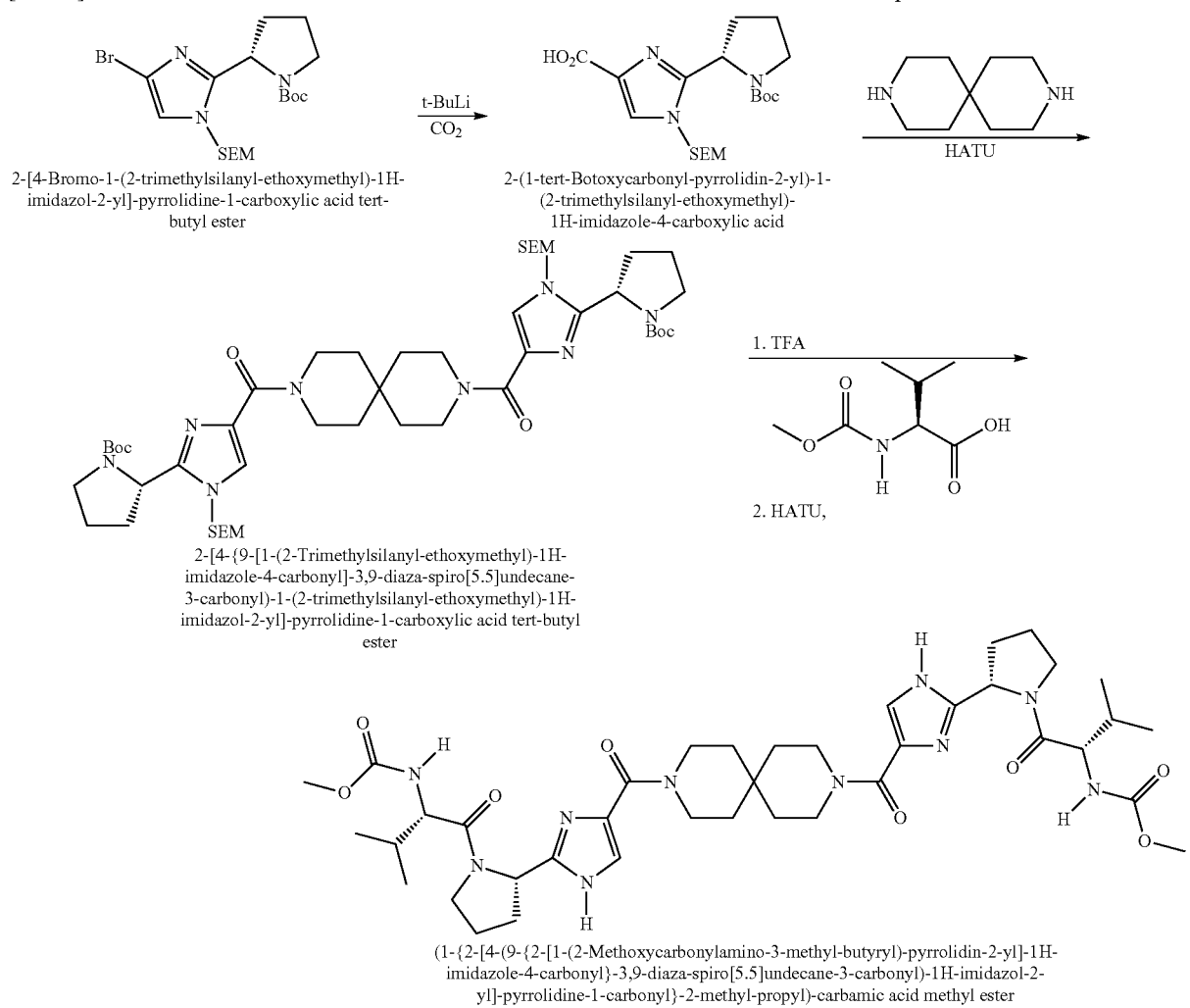

2-[4-Bromo-1-(2-trimethylsilanyl-ethoxymethyl)-1H-imidazol-2-yl]-pyrrolidine-1-carboxylic acid tert-butyl ester 2-(1-tert-Botoxycarbonyl-pyrrolidin-2-yl)-1-(2-trimethylsilanyl-ethoxymethyl)-1H-imidazole-4-carboxylic acid 2-[4-{9-[1-(2-Trimethylsilanyl-ethoxymethyl)-1H-imidazole-4-carbonyl]-3,9-diaza-spiro[5.5]undecane-3-carbonyl)-1-(2-trimethylsilanyl-ethoxymethyl)-1H-imidazol-2-yl]-pyrrolidine-1-carboxylic acid tert-butyl ester (1-{2-[4-(9-{2-[1-(2-Methoxycarbonylamino-3-methyl-butyryl)-pyrrolidin-2-yl]-1H-imidazole-4-carbonyl}-3,9-diaza-spiro[5.5]undecane-3-carbonyl)-1H-imidazol-2-yl]-pyrrolidine-1-carbonyl}-2-methyl-propyl)-carbamic acid methyl ester

2-(1-tert-Butoxycarbonyl-pyrrolidin-2-yl)-1-(2-trimethylsilanyl-ethoxymethyl)-1H-imidazole-4-carboxylic acid 2-[4-Bromo-1-(2-trimethylsilanyl-ethoxymethyl)-1H-imidazol-2-yl]-pyrrolidine-1-carboxylic acid tert-butyl ester (1.0 g, 2.2 mmol) in THF (10 mL) was cooled to −78° C. and treated with t-BuLi (1.7 M in pentane, 2.7 mL, 4.6 mmol). The reaction mixture was stirred for 1 hour and treated with solid $CO_2$ (500 mg). The mixture was warmed to ambient temperature and mixture was concentrated. The solution was dried over $MgSO_4$ and subjected to a 120 g $SiO_2$ COMBI-FLASH column (0-100% EtOAc-hexanes followed by 0-20% MeOH-EtOAc gradient) to afford 2-(1-tert-butoxycarbonyl-pyrrolidin-2-yl)-1-(2-trimethylsilanyl-ethoxymethyl)-1H-imidazole-4-carboxylic acid (200 mg, 22%): MS (ESI) m/z 412 $[M+H]^+$.

2-[4-{9-[1-(2-Trimethylsilanyl-ethoxymethyl)-1H-imidazole-4-carbonyl]-3,9-diaza-spiro[5.5]undecane-3-carbonyl}-1-(2-trimethylsilanyl-ethoxymethyl)-1H-imidazol-2-yl]-pyrrolidine-1-carboxylic acid tert-butyl ester 2-(1-tert-Butoxycarbonyl-pyrrolidin-2-yl)-1-(2-trimethylsilanyl-ethoxymethyl)-1H-imidazole-4-carboxylic acid (141 mg, 0.34 mmol) in DMF (1.0 mL) was treated with spiro-diamine (38 mg, 0.16 mmol), HATU (136 mg, 0.36 mmol), and N-methyl morpholine (0.90 mL, 0.82 mmol). The mixture was stirred for 2 hours then diluted with EtOAc (25 mL), and washed with saturated $NaHCO_3$ (3 10 mL), $H_2O$ (10 mL), and brine (10 mL) The solution was dried over $MgSO_4$ to afford crude 2-[4-{9-[1-(2-trimethylsilanyl-ethoxymethyl)-1H-imidazole-4-carbonyl]-3,9-diaza-spiro[5.5]undecane-3-carbonyl}-1-(2-trimethylsilanyl-ethoxymethyl)-1H-imidazol-2-yl]-pyrrolidine-1-carboxylic acid tert-butyl ester which was used without further purification: MS (ESI) m/z 941 $[M+H]^+$.

(1-{2-[4-(9-{2-[1-(2-Methoxycarbonylamino-3-methyl-butyryl)-pyrrolidin-2-yl]-1H-imidazole-4-carbonyl}-3,9-diaza-spiro[5.5]undecane-3-carbonyl)-1H-imidazol-2-yl]-pyrrolidine-1-carbonyl}-2-methyl-propyl)-carbamic acid methyl ester 2-[4-{9-[1-(2-Trimethylsilanyl-ethoxymethyl)-1H-imidazole-4-carbonyl]-3,9-diaza-spiro[5.5]undecane-3-carbonyl}-1-(2-trimethylsilanyl-ethoxymethyl)-1H-imidazol-2-yl]-pyrrolidine-1-carboxylic acid tert-butyl ester (153 mg, 0.17 mmol) in trifluoroacetic acid (3.0 mL) was stirred for 18 hours. The mixture was concentrated, suspended in DMF (1.7 mL), and treated with (S)-Moc-Val-OH (64 mg, 0.37 mmol), HATU (140 mg, 0.38 mmol), and N-methyl morpholine (185 mL, 1.66 mmol). The mixture was stirred for 2 hours then diluted with EtOAc (25 mL), and washed with saturated $NaHCO_3$ (3 10 mL), $H_2O$ (10 mL), and brine (10 mL). The solution was dried over $MgSO_4$ and subjected to a reverse phase HPLC column (5-95% MeCN—$H_2O$; 0.1% TFA modifier) to afford 1-{2-[4-(9-{2-[1-(2-methoxycarbonylamino-3-methyl-butyryl)-pyrrolidin-2-yl]-1H-imidazole-4-carbonyl}-3,9-diaza-spiro[5.5]undecane-3-carbonyl)-1H-imidazol-2-yl]-pyrrolidine-1-carbonyl}-2-methyl-propyl)-carbamic acid methyl ester (3.0 mg, 2%) as a white solid (TFA salt): $^1$H NMR ($CD_3OD$, 300 MHz) 7.77 (s, 2H), 5.18 (app t, J=6.9 Hz, 2H), 4.22 (d, J=7.2 Hz, 2H), 4.09 (m, 2H), 3.85 (m, 2H), 3.66 (s, 6H), 3.31 (m, 5H), 2.52 (m, 2H), 2.16 (m, 8H), 0.91 (m, 12H); MS (ESI) m/z 796 $[M+H]^+$.

Example BO

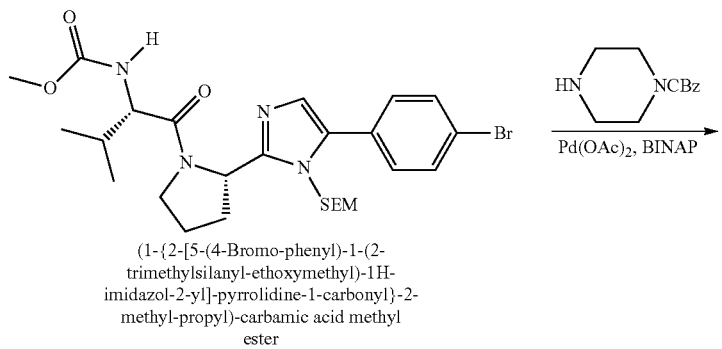

(1-{2-[5-(4-Bromo-phenyl)-1-(2-trimethylsilanyl-ethoxymethyl)-1H-imidazol-2-yl]-pyrrolidine-1-carbonyl}-2-methyl-propyl)-carbamic acid methyl ester

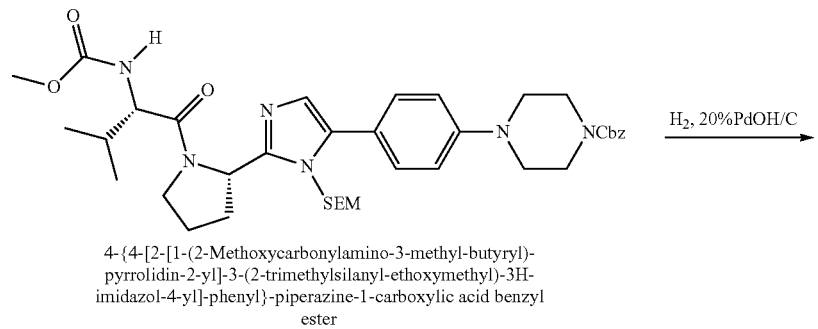

4-{4-[2-[1-(2-Methoxycarbonylamino-3-methyl-butyryl)-pyrrolidin-2-yl]-3-(2-trimethylsilanyl-ethoxymethyl)-3H-imidazol-4-yl]-phenyl}-piperazine-1-carboxylic acid benzyl ester -continued

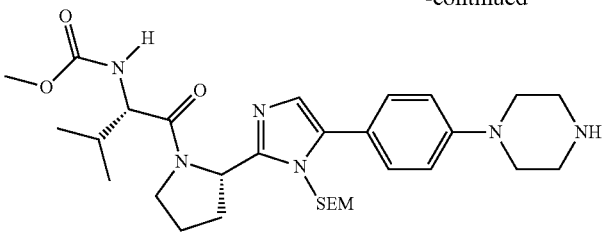

(2-Methyl-1-{2-[5-(4-piperazin-1-yl-phenyl)-
1-(2-trimethylsilanyl-ethoxymethyl)-
1H-imidazol-2-yl]-pyrrolidine-1-
carbonyl}-propyl)-carbamic acid methyl ester

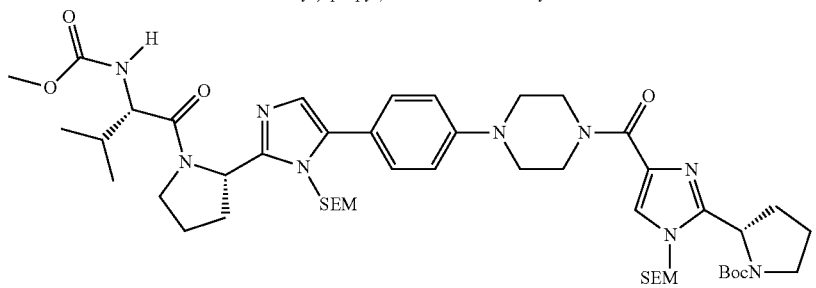

2-[4-[4-(4-{2-[1-(2-Methoxycarbonylamino-3-methyl-butyryl)-
pyrrolidin-2-yl]-3-methyl-3H-imidazol-4-yl}-phenyl)-piperazine-1-
carbonyl]-1-(2-trimethylsilanyl-ethoxymethyl)-1H-imidazol-2-yl]-
pyrrolidine-1-carboxylic acid tert-butyl ester

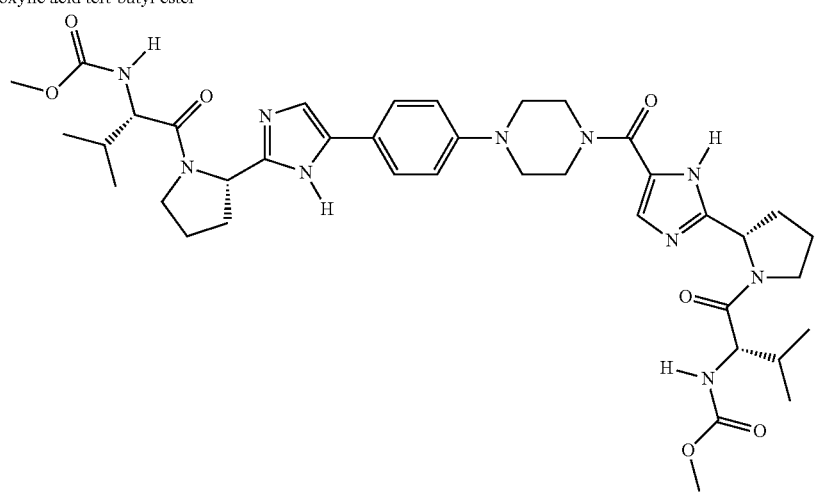

[1-(2-{5-[4-(4-{2-[1-(2-Methoxycarbonylamino-3-methyl-butyryl)-
pyrrolidin-2-yl]-3H-imidazole-4-carbonyl}-piperazin-1-yl)-phenyl]-
1H-imidazol-2-yl}-pyrrolidine-1-carbonyl)-2-methyl-propyl]-
carbamic acid methyl ester 4-{4-[2-[1-(2-Methoxycarbonylamino-3-methyl-
butyryl)-pyrrolidin-2-yl]-3-(2-trimethylsilanyl-
ethoxymethyl)-3H-imidazol-4-yl]-phenyl}-pipera-
zine-1-carboxylic acid benzyl ester (1-{2-[5-(4-Bromo-phenyl)-1-(2-trimethylsilanyl-ethoxymethyl)-1H-imidazol-2-yl]-pyrrolidine-1-carbonyl}-2-methyl-propyl)-carbamic acid methyl ester (1033 mg, 1.8 mmol) and 4-Cbz-piperazine (588 mg, 2.7 mmol) in toluene (9 mL) were treated with Pd(OAc)$_2$ (20 mg, 0.09 mmol), BINAP (110 mg, 0.1 mmol), and NaOtBu (428 mg, 4.45 mmol). The mixture was stirred in a sealed tube at 110° C. for 18 hours. The solution was concentrated, diluted with EtOAc (50 mL), and washed with saturated NaHCO$_3$ (20 mL), H$_2$O (20 mL), and brine (20 mL). The solution was dried over MgSO$_4$ and subjected to a 120 g SiO$_2$ COMBIFLASH column (0-100% EtOAc-hexanes gradient) to afford 4-{4-[2-[1-(2-methoxycarbonylamino-3-methyl-butyryl)-pyrrolidin-2-yl]-3-(2-trimethylsilanyl-ethoxymethyl)-3H-imidazol-4-yl]-phenyl}-piperazine-1-carboxylic acid benzyl ester (166 mg, 13%): MS (ESI) m/z 719 [M+H]$^+$.

(2-Methyl-1-{2-[5-(4-piperazin-1-yl-phenyl)-1-(2-trimethylsilanyl-ethoxymethyl)-1H-imidazol-2-yl]-pyrrolidine-1-carbonyl}-propyl)-carbamic acid methyl ester 4-{4-[2-[1-(2-Methoxycarbonylamino-3-methyl-butyryl)-pyrrolidin-2-yl]-3-(2-trimethylsilanyl-ethoxymethyl)-3H-imidazol-4-yl]-phenyl}-piperazine-1-carboxylic acid benzyl ester (166 mg, 0.23 mmol) in EtOH (2.5 mL) was treated with 20% PdOH/C (60 mg) and placed under an atmosphere of $H_2$. The reaction was stirred for 18 hours and filtered through a CELITE plug to afford crude (2-methyl-1-{2-[5-(4-piperazin-1-yl-phenyl)-1-(2-trimethylsilanyl-ethoxymethyl)-1H-imidazol-2-yl]-pyrrolidine-1-carbonyl}-propyl)-carbamic acid methyl ester (120 mg), which was used without further purification: MS (ESI) m/z 585 [M+H]$^+$.

2-[4-[4-(4-{2-[1-(2-Methoxycarbonylamino-3-methyl-butyryl)-pyrrolidin-2-yl]-3-methyl-3H-imidazol-4-yl}-phenyl)-piperazine-1-carbonyl]-1-(2-trimethylsilanyl-ethoxymethyl)-1H-imidazol-2-yl]-pyrrolidine-1-carboxylic acid tert-butyl ester (2-Methyl-1-{2-[5-(4-piperazin-1-yl-phenyl)-1-(2-trimethylsilanyl-ethoxymethyl)-1H-imidazol-2-yl]-pyrrolidine-1-carbonyl}-propyl)-carbamic acid methyl ester (28 mg, 0.047 mmol) and 2-(1-tert-butoxycarbonyl-pyrrolidin-2-yl)-1-(2-trimethylsilanyl-ethoxymethyl)-1H-imidazole-4-carboxylic acid (20 mg, 0.047 mmol) in DMF (1 mL) were treated with HATU (20 mg, 0.052 mmol) and N-methyl morpholine (0.26 mL, 0.23 mmol). The mixture was stirred for 18 hours then diluted with EtOAc (25 mL), and washed with saturated NaHCO$_3$ (3 10 mL), H$_2$O (10 mL), and brine (10 mL). The solution was dried over MgSO$_4$ to afford crude 2-[4-[4-(4-{2-[1-(2-methoxycarbonylamino-3-methyl-butyryl)-pyrrolidin-2-yl]-3-methyl-3H-imidazol-4-yl}-phenyl)-piperazine-1-carbonyl]-1-(2-trimethylsilanyl-ethoxymethyl)-1H-imidazol-2-yl]-pyrrolidine-1-carboxylic acid tert-butyl ester, which was used without further purification: MS (ESI) m/z 978 [M+H]$^+$.

[1-(2-{5-[4-(4-{2-[1-(2-Methoxycarbonylamino-3-methyl-butyryl)-pyrrolidin-2-yl]-3H-imidazole-4-carbonyl}-piperazin-1-yl)-phenyl]-1H-imidazol-2-yl}-pyrrolidine-1-carbonyl)-2-methyl-propyl]-carbamic acid methyl ester 2-[4-[4-(4-{2-[1-(2-Methoxycarbonylamino-3-methyl-butyryl)-pyrrolidin-2-yl]-3-methyl-3H-imidazol-4-yl}-phenyl)-piperazine-1-carbonyl]-1-(2-trimethylsilanyl-ethoxymethyl)-1H-imidazol-2-yl]-pyrrolidine-1-carboxylic acid tert-butyl ester (47 mg, 0.05 mmol) in trifluoroacetic acid (3.0 mL) was stirred for 18 hours. The mixture was concentrated, suspended in DMF (1.5 mL), and treated with (S)-Moc-Val-OH (9 mg, 0.0.053 mmol), HATU (20 mg, 0.0.053 mmol), and N-methyl morpholine (0.26 mL, 0.24 mmol). The mixture was stirred for 18 hours then diluted with EtOAc (25 mL), and washed with saturated NaHCO$_3$ (3 10 mL), H$_2$O (10 mL), and brine (10 mL). The solution was dried over MgSO$_4$ and subjected to a reverse phase HPLC column (5-95% MeCN—H$_2$O; 0.1% TFA modifier) to afford [1-(2-{5-[4-(4-{2-[1-(2-methoxycarbonylamino-3-methyl-butyryl)-pyrrolidin-2-yl]-3H-imidazole-4-carbonyl}-piperazin-1-yl)-phenyl]-1H-imidazol-2-yl}-pyrrolidine-1-carbonyl)-2-methyl-propyl]-carbamic acid methyl ester (6.6 mg, 18%) as a white solid (TFA salt): $^1$H NMR (CD$_3$OD, 300 MHz) 7.67 (s, 2H), 7.59 (d, J=8.7 Hz, 2H), 7.10 (d, J=9.3 Hz, 2H), 5.20 (app t, J=7.2 Hz, 2H), 4.22 (d, J=7.2 Hz, 2H), 4.01 (m, 5H), 3.85 (m, 2H), 3.66 (s, 6H), 3.38 (m, 2H), 2.52 (m, 2H), 2.16 (m, 8H), 0.91 (m, 12H); MS (ESI) m/z 775 [M+H]$^+$.

Example BP

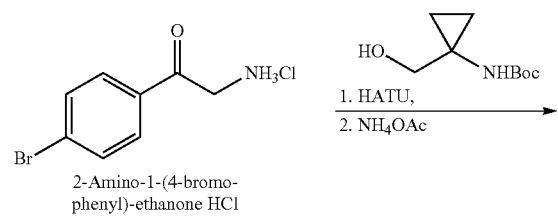

2-Amino-1-(4-bromo-phenyl)-ethanone HCl

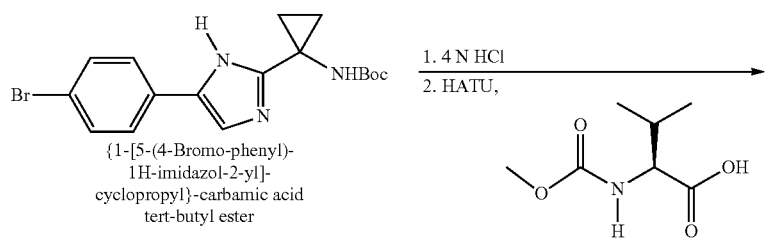

{1-[5-(4-Bromo-phenyl)-1H-imidazol-2-yl]-cyclopropyl}-carbamic acid tert-butyl ester

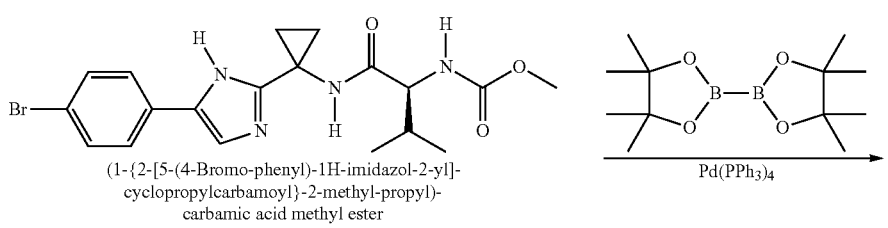

(1-{2-[5-(4-Bromo-phenyl)-1H-imidazol-2-yl]-cyclopropylcarbamoyl}-2-methyl-propyl)-carbamic acid methyl ester

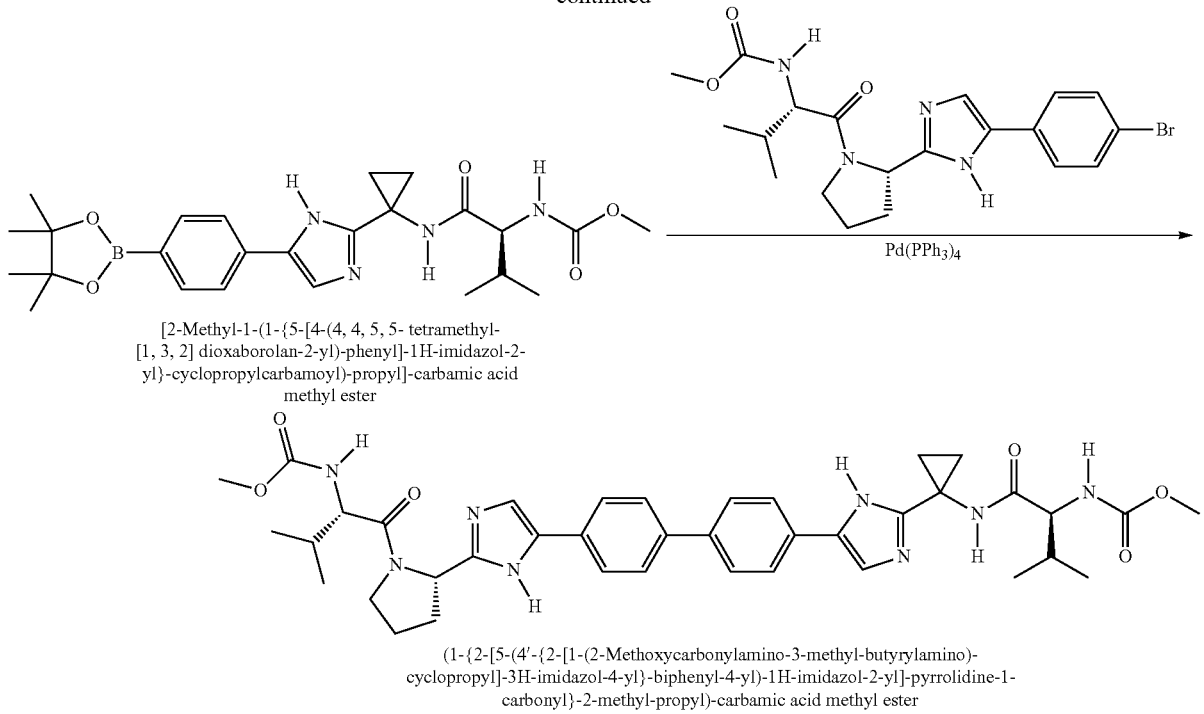

{1-[5-(4-Bromo-phenyl)-1H-imidazol-2-yl]-cyclopropyl}-carbamic acid tert-butyl ester 2-Amino-1-(4-bromo-phenyl)-ethanone HCl (2.5 g, 10 mmol) in DMF (30 mL) was treated with 1-tert-butoxycarbonylamino-cyclopropanecarboxylic acid (1.97 g, 9.8 mmol), HATU (4.02 g, 10.5 mmol), and DIPEA (5.6 mL, 31.1 mmol). The mixture was stirred for 18 hours and concentrated. The mixture was diluted with EtOAc (25 mL), and washed with saturated NaHCO$_3$ (3 10 mL), H$_2$O (10 mL), and brine (10 mL). The solution was dried over MgSO$_4$ and subjected to a 80 g SiO$_2$ COMBIFLASH column (0-100% EtOAc-hexanes gradient) to afford {1-[2-(4-bromo-phenyl)-2-oxo-ethylcarbamoyl]-cyclopropyl}-carbamic acid tert-butyl ester (3.49 g, 90%). This material (3.49 g, 8.8 mmol) in xylenes (20 mL) was treated with ammonium acetate (3.4 g, 44 mmol). The reaction was stirred at 130° C. in a sealed tube for 18 hours. The mixture was concentrated and suspended in dicholormethane (100 mL) and washed with saturated NaHCO$_3$ (50 mL). The solution was dried over MgSO$_4$ to afford crude {1-[5-(4-bromo-phenyl)-1H-imidazol-2-yl]-cyclopropyl}-carbamic acid tert-butyl ester, which was used without further purification: MS (ESI) m/z 379 [M+H]$^+$.

(1-{1-[5-(4-Bromo-phenyl)-1H-imidazol-2-yl]-cyclopropylcarbamoyl}-2-methyl-propyl)-carbamic acid methyl ester {1-[5-(4-Bromo-phenyl)-1H-imidazol-2-yl]-cyclopropyl}-carbamic acid tert-butyl ester (3.3 g, 8.77 mmol) was treated with 4 N HCl/dioxane (40 mL) and stirred for 2 hours. The mixture was concentrated and suspended in DMF (50 mL). The mixture was treated with (S)-Moc-Val-OH (1.69 g, 9.7 mmol), HATU (3.67 g, 9.7 mmol), and N-methyl morpholone (4.8 mL, 43.9 mmol). The mixture was stirred for 18 hours and concentrated. The mixture was diluted with EtOAc (100 mL), and washed with saturated NaHCO$_3$ (3 50 mL), H$_2$O (50 mL), and brine (50 mL). The solution was dried over MgSO$_4$ and subjected to a 120 g SiO$_2$ COMBIFLASH column (0-100% EtOAc-hexanes gradient) to afford (1-{1-[5-(4-bromo-phenyl)-1H-imidazol-2-yl]-cyclopropylcarbamoyl}-2-methyl-propyl)-carbamic acid methyl ester (3.37 g, 88%): MS (ESI) m/z 436 [M+H]$^+$.

[2-Methyl-1-(1-{5-[4-(4,4,5,5-tetramethyl-[1,3,2]dioxaborolan-2-yl)-phenyl]-1H-imidazol-2-yl}-cyclopropylcarbamoyl)-propyl]-carbamic acid methyl ester (1-{1-[5-(4-Bromo-phenyl)-1H-imidazol-2-yl]-cyclopropylcarbamoyl}-2-methyl-propyl)-carbamic acid methyl ester (1.38 g, 3.2 mmol) in 1,4-dioxane (25 mL) was treated with bis(pinacolato)diboron (1.69 g, 6.7 mmol), Pd(PPh$_3$)$_4$ (150 mg, 0.13 mmol), and KOAc (810 mg, 8.2 mmol). The mixture was stirred in a sealed tube at 80° C. for 18 hours. The mixture was filtered through a fritted glass funnel and concentrated. The mixture was then suspended in dichloromethane (10 mL) and filtered and subjected to a 120 g SiO$_2$ COMBIFLASH column (0-100% EtOAc-hexanes gradient) to afford [2-methyl-1-(1-{5-[4-(4,4,5,5-tetramethyl-[1,3,2]dioxaborolan-2-yl)-phenyl]-1H-imidazol-2-yl}-cyclopropylcarbamoyl)-propyl]-carbamic acid methyl ester (1.24 g, 81%): MS (ESI) m/z 483 [M+H]$^+$.

(1-{2-[5-(4'-{2-[1-(2-Methoxycarbonylamino-3-methyl-butyrylamino)-cyclopropyl]-3H-imidazol-4-yl}-biphenyl-4-yl)-1H-imidazol-2-yl]-pyrrolidine-1-carbonyl}-2-methyl-propyl)-carbamic acid methyl ester

[2-Methyl-1-(1-{5-[4-(4,4,5,5-tetramethyl-[1,3,2]dioxaborolan-2-yl)-phenyl]-1H-imidazol-2-yl}-cyclopropylcarbamoyl)-propyl]-carbamic acid methyl ester (85 mg, 0.21 mmol) and (1-{2-[5-(4-bromo-phenyl)-1H-imidazol-2-yl]- pyrrolidine-1-carbonyl}-2-methyl-propyl)-carbamic acid methyl ester (97 mg, 0.21 mmol) in 3:1 DME/H$_2$O (2.5 mL) were treated with Pd(PPh$_3$)$_4$ (10 mg, 0.0084 mmol) and K$_2$CO$_3$ (2 M solution, 0.42 mL, 0.84 mmol). The mixture was stirred in a sealed tube at 80° C. for 3 hours. The mixture was filtered through a fitted glass funnel and concentrated. The mixture was subjected to a reverse phase HPLC column (5-95% MeCN—H$_2$O; 0.1% TFA modifier) to afford (1-{2-[5-(4'-{2-[1-(2-methoxycarbonylamino-3-methyl-butyry-lamino)-cyclopropyl]-3H-imidazol-4-yl}-biphenyl-4-yl)-1H-imidazol-2-yl]-pyrrolidine-1-carbonyl}-2-methyl-propyl)-carbamic acid methyl ester (2.3 mg, 2%) as a white solid (TFA salt): $^1$H NMR (CD$_3$OD, 300 MHz) 7.93 (s, 2H), 7.84 (m, 4H), 5.20 (m, 1H), 4.23 (d, J=7.2 Hz, 2H), 4.01 (m, 2H), 3.83 (m, 4H), 3.70 (s, 3H), 3.66 (s, 3H), 3.38 (m, 2H), 2.57 (m, 2H), 2.18 (m, 4H), 2.04 (m, 4H), 1.75 (m, 4H), 1.58 (m, 4H), 0.95 (m, 12H); MS (ESI) m/z 725 [M+H]$^+$.

Example BQ

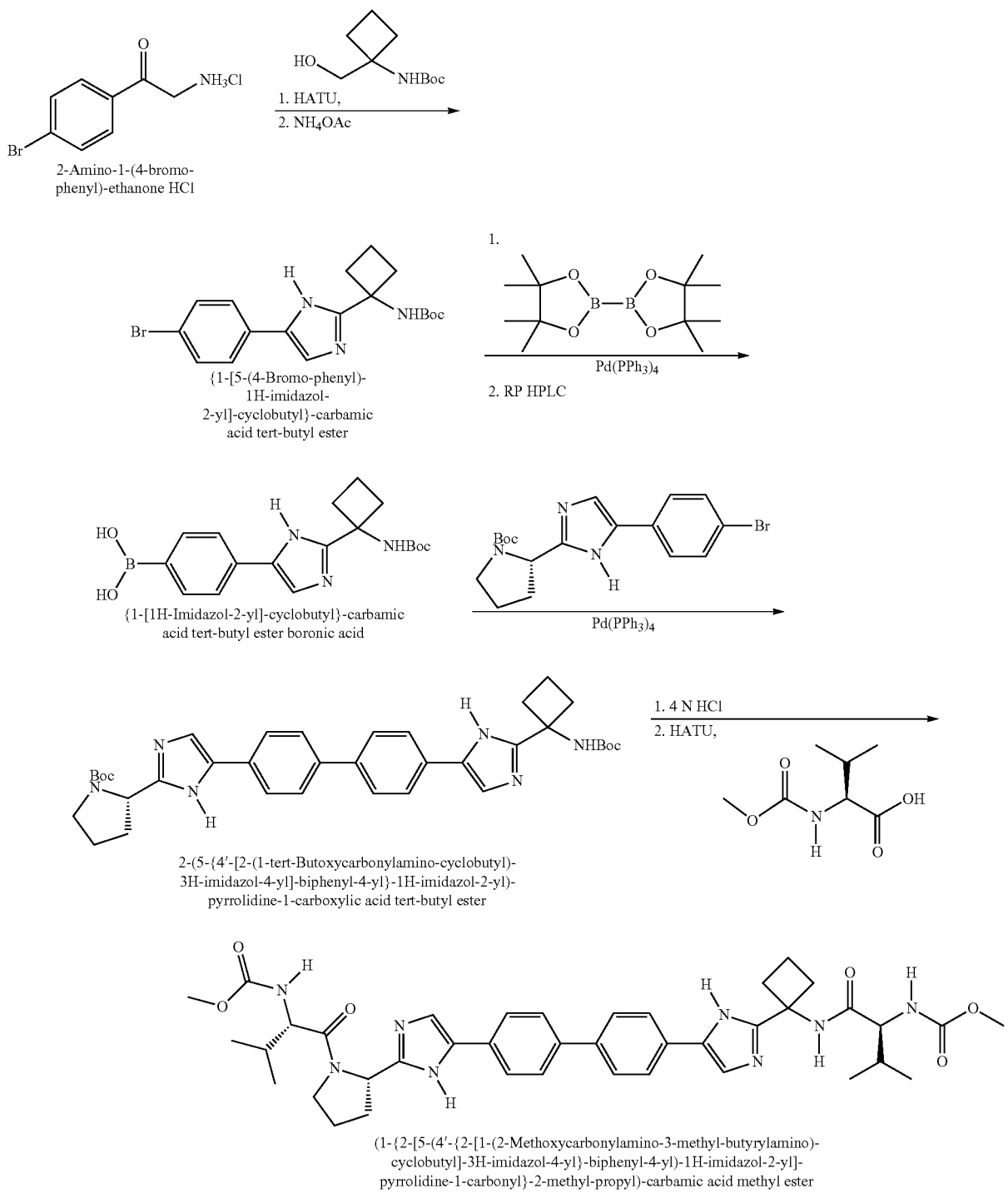

{1-[5-(4-Bromo-phenyl)-1H-imidazol-2-yl]-cyclobutyl}-carbamic acid tert-butyl ester 2-Amino-1-(4-bromo-phenyl)-ethanone HCl (5.8 g, 23 mmol) in DMF (75 mL) was treated with 1-tert-butoxycarbonylamino-cyclobutanecarboxylic acid (5.0 g, 23 mmol), HATU (9.7 g, 25 mmol), and DIPEA (12.9 mL, 34 mmol). The mixture was stirred for 18 hours and concentrated. The mixture was diluted with EtOAc (25 mL), and washed with saturated NaHCO$_3$ (3 10 mL), H$_2$O (10 mL), and brine (10 mL). The solution was dried over MgSO$_4$ to afford crude {1-[2-(4-bromo-phenyl)-2-oxo-ethylcarbamoyl]-cyclobutyl}-carbamic acid tert-butyl ester, which was used without further purification. This material (6.54 g, 16 mmol) in xylenes (40 mL) was treated with ammonium acetate (6.1 g, 80 mmol). The reaction was stirred at 130° C. in a sealed tube for 18 hours. The mixture was concentrated and suspended in dichlormethane (100 mL) and washed with saturated NaHCO$_3$ (50 mL). The solution was dried over MgSO$_4$ to afford crude {1-[5-(4-bromo-phenyl)-1H-imidazol-2-yl]-cyclobutyl}-carbamic acid tert-butyl ester, which was used without further purification: MS (ESI) m/z 393 [M+H]$^+$.

{1-[1H-Imidazol-2-yl]-cyclobutyl}-carbamic acid tert-butyl ester boronic acid {1-[5-(4-Bromo-phenyl)-1H-imidazol-2-yl]-cyclobutyl}-carbamic acid tert-butyl ester (110 mg, 0.28) in 1,4-dioxane (2.5 mL) was treated with bis(pinacolato)diboron (150 mg, 0.59 mmol), Pd(PPh$_3$)$_4$ (13 mg, 0.011 mmol), and KOAc (71 mg, 0.73 mmol). The mixture was stirred in a sealed tube at 80° C. for 18 hours. The mixture was filtered through a fritted glass funnel and concentrated. The mixture was subjected to a reverse phase HPLC column (5-95% MeCN—H$_2$O; 0.1% TFA modifier) to afford {1-[1H-imidazol-2-yl]-cyclobutyl}-carbamic acid tert-butyl ester boronic acid.

2-(5-{4'-[2-(1-tert-Butoxycarbonylamino-cyclobutyl)-3H-imidazol-4-yl]-biphenyl-4-yl}-1H-imidazol-2-yl)-pyrrolidine-1-carboxylic acid tert-butyl ester 1-[1H-Imidazol-2-yl]-cyclobutyl}-carbamic acid tert-butyl ester boronic acid (60 mg, 0.17 mmol) and 2-[5-(4-bromo-phenyl)-1H-imidazol-2-yl]-pyrrolidine-1-carboxylic acid tert-butyl ester (65 mg, 17 mmol) in 3:1 DME/H$_2$O (1.5 mL) were treated with Pd(PPh$_3$)$_4$ (10 mg, 0.0084 mmol) and K$_2$CO$_3$ (2 M solution, 0.25 mL, 0.50 mmol). The mixture was stirred in a sealed tube at 80° C. for 18 hours. The mixture was filtered through a fitted glass funnel and concentrated. The mixture was subjected to a reverse phase HPLC column (5-95% MeCN—H$_2$O; 0.1% TFA modifier) to afford 2-(5-{4'-[2-(1-tert-butoxycarbonylamino-cyclobutyl)-3H-imidazol-4-yl]-biphenyl-4-yl}-1H-imidazol-2-yl)-pyrrolidine-1-carboxylic acid tert-butyl ester (10 mg, 9%): MS (ESI) m/z 625 [M+H]$^+$.

(1-{2-[5-(4'-{2-[1-(2-Methoxycarbonylamino-3-methyl-butyrylamino)-cyclobutyl]-3H-imidazol-4-yl}-biphenyl-4-yl)-1H-imidazol-2-yl]-pyrrolidine-1-carbonyl}-2-methyl-propyl)-carbamic acid methyl ester 2-(5-{4'-[2-(1-tert-Butoxycarbonylamino-cyclobutyl)-3H-imidazol-4-yl]-biphenyl-4-yl}-1H-imidazol-2-yl)-pyrrolidine-1-carboxylic acid tert-butyl ester (9.8 mg, 0.016 mmol) was treated with 4 N HCl/dioxane (1.5 mL) and stirred for 4 hours. The mixture was concentrated and suspended in DMF (1.5 mL). The mixture was treated with (S)-Moc-Val-OH (6.0 mg, 0.032 mmol), HATU (13 mg, 0.034 mmol), and N-methyl morpholone (0.009 mL, 0.080 mmol). The mixture was stirred for 18 hours and concentrated. The mixture was subjected to a reverse phase HPLC column (5-95% MeCN—H$_2$O; 0.1% TFA modifier) to afford (1-{2-[5-(4'-{2-[1-(2-methoxycarbonylamino-3-methyl-butyrylamino)-cyclobutyl]-3H-imidazol-4-yl}-biphenyl-4-yl)-1H-imidazol-2-yl]-pyrrolidine-1-carbonyl}-2-methyl-propyl)-carbamic acid methyl ester (2.8 mg, 24%) as a white solid (TFA salt): $^1$H NMR (CD$_3$OD, 300 MHz) 7.88 (m, 10H), 5.20 (m, 1H), 4.23 (d, J=7.2 Hz, 1H), 4.12 (m, 1H), 3.88 (app d, J=7.2 Hz, 2H), 3.66 (s, 3H), 3.63 (s, 3H), 2.85 (br m, 2H), 2.65 (m, 4H), 2.09 (m, 10H), 0.95 (m, 12H); MS (ESI) m/z 739 [M+H]$^+$.

Example BR

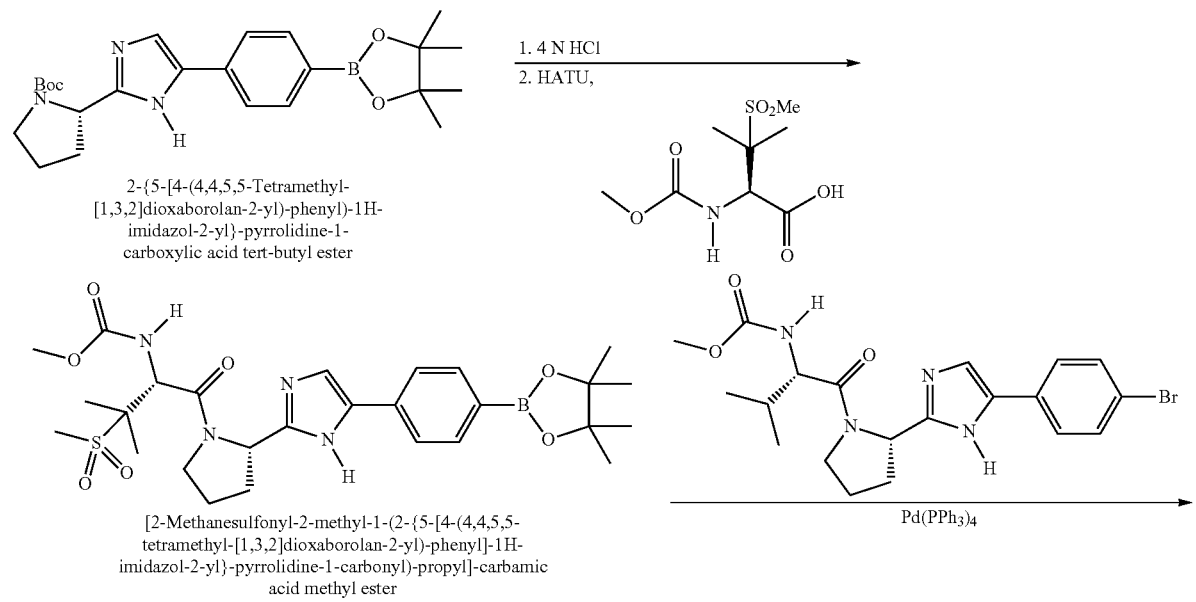

2-{5-[4-(4,4,5,5-Tetramethyl-[1,3,2]dioxaborolan-2-yl)-phenyl)-1H-imidazol-2-yl}-pyrrolidine-1-carboxylic acid tert-butyl ester

[2-Methanesulfonyl-2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester -continued

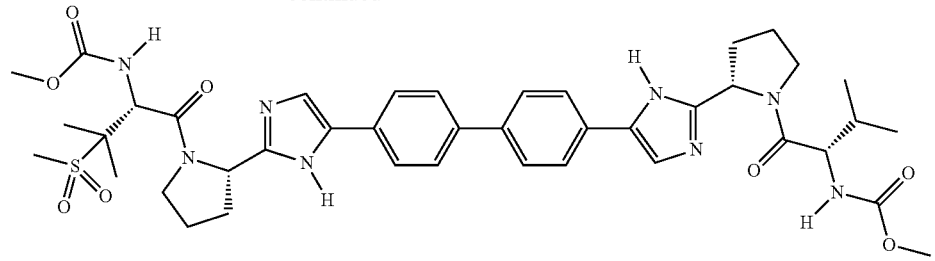

(2-Methanesulfonyl-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester

[2-Methanesulfonyl-2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (1.02 g, 1.73 mmol) was treated with 4 N HCl/dioxane (5 mL) and stirred for 4 hours. The mixture was concentrated and suspended in DMF (1.5 mL). The mixture was treated with (S)-Moc-3-methanesulfonyl-2-methoxycarbonylamino-3-methyl-butyric acid (460 mg, 1.82 mmol), HATU (772 mg, 2.03 mmol), and N-methyl morpholone (0.950 mL, 8.65 mmol). The mixture was stirred for 18 hours and concentrated. The mixture was diluted with EtOAc (100 mL), and washed with saturated NaHCO$_3$ (3 50 mL), H$_2$O (50 mL), and brine (50 mL). The solution was dried over MgSO$_4$ and subjected to a 40 g SiO$_2$ COMBIFLASH column (0-100% EtOAc-hexanes followed by 0-20% MeOH-EtOAc gradient) to afford [2-methanesulfonyl-2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (728 mg, 73%): MS (ESI) m/z 575 [M+H]$^+$.

(2-Methanesulfonyl-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester

[2-Methanesulfonyl-2-methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (700 mg, 1.22 mmol) and (1-{2-[5-(4-bromo-phenyl)-1H-imidazol-2-yl]-pyrrolidine-1-carbonyl}-2-methyl-propyl)-carbamic acid methyl ester (565 mg, 1.26 mmol) in 3:1 DME/H$_2$O (15 mL) were treated with Pd(PPh$_3$)$_4$ (56 mg, 0.0050 mmol) and NaHCO$_3$ (350 mg, 4.15 mmol). The mixture was stirred in a sealed tube at 80° C. for 24 hours. The mixture was filtered through a fritted glass funnel and concentrated. The mixture was subjected to a reverse phase HPLC column (5-95% MeCN—H$_2$O; 0.1% TFA modifier) to afford (2-methanesulfonyl-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester (150 mg, 15%) as a white solid (TFA salt): $^1$H NMR (CD$_3$OD, 300 MHz) 7.85 (m, 10H), 5.25 (m, 2H), 4.24 (d, J=7.5 Hz, 1H), 4.13 (m, 2H), 3.88 (app d, J=7.5 Hz, 2H), 3.71 (s, 3H), 3.66 (s, 3H), 2.99 (s, 3H), 2.57 (m, 2H), 2.16 (m, 10H), 1.81 (s, 3H), 1.79 (s, 1H), 0.93 (m, 6H); MS (ESI) m/z 818 [M+H]$^+$.

Example BS

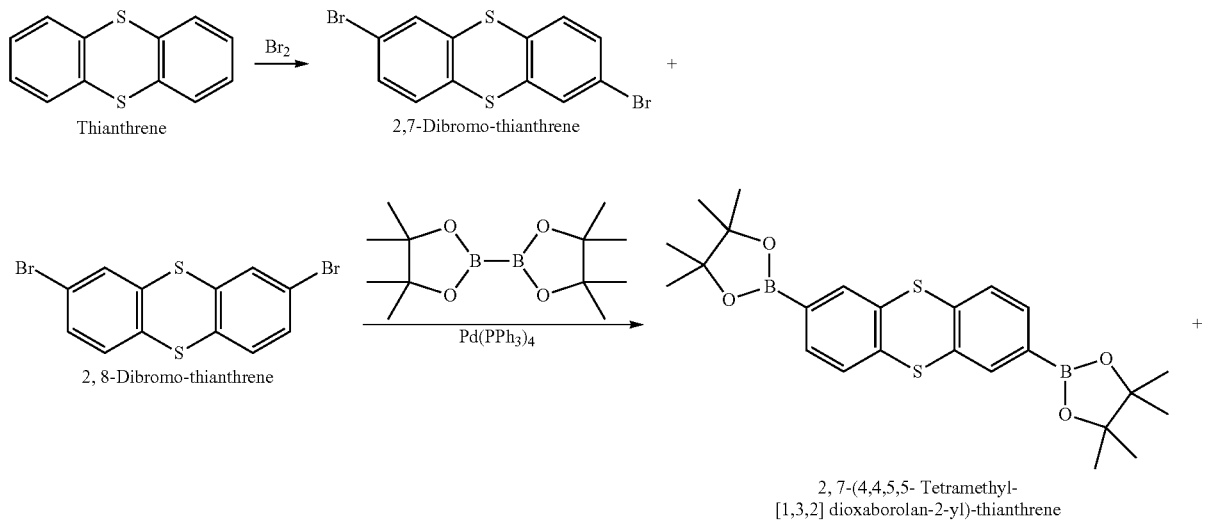

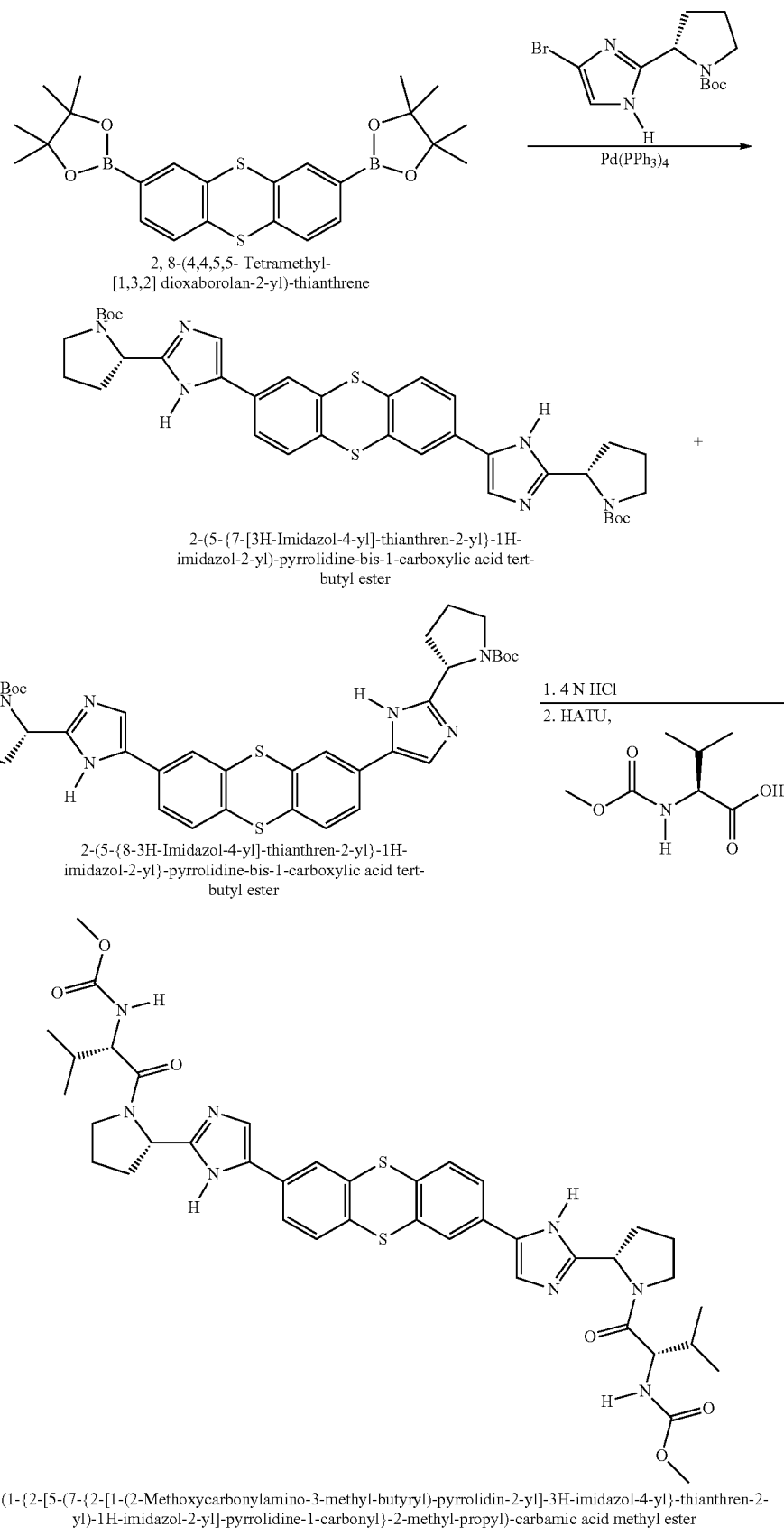

-continued

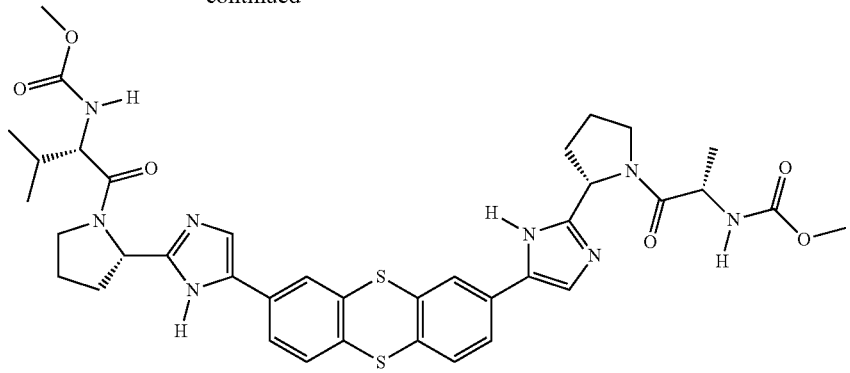

(1-{2-[5-(8-{2-[1-(2-Methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester 2,7-(4,4,5,5-Tetramethyl-[1,3,2]dioxaborolan-2-yl)-thianthrene and 2,8-(4,4,5,5-tetramethyl-[1,3,2]dioxaborolan-2-yl)-thianthrene Thianthrene (27 g, 125 mmol) in AcOH (150 mL) was treated with bromine (44 g, 275 mmol) and heated at 120° C. for 8 hours. The mixture was allowed to stand overnight at ambient temperature, at which time a white solid appeared. The solid was filtered, washed with $H_2O$ (3 50 mL) and air dried to afford a mixture of 2,7-dibromo-thianthrene and 2,8-dibromo-thianthrene which was carried forward without further purification (42 g). The 2,7-bibromo-thianthrene/2,8-dibromo-thianthrene mixture (1 g, 2.7 mmol) in DMSO (25 mL) was treated with bis(pinacolato)diboron (2.7 g, 10.7 mmol), $PdCl_2dppf$ (218 mg, 0.27 mmol), and KOAc (2.1 g, 21.4 mmol). The mixture was stirred in a sealed tube at 80° C. for 18 hours. The mixture was diluted with EtOAc (100 mL), and washed with saturated $NaHCO_3$ (3 50 mL), $H_2O$ (50 mL), and brine (50 mL). The solution was dried over $MgSO_4$ and subjected to a 40 g $SiO_2$ COMBIFLASH column (0-50% EtOAc-hexanes gradient) to afford a mixture of 2,7-(4,4,5,5-tetramethyl-[1,3,2]dioxaborolan-2-yl)-thianthrene and 2,8-(4,4,5,5-tetramethyl-[1,3,2]dioxaborolan-2-yl)-thianthrene (1.25 g, 99%): MS (ESI) m/z 796 $[M+H]^+$.

2-(5-{7-[3H-Imidazol-4-yl]-thianthren-2-yl}-1H-imidazol-2-yl)-pyrrolidine-bis-1-carboxylic acid tert-butyl ester and 2-(5-{8-3H-imidazol-4-yl]-thianthren-2-yl}-1H-imidazol-2-yl)-pyrrolidine-bis-1-carboxylic acid tert-butyl ester A mixture of 2,7-(4,4,5,5-Tetramethyl-[1,3,2]dioxaborolan-2-yl)-thianthrene and 2,8-(4,4,5,5-tetramethyl-[1,3,2]dioxaborolan-2-yl)-thianthrene (1.25 g, 2.67 mmol) and 2-(4-bromo-1H-imidazol-2-yl)-pyrrolidine-1-carboxylic acid tert-butyl ester (1.77 g, 5.6 mmol) in 3:1 DME/$H_2O$ (25 mL) were treated with $Pd(PPh_3)_4$ (185 mg, 0.160 mmol) and $NaHCO_3$ (1.12 g, 13.35 mmol). The mixture was stirred in a sealed tube at 90° C. for 24 hours. The mixture was filtered through a fitted glass funnel and concentrated. The mixture was diluted with EtOAc (100 mL), and washed with saturated $NaHCO_3$ (3 50 mL), $H_2O$ (50 mL), and brine (50 mL). The solution was dried over $MgSO_4$ and subjected to a 120 g $SiO_2$ COMBIFLASH column (0-50% EtOAc-hexanes gradient) to afford a mixture of 2-(5-{7-[3H-imidazol-4-yl]-thianthren-2-yl}-1H-imidazol-2-yl)-pyrrolidine-bis-1-carboxylic acid tert-butyl ester and 2-(5-{8-3H-imidazol-4-yl]-thianthren-2-yl}-1H-imidazol-2-yl)-pyrrolidine-bis-1-carboxylic acid tert-butyl ester.

(1-{2-[5-(7-{2-[1-(2-Methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester and (1-{2-[5-(8-{2-[1-(2-Methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester A mixture of 2-(5-{7-[3H-Imidazol-4-yl]-thianthren-2-yl}-1H-imidazol-2-yl)-pyrrolidine-bis-1-carboxylic acid tert-butyl ester and 2-(5-{8-3H-imidazol-4-yl]-thianthren-2-yl}-1H-imidazol-2-yl)-pyrrolidine-bis-1-carboxylic acid tert-butyl ester (150 mg, 0.22 mmol) was treated with 4 N HCl/dioxane (2.5 mL) and stirred for 4 hours. The mixture was concentrated and suspended in DMF (2.5 mL). The mixture was treated with (S)-Moc-Val-OH (84 mg, 0.48 mmol), HATU (191 mg, 0.50 mmol), and N-methyl morpholone (120 mL, 1.09 mmol). The mixture was stirred for 2 hours and concentrated. The mixture was diluted with EtOAc (100 mL), and washed with saturated $NaHCO_3$ (3 50 mL), $H_2O$ (50 mL), and brine (50 mL). The solution was dried over $MgSO_4$ and subjected to a 40 g $SiO_2$ COMBIFLASH column (0-100% EtOAc-hexanes followed by 0-20% MeOH-EtOAc gradient), which gave a pure mixture of 2,7/2,8 products. The 2,7/2,8 mixture was subjected to a reverse phase HPLC column (5-95% MeCN—$H_2O$; 0.1% TFA modifier) to afford (1-{2-[5-(7-{2-[1-(2-methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester (26 mg, 15%) as a white solid (TFA salt): $^1$H NMR (CD$_3$OD, 400 MHz) 7.88 (s, 2H), 7.80 (s, 2H), 7.63 (s, 4H), 5.20 (m, 2H), 4.23 (d, J=7.5 Hz, 2H), 4.13 (m, 2H), 3.88 (m, 2H), 3.72 (s, 6H), 2.99 (s, 3H), 2.52 (m, 2H), 2.16 (m, 10H), 0.95 (m, 12H); MS (ESI) m/z 818 $[M+H]^+$; and (1-{2-[5-(8-{2-[1-(2-methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester (10 mg, 5%) as a white solid (TFA salt): $^1$H NMR (CD$_3$OD, 400 MHz) 7.86 (s, 2H), 7.80 (s, 2H), 7.63 (s, 4H), 5.20 (m, 2H), 4.23 (d, J=7.5

Hz, 2H), 4.13 (m, 2H), 3.88 (m, 2H), 3.72 (s, 6H), 2.99 (s, 3H), 2.52 (m, 2H), 2.16 (m, 10H), 0.95 (m, 12H); MS (ESI) m/z 801 [M+H]$^+$.

Example BT

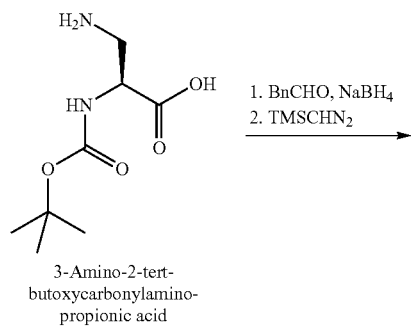

3-Amino-2-tert-butoxycarbonylamino-propionic acid

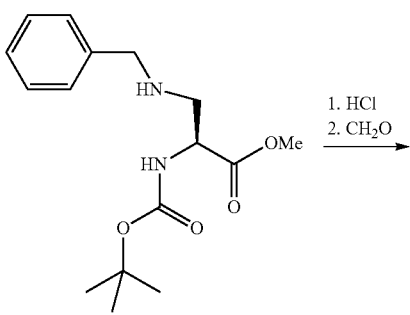

3-Benzylamino-2-tert-butoxycarbonylamino-propionic acid methyl ester

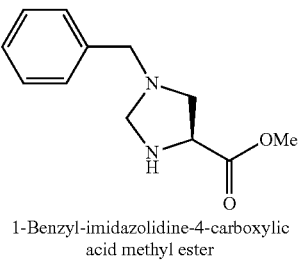

1-Benzyl-imidazolidine-4-carboxylic acid methyl ester

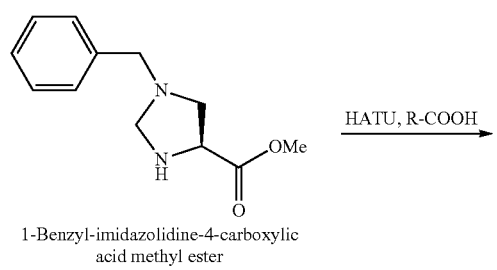

1-Benzyl-imidazolidine-4-carboxylic acid methyl ester

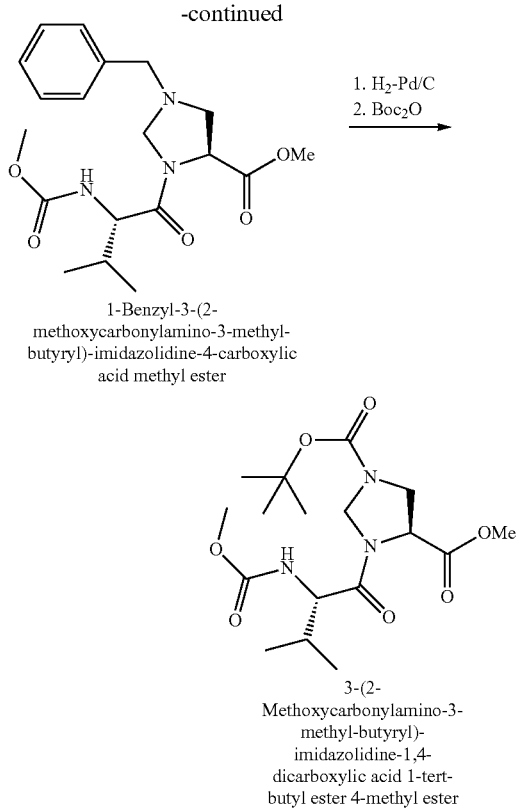

1-Benzyl-3-(2-methoxycarbonylamino-3-methyl-butyryl)-imidazolidine-4-carboxylic acid methyl ester 3-(2-Methoxycarbonylamino-3-methyl-butyryl)-imidazolidine-1,4-dicarboxylic acid 1-tert-butyl ester 4-methyl ester

3-Benzylamino-2-tert-butoxycarbonylamino-propionic acid methyl ester

3-Amino-2-tert-butoxycarbonylamino-propionic acid (5.0 g, 24.5 mmol) was suspended in methanol (100 mL) and benzaldehyde (5.2 g, 49 mmol) was added, followed by triethylamine (TEA, 10.2 mL, 73.5 mmol). The reaction mixture was stirred at ambient temperature for 90 minutes and cooled to 0° C. Solid sodium borohydride (2.78 g, 73.5 mmol) was added in small portions and the reaction was stirred for additional 60 minutes after addition was complete. All volatiles were removed in vacuo and the crude was dissolved in NaOHaq (0.1 M, 100 mL). The solution was washed with diethyl ether and acidified with HCl aq. The mixture was extracted with chloroform. The organic extracts were washed with brine and dried over sodium sulfate. Filtration and evaporation of solvents in vacuo yielded crude semi-solid (9.0 g). The crude material was dissolved in methanol (40 mL) and toluene (20 mL) and the solution was cooled to 0° C. Trimethysilyl diazomethane solution (2M, in hexanes) was added until the yellow color persisted (~25 mL). The reaction mixture was stirred for additional 60 minutes at room temperature. The volatiles were removed in vacuo and the crude product was purified via silica gel chromatography (eluent: EtOAc/hexanes) to yield the pure product 3-Benzylamino-2-tert-butoxycarbonylamino-propionic acid methyl ester (4.09 g): LCMS-ESI$^+$: calc'd for C$_{16}$H$_{24}$N$_2$O$_4$: 308.3 (M$^+$); Found: 309.2 (M+H$^+$).

1-Benzyl-imidazolidine-4-carboxylic acid methyl ester

3-Benzylamino-2-tert-butoxycarbonylamino-propionic acid methyl ester (4.01 g, 13.02 mmol) was dissolved in dichloromethane (20 mL) and HCl (4M Dioxane, 40 mL) was added. The resultant suspension was stirred at room temperature for 30 minutes, after which all volatiles were removed in vacuo. The crude material was mixed with para-formaldehyde (390 mg, 13.02 mmol), magnesium sulfate (2.6 g), potassium carbonate (2.6 g) and suspended in chloroform (40 mL). Triethylamine (5.07 mL) was added and the reaction was stirred at room temperature for 48 hours. The suspension was filtered and the volatiles were removed in vacuo. The crude material 1-Benzyl-imidazolidine-4-carboxylic acid methyl ester (3.5 g) was used in the next step without further analysis.

1-Benzyl-3-(2-methoxycarbonylamino-3-methyl-butyryl)-imidazolidine-4-carboxylic acid methyl ester Crude 1-Benzyl-imidazolidine-4-carboxylic acid methyl ester (3.0 g, 13.6 mmol) was added as a DMF suspension to a premixed solution of N-(methylcarbamoyl)(L)-valine (2.39 g, 13.6 mmol), HATU (5.16 g, 13.6 mmol) and diisopropyl ethylamine (DIEA, 3.58 g, 27.2 mmol) at room temperature. After 60 minutes, all volatiles were removed in vacuo and the crude material was taken into dichloromethane. The organic layer was washed with aqueous hydrochloric acid (0.1M), aqueous lithium chloride solution (5%), saturated aqueous sodium bicarbonate solution, brine and was dried over sodium sulfate. Filtration and evaporation of solvents yielded crude material. Purification via silica gel chromatography (eluent: EtOAc w MeOH 10%/hexanes) yielded the product 1-Benzyl-3-(2-methoxycarbonylamino-3-methyl-butyryl)-imidazolidine-4-carboxylic acid methyl ester (1.95 g, 5.15 mmol): LCMS-ESI$^+$: calc'd for $C_{19}H_{27}N_3O_5$: 377.4 (M$^+$); Found: 378.4 (M+H$^+$).

3-(2-Methoxycarbonylamino-3-methyl-butyryl)-imidazolidine-1,4-dicarboxylic acid 1-tert-butyl ester 4-methyl ester 1-Benzyl-3-(2-methoxycarbonylamino-3-methyl-butyryl)-imidazolidine-4-carboxylic acid methyl ester (1.0 g, 2.64 mmol) was dissolved in MeOH (30 mL) at room temperature. Pd on carbon (10%, 350 mg) was added and the reaction was stirred under an atmosphere of hydrogen. After three hours the reaction mixture was filtered through CELITE and the volatiles were removed in vacuo. The crude material was dissolved in tetrahydrofuran (10 mL) and Boc$_2$O (576 mg) and diiso-propyl ethylamine (340 mg) were added and the reaction was stirred at room temperature. After 60 minutes all volatiles were removed in vacuo and the crude material was purified via silica gel chromatography (eluent: EtOAc w10% MeOH/hexanes) and yielded the product (0.812 g): LCMS-ESI$^+$: calc'd for $C_{17}H_{29}N_3O_7$: 387.4 (M$^+$); Found: 388.4 (M+H$^+$).

Example BU

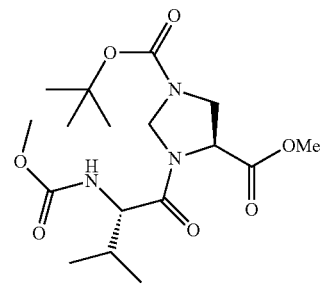

3-(2-Methoxycarbonylamino-3-methyl-butyryl)-imidazolidine-1,4-dicarboxylic acid 1-tert-butyl ester 4-methyl ester 1. LiOH
2. HATU, NH$_2$-R

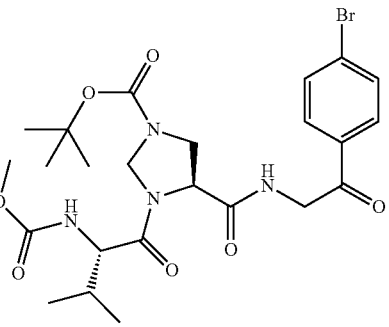

4-[2-(4-Bromo-phenyl)-2-oxo-ethylcarbamoyl]-3-(2-methoxycarbonylamino-3-methyl-butyryl)-imirazolidine-1-carboxylic acid tert-butyl ester

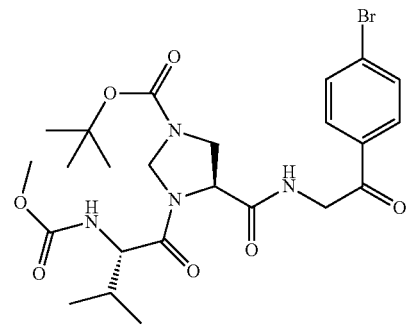

4-[2-(4-Bromo-phenyl)-2-oxo-ethylcarbamoyl]-3-(2-methoxycarbonylamino-3-methyl-butyryl)-imidazolidine-1-carboxylic acid tert-butyl ester NH$_4$OAc, m-Xyl
135° C.

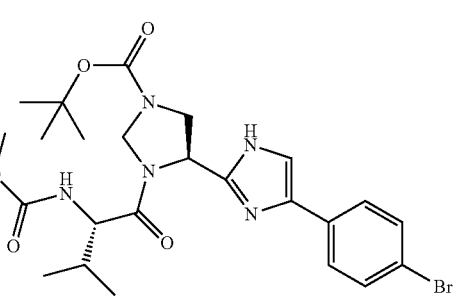

4-(4-Bromo-phenyl)-3'-(2-methoxycarbonylamino-3-methyl-butyryl)-2', 3',4', 5'-tetrahydro-1H-[2, 4']biimidazolyl-1'-carboxylic acid tert-butyl ester

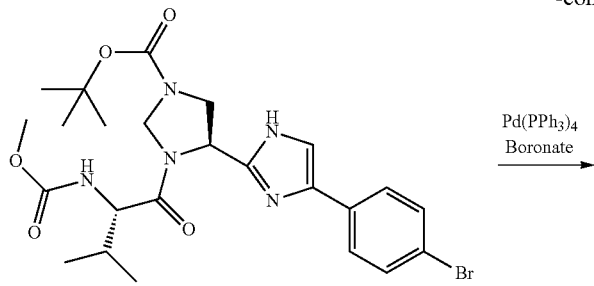

4-(4-Bromo-phenyl)-3'-(2-
methoxycarbonylamino-3-methyl-
butyryl)-2',3',4',5'-tetrahydro-1H-
[2,4']biimidazolyl-1'-carboxylic acid tert-
butyl ester Pd(PPh₃)₄
Boronate
→

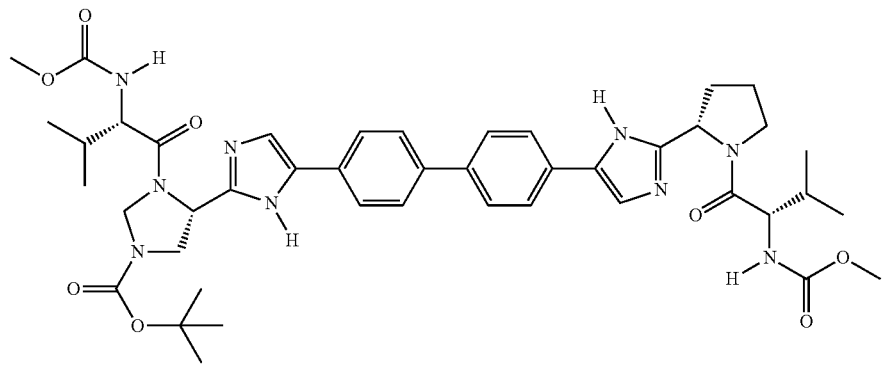

3'-(2-Methoxycarbonylamino-3-methyl-butyryl)-5-(4'-{2-
[1-(2-methoxycarbonylamino-3-methyl-butyryl)-
pyrrolidin-2-yl]-3H-imidazol-4-yl}-biphenyl-4-yl)-
2',3',4',5'-tetrahydro-1H-[2,4']biimidazolyl-1'-carboxylic
acid tert-butyl ester

4-[2-(4-Bromo-phenyl)-2-oxo-ethylcarbamoyl]-3-(2-methoxycarbonylamino-3-methyl-butyryl)-imidazolidine-1-carboxylic acid tert-butyl ester 3-(2-Methoxycarbonylamino-3-methyl-butyryl)-imidazolidine-1,4-dicarboxylic acid 1-tert-butyl ester 4-methyl ester (460 mg, 1.18 mmol) was dissolved in THF (3 mL) and MeOH (2 mL). An aqueous solution of LiOH (49.8 mg, 1.18 mmol) was added and stirring at room temperature was continued. After the hydrolysis was complete, the reaction was neutralized with aqueous HCl (1.18 mL, 1M). The organic solvents were removed in vacuo and the aqueous suspension was frozen and lyophilized. The crude material was used in the next step without further purification. The crude material was dissolved in DMF (4.0 mL) and HATU (448 mg, 1.18 mmol) and DIEA (152 mg, 1.18 mmol) were added. The reaction was stirred at room temperature for five minutes, after which the amino-(4' bromo) acetophenone hydrochloride salt (295 mg, 1.18 mmol) was added. Stirring at room temperature was continued. After 90 minutes, all volatiles were removed in vacuo and the crude material was purified via silica gel chromatography (eluent: EtOAc/hexanes) to yield the slightly impure product 4-[2-(4-Bromo-phenyl)-2-oxo-ethylcarbamoyl]-3-(2-methoxycarbonylamino-3-methyl-butyryl)-imidazolidine-1-carboxylic acid tert-butyl ester (723 mg): LCMS-ESI⁺: calc'd for $C_{24}H_{33}BrN_4O_7$: 569.4 (M⁺); Found: 570.4/572.4 (M+H⁺).

4-(4-Bromo-phenyl)-3'-(2-methoxycarbonylamino-3-methyl-butyryl)-2',3',4',5'-tetrahydro-1H-[2,4']biimidazolyl-1'-carboxylic acid tert-butyl ester 4-[2-(4-Bromo-phenyl)-2-oxo-ethylcarbamoyl]-3-(2-methoxycarbonylamino-3-methyl-butyryl)-imidazolidine-1-carboxylic acid tert-butyl ester (723 mg) was dissolved in m-xylenes (6.0 mL) and heated at 135° C. Solid ammonium acetate (500 mg, 6.48 mmol) was added and the reaction was stirred at 135° C. After 45 minutes, the reaction was cooled to room temperature and the volatiles were removed in vacuo. The crude material was purified via silica gel chromatography (eluent: EtOAc w 10% MeOH/hexanes) to yield the product 4-(4-Bromo-phenyl)-3'-(2-methoxycarbonylamino-3-methyl-butyryl)-2',3',4',5'-tetrahydro-1H-[2,4]biimidazolyl-1'-carboxylic acid tert-butyl ester (436 mg): LCMS-ESI⁺: calc'd for $C_{24}H_{32}BrN_5O_5$: 550.4 (M⁺); Found: 551.2/553.2 (M+H⁺).

3'-(2-Methoxycarbonylamino-3-methyl-butyryl)-5-(4'-{2-[1-(2-methoxycarbonylamino-3-methyl-butyryl)-pyrrolidin-2-yl]-3H-imidazol-4-yl}-biphenyl-4-yl)-2',3',4',5'-tetrahydro-1H-[2,4]biimidazolyl-1'-carboxylic acid tert-butyl ester 4-(4-Bromo-phenyl)-3'-(2-methoxycarbonylamino-3-methyl-butyryl)-2',3',4',5'-tetrahydro-1H-[2,4]biimidazolyl-1'-carboxylic acid tert-butyl ester (75 mg, 0.136 mmol) was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (67.6 mg, 0.136 mmol) under an argon atmosphere. Potassium carbonate (37.5 mg, 0.272 mmol) and Pd(PPh$_3$)$_4$ (15.7 mg, 0.014 mmol) were added, followed by DME (3 mL) and water (0.6 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product (55 mg): LCMS-ESI$^+$: calc'd for C$_{44}$H$_{57}$N$_9$O$_8$: 839.9 (M$^+$); Found: 840.5 (M+H$^+$); $^1$H-NMR: 300 MHz, (MeOH-d$_4$) δ: 7.90-7.81 (m, 10H), 5.58 (m, 1H), 5.43 (m, 1H), 5.25-5.20 (m, 2H), 4.24 (d, J=7.5 Hz, 1H), 4.11 (m, 1H), 3.99 (m, 1H), 3.86 (m, 2H), 3.67 (s, 3H), 3.66 (s, 3H), 3.46 (d, J=7.2 Hz, 1H), 2.59 (m, 1H), 2.22-2.10 (m, 5H), 1.53 & 1.44 (s, 9H) 1.04-0.89 (m, 12H).

Example BV (41.1 mg, 0.056 mmol) [prepared via reaction of 3'-(2-Methoxycarbonylamino-3-methyl-butyryl)-5-(4'-{2-[1-(2-methoxycarbonylamino-3-methyl-butyryl)-pyrrolidin-2-yl]-3H-imidazol-4-yl}-biphenyl-4-yl)-2',3',4',5'-tetrahydro-1H-[2, 4']biimidazolyl-1'-carboxylic acid tert-butyl ester with HCl-solution] in dichloromethane (5 mL). Methyl chloroformate (16.5 μL, 0.21 mmol) was added to the resulting solution. After 20 minutes the solvent was removed in vacuo. The residue was taken into tetrahydrofuran (4 mL) and methanol (2 mL) and an aqueous solution of sodium hydroxide (2 N, 1 mL) was added. After 2 hours the organic solvents were removed in vacuo and the aqueous phase was decanted. The residue was dissolved in dimethylformamide (2 mL) and purified via RP-HPLC (eluent: water/MeCN w 0.1% TFA). The product-containing fractions were combined and the solvent was removed by lyophilization to provide 3'-(2-Meth-

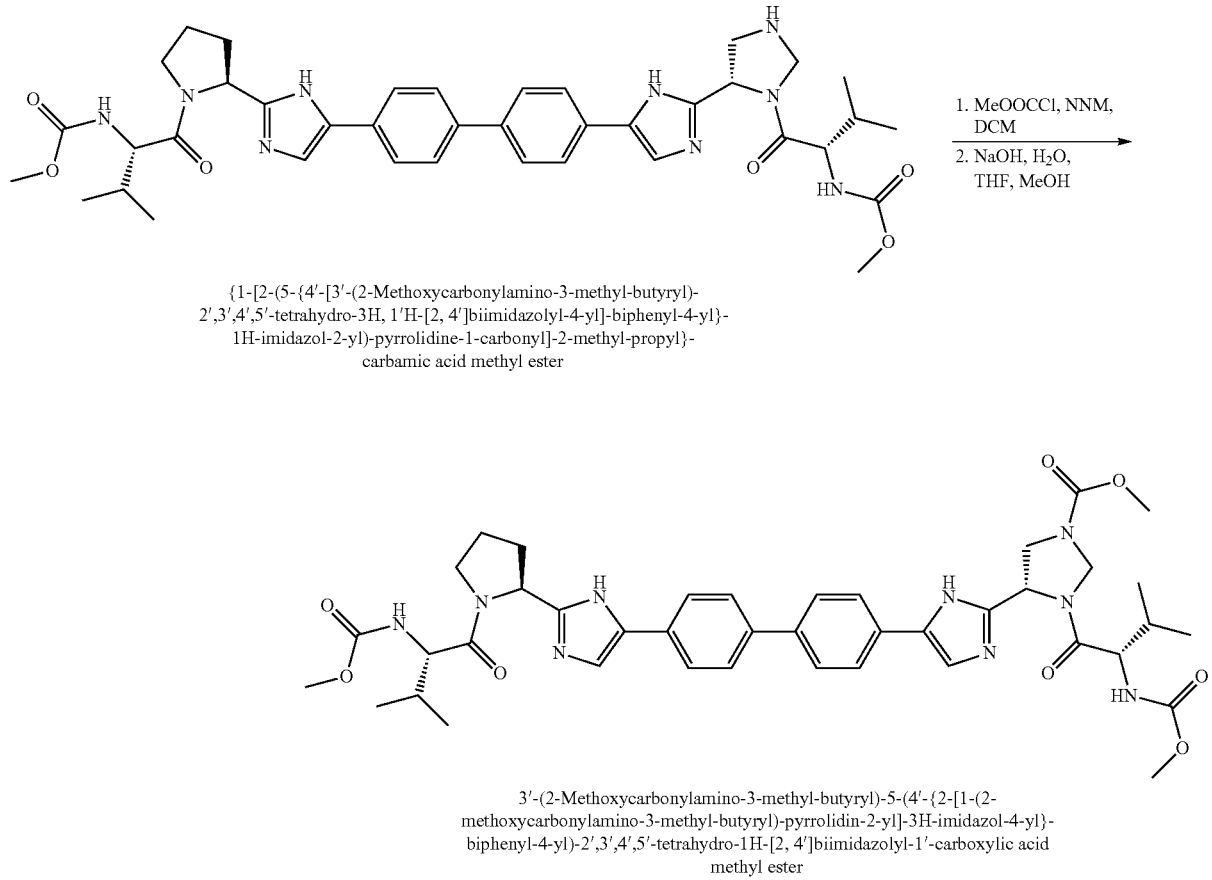 [SMILES: COC(=O)N[C@H](C(=O)N1CCC[C@H]1c1ncc(-c2ccc(-c3ccc(-c4cnc([C@@H]5CNCN5C(=O)[C@@H](NC(=O)OC)C(C)C)[nH]4)cc3)cc2)[nH]1)C(C)C ; COC(=O)N[C@H](C(=O)N1CCC[C@H]1c1ncc(-c2ccc(-c3ccc(-c4cnc([C@@H]5CN(C(=O)OC)CN5C(=O)[C@@H](NC(=O)OC)C(C)C)[nH]4)cc3)cc2)[nH]1)C(C)C]

{1-[2-(5-{4'-[3'-(2-Methoxycarbonylamino-3-methyl-butyryl)-2',3',4',5'-tetrahydro-3H, 1'H-[2, 4']biimidazolyl-4-yl]-biphenyl-4-yl}-1H-imidazol-2-yl)-pyrrolidine-1-carbonyl]-2-methyl-propyl}-carbamic acid methyl ester 3'-(2-Methoxycarbonylamino-3-methyl-butyryl)-5-(4'-{2-[1-(2-methoxycarbonylamino-3-methyl-butyryl)-pyrrolidin-2-yl]-3H-imidazol-4-yl}-biphenyl-4-yl)-2',3',4',5'-tetrahydro-1H-[2, 4']biimidazolyl-1'-carboxylic acid methyl ester 3'-(2-Methoxycarbonylamino-3-methyl-butyryl)-5-(4'-{2-[1-(2-methoxycarbonylamino-3-methyl-butyryl)-pyrrolidin-2-yl]-3H-imidazol-4-yl}-biphenyl-4-yl)-2',3',4',5'-tetrahydro-1H-[2,4']biimidazolyl-1'-carboxylic acid methyl ester 4-Methylmorpholine (31 μL, 0.28 mmol) was added to a suspension of {1-[2-(5-{4'-[3'-(2-Methoxycarbonylamino-3-methyl-butyryl)-2',3',4',5'-tetrahydro-3H,1'H-[2,4]biimidazolyl-4-yl]-biphenyl-4-yl}-1H-imidazol-2-yl)-pyrrolidine-1-carbonyl]-2-methyl-propyl}-carbamic acid methyl ester oxycarbonylamino-3-methyl-butyryl)-5-(4'-{2-[1-(2-methoxycarbonylamino-3-methyl-butyryl)-pyrrolidin-2-yl]-3H-imidazol-4-yl}-biphenyl-4-yl)-2',3',4',5'-tetrahydro-1H-[2, 4']biimidazolyl-1'-carboxylic acid methyl ester (7.5 mg) C$_{41}$H$_{51}$N$_9$O$_8$ calculated 797.4 observed [M+1]$^+$ 798.4; $^1$H (DMSO-d6): δ=8.08 (s, 1H), 7.83 (m, 8H), 7.58 (d, J=8.0 Hz, 1H), 7.29 (s, J=8.4 Hz, 1H), 5.42 (dd, J=7.6, 3.6 Hz, 1H), 5.26 (d, J=4.8 Hz, 1H), 5.18 (d, J=6.0 Hz, 1H), 5.10 (t, J=7.2 Hz, 1H), 4.88 (m, 1H), 4.08 (t, J=7.6 Hz, 2H), 3.94 (m, 1H), 3.82 (m, 4H), 3.65 (s, 3H), 3.52 (s, 3H), 3.51 (s, 3H), 2.36 (m, 1H), 2.01 (m, 5H), 0.83 (m, 12H).

Example BW

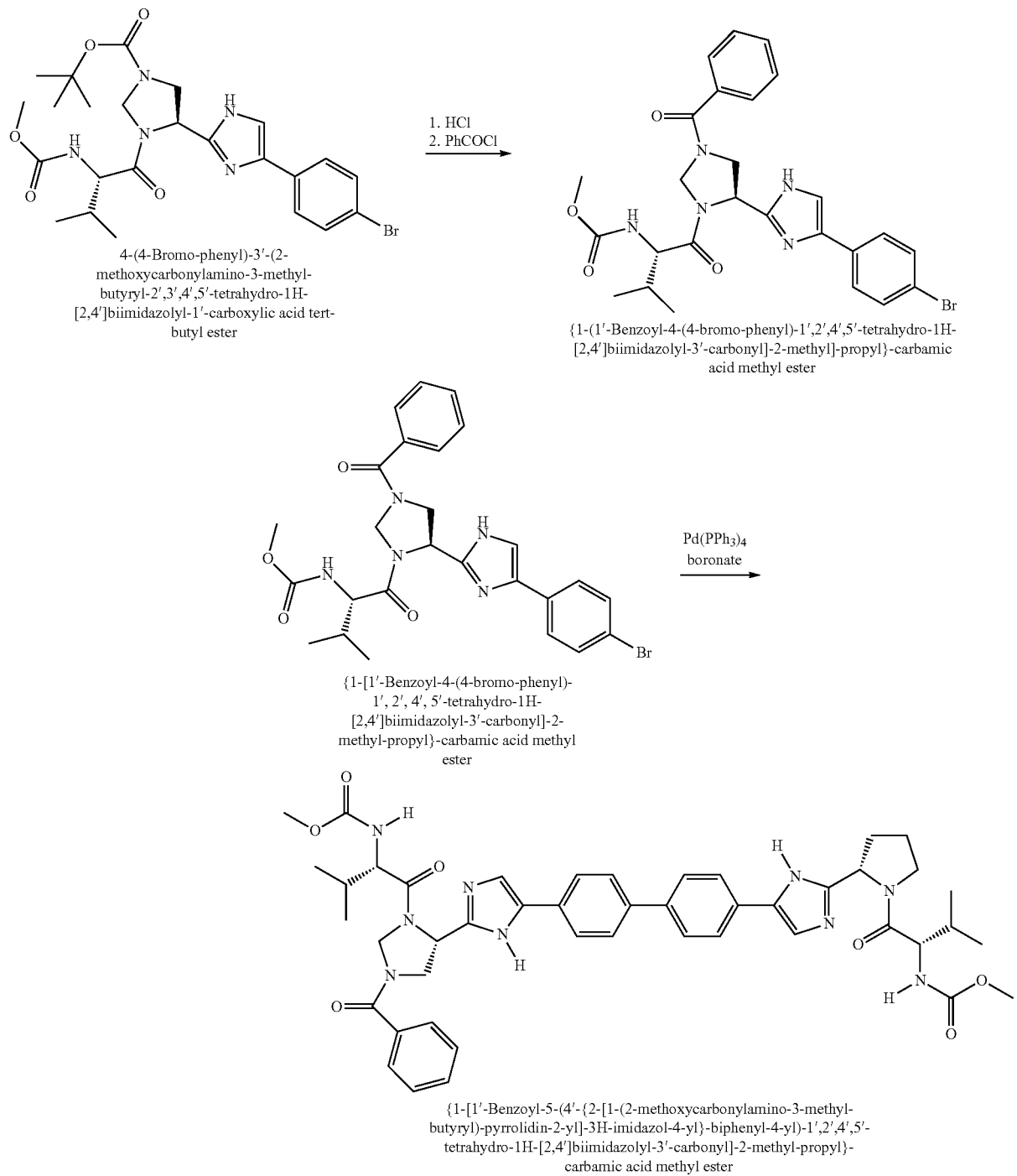

{1-[P-Benzoyl-4-(4-bromo-phenyl)-1',2',4',5'-tetrahydro-1H-[2,4']biimidazolyl-3'-carbonyl]-2-methyl-propyl}-carbamic acid methyl ester 4-(4-Bromo-phenyl)-3'-(2-methoxycarbonylamino-3-methyl-butyryl)-2',3',4',5'-tetrahydro-1H-[2,4]biimidazolyl-1'-carboxylic acid tert-butyl ester (55.6 mg, 0.101 mmol) was dissolved in dichloromethane (0.5 mL) and HCl (4M dioxane, 0.5 mL) was added. The resultant suspension was stirred at room temperature for 20 minutes, after which all volatiles were removed in vacuo. The crude material was dissolved in THF (1 mL) and diisopropyl ethylamine (26.0 mg, 0.202 mmol) was added, followed by benzoyl chloride (15.6 mg, 0.11 mmol). The reaction was stirred at room temperature. After 10 minutes, all starting material was consumed. All volatiles were removed in vacuo and the crude brown solid {1-[1'-Benzoyl-4-(4-bromo-phenyl)-1',2',4',5'-tetrahydro-1H-[2,4]biimidazolyl-3'-carbonyl]-2-methyl-propyl}-carbamic acid methyl ester was used in the coupling reaction without further analysis or purification: LCMS-ESI+: calc'd for $C_{26}H_{28}BrN_5O_4$: 554.4 (M+); Found: 554.3/556.4 (M+H+).

{1-[1'-Benzoyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-4H-[2,4']biimidazolyl-3'-carbonyl]-2-methyl-propyl}-carbamic acid methyl ester {1-[1'-Benzoyl-4-(4-bromo-phenyl)-1',2',4',5'-tetrahydro-1H-[2,4']biimidazolyl-3'-carbonyl]-2-methyl-propyl}-carbamic acid methyl ester (crude, <0.101 mmol) was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (45.1 mg, 0.091 mmol) under an argon atmosphere. Potassium carbonate (27.8 mg, 0.202 mmol) and Pd(PPh3)4 (10 mg, 0.009 mmol) were added, followed by DME (2.0 mL) and water (0.4 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product {1-[1'-Benzoyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4]biimidazolyl-3'-carbonyl]-2-methyl-propyl}-carbamic acid methyl ester (20.7 mg): LCMS-ESI+: calc'd for $C_{46}H_{53}N_9O_7$: 843.9 (M+); Found: 844.3 (M+H+); 1H-NMR: 300 MHz, (MeOH-d4) δ: 7.90-7.84 (m, 10H), 7.66-7.52 (m, 5H), 5.68 (m, 1H), 5.59 (m, 1H), 5.49 (m, 1H), 5.26 (m, 1H), 4.24 (d, J=7.5 Hz, 1H), 4.11 (m, 2H), 3.86 (m, 2H), 3.66 (s, 3H), 3.65 (s, 3H), 3.46 (d, J=5.7 Hz, 1H), 2.57 (m, 1H), 2.29-2.09 (m, 5H), 1.01-0.85 (m, 12H).

Example BX

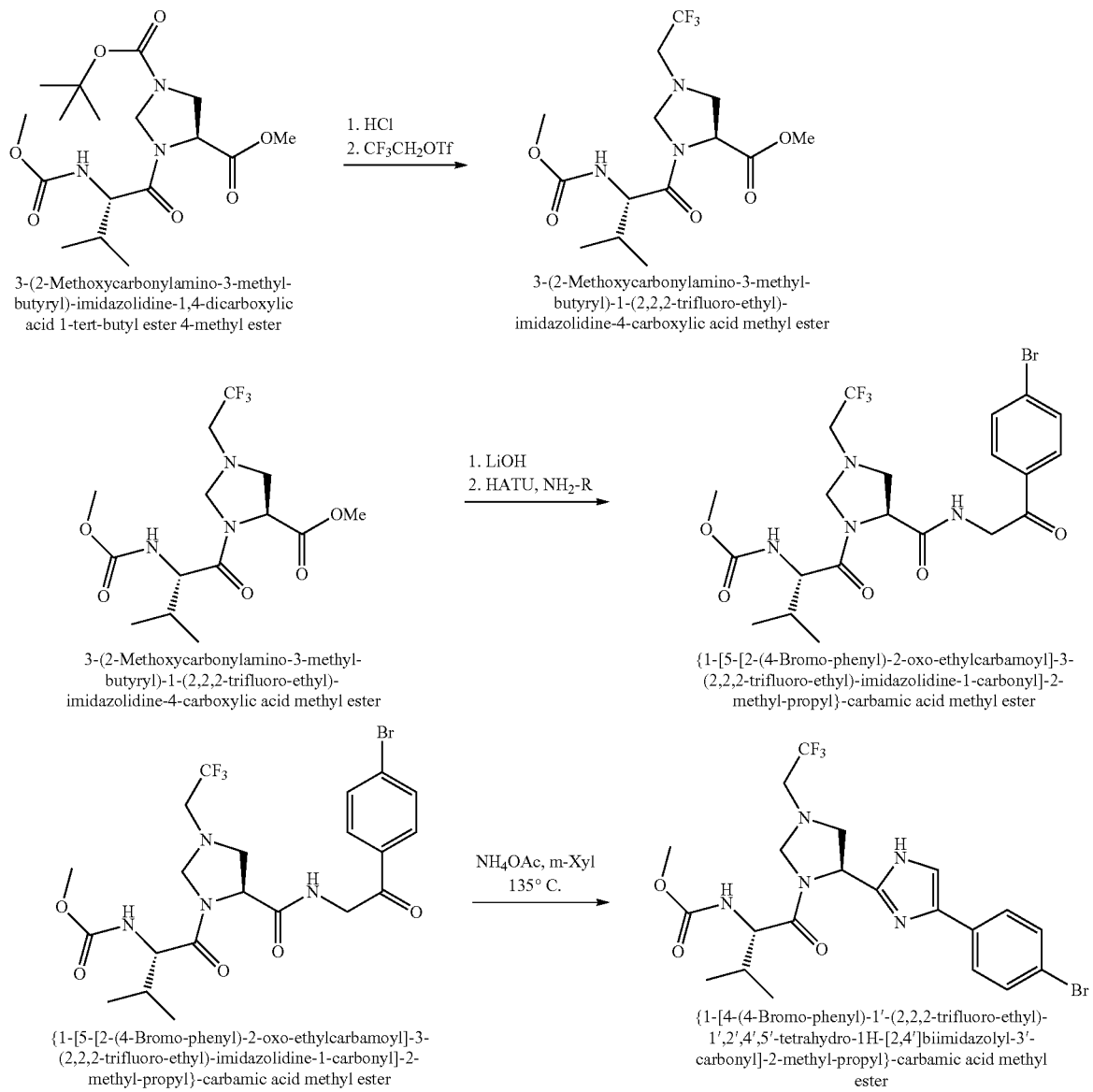

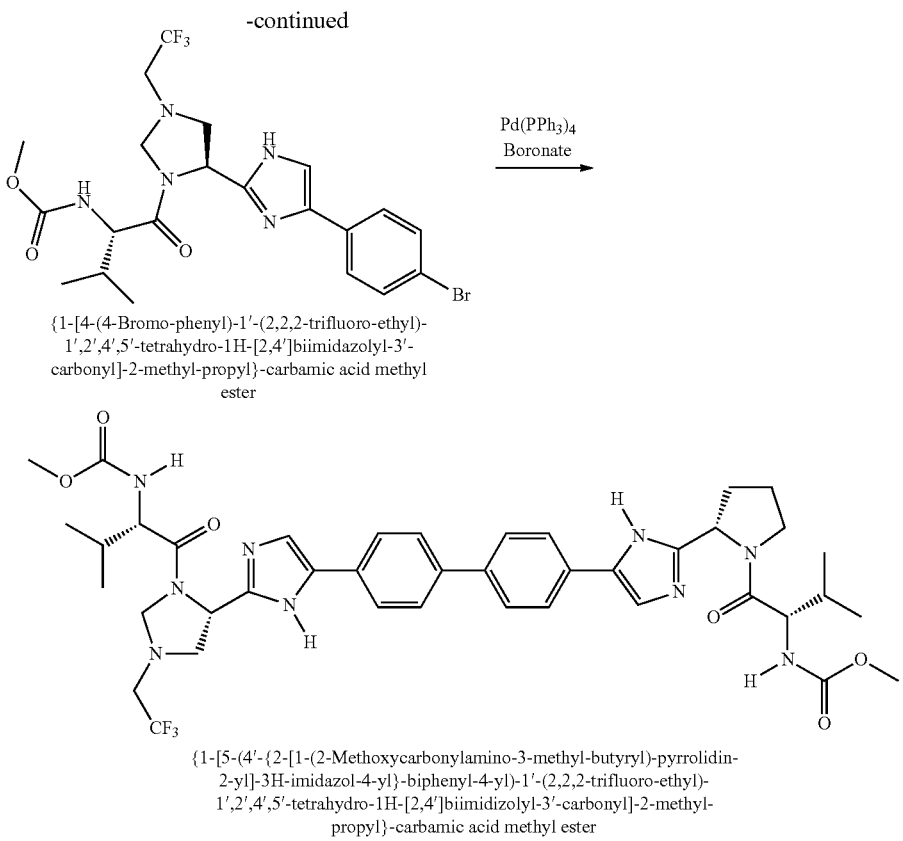

{1-[4-(4-Bromo-phenyl)-1'-(2,2,2-trifluoro-ethyl)-1',2',4',5'-tetrahydro-1H-[2,4']biimidazolyl-3'-carbonyl]-2-methyl-propyl}-carbamic acid methyl ester {1-[5-(4'-{2-[1-(2-Methoxycarbonylamino-3-methyl-butyryl)-pyrrolidin-2-yl]-3H-imidazol-4-yl}-biphenyl-4-yl)-1'-(2,2,2-trifluoro-ethyl)-1',2',4',5'-tetrahydro-1H-[2,4']biimidizolyl-3'-carbonyl]-2-methyl-propyl}-carbamic acid methyl ester

3-(2-Methoxycarbonylamino-3-methyl-butyryl)-1-(2,2,2-trifluoro-ethyl)-imidazolidine-4-carboxylic acid methyl ester 3-(2-Methoxycarbonylamino-3-methyl-butyryl)-imidazolidine-1,4-dicarboxylic acid 1-tert-butyl ester 4-methyl ester (160 mg, 0.412 mmol) was dissolved in dichloromethane (0.5 mL) and HCl (4M dioxane, 3 mL) was added. The resultant suspension was stirred at room temperature for 60 minutes, after which all volatiles were removed in vacuo. The crude material was dissolved in DMF (1.5 mL) and diisopropyl ethylamine (106 mg, 0.824 mmol) was added followed by trifluoroethyl triflate (114.7 mg, 0.494 mmol). After 14 hrs additional diisopropyl ethylamine (212 mg, 1.648 mmol) and trifluoroethyl triflate (229.4 mg, 0.988 mmol) were added. Stirring at room temperature was continued. After 40 hours, all volatiles were removed in vacuo and the crude material was purified by flash chromatography on silica gel (eluent: EtOAc/hexanes) to yield the product 3-(2-Methoxycarbonylamino-3-methyl-butyryl)-1-(2,2,2-trifluoro-ethyl)-imidazolidine-4-carboxylic acid methyl ester (95 mg, 0.257 mmol): LCMS-ESI$^+$: calc'd for $C_{14}H_{23}F_3N_3O_5$: 369.3 (M$^+$); Found: 369.9 (M$^+$).

{1-[5-[2-(4-Bromo-phenyl)-2-oxo-ethylcarbamoyl]-3-(2,2,2-trifluoro-ethyl)-imidazolidine-1-carbonyl]-2-methyl-propyl}-carbamic acid methyl ester 3-(2-Methoxycarbonylamino-3-methyl-butyryl)-1-(2,2,2-trifluoro-ethyl)-imidazolidine-4-carboxylic acid methyl ester (95 mg, 0.257 mmol) was dissolved in THF (1.8 mL) and MeOH (0.9 mL). An aqueous solution of LiOH (10.8 mg, 0.208 mmol) was added and stirring at room temperature was continued. After the hydrolysis was complete, the reaction was neutralized with aqueous HCl (1M). The organic solvents were removed in vacuo and the aqueous suspension was frozen and lyophilized. The crude material was used in the next step without further purification. The crude material was dissolved in DMF (1.5 mL) and HATU (97.6 mg, 0.257 mmol) and DIEA (66.3 mg, 0.514 mmol) were added. The reaction was stirred at room temperature for five minutes, after which the amino-(4' bromo) acetophenone hydrochloride salt (64.2 mg, 0.257 mmol) was added. Stirring at room temperature was continued. After 60 minutes, all volatiles were removed in vacuo and the crude material was purified via silica gel chromatography (eluent: EtOAc/hexanes) to yield the slightly impure product {1-[5-[2-(4-Bromo-phenyl)-2-oxo-ethylcarbamoyl]-3-(2,2,2-trifluoro-ethyl)-imidazolidine-1-carbonyl]-2-methyl-propyl}-carbamic acid methyl ester (148 mg): LCMS-ESI$^+$: calc'd for $C_{21}H_{26}BrF_3N_4O_5$: 551.3 (M$^+$); Found: 551.2/553.2 (M$^+$).

{1-[4-(4-Bromo-phenyl)-1'-(2,2,2-trifluoro-ethyl)-1',2',4',5'-tetrahydro-1H-[2,4]biimidazolyl-3'-carbonyl]-2-methyl-propyl}-carbamic acid methyl ester {1-[5-[2-(4-Bromo-phenyl)-2-oxo-ethylcarbamoyl]-3-(2,2,2-trifluoro-ethyl)-imidazolidine-1-carbonyl]-2-methyl-propyl}-carbamic acid methyl ester (148 mg, <257 mmol) was dissolved in m-xylenes (4.0 mL) and heated at 135° C. Solid ammonium acetate (150 mg, 1.9 mmol) was added and the reaction was stirred at 135° C. After 60 minutes, the reaction was cooled to room temperature and the volatiles were removed in vacuo. The crude material was purified via RP-HPLC (eluent: water/MeCN w 0.1% TFA) to yield the product {1-[4-(4-Bromo-phenyl)-1'-(2,2,2-trifluoro-ethyl)-

1',2',4',5'-tetrahydro-1H-[2,4]biimidazolyl-3'-carbonyl]-2-methyl-propyl}-carbamic acid methyl ester (15.1 mg) as the TFA salt: LCMS-ESI⁺: calc'd for $C_{21}H_{25}BrF_3N_5O_3$: 532.3 (M⁺); Found: 532.1/534.2 (M⁺).

{1-[5-(4'-{2-[1-(2-Methoxycarbonylamino-3-methyl-butyryl)-pyrrolidin-2-yl]-3H-imidazol-4-yl}-biphenyl-4-yl)-1'-(2,2,2-trifluoro-ethyl)-1',2',4',5'-tetrahydro-1H[2,4]biimidazolyl-3'-carbonyl]-2-methyl-propyl}-carbamic acid methyl ester {1-[4-(4-Bromo-phenyl)-1'-(2,2,2-trifluoro-ethyl)-1',2',4',5'-tetrahydro-1H-[2,4]biimidazolyl-3'-carbonyl]-2-methyl-propyl}-carbamic acid methyl ester (13.0 mg, 0.0244 mmol) was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (12.1 mg, 0.0244 mmol) under an argon atmosphere. Potassium carbonate (6.7 mg, 0.048 mmol) and Pd(PPh₃)₄ (2.7 mg, 0.0024 mmol) were added, followed by DME (2.0 mL) and water (0.4 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product {1-[5-(4'-{2-[1-(2-Methoxycarbonylamino-3-methyl-butyryl)-pyrrolidin-2-yl]-3H-imidazol-4-yl}-biphenyl-4-yl)-1'-(2,2,2-trifluoro-ethyl)-1',2',4',5'-tetrahydro-1H-[2,4]biimidazolyl-3'-carbonyl]-2-methyl-propyl}-carbamic acid methyl ester (6.1 mg, 0.006 mmol) as the TFA salt: LCMS-ESI⁺: calc'd for $C_{41}H_{50}F_3N_9O_6$: 821.8 (M⁺); Found: 823.4 (M+H⁺); ¹H-NMR: 300 MHz, (MeOH-$d_4$) δ: 7.89-7.82 (m, 10H), 5.39 (dd, J=6.3, 6.3 Hz, 1H), 5.25 (m, 1H), 4.78 (d, J=6.9 Hz, 1H), 4.24 (d, J=7.5 Hz, 1H), 4.10 (m, 1H), 4.00 (d, J=7.5 Hz, 1H), 3.88 (m, 1H), 3.67 (s, 3H), 3.66 (s, 3H), 3.65-3.43 (m, 4H), 2.58 (m, 1H), 2.29-2.01 (m, 5H), 1.03-0.89 (m, 12H).

Example BY

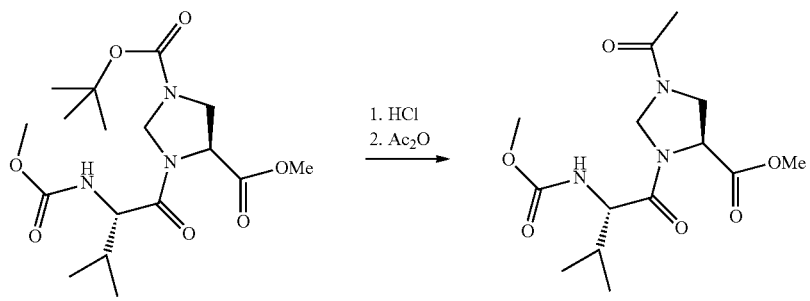

3-(2-Methoxycarbonylamino-3-methyl-butyryl)-imidazolidine-1,4-dicarboxylic acid 1-tert-butyl ester 4-methyl ester 1-Acetyl-3-(2-methoxycarbonylamino-3-methyl-butyryl)-imidazolidine-4-carboxylic acid methyl ester

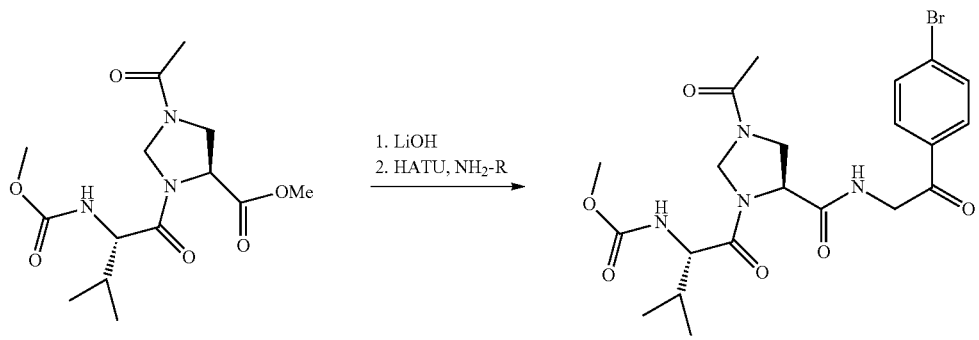

1-Acetyl-3-(2-methoxycarbonylamino-3-methyl-butyryl)-imidazolidine-4-carboxylic acid methyl ester (1-{3-Acetyl-5-[2-(4-bromo-phenyl)-2-oxo-ethylcarbamoyl]-imidazolidine-1-carbonyl}-2-methyl-propyl)-carbamic acid methyl ester

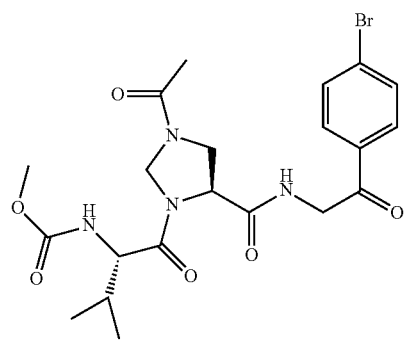

(1-{3-Acetyl-5-[2-(4-bromo-phenyl)-2-oxo-ethylcarbamoyl]-imidazolidine-1-carbonyl}-2-methyl-propyl)-carbamic acid methyl ester

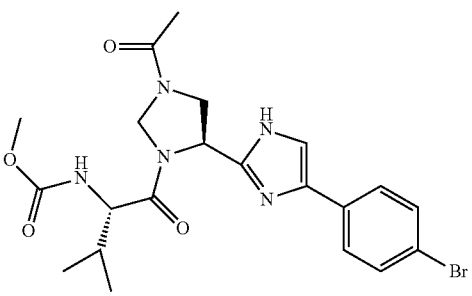

{1-[1'-Acetyl-4-(4-bromo-phenyl)-1',2',4',5'-tetrahydro-1H-[2,4']biimidazolyl-3'-carbonyl]-2-methyl-propyl}-carbamic acid methyl ester

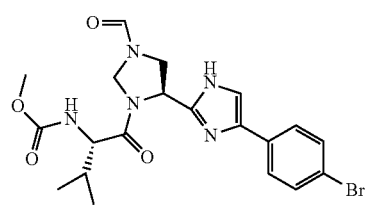

{1-[1'-Acetyl-4-(4-bromo-phenyl)-1',2',4',5'-tetrahydro-1H-[2,4']biimidazolyl-3'-carbonyl]-2-methyl-propyl}-carbamic acid methyl ester

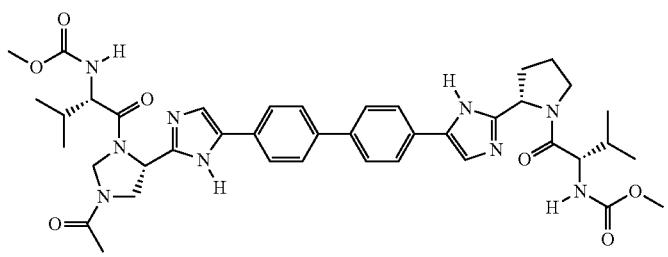

{1-[1'-Acetyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester 1-Acetyl-3-(2-methoxycarbonylamino-3-methyl-butyryl)-imidazolidine-4-carboxylic acid methyl ester 3-(2-Methoxycarbonylamino-3-methyl-butyryl)-imidazolidine-1,4-dicarboxylic acid 1-tert-butyl ester 4-methyl ester (465 mg, 1.2 mmol) was dissolved in dichloromethane (1 mL) and HCl (4M dioxane, 3 mL) was added. The resultant suspension was stirred at room temperature for 30 minutes, after which all volatiles were removed in vacuo. The crude material was dissolved in THF and diisopropyl ethylamine (154 mg, 1.2 mmol) was added, followed by acetic anhydride (122 mg, 1.2 mmol). The reaction was stirred at room temperature. After 30 minutes, all volatiles were removed in vacuo. The crude material was purified by silica gel chromatography (eluent: DCM/MeOH) to yield the product 1-Acetyl-3-(2-methoxycarbonylamino-3-methyl-butyryl)-imidazolidine-4-carboxylic acid methyl ester (273 mg, 0.829 mmol): LCMS-ESI$^+$: calc'd for $C_{14}H_{23}N_3O_6$: 329.4 (M$^+$); Found: 330.4 (M+H$^+$).

(1-{3-Acetyl-5-[2-(4-bromo-phenyl)-2-oxo-ethylcarbamoyl]-imidazolidine-1-carbonyl}-2-methyl-propyl)-carbamic acid methyl ester 1-Acetyl-3-(2-methoxycarbonylamino-3-methyl-butyryl)-imidazolidine-4-carboxylic acid methyl ester (273 mg, 0.829 mmol) was dissolved in THF (1.8 mL) and MeOH (1.2 mL). An aqueous solution of LiOH (34.8 mg, 0.829 mmol) was added and stirring at room temperature was continued. After the hydrolysis was complete, the reaction was neutralized with aqueous HCl (0.83 mL, 1M). The organic solvents were removed in vacuo and the aqueous suspension was frozen and lyophilized. The crude material was used in the next step without further purification. The crude material was dissolved in DMF (3 mL) and HATU (315 mg, 0.829 mmol) and DIEA (106 mg, 0.829 mmol) were added. The reaction was stirred at room temperature for five minutes, after which the amino-(4' bromo) acetophenone hydrochloride salt (207 mg, 0.829 mmol) was added. Stirring at room temperature was continued. After 120 minutes, all volatiles were removed in vacuo and the crude material was dissolved in DCM. The organic layer was washed with aqueous HCl (0.5 M), aqueous lithium chloride solution (5%), brine and was dried over sodium sulfate. Filtration and evaporation of solvents yielded crude product which was purified via silica gel chromatography (eluent EtOAc/hexanes) to yield the product (1-{3-Acetyl-5-[2-(4-bromo-phenyl)-2-oxo-ethylcarbamoyl]-imidazolidine-1-carbonyl}-2-methyl-propyl)-carbamic acid methyl ester (203 mg, 0.397 mmol): LCMS-ESI$^+$: calc'd for $C_{21}H_{27}BrN_4O_6$: 511.4 (M$^+$); Found: 511.3/513.2 (M+H$^+$).

{1-[1'-Acetyl-4-(4-bromo-phenyl)-1',2',4',5'-tetrahydro-1H-[2,4']biimidazolyl-3'-carbonyl]-2-methyl-propyl}-carbamic acid methyl ester (1-{3-Acetyl-5-[2-(4-bromo-phenyl)-2-oxo-ethylcarbamoyl]-imidazolidine-1-carbonyl}-2-methyl-propyl)-carbamic acid methyl ester (203 mg, 0.397 mmol) was dissolved in m-xylenes (4 mL) and heated at 135° C. Solid ammonium acetate (200 mg, 2.58 mmol) was added and the reaction was stirred at 135° C. After 120 minutes, the reaction was cooled to room temperature and the volatiles were removed in vacuo. The crude material was purified via silica gel chromatography (eluent: EtOAc w 10% MeOH/hexanes) to yield the product {1-[1'-Acetyl-4-(4-bromo-phenyl)-1',2',4',5'-tetrahydro-1H-[2,4]biimidazolyl-3'-carbonyl]-2-methyl-propyl}-carbamic acid methyl ester (162 mg, 0.329 mmol): LCMS-ESI+: calc'd for $C_{21}H_{26}BrN_5O_4$: 492.4 (M+); Found: 492.3/494.3 (M+H+).

{1-[1'-Acetyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4]biimidazolyl-3'-carbonyl]-2-methyl-propyl}-carbamic acid methyl ester {1-[1'-Acetyl-4-(4-bromo-phenyl)-1',2',4',5'-tetrahydro-1H-[2,4']biimidazolyl-3'-carbonyl]-2-methyl-propyl}-carbamic acid methyl ester (150 mg, 0.304 mmol) was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]carbamic acid methyl ester (151 mg, 0.304 mmol) under an argon atmosphere. Potassium carbonate (83.9 mg, 0.608 mmol) and Pd(PPh3)4 (34 mg, 0.030 mmol) were added, followed by DME (8 mL) and water (2 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product {1-[1'-Acetyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester (69.8 mg): LCMS-ESI+: calc'd for $C_{41}H_{51}N_9O_7$: 781.9 (M+); Found: 782.5 (M+H+); 1H-NMR: 300 MHz, (MeOH-d4) δ: 7.91-7.82 (m, 10H), 5.68 (m, 1H), 5.59-5.37 (m, 2H), 5.25 (m, 1H), 4.34 (m, 1H), 4.24 (d, J=7.5 Hz, 1H), 4.11-4.02 (m, 2H), 3.88 (m, 1H), 3.66 (s, 6H), 3.47 (d, J=7.2 Hz, 1H), 2.60 (m, 1H), 2.29-2.10 (m, 8H), 1.05-0.89 (m, 12H).

Example BZ

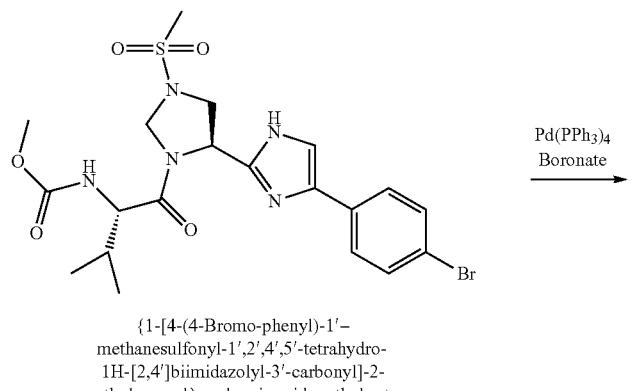

{1-[4-(4-Bromo-phenyl)-1'–methanesulfonyl-1',2',4',5'-tetrahydro-1H-[2,4']biimidazolyl-3'-carbonyl]-2-methyl-propyl}-carbamic acid methyl ester

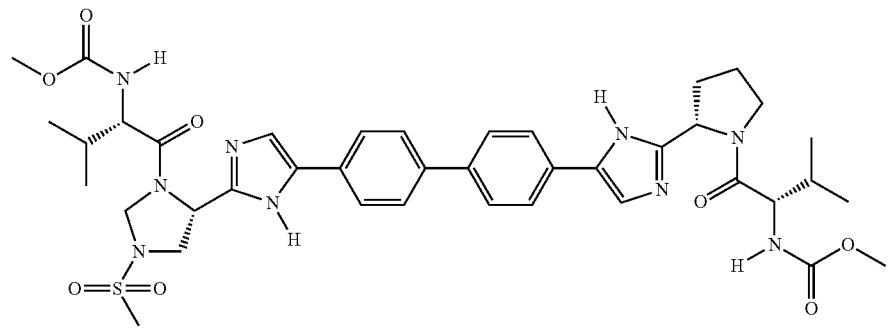

{1-[1'-Methanesulfonyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester {1-[1'-Methanesulfonyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester {1-[4-(4-Bromo-phenyl)-1'-methanesulfonyl-1',2',4',5'-tetrahydro-1H-[2,4']biimidazolyl-3'-carbonyl]-2-methyl-propyl}-carbamic acid methyl ester (62.9 mg, 0.119 mmol) [prepared as described for the synthesis of {1-[1'-Acetyl-4-(4-bromo-phenyl)-1',2',4',5'-tetrahydro-1H-[2,4]biimidazolyl-3'-carbonyl (Example BY)]-2-methyl-propyl}-carbamic acid methyl ester substituting the acetic anhydride with methyl sulfonyl chloride] was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (54.6 mg, 0.110 mmol) under an argon atmosphere. Potassium carbonate (33.1 mg, 0.240 mmol) and Pd(PPh$_3$)$_4$ (12.7 mg, 0.011 mmol) were added, followed by DME (2.0 mL) and water (0.4 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product (20.1 mg): LCMS-ESI$^+$: calc'd for C$_{40}$H$_{51}$N$_9$O$_8$S: 817.9 (M$^+$); Found: 818.6 (M+H$^+$); $^1$H-NMR: 300 MHz, (MeOH-d$_4$) δ: 7.90-7.81 (m, 10H), 5.69 (d, J=7.5 Hz, 1H), 5.48 (dd, J=6.9, 6.9 Hz, 1H), 5.27 (dd, J=8.1, 8.1 Hz, 1H), 5.17 (d, J=8.4 Hz, 1H), 4.41 (dd, J=12.0, 7.8 Hz, 1H), 4.24 (d, J=7.2 Hz, 1H), 4.11 (m, 2H), 4.00 (d, J=8.1 Hz, 1H), 3.87 (m, 2H), 3.67 (s, 3H), 3.66 (s, 3H), 3.17 (s, 3H), 2.57 (m, 1H), 2.29-1.99 (m, 5H), 1.03-0.89 (m, 12H).

Example CA

{1-[1'-Benzenesulfonyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester {1-[1'-Benzenesulfonyl-4-(4-bromo-phenyl)-1',2',4',5'-tetrahydro-1H-[2,4']biimidazolyl-3'-carbonyl]-2-methyl-propyl}-carbamic acid methyl ester (63.1 mg, 106.9 mmol) [prepared as described for the synthesis of {1-[1'-Acetyl-4-(4-bromo-phenyl)-1',2',4',5'-tetrahydro-1H-[2,4']biimidazolyl-3'-carbonyl]-2-methyl-propyl}-carbamic acid methyl ester (Example BY)] substituting the acetic anhydride with phenyl sulfonyl chloride] was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (53.1 mg, 106.9 mmol) under an argon atmosphere. Potassium carbonate (29.2 mg, 0.212 mmol) and Pd(PPh$_3$)$_4$ (12.2 mg, 0.0106 mmol) were added, followed by DME (2.5 mL) and water (0.8 mL). The mixture was heated under microwave conditions for 20 minutes at 120° C. All volatiles were removed in vacuo and the crude

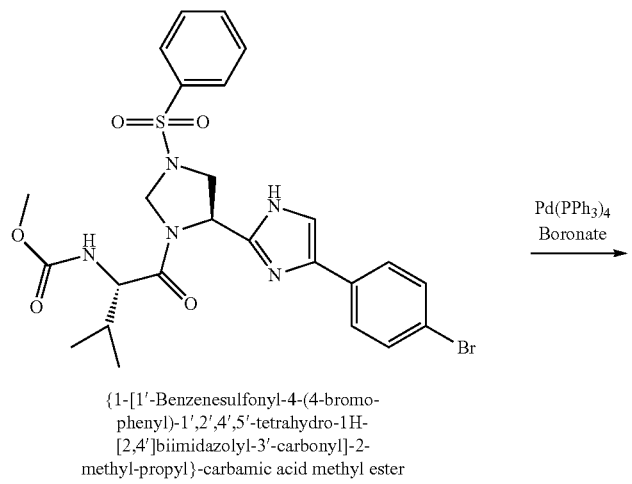

{1-[1'-Benzenesulfonyl-4-(4-bromo-phenyl)-1',2',4',5'-tetrahydro-1H-[2,4']biimidazolyl-3'-carbonyl]-2-methyl-propyl}-carbamic acid methyl ester Pd(PPh$_3$)$_4$
Boronate
→

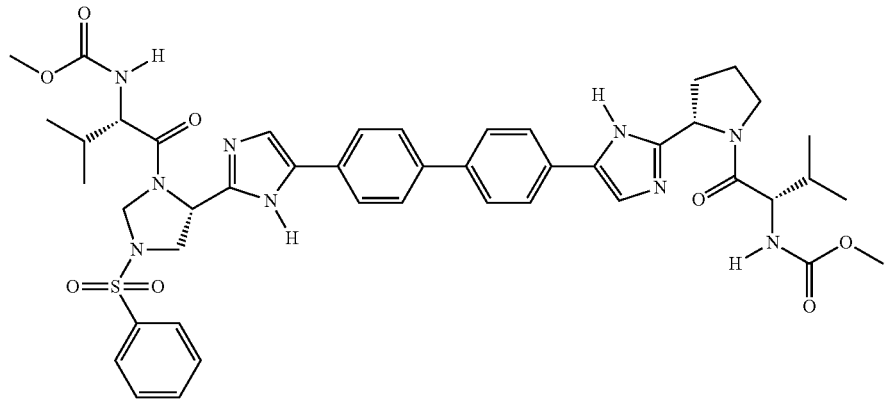

{1-[1'-Benzenesulfonyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4']biimidazolyl-3'-carbonyl]-2-methyl-propyl}-carbamic acid methyl ester material was dissolved in DMF and purified via RP-HPLC (eluent: water/MeCN w 0.1% TFA) to yield the product {1-[1'-Benzenesulfonyl-5-(4'-{2-[1-(2-methoxycarbonylamino-3-methyl-butyryl)-pyrrolidin-2-yl]-3H-imidazol-4-yl}-biphenyl-4-yl)-1',2',4',5'-tetrahydro-1H-[2,4]biimidazolyl-3'-carbonyl]-2-methyl-propyl}-carbamic acid methyl ester (27.9 mg): LCMS-ESI+: calc'd for $C_{45}H_{53}N_9O_8S$: 880.2 (M+); Found: 881.5 (M+H+); 1H-NMR: 300 MHz, (MeOH-$d_4$) δ: 8.01 (d, J=7.5 Hz, 2H), 7.90-7.76 (m, 11H), 7.65 (t, J=7.8 Hz, 2H), 5.59 (d, J=8.7 Hz, 1H), 5.25 (dd, J=7.5, 7.5 Hz, 1H), 5.19 (d, J=8.7 Hz, 1H), 4.67 (dd, J=7.5, 7.5 Hz, 1H), 4.32-4.22 (m, 2H), 4.08 (m, 2H), 3.85 (m, 1H), 3.68 (s, 3H), 3.66 (s, 3H), 3.44 (d, J=6.6 Hz, 1H), 2.57 (m, 1H), 2.29-1.99 (m, 5H), 0.99-0.86 (m, 12H).

Example CB

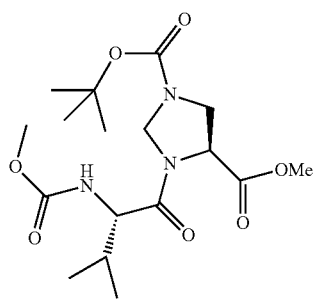

3-(2-Methoxycarbonylamino-3-methyl-butyryl)-imidazolidine-1,4-dicarboxylic acid 1-tert-butyl ester 4-methyl ester 1. HCl
2. PhB(OH)$_2$, Cu(II)

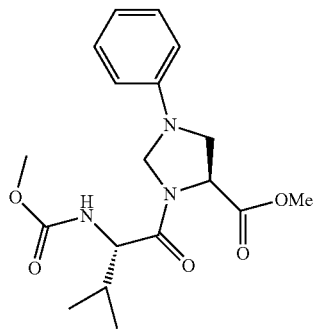

3-(2-Methoxycarbonylamino-3-methyl-butyryl)-1-phenyl-imidazolidine-4-carboxylic acid methyl ester

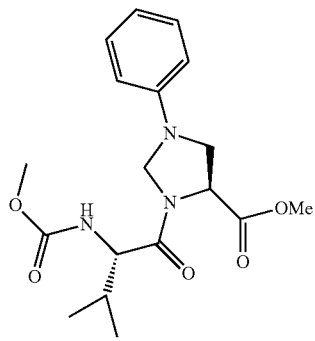

3-(2-Methoxycarbonylamino-3-methyl-butyryl)-1-phenyl-imidazolidine-4-carboxylic acid methyl ester 1. LiOH
2. HATU, NH$_2$-R

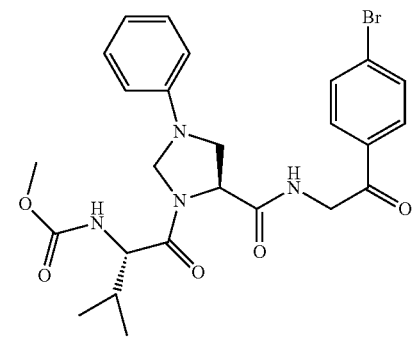

(1-{5-[2-(4-Bromo-phenyl)-2-oxo-ethylcarbamoyl]-3-phenyl-imidazolidine-1-carbonyl}-2-methyl-propyl)-carbamic acid methyl ester

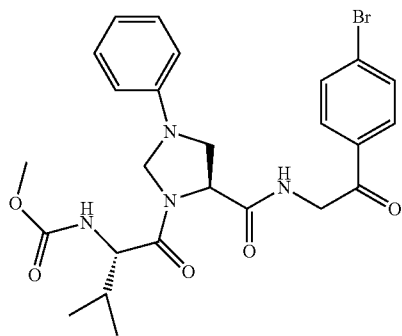

(1-{5-[2-(4-Bromo-phenyl)-2-oxo-ethylcarbamoyl]-3-phenyl-imidazolidine-1-carbonyl}-2-methyl-propyl)-carbamic acid methyl ester NH$_4$OAc, m-Xyl
135° C.

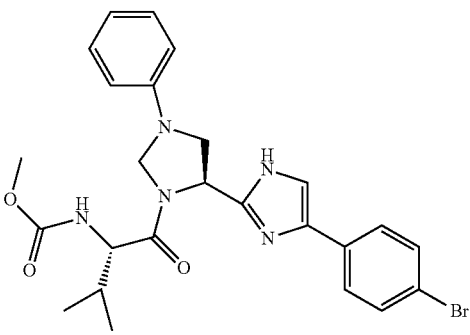

{1-[4-(4-Bromo-phenyl)-1'-phenyl-1',2',4',5'-tetrahydro-1H-[2,4']biimidazolyl-3'-carbonyl]-2-methyl-propyl}-carbamic acid methyl ester

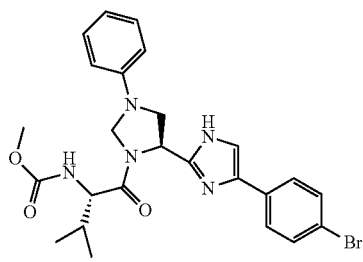

{1-[4-(4-Bromo-phenyl)-1'-phenyl-1',2',4',5'-tetrahydro-1H-[2,4']biimidazolyl-3'-carbonyl]-2-methyl-propyl}-carbamic acid methyl ester Pd(PPh$_3$)$_4$
Boronate
→

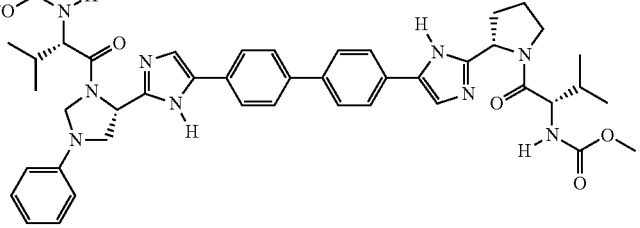

{1-[5-(4'-{2-[1-(2-Methoxycarbonylamino-3-methyl-butyryl)-pyrrolidin-2-yl]-3H-imidazol-4-yl}-biphenyl-4-yl)-1'-phenyl-1',2',4',5'-tetrahydro-1H-[2,4']biimidazolyl-3'-carbonyl]-2-methyl-propyl}-carbamic acid methyl ester

3-(2-Methoxycarbonylamino-3-methyl-butyryl)-1-phenyl-imidazolidine-4-carboxylic acid methyl ester 3-(2-Methoxycarbonylamino-3-methyl-butyryl)-imidazolidine-1,4-dicarboxylic acid 1-tert-butyl ester 4-methyl ester (0.20 g, 0.515 mmol) was dissolved in dichloromethane (1.0 mL) and HCl (4M dioxane, 1 mL) was added. The resultant suspension was stirred at room temperature for 60 minutes, after which all volatiles were removed in vacuo. The crude material was combined with phenyl boronic acid (188 mg, 1.545 mmol) and DCM (15 mL) was added. Triethylamine (1.2 mL, 8.89 mmol) was added, followed by copper(II) acetate and molecular sieves 4 Å. The reaction was stirred at room temperature. After 24 hrs, the reaction was quenched with aqueous ammonium hydroxide solution (10%) and the organic layer was isolated. The organic layer was washed with aqueous HCl solution (0.5 M), brine, and was dried over sodium sulfate. Filtration and evaporation gave crude material. Purification via flash chromatography on silica gel (eluent: EtOAc/hexanes) yielded the desired product 3-(2-Methoxycarbonylamino-3-methyl-butyryl)-1-phenyl-imidazolidine-4-carboxylic acid methyl ester (51.0 mg, 0.14 mmol): LCMS-ESI$^+$: calc'd for C$_{18}$H$_{25}$N$_3$O$_5$: 363.4 (M$^+$); Found: 364.4 (M+H$^+$).

(1-{5-[2-(4-Bromo-phenyl)-2-oxo-ethylcarbamoyl]-3-phenyl-imidazolidine-1-carbonyl}-2-methyl-propyl)-carbamic acid methyl ester 3-(2-Methoxycarbonylamino-3-methyl-butyryl)-1-phenyl-imidazolidine-4-carboxylic acid methyl ester (51 mg, 0.14 mmol) was dissolved in THF (1.2 mL) and MeOH (0.8 mL). An aqueous solution of LiOH (6.0 mg, 0.14 mmol) was added and stirring at room temperature was continued. After the hydrolysis was complete, the reaction was neutralized with aqueous HCl (1M). The organic solvents were removed in vacuo and the aqueous suspension was frozen and lyophilized. The crude material was used in the next step without further purification. The crude material was dissolved in DMF (1.5 mL) and HATU (54.3 mg, 0.14 mmol) and DIEA (36.9 mg, 0.28 mmol) were added. The reaction was stirred at room temperature for five minutes, after which the amino-(4' bromo) acetophenone hydrochloride salt (35.7 mg, 0.14 mmol) was added. Stirring at room temperature was continued. After 10 minutes, all volatiles were removed in vacuo and the crude material was purified via silica gel chromatography (eluent: EtOAc/hexanes) to yield the slightly impure product (95 mg): LCMS-ESI$^+$: calc'd for C$_{25}$H$_{29}$BrN$_4$O$_5$: 545.4 (M$^+$); Found: 545.2/547.4 (M+H$^+$).

{1-[4-(4-Bromo-phenyl)-1'-phenyl-1',2',4',5'-tetrahydro-1H-[2,4']biimidazolyl-3'-carbonyl]-2-methyl-propyl}-carbamic acid methyl ester (1-{5-[2-(4-Bromo-phenyl)-2-oxo-ethylcarbamoyl]-3-phenyl-imidazolidine-1-carbonyl}-2-methyl-propyl)-carbamic acid methyl ester (90 mg) was dissolved in m-xylenes (3 mL) and heated at 135° C. Solid ammonium acetate (100 mg, 1.29 mmol) was added and the reaction was stirred at 135° C. After 120 minutes, the reaction was cooled to room temperature and the volatiles were removed in vacuo. The crude material was purified via silica gel chromatography (eluent: EtOAc/hexanes) to yield the product {1-[4-(4-Bromo-phenyl)-1'-phenyl-1',2',4',5'-tetrahydro-1H-[2,4]biimidazolyl-3'-carbonyl]-2-methyl-propyl}-carbamic acid methyl ester (40.2 mg, 0.0764 mmol): LCMS-ESI$^+$: calc'd for C$_{25}$H$_{28}$BrN$_5$O$_3$: 526.4 (M$^+$); Found: 526.4/528.3 (M+H$^+$).

{1-[5-(4'-{2-[1-(2-Methoxycarbonylamino-3-methyl-butyryl)-pyrrolidin-2-yl]-3H-imidazol-4-yl}-biphenyl-4-yl)-1'-phenyl-1',2',4',5'-tetrahydro-1H-[2,4']biimidazolyl-3'-carbonyl]-2-methyl-propyl}-carbamic acid methyl ester {1-[4-(4-Bromo-phenyl)-1'-phenyl-1',2',4',5'-tetrahydro-1H-[2,4]biimidazolyl-3'-carbonyl]-2-methyl-propyl}-carbamic acid methyl ester (40 mg, 0.076 mmol) was combined with [2-Methyl-1-(2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (37.6 mg, 0.076 mmol) under an argon atmosphere. Potassium carbonate (20.9 mg, 0.152 mmol) and Pd(PPh$_3$)$_4$ (8.7 mg, 0.0076 mmol) were added, followed by DME (1.8 mL) and water (0.3 mL). The mixture was heated under microwave conditions for 20 minutes at 120° C. All volatiles were removed in vacuo and the crude material was dissolved in DMF and purified via RP-HPLC (eluent: water/MeCN w 0.1% TFA) to yield the product {1-[5-(4'-{2-[1-(2-Methoxycarbonylamino-3-methyl-butyryl)-pyrrolidin-2-yl]-3H-imidazol-4-yl}-biphenyl-4-yl)-1'-phenyl-1',2',4',5'-tetrahydro-1H-[2,4]biimidazolyl-3'-carbonyl]-2-methyl-propyl}-carbamic acid methyl ester (5.4 mg): LCMS-ESI$^+$: calc'd for C$_{45}$H$_{53}$N$_9$O$_6$: 815.9 (M$^+$); Found: 816.5 (M+H$^+$); $^1$H-NMR: 300 MHz, (MeOH-d$_4$) δ: 7.89-7.86 (m, 10H), 7.35 (m, 2H), 7.18 (m, 1H), 6.94 (m, 2H), 5.67 (m, 1H), 5.37 (m, 1H), 5.25 (m, 1H), 5.12 (m, 1H), 4.31-4.08 (m, 3H), 4.01-3.79 (m, 3H), 3.67 (s, 3H), 3.66 (s, 3H), 2.58 (m, 1H), 2.29-1.99 (m, 5H), 0.99-0.89 (m, 12H).

Example CD

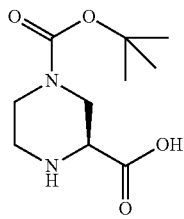

Piperazine-1,3-dicarboxylic acid 1-tert-butyl ester

1. R-COOH, HATU
2. HATU, NH$_2$-R'

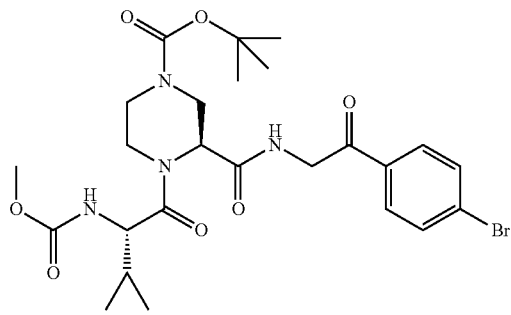

3-[2-(4-Bromo-phenyl)-2-oxo-ethylcarbamoyl]-4-(2-methoxycarbonylamino-3-methyl-butyryl)-piperazine-1-carboxylic acid tert-butyl ester NH$_4$OAc, m-Xyl
135° C.

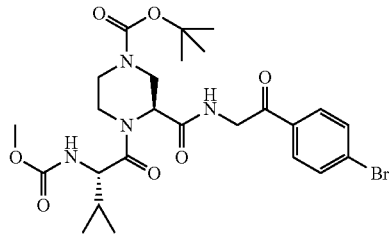

3-[2-(4-Bromo-phenyl)-2-oxo-ethylcarbamoyl]-4-(2-methoxycarbonylamino-3-methyl-butyryl)-piperazine-1-carboxylic acid tert-butyl ester

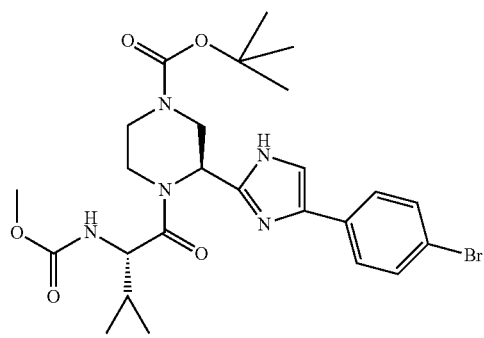

3-[4-(4-Bromo-phenyl)-1H-imidazol-2-yl]-4-(2-methoxycarbonylamino-3-methyl-butyryl)-piperazine-1-carboxylic acid tert-butyl ester

3-[2-(4-Bromo-phenyl)-2-oxo-ethylcarbamoyl]-4-(2-methoxycarbonylamino-3-methyl-butyryl)-piperazine-1-carboxylic acid tert-butyl ester N-(Methylcarbamoyl)(L)-valine (2.0 g, 11.4 mmol) was dissolved in DMF (15 mL) at room temperature. HATU (4.34 g, 11.4 mmol) and diisopropyl ethylamine (1.47 g, 11.4 mmol) were added and stirring was continued. After 10 minutes, solid piperazine-1,3-dicarboxylic acid 1-tert-butyl ester (2.62 g, 11.4 mmol) was added. To the resultant suspension was added DMF (10 mL) and diisopropyl ethylamine (1.47 g, 11.4 mmol). Stirring at room temperature was continued. After 45 min, HATU (4.34 g, 11.4 mmol) and diisopropyl ethylamine (1.47 g, 11.4 mmol) were added to the resultant yellow solution followed by amino-(4' bromo) acetophenone hydrochloride salt (2.85 g, 11.4 mmol). After 30 minutes all volatiles were removed in vacuo. The crude material was taken into EtOAc and the organic layer was washed with aqueous HCl (1 M), aqueous LiCl (5%), aqueous bicarbonate solution, brine and was dried over sodium sulfate. Filtration and evaporation of solvents in vacuo yielded crude material, which was purified by flash chromatography on silica gel (eluent: EtOAc w MeOH 10%/hexanes) to yield the product 3-[2-(4-Bromo-phenyl)-2-oxo-ethylcarbamoyl]-4-(2-methoxycarbonylamino-3-methyl-butyryl)-piperazine-1-carboxylic acid tert-butyl ester (3.62 g): LCMS-ESI$^+$: calc'd for C$_{25}$H$_{35}$BrN$_4$O$_7$: 583.4 (M$^+$); Found: 583.2/585.2 (M+H$^+$).

3-[4-(4-Bromo-phenyl)-1H-imidazol-2-yl]-4-(2-methoxycarbonylamino-3-methyl-butyryl)-piperazine-1-carboxylic acid tert-butyl ester 3-[2-(4-Bromo-phenyl)-2-oxo-ethylcarbamoyl]-4-(2-methoxycarbonylamino-3-methyl-butyryl)-piperazine-1-carboxylic acid tert-butyl ester (2.0 g, 3.43 mmol) was dissolved in m-xylenes (18 mL) and heated at 135° C. Solid ammonium acetate (1.70 g, 22.0 mmol) was added and the reaction was stirred at 135° C. After 120 minutes, the reaction was cooled to room temperature and the volatiles were removed in vacuo. The crude material was purified via silica gel chromatography (eluent: EtOAc w MeOH 10%/hexanes) to yield the product 3-[4-(4-Bromo-phenyl)-1H-imidazol-2-yl]-4-(2-methoxycarbonylamino-3-methyl-butyryl)-piperazine-1-carboxylic acid tert-butyl ester (674 mg, 1.19 mmol): LCMS-ESI$^+$: calc'd for C$_{25}$H$_{34}$BrN$_5$O$_5$: 564.5 (M$^+$); Found: 564.2/566.2 (M+H$^+$).

657      658

Example CE

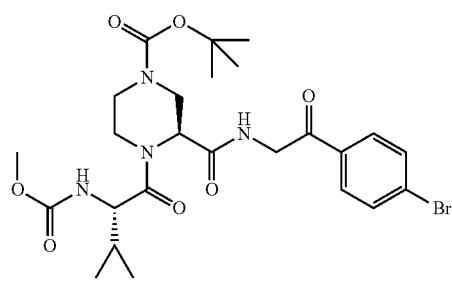

3-[4-(4-Bromo-phenyl)-1H-imidazol-2-yl]-4-(2-methoxycarbonylamino-3-methyl-butyryl)-piperazine-1-carboxylic acid tert-butyl ester 1. HCl
2. CF₃CH₂OTf

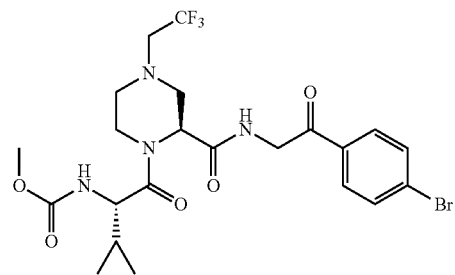

{1-[2-[2-(4-Bromo-phenyl)-2-oxo-ethylcarbamoyl]-4-(2,2,2-trifluoro-ethyl)-piperazine-1-carbonyl]-2-methyl-propyl}-carbamic acid methyl ester

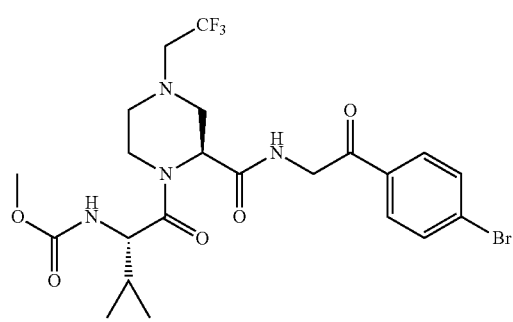

{1-[2-[2-(4-Bromo-phenyl)-2-oxo-ethylcarbamoyl]-4-(2,2,2-trifluoro-ethyl)-piperazine-1-carbonyl]-2-methyl-propyl}-carbamic acid methyl ester NH₄OAc, m-Xyl
135° C.

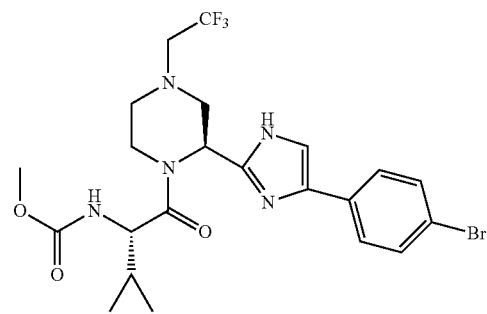

{1-[2-[4-(4-Bromo-phenyl)-1H-imidazol-2-yl]-4-(2,2,2-trifluoro-ethyl)-piperazine-1-carbonyl]-2-methyl-propyl}-carbamic acid methyl ester

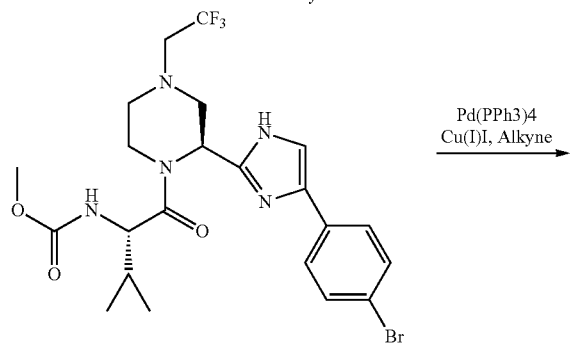

{1-[2-[4-(4-Bromo-phenyl)-1H-imidazol-2-yl]-4-(2,2,2-trifluoro-ethyl)-piperazine-1-carbonyl]-2-methyl-propyl}-carbamic acid methyl ester Pd(PPh3)4
Cu(I)I, Alkyne

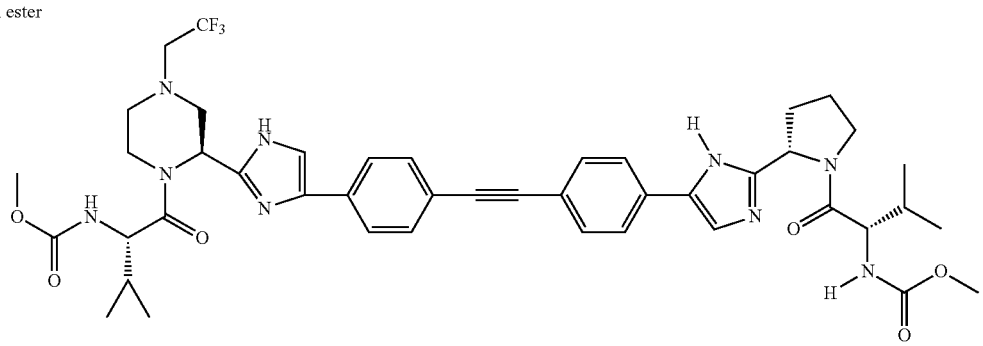

[1-(2-{5-[4-(4-{2-[1-(2-Methoxycarbonylamino-3-methyl-butyryl-4-(2,2,2-trifluoro-ethyl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester {1-[2-[2-(4-Bromo-phenyl)-2-oxo-ethylcarbamoyl]-4-(2,2,2-trifluoro-ethyl)-piperazine-1-carbonyl]-2-methyl-propyl}-carbamic acid methyl ester 3-[4-(4-Bromo-phenyl)-1H-imidazol-2-yl]-4-(2-methoxycarbonylamino-3-methyl-butyryl)-piperazine-1-carboxylic acid tert-butyl ester (400 mg, 0.686 mmol) was dissolved in dichloromethane (1.0 mL) and HCl (4M dioxane, 2 mL) was added. The resultant suspension was stirred at room temperature for 20 minutes, after which all volatiles were removed in vacuo. The crude material was dissolved in DMF (1.0 mL)/THF (1.0 mL) and diisopropyl ethylamine (88.5 mg, 0.686 mmol) was added followed by trifluoroethyl triflate (114.7 mg, 0.494 mmol). Stirring at room temperature was continued. After 14 hours, all volatiles were removed in vacuo and the crude material was purified by flash chromatography on silica gel (eluent: EtOAc w MeOH 10%/hexanes) to yield the product {1-[2-[2-(4-Bromo-phenyl)-2-oxo-ethylcarbamoyl]-4-(2,2,2-trifluoro-ethyl)-piperazine-1-carbonyl]-2-methyl-propyl}-carbamic acid methyl ester (192 mg, 0.34 mmol): LCMS-ESI$^+$: calc'd for $C_{22}H_{28}BrF_3N_4O_5$: 565.3 ($M^+$); Found: 565.2/567.2 ($M+H^+$).

{1-[2-[4-(4-Bromo-phenyl)-1H-imidazol-2-yl]-4-(2,2,2-trifluoro-ethyl)-piperazine-1-carbonyl]-2-methyl-propyl}-carbamic acid methyl ester {1-[2-[2-(4-Bromo-phenyl)-2-oxo-ethylcarbamoyl]-4-(2,2,2-trifluoro-ethyl)-piperazine-1-carbonyl]-2-methyl-propyl}-carbamic acid methyl ester (192 mg, 0.34 mmol) was dissolved in m-Xylenes (2 mL) and heated at 135° C. Solid ammonium acetate (128 mg, 1.66 mmol) was added and the reaction was stirred at 135° C. After 110 minutes, the reaction was cooled to room temperature and the volatiles were removed in vacuo. The crude material was purified via silica gel chromatography (eluent: EtOAc w MeOH 10%/hexanes) to yield the product {1-[2-[4-(4-Bromo-phenyl)-1H-imidazol-2-yl]-4-(2,2,2-trifluoro-ethyl)-piperazine-1-carbonyl]-2-methyl-propyl}-carbamic acid methyl ester (98.7 mg, 0.181 mmol): LCMS-ESI$^+$: calc'd for $C_{22}H_{27}BrF_3N_5O_3$: 546.4 ($M^+$); Found: 546.0/548.2 ($M+H^+$).

[1-(2-{5-[4-(4-{2-[1-(2-Methoxycarbonylamino-3-methyl-butyryl)-4-(2,2,2-trifluoro-ethyl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester {1-[2-[4-(4-Bromo-phenyl)-1H-imidazol-2-yl]-4-(2,2,2-trifluoro-ethyl)-piperazine-1-carbonyl]-2-methyl-propyl}-carbamic acid methyl ester (98.7 mg, 0.181 mmol) was combined with (1-{2-[5-(4-Ethynyl-phenyl)-1H-imidazol-2-yl]-pyrrolidine-1-carbonyl}-2-methyl-propyl)-carbamic acid methyl ester (71.2 mg, 0.181 mmol) and Pd(PPh$_3$)$_4$ (21.5 mg, 0.018 mmol) under an argon atmosphere. DMF (degassed with Argon) was added followed by triethylamine (181 mg, 1.8 mmol) and copper(I) iodide (3.5 mg, 0.018 mmol). The mixture was heated at 80° C. After 20 minutes, volatiles were removed in vacuo and the crude material was semi-purified via chromatography on silica gel (eluent EtOAc w MeOH 10%/hexanes) and further purified via RP-HPLC (eluent: water/MeCN w 0.1% TFA) to yield the product [1-(2-{5-[4-(4-{2-[1-(2-Methoxycarbonylamino-3-methyl-butyryl)-4-(2,2,2-trifluoro-ethyl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (12.4 mg): LCMS-ESI$^+$: calc'd for $C_{44}H_{52}F_3N_9O_6$: 859.9 ($M^+$); Found: 860.5 ($M+H^+$); $^1$H-NMR: 300 MHz, (MeOH-d$_4$) δ: 7.91-7.68 (m, 10H), 6.06 (m, 2H), 5.24 (m, 1H), 4.43 (m, 1H), 4.23 (d, J=7.8 Hz, 1H), 4.11 (m, 1H), 3.85 (m, 1H), 3.68 (s, 3H), 3.66 (s, 3H), 3.49-3.45 (m, 2H), 3.15-3.02 (m, 3H), 2.77 (m, 1H), 2.58 (m, 1H), 2.29-2.01 (m, 5H), 1.07-0.83 (m, 12H).

Example CF

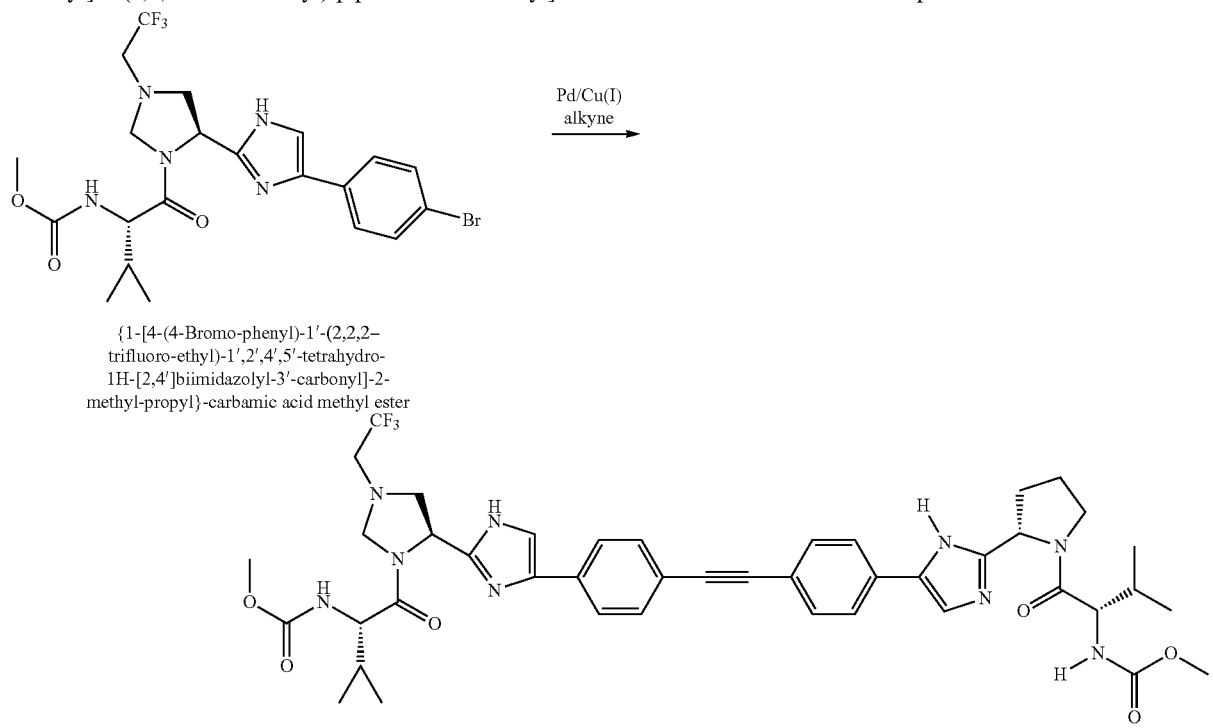

{1-[4-(4-Bromo-phenyl)-1'-(2,2,2-trifluoro-ethyl)-1',2',4',5'-tetrahydro-1H-[2,4']biimidazolyl-3'-carbonyl]-2-methyl-propyl}-carbamic acid methyl ester

[1-(2-{5-[4-(4-{2-[1-(2-Methoxycarbonylamino-3-methyl-butyryl-4N-(2,2,2-trifluoro-ethyl)-pyrrolidin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester

[1-(2-{5-[4-(4-{2-[1-(2-Methoxycarbonylamino-3-methyl-butyryl)-4N-(2,2,2-trifluoro-ethyl)-pyrrolidin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester {1-[4-(4-Bromo-phenyl)-1'-(2,2,2-trifluoro-ethyl)-1',2',4',5'-tetrahydro-1H-[2,4]biimidazolyl-3'-carbonyl]-2-methyl-propyl}-carbamic acid methyl ester (55.0 mg, 0.103 mmol) was combined with (1-{2-[5-(4-Ethynyl-phenyl)-1H-imidazol-2-yl]-pyrrolidine-1-carbonyl}-2-methyl-propyl)-carbamic acid methyl ester (37.5 mg, 0.095 mmol) and PdCl$_2$(PPh$_3$)$_2$ (7.0 mg, 0.010 mmol) under an argon atmosphere. DMF (2.0 mL, degassed with Argon) was added followed by triethylamine (104 mg, 1.03 mmol) and copper(I) iodide (1.9 mg, 0.01 mmol). The mixture was heated at 80° C. After 240 minutes, volatiles were removed in vacuo and the crude material was semi-purified via chromatography on silica gel (eluent EtOAc w MeOH 10%/hexanes) and further purified via RP-HPLC (eluent: water/MeCN w 0.1% TFA) to yield the product [1-(2-{5-[4-(4-{2-[1-(2-Methoxycarbonylamino-3-methyl-butyryl)-4N-(2,2,2-trifluoro-ethyl)-pyrrolidin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (4.9 mg): LCMS-ESI$^+$: calc'd for C$_{43}$H$_{50}$F$_3$N$_9$O$_6$: 845.9 (M$^+$); Found: 846.4 (M+H$^+$); $^1$H-NMR: 300 MHz, (MeOH-d$_4$) δ: 7.91-7.68 (m, 10H), 5.35 (dd, J=6.3, 6.3 Hz, 1H), 5.24 (m, 1H), 4.76 (d, J=6.9 Hz, 1H), 4.23 (d, J=7.5 Hz, 1H), 4.09 (m, 1H), 4.00 (d, J=7.8 Hz, 1H), 3.87 (m, 1H), 3.66 (s, 6H), 3.65-3.42 (m, 4H), 2.56 (m, 1H), 2.29-2.06 (m, 5H), 0.99-0.88 (m, 12H).

Example CG

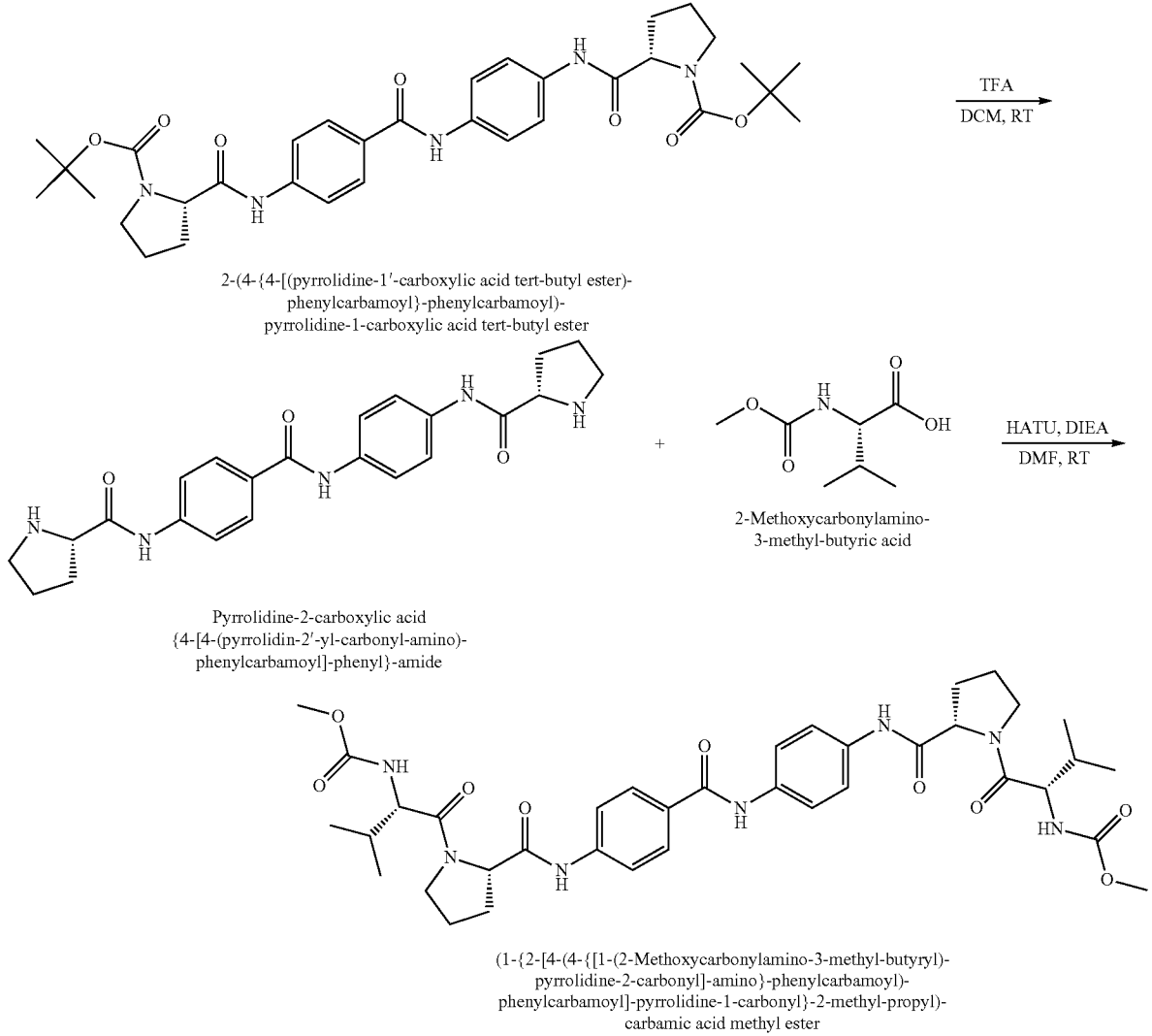

2-(4-{4-[(pyrrolidine-1'-carboxylic acid tert-butyl ester)-phenylcarbamoyl}-phenylcarbamoyl)-pyrrolidine-1-carboxylic acid tert-butyl ester 4-Amino-N-(4-amino-phenyl)-benzamide (3.00 g) and pyrrolidine-1,2-dicarboxylic acid 1-tert-butyl ester (6.55 g) were dissolved in DCM (90 mL), and 1-ethoxycarbonyl-1,2-dihydroquinoline (7.88 g) was added. The reaction mixture was stirred at ambient temperature for 17 hours and evaporated under vacuum. Oil was dissolved in ethyl acetate, forming a precipitate, which was collected by vacuum filtration and dried under vacuum, giving 2-(4-{4-[(pyrrolidine-1'-carboxylic acid tert-butyl ester)-phenylcarbamoyl}-phenylcarbamoyl)-pyrrolidine-1-carboxylic acid tert-butyl ester (7.64 g, 93%) as a white solid.

Pyrrolidine-2-carboxylic-acid {4-[4-(pyrrolidin-2'-yl-carbonyl-amino)-phenylcarbamoyl]-phenyl}-amide 2-(4-{4-[(pyrrolidine-1'-carboxylic acid tert-butyl ester)-phenylcarbamoyl}-phenylcarbamoyl)-pyrrolidine-1-carboxylic acid tert-butyl ester (2.01 g) was dissolved in DCM (46 mL), and trifluoroacetic acid (6 mL) was added. The reaction mixture was stirred at ambient temperature for 3.5 hours and evaporated under vacuum. Solid was dissolved in DCM and extracted twice with saturated NaHCO$_3$ solution. Solid was collected by vacuum filtration, washed with ethyl acetate, and dried under vacuum, giving pyrrolidine-2-carboxylic acid {4-[4-(pyrrolidin-2'-yl-carbonyl-amino)-phenylcarbamoyl]-phenyl}-amide (1.18 g, 87%) as a white solid.

(1-{2-[4-(4-{[1-(2-Methoxycarbonylamino-3-methyl-butyryl)-pyrrolidine-2-carbonyl]-amino}-phenylcarbamoyl)-phenylcarbamoyl]-pyrrolidine-1-carbonyl}-2-methyl-propyl)-carbamic acid methyl ester Pyrrolidine-2-carboxylic acid {4-[4-(pyrrolidin-2'-yl-carbonyl-amino)-phenylcarbamoyl]-phenyl}-amide (0.305 g), 2-methoxycarbonylamino-3-methyl-butyric acid (0.277 g), and HATU (0.621 g) were dissolved in anhydrous DMF (8 mL), and diisopropylethylamine (0.496 mL) was added. The reaction mixture was stirred at ambient temperature for 1 hour and evaporated under vacuum. The oil was dissolved in DCM and purified by chromatography (0-20% ethyl acetate:hexane), giving (1-{2-[4-(4-{[1-(2-methoxycarbonylamino-3-methyl-butyryl)-pyrrolidine-2-carbonyl]-amino}-phenylcarbamoyl)-phenylcarbamoyl]-pyrrolidine-1-carbonyl}-2-methyl-propyl)-carbamic acid methyl ester (0.324 g, 58%) as a white solid: $^1$H-NMR: 300 MHz, (DMSO-d6) δ: 10.3 (s, 1H), 10.1 (s, 1H), 10.0 (s, 1H), 7.9 (d, J=9.9, 2H), 7.7 (m, 4H), 7.5 (d, J=9.9, 2H), 7.3 (d, J=9.9, 2H), 4.5 (m, 2H), 4.0 (m, 2H), 3.8 (m, 2H), 3.6 (m, 2H), 3.5 (s, 6H), 2.2 (m, 2H), 1.9 (m, 8H), 0.9 (m, 12H); MS (ESI) m/z 736 [M+H]$^+$.

Example CH

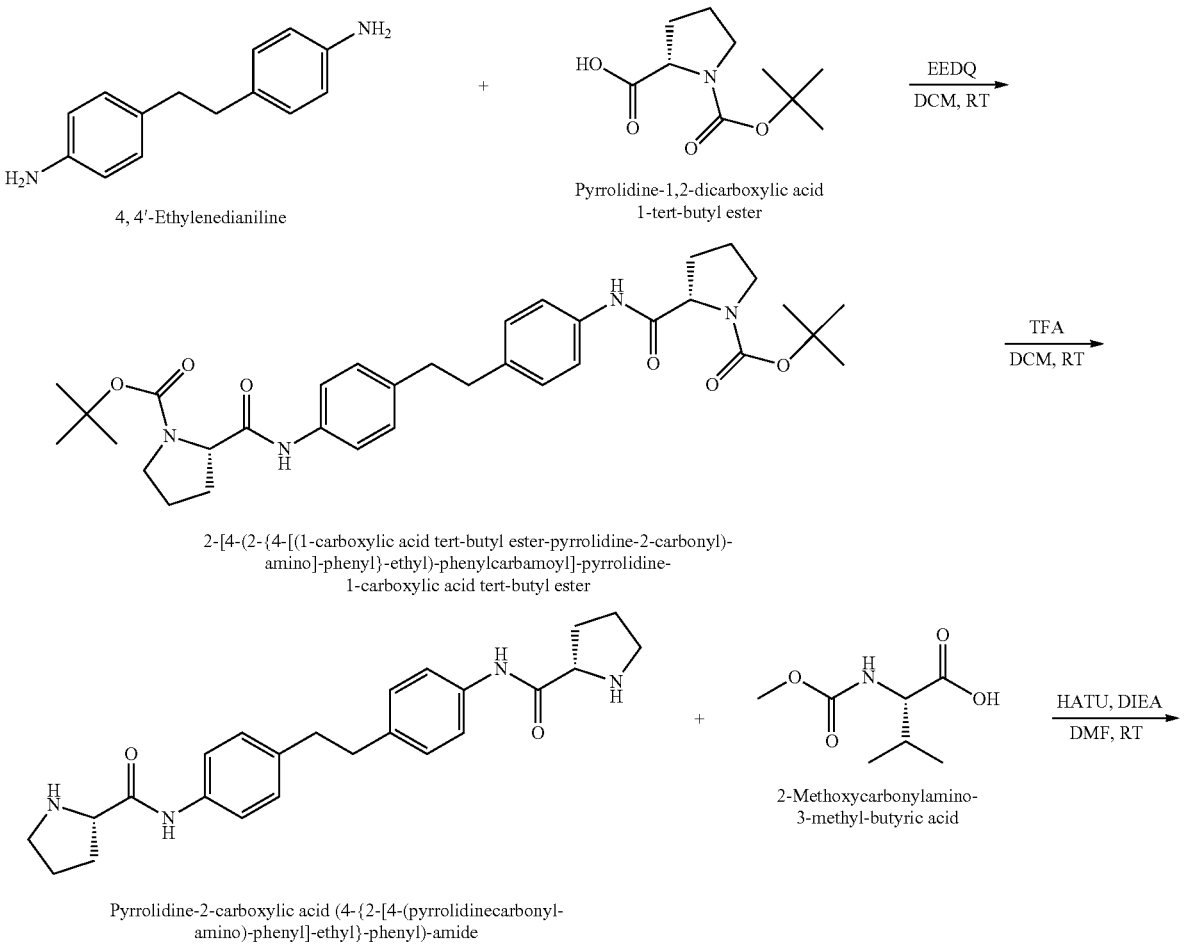


[1-(2-{4-(2-(4-{[1-(2-Methoxycarbonylamino-3-methyl-butyryl)-
pyrrolidine-2-carbonyl]-amino}-phenyl)-ethyl]-phenylcarbamoyl}-
pyrrolidine-1-carbonyl)-2-methyl-propyl]-carbamic acid methyl ester

2-[4-(2-{4-[(1-carboxylic acid tert-butyl ester-pyrrolidine-2-carbonyl)-amino]-phenyl}-ethyl)-phenylcarbamoyl]-pyrrolidine-1-carboxylic acid tert-butyl ester 4,4'-Ethylenedianiline (2.98 g) and pyrrolidine-1,2-dicarboxylic acid 1-tert-butyl ester (7.09 g) were dissolved in DCM (90 mL), and 1-ethoxycarbonyl-1,2-dihydroquinoline (8.38 g) was added. The reaction mixture was stirred at ambient temperature for 3 hours and evaporated under vacuum. Oil was dissolved in ethyl acetate, forming a precipitate, which was collected by vacuum filtration and dried under vacuum, giving 2-[4-(2-{4-[(1-carboxylic acid tert-butyl ester-pyrrolidine-2-carbonyl)-amino]-phenyl}-ethyl)-phenylcarbamoyl]-pyrrolidine-1-carboxylic acid tert-butyl ester (8.30 g, 97%) as a white solid.

Pyrrolidine-2-carboxylic acid (4-{2-[4-(pyrrolidinecarbonyl-amino)-phenyl]-ethyl}-phenyl)-amide 2-[4-(2-{4-[(1-carboxylic acid tert-butyl ester-pyrrolidine-2-carbonyl)-amino]-phenyl}-ethyl)-phenylcarbamoyl]-pyrrolidine-1-carboxylic acid tert-butyl ester (3.01 g) was dissolved in DCM (45 mL), and trifluoroacetic acid (15 mL) was added. The reaction mixture was stirred at ambient temperature for 4 hours and evaporated under vacuum. Solid was dissolved in DCM and extracted twice with saturated NaHCO₃ solution. Solid was collected by vacuum filtration, washed with ethyl acetate, and dried under vacuum, giving pyrrolidine-2-carboxylic acid (4-{2-[4-(pyrrolidinecarbonyl-amino)-phenyl]-ethyl}-phenyl)-amide (1.86 g, 93%) as a light gray solid.

[1-(2-{4-[2-(4-{[1-(2-Methoxycarbonylamino-3-methyl-butyryl)-pyrrolidine-2-carbonyl]-amino}-phenyl)-ethyl]-phenylcarbamoyl}-pyrrolidine-1-carbonyl)-2-methyl-propyl]-carbamic acid methyl ester Pyrrolidine-2-carboxylic acid (4-{2-[4-(pyrrolidinecarbonyl-amino)-phenyl]-ethyl}-phenyl)-amide (0.299 g), 2-methoxycarbonylamino-3-methyl-butyric acid (0.296 g), and HATU (0.648 g) were dissolved in anhydrous DMF (5 mL), and diisopropylethylamine (0.513 mL) was added. The reaction mixture was stirred at ambient temperature for 1 hour and evaporated under vacuum. The oil was dissolved in DCM and purified by chromatography (0-100% ethyl acetate:hexane), giving [1-(2-{4-[2-(4-{[1-(2-methoxycarbonylamino-3-methyl-butyryl)-pyrrolidine-2-carbonyl]-amino}-phenyl)-ethyl]-phenylcarbamoyl}-pyrrolidine-1-carbonyl)-2-methyl-propyl]-carbamic acid methyl ester (0.254 g, 48%) as a white solid: ¹H-NMR: 300 MHz, (DMSO-d6) δ: 9.9 (s, 2H), 8.2 (broad s, 2H), 7.4 (d, J=9.9, 4H), 7.3 (d, J=9.9, 2H), 7.1 (d, J=9.9, 4H), 4.4 (m, 2H), 4.0 (t, J=7.5, 2H), 3.8 (m, 2H), 3.6 (m, 8H), 3.5 (s, 6H), 3.1 (m, 8H), 2.8 (s, 4H), 2.1 (m, 2H), 1.9 (m, 8H), 0.9 (m, 12H); MS (ESI) m/z 721 [M+H]⁺.

Example CI

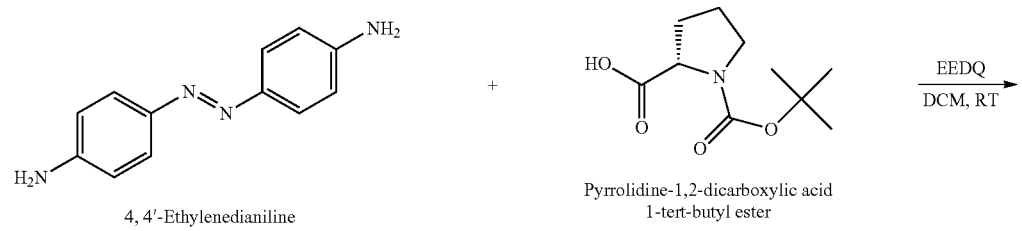

4, 4'-Ethylenedianiline

Pyrrolidine-1,2-dicarboxylic acid 1-tert-butyl ester

EEDQ
DCM, RT

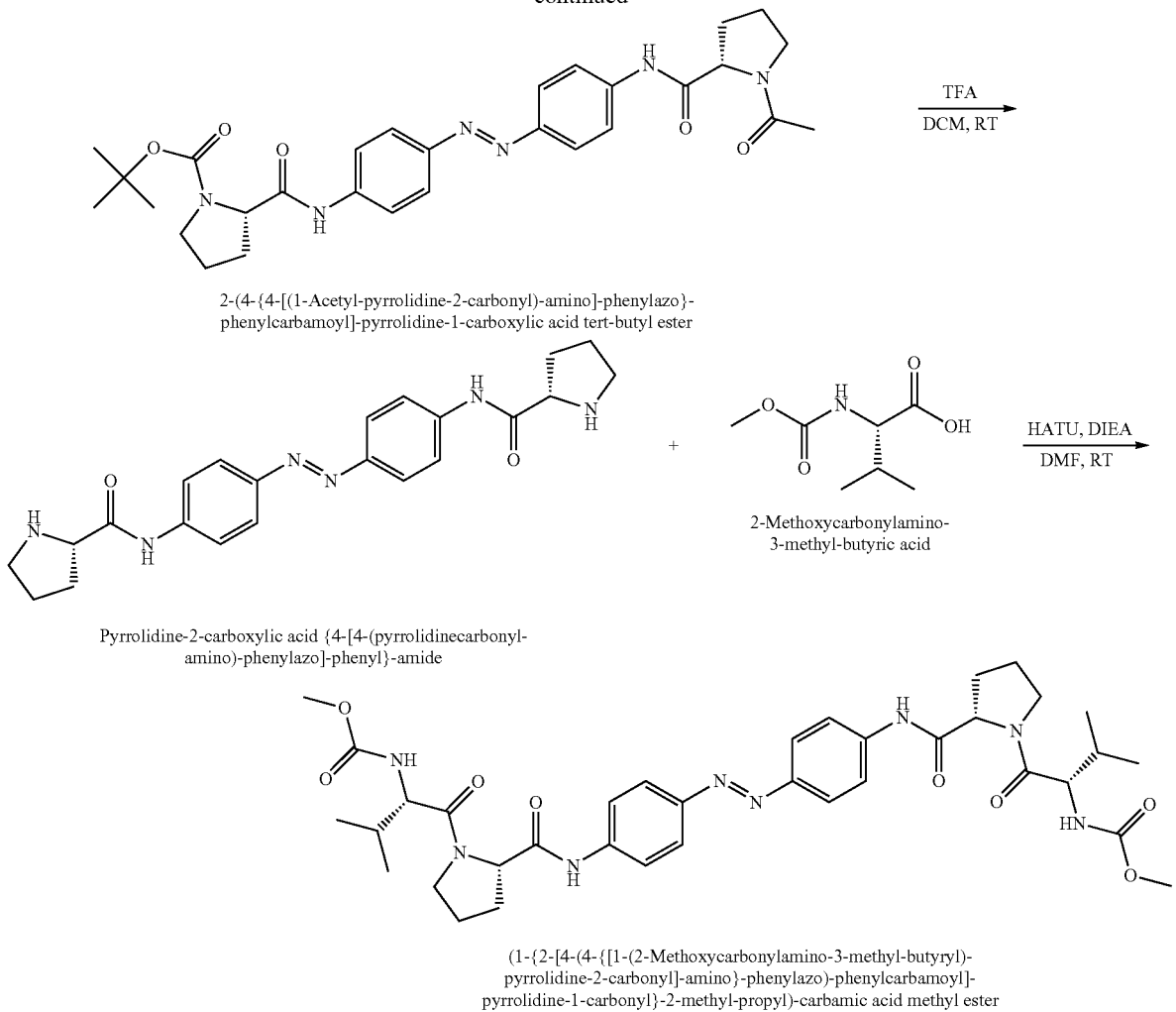

2-(4-{4-[(1-Acetyl-pyrrolidine-2-carbonyl)-amino]-phenylazo}-phenylcarbamoyl]-pyrrolidine-1-carboxylic acid tert-butyl ester Pyrrolidine-2-carboxylic acid {4-[4-(pyrrolidinecarbonyl-amino)-phenylazo]-phenyl}-amide 2-Methoxycarbonylamino-3-methyl-butyric acid (1-{2-[4-(4-{[1-(2-Methoxycarbonylamino-3-methyl-butyryl)-pyrrolidine-2-carbonyl]-amino}-phenylazo)-phenylcarbamoyl]-pyrrolidine-1-carbonyl}-2-methyl-propyl)-carbamic acid methyl ester

2-(4-{4-[(1-Acetyl-pyrrolidine-2-carbonyl)-amino]-phenylazo}-phenylcarbamoyl)-pyrrolidine-1-carboxylic acid tert-butyl ester 4-(4-aminophenylazo)-phenylamine (3.02 g) and pyrrolidine-1,2-dicarboxylic acid 1-tert-butyl ester (7.00 g) were dissolved in DCM (90 mL), and 1-ethoxycarbonyl-1,2-dihydroquinoline (8.45 g) was added. The reaction mixture was stirred at ambient temperature for 19 hours and evaporated under vacuum. Oil was dissolved in ethyl acetate, forming a precipitate, which was collected by vacuum filtration and dried under vacuum, giving 2-(4-{4-[(1-carboxylic acid tert-butyl ester-pyrrolidine-2-carbonyl)-amino]-phenylazo}-phenylcarbamoyl)-pyrrolidine-1-carboxylic acid tert-butyl ester (9.28 g) as a brown solid.

Pyrrolidine-2-carboxylic acid {4'-[4-(pyrrolidinecarbonyl-amino)-phenylazo]-phenyl}-amide 2-(4-{4-[(1-carboxylic acid tert-butyl ester-pyrrolidine-2-carbonyl)-amino]-phenylazo}-phenylcarbamoyl)-pyrrolidine-1-carboxylic acid tert-butyl ester (9.28 g, crude) was dissolved in DCM (75 mL), and trifluoroacetic acid (25 mL) was added. The reaction mixture was stirred at ambient temperature for 3 hours and evaporated under vacuum. Solid was dissolved in DCM and extracted twice with saturated NaHCO$_3$ solution. The solution was evaporated under vacuum, giving pyrrolidine-2-carboxylic acid {4-[4-(pyrrolidinecarbonyl-amino)-phenylazo]-phenyl}-amide (6.18 g, crude) as a red solid.

(1-{2-[4-(4-{[1-(2-Methoxycarbonylamino-3-methyl-butyryl)-pyrrolidine-2-carbonyl]-amino}-phenylazo)-phenylcarbamoyl]-pyrrolidine-1-carbonyl}-2-methyl-propyl)-carbamic acid methyl ester Pyrrolidine-2-carboxylic acid {4-[4-(pyrrolidinecarbonyl-amino)-phenylazo]-phenyl}-amide (0.302 g), 2-methoxycarbonylamino-3-methyl-butyric acid (0.284 g), and HATU (0.643 g) were dissolved in anhydrous DMF (5 mL), and N-methylmorpholine (0.324 mL) was added. The reaction mixture was stirred at ambient temperature for 2 hours and evaporated under vacuum. The oil was dissolved in DCM and purified by chromatography (0-100% ethyl acetate:hexane), giving (1-{2-[4-(4-{[1-(2-methoxycarbonylamino-3-methyl-butyryl)-pyrrolidine-2-carbonyl]-amino}-phenylazo)-phenylcarbamoyl]-pyrrolidine-1-carbonyl}-2-methyl-propyl)-carbamic acid methyl ester (0.158 g, 30%) as a yellow solid: $^1$H-NMR: 300 MHz, (DMSO-d$_6$) δ: 10.4 (s, 2H), 7.8 (m, 8H), 7.4 (d, J=9.9, 2H), 4.5 (m, 2H), 4.0 (t, J=7.5, 2H), 3.8 (m, 2H), 3.6 (m, 8H), 3.5 (s, 6H), 2.2 (m, 2H), 2.0 (m, 8H), 0.9 (m, 12H); MS (ESI) m/z 721 [M+H]$^+$.

Example CJ
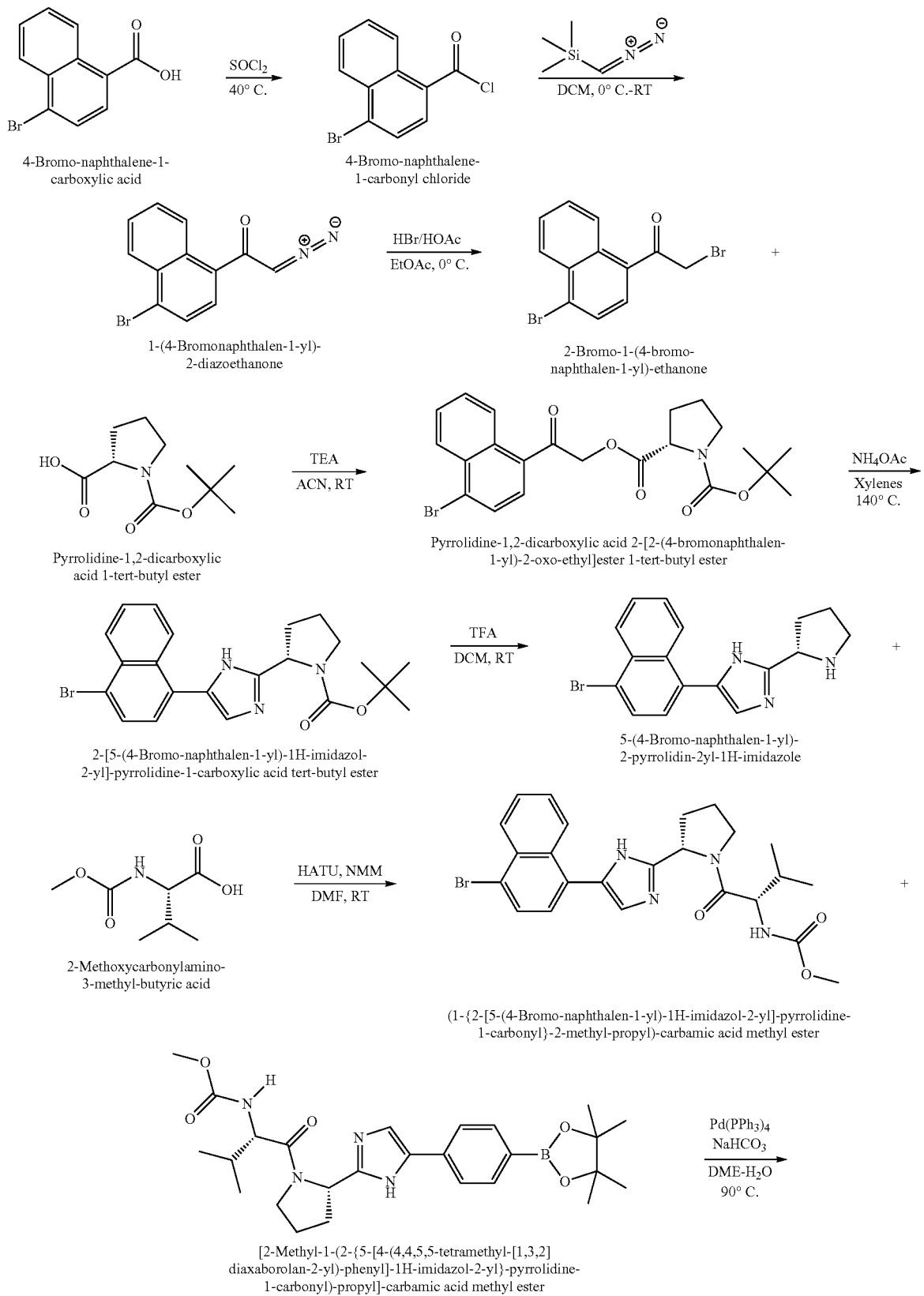

-continued

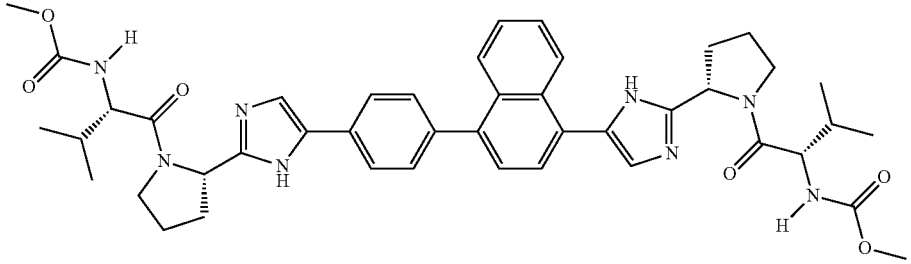

[1-(2-{5-[4-(4-{2-[1-(2-Methoxycarbonylamino-3-methyl-butyryl)-pyrrolidin-2-yl]-3H-imidazol-4-yl}-phenyl)-naphthalen-1-yl]-1H-imidazol-2-yl}-pyrrolidine-1-carbonyl)-2-methyl-propyl]-carbamic acid methyl ester

4-Bromo-naphthalene-1-carbonyl chloride

4-Bromonaphthalene-1-carboxylic acid (9.80 g) was suspended in thionyl chloride (80 mL) and stirred at 40° C. for 16 hours and evaporated under vacuum. Solid was dissolved in DCM (20 mL) and evaporated under vacuum, giving 4-bromonaphthalene-1-carbonyl chloride (13.8 g, crude) as a white solid.

1-(4-Bromonaphthalen-1-yl)-2-diazoethanone

4-Bromo-naphthalene-1-carbonyl chloride (13.8 g) was dissolved in dichloromethane (130 mL) and cooled to 0° C. TMS diazomethane solution (40 mL, 2 M in DCM) was added, and ice bath was removed. Reaction mixture was stirred for 18 hours and evaporated under vacuum, giving 1-(4-bromonaphthalen-1-yl)-2-diazoethanone (13.8 g, crude) as a brown oil.

2-Bromo-1-(4-bromo-naphthalen-1-yl)-ethanone 1-(4-Bromonaphthalen-1-yl)-2-diazoethanone (13.8 g) was dissolved in ethyl acetate (200 mL), and hydrobromic acid solution (8.4 mL, 5.7 M in acetic acid) was added at 0° C. Reaction mixture was stirred 15 minutes, NaHCO₃ solution (100 mL) was added, and mixture was stirred 10 minutes. Ethyl acetate solution was extracted twice with NaHCO₃ solution (50 mL), once with brine (50 mL), and evaporated under vacuum. The oil was dissolved in DCM and purified by chromatography (0-20% ethyl acetate:hexane), giving 2-bromo-1-(4-bromo-naphthalen-1-yl)-ethanone (6.67 g, 51%) as a tan solid.

Pyrrolidine-1,2-dicarboxylic acid 2-[2-(4-bromonaphthalen-1-yl)-2-oxo-ethyl]ester 1-tert-butyl ester Pyrrolidine-1,2-dicarboxylic acid 1-tert-butyl ester (4.85 g) was dissolved in acetonitrile (65 mL), and triethylamine (3.09 mL) was added. A solution of 2-bromo-1-(4-bromonaphthalen-1-yl)-ethanone (6.60 g) in acetonitrile (35 mL) was added. Reaction mixture was stirred 90 minutes and evaporated under vacuum. Oil was dissolved in DCM (50 mL), extracted once with water (20 mL) and once with NaHCO₃ solution (20 mL), and evaporated under vacuum to a concentrated liquid. Solution was purified by chromatography (0-50% ethyl acetate:hexane) and evaporated under vacuum, giving pyrrolidine-1,2-dicarboxylic acid 2-[2-(4-bromonaphthalen-1-yl)-2-oxo-ethyl]ester 1-tert-butyl ester (8.95 g, 95%) as a tan solid.

2-[5-(4-Bromo-naphthalen-1-yl)-1H-imidazol-2-yl]-pyrrolidine-1-carboxylic acid tert-butyl ester Pyrrolidine-1,2-dicarboxylic acid 2-[2-(4-bromonaphthalen-1-yl)-2-oxo-ethyl]ester 1-tert-butyl ester (8.80 g) and ammonium acetate (7.51 g) were suspended in xylenes. The reaction mixture was stirred at 140° C. for 15 hours and evaporated under vacuum. Solid was dissolved in ethyl acetate (50 mL) and extracted twice with water (20 mL) and once with brine (20 mL). The oil was dissolved in DCM, purified by chromatography (0-50% ethyl acetate:hexanes), and evaporated under vacuum, giving 2-[5-(4-bromo-naphthalen-1-yl)-1H-imidazol-2-yl]-pyrrolidine-1-carboxylic acid tert-butyl ester (4.34 g, 52%) as a tan solid.

5-(4-Bromo-naphthalen-1-yl)-2-pyrrolidin-2-yl-1H-imidazole

2-[5-(4-Bromo-naphthalen-1-yl)-1H-imidazol-2-yl]-pyrrolidine-1-carboxylic acid tert-butyl ester (1.00 g) was dissolved in DCM (12 mL), and trifluoroacetic acid (4 mL) was added. The reaction mixture was stirred at ambient temperature for 3 hours and evaporated under vacuum. Solid was dissolved in DCM (10 mL) and extracted with saturated NaHCO₃ solution (30 mL). A solid was collected by vacuum filtration, washed with DCM, and dried under vacuum, giving 5-(4-bromo-naphthalen-1-yl)-2-pyrrolidin-2-yl-1H-imidazole (0.940 g, crude) as an off-white solid.

(1-{2-[5-(4-Bromo-naphthalen-1-yl)-1H-imidazol-2-yl]-pyrrolidine-1-carbonyl}-2-methyl-propyl)-carbamic acid methyl ester 5-(4-bromo-naphthalen-1-yl)-2-pyrrolidin-2-yl-1H-imidazole (0.925 g), 2-methoxycarbonylamino-3-methyl-butyric acid (0.441 g), and HATU (1.00 g) were dissolved in anhydrous DMF (15 mL), and N-methylmorpholine (0.497 mL) was added. The reaction mixture was stirred at ambient temperature for 30 minutes and evaporated under vacuum. The oil was dissolved in DCM, purified by chromatography (0-100% ethyl acetate:hexanes), and evaporated under vacuum, giving (1-{2-[5-(4-bromo-naphthalen-1-yl)-1H-imidazol-2-yl]-pyrrolidine-1-carbonyl}-2-methyl-propyl)-carbamic acid methyl ester (0.814 g, 72%) as an off-white solid.

[1-(2-{5-[4-(4-{2-[1-(2-Methoxycarbonylamino-3-methyl-butyryl)-pyrrolidin-2-yl]-3H-imidazol-4-yl}-phenyl)-naphthalen-1-yl]-1H-imidazol-2-yl}-pyrrolidine-1-carbonyl)-2-methyl-propyl]carbamic acid methyl ester (1-{2-[5-(4-Bromo-naphthalen-1-yl)-1H-imidazol-2-yl]-pyrrolidine-1-carbonyl}-2-methyl-propyl)-carbamic acid methyl ester (0.115 g), [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (0.111 g), and NaHCO₃ (0.0623 g) were dissolved in a mixture of 1,2-dimethoxyethane (3 mL) and water (1 mL). The solution was degassed with nitrogen, and Pd(PPh₃)₄ (0.0114 g) was added. The reaction mixture was stirred at 85° C. for 16 hours and evaporated under vacuum. Solid was dissolved in ethyl acetate (10 mL) and extracted twice with water (10 mL) and once with brine (10 mL). Solution was evaporated, dissolved in DMF, purified by reverse phase HPLC (5-70% acetonitrile:water), and lyophilized, giving [1-(2-{5-[4-(4-{2-[1-(2-Methoxycarbonylamino-3-methyl-butyryl)-pyrrolidin-2-yl]-3H-imidazol-4-yl}-phenyl)-naphthalen-1-yl]-1H-imidazol-2-yl}-pyrrolidine-1-carbonyl)-2-methyl-propyl]-carbamic acid methyl ester (0.037 g, 21%) as a white solid: ¹H-NMR: 300 MHz, (CHCl₃-d₁) δ: 8.9 (m, 1H), 7.6 (m, 2H), 7.4 (m, 5H), 7.0 (m, 2H), 6.8 (m, 2H), 5.8 (m, 2H), 5.3 (m, 2H), 4.3 (m, 2H), 4.0 (m, 4H), 3.6 (s, 6H), 2.4 (m, 6H), 2.0 (m, 6H), 0.8 (m, 12H); MS (ESI) m/z 789 [M+H]⁺.

Example CJ

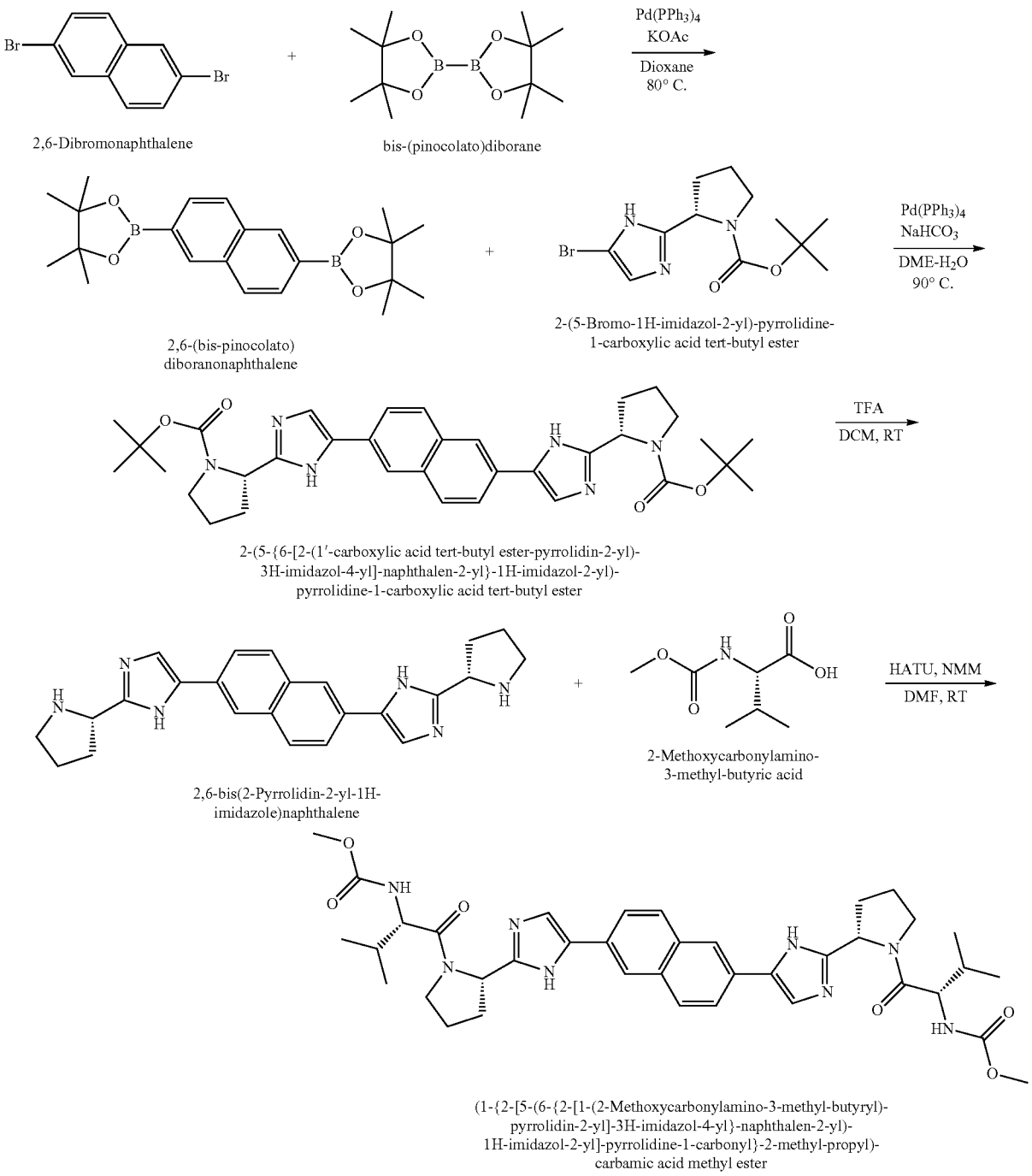

2,6-(bis-pinocolato)Diboranonaphthalene 2,6-Dibromonaphthalene (10.2 g), bis-(pinocolato)diborane (37.3 g), and potassium acetate (18.0 g) were dissolved in 1,4-dioxane (250 mL), and solution was degassed with nitrogen. Pd(PPh$_3$)$_4$ (3.13 g) was added, and the reaction mixture was stirred at 80° C. for 20 hours. The suspension was vacuum filtered, and the solid was washed with ethyl acetate, giving 2,6-(bis-pinocolato)diboranonaphthalene (7.71 g, 58%) as a yellow solid.

2-(5-{6-[2-(1'-carboxylic acid tert-butyl ester-pyrrolidin-2-yl)-3H-imidazol-4-yl]-naphthalen-2-yl}-1H-imidazol-2-yl)-pyrrolidine-1-carboxylic acid tert-butyl ester 2,6-(bis-pinocolato)diboranonaphthalene (0.501 g), 2-(5-bromo-1H-imidazol-2-yl)-pyrrolidine-1-carboxylic acid tert-butyl ester (0.885 g), and NaHCO$_3$ (0.562 g) were dissolved in a mixture of 1,2-dimethoxyethanedichloromethane (15 mL) and water (5 mL). The solution was degassed with nitrogen, and Pd(PPh$_3$)$_4$ (0.0935 g) was added. The reaction mixture was stirred at 90° C. for 16 hours and evaporated under vacuum. Solid was dissolved in DCM (20 mL) and extracted twice with water and once with brine. Solution was evaporated, recrystallized from ethyl acetate, and dried under vacuum, giving 2-(5-{6-[2-(1'-carboxylic acid tert-butyl ester-pyrrolidin-2-yl)-3H-imidazol-4-yl]-naphthalen-2-yl}-1H-imidazol-2-yl)-pyrrolidine-1-carboxylic acid tert-butyl ester (0.365 g, 46%) as a white solid.

2,6-bis(2-Pyrrolidin-2-yl-1H-imidazole)naphthalene 2-(5-{6-[2-(1'-carboxylic acid tert-butyl ester-pyrrolidin-2-yl)-3H-imidazol-4-yl]-naphthalen-2-yl}-1H-imidazol-2-yl)-pyrrolidine-1-carboxylic acid tert-butyl ester (0.365 g) was dissolved in dichloromethane (3 mL), and trifluoroacetic acid (1 mL) was added. The reaction mixture was stirred at ambient temperature for 27 hours, heated to 40° C. for 3 hours, and evaporated under vacuum. Solid was dissolved in DCM (10 mL) and extracted with saturated NaHCO$_3$ solution (30 mL) A solid was collected by vacuum filtration, washed with DCM, and dried under vacuum, giving 2,6-bis(2-pyrrolidin-2-yl-1H-imidazole)naphthalene (0.180 g, 74%) as a yellow solid.

(1-{2-[5-(6-{2-[1-(2-Methoxycarbonylamino-3-methyl-butyryl)-pyrrolidin-2-yl]-3H-imidazol-4-yl}-naphthalen-2-yl)-1H-imidazol-2-yl]-pyrrolidine-1-carbonyl}-2-methyl-propyl)-carbamic acid methyl ester 2,6-bis(2-Pyrrolidin-2-yl-1H-imidazole)naphthalene (0.170 g), 2-methoxycarbonylamino-3-methyl-butyric acid (0.168 g), and HATU (0.378 g) were dissolved in anhydrous DMF (3 mL), and N-methylmorpholine (0.188 mL) was added. The reaction mixture was stirred at ambient temperature for 30 minutes and evaporated under vacuum. The oil was dissolved in DMF and purified by reverse phase HPLC (5-70% acetonitrile:water) and lyophilized, giving (1-{2-[5-(6-{2-[1-(2-Methoxycarbonylamino-3-methyl-butyryl)-pyrrolidin-2-yl]-3H-imidazol-4-yl}-naphthalen-2-yl)-1H-imidazol-2-yl]-pyrrolidine-1-carbonyl}-2-methyl-propyl)-carbamic acid methyl ester (0.051 g, 17%) as a white solid: $^1$H-NMR: 300 MHz, (DMSO-d$_6$) δ: 8.3 (s, 2H), 8.1 (s, 2H), 8.0 (m, 4H), 7.3 (d, J=11.2, 2H), 5.1 (m, 2H), 4.1 (m, 2H), 3.9 (m, 4H), 3.5 (s, 6H), 2.4 (m, 1H), 2.0 (m, 5H), 0.8 (m, 12H); MS (ESI) m/z 713 [M+H]$^+$.

Example CK

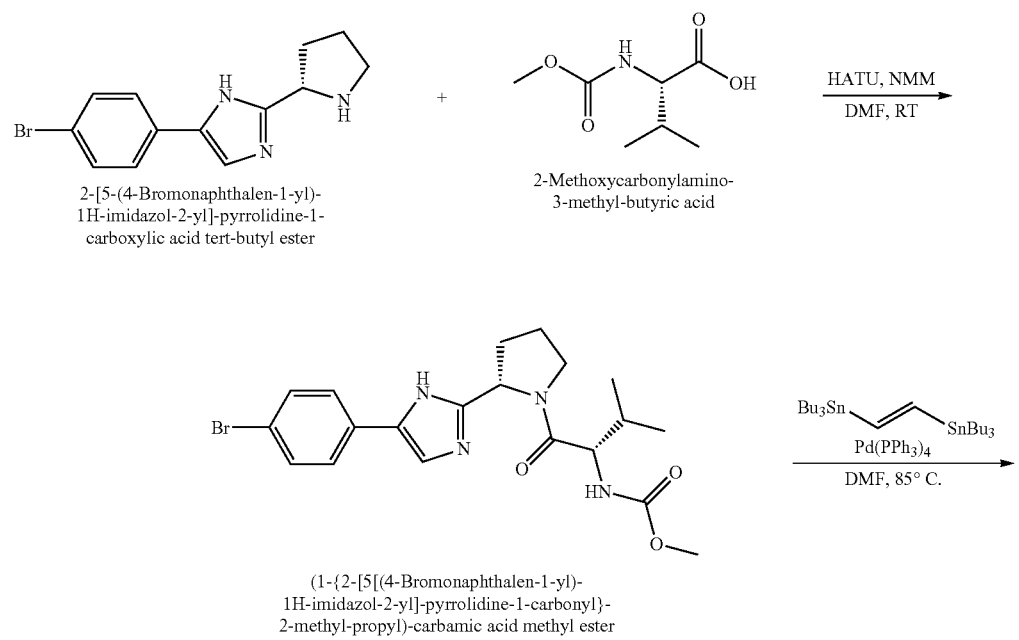

-continued

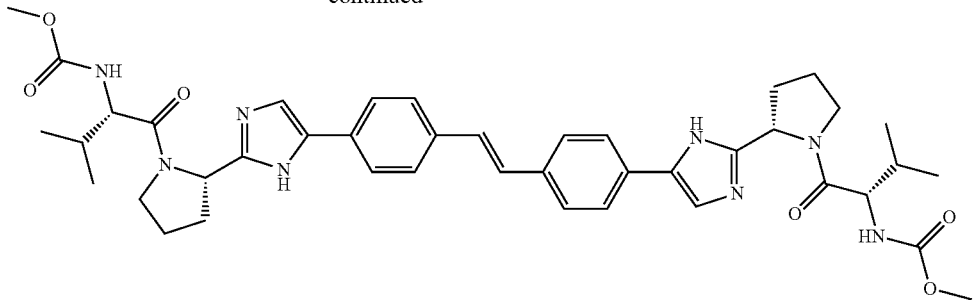

{1-[2-(5-{4-[2-(4-{2-[1-(2-Methoxycarbonylamino-3-methyl-butyryl)-
pyrrolidin-2-yl]-3H-imidazol-4-yl}-phenyl)-vinyl]-phenyl}-
1H-imidazol-2-yl)-pyrrolidine-1-carbonyl]-2-methyl-propyl}-
carbamic acid methyl ester (1-{2-[5-(4-Bromonaphthalen-1-yl)-1H-imidazol-2-yl]-pyrrolidine-1-carbonyl}-2-methyl-propyl)-carbamic acid methyl ester 2-[5-(4-Bromonaphthalen-1-yl)-1H-imidazol-2-yl]-pyrrolidine-1-carboxylic acid tert-butyl ester (3.80 g), 2-methoxycarbonylamino-3-methyl-butyric acid (2.57 g), and HATU (5.88 g) were dissolved in anhydrous DMF (85 mL), and N-methylmorpholine (2.86 mL) was added. The reaction mixture was stirred at ambient temperature for 22 hours and evaporated under vacuum. The oil was dissolved in dichloromethane, purified by chromatography (0-50% ethyl acetate:hexanes), and evaporated under vacuum, giving (1-{2-[5-(4-bromonaphthalen-1-yl)-1H-imidazol-2-yl]-pyrrolidine-1-carbonyl}-2-methyl-propyl)-carbamic acid methyl ester (6.10 g, crude) as a tan solid.

{1-[2-(5-{4-[2-(4-{2-[1-(2-Methoxycarbonylamino-3-methyl-butyryl)-pyrrolidin-2-yl]-3H-imidazol-4-yl}-phenyl)-vinyl]-phenyl}-1H-imidazol-2-yl)-pyrrolidine-1-carbonyl]-2-methyl-propyl}-carbamic acid methyl ester (1-{2-[5-(4-Bromonaphthalen-1-yl)-1H-imidazol-2-yl]-pyrrolidine-1-carbonyl}-2-methyl-propyl)-carbamic acid methyl ester (1.01 g) was dissolved in anhydrous DMF (13 mL), and (E)-bis(tributylstannyl)ethene (0.585 mL) was added. The solution was degassed with nitrogen, and Pd(PPh$_3$)$_4$ (0.0401 g) was added. The reaction mixture was stirred at 85° C. for 17 hours and evaporated under vacuum. Solid was dissolved in DMF, purified by reverse phase HPLC (5-70% acetonitrile:water), and lyophilized, giving {1-[2-(5-{4-[2-(4-{2-[1-(2-methoxycarbonylamino-3-methyl-butyryl)-pyrrolidin-2-yl]-3H-imidazol-4-yl}-phenyl)-vinyl]-phenyl}-1H-imidazol-2-yl)-pyrrolidine-1-carbonyl]-2-methyl-propyl}-carbamic acid methyl ester (25 mg, 1.5%) as a white solid: $^1$H-NMR: 300 MHz, (DMSO-d$_6$) δ: 8.0 (s, 2H), 7.8 (m, 8H), 7.4 (s, 2H), 7.3 (d, J=9.9, 2H), 5.1 (t, J=6.9, 2H), 4.1 (t, J=6.9, 2H), 3.8 (m, 4H), 3.8 (m, 2H), 3.5 (s, 6H), 2.4 (m, 2H), 2.0 (m, 6H), 0.8 (m, 12H); MS (ESI) m/z 765 [M+H]$^+$.

Example CL

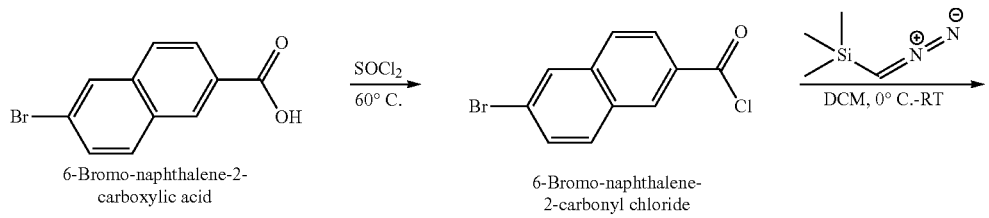

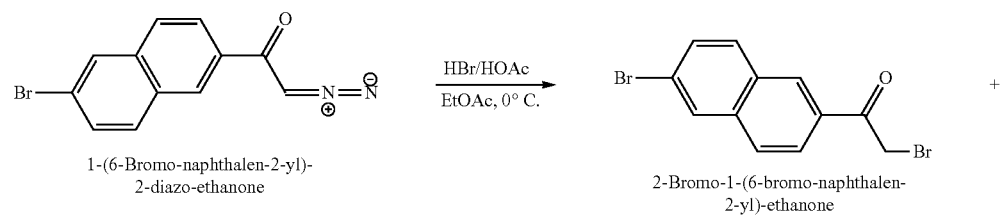

-continued

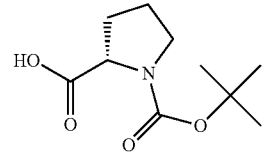
Pyrrolidine-1,2-dicarboxylic acid 1-tert-butyl ester

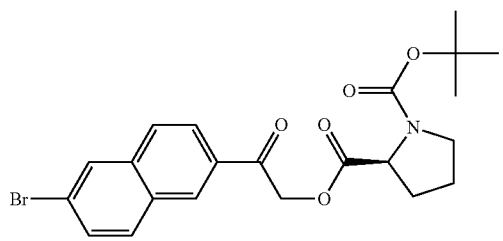
Pyrrolidine-1,2-dicarboxylic acid 2-[2-(6-bromo-naphthalen-2-yl)-2-oxo-ethyl] ester 1-tert-butyl ester

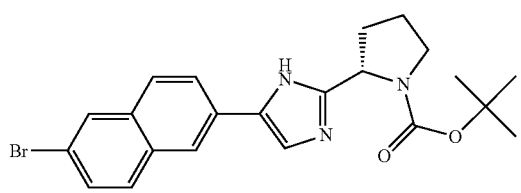
2-[5-(6-Bromo-naphthalen-2-yl)-1H-imidazol-2-yl]-pyrrolidine-1-carboxylic acid tert-butyl ester

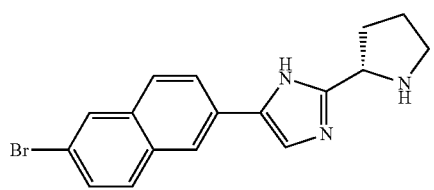
5-(6-Bromo-naphthalen-2-yl)-2-pyrrolidin-2-yl-1H-imidazole

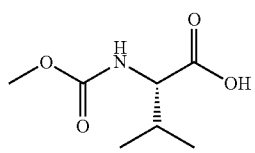
2-Methoxycarbonylamino-3-methyl-butyric acid

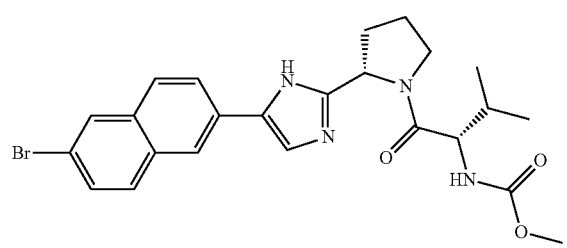
(1-{2-[5-(6-Bromonaphthalen-2-yl)-1H-imidazol-2-yl]-pyrrolidine-1-carbonyl}-2-methyl-propyl)-carbamic acid methyl ester

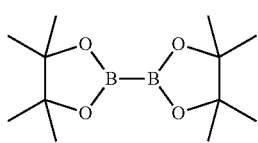
bis-(pinocolato)diborane

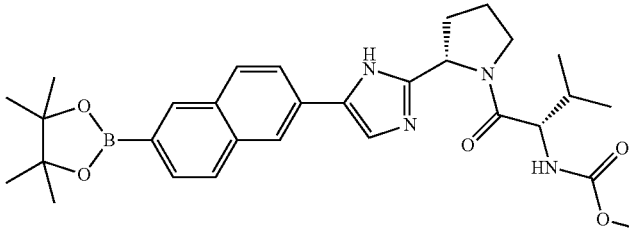
[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester

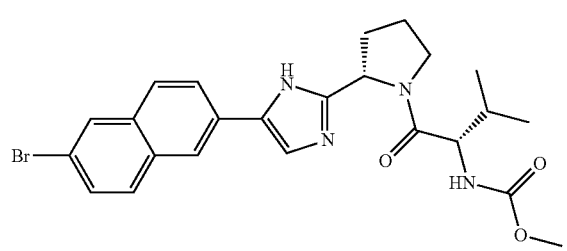
(1-{2-[5-(6-Bromonaphthalen-2-yl)-1H-imidazol-2-yl]-pyrrolidine-1-carbonyl}-2-methyl-propyl)-carbamic acid methyl ester -continued

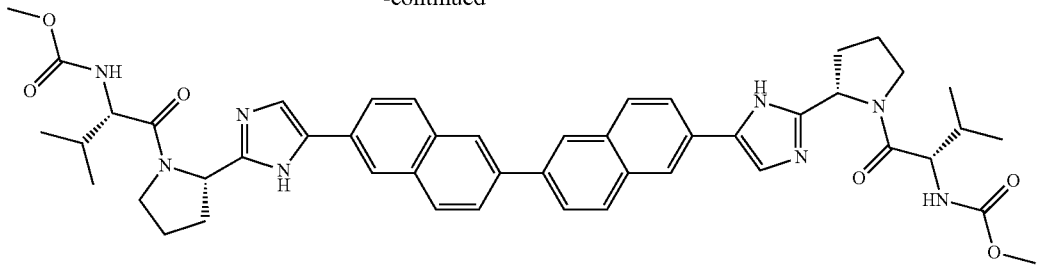

(1-{2-[5-(6'-{2-[1-(2-Methoxycarbonylamino-3-methyl-butyryl)-pyrrolidin-2-yl]-3H-imidazol-4-yl}-[2,2']binaphthalenyl-6-yl)-1H-imidazol-2-yl]-pyrrolidine-1-carbonyl}-2-methyl-propyl)-carbamic acid methyl ester

6-Bromo-naphthalene-2-carbonyl chloride

6-Bromonaphthalene-2-carboxylic acid (25.1 g) was suspended in thionyl chloride (200 mL), stirred at 60° C. for 16 hours and evaporated under vacuum. Solid was dissolved in dichloromethane (50 mL) and evaporated under vacuum, giving 6-bromonaphthalene-2-carbonyl chloride (27.0 g, crude) as a white solid.

1-(6-Bromo-naphthalen-2-yl)-2-diazo-ethanone

6-Bromonaphthalene-2-carbonyl chloride (27.0 g, crude) was dissolved in dichloromethane (330 mL) and cooled to 0° C. TMS diazomethane solution (100 mL, 2 M in DCM) was added, and ice bath was removed. Reaction mixture was stirred for 16 hours and evaporated under vacuum, giving 1-(6-bromonaphthalen-2-yl)-2-diazoethanone (34.7 g, crude) as an orange solid.

2-Bromo-1-(6-bromo-naphthalen-2-yl)-ethanone 1-(6-Bromonaphthalen-2-yl)-2-diazoethanone (34.7 g) were dissolved in ethyl acetate (500 mL), and hydrobromic acid solution (21.1 mL, 5.7 M in acetic acid) was added at 0° C. Reaction mixture was stirred 3 hours, NaHCO$_3$ solution (200 mL) was added, and mixture was stirred 10 minutes. Ethyl acetate solution was extracted twice with NaHCO$_3$ solution (50 mL), once with brine (50 mL), and evaporated under vacuum, giving 2-bromo-1-(6-bromonaphthalen-2-yl)-ethanone (33.0 g, crude) as a tan solid.

Pyrrolidine-1,2-dicarboxylic acid 2-[2-(6-bromo-naphthalen-2-yl)-2-oxo-ethyl]ester 1-tert-butyl ester Pyrrolidine-1,2-dicarboxylic acid 1-tert-butyl ester (24.0 g) was dissolved in acetonitrile (330 mL), and triethylamine (15.6 mL) was added. A solution of 2-bromo-1-(6-bromonaphthalen-2-yl)-ethanone (33.0 g) in acetonitrile (170 mL) were added. Reaction mixture was stirred over 3 days and evaporated under vacuum. Oil was dissolved in dichloromethane (100 mL), extracted with water (50 mL) and with NaHCO$_3$ solution (50 mL), and evaporated under vacuum to a concentrated liquid. Solution was purified by chromatography (0-30% ethyl acetate:hexane) and evaporated under vacuum, giving pyrrolidine-1,2-dicarboxylic acid 2-[2-(6-bromo-naphthalen-2-yl)-2-oxo-ethyl]ester 1-tert-butyl ester (39.2 g, 84%) as a tan solid.

2-[5-(6-Bromo-naphthalen-2-yl)-1H-imidazol-2-yl]pyrrolidine-1-carboxylic acid tert-butyl ester Pyrrolidine-1,2-dicarboxylic acid 2-[2-(6-bromonaphthalen-2-yl)-2-oxo-ethyl]ester 1-tert-butyl ester (39.0 g) and ammonium acetate (40.1 g) were suspended in xylenes (420 mL). The reaction mixture was stirred at 140° C. for 15 hours and evaporated under vacuum. Solid was dissolved in dichloromethane (300 mL), extracted twice with water (50 mL) and once with brine (50 mL), and evaporated under vacuum, giving 2-[5-(6-bromonaphthalen-2-yl)-1H-imidazol-2-yl]-pyrrolidine-1-carboxylic acid tert-butyl ester (30.3 g, 81%) as an off-white solid.

5-(6-Bromo-naphthalen-2-yl)-2-pyrrolidin-2-yl-1H-imidazole

2-[5-(6-Bromonaphthalen-2-yl)-1H-imidazol-2-yl]-pyrrolidine-1-carboxylic acid tert-butyl ester (5.03 g) was dissolved in dichloromethane (75 mL), and trifluoroacetic acid (25 mL) was added. The reaction mixture was stirred at ambient temperature for 5 hours and evaporated under vacuum. Solid was dissolved in dichloromethane (50 mL) and extracted with saturated NaHCO$_3$ solution (50 mL) Solid was collected by vacuum filtration, washed with dichloromethane, and dried under vacuum, giving 5-(6-Bromo-naphthalen-2-yl)-2-pyrrolidin-2-yl-1H-imidazole (98%) as an off-white solid.

(1-{2-[5-(6-Bromonaphthalen-2-yl)-1H-imidazol-2-yl]-pyrrolidine-4-carbonyl}-2-methyl-propyl)-carbamic acid methyl ester 5-(6-Bromo-naphthalen-2-yl)-2-pyrrolidin-2-yl-1H-imidazole (3.80 g), 2-methoxycarbonylamino-3-methyl-butyric acid (2.21 g), and HATU (5.06 g) were dissolved in anhydrous DMF (75 mL), and N-methylmorpholine (2.68 mL) was added. The reaction mixture was stirred at ambient temperature for 16 hours and evaporated under vacuum. The oil was dissolved in dichloromethane, purified by chromatography (0-100% ethyl acetate:hexanes), and evaporated under vacuum, giving (1-{2-[5-(6-bromo-naphthalen-2-yl)-1H-imidazol-2-yl]-pyrrolidine-1-carbonyl}-2-methyl-propyl)-carbamic acid methyl ester (0.814 g, 72%) as an off-white solid.

[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (1-{2-[5-(6-Bromonaphthalen-2-yl)-1H-imidazol-2-yl]-pyrrolidine-1-carbonyl}-2-methyl-propyl)-carbamic acid methyl ester (3.02 g), bis-(pinocolato)diborane (3.18 g), and potassium acetate (1.52 g) were dissolved in 1,4-dioxane (40 mL), and solution was degassed with nitrogen. Pd(PPh$_3$)$_4$ (0.285 g) was added, and the reaction mixture was stirred at 80° C. for 20 hours and evaporated under vacuum. Solid was dissolved in dichloromethane (50 mL), extracted with saturated NaHCO$_3$ solution (50 mL), and evaporated under vacuum. The oil was dissolved in dichloromethane, purified by chromatography (0-10% isopropanol:dichloromethane), and evaporated under vacuum, giving [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (3.65 g, crude) as a yellow solid.

(1-{2-[5-(6'-{2-[1-(2-Methoxycarbonylamino-3-methyl-butyryl)-pyrrolidin-2-yl]-3H-imidazol-4-yl}-[2,2]binaphthalenyl-6-yl)-1H-imidazol-2-yl]-pyrrolidine-1-carbonyl}-2-methyl-propyl)-carbamic acid methyl ester (1-{2-[5-(6-Bromonaphthalen-2-yl)-1H-imidazol-2-yl]-pyrrolidine-1-carbonyl}-2-methyl-propyl)-carbamic acid methyl ester (0.174 g), [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (0.202 g), and NaHCO$_3$ (0.108 g) were dissolved in a mixture of 1,2-dimethoxyethane (6 mL) and water (2 mL). The solution was degassed with nitrogen, and Pd(PPh$_3$)$_4$ (0.0176 g) was added. The reaction mixture was stirred at 85° C. for 16 hours and evaporated under vacuum. Solid was dissolved in ethyl acetate (10 mL) and extracted twice with water (10 mL) and once with brine (10 mL) Solution was evaporated, dissolved in DMF, purified by reverse phase HPLC (5-70% acetonitrile:water), and lyophilized, giving (1-{2-[5-(6'-{2-[1-(2-Methoxycarbonylamino-3-methyl-butyryl)-pyrrolidin-2-yl]-3H-imidazol-4-yl}-[2,2']binaphthalenyl-6-yl)-1H-imidazol-2-yl]-pyrrolidine-1-carbonyl}-2-methyl-propyl)-carbamic acid methyl ester (0.050 g, 16%) as a white solid: $^1$H-NMR: 300 MHz, (MeOH-d$_4$) δ: 8.3 (m, 4H), 8.1 (m, 6H), 8.0 (s, 2H), 7.8 (d, J=9.4, 2H), 5.3 (m, 2H), 4.3 (d, J=9.0, 2H), 4.1 (m, 2H), 3.9 (m, 2H), 3.7 (s, 6H), 2.6 (m, 2H), 2.2 (m, 6H), 0.9 (m, 12H); MS (ESI) m/z 839 [M+H]$^+$.

Example CM

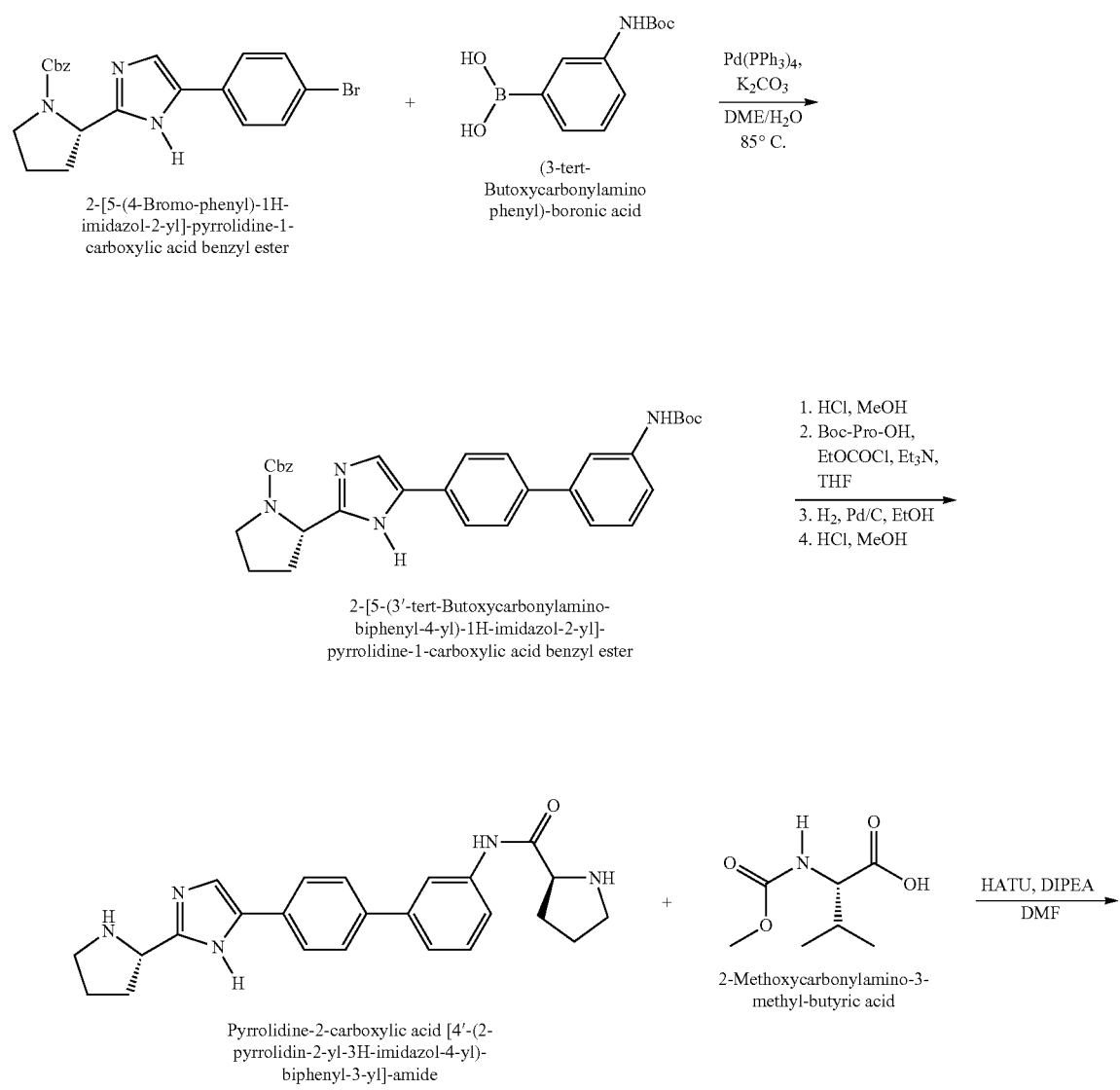

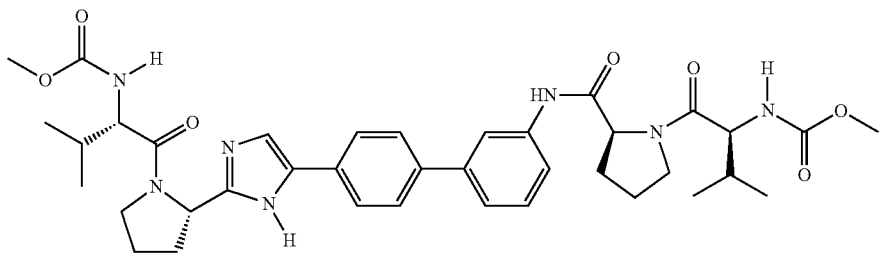

(1-{2-[5-(3'-{[1-(2-Methoxycarbonylamino-3-methyl-butyryl)-
pyrrolidine-2-carbonyl]-amino}-biphenyl-4-yl)-1H-imidazol-2-yl]-
pyrrolidine-1-carbonyl}-2-methyl-propyl)-carbamic acid methyl ester 2-[5-(3'-tert-Butoxycarbonylamino-biphenyl-4-yl)-
1H-imidazol-2-yl]-pyrrolidine-1-carboxylic acid
benzyl ester 2-[5-(4-Bromo-phenyl)-1H-imidazol-2-yl]-pyrrolidine-1-carboxylic acid benzyl ester (2.14 g, 5.01 mmol), (3-tert-Butoxycarbonylaminophenyl)-boronic acid (1.19 g, 5.01 mmol), Pd(PPh$_3$)$_4$ (289 mg, 0.251 mmol) and K$_2$CO$_3$ (5.5 mL of 2 M aqueous solution, 11.02 mmol) were combined with 1,2-dimethoxyethane (20 mL). The suspension was stirred while N$_2$ was bubbled through the solution for 24 min. A reflux condenser was attached and the suspension was heated to 85° C. for 17 hours. It was then cooled, diluted with ethyl acetate (150 mL), washed with water and brine, dried over sodium sulfate and concentrated. The crude product was purified by silica column chromatography (25% to 50% EtOAc/hexanes) to provide 2-[5-(3'-tert-Butoxycarbonylamino-biphenyl-4-yl)-1H-imidazol-2-yl]-pyrrolidine-1-carboxylic acid benzyl ester (1.73 g, 64%).

Pyrrolidine-2-carboxylic acid [4'-(2-pyrrolidin-2-yl-
3H-imidazol-4-yl)-biphenyl-3-yl]-amide 2-[5-(3'-tert-Butoxycarbonylamino-biphenyl-4-yl)-1H-imidazol-2-yl]-pyrrolidine-1-carboxylic acid benzyl ester (1.75 g, 3.25 mmol) was dissolved in methanol (40 mL) and concentrated HCl (2 mL) was added. The solution was stirred at 50° C. for 19 hours before being concentrated to a volume of 10 mL, poured into saturated NaHCO$_3$ (60 mL). The organic phase was extracted 3 times with 30 mL dichloromethane. The combined organic phases were dried with sodium sulfate and concentrated. A portion of the resulting residue (515 mg, 1.17 mmol) was dissolved in THF (2 mL) In a separate flask, ethylchloroformate (0.134 mL, 1.41 mmol) was added dropwise to a stirred 0° C. solution of Boc-Pro-OH (303 mg, 1.41 mmol) and triethylamine (0.197 mL, 1.41 mmol) in THF (4 mL). After 10 minutes, the solution of biphenyl compound was added by cannula followed by a 2 mL rinse with THF. Following addition, the mixture was warmed to RT. After 70 min, the mixture was diluted with ethyl acetate (60 mL) and washed with water and brine. The organic phase was dried over sodium sulfate and concentrated. The residue was purified by silica column chromatography (25% to 50% EtOAc/hexanes) to provide the Boc-Pro compound (470 mg, 63%). This material was dissolved in ethanol (40 mL) and 10% Pd/C (300 mg) was added before the flask was sealed and a bladder containing hydrogen gas was attached. A venting needle was placed in the septum for 30 s to allow hydrogen to bubble through the solution. After 13 h, the mixture was filtered over CELITE and concentrated. A portion of this residue (177 mg, 0.353 mmol) was dissolved in methanol (20 mL) and concentrated HCl (2 mL) was added. The mixture was stirred at 60° C. before being concentrated to provide Pyrrolidine-2-carboxylic acid [4'-(2-pyrrolidin-2-yl-3H-imidazol-4-yl)-biphenyl-3-yl]-amide (142 mg, 100%).

(1-{2-[5-(3'-{[1-(2-Methoxycarbonylamino-3-methyl-butyryl)-pyrrolidine-2-carbonyl]-amino}-biphenyl-4-yl)-1H-imidazol-2-yl]-pyrrolidine-1-carbonyl}-2-methyl-propyl)-carbamic acid methyl ester Pyrrolidine-2-carboxylic acid [4'-(2-pyrrolidin-2-yl-3H-imidazol-4-yl)-biphenyl-3-yl]-amide (142 mg, 0.353 mmol), 2-Methoxycarbonylamino-3-methyl-butyric acid (124 mg, 0.706 mmol) and HATU (295 mg, 0.777 mmol) were suspended in DMF (7 mL) and cooled to 0° C. before DIPEA (0.615 mL, 3.53 mmol) was added. After 80 min, the mixture was warmed to RT then filtered and purified by reverse phase preparative HPLC, giving (1-{2-[5-(3'-{[1-(2-Methoxycarbonylamino-3-methyl-butyryl)-pyrrolidine-2-carbonyl]-amino}-biphenyl-4-yl)-1H-imidazol-2-yl]-pyrrolidine-1-carbonyl}-2-methyl-propyl)-carbamic acid methyl ester (50 mg, 20%): $^1$H NMR (DMSO-d6, 400 MHz) 10.11 (s, 1H), 7.92 (s, 1H), 7.83 (d, J=9.0 Hz, 2H), 7.80-7.56 (m, 3H), 7.41-7.29 (m, 4H), 5.90 (m, 1H), 4.47 (m, 1H), 4.05 (m, 2H), 3.82 (m, 3H), 3.64 (m, 2H), 3.54 (m, 6H), 2.18 (m, 2H), 2.02-1.92 (m, 6H), 0.96-0.82 (m, 12H); MS (ESI) m/z 716 [M+H]$^+$.

Example CN

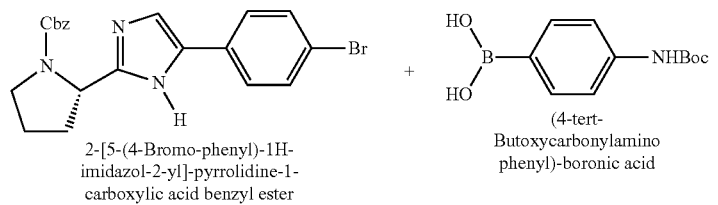

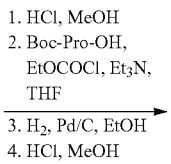

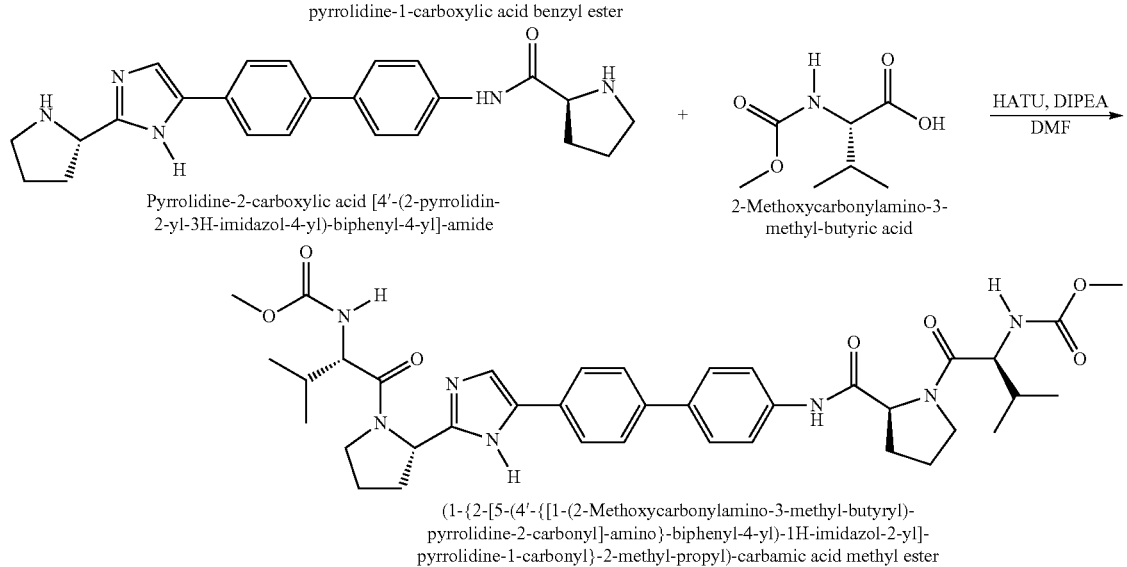

2-[5-(4'-tert-Butoxycarbonylamino-biphenyl-4-yl)-1H-imidazol-2-yl]-pyrrolidine-1-carboxylic acid benzyl ester 2-[5-(4-Bromo-phenyl)-1H-imidazol-2-yl]-pyrrolidine-1-carboxylic acid benzyl ester (2.31 g, 5.42 mmol), (4-tert-Butoxycarbonylaminophenyl)-boronic acid (1.28 g, 5.42 mmol), Pd(PPh$_3$)$_4$ (313 mg, 0.271 mmol) and K$_2$CO$_3$ (6 mL of 2 M aqueous solution, 11.92 mmol) were combined with 1,2-dimethoxyethane (20 mL). The suspension was stirred while N$_2$ was bubbled through the solution for 14 min. A reflux condenser was attached and the suspension was heated to 85° C. for 15 hours. It was then cooled, diluted with ethyl acetate (150 mL), washed with water and brine, dried over sodium sulfate and concentrated. The crude product was purified by silica column chromatography (25% to 50% EtOAc/hexanes) to provide 2-[5-(4'-tert-Butoxycarbonylamino-biphenyl-4-yl)-1H-imidazol-2-yl]-pyrrolidine-1-carboxylic acid benzyl ester (1.20 g, 41%).

Pyrrolidine-2-carboxylic acid [4'-(2-pyrrolidin-2-yl-3H-imidazol-4-yl)-biphenyl-4-yl]-amide 2-[5-(4'-tert-Butoxycarbonylamino-biphenyl-4-yl)-1H-imidazol-2-yl]-pyrrolidine-1-carboxylic acid benzyl ester (1.75 g, 3.25 mmol) was dissolved in methanol (40 mL) and concentrated HCl (2 mL) was added. The solution was stirred at 50° C. for 19 hours before being concentrated to a volume of 10 mL, poured into saturated NaHCO$_3$ (60 mL). The organic phase was extracted 3 times with 30 mL dichloromethane. The combined organic phases were dried with sodium sulfate and concentrated. A portion of the resulting residue (963 mg, 2.20 mmol) was dissolved in THF (4 mL). In a separate flask, ethylchloroformate (0.231 mL, 2.24 mmol) was added dropwise to a stirred 0° C. solution of Boc-Pro-OH (568 mg, 2.64 mmol) and triethylamine (0.368 mL, 2.69 mmol) in THF (6 mL). After 10 minutes, the solution of biphenyl compound was added by cannula followed by a 2 mL rinse with THF. Following addition, the mixture was warmed to RT. After 70 min, the mixture was diluted with ethyl acetate (60 mL) and washed with water and brine. The organic phase was dried over sodium sulfate and concentrated. The residue was purified by silica column chromatography (25% to 50% EtOAc/hexanes) to provide the Boc-Pro compound (470 mg, 63%). This material was dissolved in ethanol (40 mL) and 10% Pd/C (300 mg) was added before the flask was sealed and a bladder containing hydrogen gas was attached. A venting needle was placed in the septum for 30 s to allow hydrogen to bubble through the solution. After 14 h, the mixture was filtered over CELITE and concentrated. A portion of this residue (169 mg, 0.337 mmol) was dissolved in methanol (20 mL) and concentrated HCl (2 mL) was added. The mixture was stirred at 60° C. before being concentrated to provide Pyrrolidine-2-carboxylic acid [4'-(2-pyrrolidin-2-yl-3H-imidazol-4-yl)-biphenyl-4-yl]-amide (135 mg, 100%).

(1-{2-[5-(4'-{[1-(2-Methoxycarbonylamino-3-methyl-butyryl)-pyrrolidine-2-carbonyl]-amino}-biphenyl-4-yl)-1H-imidazol-2-yl]-pyrrolidine-1-carbonyl}-2-methyl-propyl)-carbamic acid methyl ester Pyrrolidine-2-carboxylic acid [4'-(2-pyrrolidin-2-yl-3H-imidazol-4-yl)-biphenyl-4-yl]-amide (135 mg, 0.337 mmol), 2-Methoxycarbonylamino-3-methyl-butyric acid (118 mg, 0.674 mmol) and HATU (282 mg, 0.741 mmol) were suspended in DMF (6 mL) and cooled to 0° C. before DIPEA (0.470 mL, 2.70 mmol) was added. After 60 min, the mixture was warmed to RT then filtered and purified by reverse phase preparative HPLC, giving (1-{2-[5-(4'-{[1-(2-Methoxycarbonylamino-3-methyl-butyryl)-pyrrolidine-2-carbonyl]-amino}-biphenyl-4-yl)-1H-imidazol-2-yl]-pyrrolidine-1-carbonyl}-2-methyl-propyl)-carbamic acid methyl ester (136 mg, 56%). $^1$H NMR (DMSO-d6, 400 MHz) 10.16 (s, 1H), 8.07 (s, 1H), 7.80 (d, J=4.5 Hz, 4H), 7.70 (d, J=4.5 Hz, 4H), 7.30 (m, 1H), 5.09 (m, 1H), 4.44 (m, 1H), 4.08 (m, 1H), 4.02 (m, 1H), 3.85-3.77 (m, 3H), 3.61 (m, 1H), 3.54 (s, 3H), 3.53 (s, 3H), 2.37 (m, 1H), 2.16-1.84 (m, 10H), 0.92 (d, J=6.7 Hz, 3H), 0.86 (d, 6.5 Hz, 3H), 0.80 (d, J=6.9 Hz, 3H), 0.75 (d, J=6.6 Hz, 3H); MS (ESI) m/z 716 [M+H]$^+$.

Example CO

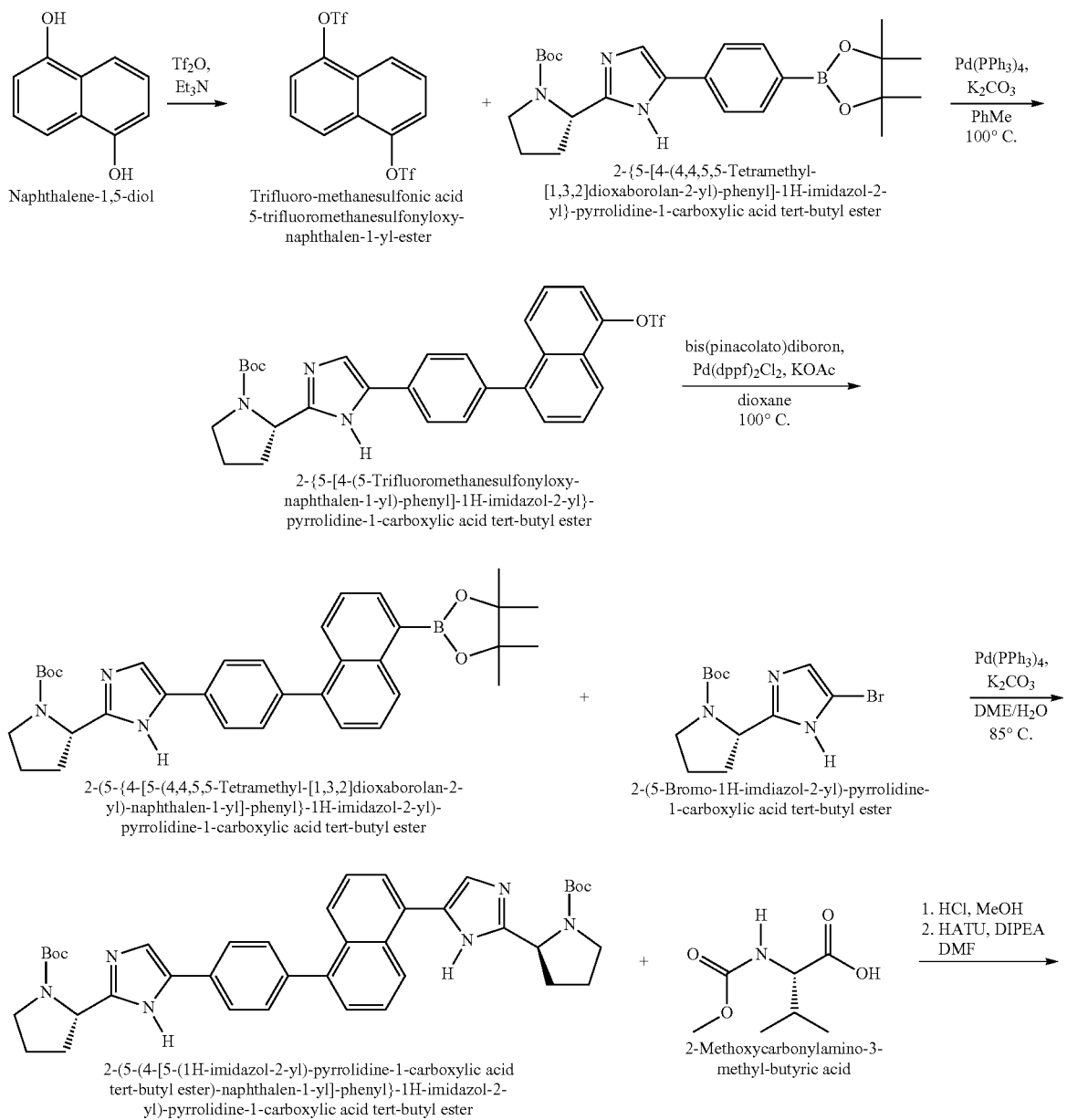

-continued

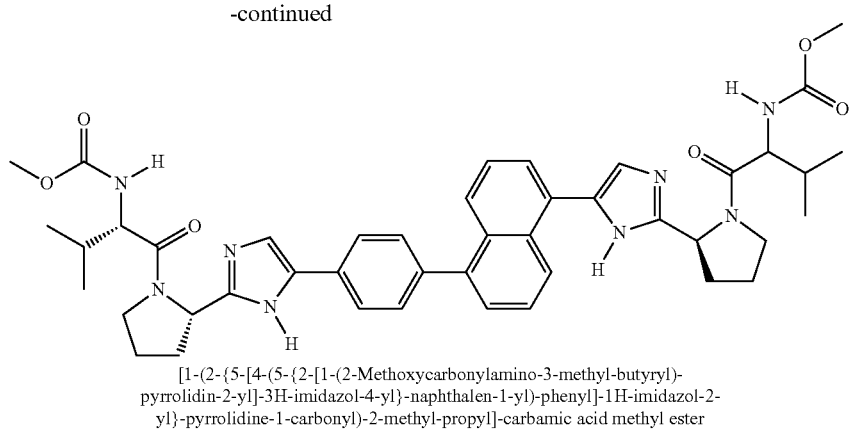

[1-(2-{5-[4-(5-{2-[1-(2-Methoxycarbonylamino-3-methyl-butyryl)-
pyrrolidin-2-yl]-3H-imidazol-4-yl}-naphthalen-1-yl)-phenyl]-1H-imidazol-2-
yl}-pyrrolidine-1-carbonyl)-2-methyl-propyl]-carbamic acid methyl ester Trifluoro-methanesulfonic acid
5-trifluoromethanesulfonyloxy-naphthalen-1-yl ester Naphthalene-1,5-diol (1 g, 6.25 mmol) was dissolved in dichloromethane (25 mL) and triethylamine (2.6 mL, 18.73 mmol) and trifluoromethanesulfonic anhydride (1.58 mL, 9.86 mmol) were added. After stirring for 16 h, the mixture was diluted with ethyl acetate (250 mL) and washed with water, saturated aqueous sodium bicarbonate and brine. The organic phase was dried over sodium sulfate, concentrated and purified by silica column chromatography (0% to 10% EtOAc/hexanes) to provide Trifluoro-methanesulfonic acid 5-trifluoromethanesulfonyloxy-naphthalen-1-yl ester (957 mg, 48%).

2-{5-[4-(5-Trifluoromethanesulfonyloxy-naphthalen-
1-yl)-phenyl]-1H-imidazol-2-yl}-pyrrolidine-1-car-
boxylic acid tert-butyl ester 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (1.30 g, 2.96 mmol), Trifluoro-methanesulfonic acid 5-trifluoromethanesulfonyloxy-naphthalen-1-yl ester (982 mg, 2.31 mmol), Pd(PPh$_3$)$_4$ (134 mg, 0.116 mmol) and potassium carbonate (639 mg, 4.62 mmol) were suspended in toluene. After degassing with nitrogen for 28 min, the stirred suspension was heated to 100° C. for 18 hours. The reaction mixture was then cooled to RT, diluted with ethyl acetate (250 mL), washed with water, brine, dried over magnesium sulfate and concentrated. The resulting residue was purified by silica column chromatography (0% to 60% EtOAc/hexanes) to provide 2-{5-[4-(5-Trifluoromethanesulfonyloxy-naphthalen-1-yl)-phenyl]-1H-imidazol-2-yl}-pyrrolidine-1-carboxylic acid tert-butyl ester (1.09 g, 80%).

2-(5-{4-[5-(4,4,5,5-Tetramethyl-[1,3,2]dioxaborolan-
2-yl)-naphthalen-1-yl]-phenyl}-1H-imidazol-2-yl)-
pyrrolidine-1-carboxylic acid tert-butyl ester 2-{5-[4-(5-Trifluoromethanesulfonyloxy-naphthalen-1-yl)-phenyl]-1H-imidazol-2-yl}-pyrrolidine-1-carboxylic acid tert-butyl ester (468 mg, 0.796 mmol), bis(pinacolato) diboron (202 mg, 0.796 mmol), Pd(dppf)$_2$Cl$_2$ (29 mg, 0.0398 mmol) and potassium acetate (234 mg, 2.39 mmol) were suspended in dioxane (4 mL) and heated to 100° C. for 90 min. After cooling to RT, the reaction mixture was diluted with ethyl acetate (100 mL) and washed with water and brine. The organic phase was dried over magnesium sulfate and concentrated. The resulting residue was purified by silica column chromatography (40% to 60% EtOAc/hexanes) to provide 2-(5-{4-[5-(4,4,5,5-Tetramethyl-[1,3,2]dioxaborolan-2-yl)-naphthalen-1-yl]-phenyl}-1H-imidazol-2-yl)-pyrrolidine-1-carboxylic acid tert-butyl ester (450 mg, 100%).

2-(5-{4-[5-(1H-imidazol-2-yl)-pyrrolidine-1-car-
boxylic acid tert-butyl ester)-naphthalen-1-yl]-phe-
nyl}-1H-imidazol-2-yl)-pyrrolidine-1-carboxylic
acid tert-butyl ester 2-(5-{4-[5-(4,4,5,5-Tetramethyl-[1,3,2]dioxaborolan-2-yl)-naphthalen-1-yl]-phenyl}-1H-imidazol-2-yl)-pyrrolidine-1-carboxylic acid tert-butyl ester (159 mg, 0.281 mmol), 2-(5-Bromo-1H-imidazol-2-yl)-pyrrolidine-1-carboxylic acid tert-butyl ester (178 mg (0.562 mmol), Pd(PPh$_3$)$_4$ (65 mg, 0.0562 mmol) and K$_2$CO$_3$ (0.281 mL of a 2 M aqueous solution, 0.562 mmol) were combined in 1,2-dimethoxyethane (3 mL) and degassed with bubbling N$_2$ for 12 min. The mixture was then heated to 85° C. for 22 hours then cooled to RT, diluted with ethyl acetate (50 mL) and washed with water and brine. The organic phase was dried over magnesium sulfate and concentrated. The crude residue was purified by silica column chromatography (80% to 100% EtOAc/hexanes) to afford 2-(5-{4-[5-(1H-imidazol-2-yl)-pyrrolidine-1-carboxylic acid tert-butyl ester)-naphthalen-1-yl]-phenyl}-1H-imidazol-2-yl)-pyrrolidine-1-carboxylic acid tert-butyl ester (42 mg, 22%).

[1-(2-{5-[4-(5-{2-[1-(2-Methoxycarbonylamino-3-
methyl-butyryl)-pyrrolidin-2-yl]-3H-imidazol-4-yl}-
naphthalen-1-yl)-phenyl]-1H-imidazol-2-yl}-pyrroli-
dine-1-carbonyl)-2-methyl-propyl]carbamic acid
methyl ester 2-(5-{4-[5-(1H-imidazol-2-yl)-pyrrolidine-1-carboxylic acid tert-butyl ester)-naphthalen-1-yl]-phenyl}-1H-imidazol-2-yl)-pyrrolidine-1-carboxylic acid tert-butyl ester (41 mg, 0.0607 mg) was dissolved in methanol (5 mL) and concentrated HCl (1 mL) was added. The mixture was stirred at 60° C. for 2 hours then cooled and concentrated. To the residue was added 2-Methoxycarbonylamino-3-methyl-butyric acid (32 mg, 0.182 mmol), HATU (51 mg, 0.133 mmol) and DMF (2 mL). The mixture was cooled to 0° C. and DIPEA (0.063 mL, 0.364 mmol) was added. After 30 min, water (1 mL) was added and the mixture was filtered and purified by reverse phase preparative HPLC, giving [1-(2-{5-

[4-(5-{2-[1-(2-Methoxycarbonylamino-3-methyl-butyryl)-pyrrolidin-2-yl]-3H-imidazol-4-yl}-naphthalen-1-yl)-phenyl]-1H-imidazol-2-yl}-pyrrolidine-1-carbonyl)-2-methyl-propyl]-carbamic acid methyl ester (17.6 mg, 38%). $^1$H NMR (MeOH-d4, 400 MHz) 8.03 (d, J=8.6 Hz, 1H), 7.98 (d, J=8.6 Hz, 1H), 7.89 (m, 2H), 7.72-7.57 (m, 6H), 7.16 (m, 1H), 5.28 (m, 2H), 4.25 (m, 2H), 4.11 (m, 3H), 3.86 (m, 3H), 3.67 (s, 3H), 3.65 (s, 3H), 2.59 (m, 2H), 2.30-2.04 (m, 8H), 0.95-0.89 (m, 12H); MS (ESI) m/z 789 [M+H]$^+$.

Example CP

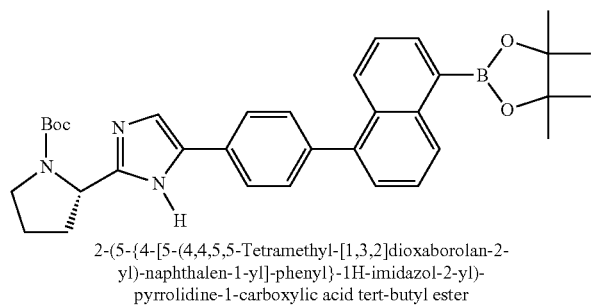

contents were then cooled to RT, diluted with ethyl acetate (50 mL), washed with water and brine, dried over magnesium sulfate and concentrated. The crude residue was purified by silica column chromatography (80% to 100% EtOAc/hexanes) to provide {1-[2-(5-{4-[5-(4-{2-[1-(2-Methoxycarbonylamino-3-methyl-butyryl)-pyrrolidin-2-yl]-3H-imidazol-4-yl}-phenyl)-naphthalen-1-yl]-phenyl}-1H-imidazol-2-yl)-pyrrolidine-1-carboxylic acid tert butyl ester (28 mg, 22%). The Suzuki product was dissolved in methanol (5 mL) and treated with concentrated HCl (1 mL). The mixture was heated to 60° C. for 100 min then cooled and concentrated. To the residue was added 2-Methoxycarbonylamino-3-methyl-

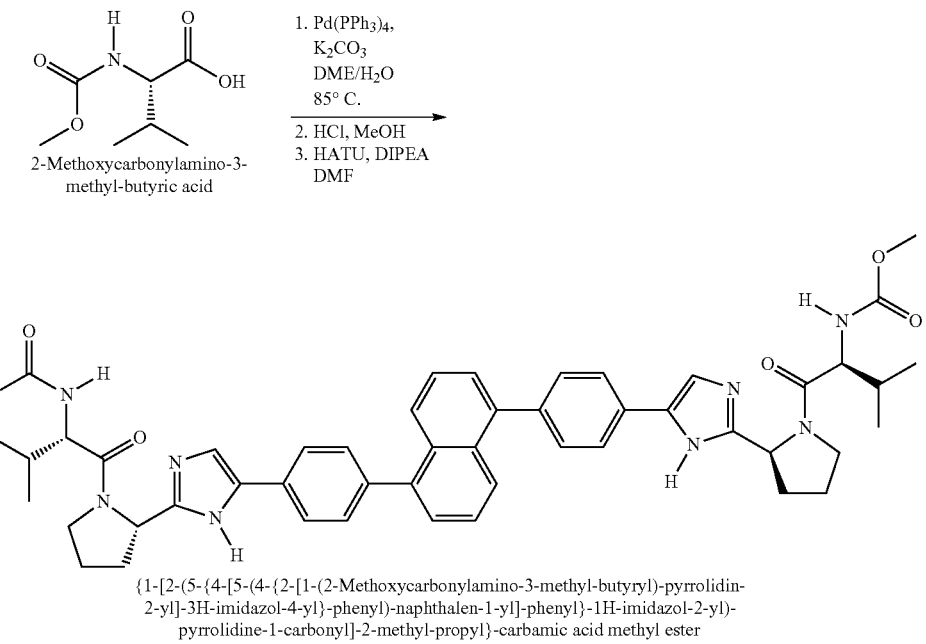

{1-[2-(5-{4-[5-(4-{2-[1-(2-Methoxycarbonylamino-3-methyl-butyryl)-pyrrolidin-2-yl]-31'-imidazol-4-yl}-phenyl)-naphthalen-1-yl]-phenyl}-1H-imidazol-2-yl)-pyrrolidine-1-carbonyl]-2-methyl-propyl}-carbamic acid methyl ester 2-(5-{4-[5-(4,4,5,5-Tetramethyl-[1,3,2]dioxaborolan-2-yl)-naphthalen-1-yl]-phenyl}-1H-imidazol-2-yl)-pyrrolidine-1-carboxylic acid tert-butyl ester (98 mg, 0.173 mmol), 2-[5-(4-Bromo-phenyl)-1H-imidazol-2-yl]-pyrrolidine-1-carboxylic acid tert-butyl ester (102 mg, 0.260 mmol), Pd(PPh$_3$)$_4$ (40 mg, 0.035 mmol) and potassium carbonate (0.173 mL of a 2 M aqueous solution, 0.346 mmol) were suspended in 1,2-dimethoxyethane. The mixture was degassed for 10 min then heated to 85° C. for 4 hours. The butyric acid (20 mg, 0.112 mmol), HATU (31 mg, 0.0821 mmol) and DMF (2 mL). The stirred mixture was cooled to 0° C. then DIPEA (0.033 mL, 0.187 mmol) was added. After 50 min, the reaction mixture was diluted with 1 mL of water and purified by reverse phase preparative HPLC to provide {1-[2-(5-{4-[5-(4-{2-[1-(2-Methoxycarbonylamino-3-methyl-butyryl)-pyrrolidin-2-yl]-3H-imidazol-4-yl}-phenyl)-naphthalen-1-yl]-phenyl}-1H-imidazol-2-yl)-pyrrolidine-1-carbonyl]-2-methyl-propyl}-carbamic acid methyl ester (12 mg, 38%). $^1$H NMR (MeOH-d$_4$, 400 MHz) 7.89-7.87 (m, 4H), 7.80-7.78 (m, 4H), 7.49-7.41 (m, 8H), 5.22 (m, 2H), 4.26 (m, 2H), 4.02 (m, 2H), 3.91 (m, 2H), 3.66 (s, 6H), 2.40-2.19 (m, 6H), 2.11-2.03 (m, 4H), 0.96 (d, J=6.6 Hz, 6H), 0.92 (d, J=6.6 Hz, 6H); MS (ESI) m/z 865 [M+H]$^+$.

Example CQ

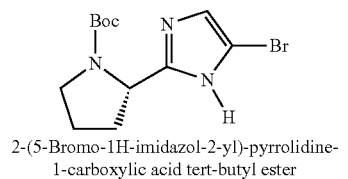

2-(5-Bromo-1H-imidazol-2-yl)-pyrrolidine-1-carboxylic acid tert-butyl ester

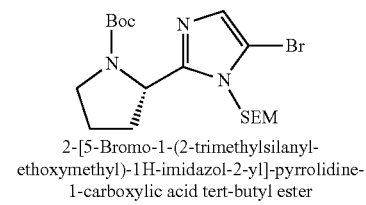

2-[5-Bromo-1-(2-trimethylsilanyl-ethoxymethyl)-1H-imidazol-2-yl]-pyrrolidine-1-carboxylic acid tert-butyl ester

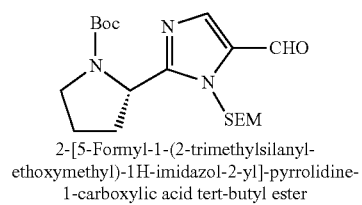

2-[5-Formyl-1-(2-trimethylsilanyl-ethoxymethyl)-1H-imidazol-2-yl]-pyrrolidine-1-carboxylic acid tert-butyl ester

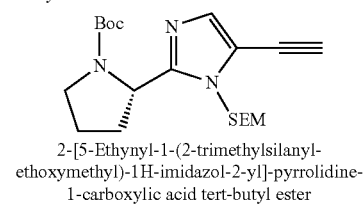

2-[5-Ethynyl-1-(2-trimethylsilanyl-ethoxymethyl)-1H-imidazol-2-yl]-pyrrolidine-1-carboxylic acid tert-butyl ester

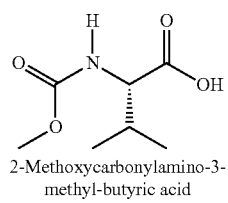

2-Methoxycarbonylamino-3-methyl-butyric acid

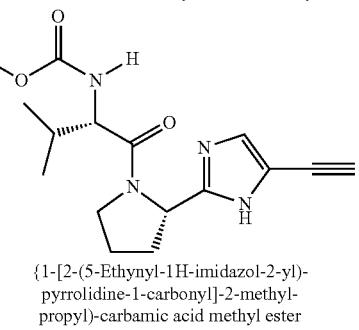

{1-[2-(5-Ethynyl-1H-imidazol-2-yl)-pyrrolidine-1-carbonyl]-2-methyl-propyl}-carbamic acid methyl ester

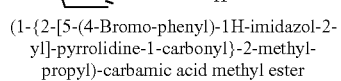

(1-{2-[5-(4-Bromo-phenyl)-1H-imidazol-2-yl]-pyrrolidine-1-carbonyl}-2-methyl-propyl)-carbamic acid methyl ester

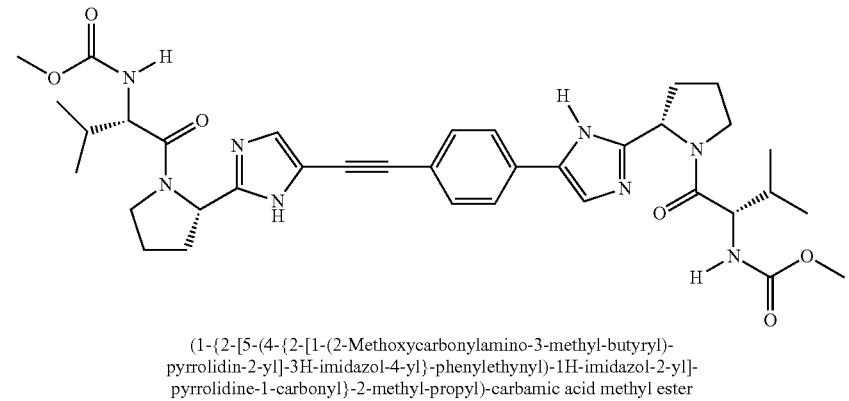

(1-{2-[5-(4-{2-[1-(2-Methoxycarbonylamino-3-methyl-butyryl)-pyrrolidin-2-yl]-3H-imidazol-4-yl}-phenylethynyl)-1H-imidazol-2-yl]-pyrrolidine-1-carbonyl}-2-methyl-propyl)-carbamic acid methyl ester

2-[5-Bromo-1-(2-trimethylsilanyl-ethoxymethyl)-1H-imidazol-2-yl]-pyrrolidine-1-carboxylic acid tert-butyl ester 2-(5-Bromo-1H-imidazol-2-yl)-pyrrolidine-1-carboxylic acid tert-butyl ester (4 g, 12.65 mmol) was dissolved in DMF and cooled to 0° C. NaH (658 mg of 60% mineral oil dispersion, 16.45 mmol) was added and the reaction mixture was aged for 13 min before addition of SEMCl (2.7 mL, 15.18 mmol) and warming to RT. After 16 h, the reaction was quenched by water, diluted with ethyl acetate (300 mL) and washed with water and brine. The organic phase was dried over magnesium sulfate and concentrated. The crude residue was purified by silica column chromatography (10% to 30% EtOAc/hexanes) to afford 2-[5-Bromo-1-(2-trimethylsilanyl-ethoxymethyl)-1H-imidazol-2-yl]-pyrrolidine-1-carboxylic acid tert-butyl ester (4.67 g, 83%).

2-[5-Formyl-1-(2-trimethylsilanyl-ethoxymethyl)-1H-imidazol-2-yl]-pyrrolidine-1-carboxylic acid tert-butyl ester 2-[5-Bromo-1-(2-trimethylsilanyl-ethoxymethyl)-1H-imidazol-2-yl]-pyrrolidine-1-carboxylic acid tert-butyl ester (3.804 g, 8.52 mmol) was dissolved in THF (42 mL) and cooled to −78° C. n-BuLi (3.4 mL of a 2.5 M hexane solution, 8.52 mmol) was added dropwise over 3 min. After 65 min, DMF (4 mL) was added and the reaction mixture was warmed to RT. After stirring at RT for 75 min, a saturated aqueous solution of ammonium chloride (50 mL) was added and the entire content of the flask was poured into saturated aqueous sodium bicarbonate. The aqueous phase was extracted 3 times with diethyl ether. The combined organic layers were dried over magnesium sulfate, concentrated and purified by silica column chromatography (30% to 70% EtOAc/hexanes) to provide 2-[5-Formyl-1-(2-trimethylsilanyl-ethoxymethyl)-1H-imidazol-2-yl]-pyrrolidine-1-carboxylic acid tert-butyl ester (1.50 g, 45%).

2-[5-Ethynyl-1-(2-trimethylsilanyl-ethoxymethyl)-1H-imidazol-2-yl]-pyrrolidine-1-carboxylic acid tert-butyl ester 2-[5-Formyl-1-(2-trimethylsilanyl-ethoxymethyl)-1H-imidazol-2-yl]-pyrrolidine-1-carboxylic acid tert-butyl ester (1.625 g, 4.11 mmol) and dimethyl-1-diazo-2-oxopropylphosphonate (1.056 g, 5.50 mmol) were dissolved in 1:1 MeOH/THF (10 mL) and potassium carbonate (1.14 g, 8.25 mmol) was added. After stirring for 200 min, more potassium carbonate (1.14 g, 8.25 mmol) was added. 45 min later, the reaction mixture was poured into 100 mL 1:1 water/saturated aqueous sodium bicarbonate. The aqueous phase was extracted 3 times with diethyl ether. The combined organic phases were dried with magnesium sulfate and concentrated. The crude residue was purified by silica column chromatography (20% to 45% EtOAc/hexanes) to afford 2-[5-Ethynyl-1-(2-trimethylsilanyl-ethoxymethyl)-1H-imidazol-2-yl]-pyrrolidine-1-carboxylic acid tert-butyl ester (1.234 g, 77%).

{1-[2-(5-Ethynyl-4H-imidazol-2-yl)-pyrrolidine-1-carbonyl]-2-methyl-propyl}-carbamic acid methyl ester 2-[5-Ethynyl-1-(2-trimethylsilanyl-ethoxymethyl)-1H-imidazol-2-yl]-pyrrolidine-1-carboxylic acid tert-butyl ester (1.002 g, 2.56 mmol) was dissolved in dioxane (5 mL) and 4 M HCl in dioxane (5 mL) was added. The reaction mixture was stirred for 3 hours and concentrated. To the residue was added 2-Methoxycarbonylamino-3-methyl-butyric acid (561 mg, 3.20 mmol), HATU (1.22 g, 3.20 mmol) and DMF (15 mL). The stirred reaction mixture was cooled to 0° C. and DIPEA (2.23 mL, 12.8 mmol) was added). After stirring for 3 h, the reaction mixture was diluted with ethyl acetate and washed with a saturated aqueous solution of sodium bicarbonate and brine. The combined organic layers were dried over magnesium sulfate and concentrated. The crude residue was purified by silica column chromatography (40% to 75% EtOAc/hexanes) to provide the coupled compound (741 mg, 65% over 2 steps). This material was dissolved in dichloromethane (10 mL) and trifluoroacetic acid (5 mL) was added. The stirred reaction mixture was heated to reflux for 4 h, then cooled to RT, and poured into a saturated aqueous solution of sodium bicarbonate. The aqueous phase was extracted 3 times with dichloromethane. The combined organic layers were dried over magnesium sulfate and concentrated. The crude residue was purified by silica column chromatography (0% to 10% MeOH/DMC) to provide {1-[2-(5-Ethynyl-1H-imidazol-2-yl)-pyrrolidine-1-carbonyl]-2-methyl-propyl}-carbamic acid methyl ester (525 mg, 100%).

(1-{2-[5-(4-{2-[1-(2-Methoxycarbonylamino-3-methyl-butyryl)-pyrrolidin-2-yl]-3H-imidazol-4-yl}-phenylethynyl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (46 mg, 0.144 mmol), (1-{2-[5-(4-Bromo-phenyl)-1H-imidazol-2-yl]-pyrrolidine-1-carbonyl}-2-methyl-propyl)-carbamic acid methyl ester (78 mg, 0.173 mmol), Pd(PPh$_3$)$_4$ (17 mg, 0.0144 mmol), CuI (5 mg, 0.0288 mmol) and triethylamine (0.200 mL, 1.44 mmol) were suspended in DMF (1.5 mL). The reaction mixture was stirred at 80° C. for 2 hours then 1 mL of water was added and the mixture was purified by reverse phase preparative HPLC, giving (1-{2-[5-(4-{2-[1-(2-Methoxycarbonylamino-3-methyl-butyryl)-pyrrolidin-2-yl]-3H-imidazol-4-yl}-phenylethynyl)-1H-imidazol-2-yl]-pyrrolidine-1-carbonyl}-2-methyl-propyl)-carbamic acid methyl ester (24 mg, 24%). $^1$H NMR (MeOH-d4, 400 MHz) 7.65 (d, J=8.2 hz, 2H), 7.45 (d, J=8.2 hz, 2H), 7.38 (s, 1H), 7.22 (s, 1H), 6.98 (m, 1H), 5.17 (m, 1H), 5.11 (m, 1H), 4.25-4.20 (m, 2H), 4.01-3.79 (m, 4H), 3.66 (s, 6H), 2.37-2.00 (m, 10H), 0.99-0.89 (m, 12H); MS (ESI) m/z 687 [M+H]$^+$.

Example CR

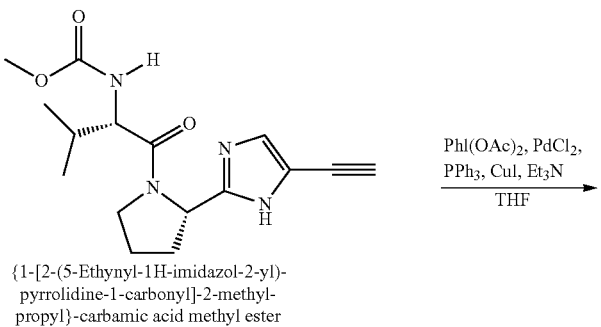

{1-[2-(5-Ethynyl-1H-imidazol-2-yl)-pyrrolidine-1-carbonyl]-2-methyl-propyl}-carbamic acid methyl ester PhI(OAc)$_2$, PdCl$_2$, PPh$_3$, CuI, Et$_3$N
THF

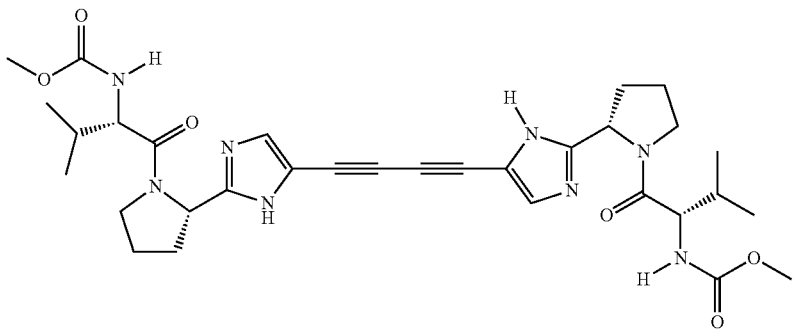

(1-{2-[5-(4-{2-[1-(2-Methoxycarbonylamino-3-methyl-butyryl)-pyrrolidin-2-yl]-3H-imidazol-4-yl}-buta-1,3-diynyl)-1H-imidazol-2-yl]-pyrrolidine-1-carbonyl}-2-methyl-propyl)-carbamic acid methyl ester (1-{2-[5-(4-{2-[1-(2-Methoxycarbonylamino-3-methyl-butyryl)-pyrrolidin-2-yl]-3H-imidazol-4-yl}-buta-1,3-diynyl)-1H-imidazol-2-yl]-pyrrolidine-1-carbonyl}-2-methyl-propyl)-carbamic acid methyl ester Triethylamine (0.270 mL, 1.92 mmol) was added to a mixture of {1-[2-(5-Ethynyl-1H-imidazol-2-yl)-pyrrolidine-1-carbonyl]-2-methyl-propyl}-carbamic acid methyl ester (61 mg, 0.192 mmol), PhI(OAc)$_2$ (247 mg, 0.766 mmol), PdCl$_2$ (7 mg, 0.0389 mmol), PPh$_3$ (30 mg, 0.115 mmol) and CuI (7 mg, 0.0389 mmol) in THF (2 mL). After 50 min, the reaction mixture was filtered, concentrated and purified by reverse phase preparative HPLC, giving (1-{2-[5-(4-{2-[1-(2-Methoxycarbonylamino-3-methyl-butyryl)-pyrrolidin-2-yl]-3H-imidazol-4-yl}-buta-1,3-diynyl)-1H-imidazol-2-yl]-pyrrolidine-1-carbonyl}-2-methyl-propyl)-carbamic acid methyl ester (3 mg, 5%). $^1$H NMR (MeOH-d4, 400 MHz) 7.33 (s, 2H), 6.95 (d, J=8.3 Hz, 2H), 5.07 (m, 2H), 4.18 (m, 2H), 3.95 (m, 2H), 3.82 (m, 2H), 3.64 (s, 6H), 2.31-1.98 (m, 10H), 1.02-0.87 (m, 12H); MS (ESI) m/z 635 [M+H]$^+$.

Example CS

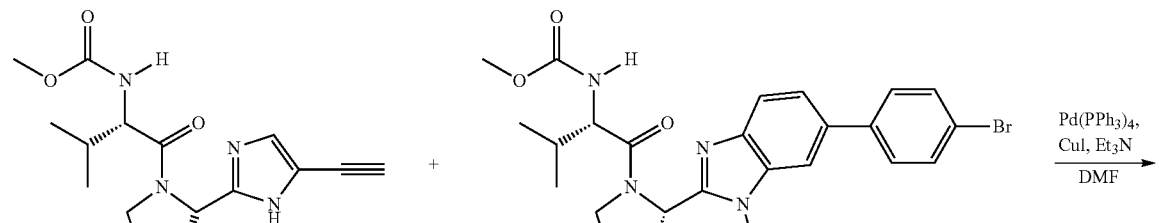

{1-[2-(5-Ethynyl-1H-imidazol-2-yl)-pyrrolidine-1-carbonyl]-2-methyl-propyl}-carbamic acid methyl ester (1-{2-[6-(4-Bromo-phenyl)-1H-benzoimidazol-2-yl]-pyrrolidine-1-carbonyl}-2-methyl-propyl)-carbamic acid methyl ester

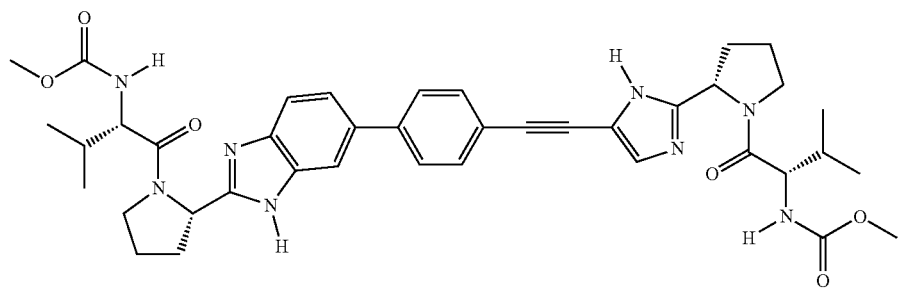

(1-{2-[6-(4-{2-[1-(2-Methoxycarbonylamino-3-methyl-butyryl)-pyrrolidin-2-yl]-3H-imidazol-4-ylethynyl}-phenyl)-1H-benzoimidazol-2-yl]-pyrroldine-1-carbonyl}-2-methyl-propyl)-carbamic acid methyl ester

(1-{2-[6-(4-{2-[1-(2-Methoxycarbonylamino-3-methyl-butyryl)-pyrrolidin-2-yl]-3H-imidazol-4-ylethynyl}-phenyl)-1H-benzoimidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (62 mg, 0.195 mmol), (1-{2-[6-(4-Bromo-phenyl)-1H-benzoimidazol-2-yl]-pyrrolidine-1-carbonyl}-2-methyl-propyl)-carbamic acid methyl ester (73 mg, 0.146 mmol), Pd(PPh$_3$)$_4$ (11 mg, 0.00975 mmol), CuI (4 mg, 0.0195 mmol) and triethylamine (0.271 mL, 1.95 mmol) were suspended in DMF (2 mL). The reaction mixture was stirred at 80° C. for 3 hours then 1 mL of water was added and the mixture was purified by reverse phase preparative HPLC, giving (1-{2-[6-(4-{2-[1-(2-Methoxycarbonylamino-3-methyl-butyryl)-pyrrolidin-2-yl]-3H-imidazol-4-ylethynyl}-phenyl)-1H-benzoimidazol-2-yl]-pyrrolidine-1-carbonyl}-2-methyl-propyl)-carbamic acid methyl ester (12 mg, 11%). $^1$H NMR (MeOH-d4, 400 MHz) 7.66-7.64 (m, 2H), 7.59-7.50 (m, 4H), 7.24 (s, 1H), 6.98 (m, 1H), 5.28 (m, 1H), 5.12 (m, 1H), 4.28-4.19 (m, 2H), 4.04-3.82 (m, 4H), 3.66 (s, 3H), 3.65 (s, 3H), 2.43-2.01 (m, 10H), 0.99-0.87 (m, 12H); MS (ESI) m/z 737 [M+H]$^+$.

Example CT

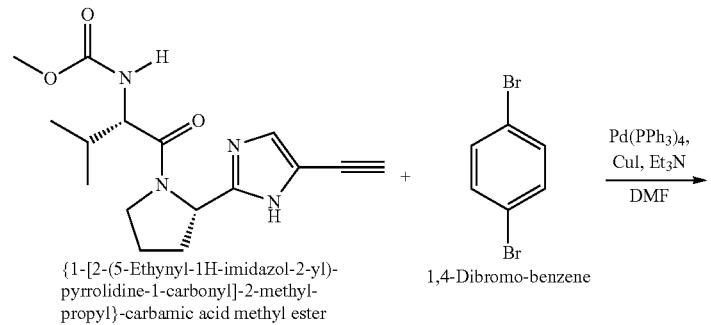

{1-[2-(5-Ethynyl-1H-imidazol-2-yl)-pyrrolidine-1-carbonyl]-2-methyl-propyl}-carbamic acid methyl ester 1,4-Dibromo-benzene

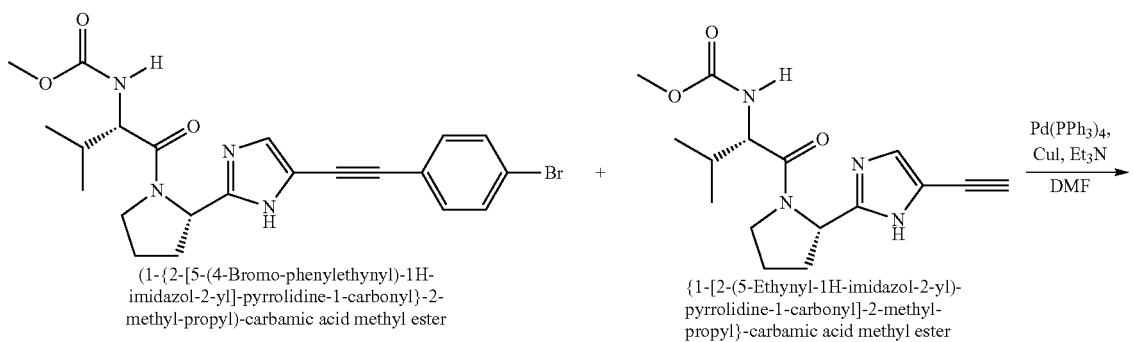

(1-{2-[5-(4-Bromo-phenylethynyl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester

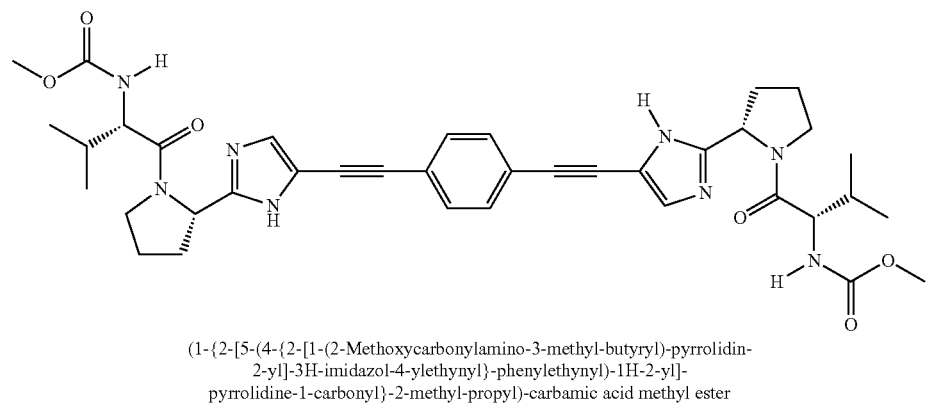

(1-{2-[5-(4-{2-[1-(2-Methoxycarbonylamino-3-methyl-butyryl)-pyrrolidin-2-yl]-3H-imidazol-4-ylethynyl}-phenylethynyl)-1H-2-yl]-pyrrolidine-1-carbonyl}-2-methyl-propyl)-carbamic acid methyl ester

(1-{2-[5-(4-Bromo-phenylethynyl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (57 mg, 0.179 mmol), 1,4-dibromobenzene (211 mg, 0.895 mmol), Pd(PPh$_3$)$_4$ (10 mg, 0.00895 mmol), CuI (3 mg, 0.0179 mmol) and triethylamine (0.249 mL, 1.79 mmol) were suspended in DMF (2 mL) and the mixture was degassed for 10 min with nitrogen. The reaction mixture was stirred at 80° C. for 70 min then diluted with 20 mL ethyl acetate and washed with saturated aqueous sodium bicarbonate and brine. The organic phase was dried with magnesium sulfate and concentrated. The crude residue was purified by silica column chromatography (0% to 5% MeOH/DCM) to afford (1-{2-[5-(4-Bromo-phenylethynyl)-1H-imidazol-2-yl]-pyrrolidine-1-carbonyl}-2-methyl-propyl)-carbamic acid methyl ester (43 mg, 51%).

(1-{2-[5-(4-{2-[1-(2-Methoxycarbonylamino-3-methyl-butyryl)-pyrrolidin-2-yl]-3H-imidazol-4-ylethynyl}-phenylethynyl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (49 mg, 0.154 mmol), (1-{2-[5-(4-bromo-phenylethynyl)-1H-imidazol-2-yl]-pyrrolidine-1-carbonyl}-2-methyl-propyl)-carbamic acid methyl ester (43 mg, 0.0908 mmol), Pd(PPh$_3$)$_4$ (10 mg, 0.00908 mmol), CuI (2 mg, 0.00908 mmol) and triethylamine (0.127 mL, 0.908 mmol) were suspended in DMF (2 mL) and the mixture was degassed for 10 min with nitrogen. The reaction mixture was stirred at 80° C. for 4 hours then cooled to RT. Formic acid (0.1 mL) and water (1 mL) were added and the mixture was purified by reverse phase preparative HPLC, giving (1-{2-[5-(4-{2-[1-(2-Methoxycarbonylamino-3-methyl-butyryl)-pyrrolidin-2-yl]-3H-imidazol-4-ylethynyl}-phenylethynyl)-1H-imidazol-2-yl]-pyrrolidine-1-carbonyl}-2-methyl-propyl)-carbamic acid methyl ester (11 mg, 17%). $^1$H NMR (MeOH-d4, 400 MHz) 7.46 (d, J=3.9 Hz, 4H), 7.25 (s, 2H), 6.96 (d, J=8.4 Hz, 2H), 5.10 (m, 2H), 4.20 (m, 2H), 3.97 (m, 2H), 3.83 (m, 2H), 3.64 (s, 6H), 2.32-2.00 (m, 10H), 0.98-0.88 (m, 12H); MS (ESI) m/z 711 [M+H]$^+$.

Example CU

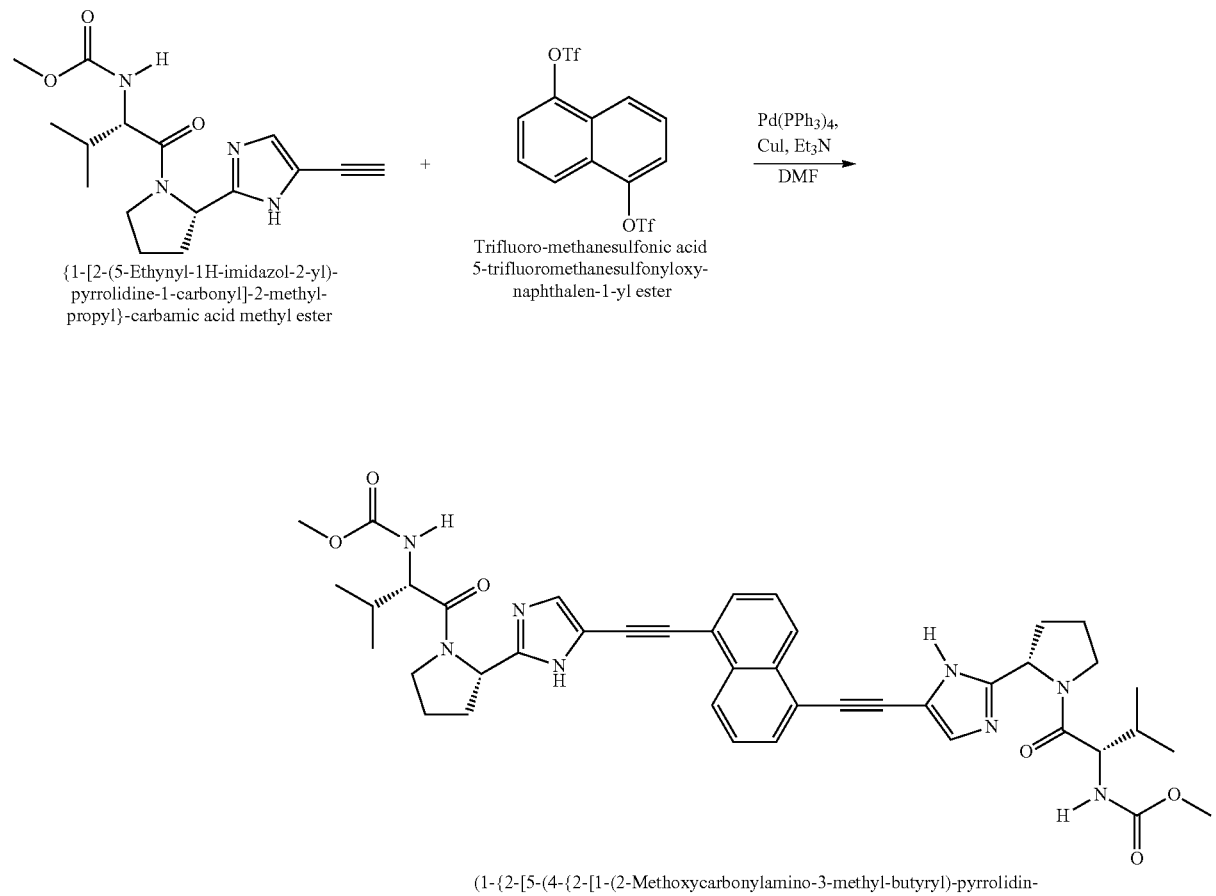

705

(1-{2-[5-(5-{2-[1-(2-Methoxycarbonylamino-3-methyl-butyryl)-pyrrolidin-2-yl]-3H-imidazol-4-ylethynyl}-naphthalen-1-ylethynyl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (98 mg, 0.207 mmol), trifluoro-methanesulfonic acid 5-trifluoromethanesulfonyloxy-naphthalen-1-yl ester (29 mg, 0.0683 mmol), Pd(PPh$_3$)$_4$ (12 mg, 0.0104 mmol), CuI (2 mg, 0.0104 mmol) and triethylamine (0.144 mL, 1.04 mmol) were suspended in DMF (2 mL) and the mixture was degassed for 10 min with nitrogen. The reaction mixture was stirred at 80° C. for 90 min then cooled to RT. Formic acid (0.1 mL) and water (1 mL) were added and the mixture was purified by reverse phase preparative HPLC, giving (1-{2-[5-(5-{2-[1-(2-Methoxycarbonylamino-3-methyl-butyryl)-pyrrolidin-2-yl]-3H-imidazol-4-ylethynyl}-naphthalen-1-ylethynyl)-1H-imidazol-2-yl]-pyrrolidine-1-carbonyl}-2-methyl-propyl)-carbamic acid methyl ester (30 mg, 58%). $^1$H NMR (MeOH-d4, 400 MHz) 8.38 (d, J=8.2 Hz, 2H), 7.71 (d, J=7.2 Hz, 2H), 7.57-7.51 (m, 2H), 7.35 (s, 2H), 6.96 (d, J=8.4 Hz, 2H), 5.13 (m, 2H), 4.20 (m, 2H), 3.95 (m, 2H), 3.83 (m, 2H), 3.63 (s, 6H), 2.33-1.98 (m, 10H), 0.97-0.87 (m, 12H); MS (ESI) m/z 761 [M+H]$^+$.

Example CV

706

(1-{2-[5-(4'-{2-[1-(2-Methoxycarbonylamino-3-methyl-butyryl)-pyrrolidin-2-yl]-3H-imidazol-4-ylethynyl}-biphenyl-4-yl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (44 mg, 0.138 mmol), (1-{2-[5-(4'-Bromo-biphenyl-4-yl)-1H-imidazol-2-yl]-pyrrolidine-1-carbonyl}-2-methyl-propyl)-carbamic acid methyl ester (67 mg, 0.128 mmol), Pd(PPh$_3$)$_4$ (15 mg, 0.0128 mmol), CuI (2 mg, 0.0128 mmol) and triethylamine (0.180 mL, 1.28 mmol) were suspended in DMF (2 mL) and the mixture was degassed for 10 min with nitrogen. The reaction mixture was stirred at 80° C. for 15 hours then cooled to RT. Formic acid (0.1 mL) and water (1 mL) were added and the mixture was purified by reverse phase preparative HPLC, giving (1-{2-[5-(4'-{2-[1-(2-Methoxycarbonylamino-3-methyl-butyryl)-pyrrolidin-2-yl]-3H-imidazol-4-ylethynyl}-biphenyl-4-yl)-1H-imidazol-2-yl]-pyrrolidine-1-carbonyl}-2-methyl-propyl)-carbamic acid methyl ester (12 mg, 12%). $^1$H NMR (MeOH-d4, 400 MHz) 7.73 (d, J=8.4 Hz, 2H), 7.66-7.64 (m, 4H), 7.52 (d, J=8.2 Hz, 2H), 7.35 (s, 1H), 7.24 (s, 1H), 6.98 (m, 2H), 5.18 (m, 1H), 5.11 (m, 1H), 4.26-4.19 (m, 2H), 4.01-3.80 (m, 4H), 3.65 (s, 6H), 2.37-2.01 (m, 10H), 1.00-0.88 (m, 12H); MS (ESI) m/z 763 [M+H]$^+$.

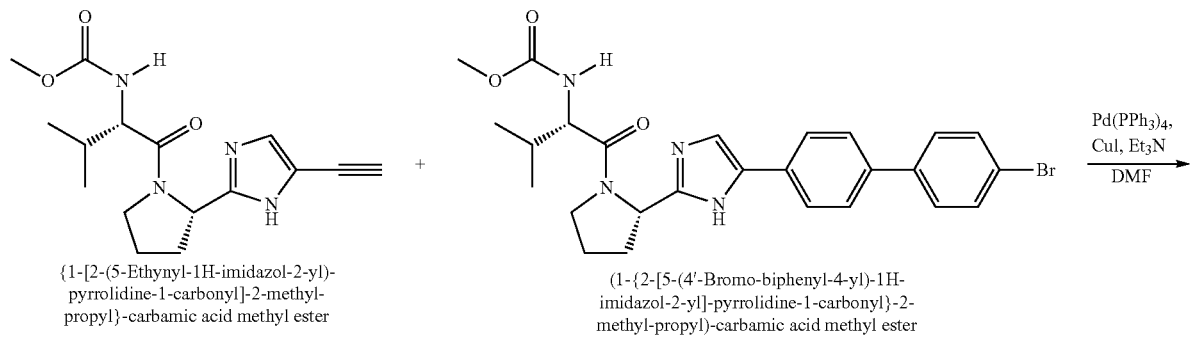

{1-[2-(5-Ethynyl-1H-imidazol-2-yl)-pyrrolidine-1-carbonyl]-2-methyl-propyl}-carbamic acid methyl ester (1-{2-[5-(4'-Bromo-biphenyl-4-yl)-1H-imidazol-2-yl]-pyrrolidine-1-carbonyl}-2-methyl-propyl)-carbamic acid methyl ester

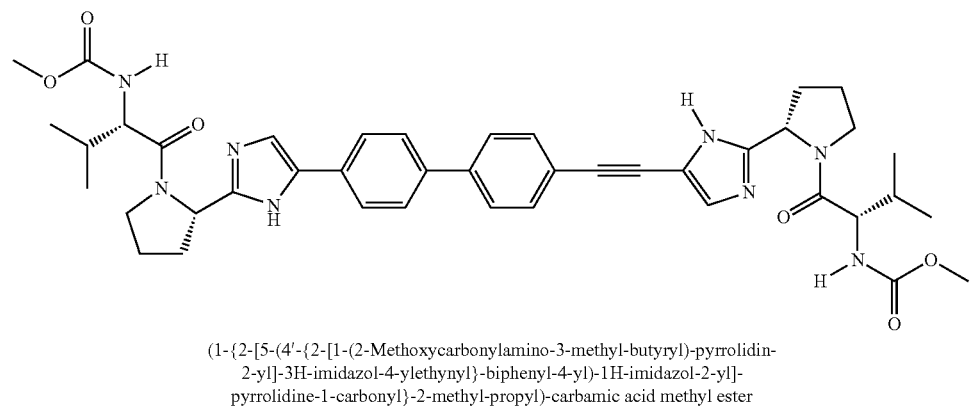

(1-{2-[5-(4'-{2-[1-(2-Methoxycarbonylamino-3-methyl-butyryl)-pyrrolidin-2-yl]-3H-imidazol-4-ylethynyl}-biphenyl-4-yl)-1H-imidazol-2-yl]-pyrrolidine-1-carbonyl}-2-methyl-propyl)-carbamic acid methyl ester Example CW

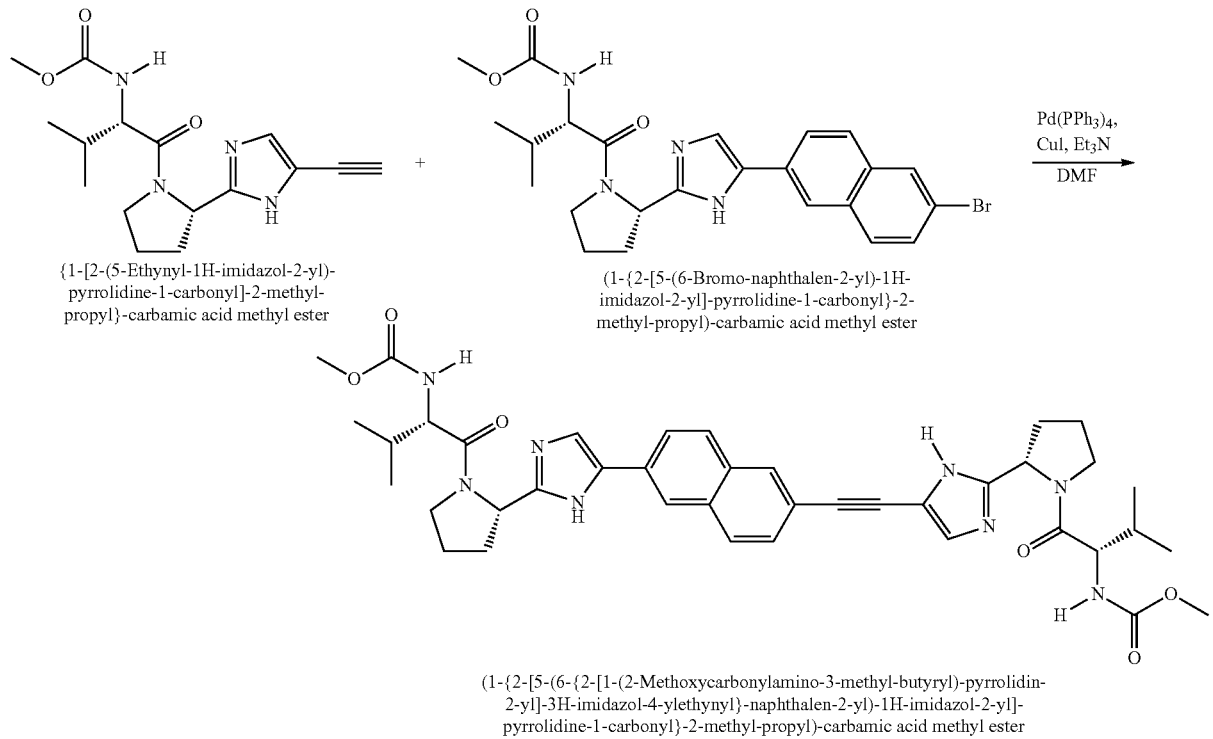

(1-{2-[5-(6-{2-[1-(2-Methoxycarbonylamino-3-methyl-butyryl)-pyrrolidin-2-yl]-3H-imidazol-4-ylethynyl}-naphthalen-2-yl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (53 mg, 0.166 mmol), (1-{2-[5-(6-Bromo-naphthalen-2-yl)-1H-imidazol-2-yl]-pyrrolidine-1-carbonyl}-2-methyl-propyl)-carbamic acid methyl ester (100 mg, 0.200 mmol), Pd(PPh$_3$)$_4$ (19 mg, 0.0166 mmol), CuI (3 mg, 0.0166 mmol) and triethylamine (0.230 mL, 1.66 mmol) were suspended in DMF (2 mL) and the mixture was degassed for 10 min with nitrogen. The reaction mixture was stirred at 80° C. for 1 hours then cooled to RT. Formic acid (0.1 mL) and water (1 mL) were added and the mixture was purified by reverse phase preparative HPLC, giving (1-{2-[5-(6-{2-[1-(2-Methoxycarbonylamino-3-methyl-butyryl)-pyrrolidin-2-yl]-3H-imidazol-4-ylethynyl}-naphthalen-2-yl)-1H-imidazol-2-yl]-pyrrolidine-1-carbonyl}-2-methyl-propyl)-carbamic acid methyl ester (24 mg, 20%). (DMSO-d6, 400 MHz) 12.00-11.85 (m, 2H), 7.99-7.83 (m, 4H), 7.64 (s, 1H), 7.48 (m, 1H), 7.42 (s, 1H), 7.29 (m, 2H), 5.10 (m, 1H), 5.03 (m, 1H), 4.06 (m, 2H), 3.82-3.76 (m, 4H), 3.54 (s, 6H), 2.15-1.97 (m, 10H), 0.94-0.81 (m, 12H); MS (ESI) m/z 737 [M+H]$^+$.

Example CX

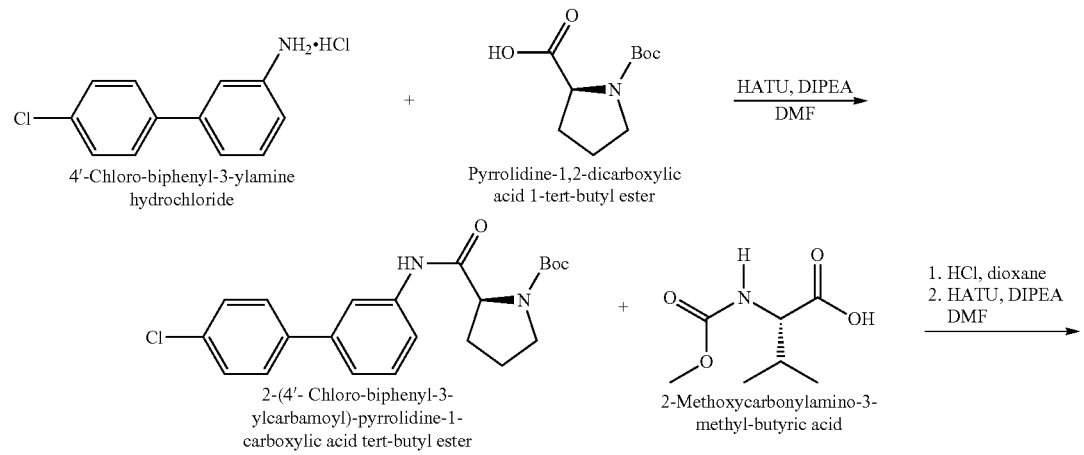

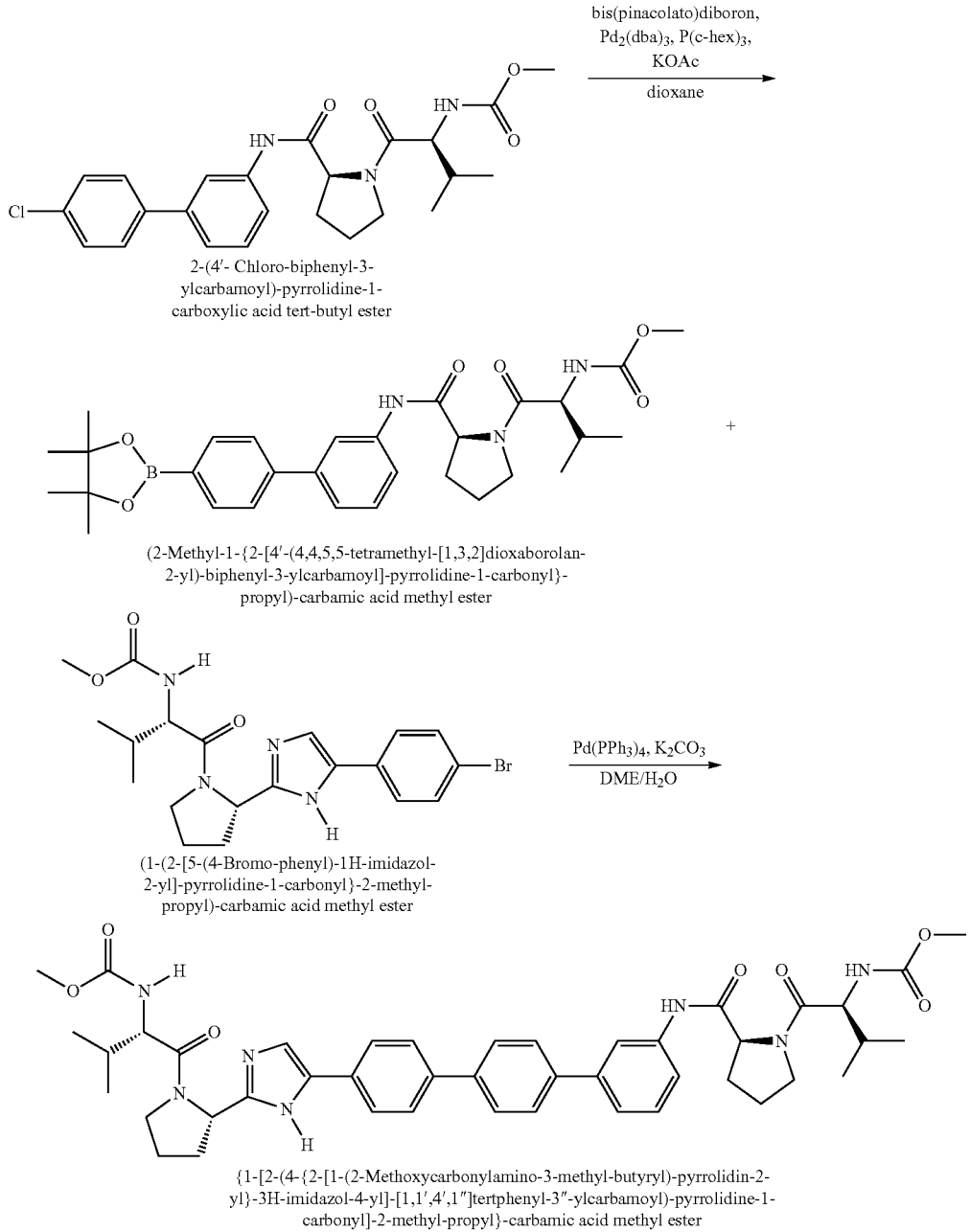

2-(4'-Chloro-biphenyl-3-ylcarbamoyl)-pyrrolidine-1-carboxylic acid tert-butyl ester 4'-Chloro-biphenyl-3-ylamine hydrochloride (1 g, 4.16 mmol), Pyrrolidine-1,2-dicarboxylic acid 1-tert-butyl ester (1.08 g, 5.00 mmol) and HATU (2.06 g, 5.41 mmol) were suspended in DMF (20 mL) and DIPEA (2.20 mL, 12.5 mmol) was added. The mixture was stirred for 16 hours before being diluted with ethyl acetate (250 mL) and washed with water and brine. The organic layer was dried over magnesium sulfate and concentrated. The crude residue was purified by silica column chromatography (25% to 45% EtOAc/hexanes) to provide 2-(4'-Chloro-biphenyl-3-ylcarbamoyl)-pyrrolidine-1-carboxylic acid tert-butyl ester (1.66 g, 99%).

{1-[2-(4'-Chloro-biphenyl-3-ylcarbamoyl)-pyrrolidine-1-carbonyl]-2-methyl-propyl}-carbamic acid methyl ester 2-(4'-Chloro-biphenyl-3-ylcarbamoyl)-pyrrolidine-1-carboxylic acid tert-butyl ester (1.66 g, 4.14 mmol) was dissolved in methanol (20 mL) and concentrated HCl (4 mL) was added. The mixture was stirred at 50° C. for 80 min then cooled and concentrated. The residue was treated with 2-methoxycarbonylamino-3-methyl-butyric acid (870 mg, 4.97 mmol) and HATU (2.05 g, 5.38 mmol) and brought up in DMF (20 mL) The mixture was cooled to 0° C. and DIPEA (3.60 mL, 20.7 mmol). After 100 min, the reaction mixture was diluted with ethyl acetate (250 mL) and washed with water and brine. The organic phase was dried over magnesium sulfate and concentrated. The resulting residue was purified by silica column chromatography (50% to 80% EtOAc/hexanes) to afford {1-[2-(4'-Chloro-biphenyl-3-yl-carbamoyl)-pyrrolidine-1-carbonyl]-2-methyl-propyl}-carbamic acid methyl ester (1.83 g, 96% over 2 steps).

(2-Methyl-1-{2-[4'-(4,4,5,5-tetramethyl-[1,3,2]diox-aborolan-2-yl)-biphenyl-3-ylcarbamoyl]-pyrrolidine-1-carbonyl}-propyl)-carbamic acid methyl ester {1-[2-(4'-Chloro-biphenyl-3-ylcarbamoyl)-pyrrolidine-1-carbonyl]-2-methyl-propyl}-carbamic acid methyl ester (409 mg, 0.893 mmol), bis(pinacolato)diboron (249 mg, 0.982 mmol), Pd$_2$(dba)$_3$ (20 mg, 0.0223 mmol), tris(cyclohexyl) phosphine (30 mg, 0.107 mmol) and potassium acetate (131 mg, 1.34 mmol) were suspended in dioxane (5 mL) and degassed with nitrogen for 4 min. The stirred suspension was heated to 80° C. for 14 hours before being cooled to RT, diluted with ethyl acetate (250 mL) and washed with water and brine. The organic phase was dried over magnesium sulfate and concentrated. The residue was purified by silica column chromatography (55% to 85% EtOAc/hexanes) to afford (2-Methyl-1-{2-[4'-(4,4,5,5-tetramethyl-[1,3,2]diox-aborolan-2-yl)-biphenyl-3-ylcarbamoyl]-pyrrolidine-1-carbonyl}-propyl)-carbamic acid methyl ester (491 mg, 100%).

{1-[2-(4-{2-[1-(2-Methoxycarbonylamino-3-methyl-butyryl)-pyrrolidin-2-yl]-3H-imidazol-4-yl}-[1,1';4',1"]terphenyl-3"-ylcarbamoyl)-pyrrolidine-1-carbonyl]-2-methyl-propyl}-carbamic acid methyl ester (2-Methyl-1-{2-[4'-(4,4,5,5-tetramethyl-[1,3,2]diox-aborolan-2-yl)-biphenyl-3-ylcarbamoyl]-pyrrolidine-1-carbonyl}-propyl)-carbamic acid methyl ester (135 mg, 0.246 mmol), (1-{2-[5-(4-Bromo-phenyl)-1H-imidazol-2-yl]-pyrrolidine-1-carbonyl}-2-methyl-propyl)-carbamic acid methyl ester (110 mg, 0.246 mmol), Pd(PPh$_3$)$_4$ (14 mg, 0.0123 mmol) and a 2 M aqueous solution of potassium carbonate (0.246 mL, 0.492 mmol) were degassed in 1,2-dimethoxyethane (2.5 mL) for 13 min. The stirred suspension was heated to 85° C. for 3 hours then concentrated, brought up in DMF/water and purified by reverse phase preparative HPLC to provide {1-[2-(4-{2-[1-(2-Methoxycarbonylamino-3-methyl-butyryl)-pyrrolidin-2-yl]-3H-imidazol-4-yl}-[1,1';4',1"]terphenyl-3"-ylcarbamoyl)-pyrrolidine-1-carbonyl]-2-methyl-propyl}-carbamic acid methyl ester (10 mg, 5%). (MeOH-d4, 400 MHz) 7.90 (s, 1H), 7.82-7.66 (m, 8H), 7.54-7.51 (m, 1H), 7.40-7.37 (m, 2H), 4.59 (m, 1H), 4.24 (m, 1H), 4.02-3.73 (m, 4H), 3.66 (s, 3H), 3.65 (s, 3H), 2.36-2.02 (m, 10H), 1.15-0.88 (m, 12H); MS (ESI) m/z 792 [M+H]$^+$.

Example CY

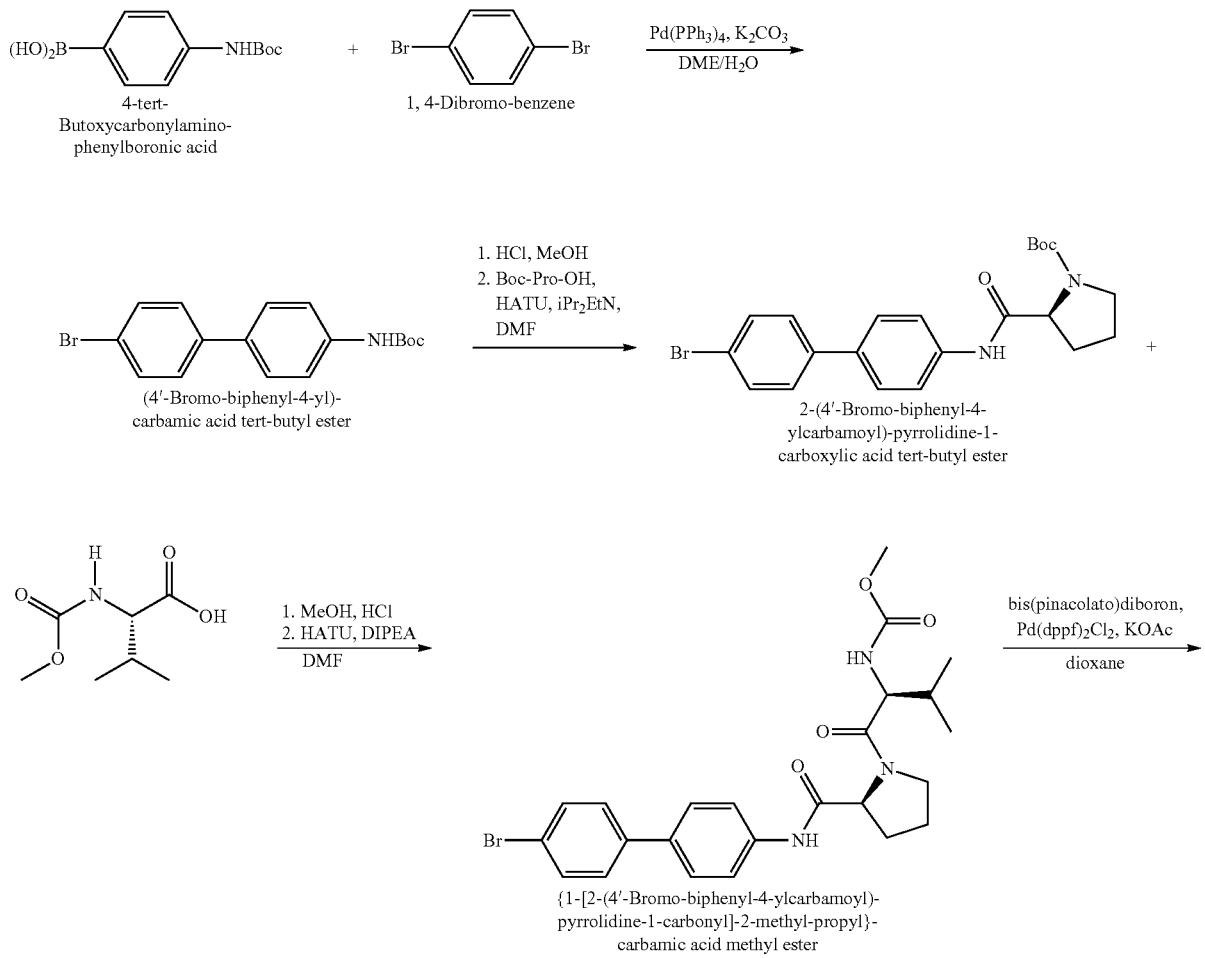

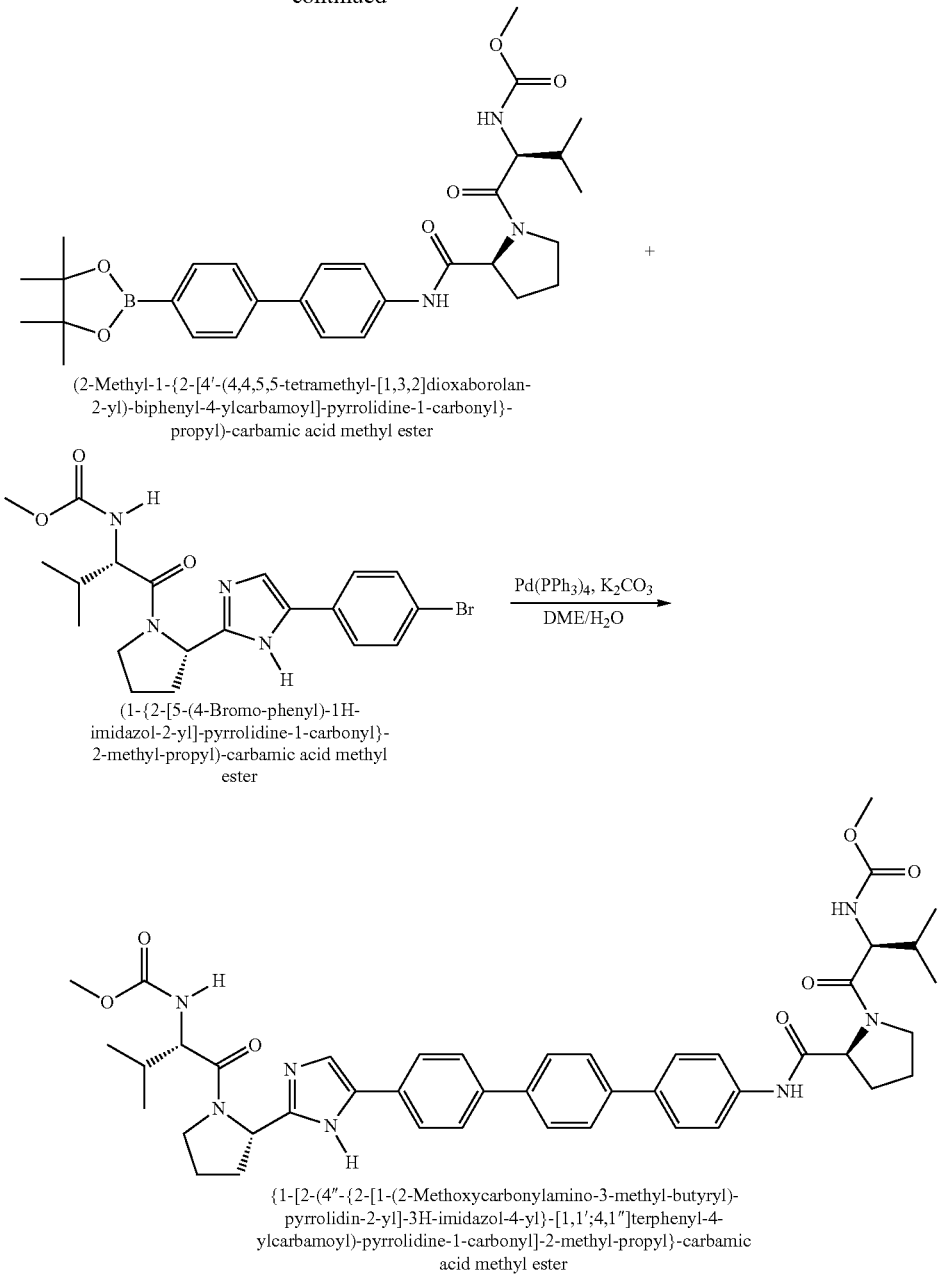

(2-Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester (1-{2-[5-(4-Bromo-phenyl)-1H-imidazol-2-yl]-pyrrolidine-1-carbonyl}-2-methyl-propyl)-carbamic acid methyl ester Pd(PPh₃)₄, K₂CO₃ / DME/H₂O {1-[2-(4''-{2-[1-(2-Methoxycarbonylamino-3-methyl-butyryl)-pyrrolidin-2-yl]-3H-imidazol-4-yl}-[1,1';4,1'']terphenyl-4-ylcarbamoyl)-pyrrolidine-1-carbonyl]-2-methyl-propyl}-carbamic acid methyl ester (4'-Bromo-biphenyl-4-yl)-carbamic acid tert-butyl ester 4-tert-Butoxycarbonylamino-phenylboronic acid (500 mg, 2.11 mmol), 1,4-dibromo-benzene (2.00 g, 8.44 mmol) Pd(PPh₃)₄ (122 mg, 0.106 mmol) and a 2 M aqueous solution of potassium carbonate (4.2 mL, 8.44 mmol) were degassed in 1,2-dimethoxyethane (20 mL) for 10 min. The stirred suspension was heated to 80° C. for 3 hours then diluted with ethyl acetate (60 mL) and washed with water and brine. The organic phase was dried over magnesium sulfate and concentrated. The residue was purified by silica column chromatography (0% to 20% EtOAc/hexanes) to provide (4'-Bromo-biphenyl-4-yl)-carbamic acid tert-butyl ester (430 mg, 59%).

2-(4'-Bromo-biphenyl-4-ylcarbamoyl)-pyrrolidine-1-carboxylic acid tert-butyl ester (4'-Bromo-biphenyl-4-yl)-carbamic acid tert-butyl ester (407 mg, 1.17 mmol) was dissolved in methanol (10 mL) and concentrated HCl (2 mL) was added. The solution was stirred at 60° C. for 1 hour then concentrated. The crude residue was treated with Boc-Pro-OH (302 mg, 1.40 mmol) and HATU (578 mg, 1.52 mmol) and suspended in DMF (6 mL). DIPEA (1.02 mL, 5.85 mmol) was added and the reaction mixture was stirred at RT for 4 hours after which it was diluted with ethyl acetate (200 mL) and washed with water and brine. The organic phase was dried over magnesium sulfate and concentrated. The residue was purified by silica column chromatography (30% to 55% EtOAc/hexanes) to afford 2-(4'-Bromobiphenyl-4-ylcarbamoyl)-pyrrolidine-1-carboxylic acid tert-butyl ester (496 mg, 95% over 2 steps).

{1-[2-(4'-Bromo-biphenyl-4-ylcarbamoyl)-pyrrolidine-1-carbonyl]-2-methyl-propyl}-carbamic acid methyl ester 2-(4'-Bromo-biphenyl-4-ylcarbamoyl)-pyrrolidine-1-carboxylic acid tert-butyl ester (496 mg, 1.11 mmol) was dissolved in methanol and concentrated HCl (2 mL) was added. The solution was stirred at 60° C. for 30 min then concentrated. The resulting residue was treated with 2-methoxycarbonylamino-3-methyl-butyric acid (233 mg, 1.33 mmol), HATU (549 mg, 1.44 mmol) and DMF (10 mL) After cooling this mixture to 0° C., DIPEA (0.970 mL, 5.55 mmol) was added. The reaction mixture was Stirred for 5 hours then diluted with ethyl acetate (150 mL) and washed with water and brine. The organic phase was dried over magnesium sulfate and concentrated. The resulting residue was purified by silica column chromatography (70% to 90% EtOAc/hexanes) to afford {1-[2-(4'-Bromo-biphenyl-4-ylcarbamoyl)-pyrrolidine-1-carbonyl]-2-methyl-propyl}-carbamic acid methyl ester (520 mg, 93% over 2 steps).

2-Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester {1-[2-(4'-Bromo-biphenyl-4-ylcarbamoyl)-pyrrolidine-1-carbonyl]-2-methyl-propyl}-carbamic acid methyl ester (154 mg, 0.307 mmol), bis(pinacolato)diboron (156 mg, 0.613 mmol), Pd(dppf)$_2$Cl$_2$ (11 mg, 0.0154 mmol) and potassium acetate (90 mg, 1.21 mmol) were suspended in dioxane and degassed for 15 min. The stirred reaction mixture was heated to 100° C. for 2 hours then cooled to RT, diluted with ethyl acetate (100 mL) and washed with water and brine. The organic phase was dried over magnesium sulfate and concentrated. The residue was purified by silica column chromatography (70% to 90% EtOAc/hexanes) to afford (2-Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester (127 mg, 75%).

{1-[2-(4"-{2-[1-(2-Methoxycarbonylamino-3-methyl-butyryl)-pyrrolidin-2-yl]-3H-imidazol-4-yl}-[1,1';4',1"]terphenyl-4-ylcarbamoyl)-pyrrolidine-1-carbonyl]-2-methyl-propyl}-carbamic acid methyl ester (2-Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester (102 mg, 0.227 mmol), (1-{2-[5-(4-Bromo-phenyl)-1H-imidazol-2-yl]-pyrrolidine-1-carbonyl}-2-methyl-propyl)-carbamic acid methyl ester (125 mg, 0.227 mmol), Pd(PPh$_3$)$_4$ (13 mg, 0.0114 mmol) and a 2 M aqueous solution of potassium carbonate (0.227 mL, 0.454 mmol) were degassed in 1,2-dimethoxyethane (2 mL) for 15 min. The stirred suspension was heated to 85° C. for 4 hours then concentrated, brought up in DMF/water and purified by reverse phase preparative HPLC to provide {1-[2-(4"-{2-[1-(2-Methoxycarbonylamino-3-methyl-butyryl)-pyrrolidin-2-yl]-3H-imidazol-4-yl}-[1,1';4',1"]terphenyl-4-ylcarbamoyl)-pyrrolidine-1-carbonyl]-2-methyl-propyl}-carbamic acid methyl ester (49 mg, 27%). (DMSO-d6, 400 MHz) 11.78 (s, 1H), 10.14 (s, 1H), 7.82-7.67 (m, 11H), 7.52 (d, J=1.8 Hz, 1H), 7.34-7.28 (m, 2H), 5.08 (m, 1H), 4.49 (m, 1H), 4.05 (m, 2H), 3.81 (m, 3H), 3.64 (m, 1H), 3.54 (s, 3H), 3.53 (s, 3H), 2.17-1.88 (m, 10H), 0.97-0.85 (m, 12H); MS (ESI) m/z 792 [M+H]$^+$.

Example CZ

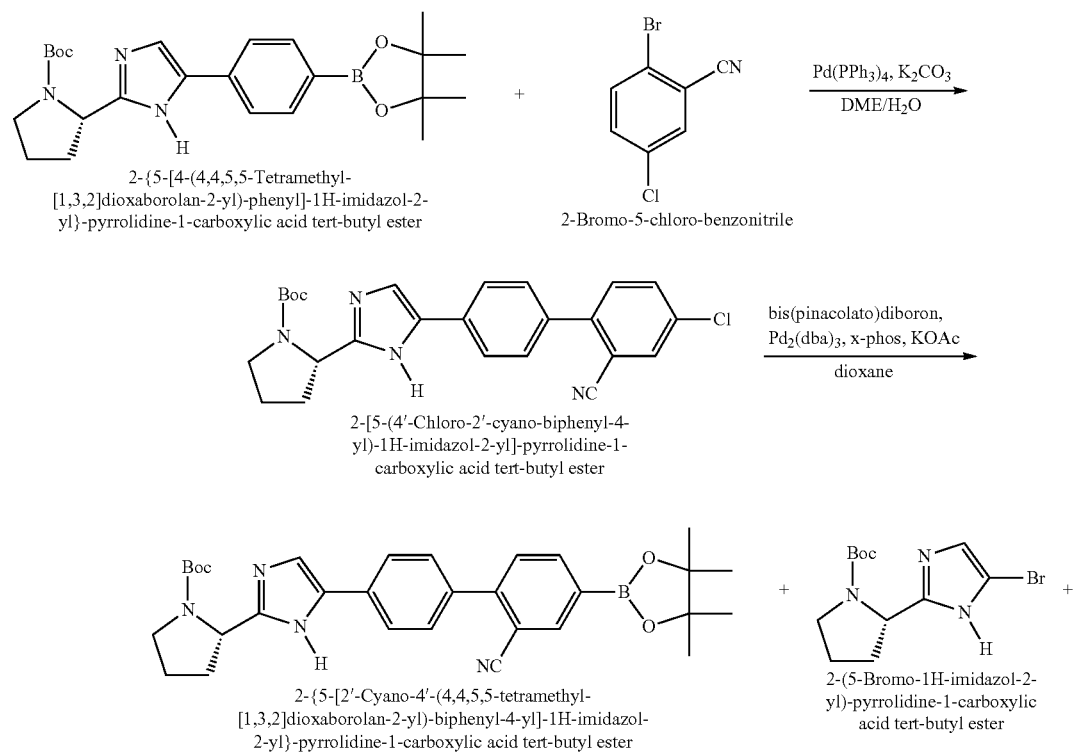

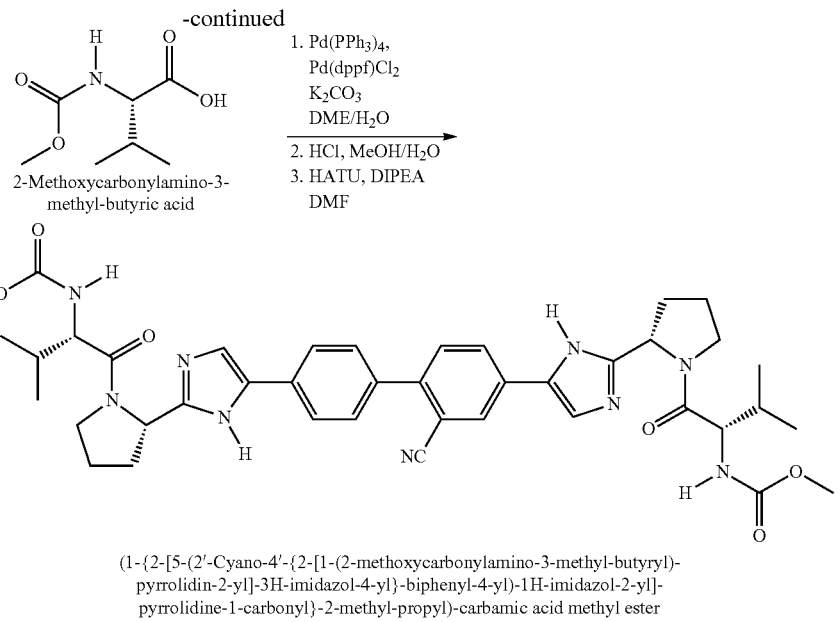

2-Methoxycarbonylamino-3-methyl-butyric acid

1. Pd(PPh$_3$)$_4$, Pd(dppf)Cl$_2$ K$_2$CO$_3$ DME/H$_2$O
2. HCl, MeOH/H$_2$O
3. HATU, DIPEA DMF (1-{2-[5-(2'-Cyano-4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester

2-[5-(4'-Chloro-2'-cyano-biphenyl-4-yl)-1H-imidazol-2-yl]-pyrrolidine-1-carboxylic acid tert-butyl ester 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (2 g, 4.55 mmol), 2-Bromo-5-chloro-benzonitrile (985 mg, 4.55 mmol), Pd(PPh$_3$)$_4$ (263 mg, 0.228 mmol) and a 2 M aqueous solution of potassium carbonate (4.6 mL, 9.2 mmol) were suspended in 1,2-methoxyethane (20 mL) and degassed for 10 min. The stirred reaction mixture was heated to 85° C. for 21 hours then poured into a saturated aqueous solution of NaHCO$_3$ (250 mL). The aqueous phase was extracted 3 times with ethyl acetate and the combined organic layers were dried over magnesium sulfate and concentrated. The crude residue was purified by silica column chromatography (65% to 90% EtOAc/hexanes) to afford 2-[5-(4'-Chloro-2'-cyano-biphenyl-4-yl)-1H-imidazol-2-yl]-pyrrolidine-1-carboxylic acid tert-butyl ester (1.65 g, 81%).

2-{5-[2'-Cyano-4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester 2-[5-(4'-Chloro-2'-cyano-biphenyl-4-yl)-1H-imidazol-2-yl]-pyrrolidine-1-carboxylic acid tert-butyl ester (1.68 g, 3.74 mmol), bis(pinacolato)diboron (1.43 g, 5.61 mmol), Pd$_2$(dba)$_3$ (86 mg, 0.0935 mmol), x-phos (214 mg, 0.449 mmol) and potassium acetate (1.10 g, 11.22 mmol) were suspended in dioxane (20 mL) and degassed for 10 min with nitrogen. The stirred reaction mixture was heated to 90° C. for 15 h, then cooled and filtered over a bed of silica, eluting with ethyl acetate until all desired product was removed. The liquid was concentrated and the resulting residue was purified by silica column chromatography (55% to 80% EtOAc/hexanes) to afford 2-{5-[2'-Cyano-4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (1.57 g, 78%).

(1-{2-[5-(2'-Cyano-4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester 2-{5-[2'-Cyano-4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (1.60 g, 2.96 mmol), 2-(5-Bromo-1H-imidazol-2-yl)-pyrrolidine-1-carboxylic acid tert-butyl ester (935 mg, 2.96 mmol), Pd(PPh$_3$)$_4$ (171 mg, 0.148 mmol), Pd(dppf)Cl$_2$ (121 mg, 0.148 mmol) and a 2 M aqueous solution of potassium carbonate (3 mL, 6 mmol) were suspended in 1,2-dimethoxyethane and degassed for 11 min. The stirred reaction mixture was heated to 85° C. for 100 min, then poured into a saturated aqueous solution of sodium bicarbonate (200 mL) and extracted 3 times with ethyl acetate. The combined organic layers were dried over magnesium sulfate and concentrated. The crude residue was purified by silica column chromatography (5% to 10% MeOH/DCM) to afford the Suzuki coupled product (438 mg, 23%). This material (174 mg, 0.268 mmol) was treated with 4 M HCl in dioxane (4 mL). Solubility was poor so 2 mL dichloromethane and 4 mL DMF were added. After stirring for 40 min, the mixture was concentrated. The crude residue was treated with 2-Methoxycarbonylamino-3-methyl-butyric acid (103 mg, 0.590 mmol), HATU (255 mg, 0.670 mmol) and DMF (5 mL) and cooled to 0° C. DIPEA (0.470 mL, 2.68 mmol) was added and the reaction mixture was stirred for 4 hours then poured into a saturated aqueous solution of sodium bicarbonate (200 mL) and extracted 3 times with ethyl acetate. The combined organic layers were dried over magnesium sulfate and concentrated. The crude residue was brought up in DMF and water and purified by reverse phase preparative HPLC, giving (1-{2-[5-(2'-Cyano-4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester (75 mg, 37%). (MeOH-d$_4$, 400 MHz) 8.19-7.35

(m, 11H), 5.18 (m, 2H), 4.24 (m, 2H), 4.03-4.86 (m, 4H), 3.65 (s, 6H), 2.37-2.00 (m, 10H), 1.00-0.90 (m, 12H); MS (ESI) m/z 764 [M+H]$^+$.
Example DA and DB
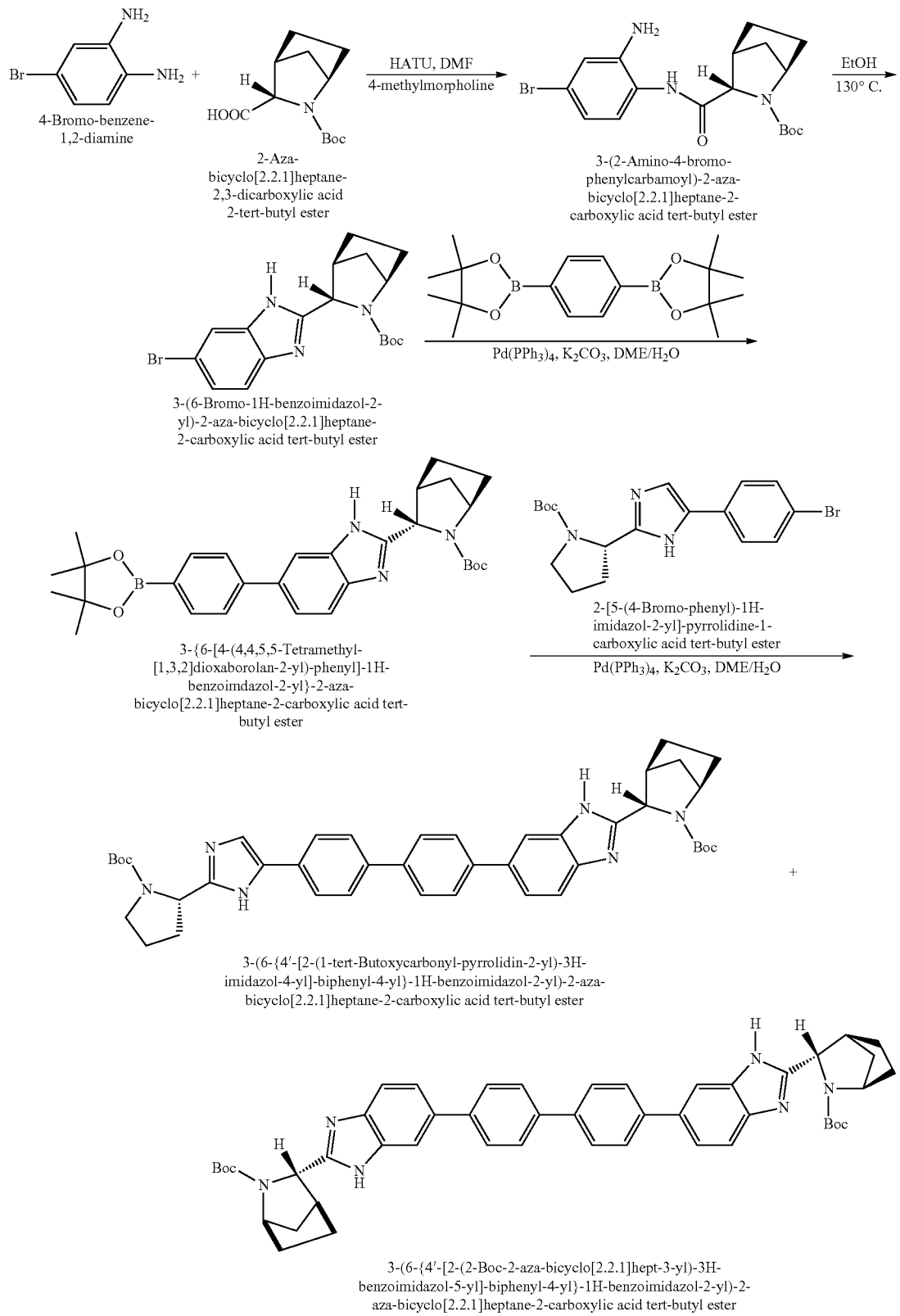

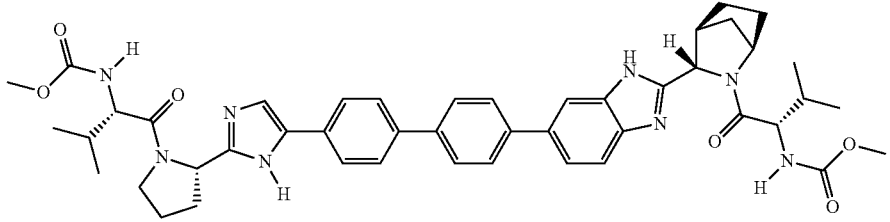
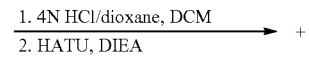
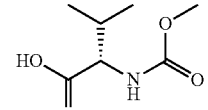

(1-{2-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-pyrrolidine-1-carbonyl}-2-methyl-propyl)-carbamic acid methyl ester 2-Methoxycarbonylamino-3-methyl-butyric acid

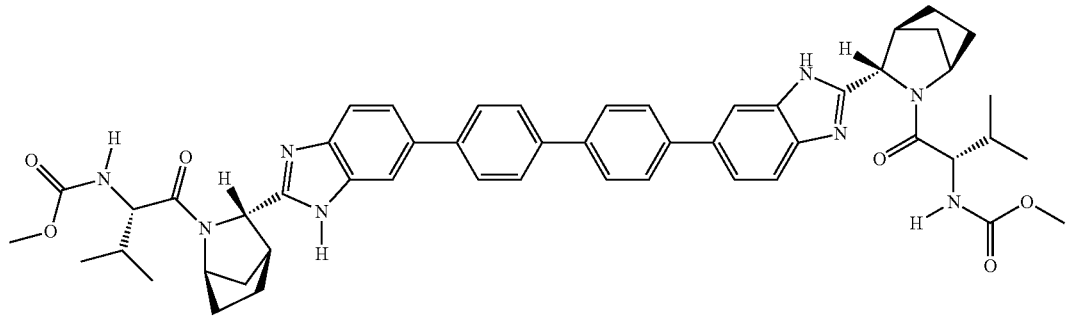

(1-{3-[6-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-benzoimidazol-2-yl]-2-aza-bicyclo[2.2.1]heptane-2-carbonyl}-2-methyl-propyl)-carbamic acid methyl ester

3-(2-Amino-4-bromo-phenylcarbamoyl)-2-aza-bicyclo[2.2.1]heptane-2-carboxylic acid tert-butyl ester To a solution of 2-Aza-bicyclo[2.2.1]heptane-2,3-dicarboxylic acid 2-tert-butyl ester (0.327 g, 1.36 mmol, 1 eq.), 4-Bromo-benzene-1,2-diamine (0.507 g, 2.71 mmol, 2 eq.) and 4-methylmorpholine (0.299 mL, 2 eq.) in 10 mL DMF was added HATU (0.543 g, 1.05 eq.). The reaction mixture was stirred at room temperature for 1 hour then concentrated down. The reaction mixture was diluted with ethyl acetate and washed with diluted NaHCO3 aqueous solution and brine. The organic layer was concentrated down and purified by flash column chromatography (silica gel, 20 to 80% ethyl acetate/hexane) to give a mixture of regioisomer 3-(2-Amino-4-bromo-phenylcarbamoyl)-2-aza-bicyclo[2.2.1]heptane-2-carboxylic acid tert-butyl ester.

3-(6-Bromo-1H-benzoimidazol-2-yl)-2-aza-bicyclo[2.2.1]heptane-2-carboxylic acid tert-butyl ester The above mixture of regioisomer 3-(2-Amino-4-bromo-phenylcarbamoyl)-2-aza-bicyclo[2.2.1]heptane-2-carboxylic acid tert-butyl ester was dissolved in ethanol and heated to 130° C. in sealed tube overnight and continue heating at 170° C. for 3 days. LC-MS showed desired product and Boc cleaved product (about 1:1 ratio). The mixture was concentrated down and dissolved DCM. Di-tert-butyl dicarbonate (0.6 eq.) was added and reaction was stirred overnight at room temperature. The reaction mixture was concentrated down and purified by flash column chromatography (silica gel, 20 to 80% ethyl acetate/hexane) to give 3-(6-Bromo-1H-benzoimidazol-2-yl)-2-aza-bicyclo[2.2.1]heptane-2-carboxylic acid tert-butyl ester (0.383 g, 72%) as an orange foam.

3-{6-[4-(4,4,5,5-Tetramethyl-[1,3,2]dioxaborolan-2-yl)-phenyl]-1H-benzoimidazol-2-yl}-2-aza-bicyclo[2.2.1]heptane-2-carboxylic acid tert-butyl ester A mixture of 3-(6-Bromo-1H-benzoimidazol-2-yl)-2-aza-bicyclo[2.2.1]heptane-2-carboxylic acid tert-butyl ester (264 mg, 0.673 mmol), Benzene-1,4-diboronic acid dipinocal ester (5 eq., 3.36 g, 6.95 mmol), tetrakis(triphenylphosphine)palladium (5%, 39 mg) and 2M potassium carbonate aqueous solution (3 eq., 1.01 mL) in 5 mL DME was heated to 90° C. under Ar for 4 hours. The reaction mixture was cooled down and diluted in ethyl acetate and washed with saturated sodium bicarbonate solution. The organic layer dried (MgSO4), concentrated and purified by flash column chromatography (silica gel, 20 to 60% ethyl acetate/hexane) to give 3-{6-[4-(4,4,5,5-Tetramethyl-[1,3,2]dioxaborolan-2-yl)-phenyl]-1H-benzoimidazol-2-yl}-2-aza-bicyclo[2.2.1]heptane-2-carboxylic acid tert-butyl ester (295 mg, yield 85%). LCMS-ESI−: calc'd for $C_{30}H_{38}BN_3O_4$: 515.45; Found: 516.1 (M+H+).

3-(6-{4'-[2-(1-tert-Butoxycarbonyl-pyrrolidin-2-yl)-3H-imidazol-4-yl]-biphenyl-4-yl}-1H-benzoimidazol-2-yl)-2-aza-bicyclo[2.2.1]heptane-2-carboxylic acid tert-butyl ester and 3-(6-{4'-[2-(2-Boc-2-aza-bicyclo[2.2.1]hept-3-yl)-3H-benzoimidazol-5-yl]-biphenyl-4-yl}-1H-benzoimidazol-2-yl)-2-aza-bicyclo[2.2.1]heptane-2-carboxylic acid tert-butyl ester A mixture of 2-[5-(4-Bromo-phenyl)-1H-imidazol-2-yl]-pyrrolidine-1-carboxylic acid tert-butyl ester (295 mg, 0.573 mmol, 1 eq.), 3-{6-[4-(4,4,5,5-Tetramethyl-[1,3,2]dioxaborolan-2-yl)-phenyl]-1H-benzoimidazol-2-yl}-2-aza-bicyclo[2.2.1]heptane-2-carboxylic acid tert-butyl ester (269 mg, 0.687 mmol), tetrakis(triphenylphosphine)palladium (5%, 33 mg) and 2M potassium carbonate aqueous solution (5 eq., 1.43 mL) in 5 mL DME was heated to 90° C. under Argon overnight. The reaction mixture was cooled and dissolved in ethyl acetate and washed with saturated sodium bicarbonate solution. The organic layer dried (MgSO4), concentrated and purified by flash column chromatography (silica gel, 50 to 100% ethyl acetate/hexane) to give 3-(6-{4'-[2-(1-tert-Butoxycarbonyl-pyrrolidin-2-yl)-3H-imidazol-4-yl]-biphenyl- 4-yl}-1H-benzoimidazol-2-yl)-2-aza-bicyclo[2.2.1]heptane-2-carboxylic acid tert-butyl ester (163 mg, yield 40%) and trace amount of byproduct 3-(6-{4'-[2-(2-Boc-2-aza-bicyclo[2.2.1]hept-3-yl)-3H-benzoimidazol-5-yl]-biphenyl-4-yl}-1H-benzoimidazol-2-yl)-2-aza-bicyclo[2.2.1]heptane-2-carboxylic acid tert-butyl ester. LCMS-ESI⁻ of 3-(6-{4'-[2-(1-tert-Butoxycarbonyl-pyrrolidin-2-yl)-3H-imidazol-4-yl]-biphenyl-4-yl}-1H-benzoimidazol-2-yl)-2-aza-bicyclo[2.2.1]heptane-2-carboxylic acid tert-butyl ester: calc'd for $C_{42}H_{48}N_6O_4$: 700.87; Found: 701.1 (M+H⁺).

(1-{2-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-pyrrolidine-1-carbonyl}-2-methyl-propyl)-carbamic acid methyl ester (Example DA) and (1-{3-[6-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-benzoimidazol-2-yl]-2-aza-bicyclo[2.2.1]heptane-2-carbonyl}-2-methyl-propyl)-carbamic acid methyl ester (Example DB)

4N HCl in dioxane (3 mL) was added to 3-(6-{4'-[2-(1-tert-Butoxycarbonyl-pyrrolidin-2-yl)-3H-imidazol-4-yl]-biphenyl-4-yl}-1H-benzoimidazol-2-yl)-2-aza-bicyclo[2.2.1]heptane-2-carboxylic acid tert-butyl ester and 3-(6-{4'-[2-(2-Boc-2-aza-bicyclo[2.2.1]hept-3-yl)-3H-benzoimidazol-5-yl]-biphenyl-4-yl}-1H-benzoimidazol-2-yl)-2-aza-bicyclo[2.2.1]heptane-2-carboxylic acid tert-butyl ester mixture (163 mg, 0.233 mmol) in 3 mL DCM and the reaction mixture was stirred at room temperature for 2 hours. The reaction mixture was concentrated and dried overnight under vacuum. The residue was dissolved in DMF (3 mL) and to this solution was added 2-Methoxycarbonylamino-3-methyl-butyric acid (2.1 eq., 85 mg), 4-methylmorpholine (6 eq., 0.15 mL), followed by HATU (2 eq., 181 mg). Reaction mixture was stirred at 0° C. for 50 minutes. The reaction mixture was dissolved in ethyl acetate and washed with dilute sodium bicarbonate solution. The organic layer was dried (MgSO₄), concentrated and purified by preparative reverse phase HPLC (GEMINI, 5 to 100% MeCN/H₂O+0.1% TFA). Product was lyophilized to give (1-{2-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-pyrrolidine-1-carbonyl}-2-methyl-propyl)-carbamic acid methyl ester (Example DA) (102 mg) and byproduct (1-{3-[6-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-benzoimidazol-2-yl]-2-aza-bicyclo[2.2.1]heptane-2-carbonyl}-2-methyl-propyl)-carbamic acid methyl ester (Example DB) (10.6 mg).

Example DA

¹H-NMR: 300 MHz, (DMSO-d₆) δ: 8.13 (s, 1H), 7.95-7.80 (m, 12H), 7.40-7.20 (m, 2H), 5.18-5.10 (m, 1H), 4.76 (m, 1H), 4.55 (m, 1H), 4.20-4.10 (m, 3H), 3.92-3.78 (m, 3H), 3.55 (d, 6H), 2.76 (m, 1H), 2.40-1.55 (m, 10H), 0.95-0.78 (m, 12H).

LCMS-ESI⁺: calc'd for $C_{46}H_{54}N_8O_6$: 814.97; Found: 815.4 (M+H⁺).

Example DB (byproduct)

¹H-NMR: 300 MHz, (DMSO-d₆) δ: 7.95-7.72 (m, 14H), 7.38-7.24 (m, 2H), 4.75 (m, 2H), 4.55 (m, 2H), 4.24-4.16 (m, 3H), 3.55 (d, 6H), 2.76 (m, 2H), 2.40-1.55 (m, 9H), 0.95-0.78 (m, 12H).

LCMS-ESI⁺: calc'd for $C_{52}H_{58}N_8O_6$: 891.07; Found: 891.4 (M+H⁺).

Example DC

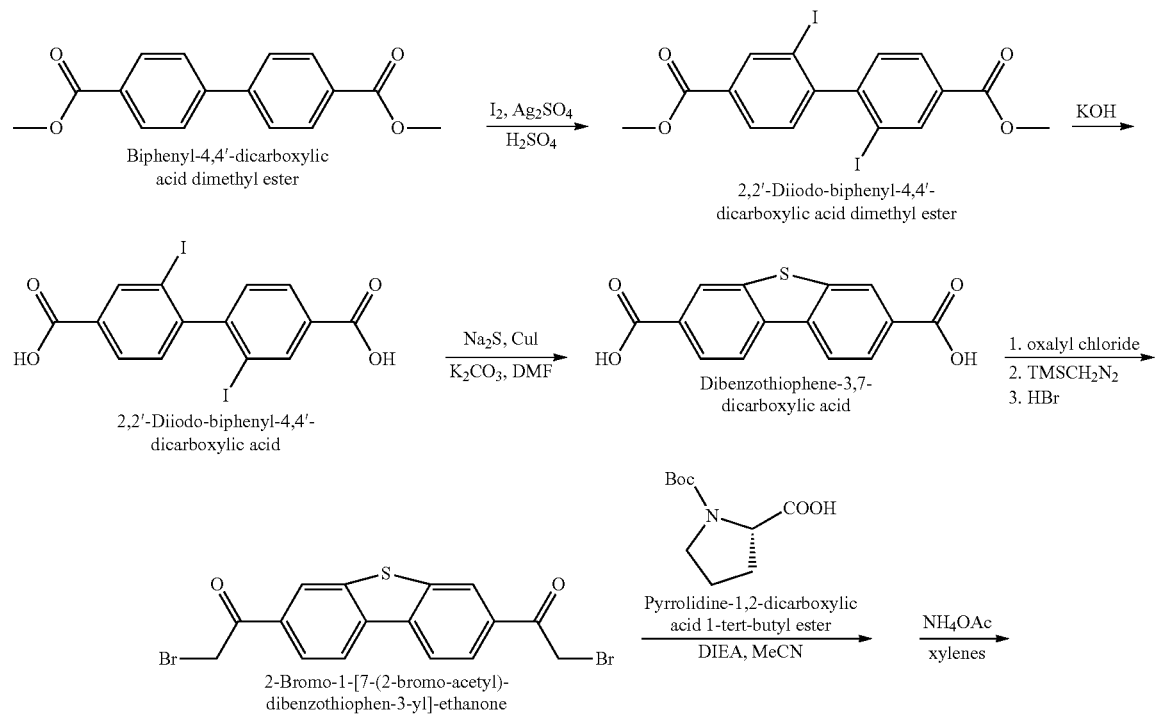

-continued

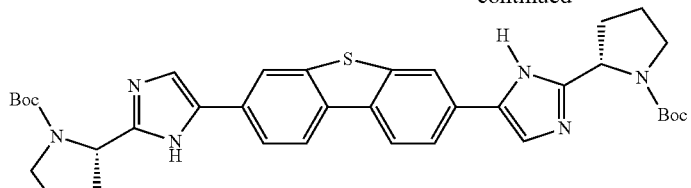

2-(5-{7-[2-(1-Boc-pyrrolidin-2-yl)-3H-imidazol-4-yl]-dibenzothiophen-3-yl}-1H-imidazol-2-yl)-pyrrolidine-1-carboxylic acid tert-butyl ester

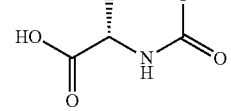

1. 4N HCl/dioxane, DCM
2. HATU, DIEA

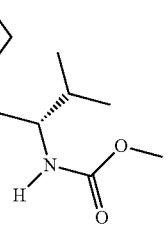

2-Methoxycarbonylamino-3-methyl-butyric acid

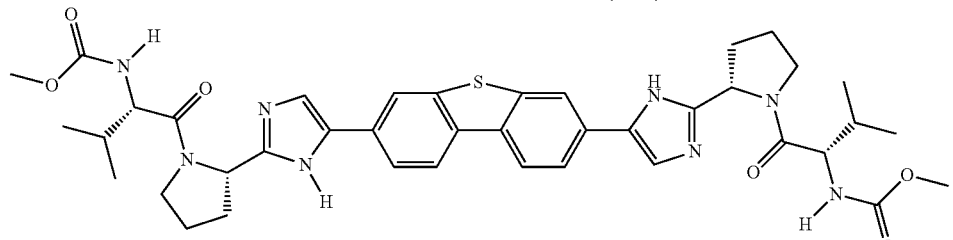

(1-{2-[5-(7-{2-[1-(2-Methoxycarbonylamino-3-methyl-butyryl)-pyrrolidin-2-yl]-3H-imidazol-4-yl}-dibenzothiophen-3-yl)-1H-imidazol-2-yl]-pyrrolidine-1-carbonyl}-2-methyl-propyl)-carbamic acid methyl ester 2,2'-Diiodo-biphenyl-4,4'-dicarboxylic acid dimethyl ester Biphenyl-4,4'-dicarboxylic acid dimethyl ester (5 g, 18.5 mmol) and silver sulfate (17 g, 54.5 mmol) were dissolved in 60 mL concentrated sulfuric acid with vigorous stirring. Iodine (11 g, 43.3 mmol) was added portion wise to give a purple solution which was stirred at room temperature for 1 hour. The reaction mixture was heated to 80° C. for overnight. The reaction mixture was cooled down, poured into ice water and sodium thiosulfate solution. Brown solid was formed, filtered and dried over vacuum at 80° C. The brown solid was extracted using a Soxhlet extraction with methanol in two batches. The product crystallized during extraction. Crystal was collected and dried to give a yellow solid 2,2'-Diiodo-biphenyl-4,4'-dicarboxylic acid dimethyl ester (5.7 g, 59%).

2,2'-Diiodo-biphenyl-4,4'-dicarboxylic acid 2,2'-Diiodo-biphenyl-4,4'-dicarboxylic acid dimethyl ester (3.24 g, 6.21 mmol) was dissolved in 20 mL THF and KOH (1.02 g, 2.5 eq.) was added, followed by 5 mL water. The reaction was stirred at room temperature overnight. The reaction was heated to 50° C. for 7 hours. The reaction was cooled to room temperature. Organic solvent was removed by rotovap. The aqueous layer was acidified with concentrated HCl to give pale white solid. The solid was filtered and dried on vacuum overnight to give the product 2,2'-Diiodo-biphenyl-4,4'-dicarboxylic acid (2.74 g, yield 89%).

Dibenzothiophene-3,7-dicarboxylic acid

A mixture of 2,2'-Diiodo-biphenyl-4,4'-dicarboxylic acid (450 mg, 0.912 mmol, 1 eq.) and potassium carbonate (189 mg, 1.5 eq.) in 5 mL DMF was heated to 100° C. to give a reddish brown mixture. Sodium sulfide (36 mg, 0.5 eq.) and copper(I) iodide (17 mg, 0.1 eq.) were added and reaction mixture was heated to 150° C. under a slow stream of Ar. CuI (100 mg) was added and followed by sodium sulfide (100 mg). The reaction was kept at 150° C. overnight. The reaction mixture was diluted with 25 mL water and active carbon (10 g) was added. The mixture was refluxed for 10 minutes then filtered through CELITE pad into 6NHCL (50 mL) and washed with water. The solid was formed and cooled to room temperature and filtered and washed with and dried to give product Dibenzothiophene-3,7-dicarboxylic acid (179 mg, 72%).

2-Bromo-1-[7-(2-bromo-acetyl)-dibenzothiophen-3-yl]-ethanone

A mixture of dibenzothiophene-3,7-dicarboxylic acid (179 mg, 0.644 mmol), oxalyl chloride (0.56 mL, 6.44 mmol) and 1 drop of DMF in 6 mL DCM was stirred at room temperature overnight. The resulting cloudy yellow solution was concentrated and co-evaporated with toluene. The residue was suspended in 6 mL DCM and cooled to 0° C. TMS diazomethane (1 ml, 3 eq.) was added to the reaction mixture dropwise. The reaction was stirred at 0° C. for 1 hour and then warmed to room temperature overnight. The mixture was concentrated to give a brown solid. The solid was suspended in 5 mL ethyl acetate and treated with 5.7 M HBr in HOAc (0.28 mL, 2.5 eq.) at 0° C. The mixture was warmed to room temperature over 2 hours. And then stirred at room temperature for 1 hour. Solid sodium bicarbonate was added and stirred for 30 minutes. The mixture was diluted with sodium bicarbonate solution and extracted with ethylacetate 3 times. The organic layer was concentrated down and purified by flash column chromatography (silica gel, 20 to 80% ethyl acetate/hexane) to give impure product 2-Bromo-1-[7-(2-bromo-acetyl)-dibenzothiophen-3-yl]-ethanone.

2-(5-{7-[2-(1-Boc-pyrrolidin-2-yl)-3H-imidazol-4-yl]-dibenzothiophen-3-yl}-1H-imidazol-2-yl)-pyrrolidine-1-carboxylic acid tert-butyl ester The mixture of above impure 2-Bromo-1-[7-(2-bromo-acetyl)-dibenzothiophen-3-yl]-ethanone, Pyrrolidine-1,2-dicarboxylic acid 1-tert-butyl ester (2.1 eq.), and DIEA (2.07 eq.) in 5 mL MeCN was stirred at room temperature overnight. The reaction mixture was concentrated down and diluted with ethyl acetate, washed with brine, dried over MgSO4, and concentrated down. The residue was dissolved in 1.5 mL xylenes and ammonium acetate (65 mg, 15 eq.) was added. The reaction was heated to 110° C. for 2 days. The mixture was diluted with EtOAc and washed with sat. NaHCO3 aqueous solution. The organic layer was concentrated down and purified by preparative reverse phase HPLC (GEMINI, 5 to 100% MeCN/H$_2$O+0.1% TFA). Product was lyophilized to give 2-(5-{7-[2-(1-Boc-pyrrolidin-2-yl)-3H-imidazol-4-yl]-dibenzothiophen-3-yl}-1H-imidazol-2-yl)-pyrrolidine-1-carboxylic acid tert-butyl ester (12.4 mg). LCMS-ESI$^-$: calc'd for C$_{36}$H$_{42}$N$_6$O$_4$S: 654.82; Found: 655.0 (M+H$^+$).

(1-{2-[5-(7-{2-[1-(2-Methoxycarbonylamino-3-methyl-butyryl)-pyrrolidin-2-yl]-3H-imidazol-4-yl}-dibenzothiophen-3-yl)-1H-imidazol-2-yl]-pyrrolidine-1-carbonyl}-2-methyl-propyl)-carbamic acid methyl ester (Example DC)

4 N HCl in dioxane (1 mL) was added to 2-(5-{7-[2-(1-Boc-pyrrolidin-2-yl)-3H-imidazol-4-yl]-dibenzothiophen-3-yl}-1H-imidazol-2-yl)-pyrrolidine-1-carboxylic acid tert-butyl ester (12.4 mg, 0.014 mmol) and the reaction mixture was stirred at room temperature for 1 hour. The reaction mixture was concentrated and dried overnight under vacuum. The residue was dissolved in DMF (1 mL) and to this solution was added 2-Methoxycarbonylamino-3-methyl-butyric acid (2.08 eq., 5.1 mg), 4-methylmorpholine (6 eq., 9.2 µL), followed by HATU (2.04 eq., 10.9 mg). Reaction mixture was stirred at 0° C. for 90 minutes. The reaction mixture was diluted with ethyl acetate and washed with saturated sodium bicarbonate solution. The organic layer was dried (MgSO$_4$), concentrated and purified by preparative reverse phase HPLC (GEMINI, 5 to 100% MeCN/H$_2$O+0.1% TFA). Product was lyophilized to give (1-{2-[5-(7-{2-[1-(2-Methoxycarbonylamino-3-methyl-butyryl)-pyrrolidin-2-yl]-3H-imidazol-4-yl}-dibenzothiophen-3-yl)-1H-imidazol-2-yl]-pyrrolidine-1-carbonyl}-2-methyl-propyl)-carbamic acid methyl ester (Example DC) (8.1 mg, 58%).

$^1$H-NMR: 300 MHz, (CD$_3$OD-d$_4$) δ: 8.41-8.25 (m, 4H), 7.92-7.78 (m, 4H), 5.22 (m, 2H), 4.22 (m, 2H), 4.08 (m, 2H), 3.86 (m, 2H), 3.62 (d, 6H), 2.60-2.50 (m, 2H), 2.30-1.92 (m, 8H), 0.97-0.82 (m, 12H). LCMS-ESI$^+$: calc'd for C$_{40}$H$_{48}$N$_8$O$_6$S: 768.92; Found: 769.3 (M+H$^+$).

Example DD

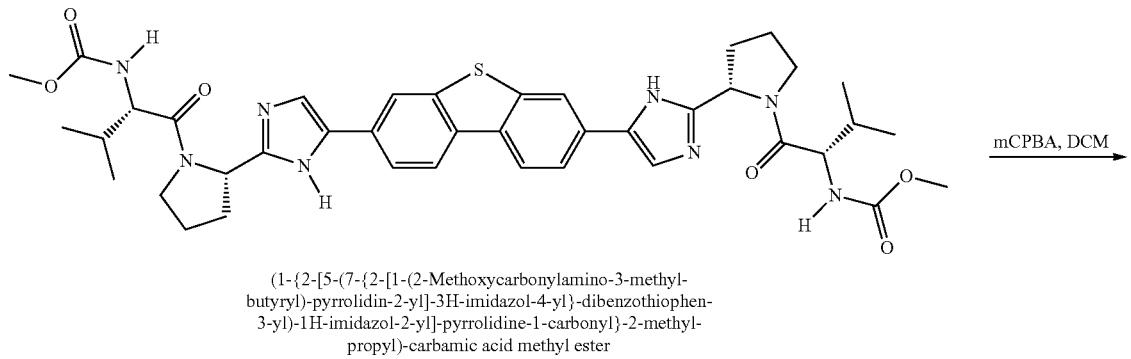

(1-{2-[5-(7-{2-[1-(2-Methoxycarbonylamino-3-methyl-butyryl)-pyrrolidin-2-yl]-3H-imidazol-4-yl}-dibenzothiophen-3-yl)-1H-imidazol-2-yl]-pyrrolidine-1-carbonyl}-2-methyl-propyl)-carbamic acid methyl ester mCPBA, DCM →

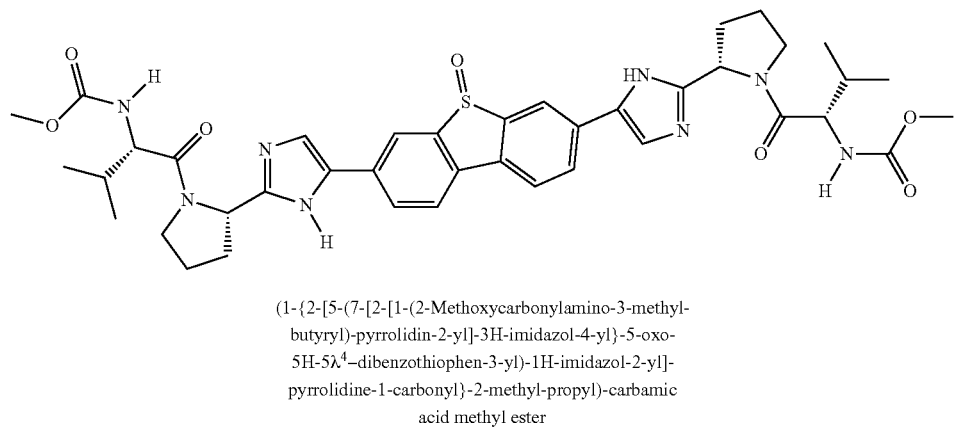

(1-{2-[5-(7-[2-[1-(2-Methoxycarbonylamino-3-methyl-butyryl)-pyrrolidin-2-yl]-3H-imidazol-4-yl}-5-oxo-5H-5λ$^4$–dibenzothiophen-3-yl)-1H-imidazol-2-yl]-pyrrolidine-1-carbonyl}-2-methyl-propyl)-carbamic acid methyl ester (1-{2-[5-(7-{2-[1-(2-Methoxycarbonylamino-3-methyl-butyryl)-pyrrolidin-2-yl]-3H-imidazol-4-yl}-5-oxo-5H-5λ⁴-dibenzothiophen-3-yl)-1H-imidazol-2-yl]-pyrrolidine-1-carbonyl}-2-methyl-propyl)-carbamic acid methyl ester (Example DD)

(1-{2-[5-(7-{2-[1-(2-Methoxycarbonylamino-3-methyl-butyryl)-pyrrolidin-2-yl]-3H-imidazol-4-yl}-dibenzothiophen-3-yl)-1H-imidazol-2-yl]-pyrrolidine-1-carbonyl}-2-methyl-propyl)-carbamic acid methyl ester (0.0041 mmol., 4 mg) was dissolved in 1 mL DCM and cooled to −40° C. mCPBA (0.4 mg, 0.9 eq.) was added. The reaction mixture was stirred at −40° C. for 2 hours and warmed up to 0° C. over 2 hours, then warmed up to room temperature overnight. The reaction mixture was diluted with ethyl acetate and washed with saturated sodium bicarbonate solution. The organic layer was dried (MgSO₄), concentrated and purified by preparative reverse phase HPLC (GEMINI, 5 to 100% ACN/H₂O+0.1% TFA). Product was lyophilized to give a yellow powder (1-{2-[5-(7-{2-[1-(2-Methoxycarbonylamino-3-methyl-butyryl)-pyrrolidin-2-yl]-3H-imidazol-4-yl}-5-oxo-5H-5λ⁴-dibenzothiophen-3-yl)-1H-imidazol-2-yl]-pyrrolidine-1-carbonyl}-2-methyl-propyl)-carbamic acid methyl ester (Example DD) (0.6 mg). $^1$H-NMR: 300 MHz, (CD$_3$OD-d$_4$) δ: 8.36 (m, 2H), 8.18-7.90 (m, 6H), 5.22 (m, 2H), 4.19 (m, 2H), 4.05 (m, 2H), 3.84 (m, 2H), 3.61 (d, 6H), 2.56-1.96 (m, 10H), 0.97-0.84 (m, 12H). LCMS-ESI$^+$: calc'd for C$_{40}$H$_{48}$N$_8$O$_6$S: 768.92; Found: 769.3 (M+H$^+$).

Example DE

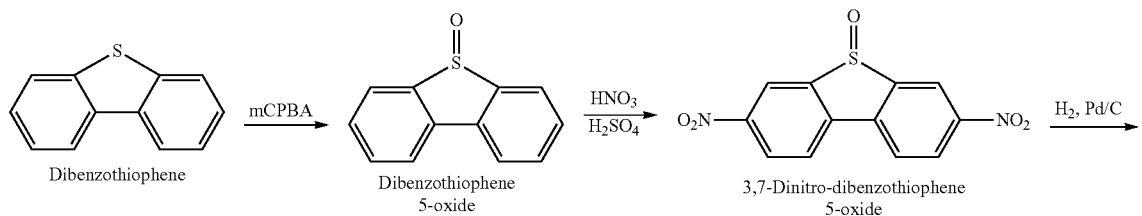

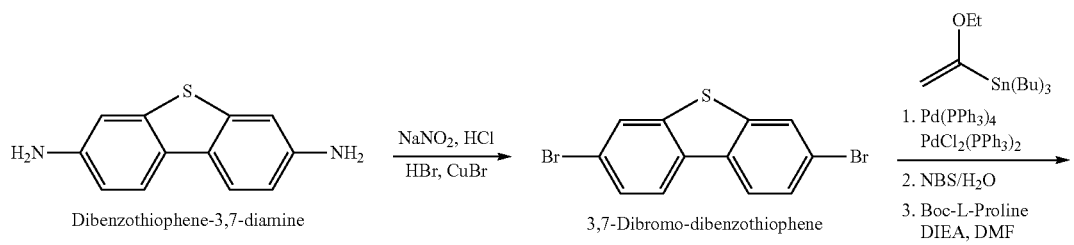

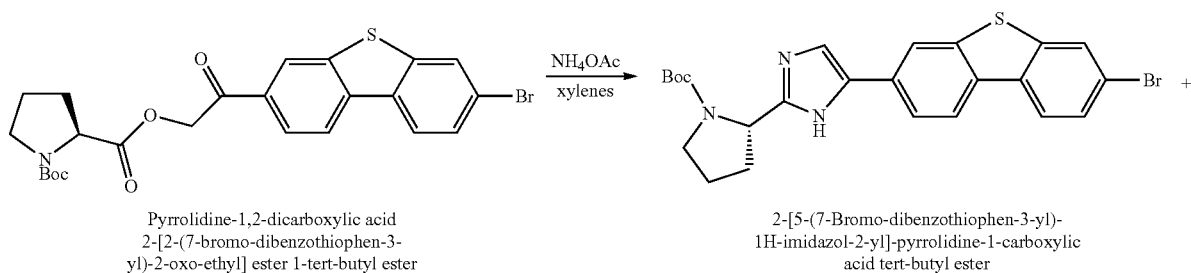

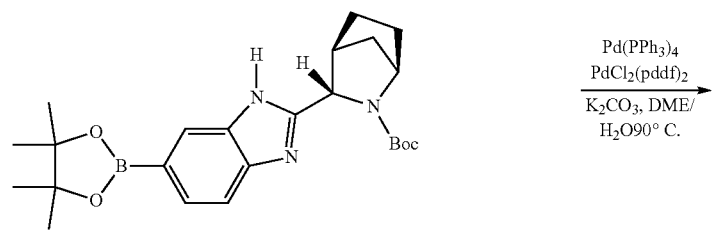

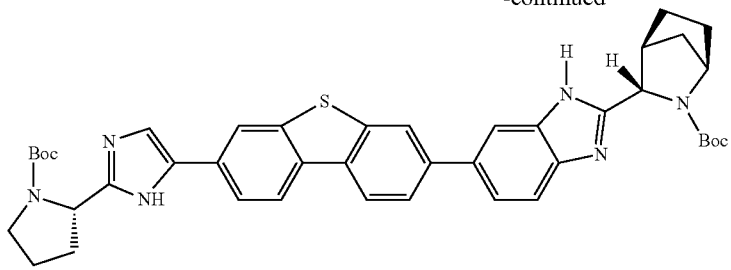

3-(6-{7-[2-(1-tert-Butoxycarbonyl-pyrrolidin-2-yl)-3H-imidazol-4-yl]-dibenzothiophen-3-yl}-1H-benzoimidazole-2-yl)-2-aza-bicyclo[2.2.1]heptane-2-carboxylic acid tert butyl ester

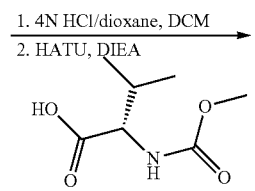

1. 4N HCl/dioxane, DCM
2. HATU, DIEA

2-Methoxycarbonylamino-3-methyl-butyric acid

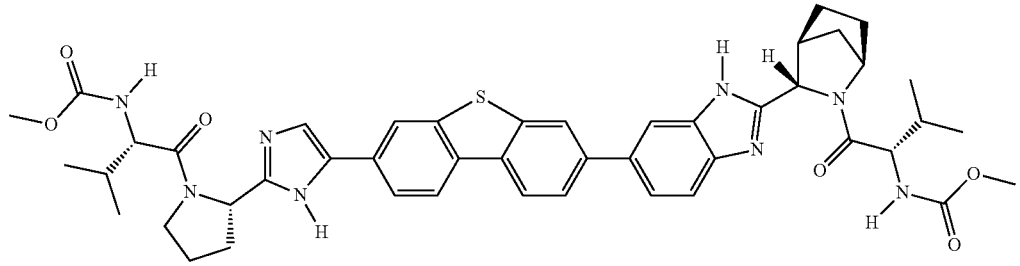

(1-{2-[5-(7-{2-[2-(2-Methoxycarbonylamino-3-methyl-butytyl-2-aza-bicyclo[2.2.1]hept-3-yl]-3H-benzoimidazol-5-yl}-dibenzothiophen-3-yl)-1H-imidazol-2-yl]-pyrrolidine-1-carbonyl}-2-methyl-propyl)-carbamic acid methyl ester

Dibenzothiophene 5-oxide

A solution of mCPBA (8.27 g, 36.9 mmol) in 71 mL chloroform was added dropwise over 30 minutes to a solution of dibenzothiophene in 89 mL chloroform at −35° C. The reaction mixture was stirred at −35° C. for 1 hour and then warmed up to room. The reaction was quenched with saturated sodium bicarbonate aqueous solution. The organic layer was washed with saturated sodium bicarbonate solution twice and dried over MgSO4, concentrated down to give an off-white solid. The solid was dissolved in refluxing ethanol and slowly cooled to room temperature to give a white crystalline solid Dibenzothiophene 5-oxide (5.65 g, 76%). LCMS-ESI⁻: calc'd for $C_{12}H_8OS$: 200.26; Found: 200.9 (M+H⁺).

3,7-Dinitro-dibenzothiophene 5-oxide

A solution of Dibenzothiophene 5-oxide (5.34 g, 26.7 mmol) in concentrated sulfuric acid (120 mL) was cooled to 6° C. Nitric acid (108 mL) was added slowly so that the internal temperature stayed at 10° C. The reaction was stirred at 10° C. for 30 minutes then warmed up to room temperature over 30 minutes. The reaction mixture was poured into ice and formed precipitate. The precipitate was washed with water and dried to give a yellow solid 3,7-Dinitro-dibenzothiophene 5-oxide (7.8 g, still containing some water and inorganic material).

Dibenzothiophene-3,7-diamine

Two batches of the above solid 3,7-dinitro-dibenzothiophene 5-oxide was hydrogenated at 45 psi in ethanol (250 mL for each batch) with 10% Pd on carbon (0.46 g each batch) for 2 hours. Two batches were combined and filtered through CELITE to give an orange solution. Hydrogen chloride gas was bubbled into the solution to form precipitate (at pH 1). The precipitate was filtered and washed with small amount of ethanol and dried on vacuum to give an orange solid Dibenzothiophene-3,7-diamine (2.46 g). LCMS-ESI⁻: calc'd for $C_{12}H_{10}N_2S$: 214.29; Found: 215.0 (M+H⁺).

3,7-Dibromo-dibenzothiophene

A suspension of Dibenzothiophene-3,7-diamine (2.46 g, 8.57 mmol) in water (16 mL) and concentrated HCl (4.3 mL) was cooled to 5° C. (internal temperature). A solution of sodium nitrite (1.54 g, 25.67 mmol) in water (5 mL) was added dropwise so that the internal temperature didn't exceed to 10° C. After 1 hour the reaction mixture was poured into a solution of CuBr (1.8 g, 12.55 mmol) in 48% HBr (18 mL) The mixture was transferred into a 1 L 3 neck flask using water (100 mL) and refluxed for 2 hours. The reaction mixture was cooled down and poured into ice water mixture. Precipitate formed and collected by filtration, dried and purified by flash column chromatography (silica gel, 0 to 10% MeOH/ethyl acetate) to give a white solid 3,7-Dibromo-dibenzothiophene (1.6 g, 55%).

Pyrrolidine-1,2-dicarboxylic acid 2-[2-(7-bromo-dibenzothiophen-3-yl)-2-oxo-ethyl]ester 1-tert-butyl ester

[1,1'-Bis(diphenylphosphino)ferrocene]dichloropalladium(II)(3%, 69 mg, 0.098 mmol) and tetrakis(triphenylphosphine)palladium (3%, 113 mg, 0.098 mmol) were added to the mixture of 3,7-Dibromo-dibenzothiophene (1.12 g, 3.27 mmol) and tributyl(1-ethoxyvinyl)tin (1.2 eq., 1.33 mL) in 25 mL dioxane. The reaction was heated to 80° C.

under Ar overnight. The reaction was cooled to room temperature. 8 mL water was added and followed by NBS (1 eq., 699 mg). The reaction was stirred at room for 1 hour. The reaction mixture was diluted with ethyl acetate and washed with saturated sodium bicarbonate solution. The organic layer dried (MgSO4), concentrated down and dried on vacuum to give a residue which was used in next step.

The residue was dissolved in 20 mL anhydrous DMF. Boc-L-Pro-OH (4 eq., 2.815 g) was added, followed by DIEA (3.5 eq., 1.60 mL) in 20 mL MeCN and 15 mL DMF dropwise. The reaction was stirred at room temperature overnight. The reaction crude was diluted with EtOAc and washed with saturated sodium bicarbonate solution. The organic layer was dried (MgSO4), concentrated and purified by flash column chromatography (silica gel, 0 to 50% ethyl acetate/hexane) to give Pyrrolidine-1,2-dicarboxylic acid 2-[2-(7-bromo-dibenzothiophen-3-yl)-2-oxo-ethyl]ester 1-tert-butyl ester (593 mg, yield 33%) and bis product. LCMS-ESI−: calc'd for $C_{24}H_{24}BrNO_5S$: 518.42; Found: 541.9 (M+Na+).

2-[5-(7-Bromo-dibenzothiophen-3-yl)-1H-imidazol-2-yl]-pyrrolidine-1-carboxylic acid tert-butyl ester 10 mL Xylenes was added to the mixture of Pyrrolidine-1,2-dicarboxylic acid 2-[2-(7-bromo-dibenzothiophen-3-yl)-2-oxo-ethyl]ester 1-tert-butyl ester (514 mg, 0.99 mmol) and ammonia acetate (20 eq., 1.53 g). The mixture was heated in microwave at 140° C. for 60 minutes. The mixture was diluted with EtOAc and washed with sat. NaHCO3 aqueous solution. The organic layer was concentrated down and purified by flash column chromatography (silica gel, 20 to 80% ethyl acetate/hexane) to give 2-[5-(7-Bromo-dibenzothiophen-3-yl)-1H-imidazol-2-yl]-pyrrolidine-1-carboxylic acid tert-butyl ester (391 mg, yield 79%). LCMS-ESI−: calc'd for $C_{24}H_{24}BrN_3O_2S$: 498.44; Found: 499.9 (M+Na+).

3-(6-{7-[2-(1-tert-Butoxycarbonyl-pyrrolidin-2-yl)-3H-imidazol-4-yl]-dibenzothiophen-3-yl}-1H-benzoimidazol-2-yl)-2-aza-bicyclo[2.2.1]heptane-2-carboxylic acid tert-butyl ester A mixture of 2-[5-(7-Bromo-dibenzothiophen-3-yl)-1H-imidazol-2-yl]-pyrrolidine-1-carboxylic acid tert-butyl ester (300 mg, 0.48 mmol, 1 eq.), 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester (1.1 eq., 530 mg), [1,1'-bis(diphenylphosphino)ferrocene]dichloropalladium(II)(3%, 12 mg), tetrakis(triphenylphosphine)palladium (3%, 17 mg) and 2N potassium carbonate aqueous solution (3.3 eq., 0.8 mL) in 2 mL DME was heated to 80° C. under Argon for 5 hours. The reaction mixture was cooled and diluted in ethyl acetate and washed with saturated sodium bicarbonate solution. The organic layer dried (MgSO4), concentrated and purified by flash column chromatography (silica gel, 20 to 100% ethyl acetate/hexane) to give a yellow foam 3-(6-{7-[2-(1-tert-Butoxycarbonyl-pyrrolidin-2-yl)-3H-imidazol-4-yl]-dibenzothiophen-3-yl}-1H-benzoimidazol-2-yl)-2-aza-bicyclo[2.2.1]heptane-2-carboxylic acid tert-butyl ester (245 mg, yield 70%). LCMS-ESI−: calc'd for $C_{42}H_{46}N_6O_4S$: 730.92; Found: 731.2 (M+H+).

(1-{2-[5-(7-{2-[2-(2-Methoxycarbonylamino-3-methyl-butyryl)-2-aza-bicyclo[2.2.1]hept-3-yl]-3H-benzoimidazol-5-yl}-dibenzothiophen-3-yl)-1H-imidazol-2-yl]-pyrrolidine-1-carbonyl}-2-methyl-propyl)-carbamic acid methyl ester (Example DE)

4N HCl in dioxane (3 mL) was added to 3-(6-{7-[2-(1-tert-Butoxycarbonyl-pyrrolidin-2-yl)-3H-imidazol-4-yl]-dibenzothiophen-3-yl}-1H-benzoimidazol-2-yl)-2-aza-bicyclo[2.2.1]heptane-2-carboxylic acid tert-butyl ester (141 mg, 0.194 mmol) in 3 mL DCM. The reaction mixture was stirred at room temperature for 1 hour. The reaction mixture was concentrated and dried overnight under vacuum. The residue was dissolved in DMF (4 mL) and to this solution was added 2-Methoxycarbonylamino-3-methyl-butyric acid (2.08 eq., 71 mg), 4-methylmorpholine (6 eq., 0.12 mL), followed by HATU (2.04 eq., 150 mg). Reaction mixture was stirred at 0° C. for 30 minutes. The reaction mixture was diluted in ethyl acetate and washed with saturated sodium bicarbonate solution. The organic layer was dried (MgSO4), concentrated and purified by flash column chromatography (silica gel, 0 to 20% MeOH/ethyl acetate), followed by preparative reverse phase HPLC (GEMINI, 5 to 100% ACN/H2O+0.1% TFA). Product was lyophilized to give (1-{2-[5-(7-{2-[2-(2-Methoxycarbonylamino-3-methyl-butyryl)-2-aza-bicyclo[2.2.1]hept-3-yl]-3H-benzoimidazol-5-yl}-dibenzothiophen-3-yl)-1H-imidazol-2-yl]-pyrrolidine-1-carbonyl}-2-methyl-propyl)-carbamic acid methyl ester (Example DE) (121 mg, 59%). $^1$H-NMR: 300 MHz, (DMSO-$d_6$) δ: 8.60-8.40 (m, 4H), 8.16 (m, 1H), 8.01 (m, 1H), 7.90 (m, 2H), 7.76 (m, 1H), 7.33 (m, 2H), 5.15 (m, 1H), 4.76 (m, 1H), 4.56 (d, 1H), 4.22-4.08 (m, 3H), 3.85 (m, 2H), 3.55 (d, 6H), 2.76 (m, 1H), 2.30-1.50 (m, 9H), 0.96-0.75 (m, 12H). $^{19}$F-NMR: 300 MHz, (CD$_3$OD-$d_4$) δ: −112.88. LCMS-ESI+: calc'd for $C_{46}H_{52}N_8O_6S$: 845.02; Found: 845.4 (M+H+).

Example DF

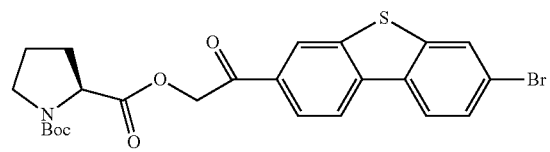

Pyrrolidine-1,2-dicarboxylic acid 2-[2-(7-bromo-dibenzothiophen-3-yl)-2-oxo-ethyl] ester 1-tert-butyl ester

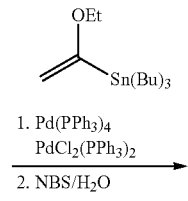

1. Pd(PPh3)4
   PdCl2(PPh3)2
2. NBS/H2O
3. DIEA, DMF

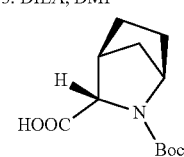

2-Aza-bicyclo[2.2.1]heptane-2,3-dicarboxylic acid 2-tert-butyl ester

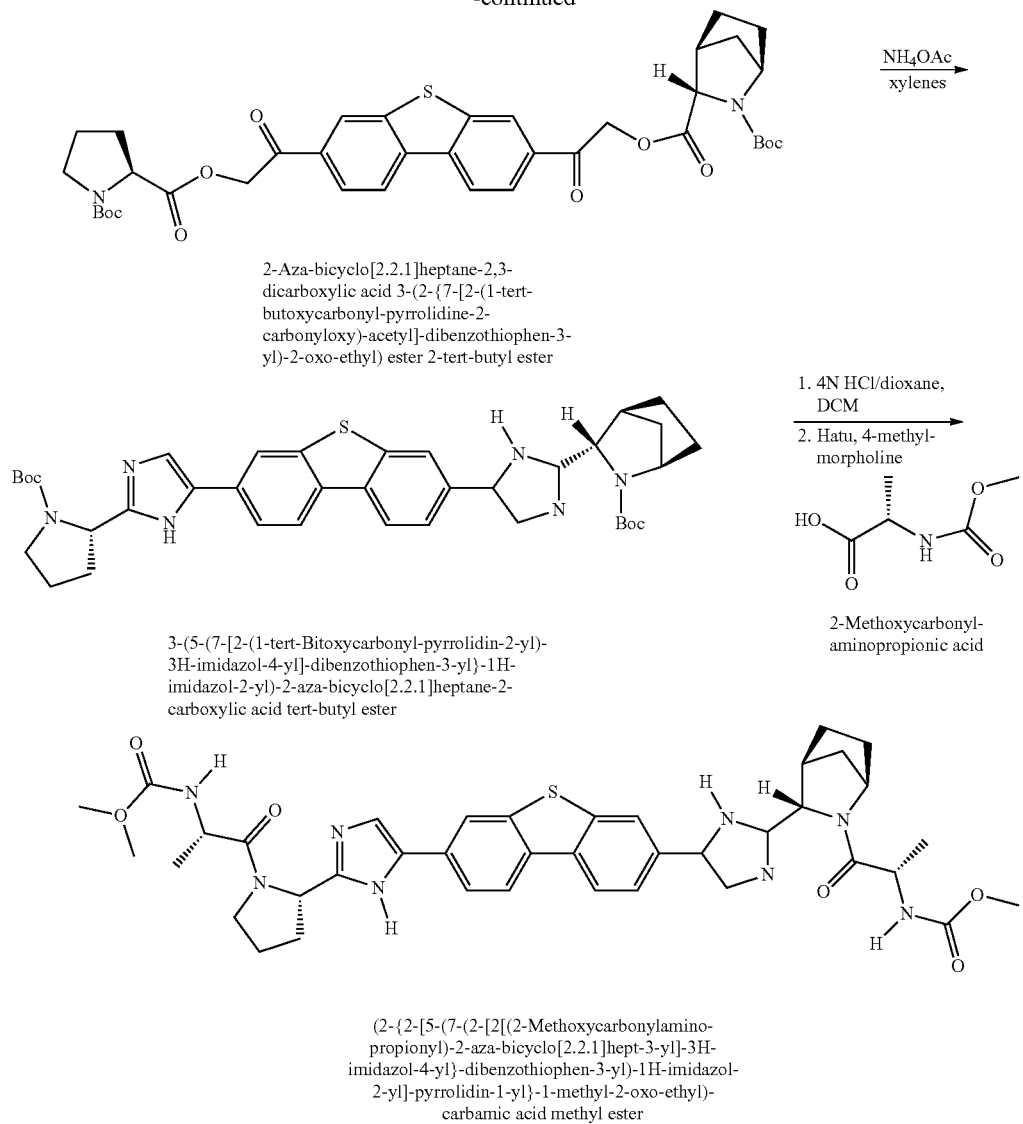

2-Aza-bicyclo[2.2.1]heptane-2,3-dicarboxylic acid 3-(2-{7-[2-(1-tert-butoxycarbonyl-pyrrolidine-2-carbonyloxy)-acetyl]-dibenzothiophen-3-yl)-2-oxo-ethyl) ester 2-tert-butyl ester 3-(5-(7-[2-(1-tert-Bitoxycarbonyl-pyrrolidin-2-yl)-3H-imidazol-4-yl]-dibenzothiophen-3-yl}-1H-imidazol-2-yl)-2-aza-bicyclo[2.2.1]heptane-2-carboxylic acid tert-butyl ester 2-Methoxycarbonyl-aminopropionic acid (2-{2-[5-(7-(2-[2[(2-Methoxycarbonylamino-propionyl)-2-aza-bicyclo[2.2.1]hept-3-yl]-3H-imidazol-4-yl}-dibenzothiophen-3-yl)-1H-imidazol-2-yl]-pyrrolidin-1-yl}-1-methyl-2-oxo-ethyl)-carbamic acid methyl ester

2-Aza-bicyclo[2.2.1]heptane-2,3-dicarboxylic acid 3-(2-{7-[2-(1-tert-butoxycarbonyl-pyrrolidine-2-carbonyloxy)-acetyl]-dibenzothiophen-3-yl]-2-oxo-ethyl) ester 2-tert-butyl ester

[1,1'-Bis(triphenylphosphine)dichloropalladium(II)(3%, 14 mg, 0.02 mmol) and tetrakis(triphenylphosphine)palladium (3%, 23 mg, 0.02 mmol) were added to the mixture of Pyrrolidine-1,2-dicarboxylic acid 2-[2-(7-bromo-dibenzothiophen-3-yl)-2-oxo-ethyl]ester 1-tert-butyl ester (345 mg, 0.665 mmol) and tributyl(1-ethoxyvinyl)tin (1.2 eq., 0.269 mL) in 5 mL dioxane. The reaction was heated to 80° C. under Are for 4 hours. The reaction was cooled to room temperature. 1.5 mL water was added and followed by NBS (1 eq., 142 mg). The reaction was stirred at room for 1 hour. The reaction mixture was diluted with ethyl acetate and washed with saturated sodium bicarbonate solution. The organic layer dried (MgSO4), concentrated down and dried on vacuum to give residue which was used in next step. The residue was dissolved in 4 mL anhydrous DMF. 2-Aza-bicyclo[2.2.1]heptane-2,3-dicarboxylic acid 2-tert-butyl ester (2 eq., 321 mg, 1.33 mmol g) was added, followed by TEA (2.2 eq., 204 mg) in 4 mL MeCN and 3 mL DMF dropwise. The reaction was stirred at room temperature overnight. The reaction crude was diluted with EtOAc and washed with saturated sodium bicarbonate solution. The organic layer dried (MgSO4), concentrated and purified by flash column chromatography (silica gel, 0 to 50% ethyl acetate/hexane) to give 2-Aza-bicyclo[2.2.1]heptane-2,3-dicarboxylic acid 3-(2-{7-[2-(1-tert-butoxycarbonyl-pyrrolidine-2-carbonyloxy)-acetyl]-dibenzothiophen-3-yl}-2-oxo-ethyl) ester 2-tert-butyl ester as a yellow residue (92.5 mg, yield 19%). LCMS-ESI⁻: calc'd for $C_{38}H_{44}N_2O_{10}S$: 720.83; Found: 743.2 (M+Na⁺).

3-(5-{7-[2-(1-tert-Butoxycarbonyl-pyrrolidin-2-yl)-3H-imidazol-4-yl]-dibenzothiophen-3-yl}-1H-imidazol-2-yl)-2-aza-bicyclo[2.2.1]heptane-2-carboxylic acid tert-butyl ester 3 mL Xylenes was added to 2-Aza-bicyclo[2.2.1]heptane-2,3-dicarboxylic acid 3-(2-{7-[2-(1-tert-butoxycarbonylpyrrolidine-2-carbonyloxy)-acetyl]-dibenzothiophen-3-yl]-2-oxo-ethyl)ester 2-tert-butyl ester (92.5 mg, 0.128 mmol) and ammonia acetate (20 eq., 198 mg). The mixture was heated in microwave at 140° C. for 60 minutes. The mixture was diluted with EtOAc and washed with sat. NaHCO3 aqueous solution. The organic layer was concentrated down and purified by flash column chromatography (silica gel, 20 to 80% ethyl acetate/hexane) to give 3-(5-{7-[2-(1-tert-Butoxycarbonyl-pyrrolidin-2-yl)-3H-imidazol-4-yl]-dibenzothiophen-3-yl}-1H-imidazol-2-yl)-2-aza-bicyclo[2.2.1]heptane-2-carboxylic acid tert-butyl ester (62 mg, yield 71%). LCMS-ESI⁻: calc'd for $C_{38}H_{44}N_6O_4S$: 680.86; Found: 681.2 (M+H⁺).

(2-{2-[5-(7-{2-[2-(2-Methoxycarbonylamino-propionyl)-2-aza-bicyclo[2.2.1]hept-3-yl]-3H-imidazol-4-yl}-dibenzothiophen-3-yl)-1H-imidazol-2-yl]-pyrrolidin-1-yl}-1-methyl-2-oxo-ethyl)-carbamic acid methyl ester (Example DF)

4N HCl in dioxane (1 mL) was added to 3-(5-{7-[2-(1-tert-Butoxycarbonyl-pyrrolidin-2-yl)-3H-imidazol-4-yl]-dibenzothiophen-3-yl}-1H-imidazol-2-yl)-2-aza-bicyclo[2.2.1]heptane-2-carboxylic acid tert-butyl ester (62 mg, 0.091 mmol) in 2 mL DCM. The reaction mixture was stirred at room temperature for 1 hour. The reaction mixture was concentrated and dried overnight under vacuum. The residue was dissolved in DMF (2 mL) and to this solution was added 2-Methoxycarbonylamino-propionic acid (2.08 eq., 28 mg), 4-methylmorpholine (6 eq., 0.06 mL), followed by HATU (2.04 eq., 71 mg). Reaction mixture was stirred at 0° C. for 30 minutes. The reaction mixture was diluted with ethyl acetate and washed with saturated sodium bicarbonate solution. The organic layer was dried (MgSO4), concentrated and purified by flash column chromatography (silica gel, 0 to 20% MeOH/ethyl acetate), followed by preparative reverse phase HPLC (GEMINI, 5 to 100% ACN/H₂O+0.1% TFA). Product was lyophilized to give (2-{2-[5-(7-{2-[2-(2-Methoxycarbonylamino-propionyl)-2-aza-bicyclo[2.2.1]hept-3-yl]-3H-imidazol-4-yl}-dibenzothiophen-3-yl)-1H-imidazol-2-yl]-pyrrolidin-1-yl}-1-methyl-2-oxo-ethyl)-carbamic acid methyl ester (Example DF) (52.7 mg, 60%).

¹H-NMR: 300 MHz, (DMSO-d₆) δ: 8.60-8.40 (m, 4H), 8.12 (m, 2H), 8.01 (m, 1H), 7.92 (m, 2H), 7.57-7.40 (m, 2H), 5.15 (m, 1H), 4.70 (m, 1H), 4.50-4.30 (m, 3H), 3.54 (d, 6H), 2.76 (m, 1H), 2.42-1.50 (m, 6H), 1.30-1.10 (m, 12H). LCMS-ESI⁺: calc'd for $C_{42}H_{44}N_8O_6S$: 738.86; Found: 739.3 (M+H⁺).

Example DG

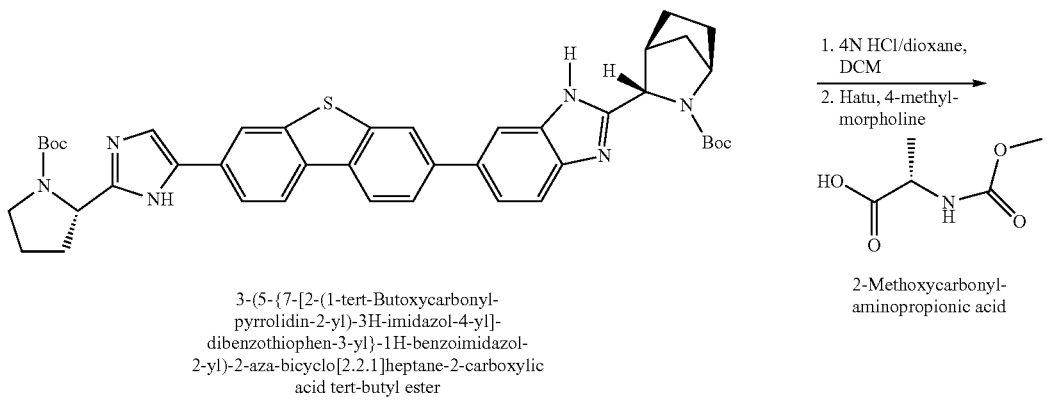

3-(5-{7-[2-(1-tert-Butoxycarbonyl-pyrrolidin-2-yl)-3H-imidazol-4-yl]-dibenzothiophen-3-yl}-1H-benzoimidazol-2-yl)-2-aza-bicyclo[2.2.1]heptane-2-carboxylic acid tert-butyl ester 2-Methoxycarbonyl-aminopropionic acid

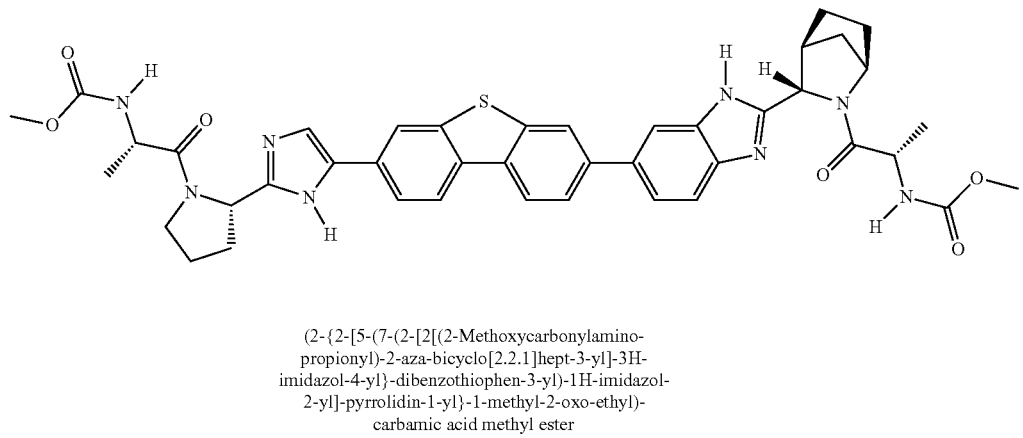

(2-{2-[5-(7-(2-[2[(2-Methoxycarbonylamino-propionyl)-2-aza-bicyclo[2.2.1]hept-3-yl]-3H-imidazol-4-yl}-dibenzothiophen-3-yl)-1H-imidazol-2-yl]-pyrrolidin-1-yl}-1-methyl-2-oxo-ethyl)-carbamic acid methyl ester (2-{2-[5-(7-{2-[2-(2-Methoxycarbonylamino-propionyl)-2-aza-bicyclo[2.2.1]hept-3-yl]-3H-benzoimidazol-5-yl}-dibenzothiophen-3-yl)-1H-imidazol-2-yl]-pyrrolidin-1-yl}-1-methyl-2-oxo-ethyl)-carbamic acid methyl ester (Example DG)

4N HCl in dioxane (2 mL) was added to 3-(6-{7-[2-(1-tert-Butoxycarbonyl-pyrrolidin-2-yl)-3H-imidazol-4-yl]-dibenzothiophen-3-yl}-1H-benzoimidazol-2-yl)-2-aza-bicyclo[2.2.1]heptane-2-carboxylic acid tert-butyl ester (103 mg, 0.141 mmol) in 3 mL DCM. The reaction mixture was stirred at room temperature for 1 hour. The reaction mixture was concentrated and dried overnight under vacuum. The residue was dissolved in DMF (2 mL) and to this solution was added 2-Methoxycarbonylamino-propionic acid (2.08 eq., 43 mg), 4-methylmorpholine (6 eq., 0.093 mL), followed by HATU (2.04 eq., 109 mg). Reaction mixture was stirred at 0° C. for 30 minutes. The reaction mixture was diluted with ethyl acetate and washed with saturated sodium bicarbonate solution. The organic layer was dried (MgSO₄), concentrated and purified by flash column chromatography (silica gel, 0 to 20% MeOH/ethyl acetate), followed by preparative reverse phase HPLC (GEMINI, 5 to 100% ACN/H₂O+0.1% TFA). Product was lyophilized to give (2-{2-[5-(7-{2-[2-(2-Methoxycarbonylamino-propionyl)-2-aza-bicyclo[2.2.1]hept-3-yl]-3H-benzoimidazol-5-yl}-dibenzothiophen-3-yl)-1H-imidazol-2-yl]-pyrrolidin-1-yl}-1-methyl-2-oxo-ethyl)-carbamic acid methyl ester (Example DG) (91.3 mg, 80%).

$^1$H-NMR: 300 MHz, (DMSO-$d_6$) δ: 8.60-8.52 (m, 2H), 8.44 (m, 2H), 8.15 (m, 1H), 8.05 (m, 1H), 7.92 (m, 2H), 7.80 (m, 2H), 7.56-7.42 (m, 2H), 5.15 (m, 1H), 4.70 (m, 1H), 4.50-4.30 (m, 3H), 3.54 (d, 6H), 2.76 (m, 1H), 2.42-1.50 (m, 12H), 1.30-1.10 (m, 6H). LCMS-ESI⁺: calc'd for $C_{42}H_{44}N_8O_6S$: 788.91; Found: 789.4 (M+H⁺).

Example DH

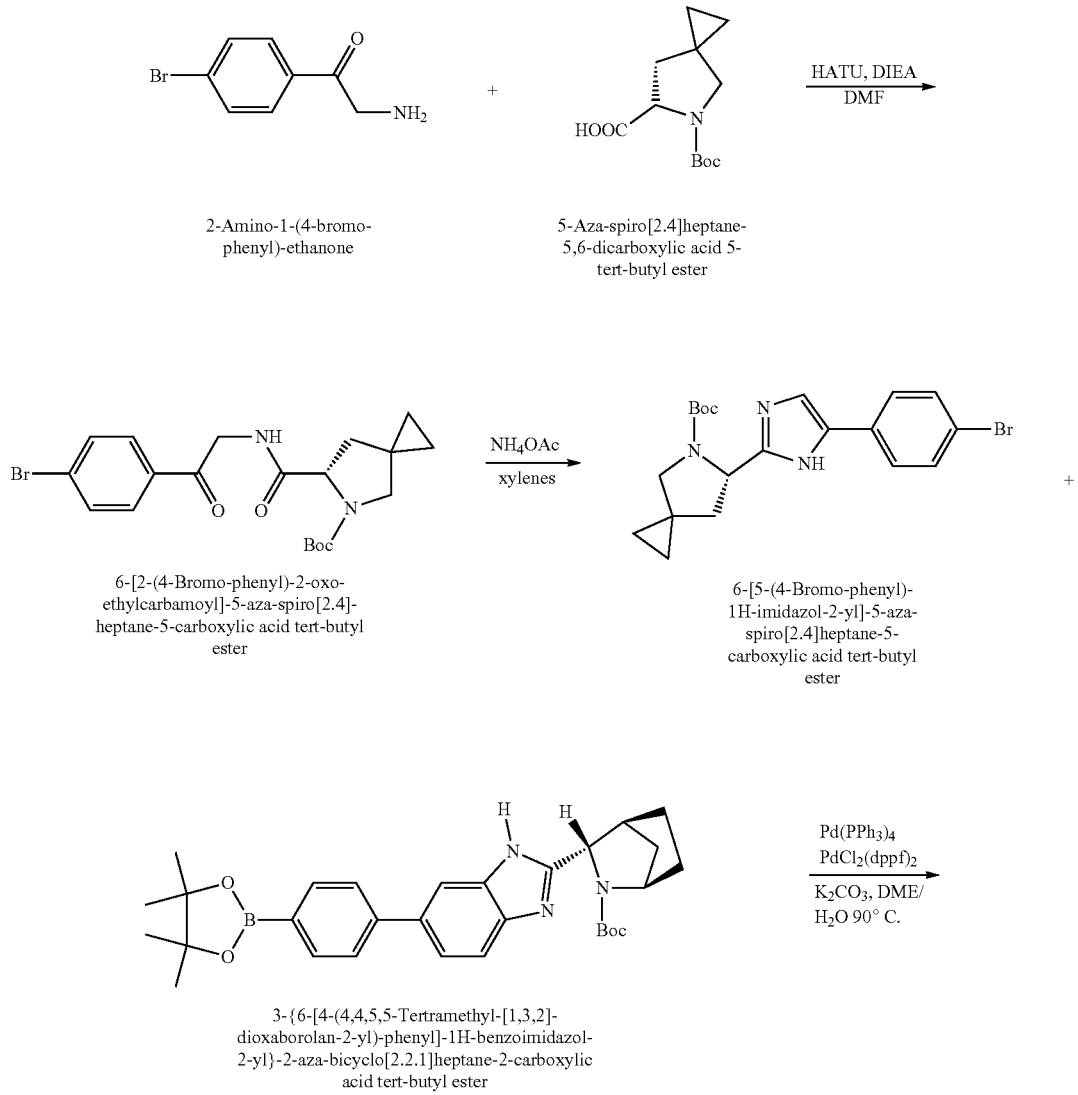

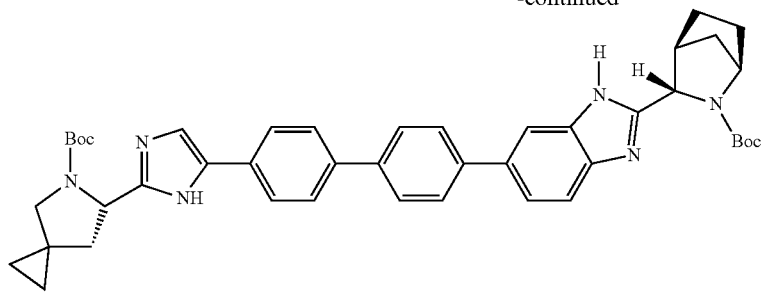

3-(6-{4'-[2-(5-tert-Butoxycarbonyl-5-aza-spiro[2.4]hept-6-yl)-3H-imidazol-4-yl]-biphenyl-4-yl}-1H-benzoimidazol-2-yl)-2-aza-bicyclo[2.2.1]heptane-2-carboxylic acid tert-butyl ester

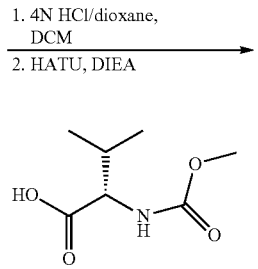

1. 4N HCl/dioxane, DCM
2. HATU, DIEA

2-Methoxycarbonylamino-3-methyl-butyric acid

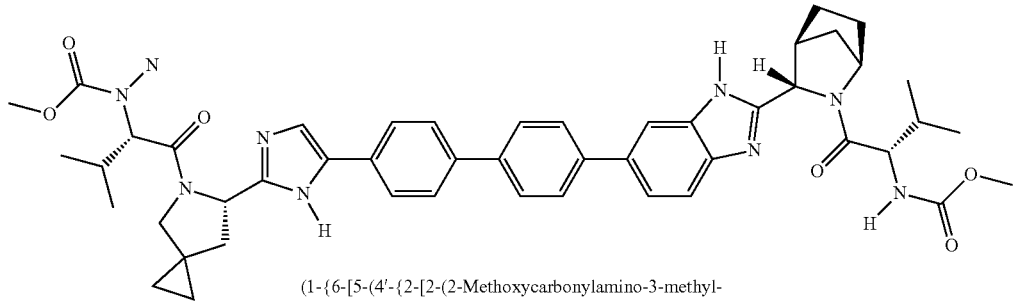

(1-{6-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-5-aza-spiro[2.4]heptane-5-carbonyl}-2-methyl-propyl)-carbamic acid methyl ester

6-[2-(4-Bromo-phenyl)-2-oxo-ethylcarbamoyl]-5-aza-spiro[2.4]heptane-5-carboxylic acid tert-butyl ester 5-Aza-spiro[2.4]heptane-5,6-dicarboxylic acid 5-tert-butyl ester (350 mg, 1.45 mmol) was mixed with HATU (551 mg, 1.45 mmol) in DMF (5 mL) and the mixture was stirred at room temperature for 30 minutes. 2-Amino-1-(4-bromo-phenyl)-ethanone bis HCl salt (416 mg, 1.45 mmol) in 2 mL DMF was added, followed by DIEA (3.5 eq., 0.88 mL) dropwise at 0° C. The reaction was stirred at 0° C. for 40 minutes. The reaction mixture was diluted in ethyl acetate and washed with saturated sodium bicarbonate solution. The organic layer was dried (MgSO4), concentrated and purified by flash column chromatography (silica gel, 20 to 100% ethyl acetate/hexane) to give 6-[2-(4-Bromo-phenyl)-2-oxo-ethylcarbamoyl]-5-aza-spiro[2.4]heptane-5-carboxylic acid tert-butyl ester (424 mg, 67%). LCMS-ESI$^-$: calc'd for $C_{20}H_{25}BrN_2O_4$: 437.33; Found: 460.1 (M+Na$^+$).

6-[5-(4-Bromo-phenyl)-1H-imidazol-2-yl]-5-aza-spiro[2.4]heptane-5-carboxylic acid tert-butyl ester 15 mL Xylenes was added to 6-[2-(4-Bromo-phenyl)-2-oxo-ethylcarbamoyl]-5-aza-spiro[2.4]heptane-5-carboxylic acid tert-butyl ester (424 mg, 0.97 mmol) and ammonium acetate (20 eq., 1.5 g). The mixture was heated in microwave at 140° C. for 60 minutes. The mixture was diluted with EtOAc and washed with sat. NaHCO3 aqueous solution. The organic layer was concentrated down and purified by flash column chromatography (silica gel, 20 to 80% ethyl acetate/hexane) to give 6-[5-(4-Bromo-phenyl)-1H-imidazol-2-yl]-5-aza-spiro[2.4]heptane-5-carboxylic acid tert-butyl ester (249 mg, yield 61%). LCMS-ESI$^-$: calc'd for $C_{20}H_{24}BrN_3O_2$: 418.33; Found: 418. (M+H$^+$).

3-(6-{4'-[2-(5-tert-Butoxycarbonyl-5-aza-spiro[2.4]hept-6-yl)-3H-imidazol-4-yl]-biphenyl-4-yl}-1H-benzoimidazol-2-yl)-2-aza-bicyclo[2.2.1]heptane-2-carboxylic acid tert-butyl ester A mixture of 6-[5-(4-Bromo-phenyl)-1H-imidazol-2-yl]-5-aza-spiro[2.4]heptane-5-carboxylic acid tert-butyl ester (101 mg, 0.243 mmol, 1 eq.), 3-{6-[4-(4,4,5,5-Tetramethyl-[1,3,2]dioxaborolan-2-yl)-phenyl]-1H-benzoimidazol-2-yl}-2-aza-bicyclo[2.2.1]heptane-2-carboxylic acid tert-butyl ester (150 mg, 0.291 mmol, 1.2 eq.), tetrakis(triphenylphosphine)palladium (5%, 17 mg) and 2M potassium carbonate aqueous solution (5 eq., 0.73 mL) in 1.5 mL DME was heated to 90° C. under Are overnight. The reaction mixture was cooled and dissolved in ethyl acetate and washed with saturated sodium bicarbonate solution. The organic layer was dried (MgSO$_4$), concentrated and purified by flash column chromatography (silica gel, 50 to 100% ethyl acetate/hexane) to give 3-(6-{4'-[2-(5-tert-Butoxycarbonyl-5-aza-spiro[2.4]hept-6-yl)-3H-imidazol-4-yl]-biphenyl-4-yl}-1H-benzoimidazol-2-yl)-2-aza-bicyclo[2.2.1]heptane-2-carboxylic acid tert-butyl ester (53 mg, yield 26%). LCMS-ESI$^-$: calc'd for $C_{44}H_{50}N_6O_4$: 726.91; Found: 727.2 (M+H$^+$).

(1-{6-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-5-aza-spiro[2.4]heptane-5-carbonyl}-2-methyl-propyl)-carbamic acid methyl ester (Example DH)

4N HCl in dioxane (2 mL) was added to 3-(6-{4'-[2-(5-tert-Butoxycarbonyl-5-aza-spiro[2.4]hept-6-yl)-3H-imidazol-4-yl]-biphenyl-4-yl}-1H-benzoimidazol-2-yl)-2-aza-bi-cyclo[2.2.1]heptane-2-carboxylic acid tert-butyl ester (53 mg, 0.073 mmol) in 2 mL DCM and the reaction mixture was stirred at room temperature for 2 hours. The reaction mixture was concentrated and dried overnight under vacuum. The residue was dissolved in DMF (1 mL) and to this solution was added 2-Methoxycarbonylamino-3-methyl-butyric acid (2.1 eq., 26.6 mg), 4-methylmorpholine (6 eq., 0.048 mL), followed by HATU (2 eq., 56 mg). Reaction mixture was stirred at 0° C. for 50 minutes. The reaction mixture was dissolved in ethyl acetate and washed with dilute sodium bicarbonate solution. The organic layer was dried (MgSO4), concentrated and purified by preparative reverse phase HPLC (GEMINI, 5 to 100% ACN/H$_2$O+0.1% TFA). Product was lyophilized to give (1-{6-[5-(4'-{2-[2-(2-Methoxycarbonylamino-3-methyl-butyryl)-2-aza-bicyclo[2.2.1]hept-3-yl]-3H-benzoimidazol-5-yl}-biphenyl-4-yl)-1H-imidazol-2-yl]-5-aza-spiro[2.4]heptane-5-carbonyl}-2-methyl-propyl)-carbamic acid methyl ester (Example DH) (41.6 mg, 53%).

$^1$H-NMR: 300 MHz, (DMSO-d$_6$) δ: 8.13 (s, 1H), 7.95-7.80 (m, 9H), 7.69 (m, 2H), 7.40-7.24 (m, 2H), 5.25 (m, 1H), 4.76 (m, 1H), 4.55 (m, 1H), 4.20-3.80 (m, 3H), 3.55 (d, 6H), 2.74 (m, 2H), 2.40-1.55 (m, 10H), 0.95-0.65 (m, 12H).

LCMS-ESI$^+$: calc'd for C$_{46}$H$_{54}$N$_8$O$_6$: 841.01; Found: 841.5 (M+H$^+$).

Example DI

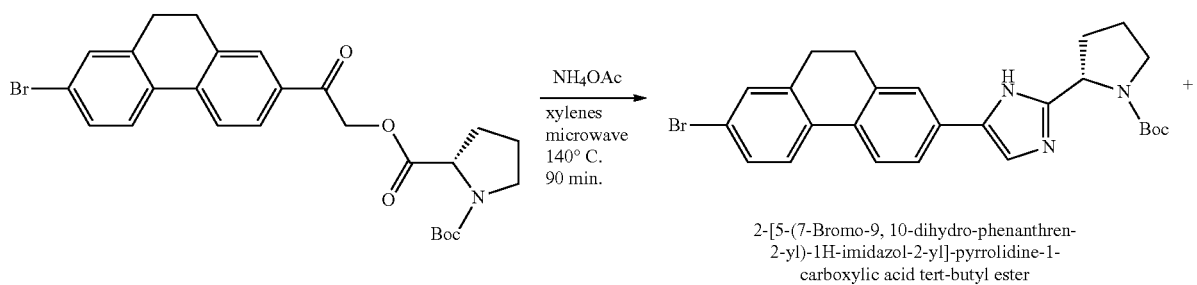

Pyrrolidine-1,2-dicarboxylic acid 2-[2-(7-bromo-9,10-dihydro-phenanthren-2-yl)-2-oxo-ethyl] ester 1-tert-butyl ester 2-[5-(7-Bromo-9,10-dihydro-phenanthren-2-yl)-1H-imidazol-2-yl]-pyrrolidine-1-carboxylic acid tert-butyl ester

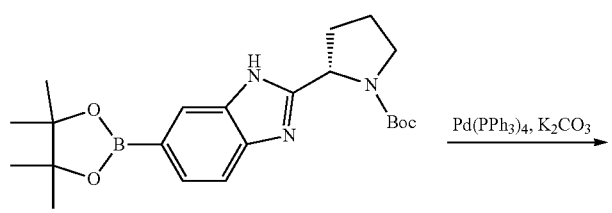

2-[6-(4,4,5,5-Tetramethyl-[1,3,2]dioxaborolan-2-yl)-1H-benzoimidazol-2-yl]-pyrrolidine-1-carboxylic acid tert-butyl ester

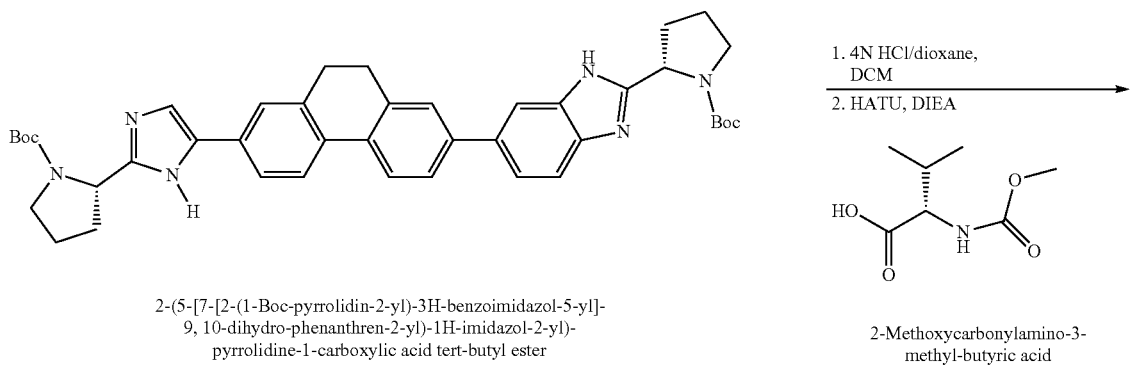

2-(5-[7-[2-(1-Boc-pyrrolidin-2-yl)-3H-benzoimidazol-5-yl]-9,10-dihydro-phenanthren-2-yl)-1H-imidazol-2-yl)-pyrrolidine-1-carboxylic acid tert-butyl ester 2-Methoxycarbonylamino-3-methyl-butyric acid

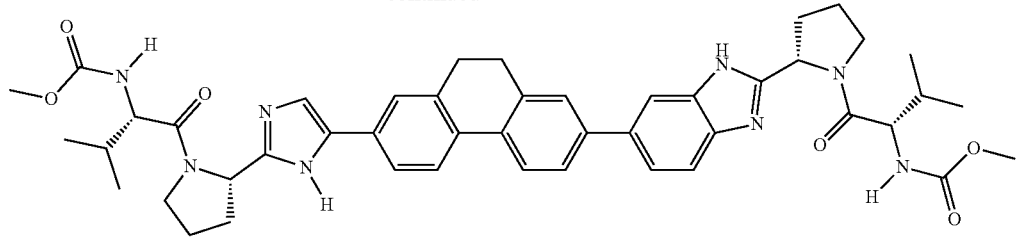

(1-{2-[5-(7-{2-[1-(2-Methoxycarbonylamino-3-methyl-butyryl)-pyrrolidin-2-yl]-3H-benzoimidazol-5-yl}-9,10-dihydro-phenanthren-2-yl)-1H-imidazol-2-yl]-pyrrolidine-1-carbonyl}-2-methyl-propyl)-carbamic acid methyl ester

2-[5-(7-bromo-9,10-dihydro-phenanthren-2-yl)-1H-imidazol-2-yl]-pyrrolidine-1-carboxylic acid tert-butyl ester 10 mL Xylenes and 10 ml DME were added to the mixture of pyrrolidine-1,2-dicarboxylic acid 2-[2-(7-bromo-9,10-dihydro-phenanthren-2-yl)-2-oxo-ethyl]ester 1-tert-butyl ester (480 mg, 0.935 mmol) and ammonia acetate (20 eq., 1.44 g). The mixture was heated in microwave at 140° C. for 90 minutes. The mixture was diluted with EtOAc and washed with sat. NaHCO3 aqueous solution. The organic layer was concentrated down and purified by flash column chromatography (silica gel, 20 to 80% ethyl acetate/hexane) to give 2-[5-(7-bromo-9,10-dihydro-phenanthren-2-yl)-1H-imidazol-2-yl]-pyrrolidine-1-carboxylic acid tert-butyl ester (246 mg, yield 53%). LCMS-ESI⁻: calc'd for $C_{26}H_{28}BrN_3O_2$: 494.42; Found: 495.5 (M+H⁺).

2-(5-{7-[2-(1-Boc-pyrrolidin-2-yl)-3H-benzoimidazol-5-yl]-9,10-dihydro-phenanthren-2-yl}-1H-imidazol-2-yl)-pyrrolidine-1-carboxylic acid tert-butyl ester A mixture of 2-[5-(7-bromo-9,10-dihydro-phenanthren-2-yl)-1H-imidazol-2-yl]-pyrrolidine-1-carboxylic acid tert-butyl ester (246 mg, 0.497 mmol), 2-[6-(4,4,5,5-tetramethyl-[1,3,2]dioxaborolan-2-yl)-1H-benzoimidazol-2-yl]-pyrrolidine-1-carboxylic acid tert-butyl ester (1 eq., 206 mg), [1,1'-bis(diphenylphosphino)ferrocene]dichloropalladium (II)(5%, 20 mg), tetrakis(triphenylphosphine)palladium (5%, 29 mg) and potassium acetate (2 eq., 137 mg) in 5 mL DME and 1 mL water was heated to 80° C. for 100 minutes. The reaction mixture was cooled and diluted with ethyl acetate and washed with saturated sodium bicarbonate solution. The organic layer dried (MgSO4), concentrated and purified by flash column chromatography (silica gel, 20 to 100% ethyl acetate/hexane) to give 2-(5-{7-[2-(1-Boc-pyrrolidin-2-yl)-3H-benzoimidazol-5-yl]-9,10-dihydro-phenanthren-2-yl}-1H-imidazol-2-yl)-pyrrolidine-1-carboxylic acid tert-butyl ester (220 mg, yield 63%). LCMS-ESI⁻: calc'd for $C_{42}H_{48}N_6O_4$: 700.87; Found: 701.1 (M+H⁺).

(1-{2-[5-(7-{2-[1-(2-Methoxycarbonylamino-3-methyl-butyryl)-pyrrolidin-2-yl]-3H-benzoimidazol-5-yl}-9,10-dihydro-phenanthren-2-yl)-1H-imidazol-2-yl]-pyrrolidine-1-carbonyl}-2-methyl-propyl)-carbamic acid methyl ester (Example A)

4N HCl in dioxane (2 mL) was added to 2-(5-{7-[2-(1-Boc-pyrrolidin-2-yl)-3H-benzoimidazol-5-yl]-9,10-dihydro-phenanthren-2-yl}-1H-imidazol-2-yl)-pyrrolidine-1-carboxylic acid tert-butyl ester (220 mg, 0.314 mmol) in 1 mL DCM and the reaction mixture was stirred at room temperature for 4 hours. The reaction mixture was concentrated and dried overnight under vacuum. The residue was dissolved in DMF (3 mL) and to this solution was added 2-Methoxycarbonylamino-3-methyl-butyric acid (2.1 eq., 116 mg), diisopropyl ethylamine (5 eq., 270 µL), followed by HATU (2 eq., 239 mg). Reaction mixture was stirred at 0° C. for 30 minutes. The reaction mixture was dissolved in ethyl acetate and washed with dilute sodium bicarbonate solution. The organic layer was dried (MgSO₄), concentrated and purified by preparative reverse phase HPLC (GEMINI, 5 to 100% ACN/H₂O+0.1% TFA). Product was lyophilized to give (1-{2-[5-(7-{2-[1-(2-Methoxycarbonylamino-3-methyl-butyryl)-pyrrolidin-2-yl]-3H-benzoimidazol-5-yl}-9,10-dihydro-phenanthren-2-yl)-1H-imidazol-2-yl]-pyrrolidine-1-carbonyl}-2-methyl-propyl)-carbamic acid methyl ester (Example DI) (115 mg, 45%).

¹H-NMR: 300 MHz, (CD₃OD-d₄) δ: 8.02-7.95 (m, 3H), 7.95-7.80 (m, 3H), 7.66-7.62 (m, 4H), 5.40-5.23 (m, 2H), 4.22 (m, 2H), 4.16 (m, 2H), 3.96-3.82 (m, 2H), 3.62 (s, 6H), 3.00 (s, 4H), 2.60 (m, 2H), 2.40-2.18 (m, 6H), 2.08 (m, 2H), 0.95-0.85 (m, 12H).

LCMS-ESI⁺: calc'd for $C_{46}H_{54}N_8O_6$: 814.97; Found: 815.4 (M+H⁺).

Example DJ

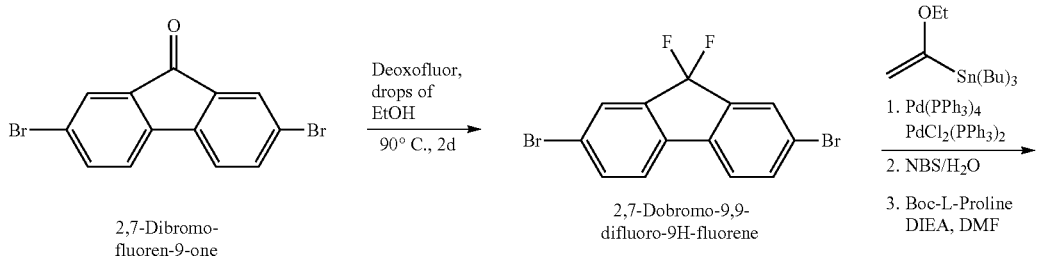

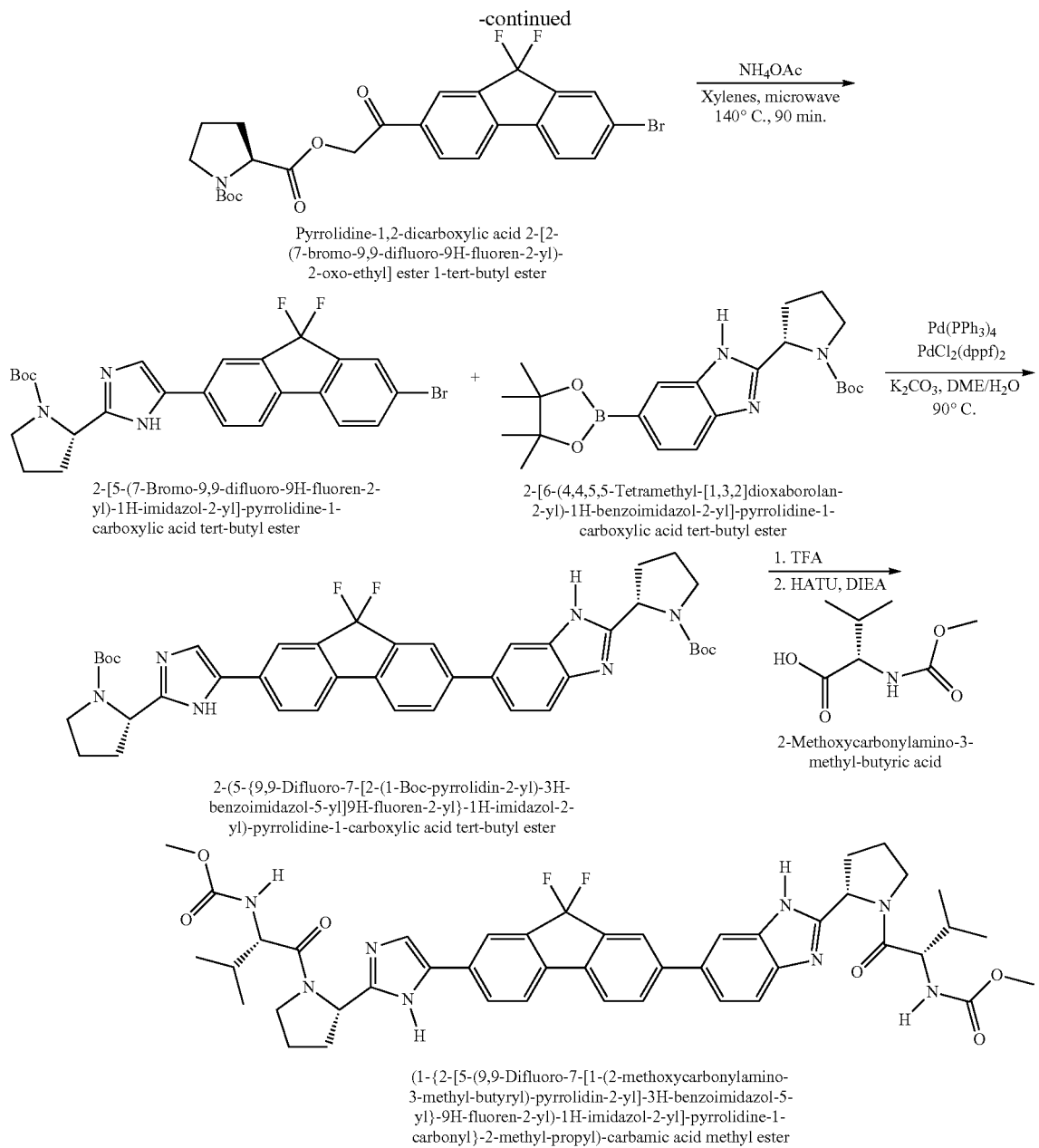

2,7-Dibromo-9,9-difluoro-9H-fluorene

Deoxofluor (bis(2-methoxyethyl)aminosulfur trifluoride, 12 mL) was added to 2,7-dibromo-fluoren-9-one (3 grams, 8.87 mmol), followed by 2 drops of ethanol. The reaction mixture was heated to 90° C. The reaction progress was monitored by analytical HPLC and TLC (in pure hexane). The product is more non-polar than the starting material. The reaction was complete after 2 days. The reaction mixture was cooled down, poured into ice water and neutralized by saturated sodium bicarbonate solution, then was extracted using ethyl acetate and washed with saturated sodium bicarbonate solution twice. The organic layer was dried (MgSO4), concentrated and purified by flash column chromatography (silica gel, 0 to 20% ethyl acetate/hexane) give product 2,7-dibromo-9,9-difluoro-9H-fluorene (3.1 gram, yield 97%).

$^1$H-NMR: 300 MHz, (CDCl$_3$) δ: 7.76 (s, 2H), 7.62 (d, 2H), 7.42 (d, 2H). F-NMR: 300 MHz, (CDCl$_3$) δ: −111.57.

Pyrrolidine-1,2-dicarboxylic acid 2-[2-(7-bromo-9,9-difluoro-9H-fluoren-2-yl)-2-oxo-ethyl]ester 1-tert-butyl ester

[1,1'-Bis(diphenylphosphino)ferrocene]dichloropalladium(II)(5%, 82 mg) and tetrakis(triphenylphosphine)palladium (5%, 115 mg) were added to the mixture of 2,7-dibromo-9,9-difluoro-9H-fluorene (720 mg, 3 mmol) and tributyl(1-ethoxyvinyl)tin (1 eq., 0.677 mL) in 12 mL dioxane. The reaction was heated to 70° C. under Argon for 4 hours. The reaction was cooled to room temperature. 3 mL water was added and followed by NBS (1 eq., 356 mg). The reaction was stirred at room temperature overnight. The reaction mixture was dissolved in ethyl acetate and washed with saturated sodium bicarbonate solution. The organic layer dried (MgSO4), concentrated down. The residue was dissolved in 15 mL anhydrous DMF. Boc-L-Pro-OH (4 eq., 1.72 g) was added, followed by DIEA (3.5 eq., 1.22 mL) in 5 mL MeCN and 5 mL DMF dropwise. The reaction was stirred at room temperature for 3 hours. The reaction crude was diluted with EtOAc and washed with saturated sodium bicarbonate solution. The organic layer dried (MgSO$_4$), concentrated and purified by flash column chromatography (silica gel, 20 to 100% ethyl acetate/hexane) to give pyrrolidine-1,2-dicarboxylic acid 2-[2-(7-bromo-9,9-difluoro-9H-fluoren-2-yl)-2-oxo-ethyl]ester 1-tert-butyl ester (363 mg, yield 34%). LCMS-ESI$^-$: calc'd for $C_{25}H_{24}BrF_2NO_5$: 536.36; Found: 560.0 (M+Na$^+$), 535.9 (M–H).

2-[5-(7-Bromo-9,9-difluoro-9H-fluoren-2-yl)-1H-imidazol-2-yl]-pyrrolidine-1-carboxylic acid tert-butyl ester 10 mL Xylenes was added to the mixture of pyrrolidine-1,2-dicarboxylic acid 2-[2-(7-bromo-9,9-difluoro-9H-fluoren-2-yl)-2-oxo-ethyl]ester 1-tert-butyl ester (363 mg, 0.677 mmol) and ammonia acetate (20 eq., 1.04 g). The mixture was heated in microwave at 140° C. for 90 minutes. The mixture was diluted with EtOAc and washed with sat. NaHCO3 aqueous solution. The organic layer was concentrated down and purified by flash column chromatography (silica gel, 20 to 80% ethyl acetate/hexane) to give 2-[5-(7-Bromo-9,9-difluoro-9H-fluoren-2-yl)-1H-imidazol-2-yl]-pyrrolidine-1-carboxylic acid tert-butyl ester (324 mg, yield 81%). LCMS-ESI$^-$: calc'd for $C_{25}H_{24}BrF_2N_3O_2$: 516.38; Found: 517.9 (M+H$^+$).

2-(5-{9,9-Difluoro-7-[2-(1-Boc-pyrrolidin-2-yl)-3H-benzoimidazol-5-yl]-9H-fluoren-2-yl}-1H-imidazol-2-yl)-pyrrolidine-1-carboxylic acid tert-butyl ester A mixture of 2-[5-(7-Bromo-9,9-difluoro-9H-fluoren-2-yl)-1H-imidazol-2-yl]-pyrrolidine-1-carboxylic acid tert-butyl ester (137 mg, 0.265 mmol), 2-[6-(4,4,5,5-Tetramethyl-[1,3,2]dioxaborolan-2-yl)-1H-benzoimidazol-2-yl]-pyrrolidine-1-carboxylic acid tert-butyl ester (1 eq., 110 mg), [1,1'-bis(diphenylphosphino)ferrocene]dichloropalladium (II)(5%, 11 mg), tetrakis(triphenylphosphine)palladium (5%, 16 mg) and potassium carbonate (2 eq., 73 mg) in 4 mL DME and 2 mL water was heated to 90° C. for 2 hours. The reaction mixture was cooled and dissolved in ethyl acetate and washed with saturated sodium bicarbonate solution. The organic layer dried (MgSO4), concentrated and purified by flash column chromatography (silica gel, 20 to 100% ethyl acetate/hexane) to give 2-(5-{9,9-Difluoro-7-[2-(1-Boc-pyrrolidin-2-yl)-3H-benzoimidazol-5-yl]-9H-fluoren-2-yl}-1H-imidazol-2-yl)-pyrrolidine-1-carboxylic acid tert-butyl ester (83 mg, yield 43%). LCMS-ESI$^-$: calc'd for $C_{41}H_{44}F_2N_6O_4$: 722.82; Found: 723.1 (M+H$^+$).

(1-{2-[5-(9,9-Difluoro-7-{2-[1-(2-methoxycarbonylamino-3-methyl-butyryl)-pyrrolidin-2-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (Example DJ)

TFA (2 mL) was added to 2-(5-{9,9-Difluoro-7-[2-(1-Boc-pyrrolidin-2-yl)-3H-benzoimidazol-5-yl]-9H-fluoren-2-yl}-1H-imidazol-2-yl)-pyrrolidine-1-carboxylic acid tert-butyl ester (83 mg, 0.115 mmol) and the reaction mixture was stirred at room temperature for 4 hours. The reaction mixture was concentrated and dried overnight under vacuum. The residue was dissolved in DMF (3 mL) and to this solution was added 2-Methoxycarbonylamino-3-methyl-butyric acid (2 eq., 40 mg), diisopropyl ethylamine (6 eq., 120 μL), followed by HATU (2 eq., 88 mg). Reaction mixture was stirred at 0° C. for 30 minutes. The reaction mixture was dissolved in ethyl acetate and washed with saturated sodium bicarbonate solution. The organic layer was dried (MgSO4), concentrated and purified by preparative reverse phase HPLC (GEMINI, 5 to 100% ACN/H$_2$O+0.1% TFA). Product was lyophilized to give (1-{2-[5-(9,9-Difluoro-7-{2-[1-(2-methoxycarbonylamino-3-methyl-butyryl)-pyrrolidin-2-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (Example DJ) (37 mg, 39%).

$^1$H-NMR: 300 MHz, (CD$_3$OD-d$_4$) δ: 8.05-7.82 (m, 9H), 5.40-5.22 (m, 2H), 4.22 (m, 2H), 4.16 (m, 2H), 4.00-3.82 (m, 2H), 3.62 (s, 6H), 2.60 (m, 2H), 2.42-2.18 (m, 6H), 2.08 (m, 2H), 0.95-0.85 (m, 12H). $^{19}$F-NMR: 300 MHz, (CD$_3$OD-d$_4$) δ: −112.88. LCMS-ESI$^+$: calc'd for $C_{45}H_{50}F_2N_8O_6$: 836.93; Found: 837.3 (M+H$^+$).

Example DK

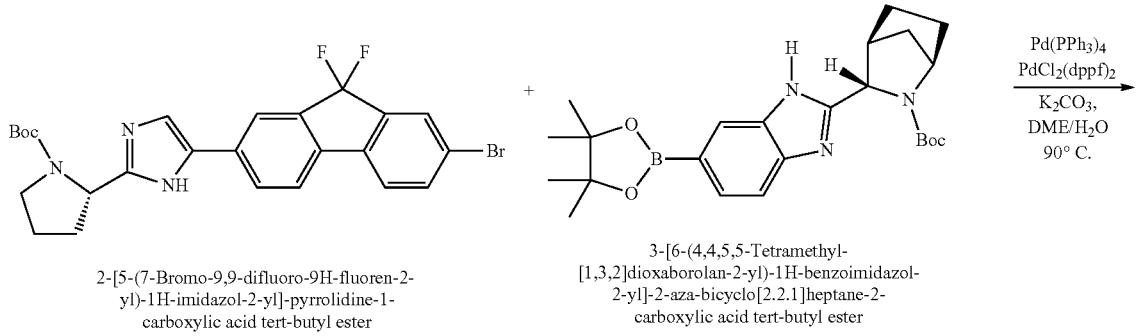

-continued

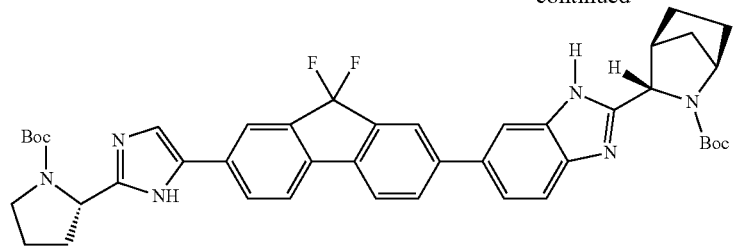

2-(5-{9,9-Difluoro-7-[2-(2-Boc-2-aza-bicyclo[2.2.1]hept-3-yl)-3H-benzoimidazol-5-yl]-9H-fluoren-2-yl)-1H-imidazol-2-yl)-pyrrolidine-1-carboxylic acid tert-butyl ester

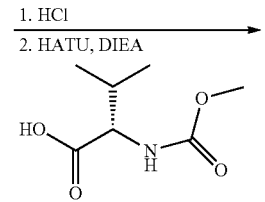

2-Methoxycarbonylamino-3-methyl-butyric acid

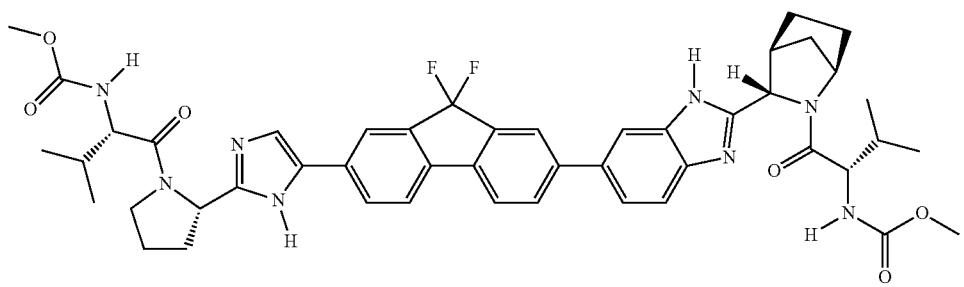

(1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester

2-(5-{9,9-Difluoro-7-[2-(2-Boc-2-aza-bicyclo[2.2.1]hept-3-yl)-3H-benzoimidazol-5-yl]-9H-fluoren-2-yl}-1H-imidazol-2-yl)-pyrrolidine-1-carboxylic acid tert-butyl ester A mixture of 2-[5-(7-Bromo-9,9-difluoro-9H-fluoren-2-yl)-1H-imidazol-2-yl]-pyrrolidine-1-carboxylic acid tert-butyl ester (324 mg, 0.627 mmol), 3-[6-(4,4,5,5-Tetramethyl-[1,3,2]dioxaborolan-2-yl)-1H-benzoimidazol-2-yl]-2-azabicyclo[2.2.1]heptane-2-carboxylic acid tert-butyl ester (1.1 eq., 304 mg), [1,1'bis(diphenylphosphino)ferrocene]dichloropalladium(II)(3%, 15 mg), tetrakis(triphenylphosphine)palladium (3%, 22 mg) and potassium carbonate (3.3 eq., 285 mg) in 10 mL DME and 3 mL water was heated to 90° C. under Argon for 3 hours. The reaction mixture was cooled and diluted with ethyl acetate and washed with saturated sodium bicarbonate solution. The organic layer was dried (MgSO4), concentrated and purified by flash column chromatography (silica gel, 20 to 100% ethyl acetate/hexane) to give 2-(5-{9,9-Difluoro-7-[2-(2-Boc-2-aza-bicyclo[2.2.1]hept-3-yl)-3H-benzoimidazol-5-yl]-9H-fluoren-2-yl}-1H-imidazol-2-yl)-pyrrolidine-1-carboxylic acid tert-butyl ester (361 mg, yield 77%). LCMS-ESI$^-$: calc'd for $C_{43}H_{46}F_2N_6O_4$: 748.86; Found: 749.2 (M+H$^+$).

(1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (Example DK)

4N HCl in dioxane (2 mL) was added to 2-(5-{9,9-Difluoro-7-[2-(2-Boc-2-aza-bicyclo[2.2.1]hept-3-yl)-3H-benzoimidazol-5-yl]-9H-fluoren-2-yl}-1H-imidazol-2-yl)-pyrrolidine-1-carboxylic acid tert-butyl ester (361 mg, 0.482 mmol) and the reaction mixture was stirred at room temperature for 4 hours. The reaction mixture was concentrated and dried overnight under vacuum. The residue was dissolved in DMF (5 mL) and to this solution was added 2-Methoxycarbonylamino-3-methyl-butyric acid (2 eq., 169 mg), diisopropyl ethylamine (6 eq., 0.5 mL), followed by HATU (2 eq., 367 mg). Reaction mixture was stirred at 0° C. for 30 minutes. The reaction mixture was dissolved in ethyl acetate and washed with saturated sodium bicarbonate solution. The organic layer was dried (MgSO4), concentrated and purified by flash column chromatography (silica gel, 0 to 20% MeOH/ethyl acetate), followed by preparative reverse phase HPLC (GEMINI, 5 to 100% ACN/H$_2$O+0.1% TFA). Product was lyophilized to give (1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (285 mg, 59%).

$^1$H-NMR: 300 MHz, (CD$_3$OD-d$_4$) δ: 8.05-7.82 (m, 9H), 5.40-5.22 (m, 2H), 4.72 (m, 1H), 4.39 (d, 1H), 4.239d, 1H), 4.17 (m, 1H), 3.91 (m, 2H), 3.62 (d, 6H), 2.98 (m, 1H), 2.58 (m, 1H), 2.37-2.18 (m, 4H), 2.18-1.92 (m, 4H), 1.80 (m, 2H), 1.09-0.85 (m, 12H). $^{19}$F-NMR: 300 MHz, (CD$_3$OD-d$_4$) δ: −112.88. LCMS-ESI$^+$: calc'd for $C_{47}H_{52}F_2N_8O_6$ 862.96; Found: 863.5 (M+H$^+$).

Example DL

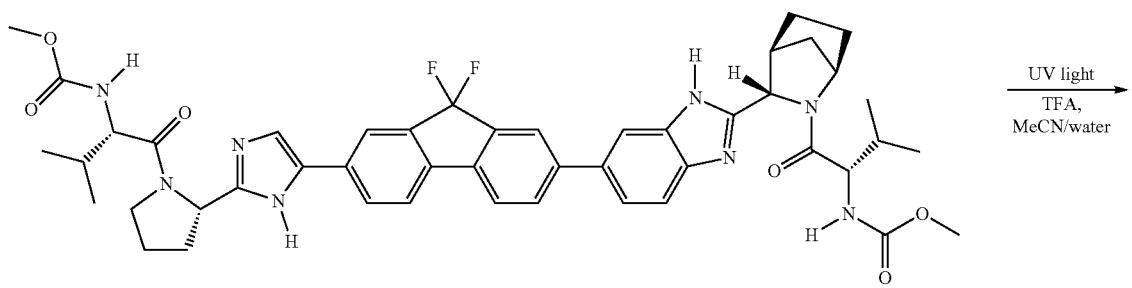

(1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester

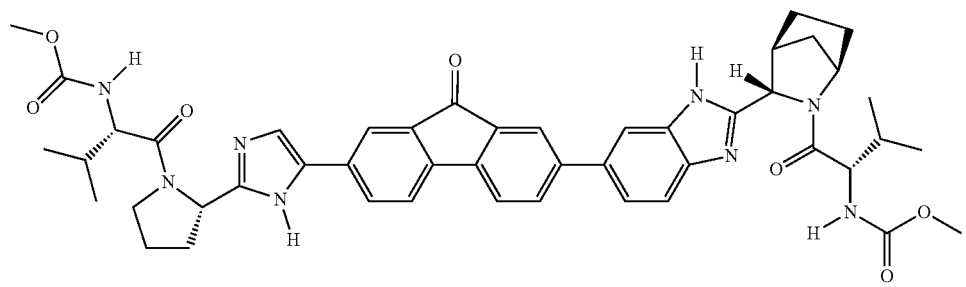

(1-{2-[5-(7-{2-[2-(2-Methoxycarbonylamino-3-methyl-butyryl)-2-aza-bicyclo[2.2.1]hept-3-yl]-3H-benzoimidazol-5-yl}-9-oxo-9H-fluoren-2-yl)-1H-imidazol-2-yl]-pyrrolidine-1-carbonyl}-2-methyl-propyl)-carbamic acid methyl ester (1-{2-[5-(7-{2-[2-(2-Methoxycarbonylamino-3-methyl-butyryl)-2-aza-bicyclo[2.2.1]hept-3-yl]-3H-benzoimidazol-5-yl}-9-oxo-9H-fluoren-2-yl)-1H-imidazol-2-yl]-pyrrolidine-1-carbonyl}-2-methyl-propyl)-carbamic acid methyl ester (Example DL)

(1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (10 mg) is dissolve in MeCN (1 mL) and water (1 mL). 1 drop of TFA was added. The mixture was treated with long wavelength UV light at room temperature for 2 hours. The reaction crude was concentrated down and purified by preparative reverse phase HPLC (GEMINI, 5 to 100% ACN/H$_2$O+0.1% TFA). Product was lyophilized to give (1-{2-[5-(7-{2-[2-(2-Methoxycarbonylamino-3-methyl-butyryl)-2-aza-bicyclo[2.2.1]hept-3-yl]-3H-benzoimidazol-5-yl}-9-oxo-9H-fluoren-2-yl)-1H-imidazol-2-yl]-pyrrolidine-1-carbonyl}-2-methyl-propyl)-carbamic acid methyl ester (Example DL) (3.7 mg).

$^1$H-NMR: 300 MHz, (CD$_3$OD-d$_4$) δ: 8.05-7.82 (m, 9H), 5.27 (m, 2H), 4.72 (m, 1H), 4.37 (d, 1H), 4.23 (d, 1H), 4.19 (m, 1H), 3.91 (m, 2H), 3.62 (d, 6H), 2.98 (m, 1H), 2.58 (m, 2H), 2.37-2.18 (m, 4H), 2.18-1.92 (m, 4H), 1.80 (m, 2H), 1.09-0.85 (m, 12H). LCMS-ESI$^+$: calc'd for C$_{47}$H$_{52}$F$_2$N$_8$O$_6$ 840.97; Found: 841.6 (M+H$^+$).

Example DM

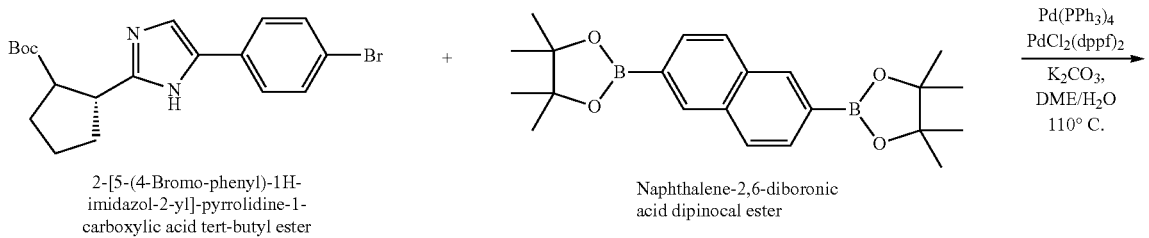

2-[5-(4-Bromo-phenyl)-1H-imidazol-2-yl]-pyrrolidine-1-carboxylic acid tert-butyl ester Naphthalene-2,6-diboronic acid dipinocal ester

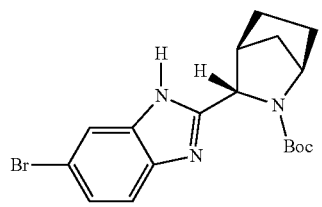

3-(6-Bromo-1H-benzoimidazol-2-yl)-2-aza-bicyclo[2.2.1]heptane-2-carboxylic acid tert-butyl ester

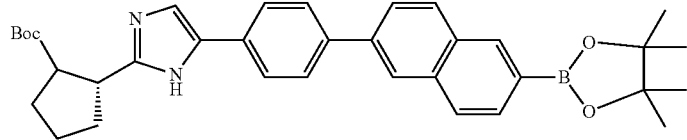

2-(5-{4-[6-(4,4,5,5-Tetramethyl-[1,3,2]dioxaborolan-2-yl)-naphthalen-2-yl]-phenyl}-1H-imidazol-2-yl)-pyrrolidine-1-carboxylic acid tert-butyl ester Pd(PPh₃)₄  K₂CO₃,
PdCl₂(dppf)₂  DME/H₂O
110° C.

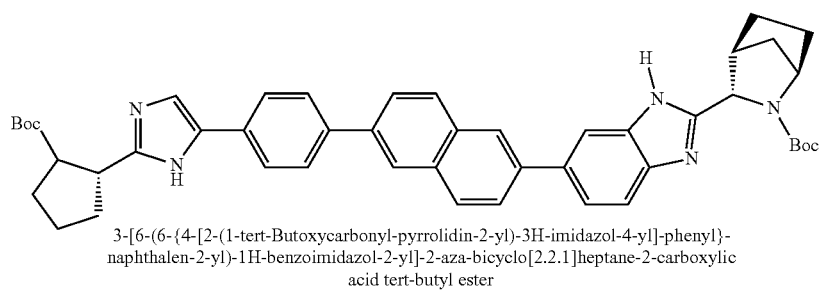

3-[6-(6-{4-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylic acid tert-butyl ester

1. TFA
2. HATU, DIEA

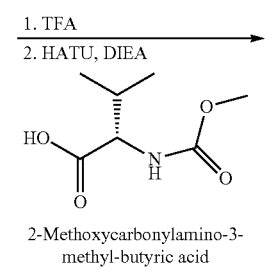

2-Methoxycarbonylamino-3-methyl-butyric acid

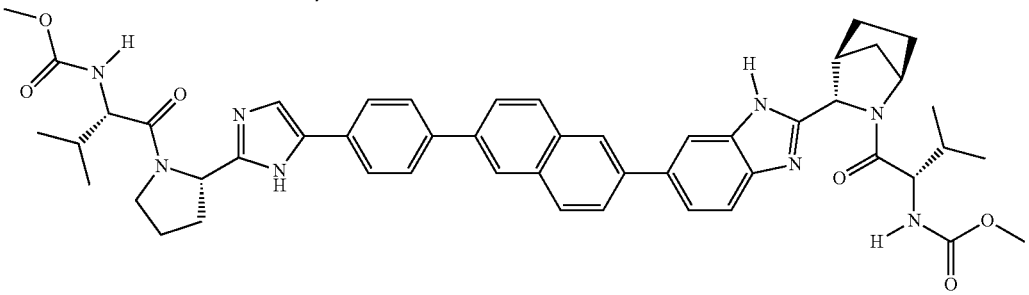

[1-(3-{6-[6-(4-{2-[1-(2-Methoxycarbonylamino-3-methyl-butyryl)-pyrrolidin-2-yl]-3H-imidazol-4-yl}-phenyl)-naphthalen-2-yl]-1H-benzoimidazol-2-yl}-2-aza-bicyclo[2.2.1]heptane-2-carbonyl)-2-methyl-propyl]-carbamic acid methyl ester 2-(5-{4-[6-(4,4,5,5-Tetramethyl-[1,3,2]dioxaborolan-2-yl)-naphthalen-2-yl]-phenyl}-1H-imidazol-2-yl)-pyrrolidine-1-carboxylic acid tert-butyl ester A mixture of 2-[5-(4-Bromo-phenyl)-1H-imidazol-2-yl]-pyrrolidine-1-carboxylic acid tert-butyl ester (1.079 g, 2.737 mmol), Naphthalene-2,6-diboronic acid dominical ester (5 eq., 5.2 g, 13.68 mmol), [1,1'-bis(diphenylphosphino)ferrocene]dichloropalladium(II)(5%, 96 mg), tetrakis(triphenylphosphine)palladium (5%, 158 mg) and potassium carbonate (5 eq., 757 mg) in 40 mL DME and 10 mL water was heated to 110° C. under Argon for 2 hours. The reaction mixture was cooled and diluted with ethyl acetate and washed with saturated sodium bicarbonate solution. The organic layer dried (MgSO4), concentrated and purified by flash column chromatography (silica gel, 20 to 100% ethyl acetate/hexane) to give 2-(5-{4-[6-(4,4,5,5-Tetramethyl-[1,3,2]dioxaborolan-2-yl)-naphthalen-2-yl]-phenyl}-1H-imidazol-2-yl)-pyrrolidine-1-carboxylic acid tert-butyl ester (730 mg, yield 47%). LCMS-ESI⁻: calc'd for $C_{34}H_{40}BN_3O_4$: 565.51; Found: 566.1 (M+H⁺).

3-[6-(6-{4-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylic acid tert-butyl ester A mixture of 2-(5-{4-[6-(4,4,5,5-Tetramethyl-[1,3,2]dioxaborolan-2-yl)-naphthalen-2-yl]-phenyl}-1H-imidazol-2-yl)-pyrrolidine-1-carboxylic acid tert-butyl ester (216 mg, 0.382 mmol), 3-(6-Bromo-1H-benzoimidazol-2-yl)-2-aza-bicyclo[2.2.1]heptane-2-carboxylic acid tert-butyl ester (1 eq., 150 mg, 0.382 mmol), [1,1'-bis(diphenylphosphino)ferrocene]dichloropalladium(II)(5%, 16 mg), tetrakis(triphenylphosphine)palladium (5%, 22 mg) and potassium carbonate (2 eq., 106 mg) in 4 mL DME and 1 mL water was heated to 90° C. under Argon for 5 hours. The reaction mixture was cooled and diluted in ethyl acetate and washed with saturated sodium bicarbonate solution. The organic layer dried (MgSO4), concentrated and purified by flash column chromatography (silica gel, 20 to 100% ethyl acetate/hexane) to give 3-[6-(6-{4-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylic acid tert-butyl ester (100 mg, yield 35%). LCMS-ESI⁻: calc'd for $C_{46}H_{50}N_6O_4$: 750.93; Found: 751.2 (M+H⁺).

[1-(3-{6-{6-(4-[2-[1-(2-Methoxycarbonylamino-3-methyl-butyryl)-pyrrolidin-2-yl]-3H-imidazol-4-yl}-phenyl)-naphthalen-2-yl]-1H-benzoimidazol-2-yl]-2-aza-bicyclo[2.2.1]heptane-2-carbonyl)-2-methyl-propyl]-carbamic acid methyl ester (Example DM)

TFA (2 mL) was added to 3-[6-(6-{4-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylic acid tert-butyl ester (100 mg, 0133 mmol) and the reaction mixture was stirred at room temperature for 2 hours. The reaction mixture was concentrated and dried overnight under vacuum. The residue was dissolved in DMF (2 mL) and to this solution was added 2-Methoxycarbonylamino-3-methyl-butyric acid (2 eq., 47 mg), diisopropyl ethylamine (6 eq., 0.14 mL), followed by HATU (2 eq., 101 mg). Reaction mixture was stirred at 0° C. for 30 minutes. The reaction mixture was diluted in ethyl acetate and washed with saturated sodium bicarbonate solution. The organic layer was dried (MgSO4), concentrated and purified by preparative reverse phase HPLC (GEMINI, 5 to 100% ACN/H₂O+0.1% TFA). Product was lyophilized to give [1-(3-{6-[6-(4-{2-[1-(2-Methoxycarbonylamino-3-methyl-butyryl)-pyrrolidin-2-yl]-3H-imidazol-4-yl}-phenyl)-naphthalen-2-yl]-1H-benzoimidazol-2-yl}-2-aza-bicyclo[2.2.1]heptane-2-carbonyl)-2-methyl-propyl]-carbamic acid methyl ester (Example DM) (19.7 mg, 17%).

¹H-NMR: 300 MHz, (CD₃OD-d₄) δ: 8.13-7.82 (m, 14H), 5.40-5.22 (m, 2H), 4.98 (m, 1H), 4.72 (m, 1H), 4.38 (d, 1H), 4.22 (m, 1H), 4.10 (m, 2H), 3.92 (m, 2H), 3.66 (d, 6H), 2.98 (m, 1H), 2.58 (m, 1H), 2.37-2.18 (m, 4H), 2.18-1.92 (m, 4H), 1.80 (m, 2H), 1.09-0.85 (m, 12H). LCMS-ESI⁺: calc'd for $C_{50}H_{56}N_8O_6$: 865.03; Found: 866.3 (M+H⁺).

Example DN

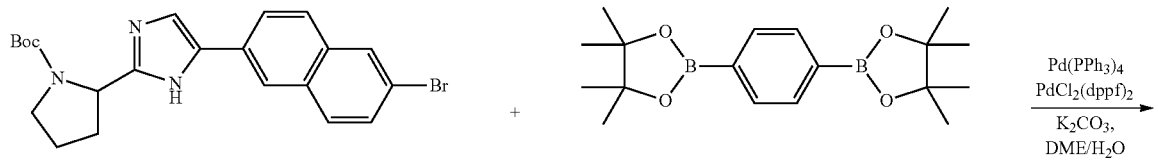

2-[5-(6-Bromo-naphthalen-2-yl)-1H-imidazol-2-yl]-pyrrolidine-1-carboxylic acid tert-butyl ester Naphthalene-2,6-diboronic acid dipinocal ester 3-(6-Bromo-1H-benzoimidazol-2-yl)-2-aza-bicyclo[2.2.1]heptane-2-carboxylic acid tert-butyl ester

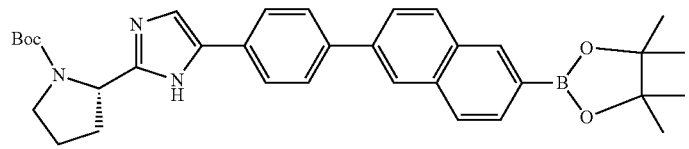

2-(5-{6-[4-(4,4,5,5-Tetramethyl-[1,3,2]dioxaborolan-2-yl)-phenyl]-naphthalen-2-yl}-1H-imidazol-2-yl)-pyrrolidine-1-carboxylic acid tert-butyl ester

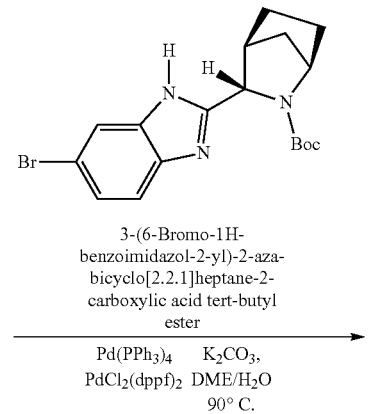

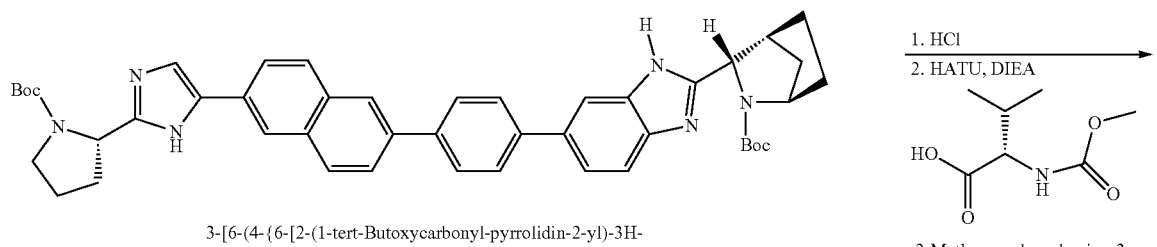

3-[6-(4-{6-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylicacid tert-butyl ester 2-Methoxycarbonylamino-3-methyl-butyric acid

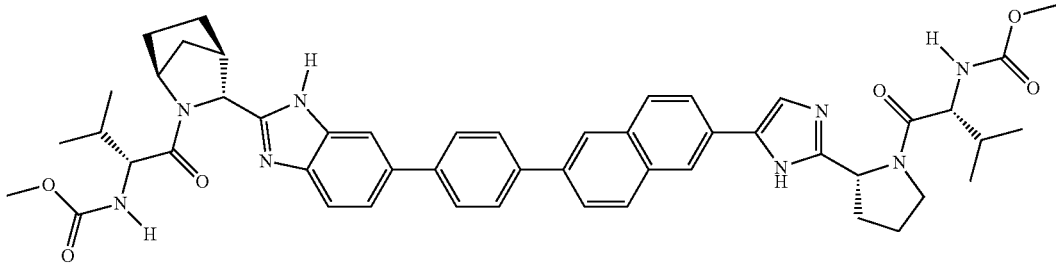

[1-(3-{6-[4-(6-{2-[1-(2-Methoxycarbonylamino-3-methyl-butyryl)-pyrrolidin-2-yl]-
3H-imidazol-4-yl}-phenyl)-naphthalen-2-yl]-1H-benzoimidazol-2-yl}-2-aza-
bicyclo[2.2.1]heptane-2-carbonyl)-2-methyl-propyl]-carbamic acid methyl ester 2-(5-{6-[4-(4,4,5,5-Tetramethyl-[1,3,2]dioxaborolan-
2-yl)-phenyl]-naphthalen-2-yl}-1H-imidazol-2-yl)-
pyrrolidine-1-carboxylic acid tert-butyl ester A mixture of 2-[5-(6-Bromo-naphthalen-2-yl)-1H-imidazol-2-yl]-pyrrolidine-1-carboxylic acid tert-butyl ester (615 mg, 1.39 mmol), Benzene-1,4-diboronic acid dipinocal ester (5 eq., 2.3 g, 6.95 mmol), [1,1'-bis(diphenylphosphino)ferrocene]dichloropalladium(II)(5%, 57 mg), tetrakis(triphenylphosphine)palladium (5%, 80 mg) and potassium carbonate (3 eq., 576 mg) in 20 mL DME and 10 mL water was heated to 90° C. under Ar for 1 hour. The reaction mixture was cooled and diluted in ethyl acetate and washed with saturated sodium bicarbonate solution. The organic layer dried (MgSO4), concentrated and purified by flash column chromatography (silica gel, 20 to 100% ethyl acetate/hexane) to give 2-(5-{6-[4-(4,4,5,5-Tetramethyl-[1,3,2]dioxaborolan-2-yl)-phenyl]-naphthalen-2-yl}-1H-imidazol-2-yl)-pyrrolidine-1-carboxylic acid tert-butyl ester (488 mg, yield 62%). LCMS-ESI−: calc'd for $C_{34}H_{40}BN_3O_4$: 565.51; Found: 566.2 (M+H+).

3-[6-(4-{6-[2-(1-tert-Butoxycarbonyl-pyrrolidin-2-
yl)-3H-imidazol-4-yl]-naphthalen-2-yl}-phenyl)-1H-
benzoimidazol-2-yl]-2-aza-bicyclo[2.2.1]heptane-2-
carboxylic acid tert-butyl ester A mixture of 2-(5-{6-[4-(4,4,5,5-Tetramethyl-[1,3,2]dioxaborolan-2-yl)-phenyl]-naphthalen-2-yl}-1H-imidazol-2-yl)-pyrrolidine-1-carboxylic acid tert-butyl ester (248 mg, 0.438 mmol, 1.1 eq.), 3-(6-Bromo-1H-benzoimidazol-2-yl)-2-aza-bicyclo[2.2.1]heptane-2-carboxylic acid tert-butyl ester (1 eq., 156 mg, 0.399 mmol), [1,1'-bis(diphenylphosphino)ferrocene]dichloropalladium(II)(3%, 10 mg), tetrakis(triphenylphosphine)palladium (3%, 14 mg) and potassium carbonate (3.3 eq., 182 mg) in 4 mL DME and 2 mL water was heated to 90° C. under Argon for 1 hour. The reaction mixture was cooled and diluted in ethyl acetate and washed with saturated sodium bicarbonate solution. The organic layer dried (MgSO4), concentrated and purified by flash column chromatography (silica gel, 20 to 100% ethyl acetate/hexane) to give 3-[6-(4-{6-[2-(1-tert-Butoxycarbonyl-pyrrolidin-2-yl)-3H-imidazol-4-yl]-naphthalen-2-yl}-phenyl)-1H-benzoimidazol-2-yl]-2-aza-bicyclo[2.2.1]heptane-2-carboxylic acid tert-butyl ester (178 mg, yield 59%). LCMS-ESI−: calc'd for $C_{46}H_{50}N_6O_4$: 750.93; Found: 751.3 (M+H+).

[1-(3-{6-[4-(6-{2-[1-(2-Methoxycarbonylamino-3-
methyl-butyryl)-pyrrolidin-2-yl]-3H-imidazol-4-yl}-
naphthalen-2-yl)-phenyl]-1H-benzoimidazol-2-yl}-
2-aza-bicyclo[2.2.1]heptane-2-carbonyl)-2-methyl-
propyl]-carbamic acid methyl ester (Example DN)

4N HCl in dioxane (1 mL) was added to 3-[6-(6-{4-[2-(1-tert-Butoxycarbonyl-pyrrolidin-2-yl)-3H-imidazol-4-yl]-phenyl}-naphthalen-2-yl)-1H-benzoimidazol-2-yl]-2-aza-bicyclo[2.2.1]heptane-2-carboxylic acid tert-butyl ester (100 mg, 0133 mmol) in 2 mL DCM and the reaction mixture was stirred at room temperature for 3 hours. The reaction mixture was concentrated and dried overnight under vacuum. The residue was dissolved in DMF (2 mL) and to this solution was added 2-Methoxycarbonylamino-3-methyl-butyric acid (2 eq., 83 mg), diisopropyl ethylamine (6 eq., 0.25 mL), followed by HATU (2 eq., 180 mg). Reaction mixture was stirred at 0° C. for 30 minutes. The reaction mixture was dissolved in ethyl acetate and washed with saturated sodium bicarbonate solution. The organic layer was dried (MgSO4), concentrated and purified by preparative reverse phase HPLC (GEMINI, 5 to 100% ACN/H2O+0.1% TFA). Product was lyophilized to give [1-(3-{6-[4-(6-{2-[1-(2-Methoxycarbonylamino-3-methyl-butyryl)-pyrrolidin-2-yl]-3H-imidazol-4-yl}-naphthalen-2-yl)-phenyl]-1H-benzoimidazol-2-yl}-2-aza-bicyclo[2.2.1]heptane-2-carbonyl)-2-methyl-propyl]-carbamic acid methyl ester (Example DN) (102 mg, 50%).

$^1$H-NMR: 300 MHz, (CD3OD-d4) δ: 8.13-7.82 (m, 14H), 5.40-5.22 (m, 2H), 4.98 (m, 1H), 4.72 (m, 1H), 4.38 (d, 1H), 4.22 (m, 1H), 4.10 (m, 2H), 3.92 (m, 2H), 3.66 (d, 6H), 2.98 (m, 1H), 2.58 (m, 1H), 2.37-2.18 (m, 4H), 2.18-1.92 (m, 4H), 1.80 (m, 2H), 1.09-0.85 (m, 12H). LCMS-ESI+: calc'd for $C_{50}H_{56}N_8O_6$: 865.03; Found: 866.4 (M+H+).

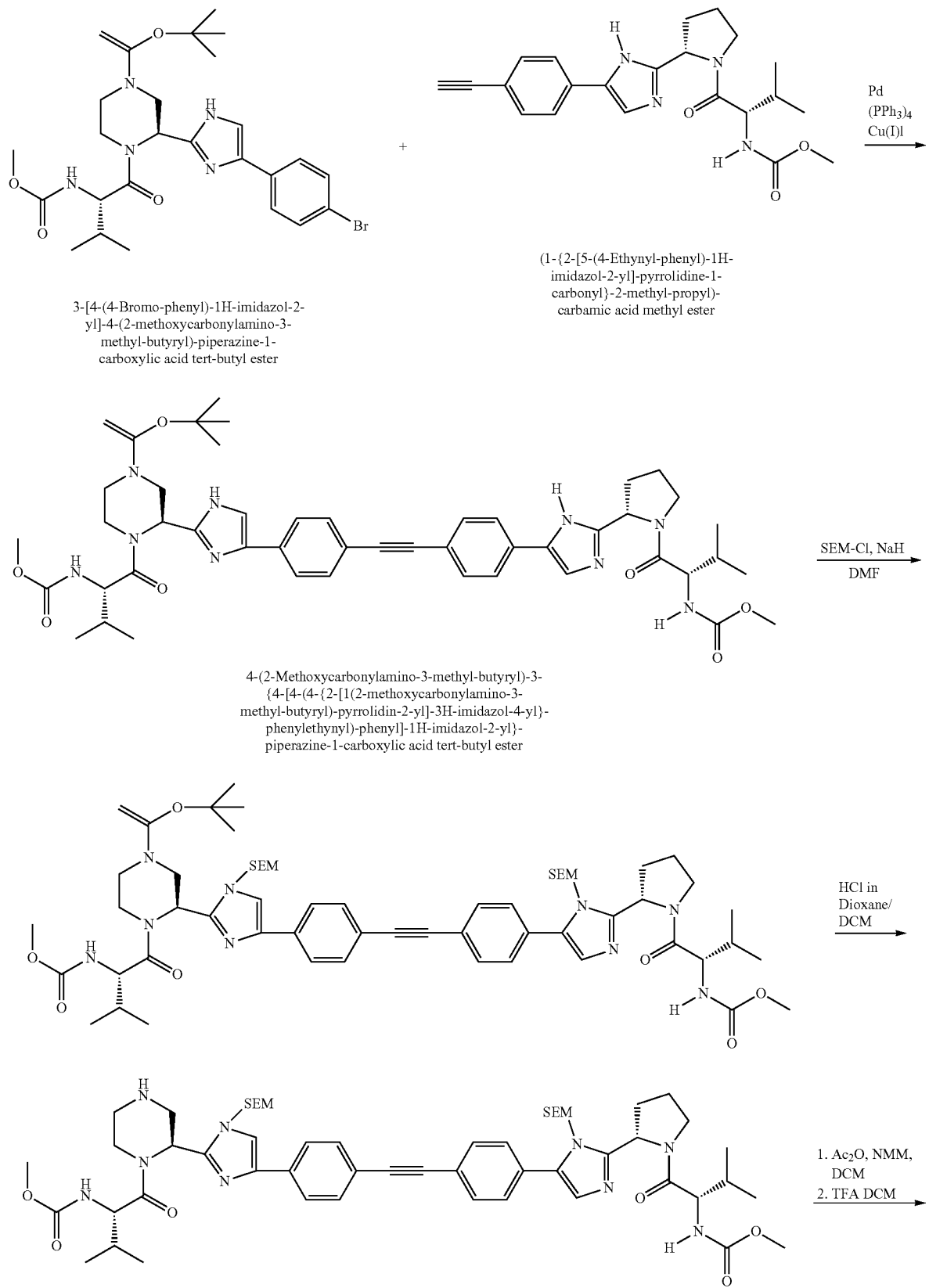

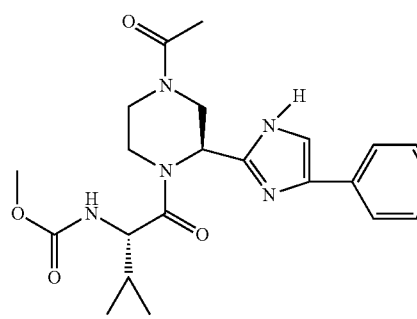
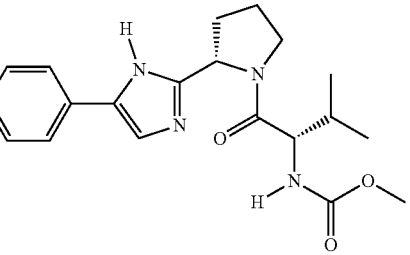

[1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester 4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid tert-butyl ester 3-[4-(4-Bromo-phenyl)-1H-imidazol-2-yl]-4-(2-methoxycarbonylamino-3-methyl-butyryl)-piperazine-1-carboxylic acid tert-butyl ester (600 mg, 1.06 mmol) was combined with (1-{2-[5-(4-Ethynyl-phenyl)-1H-imidazol-2-yl]-pyrrolidine-1-carbonyl}-2-methyl-propyl)-carbamic acid methyl ester (503 mg, 1.27 mmol) and Pd(PPh$_3$)$_4$ (122 mg, 0.106 mmol) under an argon atmosphere. DMF (degassed with Argon) was added followed by triethylamine (1.47 mL, 10.6 mmol) and copper(I) iodide (20.0 mg, 0.106 mmol). The mixture was heated at 80° C. After 20 minutes, volatiles were removed in vacuo and the crude material was semi-purified via chromatography on silica gel (eluent: EtOAc w MeOH 10%/hexanes) to yield the product 4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid tert-butyl ester (542 mg). LCMS-ESI$^+$: calc'd for $C_{47}H_{59}N_9O_8$: 878.0 (M$^+$); Found: 878.5 (M+H$^+$).

SEM Protected Imidazole Intermediate 4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid tert-butyl ester (512 mg, 0.586 mmol) was dissolved in DMF (10 mL). Sodium hydride (60% in mineral oil, 56 mg) was added at 0° C., followed by SEM-Cl (0.217 mL). After two hours, the solvents were removed in vacuo and the crude material was partitioned between DCM and water. The organic layer was dried and the crude material was purified by flash chromatography in silica gel to yield 591 mg of the SEM protected imidazole product.

LCMS-ESI$^+$: calc'd for $C_{59}H_{87}N_9O_{10}Si_2$: 1138.6 (M$^+$); Found: 1138.7 (M+H$^+$).

de-Boc Piperazine Material

The above SEM protected imidazole material was dissolved in DCM (2.5 mL) at room temperature. HCl (4M in dioxane, 5 mL) was added and stirring of the resultant suspension at room temperature was continued. After 60 minutes all volatiles were removed in vacuo and the crude material was used in the next reaction without further purification.

[1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (Example A)

The above de-Boc piperazine material (139 mg, 0.129 mmol) was dissolved in DCM (3 mL) containing NMM (0.057 mL) at room temperature. Acetic anhydride (0.0183 mL) was added and stirring at room temperature was continued. After 60 minutes all volatiles were removed in vacuo and the crude material was dissolved in a mixture of DCM (5 mL) and TFA (5 mL). Stirring at room temperature was continued. After 16 hours, the volatiles were removed in vacuo and the material was purified by RP-HPLC (eluent: water/MeCN w/0.1% TFA). The product-containing fractions were combined and lyphilized to yield the product [1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (example DO) as a TFA salt (15.7 mg).

LCMS-ESI$^+$: calc'd for $C_{44}H_{53}N_9O_7$: 819.9 (M$^+$); Found: 820.4 (M+H$^+$).

$^1$H-NMR: 300 MHz, (dmso-d$_6$) δ: 8.07 (m, 2H), 7.91-7.68 (m, 10H), 7.28 (m, 2H), 5.64 (m, 1H), 5.38 (m, 1H), 5.17 (m, 2H), 4.23 (d, J=7.8 Hz, 1H), 4.11 (m, 1H), 3.85 (m, 1H), 3.68 (s, 3H), 3.66 (s, 3H), 3.49-3.45 (m, 2H), 3.15-3.02 (m, 3H), 2.77 (m, 1H), 2.58 (m, 1H), 2.29-2.01 (m, 5H), 1.07-0.83 (m, 12H) ppm.

Example DP

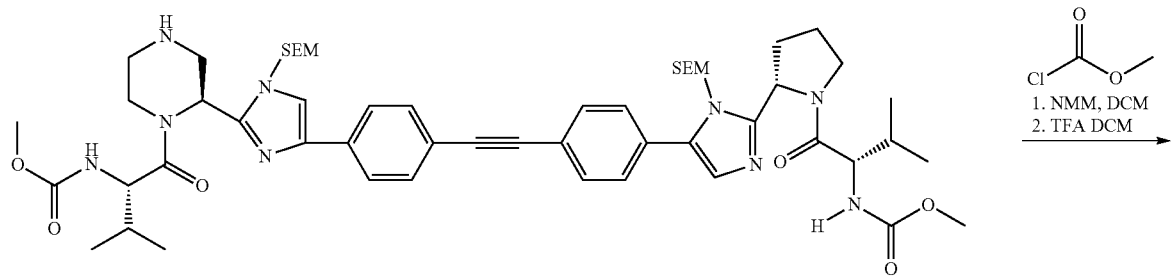

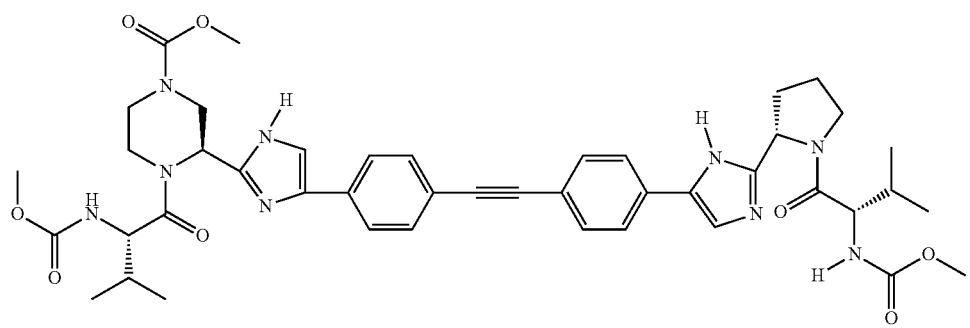

4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid methyl ester

4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenyl-ethynyl)-phenyl]-1H-imidazol-2-yl}-piperazine-1-carboxylic acid methyl ester (Example DP)

It was prepared in a similar fashion to [1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (example DO) replacing the acetic anhydride with methylchloro formate.

LCMS-ESI+: calc'd for $C_4H_{53}N_9O_8$: 835.4 (M+); Found: 835.9 (M+H+). $^1$H-NMR: 300 MHz, (dmso-d$_6$) δ: 8.08 (m, 1H), 7.76-7.54 (m, 10H), 7.30 (m, 2H), 5.58 (m, 1H), 5.08 (m, 1H), 4.36 (m, 1H), 4.26 (m, 1H), 4.03 (m, 2H), 3.95-3.75 (m, 4H), 3.50 (m, 9H), 2.29 (m, 1H), 2.13-1.95 (m, 4H), 0.87-0.68 (m, 12H) ppm.

Example DQ

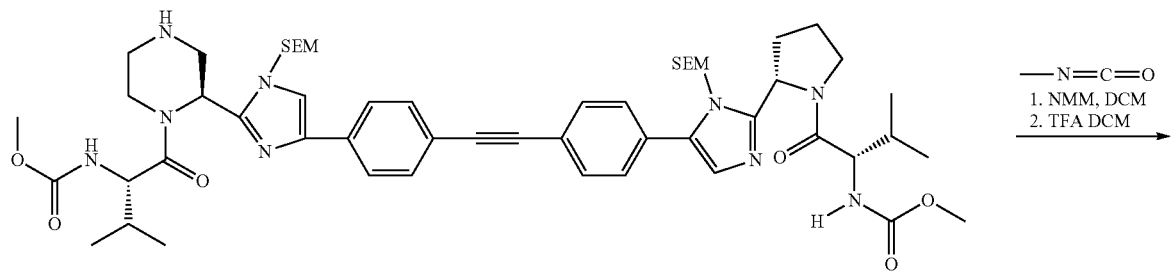

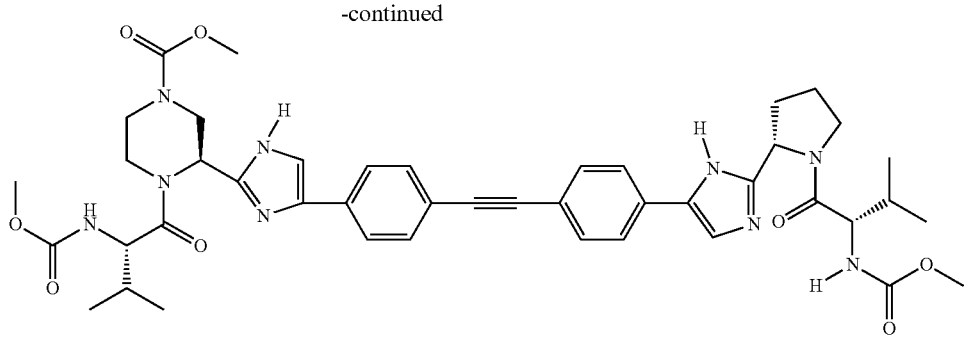

[1-(2-{5-[4-(4-{2-[1-(2-Methoxycarbonylamino-3-methyl-butyryl)-4-methylcarbamoyl-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester

[1-(2-{5-[4-(4-{2-[1-(2-Methoxycarbonylamino-3-methyl-butyryl)-4-methylcarbamoyl-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (Example DQ)

It was prepared in a similar fashion to [1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]carbamic acid methyl ester (example DO), replacing the acetic anhydride with isocyanatomethane.

LCMS-ESI$^+$: calc'd for $C_{44}H_{54}N_{10}O_7$: 834.9 (M$^+$); Found: 835.4 (M$^+$).

$^1$H-NMR: 300 MHz, (dmso-d$_6$) δ: 8.08 (m, 1H), 7.77-7.36 (m, 10H), 7.36-7.24 (m, 2H), 5.51 (m, 1H), 5.07 (m, 1H), 4.36 (m, 1H), 4.07 (m, 1H), 4.06 (m, 2H), 3.95-3.75 (m, 4H), 3.52-3.48 (m, 9H), 2.34 (m, 1H), 2.13-1.96 (m, 4H), 0.90-0.78 (m, 12H) ppm.

Example DR

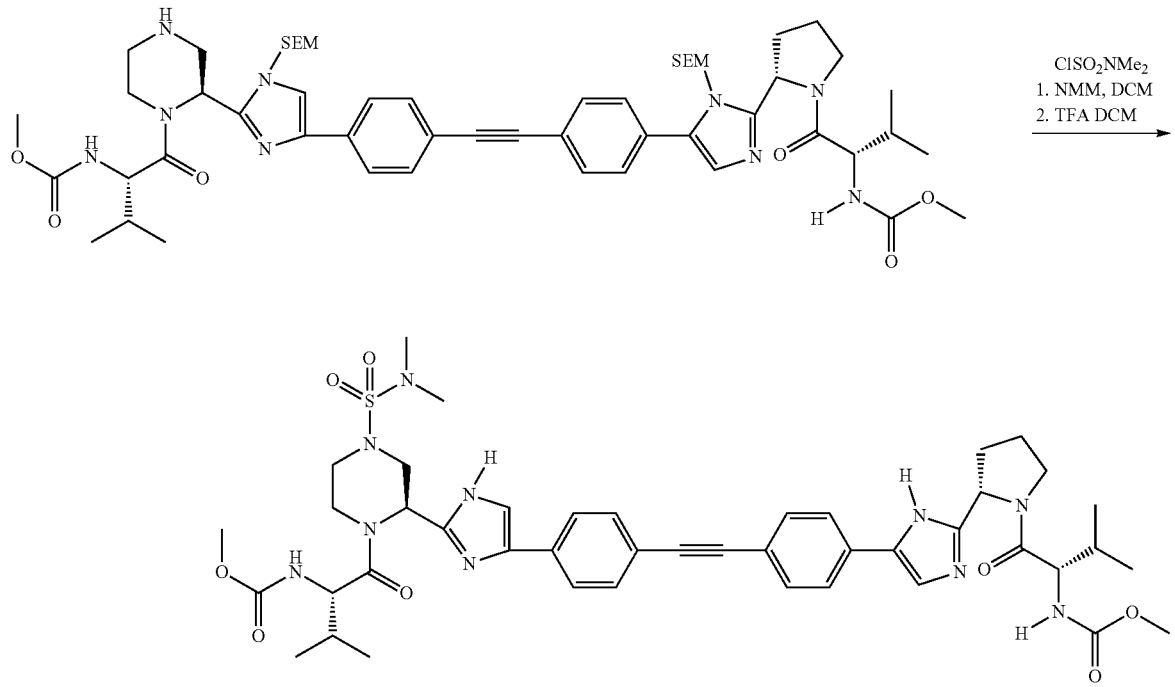

[1-(2-{5-[4-(4-{2-[4-Dimethylsulfamoyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester

[1-(2-{5-[4-(4-{2-[4-Dimethylsulfamoyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (Example DR)

It was prepared in a similar fashion to [1-(2-{5-[4-(4-{2-[4-Acetyl-1-(2-methoxycarbonylamino-3-methyl-butyryl)-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (example DO), replacing the acetic anhydride with N,N-dimethyl sulfurylamido chloride.

LCMS-ESI$^+$: calc'd for $C_{44}H_{56}N_{10}O_8S$: 885.0 (M$^+$); Found: 885.4 (M$^+$).

$^1$H-NMR: 300 MHz, (dmso-d$_6$) δ: 8.05 (m, 1H), 7.91-7.52 (m, 10H), 7.32-7.28 (m, 2H), 5.72 (s, 1H), 5.07 (m, 1H), 4.39-4.06 (m, 4H), 3.95-3.75 (m, 4H), 3.52-3.48 (m, 6H), 2.86-46 (m, 6H), 2.12-1.95 (m, 4H), 0.94-0.76 (m, 12H) ppm.

Example DS

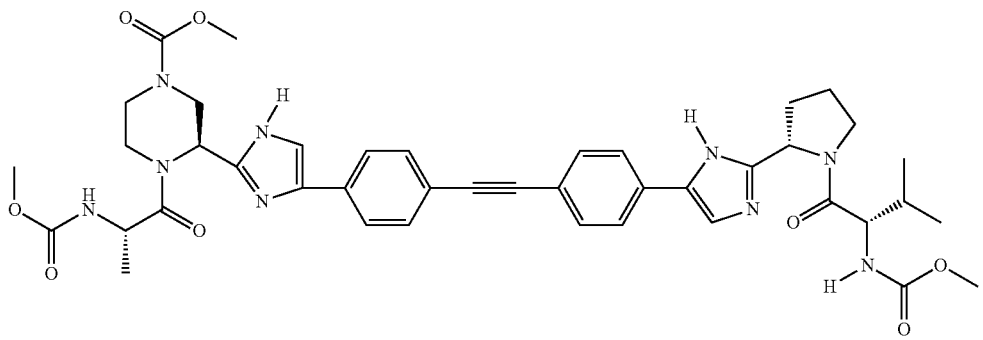

3-{4-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-4-(2-methoxycarbonylamino-propionyl)-piperazine-1-carboxylic acid methyl ester 3-{4-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-4-(2-methoxycarbonylamino-propionyl)-piperazine-1-carboxylic acid methyl ester (example DS) was prepared in a similar fashion to 4-(2-Methoxycarbonylamino-3-methyl-butyryl)-3-{4-[4-(4-{2-[1-(2-methoxycarbonylamino-3-methyl-butyryl)-pyrrolidin-2-yl]-3H-imidazol-4-yl}-phenylethynyl)-phenyl]-1H-imidazol-2-yl}-piperazine-1-carboxylic acid methyl ester (example DP), replacing the valine derived carbamate with the corresponding alanine derived carbamate.

LCMS-ESI$^+$: calc'd for $C_{40}H_{49}N_9O_8$: 783.8 (M$^+$); Found: 784.3 (M+H$^+$).

$^1$H-NMR: 300 MHz, (dmso-d$_6$) δ: 8.08 (m, 1H), 7.95-7.80 (m, 10H), 7.47 (m, 1H), 7.30 (m, 1H), 5.72 (s, 1H), 5.55 (s, 1H), 5.09 (m, 1H), 4.58 (m, 1H), 4.09 (m, 1H), 3.89-3.80 (m, 5H), 3.50-3.30 (m, 9H), 2.29 (m, 1H), 2.09-1.98 (m, 4H), 1.21 (m, 3H) 0.81-0.75 (m, 6H) ppm.

Example DT

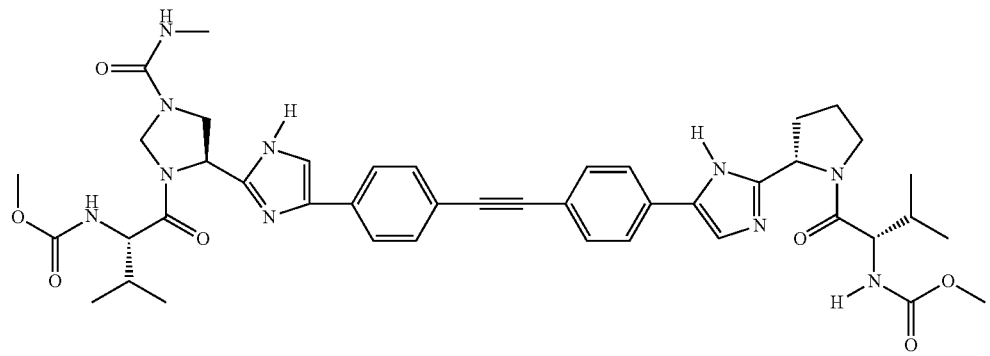

(1-{2-[5-(4-{4-[3'-(2-Methoxycarbonylamino-3-methyl-butyryl)-1'–methylcarbamoyl-2',3',4',5'-tetrahydro-1H,1'H-[2,4']biimidazolyl-4-yl]-phenylethynyl}-phenyl)-1H-imidazol-2-yl]-pyrrolidine-1-carbonyl}-2-methyl-propyl)-carbamic acid methyl ester (1-{2-[5-(4-{4-[3'-(2-Methoxycarbonylamino-3-methyl-butyryl)-1'-methylcarbamoyl-2',3',4',5'-tetrahydro-1H,1'H-[2,4']biimidazolyl-4-yl]-phenylethynyl}-phenyl)-1H-imidazol-2-yl]-pyrrolidine-1-carbonyl}-2-methyl-propyl)-carbamic acid methyl ester (example DT)

was prepared in a similar fashion to [1-(2-{5-[4-(4-{2-[1-(2-Methoxycarbonylamino-3-methyl-butyryl)-4-methylcarbamoyl-piperazin-2-yl]-1H-imidazol-4-yl}-phenylethynyl)-phenyl]-1H-imidazol-2-yl}-pyrrolidine-1-carbonyl)-2-methyl-propyl]-carbamic acid methyl ester (example DQ), replacing the piperazine carboxylic acid with the corresponding 4-amino-pyrrolidine derivative, using methodology described under examples BU and DO.

LCMS-ESI⁺: calc'd for $C_{43}H_{52}N_{10}O_7$: 820.9 (M⁺); Found: 821.4 (M⁺).

¹H-NMR: 300 MHz, (dmso-d₆) δ: 8.05 (m, 1H), 7.91 (s, 1H), 7.77-7.50 (m, 10H) 7.32 (m, 1H), 6.54 (m, 1H), 5.51 (m, 1H), 5.36 (m, 1H), 5.21 (m, 2H), 4.51 (m, 1H), 4.07 (m, 1H), 3.95-3.75 (m, 2H), 3.51 (s, 6H), 2.57 (m, 3H), 2.13 (m, 1H), 2.05-1.95 (m, 4H), 0.94-0.77 (m, 12H) ppm.

Example DU 2-(5-{6-[2-(1-boc-pyrrolidin-2-yl)-1H-benzoimidazol-5-yl]-1,5-dithia-s-indacen-2-yl}-1H-benzoimidazol-2-yl)-pyrrolidine-1-carboxylic acid tert-butyl ester 2,6-Diiodo-1,5-dithia-s-indacene (117 mg, 0.263 mmol), 2-[5-(4,4,5,5-Tetramethyl-[1,3,2]dioxaborolan-2-yl)-1H-benzoimidazol-2-yl]-pyrrolidine-1-carboxylic acid tert-butyl ester (109 mg, 0.263 mmol), Pd(PPh₃)₄ (9.1 mg), K₂CO₃ (69 mg, 0.52 mmol), were dissolved in toluene (5 mL)/water (1 mL) under an argon atmosphere. The mixture was heated for 30 minutes at 130° C. (microwave) and 30 minutes at 140° C. Removed all volatiles in vacuo and purified via silica gel chromatography (eluent: EtOAc/hexanes) to yield the product 2-(5-{6-[2-(1-Boc-pyrrolidin-2-yl)-1H-benzoimidazol-5-yl]-1,5-dithia-s-indacen-2-yl}-1H-benzoimidazol-2-yl)-pyrrolidine-1-carboxylic acid tert-butyl ester (36.3 mg).

LCMS-ESI⁺: calc'd for $C_{42}H_{44}S_2N_6O_4$: 760.3 (M⁺); Found: 761.3 (M+H⁺).

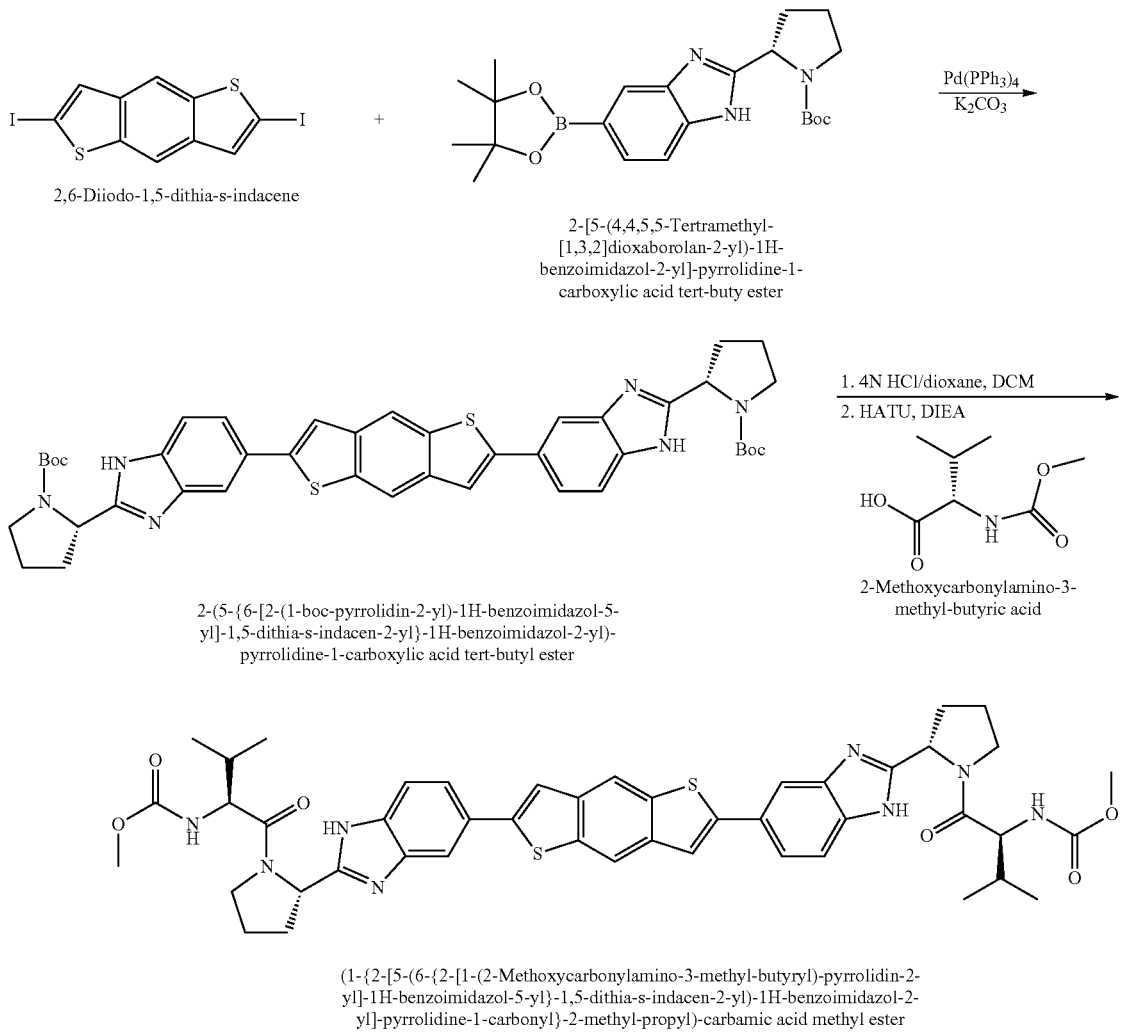

2,6-Diiodo-1,5-dithia-s-indacene

2-[5-(4,4,5,5-Tertramethyl-[1,3,2]dioxaborolan-2-yl)-1H-benzoimidazol-2-yl]-pyrrolidine-1-carboxylic acid tert-buty ester 2-(5-{6-[2-(1-boc-pyrrolidin-2-yl)-1H-benzoimidazol-5-yl]-1,5-dithia-s-indacen-2-yl}-1H-benzoimidazol-2-yl)-pyrrolidine-1-carboxylic acid tert-butyl ester 2-Methoxycarbonylamino-3-methyl-butyric acid (1-{2-[5-(6-{2-[1-(2-Methoxycarbonylamino-3-methyl-butyryl)-pyrrolidin-2-yl]-1H-benzoimidazol-5-yl}-1,5-dithia-s-indacen-2-yl)-1H-benzoimidazol-2-yl]-pyrrolidine-1-carbonyl}-2-methyl-propyl)-carbamic acid methyl ester (1-{2-[5-(6-{2-[1-(2-Methoxycarbonylamino-3-methyl-butyryl)-pyrrolidin-2-yl]-1H-benzoimidazol-5-yl}-1,5-dithia-s-indacen-2-yl)-1H-benzoimidazol-2-yl]-pyrrolidine-1-carbonyl}-2-methyl-propyl)-carbamic acid methyl ester (Example DU)

2-(5-{6-[2-(1-Boc-pyrrolidin-2-yl)-1H-benzoimidazol-5-yl]-1,5-dithia-s-indacen-2-yl}-1H-benzoimidazol-2-yl)-pyrrolidine-1-carboxylic acid tert-butyl ester (36 mg) was dissolved in DCM (3 mL) and HCl in dioxane (4M, 4 mL) was added and stirring at room temperature was continued. After 20 minutes, all volatiles were removed in vacuo. The crude material was used in the next step without further purification.

The above crude material was dissolved in DMF (3 mL) and NMM (0.025 mL) was added. A solution of 2-(L) Methoxycarbonylamino-3-methyl-butyric acid (17 mg, 0.094 mmol), HATU (36 mg, 0.094 mmol) and NMM (0.025 mL) in DMF (1 mL) was added. The reaction was stirred at room temperature. After 20 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (1-{2-[5-(6-{2-[1-(2-Methoxycarbonylamino-3-methyl-butyryl)-pyrrolidin-2-yl]-1H-benzoimidazol-5-yl}-1,5-dithia-s-indacen-2-yl)-1H-benzoimidazol-2-yl]-pyrrolidine-1-carbonyl}-2-methyl-propyl)-carbamic acid methyl ester (3.8 mg).

LCMS-ESI$^+$: calc'd for $C_{46}H_{50}N_8O_6S_2$: 875.1 (M$^+$); Found: 875.4 (M+H$^+$).

$^1$H-NMR: 300 MHz, (dmso-d$_6$) δ: 8.41 (s, 2H), 7.94-7.91 (m, 4H), 7.73-7.67 (m, 4H), 7.31 (m, 2H), 5.19 (m, 2H), 4.09 (m, 2H), 3.85 (m, 4H), 3.51 (s, 6H), 2.31-1.82 (m, 10H), 0.94-0.77 (m, 12H) ppm.

Example DV

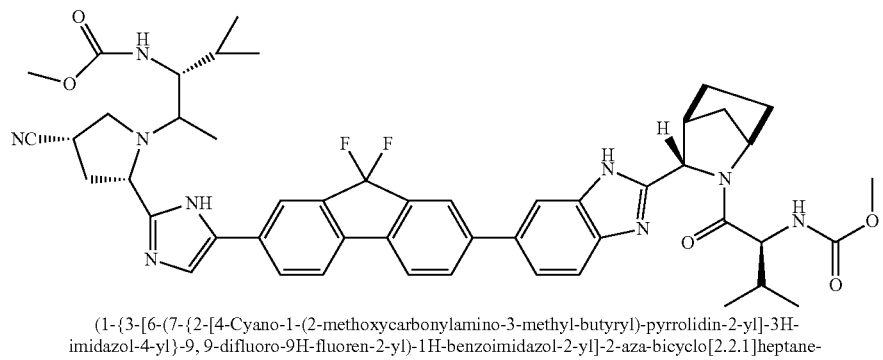

(1-{3-[6-(7-{2-[4-Cyano-1-(2-methoxycarbonylamino-3-methyl-butyryl)-pyrrolidin-2-yl]-3H-imidazol-4-yl}-9,9-difluoro-9H-fluoren-2-yl)-1H-benzoimidazol-2-yl]-2-aza-bicyclo[2.2.1]heptane-2-carbonyl}-2-methyl-propyl)-carbamic acid methyl ester (1-{3-[6-(7-{2-[4-Cyano-1-(2-methoxycarbonylamino-3-methyl-butyryl)-pyrrolidin-2-yl]-3H-imidazol-4-yl}-9,9-difluoro-9H-fluoren-2-yl)-1H-benzoimidazol-2-yl]-2-aza-bicyclo[2.2.1]heptane-2-carbonyl}-2-methyl-propyl)-carbamic acid methyl ester (Example DV) was prepared in a similar fashion to (1-{2-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-imidazol-2-yl]-pyrrolidine-1-carbonyl}-2-methyl-propyl)-carbamic acid methyl ester (Example DK), replacing the proline derivative with the corresponding 4-cyano-proline derivative.

LCMS-ESI$^+$: calc'd for $C_{48}H_{51}F_2N_9O_6$: 887.9 (M$^+$); Found: 888.3 (M+H$^+$).

$^1$H-NMR: 300 MHz, (dmso-d$_6$) δ: 8.10-7.95 (m, 8H), 7.70 (s, 2H), 7.34 (m, 1H), 7.26 (m, 1H), 5.12 (dd, J=8.4 Hz, 1H), 4.72 (s, 1H) 4.52 (s, 1H), 4.42 (m, 1H), 4.16 (m, 1H), 4.05 (m, 1H), 3.94 (m, 1H), 3.74 (m, 1H), 3.53 (s, 3H), 3.52 (s, 3H), 2.85 (m, 1H), 2.73 (m, 1H), 2.39 (m, 1H), 2.25 (m, 1H), 2.03-1.72 (m, 6H), 1.54 (m, 2H), 0.94-0.77 (m, 15H) ppm.

$^{19}$F-NMR: 282 MHz, (dmso-d$_6$) δ: −108.6 ppm [−74.3 ppm TFA].

Example DW

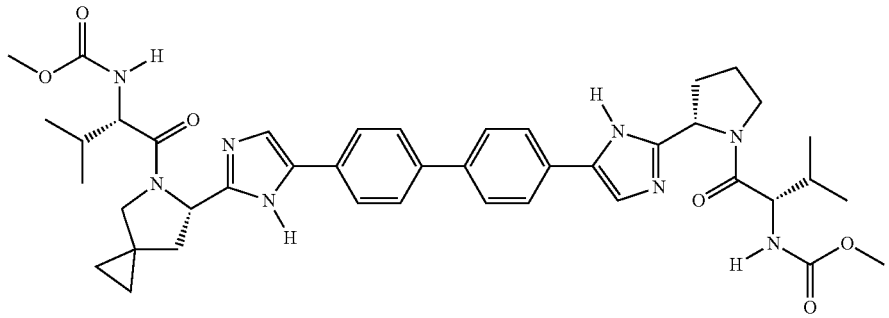

(1-{6-[5-(4'-{2-[1-(2-Methoxycarbonylamino-3-methyl-butyryl)-pyrrolidin-2-yl]-3H-imidaozl-4-yl}-biphenyl-4-yl)-1H-imidazol-2-yl]-5-aza-spiro[2.4]heptane-5-carbonyl}-2-methyl-propyl)-carbamic acid methyl ester (1-{6-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-aza-spiro[2.4]heptane-5-carbonyl}-2-methyl-propyl)-carbamic acid methyl ester (Example DW) was prepared in a similar fashion to (1-{2-[5-(4'-{2-[2-Hydroxy-1-(2-methoxycarbonylamino-3-methyl-butyrylamino)-ethyl]-3H-imidazol-4-yl}-biphenyl-4-yl)-1H-imidazol-2-yl]-pyrrolidine-1-carbonyl}-2-methyl-propyl)-carbamic acid methyl ester, replacing the oxazolidine derived carboxylic acid with the corresponding 4-cyclopropyl-proline derivative and using HCl in dioxane for the Boc deprotection.

LCMS-ESI$^+$: calc'd for $C_{42}H_{52}N_8O_6$: 764.9 (M$^+$); Found: 765.3 (M+H$^+$).

$^1$H-NMR: 300 MHz, (dmso-d$_6$) δ: 8.08 (m, 2H), 7.91-7.84 (m, 10H) 7.33 (m, 2H), 5.23 (m, 1H), 5.11 (m, 1H), 4.10 (m, H), 4.01 (m, 1H), 3.95-3.75 (m, 4H), 3.53 (s, 6H), 2.40 (m, 1H), 2.23 (m, 1H), 2.05-1.95 (m, 4H), 0.94-0.80 (m, 12H), 0.63 (m, 4H) ppm.

Example DX

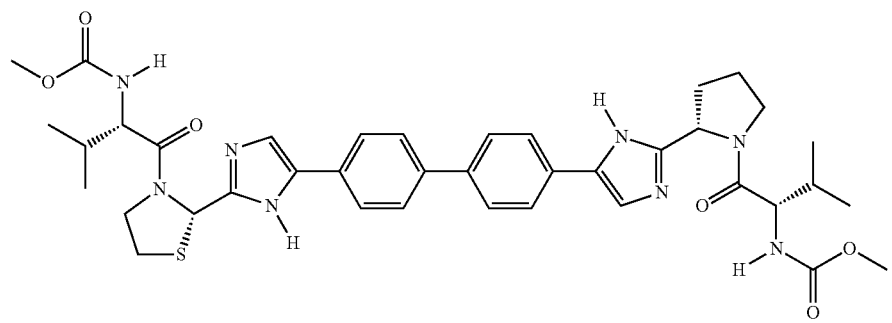

(1-{2-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-thiazolidine-3-carbonyl}-2-methyl-propyl)-carbamic acid methyl ester (1-{2-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-thiazolidine-3-carbonyl}-2-methyl-propyl)-carbamic acid methyl ester (Example DX) was prepared in a similar fashion to (1-{6-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-aza-spiro[2.4]heptane-5-carbonyl}-2-methyl-propyl)-carbamic acid methyl ester (Example DW), replacing the cyclopropyl proline carboxylic acid with the corresponding thiazolidine derivative.

LCMS-ESI$^+$: calc'd for $C_{39}H_{48}N_8O_6S$: 756.9 (M$^+$); Found: 757.0 (M$^+$).

$^1$H-NMR: 300 MHz, (dmso-d$_6$) δ: 8.06 (m, 2H), 7.86-7.70 (m, 10H), 7.45 (m, 1H), 7.22 (m, 1H), 6.33 (s, 1H), 5.09 (m, 1H), 4.18-4.08 (m, 4H), 3.80 (m, 2H), 3.56 (s, 6H), 3.30 (m, 2H), 2.40 (m, 1H), 2.05-1.95 (m, 5H), 0.94-0.75 (m, 12H) ppm.

Example DY 0.068 mmol) was dissolved in DCM (1 mL) and HCl in dioxane (4M, 1 mL) was added and stirring at room temperature was continued. After 45 minutes, all volatiles were removed in vacuo. The crude material was used in the next step without further purification. The crude material was dissolved in DMF (1.0 mL) and DIEA (26.4 mg, 0.204 mmol) was added. A solution of 2-(L) methoxycarbonylamino-propionic acid (9.95 mg, 0.068 mmol), HATU (25.9 mg, 0.068 mmol) and DIEA (8.8 mg, 0.068 mmol) in DMF (1 mL) was added. The reaction was stirred at room temperature. After 45 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (1-{6-[5-(9,9-Difluoro-7-{2-[2-(2-methoxycarbonylamino-propionyl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carbonyl}-2-methyl-propyl)-carbamic acid methyl ester (25.4 mg) as a TFA salt.

LCMS-ESI$^+$: calc'd for $C_{47}H_{50}F_2N_8O_6$: 860.9 (M$^+$); Found: 861.8 (M+H$^+$).

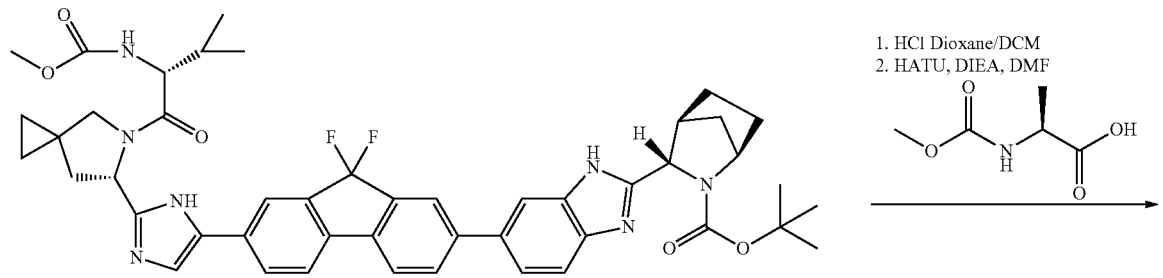

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester

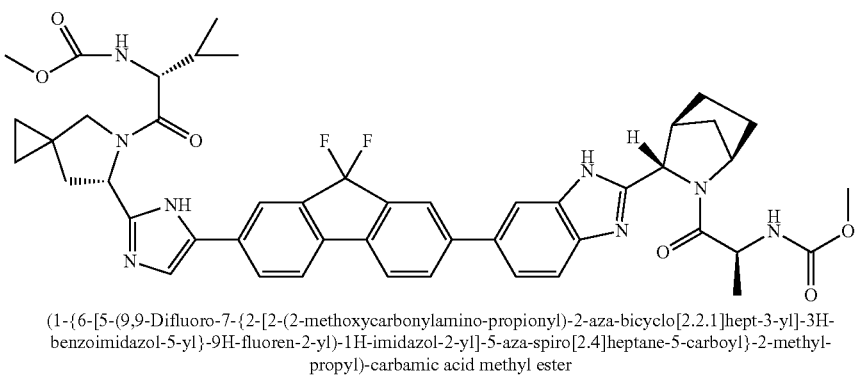

(1-{6-[5-(9,9-Difluoro-7-{2-[2-(2-methoxycarbonylamino-propionyl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carboyl}-2-methyl-propyl)-carbamic acid methyl ester (1-{6-[5-(9,9-Difluoro-7-{2-[2-(2-methoxycarbonylamino-propionyl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carbonyl}-2-methyl-propyl)-carbamic acid methyl ester 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (57.6 mg, $^1$H-NMR: 300 MHz, (dmso-d$_6$) δ: 8.20-7.99 (m, 8H), 7.73 (s, 2H), 7.37-7.27 (m, 2H), 5.24 (dd, J=7.2 Hz, 1H), 4.76 (s, 1H) 4.50 (s, 1H), 4.41 (m, 1H), 4.02 (m, 1H), 3.85 (m, 1H), 3.74 (m, 1H), 3.55 (s, 3H), 3.53 (s, 3H), 2.77 (m, 1H), 2.25 (m, 2H), 2.09-2.04 (m, 2H), 1.88-1.79 (m, 2H), 1.54 (m, 1H), 1.25 (d, J=7.8 Hz, 3H), 0.94-0.77 (m, 9H) 0.63 (m, 4H) ppm.

$^{19}$F-NMR: 282 MHz, (dmso-d$_6$) δ: −109.1 ppm [−74.8 ppm TFA].

Example DZ

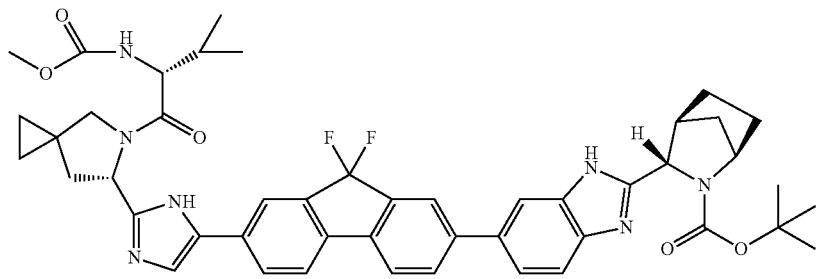

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicycol[2.2.1]heptane-2-carboxylic acid tert-butyl ester

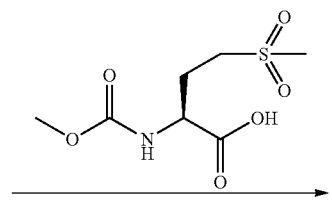

1. HCl Dioxane/DCM
2. HATU, DIEA, DMF

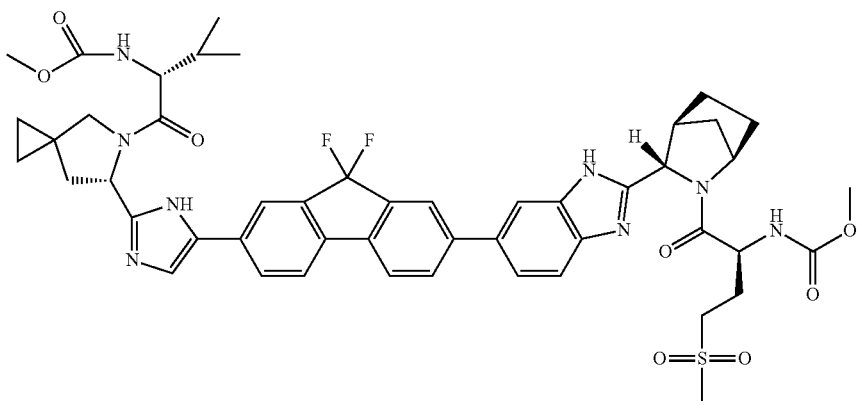

(1-{6-[5-(9,9-Difluoro-7-{2-[2-(2-methoxycarbonylamino-4-methlsulfonyl-butyryl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carboyl}-2-methyl-propyl)-carbamic acid methyl ester

(1-{6-[5-(9,9-Difluoro-7-{2-[2-(2-methoxycarbonylamino-4-methylsulfonyl-butyryl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carbonyl}-2-methyl-propyl)-carbamic acid methyl ester 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (55.6 mg, 0.067 mmol) was dissolved in DCM (1 mL) and HCl in dioxane (4M, 1 mL) was added and stirring at room temperature was continued. After 30 minutes, all volatiles were removed in vacuo. The crude material was used in the next step without further purification. The crude material was dissolved in DMF (1.0 mL) and DIEA (25.8 mg, 0.201 mmol) was added. A solution of 2-(L) methoxycarbonylamino-4-methyl-sulfonyl-butyric acid (15.9 mg, 0.067 mmol), HATU (25.4 mg, 0.067 mmol) and DIEA (8.6 mg, 0.067 mmol) in DMF (1 mL) was added. The reaction was stirred at room temperature. After 20 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (1-{6-[5-(9,9-Difluoro-7-{2-[2-(2-methoxycarbonylamino-4-methyl-sulfonyl-butyryl)-2-aza-bicyclo[2.2.1]hept-3-yl]-3H-benzoimidazol-5-yl}-9H-fluoren-2-yl)-1H-imidazol-2-yl]-5-aza-spiro[2.4]heptane-5-carbonyl}-2-methyl-propyl)-carbamic acid methyl ester (23 mg) as a TFA salt.

LCMS-ESI$^+$: calc'd for $C_{49}H_{54}F_2N_8O_8S$: 953.1 (M$^+$); Found: 954.0 (M+H$^+$).

$^1$H-NMR: 300 MHz, (dmso-d$_6$) δ: 8.20-7.99 (m, 8H), 7.77 (s, 2H), 7.65 (m, 1H), 7.35 (m, 1H), 5.25 (dd, J=7.2 Hz, 1H), 4.79 (s, 1H) 4.56 (s, 1H), 4.53 (m, 1H), 4.02 (m, 1H), 3.88 (m, 1H), 3.72 (m, 1H), 3.56 (s, 3H), 3.53 (s, 3H), 3.27 (m, 2H), 3.01 (s, 3H), 2.78 (m, 1H), 2.25 (m, 2H), 2.09-2.04 (m, 2H), 1.88-1.79 (m, 4H), 1.56 (m, 1H), 0.94-0.77 (m, 9H) 0.63 (m, 4H) ppm.

$^{19}$F-NMR: 282 MHz, (dmso-d$_6$) δ: -109.1 ppm [-74.8 ppm TFA].

Example EA

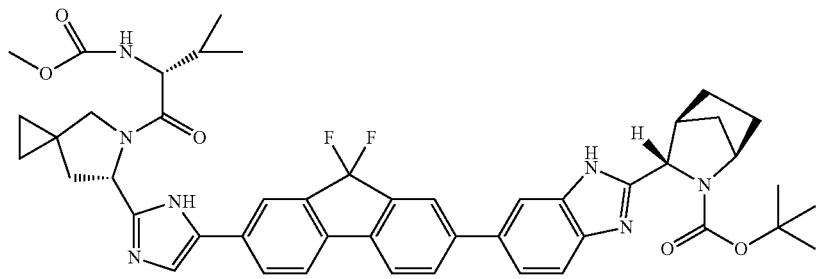
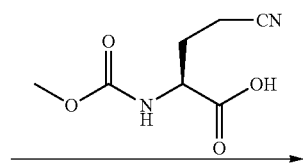

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester

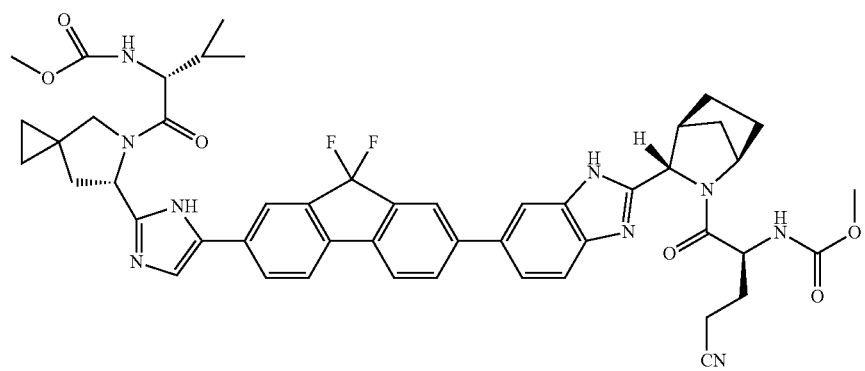

(3-Cyano-1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-propyl)-carbamic acid methyl ester

(3-Cyano-1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-propyl)-carbamic acid methyl ester 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (61.9 mg, 0.074 mmol) was dissolved in DCM (1 mL) and HCl in dioxane (4M, 1 mL) was added and stirring at room temperature was continued. After 30 minutes, all volatiles were removed in vacuo. The crude material was used in the next step without further purification. The crude material was dissolved in DMF (1.0 mL) and DIEA (28.5 mg, 0.186 mmol) was added. A solution of 2-(L) Methoxycarbonylamino-3-cyano-butyric acid (13.8 mg, 0.074 mmol), HATU (28.3 mg, 0.074 mmol) and DIEA (9.5 mg, 0.074 mmol) in DMF (0.5 mL) was added. The reaction was stirred at room temperature. After 30 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (3-Cyano-1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-propyl)-carbamic acid methyl ester (33.1 mg) as a TFA salt.

LCMS-ESI$^+$: calc'd for $C_{49}H_{51}F_2N_9O_6$: 899.9 (M$^+$); Found: 900.4 (M+H$^+$).

$^1$H-NMR: 300 MHz, (dmso-d$_6$) δ: 8.20-7.99 (m, 8H), 7.76 (s, 2H), 7.59 (m, 1H), 7.36 (m, 1H), 5.25 (dd, J=7.2 Hz, 1H), 4.79 (s, 1H) 4.55 (s, 1H), 4.41 (m, 1H), 3.99 (m, 1H), 3.86 (m, 1H), 3.74 (m, 1H), 3.56 (s, 3H), 3.54 (s, 3H), 2.77 (m, 1H), 2.62 (m, 2H), 2.25 (m, 2H), 2.14 (m, 2H), 1.88-1.79 (m, 4H), 1.54 (m, 1H), 0.94-0.77 (m, 9H) 0.63 (m, 4H) ppm.

$^{19}$F-NMR: 282 MHz, (dmso-d$_6$) β: −109.1 ppm [−74.7 ppm TFA].

Example EB

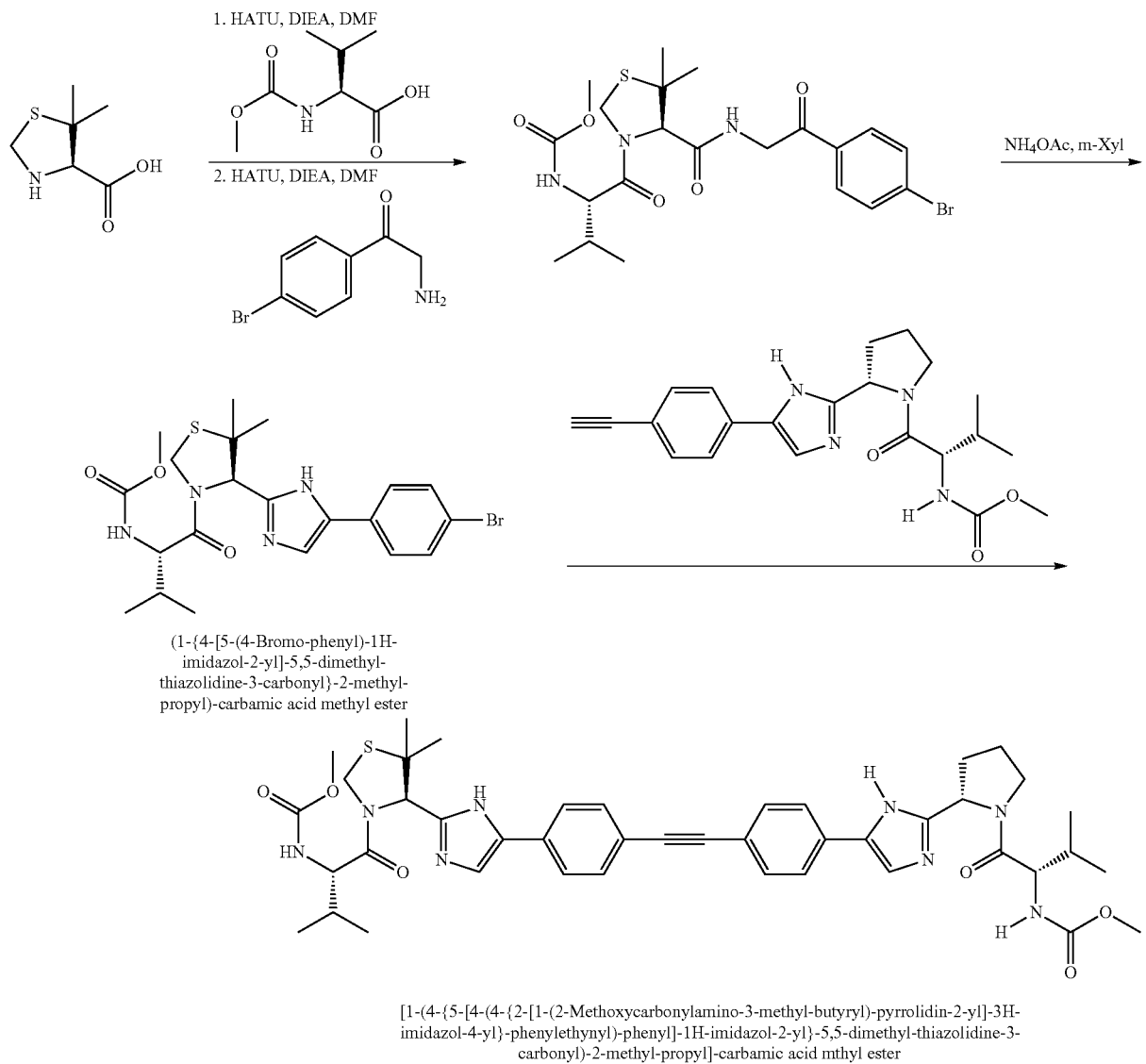

(1-{4-[5-(4-Bromo-phenyl)-1H-imidazol-2-yl]-5,5-dimethyl-thiazolidine-3-carbonyl}-2-methyl-propyl)-carbamic acid methyl ester 5,5-Dimethyl-thiazolidine-4-carboxylic acid (1.1 g, 6.91 mmol) and DIEA (891 mg, 6.91 mmol) were added as a DMF (5 mL) suspension to a premixed solution of N-(methylcarbamoyl)(L)-valine (1.21 g, 6.91 mmol), HATU (2.26 g, 6.91 mmol) and DIEA (891 mg, 6.91 mmol) at room temperature. After 20 minutes, additional HATU (2.26 g, 6.91 mmol) and DIEA (891 mg, 6.91 mmol) were added and stirring at room temperature was continued. After 5 minutes, as suspension of amino-(4' bromo) acetophenone hydrochloride salt (1.72 g, 6.91 mmol) and DIEA (891 mg, 6.91 mmol) in DMF (3 mL) was added. Stirring at room temperature was continued. After 10 minutes, all volatiles were removed in vacuo and the crude material was taken into EtOAc. The organic layer was washed with aqueous hydrochloric acid (0.1M), aqueous lithium chloride solution (5%), saturated aqueous sodium bicarbonate solution, brine and was dried over sodium sulfate. Filtration and evaporation of solvents yielded crude material. Purification via silica gel chromatography (eluent EtOAc/hexanes) yielded the product (3.46 g, 6.73 mmol).

LCMS-ESI$^+$: calc'd for $C_{21}H_{28}BrN_3O_5S$: 514.3 (M$^+$); Found: 515.4/513.4 (M+H$^+$). The product of the previous step (1.04 mg, 1.94 mmol) was dissolved in m-xylenes (9.0 mL) and heated at 135° C. Solid ammonium acetate (700 mg, 9.07 mmol) was added and the reaction was stirred at 135° C. After 240 minutes, the reaction was cooled to room temperature and the volatiles were removed in vacuo. The crude material was purified via silica gel chromatography (eluent: EtOAc/hexanes) to yield the product (1-{4-[5-(4-Bromo-phenyl)-1H-imidazol-2-yl]-5,5-dimethyl-thiazolidine-3-carbonyl}-2-methyl-propyl)-carbamic acid methyl ester (190 mg). LCMS-ESI$^+$: calc'd for $C_{21}H_{28}BrN_4O_3S$: 495.4 (M$^+$); Found: 496.4/494.4 (M+H$^+$).

[1-(4-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-5,5-dimethyl-thiazolidine-3-carbonyl)-2-methyl-propyl]-carbamic acid methyl ester (1-{4-[5-(4-Bromo-phenyl)-1H-imidazol-2-yl]-5,5-dimethyl-thiazolidine-3-carbonyl}-2-methyl-propyl)-carbamic acid methyl ester (83 mg, 0.167 mmol) was combined with (1-{2-[5-(4-Ethynyl-phenyl)-1H-imidazol-2-yl]-pyrrolidine-1-carbonyl}-2-methyl-propyl)-carbamic acid methyl ester (66.0 mg, 0.167 mmol) and PdCl$_2$(PPh$_3$)$_2$ (11.7 mg, 0.017 mmol) under an argon atmosphere. DMF (2.0 mL degassed with Argon) was added followed by triethylamine (168 mg, 1.67 mmol) and copper(I) iodide (3.2 mg, 0.017 mmol). The mixture was heated at 80° C. After 20 hours, volatiles were removed in vacuo and the crude material was semi-purified via chromatography on silica gel (eluent EtOAc w MeOH 10%/hexanes) and further purified via RP-HPLC (eluent: water/MeCN w 0.1% TFA) to yield the product [1-(4-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-5,5-dimethyl-thiazolidine-3-carbonyl)-2-methyl-propyl]-carbamic acid methyl ester (32.1 mg) as a TFA salt.

LCMS-ESI$^+$: calc'd for C$_{43}$H$_{52}$N$_8$O$_6$S: 808.9 (M$^+$); Found: 809.9 (M+H$^+$).

$^1$H-NMR: 300 MHz, (dmso-d$_6$) δ: 8.09 (m, 2H), 7.83-7.69 (m, 12H), 7.56 (m, 1H), 7.34 (m, 1H), 5.33 (s, 1H), 5.12 (m, 2H), 5.01 (m, 1H) 4.01 (m, 2H), 3.83 (m, 2H), 3.55 (s, 3H), 3.53 (s, 3H), 2.37 (m, 1H), 2.09-2.04 (m, 3H), 1.55 (s, 3H), 1.11 (s, 3H), 0.92-0.76 (m, 12H) ppm.

Example EC

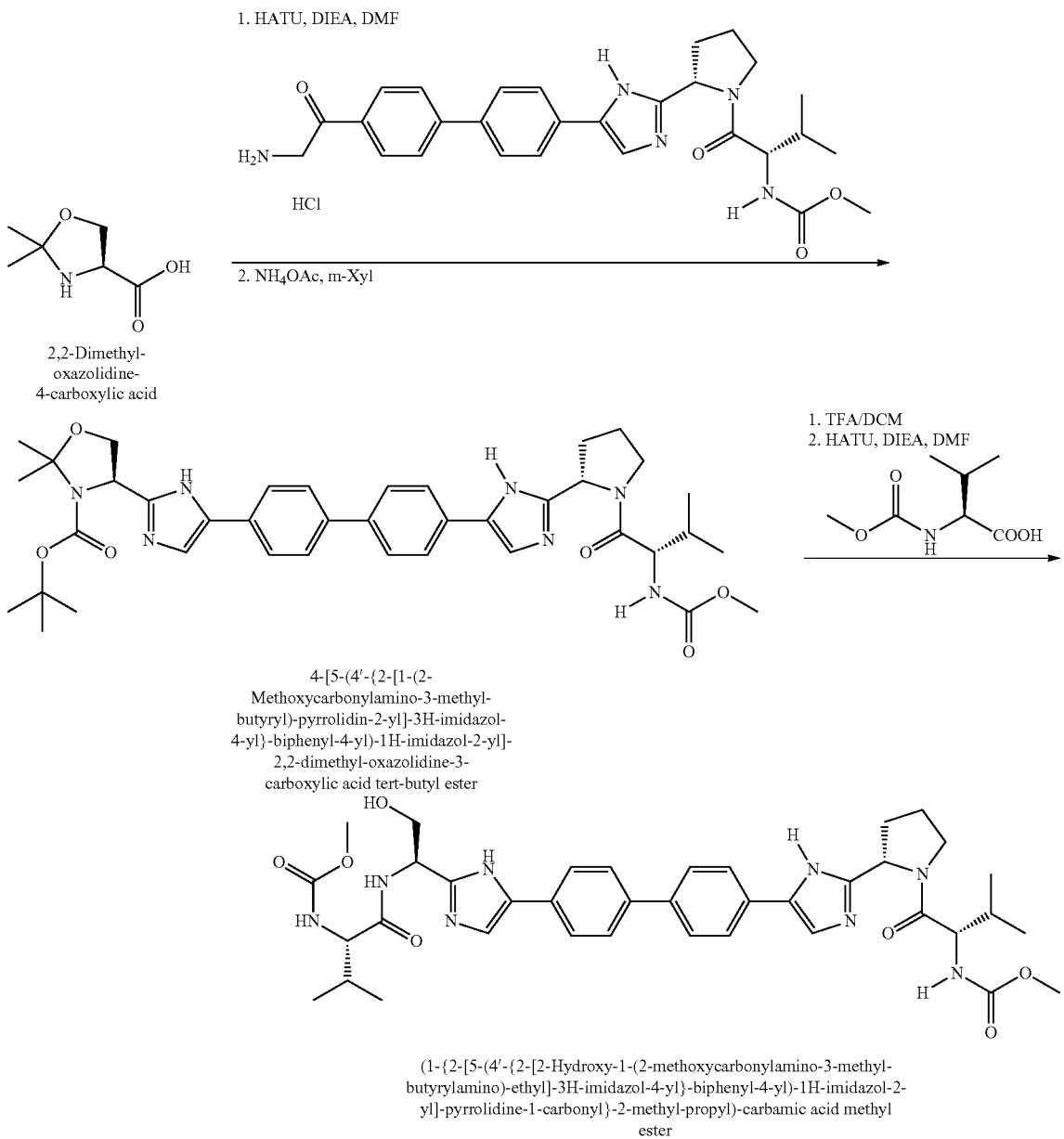

4-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-2,2-dimethyl-oxazolidine-3-carboxylic acid tert-butyl ester 2,2-Dimethyl-oxazolidine-4-carboxylic acid (350 mg, 1.02 mmol) was dissolved in DMF (2.5 mL) and HATU (387 mg, 0.102 mmol) and DIEA (129.0 mg, 1.02 mmol) were added. The reaction was stirred at room temperature for five minutes, after which [1-(2-{5-[4'-(2-Amino-acetyl)-biphenyl-4-yl]-1H-imidazol-2-yl}-pyrrolidine-1-carbonyl)-2-methyl-propyl]-carbamic acid methyl ester hydrochloride salt (503 mg, 1.0 mmol) and DIEA (129.0 mg, 1.02 mmol) were added. Stirring at room temperature was continued. After 18 hours, all volatiles were removed in vacuo and the crude material was purified via silica gel chromatography (eluent: EtOAc/hexanes) to yield the product (323 mg). The material was dissolved was dissolved in m-xylenes (5.0 mL) and heated at 135° C. Solid ammonium acetate (280 mg, 3.63 mmol) was added and the reaction was stirred at 135° C. After 180 minutes, the reaction was cooled to room temperature and the volatiles were removed in vacuo. The crude material was purified via silica gel chromatography (eluent: EtOAc/hexanes) to yield the product 4-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-2,2-dimethyl-oxazolidine-3-carboxylic acid tert-butyl ester (123 mg, 0.172 mmol).

LCMS-ESI$^+$: calc'd for $C_{39}H_{49}N_7O_6$: 711.8 (M$^+$); Found: 712.7 (M+H$^+$).

(1-{2-[5-(4'-{2-[2-Hydroxy-1-(2-methoxycarbonylamino-3-methyl-butyrylamino)-ethyl]-3H-imidazol-4-yl}-biphenyl-4-yl)-1H-imidazol-2-yl]-pyrrolidine-1-carbonyl}-2-methyl-propyl)-carbamic acid methyl ester 4-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-2,2-dimethyl-oxazolidine-3-carboxylic acid tert-butyl ester (61 mg, 0.086 mmol) was dissolved in DCM (1 mL) and TFA (4M, 0.2 mL) was added and stirring at 0° C. was continued. After 30 minutes, all volatiles were removed in vacuo. The crude material was used in the next step without further purification. The crude material was dissolved in DMF (1.5 mL) and DIEA (33.0 mg, 0.255 mmol) was added. A solution of 2-(L) Methoxycarbonylamino-3-methyl-butyric acid (15.2 mg, 0.086 mmol), HATU (32.5 mg, 0.086 mmol) and DIEA (11.0 mg, 0.086 mmol) in DMF (0.5 mL) was added. The reaction was stirred at room temperature. After 20 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (1-{2-[5-(4'-{2-[2-Hydroxy-1-(2-methoxycarbonylamino-3-methyl-butyrylamino)-ethyl]-3H-imidazol-4-yl}-biphenyl-4-yl)-1H-imidazol-2-yl]-pyrrolidine-1-carbonyl}-2-methyl-propyl)-carbamic acid methyl ester (11.2 mg) as a TFA salt.

LCMS-ESI$^+$: calc'd for $C_{38}H_{48}N_8O_7$: 728.8 (M$^+$); Found: 729.7 (M+H$^+$).

$^1$H-NMR: 300 MHz, (dmso-d$_6$) δ: 8.62 (m, 1H), 8.11 (m, 2H), 7.95-7.86 (m, 8H), 7.34 (m, 1H), 7.22 (m, 1H), 5.10 (m, 2H), 4.78 (s, 1H) 4.13 (m, 1H), 3.94 (m, 1H), 3.83 (m, 4H), 3.54 (s, 3H), 3.53 (s, 3H), 2.37 (m, 1H), 2.09-2.04 (m, 5H), 0.88-0.75 (m, 12H) ppm.

Example ED

Preparation of Intermediate 5-Aza-spiro[2.4]heptane-5,6-dicarboxylic acid 5-benzyl ester 6-methyl ester

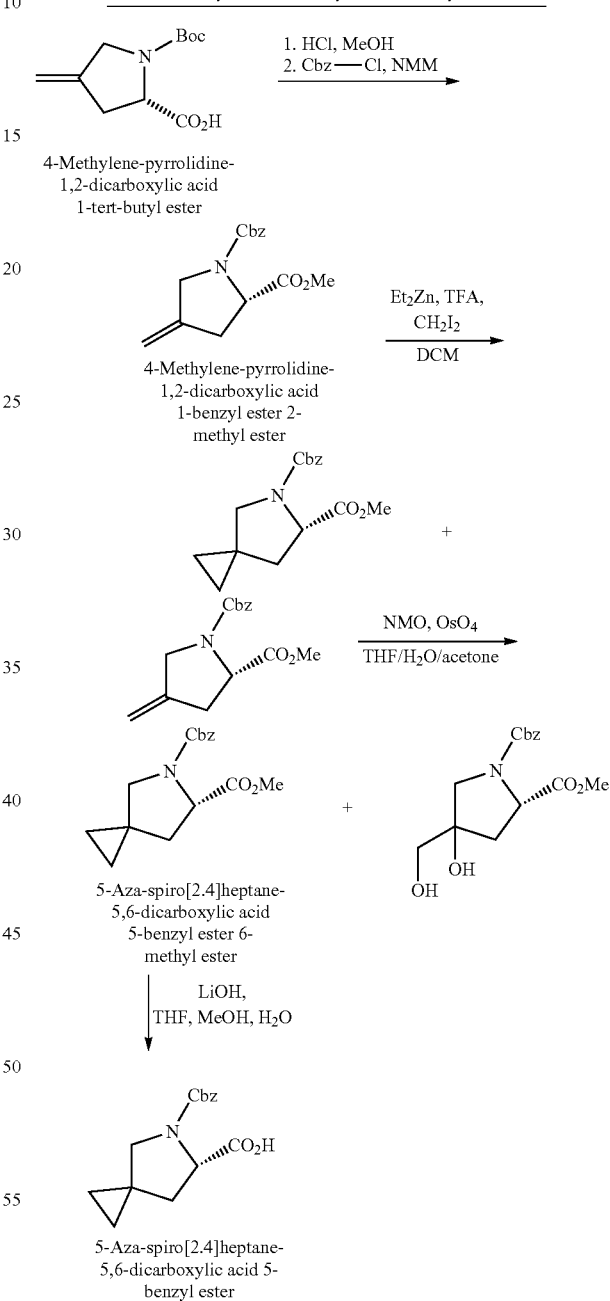

4-Methylene-pyrrolidine-1,2-dicarboxylic acid 1-benzyl ester 2-methyl ester

4-Methylene-pyrrolidine-1,2-dicarboxylic acid 1-tert-butyl ester (10.0 g, 44 mmol) was dissolved in MeOH (75 mL) at room temperature and HCl (4M in dioxane, 75 mL) was added. Stirring at room temperature was continued for 4 hours. All volatiles were removed in vacuo and a beige solid was obtained.

The crude material was suspended in DCM (100 mL) and N-Methyl morpholine (13.3 g, 132 mmol) was added. The mixture was cooled to 0° C. and benzyl chloroformate (8.26 g, 48.4 mmol) was added while stirring. After 30 minutes, the reaction was warmed to room temperature and the solution was washed with water and aqueous HCl (1M). The solution was dried over sodium sulfate. Filtration and evaporation of solvents gave crude product, which was purified by silica gel chromatography (eluent: EtOAc/hexanes) to yield the product (10.2 g). LCMS-ESI$^+$: calc'd for $C_{15}H_{17}NO_4$: 275.3 (M$^+$); Found: 276.4 (M+H$^+$).

5-aza-spiro[2.4]heptanes-5,6-dicarboxylic acid benzyl ester

An oven-dried 3-neck round bottom flask was equipped with a nitrogen inlet adaptor and a 250 mL addition funnel. The third neck was sealed with a septum. The flask was charged with a stir bar, dichlorormethane (120 mL) and diethyl zinc (1.0 M in hexane, 118 mL, 118 mmol) then cooled to 0° C. in an ice bath. The addition funnel was charged with dichloromethane (40 mL) and trifluoroacetic acid (9.1 mL, 118 mmol). After the diethyl zinc solution had cooled to 0° C. (about 25 minutes), the trifluoroacetic acid solution was added dropwise over 20 minutes to the stirred reaction mixture. After stirring for another 20 minutes at 0° C., diiodomethane (9.5 mL, 118 mmol) was added slowly over 4 minutes. After another 20 minutes, 4-methylene-pyrrolidine-1,2-dicarboxylic acid 1-benzyl ester 2-methyl ester (8.10 g, 29.4 mmol) was added in 30 mL dichloromethane by cannula. The flask containing 4-methylene-pyrrolidine-1,2-dicarboxylic acid 1-benzyl ester 2-methyl ester was then rinsed with another 10 mL dichloromethane and this solution was also transferred to the reaction mixture by cannula. The reaction mixture was allowed to warm to RT and stirred for 110 hours (about 5 days) after which the reagents were quenched with saturated aqueous ammonium chloride (~150 mL). The contents of the flask were slowly poured into a 2 L sep funnel containing saturated aqueous sodium bicarbonate (~800 mL). The aqueous phase was extracted three times with 300 mL ethyl acetate. The combined organics were dried over magnesium sulfate and concentrated to provide the crude material. The crude material was dissolved in 3:1:1 THF/water/acetone (165 mL) then treated with N-methylmorpholine-N-oxide (3.45 g, 29.4 mmol) and osmium tetroxide (4 wt % in water, 5 mL, 0.818 mmol). After stirring at RT for 7 h, the reagents were quenched with 1 M aqueous sodium thiosulfate (~100 mL). The contents of the flask were then poured into a 1 L sep funnel containing water (~300 mL). The aqueous phase was extracted three times with 300 mL dichloromethane. The combined organics were dried over magnesium sulfate and concentrated. The crude residue was purified by silica column chromatography (5% to 45% EtOAc/hexane) to provide 5-aza-spiro[2.4]heptane-5,6-dicarboxylic acid 5-benzyl ester 6-methyl ester as a clear oil (5.54 g, 19.15 mmol, 65%) as a clear oil. $^1$H NMR (CDCl$_3$) δ 7.36-7.29 (m, 5H), 5.21-5.04 (m, 2H), 4.56-4.47 (m, 1H), 3.75 (s, 1.5H), 3.60 (m, 1.5H), 03.51-3.37 (m, 2H), 2.32-2.25 (m, 1H), 1.87-1.80 (m, 1H), 0.64-0.51 (m, 4H).

5-Aza-spiro[2.4]heptane-5,6-dicarboxylic acid 5-benzyl ester

5-Aza-spiro[2.4]heptane-5,6-dicarboxylic acid 5-benzyl ester 6-methyl ester (244 mg, 0.840 mmol) was dissolved in THF (2.0 mL)/MeOH (1.5 mL) An aqueous solution of LiOH (35.5 mg, 0.84 mmol) was added and stirring at room temperature was continued. After 3 hours, the reaction was neutralized with aqueous HCl (1M) and the organic solvents were removed in vacuo. The crude mixture was diluted with water and EtOAc and the organic layer was collected. All volatiles were removed in vacuo and the crude acid was used without further purification. LCMS-ESI$^+$: calc'd for $C_{15}H_{17}NO_4$: 275.3 (M$^+$); Found: 276.3 (M+H$^+$).

Example ED'

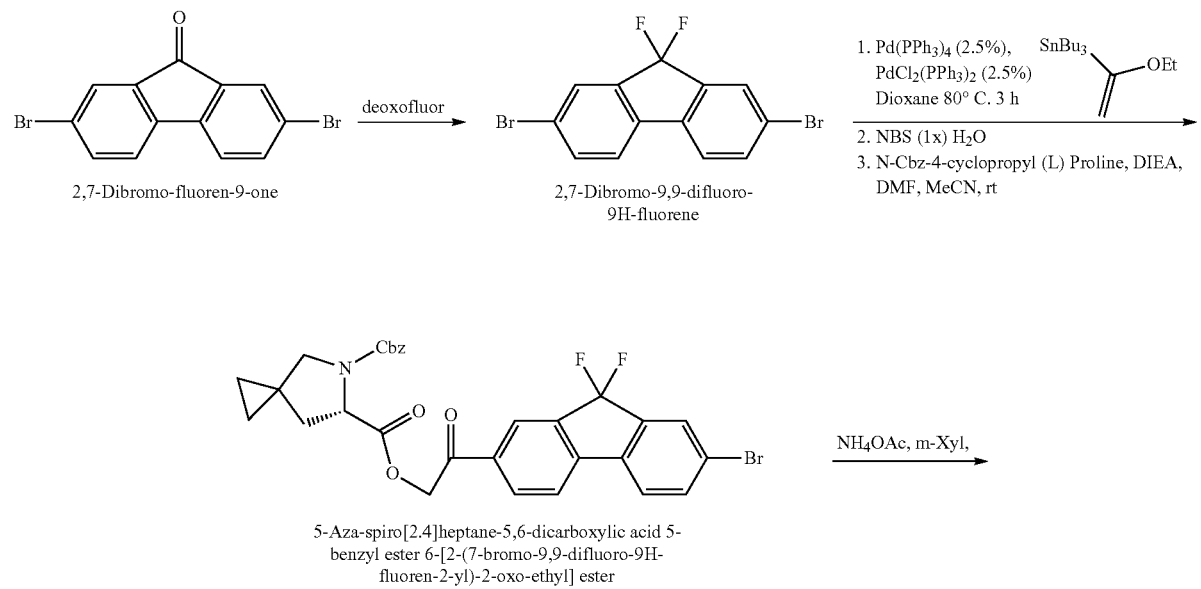

2,7-Dibromo-fluoren-9-one 2,7-Dibromo-9,9-difluoro-9H-fluorene

5-Aza-spiro[2.4]heptane-5,6-dicarboxylic acid 5-benzyl ester 6-[2-(7-bromo-9,9-difluoro-9H-fluoren-2-yl)-2-oxo-ethyl] ester -continued

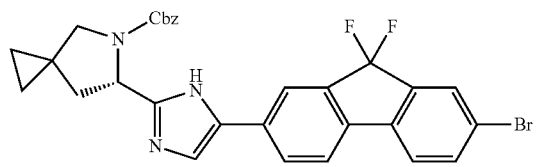

6-[5-(7-Bromo-9,9-difluoro-9H-fluoren-2-yl)-1H-imidazol-2-yl]-5-aza-spiro[2.4]heptane-5-carboxylic acid benzyl ester 1. HBr/HOAc
2. HATU, DIEA, DMF

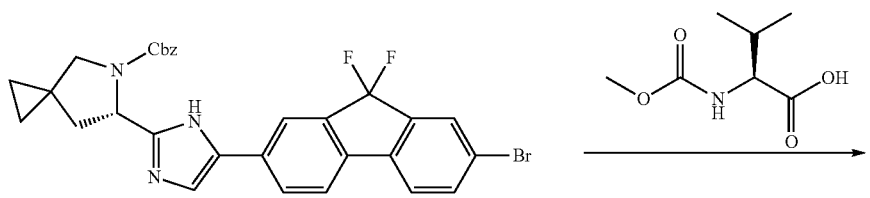

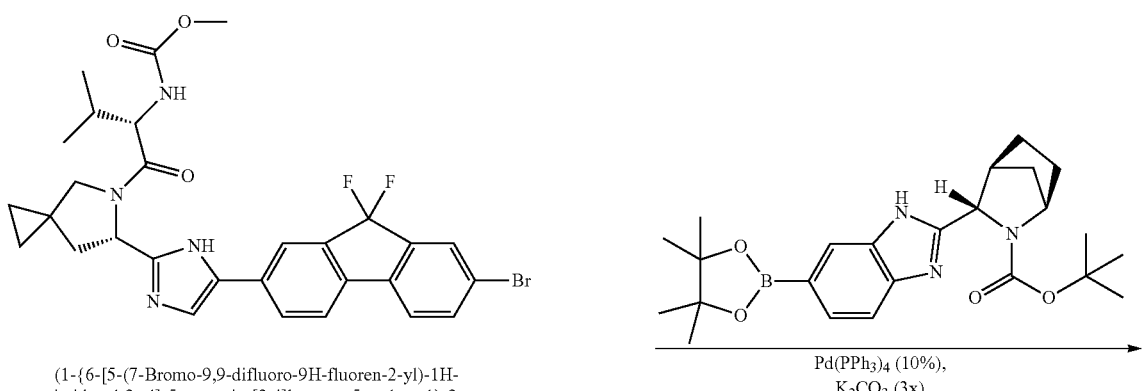

(1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester Pd(PPh$_3$)$_4$ (10%),
K$_2$CO$_3$ (3x)
DME/H$_2$O 1. HCl Dioxane/DCM
2. HATU, DIEA, DMF

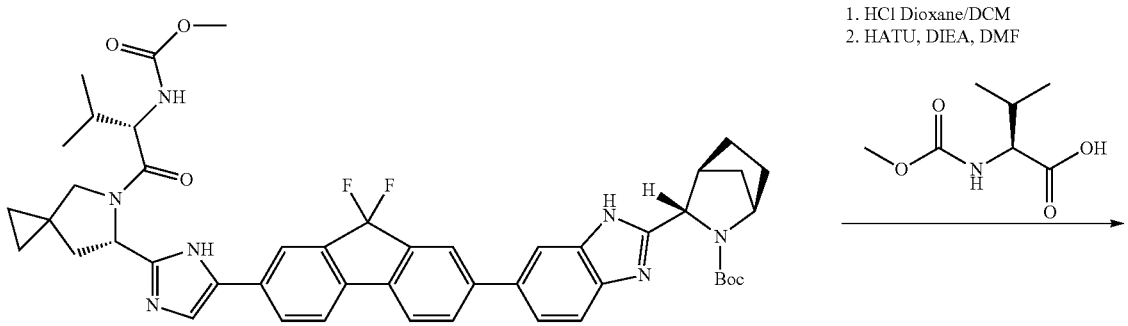

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester

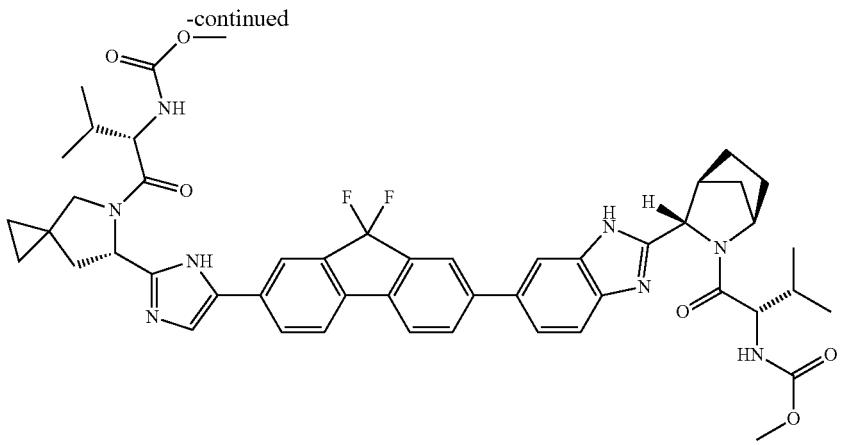

(1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester 2,7-Dibromo-9,9-difluoro-9H-fluorene 2,7-Dibromo-fluoren-9-one (4.0 g, 11.8 mmol) was suspended in deoxofluor (12 mL) at room temperature and EtOH (4 drops) was added. The stirred suspension was heated at T=90° C. for 24 hours (CAUTION: Use of deoxofluor at elevated temperatures, as described above, is strongly discouraged as rapid and violent exotherms may occur). The reaction was cooled to room temperature and poured onto ice containing sodium bicarbonate. A solid formed and was collected via filtration. The crude material was taken into EtOAc and was washed with aqueous HCl (1M) and brine. The solution was dried over sodium sulfate. Filtration and evaporation of solvents gave crude product, which was purified by silica gel chromatography (eluent: EtOAc/hexanes) to yield the product 2,7-Dibromo-9,9-difluoro-9H-fluorene (3.2 g). $^{19}$F-NMR: 282 MHz, (dmso-$d_6$) δ: −111.6 ppm.

Before using the material in the next step, it was exposed as a solution in EtOAc to charcoal.

5-Aza-spiro[2.4]heptane-5,6-dicarboxylic acid 5-benzyl ester 6-[2-(7-bromo-9,9-difluoro-9H-fluoren-2-yl)-2-oxo-ethyl]ester 2,7-Dibromo-9,9-difluoro-9H-fluorene (372 mg, 1.04 mmol), Pd(PPh$_3$)$_4$ (30.0 mg, 0.026 mmol), PdCl$_2$(PPh$_3$)$_2$ (18.2 mg, 0.026 mmol), As(PPh$_3$)$_3$ (5.0 mg) were dissolved in dioxane (10 mL) under an argon atmosphere. Ethoxyvinyltributyl tin (376.4 mg, 1.04 mmol) was added. The mixture was heated for 140 minutes at 85° C. (oil bath). The reaction was cooled to room temperature. N-bromo succinimide (177 mg, 1.0 mmol) was added followed by water (2 mL). The reaction was stirred at room temperature for 3 hours, after which the majority of the dioxane was removed in vacuo. The crude reaction mixture was diluted with EtOAc and was washed with water. All volatiles were removed in vacuo. Toluene was added and all volatiles were removed in vacuo for a second time. The crude material was dissolved in DMF/MeCN (2 mL, 1:1) at room temperature. A solution of N-Cbz-4-cyclopropyl (L) Proline (0.84 mmol) and DIEA (268 mg, 2.08 mmol) in MeCN (2 mL) was added and stirring at room temperature was continued. After 14 hours, most of the MeCN was removed in vacuo and the crude reaction mixture was diluted with EtOAc. The mixture was washed with aqueous HCl (1M), aqueous LiCl solution (5%), brine, and was dried over sodium sulfate. Filtration and evaporation of solvents gave the crude reaction product, which was purified via silica gel chromatography (eluent: EtOAc/hexanes) to yield the product 5-Aza-spiro[2.4]heptane-5,6-dicarboxylic acid 5-benzyl ester 6-[2-(7-bromo-9,9-difluoro-9H-fluoren-2-yl)-2-oxo-ethyl]ester (176 mg). LCMS-ESI$^+$: calc'd for $C_{30}H_{24}BrF_2NO_5$: 596.4 (M$^+$); Found: 595.2/597.2 (M+H$^+$).

6-[5-(7-Bromo-9,9-difluoro-9H-fluoren-2-yl)-1H-imidazol-2-yl]-5-aza-spiro[2.4]heptane-5-carboxylic acid benzyl ester 5-Aza-spiro[2.4]heptane-5,6-dicarboxylic acid 5-benzyl ester 6-[2-(7-bromo-9,9-difluoro-9H-fluoren-2-yl)-2-oxo-ethyl]ester (172 mg, 0.293 mmol) was dissolved in m-xylenes (6.0 mL). Ammonium acetate (226 mg, 2.93 mmol) was added and the reaction was stirred at 140° C. for 60 minutes under microwave conditions. The reaction was cooled to room temperature and all volatiles were removed in vacuo. The crude material was purified via silica gel chromatography (eluent: EtOAc/hexanes) to yield the product 6-[5-(7-Bromo-9,9-difluoro-9H-fluoren-2-yl)-1H-imidazol-2-yl]-5-aza-spiro[2.4]heptane-5-carboxylic acid benzyl ester (80.3 mg). LCMS-ESI$^+$: calc'd for $C_{30}H_{24}BrF_2N_3O_2$: 576.4 (M$^+$); Found: 575.2/577.2 (M+H$^+$).

(1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester 6-[5-(7-Bromo-9,9-difluoro-9H-fluoren-2-yl)-1H-imidazol-2-yl]-5-aza-spiro[2.4]heptane-5-carboxylic acid benzyl ester (800 mg, 1.38 mmol) was dissolved in DCM (15 mL) and HBr in AcOH (37%, 2 mL) was added and stirring at room temperature was continued. After 180 minutes, the suspension was diluted with hexanes and the solid was collected via filtration and was washed with hexanes and subjected to vacuum. The crude material was used in the next step without further purification. The crude material was dissolved in DMF (4.0 mL) and DIEA (356 mg, 2.76 mmol) was added. A solution of 2-(L)-Methoxycarbonylamino-3-methyl-butyric acid (242 mg, 1.38 mmol), HATU (524 mg, 1.38 mmol) and DIEA (178 mg, 1.38 mmol) in DMF (1 mL) was added. The reaction was stirred at room temperature. After 50 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by silica gel chromatography (eluent: EtOAc/hexanes) to yield the slightly impure product (1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester (878 mg). LCMS-ESI+: calc'd for $C_{29}H_{29}BrF_2N_4O_3$: 599.5 (M+); Found: 598.5/600.5 (M+H+).

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester (840 mg, 1.4 mmol), 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester (615 mg, 1.4 mmol), Pd(PPh3)4 (161 mg, 0.14 mmol), K2CO3 (579 mg, 4.2 mmol), were dissolved in DME (15 mL)/water (3 mL) under an argon atmosphere. The mixture was heated for 120 minutes at 85-90° C. (oil bath). After 120 minutes additional boronate ester (61 mg, 0.14 mmol) was added and heating was continued. After 3 hours, the reaction was cooled to room temperature. Most of the DME was removed in vacuo and the crude reaction mixture was diluted with EtOAc. The mixture was washed with brine and was dried over sodium sulfate. Filtration and evaporation of solvents gave the crude reaction product, which was purified via silica gel chromatography (eluent: EtOAc/hexanes) to yield the product 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (878 mg). LCMS-ESI+: calc'd for $C_{47}H_{51}F_2N_7O_5$: 831.9 (M+); Found: 832.7 (M+H+).

(1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (115 mg, 0.138 mmol) was dissolved in DCM (2 mL) and HCl in dioxane (4M, 2 mL) was added and stirring at room temperature was continued. After 20 minutes, all volatiles were removed in vacuo. The crude material was used in the next step without further purification. The crude material was dissolved in DMF (1.5 mL) and DIEA (53.4 mg, 0.414 mmol) was added. A solution of 2-(L) Methoxycarbonylamino-3-methyl-butyric acid (24.2 mg, 0.138 mmol), HATU (52.4 mg, 0.138 mmol) and DIEA (17.8 mg, 0.138 mmol) in DMF (1 mL) was added. The reaction was stirred at room temperature. After 20 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by RP-HPLC (eluent: water/MeCN w/0.1% TFA) to yield the product (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (76 mg). LCMS-ESI+: calc'd for $C_{49}H_{54}F_2N_8O_6$: 888.9 (M+); Found: 890.0 (M+H+).
1H-NMR: 300 MHz, (dmso-d6) δ: 8.20-7.99 (m, 8H), 7.73 (s, 2H), 7.37-7.27 (m, 2H), 5.25 (dd, J=7.2 Hz, 1H), 4.78 (s, 1H) 4.54 (s, 1H), 4.16 (m, 1H), 4.02 (m, 1H), 3.87 (m, 1H), 3.74 (m, 1H), 3.55 (s, 3H), 3.53 (s, 3H), 2.75 (m, 1H), 2.25 (m, 2H), 2.09-2.04 (m, 2H), 1.88-1.79 (m, 2H), 1.54 (m, 1H), 0.94-0.77 (m, 15H) 0.63 (m, 4H) ppm. 19F-NMR: 282 MHz, (dmso-d6) δ: −109.1 ppm [−74.8 ppm TFA]

Example EE

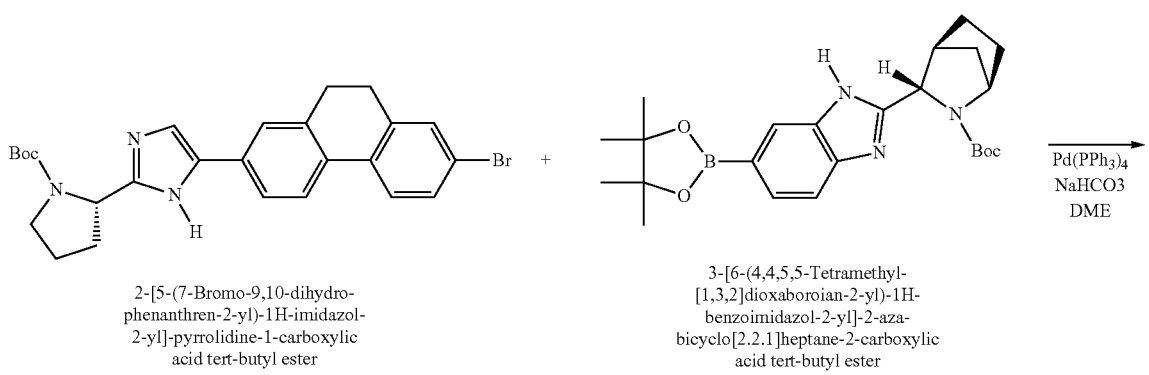

2-[5-(7-Bromo-9,10-dihydro-phenanthren-2-yl)-1H-imidazol-2-yl]-pyrrolidine-1-carboxylic acid tert-butyl ester 3-[6-(4,4,5,5-Tetramethyl-[1,3,2]dioxaboroian-2-yl)-1H-benzoimidazol-2-yl]-2-aza-bicyclo[2.2.1]heptane-2-carboxylic acid tert-butyl ester

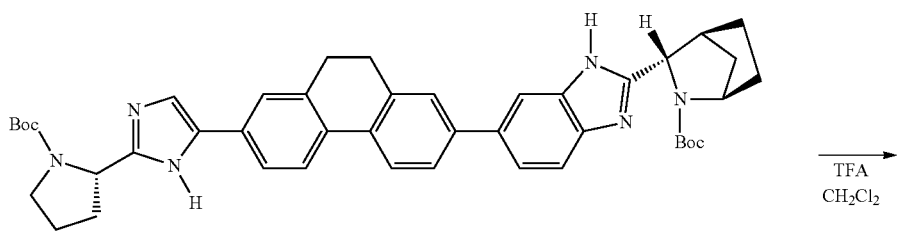

3-(6-{7-[2-(1-tert-Butoxycarbonyl-pyrrolidin-2-yl)-3H-
imidazol-4-yl]-9,10-dihydro-phenanthren-2-yl}-1H-
benzoimidazol-2-yl)-2-aza-bicyclo[2.2.1]heptane-2-
carboxylic acid tert-butyl ester

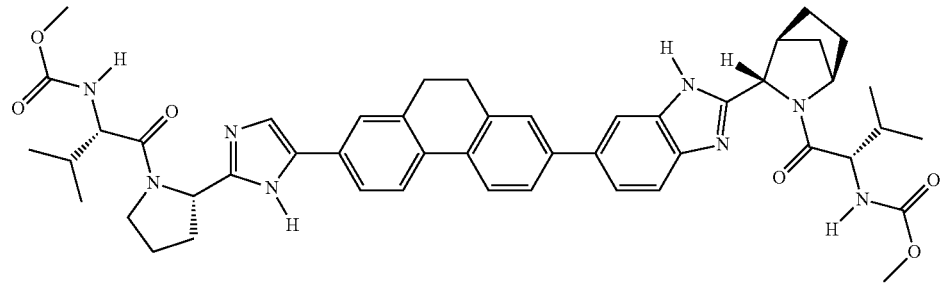

(1-{3-[6-(7-{2-[1-(2-Methoxycarbonylamino-3-methyl-butyryl)-
pyrrolidin-2-yl]-3H-imidazol-4-yl}-9,10-dihydro-phenanthren-2-
yl)-1H-benzoimidazol-2-yl]-2-aza-bicylco[2.2.1]heptane-2-
carbonyl}-2-methyl-propyl)-carbamic acid methyl ester

3-(6-{7-[2-(1-tert-Butoxycarbonyl-pyrrolidin-2-yl)-3H-imidazol-4-yl]-9,10-dihydro-phenanthren-2-yl}-1H-benzoimidazol-2-yl)-2-aza-bicyclo[2.2.1]heptane-2-carboxylic acid tert-butyl ester Pd(Ph$_3$)$_4$ (20 mg, 0.017 mmol) was added to a mixture 2-[5-(7-bromo-9,10-dihydro-phenanthren-2-yl)-1H-imidazol-2-yl]-pyrrolidine-1-carboxylic acid tert-butyl ester (173 mg, 0.35 mmol), 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester (154 mg, 0.35 mmol), NaHCO$_3$ (103 mg, 1.22 mmol) in 1,2-dimethoxyethane (5 mL) and water (1 mL). The reaction mixture was flushed with nitrogen, heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product 3-(6-{7-[2-(1-tert-Butoxycarbonyl-pyrrolidin-2-yl)-3H-imidazol-4-yl]-9,10-dihydro-phenanthren-2-yl}-1H-benzoimidazol-2-yl)-2-aza-bicyclo[2.2.1]heptane-2-carboxylic acid tert-butyl ester as a white solid (150 mg, 59%). m/z 727.4 (M+H)$^+$.

(1-{3-[6-(7-{2-[1-(2-Methoxycarbonylamino-3-methyl-butyryl)-pyrrolidin-2-yl]-3H-imidazol-4-yl}-9,10-dihydro-phenanthren-2-yl)-1H-benzoimidazol-2-yl]-2-aza-bicyclo[2.2.1]heptane-2-carbonyl}-2-methyl-propyl)-carbamic acid methyl ester To a solution of 3-(6-{7-[2-(1-tert-Butoxycarbonyl-pyrrolidin-2-yl)-3H-imidazol-4-yl]-9,10-dihydro-phenanthren-2-yl}-1H-benzoimidazol-2-yl)-2-aza-bicyclo[2.2.1]heptane-2-carboxylic acid tert-butyl ester (135 mg, 0.19 mmol) in dichloromethane (6 mL) was added trifluoroacetic acid (2 mL, excess). The mixture was stirred for 2 hours at ambient temperature and concentrated under reduced pressure. The residue was treated with ether to remove excess trifluoroacetic acid. The obtained white solid was dissolved in DMF (5 mL), to the solution was added 2-methoxycarbonylamino-3-methyl-butyric acid (65 mg, 0.37 mmol), HATU (156 mg, 0.41 mmol) and N,N-diisopropylethylamine (0.32 mL, 1.86 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (1-{3-[6-(7-{2-[1-(2-Methoxycarbonylamino-3-methyl-butyryl)-pyrrolidin-2-yl]-3H-imidazol-4-yl}-9,10-dihydro-phenanthren-2-yl)-1H-benzoimidazol-2-yl]-2-aza-bicyclo[2.2.1]heptane-2-carbonyl}-2-methyl-propyl)-carbamic acid methyl ester as a TFA salt (57 mg, 36%). $^1$H-NMR (300 MHz, CD$_3$OD) δ 8.05-7.60 (m, 10H), 5.25 (t, 1H), 4.40-4.05 (m, 3H), 3.95-3.60 (m, 8H), 3.10-2.90 (m 6H), 2.65-2.50 (m, 1H), 2.40-1.70 (m, 11H), 1.05-0.90 (m, 12H); m/z 839.2 (M+H)$^+$.

Example EF

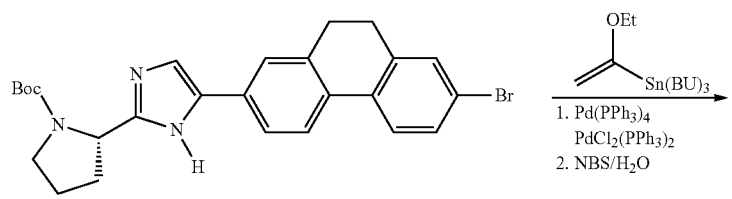

2-[5-(7-Bromo-9,10-dihydro-phenanthren-2-yl)-1H-imidazol-2-yl]-pyrrolidine-1-carboxylic acid tert-butyl ester

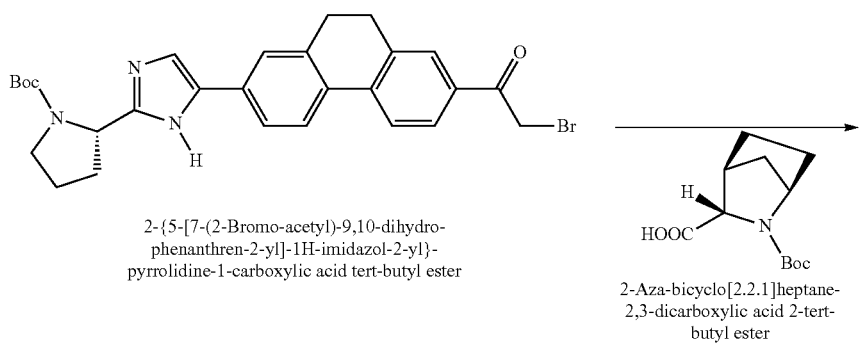

2-{5-[7-(2-Bromo-acetyl)-9,10-dihydro-phenanthren-2-yl]-1H-imidazol-2-yl}-pyrrolidine-1-carboxylic acid tert-butyl ester 2-Aza-bicyclo[2.2.1]heptane-2,3-dicarboxylic acid 2-tert-butyl ester DIE, MeCN

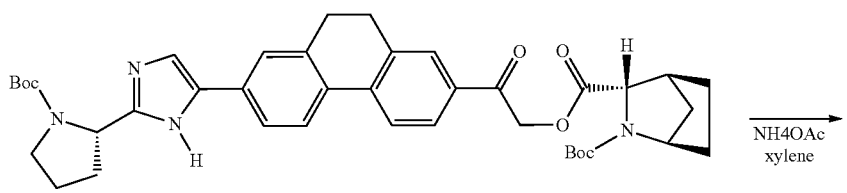

2-Aza-bicyclo[2.2.1]heptane-2,3-dicarboxylic acid 3-(2-{7-[2-(1-tert-butoxycarbonyl-pyrrolidin-2-yl)-3H-imidazol-4-yl]-9,10-dihydro-phenanthren-2-yl}-2-oxo-ethyl) ester 2-tert-butyl ester

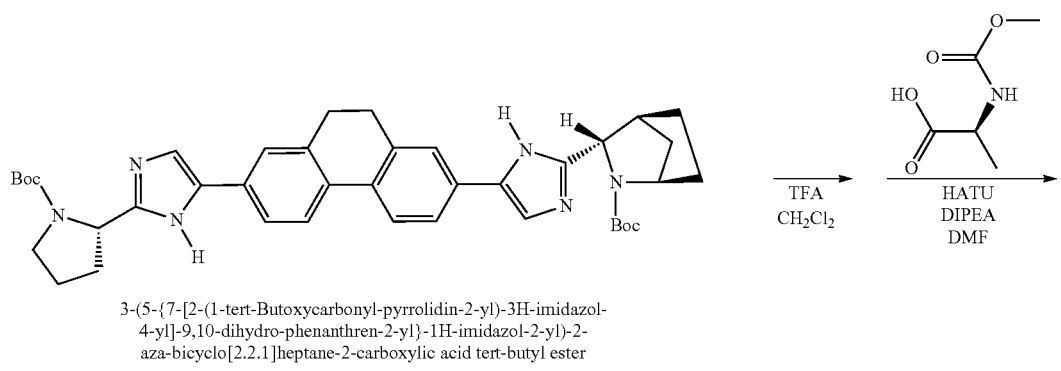

3-(5-{7-[2-(1-tert-Butoxycarbonyl-pyrrolidin-2-yl)-3H-imidazol-4-yl]-9,10-dihydro-phenanthren-2-yl}-1H-imidazol-2-yl)-2-aza-bicyclo[2.2.1]heptane-2-carboxylic acid tert-butyl ester

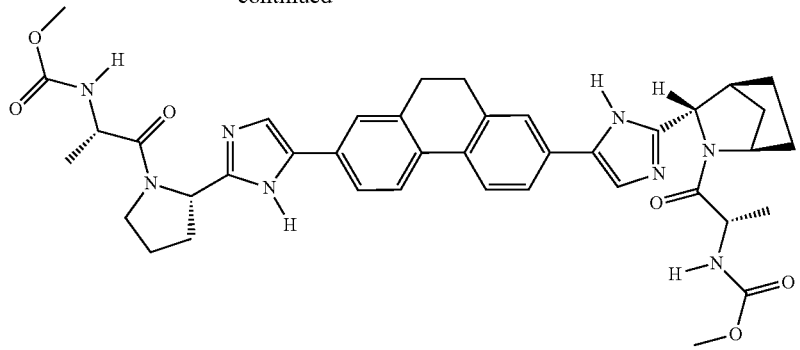

(2-{3-[5-(7-{2-[1-(2-Methoxycarbonylamino-propionyl)-
pyrrolidin-2-yl]-3H-imidazol-4-yl}-9,10-dihydro-phenanthren-
2-yl)-1H-imidazol-2-yl]-2-aza-bicyclo[2.2.1]hept-2-yl}-1-
methyl-2-oxo-ethyl)-carbamic acid methyl ester 2-{5-[7-(2-Bromo-acetyl)-9,10-dihydro-phenan-
thren-2-yl]-1H-imidazol-2-yl}-pyrrolidine-1-car-
boxylic acid tert-butyl ester Pd(Ph$_3$)$_4$ (15 mg, 0.015 mmol) and PdCl$_2$(Ph$_3$)$_2$ (10 mg, 0.015 mmol) were added to a mixture 2-[5-(7-bromo-9,10-dihydro-phenanthren-2-yl)-1H-imidazol-2-yl]-pyrrolidine-1-carboxylic acid tert-butyl ester (180 mg, 0.37 mmol) and tributyl(1-ethoxyvinyl)tin (0.15 mL, 0.44 mL) in 5 mL dioxane. The reaction mixture was flushed with nitrogen, heated at 80° C. for 16 hours, then cooled to ambient temperature. Water (1.5 mL) and NBS (78 mg, 0.44 mmol) was added and the mixture was stirred at room temperature for 40 minutes, then diluted with ethyl acetate (100 mL). Washed with water and brine, dried over Na$_2$SO$_4$, filtered and concentrated in vacuo. The obtained residue was carried on to next step reaction without purification.

2-Aza-bicyclo[2.2.1]heptane-2,3-dicarboxylic acid
3-(2-{7-[2-(1-tert-butoxycarbonyl-pyrrolidin-2-yl)-
3H-imidazol-4-yl]-9,10-dihydro-phenanthren-2-yl}-
2-oxo-ethyl)ester 2-tert-butyl ester A mixture of 2-aza-bicyclo[2.2.1]heptane-2,3-dicarboxylic acid 2-tert-butyl ester (167 mg, 0.69 mmol) and DIPEA (0.11 mL, 0.67 mmol) was added to a solution of 2-{5-[7-(2-bromo-acetyl)-9,10-dihydro-phenanthren-2-yl]-1H-imidazol-2-yl}-pyrrolidine-1-carboxylic acid tert-butyl ester (0.37 mmol, crude) in acetonitrile (5 mL). The mixture was stirred at room temperature for 16 hours, then diluted with ethyl acetate (100 mL). The organic layer was washed with NaHCO$_3$ solution and water, dried over Na$_2$SO$_4$, filtered and concentrated in vacuo. The obtained residue was purified by flash chromatography to provide the desired product 2-aza-bicyclo[2.2.1]heptane-2,3-dicarboxylic acid 3-(2-{7-[2-(1-tert-butoxycarbonyl-pyrrolidin-2-yl)-3H-imidazol-4-yl]-9,10-dihydro-phenanthren-2-yl}-2-oxo-ethyl)ester 2-tert-butyl ester as a brown solid (132 mg, 51% over two steps). m/z 697.2 (M+H)$^+$.

3-(5-{7-[2-(1-tert-Butoxycarbonyl-pyrrolidin-2-yl)-
3H-imidazol-4-yl]-9,10-dihydro-phenanthren-2-yl}-
1H-imidazol-2-yl)-2-aza-bicyclo[2.2.1]heptane-2-
carboxylic acid tert-butyl ester A mixture of 2-aza-bicyclo[2.2.1]heptane-2,3-dicarboxylic acid 3-(2-{7-[2-(1-tert-butoxycarbonyl-pyrrolidin-2-yl)-3H-imidazol-4-yl]-9,10-dihydro-phenanthren-2-yl}-2-oxo-ethyl)ester 2-tert-butyl ester (132 mg, 0.19 mmol) and ammonium acetate (292 mg, 3.8 mmol) in xylene (10 mL) was heated in a sealed tube at 140° C. for 1.5 hours under microwave condition. The volatile component was removed in vacuo, and the residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product 3-(5-{7-[2-(1-tert-Butoxycarbonyl-pyrrolidin-2-yl)-3H-imidazol-4-yl]-9,10-dihydro-phenanthren-2-yl}-1H-imidazol-2-yl)-2-aza-bicyclo[2.2.1]heptane-2-carboxylic acid tert-butyl ester as a white solid (36 mg, 28%). m/z 677.4 (M+H)$^+$.

(2-{3-[5-(7-{2-[1-(2-Methoxycarbonylamino-propio-
nyl)-pyrrolidin-2-yl]-3H-imidazol-4-yl}-9,10-dihy-
dro-phenanthren-2-yl)-1H-imidazol-2-yl]-2-aza-
bicyclo[2.2.1]hept-2-yl}-1-methyl-2-oxo-ethyl)-
carbamic acid methyl ester To a solution of 3-(5-{7-[2-(1-tert-Butoxycarbonyl-pyrrolidin-2-yl)-3H-imidazol-4-yl]-9,10-dihydro-phenanthren-2-yl}-1H-imidazol-2-yl)-2-aza-bicyclo[2.2.1]heptane-2-carboxylic acid tert-butyl ester (36 mg, 0.053 mmol) in dichloromethane (6 mL) was added trifluoroacetic acid (2 mL, excess). The mixture was stirred for 2 hours at ambient temperature and concentrated under reduced pressure. The residue was treated with ether to remove excess trifluoroacetic acid. The obtained white solid was dissolved in DMF (5 mL), to the solution was added 2-methoxycarbonylamino-propionic acid (17 mg, 0.12 mmol), HATU (50 mg, 0.13 mmol) and N,N-diisopropylethylamine (0.09 mL, 0.53 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (2-{3-[5-(7-{2-[1-(2-Methoxycarbonylamino-propionyl)-pyrrolidin-2-yl]-3H-imidazol-4-yl}-9,10-dihydro-phenanthren-2-yl)-1H-imidazol-2-yl]-2-aza-bicyclo[2.2.1]hept-2-yl}-1-methyl-2-oxo-ethyl)-carbamic acid methyl ester as a TFA salt (5.5 mg, 14%). $^1$H-NMR (300 MHz, CD$_3$OD) δ 8.05-7.60 (m, 8H), 5.35-5.25 (m, 1H), 4.65-4.40 (m, 3H), 4.05-3.80 (m, 2H), 3.75-3.50 (m, 7H), 3.00 (s, 4H), 2.87 (s, 1H), 2.65 (m, 1H), 2.30-1.70 (m, 9H), 1.45-1.20 (m, 6H); m/z 735.3 (M+H)$^+$.

Example EG

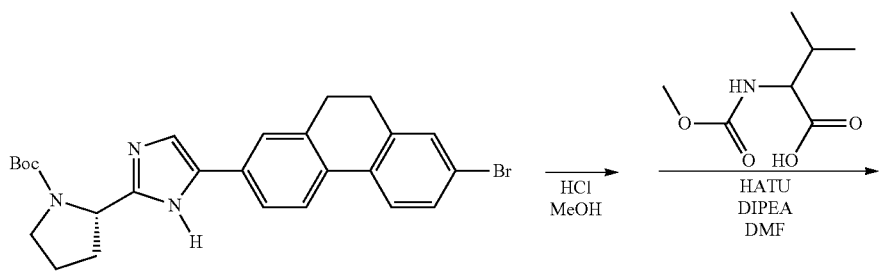

2-[5-(7-Bromo-9,10-dihydro-
phenanthren-2-yl)-1H-imidazol-
2-yl]-pyrrolidine-1-carboxylic
acid tert-butyl ester

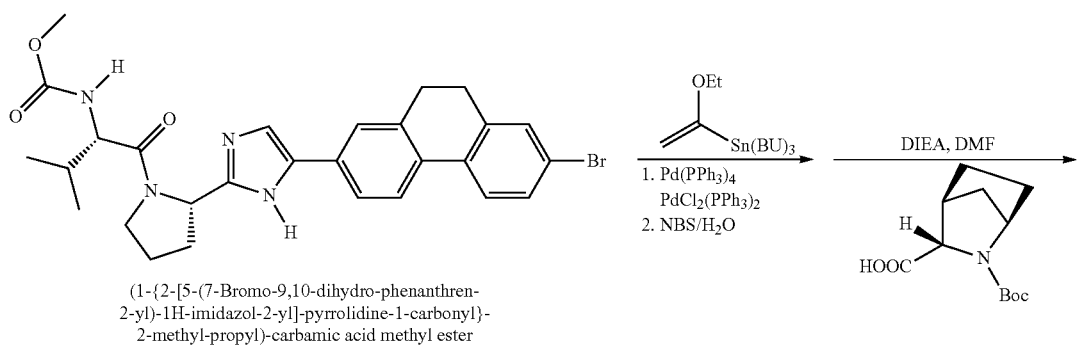

(1-{2-[5-(7-Bromo-9,10-dihydro-phenanthren-
2-yl)-1H-imidazol-2-yl]-pyrrolidine-1-carbonyl}-
2-methyl-propyl)-carbamic acid methyl ester

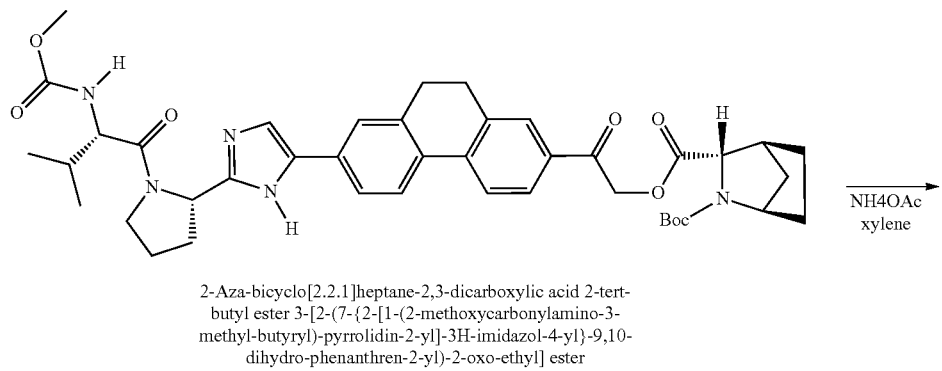

2-Aza-bicyclo[2.2.1]heptane-2,3-dicarboxylic acid 2-tert-
butyl ester 3-[2-(7-{2-[1-(2-methoxycarbonylamino-3-
methyl-butyryl)-pyrrolidin-2-yl]-3H-imidazol-4-yl}-9,10-
dihydro-phenanthren-2-yl)-2-oxo-ethyl] ester

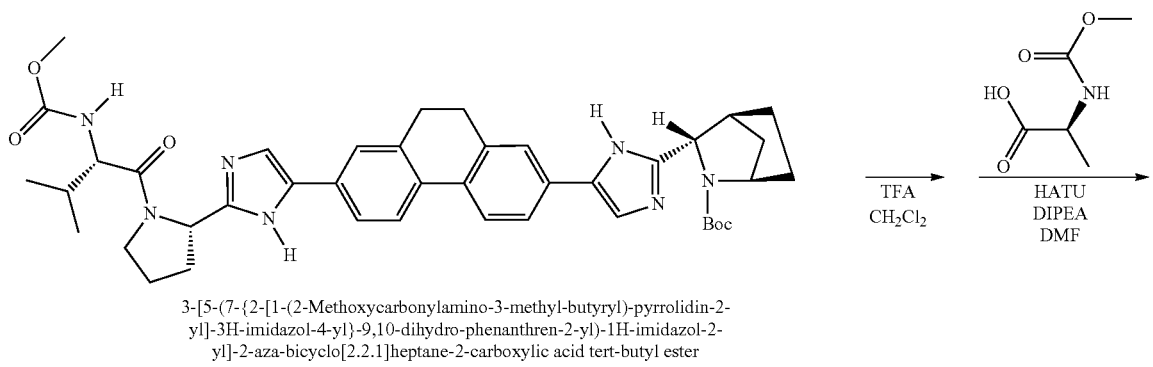

3-[5-(7-{2-[1-(2-Methoxycarbonylamino-3-methyl-butyryl)-pyrrolidin-2-
yl]-3H-imidazol-4-yl}-9,10-dihydro-phenanthren-2-yl)-1H-imidazol-2-
yl]-2-aza-bicyclo[2.2.1]heptane-2-carboxylic acid tert-butyl ester

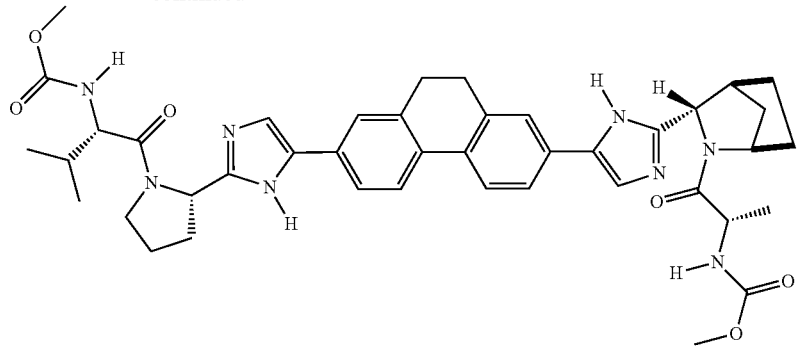

(1-{2-[5-(7-{2-[2-(2-Methoxycarbonylamino-propionyl)-2-aza-bicyclo[2.2.1]hept-3-yl]-3H-imidazol-4-yl}-9,10-dihydro-phenanthren-2-yl)-1H-imidazol-2-yl]-pyrrolidine-1-carbonyl}-2-methyl-propyl)-carbamic acid methyl ester

(1-{2-[5-(7-Bromo-9,10-dihydro-phenanthren-2-yl)-1H-imidazol-2-yl]-pyrrolidine-1-carbonyl}-2-methyl-propyl)-carbamic acid methyl ester To a solution of 2-[5-(7-bromo-9,10-dihydro-phenanthren-2-yl)-1H-imidazol-2-yl]-pyrrolidine-1-carboxylic acid tert-butyl ester (187 mg, 0.38 mmol) in methanol (5 mL) was added 4.0 M solution of HCl in dioxane (2 mL, excess). The mixture was stirred for 3 hours at 50° C. and concentrated under reduced pressure. The residue was treated with ether to remove excess HCl. The obtained white solid was dissolved in DMF (5 mL), to the solution was added 2-methoxycarbonylamino-3-methyl-butyric acid (70 mg, 0.40 mmol), HATU (173 mg, 0.46 mmol) and N,N-diisopropylethylamine (0.66 mL, 3.8 mmol). The mixture was stirred at ambient for 2 hours, and then the volatile component was removed in vacuo. The residue was dissolved in ethyl acetate (100 mL), washed with 1 N NaOH solution, water and brine, dried over $Na_2SO_4$, filtered and concentrated in vacuo. The obtained residue was purified by flash chromatography to provide the desired product (1-{2-[5-(7-bromo-9,10-dihydro-phenanthren-2-yl)-1H-imidazol-2-yl]-pyrrolidine-1-carbonyl}-2-methyl-propyl)-carbamic acid methyl ester as an oil (200 mg, 95%). m/z 551.2, 553.2 (M+H)$^+$.

2-Aza-bicyclo[2.2.1]heptane-2,3-dicarboxylic acid 2-tert-butyl ester 3-[2-(7-{2-[1-(2-methoxycarbonylamino-3-methyl-butyryl)-pyrrolidin-2-yl]-3H-imidazol-4-yl}-9,10-dihydro-phenanthren-2-yl)-2-oxo-ethyl]ester Pd(Ph$_3$)$_4$ (15 mg, 0.015 mmol) and PdCl$_2$(Ph$_3$)$_2$ (10 mg, 0.015 mmol) were added to a mixture of (1-{2-[5-(7-bromo-9,10-dihydro-phenanthren-2-yl)-1H-imidazol-2-yl]-pyrrolidine-1-carbonyl}-2-methyl-propyl)-carbamic acid methyl ester (200 mg, 0.37 mmol) and tributyl(1-ethoxyvinyl)tin (0.15 mL, 0.44 mL) in 5 mL dioxane. The reaction mixture was flushed with nitrogen, heated at 80° C. for 16 hours, then cooled to ambient temperature. Water (1.5 mL) and NBS (78 mg, 0.44 mmol) was added and the mixture was stirred at room temperature for 40 minutes, then diluted with ethyl acetate (100 mL). Washed with water and brine, dried over $Na_2SO_4$, filtered and concentrated in vacuo. The obtained residue was dissolved in acetonitrile (3 mL). To it was added a solution of 2-aza-bicyclo[2.2.1]heptane-2,3-dicarboxylic acid 2-tert-butyl ester (167 mg, 0.69 mmol) and DIPEA (0.11 mL, 0.67 mmol) in 2 mL acetonitrile. The mixture was stirred at room temperature for 16 hours, then diluted with ethyl acetate (100 mL). The organic layer was washed with NaHCO$_3$ solution and water, dried over Na$_2$SO$_4$, filtered and concentrated in vacuo. The obtained residue was purified by flash chromatography to provide the desired product 2-Aza-bicyclo[2.2.1]heptane-2,3-dicarboxylic acid 2-tert-butyl ester 3-[2-(7-{2-[1-(2-methoxycarbonylamino-3-methyl-butyryl)-pyrrolidin-2-yl]-3H-imidazol-4-yl}-9,10-dihydro-phenanthren-2-yl)-2-oxo-ethyl]ester as a brown oil (130 mg, 47% over two steps). m/z 754.3 (M+H)$^+$.

3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carboxylic acid tert-butyl ester A mixture of 2-Aza-bicyclo[2.2.1]heptane-2,3-dicarboxylic acid 2-tert-butyl ester 3-[2-(7-{2-[1-(2-methoxycarbonylamino-3-methyl-butyryl)-pyrrolidin-2-yl]-3H-imidazol-4-yl}-9,10-dihydro-phenanthren-2-yl)-2-oxo-ethyl]ester (130 mg, 0.17 mmol) and ammonium acetate (292 mg, 3.8 mmol) in xylene (10 mL) was heated in a sealed tube at 140° C. for 1.5 hours under microwave condition. The volatile component was removed in vacuo, and the residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product 3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carboxylic acid tert-butyl ester as a white solid (38 mg, 28%). m/z 734.4 (M+H)$^+$.

(1-{2-[5-(7-{2-[(2-(2-Methoxycarbonylamino-propionyl)-2-aza-bicyclo[2.2.1]hept-3-yl]-3H-imidazol-4-yl}-9,10-dihydro-phenanthren-2-yl)-1H-imidazol-2-yl]-pyrrolidine-1-carbonyl}-2-methyl-propyl)-carbamic acid methyl ester To a solution of 3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carboxylic acid tert-butyl ester (38 mg, 0.052 mmol) in dichloromethane (6 mL) was added trifluoroacetic acid (2 mL, excess). The mixture was stirred for 2 hours at ambient temperature and concentrated under reduced pressure. The residue was treated with ether to remove excess trifluoroacetic acid. The obtained white solid was dissolved in DMF (5 mL), to the solution was added 2-methoxycarbonylamino-propionic acid (9 mg, 0.06 mmol), HATU (30 mg, 0.08 mmol) and N,N-diisopropylethylamine (0.09 mL, 0.53 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (1-{2-[5-(7-{2-[2-(2-Methoxycarbonylamino-propionyl)-2-aza-bicyclo[2.2.1]hept-3-yl]-3H-imidazol-4-yl}-9,10-dihydro-phenanthren-2-yl)-1H-imidazol-2-yl]-pyrrolidine-1-carbonyl}-2-methyl-propyl)-carbamic acid methyl ester as a TFA salt (15 mg, 39%). $^1$H-NMR (300 MHz, CD$_3$OD) δ 8.10-7.60 (m, 8H), 5.35-5.25 (m, 1H), 4.70-4.45 (m, 3H), 4.30-3.80 (m, 3H), 3.67 (s, 6H), 2.70-1.60 (m, 12H), 1.41 (d, 3H), 1.05-0.80 (m, 6H); m/z 763.3 (M+H)$^+$.

Example EH

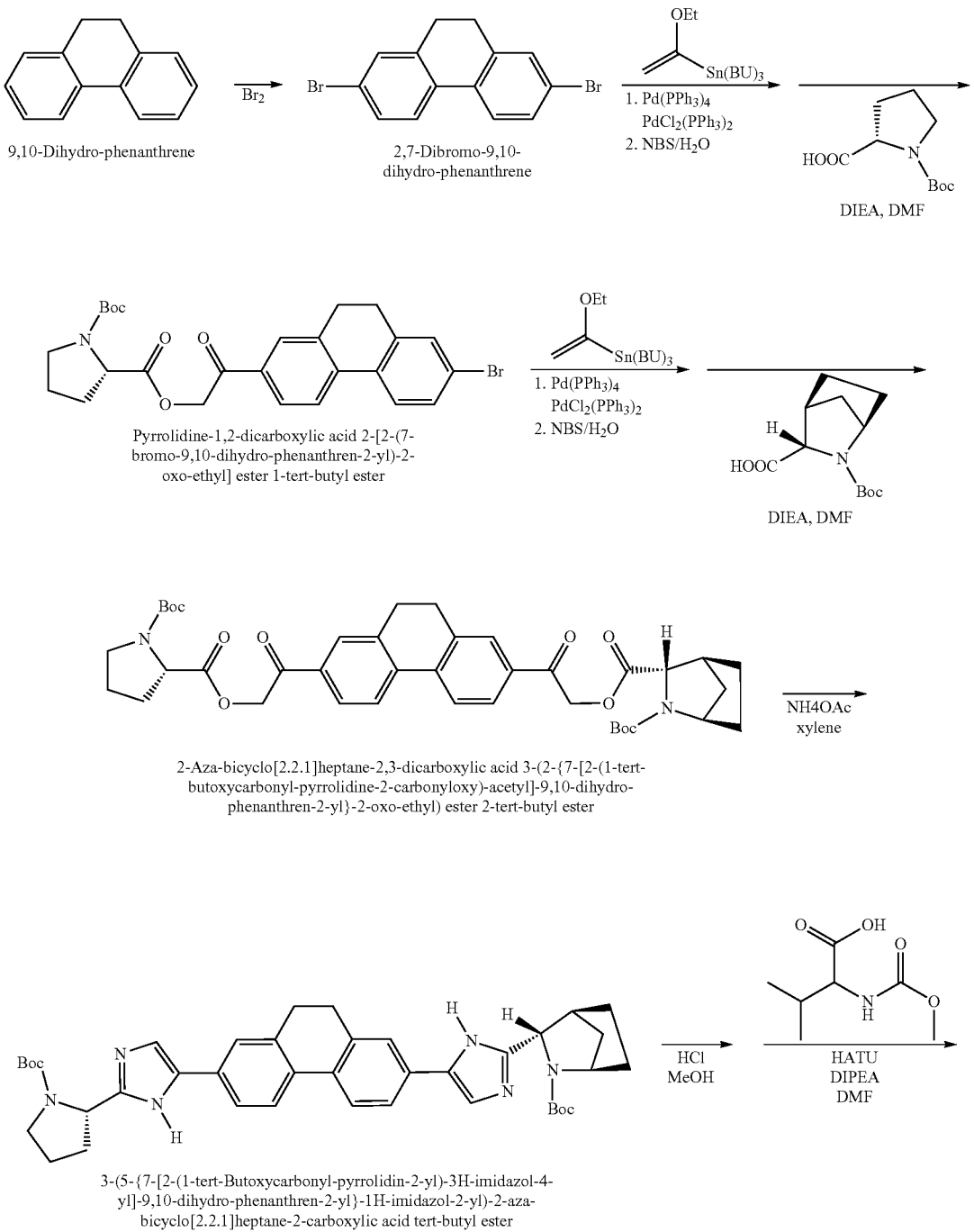

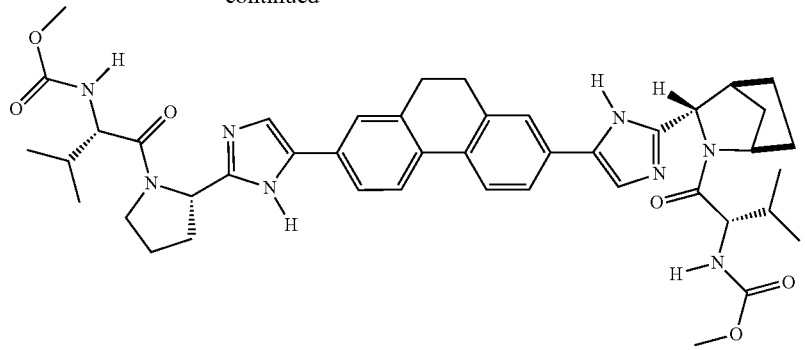

(1-{3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carbonyl}-2-methyl-propyl)-carbamic acid methyl ester 2,7-Dibromo-9,10-dihydro-phenanthrene Bromine (6.13 mL, 119.3 mmol) was added slowly to a solution of 9,10-dihydro-phenanthrene (10 g, 55.5 mmol) in trimethylphosphate (100 mL). The mixture was stirred at room temperature for 18 hours and concentrated in vacuo. The residue was recrystallized from chloroform to give product 2,7-Dibromo-9,10-dihydro-phenanthrene as a white crystal (9.45 g, 51%).

Pyrrolidine-1,2-dicarboxylic acid 2-[2-(7-bromo-9,10-dihydro-phenanthren-2-yl)-2-oxo-ethyl]ester 1-tert-butyl ester Pd(Ph$_3$)$_4$ (347 mg, 0.3 mmol) and PdCl$_2$(Ph$_3$)$_2$ (210 mg, 0.3 mmol) were added to a mixture 2,7-dibromo-9,10-dihydro-phenanthrene (2.5 g, 7.4 mmol) and tributyl(1-ethoxyvinyl)tin (2.5 mL, 7.4 mL) in 70 mL dioxane. The reaction mixture was flushed with nitrogen, heated at 80° C. for 16 hours, then cooled to ambient temperature. Water (20 mL) and NBS (1.39 g, 7.8 mmol) were added and the mixture was stirred at room temperature for 40 minutes, then diluted with ethyl acetate (300 mL). Washed with water and brine, dried over Na$_2$SO$_4$, filtered and concentrated in vacuo. The obtained residue was suspended in acetonitrile (70 mL). To it was added a solution of pyrrolidine-1,2-dicarboxylic acid 1-tert-butyl ester (3.2 g, 14.9 mmol) and DIPEA (2.4 mL, 14.1 mmol) in 20 mL acetonitrile. The mixture was stirred at room temperature for 16 hours, then diluted with ethyl acetate (300 mL). The organic layer was washed with NaHCO$_3$ solution and water, dried over Na$_2$SO$_4$, filtered and concentrated in vacuo. The obtained residue was purified by flash chromatography to provide the desired product pyrrolidine-1,2-dicarboxylic acid 2-[2-(7-bromo-9,10-dihydro-phenanthren-2-yl)-2-oxo-ethyl]ester 1-tert-butyl ester as a white solid (1.76 g, 46% over two steps). m/z 514.2, 516.2 (M+H)$^+$.

2-Aza-bicyclo[2.2.1]heptane-2,3-dicarboxylic acid 3-(2-{7-[2-(1-tert-butoxycarbonyl-pyrrolidine-2-carbonyloxy)-acetyl]-9,10-dihydro-phenanthren-2-yl}-2-oxo-ethyl)ester 2-tert-butyl ester Pd(Ph$_3$)$_4$ (37 mg, 0.03 mmol) and PdCl$_2$(Ph$_3$)$_2$ (22 mg, 0.03 mmol) were added to a mixture of pyrrolidine-1,2-dicarboxylic acid 2-[2-(7-bromo-9,10-dihydro-phenanthren-2-yl)-2-oxo-ethyl]ester 1-tert-butyl ester (410 mg, 0.8 mmol) and tributyl(1-ethoxyvinyl)tin (0.32 mL, 0.96 mmol) in 8 mL dioxane. The reaction mixture was flushed with nitrogen, heated at 80° C. for 16 hours, then cooled to ambient temperature. Water (2 mL) and NBS (171 mg, 0.96 mmol) were added and the mixture was stirred at room temperature for 40 minutes, then diluted with ethyl acetate (100 mL). Washed with water and brine, dried over Na$_2$SO$_4$, filtered and concentrated in vacuo. Half of the obtained residue was suspended in acetonitrile (5 mL) To it was added a solution of 2-aza-bicyclo[2.2.1]heptane-2,3-dicarboxylic acid 2-tert-butyl ester (100 mg, 0.41 mmol) and DIPEA (0.068 mL, 0.39 mmol) in 2 mL acetonitrile. The mixture was stirred at room temperature for 16 hours, then diluted with ethyl acetate (100 mL). The organic layer was washed with NaHCO$_3$ solution and water, dried over Na$_2$SO$_4$, filtered and concentrated in vacuo. The obtained residue was purified by flash chromatography to provide the desired product 2-aza-bicyclo[2.2.1]heptane-2,3-dicarboxylic acid 3-(2-{7-[2-(1-tert-butoxycarbonyl-pyrrolidine-2-carbonyloxy)-acetyl]-9,10-dihydro-phenanthren-2-yl}-2-oxo-ethyl)ester 2-tert-butyl ester as a white solid (171 mg, 60% over two steps). m/z 717.2 (M+H)$^+$.

3-(5-{7-[2-(1-tert-Butoxycarbonyl-pyrrolidin-2-yl)-3H-imidazol-4-yl]-9,10-dihydro-phenanthren-2-yl}-1H-imidazol-2-yl)-2-aza-bicyclo[2.2.1]heptane-2-carboxylic acid tert-butyl ester A mixture of 2-aza-bicyclo[2.2.1]heptane-2,3-dicarboxylic acid 3-(2-{7-[2-(1-tert-butoxycarbonyl-pyrrolidine-2-carbonyloxy)-acetyl]-9,10-dihydro-phenanthren-2-yl}-2-oxo-ethyl) ester 2-tert-butyl ester (171 mg, 0.24 mmol) and ammonium acetate (800 mg, 10.2 mmol) in xylene (5 mL) was heated in a sealed tube at 140° C. for 1.5 hours under microwave condition. The volatile component was removed in vacuo, and the residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product of 3-(5-{7-[2-(1-tert-butoxycarbonyl-pyrrolidin-2-yl)-3H-imidazol-4-yl]-9,10-dihydro-phenanthren-2-yl}-1H-imidazol-2-yl)-2-aza-bicyclo[2.2.1]heptane-2-carboxylic acid tert-butyl ester as a white solid (100 mg, 62%). m/z 677.9 (M+H)$^+$.

(1-{3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carbonyl}-2-methyl-propyl)-carbamic acid methyl ester To a solution of 3-(5-{7-[2-(1-tert-butoxycarbonyl-pyrrolidin-2-yl)-3H-imidazol-4-yl]-9,10-dihydro-phenanthren-2- yl}-1H-imidazol-2-yl)-2-aza-bicyclo[2.2.1]heptane-2-carboxylic acid tert-butyl ester (100 mg, 0.15 mmol) in methanol (5 mL) was added 4.0 M solution of HCl in dioxane (2 mL, excess). The mixture was stirred for 3 hours at 50° C. and concentrated under reduced pressure. The residue was treated with ether to remove excess HCl. The obtained white solid was dissolved in DMF (5 mL), to the solution was added 2-methoxycarbonylamino-3-methyl-butyric acid (54 mg, 0.31 mmol), HATU (141 mg, 0.37 mmol) and N,N-diisopropylethylamine (0.2 mL, 1.2 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (1-{3-[5-(7-{2-[1-(2-Methoxycarbonylamino-3-methyl-butyryl)-pyrrolidin-2-yl]-3H-imidazol-4-yl}-9,10-dihydro-phenanthren-2-yl)-1H-imidazol-2-yl]-2-aza-bicyclo[2.2.1]heptane-2-carbonyl}-2-methyl-propyl)-carbamic acid methyl ester as TFA salt (67 mg, 57%). $^1$H-NMR (300 MHz, CD$_3$OD) 8.05-7.65 (m, 8H), 5.35-5.20 (m, 1H), 4.40-4.05 (m, 3H), 3.95-3.80 (m, 1H), 3.67 (d, 6H), 3.05-2.80 (m, 5H), 2.70-2.50 (m, 1H), 2.40-1.60 (m, 13H), 1.10-0.85 (m, 12H); m/z 791.3 (M+H)$^+$.

Example EI

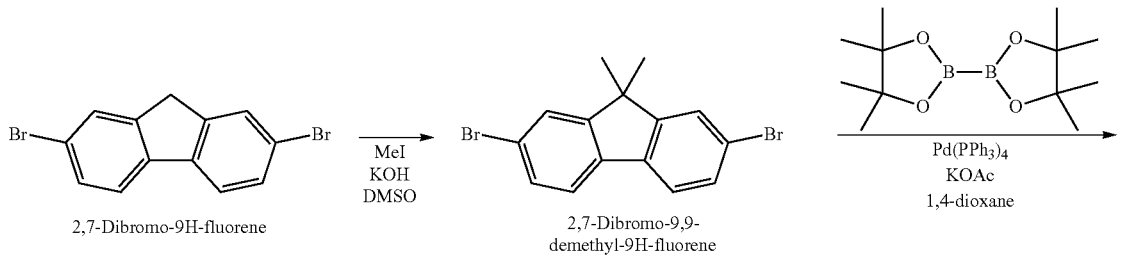

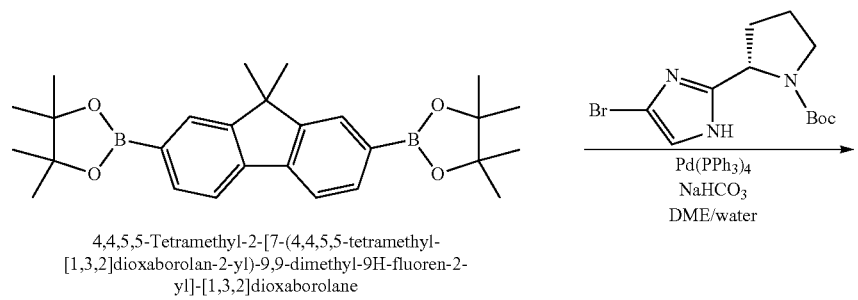

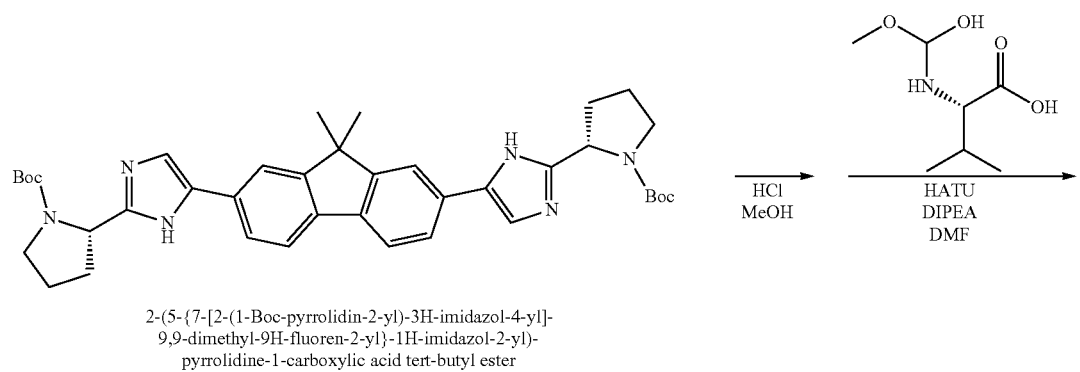

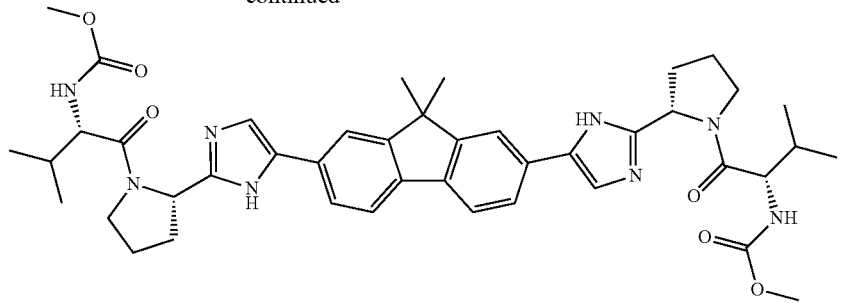

(1-{2-[5-(7-{2-[1-(2-Methoxycarbonylamino-3-methyl-
butyryl)-pyrrolidin-2-yl]-3H-imidazol-4-yl}-9,9-dimethyl-9H-
fluoren-2-yl)-1H-imidazol-2-yl]-pyrrolidine-1-carbonyl}-2-
methyl-propyl)-carbamic acid methyl ester 2,7-Dibromo-9,9-dimethyl-9H-fluorene To a stirred solution of 2,7-dibromo-9H-fluorene (1.0 g, 3.1 mmol), KI (50 mg, 0.3 mmol) and KOH (750 mg, 13.3 mmol) in DMSO was added methyl iodide (0.42 mL, 6.8 mmol). The mixture was stirred at room temperature for 16 hours, then diluted with ethyl acetate (100 mL). The organic layer was washed with water and brine, dried over Na$_2$SO$_4$, filtered and concentrated in vacuo. The obtained residue was purified by flash chromatography to provide the desired product 2,7-Dibromo-9,9-dimethyl-9H-fluorene as a white solid (1.1 g, 100%).

4,4,5,5-Tetramethyl-2-[7-(4,4,5,5-tetramethyl-[1,3,2] dioxaborolan-2-yl)-9,9-dimethyl-9H-fluoren-2-yl]-[1,3,2]dioxaborolane Pd(PPh$_3$)$_4$ (347 mg, 0.3 mmol) was added to a flask containing a mixture of 2,7-dibromo-9,9-dimethyl-9H-fluorene (1.0 g, 2.9 mmol), bis(pinacolato)diboron (2.9 g, 11.6 mmol), potassium acetate (1.4 g, 14.5 mmol) and 1,4-dioxane (30 mL). The reaction mixture was flushed with nitrogen, heated at 80° C. for 16 hours, then the volatile component was removed in vacuo. The residue was dissolved in ethyl acetate (300 mL), washed with water and brine, dried over Na$_2$SO$_4$, filtered and concentrated in vacuo. The obtained residue was purified by flash chromatography to provide the desired product 4,4,5,5-Tetramethyl-2-[7-(4,4,5,5-tetramethyl-[1,3,2]dioxaborolan-2-yl)-9,9-dimethyl-9H-fluoren-2-yl]-[1,3,2]dioxaborolane as a white solid (0.8 g, 62%).

2-(5-{7-[2-(1-Boc-pyrrolidin-2-yl)-3H-imidazol-4-yl]-9,9-dimethyl-9H-fluoren-2-yl}-1H-imidazol-2-yl)-pyrrolidine-1-carboxylic acid tert-butyl ester Pd(Ph$_3$)$_4$ (55 mg, 0.05 mmol) was added to a mixture 4,4,5,5-Tetramethyl-2-[7-(4,4,5,5-tetramethyl-[1,3,2]dioxaborolan-2-yl)-9,9-dimethyl-9H-fluoren-2-yl]-[1,3,2]dioxaborolane (205 mg, 0.48 mmol), 2-(4-bromo-1H-imidazol-2-yl)-pyrrolidine-1-carboxylic acid tert-butyl ester (309 mg, 0.98 mmol), NaHCO$_3$ (282 mg, 3.4 mmol) in 1,2-dimethoxyethane (8 mL) and water (1 mL). The reaction mixture was flushed with nitrogen, heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by HPLC to provide the desired product 2-(5-{7-[2-(1-Boc-pyrrolidin-2-yl)-3H-imidazol-4-yl]-9,9-dimethyl-9H-fluoren-2-yl}-1H-imidazol-2-yl)-pyrrolidine-1-carboxylic acid tert-butyl ester as a TFA salt (45 mg, 14%). m/z 665.4 (M+H)$^+$.

(1-{2-[5-(7-{2-[1-(2-Methoxycarbonylamino-3-methyl-butyryl)-pyrrolidin-2-yl]-3H-imidazol-4-yl}-9, 9-dimethyl-9H-fluoren-2-yl)-1H-imidazol-2-yl]-pyrrolidine-1-carbonyl}-2-methyl-propyl)-carbamic acid methyl ester To a solution of 2-(5-{7-[2-(1-Boc-pyrrolidin-2-yl)-3H-imidazol-4-yl]-9,9-dimethyl-9H-fluoren-2-yl}-1H-imidazol-2-yl)-pyrrolidine-1-carboxylic acid tert-butyl ester (45 mg, 0.07 mmol) in methanol (5 mL) was added 4.0 M solution of HCl in dioxane (1 mL, excess). The mixture was stirred for 3 hours at 50° C. and concentrated under reduced pressure. The residue was treated with ether to remove excess HCl. The obtained white solid was dissolved in DMF (5 mL), to the solution was added 2-methoxycarbonylamino-3-methyl-butyric acid (25 mg, 0.14 mmol), HATU (65 mg, 0.17 mmol) and N,N-diisopropylethylamine (0.09 mL, 0.54 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (1-{2-[5-(7-{2-[1-(2-Methoxycarbonylamino-3-methyl-butyryl)-pyrrolidin-2-yl]-3H-imidazol-4-yl}-9,9-dimethyl-9H-fluoren-2-yl)-1H-imidazol-2-yl]-pyrrolidine-1-carbonyl}-2-methyl-propyl)-carbamic acid methyl ester as TFA salt (15 mg, 28%). $^1$H-NMR (300 MHz, CD$_3$OD) δ 8.05-7.70 (m, 8H), 5.35-5.20 (m, 2H), 4.30-3.80 (m, 6H), 3.67 (s, 6H), 2.65-2.00 (m, 10H), 1.61 (s, 6H), 1.05-0.85 (m, 12H); m/z 779.4 (M+H)$^+$.

Example EJ

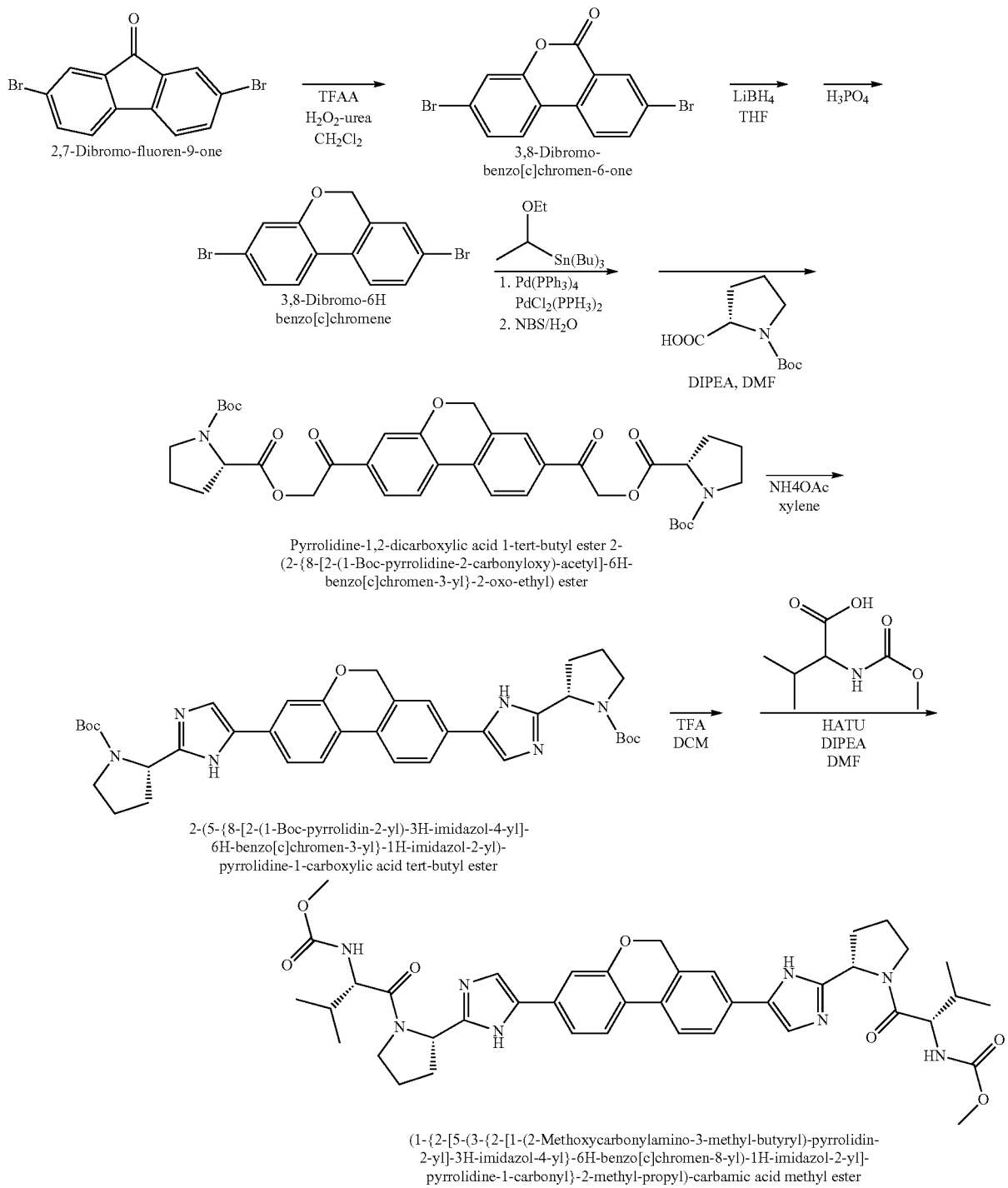

3,8-Dibromo-benzo[c]chromen-6-one

A solution of TFAA (2.1 mL, 3.15 mmol) in dichloromethane (5 mL) was added dropwise to a suspension of 2,7-dibromo-fluoren-9-one (3.3 g, 10 mmol) and $H_2O_2$-urea (1.4 g, 15 mL) in dichloromethane (50 mL). The mixture was stirred at room temperature for 48 hours, a second portion of $H_2O_2$-urea was added, and stirring was continued at room temperature for a further 72 hours. The mixture was filtered, the organic phase was extracted with water (50 mL), and dried over $Na_2SO_4$. After removal of solvent, the residue was heated with 2N NaOH at 80° C. for 10 minutes, filtered, the cooled filtrate extracted with ether. The aqueous phase was acidified with 2N HCl and extracted with ethyl acetate (200 mL). HCl (2 mL 4M solution) was added to the ethyl acetate and heated for 2 hours. The solvent was removed under vacuum, the residue was recrystallized from ethyl acetate/ethanol to give the final product 3,8-Dibromo-benzo[c]chromen-6-one as a white solid (1.5 g, 40%).

3,8-Dibromo-6H-benzo[c]chromene

To a solution of 3,8-dibromo-benzo[c]chromen-6-one (650 mg, 1.85 mmol) in THF (20 mL) was added 2 M solution of LiBH$_4$ in THF (3.7 mL, 7.4 mmol). The mixture was stirred for 3 hours at room temperature. Quenched slowly with ammonium chloride solution. The mixture was extracted with ethyl acetate, dried over Na$_2$SO$_4$, filtered and concentrated in vacuo. The obtained residue was suspended in 85% phosphoric acid (20 mL) and heated at 160° C. for 4 h. The mixture was extracted with ethyl acetate, washed with water, dried over Na$_2$SO$_4$, filtered and concentrated in vacuo. The obtained residue was purified by flash chromatography to provide the desired product 3,8-Dibromo-6H-benzo[c]chromene as a white solid (539 mg, 86%).

Pyrrolidine-1,2-dicarboxylic acid 1-tert-butyl ester 2-(2-{8-[2-(1-Boc-pyrrolidine-2-carbonyloxy)-acetyl]-6H-benzo[c]chromen-3-yl}-2-oxo-ethyl)ester Pd(PPh$_3$)$_4$ (74 mg, 0.064 mmol) and PdCl$_2$(Ph$_3$)$_2$ (45 mg, 0.064 mmol) were added to a mixture 3,8-dibromo-6H-benzo[c]chromene (539 mg, 1.6 mmol) and tributyl(1-ethoxyvinyl)tin (1.2 mL, 3.5 mL) in 20 mL dioxane. The reaction mixture was flushed with nitrogen, heated at 80° C. for 16 hours, then cooled to ambient temperature. Water (7 mL) and NBS (623 mg, 3.5 mmol) were added and the mixture was stirred at room temperature for 40 minutes, then diluted with ethyl acetate (300 mL). The solid was filtered and kept separately. The ethyl acetate layer was washed with water and brine, dried over Na$_2$SO$_4$, filtered and concentrated in vacuo. The obtained residue combine with the solid collected before was suspended in acetonitrile (20 mL) and DMF (10 mL). To it was added a solution of pyrrolidine-1,2-dicarboxylic acid 1-tert-butyl ester (1.6 g, 7.4 mmol) and DIPEA (1.2 mL, 7.1 mmol) in 5 mL acetonitrile. The mixture was stirred at room temperature for 16 hours, then diluted with ethyl acetate (300 mL). The organic layer was washed with NaHCO$_3$ solution and water, dried over Na$_2$SO$_4$, filtered and concentrated in vacuo. The obtained residue was purified by flash chromatography to provide the desired product Pyrrolidine-1,2-dicarboxylic acid 1-tert-butyl ester 2-(2-{8-[2-(1-Boc-pyrrolidine-2-carbonyloxy)-acetyl]-6H-benzo[c]chromen-3-yl}-2-oxo-ethyl)ester as a white solid (602 mg, 54% over two steps). m/z 715.2 (M+Na)$^+$.

2-(5-{8-[2-(1-Boc-pyrrolidin-2-yl)-3H-imidazol-4-yl]-6H-benzo[c]chromen-3-yl}-1H-imidazol-2-yl)-pyrrolidine-1-carboxylic acid tert-butyl ester A mixture of pyrrolidine-1,2-dicarboxylic acid 1-tert-butyl ester 2-(2-{8-[2-(1-Boc-pyrrolidine-2-carbonyloxy)-acetyl]-6H-benzo[c]chromen-3-yl}-2-oxo-ethyl) ester (168 mg, 0.24 mmol) and ammonium acetate (374 mg, 4.8 mmol) in xylene (10 mL) was heated in a sealed tube at 140° C. for 1.5 hours under microwave condition. The volatile component was removed in vacuo, and the residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product 2-(5-{8-[2-(1-Boc-pyrrolidin-2-yl)-3H-imidazol-4-yl]-6H-benzo[c]chromen-3-yl}-1H-imidazol-2-yl)-pyrrolidine-1-carboxylic acid tert-butyl ester as a white solid (100 mg, 64%). m/z 653.4 (M+H)$^+$.

(1-{2-[5-(3-{2-[1-(2-Methoxycarbonylamino-3-methyl-butyryl)-pyrrolidin-2-yl]-3H-imidazol-4-yl}-6H-benzo[c]chromen-8-yl)-1H-imidazol-2-yl]-pyrrolidine-1-carbonyl}-2-methyl-propyl)-carbamic acid methyl ester To a solution of 2-(5-{8-[2-(1-Boc-pyrrolidin-2-yl)-3H-imidazol-4-yl]-6H-benzo[c]chromen-3-yl}-1H-imidazol-2-yl)-pyrrolidine-1-carboxylic acid tert-butyl ester (300 mg, 0.46 mmol) in dichloromethane (10 mL) was added trifluoroacetic acid (2.5 mL, excess). The mixture was stirred for 2 hours at ambient temperature and concentrated under reduced pressure. The residue was treated with ether to remove excess trifluoroacetic acid. The obtained white solid was dissolved in DMF (10 mL), to the solution was added 2-methoxycarbonylamino-3-methyl-butyric acid (161 mg, 0.92 mmol), HATU (437 mg, 1.2 mmol) and N,N-diisopropylethylamine (0.64 mL, 3.7 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product (1-{2-[5-(3-{2-[1-(2-Methoxycarbonylamino-3-methyl-butyryl)-pyrrolidin-2-yl]-3H-imidazol-4-yl}-6H-benzo[c]chromen-8-yl)-1H-imidazol-2-yl]-pyrrolidine-1-carbonyl}-2-methyl-propyl)-carbamic acid methyl ester as a TFA salt (130 mg, 37%). $^1$H-NMR (300 MHz, CD$_3$OD) δ 7.80-7.20 (m, 8H), 5.40-5.05 (m, 4H), 4.65-3.80 (m, 6H), 3.75-3.40 (m, 6H), 2.40-1.90 (m, 10H), 1.05-0.80 (m, 12H); m/z 767.3 (M+H)$^+$.

Example EK

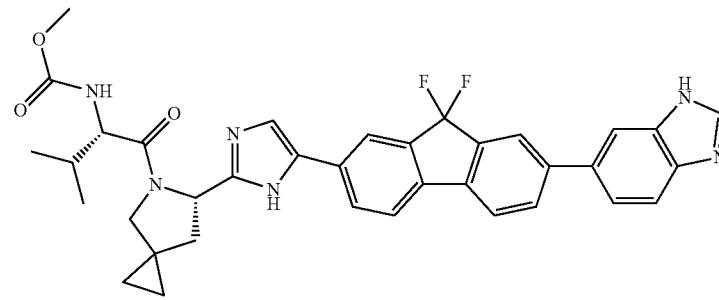 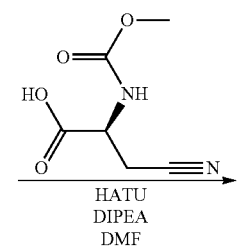

{1-[6-(5-{7-[2-(2-Aza-bicyclo[2.2.1]hept-3-yl)-3H-benzoimdazol-5-yl]-9,9-difluoro-9H-fluoren-2-yl}-1H-imidazol-2-yl)-5-aza-spiro[2.4]heptane-5-carbonyl]-2-methyl-propyl}-carbamic acid methyl ester

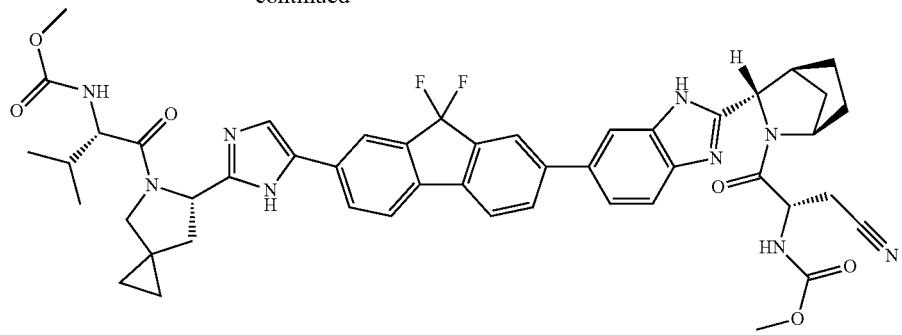

(1-{6-[5-(7-{2-[2-(3-Cyano-2-methoxycarbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl{-2-methyl-propyl)-carbamic acid methyl ester (1-{6-[5-(7-{2-[2-(3-Cyano-2-methoxycarbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl}-2-methyl-propyl)-carbamic acid methyl ester To a solution of {1-[6-(5-{7-[2-(2-aza-bicyclo[2.2.1]hept-3-yl)-3H-benzoimidazol-5-yl]-9,9-difluoro-9H-fluoren-2-yl}-1H-imidazol-2-yl)-5-aza-spiro[2.4]heptane-5-carbonyl]-2-methyl-propyl}-carbamic acid methyl ester (30 mg, 0.037 mmol) in DMF (2 mL) was added 3-cyano-2-methoxycarbonylamino-propionic acid (8 mg, 0.045 mmol), HATU (20 mg, 0.052 mmol) and N,N-diisopropylethylamine (0.051 mL, 0.3 mmol). The mixture was stirred at ambient for 2 hours, and then the volatile component was removed in vacuo. The residue was dissolved in ethyl acetate (50 mL), washed with 1 N NaOH solution, water and brine, dried over $Na_2SO_4$, filtered and concentrated in vacuo. The obtained residue was purified by HPLC to provide the desired product (1-{6-[5-(7-{2-[2-(3-Cyano-2-methoxycarbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl}-2-methyl-propyl)-carbamic acid methyl ester as a TFA salt (18 mg, 54%). $^1$H-NMR (300 MHz, DMSO-$d_6$) δ 8.30-7.70 (m, 10H), 7.45-7.30 (m, 1H), 5.26 (t, 1H), 5.00-4.80 (m, 2H), 4.60-4.45 (m, 1H), 4.10-3.70 (m, 4H), 3.63 (s, 3H), 3.54 (s, 3H), 3.00-2.65 (m, 4H), 2.30-1.10 (m, 12H), 1.00-0.60 (m, 8H); m/z 886.4 $(M+H)^+$.

Example EL

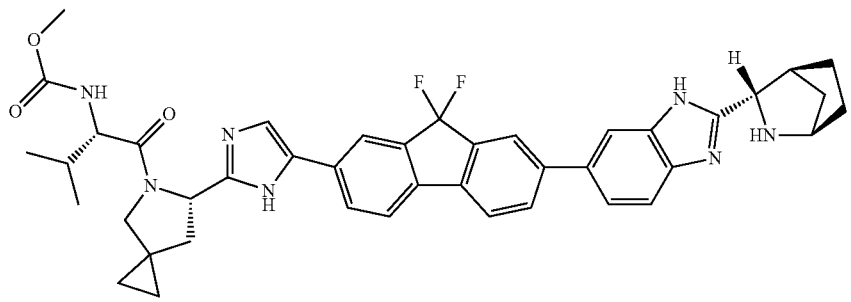

{1-[6-(5-{7-[2-(2-Aza-bicyclo[2.2.1]hept-3-yl)-3H-benzoimdazol-5-yl]-9,9-difluoro-9H-fluoren-2-yl}-1H-imidazol-2-yl)-5-aza-spiro[2.4]heptane-5-carbonyl]-2-methyl-propyl}-carbamic acid methyl ester

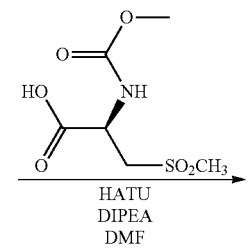

HATU
DIPEA
DMF

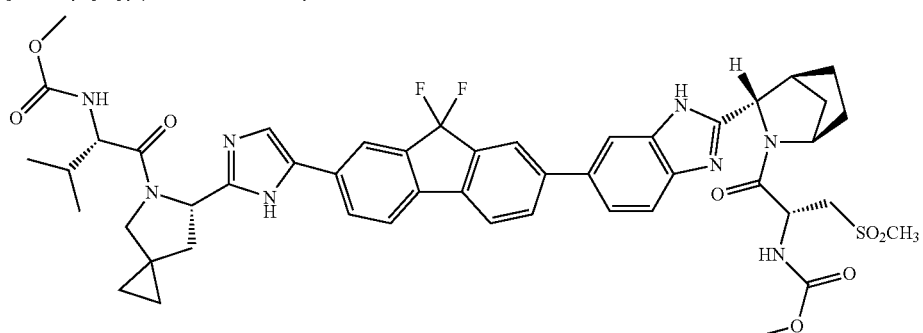

(1-{6-[5-(7-{2-[2-(3-Methanesulfonyl-2-methoxycarbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl{-2-methyl-propyl)-carbamic acid methyl ester

(1-{6-[5-(7-{2-[2-(3-Methanesulfonyl-2-methoxy-carbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl}-2-methyl-propyl)-carbamic acid methyl ester To a solution of {1-[6-(5-{7-[2-(2-aza-bicyclo[2.2.1]hept-3-yl)-3H-benzoimidazol-5-yl]-9,9-difluoro-9H-fluoren-2-yl}-1H-imidazol-2-yl)-5-aza-spiro[2.4]heptane-5-carbonyl]-2-methyl-propyl}-carbamic acid methyl ester (30 mg, 0.037 mmol) in DMF (2 mL) was added 3-methanesulfonyl-2-methoxycarbonylamino-propionic acid (8 mg, 0.045 mmol), HATU (20 mg, 0.052 mmol) and N,N-diisopropyl-ethylamine (0.051 mL, 0.3 mmol). The mixture was stirred at ambient for 2 hours, and then the volatile component was removed in vacuo. The residue was dissolved in ethyl acetate (50 mL), washed with 1 N NaOH solution, water and brine, dried over Na$_2$SO$_4$, filtered and concentrated in vacuo. The obtained residue was purified by HPLC to provide the desired product (1-{6-[5-(7-{2-[2-(3-Methanesulfonyl-2-methoxy-carbonylamino-propionyl)-2-aza-bicyclo[2.2.1]hept-3-yl]-3H-benzoimidazol-5-yl}-9,9-difluoro-9H-fluoren-2-yl)-1H-imidazol-2-yl]-5-aza-spiro[2.4]heptane-5-carbonyl}-2-methyl-propyl)-carbamic acid methyl ester as a TFA salt (18 mg, 54%). $^1$H-NMR (300 MHz, DMSO-d$_6$) δ 8.30-7.70 (m, 10H), 7.40-7.30 (m, 1H), 5.26 (t, 1H), 5.00-4.80 (m, 2H), 4.60-4.45 (m, 1H), 4.10-3.70 (m, 5H), 3.63 (s, 3H), 3.54 (s, 3H), 3.00-2.65 (m, 4H), 2.30-1.10 (m, 12H), 1.00-0.60 (m, 10H); m/z 939.4 (M+H)$^+$.

A. Example EM

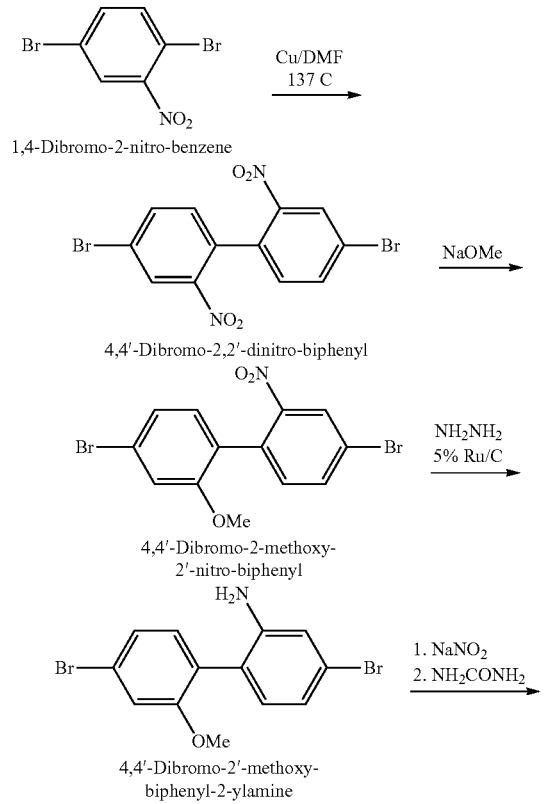

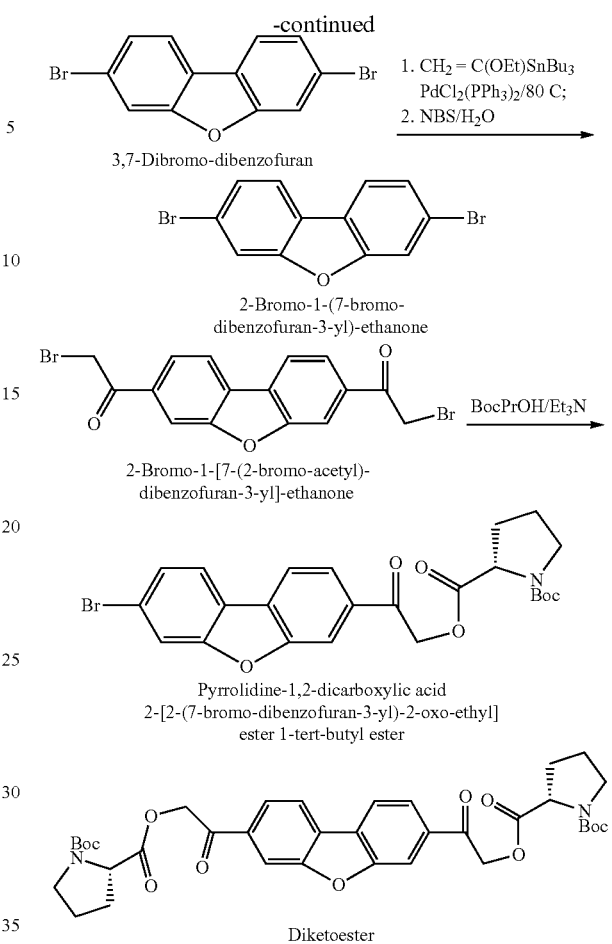

1,4-Dibromo-2-nitro-benzene

The compound was bought from Sigma-Aldrich Co.

4,4'-Dibromo-2,2'-dinitro-biphenyl

The mixture of 1,4-dibromo-2-nitro-benzene (25 g, 89 mmol) and copper powder (12.5 g, 197 mmol) in DMF (150 ml) was heated at 137 C for 2 hours. The mixture was cooled to 25° C. and was quenched with water. The mixture was extracted with EtOAc (2×). The combined organic solution was washed with water and brine and was dried with Na$_2$SO$_4$. Concentration and purification by flash column chromatography (hexanes/EtOAc) gave 4,4'-dibromo-2,2'-dinitro-biphenyl (13.6 g).

4,4'-Dibromo-2-methoxy-2'-nitro-biphenyl

To the solution of 4,4'-dibromo-2,2'-dinitro-biphenyl (6.58 g, 16.5 mmol) in DMF (50 ml) at 0° C. was added a solution of sodium methoxide in Methanol (4.4 M, 4.5 ml, 19.8 mmol). The mixture was stirred at 25° C. for 12 hours and was poured into ice-water (140 ml). The mixture was extracted with EtOAc (2×). The combined organic phase was washed with water and brine and dried with Na2SO4. Concentration under reduced pressure gave pale solid. The re-crystallization from CH3CN/MeOH gave 4,4'-dibromo-2-methoxy-2'-nitro-biphenyl as a white solid (3.76 g).

4,4'-Dibromo-2'-methoxy-biphenyl-2-ylamine

To a suspension of 4,4'-dibromo-2-methoxy-2'-nitro-biphenyl (3.76 g, 9.8 mmol) and 5% Ru/C (400 mg) in ethanol (37 ml) at 65-70° C. was added dropwise a solution of hydrazine (4.6 ml, 59 mmol) in ethanol (5 ml). The mixture was refluxed for 7 hours and filtered through a pad of CELITE. The CELITE pad was washed with ethanol. The combined solution was concentrated under reduced pressure. Coevaporation with ethanol, EtOAc and DCM gave 4,4'-dibromo-2'-methoxy-biphenyl-2-ylamine as yellow solid (3.5 g).

3,7-Dibromo-dibenzofuran

To a suspension of 4,4'-Dibromo-2'-methoxy-biphenyl-2-ylamine (3.5 g, 9.8 mmol) in H2SO4 (2.4 g) and water (8.5 ml) at 0° C. was added slowly a solution of NaNO2 (682 mg, 9.8 mmol) in water (9 ml). The mixture was stirred at 0° C. for 2 hours. Urea (1.2 g, 20 mmol) was added and the mixture was stirred for 12 hours. The mixture was diluted with water and was heated at 70° C. for 24 hours. The mixture was cooled to 25° C. and was filtered. The collected solid was re-crystallized from benzene/methanol to give 3,7-dibromo-dibenzofuran (2.27 g).

2-Bromo-1-(7-bromo-dibenzofuran-3-yl)-ethanone and 2-Bromo-1-[7-(2-bromo-acetyl)-dibenzofuran-3-yl]-ethanone To the solution of 3,7-dibromo-dibenzofuran (972 mg, 3 mmol) and tributyl(ethoxyvinyl)stannane (1.22 ml, 3.6 mmol) in dioxane (20 ml) was added PdCl$_2$(PPh$_3$)$_2$ (90 mg) and Pd(PPh$_3$)$_4$ (90 mg). The mixture was heated at 80° C. for 16 hours and was cooled to 0° C. Water (7 ml) was added, followed by slow addition of NBS (641 mg, 3.6 mmol) over 5 minutes period. The mixture was stirred at 0° C. for additional 40 minutes, and the solvent was removed under reduced pressure. The mixture was diluted with EtOAc, and was washed with water and brine and dried with sodium sulfate. Concentration under reduced pressure gave a mixture of 2-bromo-1-(7-bromo-dibenzofuran-3-yl)-ethanone and 2-Bromo-1-[7-(2-bromo-acetyl)-dibenzofuran-3-yl]-ethanone, which was used directly for the next step.

Pyrrolidine-1,2-dicarboxylic acid 2-[2-(7-bromo-dibenzofuran-3-yl)-2-oxo-ethyl]ester 1-tert-butyl ester and Diketoester To the solution of (s)Boc-PrOH (2.58 g, 12 mmol) and triethylamine (1.46 ml, 10.5 mmol) in acetonitrile (20 ml)/DMF (15 ml) was added a solution of 2-bromo-1-(7-bromo-dibenzofuran-3-yl)-ethanone and 2-bromo-1-[7-(2-bromo-acetyl)-dibenzofuran-3-yl]-ethanone in DMF (20 ml). The mixture was stirred for 10 hours, and the solvent was evaporated. The mixture was diluted with EtOAc, and washed with 0.5 N NaOH solution, water and brine, and was dried with sodium sulfate. Concentration and purification by flash column chromatography (hexanes/EtOAc) gave Pyrrolidine-1,2-dicarboxylic acid 2-[2-(7-bromo-dibenzofuran-3-yl)-2-oxo-ethyl]ester 1-tert-butyl ester (630 mg) and Diketoester (620 mg).

Example EN

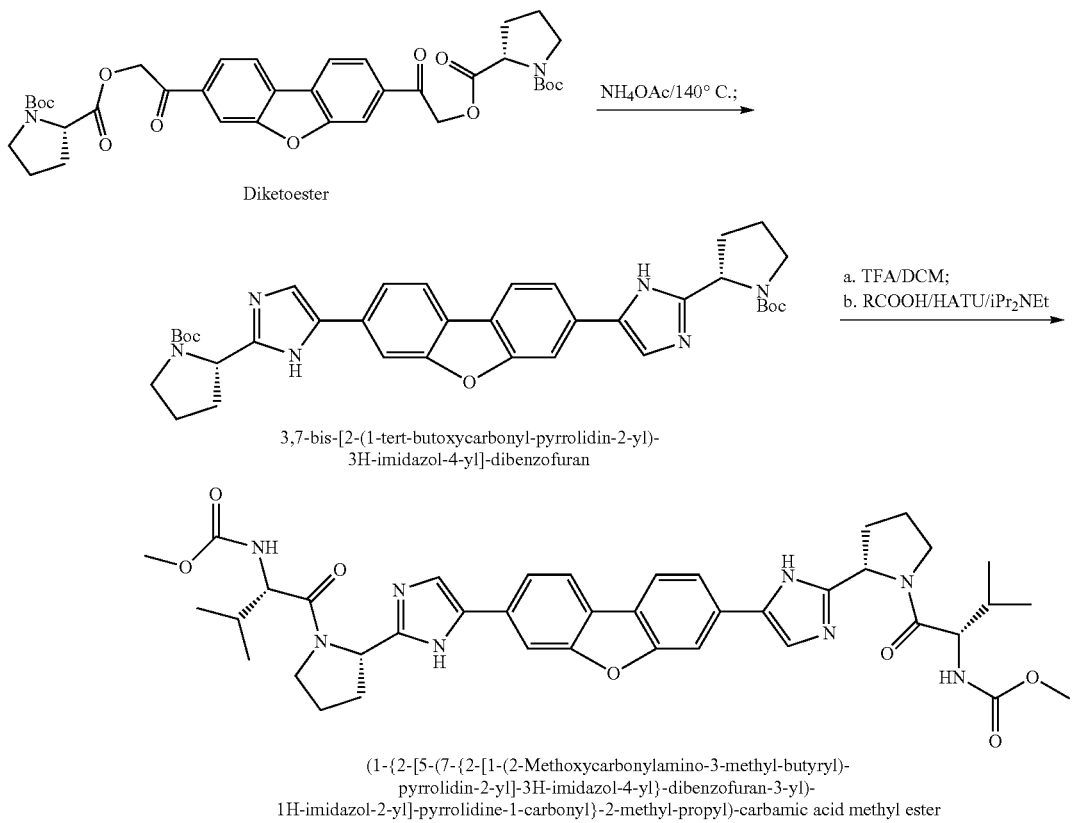

(1-{2-[5-(7-{2-[1-(2-Methoxycarbonylamino-3-methyl-butyryl)-pyrrolidin-2-yl]-3H-imidazol-4-yl}-dibenzofuran-3-yl)-1H-imidazol-2-yl]-pyrrolidine-1-carbonyl}-2-methyl-propyl)-carbamic acid methyl ester

3,7-bis-[2-(1-tert-butoxycarbonyl-pyrrolidin-2-yl)-3H-imidazol-4-yl]-dibenzofuran The mixture of diketoester (600 mg, 0.89 mmol) and ammonium acetate (1.72 g) in xylene (10 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (DCM/EtOAc) gave 3,7-bis-[2-(1-tert-butoxycarbonyl-pyrrolidin-2-yl)-3H-imidazol-4-yl]-dibenzofuran (330 mg). m/z: 639.1 (M+1), 637.3 (M−1), 320.0 (M+2)/2.

(1-{2-[(5-(7-{2-[(1-(2-Methoxycarbonylamino-3-methyl-butyryl)-pyrrolidin-2-yl]-3H-imidazol-4-yl}-dibenzofuran-3-yl)-1H-imidazol-2-yl]-pyrrolidine-1-carbonyl}-2-methy-propyl)-carbamic acid methyl ester To the solution of 3,7-bis-[2-(1-tert-butoxycarbonyl-pyrrolidin-2-yl)-3H-imidazol-4-yl]-dibenzofuran (330 mg, 0.51 mmol) in DCM (4 ml) was added TFA (2 ml). The mixture was stirred for 60 minutes, and the solvent and reagent were removed under reduced pressure. The mixture was diluted with acetonitrile and water, and was freezer-dried to give brown powder. To the solution of above powder (0.51 mmol) and MeOCO-Val-OH (179 mg, 1.02 mmol) in DMF (15 ml) was added HATU (407 mg, 1.07 mmol), followed by diisopropylethylamine (0.9 ml, 5.1 mmol). The mixture was stirred for 60 minutes and was evaporated and then diluted with EtOAc. The organic phase was washed with 1 N NaOH solution, water, and brine, and was dried with sodium sulfate. Concentration and purification by HPLC (0.1% TFA/$CH_3CN$/0.1% TFA/$H_2O$) gave (1-{2-[5-(7-{2-[1-(2-Methoxycarbonylamino-3-methyl-butyryl)-pyrrolidin-2-yl]-3H-imidazol-4-yl}-dibenzofuran-3-yl)-1H-imidazol-2-yl]-pyrrolidine-1-carbonyl}-2-methyl-propyl)-carbamic acid methyl ester (130 mg). m/z: 753.4 (M+1), 751.3 (M−1), 377.3 (M+2)/2. $^1$H NMR ($CD_3OD$, 300 MHz) δ 8.23 (2H, d, J=7.9 Hz), 8.0 (2H, s), 7.98 (2H, s), 7.78 (2H, d, J=7.9 Hz), 5.27 (2H, m), 4.24 (2H, d, J=7.0 Hz), 4.15 (2H, m), 3.90 (2H, m), 3.67 (6H, s), 2.60 (2H, m), 2.35-2.0 (8H, m), 1.0-0.8 (12H, m).

B. Example EO

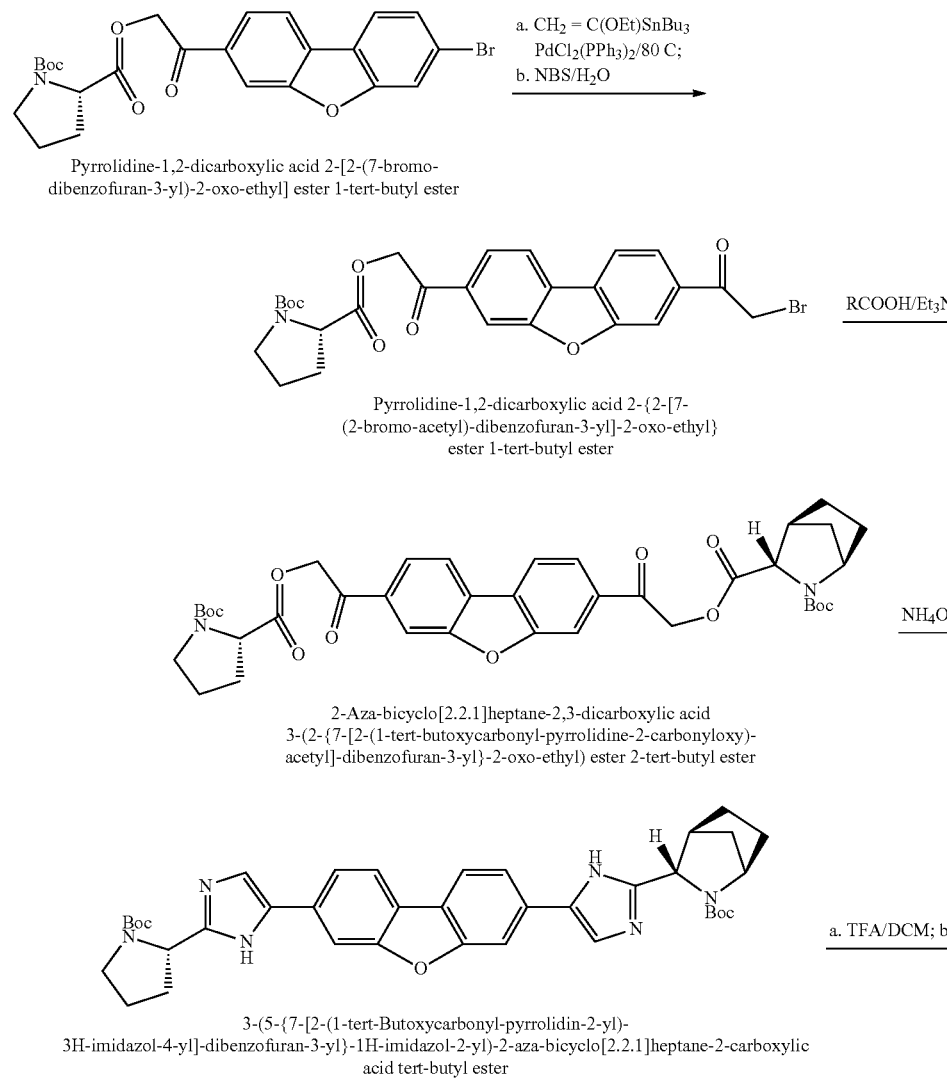

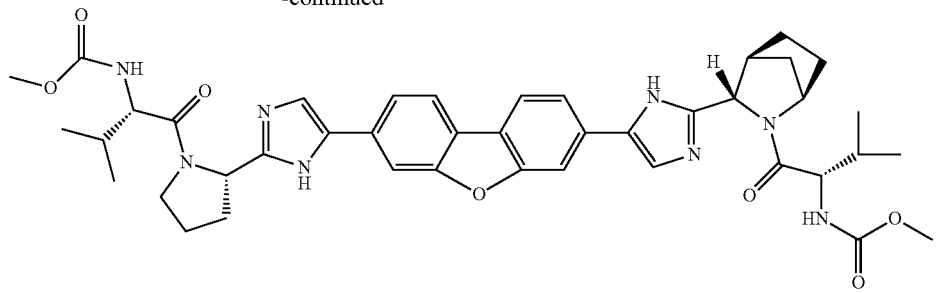

(1-{3-[5-(7-(2-[1-(2-Methoxycarbonylamino-3-methyl-butyryl)-
pyrrolidin-2-yl]-3H-imidazol-4-yl}-dibenzofuran-3-yl)-
1H-imidazol-2-yl]-2-aza-bicyclo[2.2.1]heptane-
2-carbonyl}-2-methyl-propyl)-carbamic acid methyl ester Pyrrolidine-1,2-dicarboxylic acid 2-{2-[7-(2-bromo-
acetyl)-dibenzofuran-3-yl]-2-oxo-ethyl}ester 1-tert-
butyl ester To the solution of Pyrrolidine-1,2-dicarboxylic acid 2-[2-(7-bromo-dibenzofuran-3-yl)-2-oxo-ethyl]ester 1-tert-butyl ester (250 mg, 0.5 mmol) and tributyl(ethoxyvinyl)stannane (188 μl, 0.55 mmol) in dioxane (3.3 ml) was added PdCl$_2$(PPh$_3$)$_2$ (15 mg). The mixture was heated at 80° C. for 16 hours and was cooled to 0° C. Water (1.1 ml) was added, followed by slow addition of NBS (98 mg, 0.55 mmol) over 5 minutes period. The mixture was stirred at 0° C. for additional 40 minutes, and the solvent was removed under reduced pressure. The mixture was diluted with EtOAc, and was washed with water and brine and dried with sodium sulfate. Concentration and purification by flash column chromatography (hexane/EtOAc) gave Pyrrolidine-1,2-dicarboxylic acid 2-{2-[7-(2-bromo-acetyl)-dibenzofuran-3-yl]-2-oxo-ethyl}ester 1-tert-butyl ester (205 mg).

2-Aza-bicyclo[2.2.1]heptane-2,3-dicarboxylic acid
3-(2-{7-[2-(1-tert-butoxycarbonyl-pyrrolidine-2-
carbonyloxy)-acetyl]-dibenzofuran-3-yl}-2-oxo-
ethyl) ester 2-tert-butyl ester To the solution of 2-Aza-bicyclo[2.2.1]heptane-2,3-dicarboxylic acid 2-tert-butyl ester (155 mg, 0.64 mmol) and triethylamine (77 μl, 0.55 mmol) in acetonitrile (3 ml) was added a solution of Pyrrolidine-1,2-dicarboxylic acid 2-{2-[7-(2-bromo-acetyl)-dibenzofuran-3-yl]-2-oxo-ethyl}ester 1-tert-butyl ester (200 mg, 0.37 mmol) in DMF (6 ml). The mixture was stirred for 10 hours, and the solvent was evaporated. The mixture was diluted with EtOAc, and washed with water and brine, and was dried with sodium sulfate. Concentration gave 2-Aza-bicyclo[2.2.1]heptane-2,3-dicarboxylic acid 3-(2-{7-[2-(1-tert-butoxycarbonyl-pyrrolidine-2-carbonyloxy)-acetyl]-dibenzofuran-3-yl}-2-oxo-ethyl)ester 2-tert-butyl ester (243 mg). m/z: 703.3 (M−1), 727.2 (M+Na)

3-(5-{7-[2-(1-tert-Butoxycarbonyl-pyrrolidin-2-yl)-
3H-imidazol-4-yl]dibenzofuran-3-yl}-1H-imidazol-
2-yl)-2-aza-bicyclo[2.2.1]heptane-2-carboxylic acid
tert-butyl ester The mixture of 2-Aza-bicyclo[2.2.1]heptane-2,3-dicarboxylic acid 3-(2-{7-[2-(1-tert-butoxycarbonyl-pyrrolidine-2-carbonyloxy)-acetyl]-dibenzofuran-3-yl}-2-oxo-ethyl) ester 2-tert-butyl ester (243 mg) and ammonium acetate (860 mg, 11 mmol) in xylene (5 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (DCM/EtOAc) gave 3-(5-{7-[2-(1-tert-Butoxycarbonyl-pyrrolidin-2-yl)-3H-imidazol-4-yl]dibenzofuran-3-yl}-1H-imidazol-2-yl)-2-aza-bicyclo[2.2.1]heptane-2-carboxylic acid tert-butyl ester (170 mg). m/z: 665.0 (M+1), 663.4 (M−1), 333.0 (M+2)/2.

(1-{3-[5-(7-{2-[1-(2-Methoxycarbonylamino-3-me-
thyl-butyryl)-pyrrolidin-2-yl]-3H-imidazol-4-yl}-
dibenzofuran-3-yl)-1H-imidazol-2-yl]-2-aza-bicyclo
[2.2.1]heptane-2-carbonyl}-2-methyl-propyl)-
carbamic acid methyl ester To the solution of 3-(5-{7-[2-(1-tert-Butoxycarbonyl-pyrrolidin-2-yl)-3H-imidazol-4-yl]dibenzofuran-3-yl}-1H-imidazol-2-yl)-2-aza-bicyclo[2.2.1]heptane-2-carboxylic acid tert-butyl ester (170 mg) in DCM (6 ml) was added TFA (3 ml). The mixture was stirred for 60 minutes, and the solvent and reagent were removed under reduced pressure. The mixture was diluted with acetonitrile and water, and was freezer-dried to give brown powder. To the solution of above powder (0.256 mmol) and MeOCO-Val-OH (90 mg, 0.51 mmol) in DMF (7.5 ml) was added HATU (204 mg, 0.54 mmol), followed by diisopropylethylamine (0.45 ml, 2.56 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{3-[5-(7-{2-[1-(2-Methoxycarbonylamino-3-methyl-butyryl)-pyrrolidin-2-yl]-3H-imidazol-4-yl}-dibenzofuran-3-yl)-1H-imidazol-2-yl]-2-aza-bicyclo[2.2.1]heptane-2-carbonyl}-2-methyl-propyl)-carbamic acid methyl ester (127 mg). m/z: 779.3 (M+1), 777.3 (M−1), 390.2 (M+2)/2. $^1$H NMR (CD$_3$OD, 300 MHz) δ 8.23 (2H, d, J=8.2 Hz), 8.03 (2H, s), 7.98 (2H, m), 7.88 (2H, d, J=8.2 Hz), 5.25 (1H, m), 4.85 (1H, m), 4.33 (1H, d, J=6.1 Hz), 4.24 (1H, d, J=7.0 Hz), 4.15 (1H, m), 3.88 (1H, m), 3.69 (3H, s), 3.67 (3H, s), 3.45 (1H, m), 2.89 (1H, m), 2.60 (1H, m), 2.35-1.6 (11H, m), 1.05-0.8 (12H, m).

C. Example EP

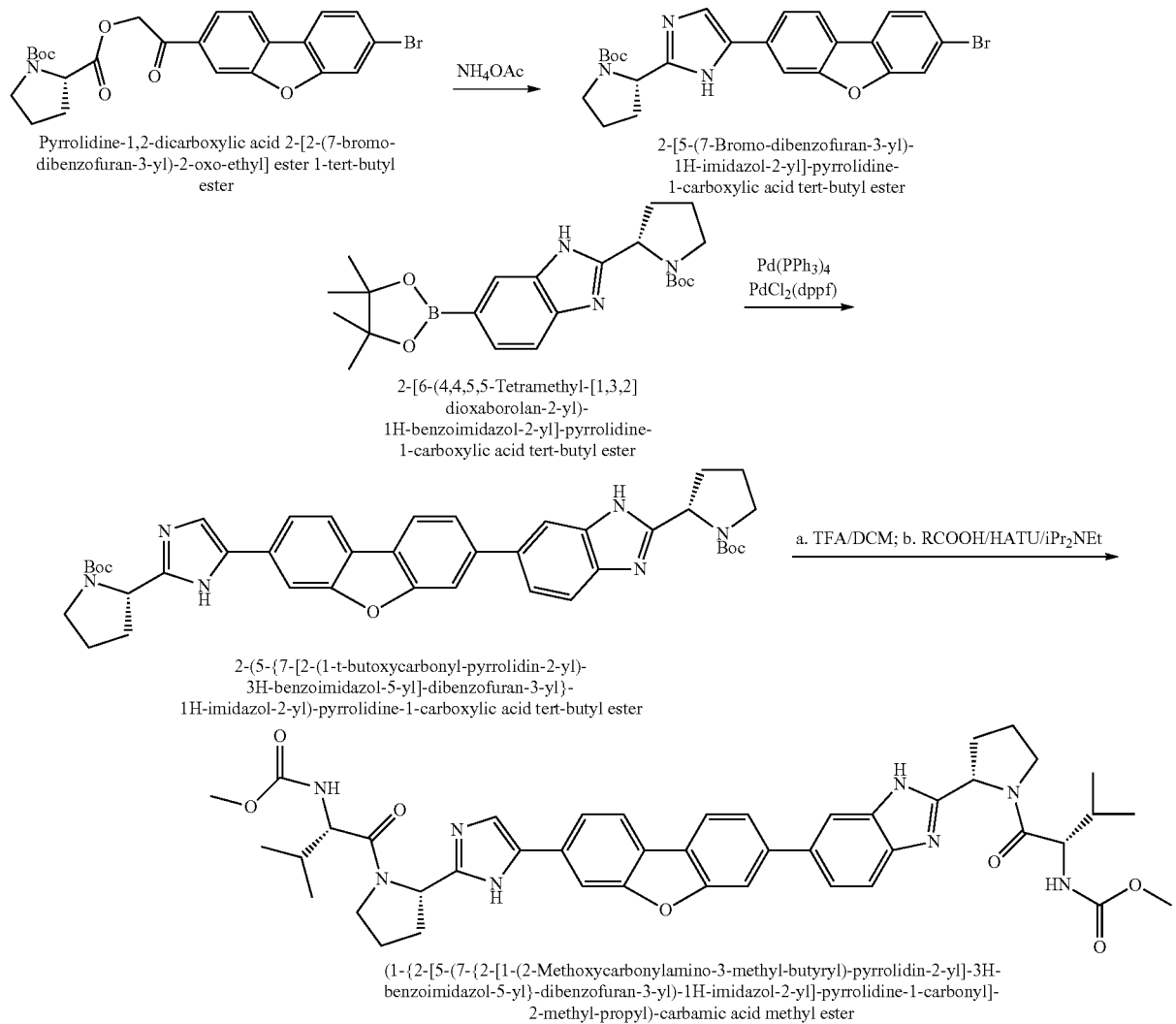

2-[5-(7-Bromo-dibenzofuran-3-yl)-1H-imidazol-2-yl]-pyrrolidine-1-carboxylic acid tert-butyl ester The mixture of Pyrrolidine-1,2-dicarboxylic acid 2-[2-(7-bromo-dibenzofuran-3-yl)-2-oxo-ethyl]ester 1-tert-butyl ester (200 mg) and ammonium acetate (860 mg, 11 mmol) in xylene (5 ml) was heated at 140° C. for 80 minutes under microwave. The mixture was quenched with water, and extracted with EtOAc. The organic phase was washed with water and brine, and was dried with sodium sulfate. Concentration and purification by flash column chromatography (DCM/EtOAc) gave 2-[5-(7-Bromo-dibenzofuran-3-yl)-1H-imidazol-2-yl]-pyrrolidine-1-carboxylic acid tert-butyl ester (124 mg). m/z: 481.9 (M+1), 480.2 (M−1).

2-(5-{7-[2-(1-t-butoxycarbonyl-pyrrolidin-2-yl)-3H-benzoimidazol-5-yl]-dibenzofuran-3-yl}-1H-imidazol-2-yl)-pyrrolidine-1-carboxylic acid tert-butyl ester To the solution of 2-[5-(7-Bromo-dibenzofuran-3-yl)-1H-imidazol-2-yl]-pyrrolidine-1-carboxylic acid tert-butyl ester (124 mg, 0.26 mmol) and 2-[6-(4,4,5,5-Tetramethyl-[1,3,2]dioxaborolan-2-yl)-1H-benzoimidazol-2-yl]-pyrrolidine-1-carboxylic acid tert-butyl ester (107 mg, 0.26 mmol) in DME (2.25 ml) and water (0.75 ml) was added potassium carbonate (72 mg, 0.52 mmol), followed by Pd(PPh$_3$)$_4$ (15 mg) and PdCl$_2$(dppf)CH$_2$Cl$_2$ (15 mg). The mixture was heated at 90° C. for 6 hours. The mixture was diluted with EtOAc, and was washed with water and brine, and was dried with sodium sulfate. Concentration and purification by flash column chromatography (EtOAc) gave 2-(5-{7-[2-(1-t-butoxycarbonyl-pyrrolidin-2-yl)-3H-benzoimidazol-5-yl]-dibenzofuran-3-yl}-1H-imidazol-2-yl)-pyrrolidine-1-carboxylic acid tert-butyl ester (83 mg). m/z: 689.1 (M+1), 687.3 (M−1), 345.0 (M+2)/2.

(1-{2-[5-(7-{2-[1-(2-Methoxycarbonylamino-3-methyl-butyryl)-pyrrolidin-2-yl]-3H-benzoimidazol-5-yl}-dibenzofuran-3-yl)-1H-imidazol-2-yl]-pyrrolidine-1-carbonyl}-2-methyl-propyl)-carbamic acid methyl ester To the solution of 2-(5-{7-[2-(1-t-butoxycarbonyl-pyrrolidin-2-yl)-3H-benzoimidazol-5-yl]-dibenzofuran-3-yl}-1H- imidazol-2-yl)-pyrrolidine-1-carboxylic acid tert-butyl ester (82 mg, 0.12) in DCM (4 ml) was added TFA (2 ml). The mixture was stirred for 60 minutes, and the solvent and reagent were removed under reduced pressure. The mixture was diluted with acetonitrile and water, and was freezer-dried to give brown powder. To the solution of above powder (0.12 mmol) and MeOCO-Val-OH (42 mg, 0.24 mmol) in DMF (3.5 ml) was added HATU (95 mg, 0.25 mmol), followed by diisopropylethylamine (0.21 ml, 1.2 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH₃CN/0.1% TFA/H₂O) gave (1-{2-[5-(7-{2-[1-(2-Methoxycarbonylamino-3-methyl-butyryl)-pyrrolidin-2-yl]-3H-benzoimidazol-5-yl}-dibenzofuran-3-yl)-1H-imidazol-2-yl]-pyrrolidine-1-carbonyl}-2-methyl-propyl)-carbamic acid methyl ester (79 mg). m/z: 803.4 (M+1), 801.1 (M−1), 402.2 (M+2)/2. ¹H NMR (CD₃OD, 300 MHz) δ 8.25 (2H, m), 8.1-7.9 (5H, m), 7.9-7.75 (3H, m), 5.4-5.2 (2H, m), 4.25 (2H, m), 4.2-3.8 (4H, m), 3.67 (6H, s), 2.60 (2H, m), 2.4-2.0 (8H, m), 1.05-0.8 (12H, m).

D. Example EQ

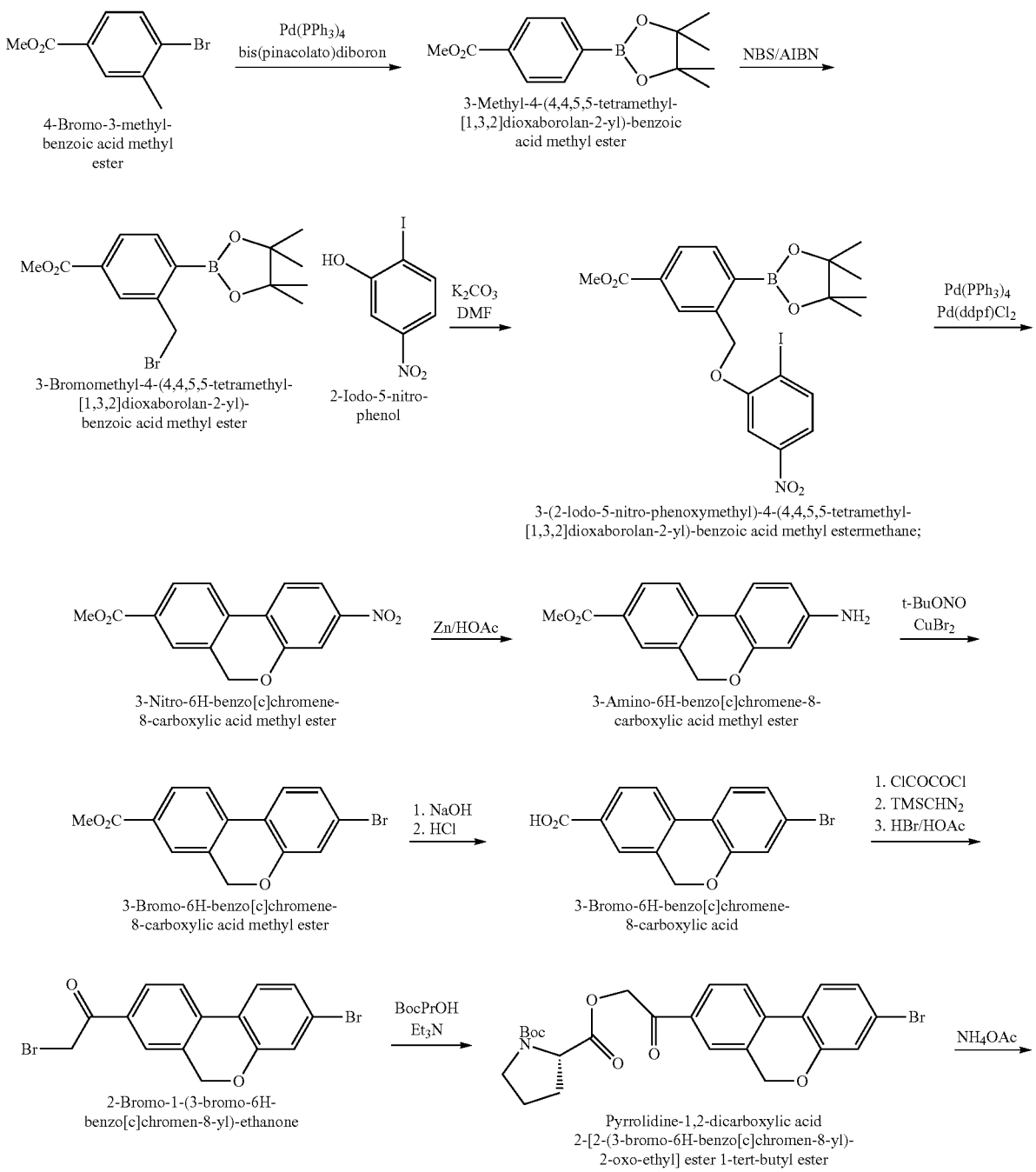

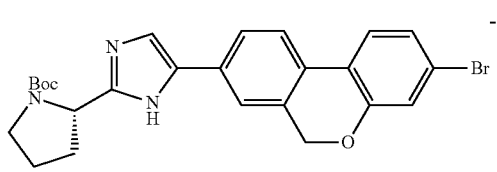

2-[5-(3-Bromo-6H-benzo[c]chromen-8-yl)-
1H-imidazol-2-yl]-pyrrolidine-1-
1-carboxylic acid tert-butyl ester -continued

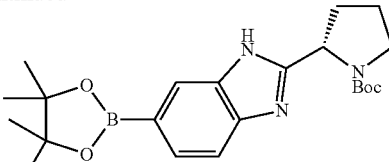

2-[6-(4,4,5,5-Tetramethyl-[1,3,2]
dioxaborolan-2-yl)-
1H-benzoimidazol-2-yl]-pyrrolidine-
1-carboxylic acid tert-butyl ester Pd(PPh₃)₄
PdCl₂(dppf) →

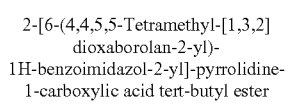

a. TFA/DCM; b. RCOOH/HATU/iPr₂NEt →

2-(5-{3-[2-(1-t-butoxycarbonyl-pyrrolidin-2-yl)-
3H-benzoimidazol-5-yl]-6H-benzo[c]chromen-8-yl}-
1H-imidazol-2-yl)-pyrrolidine-1-carboxylic acid tert-butyl ester

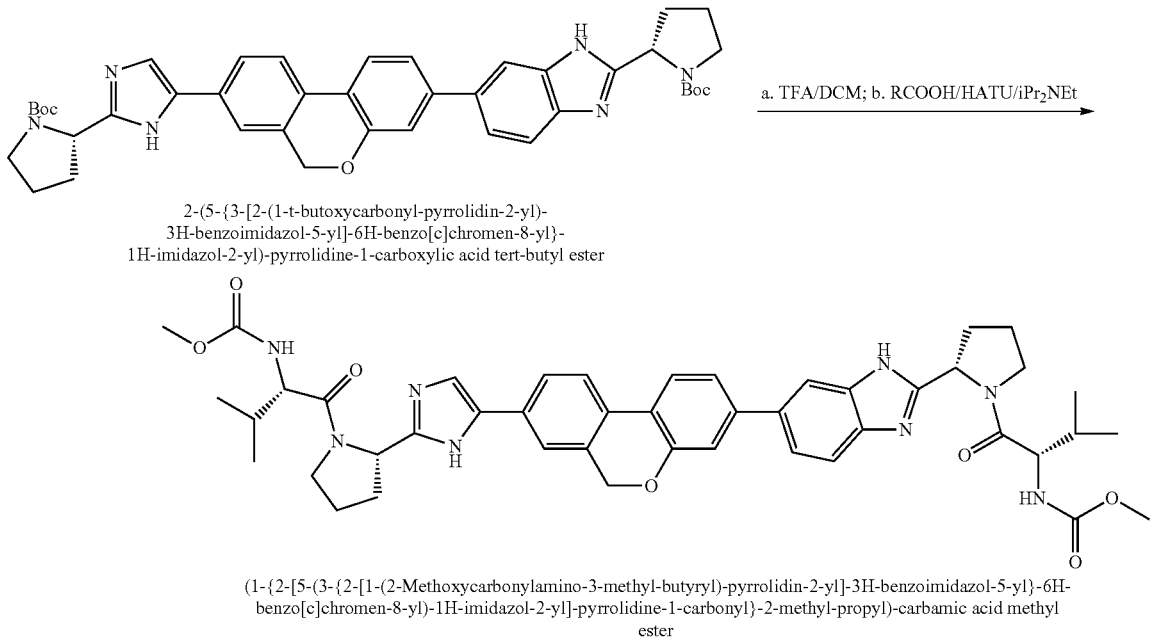

(1-{2-[5-(3-{2-[1-(2-Methoxycarbonylamino-3-methyl-butyryl)-pyrrolidin-2-yl]-3H-benzoimidazol-5-yl}-6H-
benzo[c]chromen-8-yl)-1H-imidazol-2-yl]-pyrrolidine-1-carbonyl}-2-methyl-propyl)-carbamic acid methyl
ester 4-Bromo-3-methyl-benzoic acid methyl ester The chemical was bought from Sigma-Aldrich Co.

3-Methyl-4-(4,4,5,5-tetramethyl-[1,3,2]dioxaboro-
lan-2-yl)-benzoic acid methyl ester To the solution of 4-Bromo-3-methyl-benzoic acid methyl ester (4.56 g, 20 mmol) and bis(pinacolato)diboron (10.2 g, 40 mmol) in 1,4-dioxane (160 ml) was added potassium acetate (5.0 g, 51 mmol), followed by Pd(PPh₃)₄ (924 mg). The mixture was heated at 80° C. for 16 hours. The mixture was diluted with EtOAc, and was washed with water and brine, and was dried with sodium sulfate. Concentration and purification by flash column chromatography (hexanes/EtOAc) gave 3-Methyl-4-(4,4,5,5-tetramethyl-[1,3,2]dioxaborolan-2-yl)-benzoic acid methyl ester (4.8 g).

3-Bromomethyl-4-(4,4,5,5-tetramethyl-[1,3,2]diox-
aborolan-2-yl)-benzoic acid methyl ester The solution of 3-Methyl-4-(4,4,5,5-tetramethyl-[1,3,2]dioxaborolan-2-yl)-benzoic acid methyl ester (3.71 g, 13.4 mmol), NBS (2.39 g, 13.4 mmol), and AIBN (235 mg) in CCl₄ (20 ml) was heated at 80° C. for 14 hours. The mixture was cooled to 25° C., and was filtered and washed with CCl₄. The solution was concentrated under reduced pressure, and was diluted with EtOAc. The solution was washed with water and brine and was dried with Na2SO4. Concentration gave 3-Bromomethyl-4-(4,4,5,5-tetramethyl-[1,3,2]dioxaborolan-2-yl)-benzoic acid methyl ester (4.9 g).

3-(2-Iodo-5-nitro-phenoxymethyl)-4-(4,4,5,5-tetram-
ethyl-[1,3,2]dioxaborolan-2-yl)-benzoic acid methyl
estermethane The mixture of 3-Bromomethyl-4-(4,4,5,5-tetramethyl-[1,3,2]dioxaborolan-2-yl)-benzoic acid methyl ester (3.63 g, 10.3 mmol), 2-Iodo-5-nitro-phenol (2.72 g, 10.3 mmol), and potassium carbonate (2.26 g, 16.4 mmol) in DMF (21 ml) was heated at 75° C. for 3 hours. The mixture was cooled to 25° C., and DMF was removed under reduced pressure. The mixture was diluted with EtOAc, and was acidified with 0.5 N HCl until pH=4. More water (total volume of water 100 ml) was added and the mixture was stirred for 5 minutes. The mixture was filtered and washed with water. The solid was collected and dried under reduced pressure. 3-(2-Iodo-5-nitro-phenoxymethyl)-4-(4,4,5,5-tetramethyl-[1,3,2]dioxaborolan-2-yl)-benzoic acid methyl estermethane was obtained as solid (1.8 g).

3-Nitro-6H-benzo[c]chromene-8-carboxylic acid
methyl ester

To the solution of 3-(2-Iodo-5-nitro-phenoxymethyl)-4-(4, 4,5,5-tetramethyl-[1,3,2]dioxaborolan-2-yl)-benzoic acid methyl estermethane (2.7 g, 5 mmol) in 1,2-dimethoxyether (75 ml) and water (25 ml) was added sodium bicarbonate (1.26 g, 15 mmol), followed by Pd(PPh$_3$)$_4$ (250 mg) and Pd(dppf)Cl$_2$ (250 mg). The mixture was heated at 80° C. for 16 hours. The mixture was diluted with EtOAc, and was washed with water and brine, and was dried with sodium sulfate. Concentration and purification by flash column chromatography (DCM/hexanes) gave 3-Nitro-6H-benzo[c]chromene-8-carboxylic acid methyl ester (690 mg).

3-Amino-6H-benzo[c]chromene-8-carboxylic acid methyl ester

To the solution of 3-Nitro-6H-benzo[c]chromene-8-carboxylic acid methyl ester (690 mg) in THF/DMF (5 ml/5 ml) was added acetic acid (10 ml), followed by slow addition of Zinc (800 mg). The mixture was stirred for 12 hours and solvents were removed under reduced pressure. The mixture was diluted with EtOAc, and 0.2 N sodium hydroxide solution was added until pH=10. The organic layer was separated and was washed with water and brine and dried with Na$_2$SO$_4$. Concentration and purification by flash column chromatography (DCM/EtOAc) gave 3-Amino-6H-benzo[c]chromene-8-carboxylic acid methyl ester (300 mg).

3-Bromo-6H-benzo[c]chromene-8-carboxylic acid methyl ester

To a solution of copper (II) bromide (315 mg, 1.42 mmol) and t-butyl nitrite (233 µl, 1.77 mmol) in CH$_3$CN (4 ml) at 65° C. was added dropwise a suspension of 3-Amino-6H-benzo[c]chromene-8-carboxylic acid methyl ester (300 mg, 1.18 mmol) in CH$_3$CN (5 ml). The mixture was heated at 65° C. for 3 hours. Concentration and purification by flash column chromatography (DCM/EtOAc) gave 3-Bromo-6H-benzo[c]chromene-8-carboxylic acid methyl ester (160 mg).

3-Bromo-6H-benzo[c]chromene-8-carboxylic acid

The solution of 3-Bromo-6H-benzo[c]chromene-8-carboxylic acid methyl ester (160 mg, 0.5 mmol) and sodium hydroxide (1.0 N, 1 ml, 1 mmol) in THF/MeOH (2 ml/2 ml) was heated at 50° C. for 3 hours. The mixture was cooled to 25° C. and was acidified with 2 N HCl (0.6 ml). The solvents were removed under reduced pressure. The mixture was diluted with acetonitrile and water, and was freezer-dried to give 3-Bromo-6H-benzo[c]chromene-8-carboxylic acid as brown powder.

2-Bromo-1-(3-bromo-6H-benzo[c]chromen-8-yl)-ethanone

To 3-Bromo-6H-benzo[c]chromene-8-carboxylic acid (0.5 mmol) was added a solution of oxalyl chloride in DCM (2.0 N, 5 ml, 10 mmol). The mixture was heated at 45° C. for 2 hours and cooled to 25° C. Excess reagents and solvent were removed under reduced pressure and co-evaporated with toluene. To the solution of above residue in DCM (5 ml) at 0° C. trimethylsilyldiazomethane (2.0 N, 0.75 ml, 1.5 mmol) was added dropwise. The mixture was stirred at 25° C. for 12 hours and was concentrated. The residue was dissolved in EtOAc and was cooled to 0° C. To above solution HBr/HOAc (0.28 ml, 1.5 mmol) was added dropwise. The mixture was stirred at 25° C. for 1 hour. Solid sodium bicarbonate was added and the mixture was stirred for 30 minutes. The mixture was diluted with EtOAc, and was washed with water and brine and was dried with Na$_2$SO$_4$. Concentration gave 2-Bromo-1-(3-bromo-6H-benzo[c]chromen-8-yl)-ethanone, which was used for next step without purification.

Pyrrolidine-1,2-dicarboxylic acid 2-[2-(3-bromo-6H-benzo[c]chromen-8-yl)-2-oxo-ethyl]ester 1-tert-butyl ester To the solution of (s)Boc-PrOH (1.07 g, 5 mmol) and triethylamine (0.63 ml, 4.5 mmol) in acetonitrile (20 ml) was added a solution of 2-Bromo-1-(3-bromo-6H-benzo[c]chromen-8-yl)-ethanone (0.5 mmol) in DMF (10 ml). The mixture was stirred for 10 hours, and the solvent was evaporated. The mixture was diluted with EtOAc, and washed with 0.5 N NaOH solution, water and brine, and was dried with sodium sulfate. Concentration gave Pyrrolidine-1,2-dicarboxylic acid 2-[2-(3-bromo-6H-benzo[c]chromen-8-yl)-2-oxo-ethyl]ester 1-tert-butyl ester, which was used for the next step without further purification.

2-[5-(3-Bromo-6H-benzo[c]chromen-8-yl)-1H-imidazol-2-yl]-pyrrolidine-1-carboxylic acid tert-butyl ester The mixture of Pyrrolidine-1,2-dicarboxylic acid 2-[2-(3-bromo-6H-benzo[c]chromen-8-yl)-2-oxo-ethyl]ester 1-tert-butyl ester (0.5 mmol) and ammonium acetate (860 mg, 11 mmol) in xylene (5 ml) was heated at 140° C. for 80 minutes under microwave. The mixture was quenched with water, and extracted with EtOAc. The organic phase was washed with water and brine, and was dried with sodium sulfate. Concentration and purification by HPLC (0.1% TFA/CH$_3$CN/0.1% TFA/H$_2$O) gave 2-[5-(3-Bromo-6H-benzo[c]chromen-8-yl)-1H-imidazol-2-yl]pyrrolidine-1-carboxylic acid tert-butyl ester (8 mg). m/z: 496.0 (M+1), 494.1 (M−1).

2-(5-{3-[2-(1-t-butoxycarbonyl-pyrrolidin-2-yl)-3H-benzoimidazol-5-yl]-6H-benzo[c]chromen-8-yl}-1H-imidazol-2-yl)-pyrrolidine-1-carboxylic acid tert-butyl ester To the solution of 2-[5-(3-Bromo-6H-benzo[c]chromen-8-yl)-1H-imidazol-2-yl]-pyrrolidine-1-carboxylic acid tert-butyl ester (9 mg, 0.02 mmol) and 2-[6-(4,4,5,5-Tetramethyl-[1,3,2]dioxaborolan-2-yl)-1H-benzoimidazol-2-yl]-pyrrolidine-1-carboxylic acid tert-butyl ester (9.6 mg, 0.02 mmol) in DME (0.75 ml) and water (0.25 ml) was added potassium carbonate (10 mg, 0.07 mmol), followed by Pd(PPh$_3$)$_4$ (2 mg) and PdCl$_2$(dppf)CH$_2$Cl$_2$ (2 mg). The mixture was heated at 90° C. for 6 hours. The mixture was diluted with EtOAc, and was washed with water and brine, and was dried with sodium sulfate. Concentration and purification by flash column chromatography (EtOAc) gave 2-(5-{3-[2-(1-t-butoxycarbonyl-pyrrolidin-2-yl)-3H-benzoimidazol-5-yl]-6H-benzo[c]chromen-8-yl}-1H-imidazol-2-yl)-pyrrolidine-1-carboxylic acid tert-butyl ester (4.2 mg). m/z: 729.2 (M+1), 727.3 (M−1), 365.2 (M+2)/2.

(1-{2-[5-(3-{2-[1-(2-Methoxycarbonylamino-3-methyl-butyryl)-pyrrolidin-2-yl]-3H-benzoimidazol-5-yl}-6H-benzo[c]chromen-8-yl)-1H-imidazol-2-yl]-pyrrolidine-1-carbonyl}-2-methyl-propyl)-carbamic acid methyl ester To the solution of 2-(5-{3-[2-(1-t-butoxycarbonyl-pyrrolidin-2-yl)-3H-benzoimidazol-5-yl]-6H-benzo[c]chromen-8-yl}-1H-imidazol-2-yl)-pyrrolidine-1-carboxylic acid tert-butyl ester (4.2 mg, 0.006) in DCM (2 ml) was added TFA (1 ml). The mixture was stirred for 60 minutes, and the solvent and reagent were removed under reduced pressure. The mixture was diluted with acetonitrile and water, and was freezer-dried to give brown powder. To the solution of above powder (0.006 mmol) and MeOCO-Val-OH (2 mg, 0.012 mmol) in DMF (1 ml) was added HATU (4.6 mg, 0.012 mmol), followed by diisopropylethylamine (100, 0.058 mmol). The mixture was stirred for 90 minutes and was diluted with EtOAc. The organic phase was washed with 1 N NaOH solution, water, and brine, and was dried with sodium sulfate. Concentration and purification by HPLC (0.1% TFA/CH$_3$CN/0.1% TFA/H$_2$O) gave (1-{2-[5-(3-{2-[1-(2-Methoxycarbonylamino-3-methyl-butyryl)-pyrrolidin-2-yl]-3H-benzoimidazol-5-yl}-6H-benzo[c]chromen-8-yl)-1H-imidazol-2-yl]-pyrrolidine-1-carbonyl}-2-methyl-propyl)-carbamic acid methyl ester (2.5 mg). m/z: (M+1), (M−1), (M+2)/2. $^1$H NMR (CD$_3$OD, 300 MHz) δ 8.07-7.7 (7H, m), 7.62 (1H, s), 7.45 (1H, m), 7.38 (1H, s), 5.25 (4H, m), 4.35 (1H, m), 4.22 (1H, m), 4.15 (2H, m), 3.85 (2H, m), 3.65 (6H, m), 2.98 (1H, s), 2.6 (1H, m), 2.3-1.7 (8H, m), 1.05-0.85 (12H, m).

Example ER

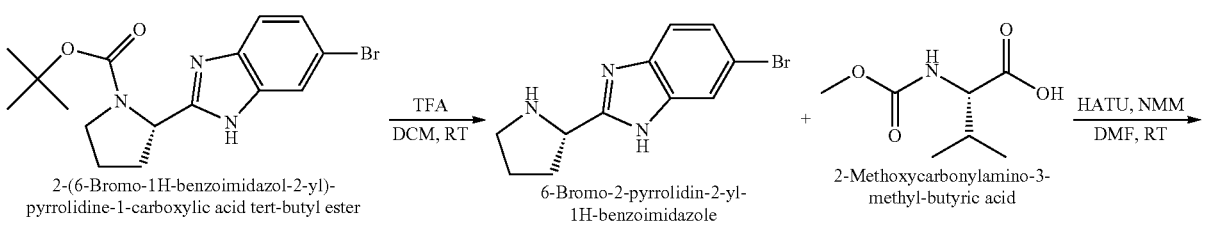

2-(6-Bromo-1H-benzoimidazol-2-yl)-pyrrolidine-1-carboxylic acid tert-butyl ester 6-Bromo-2-pyrrolidin-2-yl-1H-benzoimidazole 2-Methoxycarbonylamino-3-methyl-butyric acid

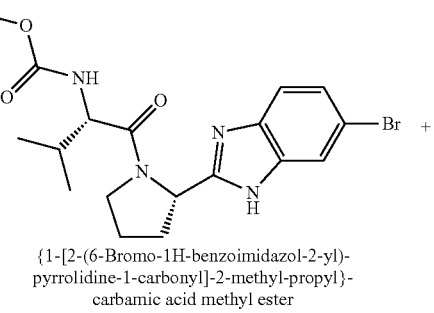

{1-[2-(6-Bromo-1H-benzoimidazol-2-yl)-pyrrolidine-1-carbonyl]-2-methyl-propyl}-carbamic acid methyl ester

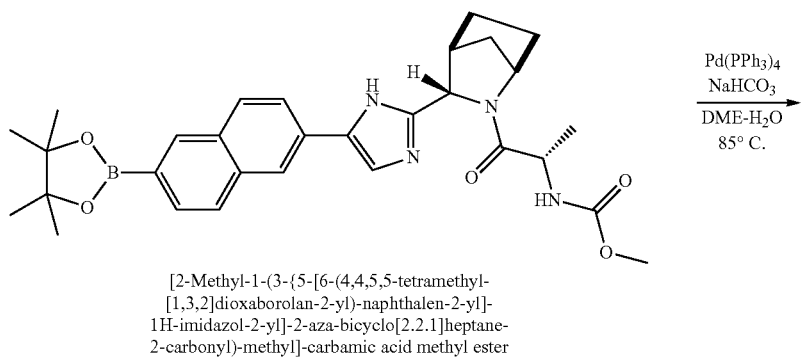

[2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester

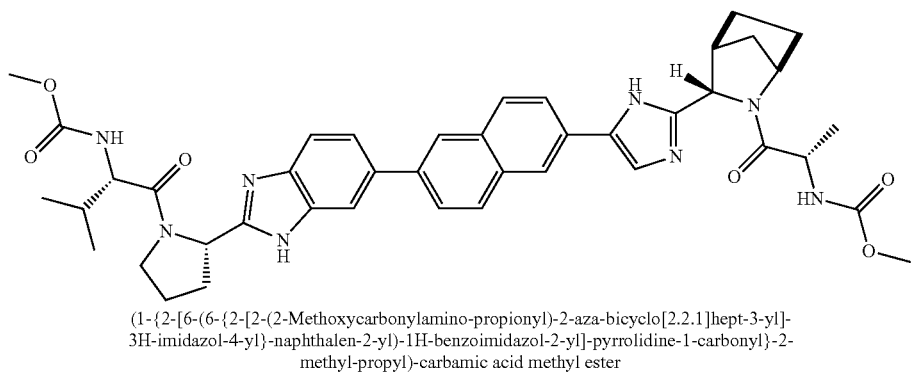

(1-{2-[6-(6-{2-[2-(2-Methoxycarbonylamino-propionyl)-2-aza-bicyclo[2.2.1]hept-3-yl]-3H-imidazol-4-yl}-naphthalen-2-yl)-1H-benzoimidazol-2-yl]-pyrrolidine-1-carbonyl}-2-methyl-propyl)-carbamic acid methyl ester

6-Bromo-2-pyrrolidin-2-yl-1H-benzoimidazole

Prepared by the same method as (1-{2-[5-(4-Bromo-phenyl)-1H-imidazol-2-yl]-pyrrolidine-1-carbonyl}-2-methyl-propyl)-carbamic acid methyl ester, except that 2-(6-Bromo-1H-benzoimidazol-2-yl)-pyrrolidine-1-carboxylic acid tert-butyl ester was used as the substrate. 120 mg light yellow solid (66% yield).

{1-[2-(6-Bromo-1H-benzoimidazol-2-yl)-pyrrolidine-1-carbonyl]-2-methyl-propyl}-carbamic acid methyl ester Prepared by the same method as (1-{2-[5-(4-Bromo-phenyl)-1H-imidazol-2-yl]-pyrrolidine-1-carbonyl}-2-methyl-propyl)-carbamic acid methyl ester but using 6-bromo-2-pyrrolidin-2-yl-1H-benzoimidazole as the substrate. 193 mg crude solid were used for the next step.

[2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester This compound was made using the same procedure as for [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]carbamic acid methyl ester, except that 2-Aza-bicyclo[2.2.1]heptane-2,3-dicarboxylic acid 2-tert-butyl ester was used in place of Pyrrolidine-1,2-dicarboxylic acid 1-tert-butyl ester and 2-Methoxycarbonylamino-propionic acid was used in place of 2-Methoxycarbonylamino-3-methyl-butyric acid 2-Methoxycarbonylamino-propionic acid.

(1-{2-[6-(6-{2-[2-(2-Methoxycarbonylamino-propionyl)-2-aza-bicyclo[2.2.1]hept-3-yl]-3H-imidazol-4-yl}-naphthalen-2-yl)-1H-benzoimidazol-2-yl]-pyrrolidine-1-carbonyl}-2-methyl-propyl)-carbamic acid methyl ester {1-[2-(6-Bromo-1H-benzoimidazol-2-yl)-pyrrolidine-1-carbonyl]-2-methyl-propyl}-carbamic acid methyl ester (0.193 g), [2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester (0.241 g), and NaHCO₃ (0.123 g) were dissolved in a mixture of 1,2-dimethoxyethane (6 mL) and water (2 mL). The solution was degassed with nitrogen, and Pd(PPh₃)₄ (0.0219 g) was added. The reaction mixture was stirred at 85° C. for 2 days and evaporated under vacuum. Solid was dissolved in ethyl acetate (15 mL) and extracted twice with water (10 mL) and once with brine (10 mL). The resulting oil was subjected to silica gel chromatography using a 40 g ISCO column and effluent of 0-5% MeOH:DCM. The fractions containing product were combined and the solvent was removed under reduced pressure. Oil was dissolved in DMF, purified by reverse phase HPLC (5-70% acetonitrile:water), and lyophilized, giving (1-{2-[6-(6-{2-[2-(2-Methoxycarbonylamino-propionyl)-2-aza-bicyclo[2.2.1]hept-3-yl]-3H-imidazol-4-yl}-naphthalen-2-yl)-1H-benzoimidazol-2-yl]-pyrrolidine-1-carbonyl}-2-methyl-propyl)-carbamic acid methyl ester (0.039 g, 12%) as a white solid.

¹H-NMR: 300 MHz, (DMSO-d₆) δ: 11.8 (s, 1H), 8.2 (d, J=27 Hz, 2H), 7.9 (m, 4H), 7.6 (m, 3H), 7.3 (m, 2H), 5.3 (m, 2H), 4.1 (m, 2H), 3.8 (m, 2H), 3.5 (s, 6H), 2.5 (s, 6H), 2.8 (m, 1H), 2.1 (m, 4H), 2.0 (m, 4H), 0.9 (m, 12H); MS (ESI): m/z 763 [M+H]⁺.

Example ES

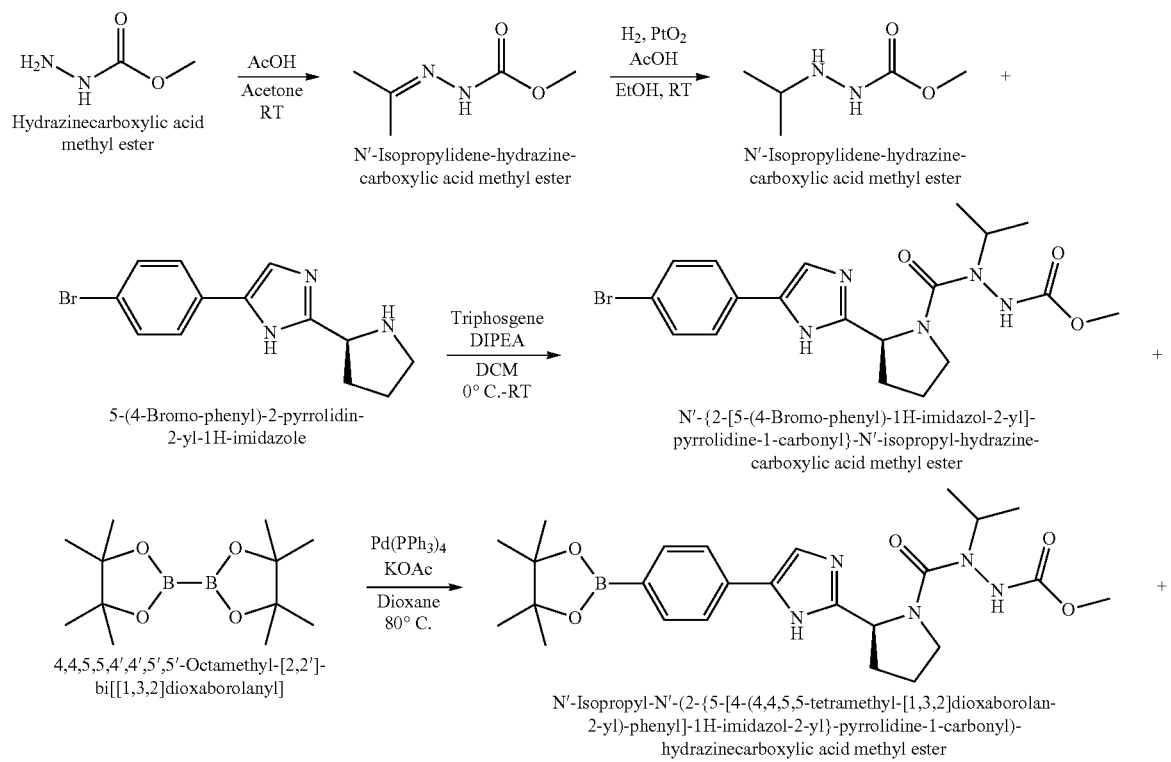

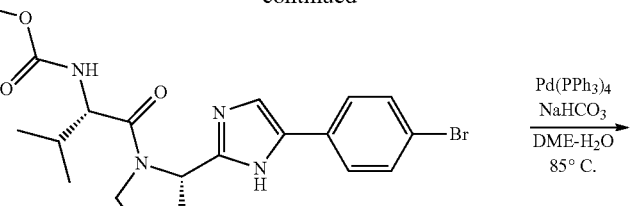

(1-{2-[5-(6-Bromonaphthalen-2-yl)-1H-imidazol-2-yl]-pyrrolidine-1-carbonyl}-2-methyl-propyl)-carbamic acid methyl ester Pd(PPh$_3$)$_4$
NaHCO$_3$
DME-H$_2$O
85° C.

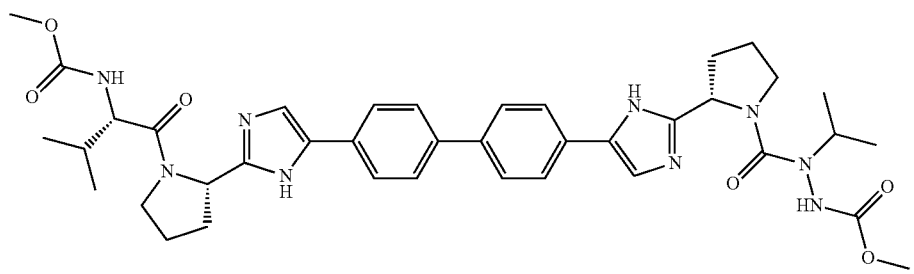

N'-Isopropyl-N'-(2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-hydrazinecarboxylic acid methyl ester N'-Isopropylidene-hydrazine-carboxylic acid methyl ester Hydrazinecarboxylic acid methyl ester (5.01 g) were dissolved in acetone (28 mL), and acetic acid (0.0636 mL) was added. The reaction mixture was stirred at room temperature for 24 hours. Water (50 mL) was added, and mixture was extracted three times with DCM (50 mL) and evaporated under vacuum, giving N'-Isopropylidene-hydrazine-carboxylic acid methyl ester (6.45 g, 89%).

N'-Isopropyl-hydrazine-carboxylic acid methyl ester

N'-Isopropylidene-hydrazine-carboxylic acid methyl ester (6.45 g) were dissolved in ethanol (50 mL) and acetic acid (50 mL) PtO$_2$ (0.231 g) was added, and reaction was stirred at room temperature for 22 hours under an atmosphere of hydrogen. Mixture was evaporated under vacuum, giving N'-Isopropyl-hydrazine-carboxylic acid methyl ester (5.08 g, 77%) as a white solid.

N'-{2-[5-(4-Bromo-phenyl)-1H-imidazol-2-yl]-pyrrolidine-1-carbonyl}-N'-isopropyl-hydrazine-carboxylic acid methyl ester Triphosgene (1.05 g) was dissolved in DCM (17 mL) and stirred at 0° C. N'-Isopropyl-hydrazine-carboxylic acid methyl ester (1.00 g) and DIPEA (1.5 mL) were dissolved in DCM (25 mL), and mixture was added to triphosgene solution and stirred for 10 minutes. 5-(4-Bromo-phenyl)-2-pyrrolidin-2-yl-1H-imidazole (2.65 g) was added. Reaction was stirred at room temperature for 1 hour and extracted twice with water (10 mL), once with brine (10 mL), and evaporated under vacuum. The resulting oil was subjected to silica gel chromatography using a 40 g ISCO column and effluent of 0-100% ethyl acetate:hexanes. The fractions containing product were combined and the solvent was removed under vacuum, giving N'-{2-[5-(4-Bromo-phenyl)-1H-imidazol-2-yl]-pyrrolidine-1-carbonyl}-N'-isopropyl-hydrazine-carboxylic acid methyl ester (533 mg, 16%).

N'-Isopropyl-N'-(2-{5-[4-(4,4,5,5-tetramethyl-[1,3,2]dioxaborolan-2-yl)-phenyl]-1H-imidazol-2-yl}-pyrrolidine-1-carbonyl)-hydrazinecarboxylic acid methyl ester N'-{2-[5-(4-Bromo-phenyl)-1H-imidazol-2-yl]-pyrrolidine-1-carbonyl}-N'-isopropyl-hydrazine-carboxylic acid methyl ester (0.533 g), 4,4,5,5,4',4',5',5'-Octamethyl-[2,2']-bi[[1,3,2]dioxaborolanyl] (0.644 g), and KOAc (0.309 g) were dissolved in dioxane (8 mL). The solution was degassed with nitrogen, and Pd(PPh$_3$)$_4$ (0.0562 g) was added, and reaction was stirred at 80° C. for 2 days. Solid was removed by vacuum filtration, and solvent was removed under vacuum. The resulting oil was subjected to silica gel chromatography using a 40 g ISCO column and effluent of 0-5% MeOH:DCM. The fractions containing product were combined and the solvent was removed under vacuum, giving N'-Isopropyl-N'-(2-{5-[4-(4,4,5,5-tetramethyl-[1,3,2]dioxaborolan-2-yl)-phenyl]-1H-imidazol-2-yl}-pyrrolidine-1-carbonyl)-hydrazinecarboxylic acid methyl ester (0.564 g, 96%) as a yellow solid.

N'-Isopropyl-N'-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-hydrazinecarboxylic acid methyl ester N'-Isopropyl-N'-(2-{5-[4-(4,4,5,5-tetramethyl-[1,3,2]dioxaborolan-2-yl)-phenyl]-1H-imidazol-2-yl}-pyrrolidine-1- carbonyl)-hydrazinecarboxylic acid methyl ester (0.295 g), (1-{2-[5-(6-Bromophenyl-2-yl)-1H-imidazol-2-yl]-pyrrolidine-1-carbonyl}-2-methyl-propyl)-carbamic acid methyl ester (0.280 g), and NaHCO₃ were dissolved in DME (9 mL) and water (3 mL). The solution was degassed with nitrogen, and Pd(PPh₃)₄ (0.0282 g) was added, and reaction was stirred at 85° C. for 19 hours. Solvent was removed under vacuum. Solid was dissolved in DMF, purified by reverse phase HPLC (5-70% acetonitrile:water) two times, and lyophilized, giving N'-Isopropyl-N'-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-hydrazinecarboxylic acid methyl ester (0.017 g, 4%) as a white solid.

¹H-NMR: 300 MHz, (CH₃OH-d₄) δ: 7.9 (m, 12H), 5.3 (m, 2H), 4.4 (m, 1H), 4.2 (d, J=7 Hz, 2H), 4.1 (m, 1H), 3.9 (m, 4H), 3.6 (m, 6H), 3.3 (s, 3H), 2.6 (m, 2H), 2.0 (m, 8H), 1.1 (m, 6H), 0.9 (m, 6H); MS (ESI): m/z 740 [M+H]⁺.

Example ET

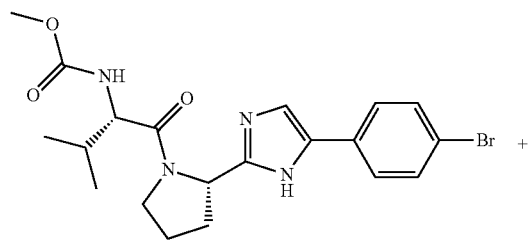

(1-{2-[5-(6-Bromonaphthalen-2-yl)-1H-imadazol-2-yl]-pyrrolidine-1-carbonyl]-2-methyl-propyl)-carbamic acid methyl ester

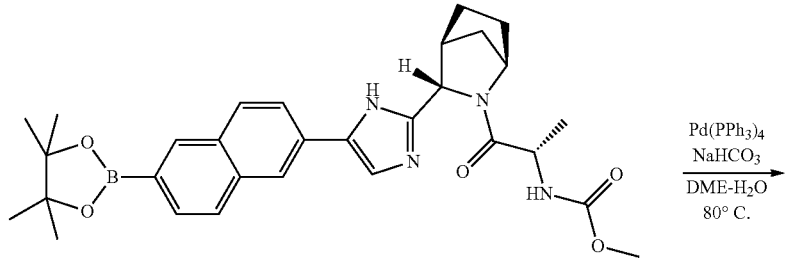

[2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester

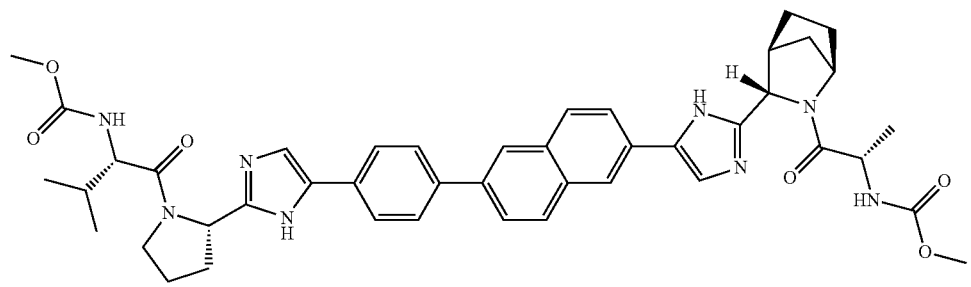

[1-(3-{5-[6-(4-{2-[1-(2-Methoxycarbonylamino-3-methyl-butyryl)-pyrrolidin-2-yl]-3H-imidazol-4-yl}-phenyl)-napthalen-2-yl]-1H-imidazol-2-yl}-2-aza-bicyclo[2.2.1]heptane-2-carbonyl)-2-methyl]-carbamic acid methyl ester

[1-(3-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl]-carbamic acid methyl ester (1-{2-[5-(6-Bromonaphthalen-2-yl)-1H-imidazol-2-yl]-pyrrolidine-1-carbonyl}-2-methyl-propyl)-carbamic acid methyl ester (0.226 g), [2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester (0.297 g), and NaHCO₃ (0.154 g) were dissolved in a mixture of 1,2-dimethoxyethane (9 mL) and water (3 mL). The solution was degassed with nitrogen, and Pd(PPh₃)₄ (0.0263 g) was added. The reaction mixture was stirred at 80° C. for 19 hours and evaporated under vacuum. Solid was dissolved in DCM (15 mL) and extracted twice with water (10 mL) and once with brine (10 mL). The resulting oil was subjected to silica gel chromatography using a 40 g ISCO column and effluent of 0-5% MeOH:DCM. The fractions containing product were combined and the solvent was removed under reduced pressure. Oil was dissolved in DMF, purified by reverse phase HPLC (5-70% acetonitrile:water), and lyophilized, giving [1-(3-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl]-carbamic acid methyl ester (0.138 g, 32%) as a white solid.

¹H-NMR: 300 MHz, (CH₃OH-d₄) δ: 8.3 (d, J=9 Hz, 2H), 8.1 (m, 2H), 8.0 (m, 4H), 7.9 (m, 4H), 5.3 (t, J=7 Hz, 2H), 4.6 (s, 2H), 4.5 (m, 2H), 4.2 (d, J=7 Hz, 2H), 4.1 (m, 2H), 3.9 (m, 2H), 3.6 (s, 6H), 3.3 (s, 2H), 2.9 (s, 1H), 2.8 (m, 1H), 2.0 (m, 8H), 1.8 (m, 1H), 1.4 (d, J=7 Hz, 3H), 0.9 (m, 6H); MS (ESI): m/z 787 [M+H]⁺.

Example EU

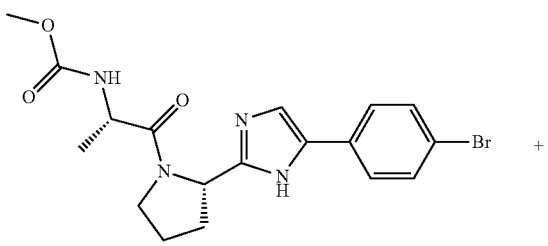

(2-{2-[5-(4-Bromo-phenyl)-1H-imadazol-2-yl]-pyrrolidine-1-yl]-1-methyl-2-oxo-ethyl)-carbamic acid methyl ester

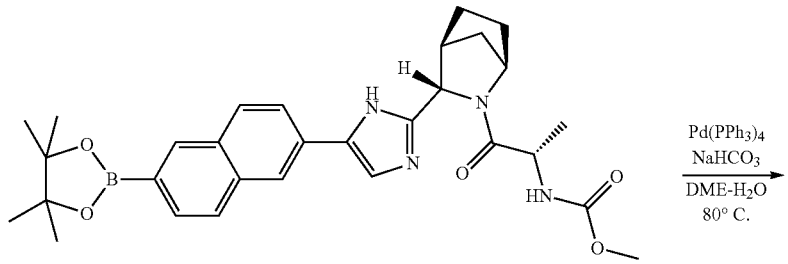

[2-Methyl-1-(3-(5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester

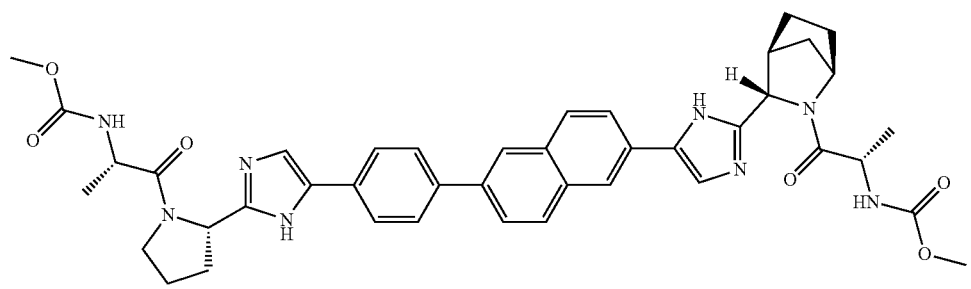

[2-(3-{5-[6-(4-[2-[1-(2-Methoxycarbonylamino-propionyl)-pyrrolidin-2-yl]-3H-imidazol-4-yl}-phenyl)-naphthalen-2-yl]-1H-imidazol-2-yl}-2-aza-bicyclo[2.2.1]hept-2-yl)-1-methyl-2-oxo-ethyl]-carbamic acid methyl ester

[2-(3-{5-[6-(4-{2-[1-(2-Methoxycarbonylamino-propionyl)-pyrrolidin-2-yl]-3H-imidazol-4-yl}-phenyl)-naphthalen-2-yl]-1H-imidazol-2-yl}-2-aza-bicyclo[2.2.1]hept-2-yl)-1-methyl-2-oxo-ethyl]-carbamic acid methyl ester (2-{2-[5-(4-Bromo-phenyl)-1H-imidazol-2-yl]-pyrrolidin-1-yl}-1-methyl-2-oxo-ethyl)-carbamic acid methyl ester (0.241 g), [2-Methyl-1-(3-{-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-methyl]-carbamic acid methyl ester (0.303 g), and NaHCO₃ (0.164 g) were dissolved in a mixture of 1,2-dimethoxyethane (9 mL) and water (3 mL). The solution was degassed with nitrogen, and Pd(PPh₃)₄ (0.0263 g) was added. The reaction mixture was stirred at 80° C. for 19 hours and evaporated under vacuum. Solid was dissolved in DCM (15 mL) and extracted twice with water (10 mL) and once with brine (10 mL). The resulting oil was subjected to silica gel chromatography using a 40 g ISCO column and effluent of 0-5% MeOH:DCM. The fractions containing product were combined and the solvent was removed under reduced pressure. Oil was dissolved in DMF, purified by reverse phase HPLC (5-70% acetonitrile:water), and lyophilized, giving [2-(3-{5-[6-(4-{2-[1-(2-Methoxycarbonylamino-propionyl)-pyrrolidin-2-yl]-3H-imidazol-4-yl}-phenyl)-naphthalen-2-yl]-1H-imidazol-2-yl}-2-aza-bicyclo[2.2.1]hept-2-yl)-1-methyl-2-oxo-ethyl]-carbamic acid methyl ester (0.159 g, 38%) as a white solid.

¹H-NMR: 300 MHz, (CH₃OH-d₄) δ: 8.3 (d, J=9 Hz, 2H), 8.1 (m, 2H), 8.0 (m, 4H), 7.9 (m, 4H), 5.3 (m, 2H), 4.6 (s, 2H), 4.5 (m, 4H), 4.0 (m, 2H), 3.9 (m, 2H), 3.7 (d, J=7 Hz, 6H), 3.3 (m, 2H), 2.9 (s, 1H), 2.8 (s, 1H), 2.6 (m, 1H), 2.0 (m, 8H), 1.8 (m, 2H), 1.4 (m, 6H); MS (ESI): m/z 759 [M+H]⁺.

Example EV

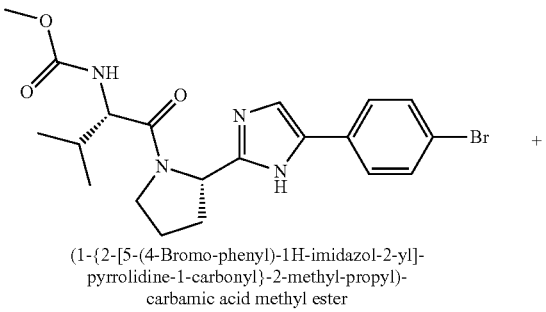

(1-{2-[5-(4-Bromo-phenyl)-1H-imidazol-2-yl]-pyrrolidine-1-carbonyl}-2-methyl-propyl)-carbamic acid methyl ester

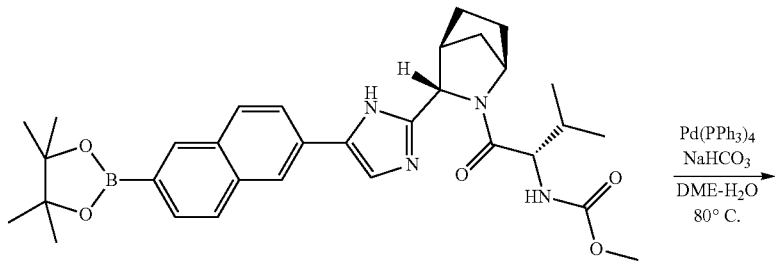

[2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-propyl]-carbamic acid methyl ester

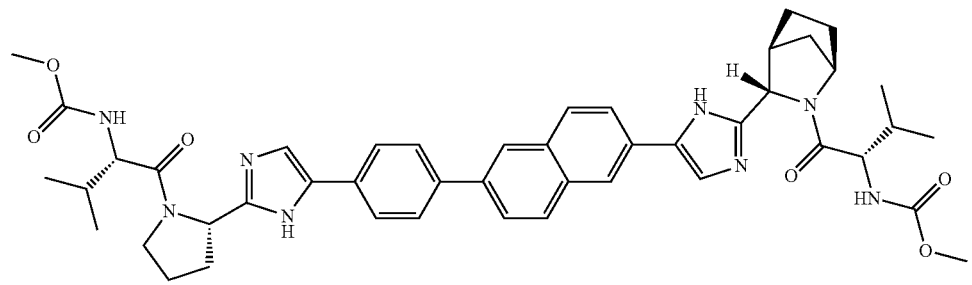

[1-(3-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester

[2-Methyl-1-(2-{5-[6-(4,4,5,5-tetramethyl-[1,3,2]
dioxaborolan-2-yl)-naphthalen-2-yl]-1H-imidazol-2-
yl}-pyrrolidine-1-carbonyl)-propyl]-carbamic acid
methyl ester This compound was made using the same procedure as for [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester, except that 2-Aza-bicyclo[2.2.1]heptane-2,3-dicarboxylic acid 2-tert-butyl ester was used in place of Pyrrolidine-1,2-dicarboxylic acid 1-tert-butyl ester as described in example CL.

[1-(3-{5-[6-(4-{2-[1-(2-Methoxycarbonylamino-3-
methyl-butyryl)-pyrrolidin-2-yl]-3H-imidazol-4-yl}-
phenyl)-naphthalen-2-yl]-1H-imidazol-2-yl}-2-aza-
bicyclo[2.2.1]heptane-2-carbonyl)-2-methyl-propyl]-
carbamic acid methyl ester (1-{2-[5-(4-Bromo-phenyl)-1H-imidazol-2-yl]-pyrrolidine-1-carbonyl}-2-methyl-propyl)-carbamic acid methyl ester (0.251 g), [2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-propyl]carbamic acid methyl ester (0.301 g), and NaHCO$_3$ (0.162 g) were dissolved in a mixture of 1,2-dimethoxyethane (9 mL) and water (3 mL) The solution was degassed with nitrogen, and Pd(PPh$_3$)$_4$ (0.0254 g) was added. The reaction mixture was stirred at 80° C. for 21 hours and evaporated under vacuum. Solid was dissolved in DCM (20 mL) and extracted twice with water (10 mL) and once with brine (10 mL). The resulting oil was subjected to silica gel chromatography using a 40 g ISCO column and effluent of 0-5% MeOH:DCM. The fractions containing product were combined and the solvent was removed under reduced pressure. Oil was dissolved in DMF, purified by reverse phase HPLC (5-70% acetonitrile: water), and lyophilized, giving [1-(3-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (0.187 g, 44%) as a white solid.

$^1$H-NMR: 300 MHz, (CH$_3$OH-d$_4$) δ: 8.3 (d, J=9 Hz, 2H), 8.1 (m, 2H), 8.0 (m, 4H), 7.9 (m, 4H), 5.3 (m, 2H), 4.7 (s, 2H), 4.3 (m, 2H), 4.1 (m, 2H), 3.9 (m, 2H), 3.7 (d, J=7 Hz, 6H), 3.3 (m, 2H), 2.9 (s, 1H), 2.6 (m, 2H), 2.1 (m, 8H), 1.8 (m, 2H), 1.4 (m, 12H); MS (ESI): m/z 815 [M+H]$^+$.

Example EW

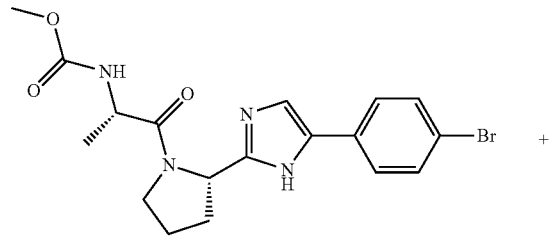

(2-{2-[5-(4-Bromo-phenyl)-1H-imidazol-2-yl]-
pyrrolidin-1-yl}-1-methyl-2-oxo-ethyl)-
carbamic acid methyl ester

+

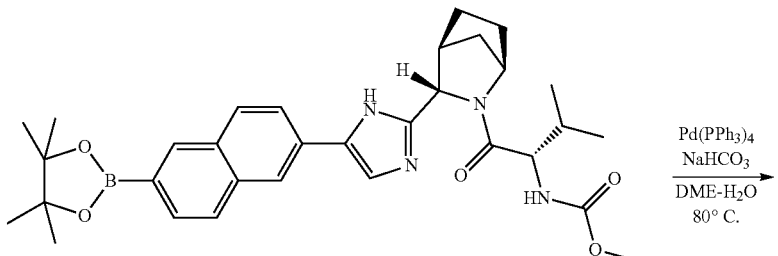

[2-Methyl-1-(3-{5-[6-(4,4,5,5-tetramethyl-
[1,3,2]dioxaborolan-2-yl)-naphthalen-2-yl]-
1H-imidazol-2-yl}-2-aza-bicyclo[2.2.1]heptane-2-carbonyl)-
propyl]-carbamic acid methyl ester

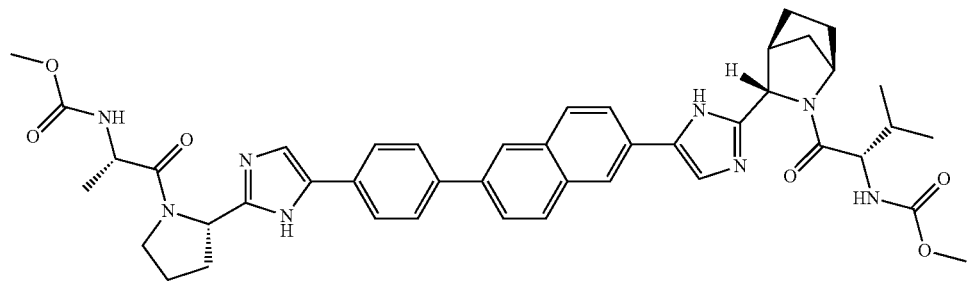

[1-(3-{5-[6-(4-{2-[1-(2-Methoxycarbonylamino-propionyl)-
pyrrolidin-2-yl]-3H-imidazol-4-yl}-phenyl)-naphthalen-2-yl]-
1H-imidazol-2-yl}-2-aza-bicyclo[2.2.1]heptane-2-carbonyl)-2-methyl-propyl]-
carbamic acid methyl ester

[1-(3-{5-[6-(4-{2-[1-(2-Methoxycarbonylamino-propionyl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (2-{2-[5-(4-Bromo-phenyl)-1H-imidazol-2-yl]-pyrrolidin-1-yl}-1-methyl-2-oxo-ethyl)-carbamic acid methyl ester (0.235 g), [2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-propyl]-carbamic acid methyl ester (0.310 g), and NaHCO₃ (0.145 g) were dissolved in a mixture of 1,2-dimethoxyethane (9 mL) and water (3 mL). The solution was degassed with nitrogen, and Pd(PPh₃)₄ (0.0260 g) was added. The reaction mixture was stirred at 80° C. for 24 hours and evaporated under vacuum. Solid was dissolved in DCM (20 mL) and extracted twice with water (10 mL) and once with brine (10 mL). The resulting oil was subjected to silica gel chromatography using a 40 g ISCO column and effluent of 0-5% MeOH:DCM. The fractions containing product were combined and the solvent was removed under reduced pressure. Oil was dissolved in DMF, purified by reverse phase HPLC (5-70% acetonitrile:water), and lyophilized, giving [1-(3-{5-[6-(4-{2-[1-(2-Methoxycarbonylamino-propionyl)-pyrrolidin-2-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (0.150 g, 36%) as a white solid.

¹H-NMR: 300 MHz, (CH₃OH-d₁) $\delta$: 8.3 (d, J=9 Hz, 2H), 8.1 (m, 2H), 8.0 (m, 4H), 7.9 (m, 4H), 5.3 (m, 2H), 4.7 (s, 2H), 4.5 (m, 1H), 4.3 (d, J=7 Hz, 1H), 4.0 (m, 2H), 3.7 (d, J=7 Hz, 6H), 3.3 (s, 6H), 2.9 (s, 1H), 2.3 (m, 2H), 2.1 (m, 8H), 2.0 (m, 2H), 1.8 (m, 2H), 1.3 (d, J=7 Hz, 3H) 1.0 (m, 6H); MS (ESI): m/z 787 [M+H]⁺.

Example EX

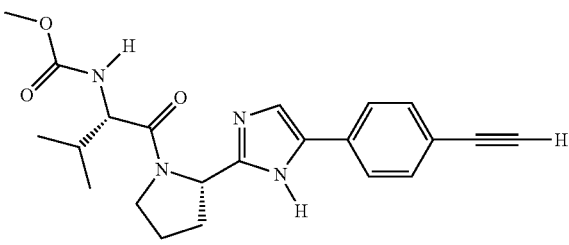

(1-{2-[5-(4-Ethynyl-phenyl)-1H-imidazol-2-yl]-pyrrolidine-1-carbonyl]-2-methyl-propyl)-carbamic acid methyl ester

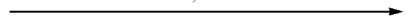

Pd(PPh₃)₄, CuI, Et₃N,
3-[5-(4-Bromo-phenyl)-1H-imidazol-2-yl]-2-aza-bicyclo[2.2.1]heptane-2-carboxylic acid tert-butyl ester
DMF, 80° C.

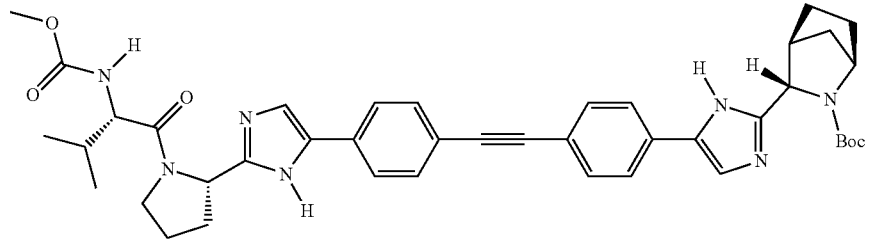

3-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carboxylic acid tert-butyl ester

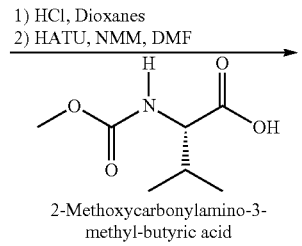

1) HCl, Dioxanes
2) HATU, NMM, DMF

2-Methoxycarbonylamino-3-methyl-butyric acid

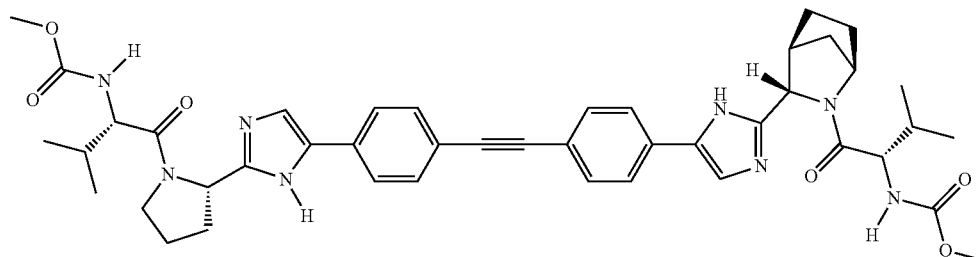

[1-(3-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carbonyl)-2-methyl-propyl]-carbamic acid methyl ester 3-{5-[4-(4-[2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carboxylic acid tert-butyl ester A solution of (1-{2-[5-(4-Ethynyl-phenyl)-1H-imidazol-2-yl]-pyrrolidine-1-carbonyl}-2-methyl-propyl)-carbamic acid methyl ester (500 mg, 1.27 mmol), 3-[5-(4-Bromo-phenyl)-1H-imidazol-2-yl]-2-aza-bicyclo[2.2.1]heptane-2-carboxylic acid tert-butyl ester (530 mg, 1.27 mmol), and triethylamine (531 □L, 3.81 mmol) in DMF (6.4 mL) was degassed with $N_2$ gas for 20 minutes. To the degassed solution was added Pd(PPh$_3$)$_4$ (150 mg, 0.13 mmol) and CuI (25 mg, 0.13 mmol). The pressure flask was sealed then heated at 80° C. overnight. After cooling to room temperature, the reaction was quenched with AcOH then purified by reverse phase preparative HPLC (10-70% MeCN—H$_2$O; 0.1% formic acid modifier) then silica gel chromatography (0-10% MeOH-EtOAc gradient) to afford 3-{5-[4-(4-[2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carboxylic acid tert-butyl ester (500 mg, 0.68 mmol, 54% yield). LCMS-ESI$^+$: calc'd for $C_{42}H_{50}N_7O_5$: 732.4 (M+H$^+$); Found: 732.2 (M+H$^+$).

[1-(3-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carbonyl)-2-methyl-propyl]-carbamic acid methyl ester To 3-{5-[4-(4-[2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carboxylic acid tert-butyl ester (150 mg, 0.20 mmol) in dioxanes (2 mL) was added 4N HCl in dioxanes (250 □L). The suspension was stirred for 2 hours then concentrated to afford the HCl salt of the crude amine. To the crude amine in DMF (4 mL) was added N-methylmorpholine (330 □L, 0.30 mmol). After all material dissolved, 2-methoxycarbonylamino-3-methyl-butyric acid (53 mg, 0.30 mmol) and HATU (76 mg, 0.20 mmol) were added. After stirring for overnight the reaction was quenched with AcOH then purified by reverse phase preparative HPLC (5-45% MeCN—H$_2$O; 0.1% formic acid modifier) to afford the title product [1-(3-{5-[4-(4-{2-[1-(2-Methoxycarbonylamino-3-methyl-butyryl)-pyrrolidin-2-yl]-3H-imidazol-4-yl}-phenylethynyl)-phenyl]-1H-imidazol-2-yl}-2-aza-bicyclo[2.2.1]heptane-2-carbonyl)-2-methyl-propyl]-carbamic acid methyl ester (83 mg, 0.11 mmol, 53% yield). $^1$H-NMR: 400 MHz, (DMSO-d$_6$) δ: 7.59-7.55 (m, 4H), 7.41-7.38 (m, 4H), 7.17 (s, 1H), 7.15 (s, 1H), 6.16 (m, 2H), 5.15 (m, 1H), 4.63 (s, 1H), 4.50 (s, 1H), 4.34-4.24 (m, 2H), 3.88-3.72 (m, 2H), 3.63 (s, 3H), 3.61 (s, 3H), 2.88 (m, 1H), 2.25-2.15 (m, 1H), 2.27-2.16 (m, 2H), 2.05-1.80 (m, 5H), 1.54 (d, 2H), 1.00-0.887 (m, 12H). LCMS-ESI$^+$: calc'd for $C_{44}H_{53}N_8O_6$: 789.4 (M+H$^+$); Found: 789.5 (M+H$^+$).

Example EY

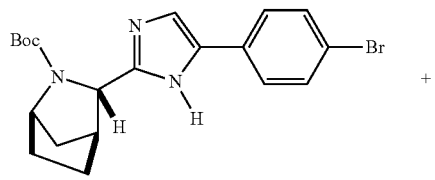

3-[5-(4-Bromo-phenyl)-1H-imidazol-2yl]-2-aza-bicyclo[2.21]heptane-2-carboxylic acid tert-butyl ester

+

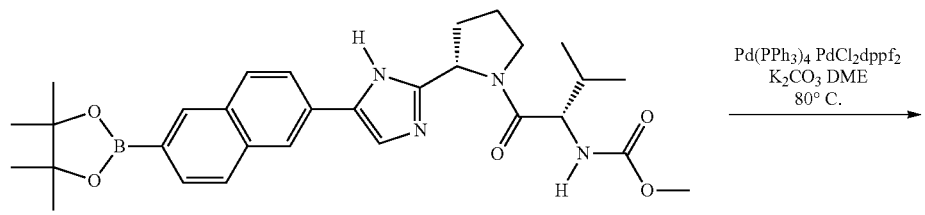

[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester

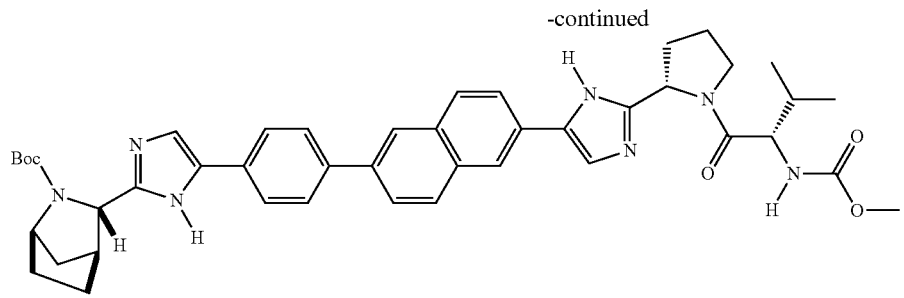
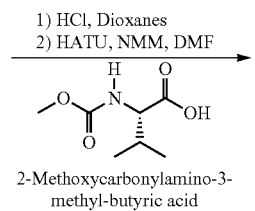

3-{5-[4-(6-{2-[1-(2-Methoxycarbonylamino-3-methyl-butyryl)-pyrrolidin-2-yl]-3H-imidazol-4-yl}-napthalen-2-yl)-phenyl]-1H-imidazol-2-yl}-2-aza-bicyclo[2.2.1]heptane-2-carboxylic acid tert-butyl ester

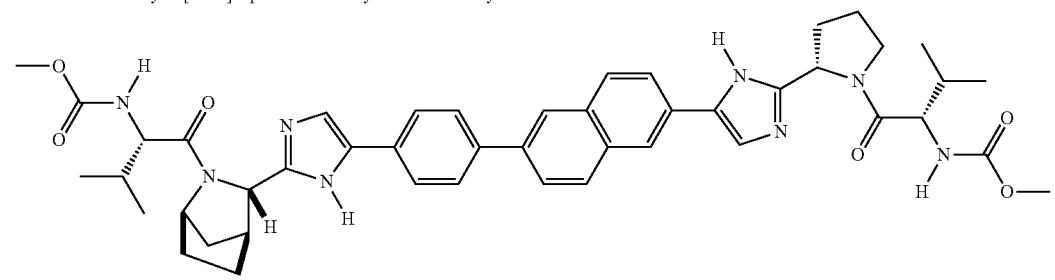

[1-(2-{5-[6-(4-{2-[2-(2-Methoxycarbonylamino-3-methyl-butyryl)-2-aza-bicyclo[2.2.1]hept-3-yl]-3H-imidazol-4-yl}phenyl)-naphthalen-2-yl]-1H-imidazol-2-yl}-pyrrolidine-1-carbonyl)-2-methyl-propyl]-carbamic acid methyl ester 3-{5-[4-(6-[2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester A solution of [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (500 mg, 0.92 mmol), 3-[5-(4-Bromo-phenyl)-1H-imidazol-2-yl]-2-aza-bicyclo[2.2.1]heptane-2-carboxylic acid tert-butyl ester (383 mg, 0.92 mmol) and aq $K_2CO_3$ (920 μl of a 2M solution, 1.84 mmol) in DME (9 mL) was degassed with $N_2$ gas for 20 minutes. To the degassed solution was added $Pd(PPh_3)_4$ (106 mg, 0.092 mmol) and $PdCl_2dppf$ (75 mg, 0.092 mmol) and then the reaction was heated to 80° C. overnight. After cooling to room temperature, the reaction was quenched with acetic acid, filtered, and then concentrated. The crude product was purified by reverse phase preparative HPLC (5-50% MeCN—$H_2O$; 0.1% formic acid modifier) to afford 3-{5-[4-(6-[2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (112 mg, 0.15 mmol, 16% yield). LCMS-ESI$^+$: calc'd for $C_4H_{52}N_7O_5$: 758.4 (M+H$^+$); Found: 758.0 (M+H$^+$).

[1-(2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester To 3-{5-[4-(6-[2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (60 mg, 0.092 mmol) in dioxanes (3 mL) was added 4N HCl in dioxanes (1 mL). The suspension was stirred overnight then concentrated to afford the HCl salt of the crude amine, which was purified by reverse phase preparative HPLC (5-45% MeCN—$H_2O$; 0.1% formic acid modifier) and concentrated. The formate salt was dissolved in MeOH then passed through an ion-exchange column (StratoSpheres SPE PL-HCO$_3$ MP SE) to afford the free amine (30 mg, 0.046 mmol, 58%). To the amine (30 mg, 0.046 mmol) in DMF (1 mL) was added N-methylmorpholine (10 □L, 0.092 mmol). After all material dissolved, 2-methoxycarbonylamino-3-methyl-butyric acid (12 mg, 0.068 mmol) and HATU (19 mg, 0.051 mmol) were added. After stirring for 3 hours the reaction was quenched with AcOH then purified by reverse phase preparative HPLC (5-45% MeCN—$H_2O$; 0.1% formic acid modifier) to afford [1-(2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (29 mg, 0.036 mmol, 77% yield). $^1$H-NMR: 400 MHz, (DMSO-d$_6$) δ: 8.04 (s, 1H), 7.86 (s, 1H), 7.71 (d, 2H), 7.63-7.58 (m, 4H), 7.52 (d, 2H), 7.26 (s, 1H), 7.14 (s, 1H), 6.17 (m, 2H), 5.21 (m, 1H), 4.67 (s, 1H), 4.52 (s, 1H), 4.35-4.26 (m, 2H), 3.86 (m, 1H), 3.79 (m, 1H), 3.64 (s, 6H), 2.90 (m, 1H), 2.43 (m, 1H), 2.30-2.1.82 (m, 9H), 1.55 (d, 2H), 1.02-0.87 (m, 12H). LCMS-ESI$^+$: calc'd for $C_{46}H_{55}N_8O_6$: 815.3 (M+H$^+$); Found: 815.4 (M+H$^+$).

Example EZ

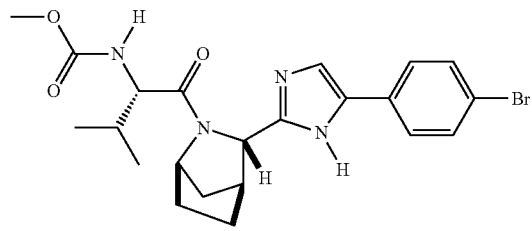

(1-{3-[5-(4-Bromo-phenyl)-1H-imidazol-2-yl]-2-aza-bicyclo[2.2.1]heptane-2-carbonyl}-2-methyl-propyl)-carbamic acid methyl ester

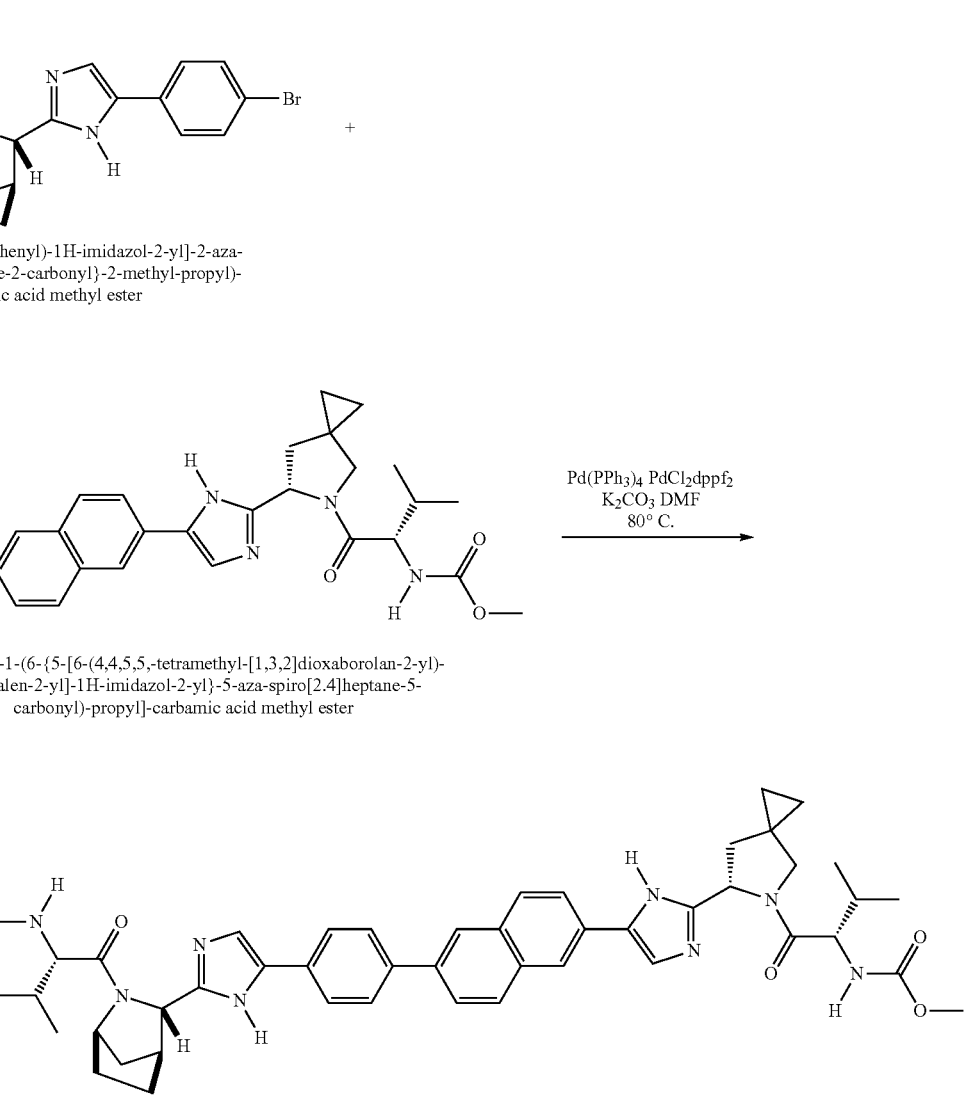

[1-(6-{5-[6-(4-{2-[2-(2-Methoxycarbonylamino-3-methyl-butyryl)-2-aza-bicyclo[2.2.1]hept-3-yl]-3H-imidazol-4yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester A solution of (1-{3-[5-(4-Bromo-phenyl)-1H-imidazol-2-yl]-2-aza-bicyclo[2.2.1]heptane-2-carbonyl}-2-methyl-propyl)-carbamic acid methyl ester (151 mg, 0.32 mmol), [2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4] heptane-5-carbonyl)-propyl]-carbamic acid methyl ester (200 mg, 0.35 mmol) and aq $K_2CO_3$ (438 µl of a 2M solution, 0.88 mmol) in DME (4 mL) was degassed with $N_2$ gas for 20 minutes. To the degassed solution was added Pd(PPh$_3$)$_4$ (40 mg, 0.035 mmol) and then the reaction was heated to 80° C. overnight. After cooling to room temperature, the reaction was quenched with acetic acid, filtered, and then concentrated. The crude product was purified by reverse phase preparative HPLC (5-50% MeCN—$H_2O$; 0.1% formic acid modifier) to afford [1-(6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester (40 mg, 0.047 mmol, 14% yield). $^1$H-NMR: 400 MHz, (DMSO-d$_6$) δ: 11.75 (s, 1H), 11.72 (s, 1H), 8.24 (s, 1H), 8.15 (d, 1H), 7.93-7.74 (m, 8H), 7.63 (s, 1H), 7.54 (s, 1H), 7.30 (d, 1H), 7.16 (d, 1H), 5.22 (t, 1H), 4.52-4.50 (m, 2H), 4.16 (t, 1H), 4.00 (t, 1H), 3.81 (d, 1H), 3.75 (d, 1H), 3.72 (s, 3H), 3.31 (s, 3H), 2.55 (m, 1H), 2.32-1.41 (m, 10H), 1.01-0.57 (m, 16H). LCMS-ESI$^+$: calc'd for $C_{48}H_{57}N_8O_6$: 841.4 (M+H$^+$); Found: 842.1 (M+H$^+$).

Example FA and FB
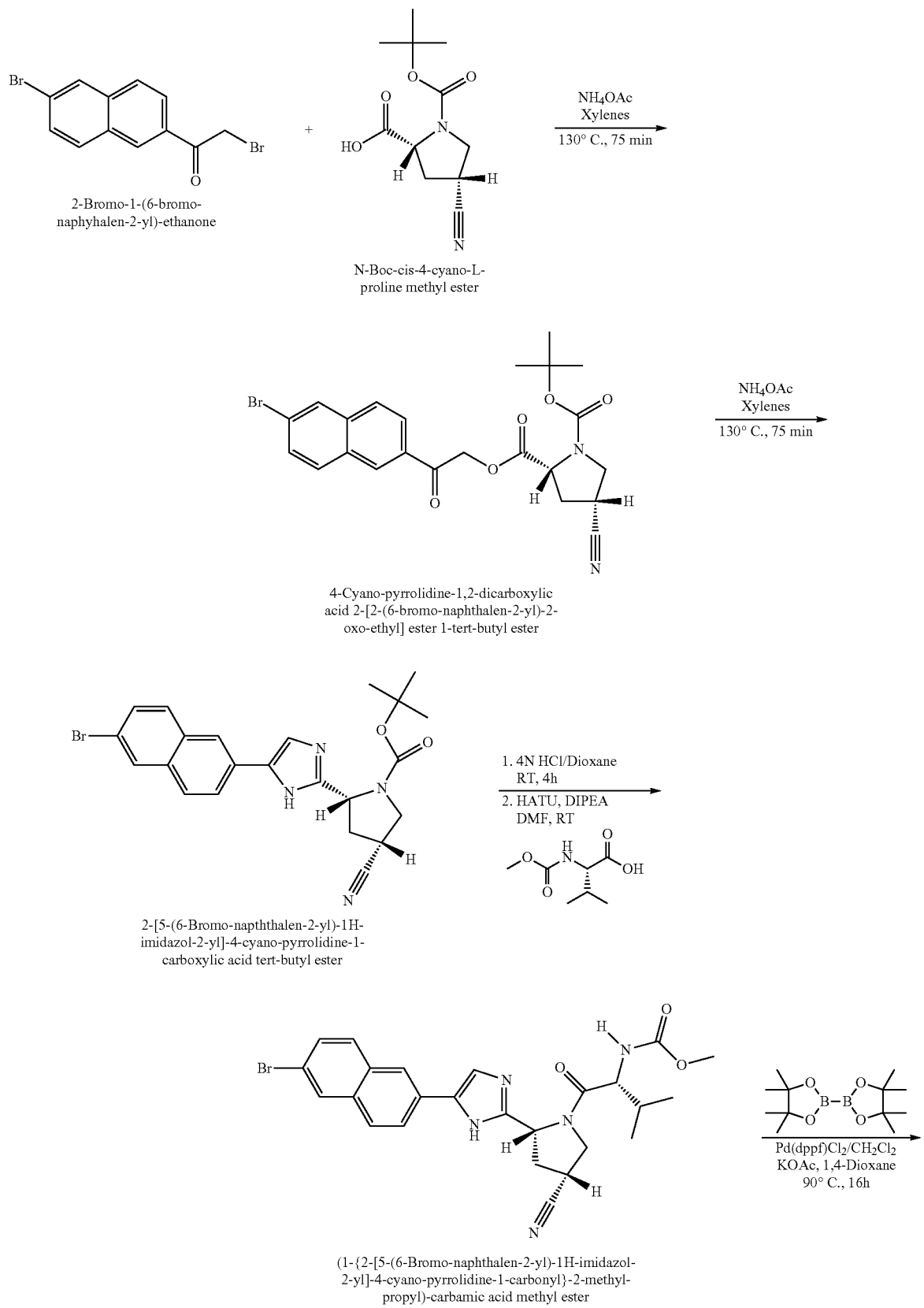

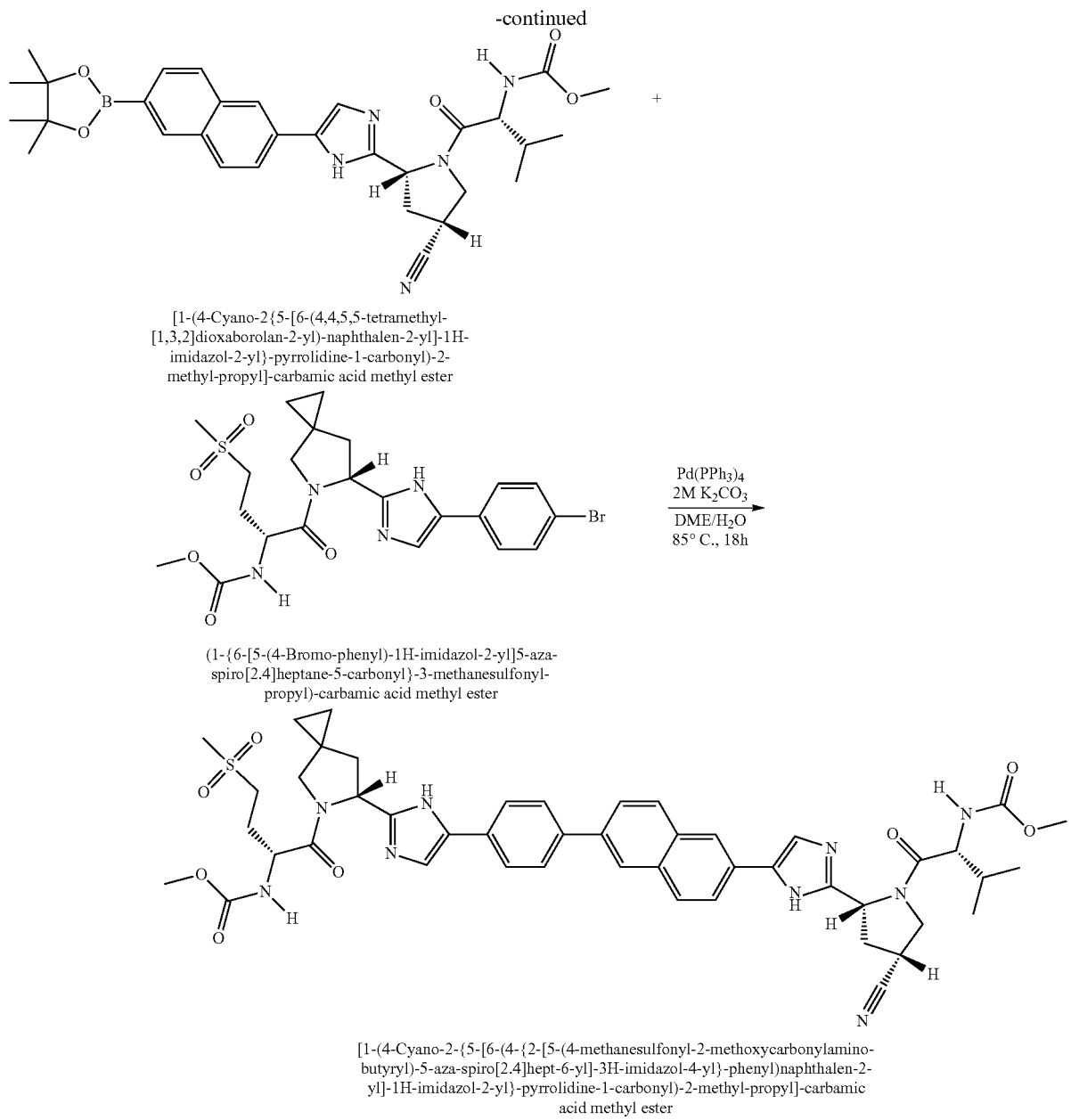

[1-(4-Cyano-2{5-[6-(4,4,5,5-tetramethyl-[1,3,2]dioxaborolan-2-yl)-naphthalen-2-yl]-1H-imidazol-2-yl}-pyrrolidine-1-carbonyl)-2-methyl-propyl]-carbamic acid methyl ester (1-{6-[5-(4-Bromo-phenyl)-1H-imidazol-2-yl]5-aza-spiro[2.4]heptane-5-carbonyl}-3-methanesulfonyl-propyl)-carbamic acid methyl ester

[1-(4-Cyano-2-{5-[6-(4-{2-[5-(4-methanesulfonyl-2-methoxycarbonylamino-butyryl)-5-aza-spiro[2.4]hept-6-yl]-3H-imidazol-4-yl}-phenyl)naphthalen-2-yl]-1H-imidazol-2-yl}-pyrrolidine-1-carbonyl)-2-methyl-propyl]-carbamic acid methyl ester

4-Cyano-pyrrolidine-1,2-dicarboxylic acid 2-[2-(6-bromo-naphthalen-2-yl)-2-oxo-ethyl]ester 1-tert-butyl ester Title compound was prepared according to the method employed to prepare pyrrolidine-1,2-dicarboxylic acid 2-[2-(6-bromo-naphthalen-2-yl)-2-oxo-ethyl]ester 1-tert-butyl ester in Example CL, substituting pyrrolidine-1,2-dicarboxylic acid 1-tert-butyl ester with N-Boc-cis-4-cyano-L-proline methyl ester (643 mg, 67%)

2-[5-(6-Bromo-naphthalen-2-yl)-1H-imidazol-2-yl]-4-cyano-pyrrolidine-1-carboxylic acid tert-butyl ester Title compound was prepared according to the method employed to prepare 2-[5-(6-Bromo-naphthalen-2-yl)-1H-imidazol-2-yl]-pyrrolidine-1-carboxylic acid tert-butyl ester: in Example CL, changing the reaction temperature to 130° C. and the reaction time to 75 minutes. (396 mg, 64%) MS (ESI) m/z 468.99 [M+H]⁺.

(1-{2-[5-(6-Bromo-naphthalen-2-yl)-1H-imidazol-2-yl]-4-cyano-pyrrolidine-1-carbonyl}-2-methyl-propyl)-carbamic acid methyl ester Title compound was prepared according to the method employed to prepare (1-{2-[5-(7-{2-[1-(2-Methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester and (1-{2-[5-(8-[2-[1-(2-Methoxycarbonylamino-3-methyl-butyryl)-pyrrolidin-2-yl]-3H-imidazol-4-yl}-thianthren-2-yl)-1H-imidazol-2-yl]-pyrrolidine-1-carbonyl}-2-methyl-propyl)-carbamic acid methyl ester in Example BS, substituting N-methylmorpholine with five equivalents of diisopropyl-ethylamine. (430 mg, 97%) MS (ESI) m/z 525.94 [M+H]⁺.

[1-(4-Cyano-2-{5-[6-(4,4,5,5-tetramethyl-[1,3,2] dioxaborolan-2-yl)-naphthalen-2-yl]-1H-imidazol-2-yl}-pyrrolidine-1-carbonyl)-2-methyl-propyl]-carbamic acid methyl ester Title compound was prepared according to the method employed to prepare 2-[6-(4,4,5,5-Tetramethyl-[1,3,2]dioxaborolan-2-yl)-1H-benzoimidazol-2-yl]-pyrrolidine-1-carboxylic acid tert-butyl ester in Example CL, replacing N-Boc Proline with N-Boc-4-cyano-proline. (407 mg, 87%) MS (ESI) m/z 572.46 [M+H]⁺.

(1-{6-[5-(4-Bromo-phenyl)-1H-imidazol-2-yl]-5-aza-spiro[2.4]heptane-5-carbonyl}-3-methanesulfonyl-propyl)-carbamic acid methyl ester

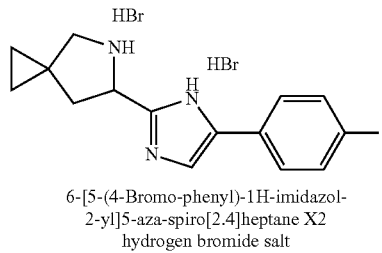

6-[5-(4-Bromo-phenyl)-1H-imidazol-2-yl]5-aza-spiro[2.4]heptane X2 hydrogen bromide salt

+

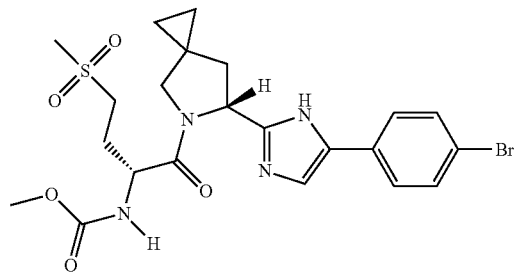

(1-{6-[5-(4-Bromo-phenyl)-1H-imidazol-2-yl}-5-aza-spiro[2.4]heptane-5-carbonyl}-3-methanesulfonyl-propl)-carbamic acid methyl ester

+

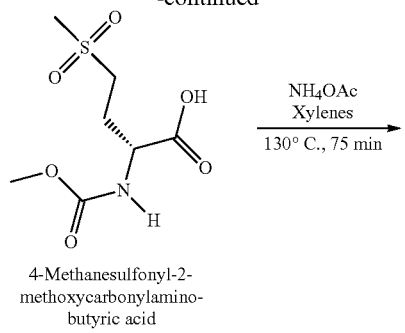

4-Methanesulfonyl-2-methoxycarbonylamino-butyric acid

NH₄OAc
Xylenes
130° C., 75 min
→

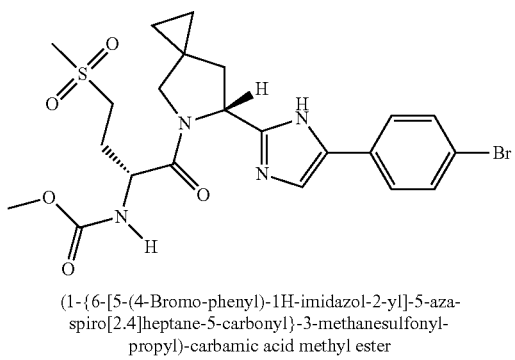

(1-{6-[5-(4-Bromo-phenyl)-1H-imidazol-2-yl]-5-aza-spiro[2.4]heptane-5-carbonyl}-3-methanesulfonyl-propyl)-carbamic acid methyl ester Title compound was prepared according to the method employed to prepare (1-{2-[5-(4-Bromonaphthalen-1-yl)-1H-imidazol-2-yl]-pyrrolidine-1-carbonyl}-2-methyl-propyl)-carbamic acid methyl ester in Example CK, substituting N-methylmorpholine with five equivalents of diisopropyl-ethylamine. (99%)

Example FA

[1-(4-Cyano-2-{5-[6-(4-{2-[5-(4-methanesulfonyl-2-methoxycarbonylamino-butyryl)-5-aza-spiro[2.4] hept-6-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Pd(PPh₃)₄
2M K₂CO₃
DME/H₂O
85° C., 18h
→

-continued

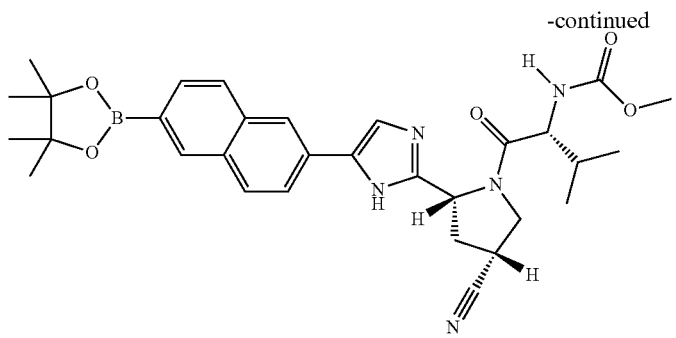

[1-(4-Cyano-2-{5-[6-(4,4,5,5-tetramethyl-
[1,3,2]dioxaborolan-2-yl)-naphthalen-2-yl]-1H-imidazol-
2-yl}-pyrrolidine-1-carbonyl)-2-methyl-propyl]-
carbamic acid methyl ester

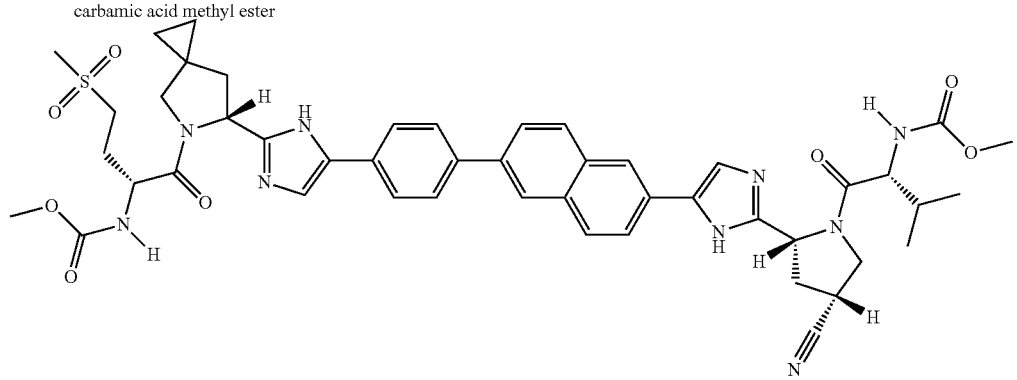

[1-(4-Cyano-2-{5-[6-(4-{2-[5-(4-methanesulfonyl-2-methoxycarbonylamino-
butyryl)-5-aza-spiro[2.4]hept-6-yl]-3H-imidazol-4-yl}-phenyl)-naphthalen-2-
yl]-1H-imidazol-2-yl}-pyrrolidine-1-carbonyl)-2-methyl-propyl]-carbamic
acid methyl ester Title compound was prepared according to the method employed to prepare (1-{2-[5-(6'-{2-[1-(2-Methoxycarbonylamino-3-methyl-butyryl)-pyrrolidin-2-yl]-3H-imidazol-4-yl}-[2,2']binaphthalenyl-6-yl)-1H-imidazol-2-yl]-pyrrolidine-1-carbonyl}-2-methyl-propyl)-carbamic acid methyl ester in Example CL. (30%)

$^1$H-NMR: 400 MHz, (CD$_3$OD) δ 8.14 (s, 2H), 8.09 (d, J=5.6 Hz, 1H), 7.92 (d, J=7.6 Hz, 2H), 7.85-7.78 (m, 5H), 7.46 (s, 1H), 7.41 (s, 1H), 5.33 (dd, J=5.6 Hz, 7.6 Hz, 1H), 5.21 (t, J=8.4 Hz, 1H), 4.63-4.58 (m, 2H), 4.17-4.13 (m, 1H), 4.05 (t, J=10.4 Hz, 1H), 3.83 (s, 2H), 3.65 (d, J=5.2 Hz, 6H), 3.48-3.42 (m, 3H), 3.21 (t, J 7.6 Hz, 2H), 2.98 (s, 1H), 2.95 (s, 2H), 2.92-2.84 (m, 1H), 2.64-2.55 (m, 1H), 2.35-2.27 (m, 2H), 2.14-1.92 (m, 4H), 0.98-0.87 (m, 7H), 0.79-0.59 (m, 4H). MS (ESI) m/z 904.58 [M+H]$^+$.

Example FB

[1-(4-Cyano-2-{5-[6-(4-{2-[2-(2-methoxycarbony-
lamino-3-methyl-butyryl)-2-aza-bicyclo[2.2.1]hept-
3-yl]-3H-imidazol-4-yl}-phenyl)-naphthalen-2-yl]-
1H-imidazol-2-yl}-pyrrolidine-1-carbonyl)-2-
methyl-propyl]-carbamic acid methyl ester

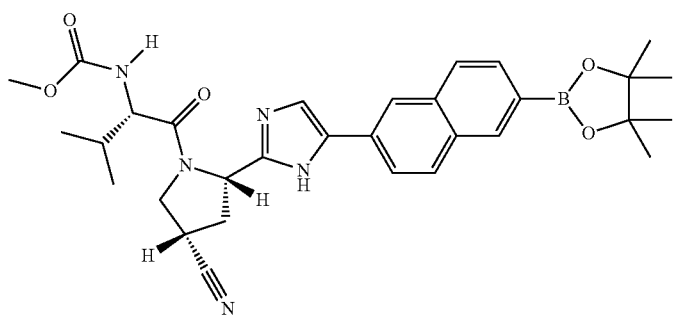

[1-(4-Cyano-2-(5-[6-(4,4,5,5-tetramethyl-
[1,3,2]dioxaborolan-2-yl)-naphthalen-2-yl]-1H-
imidazol-2-yl}-pyrrolidine-1-carbonyl)-2-methyl-
propyl]-carbamic acid methyl ester

+

Pd(PPh$_3$)$_4$
2M K$_2$CO$_3$
―――――→
DME/H$_2$O
85° C., 18h

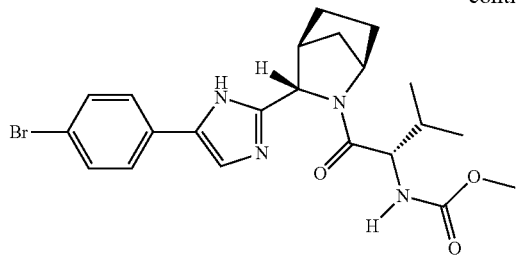

(1-{3-[5-(4-Bromo-phenyl)-1H-imidazol-2-yl]-
2-aza-bicyclo[2.2.1]heptane-2-carbonyl]-2-
methyl-propyl)-carbamic acid methyl ester

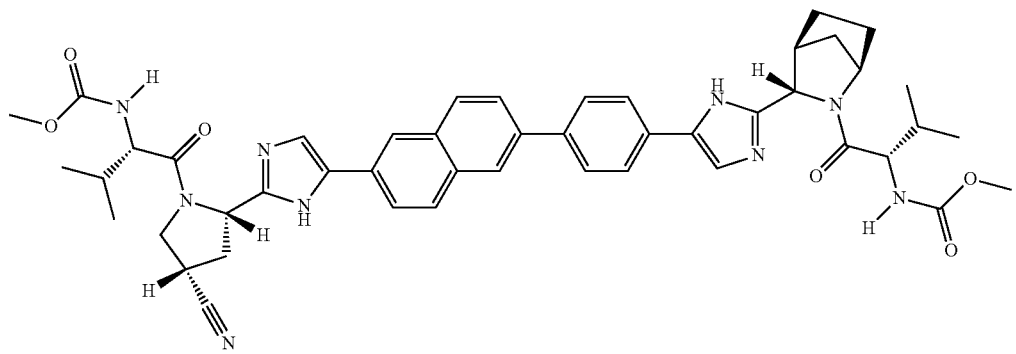

[1-(4-Cyano-2-{5-[6-(4-{2-[2-(2-methoxycarbonylamino-3-methyl-butyryl)-2-aza-
bicyclo[2.2.1]hept-3-yl]-3H-imidazol-4-yl}-phenyl)-naphthalen-2-yl]-1H-imidazol-
2-yl}pyrrolidine-1-carbonyl)-2-methyl-propyl]carbamic acid methyl ester Title compound was prepared according to the method employed to prepare (1-{2-[5-(6'-{2-[1-(2-Methoxycarbonylamino-3-methyl-butyryl)-pyrrolidin-2-yl]-3H-imidazol-4-yl}-[2,2']binaphthalenyl-6-yl)-1H-imidazol-2-yl]-pyrrolidine-1-carbonyl}-2-methyl-propyl)-carbamic acid methyl ester in Example CL. (35%)

:$^1$H-NMR: 400 MHz, (CD$_3$OD) δ 8.22 (s, 1H), 8.15 (s, 1H), 8.07 (s, 1H), 7.92 (dd, J=2 Hz, 8.4 Hz, 2H), 7.85-7.76 (m, 6H), 7.44 (s, 1H), 7.33 (s, 1H), 5.21 (t, J=8.8 Hz, 1H), 4.71 (s, 1H), 4.62-4.55 (m, 2H), 4.33-4.27 (m, 1H), 4.16 (d, J=7.6 Hz, 1H), 4.05 (t, J=10.4 Hz, 1H), 3.65 (d, J=5.6 Hz, 4H), 3.51 (m, 2H), 2.90 (m, 1H), 2.76 (s, 1H), 2.64 (m, 1H), 2.29 (d, J=9.6 Hz, 1H), 2.19-2.10 (m, 1H), 2.00-1.84 (m, 4H), 1.65-1.56 (m, 2H), 1.31 (m, 1H), 1.02 (d, J=6.8 Hz, 2H), 0.971-0.86 (m, 8H). MS (ESI) m/z 840.64 [M+H]$^+$.

Example FC

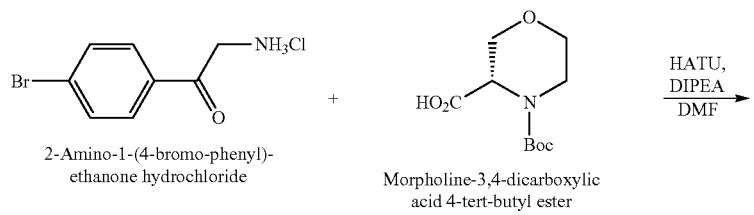

2-Amino-1-(4-bromo-phenyl)-
ethanone hydrochloride

Morpholine-3,4-dicarboxylic
acid 4-tert-butyl ester

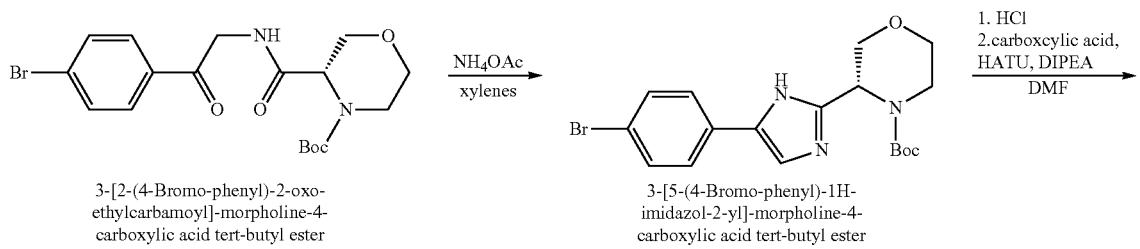

3-[2-(4-Bromo-phenyl)-2-oxo-
ethylcarbamoyl]-morpholine-4-
carboxylic acid tert-butyl ester 3-[5-(4-Bromo-phenyl)-1H-
imidazol-2-yl]-morpholine-4-
carboxylic acid tert-butyl ester

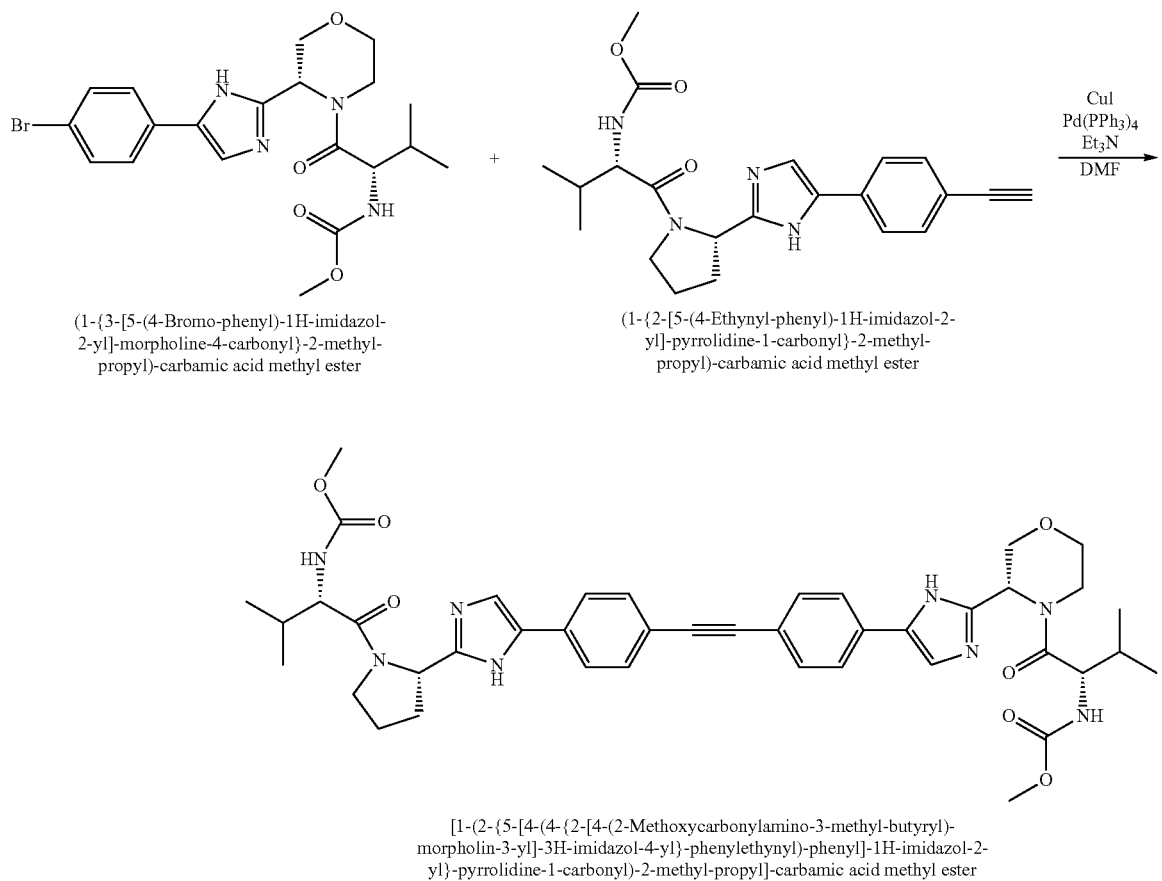

(1-{3-[5-(4-Bromo-phenyl)-1H-imidazol-2-yl]-morpholine-4-carbonyl}-2-methyl-propyl)-carbamic acid methyl ester (1-{2-[5-(4-Ethynyl-phenyl)-1H-imidazol-2-yl]-pyrrolidine-1-carbonyl}-2-methyl-propyl)-carbamic acid methyl ester

[1-(2-{5-[4-(4-{2-[4-(2-Methoxycarbonylamino-3-methyl-butyryl)-morpholin-3-yl]-3H-imidazol-4-yl}-phenylethynyl)-phenyl]-1H-imidazol-2-yl}-pyrrolidine-1-carbonyl)-2-methyl-propyl]-carbamic acid methyl ester

3-[2-(4-Bromo-phenyl)-2-oxo-ethylcarbamoyl]-morpholine-4-carboxylic acid tert-butyl ester Title compound was prepared according to the method employed to prepare 3-[2-(4-Bromo-phenyl)-2-oxo-ethylcarbamoyl]-2-aza-bicyclo[2.2.1]heptane-2-carboxylic acid tert-butyl ester (Example AE), substituting Morpholine-3,4-dicarboxylic acid 4-tert-butyl ester for 2-aza-bicyclo[2.2.1]heptane-2,3-dicarboxylic acid 2-tert-butyl ester.

3-[5-(4-Bromo-phenyl)-1H-imidazol-2-yl]-morpholine-4-carboxylic acid tert-butyl ester Title compound was prepared according to the method employed to prepare 3-[5-(4-Bromo-phenyl)-1H-imidazol-2-yl]-2-aza-bicyclo[2.2.1]heptane-2-carboxylic acid tert-butyl ester (Example AS), substituting 3-[2-(4-Bromo-phenyl)-2-oxo-ethylcarbamoyl]-morpholine-4-carboxylic acid tert-butyl ester for 3-[2-(4-bromo-phenyl)-2-oxo-ethylcarbamoyl]-2-aza-bicyclo[2.2.1]heptane-2-carboxylic acid tert-butyl ester.

(1-{3-[5-(4-Bromo-phenyl)-1H-imidazol-2-yl]-morpholine-4-carbonyl}-2-methyl-propyl)-carbamic acid methyl ester Title compound was prepared according to the method employed to prepare {1-[2-(4'-Bromo-biphenyl-4-ylcarbamoyl)-pyrrolidine-1-carbonyl]-2-methyl-propyl}-carbamic acid methyl ester (Example CY), substituting 3-[5-(4-Bromo-phenyl)-1H-imidazol-2-yl]-morpholine-4-carboxylic acid tert-butyl ester for 2-(4'-Bromo-biphenyl-4-ylcarbamoyl)-pyrrolidine-1-carboxylic acid tert-butyl ester.

[1-(2-{5-[4-(4-{2-[4-(2-Methoxycarbonylamino-3-methyl-butyryl)-morpholin-3-yl]-3H-imidazol-4-yl}-phenylethynyl)-phenyl]-1H-imidazol-2-yl}-pyrrolidine-1-carbonyl)-2-methyl-propyl]-carbamic acid methyl ester Title compound was prepared according to the method employed to prepare Methoxycarbonylamino-3-methyl-butyryl)-pyrrolidin-2-yl]-3H-imidazol-4-ylethynyl}-phenylethynyl)-1H-imidazol-2-yl]-pyrrolidine-1-carbonyl}-2-methyl-propyl)-carbamic acid methyl ester (Example CT), substituting (1-{3-[5-(4-Bromo-phenyl)-1H-imidazol-2-yl]-morpholine-4-carbonyl}-2-methyl-propyl)-carbamic acid methyl ester for (1-{2-[5-(4-bromo-phenylethynyl)-1H-imidazol-2-yl]-pyrrolidine-1-carbonyl}-2-methyl-propyl)-carbamic acid methyl ester. $^1$H-NMR: 400 MHz, (DMSO-$d_6$) δ 12.05 (s, 1H), 11.84 (s, 1H), 7.81-7.74 (m, 4H), 7.69 (s, 1H), 7.56 (s, 1H), 7.50-7.47 (m, 4H), 7.32-7.27 (m, 2H), 4.42-4.34 (m, 2H), 4.08-3.95 (m, 2H), 3.85-3.79 (m, 3H), 3.72-3.68 (m, 2H), 3.56 (d, J=7.6 Hz, 5H), 3.46-3.40 (m, 2H), 2.2-2.07 (m, 3H), 2.01-1.90 (m, 4H), 1.02-1.00 (d, J=6.4 Hz, 2H), 0.953-0.837 (m, 12H); MS (ESI) m/z 779 [M+H]$^+$.

Example FD
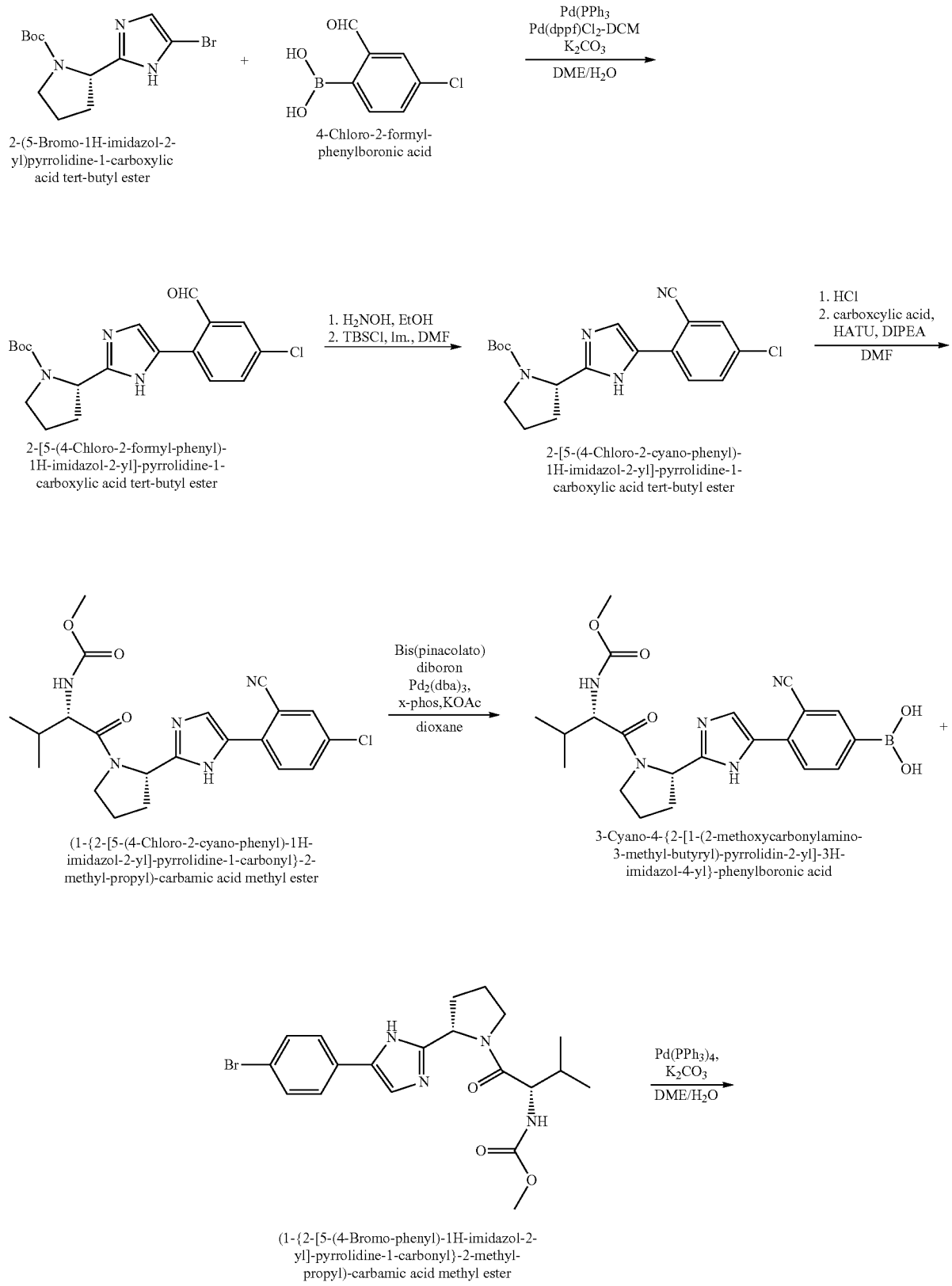

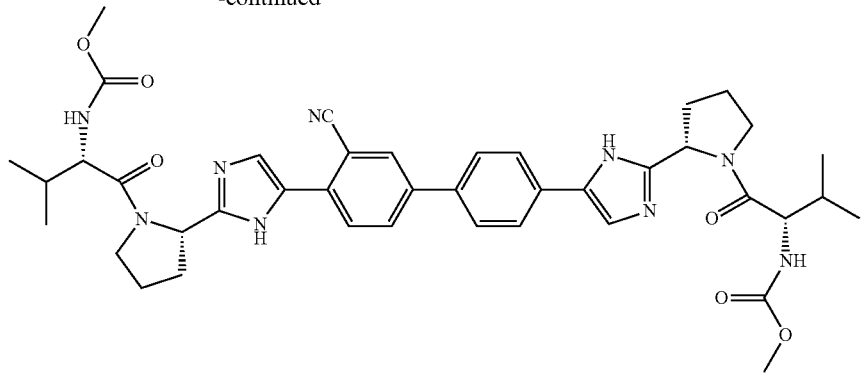

(1-{2-[5-(3-Cyano-4'-{2-[1-(2-methoxycarbonylamino-3-methyl-butyryl)-
pyrrolidin-2-yl]-3H-imidazol-4-yl}-biphenyl-4-yl)-1H-imidazol-2-yl]-
pyrrolidine-1-carbonyl}-2-methyl-propyl)-carbamic acid methyl ester 2-[5-(4-Chloro-2-formyl-phenyl)-1H-imidazol-2-yl]-pyrrolidine-1-carboxylic acid tert-butyl ester 2-(5-Bromo-1H-imidazol-2-yl)-pyrrolidine-1-carboxylic acid tert-butyl ester (2.00 g, 6.32 mmol), 4-Chloro-2-formyl-phenylboronic acid (1.17 g, 6.32 mmol), Pd(PPh$_3$)$_4$ (365 mg, 0.316 mmol), Pd(dppf)C$_{12}$-DCM (258 mg, 0.316 mmol) K$_2$CO$_3$ (2 M, 6.3 mL, 12.6 mmol) and DME (30 mL) were combined in a round bottom flask. The stirred suspension was degassed for 10 minutes with bubbling N$_2$ then heated to 85° C. After 4 h, the reaction mixture was poured into saturated aqueous NaHCO$_3$. The aqueous phase was extracted 3× with EtOAc and the combined organics were dried over MgSO$_4$, filtered and concentrated under reduced pressure. The crude residue was purified by silica column chromatography (25% to 75% EtOAc/Hexane) to afford the title compound 2-[5-(4-Chloro-2-formyl-phenyl)-1H-imidazol-2-yl]-pyrrolidine-1-carboxylic acid tert-butyl ester (1.85 g, 78%).

2-[5-(4-Chloro-2-cyano-phenyl)-1H-imidazol-2-yl]-pyrrolidine-1-carboxylic acid tert-butyl ester 2-[5-(4-Chloro-2-formyl-phenyl)-1H-imidazol-2-yl]-pyrrolidine-1-carboxylic acid tert-butyl ester (985 mg, 2.62 mmol) was dissolved in ethanol (20 mL) and hydroxylamine (50% w/w in H$_2$O, 642 µL, 10.48 mmol) was added. After stirring at room temperature for 15 h, the solution was concentrated. To the crude oxime was added TBSCl (474 mg, 3.14 mmol), imidazole (357 mg, 5.24 mmol) and DMF (10 mL). The reaction mixture was stirred at 120° C. for 80 minutes at which point more TBSCl (237 mg, 1.58 mmol) and imidazole (177 mg, 2.60 mmol) were added. The reaction mixture was stirred an additional 17 hours at 120° C. then cooled to room temperature, diluted with EtOAc. The organic phase was washed with saturated aqueous NaHCO$_3$ and brine then dried over MgSO$_4$, filtered and concentrated under reduced pressure. The crude residue was purified by silica column chromatography (25% to 50% EtOAc/Hexane) to afford the title compound 2-[5-(4-Chloro-2-cyano-phenyl)-1H-imidazol-2-yl]-pyrrolidine-1-carboxylic acid tert-butyl ester (500 mg, 51%).

(1-{2-[5-(4-Chloro-2-cyano-phenyl)-1H-imidazol-2-yl]-pyrrolidine-1-carbonyl}-2-methyl-propyl)-carbamic acid methyl ester Title compound was prepared according to the method employed to prepare {1-[2-(4'-Chloro-biphenyl-3-ylcarbamoyl)-pyrrolidine-1-carbonyl]-2-methyl-propyl}-carbamic acid methyl ester (Example CX), substituting 2-[5-(4-Chloro-2-cyano-phenyl)-1H-imidazol-2-yl]-pyrrolidine-1-carboxylic acid tert-butyl ester for 2-(4'-Chloro-biphenyl-3-ylcarbamoyl)-pyrrolidine-1-carboxylic acid tert-butyl ester.

3-Cyano-4-{2-[1-(2-methoxycarbonylamino-3-methyl-butyryl)-pyrrolidin-2-yl]-3H-imidazol-4-yl}-phenylboronic acid Title compound was prepared according to the method employed to prepare 2-{5-[2'-Cyano-4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (Example CZ), substituting (1-{2-[5-(4-Chloro-2-cyano-phenyl)-1H-imidazol-2-yl]-pyrrolidine-1-carbonyl}-2-methyl-propyl)-carbamic acid methyl ester for 2-[5-(4'-Chloro-2'-cyano-biphenyl-4-yl)-1H-imidazol-2-yl]-pyrrolidine-1-carboxylic acid tert-butyl ester.

(1-{2-[5-(3-Cyano-4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting 3-Cyano-4-{2-[1-(2-methoxycarbonylamino-3-methyl-butyryl)-pyrrolidin-2-yl]-3H-imidazol-4-yl}-phenylboronic acid for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H-NMR: 400 MHz, (DMSO-d$_6$) δ 12.13 (s, 1H), 8.13-8.04 (m, 2H), 7.85-7.75 (m, 4H), 7.57 (s, 1H), 7.31 (dd, J=3.6 Hz, 8.4 Hz, 1H), 5.13-5.10 (m, 2H); MS (ESI) m/z 764 [M+H]$^+$.

Example FE

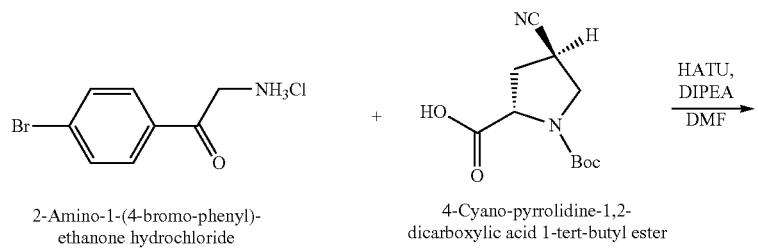

2-Amino-1-(4-bromo-phenyl)-
ethanone hydrochloride

4-Cyano-pyrrolidine-1,2-
dicarboxylic acid 1-tert-butyl ester

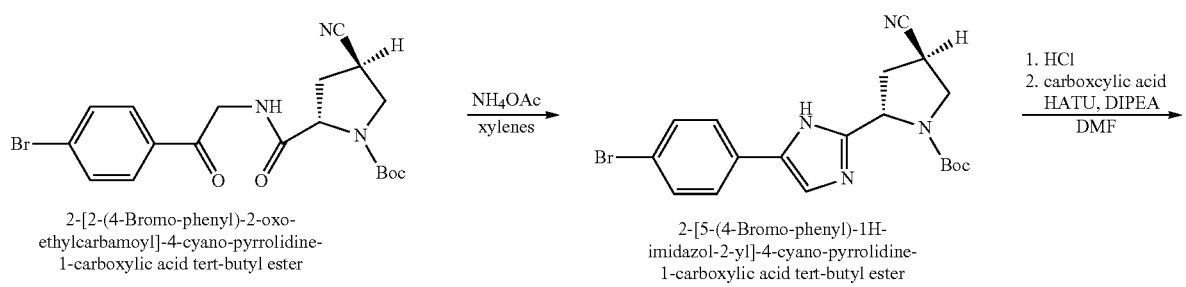

2-[2-(4-Bromo-phenyl)-2-oxo-
ethylcarbamoyl]-4-cyano-pyrrolidine-
1-carboxylic acid tert-butyl ester 2-[5-(4-Bromo-phenyl)-1H-
imidazol-2-yl]-4-cyano-pyrrolidine-
1-carboxylic acid tert-butyl ester

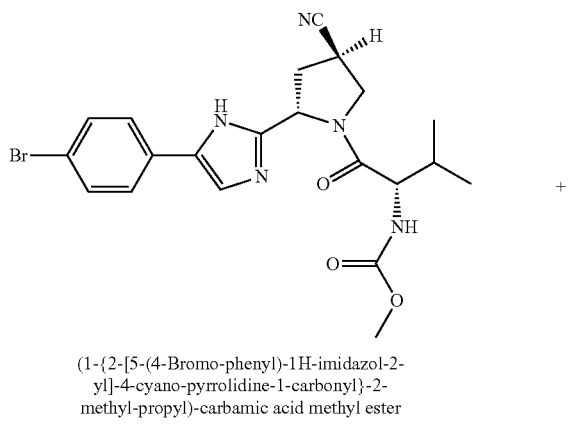

(1-{2-[5-(4-Bromo-phenyl)-1H-imidazol-2-
yl]-4-cyano-pyrrolidine-1-carbonyl}-2-
methyl-propyl)-carbamic acid methyl ester

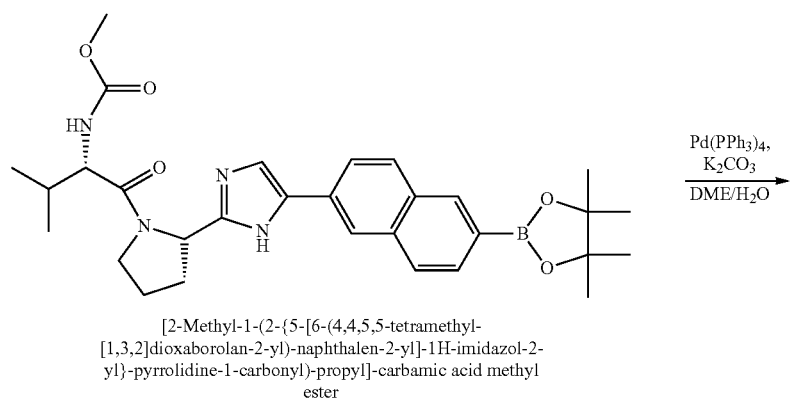

[2-Methyl-1-(2-{5-[6-(4,4,5,5-tetramethyl-
[1,3,2]dioxaborolan-2-yl)-naphthalen-2-yl]-1H-imidazol-2-
yl}-pyrrolidine-1-carbonyl)-propyl]-carbamic acid methyl
ester

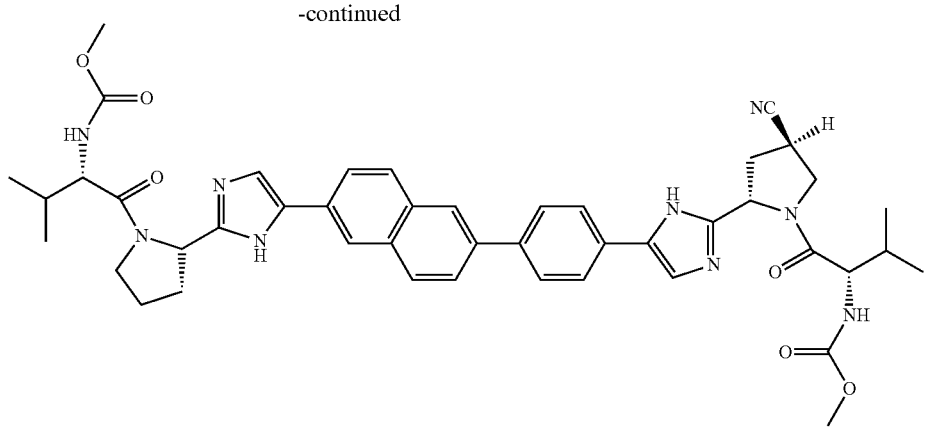

[1-(2-{5-[6-(4-{2-[4-Cyano-1-(2-methoxycarbonylamino-3-methyl-butyryl)-
pyrrolidin-2-yl]-3H-imidazol-4-yl}-phenyl)-naphthalen-2-yl]-1H-imidazol-2-
yl}-pyrrolidine-1-carbonyl)-2-methyl-propyl]-carbamic acid methyl ester

2-[2-(4-Bromo-phenyl)-2-oxo-ethylcarbamoyl]-4-cyano-pyrrolidine-1-carboxylic acid tert-butyl ester Title compound was prepared according to the method employed to prepare 3-[2-(4-Bromo-phenyl)-2-oxo-ethylcarbamoyl]-2-aza-bicyclo[2.2.1]heptane-2-carboxylic acid tert-butyl ester (Example AE), substituting 4-Cyano-pyrrolidine-1,2-dicarboxylic acid 1-tert-butyl ester for 2-aza-bicyclo[2.2.1]heptane-2,3-dicarboxylic acid 2-tert-butyl ester.

2-[5-(4-Bromo-phenyl)-1H-imidazol-2-yl]-4-cyano-pyrrolidine-1-carboxylic acid tert-butyl ester Title compound was prepared according to the method employed to prepare 3-[5-(4-Bromo-phenyl)-1H-imidazol-2-yl]-2-aza-bicyclo[2.2.1]heptane-2-carboxylic acid tert-butyl ester (Example AS), 2-[2-(4-Bromo-phenyl)-2-oxo-ethylcarbamoyl]-4-cyano-pyrrolidine-1-carboxylic acid tert-butyl ester for 3-[2-(4-bromo-phenyl)-2-oxo-ethylcarbamoyl]-2-aza-bicyclo[2.2.1]heptane-2-carboxylic acid tert-butyl ester.

(1-{2-[5-(4-Bromo-phenyl)-1H-imidazol-2-yl]-4-cyano-pyrrolidine-1-carbonyl}-2-methyl-propyl)-carbamic acid methyl ester Title compound was prepared according to the method employed to prepare {1-[2-(4'-Chloro-biphenyl-3-ylcarbamoyl)-pyrrolidine-1-carbonyl]-2-methyl-propyl}-carbamic acid methyl ester (Example CX), substituting 2-[5-(4-Bromo-phenyl)-1H-imidazol-2-yl]-4-cyano-pyrrolidine-1-carboxylic acid tert-butyl ester for 2-(4'-Chloro-biphenyl-3-ylcarbamoyl)-pyrrolidine-1-carboxylic acid tert-butyl ester.

[1-(2-{5-[6-(4-{2-[4-Cyano-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting (1-{2-[5-(4-Bromo-phenyl)-1H-imidazol-2-yl]-4-cyano-pyrrolidine-1-carbonyl}-2-methyl-propyl)-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H-NMR: 400 MHz, (DMSO-d$_6$) δ 11.98 (s, 1H), 11.82 (s, 1H), 8.22 (m, 2H), 7.92-7.77 (m, 6H), 7.62 (m, 2H), 7.44 (d, J=7.6 Hz, 1H), 7.31 (d, J=8.0, 1H), 5.24 (t, J=5.2 Hz, 1H), 5.12 (d, J=4.0, 1H), 4.22-4.19 (m, 1H), 4.09-4.0 (m, 4H), 3.89-3.83 (m, 4H), 3.56 (d, J=5.6 Hz, 6H), 2.17 (brs, 2H), 2.06-1.90 (m, 4H), 0.95-0.84 (m, 14H); MS (ESI) m/z 814 [M+H]$^+$.

Example FF

1. TMS-acetylene, CuI, Pd(PPh$_3$)$_4$, Et$_3$N, DMF
2. K$_2$CO$_3$, MeOH

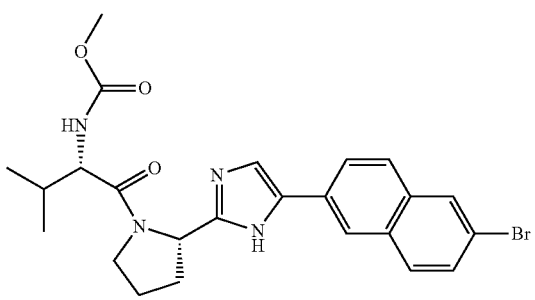

(1-{2-[5-(6-Bromo-naphthalen-2-yl)-1H-imidazol-2-yl]-pyrrolidine-1-carbonyl}-2-methyl-propyl)-carbamic acid methyl ester

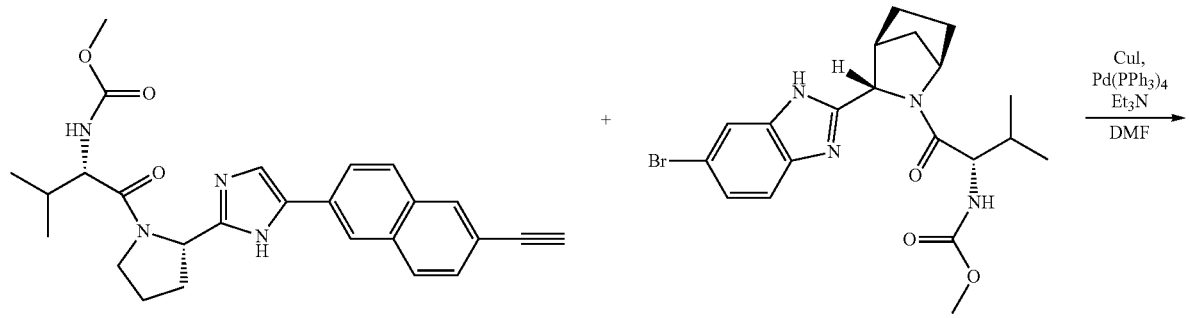

(1-{2-[5-(6-Ethynyl-naphthalen-2-yl)-1H-imidazol-2-yl]-pyrrolidine-1-carbonyl}-2-methyl-propyl)-carbamic acid methyl ester {1-[3-(6-Bromo-1H-benzoimidazol-2-yl)-2-aza-bicyclo[2.2.1]heptane-2-carbonyl]-2-methyl-propyl}-carbamic acid methyl ester

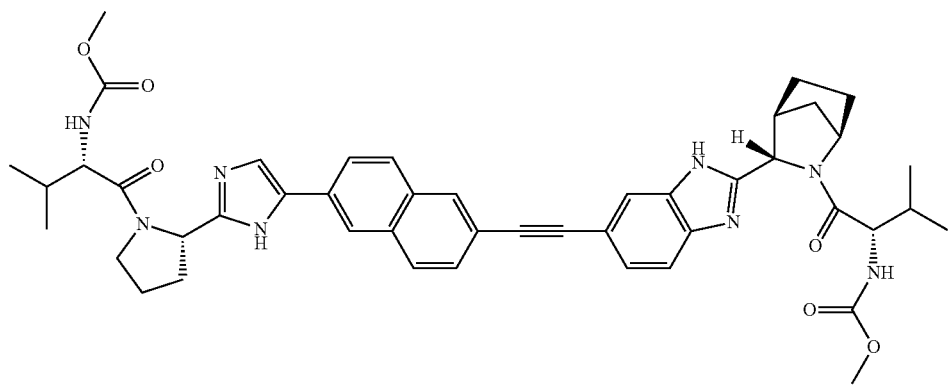

(1-{2-[5-(6-{2-[2-(2-Methoxycarbonylamino-3-methyl-butyryl)-2-aza bicyclo[2.2.1]hept-3-yl]-3H-benzoimidazol-5-ylethynyl}-naphthalen-2-yl)-1H-imidazol-2-yl]-pyrrolidine-1-carbonyl}-2-methyl-propyl)-carbamic acid methyl ester

(1-{2-[5-(6-Ethynyl-naphthalen-2-yl)-1H-imidazol-2-yl]-pyrrolidine-1-carbonyl}-2-methyl-propyl)-carbamic acid methyl ester Title compound was prepared according to the method employed to prepare (1-{2-[5-(4-Ethynyl-phenyl)-1H-imidazol-2-yl]-pyrrolidine-1-carbonyl}-2-methyl-propyl)-carbamic acid methyl ester from (1-{2-[5-(4-bromo-phenyl)-1H-imidazol-2-yl]-pyrrolidine-1-carbonyl}-2-methyl-propyl)-carbamic acid methyl ester (Example AY), substituting (1-{2-[5-(6-Bromo-naphthalen-2-yl)-1H-imidazol-2-yl]-pyrrolidine-1-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester.

(1-{2-[5-(6-{2-[2-(2-Methoxycarbonylamino-3-methyl-butyryl)-2-aza-bicyclo[2.2.1]hept-3-yl]-3H-benzoimidazol-5-ylethynyl}-naphthalen-2-yl)-1H-imidazol-2-yl]-pyrrolidine-1-carbonyl}-2-methyl-propyl)-carbamic acid methyl ester Title compound was prepared according to the method employed to prepare Methoxycarbonylamino-3-methyl-butyryl)-pyrrolidin-2-yl]-3H-imidazol-4-ylethynyl}-phenylethynyl)-1H-imidazol-2-yl]-pyrrolidine-1-carbonyl}-2-methyl-propyl)-carbamic acid methyl ester (Example CT), substituting {1-[3-(6-Bromo-1H-benzoimidazol-2-yl)-2-aza-bicyclo[2.2.1]heptane-2-carbonyl]-2-methyl-propyl}-carbamic acid methyl ester for (1-{2-[5-(4-bromo-phenylethynyl)-1H-imidazol-2-yl]-pyrrolidine-1-carbonyl}-2-methyl-propyl)-carbamic acid methyl ester and (1-{2-[5-(6-Ethynyl-naphthalen-2-yl)-1H-imidazol-2-yl]-pyrrolidine-1-carbonyl}-2-methyl-propyl)-carbamic acid methyl ester for {1-[2-(5-Ethynyl-1H-imidazol-2-yl)-pyrrolidine-1-carbonyl]-2-methyl-propyl}-carbamic acid methyl ester. NMR (MeOH-d4, 400 MHz) δ: 8.19-8.11 (m, 1H), 8.01-7.99 (m, 1H), 7.86-7.71 (m, 3H), 7.57-7.39 (m, 3H), 7.02-6.99 (m, 1H); MS (ESI) m/z 813 [M+H]+.

Example FG

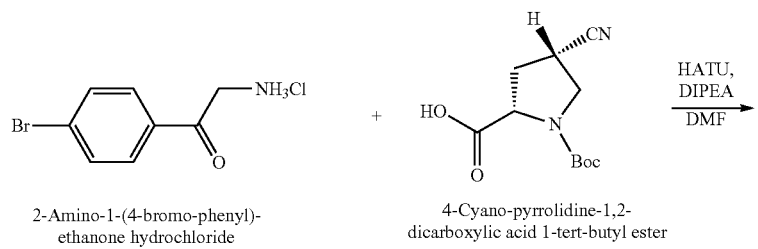

2-Amino-1-(4-bromo-phenyl)-ethanone hydrochloride

4-Cyano-pyrrolidine-1,2-dicarboxylic acid 1-tert-butyl ester

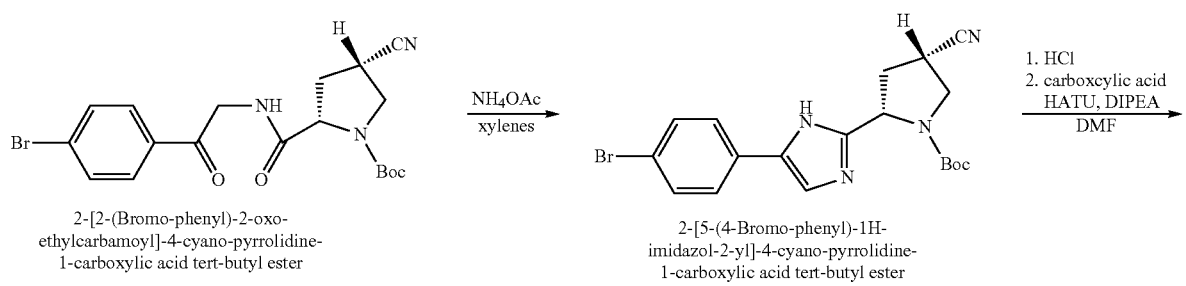

2-[2-(Bromo-phenyl)-2-oxo-ethylcarbamoyl]-4-cyano-pyrrolidine-1-carboxylic acid tert-butyl ester 2-[5-(4-Bromo-phenyl)-1H-imidazol-2-yl]-4-cyano-pyrrolidine-1-carboxylic acid tert-butyl ester

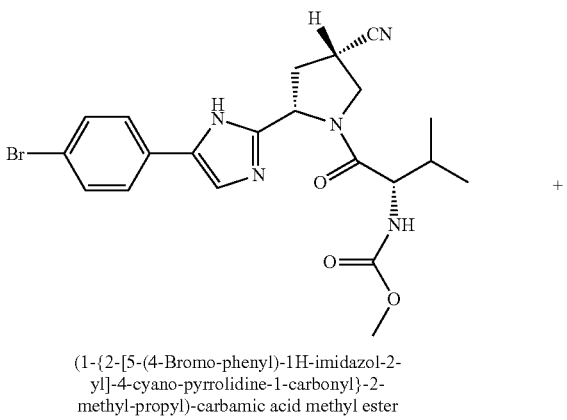

(1-{2-[5-(4-Bromo-phenyl)-1H-imidazol-2-yl]-4-cyano-pyrrolidine-1-carbonyl}-2-methyl-propyl)-carbamic acid methyl ester

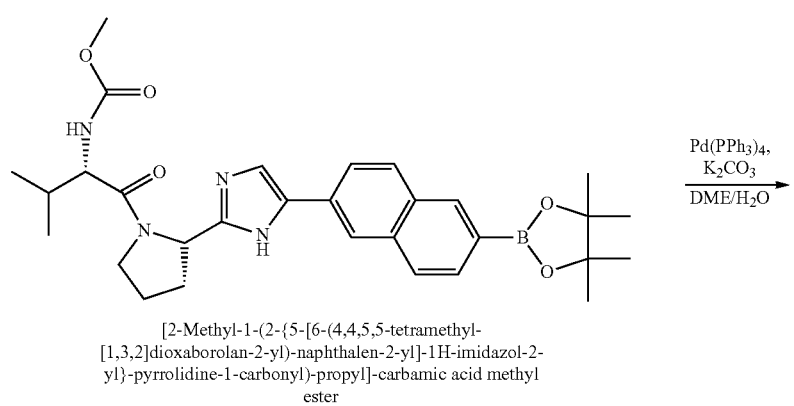

[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester -continued

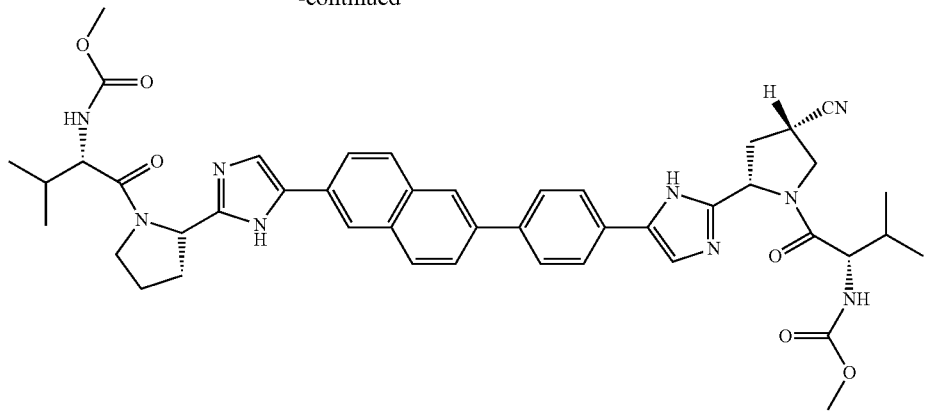

[1-(2-{5-[6-(4-{2-[4-Cyano-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

2-[2-(4-Bromo-phenyl)-2-oxo-ethylcarbamoyl]-4-cyano-pyrrolidine-1-carboxylic acid tert-butyl ester Title compound was prepared according to the method employed to prepare 3-[2-(4-Bromo-phenyl)-2-oxo-ethylcarbamoyl]-2-aza-bicyclo [2.2.1]heptane-2-carboxylic acid tert-butyl ester (Example AE), substituting 4-Cyano-pyrrolidine-1,2-dicarboxylic acid 1-tert-butyl ester for 2-aza-bicyclo[2.2.1]heptane-2,3-dicarboxylic acid 2-tert-butyl ester.

2-[5-(4-Bromo-phenyl)-1H-imidazol-2-yl]-4-cyano-pyrrolidine-1-carboxylic acid tert-butyl ester Title compound was prepared according to the method employed to prepare 3-[5-(4-Bromo-phenyl)-1H-imidazol-2-yl]-2-aza-bicyclo[2.2.1]heptane-2-carboxylic acid tert-butyl ester (Example AS), and substituting 2-[2-(4-Bromo-phenyl)-2-oxo-ethylcarbamoyl]-4-cyano-pyrrolidine-1-carboxylic acid tert-butyl ester for 3-[2-(4-bromo-phenyl)-2-oxo-ethylcarbamoyl]-2-aza-bicyclo[2.2.1]heptane-2-carboxylic acid tert-butyl ester.

(1-{2-[5-(4-Bromo-phenyl)-1H-imidazol-2-yl]-4-cyano-pyrrolidine-1-carbonyl}-2-methyl-propyl)-carbamic acid methyl ester Title compound was prepared according to the method employed to prepare {1-[2-(4'-Chloro-biphenyl-3-ylcarbamoyl)-pyrrolidine-1-carbonyl]-2-methyl-propyl}-carbamic acid methyl ester (Example CX), substituting 2-[5-(4-Bromo-phenyl)-1H-imidazol-2-yl]-4-cyano-pyrrolidine-1-carboxylic acid tert-butyl ester for 2-(4'-Chloro-biphenyl-3-ylcarbamoyl)-pyrrolidine-1-carboxylic acid tert-butyl ester.

[1-(2-{5-[6-(4-{2-[4-Cyano-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting (1-{2-[5-(4-Bromo-phenyl)-1H-imidazol-2-yl]-4-cyano-pyrrolidine-1-carbonyl}-2-methyl-propyl)-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. NMR (MeOH-d4, 400 MHz) δ: 8.12-8.03 (m, 2H), 7.89-7.74 (m, 6H), 7.48-7.36 (m, 2H), 5.20 (m, 2H), 4.60 (m, 1H), 4.28-3.88 (m, 6H), 3.66 (s, 6H), 2.86 (m, 1H), 2.60 (m, 1H), 2.40-2.19 (m, 3H), 2.11-1.97 (m, 3H), 1.00-0.88 (m, 12H); MS (ESI) m/z 814 [M+H]$^+$.

Example FH

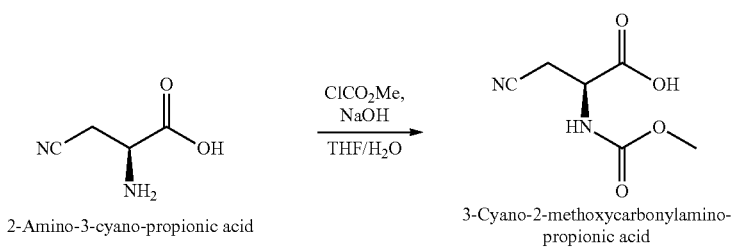

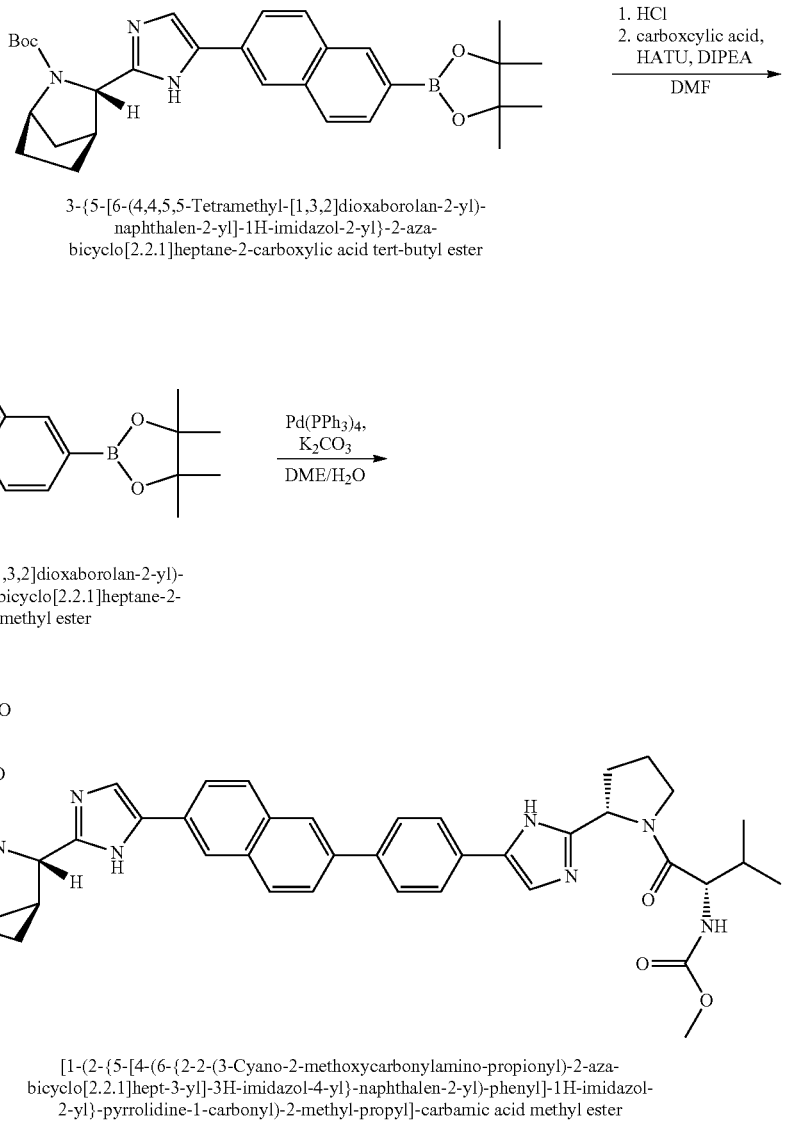

3-{5-[6-(4,4,5,5-Tetramethyl-[1,3,2]dioxaborolan-2-yl)-naphthalen-2-yl]-1H-imidazol-2-yl}-2-aza-bicyclo[2.2.1]heptane-2-carboxylic acid tert-butyl ester

[2-Cyano-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-ethyl]-carbamic acid methyl ester

[1-(2-{5-[4-(6-{2-2-(3-Cyano-2-methoxycarbonylamino-propionyl)-2-aza-bicyclo[2.2.1]hept-3-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester 3-Cyano-2-methoxycarbonylamino-propionic acid Methyl chloroformate (0.81 mL, 10.51 mmol) was added dropwise to a stirred suspension of 2-Amino-3-cyano-propionic acid (1.00 g, 8.76 mmol) and NaOH (5 N in H$_2$O, 4.2 mL, 21.0 mmol) in THF (20 mL). After stirring at room temperature for 7 h, the reaction mixture was poured into 10% HCl and the aqueous phase was extracted 3× with diethyl ether. The combined organics were dried over MgSO$_4$, filtered and concentrated to afford 3-Cyano-2-methoxycarbonylamino-propionic acid (295 mg, 20%).

[2-Cyano-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-ethyl]-carbamic acid methyl ester Title compound was prepared according to the method employed to prepare {1-[2-(4'-Chloro-biphenyl-3-ylcarbamoyl)-pyrrolidine-1-carbonyl]-2-methyl-propyl}-carbamic acid methyl ester (Example CX), substituting 3-{5-[6-(4,4,5,5-Tetramethyl-[1,3,2]dioxaborolan-2-yl)-naphthalen-2-yl]-1H-imidazol-2-yl}-2-aza-bicyclo[2.2.1]heptane-2-carboxylic acid tert-butyl ester for 2-(4'-Chloro-biphenyl-3-ylcarbamoyl)-pyrrolidine-1-carboxylic acid tert-butyl ester and 3-Cyano-2-methoxycarbonylamino-propionic acid for 2-methoxycarbonylamino-3-methyl-butyric acid.

[1-(2-{5-[4-(6-{2-[2-(3-Cyano-2-methoxycarbonylamino-propionyl)-2-aza-bicyclo[2.2.1]hept-3-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting [2-Cyano-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-ethyl]-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H NMR (DMSO-d6, 400 MHz) δ: 8.24-8.18 (m, 2H), 7.99-7.79 (m, 6H), 7.63-7.54 (m, 2H), 5.09 (m, 1H), 4.84 (m, 1H), 4.53 (s, 1H), 4.41 (s, 1H), 4.07 (m, 1H), 3.82 (m, 2H), 3.62 (s, 3H), 3.54 (s, 3H), 2.92-2.87 (m, 1H), 2.79-2.75 (m, 1H), 2.72-2.67 (m, 1H), 2.16-1.42 (m, 9H), 0.91-0.87 (m, 12H); MS (ESI) m/z 812 [M+H]⁺.

Example FI

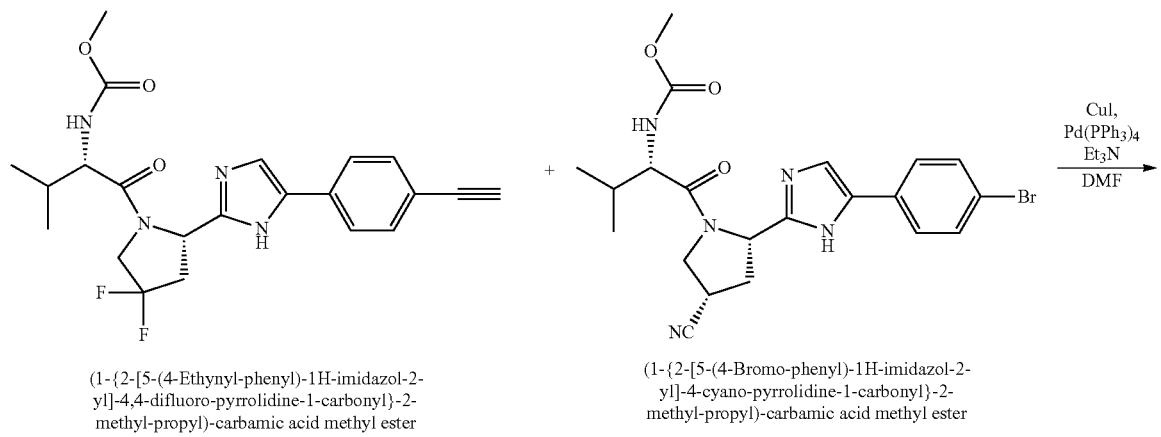

(1-{2-[5-(4-Ethynyl-phenyl)-1H-imidazol-2-yl]-4,4-difluoro-pyrrolidine-1-carbonyl}-2-methyl-propyl)-carbamic acid methyl ester (1-{2-[5-(4-Bromo-phenyl)-1H-imidazol-2-yl]-4-cyano-pyrrolidine-1-carbonyl}-2-methyl-propyl)-carbamic acid methyl ester

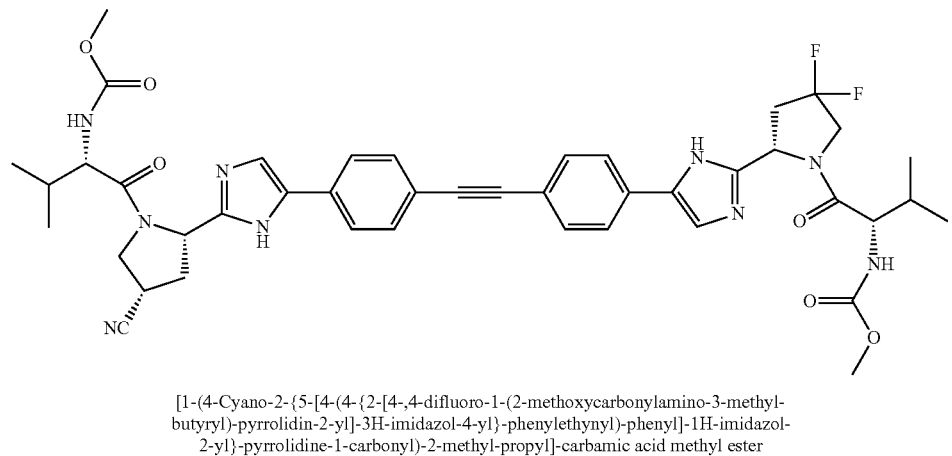

[1-(4-Cyano-2-{5-[4-(4-{2-[4-,4-difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester

[1-(4-Cyano-2-{5-[4-(4-{2-[4,4-difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester Title compound was prepared according to the method employed to prepare [1-(2-{5-[4-(4-{2-[4,4-Difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester (Example AB1) substituting (1-{2-[5-(4-Bromo-phenyl)-1H-imidazol-2-yl]-4-cyano-pyrrolidine-1-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester (400 mg, 0.89 mmol), and (1-{2-[5-(4-ethynyl-phenyl)-1H-imidazol-2-yl]-4,4-difluoro-pyrrolidine-1-carbonyl}-2-methyl-propyl)-carbamic acid methyl ester for (1-{2-[5-(4-ethynyl-phenyl)-1H-imidazol-2-yl]-pyrrolidine-1-carbonyl}-2-methyl-propyl)-carbamic acid methyl ester. ¹H NMR (MeOH-d4, 400 MHz) δ: 7.71-7.61 (m, 4H) 7.46-7.34 (m, 4H), 5.30 (m, 1H), 5.14 (m, 1H), 4.55-4.45 (m, 2H), 4.20-3.94 (m, 5H), 3.61 (s, 6H), 3.47-3.40 (m, 2H), 2.84-2.76 (m, 3H), 2.52 (m, 1H), 1.96-1.91 (m, 2H), 0.96-0.83 (m, 12H); MS (ESI) m/z 824 [M+H]⁺.

Example FJ

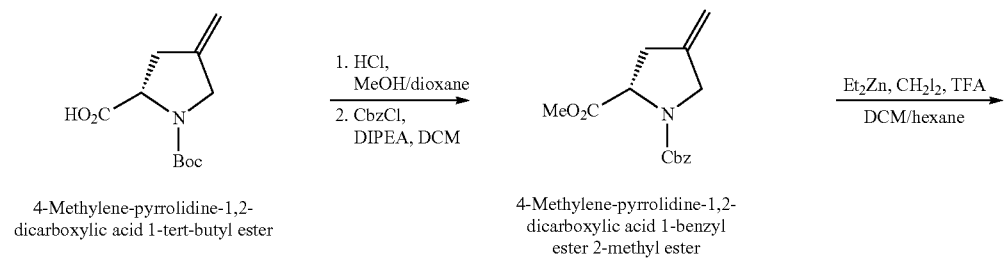

4-Methylene-pyrrolidine-1,2-dicarboxylic acid 1-tert-butyl ester

4-Methylene-pyrrolidine-1,2-dicarboxylic acid 1-benzyl ester 2-methyl ester

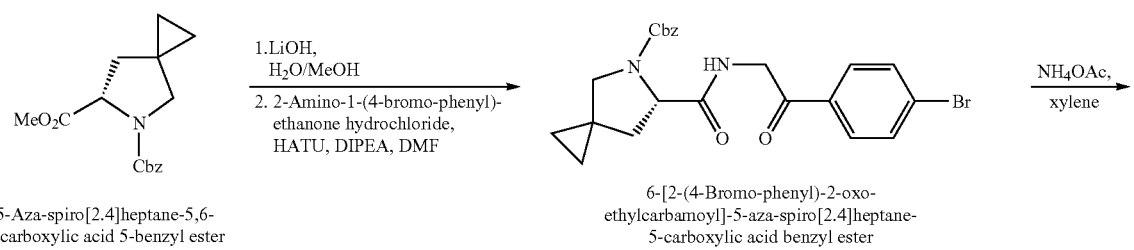

5-Aza-spiro[2.4]heptane-5,6-dicarboxylic acid 5-benzyl ester

6-[2-(4-Bromo-phenyl)-2-oxo-ethylcarbamoyl]-5-aza-spiro[2.4]heptane-5-carboxylic acid benzyl ester

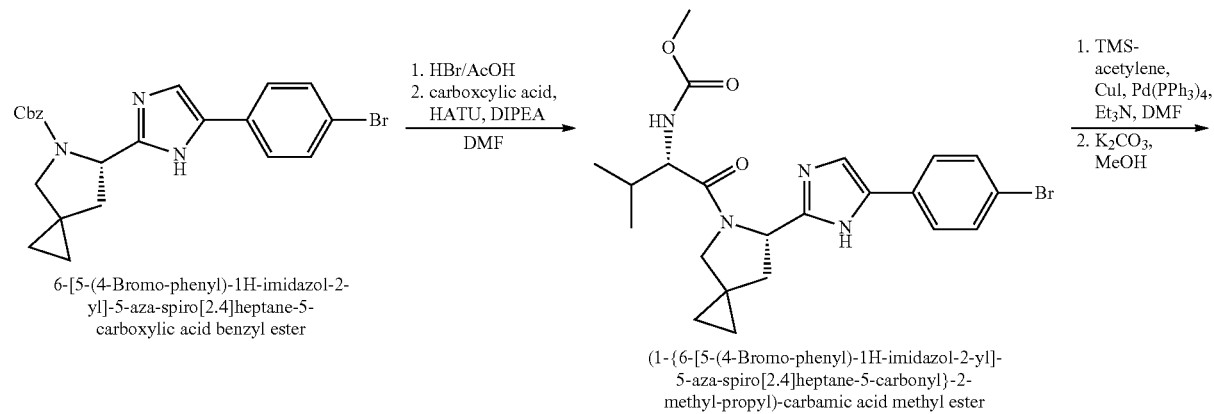

6-[5-(4-Bromo-phenyl)-1H-imidazol-2-yl]-5-aza-spiro[2.4]heptane-5-carboxylic acid benzyl ester (1-{6-[5-(4-Bromo-phenyl)-1H-imidazol-2-yl]-5-aza-spiro[2.4]heptane-5-carbonyl}-2-methyl-propyl)-carbamic acid methyl ester

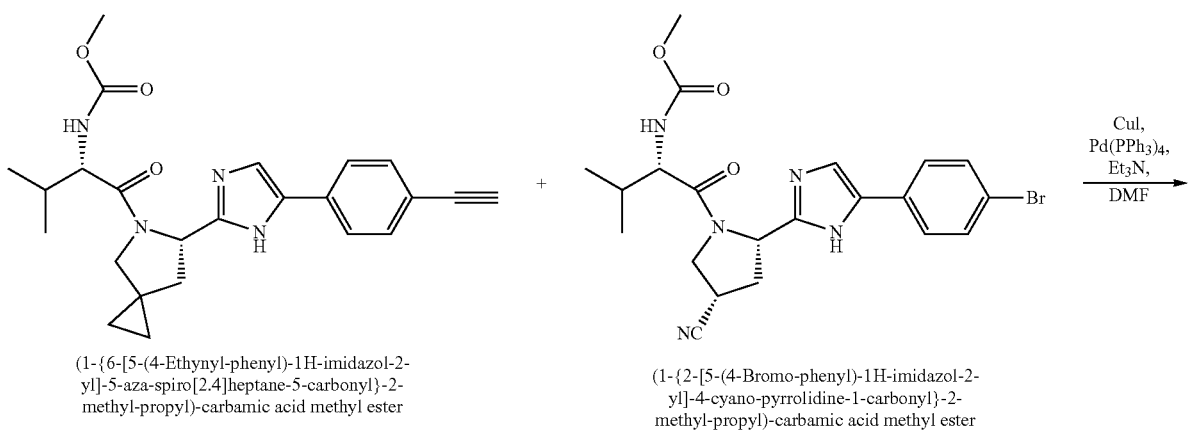

(1-{6-[5-(4-Ethynyl-phenyl)-1H-imidazol-2-yl]-5-aza-spiro[2.4]heptane-5-carbonyl}-2-methyl-propyl)-carbamic acid methyl ester (1-{2-[5-(4-Bromo-phenyl)-1H-imidazol-2-yl]-4-cyano-pyrrolidine-1-carbonyl}-2-methyl-propyl)-carbamic acid methyl ester

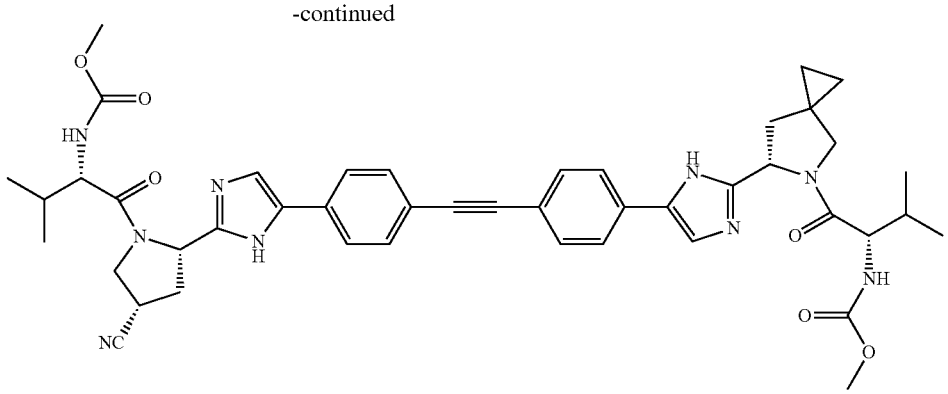

[1-(4-Cyano-2-{5-[4-(4-{2-[5-(2-methoxycarbonylamino-3-methyl-butyryl)-5-aza-spiro[2.4]hept-6-yl]-3H-imidazol-4-yl}-phenylethynyl)-phenyl]-1H-imidazol-2-yl}-pyrrolidine-1-carbonyl)-2-methyl-propyl]-carbamic acid methyl ester

4-Methylene-pyrrolidine-1,2-dicarboxylic acid 1-benzyl ester 2-methyl ester

4-Methylene-pyrrolidine-1,2-dicarboxylic acid 1-tert-butyl ester (12.00 g, 52.80 mmol) was dissolved in MeOH (200 mL) and treated with 4.0 M HCl/dioxane (50 mL) After stirring for 3.5 hours at room temperature, the reaction mixture was concentrated under reduced pressure. The crude residue was dissolved in DCM (200 mL) and treated with DIPEA (22 mL, 127 mmol) and BnOCOCl (9.64 mL, 63.4 mmol). After stirring for 1 hours at room temperature, the reaction mixture was poured into $H_2O$. The aqueous layer was extracted 3× with DCM. The combined organics were dried over $MgSO_4$, filtered and concentrated. The residue was purified by silica column chromatography (10% to 25% EtOAc/hexane) to provide 4-Methylene-pyrrolidine-1,2-dicarboxylic acid 1-benzyl ester 2-methyl ester (8.20 g, 56%).

5-Aza-spiro[2.4]heptane-5,6-dicarboxylic acid 5-benzyl ester

Diethyl zinc (1.0 M in hexane (118 mL, 118 mmol) was added to a 3-neck round bottom flask containing a stir bar, DCM (120 mL) and equipped with an addition funnel and an Argon inlet adaptor. The solution was cooled to 0° C. before TFA (9.5 mL, 118 mmol) in DCM (40 mL) was added dropwise by addition funnel over 22 minutes. 20 minutes after completion of the addition, $CH_2I_2$ was added slowly over 4 minutes. 20 minutes after completion of addition, 4-Methylene-pyrrolidine-1,2-dicarboxylic acid 1-benzyl ester 2-methyl ester (8.10 g, 29.4 mmol) in DCM (30 mL) was added by cannula followed by a rinse with DCM (10 mL). 10 minutes later, the reaction mixture was warmed to room temperature and stirred for 110 hours. The reaction was quenched by addition of 100 mL saturated aqueous $NH_4Cl$. The entire contents of the flask were poured into saturated aqueous $NaHCO_3$ and the aqueous phase was extracted 3× with EtOAc. The combined organics were dried over $MgSO_4$, filtered and concentrated. The residue was dissolved in THF (100 mL), acetone (33 mL) and $H_2O$ (33 mL) and N-methylmorpholine-N-oxide (3.45 g, 29.41 mmol) and osmium tetroxide (4 wt % in $H_2O$, 5 mL, 0.818 mmol) were added sequentially. The reaction mixture was stirred 7 hours at room temperature then quenched with 100 mL saturated aqueous $Na_2S_2O_3$. The entire contents of the flask was poured into $H_2O$ and the aqueous layer was extracted 3× with DCM. The combined organics were dried over $MgSO_4$, filtered and concentrated. The resulting residue was purified by silica column chromatography (10% to 25% EtOAc/hexane) to provide 5-Aza-spiro[2.4]heptane-5,6-dicarboxylic acid 5-benzyl ester (5.54 g, 65%).

6-[2-(4-Bromo-phenyl)-2-oxo-ethylcarbamoyl]-5-aza-spiro[2.4]heptane-5-carboxylic acid benzyl ester 5-Aza-spiro[2.4]heptane-5,6-dicarboxylic acid 5-benzyl ester (361 mg, 1.25 mmol) was dissolved in MeOH (10 mL) and LiOH (1 M in $H_2O$, 5 mL, 5 mmol) was added. After stirring for 15 hours at room temperature, the reaction mixture was poured into 10% HCl and the aqueous phase was extracted 3× with DCM. The combined organics were dried over $MgSO_4$, filtered and concentrated. The residue was treated with 2-Amino-1-(4-bromo-phenyl)-ethanone hydrochloride (344 mg, 1.38 mmol), HATU (525 mg, 1.38 mmol) and DMF (14 mL). The suspension was stirred at 0° C. for 21 minutes before DIPEA (0.72 mL, 4.1 mmol) was added dropwise. Immediately after addition, the reaction mixture was warmed to room temperature. 40 minutes later the mixture was diluted with EtOAc. The organic layer was washed with saturated aqueous $NaHCO_3$ and brine, then dried over $MgSO_4$, filtered and concentrated. The crude residue was purified by silica column chromatography (30% to 50% EtOAc/hexane) to afford 6-[2-(4-Bromo-phenyl)-2-oxo-ethylcarbamoyl]-5-aza-spiro[2.4]heptane-5-carboxylic acid benzyl ester (589 mg, 100%).

6-[5-(4-Bromo-phenyl)-1H-imidazol-2-yl]-5-aza-spiro[2.4]heptane-5-carboxylic acid benzyl ester Title compound was prepared according to the method employed to prepare 3-[5-(4-Bromo-phenyl)-1H-imidazol-2-yl]-2-aza-bicyclo[2.2.1]heptane-2-carboxylic acid tert-butyl ester (Example AS), substituting 6-[2-(4-Bromo-phenyl)-2-oxo-ethylcarbamoyl]-5-aza-spiro[2.4]heptane-5-carboxylic acid benzyl ester for 3-[2-(4-bromo-phenyl)-2-oxo-ethylcarbamoyl]-2-aza-bicyclo[2.2.1]heptane-2-carboxylic acid tert-butyl ester.

(1-{6-[5-(4-Bromo-phenyl)-1H-imidazol-2-yl]-5-aza-spiro[2.4]heptane-5-carbonyl}-2-methyl-propyl)-carbamic acid methyl ester 6-[5-(4-Bromo-phenyl)-1H-imidazol-2-yl]-5-aza-spiro[2.4]heptane-5-carboxylic acid benzyl ester (478 mg, 1.04 mmol) was treated with DCM (5 mL) then HBr (33 wt % in AcOH, 5 mL). The mixture was stirred for 160 minutes at room temperature, concentrated under reduced pressure then coevaporated 2× with toluene to remove excess AcOH. The crude residue was treated with 2-Methoxycarbonylamino-3-methyl-butyric acid (274 mg, 1.56 mmol), HATU (435 mg, 1.14 mmol) and DMF (10 mL) The stirred mixture was cooled to 0° C. and DIPEA (0.91 mL, 5.2 mmol) was added before the warming to room temperature. After 1 h, the reaction mixture was diluted with EtOAc and washed with saturated aqueous NaHCO$_3$ and brine. The organic layer was dried over MgSO$_4$, filtered and concentrated and the crude residue was purified by silica column chromatography (75% to 100% EtOAc/hexane) to yield (1-{6-[5-(4-Bromo-phenyl)-1H-imidazol-2-yl]-5-aza-spiro[2.4]heptane-5-carbonyl}-2-methyl-propyl)-carbamic acid methyl ester (297 mg, 60%).

(1-{6-[5-(4-Ethynyl-phenyl)-1H-imidazol-2-yl]-5-aza-spiro[2.4]heptane-5-carbonyl}-2-methyl-propyl)-carbamic acid methyl ester Title compound was prepared according to the method employed to prepare (1-{2-[5-(4-Ethynyl-phenyl)-1H-imidazol-2-yl]-pyrrolidine-1-carbonyl}-2-methyl-propyl)-carbamic acid methyl ester from (1-{2-[5-(4-bromo-phenyl)-1H-imidazol-2-yl]-pyrrolidine-1-carbonyl}-2-methyl-propyl)-carbamic acid methyl ester (Example AY), substituting (1-{6-[5-(4-Bromo-phenyl)-1H-imidazol-2-yl]-5-aza-spiro[2.4]heptane-5-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester.

[1-(4-Cyano-2-{5-[4-(4-{2-[5-(2-methoxycarbonylamino-3-methyl-butyryl)-5-aza-spiro[2.4]hept-6-yl]-3H-imidazol-4-yl}-phenylethynyl)-phenyl]-1H-imidazol-2-yl}-pyrrolidine-1-carbonyl)-2-methyl-propyl]-carbamic acid methyl ester Title compound was prepared according to the method employed to prepare [1-(2-{5-[4-(4-{2-[4,4-Difluoro-1-(2-methoxycarbonylamino-3-methyl-butyryl)-pyrrolidin-2-yl]-3H-imidazol-4-yl}-phenylethynyl)-phenyl]-1H-imidazol-2-yl}-pyrrolidine-1-carbonyl)-2-methyl-propyl]-carbamic acid methyl ester (Example AB1), substituting (1-{2-[5-(4-Bromo-phenyl)-1H-imidazol-2-yl]-4-cyano-pyrrolidine-1-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester (400 mg, 0.89 mmol), and (1-{6-[5-(4-Ethynyl-phenyl)-1H-imidazol-2-yl]-5-aza-spiro[2.4]heptane-5-carbonyl}-2-methyl-propyl)-carbamic acid methyl ester for (1-{2-[5-(4-Ethynyl-phenyl)-1H-imidazol-2-yl]-4,4-difluoro-pyrrolidine-1-carbonyl}-2-methyl-propyl)-carbamic acid methyl ester. $^1$H NMR (MeOH-d4, 400 MHz) δ: 7.78-7.66 (m, 4H), 7.52-7.37 (m, 4H), 5.29 (m, 1H), 5.17 (m, 1H), 4.59 (m, 1H), 4.17-4.09 (m, 3H), 4.01 (m, 1H), 3.93-3.80 (m, 2H), 3.65 (s, 6H), 3.50-3.42 (m, 2H), 2.88-2.81 (m, 1H), 2.66-2.52 (m, 2H), 2.36-2.31 (m, 1H), 2.18-2.13 (m, 1H), 2.05-1.94 (m, 3H), 1.01-0.87 (m, 12H), 0.82-0.63 (m, 4H); MS (ESI) m/z 814 [M+H]$^+$.

Example FK

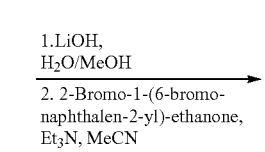

5-Aza-spiro[2.4]heptane-5,6-dicarboxylic acid 5-benzyl ester

1. LiOH, H$_2$O/MeOH
2. 2-Bromo-1-(6-bromo-naphthalen-2-yl)-ethanone, Et$_3$N, MeCN

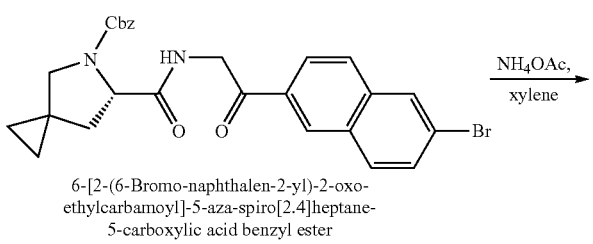

6-[2-(6-Bromo-naphthalen-2-yl)-2-oxo-ethylcarbamoyl]-5-aza-spiro[2.4]heptane-5-carboxylic acid benzyl ester NH$_4$OAc, xylene

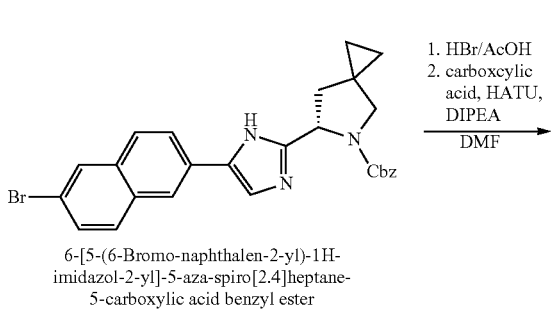

6-[5-(6-Bromo-naphthalen-2-yl)-1H-imidazol-2-yl]-5-aza-spiro[2.4]heptane-5-carboxylic acid benzyl ester 1. HBr/AcOH
2. carboxylic acid, HATU, DIPEA DMF

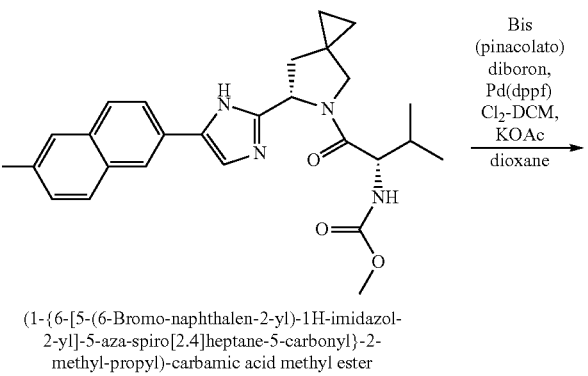

(1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester Bis(pinacolato)diboron, Pd(dppf)Cl$_2$-DCM, KOAc dioxane -continued

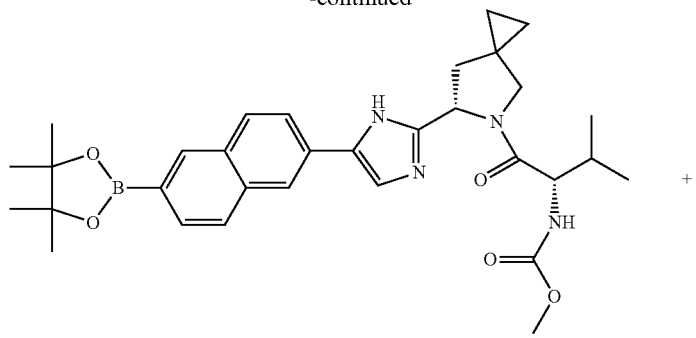

[2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4]heptane-5-carbonyl)-propyl]-carbamic acid methyl ester

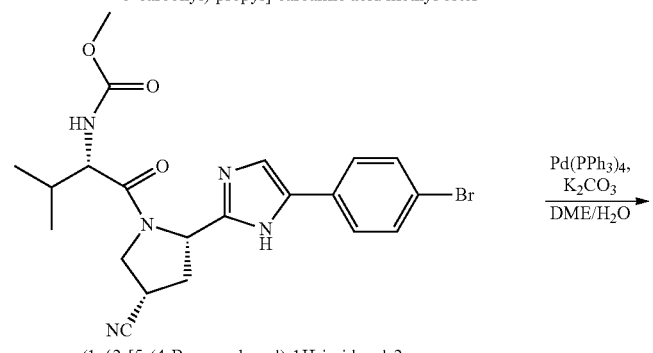

(1-{2-[5-(4-Bromo-phenyl)-1H-imidazol-2-yl]-4-cyano-pyrrolidine-1-carbonyl}-2-methyl-propyl)-carbamic acid methyl ester

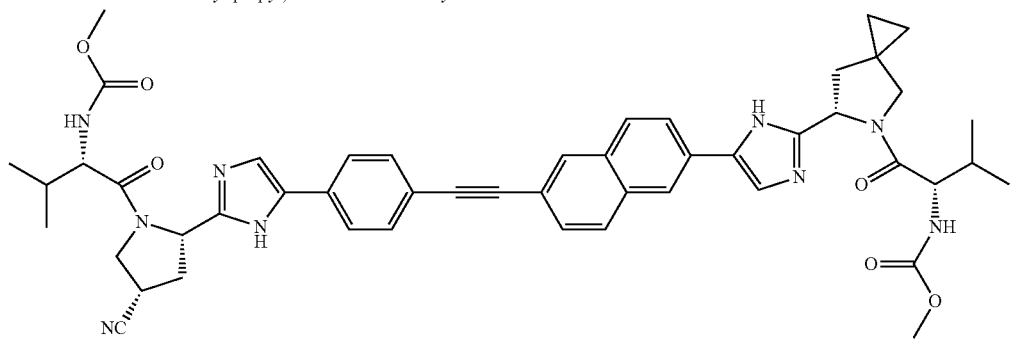

[1-(4-Cyano-2-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester

6-[2-(6-Bromo-naphthalen-2-yl)-2-oxo-ethylcarbamoyl]-5-aza-spiro[2.4]heptane-5-carboxylic acid benzyl ester 5-Aza-spiro[2.4]heptane-5,6-dicarboxylic acid 5-benzyl ester (2.217 g, 7.66 mmol) was dissolved in MeOH (30 mL) and LiOH (1 M in H$_2$O, 15 mL, 15 mmol) was added. After stirring for 15 hours at room temperature, the reaction mixture was poured into 10% HCl and the aqueous phase was extracted 3× with DCM. The combined organics were dried over MgSO$_4$, filtered and concentrated. The residue was treated with MeCN (40 mL), Et$_3$N (1.2 mL, 8.4 mmol) and 2-Bromo-1-(6-bromo-naphthalen-2-yl)-ethanone and the mixture was stirred at room temperature for 20 hours before being filtered over CELITE and concentrated. The resulting oil was dissolved in the minimum amount of DCM and EtOAc (30 mL) was added causing the product to precipitate. The mixture was cooled to 0° C. then the solid was filtered off and rinsed with EtOAc giving clean product (4.00 g, 100%).

6-[5-(6-Bromo-naphthalen-2-yl)-1H-imidazol-2-yl]-5-aza-spiro[2.4]heptane-5-carboxylic acid benzyl ester Title compound was prepared according to the method employed to prepare 3-[5-(4-Bromo-phenyl)-1H-imidazol-2-yl]-2-aza-bicyclo[2.2.1]heptane-2-carboxylic acid tert-butyl ester (Example AS), substituting 6-[2-(6-Bromo-naphthalen-2-yl)-2-oxo-ethylcarbamoyl]-5-aza-spiro[2.4]heptane-5-carboxylic acid benzyl ester for 3-[2-(4-bromo-phenyl)-2-oxo-ethylcarbamoyl]-2-aza-bicyclo[2.2.1]heptane-2-carboxylic acid tert-butyl ester.

(1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester Title compound was prepared according to the method employed to prepare (1-{6-[5-(4-Bromo-phenyl)-1H-imidazol-2-yl]-5-aza-spiro[2.4]heptane-5-carbonyl}-2-methyl-propyl)-carbamic acid methyl ester, substituting 6-[5-(6-Bromo-naphthalen-2-yl)-1H-imidazol-2-yl]-5-aza-spiro[2.4]heptane-5-carboxylic acid benzyl ester for 6-[2-(4-Bromo-phenyl)-2-oxo-ethylcarbamoyl]-5-aza-spiro[2.4]heptane-5-carboxylic acid benzyl ester according to example FJ.

[2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4]heptane-5-carbonyl)-propyl]-carbamic acid methyl ester Title compound was prepared according to the method employed to prepare Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester (Example CY), substituting (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester for {1-[2-(4'-Bromo-biphenyl-4-ylcarbamoyl)-pyrrolidine-1-carbonyl]-2-methyl-propyl}-carbamic acid methyl ester.

[1-(4-Cyano-2-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting (1-{2-[5-(4-Bromo-phenyl)-1H-imidazol-2-yl]-4-cyano-pyrrolidine-1-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester and [2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4]heptane-5-carbonyl)-propyl]-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H NMR (DMSO-d6, 400 MHz) δ: 8.20-8.10 (m, 2H), 7.90-7.68 (m, 6H), 7.60-7.55 (m, 2H), 7.33-7.30 (m, 2H), 5.18 (m, 1H), 5.07 (m, 1H), 4.44 (m, 1H), 4.04-3.69 (m, 6H), 3.40-3.38 (m, 1H), 3.30 (s, 6H), 2.71 (m, 1H), 2.40-1.90 (m, 5H), 0.90-0.79 (m, 12H), 0.70-0.54 (m, 4H); MS (ESI) m/z 841 [M+H]$^+$.

Example DL

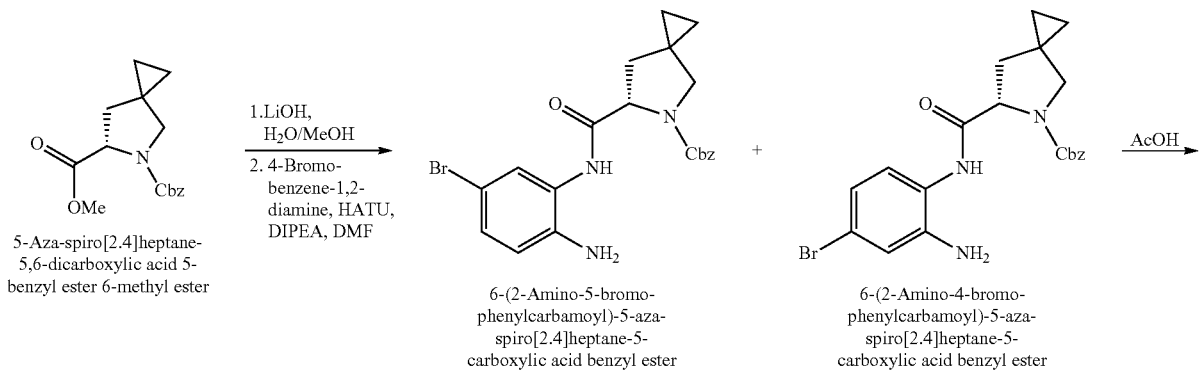

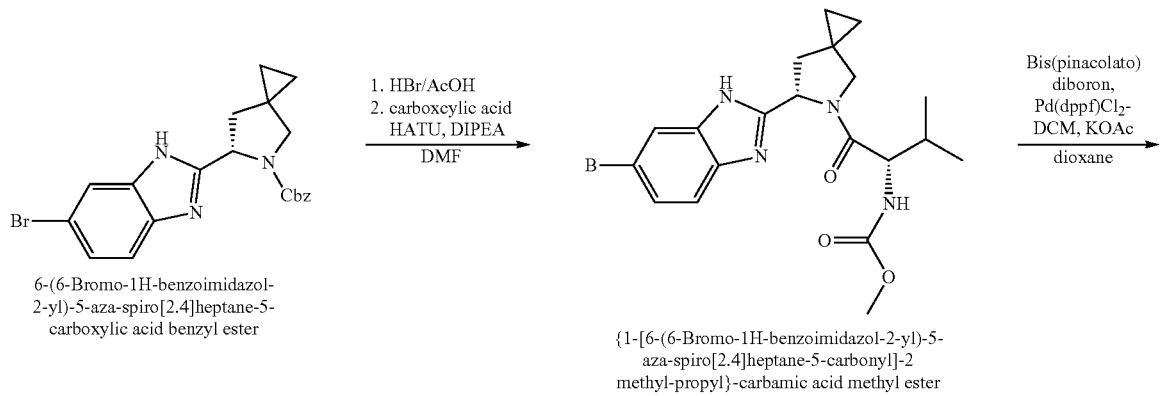

901 902

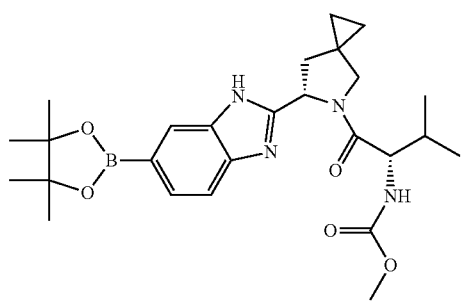

(2-Methyl-1-{6-[6-(4,4,5,5-tetramethyl-[1,3,2]dioxaborolan-2-yl)-1H-benzoimidazol-2-yl]-5-aza-spiro[2.4]heptane-5-carbonyl}-propyl)-carbamic acid methyl ester

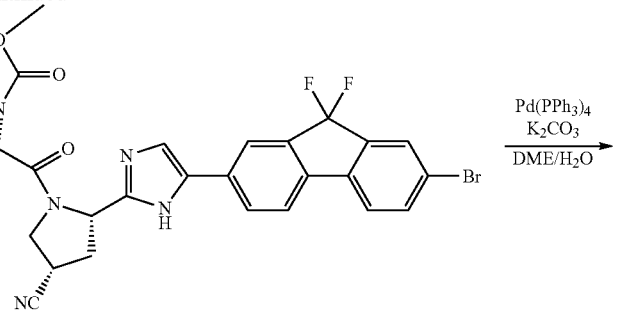

(1-{2-[5-(7-Bromo-9,9-difluoro-9H-fluoren-2-yl)-1H-imidazol-2-yl]-4-cyano-pyrrolidine-1-carbonyl}-2-methyl-propyl)-carbamic acid methyl ester

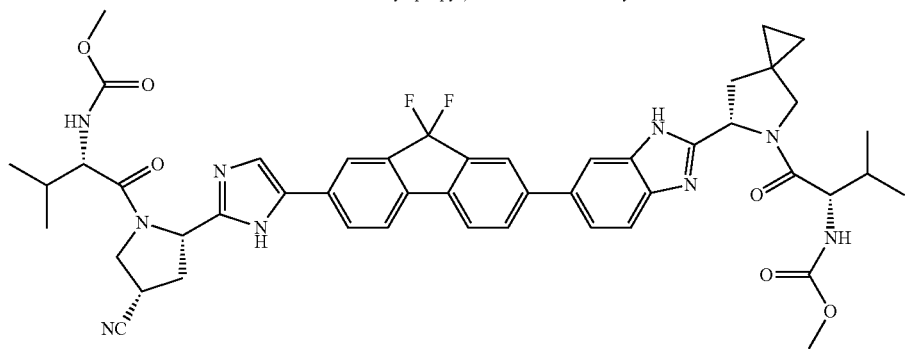

(1-{4-Cyano-2-[5-(9,9-difluoro-7-{2-[5-(2-methoxycarbonylamino-3-methyl-butyryl)-5-aza-spiro[2.4]hept-6-yl]-3H-benzoimidazol-5-yl}-9H-fluoren-2-yl)-1H-imidazol-2-yl]-pyrrolidine-1-carbonyl}-2-methyl-propyl)-carbamic acid methyl ester

6-(2-Amino-5-bromo-phenylcarbamoyl)-5-aza-spiro[2.4]heptane-5-carboxylic acid benzyl ester and 6-(2-Amino-4-bromo-phenylcarbamoyl)-5-aza-spiro[2.4]heptane-5-carboxylic acid benzyl ester 5-Aza-spiro[2.4]heptane-5,6-dicarboxylic acid 5-benzyl ester 6 methyl ester (987 mg, 3.41 mmol) was dissolved in EtOH (10 mL) and LiOH (1 M in H₂O, 5 mL, 5 mmol) was added. After stirring for 2 hours at 50° C., the reaction mixture was poured into 10% HCl and the aqueous phase was extracted 3× with DCM. The combined organics were dried over MgSO₄, filtered and concentrated. The residue was treated with 4-Bromo-benzene-1,2-diamine (1.60 g, 8.53 mmol), HATU (1.43 g, 3.75 mmol) and DMF (17 mL) then cooled to 0° C. DIPEA (0.712 mL, 4.09 mmol) was added and the reaction mixture was allowed to warm to room temperature slowly overnight. The reaction mixture was then diluted with EtOAc and the organic layer was washed with saturated aqueous NaHCO₃ and brine then dried over MgSO₄, filtered and concentrated. The crude material was purified by silica column chromatography to afford a mixture of 6-(2-Amino-5-bromo-phenylcarbamoyl)-5-aza-spiro[2.4]heptane-5-carboxylic acid benzyl ester and 6-(2-Amino-4-bromo-phenylcarbamoyl)-5-aza-spiro[2.4]heptane-5-carboxylic acid benzyl ester (1.47 g, 97%).

6-(6-Bromo-1H-benzoimidazol-2-yl)-5-aza-spiro[2.4]heptane-5-carboxylic acid benzyl ester A mixture of 6-(2-Amino-5-bromo-phenylcarbamoyl)-5-aza-spiro[2.4]heptane-5-carboxylic acid benzyl ester and 6-(2-Amino-4-bromo-phenylcarbamoyl)-5-aza-spiro[2.4]heptane-5-carboxylic acid benzyl ester (1.446 g, 3.25 mmol) was dissolved in AcOH (20 mL) and the reaction mixture was stirred at 40° C. for 18 hours then concentrated under reduced pressure. The residue was dissolved in EtOAc and washed with saturated aqueous NaHCO₃. The aqueous layer was extracted 2× with EtOAc and the combined organics were dried over MgSO₄, filtered and concentrated to provide 6-(6-Bromo-1H-benzoimidazol-2-yl)-5-aza-spiro[2.4]heptane-5-carboxylic acid benzyl ester (1.385 g, 100%).

{1-[6-(6-Bromo-1H-benzoimidazol-2-yl)-5-aza-spiro[2.4]heptane-5-carbonyl]-2-methyl-propyl}-carbamic acid methyl ester 6-(6-Bromo-1H-benzoimidazol-2-yl)-5-aza-spiro[2.4]heptane-5-carboxylic acid benzyl ester (301 mg, 0.706 mmol) was dissolved in DCM (10 mL) and HBr (33 wt % in AcOH, 5 mL) was added. After 2 h the reaction mixture was concentrated and placed under hi-vac. The residue was co-evaporated with PhMe, MeOH, then again with PhMe and MeOH and placed under hi-vac. The residue was treated with 2-Methoxycarbonylamino-3-methyl-butyric acid (130 mg, 0.741 mmol, HATU (282 mg, 0.741 mmol) and DMF (7 mL). The reaction mixture was cooled to 0° C. then DIPEA (0.615 mL, 3.53 mmol) was added before warming to room temperature. After 30 minutes, the reaction mixture was diluted with EtOAc and the organic phase was washed with saturated aqueous NaHCO₃ and brine, then dried over MgSO₄, filtered and concentrated. The crude residue was purified by silica column chromatography (50% to 80% EtOAc/hexane) to afford {1-[6-(6-Bromo-1H-benzoimidazol-2-yl)-5-aza-spiro[2.4]heptane-5-carbonyl]-2-methyl-propyl}-carbamic acid methyl ester (238 mg, 75%).

(2-Methyl-1-{6-[6-(4,4,5,5-tetramethyl-[1,3,2]dioxaborolan-2-yl)-1H-benzoimidazol-2-yl]-5-aza-spiro[2.4]heptane-5-carbonyl}-propyl)-carbamic acid methyl ester Title compound was prepared according to the method employed to prepare Methyl-1-{2-[4'-(4,4,5,5-tetramethyl-[1,3,2]dioxaborolan-2-yl)-biphenyl-4-ylcarbamoyl]-pyrrolidine-1-carbonyl}-propyl)-carbamic acid methyl ester (Example CY), substituting {1-[6-(6-Bromo-1H-benzoimidazol-2-yl)-5-aza-spiro[2.4]heptane-5-carbonyl]-2-methyl-propyl}-carbamic acid methyl ester for {1-[2-(4'-Bromo-biphenyl-4-ylcarbamoyl)-pyrrolidine-1-carbonyl]-2-methyl-propyl}-carbamic acid methyl ester.

(1-{4-Cyano-2-[5-(9,9-difluoro-7-{2-[5-(2-methoxycarbonylamino-3-methyl-butyryl)-5-aza-spiro[2.4]hept-6-yl]-3H-benzoimidazol-5-yl}-9H-fluoren-2-yl)-1H-imidazol-2-yl]-pyrrolidine-1-carbonyl}-2-methyl-propyl)-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example AZ), substituting (1-{2-[5-(7-Bromo-9,9-difluoro-9H-fluoren-2-yl)-1H-imidazol-2-yl]-4-cyano-pyrrolidine-1-carbonyl}-2-methyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester and (2-Methyl-1-{6-[6-(4,4,5,5-tetramethyl-[1,3,2]dioxaborolan-2-yl)-1H-benzoimidazol-2-yl]-5-aza-spiro[2.4]heptane-5-carbonyl}-propyl)-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H NMR (DMSO-d6, 400 MHz) δ: 8.07-7.55 (m, 9H), 7.34 (m, 2H), 5.31 (m, 1H), 5.11 (m, 1H), 4.45 (m, 1H), 4.08-3.87 (m, 6H), 3.63-3.54 (m, 9H), 3.41-3.28 (m, 4H), 2.73 (m, 1H), 2.40-2.25 (m, 2H), 2.15-2.13 (m, 1H), 1.95 (m, 3H), 0.93-0.83 (m, 12H), 0.74-0.57 (m, 4H); MS (ESI) m/z 889 [M+H]$^+$.

Example FM

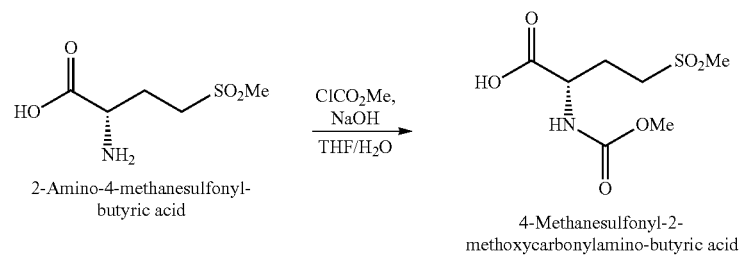

2-Amino-4-methanesulfonyl-butyric acid → 4-Methanesulfonyl-2-methoxycarbonylamino-butyric acid

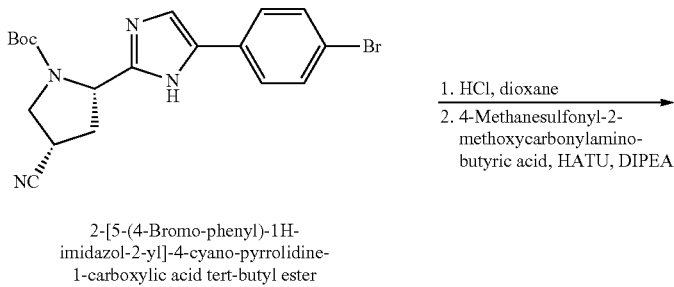

2-[5-(4-Bromo-phenyl)-1H-imidazol-2-yl]-4-cyano-pyrrolidine-1-carboxylic acid tert-butyl ester 1. HCl, dioxane
2. 4-Methanesulfonyl-2-methoxycarbonylamino-butyric acid, HATU, DIPEA

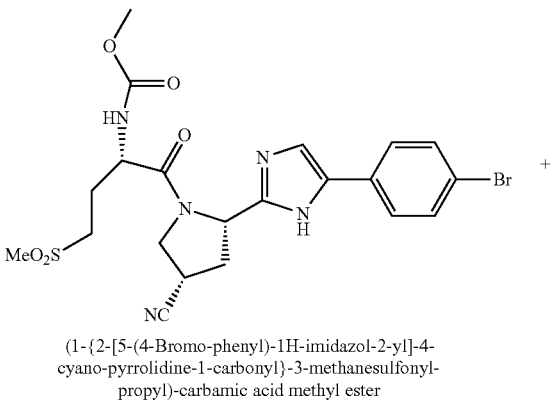

(1-{2-[5-(4-Bromo-phenyl)-1H-imidazol-2-yl]-4-cyano-pyrrolidine-1-carbonyl}-3-methanesulfonyl-propyl)-carbamic acid methyl ester

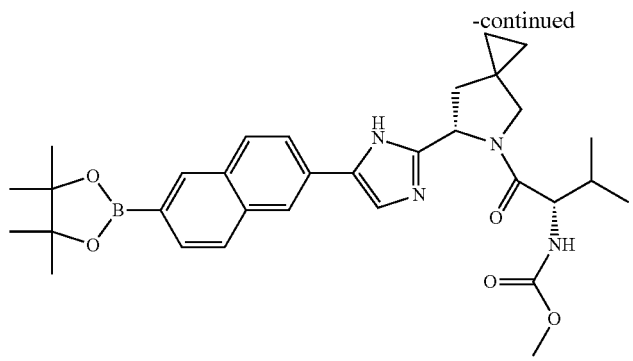

[2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4]heptane-5-carbonyl)-propyl]-carbamic acid methyl ester

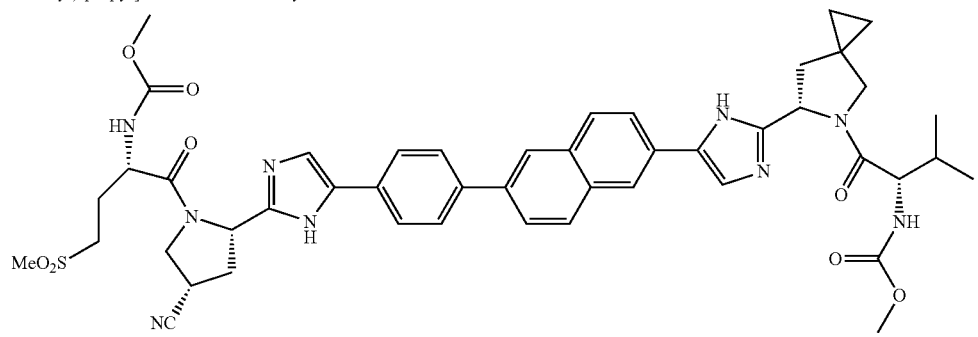

[1-(6-{5-[6-(4-{2-[4-Cyano-1-(4-methanesulfonyl-2-methoxycarbonyonylamino-butyryl)-pyrrolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester 4-Methanesulfonyl-2-methoxycarbonylamino-butyric acid Methyl chloroformate (2.6 mL, 33 mmol) was added dropwise to a stirred suspension of 2-Amino-4-methanesulfonyl-butyric acid (5.03 g, 27.8 mmol) and NaOH (5 N in $H_2O$, 13.3 mL, 66.6 mmol) in THF (50 mL). After stirring at room temperature for 9 h, additional methyl chloroformate (5.2 mL, 66.6 mmol) and NaOH (5 N in $H_2O$, 30 mL, 150 mmol) were added. After another 14 h, the reaction mixture was poured into $H_2O$. The aqueous phase was washed with DCM 2× then acidified to pH 1 with 10% HCl. The acidified aqueous phase was extracted 3× with EtOAc. The combined organics were dried over $MgSO_4$, filtered and concentrated to provide 4-Methanesulfonyl-2-methoxycarbonylamino-butyric acid (970 mg, 15%).

(1-{2-[5-(4-Bromo-phenyl)-1H-imidazol-2-yl]-4-cyano-pyrrolidine-1-carbonyl}-3-methanesulfonyl-propyl)-carbamic acid methyl ester Title compound was prepared according to the method employed to prepare {1-[2-(4'-Chloro-biphenyl-3-ylcarbamoyl)-pyrrolidine-1-carbonyl]-2-methyl-propyl}-carbamic acid methyl ester (Example CX), substituting 2-[5-(4-Bromo-phenyl)-1H-imidazol-2-yl]-4-cyano-pyrrolidine-1-carboxylic acid tert-butyl ester for 2-(4'-Chloro-biphenyl-3-ylcarbamoyl)-pyrrolidine-1-carboxylic acid tert-butyl ester and 4-Methanesulfonyl-2-methoxycarbonylamino-butyric acid for 2-methoxycarbonylamino-3-methyl-butyric acid.

[1-(6-{5-[6-(4-{2-[4-Cyano-1-(4-methanesulfonyl-2-methoxycarbonylamino-butyryl)-pyrrolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester Title compound was prepared according to the method employed to prepare [1-(2-{5-[6-(4-{2-[1-(2-Methoxycarbonylamino-3-methyl-butyryl)-pyrrolidin-2-yl]-phenyl)-naphthalen-2-yl]-1H-imidazol-2-yl}-pyrrolidine-1-carbonyl)-2-methyl-propyl]-carbamic acid methyl ester (Example AZ), substituting (1-{2-[5-(4-Bromo-phenyl)-1H-imidazol-2-yl]-4-cyano-pyrrolidine-1-carbonyl}-3-methanesulfonyl-propyl)-carbamic acid methyl ester for (1-{2-[5-(4-bromo-phenyl)-1H-imidazol-2-yl]-pyrrolidine-1-carbonyl}-2-methyl-propyl)-carbamic acid methyl ester and [2-Methyl-1-(6-{5-[6-(4,4,5,5-tetramethyl-[1,3,2]dioxaborolan-2-yl)-naphthalen-2-yl]-1H-imidazol-2-yl}-5-aza-spiro[2.4]heptane-5-carbonyl)-propyl]-carbamic acid methyl ester for [2-methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. $^1$H NMR (MeOH-d4, 400 MHz) δ: 8.09-8.07 (m, 2H), 7.92-7.22 (m, 8H), 7.42-7.38 (m, 2H), 5.33 (t, J=7.5 Hz, 1H), 5.21 (t, J=8.0 Hz, 1H), 4.65 (m, 1H), 4.49 (m, 1H), 4.17-4.11 (m, 2H), 3.95 (d, J=9.6 Hz, 1H), 3.83 (d, J=10.2 Hz, 1H), 3.66 (s, 6H), 3.55-3.49 (m, 3H), 3.19-3.15 (m, 3H), 2.94 (s, 3H), 2.89-2.03 (m, 10H), 1.03-0.64 (m, 14H); MS (ESI) m/z 904 [M+H]$^+$.

907 908

Example FN

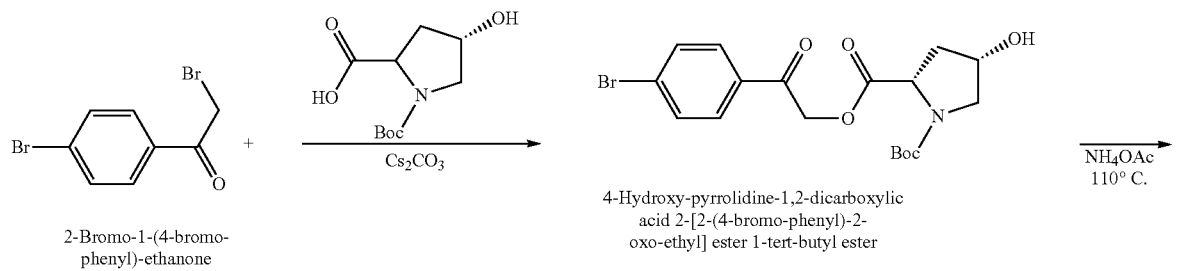

2-Bromo-1-(4-bromo-phenyl)-ethanone

4-Hydroxy-pyrrolidine-1,2-dicarboxylic acid 2-[2-(4-bromo-phenyl)-2-oxo-ethyl] ester 1-tert-butyl ester

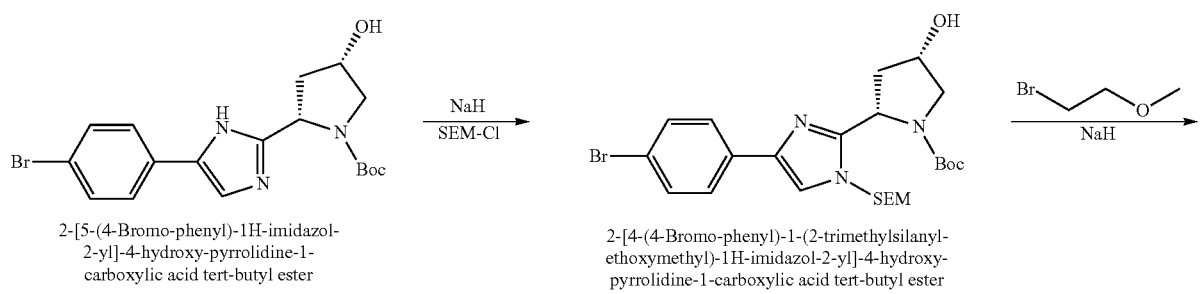

2-[5-(4-Bromo-phenyl)-1H-imidazol-2-yl]-4-hydroxy-pyrrolidine-1-carboxylic acid tert-butyl ester 2-[4-(4-Bromo-phenyl)-1-(2-trimethylsilanyl-ethoxymethyl)-1H-imidazol-2-yl]-4-hydroxy-pyrrolidine-1-carboxylic acid tert-butyl ester

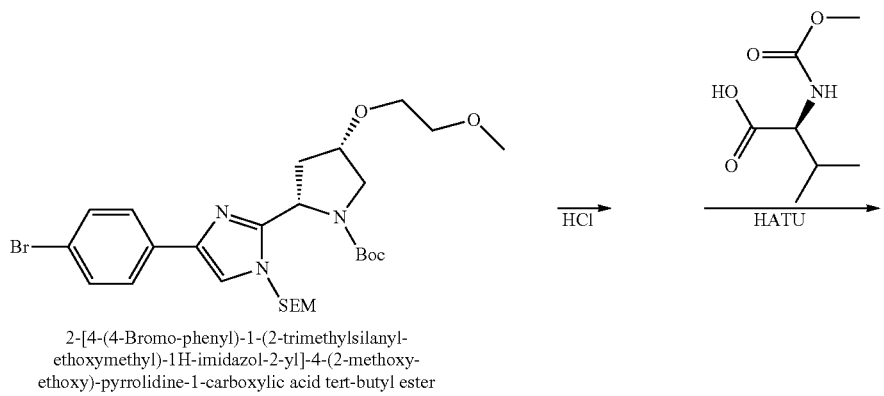

2-[4-(4-Bromo-phenyl)-1-(2-trimethylsilanyl-ethoxymethyl)-1H-imidazol-2-yl]-4-(2-methoxy-ethoxy)-pyrrolidine-1-carboxylic acid tert-butyl ester

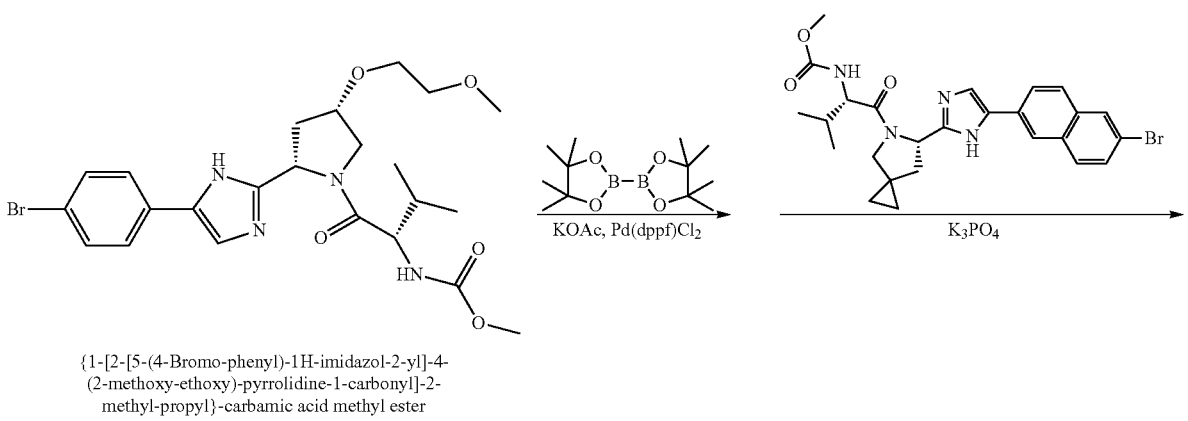

{1-[2-[5-(4-Bromo-phenyl)-1H-imidazol-2-yl]-4-(2-methoxy-ethoxy)-pyrrolidine-1-carbonyl]-2-methyl-propyl}-carbamic acid methyl ester

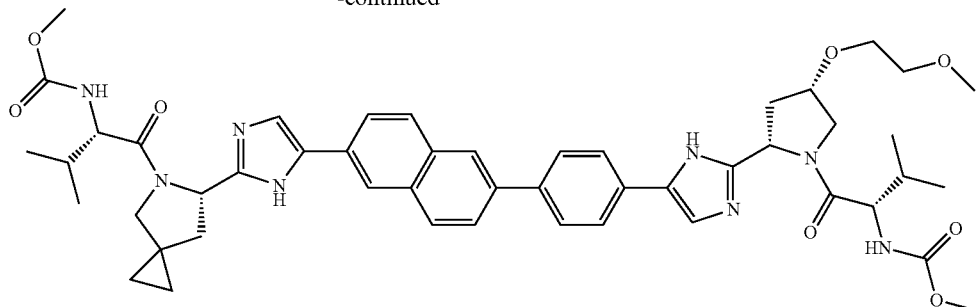

[1-(6-{5-[6-(4-{2-[1-(2-Methoxycarbonylamino-3-methyl-butyryl)-
4-(2-methoxy-ethoxy)-pyrrolidin-2-yl]-3H-imidazol-4-yl}-phenyl)-
naphthalen-2-yl]-1H-imidazol-2-yl}-5-aza-spiro[2.4]heptane-5-
carbonyl)-2-methyl-propyl]-carbamic acid methyl ester

4-Hydroxy-pyrrolidine-1,2-dicarboxylic acid 2-[2-(4-bromo-phenyl)-2-oxo-ethyl]ester 1-tert-butyl ester 4-Hydroxy-pyrrolidine-1,2-dicarboxylic acid 1-tert-butyl ester (5.0 g) was dissolved in methanol (87 mL), and $Cs_2CO_3$ (3.5 g) in water (56 mL) was added. The mixture was stirred over 10 min. and evaporated under vacuum. The solid was dissolved in DMF (100 mL), and 2-bromo-1-(4-bromo-phenyl)-ethanone (6.0 g) was added. Reaction mixture was stirred over 3 hours and evaporated under vacuum. The crude solid was used for the next step.

2-[5-(4-Bromo-phenyl)-1H-imidazol-2-yl]-4-hydroxy-pyrrolidine-1-carboxylic acid tert-butyl ester The crude 4-Hydroxy-pyrrolidine-1,2-dicarboxylic acid 2-[2-(4-bromo-phenyl)-2-oxo-ethyl]ester 1-tert-butyl ester (10.8 g) and ammonium acetate (13.3 g) were suspended in toluene (80 mL). The reaction mixture was stirred at 110° C. for 80 min. and evaporated under reduced pressure and resulting residue was taken up in ethyl acetate (200 mL). The organic phase was washed with saturated sodium bicarbonate (1×150 mL) and dried over sodium sulfate. After the solvent was removed, the resulting oil was subjected to silica gel chromatography using effluent of 50-90% ethyl acetate and hexanes. The fractions containing product were combined and the solvent was removed under reduced pressure to provide 2-[5-(4-Bromo-phenyl)-1H-imidazol-2-yl]-4-hydroxy-pyrrolidine-1-carboxylic acid tert-butyl ester (2.3 g, 32% over 2 steps) as an off-white solid.

2-[4-(4-Bromo-phenyl)-1-(2-trimethylsilanyl-ethoxymethyl)-1H-imidazol-2-yl]-4-hydroxy-pyrrolidine-1-carboxylic acid tert-butyl ester 2-[5-(4-Bromo-phenyl)-1H-imidazol-2-yl]-4-hydroxy-pyrrolidine-1-carboxylic acid tert-butyl ester (500 mg) was dissolved in DMF (8 mL), and NaH (54 mg) was added. The mixture was stirred over 10 min. and SEM-Cl was added slowly, and then stirred for 2 hours. The mixture was quenched with 3 mL of sat. $NH_4Cl$ and was taken up in ethyl acetate (100 mL). The organic phase was washed with saturated sodium bicarbonate (1×100 mL) and dried over sodium sulfate. After the solvent was removed, the resulting oil was subjected to silica gel chromatography using effluent of 20-50% ethyl acetate and hexanes. The fractions containing product were combined and the solvent was removed under reduced pressure to provide 2-[4-(4-Bromo-phenyl)-1-(2-trimethylsilanyl-ethoxymethyl)-1H-imidazol-2-yl]-4-hydroxy-pyrrolidine-1-carboxylic acid tert-butyl ester (648 mg, 98%) as an off-white solid.

2-[4-(4-Bromo-phenyl)-1-(2-trimethylsilanyl-ethoxymethyl)-1H-imidazol-2-yl]-4-(2-methoxy-ethoxy)-pyrrolidine-1-carboxylic acid tert-butyl ester 2-[4-(4-Bromo-phenyl)-1-(2-trimethylsilanyl-ethoxymethyl)-1H-imidazol-2-yl]-4-hydroxy-pyrrolidine-1-carboxylic acid tert-butyl ester (222 mg) was dissolved in DMF (4 mL), and NaH (25 mg) was added. The mixture was stirred over 20 min. and 1-bromo-2-methoxy-ethane was added slowly, and then stirred for 2.5 hours. The mixture was quenched with 3 mL of sat. $NH_4Cl$ and was taken up in ethyl acetate (50 mL). The organic phase was washed with saturated sodium bicarbonate (1×50 mL) and dried over sodium sulfate. After the solvent was removed, the resulting oil was subjected to silica gel chromatography using effluent of 20-60% ethyl acetate and hexanes. The fractions containing product were combined and the solvent was removed under reduced pressure to provide 2-[4-(4-Bromo-phenyl)-1-(2-trimethylsilanyl-ethoxymethyl)-1H-imidazol-2-yl]-4-(2-methoxy-ethoxy)-pyrrolidine-1-carboxylic acid tert-butyl ester (209 mg, 85%) as a clear oil.

{1-[2[5-(4-Bromo-phenyl)-1H-imidazol-2-yl]-4-(2-methoxy-ethoxy)-pyrrolidine-1-carbonyl]-2-methyl-propyl}-carbamic acid methyl ester To 2-[4-(4-Bromo-phenyl)-1-(2-trimethylsilanyl-ethoxymethyl)-1H-imidazol-2-yl]-4-(2-methoxy-ethoxy)-pyrrolidine-1-carboxylic acid tert-butyl ester (209 mg) in DCM (3 mL) was added 4N HCl in dioxane (2.6 mL). The suspension was stirred for 16 hours then concentrated to afford the HCl salt of the crude amine. To the crude amine in DMF (3 mL) was added N-methylmorpholine (193 µL). After all material dissolved, 2-methoxycarbonylamino-3-methyl-butyric acid (123 mg) and HATU (267 mg) were added. After stirring for 30 min. the reaction was purified by a preparative HPLC (10-60% MeCN—$H_2O$; 0.1% formic acid modifier) to afford the title product (169 mg, 92%).

[1-(6-{5-[6-(4-{2-[1-(2-Methoxycarbonylamino-3-methyl-butyryl)-4-(2-methoxy-ethoxy)-pyrrolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester A mixture of {1-[2[5-(4-Bromo-phenyl)-1H-imidazol-2-yl]-4-(2-methoxy-ethoxy)-pyrrolidine-1-carbonyl]-2-methyl-propyl}-carbamic acid methyl ester (169 mg), bis(pinacolato)diboron (107 mg), [1,1'-bis(diphenylphosphino)ferrocene]dichloropalladium(II)(24 mg) and potassium acetate (95 mg) in 1.6 mL of dioxane was heated to 90° C. for 1.5 hour. (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester (170 mg) in 1 mL of dioxane and 2M tripotassium phosphate (565 μl) were added and stirred at 90° C. for overnight. The mixture was purified by a preparative HPLC (10-60% MeCN—H$_2$O; 0.1% formic acid modifier) to afford the title product (119 mg, 41%). $^1$H NMR (DMSO-d6, 400 MHz) δ: 8.20-8.10 (m, 2H), 7.90-7.68 (m, 6H), 7.60-7.55 (m. 2H), 7.33-7.30 (m, 2H), 5.18 (m, 1H), 5.07 (m, 1H), 4.44 (m, 1H), 4.04-3.69 (m, 6H), 3.80-3.38 (m, 5H), 3.30 (m, 9H), 2.71 (m, 1H), 2.40-1.90 (m, 5H), 0.90-0.79 (m, 12H), 0.70-0.54 (m, 4H); MS (ESI) m/z 889.5 [M+H]$^+$.

Example FO

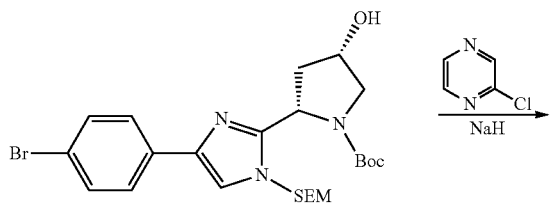

2-[4-(4-Bromo-phenyl)-1-(2-trimethylsilanyl-ethoxymethyl)-1H-imidazol-2-yl]-4-hydroxy-pyrrolidine-1-carboxylic acid tert-butyl ester

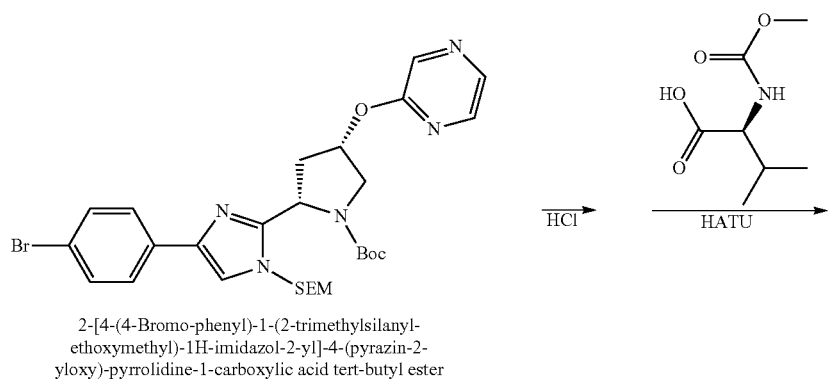

2-[4-(4-Bromo-phenyl)-1-(2-trimethylsilanyl-ethoxymethyl)-1H-imidazol-2-yl]-4-(pyrazin-2-yloxy)-pyrrolidine-1-carboxylic acid tert-butyl ester

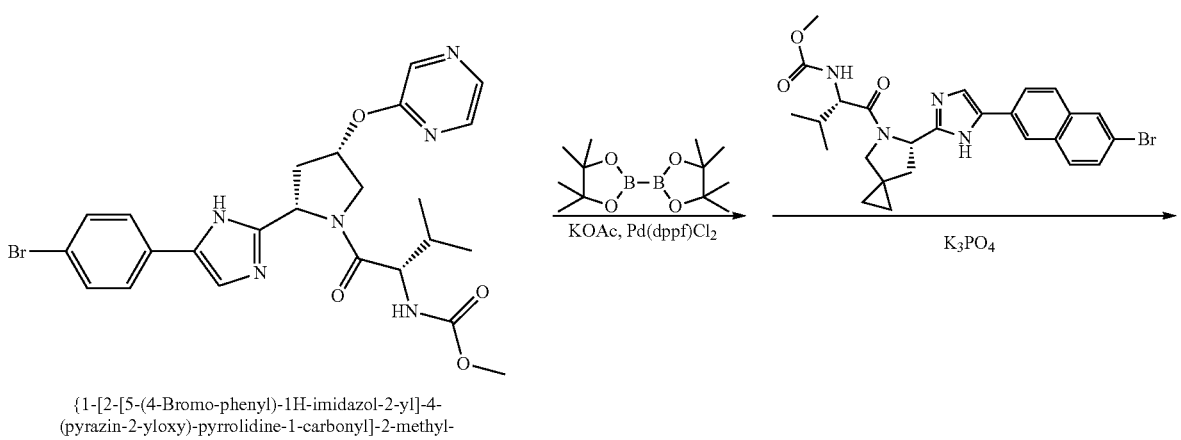

{1-[2-[5-(4-Bromo-phenyl)-1H-imidazol-2-yl]-4-(pyrazin-2-yloxy)-pyrrolidine-1-carbonyl]-2-methyl-propyl}-carbamic acid methyl ester -continued

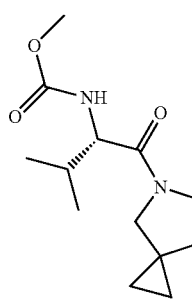

[1-(6-{5-[6-(4-{2-[1-(2-Methoxycarbonylamino-3-methyl-butyryl)-
4-(pyrazin-2-yloxy)-pyrrolidin-2-yl]-3H-imidazol-4-yl}-phenyl)-
naphthalen-2-yl]-1H-imidazol-2-yl}-5-aza-spiro[2.4]heptane-5-
carbonyl)-2-methyl-propyl]-carbamic acid methyl ester 2-[4-(4-Bromo-phenyl)-1-(2-trimethylsilanyl-
ethoxymethyl)-1H-imidazol-2-yl]-4-(pyrazin-2-
yloxy)-pyrrolidine-1-carboxylic acid tert-butyl ester Title compound was prepared according to the method employed to prepare 2-[4-(4-Bromo-phenyl)-1-(2-trimethyl-silanyl-ethoxymethyl)-1H-imidazol-2-yl]-4-(2-methoxy-ethoxy)-pyrrolidine-1-carboxylic acid tert-butyl ester (Example 1), substituting 2-chloro-pyrazine (50 µl) for 1-bromo-2-methoxy-ethane (94 mg, 40%).

{1-[2[5-(4-Bromo-phenyl)-1H-imidazol-2-yl]-4-
(pyrazin-2-yloxy)-pyrrolidine-1-carbonyl]-2-methyl-
propyl}-carbamic acid methyl ester Title compound was prepared according to the method employed to prepare {1-[2-[5-(4-Bromo-phenyl)-1H-imida-zol-2-yl]-4-(2-methoxy-ethoxy)-pyrrolidine-1-carbonyl]-2-methyl-propyl}-carbamic acid methyl ester (Example 1), substituting 2-[4-(4-Bromo-phenyl)-1-(2-trimethylsilanyl-ethoxymethyl)-1H-imidazol-2-yl]-4-(pyrazin-2-yloxy)-pyr-rolidine-1-carboxylic acid tert-butyl ester (94 mg) for 2-[4-(4-Bromo-phenyl)-1-(2-trimethylsilanyl-ethoxymethyl)-1H-imidazol-2-yl]-4-(2-methoxy-ethoxy)-pyrrolidine-1-carboxylic acid tert-butyl ester (88 mg, 99%).

[1-(6-{5-[6-(4-{2-[1-(2-Methoxycarbonylamino-3-
methyl-butyryl)-4-(pyrazin-2-yloxy)-pyrrolidin-2-
yl]-3H-imidazol-4-yl}-phenyl)-naphthalen-2-yl]-1H-
imidazol-2-yl}-5-aza-spiro[2.4]heptane-5-carbonyl)-
2-methyl-propyl]-carbamic acid methyl ester Title compound was prepared according to the method employed to prepare [1-(6-{5-[6-(4-{2-[1-(2-Methoxycarbo-nylamino-3-methyl-butyryl)-4-(2-methoxy-ethoxy)-pyrroli-din-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester (Example 1), substituting {1-[2[5-(4-Bromo-phenyl)-1H-imidazol-2-yl]-4-(pyrazin-2-yloxy)-pyrrolidine-1-carbonyl]-2-methyl-pro-pyl}-carbamic acid methyl ester (88 mg) for {1-[2[5-(4-Bromo-phenyl)-1H-imidazol-2-yl]-4-(2-methoxy-ethoxy)-pyrrolidine-1-carbonyl]-2-methyl-propyl}-carbamic acid methyl ester (38 mg, 26%). $^1$H NMR (MeOH-d4, 400 MHz) δ: 8.20-8.10 (m, 3H), 7.90-7.68 (m, 8H), 7.60-7.55 (m, 2H), 7.33-7.30 (m, 2H), 5.68 (m, 1H), 5.39 (m, 1H), 4.44 (m, 1H), 4.04-3.69 (m, 6H), 3.80-3.38 (m, 1H), 3.30 (m, 6H), 2.71 (m, 1H), 2.40-1.90 (m, 5H), 0.90-0.79 (m, 12H), 0.70-0.54 (m, 4H); MS (ESI) m/z 910.5 [M+H]$^+$.

Example FP

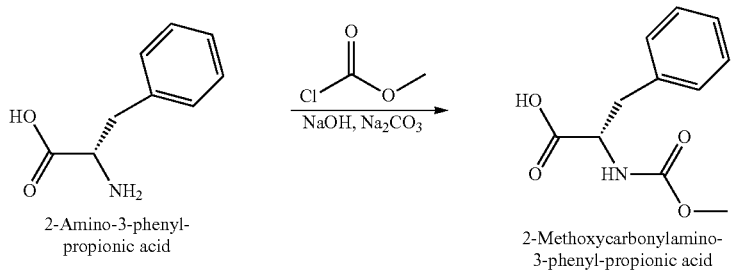

2-Amino-3-phenyl-
propionic acid

2-Methoxycarbonylamino-
3-phenyl-propionic acid

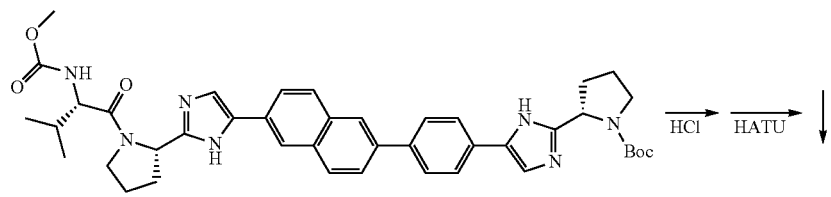

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

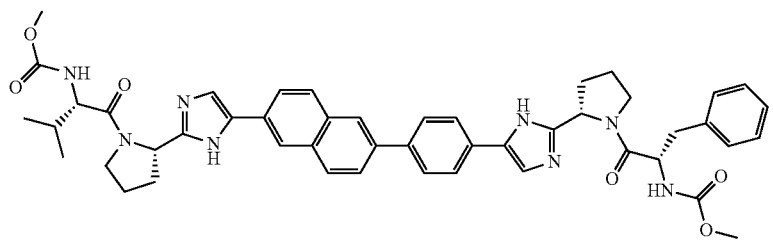

[1-(2-{5-[6-(4-{2-[1-(2-Methoxycarbonylamino-3-phenyl-propionyl)-pyrrolidin-2-yl]-3H-imidazol-4-yl}phenyl)-naphthalen-2-yl]-1H-imidazol-2-yl}-pyrrolidine-1-carbonyl)-2-methyl-propyl]-carbamic acid methyl ester

2-Methoxycarbonylamino-3-phenyl-propionic acid

2-Amino-3-phenyl-propionic acid (1.65 g) was dissolved in 1 N NaOH (10 mL), and $Na_2CO_3$ (530 mg) was added. The mixture was cooled to 0° C. and methyl chloroformate was added slowly, and then stirred for overnight at room temperature. The mixture was washed with DCM and acidified with 3 mL of 2N HCl, and then was taken up in ether (200 mL). The organic phase was dried over sodium sulfate. Removing the solvent to give 2-Methoxycarbonylamino-3-phenyl-propionic acid (1.95 g, 87%) as an off-white solid.

[1-(2-{5-[6-(4-{2-[1-(2-Methoxycarbonylamino-3-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester To 2-{5-[4-(6-{2-[1-(2-Methoxycarbonylamino-3-methyl-butyryl)-pyrrolidin-2-yl]-3H-imidazol-4-yl}-naphthalen-2-yl]-1H-imidazol-2-yl}-pyrrolidine-1-carboxylic acid tert-butyl ester (40 mg) in methanol (0.5 mL) was added 4N HCl in dioxanes (0.5 mL). The mixture was stirred for 1.5 hours then concentrated to afford the HCl salt of the crude amine. To the crude amine in DMF (2 mL) was added N-methylmorpholine (30 μL). After all material dissolved, 2-methoxy carbonylamino-3-phenyl-propionic acid (24 mg) and HATU (42 mg) were added. After stirring for 30 min. the reaction was purified by a preparative HPLC (10-60% MeCN—$H_2O$; 0.1% formic acid modifier) to afford the title product (34 mg, 37%). $^1H$ NMR (MeOH-d4, 400 MHz) δ: 8.22-8.03 (m, 4H), 7.89-7.74 (m, 8H), 7.54-7.05 (m, 5H), 5.20 (m, 2H), 4.63 (m, 1H), 4.48 (m, 1H), 4.25 (m, 1H), 4.15-3.88 (m, 4H), 3.69-3.51 (m, 8H), 3.45-3.15 (m, 4H) 3.10 (m, 1H), 2.95 (m, 1H), 2.86 (m, 1H), 2.45-2.04 (m, 7H), 1.00-0.88 (m, 6H); MS (ESI) m/z 837.4 $[M+H]^+$.

Example FQ

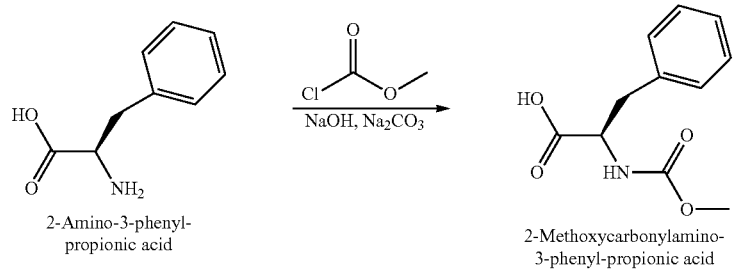

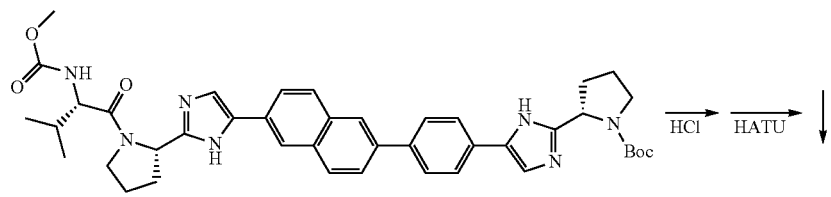

2-{5-[4-(6-{2-[1-(2-Methoxycarbonylamino-3-methyl-butyryl)-
pyrrolidin-2-yl]-3H-imidazol-4-yl}-naphthalen-2-yl)-phenyl]-1H-
imidazol-2-yl}-pyrrolidine-1-carboxylic acid tert-butyl esterw

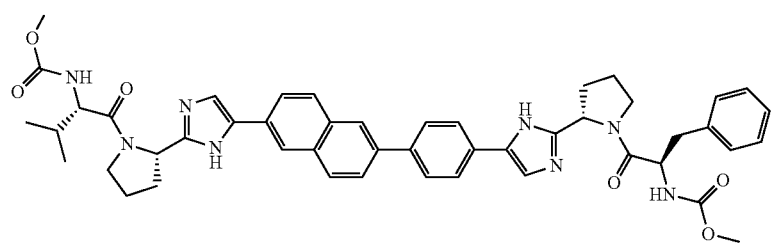

[1-(2-{5-[6-(4-{2-[1-(2-Methoxycarbonylamino-3-phenyl-propionyl)-
pyrrolidin-2-yl]-3H-imidazol-4-yl}phenyl)-naphthalen-2-yl]-1H-imidazol-
2-yl}-pyrrolidine-1-carbonyl)-2-methyl-propyl]-carbamic acid methyl ester

[1-(2-{5-[6-(4-{2-[1-(2-Methoxycarbonylamino-3-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Title compound was prepared according to the method employed to prepare [1-(2-{5-[6-(4-{2-[1-(2-Methoxycarbonylamino-3-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (Example 3), (33 mg, 36%). $^1$H NMR (MeOH-d4, 400 MHz) δ: 8.22-8.03 (m, 4H), 7.89-7.74 (m, 9H), 7.54-7.05 (m, 4H), 5.20 (m, 2H), 4.63 (m, 1H), 4.48 (m, 1H), 4.25 (m, 1H), 4.15-3.88 (m, 4H), 3.69-3.51 (m, 8H), 3.45-3.15 (m, 4H) 3.10 (m, 1H), 2.95 (m, 1H), 2.86 (m, 1H), 2.45-1.97 (m, 5H), 1.80 (m, 1H), 1.63 (m, 1H), 1.00-0.88 (m, 6H); MS (ESI) m/z 837.4 [M+H]$^+$.

Example FR

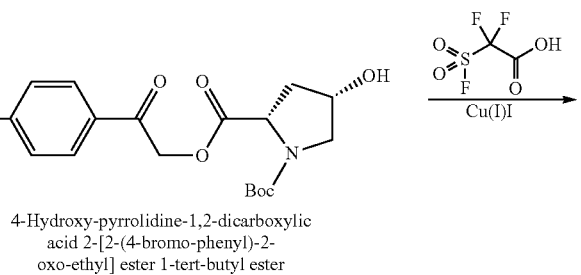

4-Hydroxy-pyrrolidine-1,2-dicarboxylic
acid 2-[2-(4-bromo-phenyl)-2-
oxo-ethyl] ester 1-tert-butyl ester

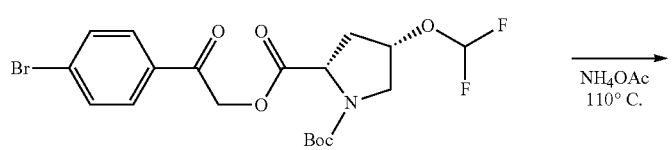

4-Difluoromethoxy-pyrrolidine-1,2-
dicarboxylic acid 2-[2-(4-bromo-phenyl)-
2-oxo-ethyl] ester 1-tert-butyl ester

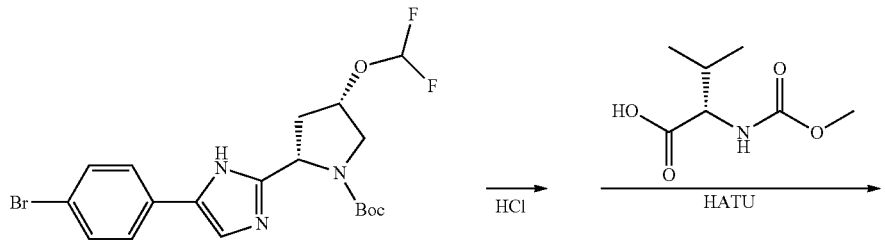

2-[5-(4-Bromo-phenyl)-1H-imidazol-
2-yl]-4-difluoromethoxy-pyrrolidine-
1-carboxylic acid tert-butyl ester

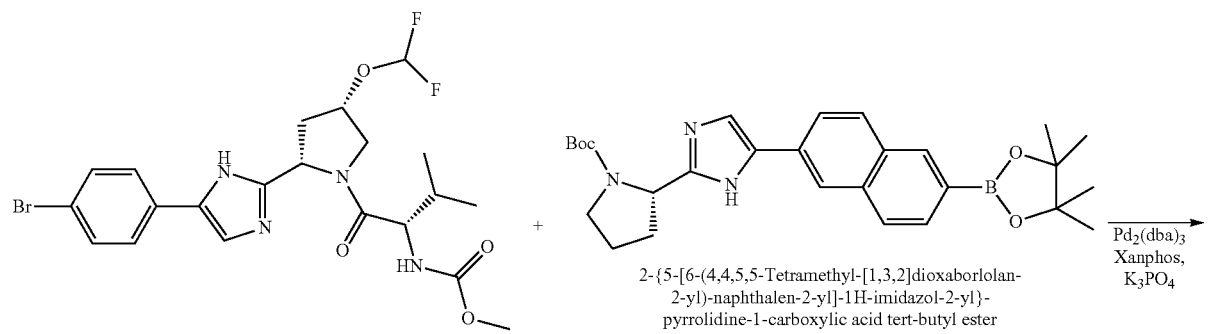

(1-{2-[5-(4-Bromo-phenyl)-1H-imidazol-2-yl]-4-
difluoromethoxy-pyrrolidine-1-carbonyl}-
2-methyl-propyl)-carbamic acid methyl ester 2-{5-[6-(4,4,5,5-Tetramethyl-[1,3,2]dioxaborlolan-
2-yl)-naphthalen-2-yl]-1H-imidazol-2-yl}-
pyrrolidine-1-carboxylic acid tert-butyl ester

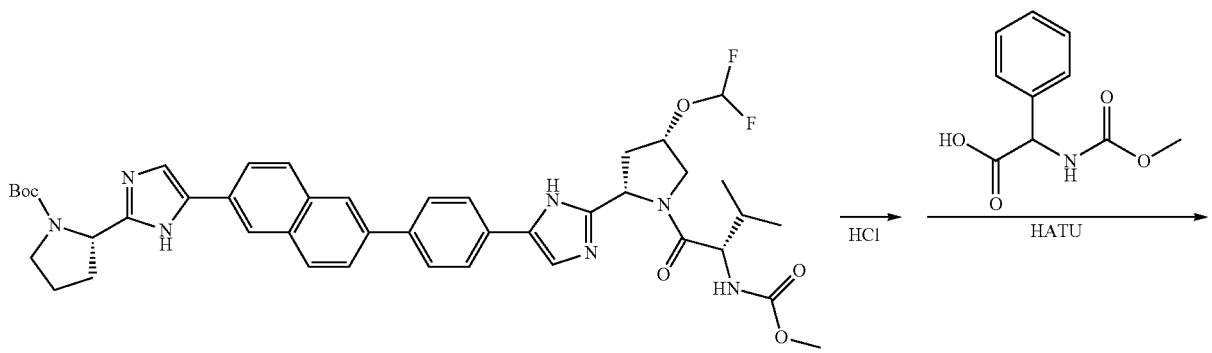

2{5-[6-(4-{2-[4-Difluoromethoxy-1-(2-methoxycarbonylamino-3-
methyl-butyryl)-pyrrolidin-2-yl]-3H-imidazol-4-yl}-phenyl)-naphthalen-
2-yl]-1H-imidazol-2-yl}-pyrrolidine-1-carboxylic acid tert-butyl ester

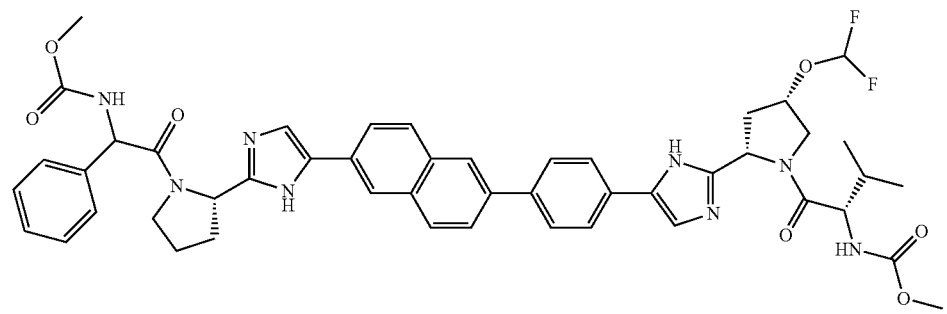

[1-(4-Difluoromethoxy-2-(5-[4-(6-{2-[1-(2-methoxycarbonylamino-2-phenyl-
acetyl)-pyrrolidin-2-yl]-3H-imidazol-4-yl}-naphthalen-2-yl)-phenyl]-1H-imidazol-
2-yl}-pyrrolidine-1-carbonyl)-2-methyl-propyl]-carbamic acid methyl ester

4-Difluoromethoxy-pyrrolidine-1,2-dicarboxylic acid 2-[2-(4-bromo-phenyl)-2-oxo-ethyl]ester 1-tert-butyl ester To 4-Hydroxy-pyrrolidine-1,2-dicarboxylic acid 2-[2-(4-bromo-phenyl)-2-oxo-ethyl]ester 1-tert-butyl ester (500 mg) and Cu(I)I (45 mg) in MeCN (8 mL) at 45° C. was added 242 μl of difluoro-fluorosulfonyl-acetic acid in 2 mL of MeCN dropwise for 60 min. The reaction mixture was stirred at 45° C. for 60 min. and evaporated under reduced pressure, and resulting residue was taken up in ethyl acetate (100 mL). The organic phase was washed with brine (1×100 mL) and dried over sodium sulfate. After the solvent was removed, the resulting oil was subjected to silica gel chromatography using effluent of 10-50% ethyl acetate and hexanes. The fractions containing product were combined and the solvent was removed under reduced pressure to provide 4-Difluoromethoxy-pyrrolidine-1,2-dicarboxylic acid 2-[2-(4-bromo-phenyl)-2-oxo-ethyl]ester 1-tert-butyl ester (339 mg, 61%) as a clear oil.

2-[5-(4-Bromo-phenyl)-1H-imidazol-2-yl-4-difluoromethoxy-pyrrolidine-1-carboxylic acid tert-butyl ester Title compound was prepared according to the method employed to prepare 2-[5-(4-Bromo-phenyl)-1H-imidazol-2-yl]-4-hydroxy-pyrrolidine-1-carboxylic acid tert-butyl ester (Example 1), substituting 4-Difluoromethoxy-pyrrolidine-1,2-dicarboxylic acid 2-[2-(4-bromo-phenyl)-2-oxo-ethyl]ester 1-tert-butyl ester (305 mg) for 4-Hydroxy-pyrrolidine-1,2-dicarboxylic acid 2-[2-(4-bromo-phenyl)-2-oxo-ethyl]ester 1-tert-butyl ester (244 mg, 83%).

(1-{2-[5-(4-Bromo-phenyl)-1H-imidazol-2-yl-4-difluoromethoxy-pyrrolidine-1-carbonyl}-2-methoxy-propyl)-carbamic acid methyl ester To 2-[5-(4-Bromo-phenyl)-1H-imidazol-2-yl-4-difluoromethoxy-pyrrolidine-1-carboxylic acid tert-butyl ester (244 mg) in DCM (4 mL) was added 4N HCl in dioxanes (1.3 mL). The mixture was stirred for 1 hours then concentrated to afford the HCl salt of the crude amine. To the crude amine in DMF (2.7 mL) was added N-methylmorpholine (234 μL). After all material dissolved, 2-methoxycarbonylamino-3-methyl-butyric acid (103 mg) and HATU (263 mg) were added. After stirring for 60 min. the reaction was evaporated under reduced pressure, and resulting residue was taken up in ethyl acetate (100 mL). The organic phase was washed with saturated sodium bicarbonate (1×100 mL) and dried over sodium sulfate. After the solvent was removed, the resulting oil was subjected to silica gel chromatography using effluent of 80-100% ethyl acetate and hexanes. The fractions containing product were combined and the solvent was removed under reduced pressure to provide (1-{2-[5-(4-Bromo-phenyl)-1H-imidazol-2-yl-4-difluoromethoxy-pyrrolidine-1-carbonyl}-2-methoxy-propyl)-carbamic acid methyl ester (166 mg, 61%) as a clear oil.

2-{5-[6-(4-{2-[4-Difluoromethoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-bytyl ester To (1-{2-[5-(4-Bromo-phenyl)-1H-imidazol-2-yl-4-difluoromethoxy-pyrrolidine-1-carbonyl}-2-methoxy-propyl)-carbamic acid methyl ester (166 mg) and 2-{5-[6-(4,4,5,5-tetramethyl-[1,3,2]dioxaborolan-2-yl)-naphthalen-2-yl]-1H-imidazol-2-yl}-pyrrolidine-1-carboxylic acid tert-butyl ester (237 mg) in DME (1.6 mL) were added $Pd_2(dba)_3$ (15 mg), Xanphos (19 mg), and 2M $K_3PO_4$ (483 μl). After stirring for overnight at 80° C., the mixture was filtered and evaporated under reduced pressure, and resulting residue was subjected to silica gel chromatography using effluent of 10-15% MeOH and DCM. The fractions containing product were combined and the solvent was removed under reduced pressure to provide the title product (30 mg, 12%) as a clear film.

[1-(4-Difluoromethoxy-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester Title compound was prepared according to the method employed to prepare (1-{2-[5-(4-Bromo-phenyl)-1H-imidazol-2-yl-4-difluoromethoxy-pyrrolidine-1-carbonyl}-2-methoxy-propyl)-carbamic acid methyl ester (Example 5), substituting methoxycarbonylamino-phenyl-acetic acid (30 mg) for 2-methoxycarbonylamino-3-methyl-butyric acid (22 mg, 58%). $^1$H NMR (MeOH-d4, 400 MHz) δ: 8.20-8.05 (m, 3H), 7.95-7.72 (m, 5H), 7.56-7.35 (m. 8H), 7.15 (m, 1H), 6.71-6.35 (m, 1H), 5.55 (m, 1H), 5.30-5.20 (m, 3H), 5.05-4.90 (m, 3H), 4.36 (m, 1H), 4.20 (m, 1H), 4.12-3.82 (m, 2H), 3.65 (m, 6H), 3.50 (m, 1H), 2.75 (m, 1H), 2.45 (m, 1H), 2.35-1.90 (m, 2H), 0.98-0.85 (m, 6H); MS (ESI) m/z 889.3 $[M+H]^+$.

Example FS

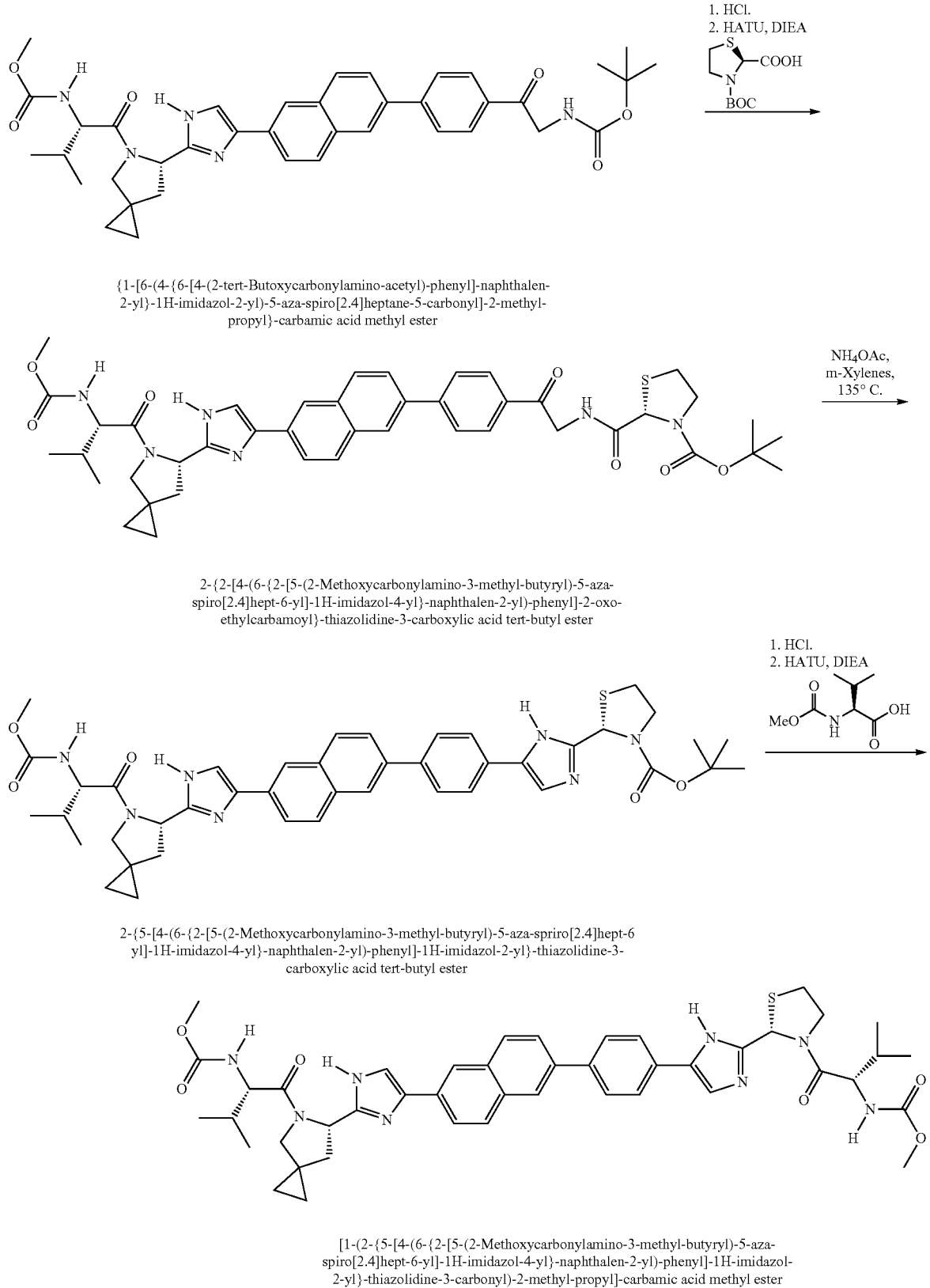

{1-[6-(4-{6-[4-(2-tert-Butoxycarbonylamino-acetyl)-phenyl]-naphthalen-2-yl}-1H-imidazol-2-yl)-5-aza-spiro[2.4]heptane-5-carbonyl]-2-methyl-propyl}-carbamic acid methyl ester 2-{2-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-2-oxo-ethylcarbamoyl}-thiazolidine-3-carboxylic acid tert-butyl ester 2-{5-[4-(6-{2-[5-(2-Methoxycarbonylamino-3-methyl-butyryl)-5-aza-spriro[2.4]hept-6-yl]-1H-imidazol-4-yl}-naphthalen-2-yl)-phenyl]-1H-imidazol-2-yl}-thiazolidine-3-carboxylic acid tert-butyl ester

[1-(2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carbonyl)-2-methyl-propyl]-carbamic acid methyl ester

2-{2-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-2-oxo-ethylcarbamoyl}-thiazolidine-3-carboxylic acid tert-butyl ester {1-[6-(4-{6-[4-(2-tert-Butoxycarbonylamino-acetyl)-phenyl]-naphthalen-2-yl}-1H-imidazol-2-yl)-5-aza-spiro[2.4]heptane-5-carbonyl]-2-methyl-propyl}-carbamic acid methyl ester (395.0 mg, 0.581 mmol) was dissolved in DCM (4 mL) and HCl in dioxane (4M, 4 mL) was added and stirring at room temperature was continued. After 60 minutes, all volatiles were removed in vacuo. The crude material was used in the next step without further purification. The crude material was dissolved in DMF (2.0 mL) and DIEA (110.8 mg, 0.860 mmol) was added. A solution of N-Boc (S) thiazolidine-2-carboxylic acid (100.0 mg, 0.430 mmol), HATU (163.0 mg, 0.430 mmol) and DIEA (55.4 mg, 0.430 mmol) in DMF (1 mL) was added. The reaction was stirred at room temperature. After 20 minutes, the reaction was diluted with EtOAc and was washed with brine, sodium hydroxyl solution (1M), brine, and was dried over sodium sulfate. Filtration and removal of solvents in vacuo gave the crude material (350 mg), which was used in the next step without further purification.

LCMS-ESI$^+$: calc'd for $C_{43}H_{50}N_6O_7S$: 794.9 ($M^+$); Found: 795.8 ($M+H^+$).

2-{5-[4-(6-{2-[5-(2-Methoxycarbonylamino-3-methyl-butyryl)-5-aza-spiro hept-6-yl]-1H-imidazol-4-yl}-naphthalen-2-yl)-phenyl]-1H-imidazol-2-yl}-thiazolidine-3-carboxylic acid tert-butyl ester 2-{2-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-2-oxo-ethylcarbamoyl}-thiazolidine-3-carboxylic acid tert-butyl ester (350 mg, 0.44 mmol) was dissolved in m-xylenes (3.0 mL) and heated at 135° C. Solid ammonium acetate (400 mg, 9.07 mmol) was added and the reaction was stirred at 135° C. After 45 minutes, the reaction was cooled to room temperature and the volatiles were removed in vacuo. The crude reaction product was partitioned between chloroform and water. The organic layer was collected and dried over sodium sulfate. Filtration and evaporation of solvents gave the crude product. The crude material was purified via silica gel chromatography (eluent: EtOAc/hexanes) to yield the product (151.3 mg, 0.195 mmol).

LCMS-ESI$^+$: calc'd for $C_{43}H_{49}N_7O_5S$: 775.9 ($M^+$); Found: 776.8 ($M+H^+$).

[1-(2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carbonyl)-2-methyl-propyl]-carbamic acid methyl ester 2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carboxylic acid tert-butyl ester (49.9 mg, 0.064 mmol) was dissolved in DCM (0.33 mL) and HCl in dioxane (4M, 0.33 mL) was added and stirring at room temperature was continued. After 45 minutes, all volatiles were removed in vacuo. The crude material was used in the next step without further purification. The crude material was dissolved in DMF (0.5 mL) and DIEA (24.6 mg, 0.191 mmol) was added. A solution of 2-(L) methoxycarbonylamino-3-methyl-butyric acid (11.2 mg, 0.064 mmol), HATU (24.1 mg, 0.064 mmol) and DIEA (8.2 mg, 0.064 mmol) in DMF (0.5 mL) was added. The reaction was stirred at room temperature. After 18 hrs all volatiles were removed in vacuo. The crude material, which was purified by RP-HPLC (eluent: water/MeCN w/0.1% TFA) to yield the product (8.5 mg) as a TFA salt.

LCMS-ESI$^+$: calc'd for $C_{45}H_{52}N_8O_6S$: 833.0 ($M^+$); Found: 833.7 ($M+H^+$).

$^1$H-NMR: 300 MHz, (dmso-d$_6$) δ: 8.35-7.88 (m, 14H), 7.36-7.33 (m, 2H), 6.36 (m, 1H), 5.28 (dd, J=7.2 Hz, 1H), 4.24 (m, 1H) 4.16 (m, 1H), 4.03-3.74 (m, 6H), 3.55 (s, 3H), 3.54 (s, 3H), 2.27 (m, 2H), 2.08 (m, 2H), 0.90-0.76 (m, 12H) 0.65 (m, 4H) ppm.

Example FT

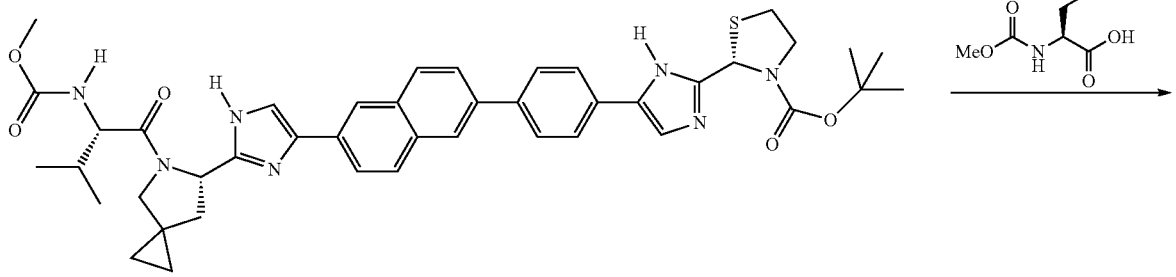

2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carboxylic acid tert-butyl ester

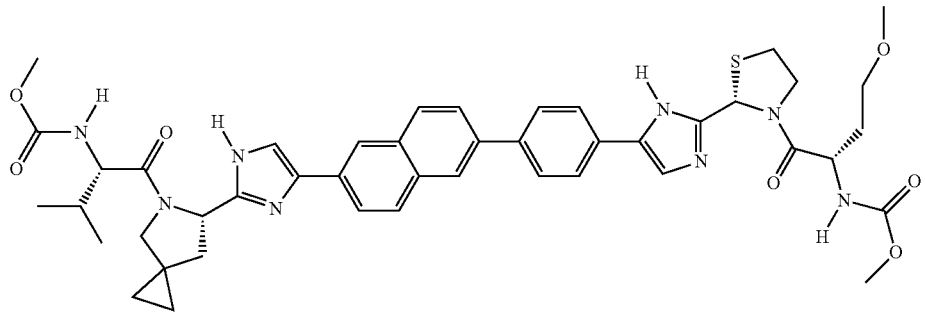

[1-(6-{4-[6-(4-{2-[3-(4-Methoxy-2-methoxycarbonylamino-butyryl)-thiazolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{4-[6-(4-{2-[3-(4-Methoxy-2-methoxycarbonylamino-butyryl)-thiazolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester 2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carboxylic acid tert-butyl ester (49.9 mg, 0.064 mmol) was dissolved in DCM (0.33 mL) and HCl in dioxane (4M, 0.33 mL) was added and stirring at room temperature was continued. After 45 minutes, all volatiles were removed in vacuo. The crude material was used in the next step without further purification. The crude material was dissolved in DMF (0.5 mL) and DIEA (24.6 mg, 0.191 mmol) was added. A solution of (L) 4-methoxy-2-methoxycarbonylamino-butyric acid (12.1 mg, 0.064 mmol), HATU (24.1 mg, 0.064 mmol) and DIEA (8.2 mg, 0.064 mmol) in DMF (0.5 mL) was added. The reaction was stirred at room temperature. After 3 hrs all volatiles were removed in vacuo. The crude material, which was purified by RP-HPLC (eluent: water/MeCN w/0.1% TFA) to yield the product (21.3 mg) as a TFA salt.

LCMS-ESI$^+$: calc'd for $C_{45}H_{52}N_8O_7S$: 849.0 (M$^+$); Found: 849.7 (M+H$^+$).

$^1$H-NMR: 300 MHz, (dmso-d$_6$) δ: 8.37 (m, 2H), 8.20-8.14 (m, 2H), 8.06-7.88 (m, 10H), 7.36-7.33 (m, 2H), 6.36 (m, 1H), 5.30 (dd, J=7.2 Hz, 1H), 4.45 (m, 1H) 4.06 (m, 1H), 4.06-3.69 (m, 6H), 3.55 (s, 3H), 3.54 (s, 3H), 3.36 (m, 2H), 3.25 (m, 3H), 2.26 (m, 2H), 2.02 (m, 2H), 1.81 (m, 1H), 0.90-0.76 (m, 6H) 0.65 (m, 4H) ppm.

Example FU

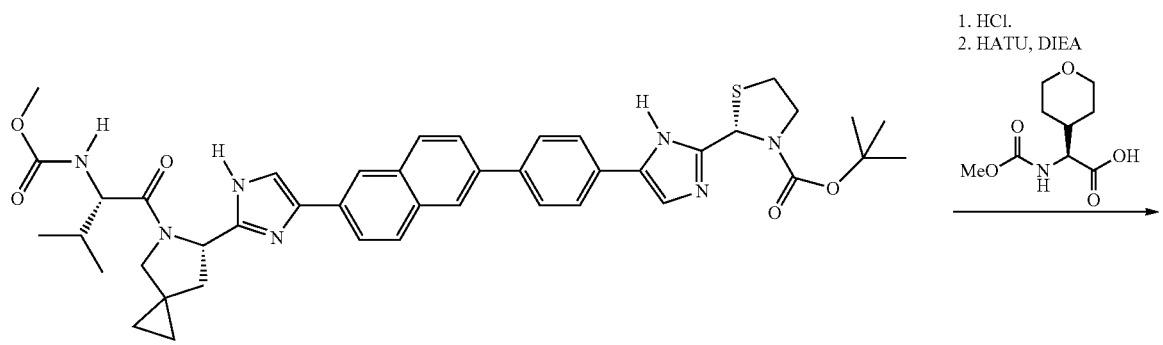

2-{5-[4-(6-{2-[5-(2-Methoxycarbonylamino-3-methyl-butyryl)-5-aza-spiro[2.4]hept-6-yl]-1H-imidazol-4-yl-naphthalen-2-yl)-phenyl]-1H-imidazol-2-yl}-thiazolidine-3-carboxylic acid tert-butyl ester

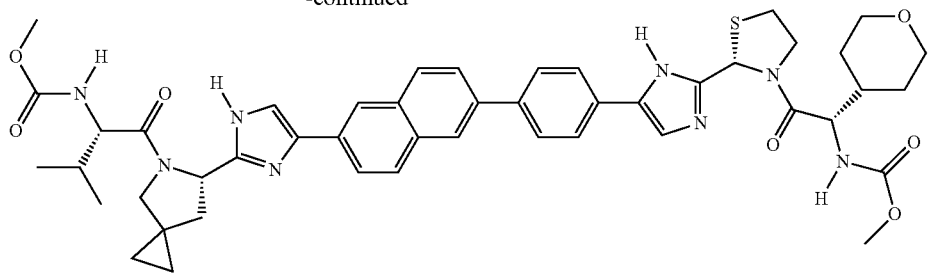

{1-[6-(4-{6-[4-(2-{3-[2-Methoxycarbonylamino-2-(tetrahydro-pyran-4-yl)-
acetyl]-thiazolidin-2-yl}-3H-imidazol-4-yl)-phenyl]-naphthalen-2-yl}-1H-
imidazol-2-yl)-5-aza-spiro[2.4]heptane-5-carbonyl]-2-methyl-propyl}-
carbamic acid methyl ester {1-[6-(4-{6-[4-(2-{3-[2-Methoxycarbonylamino-2-(tetrahydro-pyran-4-yl)-acetyl]-thiazolidin-2-yl}-3H-imidazol-4-yl)-phenyl]-naphthalen-2-yl}-1H-imidazol-2-yl)-5-aza-spiro[2.4]heptane-5-carbonyl]-2-methyl-propyl}-carbamic acid methyl ester 2-{5-[4-(6-{2-[5-(2-Methoxycarbonylamino-3-methyl-butyryl)-5-aza-spiro[2.4]hept-6-yl]-1H-imidazol-4-yl}-naphthalen-2-yl)-phenyl]-1H-imidazol-2-yl}-thiazolidine-3-carboxylic acid tert-butyl ester (49.9 mg, 0.064 mmol) was dissolved in DCM (0.33 mL) and HCl in dioxane (4M, 0.33 mL) was added and stirring at room temperature was continued. After 45 minutes, all volatiles were removed in vacuo. The crude material was used in the next step without further purification. The crude material was dissolved in DMF (0.5 mL) and DIEA (24.6 mg, 0.191 mmol) was added. A solution of 2-(L) methoxycarbonylamino-(tetrahydro-pyran-4-yl)-acetic acid (13.8 mg, 0.064 mmol), HATU (24.1 mg, 0.064 mmol) and DIEA (8.2 mg, 0.064 mmol) in DMF (0.5 mL) was added. The reaction was stirred at room temperature. After 18 hrs all volatiles were removed in vacuo. The crude material, which was purified by RP-HPLC (eluent: water/MeCN w/0.1% TFA) to yield the product (6.2 mg) as a TFA salt.

LCMS-ESI$^+$: calc'd for $C_{47}H_{52}N_8O_7S$: 875.0 (M$^+$); Found: 875.7 (M+H$^+$).

$^1$H-NMR: 300 MHz, (dmso-d$_6$) δ: $^1$H-NMR: 300 MHz, (dmso-d$_6$) δ: 8.31-7.89 (m, 14H), 7.36-7.33 (m, 2H), 6.34 (m, 1H), 5.27 (m, 1H), 4.30 (m, 1H) 4.03 (m, 1H), 4.06-3.69 (m, 6H), 3.57 (s, 3H), 3.54 (s, 3H), 3.28-2.95 (m, 4H), 2.26 (m, 2H), 2.02 (m, 2H), 1.50-1.32 (m, 4H), 0.85-0.73 (m, 6H) 0.65 (m, 4H) ppm.

Example FV

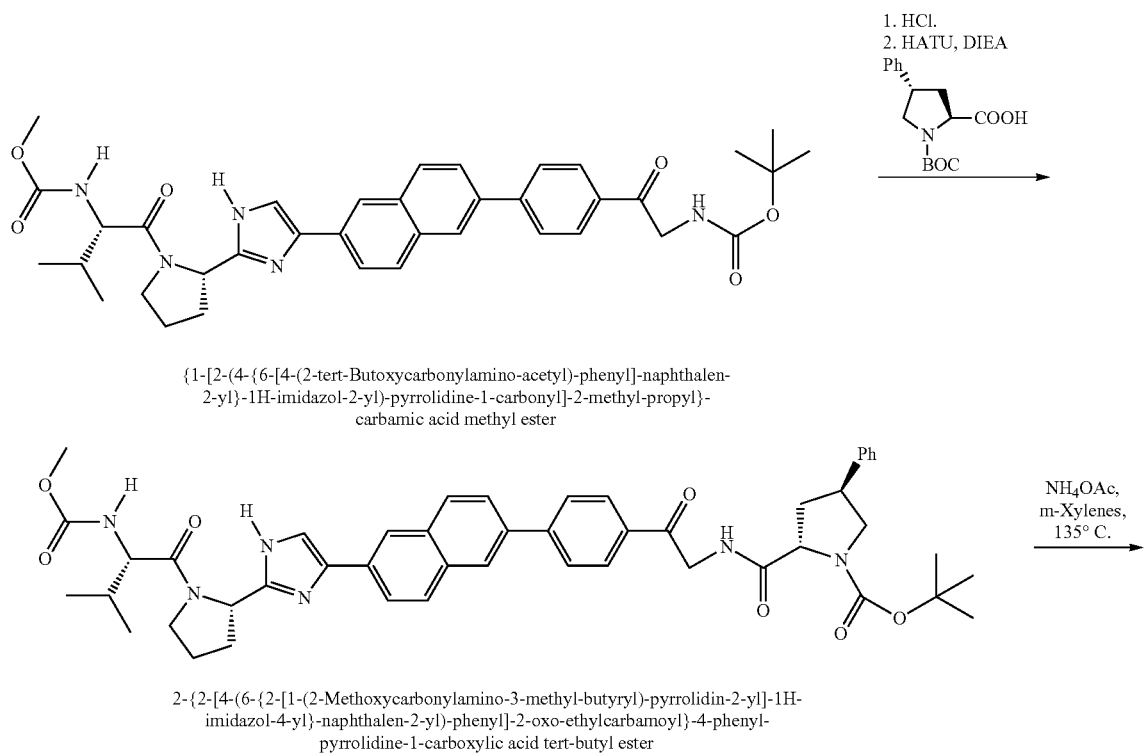

{1-[2-(4-{6-[4-(2-tert-Butoxycarbonylamino-acetyl)-phenyl]-naphthalen-
2-yl}-1H-imidazol-2-yl)-pyrrolidine-1-carbonyl]-2-methyl-propyl}-
carbamic acid methyl ester 2-{2-[4-(6-{2-[1-(2-Methoxycarbonylamino-3-methyl-butyryl)-pyrrolidin-2-yl]-1H-
imidazol-4-yl}-naphthalen-2-yl)-phenyl]-2-oxo-ethylcarbamoyl}-4-phenyl-
pyrrolidine-1-carboxylic acid tert-butyl ester -continued

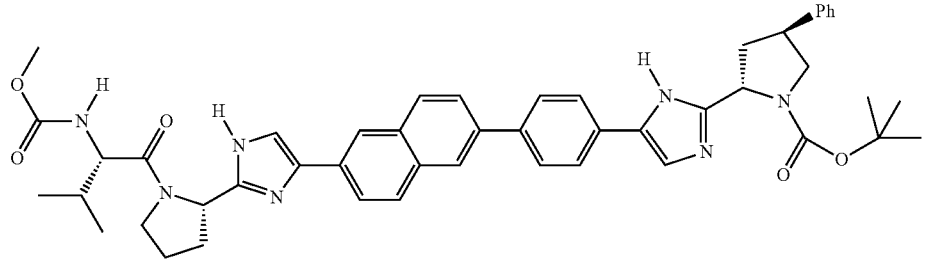
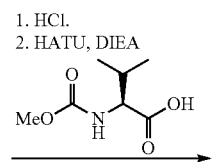

2-{5-[4-(6-{2-[1-(2-Methoxycarbonylamino-3-methyl-butyryl)-pyrrolidin-2-yl]-1H-imidazol-4-yl}naphthalen-2-yl)-phenyl]-1H-imidazol-2-yl}-4-phenyl-pyrrolididne-1-carboxylic acid tert-butyl ester

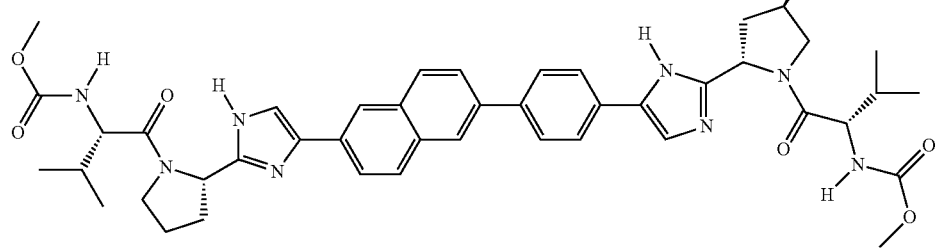

[1-(2-{5-[4-(6-{2-[1-(2-Methoxycarbonylamino-3-methyl-butyryl)-pyrrolidine-2-yl]-1H-imidazol-4-yl}naphthalen-2-yl)-phenyl]-1H-imidazol-2-yl}-4-phenyl-pyrrolidine-1-carbonyl)-2-methyl-propyl]-carbamic acid methyl ester 2-{2-[4-(6-{2-[1-(2-Methoxycarbonylamino-3-methyl-butyryl)-pyrrolidin-2-yl]-1H-imidazol-4-yl}-naphthalen-2-yl)-phenyl]-2-oxo-ethylcarbamoyl}-4-phenyl-pyrrolidine-1-carboxylic acid tert-butyl ester {1-[2-(4-{6-[4-(2-tert-Butoxycarbonylamino-acetyl)-phenyl]-naphthalen-2-yl}-1H-imidazol-2-yl)-pyrrolidine-1-carbonyl]-2-methyl-propyl}-carbamic acid methyl ester (61.0 mg, 0.095 mmol) was dissolved in DCM (1 mL) and HCl in dioxane (4M, 1 mL) was added and stirring at room temperature was continued. After 90 minutes, all volatiles were removed in vacuo. The crude material was used in the next step without further purification. The crude material was dissolved in DMF (1.0 mL) and DIEA (23.7 mg, 0.183 mmol) was added. A solution of 4-Phenyl-pyrrolidine-1,2-dicarboxylic acid 1-tert-butyl ester (17.8 mg, 0.061 mmol), HATU (23.3 mg, 0.061 mmol) and DIEA (7.9 mg, 0.061 mmol) in DMF (0.5 mL) was added. The reaction was stirred at room temperature. After 20 minutes, the reaction was diluted with EtOAc and was washed with brine, saturated sodium bicarbonate solution, brine, and was dried over sodium sulfate. Filtration and removal of solvents in vacuo gave the crude material (88 mg), which was used in the next step without further purification.

LCMS-ESI$^+$: calc'd for $C_{48}H_{54}N_6O_7$: 826.9 (M$^+$); Found: 827.7 (M+H$^+$).

2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-phenyl-pyrrolidine-1-carboxylic acid tert-butyl ester 2-{2-[4-(6-{2-[1-(2-Methoxycarbonylamino-3-methyl-butyryl)-pyrrolidin-2-yl]-1H-imidazol-4-yl}-naphthalen-2-yl)-phenyl]-2-oxo-ethylcarbamoyl}-4-phenyl-pyrrolidine-1-carboxylic acid tert-butyl ester (88 mg) was dissolved in m-xylenes (1.0 mL) and heated at 135° C. Solid ammonium acetate (100 mg, 1.2 mmol) was added and the reaction was stirred at 135° C. After 180 minutes, the reaction was cooled to room temperature and the volatiles were removed in vacuo. The crude reaction product was partitioned between chloroform and water. The organic layer was collected and dried over sodium sulfate. Filtration and evaporation of solvents gave the crude product. The crude material was purified via silica gel chromatography (eluent: EtOAc/hexanes) to yield the product (51.0 mg, 0.195 mmol).

LCMS-ESI$^+$: calc'd for $C_{48}H_{53}N_7O_5$: 807.9 (M$^+$); Found: 808.4 (M+H$^+$).

[1-(2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-phenyl-pyrrolidine-1-carbonyl)-2-methyl-propyl]-carbamic acid methyl ester 2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-phenyl-pyrrolidine-1-carboxylic acid tert-butyl ester (51.0 mg, 0.063 mmol) was dissolved in DCM (1.0 mL) and HCl in dioxane (4M, 1.0 mL) was added and stirring at room temperature was continued. After 30 minutes, all volatiles were removed in vacuo. The crude material was used in the next step without further purification. The crude material was dissolved in DMF (0.5 mL) and DIEA (24.3 mg, 0.190 mmol) was added. A solution of 2-(L) methoxycarbonylamino-3-methyl-butyric acid (11.1 mg, 0.063 mmol), HATU (24.0 mg, 0.063 mmol) and DIEA (8.1 mg, 0.063 mmol) in DMF (0.5 mL) was added. The reaction was stirred at room temperature. After 60 minutes, the crude reaction was quenched with aqueous hydrochloric acid (0.1 mL, 2 M) and was purified by RP-HPLC (eluent: water/MeCN w/0.1% TFA) to yield the product (12.1 mg) as a TFA salt.

LCMS-ESI$^+$: calc'd for $C_{50}H_{56}N_8O_6$: 865.0 (M$^+$); Found: 865.4 (M+H$^+$).

$^1$H-NMR: 300 MHz, (dmso-d$_6$) δ: 8.31-8.30 (d, J=3 Hz, 2H), 8.08 (d, J=6.6 Hz, 2h), 7.98-7.86 (m, 10H), 7.34-7.21 (m, 7H), 5.28 (dd, J=6.0/2.7 Hz, 1H), 5.10 (dd, J=6.0/5.7 Hz, 1H), 4.26 (m, 1H) 4.11 (m, 1H), 4.06 (m, 1H) 3.85-3.73 (m, 3H), 3.48 (s, 3H), 3.47 (s, 3H), 2.27 (m, 2H), 2.14-2.09 (m, 7H), 0.89-0.72 (m, 12H) ppm.

Example FW

[1-(2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-phenyl-pyrrolidine-1-carbonyl)-2-methyl-propyl]-carbamic acid methyl ester 2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-phenyl-pyrrolidine-1-carboxylic acid tert-butyl ester (88. mg, 0.107 mmol) was dissolved in DCM (1.0 mL) and HCl in dioxane (4M, 1.0 mL) was added and stirring at room temperature was continued. After 40 minutes, all volatiles were removed in vacuo. The crude material was used in the next step without further purification. The crude material was dissolved in DMF (0.4 mL) and DIEA (40.8 mg, 0.321 mmol) was added. A solution of 2-(L) methoxycarbonylamino-3-methyl-butyric acid (18.7 mg, 0.107 mmol), HATU (40.6 mg, 0.107 mmol) and DIEA (13.6 mg, 0.107 mmol) in DMF (0.4 mL) was added. The reaction was stirred at room temperature. After 20 minutes, the crude reaction was quenched with aqueous hydrochloric acid (0.1 mL, 2 M) and was purified by RP-HPLC (eluent: water/MeCN w/0.1% TFA) to yield the product (38.7 mg) as a TFA salt.

LCMS-ESI$^+$: calc'd for $C_{50}H_{56}N_8O_6$: 865.0 (M$^+$); Found: 865.4 (M+H$^+$).

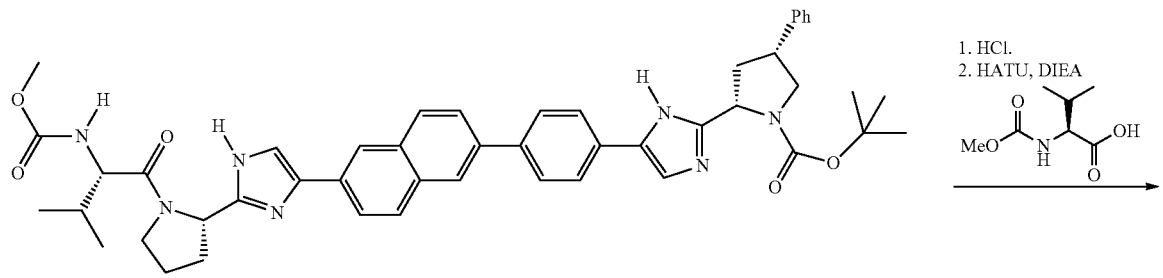

2-{5-[4-{6-{2-[1-(2-Methoxycarbonylamino-3-methyl-butyryl)-pyrrolidien-2-yl}-1H-imidazol-4-yl}-naphthalen-2-yl)-phenyl]-1H-imidazol-2-yl}-4-phenyl-pyrrolidine-1-carboxylic acid tert-butyl ester

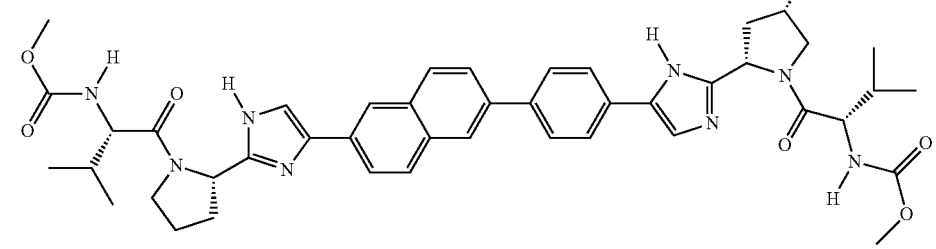

[1-(2-{5-[4-(6-{2-[1-(2-Methoxycarbonylamino-3-methyl-butyryl)-pyrrolidine-2-yl]-1H-imidazol-4-yl}-naphthalen-2-yl)-phenyl]-1H-imidazol-2-yl}-4-phenyl-pyrrolidine-1-carbonyl)-2-methyl-propyl]-carbamic acid methyl ester ¹H-NMR: 300 MHz, (dmso-d₆) δ: 8.37-8.35 (m, 2H), 8.16-7.91 (m, 12H), 7.47-7.28 (m, 7H), 5.24 (dd, J=7.8/5.4 Hz, 1H), 5.16 (dd, J=4.8/4.8 Hz, 1H), 4.44 (dd, J=6.3/6.3 Hz, 1H) 4.16-4.09 (m, 2H) 3.85-3.80 (m, 3H), 3.57 (s, 3H), 3.56 (s, 3H), 2.78 (m, 1H), 2.30-1.96 (m, 8H), 0.90-0.75 (m, 12H) ppm.

Example FX

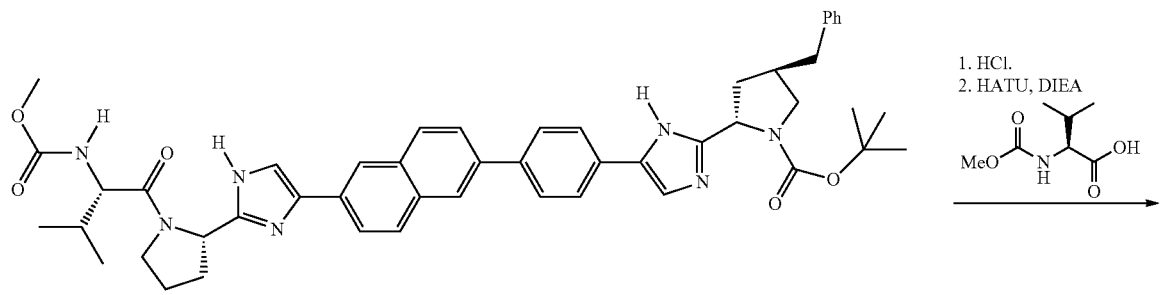

4-Benzyl-2-{5-[4-(6-{2-[1-(2-Methoxycarbonylamion-3-methyl-butyryl)-pyrrolidin-2-yl]-1H-imidazol-4-yl}-naphthalen-2-yl)-phenyl]-1H-imidazol-2-yl}-pyrrolidine-1-carboxylic acid tert-butyl ester

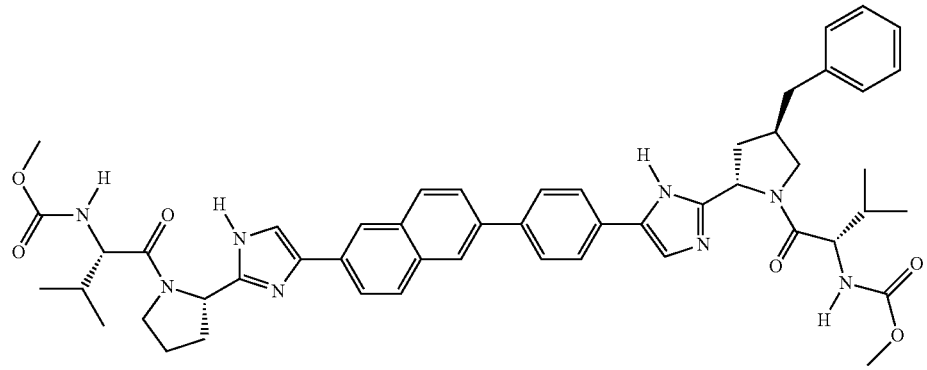

[1-(4-Benzyl-2-{5-[4-(6-{2-[1-(2-methoxycarbonylamino-3-methyl-butyryl)-pyrrolidin-2-yl]-1H-imidazol-4-yl}-naphthalen-2-yl)-phenyl]-1H-imidazol-2-yl}-pyrrolidine-1-carbonyl)-2-methyl-propyl]-carbamic acid methyl ester

[1-(4-Benzyl-2-{5-[4-(6-{2-[1-(2-methoxycarbonylamino-3-methyl-butyryl)-pyrrolidin-2-yl]-1H-imidazol-4-yl}-naphthalen-2-yl)-phenyl]-1H-imidazol-2-yl}-pyrrolidine-1-carbonyl)-2-methyl-propyl]-carbamic acid methyl ester 4-Benzyl-2-{5-[4-(6-{2-[1-(2-methoxycarbonylamino-3-methyl-butyryl)-pyrrolidin-2-yl]-1H-imidazol-4-yl}-naphthalen-2-yl)-phenyl]-1H-imidazol-2-yl}-pyrrolidine-1-carboxylic acid tert-butyl ester (58.0 mg, 0.071 mmol) was dissolved in DCM (1.0 mL) and HCl in dioxane (4M, 1.0 mL) was added and stirring at room temperature was continued. After 30 minutes, all volatiles were removed in vacuo. The crude material was used in the next step without further purification. The crude material was dissolved in DMF (0.5 mL) and DIEA (27.3 mg, 0.211 mmol) was added. A solution of 2-(L) methoxycarbonylamino-3-methyl-butyric acid (12.3 mg, 0.071 mmol), HATU (26.8 mg, 0.071 mmol) and DIEA (9.1 mg, 0.071 mmol) in DMF (0.5 mL) was added. The reaction was stirred at room temperature. After 30 minutes, the crude reaction was quenched with aqueous hydrochloric acid (0.1 mL, 2 M) and was purified by RP-HPLC (eluent: water/MeCN w/0.1% TFA) to yield the product (25.1 mg) as a TFA salt.

LCMS-ESI⁺: calc'd for $C_{51}H_{57}N_8O_6$: 878.0 (M⁺); Found: 879.6 (M+H⁺). ¹H-NMR: 300 MHz, (dmso-d₆) δ: 8.36 (s, 2H), 8.16-7.89 (m, 12H), 7.38-7.19 (m, 7H), 5.29 (dd, J=5.7/3.9 Hz, 1H), 5.16 (dd, J=5.1/5.1 Hz, 1H), 4.18-4.05 (m, 2H), 3.93-3.86 (m, 2H), 3.56 (s, 3H), 3.53 (s, 3H), 3.52 (m, 2H), 2.79 (m, 1H), 2.48 (m, 2H), 2.39 (m, 1H), 2.18-2.01 (m, 7H), 0.91-0.77 (m, 12H) ppm.

Example FY

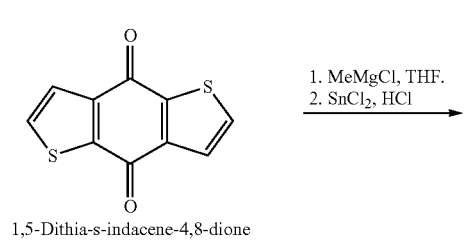
1,5-Dithia-s-indacene-4,8-dione

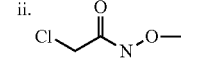
4,8-Dimethyl-1,5-dithia-s-indacene

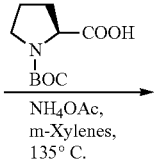
2-Chloro-1-[6-(2-chloro-acetyl)-4,8-dimethyl-1,5-dithia-s-indacen-2-yl-ethanone

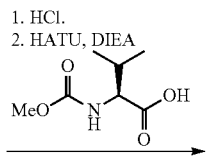

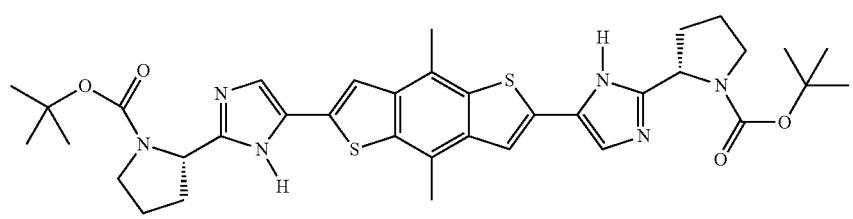
1-{2-[5-(6-{2-[1-carbamic acid tert. buty ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert. butyl ester

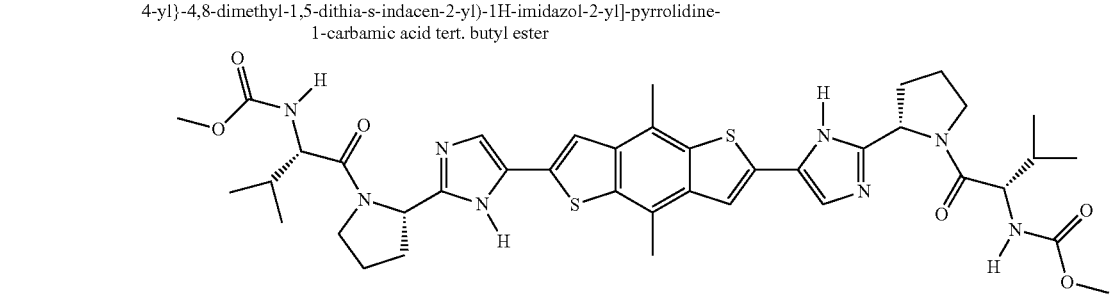
(1-{2-[5-(6-{2-[1-(2-Methoxycarbonylamino-3-methyl-butyryl)-pyrrolidin-2-yl]-3H-imidazol-4-yl}-4,8-dimethyl-1,5-dithia-s-indacen-2-yl)-1H-imidazol-2-yl]-pyrrolidine-1-carbonyl}-2-methyl-propyl)-carbamic acid methyl ester

4,8-Dimethyl-1,5-dithia-s-indacene 1,5-Dithia-s-indacene-4,8-dione (2.0 g, 9.17 mmol) was added to a methyl magnesium chloride solution (60 mmol) in THF (80 mL) [Org. Lett., 2008, 10:4421-4424]. The reaction mixture was heated at 55° C. (oil bath). After 14 hrs, a solution of tin(II)chloride (10 g) in aqueous HCl (2M, 50 mL) was added carefully and the heating was continued for 4 additional hours. The reaction was cooled to room temperature and the THF was removed in vacuo. The crude mixture was partitioned between chloroform and brine. The resultant thick suspension was filtered and the solid was discarded. The organic layer was dried over sodium sulfate. Filtration and removal of solvents in vacuo gave the crude material, which was via silica gel chromatography (eluent: EtOAc/hexanes) to yield the product (355.0 mg, 1.63 mmol).

$^1$H-NMR: 300 MHz, (CDCl$_3$) δ: 7.49 (d, J=4.2 Hz, 2H), 7.46 (d, J=4.2 Hz, 2H), 2.81 (s, 6H) ppm.

2-Chloro-1-[6-(2-chloro-acetyl)-4,8-dimethyl-1,5-dithia-s-indacen-2-yl]-ethanone 4,8-Dimethyl-1,5-dithia-s-indacene (61.0 mg, 0.095 mmol) was dissolved in THF (9 mL) and was cooled to −78° C. A solution of n-BuLi (1.6 M hexanes, 0.946 mL) was added and stirring at −78° C. was continued for 90 minutes. To the resultant suspension was added a solution of N-Methyl, N-Methoxy-2-chloroacetate (209 mg, 1.51 mmol) in THF (1 mL) Stirring at −78° C. was continued for 45 minutes. The reaction was quenched with ammonium chloride solution and methanol and was warmed to room temperature. The bright yellow solid was collected and used in the next step without further purification.

1-{2-[5-(6-{2-[1-carbamic acid tert. butyl ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert-butyl ester 2-Chloro-1-[6-(2-chloro-acetyl)-4,8-dimethyl-1,5-dithia-s-indacen-2-yl]-ethanone (crude solid from previous step)) was combined and with (L)-N-Boc Proline carboxylic acid (324 mg, 1.51 mmol), potassium carbonate (304 mg, 2.2 mmol), sodium iodide (21.6 mg) and was heated in acetone (10 mL) at −78° C. After 120 minutes, all volatiles were removed in vacuo. The reaction was diluted with chloroform and was washed with brine, saturated sodium bicarbonate solution, brine, and was dried over sodium sulfate. Filtration and removal of solvents in vacuo gave the crude material (580 mg, 0.797 mmol), which was used in the next step without further purification.

The crude product from the previous step (580.1 mg, 0.797 mol) was dissolved in m-xylenes (7.0 mL) and heated at 140° C. Solid ammonium acetate (500 mg, 6.41 mmol) was added and the reaction was stirred at 140° C. After 240 minutes, the reaction was cooled to room temperature and the volatiles were removed in vacuo. The crude reaction product was partitioned between chloroform and aqueous sodium bicarbonate solution. The organic layer was collected, washed with brine and dried over sodium sulfate. Filtration and evaporation of solvents gave the crude product (303.0 mg, 0.440 mmol).

LCMS-ESI$^+$: calc'd for $C_{36}H_{44}N_6O_4S_2$: 688.9 (M$^+$); Found: 688.3 (M+H$^+$).

(1-{2-[5-(6-{2-[1-(2-Methoxycarbonylamino-3-methyl-butyryl)-pyrrolidin-2-yl]-3H-imidazol-4-yl}-4,8-dimethyl-1,5-dithia-s-indacen-2-yl)-1H-imidazol-2-yl]-pyrrolidine-1-carbonyl}-2-methyl-propyl)-carbamic acid methyl ester 1-{2-[5-(6-{2-[1-carbamic acid tert-butyl ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert-butyl ester (51.0 mg, 0.073 mmol) was dissolved in DCM (0.67 mL) and HCl in dioxane (4M, 0.67 mL) was added and stirring at room temperature was continued. After 45 minutes, all volatiles were removed in vacuo. The crude material was used in the next step without further purification. The crude material was dissolved in DMF (0.8 mL) and DIEA (37.6 mg, 0.292 mmol) was added. A solution of 2-(L) methoxycarbonylamino-3-methyl-butyric acid (25.5 mg, 0.146 mmol), HATU (55.5 mg, 0.146 mmol) and DIEA (18.8 mg, 0.146 mmol) in DMF (0.5 mL) was added. The reaction was stirred at room temperature. After 30 minutes, the reaction was quenched with aqueous hydrochloric acid (0.2 mL, 2 M) and was purified by RP-HPLC (eluent: water/MeCN w/0.1% TFA) to yield the product (5.1 mg) as a TFA salt.

LCMS-ESI$^+$: calc'd for $C_{40}H_{50}N_8O_6S_2$: 803.0 (M$^+$); Found: 803.2 (M+H$^+$).

$^1$H-NMR: 300 MHz, (dmso-d$_6$) δ: 7.88 (s, 4H), 7.30 (m, 2H), 5.10 (m, 2H), 4.12 (dd, J=8.1/8.1 Hz, 2H), 3.83 (m, 4H) 3.53 (s, 6H), 2.73 (s, 6H), 2.27 (m, 2H), 2.14-1.98 (m, 8H), 0.89-0.80 (m, 12H) ppm.

Example FZ

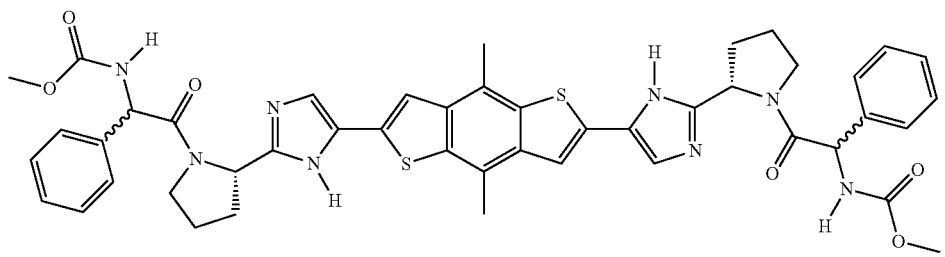

(2-{2-[5-(6-{2-[1-(2-Methoxycarbonylamino-2-phenyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-phenyl-ethyl)-carbamic acid methyl ester

(2-{2-[5-(6-{2-[1-(2-Methoxycarbonylamino-2-phenyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-phenyl-ethyl)-carbamic acid methyl ester 1-{2-[5-(6-{2-[1-carbamic acid tert-butyl ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert-butyl ester (51.0 mg, 0.073 mmol) was dissolved in DCM (0.67 mL) and HCl in dioxane (4M, 0.67 mL) was added and stirring at room temperature was continued. After 45 minutes, all volatiles were removed in vacuo. The crude material was used in the next step without further purification. The crude material was dissolved in DMF (0.8 mL) and DIEA (37.6 mg, 0.292 mmol) was added. A solution of 2-(D) methoxycarbonylamino-2-phenyl-acetic acid (30.5 mg, 0.146 mmol), HATU (55.5 mg, 0.146 mmol) and DIEA (18.8 mg, 0.146 mmol) in DMF (0.5 mL) was added. The reaction was stirred at room temperature. After 30 minutes, the reaction was quenched with aqueous hydrochloric acid (0.2 mL, 2 M) and was purified by RP-HPLC (eluent: water/MeCN w/0.1% TFA) to yield the product (6.7 mg) as a mixture of isomers and in the form of the TFA salt.

LCMS-ESI$^+$: calc'd for $C_{40}H_{50}N_8O_6S_2$: 871.0 (M$^+$); Found: 871.7 (M+H$^+$).

$^1$H-NMR: 300 MHz, (dmso-d$_6$) δ: 7.95-7.66 (m, 6H), 7.40-7.34 (m, 8H), 7.06 (m, 2H), 5.51 (m, 2H), 5.13 (m, 2H), 3.91 (m, 2H), 3.54 and 3.52 (2×s, 6H), 3.16 (m, 2H), 2.76 (s, 6H), 2.19-1.98 (m, 8H) ppm.

Example GA

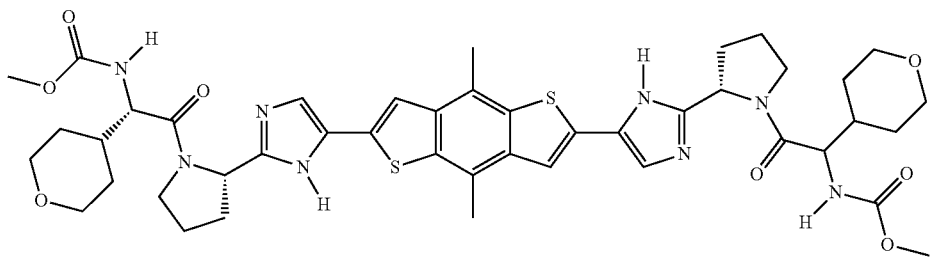

(2-{2-[5-(6-{2-[1-(2-Methoxycarbonylamino-2-tetrahydropyranyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-tetrahydropyranyl-ethyl)-carbamic acid methyl ester (2-{2-[5-(6-{2-[1-(2-Methoxycarbonylamino-2-tetrahydropyranyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-tetrahydropyranyl-ethyl)-carbamic acid methyl ester 1-{2-[5-(6-{2-[1-carbamic acid tert-butyl ester-pyrrolidin-2-yl]-3H-imidazol-4-yl}-4,8-dimethyl-1,5-dithia-s-indacen-2-yl)-1H-imidazol-2-yl]-pyrrolidine-1-carbamic acid tert-butyl ester (51.0 mg, 0.073 mmol) was dissolved in DCM (0.67 mL) and HCl in dioxane (4M, 0.67 mL) was added and stirring at room temperature was continued. After 45 minutes, all volatiles were removed in vacuo. The crude material was used in the next step without further purification. The crude material was dissolved in DMF (0.8 mL) and DIEA (37.6 mg, 0.292 mmol) was added. A solution of 2-(L) methoxycarbonylamino-2-(4-tetrahydropyranyl)-acetic acid (31.6 mg, 0.146 mmol), HATU (55.5 mg, 0.146 mmol) and DIEA (18.8 mg, 0.146 mmol) in DMF (0.5 mL) was added. The reaction was stirred at room temperature. After 20 minutes, the reaction was quenched with aqueous hydrochloric acid (0.2 mL, 2 M) and was purified by RP-HPLC (eluent: water/MeCN w/0.1% TFA) to yield the product (8.1 mg) as a TFA salt.

LCMS-ESI+: calc'd for $C_4H_{54}N_8O_8S_2$: 887.0 (M+); Found: 887.9 (M+H+).

1H-NMR: 300 MHz, (dmso-$d_6$) δ: 7.81 (s, 4H), 7.39 (m, 2H), 5.08 (m, 2H), 4.18 (m, 2H), 3.85 (m, 8H) 3.53 (s, 6H), 3.22 (m, 4H), 2.72 (s, 6H), 2.27 (m, 2H), 2.14-1.98 (m, 8H), 1.58-1.25 (m, 8H) ppm.

Example GB (1-{2-[5-(4,8-Dimethoxy-6-{2-[1-(2-methoxycarbonylamino-3-methyl-butyryl)-pyrrolidin-2-yl]-3H-imidazol-4-yl}-1,5-dithia-s-indacen-2-yl)-1H-imidazol-2-yl]-pyrrolidine-1-carbonyl}-2-methyl-propyl)-carbamic acid methyl ester 1-{2-[5-(6-{2-[1-carbamic acid tert-butyl ester-pyrrolidin-2-yl]-3H-imidazol-4-yl}-4,8-dimethoxy-1,5-dithia-s-indacen-2-yl)-1H-imidazol-2-yl]-pyrrolidine-1-carbamic acid tert-butyl ester (49.3 mg, 0.070 mmol) was dissolved in DCM (0.67 mL) and HCl in dioxane (4M, 0.67 mL) was added and stirring at room temperature was continued. After 45 minutes, all volatiles were removed in vacuo The crude material was used in the next step without further purification. The crude material was dissolved in DMF (0.8 mL) and DIEA (36.0 mg, 0.280 mmol) was added. A solution of 2-(L) methoxycarbonylamino-3-methyl-butyric acid (24.5 mg, 0.140 mmol), HATU (53.2 mg, 0.140 mmol) and DIEA (18.0 mg, 0.140 mmol) in DMF (0.5 mL) was added. The reaction was stirred at room temperature. After 45 minutes, the crude reaction was quenched with aqueous hydrochloric acid (0.2 mL, 2 M) and was purified by RP-HPLC (eluent: water/MeCN w/0.1% TFA) to yield the product (5.1 mg) as a TFA salt. [The required starting material for the modified sequence was described in Org. Lett., 2008, 10:4421-4424.]

LCMS-ESI+: calc'd for $C_{40}H_{50}N_8O_8S_2$: 835.0 (M+); Found: 835.2 (M+H+).

1H-NMR: 300 MHz, (dmso-$d_6$) δ: 7.95 (s, 2H), 7.85 (s, 2H), 7.30 (d, J=8.4 Hz, 2H), 5.09 (dd, J=4.8/4.8 Hz, 2H), 4.10-4.07 (m, 8H), 3.82 (m, 4H) 3.57 (s, 6H), 2.30 (m, 2H), 2.15-1.96 (m, 8H), 0.87-0.80 (m, 12H) ppm.

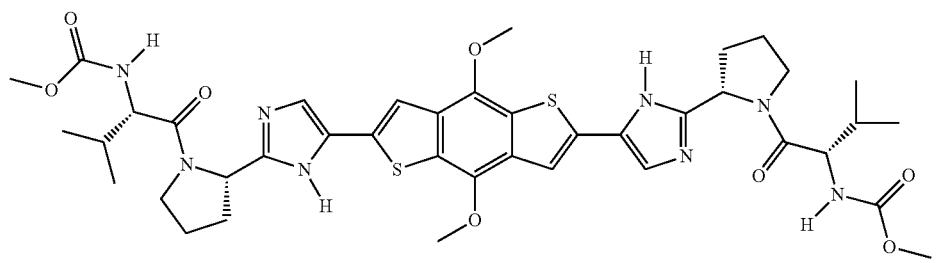

(1-{2-[5-(4,8-Dimethoxy-6-{2-[1-(2-methoxycarbonylamino-3-methyl-butyryl)-pyrrolidin-2-yl]-3H-imidazol-4-yl}-1,5-dithia-s-indacen-2-yl)-1H-imidazol-2-yl]-pyrrolidine-1-carbonyl}-2-methyl-propyl)-carbamic acid methyl ester

Example GC

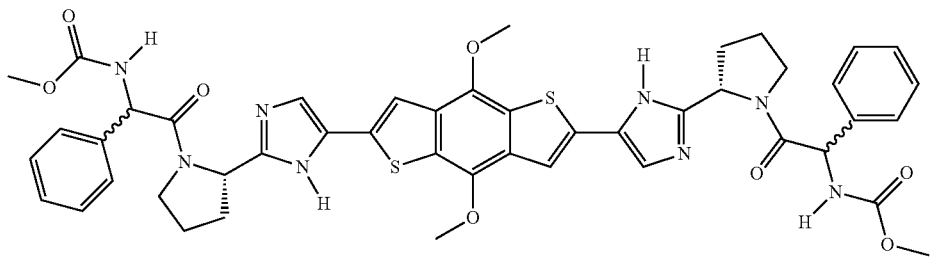

(2-{2-[5-(4,8-Dimethoxy-6-{-2-[1-(2-methoxycarbonylamino-2-phenyl-acetyl)-pyrrolidin-2-yl]-3H-imidazol-4-yl}-1,5-dithia-s-indacen-2-yl)-1H-imidazol-2-yl]-pyrrolidin-1-yl}-2-oxo-1-phenyl-ethyl)-carbamic acid methyl ester

(2-{2-[5-(4,8-Dimethoxy-6-{2-[1-(2-methoxycarbonylamino-2-phenyl-acetyl)-pyrrolidin-2-yl]-3H-imidazol-4-yl}-1,5-dithia-s-indacen-2-yl)-1H-imidazol-2-yl]-pyrrolidin-1-yl}-2-oxo-1-phenyl-ethyl)-carbamic acid methyl ester 1-{2-[5-(6-{2-[1-carbamic acid tert-butyl ester-pyrrolidin-2-yl]-3H-imidazol-4-yl}-4,8-dimethoxy-1,5-dithia-s-indacen-2-yl)-1H-imidazol-2-yl]-pyrrolidine-1-carbamic acid tert-butyl ester (49.3 mg, 0.070 mmol) was dissolved in DCM (0.67 mL) and HCl in dioxane (4M, 0.67 mL) was added and stirring at room temperature was continued. After 45 minutes, all volatiles were removed in vacuo. The crude material was used in the next step without further purification. The crude material was dissolved in DMF (0.8 mL) and DIEA (36.0 mg, 0.280 mmol) was added. A solution of 2-(D) methoxycarbonylamino-2-phenyl-acetic acid (29.3 mg, 0.140 mmol), HATU (53.2 mg, 0.140 mmol) and DIEA (18.0 mg, 0.140 mmol) in DMF (0.5 mL) was added. The reaction was stirred at room temperature. After 45 minutes, the crude reaction was quenched with aqueous hydrochloric acid (0.2 mL, 2 M) and was purified by RP-HPLC (eluent: water/MeCN w/0.1% TFA) to yield the product (6.7 mg) as a mixture of isomers and in the form of the TFA salt.

LCMS-ESI$^+$: calc'd for $C_{40}H_{50}N_8O_6S_2$: 871.0 (M$^+$); Found: 871.7 (M+H$^+$).

$^1$H-NMR: 300 MHz, (dmso-d$_6$) δ: 8.01-7.67 (m, 6H), 7.39-7.35 (m, 8H), 7.06 (m, 2H), 5.51 (m, 2H), 5.13 (m, 2H), 4.13 (s, 6H), 3.91 (m, 2H), 3.54 and 3.52 (2×s, 6H), 3.16 (m, 2H), 2.19-1.87 (m, 8H) ppm.

(2-{2-[5-(6-{2-[1-(2-Methoxycarbonylamino-2-tetrahydropyranyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-tetrahydropyranyl-ethyl)-carbamic acid methyl ester 1-{2-[5-(6-{2-[1-carbamic acid tert-butyl ester-pyrrolidin-2-yl]-3H-imidazol-4-yl}-4,8-dimethoxy-1,5-dithia-s-indacen-2-yl)-1H-imidazol-2-yl]-pyrrolidine-1-carbamic acid tert-butyl ester (49.3 mg, 0.070 mmol) was dissolved in DCM (0.67 mL) and HCl in dioxane (4M, 0.67 mL) was added and stirring at room temperature was continued. After 45 minutes, all volatiles were removed in vacuo. The crude material was used in the next step without further purification. The crude material was dissolved in DMF (0.8 mL) and DIEA (36.0 mg, 0.280 mmol) was added. A solution of 2-(L) methoxycarbonylamino-2-(4-tetrahydropyranyl)-acetic acid (30.4 mg, 0.140 mmol), HATU (53.2 mg, 0.140 mmol) and DIEA (18.0 mg, 0.140 mmol) in DMF (0.5 mL) was added. The reaction was stirred at room temperature. After 20 minutes, the reaction was quenched with aqueous hydrochloric acid (0.2 mL, 2 M) and was purified by RP-HPLC (eluent: water/MeCN w/0.1% TFA) to yield the product (8.1 mg) as a TFA salt.

LCMS-ESI$^+$: calc'd for $C_{44}H_{54}N_8O_8S_2$: 919.0 (M$^+$); Found: 919.6 (M+H$^+$).

$^1$H-NMR: 300 MHz, (dmso-d$_6$) δ: 7.86 (s, 2H), 7.74 (s, 2H), 7.39 (m, 2H), 5.07 (m, 2H), 4.18 (m, 2H), 4.08 (s, 6H), 3.84 (m, 8H), 3.53 (s, 6H), 3.21 (m, 4H), 2.26 (m, 2H), 2.15-1.92 (m, 8H), 1.64-1.27 (m, 8H) ppm.

Example GD

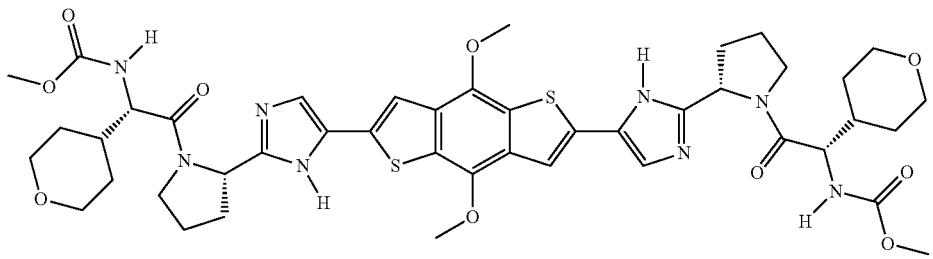

(2-{2-[5-(4,8-Dimethoxy-6-{2-[1-(2-methoxycarbonylamino-2-tetrahydropyranyl-acetyl)-pyrrolidin-2-yl]-3H-imidazol-4-yl}-1,5-dithia-s-indacen-2-yl)-1H-imidazol-2-yl]-pyrrolidin-1-yl}-2-oxo-1-tetrahydropyranyl-ethyl)-carbamic acid methyl ester Example GE

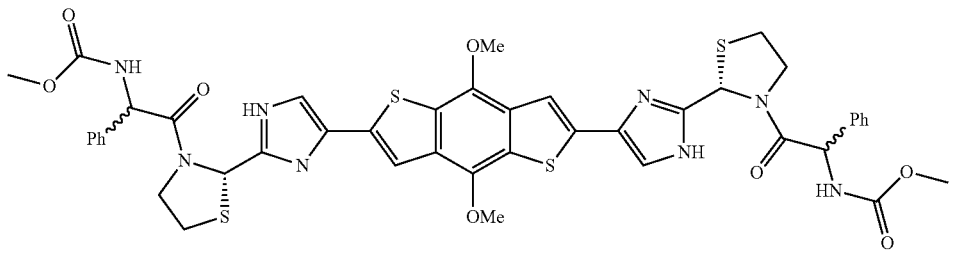

(2-{2-[4-(4,8-Dimethoxy-6-{2-[3-(2-methoxycarbonylamino-2-phenyl-acetyl)-thiazolidin-2-yl]-1H-imidazol-4-yl}-1,5-dithia-s-indacen-2-yl)-1H-imidazol-2-yl]-thiazolidin-3-yl}-2-oxo-1-phenyl-ethyl)-carbamic acid methyl ester (2-{2-[5-(6-{2-[1-(2-Methoxycarbonylamino-2-phenyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-phenyl-ethyl)-carbamic acid methyl ester (2-{2-[5-(6-{2-[1-(2-Methoxycarbonylamino-2-phenyl-acetyl)-pyrrolidin-2-yl]-3H-imidazol-4-yl}-4,8-dimethyl-1,5-dithia-s-indacen-2-yl)-1H-imidazol-2-yl]-pyrrolidin-1-yl}-2-oxo-1-phenyl-ethyl)-carbamic acid methyl ester was prepared following method used for (2-{2-[5-(4,8-Dimethoxy-6-{2-[1-(2-methoxycarbonylamino-2-phenyl-acetyl)-pyrrolidin-2-yl]-3H-imidazol-4-yl}-1,5-dithia-s-indacen-2-yl)-1H-imidazol-2-yl]-pyrrolidin-1-yl}-2-oxo-1-phenyl-ethyl)-carbamic acid methyl ester substituting L-thiazolidine-2,3-dicarboxylic acid 3-tert-butyl ester for L-pyrrolidine-1,2-dicarboxylic acid 1-tert-butyl ester.

LCMS-ESI$^+$: calc'd for $C_4H_{42}N_8O_8S_4$: 938.2 (M$^+$) found: 939.1 (M+H$^+$)

$^1$H-NMR: 300 MHz, (dmso-d$_6$) δ: 7.85-7.63 (m 2H), 7.46-7.29 (m 10H), 7.08-7.01 (m, 2H), 6.31 (m, 2H), 5.60 (d, J=7.6 Hz, 2H), 4.24 (m 2H), 4.13 (s, 6H), 4.06-3.76 (m 2H), 3.54 (m, 6H), 3.28 (m, 2H), 3.15 (m, 2H).

Example GF

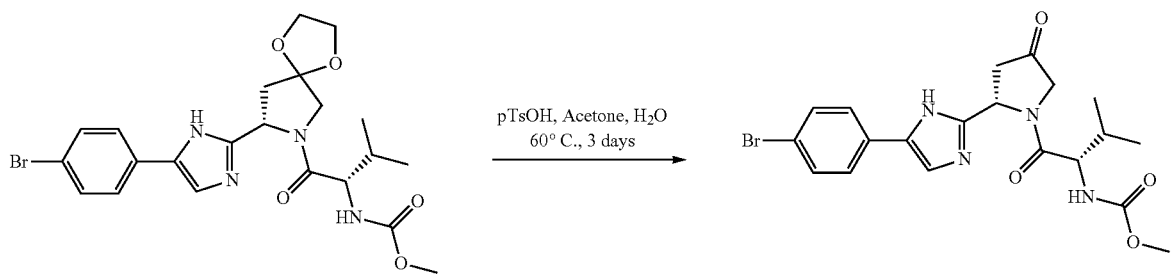

(1-{8-[5-(4-Bromo-phenyl)-1H-imidazol-2-yl]-1,4-dioxa-7-aza-spiro[4.4]nonane-7-carbonyl}-2-methyl-propyl)-carbamic acid methyl ester (1-{2-[5-(4-Bromo-phenyl)-1H-imidazol-2-yl]-4-oxo-pyrrolidine-1-carbonyl}-2-methyl-propyl)-carbamic acid methyl ester

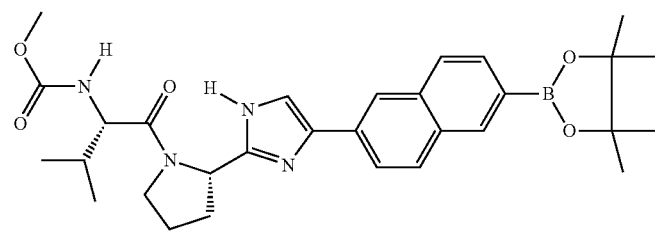

[2-Methyl-1-(2-{4-[6-(4,4,5,5-tetramethyl-[1,3,2]dioxaborolan-2-yl)-napthalen-2-yl]-1H-imidazol-2-yl}-pyrrolidine-1-carbonyl)-propyl]-carbamic acid methyl ester

+

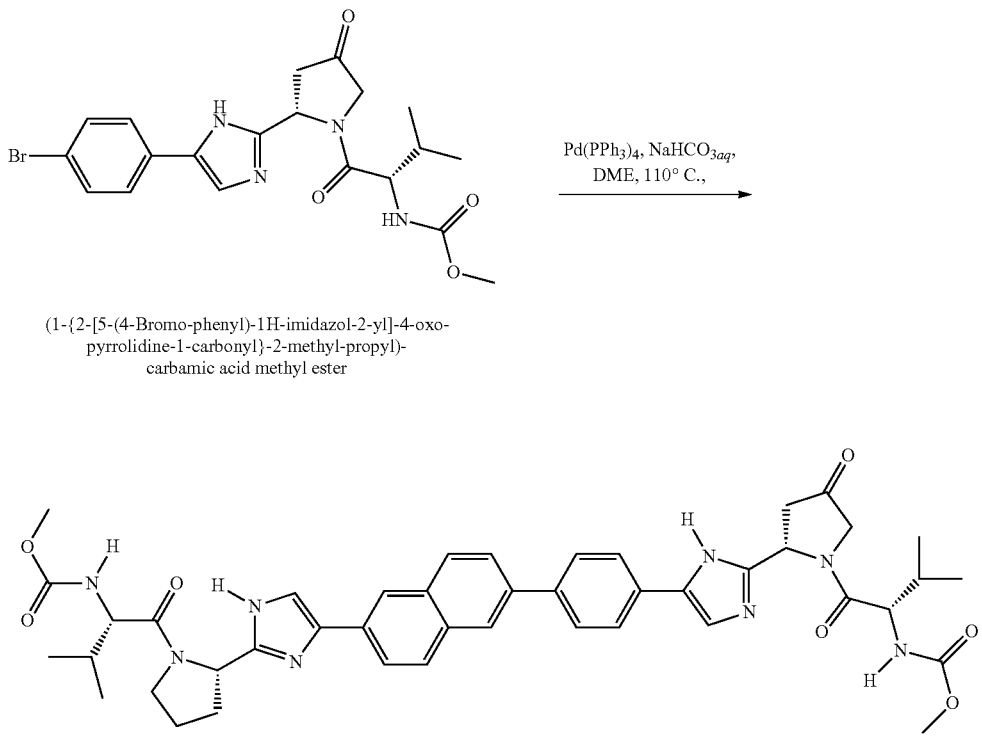

(1-{2-[5-(4-Bromo-phenyl)-1H-imidazol-2-yl]-4-oxo-pyrrolidine-1-carbonyl}-2-methyl-propyl)-carbamic acid methyl ester

[1-(2-{5-[4-(6-{2-[1-(2-Methoxycarbonylamino-3-methyl-butyryl-pyrrolidin-2-yl]-1H-imidazol-4-yl}-napthalen-2-yl)-phenyl]-1H-imidazol-2-yl}-4-oxo-pyrrolidine-1-carbonyl)-2-methyl-propyl]-carbamic acid methyl ester (1-{2-[5-(4-Bromo-phenyl)-1H-imidazol-2-yl]-4-oxo-pyrrolidine-1-carbonyl}-2-methyl-propyl)-carbamic acid methyl ester (1-{8-[5-(4-Bromo-phenyl)-1H-imidazol-2-yl]-1,4-dioxa-7-aza-spiro[4.4]nonane-7-carbonyl}-2-methyl-propyl)-carbamic acid methyl ester (230.0 mg, 0.453 mmol) was dissolved in acetone (10 mL) and water (0.2 mL) and p-TsOH∘H2O (53 mg, 0.278 mmol) were added. The reaction was heated at 60° C. for 20 hours, after which additional p-TsOH∘H$_2$O (53 mg, 0.278 mmol) was added heating at 60° C. was continued. After three days, all volatiles were removed in vacuo. The crude material was taken into EtOAc and was washed with aqueous sodium bicarbonate solution and dried over sodium sulfate. Filtration and evaporation of solvents in vacuo gives the crude product. The crude material was purified via silica gel chromatography (eluent: EtOAc containing 10% MeOH/hexanes) to yield the product (93.9 mg, 0.202 mmol).

LCMS-ESI$^+$: calc'd for $C_{20}H_{23}BrN_4O_4$: 463.3 (M$^+$); Found: 463.6 (M+H$^+$).

$^1$H-NMR: 300 MHz, (dmso-d$_6$) δ: 7.92 (m, 1H), 7.64 (m, 5H), 7.49 (d, J=6.5 Hz, 1H), 5.56 (dd, J=7.5/3.6 Hz, 1H), 4.34 (m, 2H), 3.91 (dd, J=6.3/6.3 Hz, 1H), 3.52 (s, 3H), 3.20 (dd, J=14.4/7.8 Hz, 1h), 2.82 (br-d, J=14.4 Hz, 1H), 1.87 (m, 1H), 0.78 (d, J=5.1 Hz, 3H), 0.71 (d, J=4.8 Hz, 3H) ppm.

[1-(2-{5-[4-(6-{2-[1-(2-Methoxycarbonylamino-3-methyl-butyryl)-pyrrolidin-2-yl]-1H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester (1-{2-[5-(4-Bromo-phenyl)-1H-imidazol-2-yl]-4-oxo-pyrrolidine-1-carbonyl}-2-methyl-propyl)-carbamic acid methyl ester (46.0 mg, 0.1 mmol), [2-Methyl-1-(2-{4-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (54 mg, 0.1 mmol), and Pd[PPh$_3$]$_4$ (11.5 mg, 0.01 mmol) were dissolved in DME (2 mL) under an atmosphere of argon. Saturated, aqueous sodium bicarbonate solution (0.3 mL) was added and the reaction was heated under microwave conditions at 120° C. for 20 minutes. The solids were discarded and the volatiles were removed in vacuo. The crude reaction mixture was purified by RP-HPLC (eluent: water/MeCN w/0.1% TFA) to yield the product (4.0 mg) as a TFA salt.

LCMS-ESI$^+$: calc'd for $C_4H_{50}N_8O_7$: 802.9 (M$^+$); Found: 803.4 (M+H$^+$).

$^1$H-NMR: 300 MHz, (dmso-d$_6$) δ: 8.32 (m, 2H), 8.12-7.84 (m, 10H), 7.52 (d, J=7.8 Hz, 1H), 7.32 (d, J=8.4 Hz, 1H), 5.61 (m, 1H), 5.14 (m, 1H), 4.39 (m, 2H), 4.12 (dd, J=7.5 Hz, 1H), 3.94 (dd, J=8.4/8.4 Hz, 1H), 3.85 (m, 2H), 3.54 (2xs, 6H), 3.26 (m, 1H), 2.90 (m, 1H), 2.13-1.90 (m, 6H), 0.86-0.74 (m, 12H) ppm.

Example GG

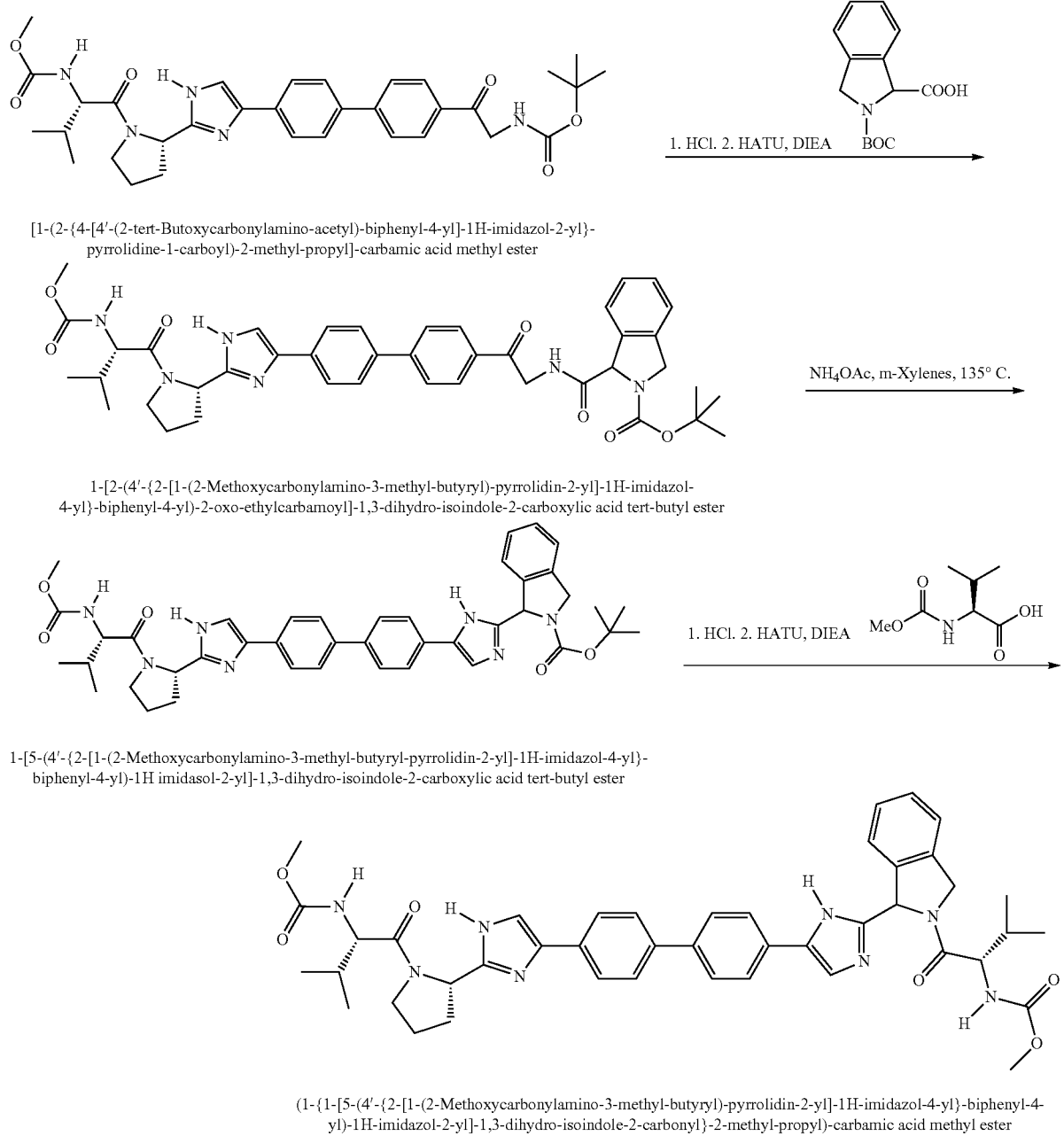

[1-(2-{4-[4'-(2-tert-Butoxycarbonylamino-acetyl)-biphenyl-4-yl]-1H-imidazol-2-yl}-pyrrolidine-1-carboyl)-2-methyl-propyl]-carbamic acid methyl ester 1-[2-(4'-{2-[1-(2-Methoxycarbonylamino-3-methyl-butyryl)-pyrrolidin-2-yl]-1H-imidazol-4-yl}-biphenyl-4-yl)-2-oxo-ethylcarbamoyl]-1,3-dihydro-isoindole-2-carboxylic acid tert-butyl ester 1-[5-(4'-{2-[1-(2-Methoxycarbonylamino-3-methyl-butyryl-pyrrolidin-2-yl]-1H-imidazol-4-yl}-biphenyl-4-yl)-1H imidasol-2-yl]-1,3-dihydro-isoindole-2-carboxylic acid tert-butyl ester (1-{1-[5-(4'-{2-[1-(2-Methoxycarbonylamino-3-methyl-butyryl)-pyrrolidin-2-yl]-1H-imidazol-4-yl}-biphenyl-4-yl)-1H-imidazol-2-yl]-1,3-dihydro-isoindole-2-carbonyl}-2-methyl-propyl)-carbamic acid methyl ester

1-[2-(4'-{2-[1-(2-Methoxycarbonylamino-3-methyl-butyryl)-pyrrolidin-2-yl]-1H-imidazol-4-yl}-biphenyl-4-yl)-2-oxo-ethylcarbamoyl]-1,3-dihydro-isoindole-2-carboxylic acid tert-butyl ester

[1-(2-{4-[4'-(2-tert-Butoxycarbonylamino-acetyl)-biphenyl-4-yl]-1H-imidazol-2-yl}-pyrrolidine-1-carbonyl)-2-methyl-propyl]-carbamic acid methyl ester (107.0 mg, 0.177 mmol) was dissolved in DCM (1 mL) and HCl in dioxane (4M, 1 mL) was added and stirring at room temperature was continued. After 45 minutes, all volatiles were removed in vacuo. The crude material was used in the next step without further purification. The crude material was dissolved in DMF (0.6 mL) and DIEA (68.4 mg, 0.531 mmol) was added. A solution of racemic 1,3-dihydro-isoindole-1,2-dicarboxylic acid 2-tert-butyl ester (46.6 mg, 0.177 mmol), HATU (67.3 mg, 0.177 mmol) and DIEA (22.8 mg, 0.177 mmol) in DMF (0.4 mL) was added. The reaction was stirred at room temperature. After 15 minutes, the reaction was diluted with EtOAc and was washed with brine, saturated sodium bicarbonate solution, brine, and was dried over sodium sulfate. Filtration and removal of solvents in vacuo gave the crude material (147.8 mg), which was used in the next step without further purification.

LCMS-ESI$^+$: calc'd for $C_{42}H_{48}N_6O_7$: 748.8 (M$^+$); Found: 749.2 (M+H$^+$).

1-[5-(4'-{2-[1-(2-Methoxycarbonylamino-3-methyl-butyryl)-pyrrolidin-2-yl]-1H-imidazol-4-yl}-biphenyl-4-yl)-1H-imidazol-2-yl]-1,3-dihydro-isoindole-2-carboxylic acid tert-butyl ester 1-[2-(4'-{2-[1-(2-Methoxycarbonylamino-3-methyl-butyryl)-pyrrolidin-2-yl]-1H-imidazol-4-yl}-biphenyl-4-yl)-2-oxo-ethylcarbamoyl]-1,3-dihydro-isoindole-2-carboxylic acid tert-butyl ester (147.8 mg) was taken into m-xylenes (2.0 mL) and heated at 135° C. Solid ammonium acetate (120 mg, 1.5 mmol) was added and the reaction was stirred at 135° C. After 180 minutes, the reaction was cooled to room temperature and the volatiles were removed in vacuo. The crude reaction product was partitioned between EtOAc and water. The organic layer was collected and dried over sodium sulfate. Filtration and evaporation of solvents gave the crude product (142 mg).

LCMS-ESI$^+$: calc'd for $C_{42}H_{47}N_7O_5$: 729.8 (M$^+$); Found: 730.4 (M+H$^+$).

$^1$H-NMR: 300 MHz, (dmso-d$_6$) δ: 8.07 (m, 2H), 7.90-7.85 (m, 8H), 7.49-7.27 (m, 5H), 6.31 (s, 1H), 5.12 (dd, J=6.9/6.9 Hz, 1H), 4.95-4.70 (m, 2H), 4.11 (dd, J=7.5/7.5 Hz, 1H), 3.83 (m, 2H), 3.53 (s, 3H), 2.41 (m, 1H), 2.13-1.95 (m, 4H), 1.45 and 1.22 (2×s, 9H), 0.88-0.78 (m, 6H) ppm.

(1-{1-[5-(4'-{2-[1-(2-Methoxycarbonylamino-3-methyl-butyryl)-pyrrolidin-2-yl]-1H-imidazol-4-yl}-biphenyl-4-yl)-1H-imidazol-2-yl]-1,3-dihydro-isoindole-2-carbonyl}-2-methyl-propyl)-carbamic acid methyl ester 1-[5-(4'-{2-[1-(2-Methoxycarbonylamino-3-methyl-butyryl)-pyrrolidin-2-yl]-1H-imidazol-4-yl}-biphenyl-4-yl)-1H-imidazol-2-yl]-1,3-dihydro-isoindole-2-carboxylic acid tert-butyl ester (71.0 mg, 0.086 mmol) was dissolved in DCM (1.0 mL) and HCl in dioxane (4M, 0.5 mL) was added and stirring at room temperature was continued. After 5 minutes, all volatiles were removed in vacuo. The crude material was used in the next step without further purification. The crude material was dissolved in DMF (0.5 mL) and DIEA (30.9 mg, 0.24 mmol) was added. A solution of 2-(L) methoxycarbonylamino-3-methyl-butyric acid (14.0 mg, 0.080 mmol), HATU (30.4 mg, 0.08 mmol) and DIEA (10.3 mg, 0.08 mmol) in DMF (0.4 mL) was added. The reaction was stirred at room temperature. After 120 minutes, the crude reaction was quenched with aqueous hydrochloric acid (0.1 mL, 2 M) and was purified by RP-HPLC (eluent: water/MeCN w/0.1% TFA) to yield the two diastereomeric products (1.5 mg and 2.4 mg) as TFA salts.

Compound A (Faster Eluding Material on RP-HPLC)

LCMS-ESI$^+$: calc'd for $C_4H_{50}N_8O_6$: 786.9 (M$^+$); Found: 787.4 (M+H$^+$).

$^1$H-NMR: 300 MHz, (dmso-d$_6$) δ: 7.90-7.75 (m, 10H), 7.50-7.27 (m, 6H), 6.42 (m, 1H), 5.39-5.21 (m, 2H), 5.09 (m, 1H), 4.16-4.08 (m, 2H), 3.81 (m, 2H), 3.52 (s, 6H), 2.41 (m, 1H), 2.13-1.95 (m, 5H), 0.91-0.79 (m, 12H) ppm.

Compound B (Later Eluding Material on RP-HPLC)

LCMS-ESI$^+$: calc'd for $C_{44}H_{50}N_8O_6$: 786.9 (M$^+$); Found: 787.4 (M+H$^+$).

$^1$H-NMR: 300 MHz, (dmso-d$_6$) δ: 7.80-7.58 (m, 10H), 7.40-7.13 (m, 6H), 6.29 (m, 1H), 5.09-4.70 (m, 3H), 4.06 (m, 1H), 3.91 (m, 1H), 3.65 (m, 2H), 3.34 (s, 3H), 3.33 (s, 3H), 2.18 (m, 1H), 1.98-1.82 (m, 5H), 0.75-0.59 (m, 12H) ppm.

Example GH

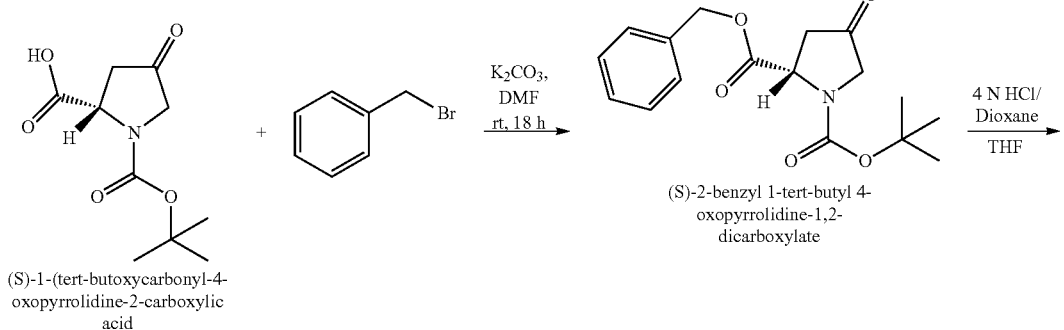

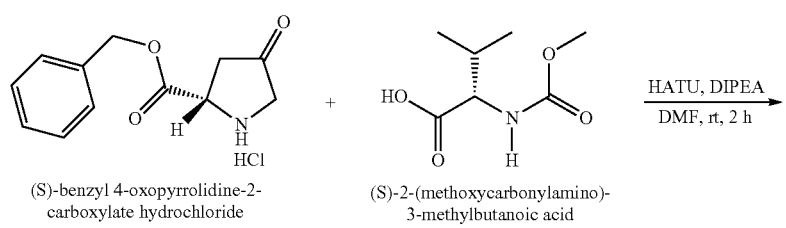

-continued
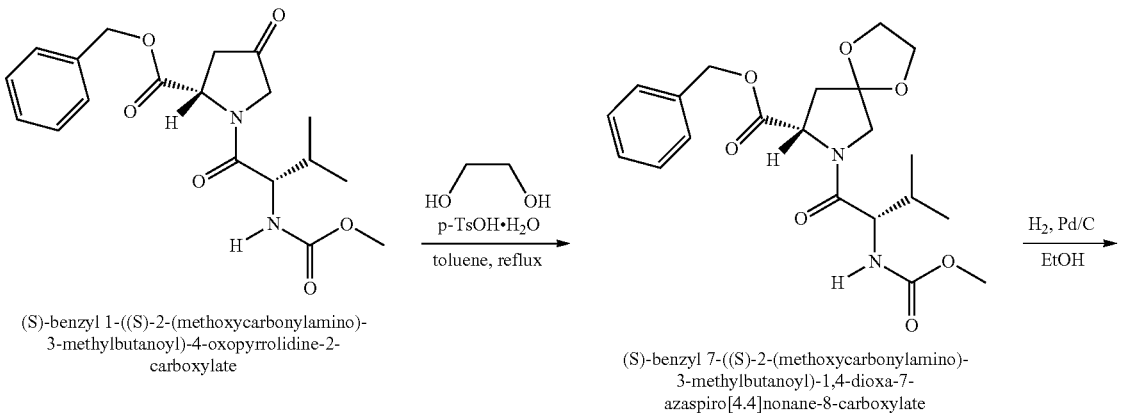
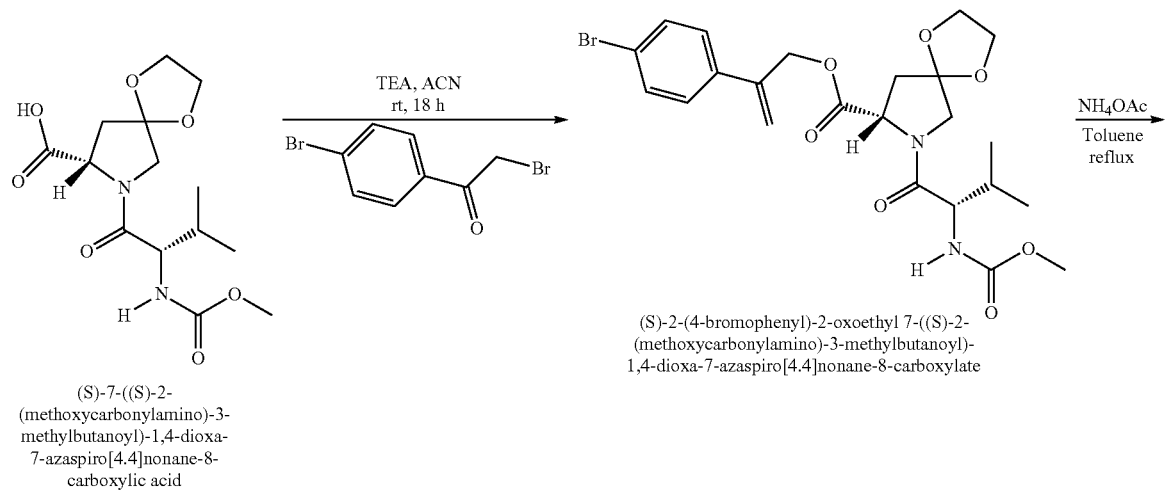
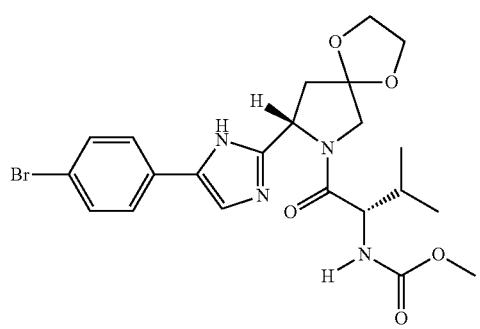
methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

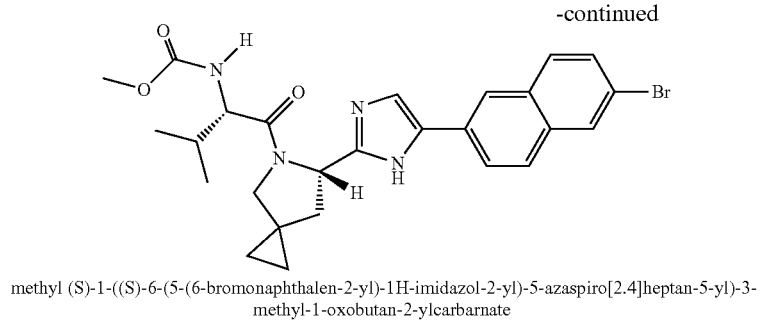

methyl (S)-1-((S)-6-(5-(6-bromonaphthalen-2-yl)-1H-imidazol-2-yl)-5-azaspiro[2.4]heptan-5-yl)-3-methyl-1-oxobutan-2-ylcarbarnate

+

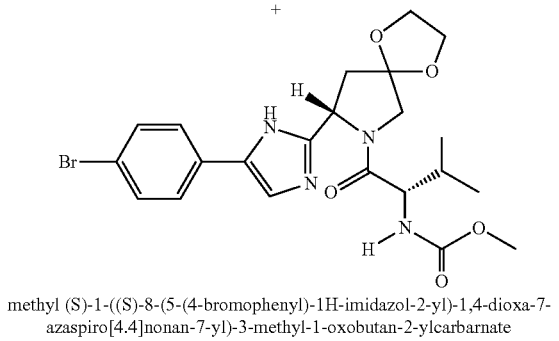

methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbarnate

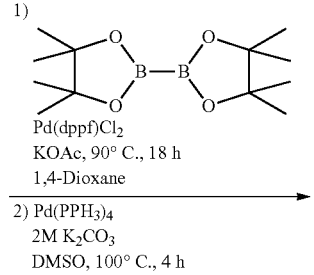

1)
Pd(dppf)Cl₂
KOAc, 90° C., 18 h
1,4-Dioxane

2) Pd(PPH₃)₄
2M K₂CO₃
DMSO, 100° C., 4 h

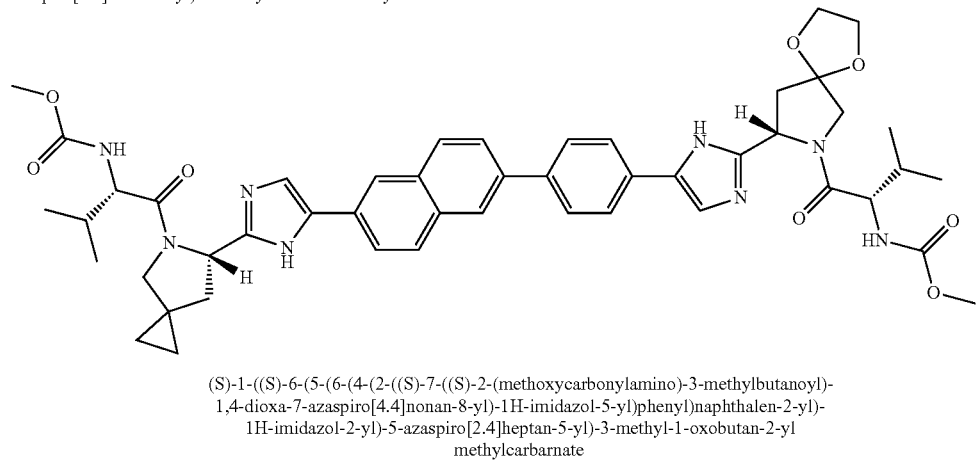

(S)-1-((S)-6-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)-5-azaspiro[2.4]heptan-5-yl)-3-methyl-1-oxobutan-2-yl methylcarbarnate

(S)-2-benzyl 1-tert-butyl 4-oxopyrrolidine-1,2-dicarboxylate

To a stirring solution of a mixture of (S)-1-(tert-butoxycarbonyl)-4-oxopyrrolidine-2-carboxylic acid (2.85 g, 12.43 mmol) and potassium carbonate (4.33 g, 24.87 mmol) in anhydrous N,N-dimethylformamide (60 mL) was added benzyl bromide (4.25 g, 24.87 mmol). The mixture was stirred at room temperature overnight.

The resulting crude mixture was diluted with ethylacetate and the organic layer was washed with 10% sodium carbonate and brine. The organic layer was dried over sodium sulfate and volatiles were removed in-vacuo. The residue was purified on normal phase column to yield 2.82 g (71%) of desired product.

(S)-benzyl 4-oxopyrrolidine-2-carboxylate hydrochloride

To a stirring solution of (S)-2-benzyl 1-tert-butyl 4-oxopyrrolidine-1,2-dicarboxylate (2.82 g, 8.8 mmol) in anhydrous tetrahydrofuran (44 mL) was added 4N HCl in 1,4-dioxane (9.3 mL) at room temperature. The mixture was stirred for 18 hours at room temperature. The product was then three times with toluene on rotovap to dryness to remove all the excess acid and further dried on a high vacuum overnight and used as is in the next step. Quantitative yield.

(S)-benzyl 1-((S)-2-(methoxycarbonylamino)-3-methylbutanoyl)-4-oxopyrrolidine-2-carboxylate Following the procedure used to prepare compound (S)-benzyl 1-((S)-2-(methoxycarbonylamino)-3-methylbutanoyl)-4-oxopyrrolidine-2-carboxylate, except that (S)-benzyl 4-oxopyrrolidine-2-carboxylate and (S)-2-(methoxycarbonylamino)-3-methylbutanoic acid were used instead of 2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester and 3-[5-(4-bromo-phenyl)-1H-imidazol-2-yl]-pyrrolidine-1-carboxylic acid tert-butyl ester.

(S)-benzyl 7-((S)-2-(methoxycarbonylamino)-3-methylbutanoyl)-1,4-dioxa-7-azaspiro[4.4]nonane-8-carboxylate (S)-benzyl 1-((S)-2-(methoxycarbonylamino)-3-methylbutanoyl)-4-oxopyrrolidine-2-carboxylate (2.45 g, 6.51 mmol) in a round bottom flask was dissolved in anhydrous toluene (200 mL) and p-toluene sulfonic acid monohydride (124 mg, 0.1 mmol) and ethylene glycol (808 mg, 13.02 mmol) were added and the mixture was refluxed for 18 hours, removing the generated byproduct water with a Dean-Stark apparatus. The crude mixture was then diluted with ethyl acetate and washed, respectively, with 10% citric acid, saturated ammonium chloride, 10% sodium carbonate and finally with brine. The organic layers were combined and dried over sodium sulfate and concentrated down on rotovap. The crude residue was then purified on normal phase column chromatography with 5% MeOH/DCM. (2.3 g, 84%)

(S)-7-((S)-2-(methoxycarbonylamino)-3-methylbutanoyl)-1,4-dioxa-7-azaspiro[4.4]nonane-8-carboxylic acid (S)-benzyl 7-((S)-2-(methoxycarbonylamino)-3-methylbutanoyl)-1,4-dioxa-7-azaspiro[4.4]nonane-8-carboxylate (2.3 g, 5.47 mmol) was dissolved in ethyl alcohol (55 mL) and under Argon charged with 10% Pd/C in a round bottom flask. The flask was then sealed with a rubber septa and the air was removed by vacuum and replaced with H2 from a balloon. This process repeated three times and the mixture was stirred under H2 atmosphere for 18 hours. The resulting mixture was then passed through a elite plug and concentrated down on rotovap to yield 1.76 g, 98% desired product.

(S)-2-(4-bromophenyl)-2-oxoethyl 7-((S)-2-(methoxycarbonylamino)-3-methylbutanoyl)-1,4-dioxa-7-azaspiro[4.4]nonane-8-carboxylate Title compound was prepared according to the method employed to prepare (S)-2-(4-bromophenyl)-2-oxoethyl 5-((S)-2-(methoxycarbonylamino)-3-methylbutanoyl)-5-azaspiro[2.4]heptane-6-carboxylate (2.07 g, 74%)

Methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate Title compound was prepared according to the method employed to prepare methyl (S)-1-((S)-6-(5-(4-bromophenyl)-1H-imidazol-2-yl)-5-azaspiro[2.4]heptan-5-yl)-3-methyl-1-oxobutan-2-ylcarbamate (1.64 g, 82.2%)

(S)-1-((S)-6-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl) naphthalen-2-yl)-1H-imidazol-2-yl)-5-azaspiro[2.4] heptan-5-yl)-3-methyl-1-oxobutan-2-yl-carbamic acid methyl ester Methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (200 mg, 0.39 mmol), bis(pinacolato)diboron (130 mg, 0.51 mmol), potassium acetate (116 mg, 1.18 mmol), and Pd(dppf)Cl₂ (29 mg, 0.039 mmol) were all weighed out in a glass pressure vessel and anhydrous 1,4-Dioxane (2 mL) was added. The mixture was bubbled with nitrogen gas for about 5 min. The vessel was then capped and sealed and heated in an oil bath at 90° C. overnight with continuous stirring.

The reaction vessel was cooled down to room temperature and methyl (S)-1-((S)-6-(5-(6-bromonaphthalen-2-yl)-1H-imidazol-2-yl)-5-azaspiro[2.4]heptan-5-yl)-3-methyl-1-oxobutan-2-ylcarbamate (215 mg, 0.41 mmol), 2M $K_2CO_3$, and Pd(PPh₃)₄ (46 mg, 0.04 mmol) were all added along with 2 mL of DMSO and the mixture was bubbled with nitrogen gas for 5 minutes. The vessel, again, was capped, sealed and placed in an oil bath at 100° C. for 4 hours. The resulting crude mixture was diluted with ethyl acetate and washed, respectively, with brine, 10% $Na_2CO_3$, 10% citric acid, saturated solution of $NH_4Cl$, and brine. The organic layer was then dried over $Na_2SO_4$ and the volatiles were removed on rotovap. The residue was first purified on normal phase chromatography and then on prep HPLC. Yield=205 mg (60%). ¹H-NMR: 400 MHz, (CDCl₃) δ 8.18-7.97 (m, 1H), 7.83-7.6 (m, 8H), 7.82-7.22 (m, 3H), 5.47-5.34 (m, 4H), 4.33-4.26 (m, 1H), 4.08-4.03 (m, 4H), 3.94-3.89 (m, 1H), 3.78-3.69 (m, 8H), 3.22 (brs, 1H), 2.96-2.94 (m, 1H), 2.49-2.46 (m, 1H), 2.22-2.17 (m, 1H), 1.99 (brs, 1H), 1.08-1.04 (m, 2H), 0.94-0.79 (m, 12H), 0.71 (m, 4H). MS (ESI) m/z 873.79 [M+H]⁺.

Example GI

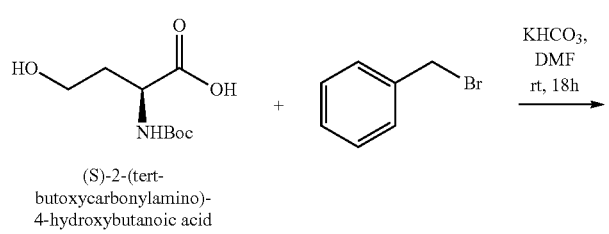

(S)-2-(tert-butoxycarbonylamino)-4-hydroxybutanoic acid

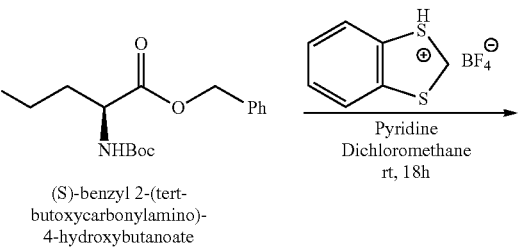

(S)-benzyl 2-(tert-butoxycarbonylamino)-4-hydroxybutanoate

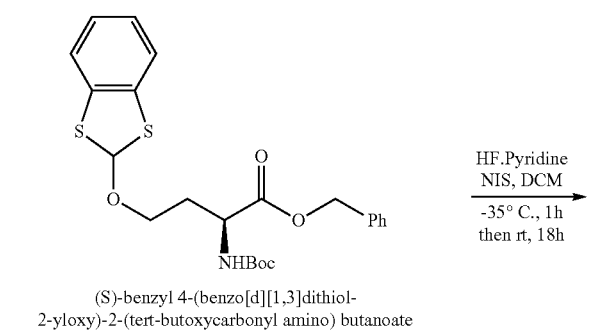

(S)-benzyl 4-(benzo[d][1,3]dithiol-2-yloxy)-2-(tert-butoxycarbonyl amino) butanoate

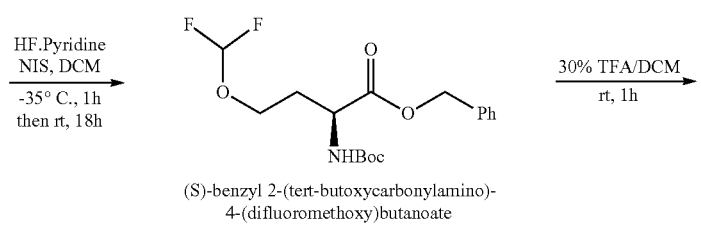

(S)-benzyl 2-(tert-butoxycarbonylamino)-4-(difluoromethoxy)butanoate

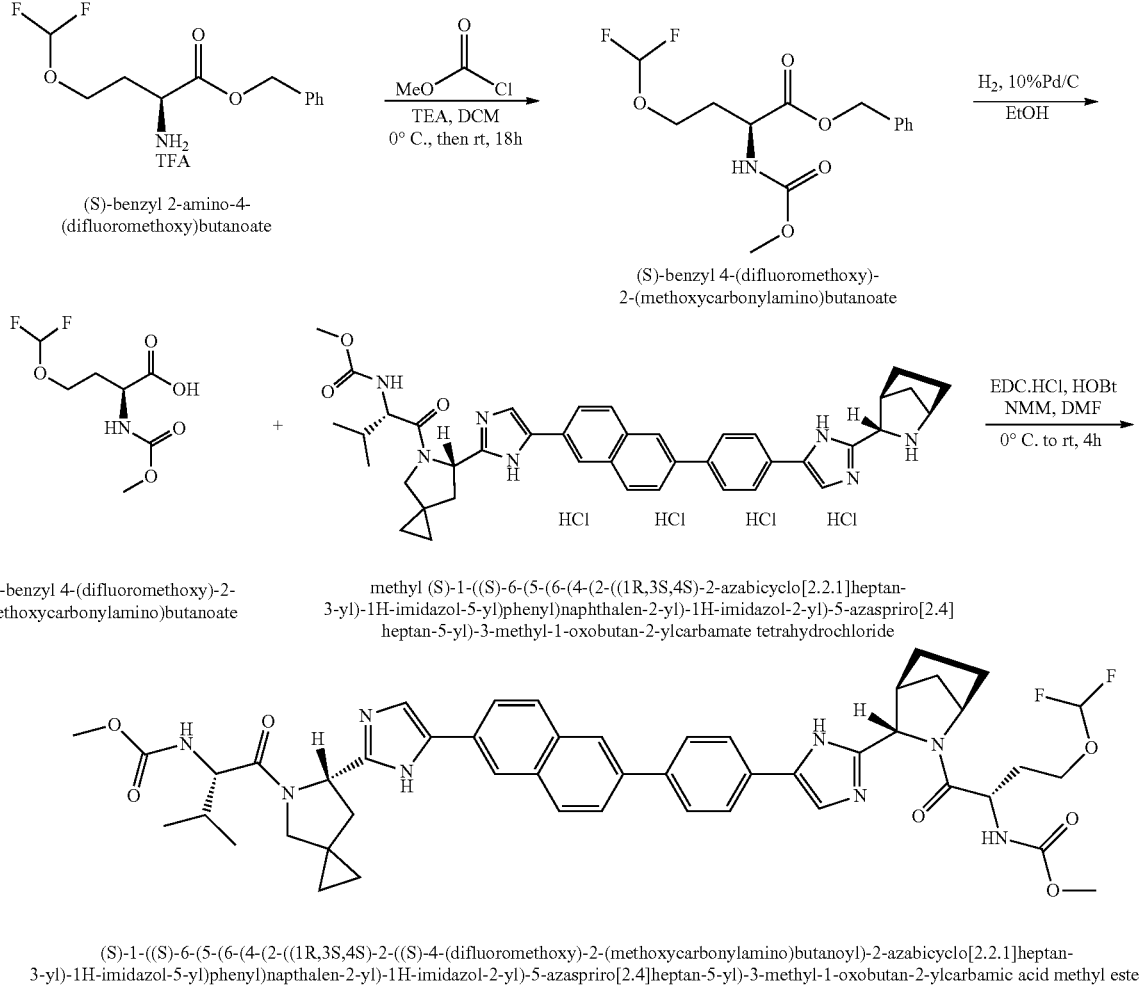

(S)-benzyl 2-(tert-butoxycarbonylamino)-4-hydroxybutanoate

N-t-Boc-L-homoserine (5.14 g, 23.45 mmol) and potassium bicarbonate (2.46 g, 24.6 mmol) was weighed out in a round bottom flask and to it was added anhydrous N,N-dimethylformamide (100 mL) and benzyl bromide (4.2 g, 24.6 mmol). The mixture was stirred at room temperature for 18 hours. The crude mixture was then diluted with ethyl acetate and washed, respectively, with brine, saturated $NaHCO_3$ and brine, and dried over $Na_2SO_4$. The organic layer was then concentrated down on rotovap and purified on normal phase column chromatography. Yield=7.27 g (100%).

(S)-benzyl 4-(benzo[d][1,3]dithiol-2-yloxy)-2-(tert-butoxycarbonyl amino)butanoate (S)-Benzyl 2-(tert-butoxycarbonylamino)-4-hydroxybutanoate (5.76 g, 18.62 mmol) and 1,3-benzodithiol-2-ylium tetrafluoroborate (4.69 g, 19.55 mmol) were dissolved in dichloromethane (186 mL) and pyridine (4.42 g, 55.86 mmol) was added at room temperature. The mixture was stirred overnight. Upon completion of the reaction, it was quenched with triethylamine (11.5 g, 113.5 mmol) and diluted with dichloromethane. The organic layer was then washed with saturated NaHCO3 and brine. The organic layer was dried over $MgSO_4$ and concentrated down in vacuo. The residue was then purified on normal phase column to obtain a clear oil. 7.6 g (88%).

(S)-Benzyl 2-(tert-butoxycarbonylamino)-4-(difluoromethoxy)butanoate

N-Iodosuccinimide (783 mg, 3.48 mmol) was suspended in anhydrous dichloromethane (10 mL) and at −35° C. was slowly added HF.pyridine (70% HF)(50 µl, 1.91 mmol) and the mixture was stirred for 5-10 min. At this temperature was then dropwise added a solution of (S)-benzyl 4-(benzo[d][1,3]dithiol-2-yloxy)-2-(tert-butoxycarbonyl amino)butanoate (400 mg, 0.87 mmol) in dichloromethane (3 mL). The reaction content was then stirred for 1 hour at −35° C. and 1 hour at room temperature.

To the reaction mixture was added ice-cold saturated $NaHCO_3$ and extracted with dichloromethane. The organic layer was washed with a saturated solution of sodium thiosulfate and washed with brine and dried over sodium sulfate. The volatiles were removed in vacuo and the residue was purified on normal phase column. 161 mg (52%).

(S)-benzyl 2-amino-4-(difluoromethoxy)butanoate (S)-benzyl 2-(tert-butoxycarbonylamino)-4-(difluoromethoxy)butanoate (161 mg, 0.448 mmol) was stirred in 30% TFA in dichloromethane (5 mL) for 1 h. The resulting mixture was concentrated down on rotovap and redissolved and concentrated down with toluene three times, and finally the residue was dried on high vacuum pump. The desired product was used as-is in the next step.

(S)-benzyl 4-(difluoromethoxy)-2-(methoxycarbonylamino)butanoate (S)-Benzyl 2-amino-4-(difluoromethoxy)butanoate (116 mg, 0.448 mmol) was dissolved in anhydrous dichloromethane (2.5 mL) and cooled down to 0° C. and TEA (181 mg, 1.79 mmol) and methylchloroformate (51 mg, 0.538 mmol) were added respectively. The mixture was stirred for 30 minutes and then it was stirred at room temperature overnight. The resulting product mixture was quenched with saturated NaHCO$_3$ and extracted with dichloromethane. The organic layer was washed with saturated NH$_4$Cl solution and brine and dried over Na$_2$SO$_4$. The volatiles were removed in vacuo to afford 56 mg (40%) of desired product after column purification.

(S)-4-(Difluoromethoxy)-2-(methoxycarbonylamino)butanoic acid (S)-Benzyl 4-(difluoromethoxy)-2-(methoxycarbonylamino)butanoate (56 mg, 0.176 mmol) was dissolved in ethyl alcohol (3.5 mL) and under Argon charged with 10% Pd/C (19 mg). The flask was sealed with a rubber septa and the air atmosphere was replaced with H$_2$ from a balloon by applying vacuum and then releasing H$_2$ and repeating this three times. The mixture was stirred for 4 hours at room temperature. Upon completion, the crude mixture was passed through a Elite plug, concentrated down on rotovap and used as-is in the next step. 40 mg (100%).

(S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester Methyl (S)-1-((S)-6-(5-(6-(4-(2-((1R,3S,4S)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamate tetrahydrochloride (66 mg, 0.096 mmol), (S)-4-(difluoromethoxy)-2-(methoxycarbonylamino)butanoic acid (20 mg, 0.088 mmol), N-(3-dimethylaminopropyl)-N'-ethylcarbodiimide hydrochloride (24 mg, and hydroxybenzotriazole hydrate (HOBt)(17 mg, 0.125 mmol) were all weighed out in a flask and anhydrous N,N-dimethylformamide (1 mL) was added. The mixture was cooled down in an ice bath to 0° C. and N-methylmorpholine (NMM) (58 mg, 0.576 mmol) was added from a syringe to the mixture. The reaction content was stirred for 4 hours at room temperature. The resulting mixture was then directly purified on reverse phase prep. HPLC. 37 mg, (43%). $^1$H-NMR: 400 MHz, (CD$_3$OD) δ 8.08 (s, 1H), 8.01 (d, J=16 Hz, 1H), 7.86-7.66 (m, 10H), 7.38 (s, 1H), 7.27 (s, 1H), 7.03 (d, J=8.4 Hz, 1H), 6.58 (t, J=75.6 Hz, 1H), 5.32 (t, J=7.2 Hz, 1H), 4.70 (s, 1H), 6.66-6.25 (m, 1H), 4.51 (s, 1H), 4.14 (m, 1H), 3.98-3.78 (m, 4H), 3.63 (s, 6H), 3.50-3.46 (m, 1H), 2.70 (brs, 1H), 2.39-1.78 (m, 7H), 1.71-1.40 (m, 2H), 0.99-0.90 (m, 5H), 0.82-0.60 (m, 4H). MS (ESI) m/z 894.16 [M+H]$^+$.

Example GJ

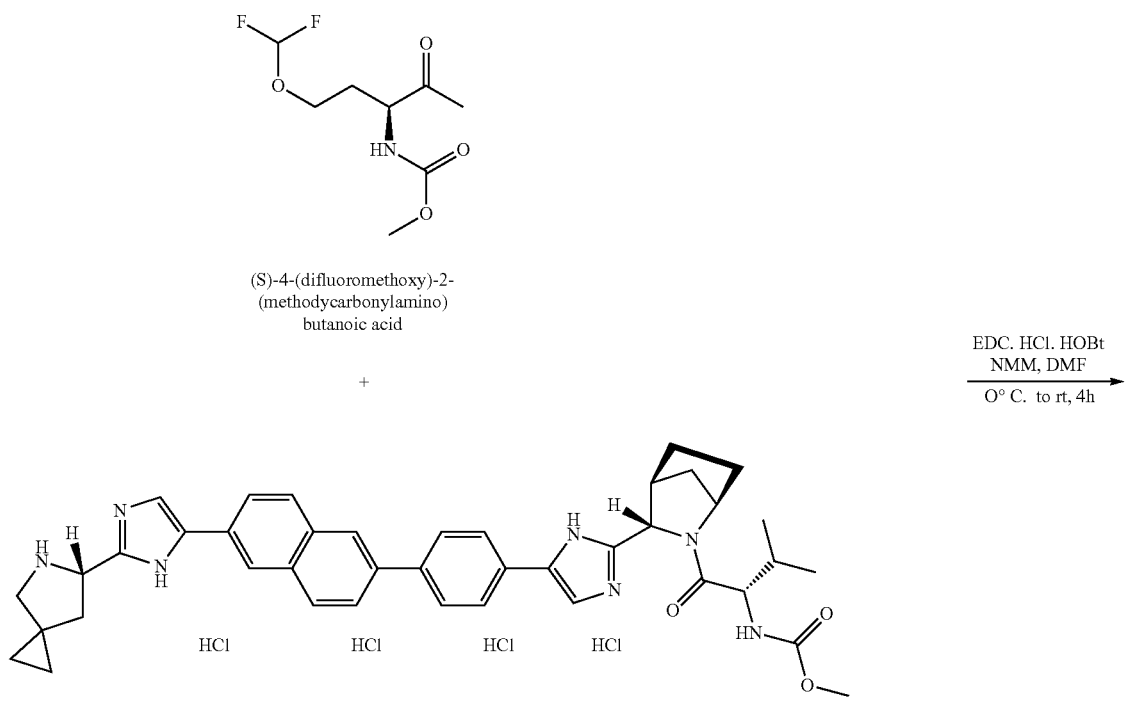

(S)-4-(difluoromethoxy)-2-(methodycarbonylamino)butanoic acid

+

EDC. HCl. HOBt
NMM, DMF
0° C. to rt, 4h methyl (S)-1-((1R, 3S, 4S)-3-(5-(4-(6-(2-((S)-5-azaspiro[2.4]heptan-6-yl)-1H-imidazol-5-yl)naphthalen-2-yl)phenyl)-1H-imidazol-2-yl)-2-azabicyclo[2.2.1]heptan-2-yl)-3-methyl-1-oxubutan-2-ylcarbamate tetrahydrochloride -continued

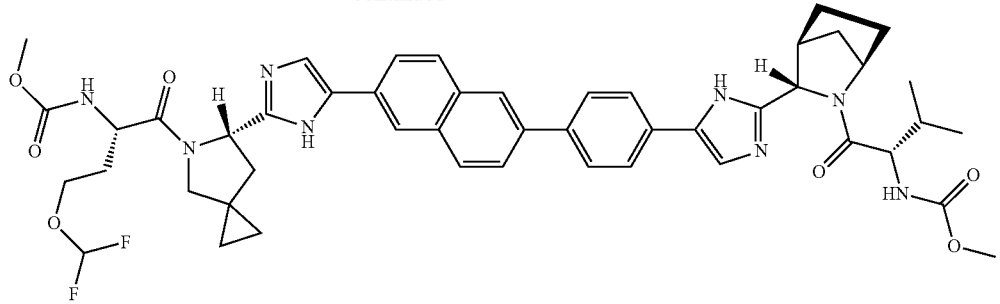

(S)-4-(difluoromethoxy)-1-((S-(6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)-phenyl)naphthalen-2-yl)-1H-imidazol-2-yl)-5-azaspiro[2.4]heptan-5-yl)-1-oxobutan-2-ylcarbamic acid methyl ester (S)-4-(difluoromethoxy)-1-((S)-6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-1-oxobutan-2-ylcarbamic acid methyl ester Title compound was prepared according to the method employed to prepare (S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester. $^1$H-NMR: 400 MHz, (CD$_3$OD) δ 8.13 (s, 1H), 8.03 (m, 1H), 7.91-7.85 (m, 2H), 7.80-7.71 (m, 6H), 7.42 (s, 1H), 7.31 (s, 1H), 6.97 (m, 1H), 6.56 (t, J=76 Hz, 1H), 5.40-5.35 (m, 1H), 4.83 (m, 1H), 4.71 (s, 1H), 4.56 (m, 1H), 4.44-4.33 (m, 1H), 3.93 (brs, 2H), 3.82 (m, 2H), 3.76-3.66 (m, 5H), 3.51-3.42 (m, 1H), 2.80-2.64 (m, 1H), 2.32-2.25 (m, 1H), 2.17-2.12 (m, 2H), 2.07-1.86 (m, 5H), 1.73-1.57 (m, 2H), 1.03-0.9 (m, 4H), 0.77-0.57 (m, 4H). MS (ESI) m/z 894.00 [M+H]$^+$.

Example GK

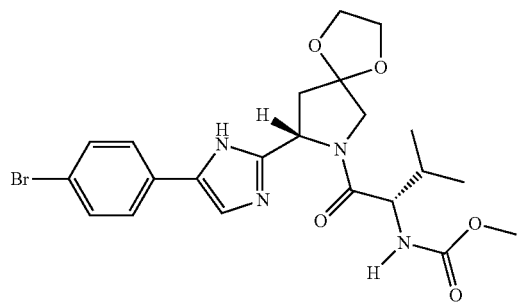

methyl(S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

+

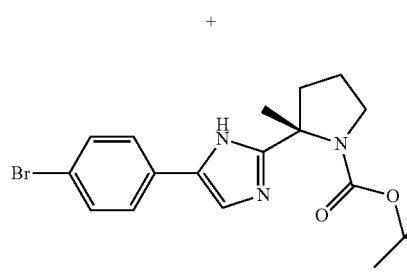

(S)-tert-butyl-2-(5-(4-bromophenyl)-1H-imidazol-2-yl)pyrrolidine-1-carboxylate

1)
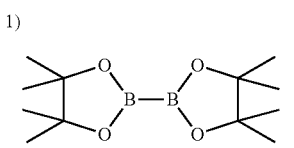

Pd(dppf)Cl$_2$
KOAc, 90° C., 18h
1,4-Dioxane

2) 
Pd(PPh$_3$)$_4$
2M K$_2$CO$_3$
DMSO, 100° C., 4h

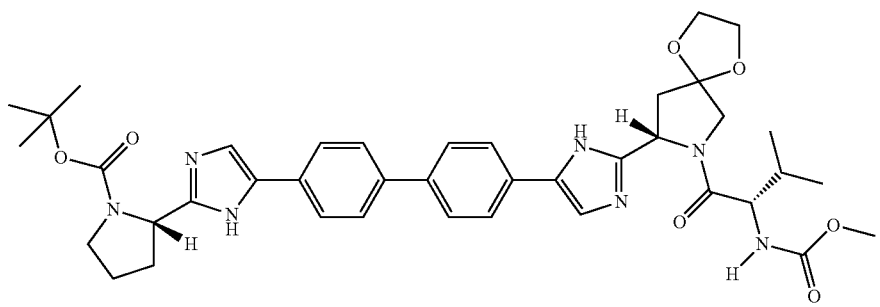

(S)-tert-butyl 2-(5-(4'(2-((S)-7-((S)-2-)methoxycarbonylamino-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-carboxylate

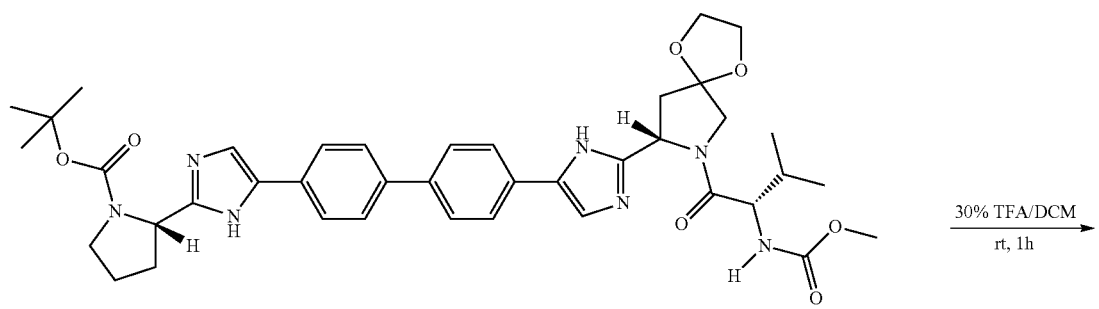

(S)-tert-butyl 2-(5-(4'(2-((S)-7-((S)-2-)methoxycarbonylamino-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-carboxylate → 30% TFA/DCM, rt, 1h

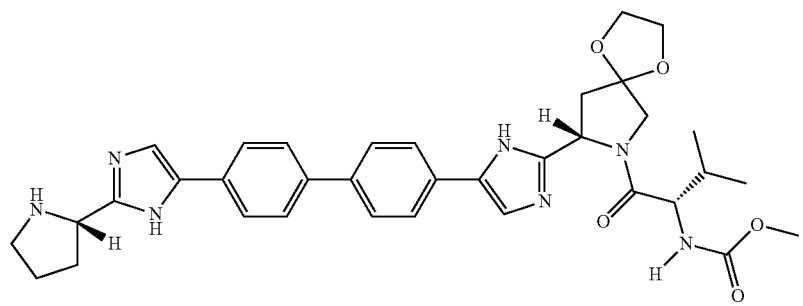

methyl (S)-3-methyl-1-oxo-1-((S)-8-(5-(4'-(2-((S)-pyrrolidin-2-yl)-1H-imidazol-5-yl)biphenyl-4-yl)-1H-imidazol-2-yl)-1,4-dioxa-7-azaspiro[4.4]nonan-7yl)butan-2-ylcarbamate

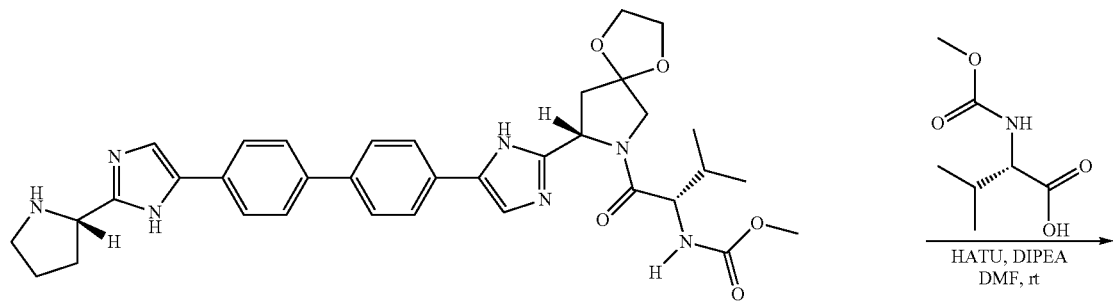

methyl (S)-3-methyl-1-oxo-1-((S)-8-(5-(4'-(2-((S)-pyrrolidin-2-yl)-1H-imidazol-5-yl)biphenyl-4-yl)-1H-imidazol-2-yl)-1,4-dioxa-7-azaspiro[4.4]nonan-7-yl)butan-2-ylcarbamate → HATU, DIPEA, DMF, rt

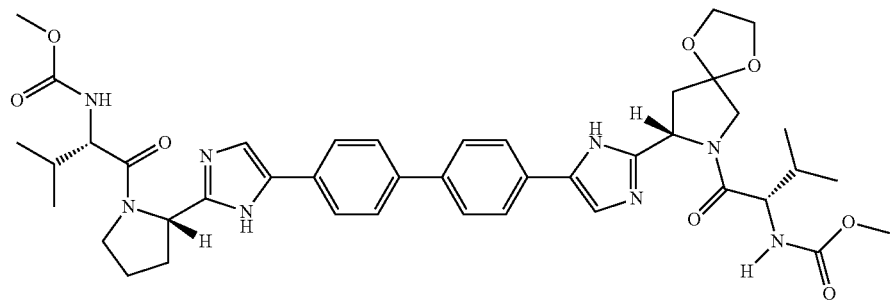

(S)-1-((S)-2-(5-(4'(2-((S)-7-((S)-2-)methoxycarbonylamino-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-yl)-3-methyl-1-oxobutan-2-ylcarbamic acid methyl ester

(S)-Tert-butyl 2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-carboxylate Title compound was prepared according to the method employed to prepare (S)-1-((S)-6-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)-5-azaspiro[2.4]heptan-5-yl)-3-methyl-1-oxobutan-2-yl-carbamic acid methyl ester, except instead of methyl (S)-1-((S)-6-(5-(6-bromonaphthalen-2-yl)-1H-imidazol-2-yl)-5-azaspiro[2.4]heptan-5-yl)-3-methyl-1-oxobutan-2-ylcarbamate and methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate, methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (600 mg, 1.182 mmol) and (S)-tert-butyl 2-(5-(4-bromophenyl)-1H-imidazol-2-yl)pyrrolidine-1-carboxylate (510 mg, 1.3 mmol). The amount for all the other reagents were adjusted accordingly. 489 mg (56%).

Methyl (S)-3-methyl-1-oxo-1-((S)-8-(5-(4'-(2-((S)-pyrrolidin-2-yl)-1H-imidazol-5-yl)biphenyl-4-yl)-1H-imidazol-2-yl)-1,4-dioxa-7-azaspiro[4.4]nonan-7-yl)butan-2-ylcarbamate Title compound was prepared according to the method employed to prepare (S)-benzyl 2-amino-4-(difluoromethoxy)butanoate, except it was freebased as follows: The volatiles were removed and the residue was taken up in EtOAc and washed with water to get the desired product in aqueous layer. The organic layer was again washed with some more water and the aqueous layers were combined and basified with 50% NaOH solution to adjust the pH to 9. The desired product was then back-extracted into EtOAc layer and the aqueous layer was extracted three times with EtOAc. The organic phase was dried over $Na_2SO_4$ and concentrated down on rotovap to afford 290 mg (69%) of desired compound as free base.

(S)-1-((S)-2-(5-(4'-(2-((S)-7-((S)-2-(methoxycarbonylamino)-3-methylbutanoyl)-1,4-dioxa-7-azaspiro [4.4]nonan-8-yl)-1H-imidazol-5-yl)biphenyl-4-yl)-1H-imidazol-2-yl)pyrrolidin-1-yl)-3-methyl-1-oxobutan-2-ylcarbamic acid methyl ester Title compound was prepared according to the method employed to prepare 1-{2-[5-(9-{2-[1-(2-Methoxycarbonylamino-3-methyl-butyryl)-pyrrolidin-2-yl]-3H-imidazol-4-yl}-6-methyl-6,7-dihydro-5H-dibenzo[c,e]azepin-3-yl)-1H-imidazol-2-yl]-pyrrolidine-1-carbonyl}-2-methyl-propyl)-carbamic acid methyl ester. $^1$H-NMR: 400 MHz, (CD$_3$OD) δ 7.80 (d, J=8.0 Hz, 1H), 7.74-7.70 (m, 4H), 7.66-7.62 (m, 5H), 7.36-7.31 (m, 2H), 7.02 (t, J=7.6 Hz, 1H), 5.24 (m, 2H), 4.25 (d, J=7.2 Hz, 1H), 4.17 (d, J=7.6 Hz, 1H), 4.11-3.85 (m, 8H), 3.66 (s, 5H), 3.50-3.45 (m, 1H), 2.56-2.44 (m, 2H), 2.36-2.17 (m, 3H), 2.09-1.99 (m, 3H), 1.01-0.86 (m, 12H). MS (ESI) m/z 797.84 [M+H]$^+$.

Example GL

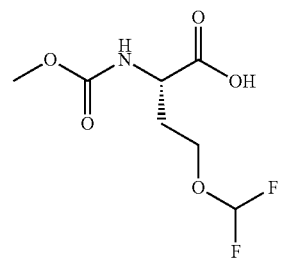

(S)-4-(difluoromethoxy)-2-(methoxycarbonylamino)butanoic acid

+

HATU, DIPEA
DMF, rt
→

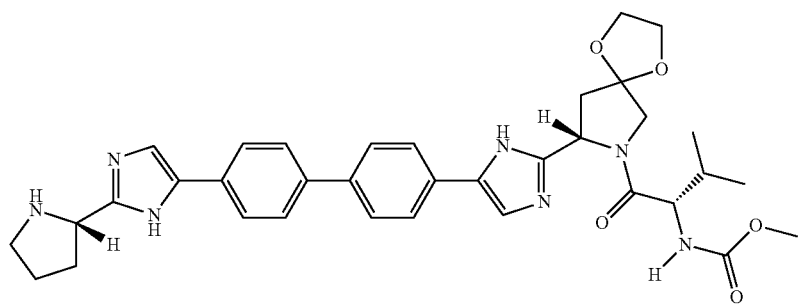

methyl (S)-3-methyl-1-oxo-1-((S)-8-(5-(4'-(2-((S)-pyrrolidin-2-yl)-1H-imidazol-5-yl)biphenyl-4-yl)-1H-imidazol-2-yl)-1,4-dioxa-7-azaspiro[4.4]nonan-7-yl)butan-2-ylcarbamate

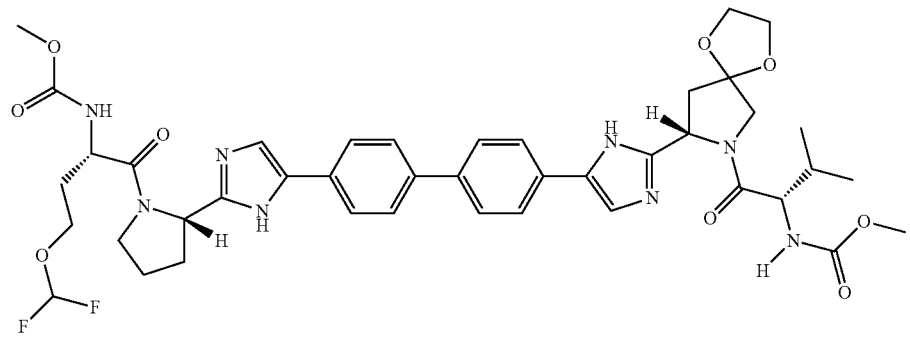

(S)-4-(difluoromethoxy)-1-((S)-2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidin-1-yl)-1-oxobutan-2-ylcarbamic acid methyl ester (S)-4-(difluoromethoxy)-1-((S)-2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidin-1-yl)-1-oxobutan-2-ylcarbamic acid methyl ester Title compound was prepared according to the method employed to prepare 1-{2-[5-(9-{2-[1-(2-Methoxycarbonylamino-3-methyl-butyryl)-pyrrolidin-2-yl]-3H-imidazol-4-yl}-6-methyl-6,7-dihydro-5H-dibenzo[c,e]azepin-3-yl)-1H-imidazol-2-yl]-pyrrolidine-1-carbonyl}-2-methyl-propyl)-carbamic acid methyl ester.

$^1$H-NMR: 400 MHz, (CD$_3$OD) δ 7.69 (d, J=8.0 Hz, 1H), 7.61-7.57 (m, 4H), 7.56-7.52 (m, 5H), 7.28-7.24 (m, 2H), 6.46 (t, J=7.6 Hz, 1H), 5.14 (m, 2H), 4.62 (m, 1H), 4.24 (m, 11H), 3.64 (s, 5H), 2.54-2.43 (m, 2H), 2.36-1.81 (m, 8H), 099-0.84 (m, 6H). MS (ESI) m/z 849.76 [M+H]$^+$.

Example GM

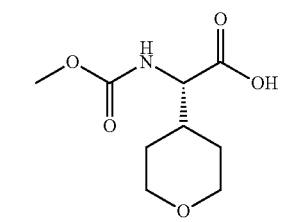

(S)-2-(methoxycarbonylamino)-2-(tetrahydro-2H-pyran-4-yl)acetic acid

+

HATU, DIPEA
DMF, rt
→

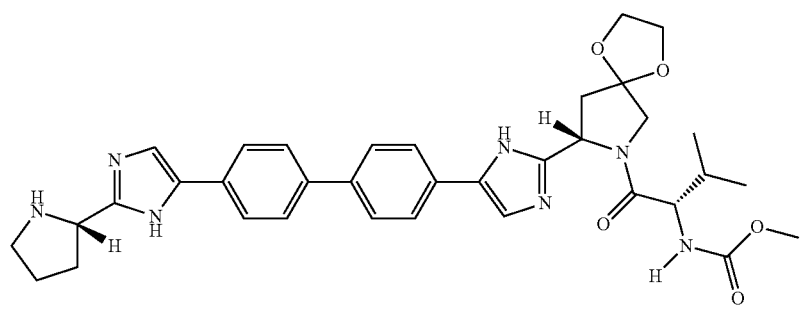

methyl (S)-3-methyl-1-oxo-1-((S)-8-(5-(4'-(2-((S)-pyrrolidin-2-yl)-1H-imidazol-5-yl)biphenyl-4-yl)-1H-imidazol-2-yl)-1,4-dioxa-7-azaspiro[4.4]nonan-7-yl)butan-2-ylcarbamate

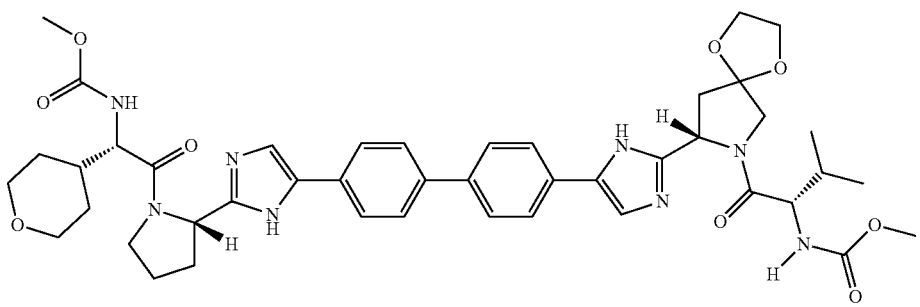

(S)-2-((S)-2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidin-1-yl)-2-oxo-1-(tetrahydro-2H-pyran-4-yl)ethylcarbamic acid methyl ester

(S)-2-((S)-2-(5-(4'-(2-((S)-7-((S)-2-(Methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidin-1-yl)-2-oxo-1-(tetrahydro-2H-pyran-4-yl)ethylcarbamic acid methyl ester Title compound was prepared according to the method employed to prepare 1-{2-[5-(9-{2-[1-(2-Methoxycarbonylamino-3-methyl-butyryl)-pyrrolidin-2-yl]-3H-imidazol-4-yl}-6-methyl-6,7-dihydro-5H-dibenzo[c,e]azepin-3-yl)-1H-imidazol-2-yl]-pyrrolidine-1-carbonyl}-2-methyl-propyl)-carbamic acid methyl ester. $^1$H-NMR: 400 MHz, (CD$_3$OD) δ 7.68 (d, J=8.0 Hz, 1H), 7.63-7.50 (m, 8H), 7.25-7.19 (m, 2H), 5.13-5.05 (m, 2H), 4.22 (d, J=8.4 Hz, 1H), 4.07 (d, J=7.2 Hz, 1H), 4.01-3.80 (m, 10H), 3.56 (s, 5H), 3.36 (s, 1H), 3.29-3.18 (m, 3H), 2.46-2.34 (m, 2H), 2.27-2.07 (m, 3H), 1.99-1.87 (m, 4H), 1.54-1.19 (m, 5H), 0.85-0.76 (m, 6H). MS (ESI) m/z 839.84 [M+H]$^+$.

Example GN

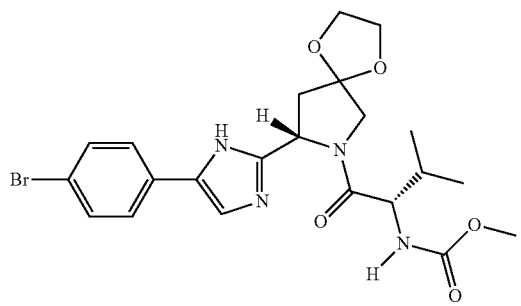

methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

+

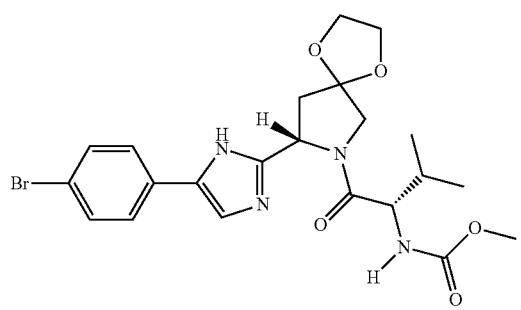

methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

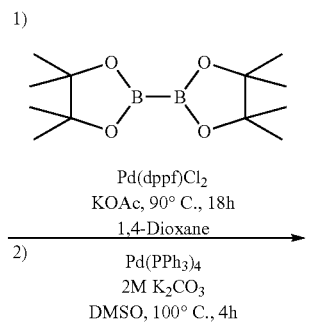

1) Pd(dppf)Cl$_2$
KOAc, 90° C., 18h
1,4-Dioxane

2) Pd(PPh$_3$)$_4$
2M K$_2$CO$_3$
DMSO, 100° C., 4h

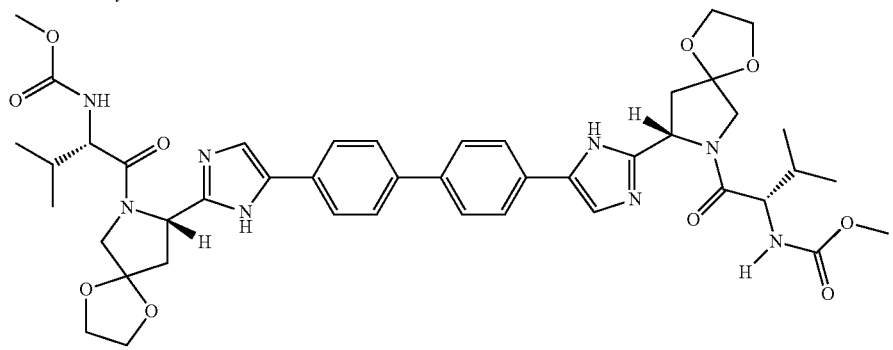

(S)-1-((S)-8-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)-1,4-dioxa-7-azaspiro[4.4]nonan-7-yl)-3-methyl-1-oxobutan-2-ylcarbamic acid methyl ester (S)-1-((S)-8-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)-1,4-dioxa-7-azaspiro[4.4]nonan-7-yl)-3-methyl-1-oxobutan-2-ylcarbamic acid methyl ester Title compound was prepared according to the method employed to prepare (S)-tert-butyl 2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-carboxylate. $^1$H-NMR: 400 MHz, (CD$_3$OD) δ 7.78 (d, J=8.0 Hz, 1H), 7.71-7.69 (m, 4H), 7.65-7.61 (m, 5H), 5.23 (t, J=8.4 Hz, 2H), 4.17 (d, J=7.6 Hz, 1H), 4.10 (m, 14H), 3.65 (s, 5H), 3.46 (s, 1H), 2.65 (s, 1H), 2.55-2.44 (m, 4H), 2.04-1.96 (m, 2H), 1.00 (d, J=6.8 Hz, 1H), 0.95-0.85 (m, 12H). MS (ESI) m/z 855.80 [M+H]$^+$.

Example GO

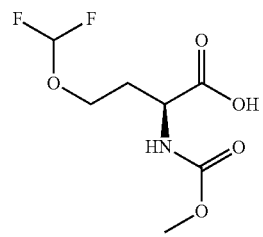

(S)-4-(difluoromethoxy)-2-(methoxycarbonylamino)butanoic acid

+

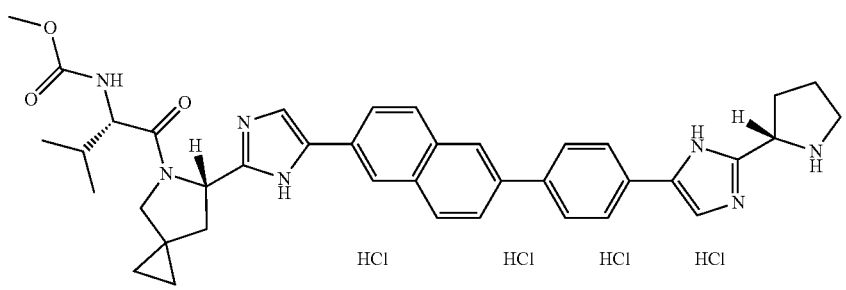

methyl (S)-3-methyl-1-oxo-1-((S)-6-(5-(6-(4-(2-((S)-pyrrolidin-2-yl)-1H-imidazol-5-yl)phenyl)naphthalen-2-yl)-1H-imidazol-2-yl)-5-azaspiro[2.4]heptan-5-yl)butan-2-ylcarbamate tetrahydrochloride EDC. HCl, HOBt
NMM, DMF
0° C. to rt, 4h

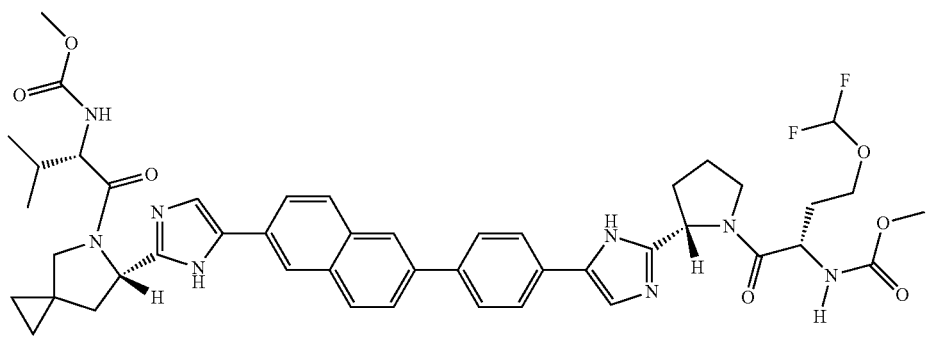

(S)-1-((S)-6-(5-(6-(4-(2-((S)-1-((S)-4-(difluoromethoxy)-2-(methoxycarbonylamino)butanoyl)pyrrolidin-2-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester (S)-1-((S)-6-(5-(6-(4-(2-((S)-1-((S)-4-(Difluoromethoxy)-2-(methoxycarbonylamino)butanoyl)pyrrolidin-2-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester Title compound was prepared according to the method employed to prepare (S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester. $^1$H-NMR: 400 MHz, (CD$_3$OD) δ 8.00-7.98 (m, 1H), 7.91-7.84 (m, 1H), 7.78-7.55 (m, 8H), 7.37-7.20 (m, 2H), 6.49 (t, J=75.6 Hz, 1H), 5.25-5.20 (m, 1H), 5.14 (m, 1H), 4.57 (m, 1H), 4.12-4.01 (m, 1H), 3.89-3.81 (m, 4H), 3.75-3.66 (m, 1H), 3.58 (s, 5H), 3.42-3.39 (m, 1H), 2.33-1.77 (m, 9H), 0.94-0.83 (m, 6H), 0.72-0.52 (m, 4H). MS (ESI) m/z 867.86 [M+H]$^+$.

Example GP and GQ

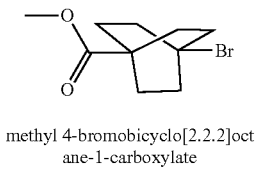

methyl 4-bromobicyclo[2.2.2]octane-1-carboxylate

AlCl$_3$
bromobenzene
$\xrightarrow{0° C., 30 min \\ then rt, 18h}$

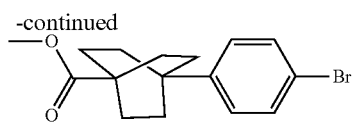

methyl 4-(4-bromophenyl)bicyclo[2.2.2]octane-1-carboxylate

+

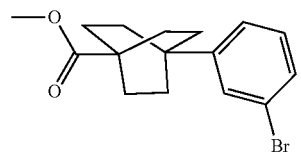

methyl 4-(3-bromophenyl)bicyclo[2.2.2]octane-1-carboxylate

Mixture of methyl 4-(4-bromophenyl)bicyclo[2.2.2]octane-1-carboxylate and methyl 4-(3-bromophenyl)bicyclo[2.2.2]octane-1-carboxylate A solution of methyl 4-bromobicyclo[2.2.2]octane-1-carboxylate (1 g, 4.05 mmol) in anhydrous bromobenzene (6.75 mL) was added dropwise to an ice-water cooled suspension of aluminum chloride (2.16 g, 16.2 mmol) in bromobenzene (3.25 mL) under nitrogen. The resulting reaction mixture was allowed to stir in the ice bath for 30 min and then at ambient temperature overnight.

The mixture was cautiously poured onto ice (100 g) and concentrated HCl (3.3 mL) and the mixture was extracted into ether (4 100 mL) The ether extracts were combined, washed with brine (100 mL), separated, and dried over MgSO$_4$ to leave a-brown solid. Purification by silica chromatography (5% ethyl acetate/hexane) gave a mixture of para- and meta substituted derivatives. (970 mg, 74%). (For a more detailed procedure see *J. Med. Chem.,* 2009, 52, 6, 1563).

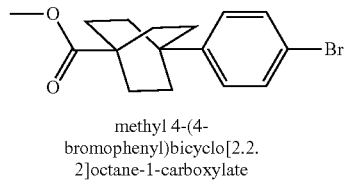

methyl 4-(4-bromophenyl)bicyclo[2.2.2]octane-1-carboxylate

+

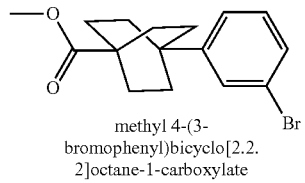

methyl 4-(3-bromophenyl)bicyclo[2.2.2]octane-1-carboxylate $\xrightarrow{2.5M\ LiOH}$

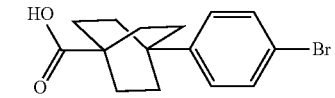

4-(4-bromophenyl)bicyclo[2.2.2]octane-1-carboxylic acid

+

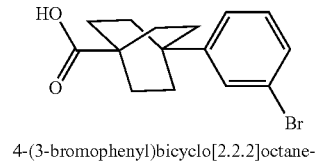

4-(3-bromophenyl)bicyclo[2.2.2]octane-1-carboxylic acid

Mixture of 4-(4-bromophenyl)bicyclo[2.2.2]octane-1-carboxylic acid and 4-(3-bromophenyl)bicyclo[2.2.2]octane-1-carboxylic acid A mixture of the title compounds were prepared according to the method employed to prepare (1-{3-Acetyl-5-[2-(4-bromo-phenyl)-2-oxo-ethylcarbamoyl]-imidazolidine-1-carbonyl}-2-methyl-propyl)-carbamic acid methyl ester. (638 mg, 94%)

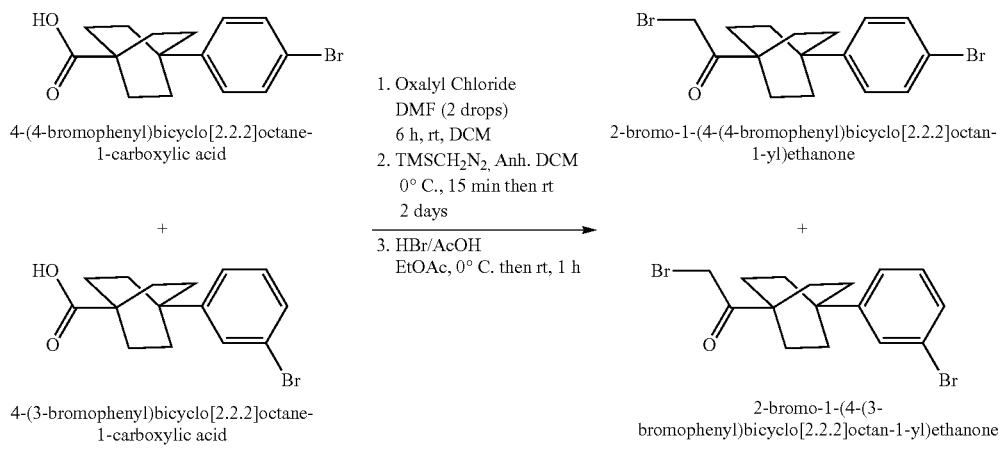 [SMILES: O=C(O)C12CCC(c3ccc(Br)cc3)(CC1)CC2 ; O=C(CBr)C12CCC(c3ccc(Br)cc3)(CC1)CC2 ; O=C(O)C12CCC(c3cccc(Br)c3)(CC1)CC2 ; O=C(CBr)C12CCC(c3cccc(Br)c3)(CC1)CC2]

Mixture of 2-bromo-1-(4-(4-bromophenyl)bicyclo[2.2.2]octan-1-yl)ethanone and 2-bromo-1-(4-(3-bromophenyl)bicyclo[2.2.2]octan-1-yl)ethanone A mixture of the title compounds were prepared according to the method employed to prepare 2-Bromo-1-{4-[3-(2-bromo-acetyl)-phenoxy]-phenyl}-ethanone. (290 mg, 43%)

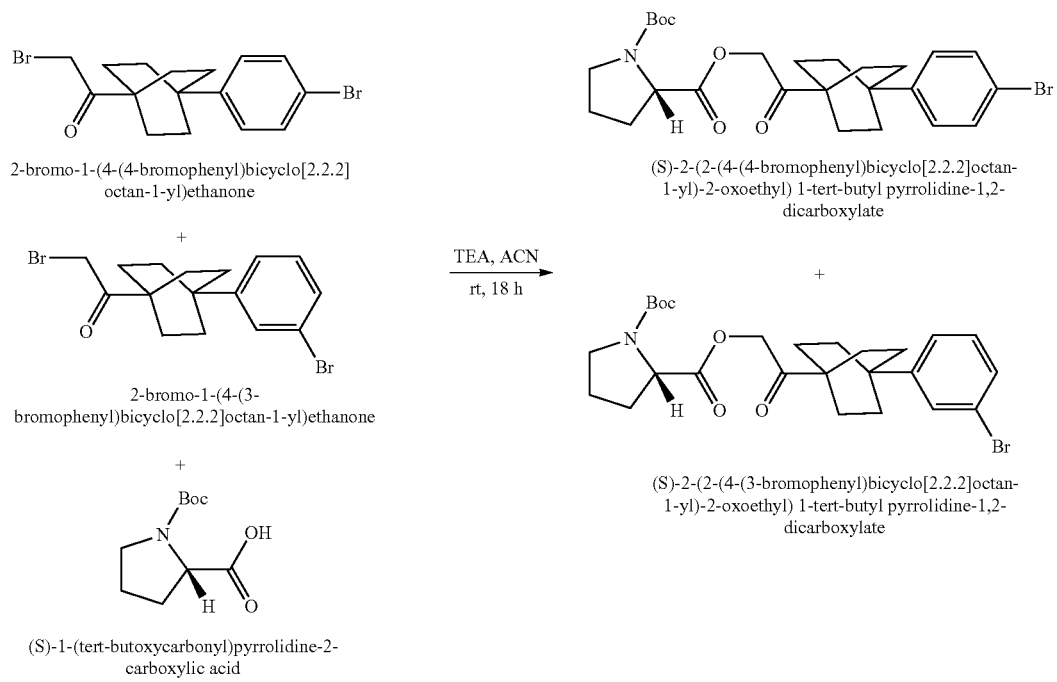 [SMILES: O=C(CBr)C12CCC(c3ccc(Br)cc3)(CC1)CC2 ; CC(C)(C)OC(=O)N1CCC[C@H]1C(=O)OCC(=O)C12CCC(c3ccc(Br)cc3)(CC1)CC2 ; O=C(CBr)C12CCC(c3cccc(Br)c3)(CC1)CC2 ; CC(C)(C)OC(=O)N1CCC[C@H]1C(=O)OCC(=O)C12CCC(c3cccc(Br)c3)(CC1)CC2 ; CC(C)(C)OC(=O)N1CCC[C@H]1C(=O)O]

Mixture of (S)-2-(2-(4-(4-bromophenyl)bicyclo[2.2.2]octan-1-yl)-2-oxoethyl) 1-tert-butyl pyrrolidine-1,2-dicarboxylate and (S)-2-(2-(4-(3-bromophenyl)bicyclo[2.2.2]octan-1-yl)-2-oxoethyl) 1-tert-butyl pyrrolidine-1,2-dicarboxylate A mixture of the title compounds were prepared according to the method employed to prepare 2-Aza-bicyclo[2.2.1]heptane-2,3-dicarboxylic acid 3-(2-{9-[2-(1-tert-butoxycarbonyl-pyrrolidine-2-carbonyloxy)-acetyl]-5,7-dihydro-dibenzo[c,e]oxepin-3-yl}-2-oxo-ethyl) ester 2-tert-butyl ester. (365 mg, 94%).

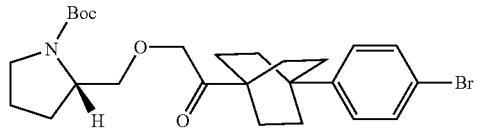

(S)-2-(2-(4-(4-bromophenyl)bicyclo[2.2.2]octan-1-yl)-2-oxoethyl 1-tert-butyl pyrrolidine-1,2-dicarboxylate

+

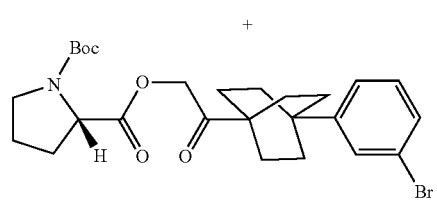

(S)-2-(2-(4-(3-bromophenyl)bicyclo[2.2.2]octan-1-yl)-2-oxoethyl) 1-tert-butyl pyrrolidine-1,2-dicarboxylate $\xrightarrow{\text{NH}_4\text{OAc}}_{\text{Toluene, reflux} \atop 18 \text{ h}}$

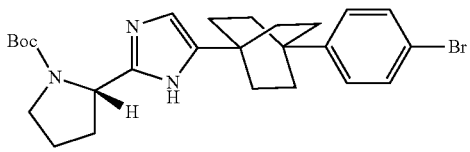

(S)-tert-butyl 2-(5-(4-(4-bromophenyl)bicyclo[2.2.2]octan-2-yl)-1H-imidazol-2-yl)pyrrolidine-1-carboxylate

+

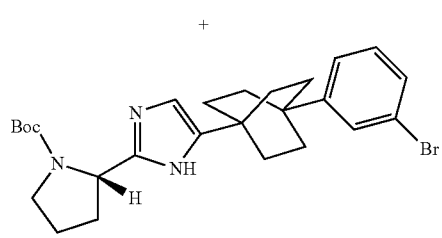

(S)-tert-butyl 2-(5-(4-(3-bromophenyl)bicyclo[2.2.2]octan-1-yl)-1H-imidazol-2-yl)pyrrolidine-1-carboxylate Mixture of (S)-tert-butyl 2-(5-(4-(4-bromophenyl)bicyclo[2.2.2]octan-1-yl)-1H-imidazol-2-yl)pyrrolidine-1-carboxylate and (S)-tert-butyl 2-(5-(4-(3-bromophenyl)bicyclo[2.2.2]octan-1-yl)-1H-imidazol-2-yl)pyrrolidine-1-carboxylate A mixture of the title compounds were prepared according to the method employed to prepare methyl (S)-1-((S)-6-(5-(4-bromophenyl)-1H-imidazol-2-yl)-5-azaspiro[2.4]heptan-5-yl)-3-methyl-1-oxobutan-2-ylcarbamate. (298 mg, 85%).

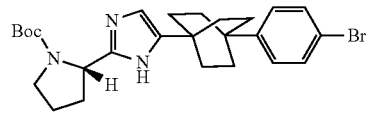

(S)-tert-butyl 2-(5-(4-(4-bromophenyl)bicyclo[2.2.2]octan-1-yl)-1H-imidazol-2-yl)pyrrolidine-1-carboxylate

+

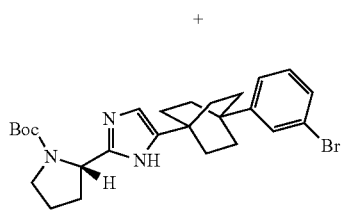

(S)-tert-butyl 2-(5-(4-(3-bromophenyl)bicyclo[2.2.2]octan-1-yl)-1H-imidazol-2-yl)pyrrolidine-1-carboxylate

1)

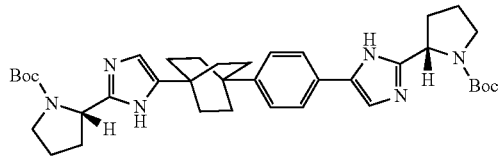

Pd(dppf)Cl$_2$
KOAc, 90° C., 18 h
1,4-Dioxane

2) Pd(PPh$_3$)$_4$
2M K$_2$CO$_3$
DMSO, 100° C., 4 h (S)-tert-butyl 2-(5-(4-(4-(2-((S)-1-(tert-butoxycarbonyl)pyrrolidin-2-yl)-1H-imidazol-5-yl)bicyclo(2.2.2)octan-1-yl)phenyl)-1H-imidazol-2-yl)pyrrolidine-1-carboxylate

+

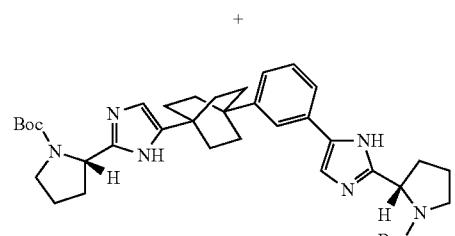

(S)-tert-butyl 2-(5-(3-(4-2-((S)-1-(tert-butoxycarbonyl)pyrrolidin-2-yl)-1H-imidazol-5-yl)bicyclo[2.2.2]octan-1-yl)phenyl)-1H-imidazol-2-yl)pyrrolidine-1-carboxylate

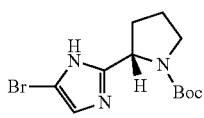

(S)-tert-butyl 2-(5-bromo-1H-imidazol-2-yl)pyrrolidine-1-carboxylate

Mixture of (S)-tert-butyl 2-(5-(4-(4-(2-((S)-1-(tert-butoxycarbonyl)pyrrolidin-2-yl)-1H-imidazol-5-yl)bicyclo[2.2.2]octan-1-yl)phenyl)-1H-imidazol-2-yl)pyrrolidine-1-carboxylate and (S)-tert-butyl 2-(5-(3-(4-(2-((S)-1-(tert-butoxycarbonyl)pyrrolidin-2-yl)-1H-imidazol-5-yl)bicyclo[2.2.2]octan-1-yl)phenyl)-1H-imidazol-2-yl)pyrrolidine-1-carboxylate A mixture of the title compounds were prepared according to the method employed to prepare (S)-tert-butyl 2-(5-(4'-(2-((S)-7-((S)-2-(methoxycarbonylamino)-3-methylbutanoyl)-1,4-dioxa-7-azaspiro[4.4]nonan-8-yl)-1H-imidazol-5-yl)biphenyl-4-yl)-1H-imidazol-2-yl)pyrrolidine-1-carboxylate. (287 mg, 73%).

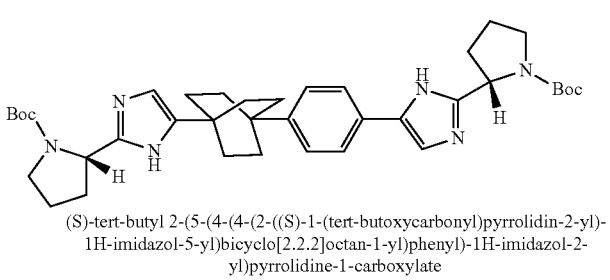

(S)-tert-butyl 2-(5-(4-(4-(2-((S)-1-(tert-butoxycarbonyl)pyrrolidin-2-yl)-1H-imidazol-5-yl)bicyclo[2.2.2]octan-1-yl)phenyl)-1H-imidazol-2-yl)pyrrolidine-1-carboxylate

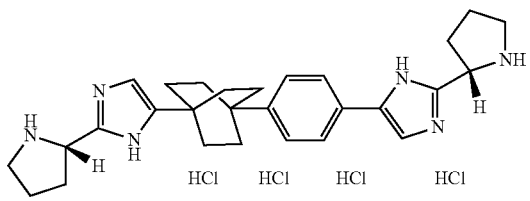

2-((S)-pyrrolidin-2-yl)-5-(4-(4-(2-((S)-pyrrolidin-2-yl)-1H-imidazol-5-yl)bicyclo[2.2.2]octan-1-yl)phenyl)-1H-imidazole tetrahydrochloride 4N HCl/Dioxane
THF

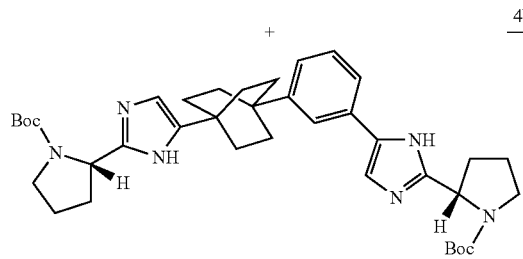

(S)-tert-butyl 2-(5-(3-(4-(2-((S)-1-(tert-butoxycarbonyl)pyrrolidin-2-yl)-1H-imidazol-5-yl)bicyclo[2.2.2]octan-1-yl)phenyl)-1H-imidazol-2-yl)pyrrolidine-1-carboxylate

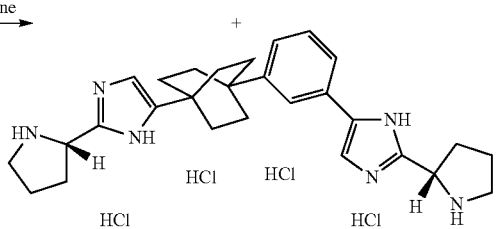

2-((S)-pyrrolidin-1-yl)-5-(3-(4-(2-((S)-pyrrolidin-1-yl)-1H-imidazol-5-yl)bicyclo[2.2.2]octan-1-yl)phenyl)-1H-imidazole tetrahydrochloride Mixture of 2-((S)-pyrrolidin-2-yl)-5-(4-(4-(2-((S)-pyrrolidin-2-yl)-1H-imidazol-5-yl)bicyclo[2.2.2]octan-1-yl)phenyl)-1H-imidazole tetrahydrochloride and 2-((S)-pyrrolidin-2-yl)-5-(3-(4-(2-((S)-pyrrolidin-2-yl)-1H-imidazol-5-yl)bicyclo[2.2.2]octan-1-yl)phenyl)-1H-imidazole tetrahydrochloride A mixture of the title compounds were prepared according to the method employed to prepare (S)-benzyl 4-oxopyrrolidine-2-carboxylate hydrochloride.

pyrrolidin-2-yl)-1H-imidazol-5-yl)phenyl)bicyclo[2.2.2]octan-1-yl)-1H-imidazol-2-yl)pyrrolidin-1-yl)-3-methyl-1-oxobutan-2-ylcarbamic acid methyl ester by prep HPLC. (41 mg, 23%) $^1$H-NMR: 400 MHz, (CD$_3$OD) δ 7.63 (d, J=8 Hz, 1H), 7.55 (d, J=8.4 Hz, 2H), 7.42 (s, 1H), 7.34 (d, J=8.4 Hz, 2H), 7.20 (s, 1H), 7.01-6.95 (m, 1H), 5.17-5.11 (m, 2H), 4.24-4.19 (m, 2H), 4.00-3.96 (m, 2H), 3.88-3.81 (m, 2H), 3.64 (s, 5H), 3.54-3.48 (m, 1H), 2.34-1.96 (m, 10H), 1.91 (brs, 12H), 1.01-0.88 (m, 12H). MS (ESI) m/z 772.56 [M+H]$^+$.

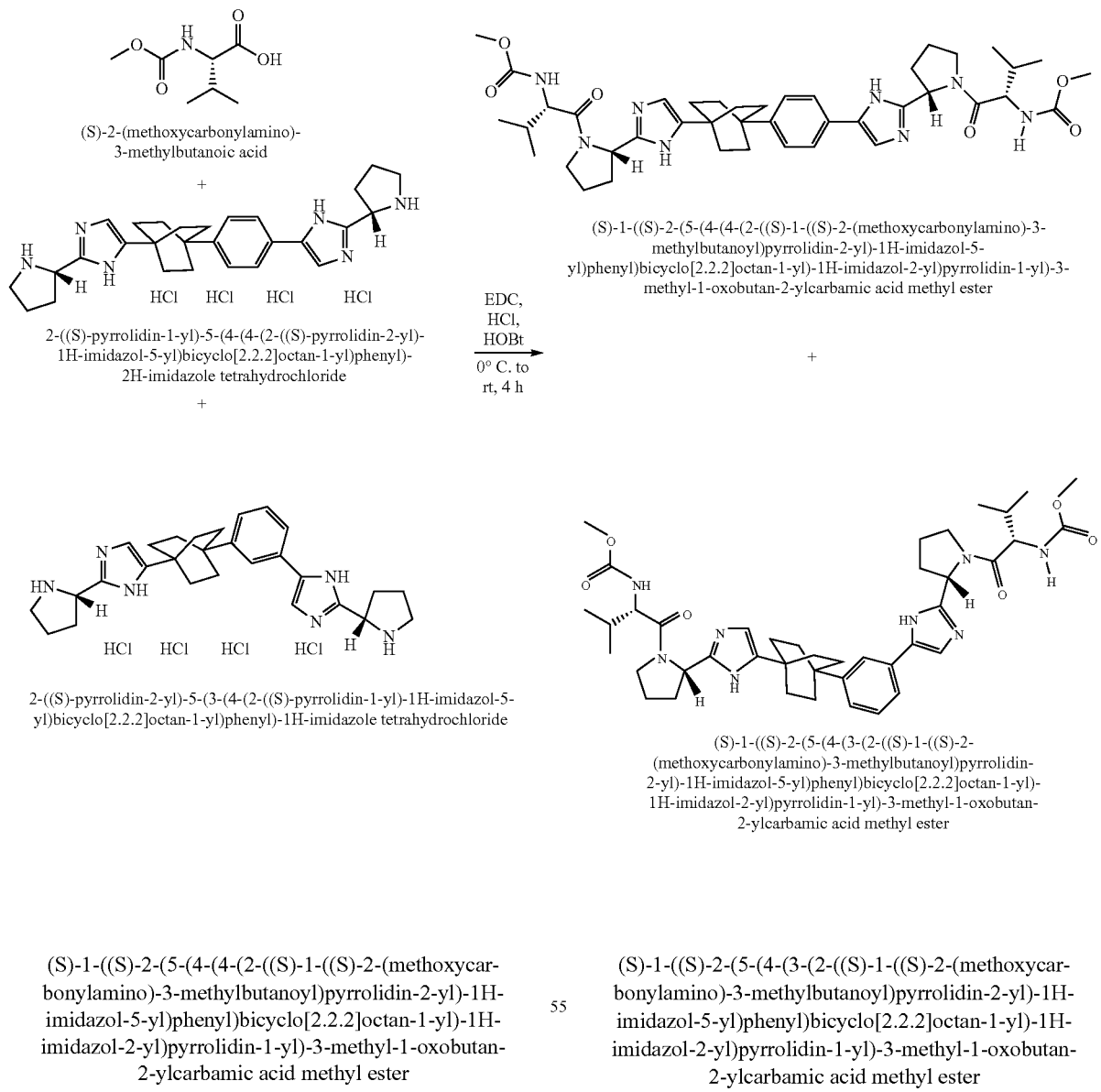

(S)-1-((S)-2-(5-(4-(4-(2-((S)-1-((S)-2-(methoxycarbonylamino)-3-methylbutanoyl)pyrrolidin-2-yl)-1H-imidazol-5-yl)phenyl)bicyclo[2.2.2]octan-1-yl)-1H-imidazol-2-yl)pyrrolidin-1-yl)-3-methyl-1-oxobutan-2-ylcarbamic acid methyl ester Title compound was prepared according to the method employed to prepare (S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester and separated from (S)-1-((S)-2-(5-(4-(3-(2-((S)-1-((S)-2-(methoxycarbonylamino)-3-methylbutanoyl)

(S)-1-((S)-2-(5-(4-(3-(2-((S)-1-((S)-2-(methoxycarbonylamino)-3-methylbutanoyl)pyrrolidin-2-yl)-1H-imidazol-5-yl)phenyl)bicyclo[2.2.2]octan-1-yl)-1H-imidazol-2-yl)pyrrolidin-1-yl)-3-methyl-1-oxobutan-2-ylcarbamic acid methyl ester Title compound was prepared according to the method employed to prepare (S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester and separated from (S)-1-((S)-2-(5-(4-(4-(2-

987

((S)-1-((S)-2-(methoxycarbonylamino)-3-methylbutanoyl)pyrrolidin-2-yl)-1H-imidazol-5-yl)phenyl)bicyclo[2.2.2]octan-1-yl)-1H-imidazol-2-yl)pyrrolidin-1-yl)-3-methyl-1-oxobutan-2-ylcarbamic acid methyl ester by prep HPLC. (54 mg, 30%). $^1$H-NMR: 400 MHz, (CD$_3$OD) δ 7.66 (s, 1H), 7.43 (d, J=8 Hz, 2H), 7.28-7.21 (m, 3H), 7.01-6.95 (m, 1H), 5.17-5.11 (m, 2H), 4.25-4.20 (m, 2H), 3.99-3.94 (m, 2H), 3.89-3.81 (m, 2H), 3.64 (s, 5H), 3.57-3.45 (m, 1H), 2.34-1.88 (m, 22H), 1.02-0.89 (m, 12H). MS (ESI) m/z 772.96 [M+H]$^+$.

Example GR

988

(S)-1-((S)-2-(5-(6-(4-(2-((2S,5R)-1-((S)-2-(methoxycarbonylamino)propanoyl)-5-phenylpyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester Title compound was prepared according to the method employed to prepare (S)-1-((S)-6-(5-(6-(4-(2-((1R,3S,4S)-2-((S)-4-(difluoromethoxy)-2-(methoxycarbonylamino)butanoyl)-2-azabicyclo[2.2.1]heptan-3-yl)-1H-imidazol-5-yl)

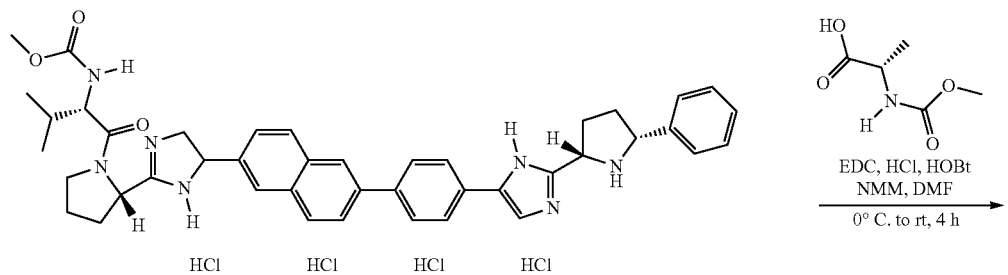

methyl (S)-3-methyl-1-oxo-1-((S)-2-(5-(6-(4-(2-((2S,5R)-5-phenylpyrrolidin-2-yl)-1H-imidazol-5-yl)phenyl)naphthalen-2-yl)-1H-imidazol-2-yl)pyrrolidin-1-yl)butan-2-ylcarbamate tetrahydrochloride

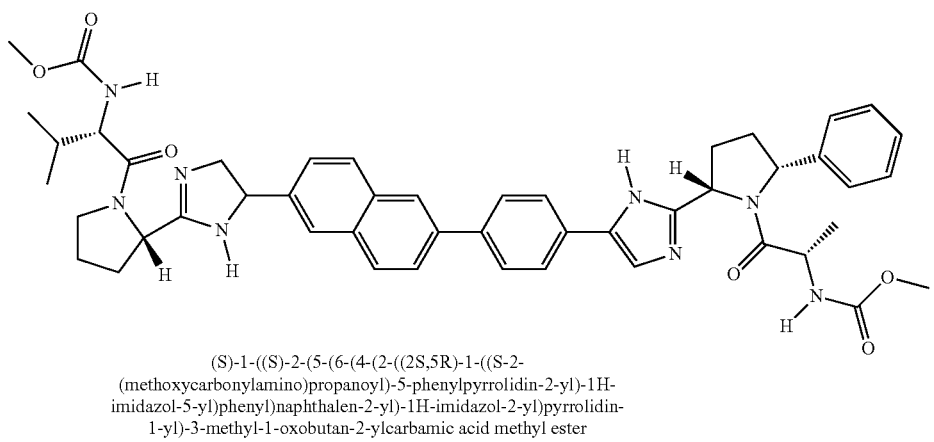

(S)-1-((S)-2-(5-(6-(4-(2-((2S,5R)-1-((S-2-(methoxycarbonylamino)propanoyl)-5-phenylpyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester phenyl)naphthalen-2-yl)-1H-imidazol-2-yl)-5-azaspiro[2.4]heptan-5-yl)-3-methyl-1-oxobutan-2-ylcarbamic acid methyl ester.

$^1$H-NMR: 400 MHz, (CD$_3$OD) δ 8.13 (s, 1H), 8.08 (s, 1H), 7.94-7.77 (m, 8H), 7.50-7.42 (m, 3H), 7.36-7.25 (m, 2H), 7.17-6.99 (m, 2H), 5.49-5.36 (m, 2H), 5.23 (d, J=5.2 Hz, 1H), 4.27-4.21 (m, 2H), 4.04-3.99 (m, 1HN, 3.93-3.87 (m, 1H), 3.70 (s, 1H), 3.66 (s, 4H), 2.68-2.48 (m, 2H), 2.39-2.20 (m, 4H), 2.11-2.03 (m, 2H), 1.39 (d, J=6.8 Hz, 1H), 1.04-0.96 (m, 4H), 0.93 (d, J=6.8 Hz, 2H), 0.70 (d, J=6.8 Hz, 2H). MS (ESI) m/z 837.92 [M+H]$^+$.

Example GS

[1-(2-{5-[6-(4-{2-[1-(2-Dimethylcarbamoyloxy-2-phenyl-acetyl)-pyrrolidin-2-yl]-3H-imidazol-4-yl}-naphthalen-2-yl]-1H-imidazol-2-yl}-pyrrolidine-1-carbonyl)-2-methyl-propyl]-carbamic acid methyl ester To 2-{5-[4-(6-{2-[1-(2-Methoxycarbonylamino-3-methyl-butyryl)-pyrrolidin-2-yl]-3H-imidazol-4-yl}-naphthalen-2-yl]-1H-imidazol-2-yl}-pyrrolidine-1-carboxylic acid tert-butyl ester (40 mg) in methanol (0.5 mL) was added 4N HCl in dioxanes (0.5 mL). The mixture was stirred for 2 hours

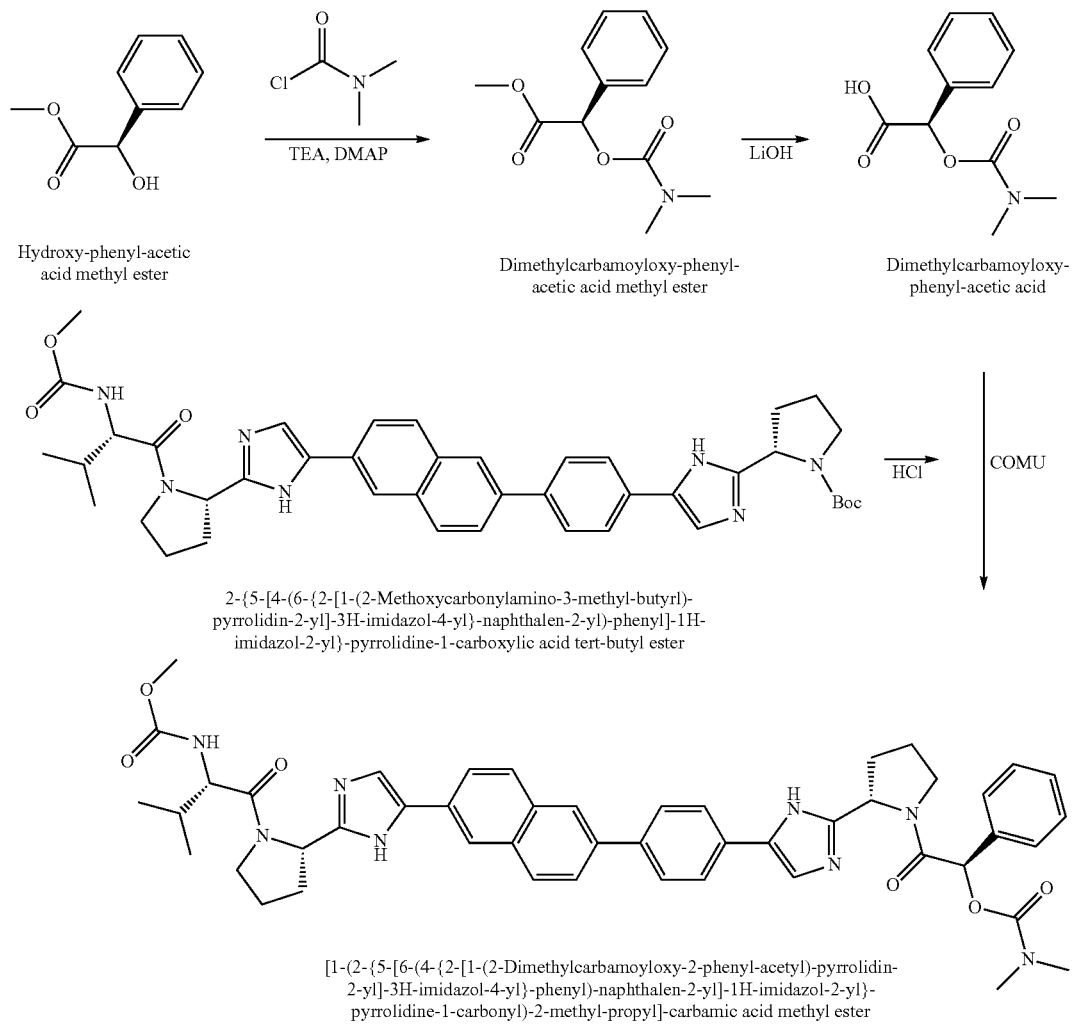

Dimethylcarbamoyloxy-phenyl-acetic acid

To hydroxyl-phenyl-acetic acid methyl ester (500 mg) in THF (10 mL) were added dimethylcarbamoyl chloride (304 μl), TEA (503 μl), and DMAP (37 mg). After stirring for overnight at room temperature, the mixture was taken up in ethyl acetate (150 mL). The organic phase was washed with 1 N HCl (1×100 mL) and saturated sodium bicarbonate (1×100 mL), and dried over sodium sulfate. After the solvent was removed, the resulting solid was dissolved in THF (6 mL). To the solution was added 2 M LiOH (3 mL). After stirring for 90 min. at room temperature, the reaction mixture was acidified with 2 N HCl (3.2 mL). The mixture was extracted with ethyl acetate (50 mL). The organic phase was dried over sodium sulfate. The solvent was removed under reduced pressure to provide dimethylcarbamoyloxy-phenyl-acetic acid (561 mg, 83%) as an off-white solid.

then concentrated to afford the HCl salt of the crude amine. To the crude amine in DMF (1 mL) was added DIEA (14 μl). After all material dissolved, dimethylcarbamoyloxy-phenyl-acetic acid (12 mg) and (1-cyano-2-ethoxy-2-oxoethylidenaminooxy)dimethylamino-morpholino-carbenium hexafluorophosphate (COMU, 23 mg) were added. After stirring for 30 min. the reaction was purified by a preparative HPLC (10-60% MeCN—H$_2$O; 0.1% formic acid modifier) to afford the title product (22 mg, 48%). $^1$H NMR (MeOH-d4, 400 MHz) δ: 8.22-8.05 (m, 2H), 7.92-7.69 (m, 9H), 7.56-7.44 (m, 6H), 6.08-5.92 (d, 1H), 5.27-5.20 (m, 2H), 4.28-4.24 (m, 1H), 4.13-4.00 (m, 2H), 3.90-3.68 (m, 2H), 3.66 (s, 3H), 3.45-3.38 (m, 2H), 2.92-2.90 (m, 6H), 2.47-1.96 (m, 10H), 1.05-0.91 (m, 6H); MS (ESI) m/z 837.3 [M+H]$^+$.

Example GT

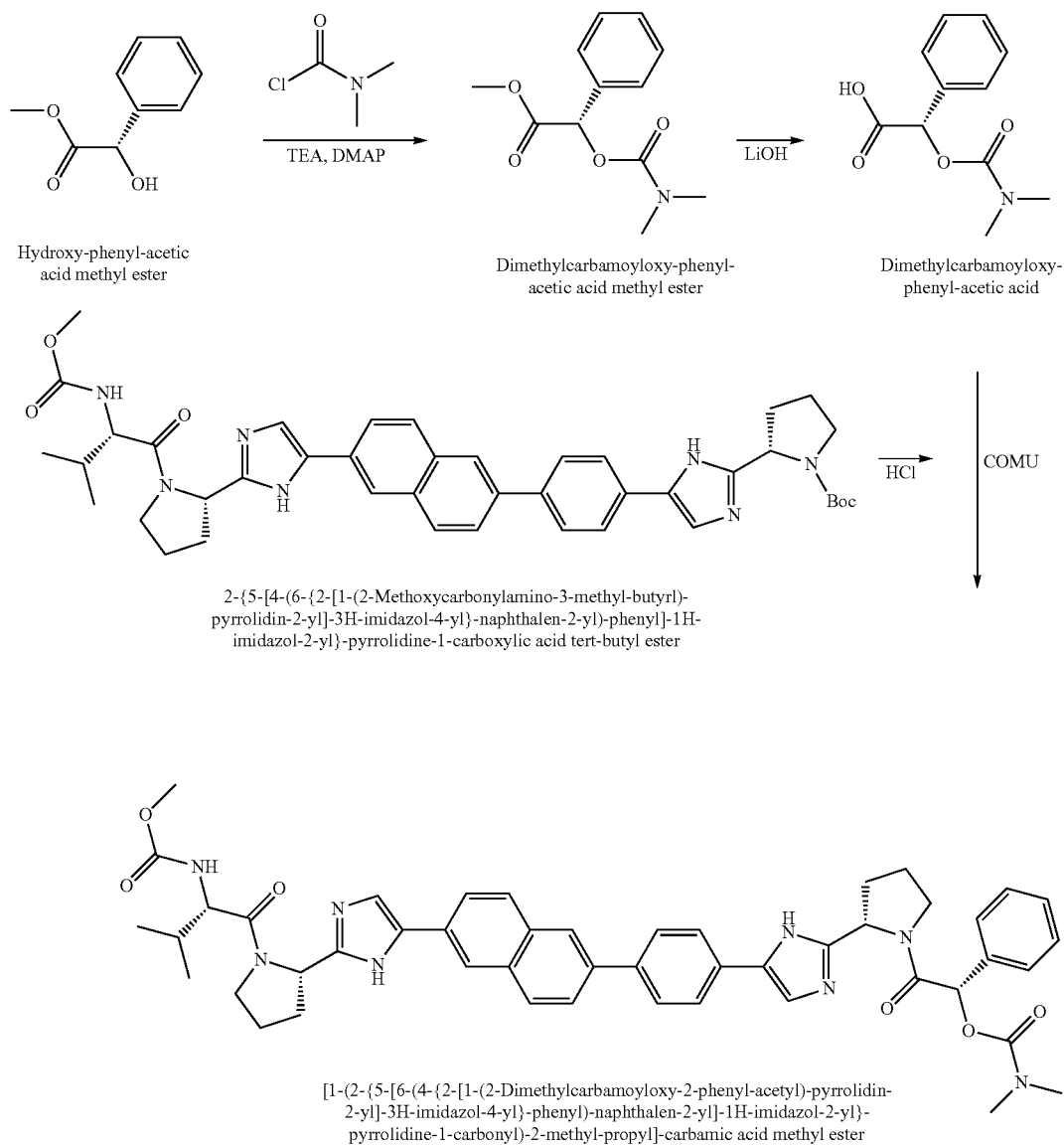

[1-(2-{5-[6-(4-{2-[1-(2-Dimethylcarbamoyloxy-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Title compound was prepared according to the method employed to [1-(2-{5-[6-(4-{2-[1-(2-Dimethylcarbamoyloxy-2-phenyl-acetyl)-pyrrolidin-2-yl]-3H-imidazol-4-yl)-naphthalen-2-yl]-1H-imidazol-2-yl}-pyrrolidine-1-carbonyl)-2-methyl-propyl]-carbamic acid methyl ester (Example 6), (20 mg, 43%). $^1$H NMR (MeOH-d4, 400 MHz) δ: 8.21-8.04 (m, 2H), 7.93-7.89 (m, 3H), 7.81-7.68 (m, 5H), 7.53-7.41 (m, 7H), 6.10-5.78 (d, 1H), 5.28-5.21 (m, 2H), 4.28-4.26 (m, 1H), 4.03-3.81 (m, 4H), 3.66 (s, 3H), 3.62-3.45 (m, 2H), 2.92-2.85 (m, 6H), 2.42-1.90 (m, 10H), 1.01-0.89 (m, 6H); MS (ESI) m/z 837.5 [M+H]$^+$.

Example GU

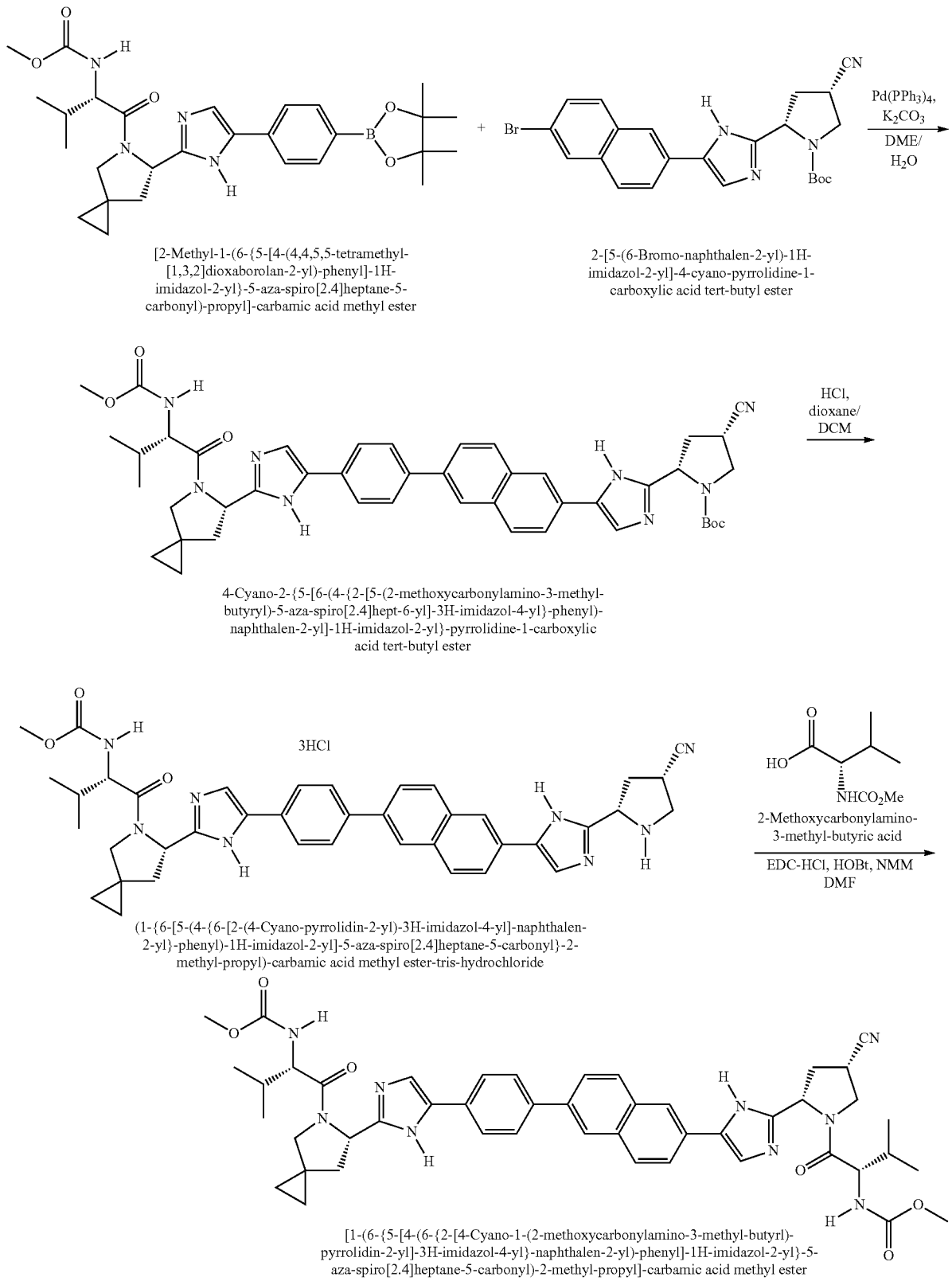

[2-Methyl-1-(6-{5-[4-(4,4,5,5-tetramethyl-[1,3,2]dioxaborolan-2-yl)-phenyl]-1H-imidazol-2-yl}-5-aza-spiro[2.4]heptane-5-carbonyl)-propyl]-carbamic acid methyl ester 2-[5-(6-Bromo-naphthalen-2-yl)-1H-imidazol-2-yl]-4-cyano-pyrrolidine-1-carboxylic acid tert-butyl ester 4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carboxylic acid tert-butyl ester (1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride 2-Methoxycarbonylamino-3-methyl-butyric acid

[1-(6-{5-[4-(6-{2-[4-Cyano-1-(2-methoxycarbonylamino-3-methyl-butyryl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester

4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carboxylic acid tert-butyl ester

[2-Methyl-1-(6-{5-[4-(4,4,5,5-tetramethyl-[1,3,2]dioxaborolan-2-yl)-phenyl]-1H-imidazol-2-yl}-5-aza-spiro[2.4]heptane-5-carbonyl)-propyl]-carbamic acid methyl ester (997 mg, 1.91 mmol), 2-[5-(6-Bromo-naphthalen-2-yl)-1H-imidazol-2-yl]-4-cyano-pyrrolidine-1-carboxylic acid tert-butyl ester, Pd(PPh$_3$)$_4$ (184 mg, 0.159 mmol), and K$_2$CO$_3$ (2 M in H$_2$O, 1.9 mL, 3.8 mmol) were combined in 1,2-dimethoxyethane (16 mL) The reaction mixture was degassed with bubbling N$_2$ for 10 minutes then heated to reflux for 3.5 h. After heating, the reaction mixture was cooled to RT, diluted with EtOAc and washed with H$_2$O and brine. The organic phase was dried over MgSO$_4$, then filtered and concentrated. The resulting residue was purified with silica column chromatography 0% to 100% (10% MeOH/DCM)/EtOAc to afford the title compound (641 mg, 51%).

(1-{(6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride 4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carboxylic acid tert-butyl ester (639 mg, 0.816 mmol) was dissolved in DCM (8 mL) and 4.0 M HCl in dioxane (2 mL, 8 mmol) was added. After stirring for 37 min, the solid was filtered off and rinsed with EtOAc, affording the title compound (597 mg, 92%).

[1-(6-{5-[4-(6-{2-[4-Cyano-1-(2-methoxycarbonylamino-3-methyl-butyryl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester 2-Methoxycarbonylamino-3-methyl-butyric acid (40 mg, 0.227 mmol) EDC-HCl (44 mg, 0.227 mmol) and HOBt (32 mg, 0.237 mmol) were combined in DMF (2 mL) and stirred for 20 min at RT. (1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride (150 mg, 0.189 mg) was added, the reaction mixture was cooled to 0° C. and NMM (0.104 mL, 0.947 mmol) was added dropwise. After 1.5 h, the reaction mixture was warmed to RT. 30 min later, the mixture was diluted with EtOAc and washed with NaHCO$_3$, then 1:1 brine/5M NaOH. The organic phase was dried over MgSO$_4$, then filtered and concentrated. The resulting residue was purified by HPLC to afford the title compound (18 mg, 11%). MS (ESI) m/z 840 [M+H]$^+$.

Example GV

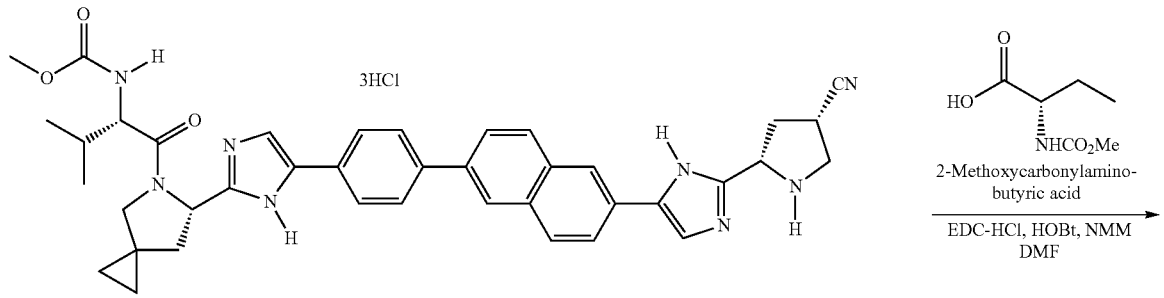

(1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride

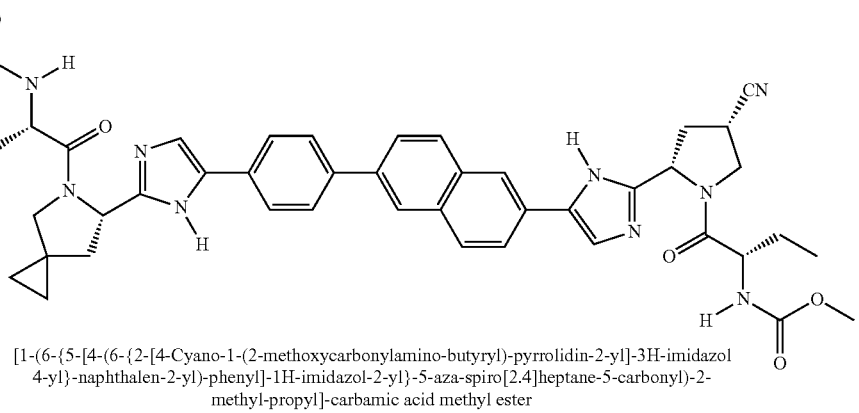

[1-(6-{5-[4-(6-{2-[4-Cyano-1-(2-methoxycarbonylamino-butyryl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester

997

[1-(6-{5-[4-(6-{2-[4-Cyano-1-(2-methoxycarbony-lamino-butyryl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester 2-Methoxycarbonylamino-butyric acid (37 mg, 0.227 mmol) EDC-HCl (44 mg, 0.227 mmol) and HOBt (32 mg, 0.237 mmol) were combined in DMF (2 mL) and stirred for 20 min at RT. (1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride (150 mg, 0.189 mg) was added, the reaction mixture was cooled to 0° C. and NMM (0.104 mL, 0.947 mmol) was added dropwise. After 1.5 h, the reaction mixture was warmed to RT. 30 min later, the mixture was diluted with EtOAc and washed with NaHCO₃, then 1:1 brine/5M NaOH. The organic phase was dried over MgSO₄, then filtered and concentrated. The resulting residue was purified by HPLC to afford the title compound (85 mg, 54%). MS (ESI) m/z 826 [M+H]$^+$.

Example GW

998

[1-(4-Cyano-2-{5-[6-(4-{2-[5-(2-methoxycarbony-lamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carbonyl)-2,2-dimethyl-propyl]-carbamic acid methyl ester 2-Methoxycarbonylamino-3,3-dimethyl-butyric acid (37 mg, 0.227 mmol) EDC-HCl (44 mg, 0.227 mmol) and HOBt (32 mg, 0.237 mmol) were combined in DMF (2 mL) and stirred for 20 min at RT. (1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride (150 mg, 0.189 mg) was added, the reaction mixture was cooled to 0° C. and NMM (0.104 mL, 0.947 mmol) was added dropwise. After 1.5 h, the reaction mixture was warmed to RT. 30 min later, the mixture was diluted with EtOAc and washed with NaHCO₃, then 1:1 brine/5M NaOH. The organic phase was dried over MgSO₄, then filtered and concentrated. The resulting residue was purified by HPLC to afford the title compound (77 mg, 48%). MS (ESI) m/z 855 [M+H]$^+$.

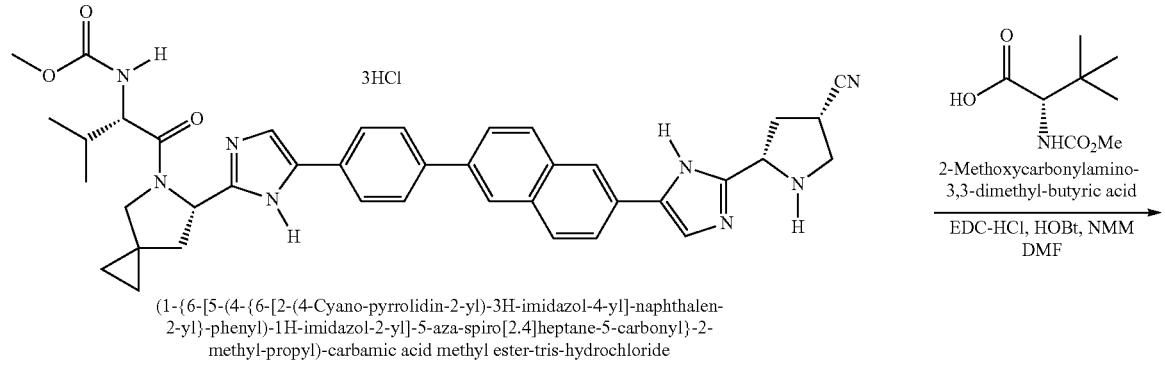

(1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride

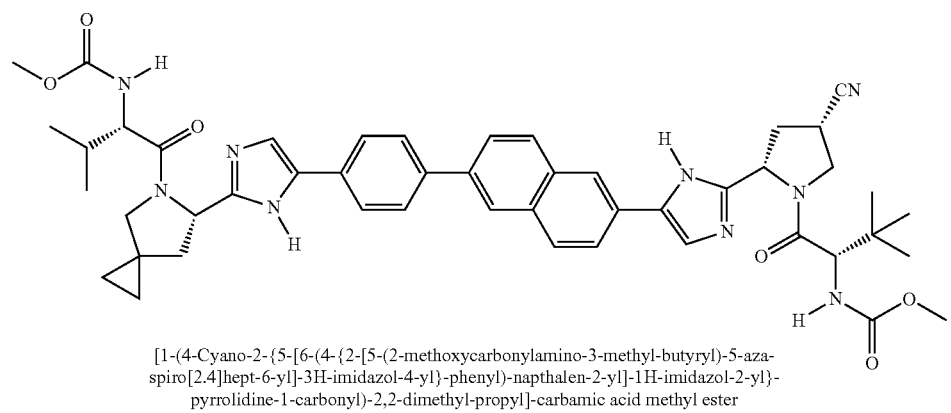

[1-(4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-napthalen-2-yl]-1H-imidazol-2-yl}-pyrrolidine-1-carbonyl)-2,2-dimethyl-propyl]-carbamic acid methyl ester

Example GX
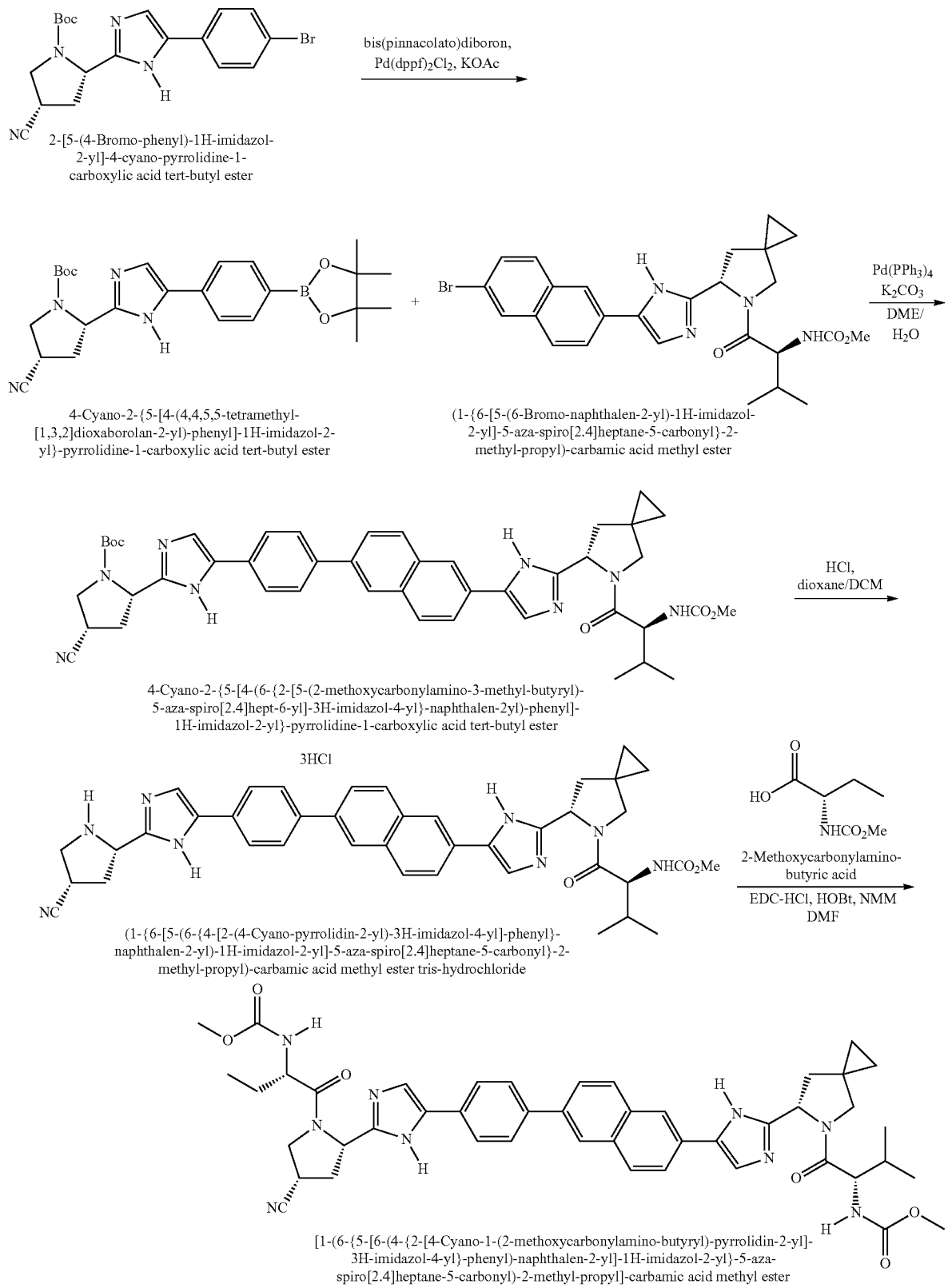

4-Cyano-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester 2-[5-(4-Bromo-phenyl)-1H-imidazol-2-yl]-4-cyano-pyrrolidine-1-carboxylic acid tert-butyl ester (2.895 g, 6.94 mmol), bis(pinacolato)diboron (2.64 g, 10.41 mmol), Pd(dppf)$_2$Cl$_2$ (254 mg, 0.347 mmol) and KOAc (2.04 g, 20.82 mmol) were combined in dioxane and degassed for 12 min with bubbling N$_2$. The reaction mixture was then stirred at 90° C. for 18 h, cooled to RT and diluted with EtOAc. The organic mixture was washed with saturated aqueous NaHCO$_3$ and brine before being dried over MgSO$_4$, filtered and concentrated. The crude residue was purified by silica column chromatography (50% to 100% EtOAc/Hex) to provide the title compound (1.56 g, 48%).

4-Cyano-2-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-pyrrolidine-1-carboxylic acid tert-butyl ester 4-Cyano-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (0.990 g, 2.13 mmol), (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester (1.007 g, 1.92 mmol), Pd(PPh$_3$)$_4$ (222 mg, 0.192 mmol) and K$_2$CO$_3$ (2.0 M in H$_2$O, 2.1 mL, 4.2 mmol) were combined in 1,2-dimethoxymethane. The mixture was degassed for 10 min with bubbling N$_2$ then heated to reflux for 4 h then cooled. The reaction mixture was diluted with EtOAc and washed with saturated aqueous NaHCO$_3$ and brine before being dried over MgSO$_4$, filtered and concentrated. The crude residue was purified by silica column chromatography (EtOAc, then 2% MeOH/DCM, then 4% MeOH/DCM) to provide the title compound (1.028 g, 68%).

(1-{6-[5-(6-{4-[2-(4-Cyano-pyrrolidin-2-yl)-3H-imidazol-4-yl]-phenyl}-naphthalen-2-yl)-1H-imidazol-2-yl]-5-aza-spiro[2.4]heptane-5-carbonyl}-2-methyl-propyl)-carbamic acid methyl ester tris-hydrochloride A solution of 4-Cyano-2-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-pyrrolidine-1-carboxylic acid tert-butyl ester (1.000 g, 1.28 mmol) in DCM (16 mL) was treated with HCl (4.0 M in dioxane, 3.2 mL, 12.8 mmol). After 2.5 h, the solid was filtered off and rinsed with EtOAc to provide the title compound (1.004 g, 99%).

[1-(6-{5-[6-(4-{2-[4-Cyano-1-(2-methoxycarbonylamino-butyryl)-pyrrolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester 2-2-Methoxycarbonylamino-butyric acid (37 mg, 0.227 mmol) EDC-HCl (44 mg, 0.227 mmol) and HOBt (32 mg, 0.237 mmol) were combined in DMF (2 mL) and stirred for 20 min at RT. (1-{6-[5-(6-{4-[2-(4-Cyano-pyrrolidin-2-yl)-3H-imidazol-4-yl]-phenyl}-naphthalen-2-yl)-1H-imidazol-2-yl]-5-aza-spiro[2.4]heptane-5-carbonyl}-2-methyl-propyl)-carbamic acid methyl ester tris-hydrochloride (150 mg, 0.189 mg) was added, the reaction mixture was cooled to 0° C. and NMM (0.104 mL, 0.947 mmol) was added dropwise. After 1.5 h, the reaction mixture was warmed to RT. 30 min later, the mixture was diluted with EtOAc and washed with NaHCO$_3$, then brine. The organic phase was dried over MgSO$_4$, then filtered and concentrated. The resulting residue was purified by HPLC to afford the title compound (78 mg, 49%). MS (ESI) m/z 826 [M+H]$^+$.

Example GY

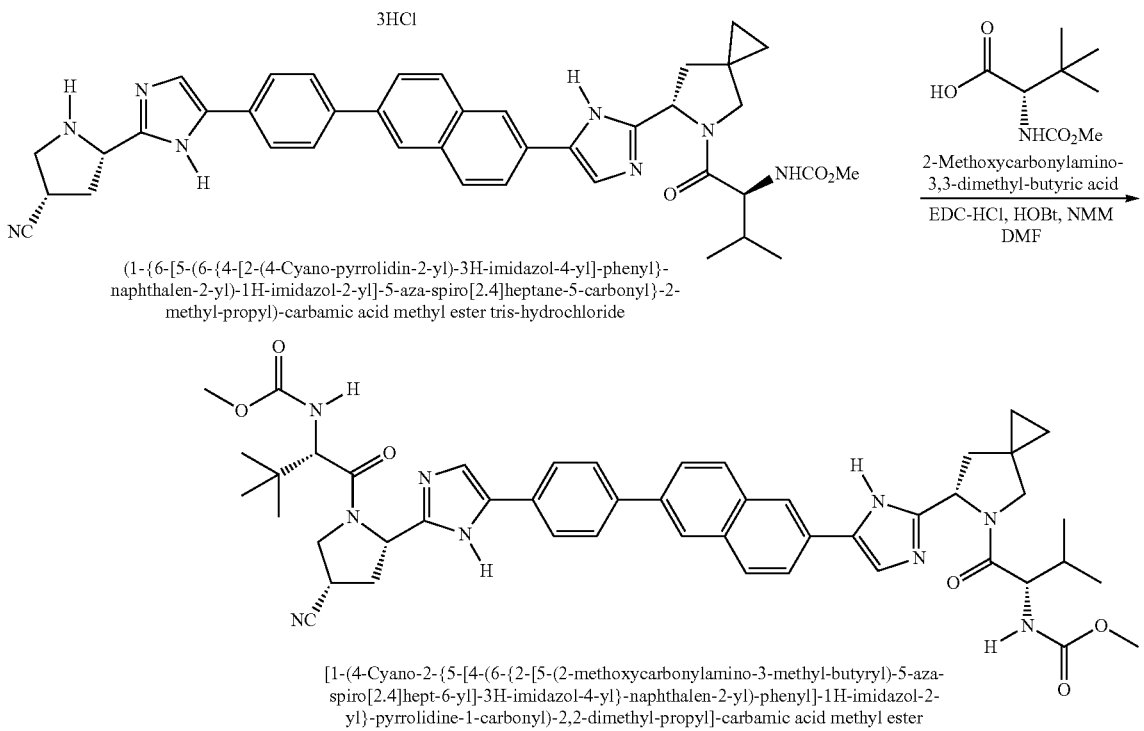

[1-(4-Cyano-2-{5-[4-(6-{2-[5-(2-methoxycarbonyl-lamino-3-methyl-butyryl)-5-aza-spiro[2.4]hept-6-yl]-3H-imidazol-4-yl}-naphthalen-2-yl)-phenyl]-1H-imidazol-2-yl}-pyrrolidine-1-carbonyl)-2,2-dimethyl-propyl]-carbamic acid methyl ester 2-Methoxycarbonylamino-3,3-dimethyl-butyric acid (43 mg, 0.227 mmol) EDC-HCl (44 mg, 0.227 mmol) and HOBt (32 mg, 0.237 mmol) were combined in DMF (2 mL) and stirred for 20 min at RT. (1-{6-[5-(6-{4-[2-(4-Cyano-pyrrolidin-2-yl)-3H-imidazol-4-yl]-phenyl}-naphthalen-2-yl)-1H-imidazol-2-yl]-5-aza-spiro[2.4]heptane-5-carbonyl}-2,2- methyl-propyl)-carbamic acid methyl ester tris-hydrochloride (150 mg, 0.189 mmol) was added, the reaction mixture was cooled to 0° C. and NMM (0.104 mL, 0.947 mmol) was added dropwise. After 20, the reaction mixture was warmed to RT. 30 min later, the mixture was diluted with EtOAc and washed with NaHCO$_3$, then brine. The organic phase was dried over MgSO$_4$, then filtered and concentrated. The resulting residue was purified by HPLC to afford the title compound (73 mg, 45%). MS (ESI) m/z 854 [M+H]$^+$.

Example GZ

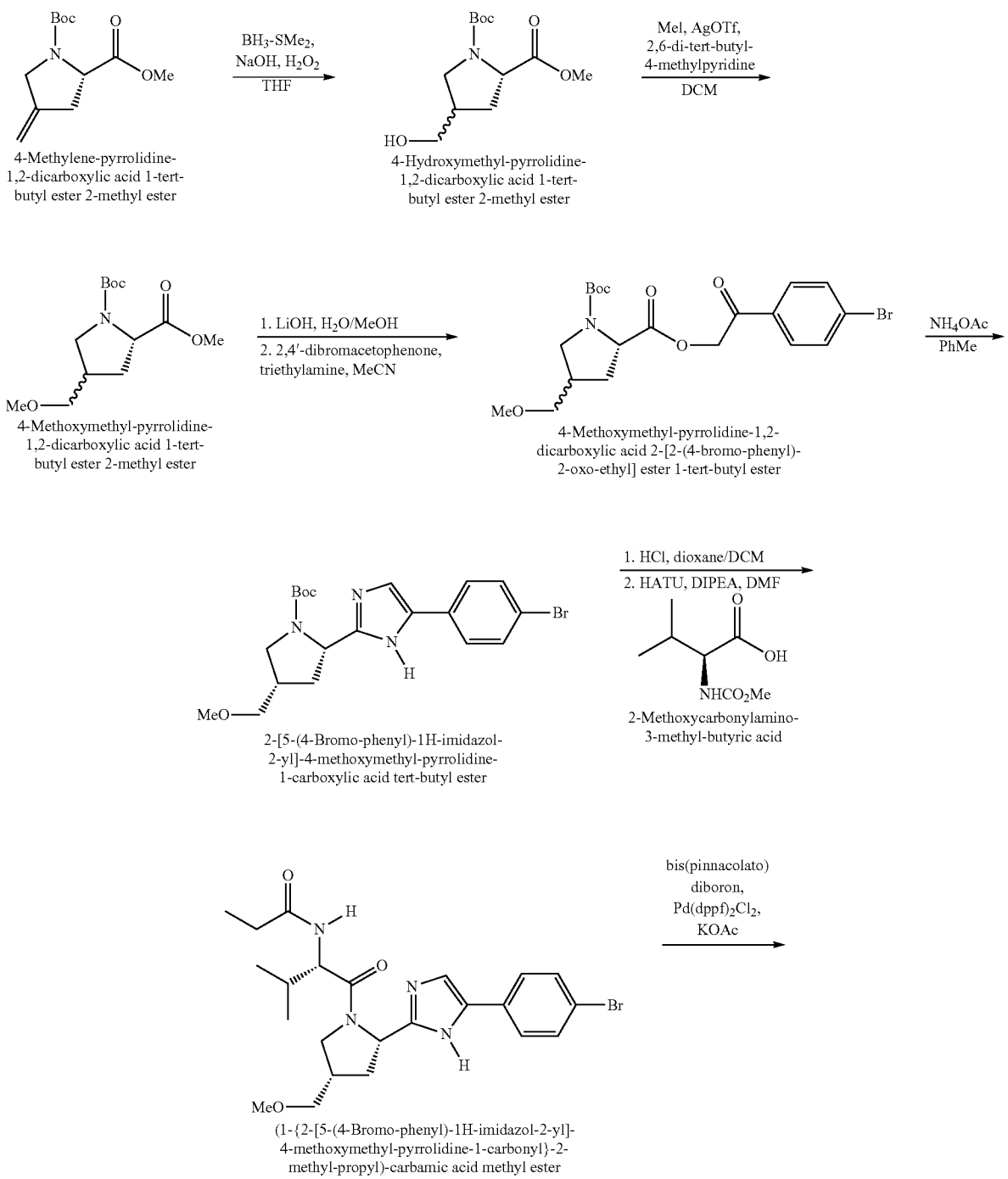

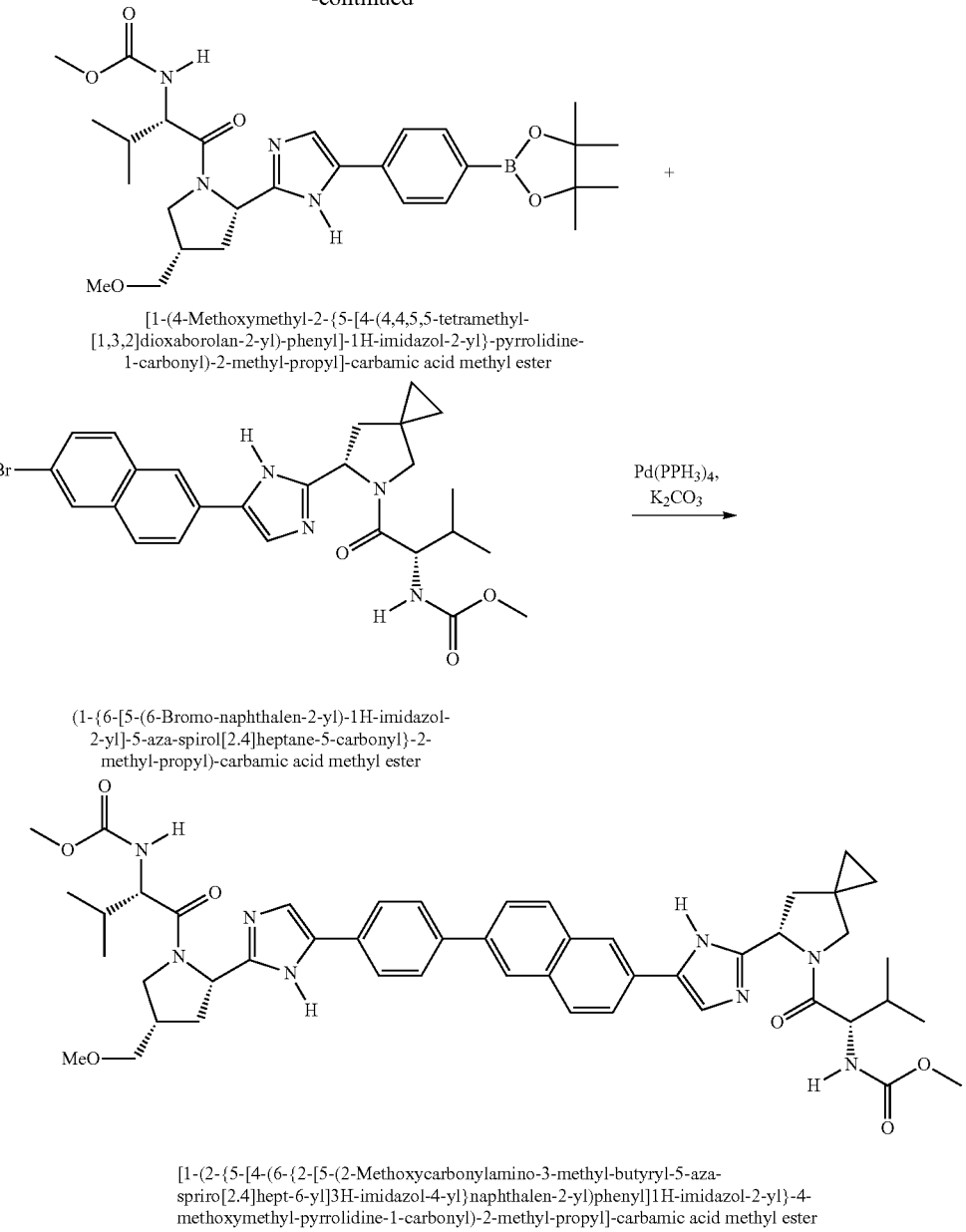

[1-(4-Methoxymethyl-2-{5-[4-(4,4,5,5-tetramethyl-
[1,3,2]dioxaborolan-2-yl)-phenyl]-1H-imidazol-2-yl}-pyrrolidine-
1-carbonyl)-2-methyl-propyl]-carbamic acid methyl ester (1-{6-[5-(6-Bromo-naphthalen-2-yl)-1H-imidazol-
2-yl]-5-aza-spiro[2.4]heptane-5-carbonyl}-2-
methyl-propyl)-carbamic acid methyl ester

[1-(2-{5-[4-(6-{2-[5-(2-Methoxycarbonylamino-3-methyl-butyryl-5-aza-
spriro[2.4]hept-6-yl]3H-imidazol-4-yl}naphthalen-2-yl)phenyl]1H-imidazol-2-yl}-4-
methoxymethyl-pyrrolidine-1-carbonyl)-2-methyl-propyl]-carbamic acid methyl ester

4-Hydroxymethyl-pyrrolidine-1,2-dicarboxylic acid 1-tert-butyl ester 2-methyl ester 4-Methylene-pyrrolidine-1,2-dicarboxylic acid 1-tert-butyl ester 2-methyl ester (4.48 g, 19.71 mmol) was dissolved in THF (100 mL) and the stirred solution was cooled to 0° C. Borane-dimethylsulfide complex (1.9 mL, 19.7 mmol) was added and the reaction mixture was allowed to warm to RT o/n. After 16 h, water was added dropwise until no bubbling was observed. The stirred mixture was then cooled to 0° C. Aqueous NaOH (5M in H$_2$O, 5.3 mL, 26.6 mmol), then H$_2$O$_2$ (30 wt % in H$_2$O, 6.0 mL, 58.5 mmol) were added dropwise. The reaction was then warmed to 50° C. After 30 min, the mixture was diluted with ethyl ether and washed with water and brine. The organic phase was dried over MgSO$_4$, filtered and concentrated. The crude residue was purified by silica column chromatography (25% to 75% EtOAc/Hex) to afford the title compound (2.08 g, 41%).

4-Methoxymethyl-pyrrolidine-1,2-dicarboxylic acid 1-tert-butyl ester 2-methyl ester 4-Hydroxymethyl-pyrrolidine-1,2-dicarboxylic acid 1-tert-butyl ester 2-methyl ester (861 mg, 3.32 mmol) was dissolved in DCM (6.6 mL) then 2,6-di-tert-butyl-4-methylpyridine (1.023 g, 4.98 mmol) and AgOTf (938 mg, 3.65 mmol) were added. The reaction mixture was cooled to 0° C. and iodomethane (0.25 mL, 3.98 mmol) was added. After 4 min, the reaction mixture was diluted with DCM and it was filtered over elite. The filtrate was concentrated to a residue which was dissolved in diethyl ether. The organic solution was washed with 10% HCl and brine, then dried over MgSO$_4$, filtered and concentrated. The crude residue was purified by silica column chromatography (20% to 80% EtOAc/Hex) to afford the title compound (479 mg, 53%).

4-Methoxymethyl-pyrrolidine-1,2-dicarboxylic acid 2-[2-(4-bromo-phenyl)-2-oxo-ethyl]ester 1-tert-butyl ester 4-Methoxymethyl-pyrrolidine-1,2-dicarboxylic acid 1-tert-butyl ester 2-methyl ester (461 mg, 1.68 mmol) was dissolved in MeOH (17 mL) and LiOH (1 M in $H_2O$, 8.5 mL, 8.5 mmol) was added. After stirring at RT for 5 h, the MeOH was removed under reduced pressure. The aqueous solution was poured into a separatory funnel, diluted with 1 M HCl (9 mL, 9 mmol) and extracted with DCM (3×). The combined organics were dried over $MgSO_4$, filtered and concentrated. The residue was dissolved in MeCN (17 mL) and treated with 2,4'-dibromoacetophenone (514 mg, 1.85 mmol), and triethylamine (0.258 mL, 1.85 mmol). After stirring for 2 h, the solvent was removed and the solid was suspended in EtOAc. The organic layer was washed with saturated aqueous $NaHCO_3$ and brine then dried over $MgSO_4$, filtered and concentrated. The crude residue was purified by silica column chromatography (15% to 35% EtOAc/Hex) to afford the title compound (746 mg, 97%).

2-[5-(4-Bromo-phenyl)-1H-imidazol-2-yl]-4-methoxymethyl-pyrrolidine-1-carboxylic acid tert-butyl ester 4-Methoxymethyl-pyrrolidine-1,2-dicarboxylic acid 2-[2-(4-bromo-phenyl)-2-oxo-ethyl]ester 1-tert-butyl ester (746 mg, 1.63 mmol) was dissolved in PhMe (16 mL) and treated with $NH_4OAc$ (2.52 g, 32.7 mmol). The stirred mixture was refluxed for 19 h then cooled to RT and diluted with EtOAc. The organic phase was washed with saturated aqueous $NaHCO_3$ and brine then dried over $MgSO_4$, filtered and concentrated. The crude residue was purified by silica column chromatography (35% to 65% EtOAc/Hex) to afford the title compound (334 mg, 47%).

(1-{2-[5-(4-Bromo-phenyl)-1H-imidazol-2-yl]-4-methoxymethyl-pyrrolidine-1-carbonyl}-2-methyl-propyl)-carbamic acid methyl ester 2-[5-(4-Bromo-phenyl)-1H-imidazol-2-yl]-4-methoxymethyl-pyrrolidine-1-carboxylic acid tert-butyl ester (334 mg, 0.765 mmol) was dissolved in DCM (4 mL) and treated with HCl (4.0M in dioxane, 0.960 mL, 3.83 mmol). After 2.5 h, the solution was concentrated and the residue was treated with 2-Methoxycarbonylamino-3-methyl-butyric acid (146 mg, 0.832 mmol) and HATU (316 mg, 0.832 mmol). The solids were suspended in DMF (4 mL) and the reaction mixture was cooled to 0° C. before triethylamine (0.67 mL, 3.83 mmol) was added in a dropwise fashion. After 30 min, the mixture was warmed to RT. After another 1 h, it was diluted with EtOAc and washed with saturated aqueous $NaHCO_3$ and brine. Then it was dried over $MgSO_4$, filtered and concentrated. The crude residue was purified by silica column chromatography (80% to 100% EtOAc/Hex) to afford the title compound (369 mg, 98%).

[1-(4-Methoxymethyl-2-{5-[4-(4,4,5,5-tetramethyl-[1,3,2]dioxaborolan-2-yl)-phenyl]-1H-imidazol-2-yl}-pyrrolidine-1-carbonyl)-2-methyl-propyl]-carbamic acid methyl ester (1-{2-[5-(4-Bromo-phenyl)-1H-imidazol-2-yl]-4-methoxymethyl-pyrrolidine-1-carbonyl}-2-methyl-propyl)-carbamic acid methyl ester (348 mg, 0.705 mmol), bis(pinacolato)diboron (269 mg, 1.06 mmol), $Pd(dppf)_2Cl_2$ (52 mg, 0.0705 mmol) and KOAc (208 g, 2.12 mmol) were combined in dioxane and degassed for 12 min with bubbling $N_2$. The reaction mixture was then stirred at 90° C. for 18 h, cooled to RT and diluted with EtOAc. The organic mixture was washed with saturated aqueous $NaHCO_3$ and brine before being dried over $MgSO_4$, filtered and concentrated. The crude residue was purified by silica column chromatography (80% to 100% EtOAc/Hex) to provide the title compound (297 mg, 78%).

[1-(2-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-4-methoxymethyl-pyrrolidine-1-carbonyl)-2-methyl-propyl]-carbamic acid methyl ester

[1-(4-Methoxymethyl-2-{5-[4-(4,4,5,5-tetramethyl-[1,3,2]dioxaborolan-2-yl)-phenyl]-1H-imidazol-2-yl}-pyrrolidine-1-carbonyl)-2-methyl-propyl]-carbamic acid methyl ester (132 mg, 0.244 mmol), (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester (154 mg, 0.293 mmol) $Pd(PPh_3)_4$ (28 mg, 0.0244 mmol) and $K_2CO_3$ (2M in $H_2O$, 0.488 mL, 0.976 mmol) were combined in 1,2-dimethoxyethane (5 mL). The mixture was degassed with bubbling $N_2$ for 12 min then heated to 85° C. for 4 h. After cooling to RT, the reaction mixture was diluted with EtOAc then washed with water and brine. The organic layer was dried over $MgSO_4$, filtered and concentrated. The crude residue was purified by HPLC to provide the title compound (118 mg, 56%). MS (ESI) m/z 859 [M+H]$^+$.

Example HA

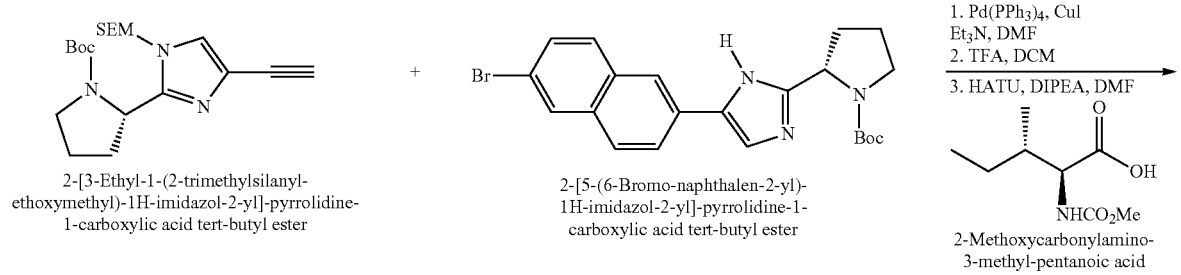

2-[3-Ethyl-1-(2-trimethylsilanyl-ethoxymethyl)-1H-imidazol-2-yl]-pyrrolidine-1-carboxylic acid tert-butyl ester 2-[5-(6-Bromo-naphthalen-2-yl)-1H-imidazol-2-yl]-pyrrolidine-1-carboxylic acid tert-butyl ester 1. $Pd(PPh_3)_4$, CuI
Et$_3$N, DMF
2. TFA, DCM
3. HATU, DIPEA, DMF 2-Methoxycarbonylamino-3-methyl-pentanoic acid

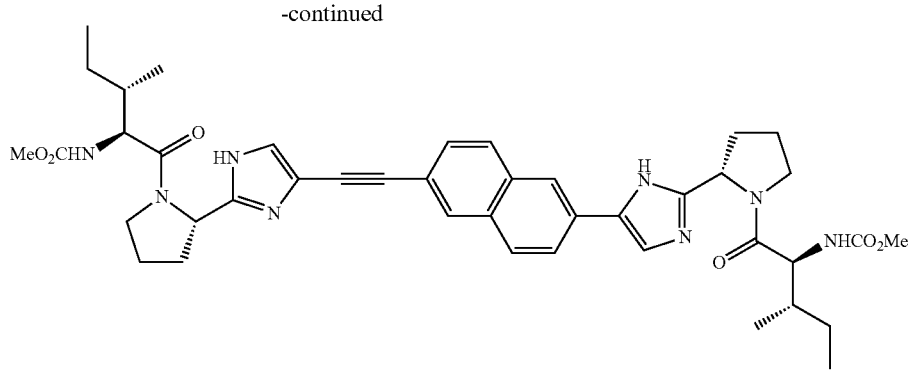

(1-{2-[4-(6-{2-{1(2-Methoxycarbonylamino-3-methyl-pentanoyl)-pyrrolidin-2-yl]3H-imidazol-4-yl}naphthalen-2-ylethynyl)-1H-imidazol-2-yl]-pyrrolidine-1-carbonyl}-2-methyl-butyl)-carbamic acid methyl ester

(1-{2-[4-(6-{2-[1-(2-Methoxycarbonylamino-3-methyl-pentanoyl)-pyrrolidin-2-yl]-3H-imidazol-4-yl}-naphthalen-2-ylethynyl)-1H-imidazol-2-yl]-pyrrolidine-1-carbonyl}-2-methyl-butyl)-carbamic acid methyl ester 2-[4-Ethynyl-1-(2-trimethylsilanyl-ethoxymethyl)-1H-imidazol-2-yl]-pyrrolidine-1-carboxylic acid tert-butyl ester (192 mg, 0.490 mmol), 2-[5-(6-Bromo-naphthalen-2-yl)-1H-imidazol-2-yl]-pyrrolidine-1-carboxylic acid tert-butyl ester (260 mg, 0.588 mmol), Pd(PPh$_3$)$_4$ (57 mg, 0.0490 mmol), CuI (19 mg, 0.0980 mmol) and Et$_3$N (0.683 mL, 4.90 mmol) were combined in DMF (5 mL). The stirred reaction mixture was degassed for 10 min, then heated to 80° C. for 3 h, after which it was diluted with EtOAc, washed with H$_2$O and brine. The organic phase was dried over MgSO$_4$, filtered and concentrated. The crude residue was purified by silica column chromatography (45% to 75% EtOAc/Hex) to provide the naphthyl alkyne compound (147 mg, 40%). This product was dissolved in DCM (10 mL) and treated with TFA (5 mL) After stirring for 20 h, the mixture was concentrated. The residue was free-based then treated with 2-Methoxycarbonylamino-3-methyl-pentanoic acid (52 mg, 0.276 mmol), HATU (84 mg, 0.222 mmol) and DMF (2 mL). The stirred mixture was cooled to 0° C. and DIPEA (0.160 mL, 0.923 mmol) was added dropwise. The reaction was allowed to come to RT slowly o/n. After 30 h, 6 drops of 5 M NaOH were added and the mixture was stirred for 20 min, after which it was diluted with EtOAc and washed with 1M LiOH and brine. The organic phase was dried over MgSO$_4$, filtered and concentrated. The crude residue was purified by HPLC to afford the title compound (33 mg, 22%). MS (ESI) m/z 765 [M+H]$^+$.

Example HB

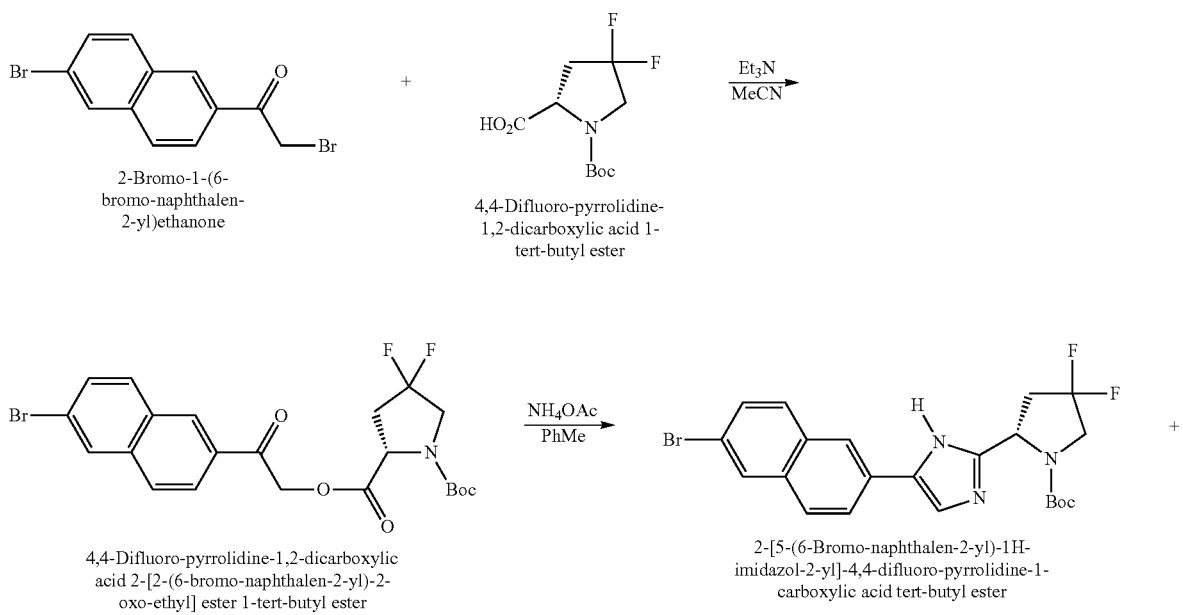

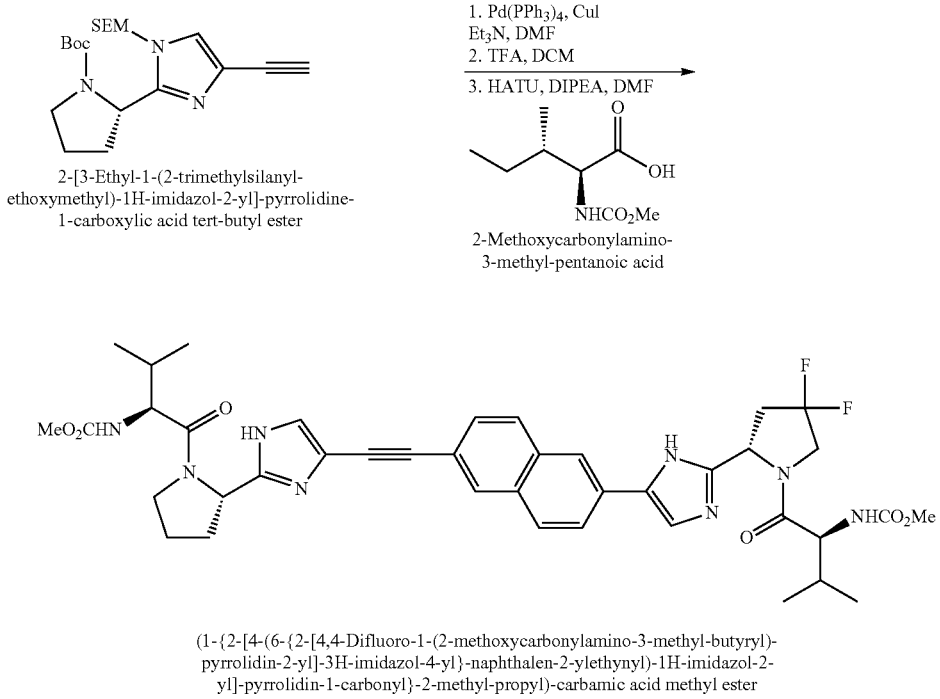

4,4-Difluoro-pyrrolidine-1,2-dicarboxylic acid 2-[2-(6-bromo-naphthalen-2-yl)-2-oxo-ethyl]ester 1-tert-butyl ester 2-Bromo-1-(6-bromo-naphthalen-2-yl)-ethanone (1 g, 3.07 mmol) and 4,4-Difluoro-pyrrolidine-1,2-dicarboxylic acid 1-tert-butyl ester (849 mg, 3.38 mmol) were suspended in MeCN (15 mL) and treated with Et₃N (0.45 mL, 3.22 mmol). After stirring o/n, the reaction mixture was concentrated. The resulting residue was dissolved in EtOAc and washed with water, saturated aqueous NaHCO₃ and brine. The organic layer was dried over MgSO₄, filtered and concentrated. The crude material was purified by silica column chromatography (0% to 20% EtOAc/Hex) to provide the title compound (1.27 g, 83%).

2-[5-(6-Bromo-naphthalen-2-yl)-1H-imidazol-2-yl]-4,4-difluoro-pyrrolidine-1-carboxylic acid tert-butyl ester 4,4-Difluoro-pyrrolidine-1,2-dicarboxylic acid 2-[2-(6-bromo-naphthalen-2-yl)-2-oxo-ethyl]ester 1-tert-butyl ester (1.2 g, 2.41 mmol) was treated with NH₄OAc (3.72 g, 96.4 mmol) and PhMe (48 mL). The reaction mixture was refluxed with stirring for 18 h. After this period, it was cooled to RT, diluted with EtOAc and washed with saturated aqueous NaHCO₃ and brine. Filtration and concentration provided a crude residue that was purified by silica column chromatography (20% to 60% EtOAc/Hex) to provide the title compound (803 mg, 70%).

(1-{2-[4-(6-{2-[4,4-Difluoro-1-(2-methoxycarbonylamino-3-methyl-butyryl)-pyrrolidin-2-yl]-3H-imidazol-4-yl}-naphthalen-2-ylethynyl)-1H-imidazol-2-yl]-pyrrolidine-1-carbonyl}-2-methyl-propyl)-carbamic acid methyl ester 2-[4-Ethynyl-1-(2-trimethylsilanyl-ethoxymethyl)-1H-imidazol-2-yl]-pyrrolidine-1-carboxylic acid tert-butyl ester (199 mg, 0.508 mmol), 2-[5-(6-Bromo-naphthalen-2-yl)-1H-imidazol-2-yl]-4,4-difluoro-pyrrolidine-1-carboxylic acid tert-butyl ester (364 mg, 0.762 mmol), Pd(PPh₃)₄ (118 mg, 0.102 mmol), CuI (19 mg, 0.102 mmol) and triethylamine (0.71 mL, 5.08 mmol) were suspended in DMF (5 mL). The reaction mixture was degassed with bubbling N₂ then heated to 80° C. for 4 h. Following this period, the mixture was cooled to RT, diluted with EtOAc and washed with water, saturated aqueous NaHCO₃ and brine. The organic layer was dried over MgSO₄, filtered and concentrated. The crude material was purified by silica column chromatography (50% to 100% EtOAc/Hex) to provide the naphthyl alkyne (284 mg, 71%). A fraction of this material (123 mg, 0.156 mg) was dissolved in EtOH (4 mL) and treated with conc. HCl. The reaction mixture was stirred at reflux for 18 h. The solution was then concentrated. The resulting residue treated with 2-Methoxycarbonylamino-3-methyl-butyric acid (60 mg, 0.343 mmol) and HATU (130 mg, 0.343 mmol), suspended in DMF (3 mL) and cooled to 0° C. DIPEA (0.272 mL, 1.56 mmol) was added dropwise. After stirring for 4 h, NaOH (5M in H₂O, 0.300 mL, 1.5 mmol) was added. This mixture was stirred for 3 h then diluted with EtOAc and washed with 1 M LiOH (2×) then brine. The organic phase was dried over MgSO₄, filtered and concentrated. The crude residue was then purified by HPLC to afford the title compound (53 mg, 44%). MS (ESI) m/z 773 [M+H]⁺.

Example HC

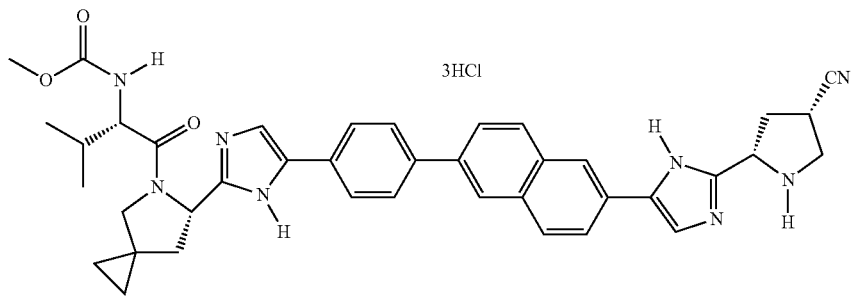 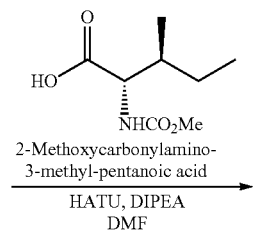

(1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-spiro[2.4]heptane-5-carbonyl}-2-methyl-propyl)-carbamic acid methyl ester-tris-hydrochloride

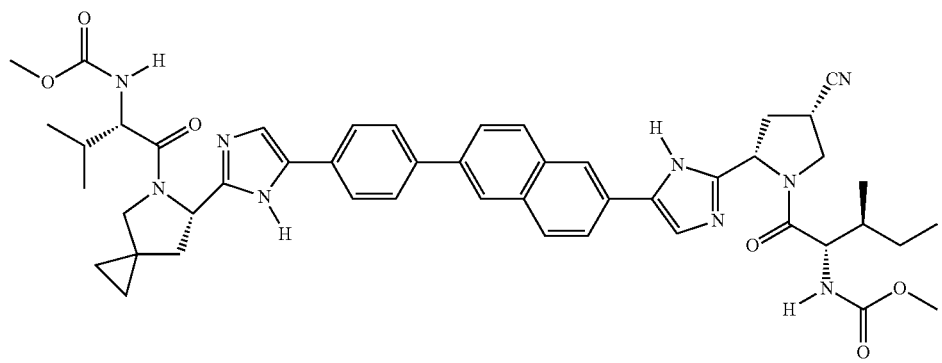

[1-(4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carbonyl)-2-methyl-butyl]-carbamic acid methyl ester

[1-(4-Cyano-2-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-pyrrolidine-1-carbonyl)-2-methyl-butyl]-carbamic acid methyl ester (1-{6-[5-(4-{6-[2-(4-Cyano-pyrrolidin-2-yl)-3H-imidazol-4-yl]-naphthalen-2-yl}-phenyl)-1H-imidazol-2-yl]-5-aza-Spiro[2.4]heptane-5-carbonyl}-2-methyl-propyl)-carbamic acid methyl ester-tris-hydrochloride (148 mg, 0.187 mmol), 2-2-Methoxycarbonylamino-3-methyl-pentanoic acid (42 mg, 0.224 mmol) and HATU (78 mg, 0.206 mmol) were combined in DMF (2 mL) and cooled to 0° C. DIPEA (0.163 mL, 0.935 mmol) was added dropwise. The reaction mixture was allowed to warm to RT slowly. After 12 h, it was diluted with EtOAc and washed with saturated aqueous NaHCO$_3$, then brine. The organic phase was dried over MgSO$_4$, filtered and concentrated. The crude residue was purified by HPLC to afford the title compound (80 mg, 50%). MS (ESI) m/z 854 [M+H]$^+$.

Example HD

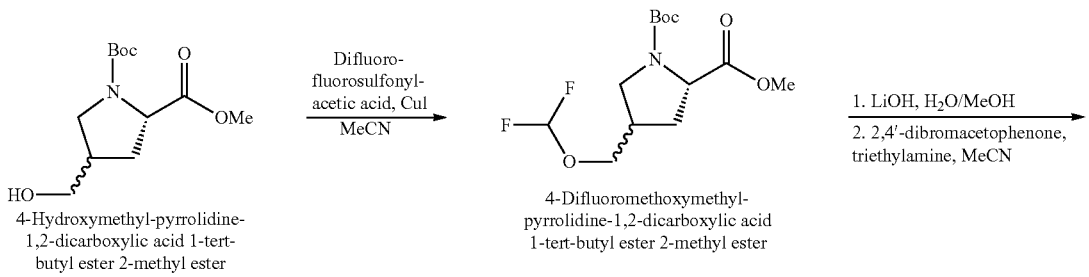

4-Hydroxymethyl-pyrrolidine-1,2-dicarboxylic acid 1-tert-butyl ester 2-methyl ester 4-Difluoromethoxymethyl-pyrrolidine-1,2-dicarboxylic acid 1-tert-butyl ester 2-methyl ester 1. LiOH, H$_2$O/MeOH
2. 2,4'-dibromacetophenone, triethylamine, MeCN -continued

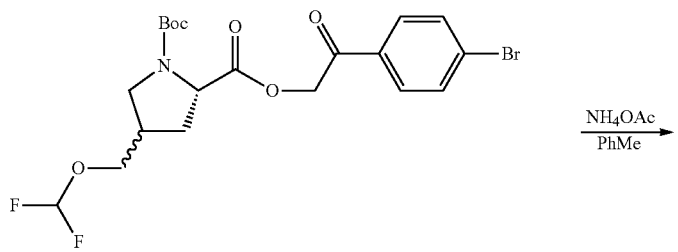

4-Difluoromethoxymethyl-pyrrolidine-1,2-
dicarboxylic acid 2-[2-(4-bromo-phenyl)-
2-oxo-ethyl] ester 1-tert-butyl ester $\xrightarrow{\text{NH}_4\text{OAc}}{\text{PhMe}}$

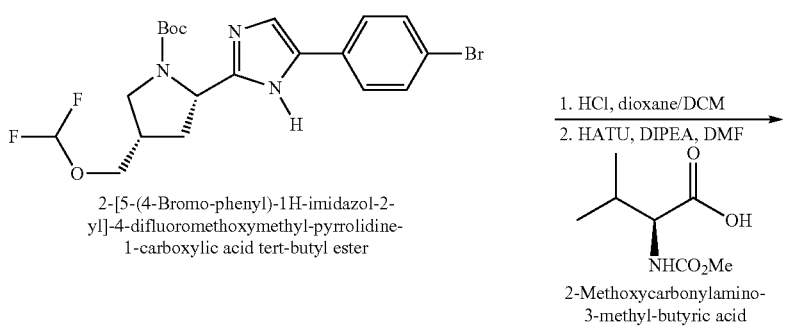

2-[5-(4-Bromo-phenyl)-1H-imidazol-2-
yl]-4-difluoromethoxymethyl-pyrrolidine-
1-carboxylic acid tert-butyl ester 1. HCl, dioxane/DCM
2. HATU, DIPEA, DMF 2-Methoxycarbonylamino-
3-methyl-butyric acid

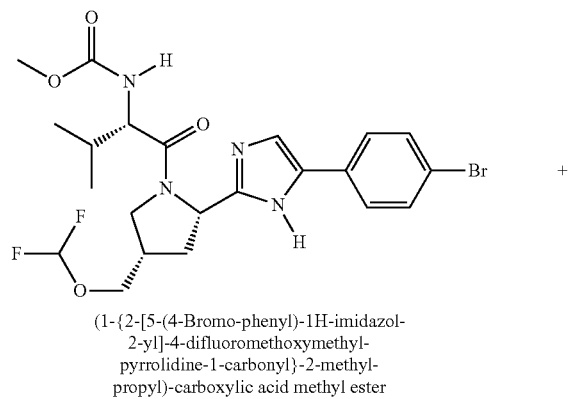

(1-{2-[5-(4-Bromo-phenyl)-1H-imidazol-
2-yl]-4-difluoromethoxymethyl-
pyrrolidine-1-carbonyl}-2-methyl-
propyl)-carboxylic acid methyl ester

+

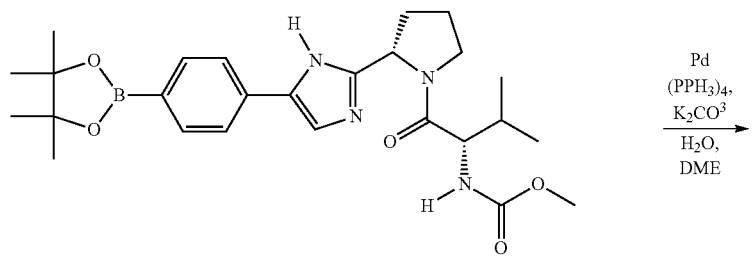

[2-Methyl-1-(2-{5-[4-(4,4,5,5-tetramethyl-
[1,3,2]dioxaborolan-2-yl)-phenyl]-1H-
imidazol-2-yl}-pyrrolidine-1-carbonyl)-
propyl]-carbamic acid methyl ester $\xrightarrow[\text{H}_2\text{O, DME}]{\text{Pd(PPH}_3)_4, \text{K}_2\text{CO}_3}$

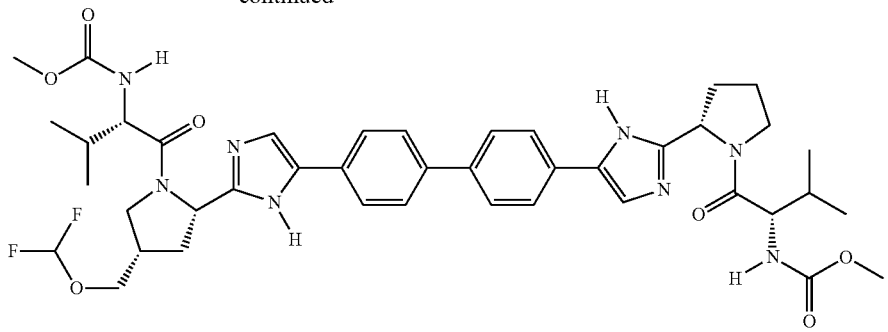

(1-{4-Difluoromethoxymethyl-2-[5-(4'-{2-[1-(2-methoxycarbonylamino-3-
methyl-butyryl)-pyrrolidin-2-yl]-3H-imidazol-4-yl}-biphenyl-4-yl)-1H-imidazol-
2-yl]-pyrrolidine-1-carbonyl}-2-methyl-propyl)-carbamic acid methyl ester

4-Difluoromethoxymethyl-pyrrolidine-1,2-dicarboxylic acid 1-tert-butyl ester 2-methyl ester 4-Hydroxymethyl-pyrrolidine-1,2-dicarboxylic acid 1-tert-butyl ester 2-methyl ester (584 mg, 2.25 mmol) and CuI (86 mg, 0.45 mmol) were suspended in MeCN (10 mL). The reaction mixture was heated to 45° C. and difluoro-fluorosulfonyl-acetic acid (0.465 mL, 4.5 mmol) was added dropwise over the course of 30 min. Stirring was continued for another 3 h, after which the reaction mixture was cooled to RT and concentrated. The residue was taken up in EtOAc and washed with saturated aqueous NaHCO$_3$ and brine then dried over MgSO$_4$, filtered and concentrated. The crude residue was purified by silica column chromatography (19% to 40% EtOAc/Hex) to afford the title compound (394 mg, 57%).

4-Difluoromethoxymethyl-pyrrolidine-1,2-dicarboxylic acid 2-[2-(4-bromo-phenyl)-2-oxo-ethyl] ester 1-tert-butyl ester 4-Difluoromethoxymethyl-pyrrolidine-1,2-dicarboxylic acid 1-tert-butyl ester 2-methyl ester (398 mg, 1.29 mmol) was dissolved in MeOH (8 mL) and LiOH (1 M in H$_2$O, 2 mL, 2 mmol) was added. After stirring at RT for 5 h, the MeOH was removed under reduced pressure. The aqueous solution was poured into a separatory funnel, diluted with 1 M HCl (2 mL, 2 mmol) and extracted with DCM (3×). The combined organics were dried over MgSO$_4$, filtered and concentrated. The residue was dissolved in MeCN (4 mL) and treated with 2,4'-dibromoacetophenone (200 mg, 0.719 mmol), and triethylamine (0.100 mL, 0.719 mmol). After stirring for 15 h, the solvent was removed. The crude residue was purified by silica column chromatography (10% to 35% EtOAc/Hex) to afford the title compound (303 mg, 94%).

2-[5-(4-Bromo-phenyl)-1H-imidazol-2-yl]-4-difluoromethoxymethyl-pyrrolidine-1-carboxylic acid tert-butyl ester 4-Difluoromethoxymethyl-pyrrolidine-1,2-dicarboxylic acid 2-[2-(4-bromo-phenyl)-2-oxo-ethyl]ester 1-tert-butyl ester (303 mg, 0.615 mmol) was dissolved in PhMe (12 mL) and treated with NH$_4$OAc (948 mg, 12.3 mmol). The stirred mixture was refluxed for 23 h then cooled to RT and diluted with EtOAc. The organic phase was washed with saturated aqueous NaHCO$_3$ and brine then dried over MgSO$_4$, filtered and concentrated. The crude residue was purified by silica column chromatography (25% to 50% EtOAc/Hex) to afford the title compound (130 mg, 45%).

(1-{2-[5-(4-Bromo-phenyl)-1H-imidazol-2-yl]-4-difluoromethoxymethyl-pyrrolidine-1-carbonyl}-2-methyl-propyl)-carbamic acid methyl ester 2-[5-(4-Bromo-phenyl)-1H-imidazol-2-yl]-4-difluoromethoxymethyl-pyrrolidine-1-carboxylic acid tert-butyl ester was dissolved in DCM (4 mL) and treated with HCl (4.0M in dioxane, 1 mL, 4 mmol). After 2.5 h, the solution was concentrated and the residue was treated with 2-Methoxycarbonylamino-3-methyl-butyric acid (55 mg, 0.315 mmol) and HATU (120 mg, 0.315 mmol). The solids were suspended in DMF (3 mL) and the reaction mixture was cooled to 0° C. before triethylamine (0.25 mL, 1.43 mmol) was added in a dropwise fashion. After 30 min, the mixture was warmed to RT. After another 1 h, it was diluted with EtOAc and washed with saturated aqueous NaHCO$_3$ and brine. Then it was dried over MgSO$_4$, filtered and concentrated. The crude residue was purified by silica column chromatography (60% to 100% EtOAc/Hex) to afford the title compound (92 mg, 61%).

(1-{4-Difluoromethoxymethyl-2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester (1-{2-[5-(4-Bromo-phenyl)-1H-imidazol-2-yl]-4-difluoromethoxymethyl-pyrrolidine-1-carbonyl}-2-methyl-propyl)-carbamic acid methyl ester (42 mg, 0.174 mmol), [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (95 mg, 0.191 mmol), Pd(PPh$_3$)$_4$ (20 mg, 0.0174 mmol) and K$_2$CO$_3$ (2M in H$_2$O, 0.191 mL, 0.383 mmol) were combined in 1,2-dimethoxyethane (2 mL). The mixture was degassed with bubbling N$_2$ for 12 min then heated to 85° C. for 4 h. After cooling to RT, the reaction mixture was diluted with EtOAc then washed with water and brine. The organic layer was dried over MgSO$_4$, filtered and concentrated. The crude residue was purified by HPLC to provide the title compound (42 mg, 30%). MS (ESI) m/z 819 [M+H]$^+$.

Example HE
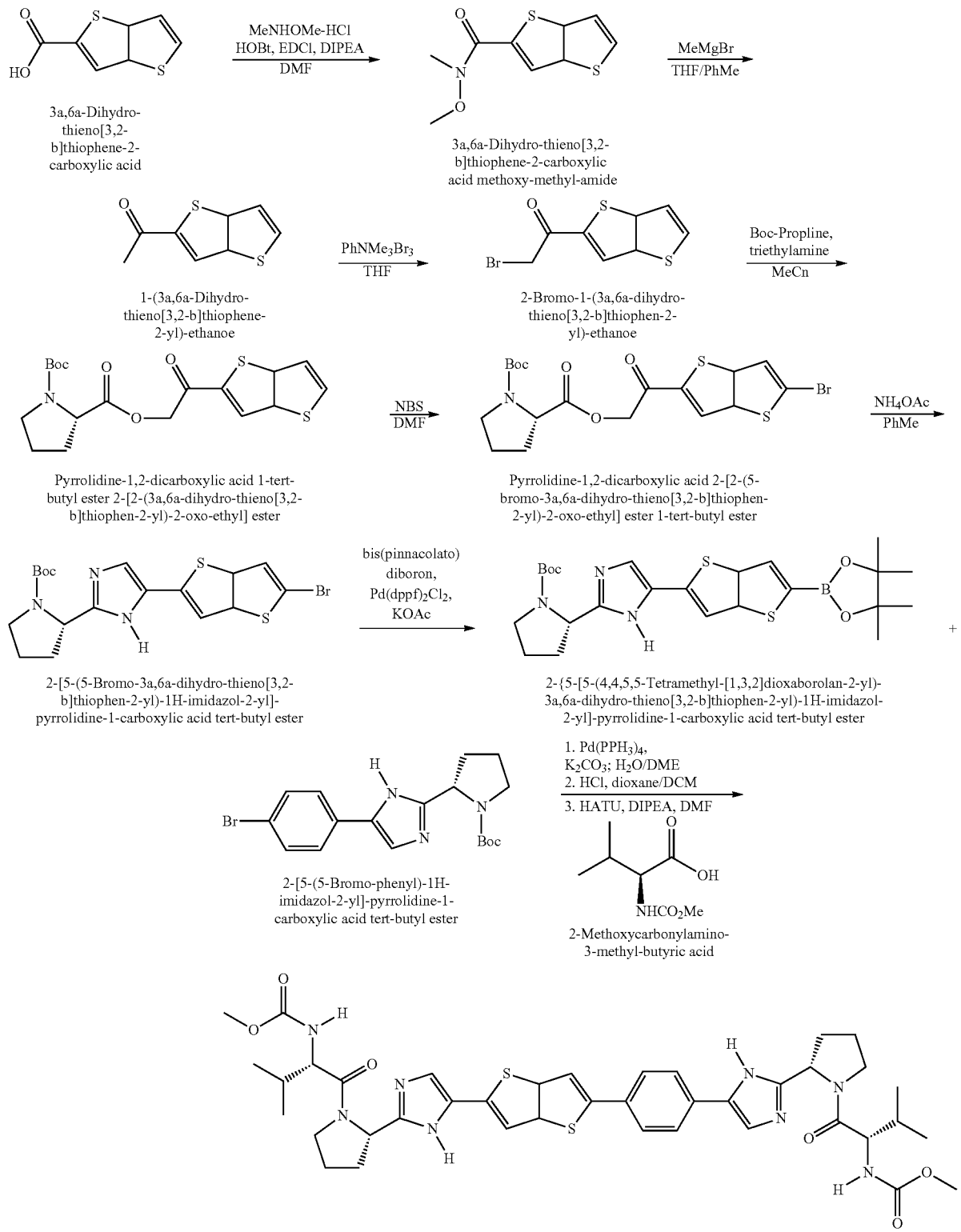
[1-(2-{5-[5-(4-{2-[1-(2-Methoxycarbonylamino-3-methyl-butyryl)-pyrrolidin-2-yl]-
3H-imidazol-4-yl}-phenyl)-3a,6a-dihydro-thieno[3,2-b]thiophen-2-yl]-1H-imidazol-
2-yl}-pyrrolidine-1-carbonyl)-2-methyl-propyl]-carbamic acid methyl ester

3a,6a-Dihydro-thieno[3,2-b]thiophene-2-carboxylic acid methoxy-methyl-amide 3a,6a-Dihydro-thieno[3,2-b]thiophene-2-carboxylic acid (2 g, 10.86 mmol) MeNHOMe-HCl (1.06 g, 10.86 mmol), HOBt (1.47 g, 10.86 mmol) and DIPEA (5.9 mL, 33.67 mmol) were combined in DMF (40 mL). To the stirred mixture was added EDCI (2.72 g, 14.12 mmol). After 5 h, EtOAc (100 mL) was added and the organics were washed with saturated aqueous $NaHCO_3$ and brine then dried over $MgSO_4$, filtered and concentrated. The crude residue was purified by silica column chromatography (20% to 45% EtOAc/Hex) to afford the title compound (1.98 g, 80%).

1-(3a,6a-Dihydro-thieno[3,2-b]thiophen-2-yl)-ethanone 3a,6a-Dihydro-thieno[3,2-b]thiophene-2-carboxylic acid methoxy-methyl-amide (1.955 g, 8.60 mmol) was dissolved in THF. The stirred solution was cooled to 0° C. before methylmagnesium bromide (1.4 M in PhMe, 8.6 mL, 12.04 mmol) was added. The reaction was allowed to gradually warm to RT o/n, then it was quenched by addition of 10% HCl. The aqueous phase was extracted with diethyl ether. The organic phase was washed with brine then dried over $MgSO_4$, filtered and concentrated to afford the title compound (1.98 g, 80%).

2-Bromo-1-(3a,6a-dihydro-thieno[3,2-b]thiophen-2-yl)-ethanone 1-(3a,6a-Dihydro-thieno[3,2-b]thiophen-2-yl)-ethanone (453 mg, 2.48 mmol) was dissolved in THF (12 mL) and phenyltrimethylammonium tribromide (932 mg, 2.48 mmol) was added. After stirring for 1 h, the suspension was filtered over CELITE. The filtrate was diluted with diethyl ether, then washed with saturated aqueous $NaHCO_3$ and brine then dried over $MgSO_4$, filtered and concentrated to afford the title compound which was carried on without purification.

Pyrrolidine-1,2-dicarboxylic acid 1-tert-butyl ester 2-[2-(3a,6a-dihydro-thieno[3,2-b]thiophen-2-yl)-2-oxo-ethyl]ester Crude 2-Bromo-1-(3a,6a-dihydro-thieno[3,2-b]thiophen-2-yl)-ethanone (2.48 mmol assuming complete conversion from starting material) was treated with Boc-proline and MeCN (25 mL). Triethylamine was added and the solution was stirred at RT for 1 h then concentrated. The crude residue was purified by silica column chromatography (14% to 35% EtOAc/Hex) to afford the title compound (595 mg, 61%).

Pyrrolidine-1,2-dicarboxylic acid 2-[2-(5-bromo-3a,6a-dihydro-thieno[3,2-b]thiophen-2-yl)-2-oxo-ethyl] ester 1-tert-butyl ester Pyrrolidine-1,2-dicarboxylic acid 1-tert-butyl ester 2-[2-(3a,6a-dihydro-thieno[3,2-b]thiophen-2-yl)-2-oxo-ethyl]ester (595 mg, 1.5 mmol) was dissolved in DMF (7.5 mL) and treated with N-bromosuccinimide (295 mg, 1.65 mmol). The reaction mixture was stirred for 4d at RT then diluted with EtOAc and washed with saturated aqueous $NaHCO_3$ and brine. The organic layer was dried over $MgSO_4$, filtered and concentrated. The crude residue was purified by silica column chromatography (20% to 50% EtOAc/Hex) to afford the title compound (469 mg, 66%).

2-[5-(5-Bromo-3a,6a-dihydro-thieno[3,2-b]thiophen-2-yl)-1H-imidazol-2-yl]-pyrrolidine-1-carboxylic acid tert-butyl ester Pyrrolidine-1,2-dicarboxylic acid 2-[2-(5-bromo-3a,6a-dihydro-thieno[3,2-b]thiophen-2-yl)-2-oxo-ethyl]ester 1-tert-butyl ester (480 mg, 1.01 mmol) was treated with PhMe (10 mL) and ammonium acetate (1.56 g, 20.24 mmol). The reaction mixture was refluxed while stirring for 16 h, then cooled to RT. EtOAc was added and the organic phase was washed with saturated aqueous $NaHCO_3$ and brine. After it was dried over $MgSO_4$, it was filtered and concentrated. The crude residue was purified by silica column chromatography (25% to 60% EtOAc/Hex) to afford the title compound (378 mg, 82%).

2-{5-[5-(4,4,5,5-Tetramethyl-[1,3,2]dioxaborolan-2-yl)-3a,6a-dihydro-thieno[3,2-b]thiophen-2-yl]-1H-imidazol-2-yl}-pyrrolidine-1-carboxylic acid tert-butyl ester 2-[5-(5-Bromo-3a,6a-dihydro-thieno[3,2-b]thiophen-2-yl)-1H-imidazol-2-yl]-pyrrolidine-1-carboxylic acid tert-butyl ester (273 mg, 0.598 mmol), bis(pinacolato)diboron (0.228 mg, 0.897 mmol), $Pd(dppf)_2Cl_2$ (44 mg, 0.0598 mmol) and KOAc (176 mg, 1.79 mmol) were combined in dioxane and degassed for 12 min with bubbling $N_2$. The reaction mixture was then stirred at 85° C. for 2.5 h, cooled to RT and diluted with EtOAc. The organic mixture was washed with saturated aqueous $NaHCO_3$ and brine before being dried over $MgSO_4$, filtered and concentrated. The crude residue was purified by silica column chromatography (25% to 60% EtOAc/Hex) to provide the title compound (0.159 g, 53%). The product was contaminated with an equimolar amount of a byproduct which was believed to be the proteodebrominated starting material.

[1-(2-{5-[5-(4-{2-[1-(2-Methoxycarbonylamino-3-methyl-butyryl)-pyrrolidin-2-yl]-3H-imidazol-4-yl}-phenyl)-3a,6a-dihydro-thieno[3,2-b]thiophen-2-yl]-1H-imidazol-2-yl}-pyrrolidine-1-carbonyl)-2-methyl-propyl]-carbamic acid methyl ester 2-{5-[5-(4,4,5,5-Tetramethyl-[1,3,2]dioxaborolan-2-yl)-3a,6a-dihydro-thieno[3,2-b]thiophen-2-yl]-1H-imidazol-2-yl}-pyrrolidine-1-carboxylic acid tert-butyl ester (159 mg, 0.317 mmol), 2-[5-(4-Bromo-phenyl)-1H-imidazol-2-yl]-pyrrolidine-1-carboxylic acid tert-butyl ester (124 mg, 0.317 mmol), $Pd(PPh_3)_4$ (37 mg, 0.0317 mmol) and $K_2CO_3$ (2 M in $H_2O$, 0.32 mL, 0.64 mmol) were combined in 1,2-dimethoxyethane (3 mL) and degassed with bubbling $N_2$ for 10 min. The stirred reaction mixture was warmed to 85° C. for 3.5 h then cooled to RT and diluted with EtOAc. The organic phase was washed with saturated aqueous $NaHCO_3$ and brine before being dried over $MgSO_4$, filtered and concentrated. The crude residue was purified by silica column chromatography (EtOAc then 5% MeOH/DCM) to afford the Suzuki-coupled product (89 mg, 41%). This material was dissolved in DCM (4 mL) and treated with HCl (4 M in dioxane, 1 mL, 4 mmol). After stirring for 73 min, the reaction mixture was diluted with EtOAc and the solid was filtered off and rinsed with EtOAc. The solid was dried, then combined with 2-Methoxycarbonylamino-3-methyl-butyric acid (37 mg, 0.212 mmol), HATU (81 mg, 0.212 mmol) and DMF (2 mL). The stirred reaction mixture was cooled to 0° C. and DIPEA (0.17 mL, 0.96 mmol) was added dropwise. After 15 min, it was warmed to RT. 17 h later, the reaction mixture was diluted with EtOAc. The organic phase was washed with saturated aqueous NaHCO₃ and brine before being dried over MgSO₄, filtered and concentrated. The crude residue was purified by HPLC to afford the title compound (23 mg, 22%). MS (ESI) m/z 801 [M+H]⁺.

Example HF

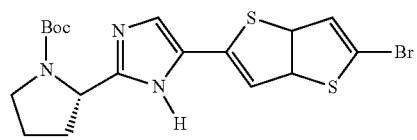

2-[5-(5-Bromo-3a,6a-dihydro-thieno[3,2-b]thiophen-2-yl)-1H-imidazol-2-yl]-pyrrolidine-1-carboxylic acid tert-butyl ester

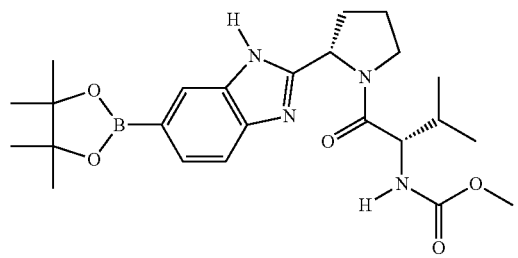

(2-Methyl-1-{2-6[-(4,4,5,5-tetramethyl-[1,3,2]dioxaborolan-2-yl)-1H-benzoimidazol-2-yl]-pyrrolidine-1-carbonyl}-propyl)-carbamic acid methyl ester

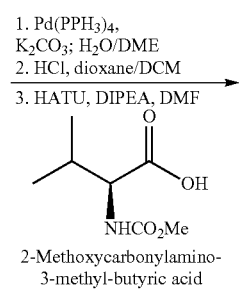

1. Pd(PPh₃)₄, K₂CO₃; H₂O/DME
2. HCl, dioxane/DCM
3. HATU, DIPEA, DMF

2-Methoxycarbonylamino-3-methyl-butyric acid

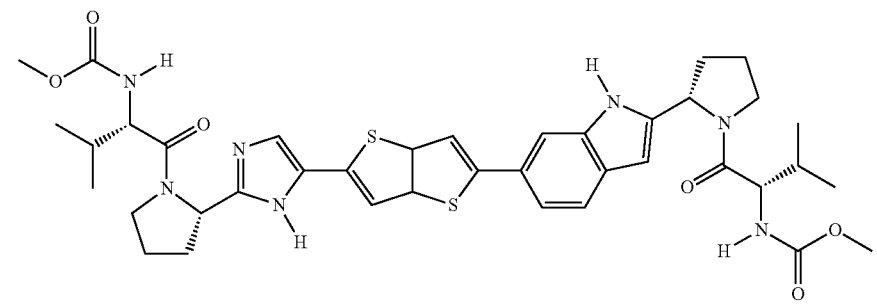

(1-{2-[5-(5-{2-[1-(2-Methoxycarbonylamino-3-methyl-butyryl)-pyrrolidin-2-yl]-3H-benzoimidazol-5-yl}-3a,6a-dihydro-thieno[3,2-b]thiophen-2-yl)-1H-imidazol-2-yl]-pyrrolidine-1-carbonyl}-2-methyl-propyl)-carbamic acid methyl ester (1-{2-[5-(5-{2-[1-(2-Methoxycarbonylamino-3-methyl-butyryl)-pyrrolidin-2-yl]-3H-benzoimidazol-5-yl}-3a,6a-dihydro-thieno[3,2-b]thiophen-2-yl)-1H-imidazol-2-yl]-pyrrolidine-1-carbonyl}-2-methyl-propyl)-carbamic acid methyl ester 2-[5-(5-Bromo-3a,6a-dihydro-thieno[3,2-b]thiophen-2-yl)-1H-imidazol-2-yl]-pyrrolidine-1-carboxylic acid tert-butyl ester (100 mg, 0.219 mmol), (2-Methyl-1-{2-[6-(4,4,5,5-tetramethyl-[1,3,2]dioxaborolan-2-yl)-1H-benzoimidazol-2-yl]-pyrrolidine-1-carbonyl}-propyl)-carbamic acid methyl ester (117 mg, 0.283 mmol), Pd(PPh₃)₄ (51 mg, 0.0438 mmol) and K₂CO₃ (2 M in H₂O, 0.33 mL, 0.66 mmol) were combined in 1,2-dimethoxyethane (4 mL) and degassed with bubbling N₂ for 10 min. The stirred reaction mixture was warmed to 85° C. for 3.5 h then cooled to RT and diluted with EtOAc. The organic phase was washed with saturated aqueous NaHCO₃ and brine before being dried over MgSO₄, filtered and concentrated. The crude residue was purified by silica column chromatography (EtOAc) to afford the Suzuki-coupled product (71 mg, 49%). This material was dissolved in DCM (4 mL) and treated with HCl (4 M in dioxane, 1 mL, 4 mmol).

After stirring for 97 min, the reaction mixture was concentrated. The solid was dried, then combined with 2-Methoxycarbonylamino-3-methyl-butyric acid (39 mg, 0.225 mmol), HATU (86 mg, 0.225 mmol) and DMF (4 mL). The stirred reaction mixture was cooled to 0° C. and DIPEA (0.18 mL, 1.07 mmol) was added dropwise. After 30 min, it was warmed to RT. 12 min later, the reaction mixture was diluted with EtOAc. The organic phase was washed with saturated aqueous NaHCO₃ and brine before being dried over MgSO₄, filtered and concentrated. The crude residue was purified by HPLC to afford the title compound (32 mg, 39%). MS (ESI) m/z 775 [M+H]⁺.

Example HG

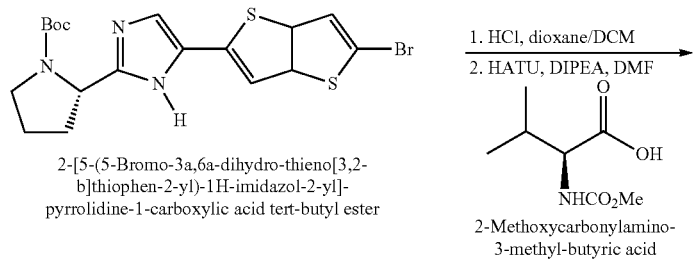

2-[5-(5-Bromo-3a,6a-dihydro-thieno[3,2-b]thiophen-2-yl)-1H-imidazol-2-yl]-pyrrolidine-1-carboxylic acid tert-butyl ester 2-Methoxycarbonylamino-3-methyl-butyric acid

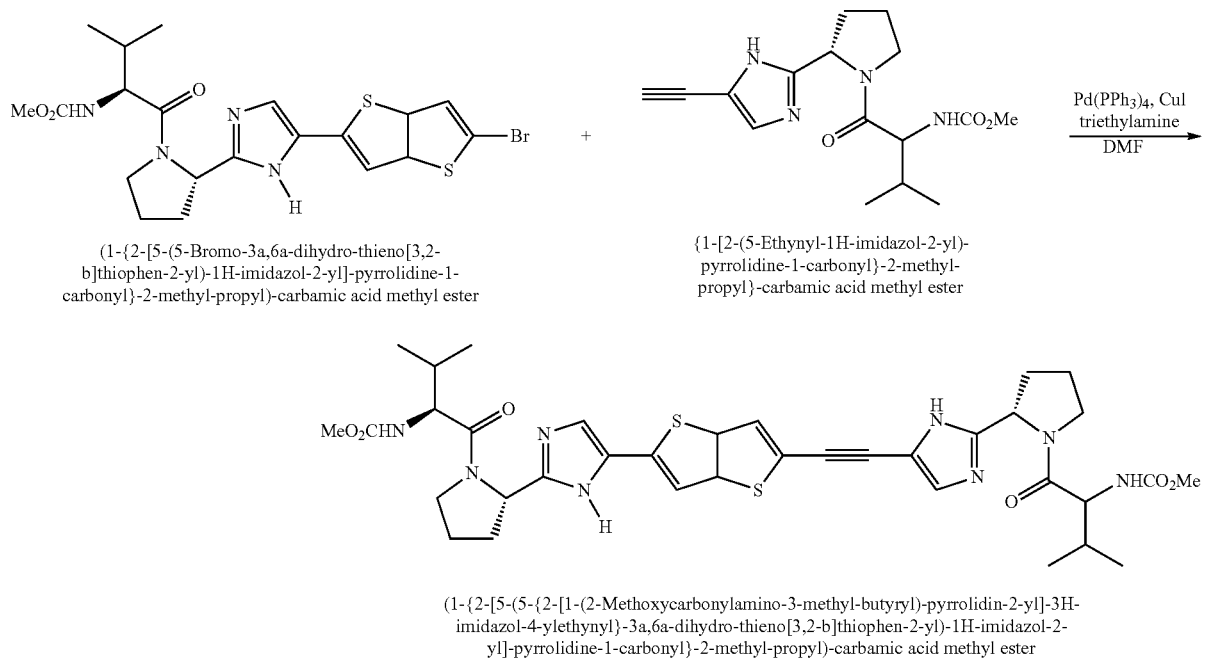

(1-{2-[5-(5-Bromo-3a,6a-dihydro-thieno[3,2-b]thiophen-2-yl)-1H-imidazol-2-yl]-pyrrolidine-1-carbonyl}-2-methyl-propyl)-carbamic acid methyl ester {1-[2-(5-Ethynyl-1H-imidazol-2-yl)-pyrrolidine-1-carbonyl]-2-methyl-propyl}-carbamic acid methyl ester (1-{2-[5-(5-{2-[1-(2-Methoxycarbonylamino-3-methyl-butyryl)-pyrrolidin-2-yl]-3H-imidazol-4-ylethynyl}-3a,6a-dihydro-thieno[3,2-b]thiophen-2-yl)-1H-imidazol-2-yl]-pyrrolidine-1-carbonyl}-2-methyl-propyl)-carbamic acid methyl ester

(1-{2-[5-(5-Bromo-3a,6a-dihydro-thieno[3,2-b]thiophen-2-yl)-1H-imidazol-2-yl]-pyrrolidine-1-carbonyl}-2-methyl-propyl)-carbamic acid methyl ester 2-[5-(5-Bromo-3a,6a-dihydro-thieno[3,2-b]thiophen-2-yl)-1H-imidazol-2-yl]-pyrrolidine-1-carboxylic acid tert-butyl ester (250 mg, 0.548 mmol) was dissolved in DCM (4 mL) and treated with HCl (4 M in dioxane, 1 mL, 4 mmol). After stirring for 1.5 h, the reaction mixture was concentrated. The solid was dried, then combined with 2-Methoxycarbonylamino-3-methyl-butyric acid (106 mg, 0.603 mmol), HATU (229 mg, 0.603 mmol) and DMF (6 mL). The stirred reaction mixture was cooled to 0° C. and DIPEA (0.48 mL, 2.74 mmol) was added dropwise. After 50 min, it was warmed to RT. 12 min later, the reaction mixture was diluted with EtOAc. The organic phase was washed with saturated aqueous NaHCO$_3$ and brine before being dried over MgSO$_4$, filtered and concentrated. The crude residue was purified by silica column chromatography to afford the title compound (252 mg, 90%).

(1-{2-[5-(5-{2-[1-(2-Methoxycarbonylamino-3-methyl-butyryl)-pyrrolidin-2-yl]-3H-imidazol-4-ylethynyl}-3a,6a-dihydro-thieno[3,2-b]thiophen-2-yl)-1H-imidazol-2-yl]-pyrrolidine-1-carbonyl}-2-methyl-propyl)-carbamic acid methyl ester (1-{2-[5-(5-Bromo-3a,6a-dihydro-thieno[3,2-b]thiophen-2-yl)-1H-imidazol-2-yl]-pyrrolidine-1-carbonyl}-2-methyl-propyl)-carbamic acid methyl ester (140 mg, 0.440 mmol), {1-[2-(5-Ethynyl-1H-imidazol-2-yl)-pyrrolidine-1-carbonyl]-2-methyl-propyl}-carbamic acid methyl ester (130 mg, 0.254 mmol), Pd(PPh$_3$)$_4$ (29 mg, 0.0254 mmol), CuI (10 mg, 0.0508 mmol) and triethylamine (0.354 mmol, 2.54 mmol) were combined in DMF (2.5 mL) and degassed with N$_2$ for 17 min. The reaction was heated to 85° C. for 4 h then cooled to RT, diluted with EtOAc and washed with saturated aqueous NaHCO$_3$ (2×) and brine. The organic layer was dried over MgSO$_4$, filtered and concentrated. The crude residue was purified by HPLC chromatography to afford the title compound (34 mg, 18%). MS (ESI) m/z 749 [M+H]$^+$.

Example HH

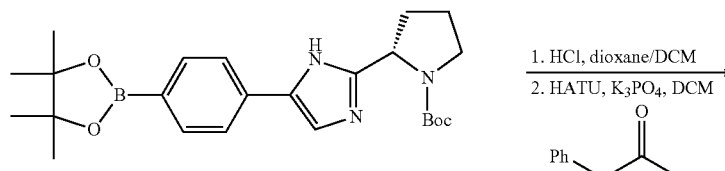

2-{5-[4-(4,4,5,5-Tetramethyl-[1,3,2]dioxaborolan-2-yl)-phenyl]-1H-imidazol-2-yl}-pyrrolidine-1-caboxylic acid tert-butyl ester

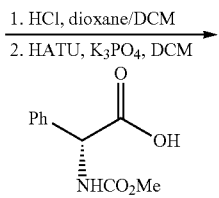

Methoxycarbonylamino-phenyl-acetic acid

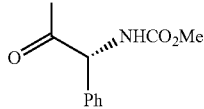

[2-Oxo-1-phenyl-2-(2-{5-(4,4,5,5-tetramethyl-[1,3,2]dioxaborolan-2-yl)-phenyl]-1H-imidazol-2-yl}-pyrrolidine-1-yl)-ethyl]-carbamic acid methyl ester

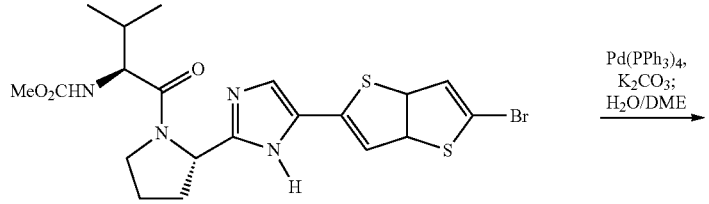

(1-{2-[5-(5-Bromo-3a,6a-dihydro-thieno[3,2-b]thiophen-2-yl)-1H-imidazol-2-yl]-pyrrolidine-1-carbonyl}-2-methyl-propyl)-carbamic acid methyl ester

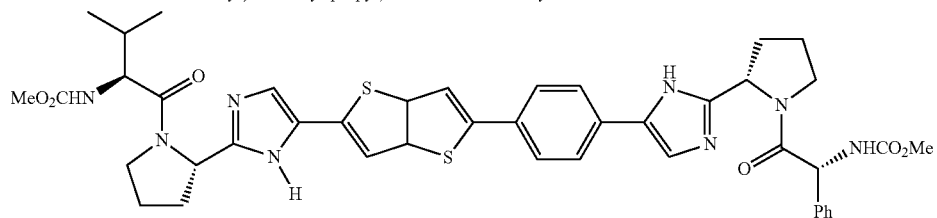

{2-Methyl-1-[2-(5-{5-[4-(2-{1-[2-(methylperoxymethyl-amino)-2-acetyl]-pyrrolidin-2-yl}-3H-imidazol-4-yl)phenyl]-3a,6a-dihydro-thieno[3,2-b]thiophen-2-yl}-1H-imidazol-2-yl)-pyrrolidine-1-carbonyl]-propyl}-carbamic acid methyl ester

[2-oxo-1-phenyl-2-(2-{5-[4-(4,4,5,5-tetramethyl-[1,3,2]dioxaborolan-2-yl)-phenyl]-1H-imidazol-2-yl}-pyrrolidin-1-yl)-ethyl]-carbamic acid methyl ester 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (530 mg, 1.21 mmol) was dissolved in DCM (4 mL) and treated with HCl (4M in dioxane, 1 mL, 4 mmol). The reaction mixture was stirred at RT for 19 h then the solid was filtered off and rinsed with DCM. After being thoroughly dried (461 mg, 92%), a portion of this solid (200 mg, 0.485 mmol) was combined with Methoxycarbonylamino-phenyl-acetic acid (122 mg, 0.582 mmol) and HATU (221 mg, 0.582 mmol) were suspended in DCM (5 mL) and K$_3$PO$_4$ (309 mg, 1.455 mmol) was added. After stirring 24 h, the reaction mixture was diluted with EtOAc and washed with 1M LiOH and brine. The organic layer was dried over MgSO$_4$, filtered and concentrated. The crude residue was purified by silica column chromatography (75% to 100% EtOAc) to provide the title compound (204 mg, 79%).

{2-Methyl-1-[2-(5-{5-[4-(2-{1-[2-(methylperoxymethyl-amino)-2-phenyl-acetyl]-pyrrolidin-2-yl}-3H-imidazol-4-yl)-phenyl]-3a,6a-dihydro-thieno[3,2-b]thiophen-2-yl}-1H-imidazol-2-yl)-pyrrolidine-1-carbonyl]-propyl}-carbamic acid methyl ester

[2-oxo-1-phenyl-2-(2-{5-[4-(4,4,5,5-tetramethyl-[1,3,2]dioxaborolan-2-yl)-phenyl]-1H-imidazol-2-yl}-pyrrolidin-1-yl)-ethyl]-carbamic acid methyl ester (204 mg, 0.385 mmol), (1-{2-[5-(5-Bromo-3a,6a-dihydro-thieno[3,2-b]thiophen-2-yl)-1H-imidazol-2-yl]-pyrrolidine-1-carbonyl}-2-methyl-propyl)-carbamic acid methyl ester (137 mg, 0.268 mmol), Pd(PPh$_3$)$_4$ (31 mg, 0.0268 mmol) and K$_2$CO$_3$ (2M in H$_2$O, 0.4 mL, 0.8 mmol) were combined in 1,2-dimethoxy-ethane (2.7 mL). After 10 min of degassing with bubbling N$_2$, the reaction mixture was heated to 85° C. for 19 h. After this period, it was cooled and diluted MeOH. The suspension was filtered over a thiol SPE cartridge to remove the palladium, then concentrated. The crude residue was purified by HPLC to afford the title compound (103 mg, 46%). MS (ESI) m/z 835 [M+H]$^+$.

Example HI
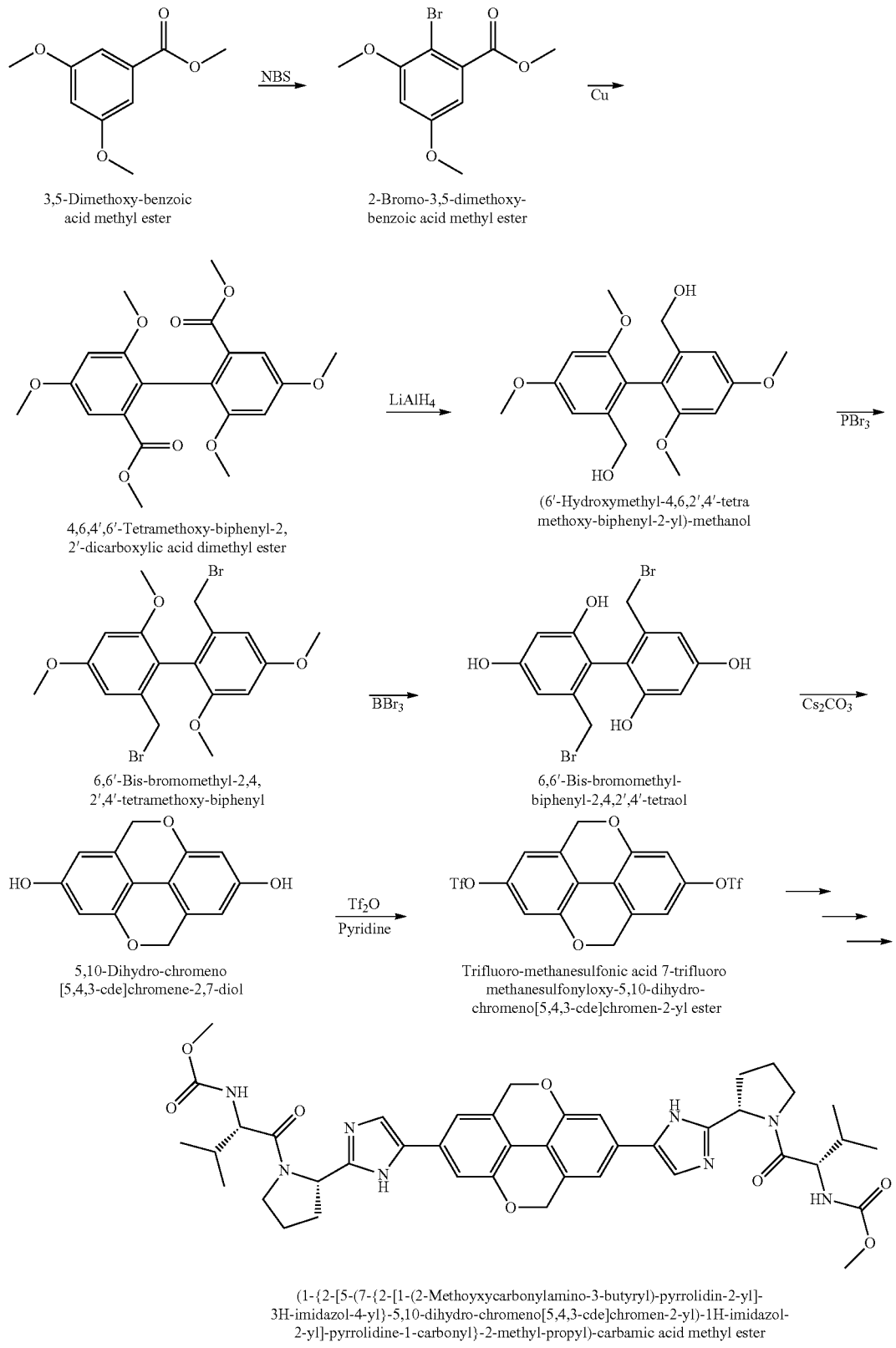
(1-{2-[5-(7-{2-[1-(2-Methoyxycarbonylamino-3-butyryl)-pyrrolidin-2-yl]-
3H-imidazol-4-yl}-5,10-dihydro-chromeno[5,4,3-cde]chromen-2-yl)-1H-imidazol-
2-yl]-pyrrolidine-1-carbonyl}-2-methyl-propyl)-carbamic acid methyl ester

2-Bromo-3,5-dimethoxy-benzoic acid methyl ester 3,5-Dimethoxy-benzoic acid methyl ester (4.0 g) was dissolved in MeCN (28 mL), and NBS (4.4 g) was added at 0° C. After stirring at room temperature for 3 hours, saturated $Na_2SO_3$ (15 mL) was added. The mixture was evaporated under vacuum and extracted with ether (1×, 500 mL). After the solvent was removed, the crude material was subjected to silica gel chromatography using effluent of 10-40% ethyl acetate and hexanes. The fractions containing product were combined and the solvent was removed under reduced pressure to provide 2-bromo-3,5-dimethoxy-benzoic acid methyl ester (5.2 g, 93%) as a clear oil.

4,6,4',6'-Tetramethoxy-biphenyl-2,2'-dicarboxylic acid dimethyl ester

2-Bromo-3,5-dimethoxy-benzoic acid methyl ester (5.2 g) was dissolved in DMF (16 mL), and Cu powder (2.4 g) was added. After stirring at 150° C. for 3 days, the mixture was filtered and evaporated under vacuum. The crude material was subjected to silica gel chromatography using effluent of 30-60% ethyl acetate and hexanes. The fractions containing product were combined and the solvent was removed under reduced pressure to provide 4,6,4',6'-tetramethoxy-biphenyl-2,2'-dicarboxylic acid dimethyl ester (2.5 g, 68%) as a clear oil.

(6'-Hydroxymethyl-4,6,2',4% tetramethoxy-biphenyl-2-yl)-methanol 4,6,4',6'-tetramethoxy-biphenyl-2,2'-dicarboxylic acid dimethyl ester (2.5 g) was dissolved in THF (96 mL), and 1M $LiAlH_4$ in THF (9.6 mL) was added. After stirring at room temperature for overnight, the mixture was quenched with water and 2N HCl (24 mL) was added. The mixture was evaporated under vacuum and partitioned with DCM (300 mL) and water (200 mL). The organic layer was dried over $Na_2SO_4$ and crystallized with DCM to provide (6'-hydroxymethyl-4,6,2',4'-tetramethoxy-biphenyl-2-yl)-methanol (1.7 g, 77%) as a pale blue white triclinic crystals.

6,6'-Bis-bromomethyl-2,4,2',4' tetramethoxy-biphenyl (6'-hydroxymethyl-4,6,2',4'-tetramethoxy-biphenyl-2-yl)-methanol (779 mg) was dissolved in DCM (5.8 mL), and $PBr_3$ (527 µl) was slowly added at 0° C. After stirring at 0° C. for 30 min. and at room temperature for 1 hour, $H_2O$ (40 mL) was added. The mixture was extracted with ether (1×, 50 mL). After the solvent was removed, the crude material was subjected to silica gel chromatography using effluent of 10-40% ethyl acetate and hexanes. The fractions containing product were combined and the solvent was removed under reduced pressure to provide 6,6'-bis-bromomethyl-2,4,2',4'-tetramethoxy-biphenyl (700 mg, 65%) as a thick oil.

6,6'-Bis-bromomethyl-biphenyl-2,4,2',4'-tetraol 6,6'-bis-bromomethyl-2,4,2',4'-tetramethoxy-biphenyl (685 mg) was dissolved in DCM (3.0 mL), and 1M $BBr_3$ in DCM (16.4 mL) was slowly added. After stirring for 2 days, the mixture was poured on to ice and concentrated. The crude material was used for the next step without a further purification.

5-10-Dihydro-chromeno[5,4,3-cde]chromene-2,7-diol

The crude 6,6'-bis-bromomethyl-biphenyl-2,4,2',4'-tetraol was dissolved in DMF (30 mL), and $Cs_2CO_3$ (1.9 g) was added. After stirring at room temperature for 1 hour, the mixture was partitioned with 1 N HCl (100 mL) and ethyl acetate (100 mL), and extracted with ethyl acetate (3×, 100 mL). After the solvent was removed, the crude material was subjected to silica gel chromatography using effluent of 10-15% methanol and DCM. The fractions containing product were combined and the solvent was removed under reduced pressure to provide 5-10-dihydro-chromeno[5,4,3-cde]chromene-2,7-diol (301 mg, 84%) as a white solid.

Trifluoro-methanesulfonic acid 7-trifluoromethane-sulfonyloxy-5,10-dihydro-chromeno[5,4,3-cde] chromen-2-yl ester 5-10-Dihydro-chromeno[5,4,3-cde]chromene-2,7-diol (290 mg) was dissolved in DCM (12 mL), and $Tf_2O$ (1.2 mL) and pyridine (969 µl) were added. After stirring at room temperature for overnight, the mixture was partitioned with 2 N HCl (50 mL) and DCM (50 mL), and washed with 2 N HCl (2×50 mL) and saturated sodium bicarbonate (1×50 mL). After the solvent was removed, the resulting oil was subjected to silica gel chromatography using effluent of 0-30% ethyl acetate and hexanes. The fractions containing product were combined and the solvent was removed under reduced pressure to provide trifluoro-methanesulfonic acid 7-trifluoromethanesulfonyloxy-5,10-dihydro-chromeno[5,4,3-cde]chromen-2-yl ester (472 mg, 78%) as an off-white solid.

(1-{2-[5-(7-{2-[1-(2-Methoxycarbonylamino-3-methyl-butyryl)-pyrrolidin-2-yl]-3H-imidazol-4-yl}-5,10-dihydro-chromeno[5,4,3-cde]chromen-2-yl)-1H-imidazol-2-yl]-pyrrolidine-1-carbonyl}-2-methyl-propyl)-carbamic acid methyl ester Title compound was prepared according to the method employed to prepare (1-{2-[5-(2-{2-[1-(2-Methoxycarbonylamino-3-methyl-butyryl)-pyrrolidin-2-yl]-3H-imidazol-4-yl}-6-H-dibenzo[c,h]chromen-8-yl)-1H-imidazol-2-yl]-pyrrolidine-1-carbonyl}-2-methyl-propyl)-carbamic acid methyl ester, substituting trifluoro-methanesulfonic acid 7-trifluoromethane sulfonyloxy-5,10-dihydro-chromeno[5,4,3-cde]chromen-2-yl ester for trifluoro-methanesulfonic acid 2-trifluoromethanesulfonyloxy-6-H-dibenzo[c,h]chromen-8-yl ester.

Example HJ

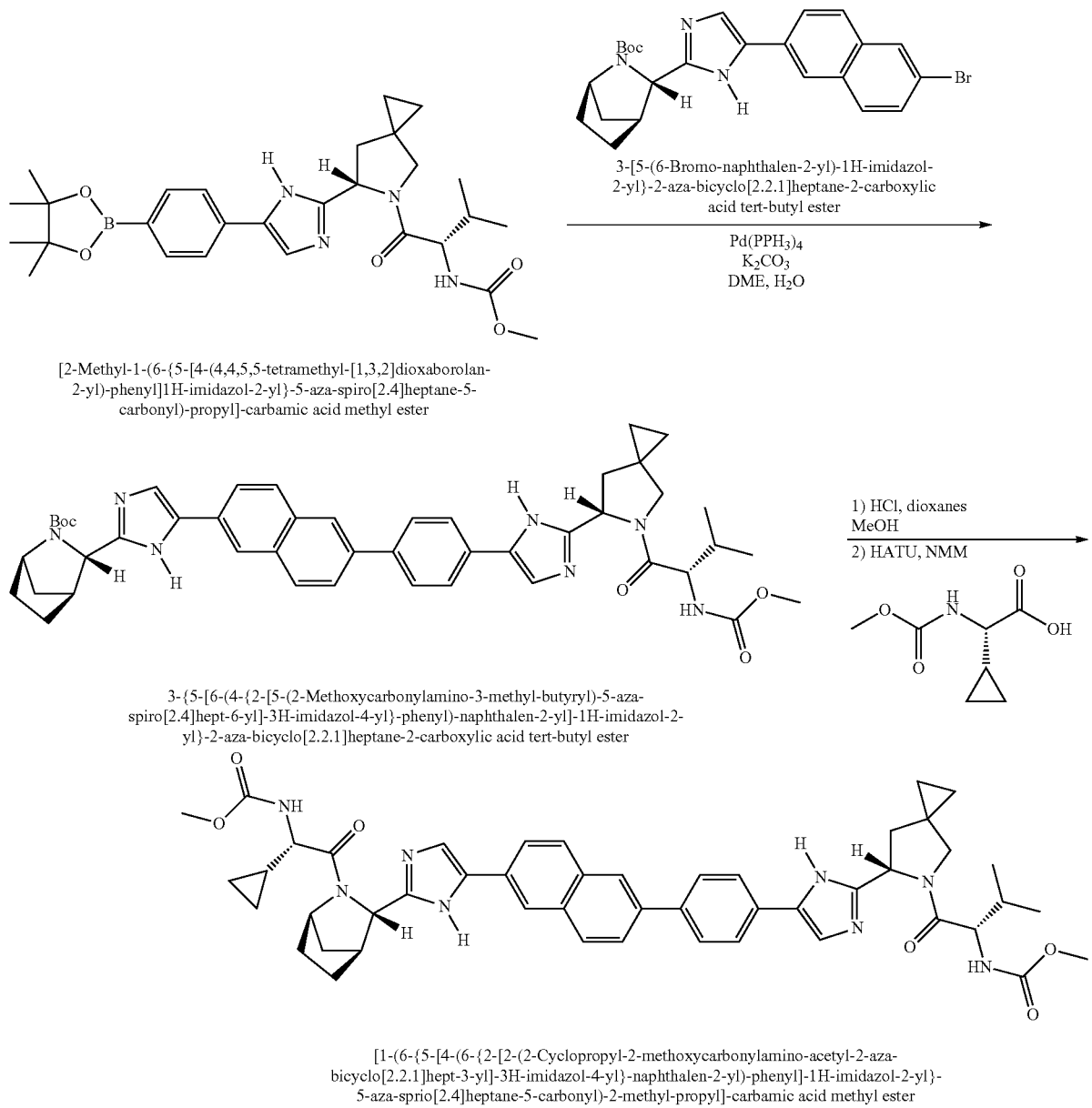

3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carboxylic acid tert-butyl ester To a solution of [2-Methyl-1-(6-{5-[4-(4,4,5,5-tetramethyl-[1,3,2]dioxaborolan-2-yl)-phenyl]-1H-imidazol-2-yl}-5-aza-spiro[2.4]heptane-5-carbonyl)-propyl]-carbamic acid methyl ester (0.95 g, 1.82 mmol) and 3-[5-(6-Bromo-naphthalen-2-yl)-1H-imidazol-2-yl]-2-aza-bicyclo[2.2.1]heptane-2-carboxylic acid tert-butyl ester (0.96 g, 1.82 mmol, 1 equiv.) in DME (20 mL) was added $K_2CO_3$ (aqueous, 2 M, 3.6 mL, 7.2 mmol, 4 equiv.) and Pd(PPh$_3$)$_4$ (0.11 g, 0.09 mmol, 0.05 equiv.). The slurry was degassed with argon for 5 minutes and heated to 80° C. for 12 hours. The resulting reaction mixture was diluted with EtOAc and washed with water. The aqueous layer was back-extracted with EtOAc and the combined organic layers were dried over $Na_2SO_4$ and concentrated. The crude oil was purified by column chromatography (SiO$_2$, 50→100% EtOAc in Hexanes) to provide 3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carboxylic acid tert-butyl ester (0.53 g, 37%) as a yellow powder.

LCMS-ESI$^+$: calc'd for $C_{46}H_{53}N_7O_5$: 783.4 (M$^+$); Found: 784.3 (M+H$^+$).

[1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro PA heptane-5-carbonyl)-2-methyl-propyl]-carbamic acid methyl ester To a slurry of 3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carboxylic acid tert-butyl ester (0.05 g, 0.06 mmol) in MeOH (0.1 mL) was added HCl in dioxanes (4 M, 0.6 mL). The resulting solution was stirred at room temperature for 1 hour and the concentrated to dryness. Cyclopropyl-methoxycarbonylamino-acetic acid (0.02 g, 0.09 mmol, 1.5 equiv.) and CH$_2$Cl$_2$ (0.6 mL) were then added, followed by HATU (0.03 g, 0.08 mmol, 1.25 equiv.) and NMM (0.05 mL, 0.45 mmol, 5 equiv.). The resulting solution was stirred at room temperature for 18 hours. The reaction mixture was concentrated and purified by preparative HPLC (Gemini, 15-40% MeCN in H$_2$O (0.1% formic acid)) and lyophilized to provide [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (0.03 g, 49%) as a white powder. LCMS-ESI$^+$: calc'd for C$_{48}$H$_{54}$N$_8$O$_6$: 838.4 (M$^+$); Found: 839.9 (M+H$^+$). $^1$H-NMR: 400 MHz, (CDCl$_3$) δ: (mixture of rotomers) 8.22 (s, 2H), 7.81-7.96 (m, 10H), 7.63 (d, 1H), 7.29 (d, 1H), 5.18 (t, 1H), 4.56 (d, 1H), 3.96 (t, 1H), 3.74 (m, 1H), 3.51 (s, 6H), 3.12 (t, 1H), 2.48 (s, 1H), 1.93-2.29 (m, 6H), 1.58-1.77 (m, 5H), 0.85 (d, 3H), 0.80 (d, 3H), 0.58 (m, 4H), 0.34 (m, 1H), 0.26 (m, 1H), 0.03 (m, 1H), −0.12 (m, 1H).

Example HK

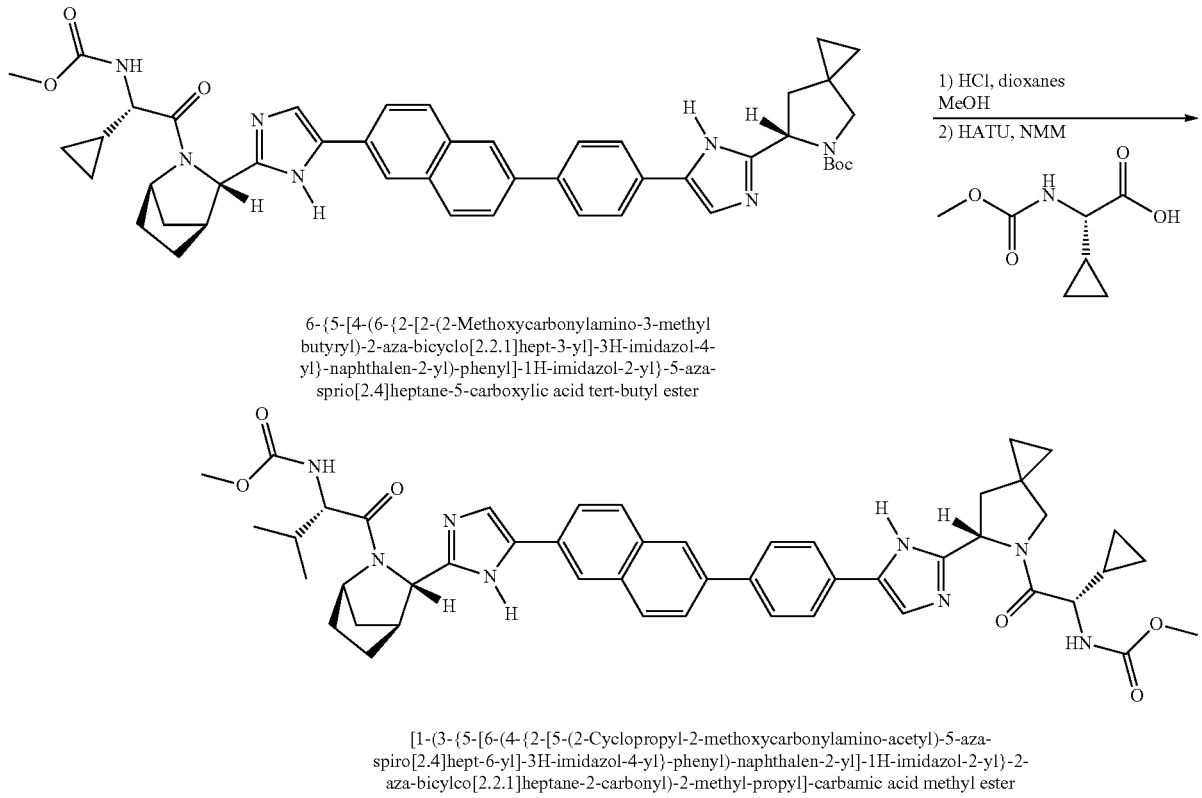

6-{5-[4-(6-{2-[2-(2-Methoxycarbonylamino-3-methyl butyryl)-2-aza-bicyclo[2.2.1]hept-3-yl]-3H-imidazol-4-yl}-naphthalen-2-yl)-phenyl]-1H-imidazol-2-yl}-5-aza-sprio[2.4]heptane-5-carboxylic acid tert-butyl ester

[1-(3-{5-[6-(4-{2-[5-(2-Cyclopropyl-2-methoxycarbonylamino-acetyl)-5-aza-spiro[2.4]hept-6-yl]-3H-imidazol-4-yl}-phenyl)-naphthalen-2-yl]-1H-imidazol-2-yl}-2-aza-bicylco[2.2.1]heptane-2-carbonyl)-2-methyl-propyl]-carbamic acid methyl ester

[1-(3-{5-[6-(4-{2-[5-(2-Cyclopropyl-2-methoxycarbonylamino-acetyl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]carbamic acid methyl ester This compound was prepared following the procedure for [1-(6-{5-{4-(6-[2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester using 6-{5-[4-(6-{2-[2-(2-Methoxycarbonylamino-3-methyl-butyryl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carboxylic acid tert-butyl ester (0.05 g, 0.06 mmol) to provide [1-(3-{5-[6-(4-{2-[5-(2-Cyclopropyl-2-methoxycarbonylamino-acetyl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (0.02 g, 46%) as a white powder. LCMS-ESI$^+$: calc'd for C$_{48}$H$_{54}$N$_8$O$_6$: 838.4 (M$^+$); Found: 839.9 (M+H$^+$). $^1$H-NMR:

400 MHz, (CDCl₃) δ: (mixture of rotomers) 8.18 (s, 2H), 7.80-7.91 (m, 10H), 7.58 (s, 1H), 7.14 (d, 1H), 5.19 (d, 1H), 4.50 (d, 1H), 4.13 (t, 1H), 3.57 (m, 1H), 3.51 (s, 6H), 3.28 (m, 1H), 2.48 (s, 1H), 1.94-2.04 (m, 2H), 1.71-1.83 (m, 5H), 1.42-1.49 (m, 4H), 0.97 (d, 3H), 0.87 (d, 3H), 0.52-0.68 (m, 4H), 0.33 (m, 1H), 0.23 (m, 1H), 0.03 (m, 1H), −0.12 (m, 1H).
Example HL
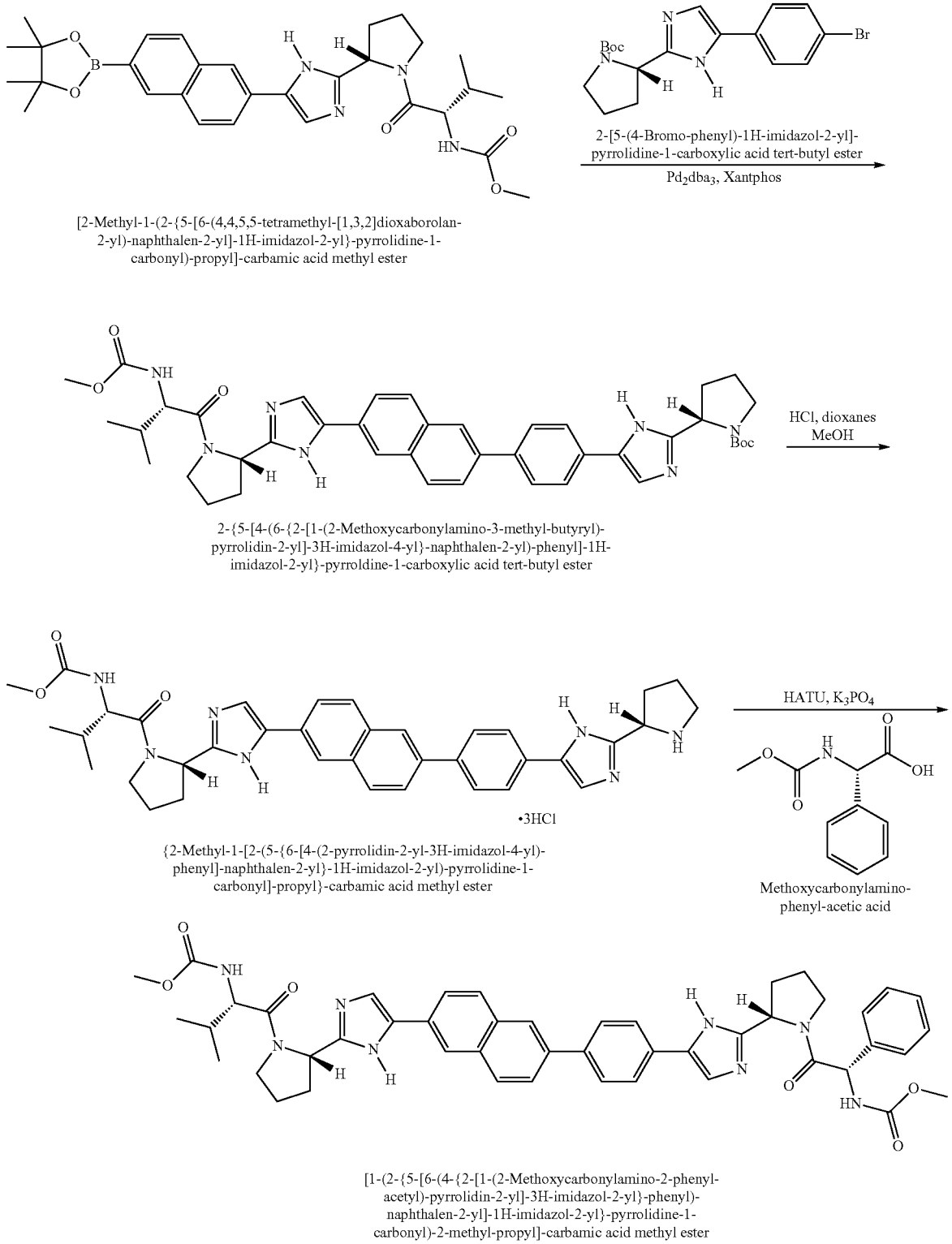

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester To a solution of 2-[5-(4-Bromo-phenyl)-1H-imidazol-2-yl]-pyrrolidine-1-carboxylic acid tert-butyl ester (1.00 g, 2.5 mmol) and [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (1.97 g, 3.6 mmol, 1.5 equiv.) in DME (12.5 mL) was added $K_3PO_4$ (aqueous, 2 M, 3.9 mL, 7.8 mmol, 3 equiv.), $Pd_2dba_3$ (0.12 g, 0.13 mmol, 0.05 equiv.), and Xantphos (0.15 g, 0.26 mmol, 0.1 equiv.). The slurry was degassed with argon for 5 minutes and heated to 80° C. for 18 hours. The resulting reaction mixture was diluted with EtOAc/MeOH (10:1) and filtered through CELITE. The solution was washed with water and brine. The aqueous layer was back-extracted with EtOAc and the combined organic layers were dried over $Na_2SO_4$ and concentrated. The crude oil was purified by column chromatography ($SiO_2$, 50→100% EtOAc in Hexanes) to provide 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.93 g, 49%) as a yellow powder. LCMS-ESI$^+$: calc'd for $C_{42}H_{49}N_7O_5$: 731.4 (M$^+$); Found: 732.9 (M+H$^+$).

{2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester To a slurry of 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.1 g, 0.14 mmol) in MeOH (0.15 mL) was added HCl in dioxanes (4 M, 0.7 mL). The resulting solution was stirred at room temperature for 1 hour and diluted with $Et_2O$. The resulting precipitate was filtered and dried to provide {2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester trihydrochloric acid salt (0.09 g, 87%) as a white powder. LCMS-ESI$^+$: calc'd for $C_{37}H_{41}N_7O_3$: 631.3 (M$^+$); Found: 632.7 (M+H$^+$).

[1-(2-{5-[6-(4-{2-[1-(2S)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester To a slurry of {2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester (0.045 g, 0.06 mmol) and (S)-methoxycarbonylamino-phenyl-acetic acid (0.02 g, 0.09 mmol, 1.5 equiv.) in $CH_2Cl_2$ (0.6 mL) was added HATU (0.03 g, 0.08, 1.25 equiv.) and $K_3PO_4$ (0.05 g, 0.22 mmol, 3 equiv.). The reaction mixture was stirred at room temperature for 18 hours and diluted with $CH_2Cl_2$. The salts were filtered and the filtrate was concentrated. The crude oil was purified by preparative HPLC (Gemini, 15-40% MeCN in $H_2O$ (0.1% formic acid)) and lyophilized to provide [1-(2-{5-[6-(4-{2-[1-(2S)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.03 g, 65%) as a white powder. LCMS-ESI$^+$: calc'd for $C_{47}H_{50}N_8O_6$: 822.4 (M$^+$); Found: 823.5 (M+H$^+$). $^1$H-NMR: 400 MHz, (CDCl$_3$) δ: (Mixture of rotomers) 7.64-8.03 (m, 9H), 7.20-7.40 (m, 6H), 7.17 (s, 2H), 6.14 (m, 1H), 5.53 (dd, 2H), 5.25-5.33 (m, 2H), 4.33 (t, 1H), 3.85 (m, 1H), 3.73 (m, 1H), 3.68 (s, 3H), 3.66 (s, 3H), 3.27 (m, 1H), 2.86-2.96 (m, 3H), 2.35 (m, 1H), 1.94-2.23 (m, 6H), 0.87-0.90 (m, 6H).

Example HM

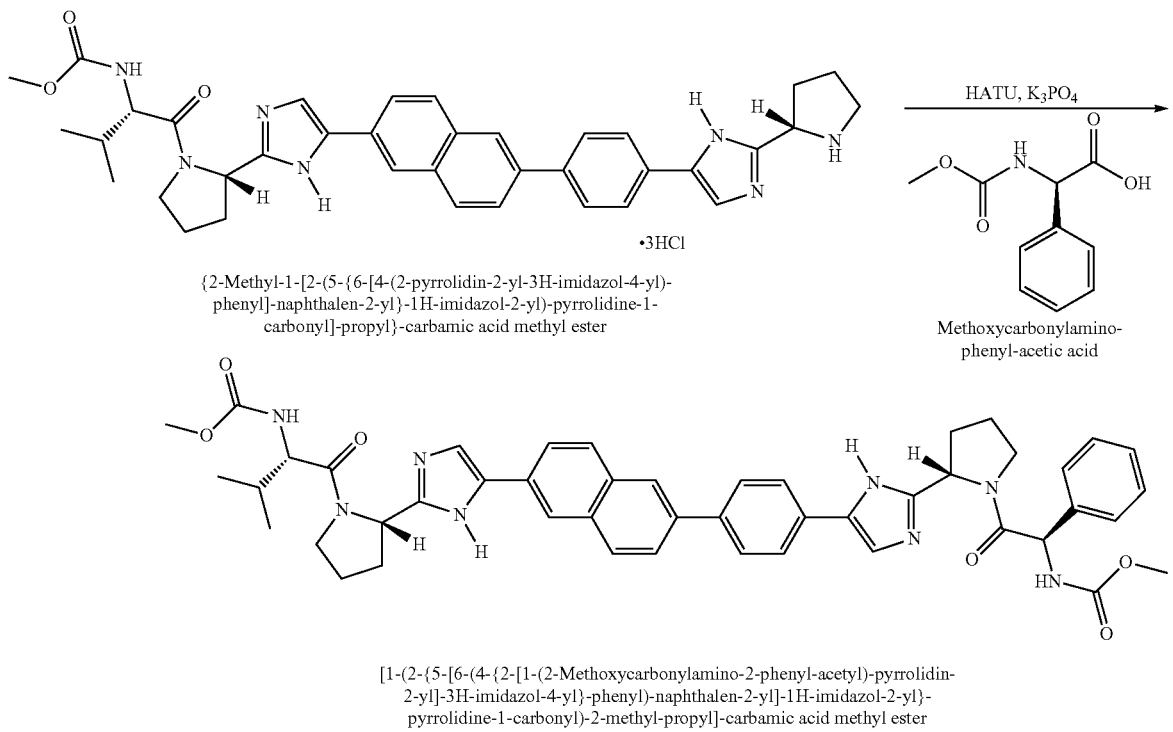

{2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester Methoxycarbonylamino-phenyl-acetic acid

[1-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

1041

[1-(2-{5-[6-(4-{2-[1-(2R)-(2-Methoxycarbony-lamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester This compound was prepared following the procedure for [1-(2-{5-[6-(4-{2-[1-(2S)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using (R)-methoxycarbonylamino-phenyl-acetic acid (0.02 g, 0.09 mmol, 1.5 equiv.) to provide [1-(2-{5-[6-(4-{2-[1-(2R)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.03 g, 65%) as a white powder. LCMS-ESI$^+$: calc'd for $C_{47}H_{50}N_8O_6$: 822.4 (M$^+$); Found: 823.8 (M+H$^+$). $^1$H-NMR: 400 MHz, (CDCl$_3$) δ: (Mixture of rotomers) 7.62-8.02 (m, 9H), 7.36-7.43 (m, 6H), 7.22 (s, 2H), 6.01 (s, 1H), 5.29-5.53 (m, 4H), 4.35 (t, 1H), 3.73-3.87 (m, 2H), 3.68 (s, 3H), 3.63 (s, 3H), 3.22 (q, 2H), 2.82-2.96 (m, 2H), 2.37 (m, 1H), 2.23 (m, 2H), 1.90-2.11 (m, 4H), 0.87-0.93 (m, 6H).

Example HN

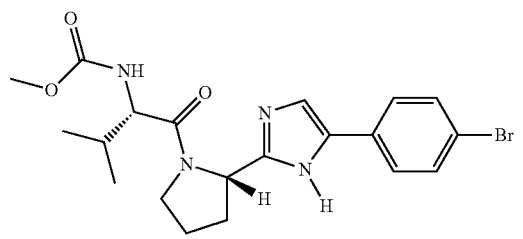

(1-{2-[5-(4-Bromo-phenyl)-1H-imidazol-2-yl]-pyrrolidine-1-carbonyl}-2-methyl-propyl)-carbamic acid methyl ester

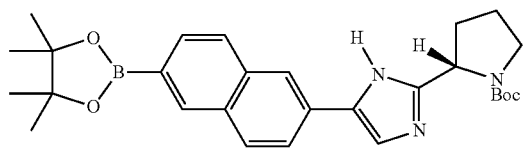

2-{5-[6-(4,4,5,5-Tetramethyl-[1,3,2]dioxaborolan-2-yl)-naphthalen-2-yl]-1H-imidazol-2-yl}-pyrrolidine-1-carboxylic acid tert-butyl ester Pd$_2$dba$_3$, Xantphos

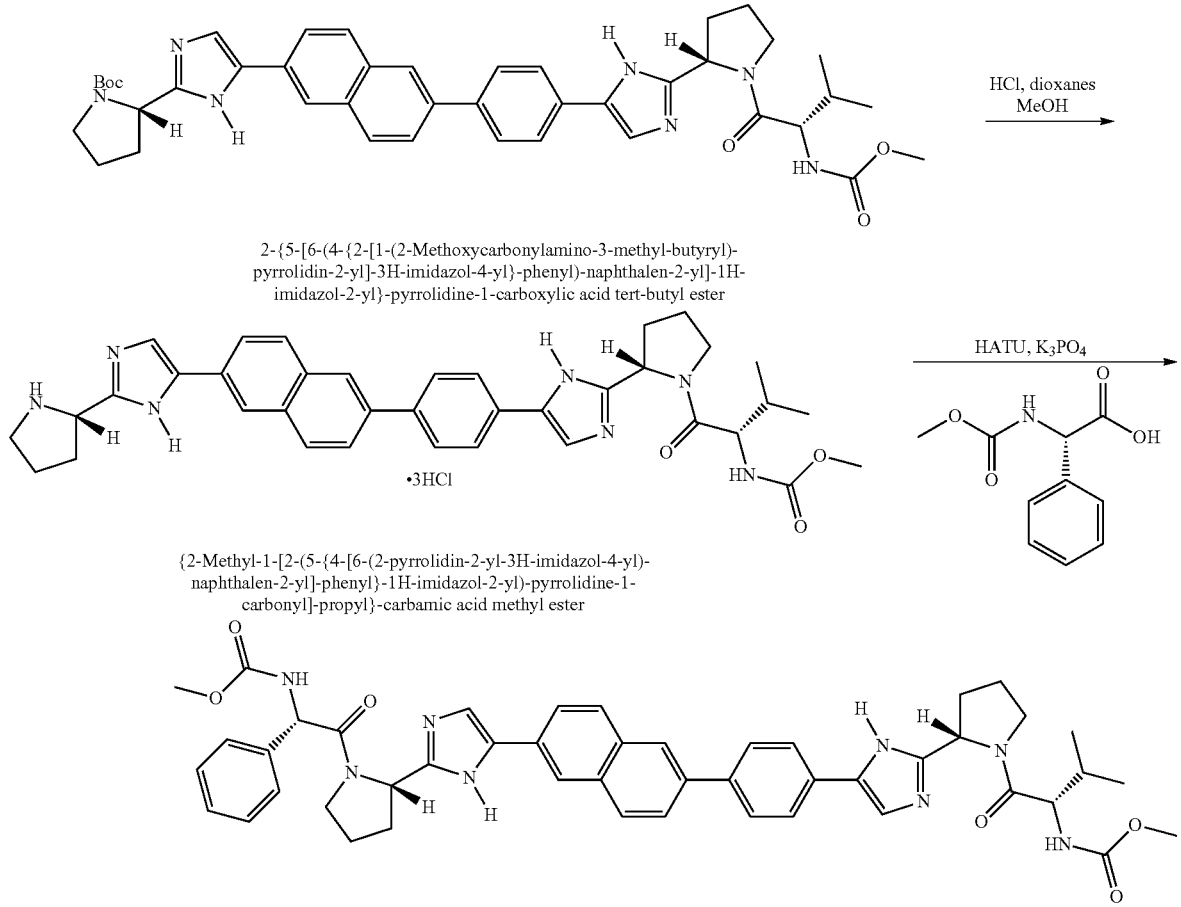

2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester HCl, dioxanes
MeOH ·3HCl {2-Methyl-1-[2-(5-{4-[6-(2-pyrrolidin-2-yl-3H-imidazol-4-yl)-naphthalen-2-yl]-phenyl}-1H-imidazol-2-yl)-pyrrolidine-1-carbonyl]-propyl}-carbamic acid methyl ester

HATU, K$_3$PO$_4$

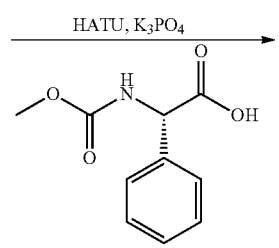

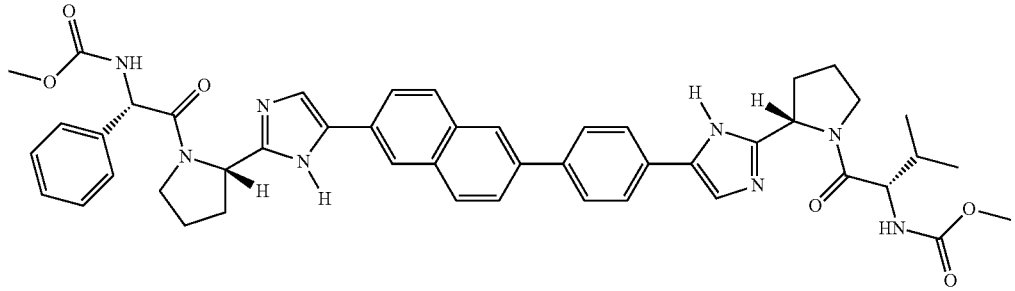

[1-(2-{5-[4-(6-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

1043

[1-(2-{5-[4-(6-{2-[1-(2S)-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester This compound was prepared following the procedure for [1-(2-{5-[6-(4-{2-[1-(2S)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using (1-{2-[5-(4-Bromo-phenyl)-1H-imidazol-2-yl]-pyrrolidine-1-carbonyl}-2-methyl-propyl)-carbamic acid methyl ester (1.0 g, 2.2 mmol) and 2-{5-[6-(4,4,5,5-Tetramethyl-[1,3,2]dioxaborolan-2-yl)-naphthalen-2-yl]-1H-imidazol-2-yl}-pyrrolidine-1-carboxylic acid tert-butyl ester (1.6 g, 3.4 mmol, 1.5 equiv.) to provide [1-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester (0.03 g, 54%) as a white powder. LCMS-ESI⁺: calc'd for $C_{47}H_{50}N_8O_6$: 822.4 (M⁺); Found: 823.9 (M+H⁺). ¹H-NMR: 400 MHz, (CDCl₃) δ: (Mixture of rotomers) 7.52-7.93 (m, 9H), 7.27-7.42 (m, 6H), 7.16 (s, 2H), 6.08 (m, 1H), 5.48-5.56 (m, 2H), 5.34 (s, 1H), 5.24 (s, 1H), 4.35 (t, 1H), 3.93 (m, 1H), 3.73 (m, 1H), 3.68 (s, 3H), 3.66 (s, 3H), 3.38 (m, 1H), 2.78-2.83 (m, 3H), 2.36 (m, 1H), 2.04-2.23 (m, 6H), 0.86-0.97 (m, 6H).

Example HO

1044

[1-(2-{5-[4-(6-{2-[1-(2R)-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester This compound was prepared following the procedure for [1-(2-{5-[4-(6-{2-[1-(2S)-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester using (R)-methoxycarbonylamino-phenyl-acetic acid (0.02 g, 0.09 mmol, 1.5 equiv.) to provide [1-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester (0.03 g, 58%) as a white powder. LCMS-ESI⁺: calc'd for $C_{47}H_{50}N_8O_6$: 822.4 (M⁺); Found: 823.8 (M+H⁺). ¹H-NMR: 400 MHz, (CDCl₃) δ: (Mixture of rotomers) 7.62-7.87 (m, 9H), 7.29-7.43 (m, 6H), 7.18 (s, 2H), 6.09 (m, 1H), 5.46 (m, 2H), 5.33 (s, 1H), 5.27 (s, 1H), 4.33 (t, 1H), 3.84 (m, 1H), 3.71 (m, 1H), 3.68 (s, 3H), 3.61 (s, 3H), 3.24 (m, 1H), 2.83-2.93 (m, 3H), 2.35 (m, 1H), 1.92-2.23 (m, 6H), 0.86-0.97 (m, 6H).

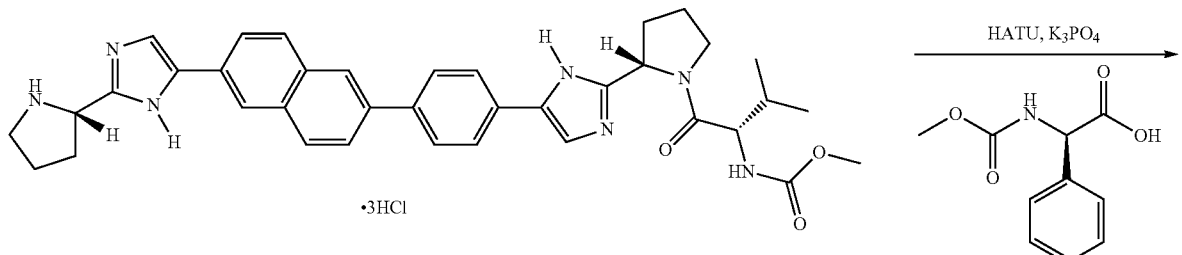

{2-Methyl-1-[2-(5-{4-[6-(2-pyrrolidin-2-yl-3H-imidazol-4-yl)-naphthalen-2-yl]-phenyl}-1H-imidazol-2-yl)-pyrrolidine-1-carbonyl]-propyl}-carbamic acid methyl ester

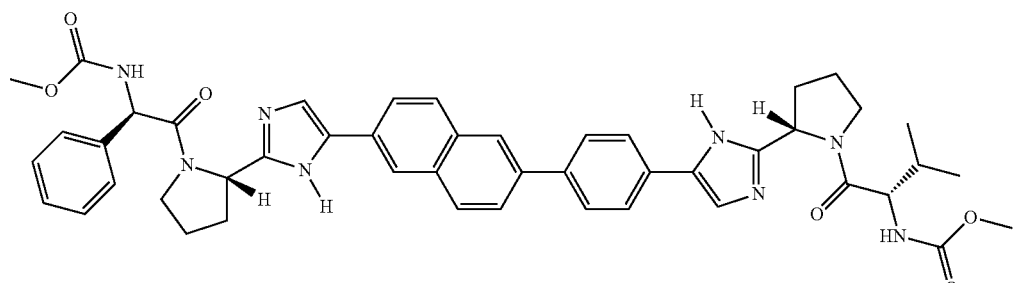

[1-(2-{5-[4-(6-{2-[1-(2-Methoxycarbonylamino-2-phenyl-acetyl-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester

Example HP

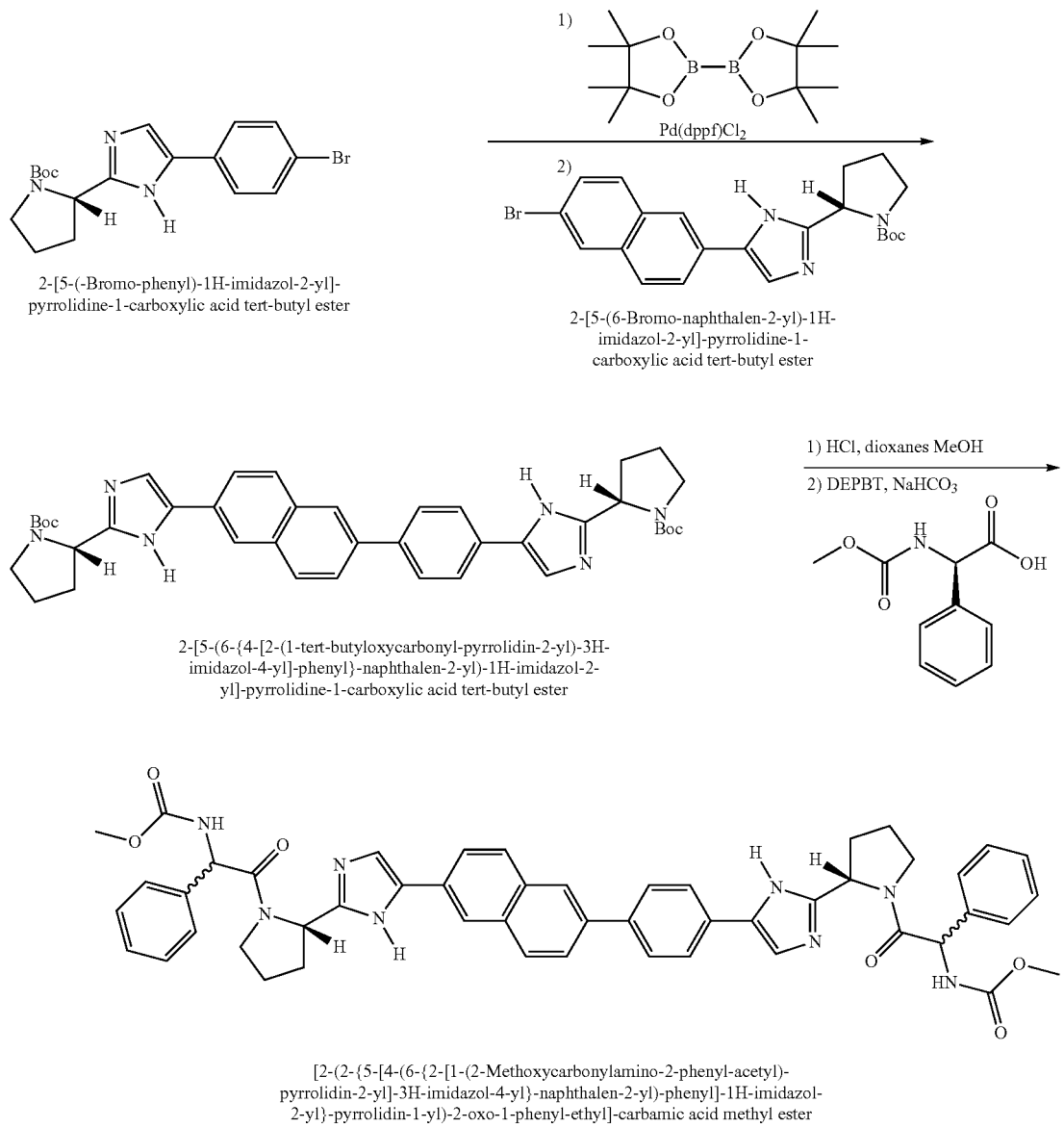

2-[5-(6-{4-[2-(1-tert-butyloxycarbonyl-pyrrolidin-2-yl)-3H-imidazol-4-yl]-phenyl}-naphthalen-2-yl)-1H-imidazol-2-yl]-pyrrolidine-1-carboxylic acid tert-butyl ester To a solution of 2-[5-(4-Bromo-phenyl)-1H-imidazol-2-yl]-pyrrolidine-1-carboxylic acid tert-butyl ester (0.39 g, 1.0 mmol) and bis(pinacolato)diborane (0.31 g, 1.2 mmol, 1.2 equiv.) in dioxane (5 mL) was added KOAc (0.30 g, 3.0 mmol, 3 equiv.) and Pd(dppf)Cl$_2$ (0.04 g, 0.05 mmol, 0.05 equiv.). The slurry was degassed with argon for 5 minutes and heated to 85° C. for 2.5 hours. The resulting solution was cooled to room temperature and 2-[5-(6-Bromo-naphthalen-2-yl)-1H-imidazol-2-yl]-pyrrolidine-1-carboxylic acid tert-butyl ester (0.45 g, 1.0 mmol, 1 equiv.) and K$_3$PO$_4$ (aqueous, 2 M, 1.75 mL, 3.5 mmol, 3.5 equiv.) was added. The reaction mixture was heated to 85° C. for 6 hours. The slurry was filtered through CELITE and concentrated. The crude product was purified by column chromatography (SiO$_2$, 50-100% EtOAc in Hexanes (2% MeOH)) and preparative HPLC (Gemini, 15-40% MeCN in H$_2$O (0.1% formic acid)) to provide 2-[5-(6-{4-[2-(1-tert-butyloxycarbonyl-pyrrolidin-2-yl)-3H-imidazol-4-yl]-phenyl}-naphthalen-2-yl)-1H-imidazol-2-yl]-pyrrolidine-1-carboxylic acid tert-butyl ester (0.07 g, 10%) as a white powder. LCMS-ESI$^+$: calc'd for C$_{40}$H$_{46}$N$_6$O$_4$: 674.4 (M$^+$); Found: 675.6 (M+H$^+$).

[2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-phenyl-ethyl]-carbamic acid methyl ester To a slurry of 2-[5-(6-{4-[2-(1-tert-butyloxycarbonyl-pyrrolidin-2-yl)-3H-imidazol-4-yl]-phenyl}-naphthalen-2-yl)-1H-imidazol-2-yl]-pyrrolidine-1-carboxylic acid tert-butyl ester (0.07 g, 0.09 mmol) in MeOH (0.1 mL) was added HCl in dioxanes (4 M, 1.5 mL). The resulting solution was stirred at room temperature for 2 hour and basified with NaOH (2 N). The crude product was extracted with $CH_2Cl_2$. The organic extracts were combined, dried over $Na_2SO_4$ and concentrated. (R)-Methoxycarbonylamino-phenyl-acetic acid (0.08 g, 0.4 mmol, 4.4 equiv.) and DMF (1.0 mL) were then added, followed by DEPBT (0.12 g, 0.4, 4 equiv.) and $NaHCO_3$ (0.04 g, 0.43 mmol, 4 equiv.). The resulting slurry was stirred at room temperature for 7 days. The reaction mixture was purified by preparative HPLC (Gemini, 15→40% MeCN in $H_2O$ (0.1% formic acid)) and lyophilized to provide [2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-phenyl-ethyl]-carbamic acid methyl ester (0.04 g, 49%) as a white powder. LCMS-ESI$^+$: calc'd for $C_{50}H_{48}N_8O_6$: 856.4 (M$^+$); Found: 858.1 (M+H$^+$). $^1$H-NMR: 400 MHz, (CDCl$_3$) δ: (Mixture of rotomers) 10.32-10.45 (m, 2H), 8.26 (s, 1H), 8.00 (s, 1H), 7.72-7.98 (m, 8H), 7.19-7.50 (m, 12H), 6.07 (m, 2H), 5.28-5.55 (m, 4H), 3.73 (m, 2H), 3.66 (s, 3H), 3.65 (s, 3H), 3.22 (m, 2H), 2.86-2.96 (m, 2H), 2.22 (m, 2H), 2.04 (m, 2H), 1.92 (m, 2H).

Example HQ

[1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester This compound was prepared following the procedure for [1-(2-{5-[6-(4-{2-[1-(2S)-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-o-tolyl-acetic acid (0.03 g, 0.12 mmol, 1.75 equiv.) to provide [1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.03 g, 50%) as a white powder. LCMS-ESI$^+$: calc'd for $C_{48}H_{52}N_8O_6$: 836.4 (M$^+$); Found: 837.4 (M+H$^+$). 400 MHz, (CDCl$_3$) δ: (Mixture of diastereomers) 7.61-8.00 (m, 16H), 7.18-7.41 (m, 12H), 7.10 (s, 2H), 5.28-5.63 (m, 10H), 4.36 (t, 2H), 3.72-3.86 (m, 4H), 3.68 (s, 6H), 3.66 (s, 6H), 2.79-3.07 (m, 8H), 2.50 (s, 3H), 2.44 (s, 3H), 2.38 (m, 4H), 1.86-2.28 (m, 8H), 0.88-0.94 (m, 12H).

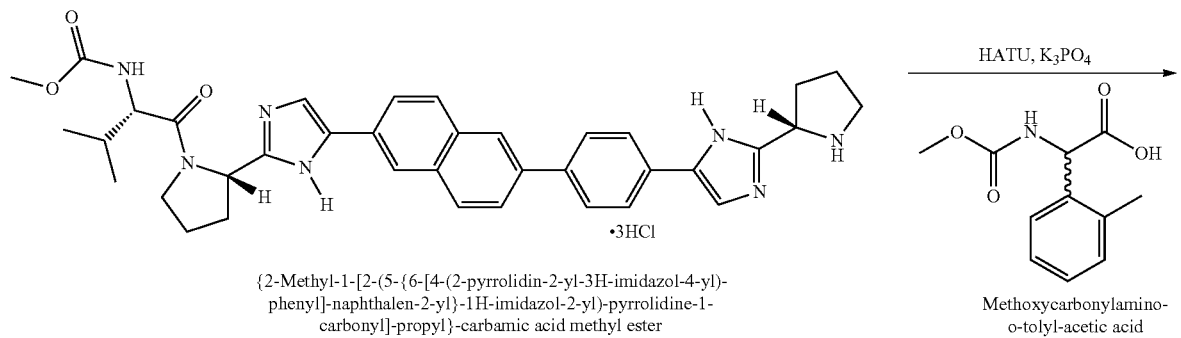

{2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester Methoxycarbonylamino-o-tolyl-acetic acid

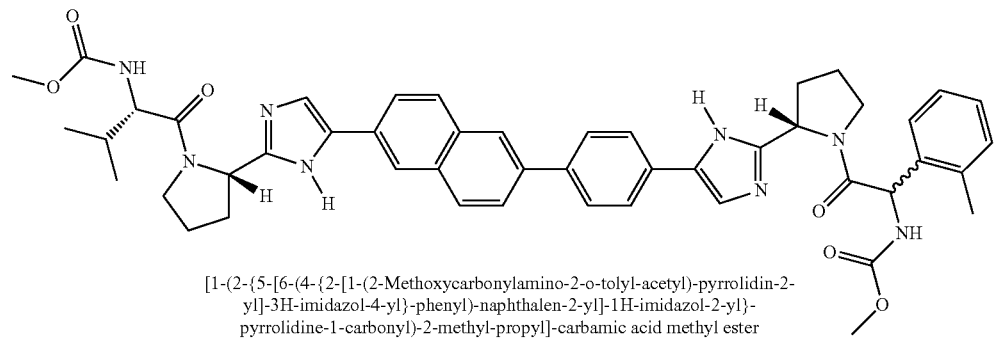

[1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

Example HR

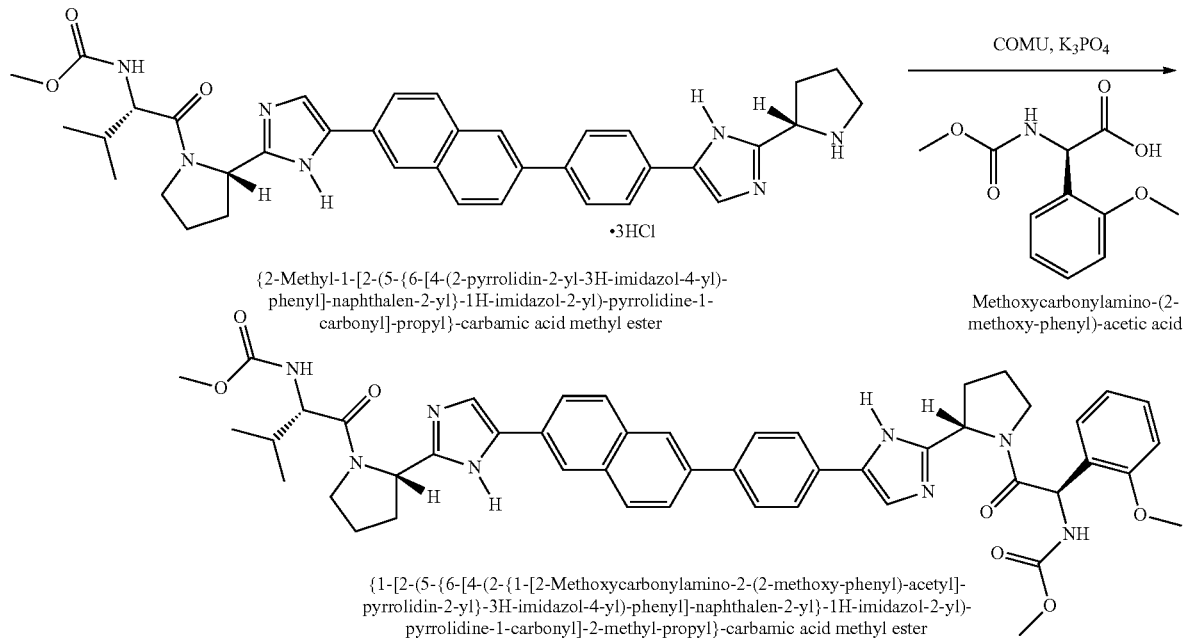

{2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester Methoxycarbonylamino-(2-methoxy-phenyl)-acetic acid {1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester {1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl]-carbamic acid methyl ester To a solution of {2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester (0.04 g, 0.05 mmol) and (S)-Methoxycarbonylamino-(2-methoxy-phenyl)-acetic acid (0.02 g, 0.08 mmol, 1.5 equiv.) in CH$_2$Cl$_2$ (0.5 mL) was added K$_3$PO$_4$ (0.03 g, 0.15 mmol, 3 equiv.). The slurry was cooled to 0° C. and COMU (0.03 g, 0.06 mmol, 1.25 equiv.) and the reaction was stirred at 0° C. for 1 hour. The slurry was diluted with CH$_2$Cl$_2$ and filtered. The filtrate was concentrated and the crude product was purified by preparative HPLC (Gemini, 15-40% MeCN in H$_2$O (0.1% formic acid)) and lyophilized to provide {1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.02 g, 50%) as a white powder. LCMS-ESI$^+$: calc'd for C$_{48}$H$_{52}$N$_8$O$_7$: 852.4 (M$^+$); Found: 853.6 (M+H$^+$). $^1$H-NMR: 400 MHz, (acetone-d$_6$) δ: (Mixture of rotamers) 10.96-11.01 (m, 2H), 8.29 (s, 1H), 8.07 (s, 1H), 7.73-7.89 (m, 7H), 7.35-7.48 (m, 4H), 7.33 (t, 1H), 7.05 (d, 1H), 6.96 (t, 1H), 6.36 (d, 1H), 5.91 (d, 1H), 5.21-5.26 (m, 3H), 4.29 (t, 1H), 3.90 (s, 3H), 3.78-3.93 (m, 2H), 3.60 (s, 3H), 3.58 (s, 3H), 3.30 (q, 2H), 2.59-2.65 (m, 2H), 2.36 (m, 1H), 1.90-2.21 (m, 6H), 0.85-0.93 (m, 6H).

Example HS (1-{2-[5-(6-{2-[1-(2-Methoxycarbonylamino-3-methyl-butyryl)-pyrrolidin-2-yl]-3H-imidazol-4-yl}-naphthalen-2-yl)-1H-benzoimidazol-2-yl]-azetidine-1-carbonyl}-2-methyl-propyl)-carbamic acid methyl ester

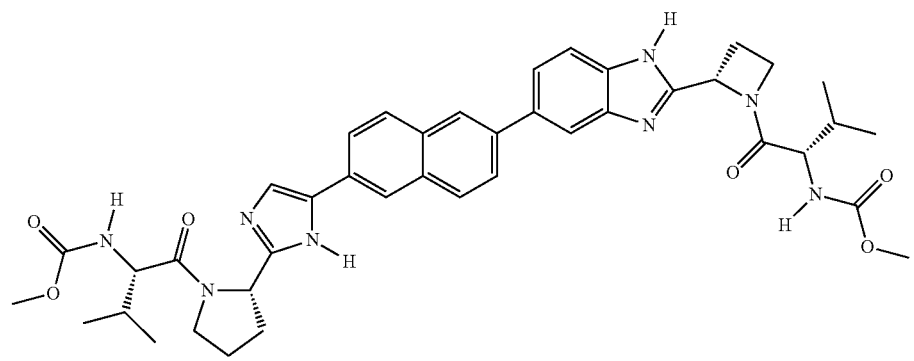

(1-{2-[5-(6-{2-[1-(2-Methoxycarbonylamino-3-methyl-butyryl)-pyrrolidin-2-yl]-3H-imidazol-4-yl}-naphthalen-2-yl)-1H-benzoimidazol-2-yl]-azetidine-1-carbonyl}-2-methyl-propyl)-carbamic acid methyl ester (1-{2-[5-(6-{2-[1-(2-Methoxycarbonylamino-3-methyl-butyryl)-pyrrolidin-2-yl]-3H-imidazol-4-yl}-naphthalen-2-yl)-1H-benzoimidazol-2-yl]-azetidine-1-carbonyl}-2-methyl-propyl)-carbamic acid methyl ester was prepared following method YYY substituting azetidine-1,2-dicarboxylic acid 1-tert-butyl ester for pyrrolidine-1,2-dicarboxylic acid 1-tert-butyl ester. $C_{41}H_{48}N_8O_6$ calculated 748.4 observed $[M+1]^+$ 749.4; rt=1.59 min. $^1$H(DMSO-d6): δ=8.31 (d, J=6.4 Hz, 2H), 8.16 (m, 2H), 8.04 (m, 2H), 7.98 (m, 1H), 7.90 (d, J=8.8 Hz, 1H), 7.78 (s, 2H), 7.42 (d, J=7.6 Hz, 1H), 7.32 (d, J=8.8 Hz, 1H), 5.49 (t, J=6.8 Hz, 1H), 5.15 (t, J=6.8 Hz, 1H), 4.41 (m, 2H), 4.12 (t, J=8.0 Hz, 2H), 3.85 (m, 1H), 3.78 (t, J=8.0 Hz, 1H), 3.55 (s, 3H), 3.53 (s, 3H), 2.76 (m, 1H), 2.65 (m, 1H), 2.41 (m, 1H), 2.17-2.08 (m, 2H), 2.03 (m, 2H), 1.86 (m, 1H), 0.83 (m, 6H).

Example HT (1-{2-[5-(4'-{2-[1-(2-Methoxycarbonylamino-3-methyl-butyryl)-azetidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester

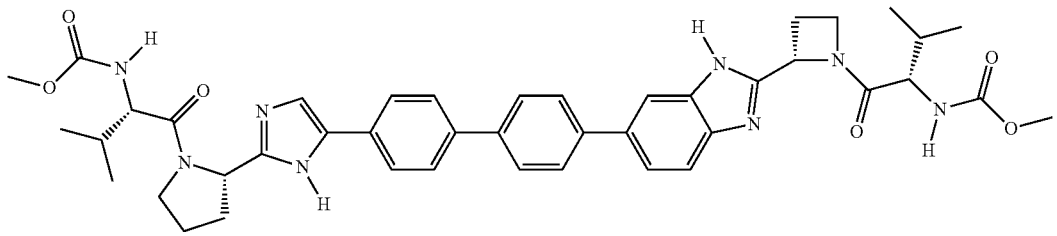

(1-{2-[5-(4'-{2-[1-(2-Methoxycarbonylamino-3-methyl-butyryl)-azetidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester (1-{2-[5-(4'-{2-[1-(2-Methoxycarbonylamino-3-methyl-butyryl)-azetidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester was prepared following method YYY substituting azetidine-1,2-dicarboxylic acid 1-tert-butyl ester for pyrrolidine-1,2-dicarboxylic acid 1-tert-butyl ester. $C_{43}H_{50}N_8O_6$: calculated 774.4 observed $[M+1]^+$ 775.8; rt=1.66 min. $^1$H (DMSO-d6): δ=8.11 (s, 1H), 7.91 (m, 3H), 7.86 (m, 5H), 7.72 (d, J=8.0 Hz, 1H), 7.65 (d, J=8.4 Hz, 1H), 7.42 (d, J=7.6 Hz, 1H), 7.32 (d, J=8.4 Hz, 1H), 5.47 (t, J=6.4 Hz, 1H), 5.12 (t, J=7.2 Hz, 1H), 4.40 (m, 2H), 4.11 (t, J=7.6 Hz, 1H), 3.84 (m, 2H), 3.69 (m, 2H), 3.55 (s, 3H), 3.53 (s, 3H), 2.75 (m, 1H), 2.63 (m, 1H), 2.39 (m, 1H), 2.18-2.03 (m, 2H), 2.01 (m, 2H), 1.86 (m, 1H), 0.83 (m, 6H).

Example HU

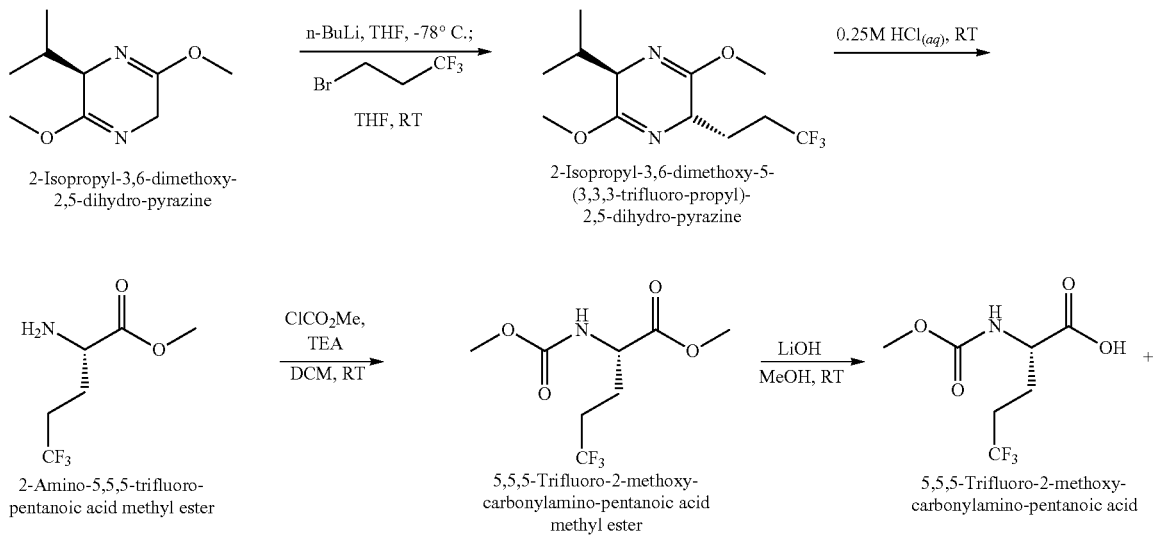

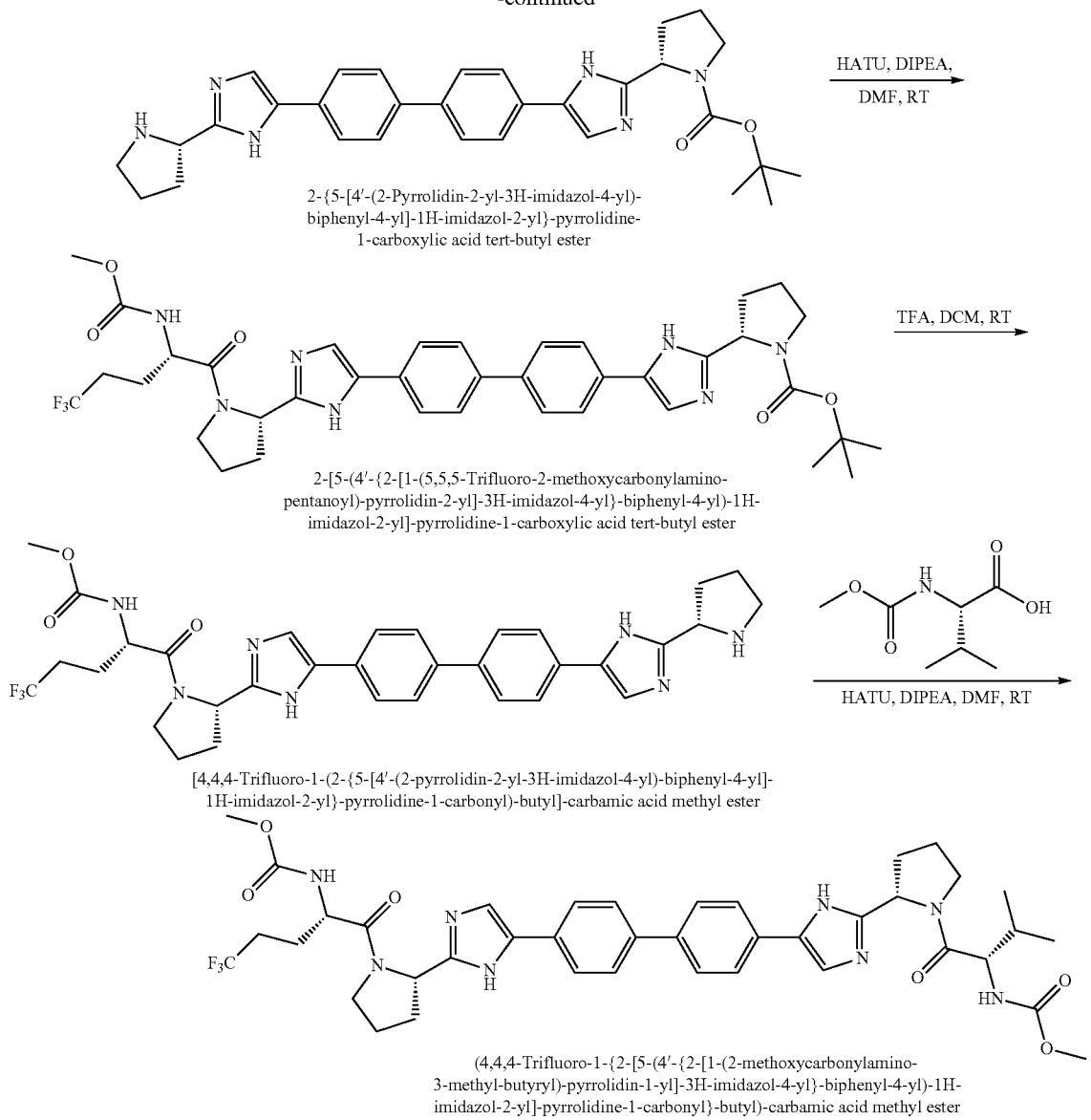

2-{5-[4'-(2-Pyrrolidin-2-yl-3H-imidazol-4-yl)-biphenyl-4-yl]-1H-imidazol-2-yl}-pyrrolidine-1-carboxylic acid tert-butyl ester 2-[5-(4'-{2-[1-(5,5,5-Trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carboxylic acid tert-butyl ester

[4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester (4,4,4-Trifluoro-1-{2-[5-(4'-{2-[1-(2-methoxycarbonylamino-3-methyl-butyryl)-pyrrolidin-1-yl]-3H-imidazol-4-yl}-biphenyl-4-yl)-1H-imidazol-2-yl]-pyrrolidine-1-carbonyl}-butyl)-carbamic acid methyl ester 2-Isopropyl-3,6-dimethoxy-5-(3,3,3-trifluoro-propyl)-2,5-dihydro-pyrazine To a stirred solution of 2-isopropyl-3,6-dimethoxy-2,5-dihydro-pyrazine (1 mL, 5.58 mmol) in THF (13.5 mL) under argon at −78° C. was added a solution of n-butyllithium (2.5 M, 2.3 mL, 5.75 mmol). The solution was stirred at −78° C. for 30 minutes. A solution of 1-Iodo-3,3,3-trifluoropropane (925 µL, 5.87 mmol) in THF (11.5 mL) was added slowly. The resulting solution was stirred at −78° C. for 5 hours, warmed to room temperature and diluted with ethyl acetate. The organic layer was washed successively with saturated aqueous NH$_4$Cl solution, water and brine. The organic layer was then dried (MgSO$_4$), concentrated and purified by flash chromatography to yield 2-Isopropyl-3,6-dimethoxy-5-(3,3,3-trifluoro-propyl)-2,5-dihydro-pyrazine (915 mg, 59%). $^1$H-NMR: 400 MHz, (CDCl$_3$) δ: 4.04-3.99 (m, 1H), 3.98-3.95 (m, 1H), 3.71 (s, 3H), 3.68 (s, 3H), 2.29-2.20 (m, 1H), 2.18-2.04 (m, 3H), 1.94-1.84 (m, 1H), 1.03 (d, J=6.9 Hz, 3H), 0.71 (d, J=6.8 Hz, 3H) ppm.

5,5,5-Trifluoro-2-methoxycarbonylamino-pentanoic acid methyl ester

A solution of 2-Isopropyl-3,6-dimethoxy-5-(3,3,3-trifluoro-propyl)-2,5-dihydro-pyrazine (725 mg, 2.59 mmol) in 0.25N HCl was stirred at room temperature for 3 hours. The aqueous solution was washed once with ethyl acetate. The ethyl acetate rinsing was discarded and the aqueous layer was basified to pH-10 with saturated aqueous NaHCO$_3$. The aqueous layer was extracted twice with ethyl acetate. The combined organics were washed with brine, dried (MgSO$_4$) and concentrated to give crude (2S)-amino-5,5,5-trifluoro-pentanoic acid methyl ester contaminated with D-valine methyl ester. The crude material was dissolved in dichloromethane (20 mL) and cooled to 0° C. Triethylamine (1.75 mL, 12.6 mmol) and methyl chloroformate (480 µL, 6.2 mmol) were successively added to the solution. After 1 hour the reaction was concentrated and purified by flash chromatography to yield 5,5,5-Trifluoro-2-methoxy-carbonylamino-pentanoic acid methyl ester (465 mg, 74%). $^1$H-NMR: 400 MHz, (CDCl$_3$) δ: 5.27 (br, 1H), 4.42 (br, 1H), 3.79 (s, 3H), 3.70 (s, 3H), 2.29-2.09 (m, 3H), 1.94-1.84 (m, 1H) ppm.

2-[5-(4'-{2-[1-(5,5,5-Trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carboxylic acid tert-butyl ester To a solution of 5,5,5-Trifluoro-2-methoxycarbonylamino-pentanoic acid methyl ester (194 mg, 0.80 mmol) in methanol (3 mL) was added an aqueous LiOH solution (1M, 2 mL, 2 mmol). The resulting solution was stirred at room temperature for 45 minutes and then washed with ethyl acetate. The ethyl acetate washing was discarded and the aqueous layer was acidified with concentrated HCl. The acidified aqueous layer was extracted twice with ethyl acetate. The combined organics were washed with brine, dried (MgSO$_4$), and concentrated to give clean 5,5,5-Trifluoro-2-methoxy-carbonylamino-pentanoic acid. To a solution of the pentanoic acid in dimethylformamide (2 mL) was added HATU (300 mg, 0.79 mmol). After stirring for 5 minutes, a solution of 2-{5-[4'-(2-pyrrolidin-2-yl-3H-imidazol-4-yl)-biphenyl-4-yl]-1H-imidazol-2-yl}-pyrrolidine-1-carboxylic acid tert-butyl ester (412 mg, 0.79 mmol) in dimethylformamide (1.9 mL) was added to the reaction, followed immediately by diisopropylethylamine (275 µL, 1.58 mmol). The reaction was stirred for 1 hour at room temperature then diluted with ethyl acetate. The organic layer was washed with water and brine, dried (MgSO$_4$), concentrated and purified by flash chromatography to yield 2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carboxylic acid tert-butyl ester (340 mg, 59%). LCMS-ESI$^+$: calculated for C$_{38}$H$_{44}$F$_3$N$_7$O$_5$: 735.34; observed [M+1]$^+$: 736.05.

[4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester To a solution of 2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carboxylic acid tert-butyl ester (340 mg, 0.46 mmol) in dichloromethane (5 mL) was added trifluoroacetic acid (1 mL) The reaction was stirred at room temperature for 3 hours and then thoroughly concentrated. The resulting residue was dissolved in dichloromethane and washed three times with saturated aqueous NaHCO$_3$ solution. The organic layer was dried (MgSO$_4$), and concentrated to give the crude free pyrrolidine (270 mg, 92%), which was clean enough to use without further purification. LCMS-ESI$^+$: calculated for C$_{33}$H$_{36}$F$_3$N$_7$O$_3$: 635.28; observed [M+1]$^+$: 636.17.

(4,4,4-Trifluoro-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester To a solution of crude [4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester (125 mg, 0.20 mmol) in dimethylformamide (0.6 mL) was added a solution of 2-methoxycarbonylamino-3-methyl-butyric acid (38 mg, 0.22 mmol) and HATU (82 mg, 0.22 mmol) in dimethylformamide (0.6 mL). Diisopropylethylamine (70 µL, 0.40 mmol) was then added and the reaction was stirred at room temperature for 16 hours. The solution was concentrated and purified by preparative reverse phase HPLC (Gemini, 15 to 50% ACN/H$_2$O+0.1% HCO$_2$H) to yield (4,4,4-trifluoro-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester (73 mg, 47%). LCMS-ESI$^+$: calculated for C$_{40}$H$_{47}$F$_3$N$_8$O$_6$: 792.85; observed [M+1]$^+$: 794.33. $^1$H-NMR: 400 MHz, (CD$_3$OD) δ: 7.82-7.70 (m, 4H), 7.68-7.63 (m, 4H), 7.32-7.31 (m, 2H), 5.20-5.16 (m, 2H), 4.56-4.51 (m, 1H), 4.26-4.22 (m, 1H), 4.04-3.96 (m, 1H), 3.91-3.84 (m, 2H), 3.67 (s, 3H), 3.66 (s, 3H), 3.51-3.46 (m, 1H), 2.38-1.96 (m, 12H), 1.90-1.78 (m, 1H), 1.01-0.89 (m, 6H) ppm.

Example HV

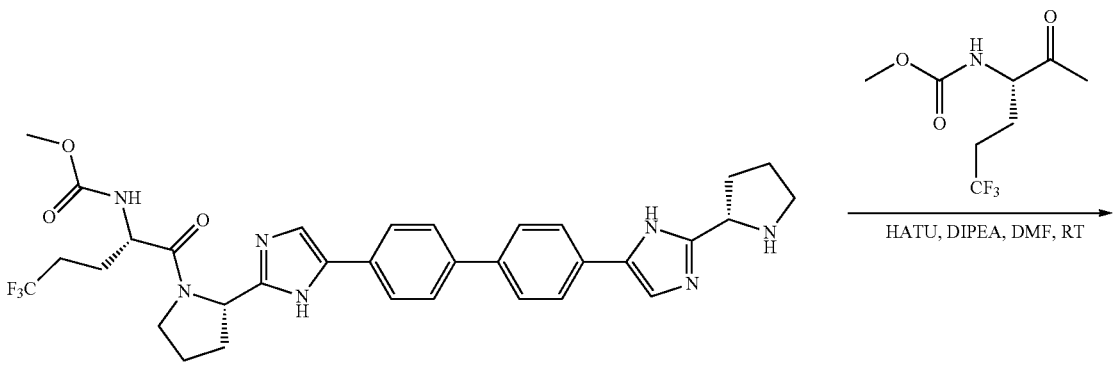

[4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester

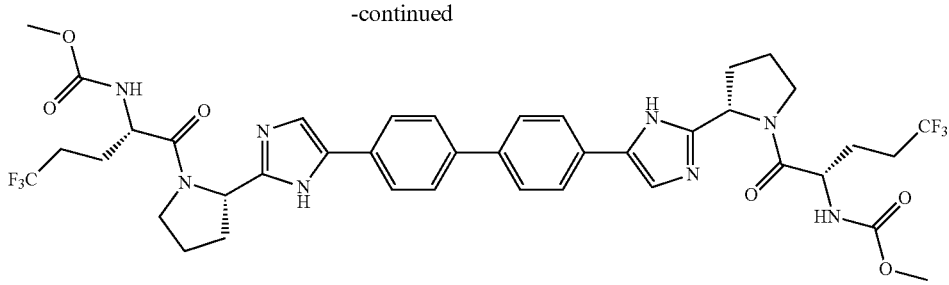

(4,4,4-Trifluoro-1-{2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester

(4,4,4-Trifluoro-1-{2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester To a solution of crude [4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester (115 mg, 0.18 mmol) in dimethylformamide (0.5 mL) was added a solution of 5,5,5-Trifluoro-2-methoxycarbonylamino-pentanoic acid (44 mg, 0.19 mmol) and HATU (72 mg, 0.19 mmol) in dimethylformamide (0.5 mL). Diisopropylethylamine (65 µL, 0.37 mmol) was then added and the reaction was stirred at room temperature for 16 hours. The solution was concentrated and purified by preparative reverse phase HPLC (Gemini, 15 to 50% ACN/H$_2$O+0.1% HCO$_2$H) to yield (4,4,4-Trifluoro-1-{2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester (35 mg, 23%). LCMS-ESI$^+$: calculated for C$_{40}$H$_{44}$F$_6$N$_8$O$_6$: 846.82; observed [M+1]$^+$: 847.34.

$^1$H-NMR: 400 MHz, (CD$_3$OD) δ: 7.81-7.72 (m, 4H), 7.67-7.64 (m, 4H), 7.38-7.32 (m, 2H), 5.20-5.16 (m, 2H), 4.55-4.51 (m, 2H), 3.91-3.86 (m, 4H), 3.67 (s, 6H), 2.38-2.20 (m, 8H), 2.18-1.79 (m, 8H) ppm.

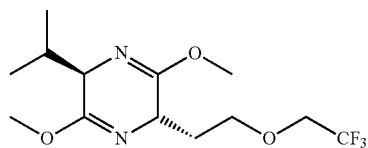

2-Isopropyl-3,6-dimethoxy-5-[2-(2,2,2-trifluoro-ethoxy)-ethyl]-2,5-dihydro-pyrazine

2-Isopropyl-3,6-dimethoxy-5-[2-(2,2,2-trifluoro-ethoxy)-ethyl]-2,5-dihydro-pyrazine This compound was made in 65% yield by the same procedure as 2-Isopropyl-3,6-dimethoxy-5-(3,3,3-trifluoro-propyl)-2,5-dihydro-pyrazine, substituting 1-Iodo-3,3,3-trifluoropropane with 2-(2-Bromoethoxy)-1,1,1-trifluoroethane.
$^1$H-NMR: 400 MHz, (CDCl$_3$) δ: 4.11-4.05 (m, 1H), 3.95 (t, J=3.5 Hz, 1H), 3.86-3.75 (m, 3H), 3.74-3.66 (m, 7H), 2.30-2.18 (m, 2H), 1.92-1.82 (m, 1H), 1.03 (d, J=6.9 Hz, 3H), 0.70 (d, J=6.8 Hz, 3H) ppm.

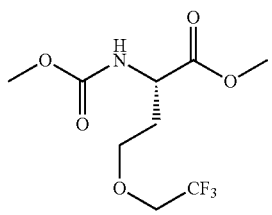

2-Methoxycarbonylamino-4-(2,2,2-trifluoro-ethoxy)-butyric acid methyl ester

2-Methoxycarbonylamino-4-(2,2,2-trifluoro-ethoxy)-butyric acid methyl ester

This compound was made by the same procedure as 5,5,5-Trifluoro-2-methoxycarbonylamino-pentanoic acid methyl ester, using 2-Isopropyl-3,6-dimethoxy-5-[2-(2,2,2-trifluoro-ethoxy)-ethyl]-2,5-dihydropyrazine as the starting material. $^1$H-NMR: 400 MHz, (CDCl$_3$) δ: 5.51-5.43 (br, 1H), 4.51-4.43 (m, 1H), 3.83-3.63 (m, 10H), 2.22-2.13 (m, 1H), 2.13-2.03 (m, 1H) ppm.

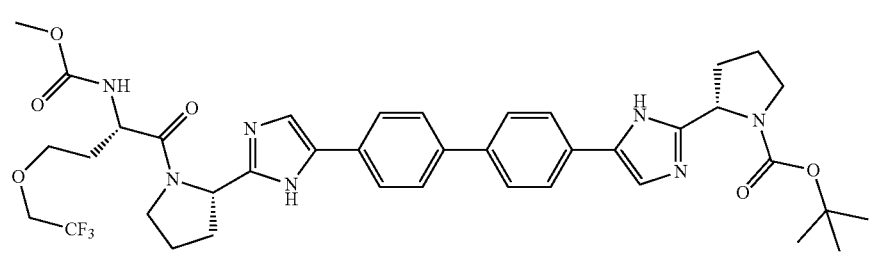

2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carboxylic acid tert-butyl ester

2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carboxylic acid tert-butyl ester This compound was made in 74% yield by the same procedure as 2-[5-(4'-{2-[1-(5,5,5-Trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carboxylic acid tert-butyl ester, using 2-Methoxycarbonylamino-4-(2,2,2-trifluoro-ethoxy)-butyric acid methyl ester as the starting material. LCMS-ESI$^+$: calculated for $C_{39}H_{46}F_3N_7O_6$: 765.35; observed [M+1]$^+$: 766.12.

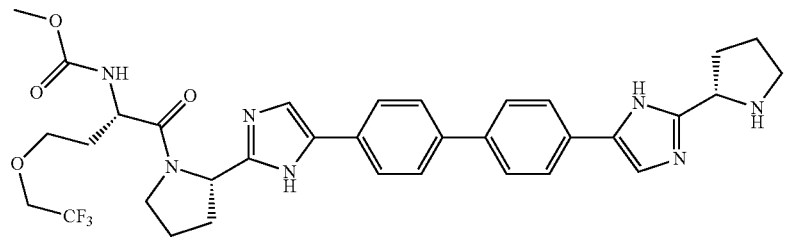

[1-(2-{5-[4'-(2-Pyrrolidin-2-yl-3H-imidazol-4-yl)-biphenyl-4-yl]-1H-imidazol-2-yl}-pyrrolidine-1-carbonyl)-3-(2,2,2-trifluoro-ethoxy)-propyl]-carbamic acid methyl ester

[1-(2-{5-[4'-(2-Pyrrolidin-2-yl-3H-imidazol-4-yl)-biphenyl-4-yl]-1H-imidazol-2-yl}-pyrrolidine-1-carbonyl)-3-(2,2,2-trifluoroethoxy)-propyl]-carbamic acid methyl ester This compound was made by the same procedure as [4,4,4-Trifluoro-1-(2-{5-[4'-(2-pyrrolidin-2-yl-3H-imidazol-4-yl)-biphenyl-4-yl]-1H-imidazol-2-yl}-pyrrolidine-1-carbonyl)-butyl]-carbamic acid methyl ester, using 2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carboxylic acid tert-butyl ester as the starting material. LCMS-ESI$^+$: calculated for $C_{34}H_{38}F_3N_7O_4$: 665.29; observed [M+1]$^+$: 666.20.

Example HW

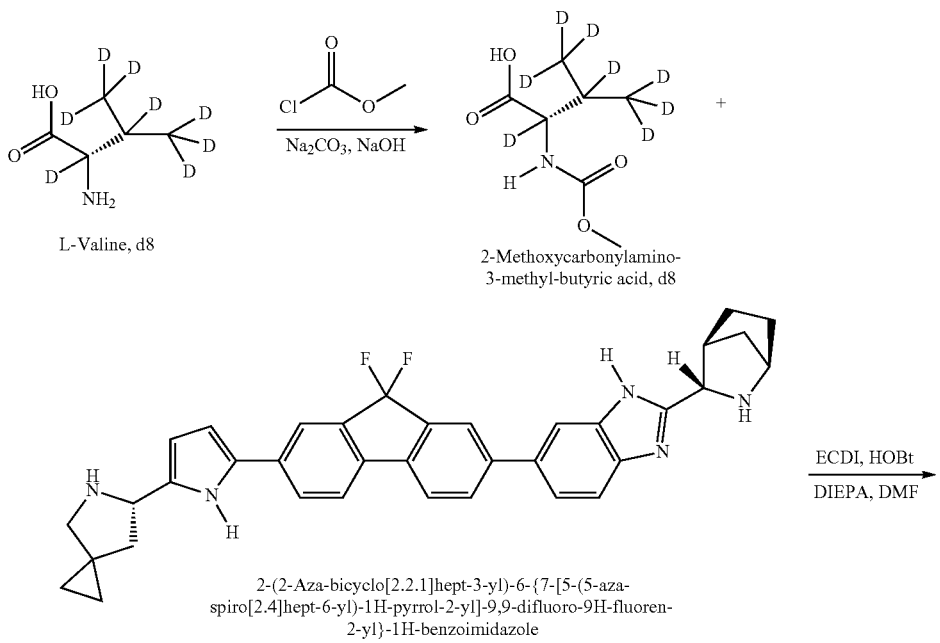

-continued

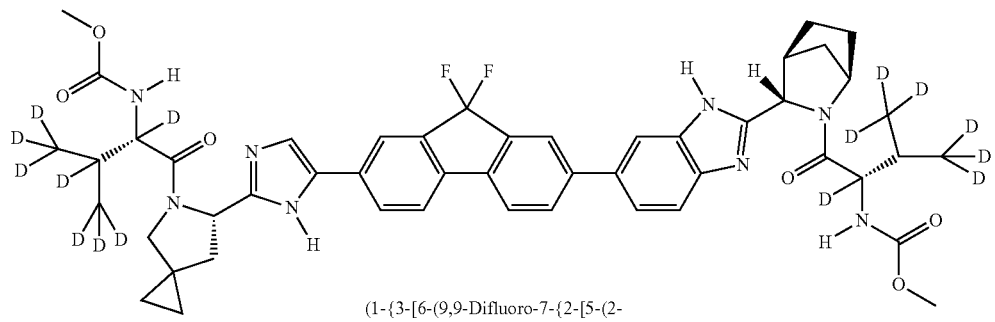

(1-{3-[6-(9,9-Difluoro-7-{2-[5-(2-methoxycarbonylamino-3-methyl-butyryl, d8)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester,d8

To a solution of L-valine, d8 (Cambridge Isotope Laboratories, 0.4949 g) in 1N sodium hydroxide (3.95 mL) was added sodium carbonate (0.419 g). The solution was cooled to 0° C. and methyl chloroformate (0.289 mL) was added dropwise over 30 minutes and reaction mixture was stirred for 3 h at 0° C. Reaction mixture was washed with ethyl ether (3×15 mL) and aqueous layer was acidified to pH=1 with concentrated HCl. Aqueous layer was extracted dichloromethane (3×15 mL) and organic layers were dried (MgSO$_4$) and concentrated to give 2-Methoxycarbonylamino-3-methyl-butyric acid, d8 as a white solid (0.5681 g).

LCMS-ESI$^-$: calc'd for $C_7H_5D_8NO_4$: 184.2 (M+H$^+$); Found: 184.0 (M+H$^+$).

A solution of hydroxybenzotriazole (0.242 g), 1-(3-dimethylaminepropyl)-3-ethylcarbodiimide-HCl (0.328 g) and 2-Methoxycarbonylamino-3-methyl-butyric acid, d8 (0.315 g) in DMF (5.0 mL) was stirred at rt for 1 hr. Reaction mixture was cooled to 0° C. and a solution of 2-(2-Aza-bicyclo[2.2.1]hept-3-yl)-6-{7-[5-(5-aza-spiro[2.4]hept-6-yl)-1H-pyrrol-2-yl]-9,9-difluoro-9H-fluoren-2-yl}-1H-benzoimidazole in DMF (2.0 mL) was added, followed by dropwise addition of diisopropylethylamine over 15 min. Reaction mixture was warmed to rt overnight, diluted with ethyl acetate and washed with brine, brine/saturated sodium bicarbonate solution (1:1) and aqueous layers back-extracted with ethyl acetate. The combined organic layer was dried (MgSO$_4$), concentrated and purified by flash column chromatography (silica gel, 0 to 5% methanol/ethyl acetate), then and purified by preparative reverse phase HPLC (Gemini, 25 to 100% ACN/H$_2$O+0.1% TFA). The product-containing fractions were pooled and treated with saturated sodium bicarbonate solution at 0° C. for 1 h. Product was extracted with ethyl acetate (2×), combined organic layer was dried (MgSO$_4$), concentrated and lyophilized from ACN/H$_2$O to give (1-{3-[6-(9,9-Difluoro-7-{2-[5-(2-methoxycarbonylamino-3-methyl-butyryl, d8)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester,d8 as a white powder (0.3947)

$^1$H-NMR: 300 MHz, (DMSO-d$_6$) δ: 12.13 (s, 1H), 11.77 (s, 1H), 8.1-7.1 (m, 12H), 7.23 (s, 1H), 7.14 (s, 1H), 5.2-5.1 (m, 1H), 4.60 (d, J=4.5 Hz, 1H), 4.48 (s, 1H), 3.8-3.6 (m, 2H), 3.48 (s, 6H), 2.60 (s, 1H), 2.40-2.01 (m, 10H), 0.64-0.52 (m, 4H).

LCMS-ESI$^+$: calc'd for $C_{49}H_{38}D_{16}F_2N_8O_6$: 906.1 (M+H$^+$); Found: 905.6 (M+H$^+$).

Example HX

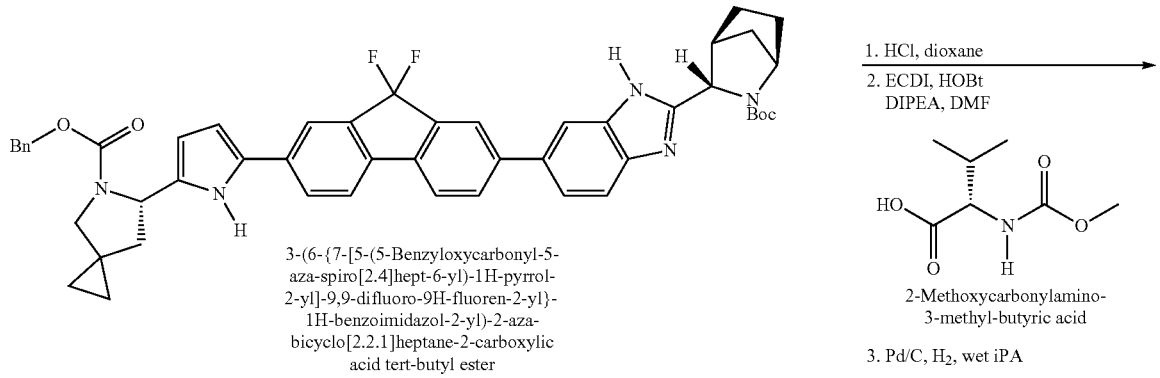

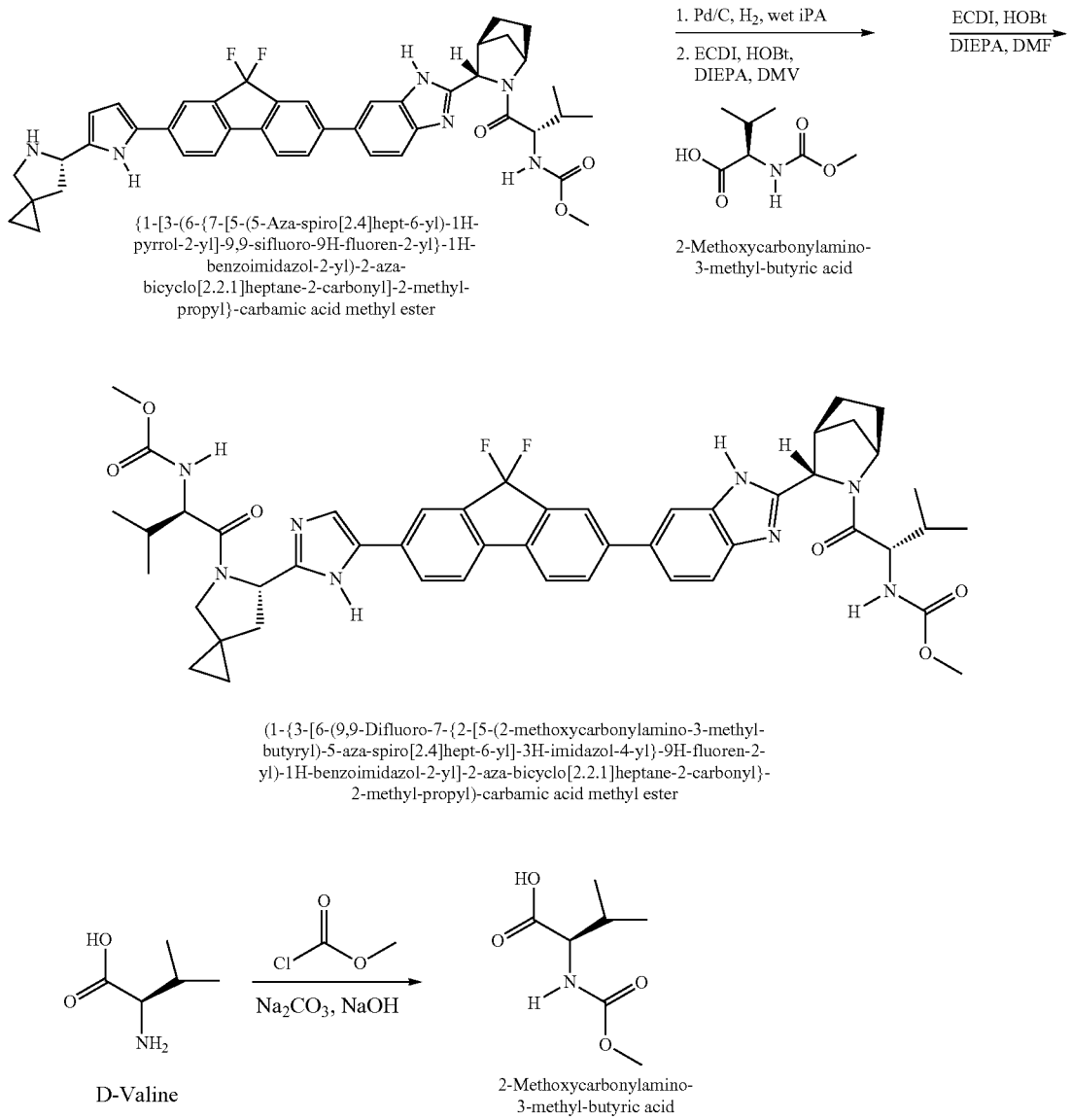

To a solution of 3-(6-{7-[5-(5-Benzyloxycarbonyl-5-aza-spiro[2.4]hept-6-yl)-1H-pyrrol-2-yl]-9,9-difluoro-9H-fluoren-2-yl}-1H-benzoimidazol-2-yl)-2-aza-bicyclo[2.2.1]heptane-2-carboxylic acid tert-butyl ester (1.0 g), in CH₂Cl₂ (10 mL) at 0° C. was added 4 N HCl in dioxane (2.0 mL). Reaction mixture was stirred at 0° C. for 5 minutes, then warmed to rt. After stirring for 1.5 h, reaction mixture was concentrated and dried overnight under vacuum to give an off-white powder (0.8826 g). Powder was suspended in ethyl acetate and saturated sodium bicarbonate solution and stirred for 1 h. Aqueous layer was extracted with ethyl acetate (2×), dried (MgSO₄), and concentrated. A portion of this residue was used in the next step. A solution of hydroxybenzotriazole (40 mg), 1-(3-dimethylaminepropyl)-3-ethylcarbodiimide-HCl (57 mg) and 2-Methoxycarbonylamino-3-methyl-butyric acid (54 mg) in DMF (0.5 mL) and CH₂Cl₂ (0.5 mL) was stirred at 0° C. for 1 hr. This solution was added to a solution the above amine (150 mg) in DMF (0.5 mL) and CH₂Cl₂ (0.5 mL) at −20° C. and stirred at this temperature overnight. Reaction mixture was diluted with ethyl acetate and washed with brine, brine/saturated sodium bicarbonate solution (1:1) and aqueous layers back-extracted with ethyl acetate. The combined organic layer was dried (MgSO₄), concentrated and purified by flash column chromatography (silica gel, 0 to 5% methanol/ethyl acetate) to 6-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2- yl)-1H-pyrrol-2-yl]-5-aza-spiro[2.4]heptane-5-carboxylic acid benzyl ester as a yellow foam (127 mg).

LCMS-ESI+: calc'd for C50H49F2N7O5: 865.96 (M+H+); Found: 866.3 (M+H+).

A mixture of 6-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-pyrrol-2-yl]-5-aza-spiro[2.4]heptane-5-carboxylic acid benzyl ester (127 mg) and 10% palladium on carbon, wet (29 mg) in ethanol (4 mL) was stirred under an hydrogen atmosphere for 18 h. Added more and 10% palladium on carbon, wet (50 mg) and continued reaction for 30 h. Reaction mixture was filtered through a pad of CELITE, concentrated and purified by flash column chromatography (silica gel, 5 to 20% methanol/dichloromethane) to give {1-[3-(6-{7-[5-(5-Aza-spiro[2.4]hept-6-yl)-1H-pyrrol-2-yl]-9,9-difluoro-9H-fluoren-2-yl}-1H-benzoimidazol-2-yl)-2-aza-bicyclo[2.2.1]heptane-2-carbonyl]-2-methyl-propyl}-carbamic acid methyl ester as a pale yellow film (21 mg).

LCMS-ESI+: calc'd for C42H43F2N7O3: 732.8 (M+H+); Found: 732.4 (M+H+).

A solution of hydroxybenzotriazole (5.4 mg), 1-(3-dimethylaminepropyl)-3-ethylcarbodiimide-HCl (7.7 mg) and 2-Methoxycarbonylamino-3-methyl-butyric acid (7.0 mg) in DMF (0.2 mL) and CH2Cl2 (0.2 mL) was stirred at 0° C. for 1 hr. This solution was added to a solution {1-[3-(6-{7-[5-(5-Aza-spiro[2.4]hept-6-yl)-1H-pyrrol-2-yl]-9,9-difluoro-9H-fluoren-2-yl}-1H-benzoimidazol-2-yl)-2-aza-bicyclo[2.2.1]heptane-2-carbonyl]-2-methyl-propyl}-carbamic acid methyl ester (21 mg) in DMF (0.4 mL) and CH2Cl2 (0.4 mL) at −25° C. and stirred at this temperature overnight. Reaction mixture was diluted with ethyl acetate and washed with brine, brine/saturated sodium bicarbonate solution (1:1) and aqueous layers back-extracted with ethyl acetate. The combined organic layer was dried (MgSO4), concentrated and purified by preparative reverse phase HPLC (Gemini, 25 to 100% ACN/H2O+0.1% TFA). The product-containing fractions were pooled, diluted with ethyl acetate and treated with saturated sodium bicarbonate solution at for 1 h. Product was extracted with ethyl acetate (2×), combined organic layer was dried (MgSO4), concentrated and lyophilized from ACN/H2O to (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester as a white powder (11.8 mg)

1H-NMR: 300 MHz, (DMSO-d6) δ: 12.18 (s, 1H), 12.05 (s 0.5H), 11.48 (s, 0.5H), 8.1-7.1 (m, 10H), 5.75 (d, J=4.5 Hz, 0.5H), 5.190 (d, J=4.5 Hz, 0.5H), 4.63 (d, J=4.8 Hz, 1H), 4.54 (s, 1H), 4.12-4.0 (m, 2H), 3.8-3.2 (m, 9H), 2.65 (s, 1H), 2.40-2.01 (m, 27H).

LCMS-ESI+: calc'd for C49H54F2N8O6: 890.0 (M+H+); Found: 889.4 (M+H+).

To a solution of d-valine, (5.0 g) in 1N sodium hydroxide (42.7 mL) was added sodium carbonate (4.53 g). The solution was cooled to 0° C. and methyl chloroformate (0.289 mL) was added dropwise over 2 h and reaction mixture was stirred for 2 h at 0° C. White reaction mixture was diluted with enough H2O to form a colorless solution and washed with ethyl ether (3×30 mL). Aqueous layer was acidified to pH=2 with concentrated HCl to give a white precipitate that collected by filtration, washed with H2O and dried under high vacuum to give 2-Methoxycarbonylamino-3-methyl-butyric acid as a crystalline white solid (4.668 g). LCMS-ESI−: calc'd for C7H13NO4: 176.2 (M+H+); Found: 175.9 (M+H+).

Example HY

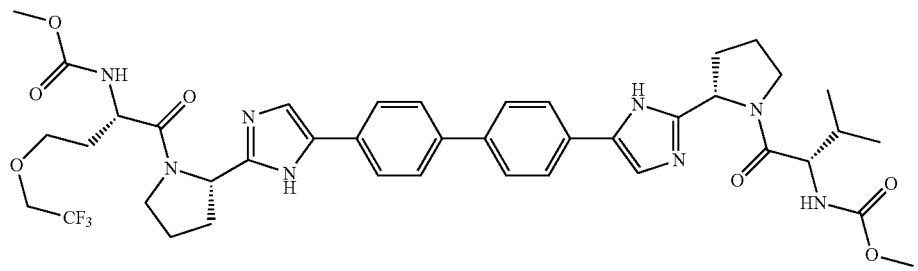

[1-(2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carbonyl)-2-methyl-propyl]-carbamic acid methyl ester

[1-(2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carbonyl)-2-methyl-propyl]-carbamic acid methyl ester This compound was made in 45% yield by the same procedure as (4,4,4-Trifluoro-1-{2-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester, using [1-(2-{5-[4'-(2-Pyrrolidin-2-yl-3H-imidazol-4-yl)-biphenyl-4-yl]-1H-imidazol-2-yl}-pyrrolidine-1-carbonyl)-3-(2,2,2-trifluoroethoxy)-propyl]-carbamic acid methyl ester as the starting material. LCMS-ESI+: calculated for C41H49F3N8O7: 822.87; observed [M+1]+: 823.45. 1H-NMR: 400 MHz, (CD3OD) δ: 7.82-7.72 (m, 4H), 7.69-7.65 (m, 4H), 7.38-7.32 (m, 2H), 5.22-5.16 (m, 2H), 4.65-4.61 (m, 1H), 4.26-4.21 (m, 1H), 4.04-3.84 (m, 6H), 3.72-3.48 (m, 8H), 2.39-1.98 (m, 10H), 1.88-1.78 (m, 1H), 1.01-0.89 (m, 6H) ppm.

Example HZ

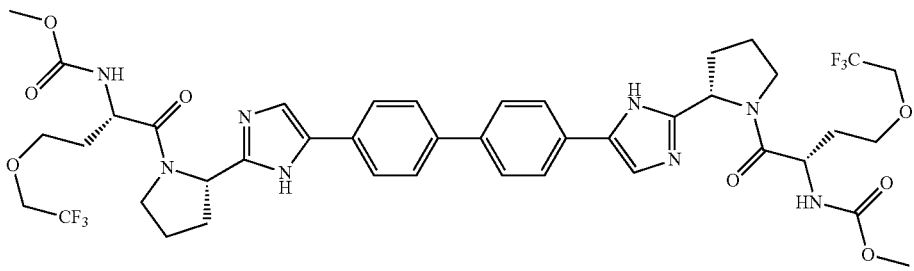

[1-(2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carbonyl)-3-(2,2,2-trifluoro-ethoxy)-propyl]-carbamic acid methyl ester

[1-(2-{5-[4'-(2-{1-[2-Methoxycarbonylamino-4-(2,2,2-trifluoro-ethoxy)-butyryl]-pyrrolidin-2-yl}-3H-imidazol-4-yl)-biphenyl-4-yl]-1H-imidazol-2-yl}-pyrrolidine-1-carbonyl)-3-(2,2,2-trifluoro-ethoxy)-propyl]-carbamic acid methyl ester This compound was made in 27% yield by the same procedure as (4,4,4-Trifluoro-1-{2-[5-(4'-{2-[1-(5,5,5-trifluoro-2-methoxycarbonylamino-pentanoyl)-pyrrolidin-2-yl]-3H-imidazol-4-yl}-biphenyl-4-yl)-1H-imidazol-2-yl]-pyrrolidine-1-carbonyl}-butyl)-carbamic acid methyl ester, using [1-(2-{5-[4'-(2-Pyrrolidin-2-yl-3H-imidazol-4-yl)-biphenyl-4-yl]-1H-imidazol-2-yl}-pyrrolidine-1-carbonyl)-3-(2,2,2-trifluoroethoxy)-propyl]-carbamic acid methyl ester as the starting material. LCMS-ESI[+]: calculated for $C_{42}H_{48}F_6N_8O_8$: 906.87; observed [M+1][+]: 907.45. $^1$H-NMR: 400 MHz, (CD$_3$OD) δ: 7.73-7.65 (m, 4H), 7.62-7.59 (m, 4H), 7.38-7.35 (m, 2H), 5.14-5.10 (m, 2H), 4.55-4.51 (m, 2H), 3.86-3.77 (m, 8H), 3.63-3.43 (m, 10H), 2.34-2.24 (m, 2H), 2.22-1.87 (m, 8H), 1.86-1.68 (m, 2H) ppm.

Example IA

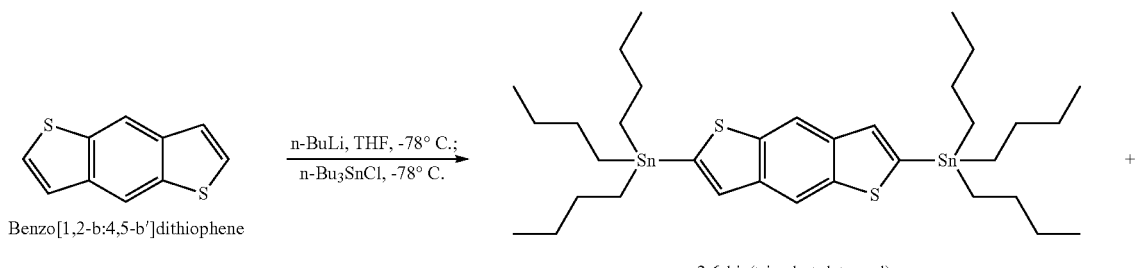

Benzo[1,2-b:4,5-b']dithiophene 2,6-bis(tri-n-butylstannyl)-benzo[1,2-b:4,5-b']dithiophene

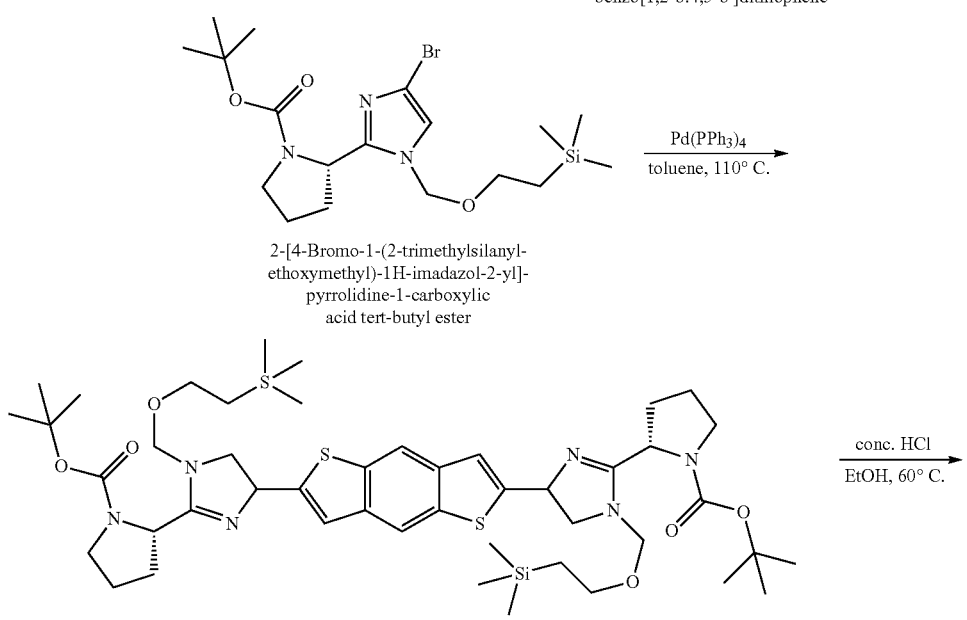

2-[4-Bromo-1-(2-trimethylsilanyl-ethoxymethyl)-1H-imadazol-2-yl]-pyrrolidine-1-carboxylic acid tert-butyl ester

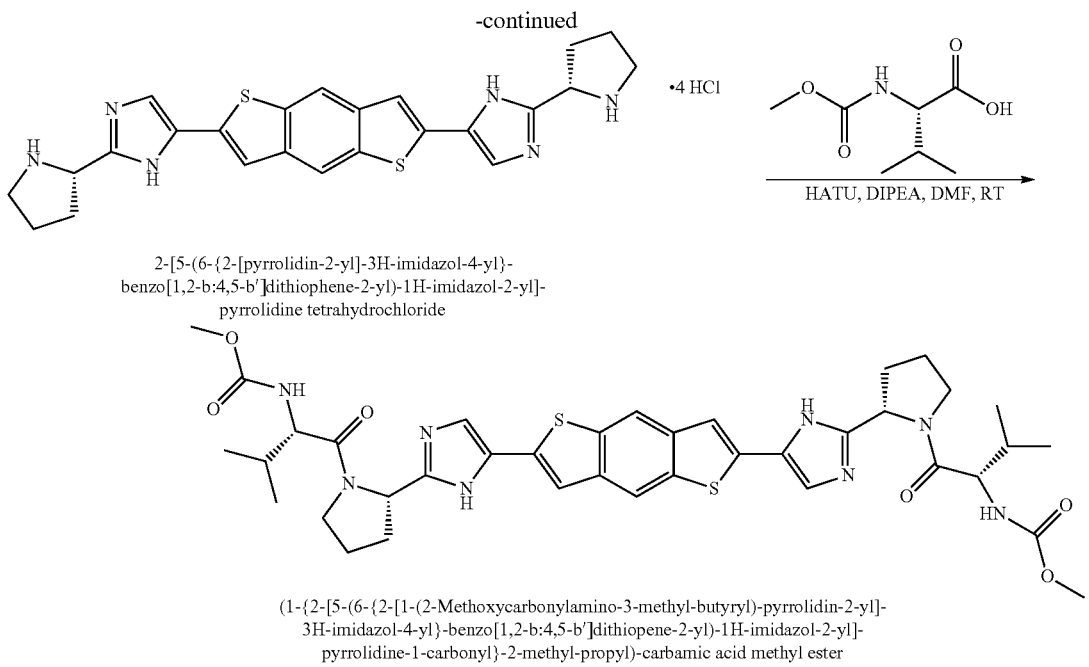

2-[5-(6-{2-[pyrrolidin-2-yl]-3H-imidazol-4-yl}-benzo[1,2-b:4,5-b']dithiophene-2-yl)-1H-imidazol-2-yl]-pyrrolidine tetrahydrochloride (1-{2-[5-(6-{2-[1-(2-Methoxycarbonylamino-3-methyl-butyryl)-pyrrolidin-2-yl]-3H-imidazol-4-yl}-benzo[1,2-b:4,5-b']dithiopene-2-yl)-1H-imidazol-2-yl]-pyrrolidine-1-carbonyl}-2-methyl-propyl)-carbamic acid methyl ester

2,6-Bis(tri-n-butylstannyl)-benzo[1,2-b:4,5-b']dithiophene

To a stirred solution of benzo[1,2-b:4,5-b']dithiophene (820 mg, 4.3 mmol) in THF (100 mL) under argon at −78° C. was added a solution of n-butyllithium (2.5 M, 3.44 mL, 8.6 mmol). The solution was stirred at −78° C. for 30 minutes and then warmed to −20° C. for 30 minutes. Tri-n-butyltin chloride (2.34 mL, 8.6 mmol) was added and the reaction mixture was stirred at −20° C. for 30 minutes and then allowed to warm to room temperature. After 16 hours, hexane was added and the reaction was successively washed with water and brine, dried (MgSO$_4$), concentrated and purified by flash chromatography (100% hexanes). 2,6-bis(tri-n-butylstannyl)-benzo[1,2-b:4,5-b']dithiophene (1.4 g, 42%) was isolated along with product contaminated with the monostannylated benzodithiophene. $^1$H-NMR: 400 MHz, (CDCl$_3$) δ: 8.27 (s, 2H), 7.38 (s, 2H), 1.65-1.57 (m, 12H), 1.41-1.32 (m, 12H), 1.26-1.11 (m, 12H), 0.91 (t, J=7.3 Hz, 18H) ppm.

Fully protected 2-[5-(6-{2-[pyrrolidin-2-yl]-3H-imidazol-4-yl}-benzo[1,2-b:4,5-b']dithiophene-2-yl)-1H-imidazol-2-yl]-pyrrolidine Pd(PPh$_3$)$_4$ (61 mg, 0.053 mmol) was added to a degassed solution of 2,6-bis(tri-n-butylstannyl)-benzo[1,2-b:4,5-b']dithiophene (202 mg, 0.26 mmol) and 2-[4-Bromo-1-(2-trimethylsilanyl-ethoxymethyl)-1H-imidazol-2-yl]-pyrrolidine-1-carboxylic acid tert-butyl ester (260 mg, 0.58 mmol) in toluene (4 mL). The reaction was refluxed for 24 hours, then cooled to room temperature and filtered through CELITE and a palladium scavenging column (Stratospheres™ PL-Guanidine MP SPE+, Part #: PL3514-CM89). The solids were rinsed twice with toluene. The filtrate was concentrated and the crude product purified by flash chromatography to yield the desired, fully protected product (100 mg, 41%). LCMS-ESI$^+$: calculated for C$_{46}$H$_{68}$N$_6$O$_6$S$_2$Si$_2$: 920.42; observed [M+1]$^+$ : 921.45.

(1-{2-[5-(6-{2-[1-(2-Methoxycarbonylamino-3-methyl-butyryl)-pyrrolidin-2-yl]-3H-imidazol-4-yl}-benzo[1,2-b:4,5-b]dithiophene-2-yl)-1H-imidazol-2-yl]-pyrrolidine-1-carbonyl}-2-methyl-propyl)-carbamic acid methyl ester A solution of fully protected 2-[5-(6-{2-[pyrrolidin-2-yl]-3H-imidazol-4-yl}-benzo[1,2-b:4,5-b']dithiophene-2-yl)-1H-imidazol-2-yl]-pyrrolidine (100 mg, 0.11 mmol), ethanol (4 mL) and concentrated HCl (1 mL) was heated to 60° C. for 16 hours. The reaction was concentrated and the crude material dissolved in DCM (10 mL). This solution was concentrated to yield crude 2-[5-(6-{2-[pyrrolidin-2-yl]-3H-imidazol-4-yl}-benzo[1,2-b:4,5-b']dithiophene-2-yl)-1H-imidazol-2-yl]-pyrrolidine tetrahydrochloride. To this material was added a solution of 2-methoxycarbonylamino-3-methylbutyric acid (38 mg, 0.22 mmol) and HATU (83 mg, 0.22 mmol) in DMF (1.5 mL). To the resulting solution was added diisopropylethylamine (190 μL, 1.1 mmol). After stirring for 2 hours at room temperature, the reaction was concentrated and purified twice by preparative reverse phase HPLC (Gemini, 10 to 45% ACN/H$_2$O+0.1% HCO$_2$H). The product fractions were passed through a freebasing column (STRATOSPHERES™ PL-HCO$_3$ MP SPE, Part #: PL3540-C603) and lyophilized to give (1-{2-[5-(6-{2-[1-(2-methoxycarbonylamino-3-methyl-butyryl)-pyrrolidin-2-yl]-3H-imidazol-4-yl}-benzo[1,2-b:4,5-b']dithiophene-2-yl)-1H-imidazol-2-yl]-pyrrolidine-1-carbonyl}-2-methyl-propyl)-carbamic acid methyl ester (29 mg, 34%). LCMS-ESI$^+$: calculated for C$_{38}$H$_{46}$N$_8$O$_6$S$_2$: 774.95; observed [M+1]$^+$: 775.96. $^1$H-NMR: 400 MHz, (CD$_3$OD) δ: 8.16-8.11 (m, 2H), 7.49-7.47 (m, 2H), 7.38-7.29 (m, 2H), 5.18-5.15 (m, 2H), 4.24 (d, J=7.4 Hz, 2H), 4.04-3.96 (m, 2H), 3.91-3.86 (m, 2H), 3.66 (br s, 6H), 2.38-2.17 (m, 6H), 2.11-1.98 (m, 4H), 1.00-0.89 (m, 12H) ppm.

Example IB

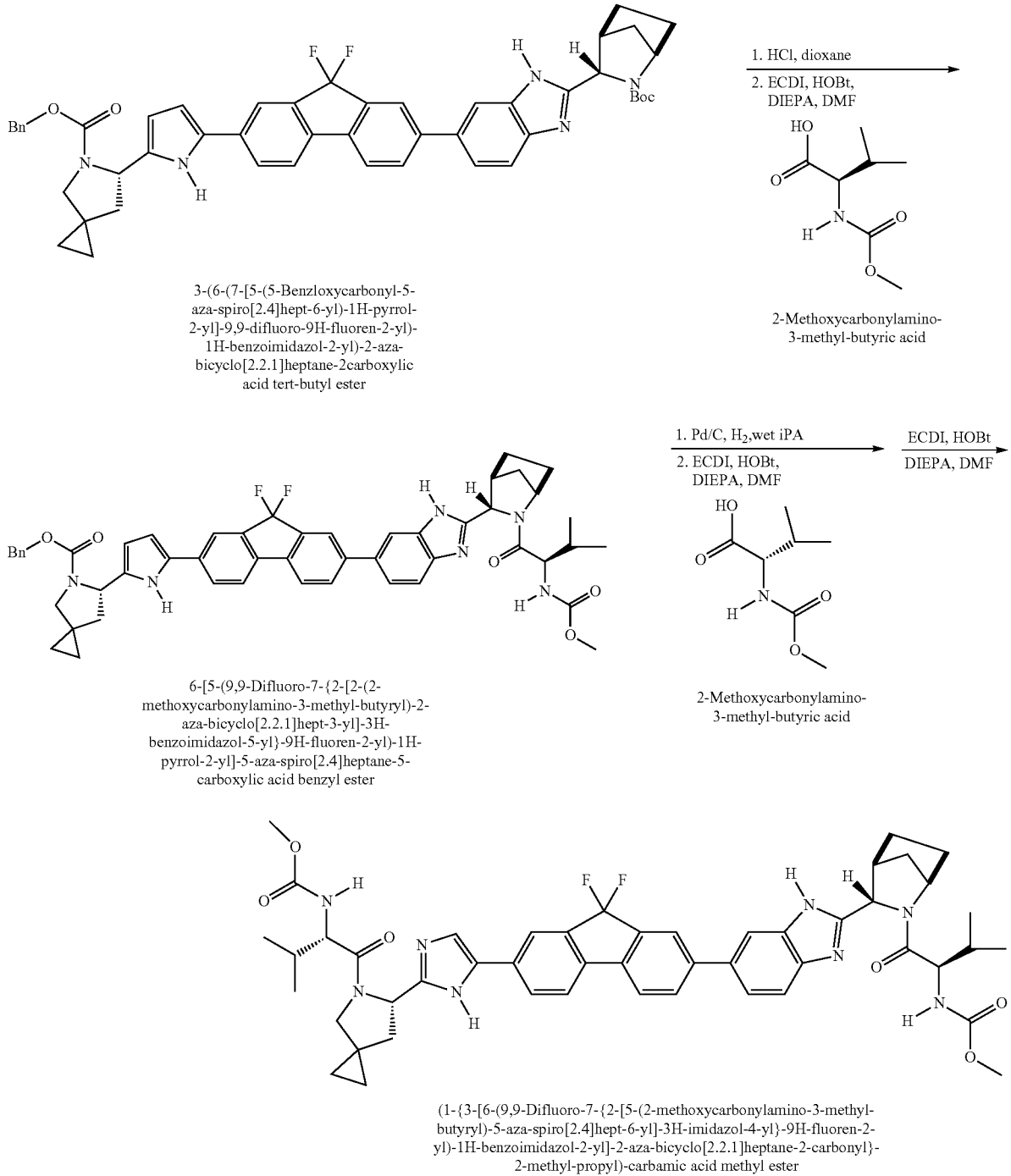

3-(6-(7-[5-(5-Benzloxycarbonyl-5-aza-spiro[2.4]hept-6-yl)-1H-pyrrol-2-yl]-9,9-difluoro-9H-fluoren-2-yl)-1H-benzoimidazol-2-yl)-2-aza-bicyclo[2.2.1]heptane-2carboxylic acid tert-butyl ester 2-Methoxycarbonylamino-3-methyl-butyric acid 6-[5-(9,9-Difluoro-7-{2-[2-(2-methoxycarbonylamino-3-methyl-butyryl)-2-aza-bicyclo[2.2.1]hept-3-yl]-3H-benzoimidazol-5-yl}-9H-fluoren-2-yl)-1H-pyrrol-2-yl]-5-aza-spiro[2.4]heptane-5-carboxylic acid benzyl ester 2-Methoxycarbonylamino-3-methyl-butyric acid (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester was prepared in a similar manner as Example B to give title compound as a white powder (88.9 mg). $^1$H-NMR: 300 MHz, (DMSO-$d_6$) δ: 12.56 (d, J=13.5 Hz, 0.5H), 12.04 (d, J=17.1 Hz, 0.5H), 11.84 (s, 1H), 8.1-7.1 (m, 12H), 5.3-5.1 (m, 1H), 4.8-4.5 (m, 1H), 4.1-3.7 (m, 4H), 3.6-3.2 (m, 20H), 2.8-1.1 (m, 12H), 0.9-0.4 (m, 16H).

LCMS-ESI$^+$: calc'd for $C_{49}H_{54}F_2N_8O_6$: 890.0 (M+H$^+$); Found: 889.4 (M+H$^+$).

Example IC

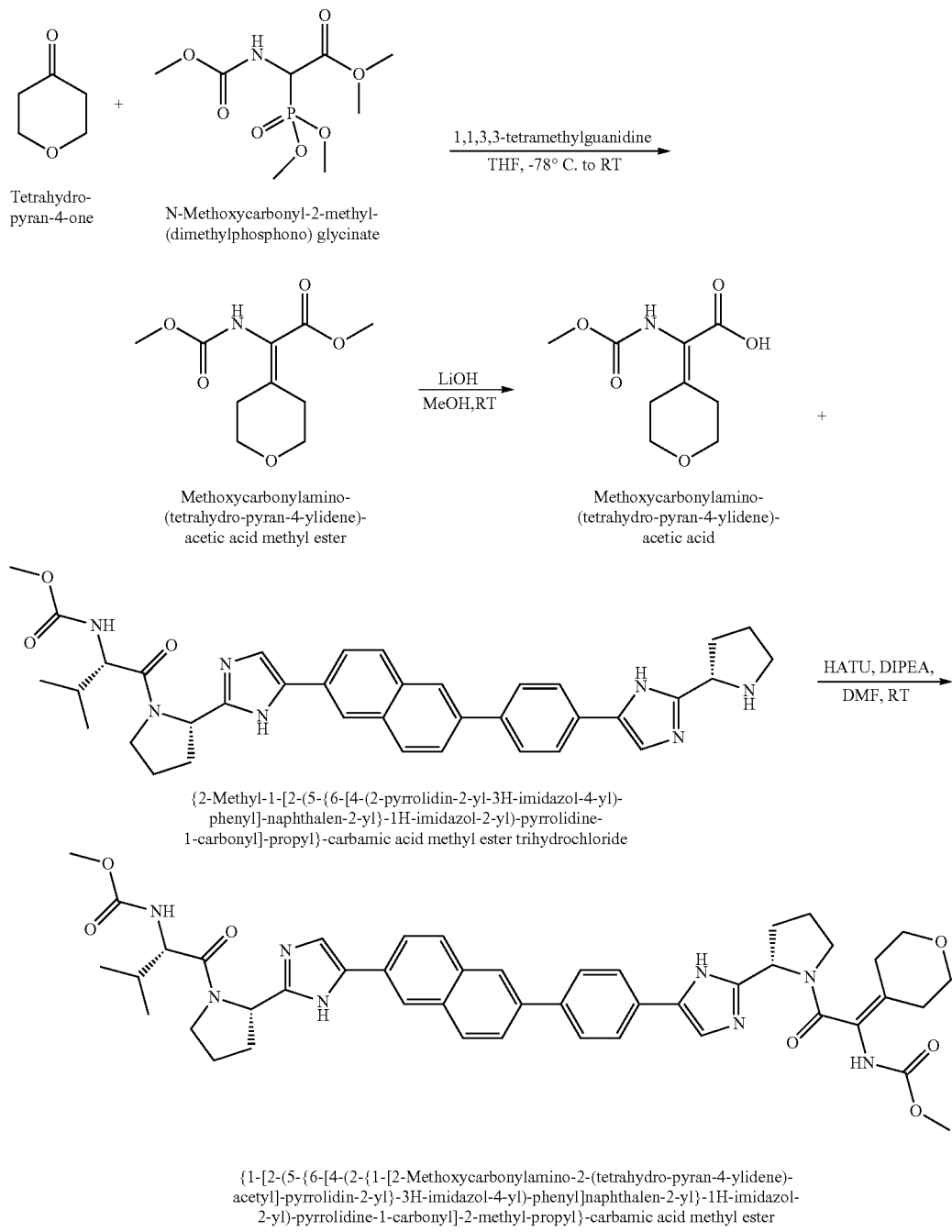

{2-Methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester trihydrochloride {1-[2-(5-{6-[4-(2-{1-[2-Methoxycarbonylamino-2-(tetrahydro-pyran-4-ylidene)-acetyl]-pyrrolidin-2-yl}-3H-imidazol-4-yl)-phenyl]naphthalen-2-yl}-1H-imidazol-2-yl)-pyrrolidine-1-carbonyl]-2-methyl-propyl}-carbamic acid methyl ester Methoxycarbonylamino-(tetrahydropyran-4-ylidene)-acetic acid methyl ester A solution of N-methoxycarbonyl-2-methyl-(dimethylphosphono)glycinate (1.45 g, 5.68 mmol) in tetrahydrofuran (22 mL) was cooled to −78° C. 1,1,3,3-Tetramethylguanidine (0.680 mL, 5.42 mmol) was added and the resulting solution was stirred at −78° C. for 30 minutes. Tetrahydropyran-4-one (0.500 mL, 5.42 mmol) was added and the reaction was stirred at −78° C. for 1 hour. The ice bath was removed and the reaction was allowed to warm to room temperature overnight. In the morning, the reaction was diluted with ethyl acetate. The organics were washed with 1N aqueous HCl and brine, dried (MgSO$_4$) and concentrated. The crude residue was purified by flash chromatography to yield methoxycarbonylamino-(tetrahydropyran-4-ylidene)-acetic acid methyl ester. $^1$H-NMR: 400 MHz, (CDCl$_3$) δ: 5.94 (br s, 1H), 3.80-3.74 (m, 7H), 3.71 (s, 3H), 2.95-2.91 (m, 2H), 2.45-2.41 (m, 2H) ppm.

{1-[2-(5-{6-[4-(2-{1-[2-Methoxycarbonylamino-2-(tetrahydropyran-4-ylidene)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester To a solution of methoxycarbonylamino-(tetrahydropyran-4-ylidene)-acetic acid methyl ester (141 mg, 0.62 mmol) in methanol (1.8 mL) was added an aqueous LiOH solution (1 M, 1.8 mL, 1.8 mmol). The resulting solution was stirred at room temperature for 16 hours and then washed with ethyl acetate. The ethyl acetate washing was discarded and the aqueous layer was acidified with concentrated HCl. The acidified aqueous layer was extracted twice with ethyl acetate. The combined organics were washed with brine, dried (MgSO$_4$), and concentrated to give methoxycarbonylamino-(tetrahydropyran-4-ylidene)-acetic acid. To a solution of methoxycarbonylamino-(tetrahydropyran-4-ylidene)-acetic acid (23 mg, 0.11 mmol) in dimethylformamide (0.6 mL) was added HATU (41 mg, 0.11 mmol). After stirring for 5 minutes, a solution of {2-methyl-1-[2-(5-{6-[4-(2-pyrrolidin-2-yl-3H-imidazol-4-yl)-phenyl]-naphthalen-2-yl}-1H-imidazol-2-yl)-pyrrolidine-1-carbonyl]-propyl}-carbamic acid methyl ester trihydrochloride (50 mg, 0.068 mmol) in dimethylformamide (0.6 mL) was added to the reaction, followed immediately by diisopropylethylamine (85 µL, 0.49 mmol). The reaction was stirred for 1 hour at room temperature then diluted with ethyl acetate. The organic layer was washed successively with saturated aqueous NaHCO$_3$ solution, water and brine, dried (MgSO$_4$), concentrated and purified by preparative reverse phase HPLC (Gemini, 15 to 50% ACN/H$_2$O+0.1% HCO$_2$H) to yield {1-[2-(5-{6-[4-(2-{1-[2-methoxycarbonylamino-2-(tetrahydropyran-4-ylidene)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (28 mg, 50%).

LCMS-ESI$^+$: calculated for C$_{46}$H$_{52}$N$_8$O$_7$: 828.95; observed [M+1]$^+$: 830.32. $^1$H-NMR: 400 MHz, (CD$_3$OD) δ: 8.24-8.07 (m, 3H), 7.96-7.76 (m, 7H), 7.45-7.34 (m, 2H), 5.28-5.18 (m, 2H), 4.27-4.23 (m, 1H), 4.05-3.98 (m, 1H), 3.94-3.86 (m, 1H), 3.84-3.41 (m, 12H), 2.48-1.98 (m, 13H), 1.02-0.90 (m, 6H) ppm.

Example ID

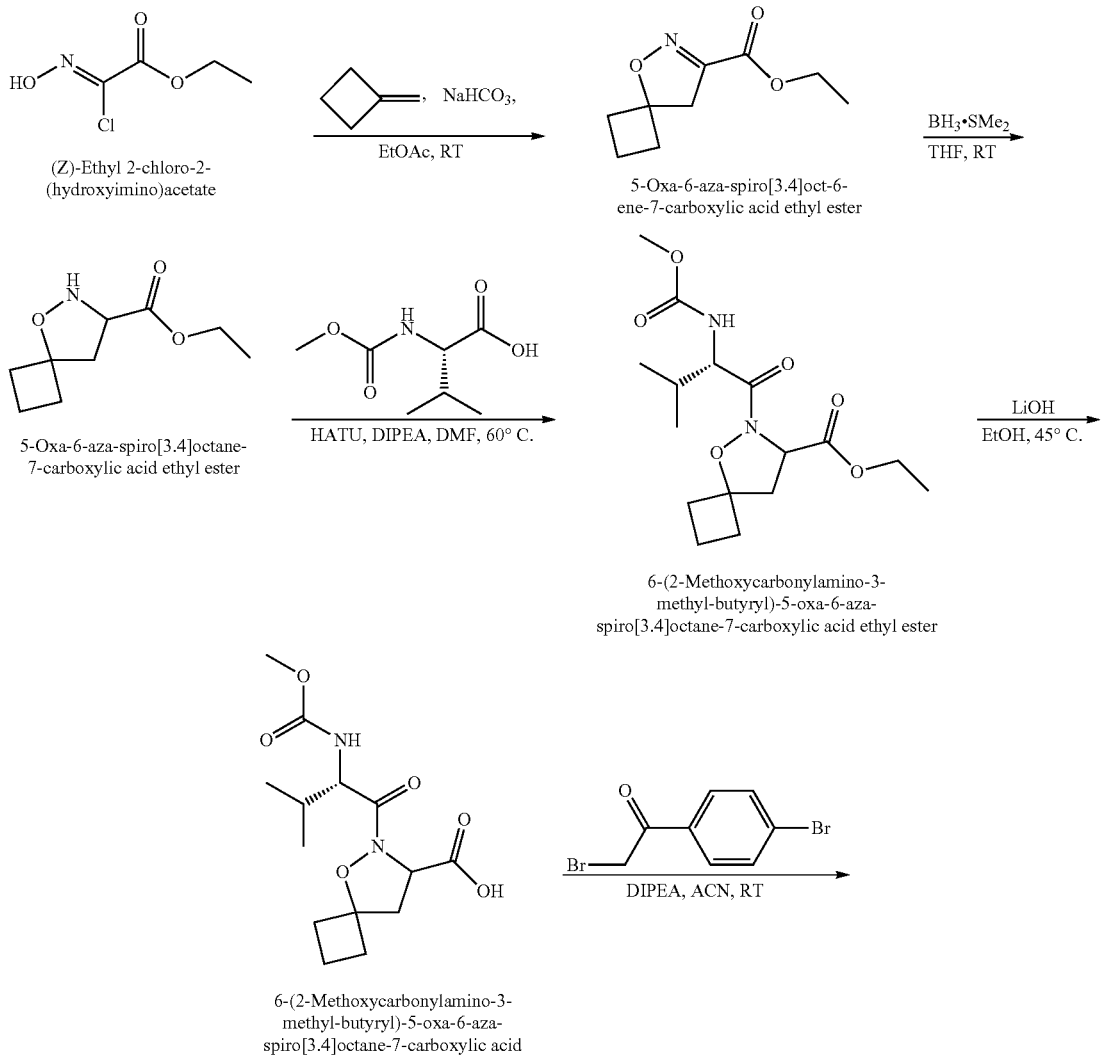

-continued

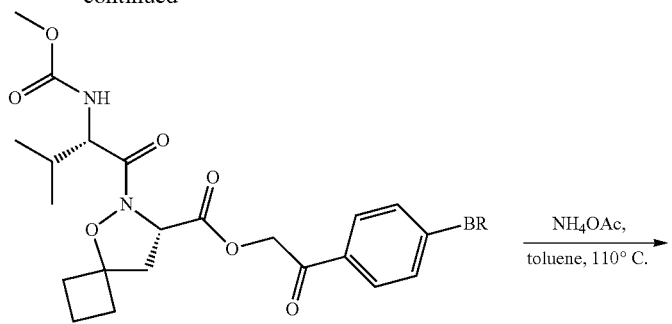

6-(2-Methoxycarbonylamino-3-methyl-butyryl)-
5-oxa-6-aza-spiro[3.4]octane-7-carboxylic acid 2-
(4-bromo-phenyl)-2-oxo-ethyl ester

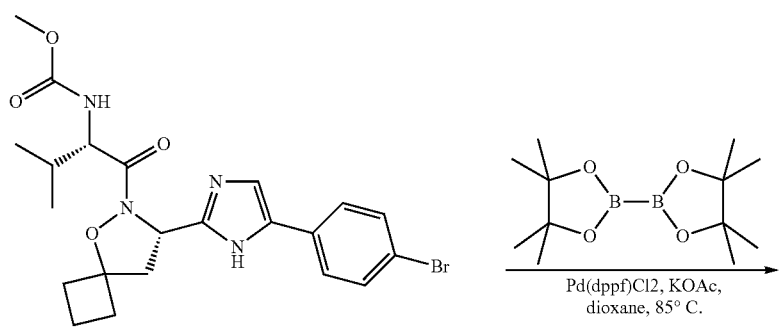

(1-{7-[5-(4-Bromo-phenyl)-1H-imidazol-2yl]-
5-oxa-6-aza-spiro[3.4]octane-6-carbonyl}-2-
methyl-propyl)-carbamic acid methyl ester

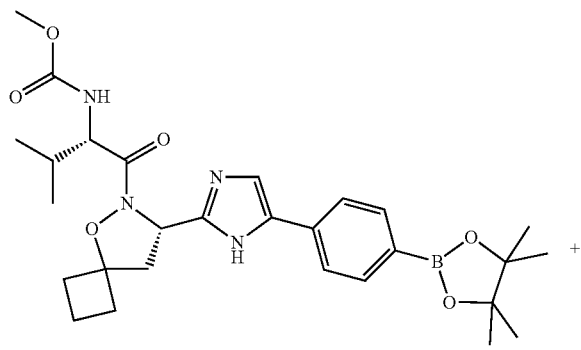

[2-Methyl-1-(7-{5-[4-(4,4,5,5-tetramethyl-
[1,3,2]dioxaborolan-2-yl)-phenyl]-1H-imidazol-2-yl}-
5-oxa-6-aza-spiro[3.4]octane-6-carbonyl)-
propyl]-carbamic acid methyl ester

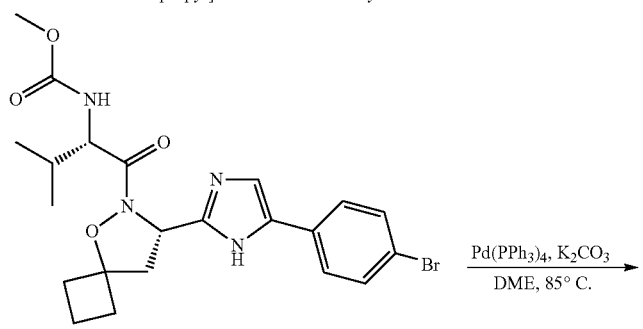

(1-{7-[5-(4-Bromo-phenyl)-1H-imidazol-2-yl]-
5-oxa-6-aza-spiro[3.4]octane-6-carboyl}-2-
methyl-propyl)-carbamic acid methyl ester

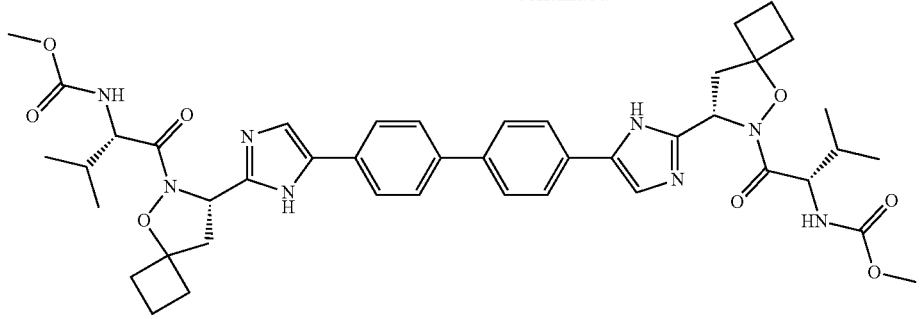

(1-{7-[5-(4'-{2-[6-(2-Methoxycarbonylamino-3methyl-butyrl)-5-oxa-6-aza-spiro[3.4]oct-7-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester

5-Oxa-6-aza-spiro[3.4]oct-6-ene-7-carboxylic acid ethyl ester

To a solution of methylenecyclobutane (2 mL, 21.6 mmol) in ethyl acetate (125 mL) was added (Z)-ethyl 2-chloro-2-(hydroxyimino)acetate (6.55 g, 43.2 mmol) and solid sodium bicarbonate (16.3 g, 194 mmol). The reaction mixture was sealed and stirred at room temperature for 6 hours. More (Z)-ethyl 2-chloro-2-(hydroxyimino)acetate (4 g, 26.4 mmol) and sodium bicarbonate (8 g, 95.2 mmol) were added and the reaction was stirred at room temperature for an additional 12 hours. The reaction was diluted with ethyl acetate and washed successively with water and brine, dried (MgSO$_4$) and concentrated to yield crude 5-oxa-6-aza-spiro[3.4]oct-6-ene-7-carboxylic acid ethyl ester, contaminated with (Z)-Ethyl 2-chloro-2-(hydroxyimino)acetate and related compounds.

5-Oxa-6-aza-spiro[3.4]octane-7-carboxylic acid ethyl ester

To a solution of crude 5-oxa-6-aza-spiro[3.4]oct-6-ene-7-carboxylic acid ethyl ester (7.5 g, <40.9 mmol) in tetrahydrofuran (270 mL) at 0° C. was slowly added a solution of borane-dimethyl sulfide complex (10 M in THF, 16.4 mL, 164 mmol). The reaction was allowed to warm to room temperature overnight then recooled to 0° C., and quenched by the careful addition of water. The mixture was diluted with ethyl acetate, washed with water and brine, dried (MgSO$_4$), and concentrated to yield a large amount of white solids. These solids were thoroughly triturated three times with dichloromethane (150 mL). The combined dichloromethane washings were concentrated and the resulting oil was purified by flash chromatography to yield 5-oxa-6-aza-spiro[3.4]octane-7-carboxylic acid ethyl ester (1.08 g, 29% over 2 steps). $^1$H-NMR: 400 MHz, (CDCl$_3$) δ: 8.01-7.95 (br, 1H), 4.39-4.28 (m, 2H), 4.18-4.10 (m, 1H), 2.80-2.75 (m, 1H), 2.62-2.49 (m, 2H), 2.37-2.29 (m, 1H), 2.25-2.17 (m, 1H), 2.13-1.95 (m, 1H), 1.88-1.79 (m, 1H), 1.68-1.56 (m, 1H), 1.34 (t, J=7.1 Hz, 3H) ppm.

6-(2-Methoxycarbonylamino-3-methyl-butyryl)-5-oxa-6-aza-spiro[3.4]octane-7-carboxylic acid ethyl ester To a solution of 2-methoxycarbonylamino-3-methyl-butyric acid (1.11 g, 6.33 mmol) and HATU (2.41 g, 6.34 mmol) in dimethylformamide (13 mL) was added a solution of 5-oxa-6-aza-spiro[3.4]octane-7-carboxylic acid ethyl ester (980 mg, 5.3 mmol) in dimethylformamide (13 mL). To the resulting reaction mixture was added diisopropylethylamine (1.85 mL, 10.6 mmol) and the reaction was heated to 60° C. for 16 hours. The reaction was diluted with ethyl acetate, washed with water and brine, dried (MgSO$_4$) and concentrated. The resulting residue was purified by flash chromatography to give 6-(2-methoxycarbonylamino-3-methyl-butyryl)-5-oxa-6-aza-spiro[3.4]octane-7-carboxylic acid ethyl ester (1.31 g, 72%). LCMS-ESI$^+$: calculated for $C_{16}H_{26}N_2O_6$: 342.18; observed [M+1]$^+$: 342.90.

6-(2-Methoxycarbonylamino-3-methyl-butyryl)-5-oxa-6-aza-spiro[3.4]octane-7-carboxylic acid To a solution of 6-(2-methoxycarbonylamino-3-methyl-butyryl)-5-oxa-6-aza-spiro[3.4]octane-7-carboxylic acid ethyl ester (1.31 g, 3.83 mmol) in ethanol (10 mL) was added a solution of lithium hydroxide (1M in water, 7.6 mL, 7.6 mmol). The reaction was stirred at room temperature for 30 minutes. The reaction was partially concentrated and the resulting aqueous solution was washed with ethyl acetate. The ethyl acetate layer was discarded and the aqueous layer was acidified using concentrated HCl. The acidic aqueous layer was extracted twice with ethyl acetate. The combined organic layers were washed with brine, dried (MgSO$_4$) and concentrated to yield crude 6-(2-methoxycarbonylamino-3-methyl-butyryl)-5-oxa-6-aza-spiro[3.4]octane-7-carboxylic acid, which was used without further purification.

6-(2-Methoxycarbonylamino-3-methyl-butyryl)-5-oxa-6-aza-spiro[3.4]octane-7-carboxylic acid 2-(4-bromophenyl)-2-oxo-ethyl ester To a solution of 6-(2-methoxycarbonylamino-3-methyl-butyryl)-5-oxa-6-aza-spiro[3.4]octane-7-carboxylic acid (~3.83 mmol) and 2,4'-dibromoacetophenone (1.1 g, 3.96 mmol) in acetonitrile (19 mL) was added diisopropylethylamine (1.32 mL, 7.59 mmol). The reaction was stirred at room temperature for 16 hours and was then diluted with ethyl acetate. The organics were washed with water and brine, dried (MgSO$_4$) and concentrated. The resulting crude residue was purified by flash chromatography, cleanly separating the two diastereomers of 6-(2-methoxycarbonylamino-3-methyl-butyryl)-5-oxa-6-aza-spiro[3.4]octane-7-carboxylic acid 2-(4-bromophenyl)-2-oxo-ethyl ester (330 mg of the (R) diastereomer, 360 mg of the (S) diastereomer, 35% total yield over 2 steps). $^1$H-NMR for the desired (S) diastereomer: 400

MHz, (CDCl$_3$) δ: 7.74-7.71 (m, 2H), 7.62-7.60 (m, 2H), 5.47 (d, J=16.4 Hz, 1H), 5.40-5.35 (m, 1H), 5.20 (d, J=16.4 Hz, 1H), 4.92 (dd, J$^1$=7.1 Hz, J$^2$=9.0 Hz, 1H), 4.74-4.70 (m, 1H), 3.65 (s, 3H), 2.84 (dd, J$^1$=9.0 Hz, J$^2$=12.6 Hz, 1H), 2.60 (dd, J$^1$=7.0 Hz, J$^2$=12.6 Hz, 1H), 2.52-2.12 (m, 5H), 2.07-1.86 (m, 2H), 1.75-1.65 (m, 1H), 1.01 (d, J=6.6 Hz, 3H), 0.89 (d, J=7.1 Hz, 3H) ppm.

(1-{7-[5-(4-Bromo-phenyl)-1H-imidazol-2-yl]-5-oxa-6-aza-spiro[3.4]octane-6-carbonyl}-2-methyl-propyl)-carbamic acid methyl ester To a solution of 6-(2-methoxycarbonylamino-3-methyl-butyryl)-5-oxa-6-aza-spiro[3.4]octane-7-carboxylic acid 2-(4-bromophenyl)-2-oxo-ethyl ester (150 mg, 0.29 mmol) in toluene (3 mL) was added ammonium acetate (230 mg, 3.0 mmol). The reaction mixture was vigorously refluxed for 3 hours, cooled to room temperature and diluted with ethyl acetate. The organics were washed with water and brine, dried (MgSO$_4$), and concentrated. The crude residue was purified by flash chromatography to yield (1-{7-[5-(4-bromophenyl)-1H-imidazol-2-yl]-5-oxa-6-aza-spiro[3.4]octane-6-carbonyl}-2-methyl-propyl)-carbamic acid methyl ester (95 mg, 66%). LCMS-ESI$^+$: calculated for C$_{22}$H$_{27}$BrN$_4$O$_4$: 490.12/492.12; observed [M+1]$^+$: 490.99/492.99. $^1$H-NMR: 400 MHz, (CDCl$_3$) δ: 7.60-7.55 (m, 2H), 7.50-7.46 (m, 2H), 7.26 (s, 1H), 5.38-5.29 (m, 2H), 4.76-4.70 (br, 1H), 3.70 (s, 3H), 3.36-3.29 (m, 1H), 2.84 (dd, J$^1$=8.2 Hz, J$^2$=12.5 Hz, 1H), 2.51-2.32 (m, 3H), 2.13-2.03 (m, 2H), 2.00-1.89 (m, 1H), 1.83-1.71 (m, 1H), 0.97 (d, J=6.7 Hz, 3H), 0.84 (d, J=6.8 Hz, 3H), ppm.

[2-Methyl-1-(7-{5-[4-(4,4,5,5-tetramethyl[1,3,2]dioxaborolan-2-yl)-phenyl]-1H-imidazol-2-yl}-5-oxa-6-azaspiro[3.4]octane-6-carbonyl)-propyl]-carbamic acid methyl ester A degassed mixture of (1-{7-[5-(4-bromophenyl)-1H-imidazol-2-yl]-5-oxa-6-aza-spiro[3.4]octane-6-carbonyl}-2-methyl-propyl)-carbamic acid methyl ester (85 mg, 0.17 mmol), bis(pinacolato)diboron (66 mg, 0.26 mmol), potassium acetate (51 mg, 0.52 mmol) and dichloro[1,1'-bis(diphenylphosphino)ferrocene]palladium(II) (13 mg, 0.018 mmol) in 1,4-dioxane (1.7 mL) was heated to 85° C. for 75 minutes. After cooling to room temperature, the reaction was filtered through a palladium scavenging column (STRATOSPHERES™ PL-Guanidine MP SPE+, Part #: PL3514-CM89) and the solids were rinsed with ethyl acetate. The filtrate was washed with water and brine, dried (MgSO$_4$), and concentrated. The crude residue was purified by flash chromatography to yield [2-methyl-1-(7-{5-[4-(4,4,5,5-tetramethyl[1,3,2]dioxaborolan-2-yl)-phenyl]-1H-imidazol-2-yl}-5-oxa-6-azaspiro[3.4]octane-6-carbonyl)-propyl]-carbamic acid methyl ester (81 mg, 87%). LCMS-ESI$^+$: calculated for C$_{28}$H$_{39}$BN$_4$O$_6$: 538.30; observed [M+1]$^+$: 539.12.

(1-{7-[5-(4'-{2-[6-(2-Methoxycarbonylamino-3-methyl-butyryl)-5-oxa-6-aza-spiro[3.4]oct-7-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester To a solution of [2-methyl-1-(7-{5-[4-(4,4,5,5-tetramethyl-[1,3,2]dioxaborolan-2-yl)-phenyl]-1H-imidazol-2-yl}-5-oxa-6-azaspiro[3.4]octane-6-carbonyl)-propyl]-carbamic acid methyl ester (81 mg, 0.15 mmol), (1-{7-[5-(4-bromophenyl)-1H-imidazol-2-yl]-5-oxa-6-aza-spiro[3.4]octane-6-carbonyl}-2-methyl-propyl)-carbamic acid methyl ester (60 mg, 0.12 mmol) and tetrakis(triphenylphosphine)palladium(0) (14 mg, 0.012 mmol) in 1,2-dimethoxyethane (2.0 mL) was added a solution of potassium carbonate (2M in water, 0.250 mL, 0.50 mmol). The resulting mixture was degassed for 15 minutes with a stream of argon and then heated to 85° C. for 3 hours. After cooling to room temperature, the reaction was filtered through a palladium scavenging column (STRATOSPHERES™ PL-Guanidine MP SPE+, Part #: PL3514-CM89) and the solids were rinsed with methanol. The filtrate was concentrated and purified by preparative reverse phase HPLC (Gemini, 15 to 51% ACN/H$_2$O+ 0.1% HCO$_2$H) to yield (1-{7-[5-(4'-{2-[6-(2-Methoxycarbonylamino-3-methyl-butyryl)-5-oxa-6-aza-spiro[3.4]oct-7-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester (26 mg, 26%). LCMS-ESI$^+$: calculated for C$_{44}$H$_{54}$N$_8$O$_8$: 822.41; observed [M+1]$^+$: 823.43. $^1$H-NMR: 400 MHz, (CD$_3$OD) δ: 7.78-7.75 (m, 4H), 7.68-7.65 (m, 4H), 7.38 (s, 2H), 6.94-6.89 (br, 2H), 5.47-5.42 (m, 2H), 4.74-4.68 (br, 2H), 3.66 (s, 6H), 3.00-2.94 (m, 2H), 2.78-2.71 (m, 2H), 2.61-2.53 (m, 2H), 2.49-2.40 (m, 2H), 2.38-2.30 (m, 2H), 2.22-2.09 (m, 4H), 2.00-1.90 (m, 2H), 1.84-1.75 (m, 2H), 0.98 (d, J=6.8 Hz, 6H), 0.88 (d, J=6.7 Hz, 6H) ppm.

Example IE

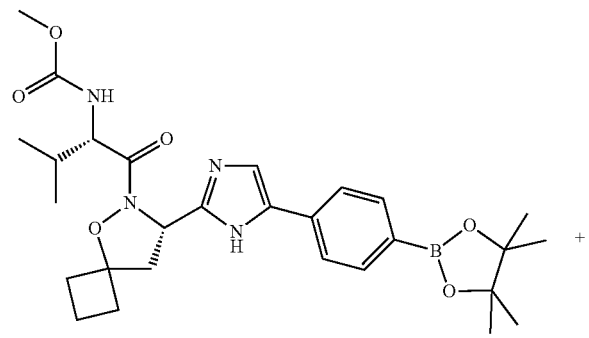

[2-Methyl-1-(7-{5-[4-(4,4,5,5-tetramethyl-[1.3.2]dioxaborlan-2-yl)-phenyl]-1H-imidazol-2-yl}-5-oxa-6-aza-spiro[3.4]octane-6-carbonyl)-propyl]-carbamic acid methyl ester -continued

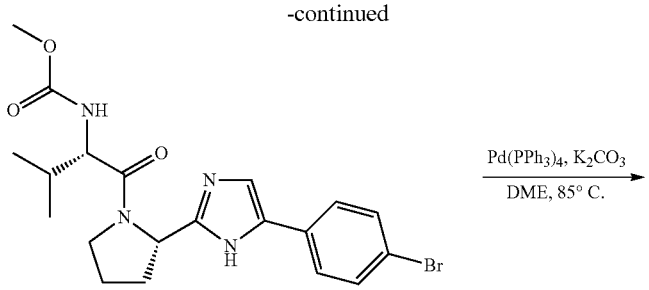

(1-{2-[5-(4-Bromo-phenyl)-1H-imidazol-2-yl]-pyrrolidine-1-carbonyl}-2-methyl-propyl)-carbamic acid methyl ester

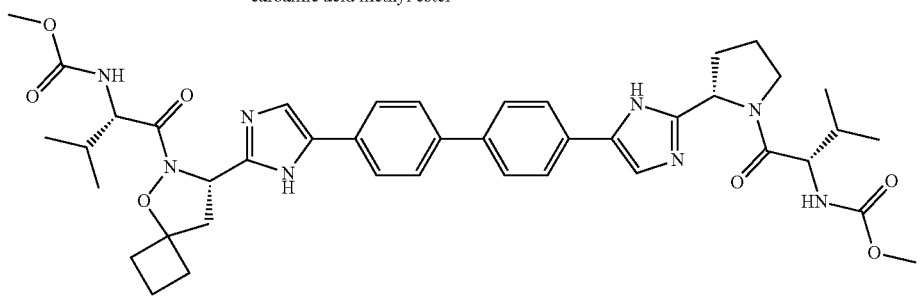

(1-{7-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester (1-{7-[5-(4'-{2-[1-(2-Methoxycarbonylamino-3-methyl-butyryl)-pyrrolidin-2-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester To a solution of [2-methyl-1-(7-{5-[4-(4,4,5,5-tetramethyl[1,3,2]dioxaborolan-2-yl)-phenyl]-1H-imidazol-2-yl}-5-oxa-6-azaspiro[3.4]octane-6-carbonyl)-propyl]-carbamic acid methyl ester (81 mg, 0.15 mmol), (1-{2-[5-(4-bromophenyl)-1H-imidazol-2-yl]-pyrrolidine-1-carbonyl}-2-methyl-propyl)-carbamic acid methyl ester (81 mg, 0.18 mmol) and tetrakis(triphenylphosphine)palladium(0) (18 mg, 0.015 mmol) in 1,2-dimethoxyethane (3.0 mL) was added a solution of potassium carbonate (2M in water, 0.300 mL, 0.60 mmol). The resulting mixture was degassed for 15 minutes with a stream of argon and then heated to 85° C. for 3 hours. After cooling to room temperature, the reaction was filtered through a palladium scavenging column (STRATOSPHERES™ PL-Guanidine MP SPE+, Part #: PL3514-CM89) and the solids were rinsed with methanol. The filtrate was concentrated and purified by flash chromatography (0%-5% methanol/dichloromethane). The resulting residue was repurified by preparative reverse phase HPLC (Gemini, 15 to 50% ACN/H$_2$O+0.1% HCO$_2$H) to yield (1-{7-[5-(4'-{2-[1-(2-methoxycarbonylamino-3-methyl-butyryl)-pyrrolidin-2-yl]-3H-imidazol-4-yl}-biphenyl-4-yl)-1H-imidazol-2-yl]-5-oxa-6-aza-spiro[3.4]octane-6-carbonyl}-2-methyl-propyl)-carbamic acid methyl ester (35 mg, 30%). LCMS-ESI$^+$: calculated for C$_{42}$H$_{52}$N$_8$O$_7$: 780.40; observed [M+1]$^+$: 781.29. $^1$H-NMR: 400 MHz, (CD$_3$OD) δ: 7.82-7.72 (m, 4H), 7.69-7.65 (m, 4H), 7.38 (s, 1H), 7.32 (s, 1H), 6.99-6.90 (m, 2H), 5.47-5.42 (m, 1H), 5.20-5.16 (m, 1H), 4.75-4.68 (m, 1H), 4.226-4.21 (m, 1H), 4.03-3.96 (m, 1H), 3.91-3.85 (m, 1H), 3.71-3.48 (m, 7H), 3.00-2.94 (m, 1H), 2.78-2.71 (m, 1H), 2.61-1.90 (m, 10H), 1.83-1.73 (m, 1H), 1.00-0.86 (m, 12H) ppm.

Example IF (S)-2-(methoxycarbonylamino)-2-(tetrahydro-2H-pyran-4-yl) acetic acid (3)

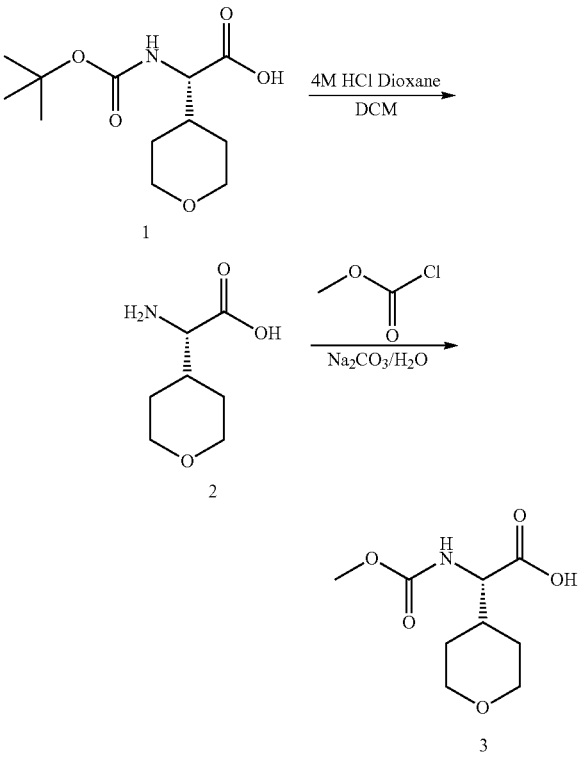

To (S)-2-(tert-butoxycarbonylamino)-2-(tetrahydro-2H-pyran-4-yl)acetic acid 1 (1.5 g, 5.8 mmol) in dichloromethane (5 mL) was added 4M HCl in dioxane (5 mL) and the reaction mixture was cooled to 0° C. and then stirred for 2 hours. After concentrated in vacuo to afford 2 To (S)-2-amino-2-(tetrahydro-2H-pyran-4-yl)acetic acid 2 (780 mg; 5 mmol) in water (25 ml) was added sodium carbonate (1.06 g; 10 mmol), and the resultant mixture was cooled to 0 .deg. C. and then methyl chloroformate (0.53 ml; 5.5 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford 3a colorless residue. MS (ESI) m/z: 218 [M+H]$^+$.

4

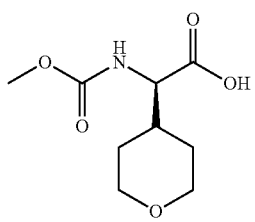

5

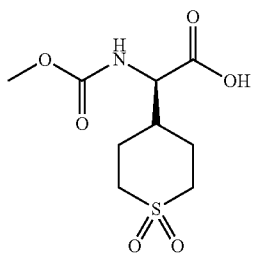

6

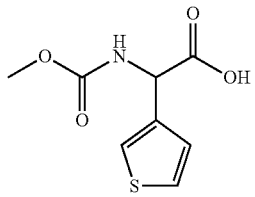

7

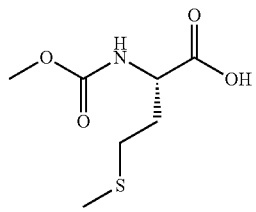

8

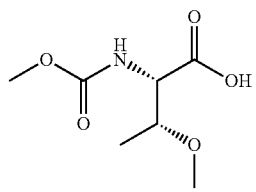

9

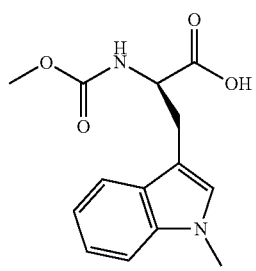

10

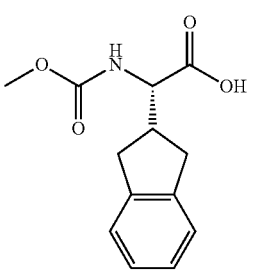

Compounds 4-10 were prepared according to the method employed to prepare ((S)-2-(methoxycarbonylamino)-2-(tetrahydro-2H-pyran-4-yl)acetic acid (3)

(S)-2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(tetrahydro-2H-pyran-4-yl)ethylcarbamic acid methyl ester

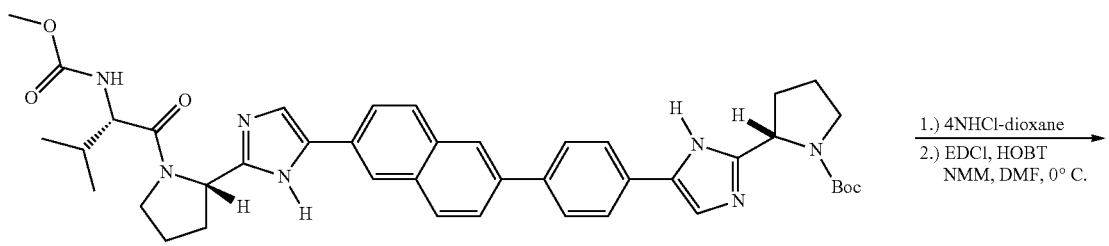

11

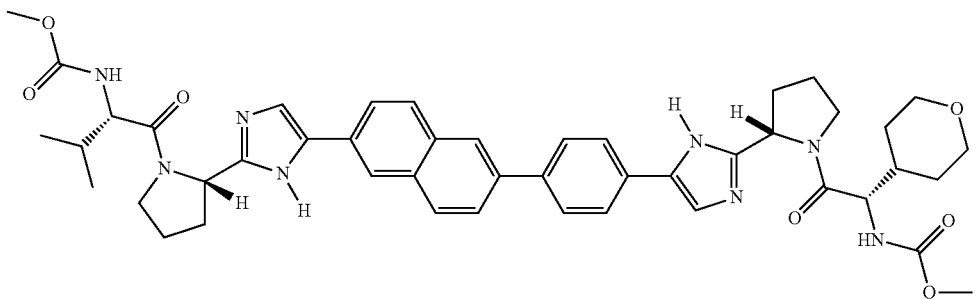

(S)-2-((S)-2-(5-(4-(6-(2-((S)-2-(methoxycarbonylamino)-
3-methylbutanoyl)pyrrolidin-2-yl)-1H-imidazol-5-yl)naphthalen-
2-yl)phenyl)-1H-imidazol-2-yl)pyrrolidin-1-yl)-2-oxo-1-
(tetrahydro-2H-pyran-4-yl)ethylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 3 (20 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 μL, 0.18 mmol) was added from a syringe to the mixture. The reaction content was stirred for 4 hours at room temperature. The resulting mixture was then directly purified on reverse phase prep. HPLC to afford title compound as white solid (36 mg, 65%).

$^1$H-NMR: 400 MHz, (CD$_3$OD) δ 8.03 (s, 1H), 7.99 (s, 1H), 7.79-7.66 (m, 10H), 7.33 (s, 1H), 7.24 (s, 1H), 7.05-6.91 (m, 1H), 5.22-5.09 (m, 1H), 4.23-4.15 (m, 1H), 3.98-3.78 (m, 4H), 3.57 (s, 6H), 3.38-3.31 (m, 8H), 2.65 (m, 1H), 2.30-2.09 (m, 5H), 2.02-1.95 (m, 2H), 1.56-1.29 (m, 5H), 0.92-0.82 (m, 6H). MS (ESI) m/z 832 [M+H]$^+$.

Example IG (S)-1-(2,3-dihydro-1H-inden-2-yl)-2-((S)-2-(5-(4-(6-
(2-((S)-1-((S)-2-(methoxycarbonylamino)-3-meth-
ylbutanoyl)pyrrolidin-2-yl)-1H-imidazol-5-yl)naph-
thalen-2-yl)phenyl)-1H-imidazol-2-yl)pyrrolidin-1-
yl)-2-oxoethylcarbamic acid methyl ester

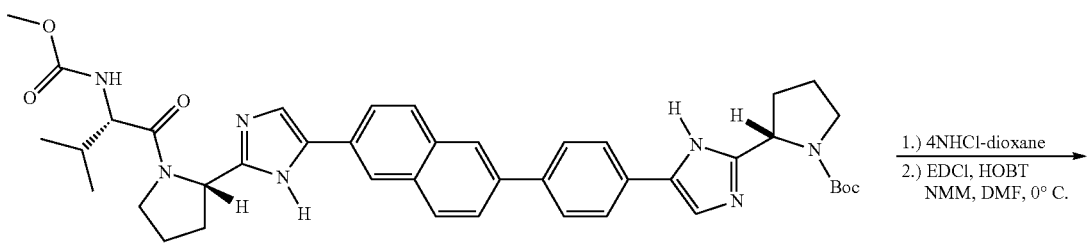

-continued

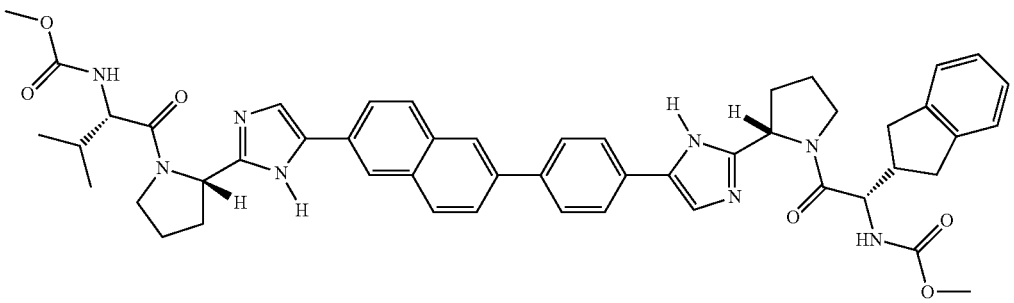

(S)-1-(2,3-dihydro-1H-inden-2-yl)-2-((S)-2-(5-(4-(6-(2-((S)-1-
((S)-2-(methoxycarbonylamino)-3-methylbutanoyl)pyrrolidin-2-
yl)-1H-imidazol-5-yl)naphthalen-2-yl-)phenyl)-1H-imidazol-2-
yl)pyrrolidin-1-yl)-2-oxoethylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (32 mg) in DMF (0.7 mL) was added compound 10 (16 mg, 0.063 mmol), N-(3-dimethylaminopropyl)-N'-ethylcarbodiimide hydrochloride (12 mg, 0.063 mmol) and hydroxybenzotriazole hydrate (HOBt), (9 mg, 0.063 mmol). The mixture was cooled down in an ice bath to 0° C. and N-methylmorpholine (NMM) (20 µL, 0.12 mmol) was added from a syringe to the mixture. The reaction content was stirred for 4 hours at room temperature. The resulting mixture was then directly purified on reverse phase prep. HPLC to afford title compound as white solid (23 mg, 62%). MS (ESI) m/z 864 [M+H]$^+$.

Example 1H (R)-2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(tetrahydro-2H-pyran-4-yl)ethylcarbamic acid methyl ester

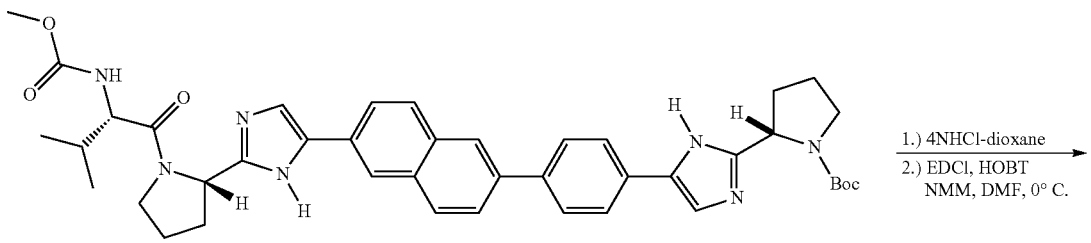

11

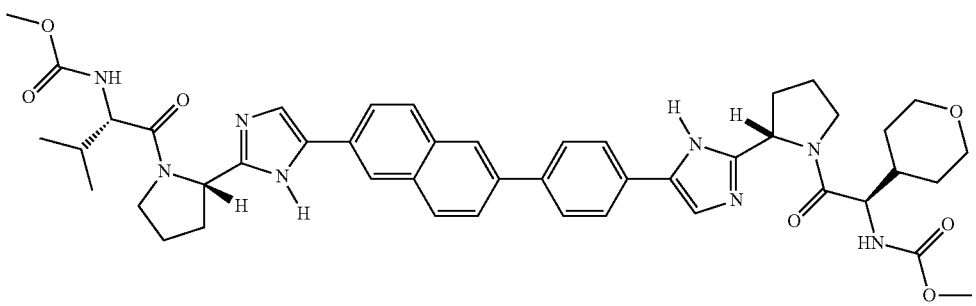

(R)-2-((S)-2-(5-(4-(6-(2-((S)-2-(methoxycarbonylamino)-
3-methylbutanoyl)pyrrolidin-2-yl)-1H-imidazol-5-yl)naphthalen-
2-yl)phenyl)-1H-imidazol-2-yl)pyrrolidin-1-yl)-2-oxo-1-
(tetrahydro-2H-pyran-4-yl)ethylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (33 mg) in DMF (0.8 mL) was added compound 4 (15 mg, 0.068 mmol), N-(3-dimethylaminopropyl)-N'-ethylcarbodiimide hydrochloride (13 mg, 0.068 mmol) and hydroxybenzotriazole hydrate (HOBt), (11 mg, 0.068 mmol). The mixture was cooled down in an ice bath to 0° C. and N-methylmorpholine (NMM) (14 μL, 0.13 mmol) was added from a syringe to the mixture. The reaction content was stirred for 4 hours at room temperature. The resulting mixture was then directly purified on reverse phase prep. HPLC to afford title compound as white solid (25 mg, 67%).
MS (ESI) m/z 832 [M+H]$^+$.

Example II (2S)-1-((2S)-2-(5-(6-(4-(2-((2S)-1-(2-(1,1-dioxo-hexahydro-thiopyran-4-yl)-2-(methoxycarbonylamino)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (33 mg) in DMF (0.8 mL) was added compound 5 (18 mg, 0.068 mmol), N-(3-dimethylaminopropyl)-N'-ethylcarbodiimide hydrochloride (13 mg, 0.068 mmol) and hydroxybenzotriazole hydrate (HOBt), (11 mg, 0.068 mmol). The mixture was cooled down in an ice bath to 0° C. and N-methylmorpholine (NMM) (14 μL, 0.13 mmol) was added from a syringe to the mixture. The reaction content was stirred for 4 hours at room temperature. The resulting mixture was then directly purified on reverse phase prep. HPLC to afford title compound as white solid (16 mg, 40%).

MS (ESI) m/z 880 [M+H]$^+$.

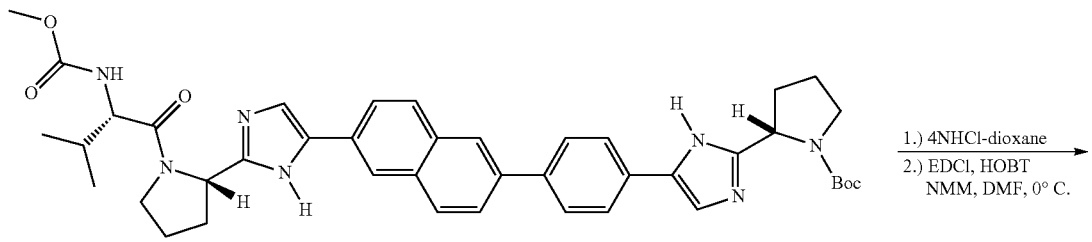

11

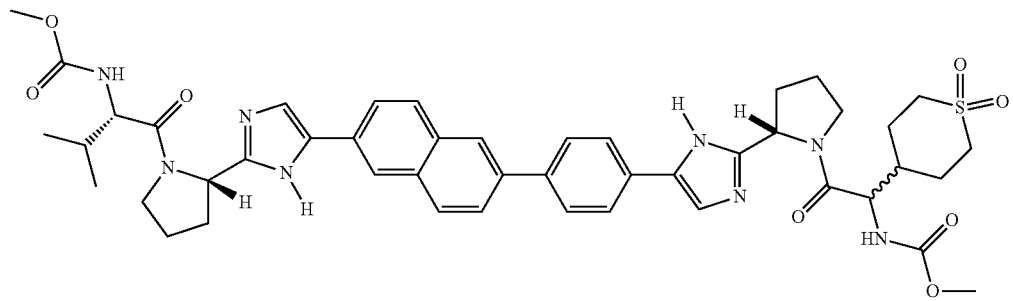

(2S)-1-((2S)-2-(5-(6-(4-(2-((2S)-1-(2-(1,1-dioxo-hexahydro-thiopyran-4-yl)-2-(methoxycarbonylamino)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester

Example IJ (S)-1-((S)-2-(5-(6-(4-(2-((S)-1-(2-(methoxycarbonylamino)-2-(thiophen-3-yl)acetyl)pyrrolidin-2-yl)-1H-imidazol-5-yl)phenyl)naphthalen-2-yl)-1H-imidazol-2-yl)-2-methylpyrrolidin-1-yl)-3-methyl-1-oxobutan-2-ylcarbamic acid methyl ester

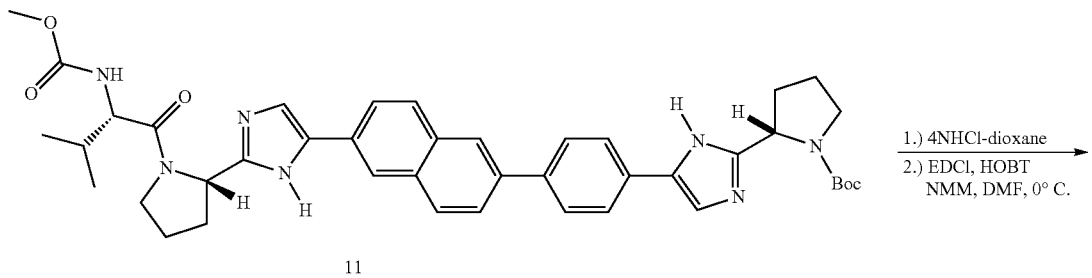

11

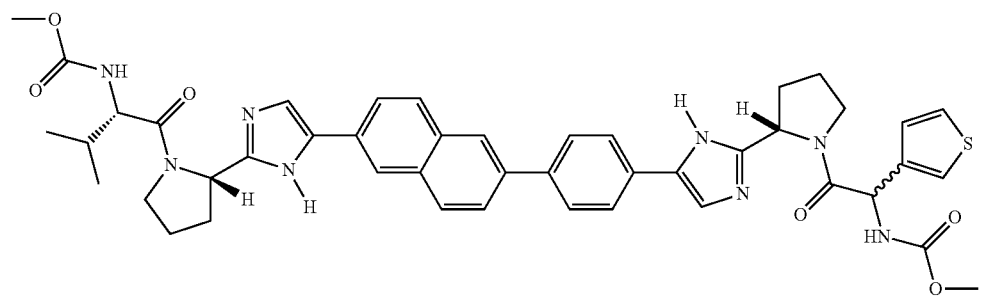

(S)-1-((S)-2-(5-(6-(4-(2-((S)-1-(2-(methoxycarbonylamino)-2-(thiophen-3-yl)acetyl)pyrrolidin-2-yl)-1H-imidazol-5-yl)phenyl)naphthalen-2-yl)-1H-imidazol-2-yl)-2-methylpyrrolidin-1-yl)-3-methyl-1-oxobutan-2-ylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (33 mg) in DMF (0.8 mL) was added compound 6 (15 mg, 0.068 mmol), N-(3-dimethylaminopropyl)-N'-ethylcarbodiimide hydrochloride (13 mg, 0.068 mmol) and hydroxybenzotriazole hydrate (HOBt), (11 mg, 0.068 mmol). The mixture was cooled down in an ice bath to 0° C. and N-methylmorpholine (NMM) (14 µL, 0.13 mmol) was added from a syringe to the mixture. The reaction content was stirred for 4 hours at room temperature. The resulting mixture was then directly purified on reverse phase prep. HPLC to afford title compound as white solid (22 mg, 60%).

MS (ESI) m/z 830 [M+H]⁺.

Example IK (S)-1-((S)-2-(5-(6-(4-(2-((S)-1-((R)-2-(methoxycarbonylamino)-3-(1-methyl-1H-indol-3-yl)propanoyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester

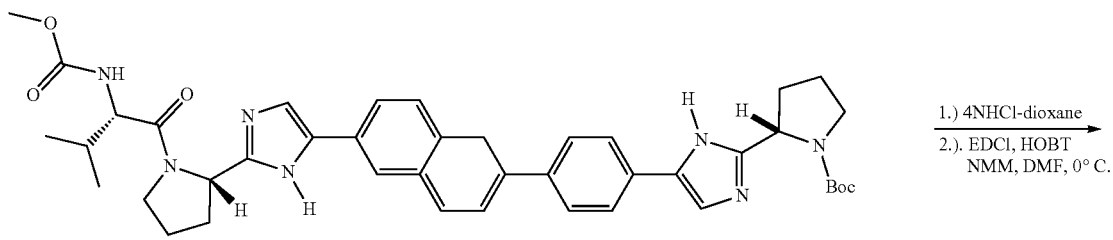

11

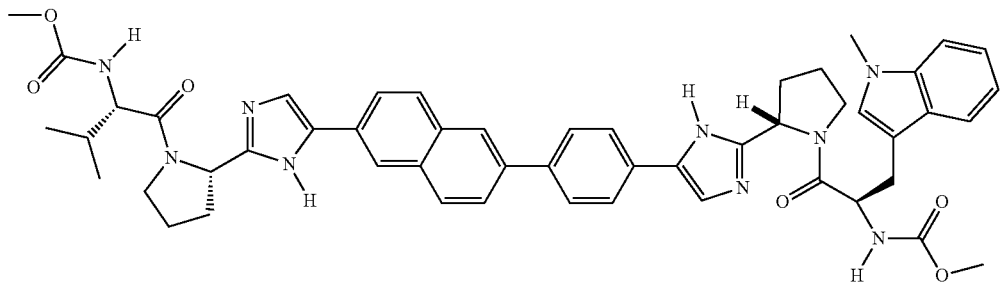

(S)-1-((S)-2-(5-(6-(4-(2-((S)-1-((R)-2(methoxycarbonylamino)-3-
(1-methyl-1H-indol-3-yl)propanoyl)pyrrolidin-2-yl)-1H-imidazol-5-
yl)phenyl)naphthalen-2-yl)-1H-imidazol-2-yl)pyrrolidin-1-yl)-3-
methyl-1-oxobutan-2-ylcarbamic acid methyl ester To compound 11 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (20 mg) in DMF (0.5 mL) was added compound 9 (11 mg, 0.039 mmol), N-(3-dimethylaminopropyl)-N'-ethylcarbodiimide hydrochloride (8 mg, 0.039 mmol) and hydroxybenzotriazole hydrate (HOBt), (6 mg, 0.039 mmol). The mixture was cooled down in an ice bath to 0° C. and N-methylmorpholine (NMM) (8.3 μL, 0.075 mmol) was added from a syringe to the mixture. The reaction content was stirred for 4 hours at room temperature. The resulting mixture was then directly purified on reverse phase prep. HPLC to afford title compound as white solid (10 mg, 42%).

MS (ESI) m/z 891 [M+H]$^+$.

Example IL (S)-2-((S)-2-(5-(6-(4-(2-((S)-1-((S)-2-(methoxycarbonylamino)-3-methylbutanoyl)pyrrolidin-2-yl)-1H-imidazol-5-yl)phenyl)naphthalen-2-yl)-1H-imidazol-2-yl)pyrrolidin-1-yl)-2-oxo-1-(tetrahydro-2H-pyran-4-yl)ethylcarbamic acid methyl ester

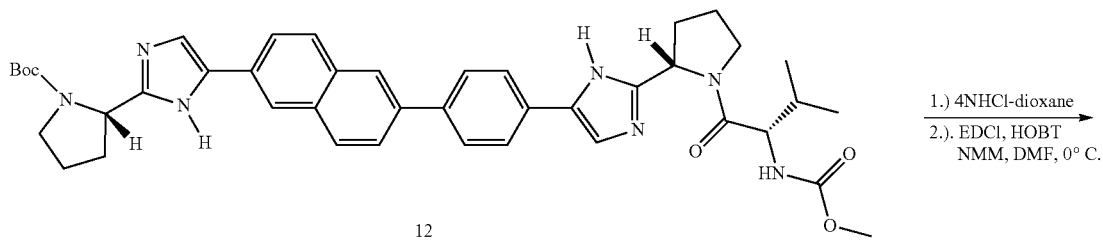

12

1.) 4NHCl-dioxane
2.). EDCl, HOBT
NMM, DMF, 0° C.

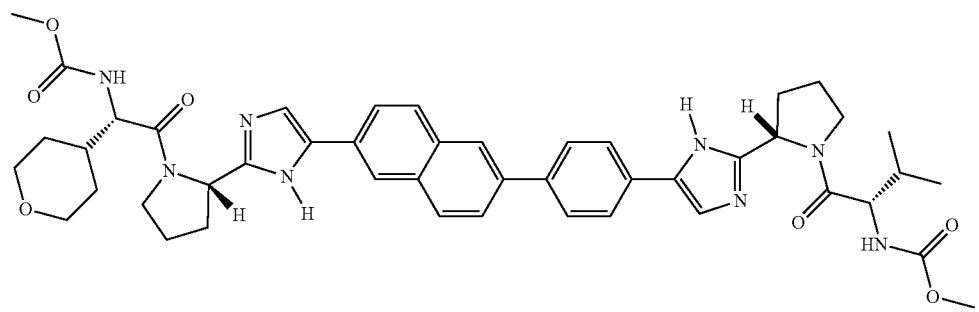

(S)-2-((S)-2-(5-(6-(4-(2-((S)-1-((S)-2(methoxycarbonylamino)-3-
methylbutanoyl)pyrrolidin-2-yl)-1H-imidazol-5-
yl)phenyl)naphthalen-2-yl)-1H-imidazol-2-yl)pyrrolidin-1-yl)-2-
oxo-1-(tetrahydro-2H-pyran-4-yl)ethylcarbamic acid methyl ester To compound 12 (50 mg, 0.068 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts (43 mg) in DMF (0.8 mL) was added compound 3 (20 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 μL, 0.18 mmol) was added from a syringe to the mixture. The reaction content was stirred for 4 hours at room temperature. The resulting mixture was then directly purified on reverse phase prep. HPLC to afford title compound as white solid (32 mg, 465%).

MS (ESI) m/z 832 [M+H]$^+$.

Example IM (S)-2-((S)-2-(5-(6-(4-(2-((S)-1-((S)-2-(methoxycarbonylamino)-2-(tetrahydro-2H-pyran-4-yl)acetyl)pyrrolidin-2-yl)-1H-imidazol-5-yl)phenyl)naphthalen-2-yl)-1H-imidazol-2-yl)pyrrolidin-1-yl)-2-oxo-1-(tetrahydro-2H-pyran-4-yl)ethylcarbamic acid methyl ester To compound 13 (50 mg, 0.074 mmol) in dichloromethane (0.9 mL) was added 4M HCl in dioxane (0.9 mL) and the reaction mixture was cooled to 0° C. and then stirred for 2 hours. After concentrated in vacuo to afford HCl salts.

To these HCl salts in DMF (0.8 mL) was added compound 3 (41 mg, 0.19 mmol), N-(3-dimethylaminopropyl)-N'-ethylcarbodiimide hydrochloride (36 mg, 0.19 mmol) and hydroxybenzotriazole hydrate (HOBt), (26 mg, 0.19 mmol). The mixture was cooled down in an ice bath to 0° C. and N-methylmorpholine (NMM) (25 μL, 0.22 mmol) was added from a syringe to the mixture. The reaction content was stirred for 4 hours at room temperature. The resulting mixture was then directly purified on reverse phase prep. HPLC to afford title compound as white solid (32 mg, 50%).

MS (ESI) m/z 874 [M+H]$^+$.

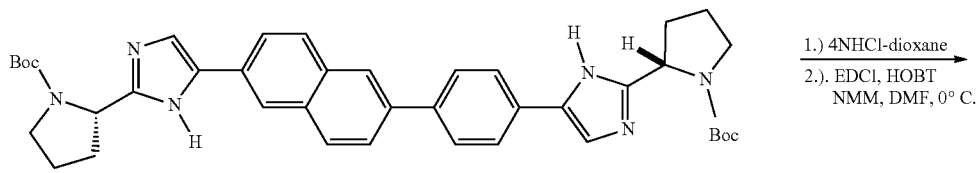

13

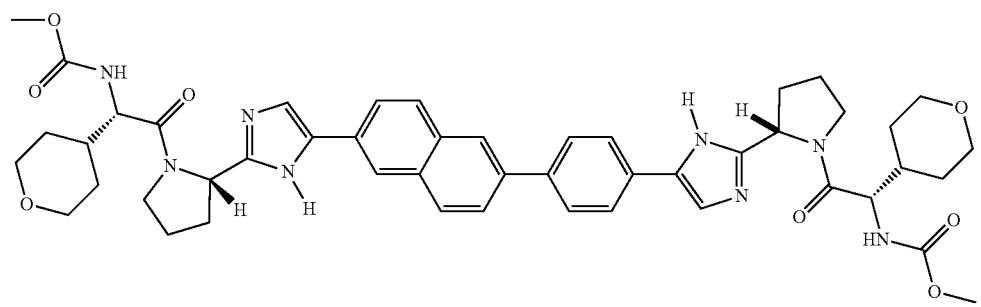

(S)-2-((S)-2-(5-(6-(4-(2-((S)-1-((S)-2(methoxycarbonylamino)-2-(tetrahydro-2H-pyran-4-yl)acetyl)pyrrolidin-2-yl)-1H-imidazol-5-yl)phenyl)naphthalen-2-yl)-1H-imidazol-2-yl)pyrrolidin-1-yl)-2-oxo-1-(tetrahydro-2H-pyran-4-yl)ethylcarbamic acid methyl ester

Example IN (S)-2-((S)-6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-2-oxo-1-(tetrahydro-2H-pyran-4-yl)ethylcarbamic acid methyl ester

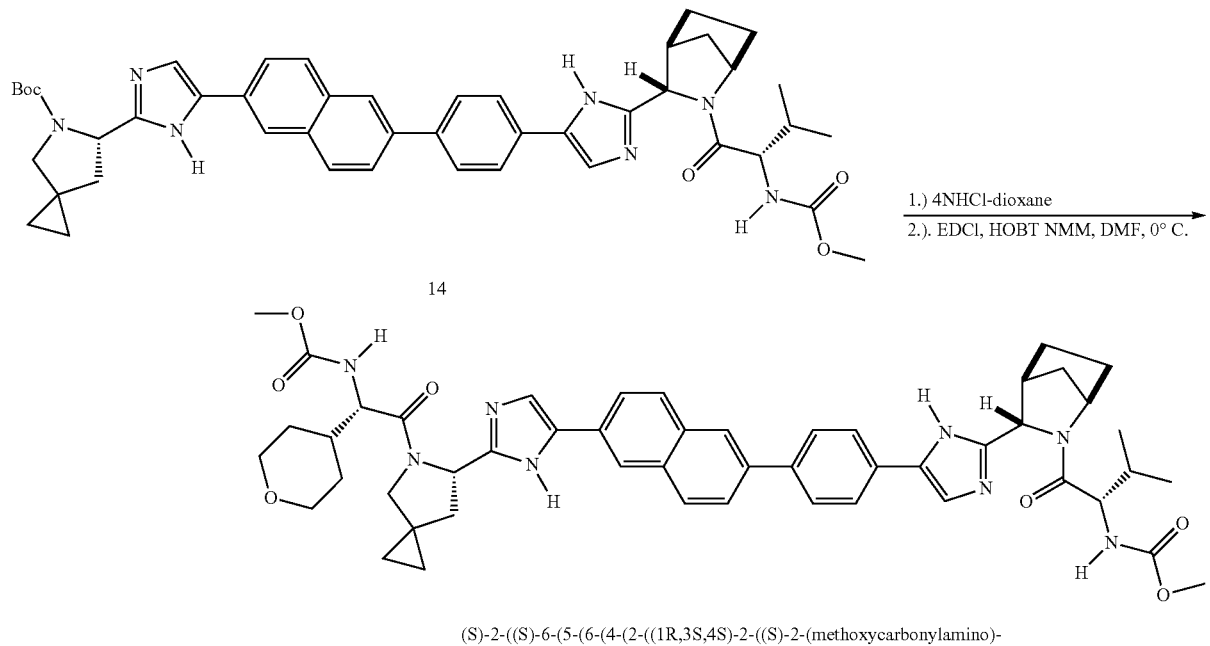

(S)-2-((S)-6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-2-oxo-1-(tetrahydro-2H-pyran-4-yl)ethylcarbamic acid methyl ester To compound 14 (50 mg, 0.064 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 3 (20 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (18 µL, 0.16 mmol) was added from a syringe to the mixture. The reaction content was stirred for 4 hours at room temperature. The resulting mixture was then directly purified on reverse phase prep. HPLC to afford title compound as white solid (30 mg, 54%).

MS (ESI) m/z 884 [M+H]+.

Example IO (2S,3R)-3-methoxy-1-((S)-6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-1-oxobutan-2-ylcarbamic acid methyl ester

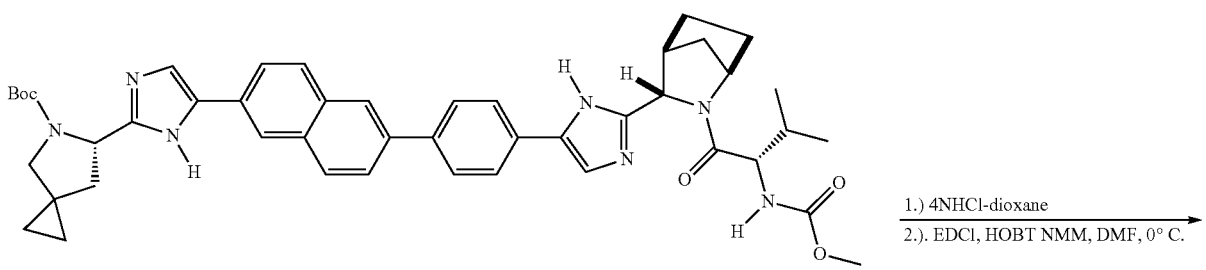

-continued

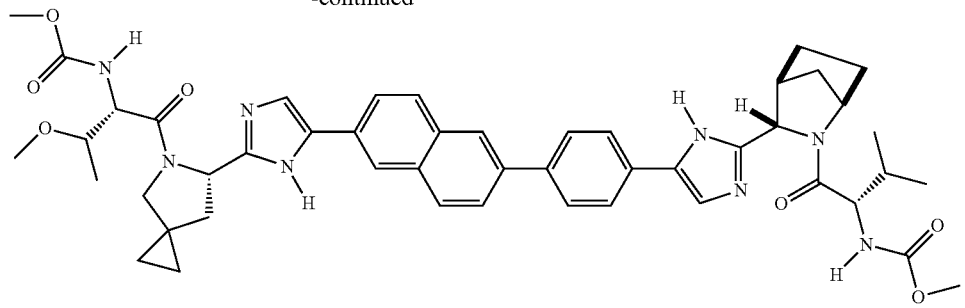

(2S,3R)-3-methoxy-1-((S)-6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-1-oxobutan-2-ylcarbamic acid methyl ester To compound 14 (50 mg, 0.064 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 8 (17 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (18 μL, 0.16 mmol) was added from a syringe to the mixture. The reaction content was stirred for 4 hours at room temperature. The resulting mixture was then directly purified on reverse phase prep. HPLC to afford title compound as white solid (30 mg, 54%).

MS (ESI) m/z 858 [M+H]⁺.

Example IP (S)-1-((S)-6-(5-(6-(4-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester

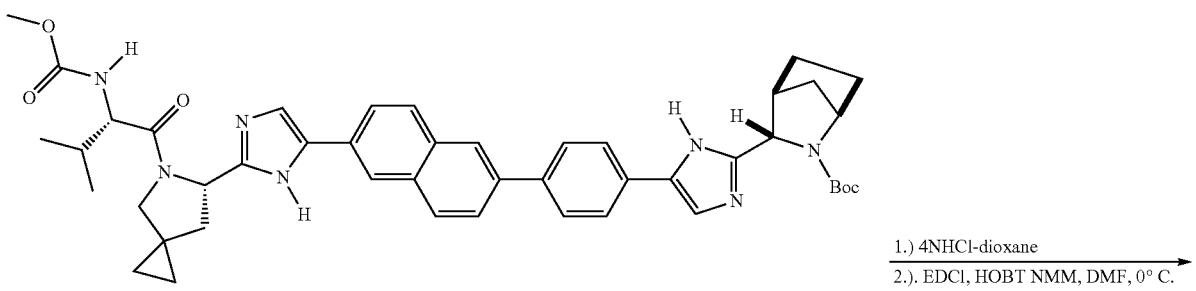

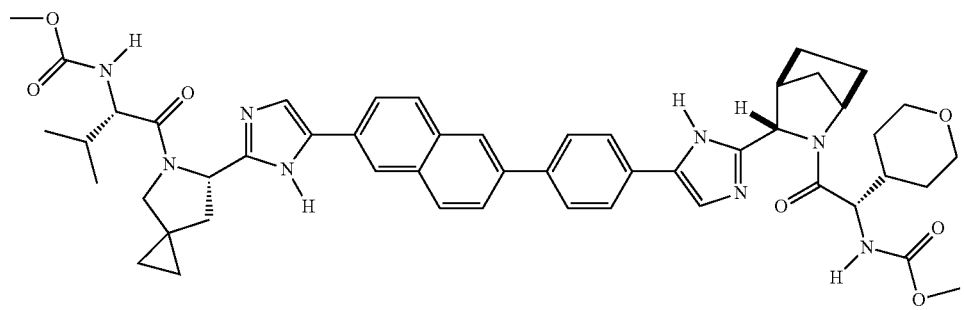

(S)-1-((S)-6-(5-(6-(4-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-3-methyl-1-oxobutan-2-ylcarbamic acid methyl ester To compound 15 (50 mg, 0.064 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 3 (20 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 μL, 0.16 mmol) was added from a syringe to the mixture. The reaction content was stirred for 4 hours at room temperature. The resulting mixture was then directly purified on reverse phase prep. HPLC to afford title compound as white solid (25 mg, 45%).

MS (ESI) m/z 884 [M+H]$^+$.

Example IQ (S)-2-((S)-6-(5-(6-(4-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-2-oxo-1-(tetrahydro-2H-pyran-4-yl)ethylcarbamic acid methyl ester To compound 16 (50 mg, 0.069 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 3 (41 mg, 0.19 mmol), N-(3-dimethylaminopropyl)-N'-ethylcarbodiimide hydrochloride (36 mg, 0.19 mmol) and hydroxybenzotriazole hydrate (HOBt), (26 mg, 0.19 mmol). The mixture was cooled down in an ice bath to 0° C. and N-methylmorpholine (NMM) (25 μL, 0.22 mmol) was added from a syringe to the mixture. The reaction content was stirred for 4 hours at room temperature. The resulting mixture was then directly purified on reverse phase prep. HPLC to afford title compound as white solid (28 mg, 44%).

MS (ESI) m/z 926 [M+H]$^+$.

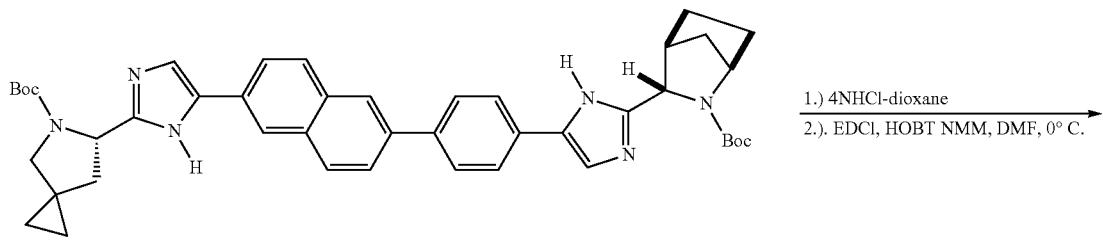

16

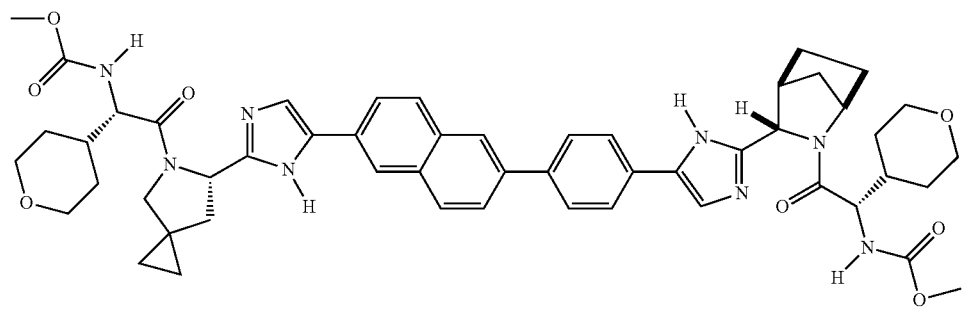

(S)-2-((S)-6-(5-(6-(4-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-2-oxo-1-(tetrahydro-2H-pyran-4-yl)ethylcarbamic acid methyl ester

Example IR (2S,3R)-3-methoxy-1-((S)-6-(5-(6-(4-(2-((1R,3S,4S)-2-((2S,3R)-3-methoxy-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-1-oxobutan-2-ylcarbamic acid methyl ester

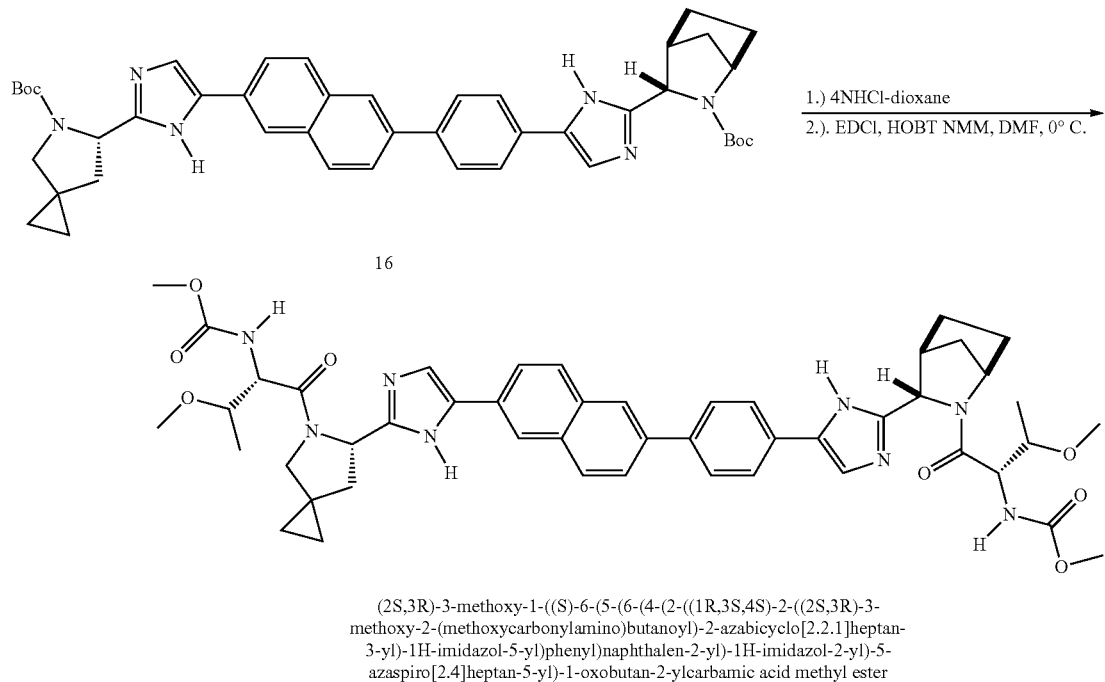

(2S,3R)-3-methoxy-1-((S)-6-(5-(6-(4-(2-((1R,3S,4S)-2-((2S,3R)-3-methoxy-2-(methoxycarbonylamino)butanoyl)-2-azabicyclo[2.2.1]heptan-3-yl)-1H-imidazol-5-yl)phenyl)naphthalen-2-yl)-1H-imidazol-2-yl)-5-azaspiro[2.4]heptan-5-yl)-1-oxobutan-2-ylcarbamic acid methyl ester To compound 16 (50 mg, 0.069 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 8 (38 mg, 0.2 mmol), N-(3-dimethylaminopropyl)-N'-ethylcarbodiimide hydrochloride (38 mg, 0.2 mmol) and hydroxybenzotriazole hydrate (HOBt), (27 mg, 0.2 mmol). The mixture was cooled down in an ice bath to 0° C. and N-methylmorpholine (NMM) (55 µL, 0.5 mmol) was added from a syringe to the mixture. The reaction content was stirred for 4 hours at room temperature. The resulting mixture was then directly purified on reverse phase prep. HPLC to afford title compound as white solid (29 mg, 40%).

MS (ESI) m/z 874 [M+H]$^+$.

Example IS (S)-1-((S)-6-(5-(9,9-difluoro-7-(2-((S)-1-((S)-2-(methoxycarbonylamino)-3-methylbutanoyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester

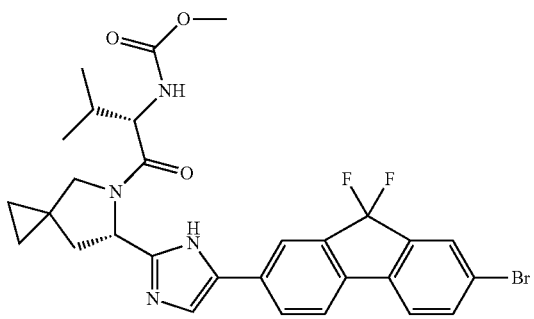

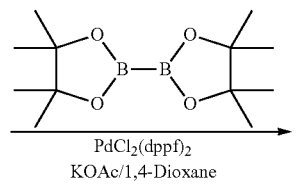

PdCl$_2$(dppf)$_2$
KOAc/1,4-Dioxane

-continued

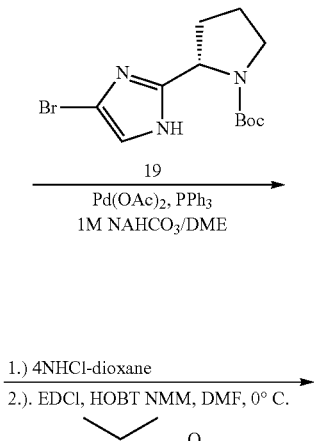

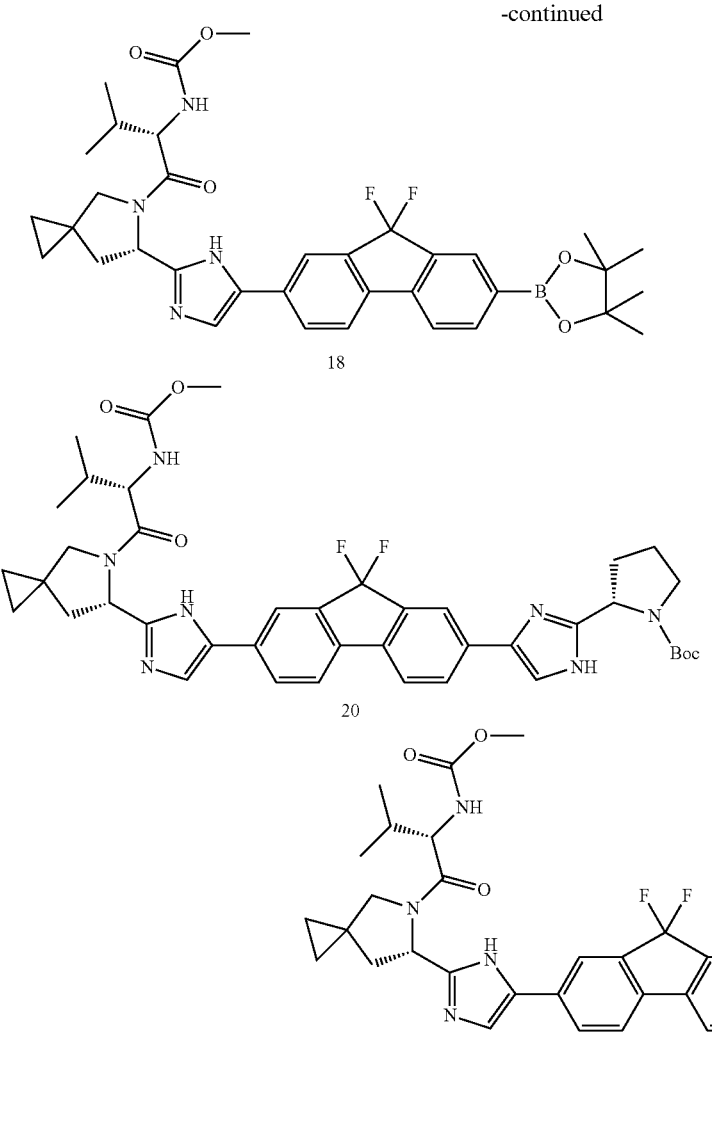

(S)-1-((S)-6-(5-(9,9-difluoro-7-(2-((S)-1-((S)-2-(methoxycarbonylamino)-3-methylbutanoyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester Compound 17 (1.2 g, 2 mmol), bis(pinacolato)diboron (1 g, 4 mmol), potassium acetate (510 mg, 5.2 mmol), and Pd(dppf)Cl$_2$ (82 mg, 0.1 mmol) were all weighed out in a glass pressure vessel and anhydrous 1,4-Dioxane (10 mL) was added. The mixture was bubbled with nitrogen gas for about 5 min. The vessel was then capped and sealed and heated in an oil bath at 90° C. overnight with continuous stirring. The reaction vessel was cooled down to room temperature and all volatiles were removed under reduced pressure and the resulting oil was subjected to silica gel chromatography with an eluent of ethyl acetate and hexane at a gradient of 0-50% with an ISCO column (12 g silica gel). The fractions containing product were combined and the solvent was removed under reduced pressure to provide (18) (968 mg, 75%).

To compound 18 (950 mg, 1.47 mmol), compound 19 (488 mg, 1.54 mmol.), Pd(OAc)$_2$ (23 mg, 0.1 mmol) and PPh$_3$ (42 mg, 0.16 mmol). DME (16 mL) was added and followed by 6 mL 1M NaHCO3 aqueous solution. The reaction was purged with Argon and heated to 90° C. for 3 hours under Ar. The reaction was cooled to room temperature and concentrated down. EtOAc was added and washed with sat. NaHCO3 aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide product 20 (1 g, 90%). MS (ESI) m/z 757 [M+H]$^+$.

To compound 20 (50 mg, 0.066 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 21 (16 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 µL, 0.18 mmol) was added from a syringe to the mixture. The reaction content was stirred for 4 hours at room temperature. The resulting mixture was then directly purified on reverse phase prep. HPLC to afford title compound as white solid (33 mg, 62%). MS (ESI) m/z 814 [M+H]$^+$.

Example IT (S)-1-((S)-6-(5-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester To compound 20 (50 mg, 0.066 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 3 (20 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 µL, 0.18 mmol) was added from a syringe to the mixture. The reaction content was stirred for 4 hours at room temperature. The resulting mixture was then directly purified on reverse phase prep. HPLC to afford title compound as white solid (30 mg, 54%). MS (ESI) m/z 856 [M+H]$^+$.

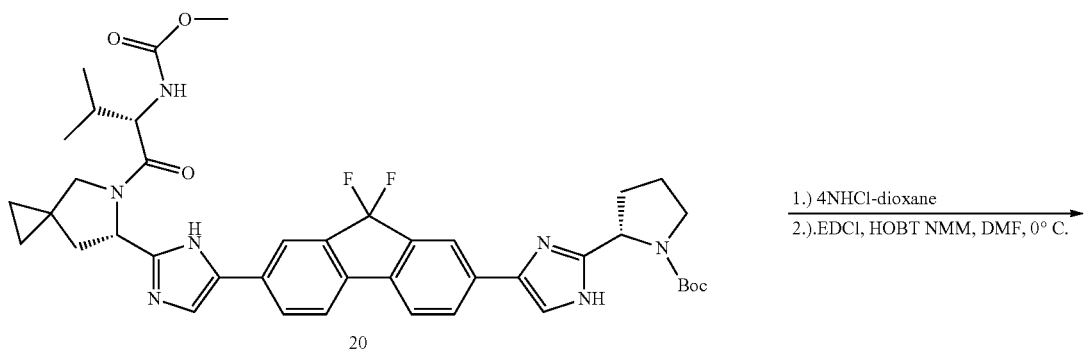

1.) 4NHCl-dioxane
2.) EDCl, HOBT NMM, DMF, 0° C.

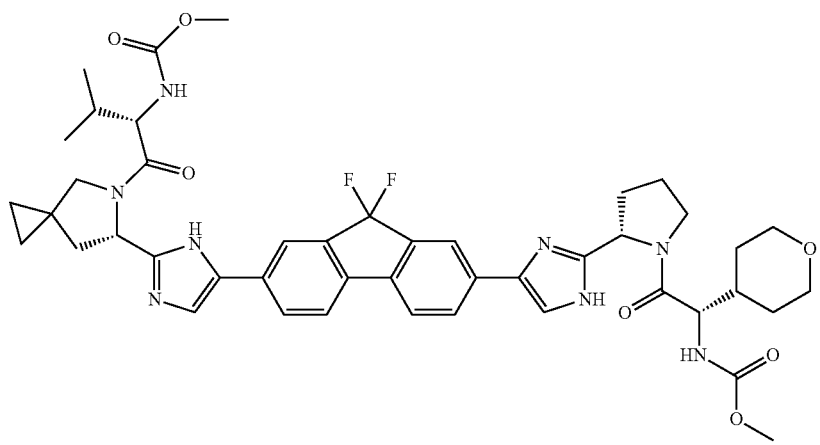

(S)-1-((S)-6-(5-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester

Example IU (S)-1-((S)-6-(5-(9,9-difluoro-7-(2-((S)-1-((S)-2-(methoxycarbonylamino)-4-(methylthio)butanoyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester

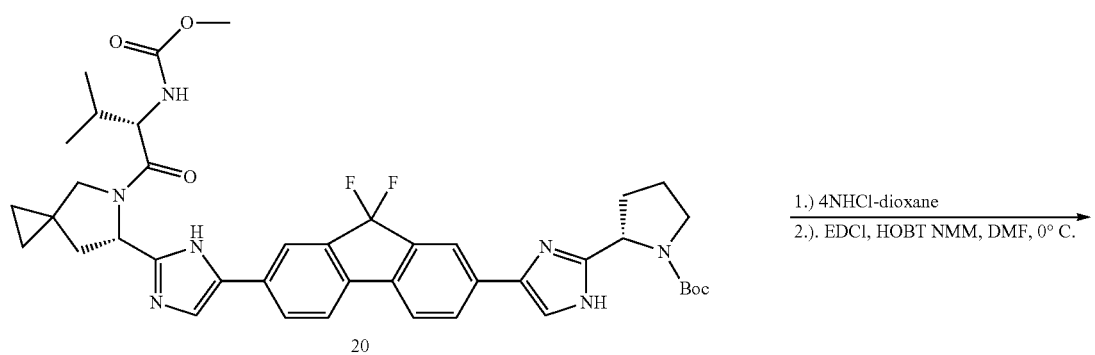

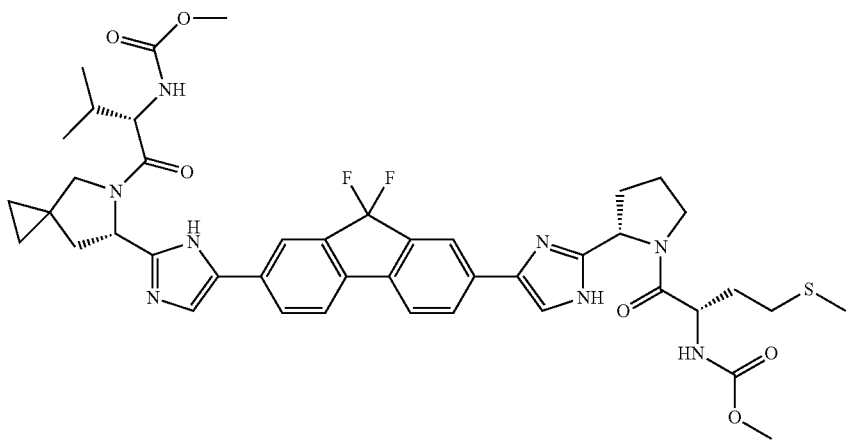

(S)-1-((S)-6-(5-(9,9-difluoro-7-(2-((S)-1-((S)-2-(methoxycarbonylamino)-4-(methylthio)butanoyl)pyrrolidin-2-yl)-1H-imidazol-4-yl)-9H-fluoren-2-yl)-1H-imidazol-2-yl)-5-azaspiro[2.4]heptan-5-yl)-3-methyl-1-oxobutan-2-ylcarbamic acid methyl ester To compound 20 (50 mg, 0.066 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

To these HCl salts in DMF (0.8 mL) was added compound 7 (19 mg, 0.09 mmol), N-(3-dimethylaminopropyl)-N'-ethylcarbodiimide hydrochloride (18 mg, 0.09 mmol) and hydroxybenzotriazole hydrate (HOBt), (13 mg, 0.09 mmol). The mixture was cooled down in an ice bath to 0° C. and N-methylmorpholine (NMM) (20 µL, 0.18 mmol) was added from a syringe to the mixture. The reaction content was stirred for 4 hours at room temperature. The resulting mixture was then directly purified on reverse phase prep. HPLC to afford title compound as white solid (30 mg, 55%). MS (ESI) m/z 846 [M+H]$^+$.

Example IV (S)-1-((S)-6-(5-(9,9-difluoro-7-(4-(2-((S)-1-((S)-2-(methoxycarbonylamino)-3-methylbutanoyl)pyrrolidin-2-yl)-1H-imidazol-5-yl)phenyl)-9H-fluoren-2-yl)-1H-imidazol-2-yl)-5-azaspiro[2.4]heptan-5-yl)-3-methyl-1-oxobutan-2-ylcarbamic acid methyl ester

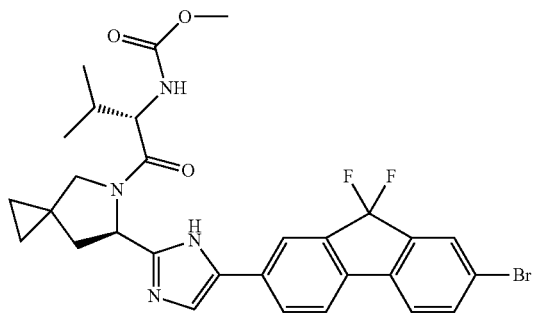

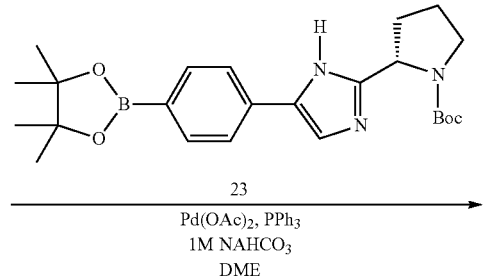

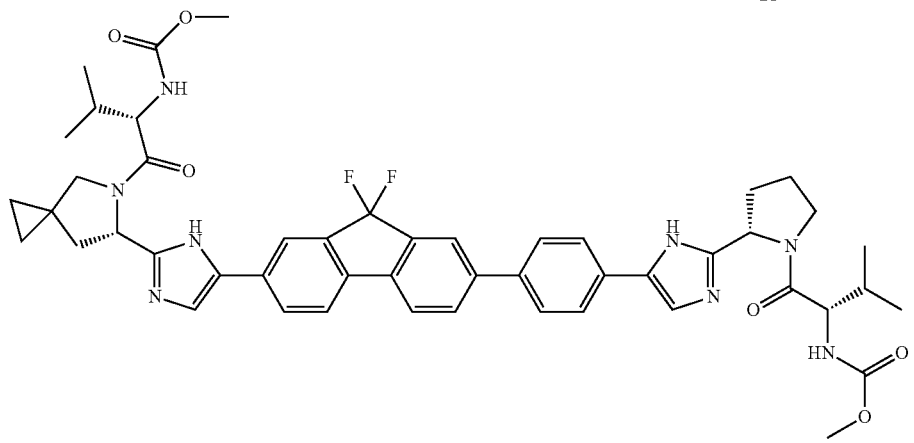

(S)-1-((S)-6-(5-(9,9-difluoro-7-(4-(2-((S)-1-((S)-2-(methoxycarbonylamino)-3-methylbutanoyl)pyrrolidin-2-yl)-1H-imidazol-5-yl)phenyl)-9H-fluoren-2-yl)-1H-imidazol-2-yl)-5-azaspiro[2.4]heptan-5-yl)-3-methyl-1-oxobutan-2-ylcarbamic acid methyl ester To compound 22 (320 mg, 0.53 mmol), compound 23 (282 mg, 0.64 mmol.), Pd(OAc)₂ (8.4 mg, 0.04 mmol) and PPh3 (16 mg, 0.06 mmol). DME (5.5 mL) was added and followed by 2.2 mL 1M NaHCO3 aqueous solution. The reaction was purged with Argon and heated to 90° C. for 3 hours under Ar. The reaction was cooled to room temperature and concentrated down. EtOAc was added and washed with sat. NaHCO3 aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide product 24 (266 mg, 60%). MS (ESI) m/z 833 [M+H]+.

To compound 24 (120 mg, 0.15 mmol) in dichloromethane (1.5 mL) was added 4M HCl in dioxane (1.5 mL) and the reaction mixture was cooled to 0° C. and then stirred for 2 hours. After concentrated in vacuo to afford HCl salts.

To these HCl salts in DMF (1.5 mL) was added compound 21 (35 mg, 0.2 mmol), N-(3-dimethylaminopropyl)-N'-ethylcarbodiimide hydrochloride (38 mg, 0.2 mmol) and hydroxybenzotriazole hydrate (HOBt), (27 mg, 0.2 mmol). The mixture was cooled down in an ice bath to 0° C. and N-methylmorpholine (NMM) (50 µL, 0.45 mmol) was added from a syringe to the mixture. The reaction content was stirred for 4 hours at room temperature. The resulting mixture was then directly purified on reverse phase prep. HPLC to afford title compound as white solid (65 mg, 56%). MS (ESI) m/z 890 [M+H]+.

Example IW

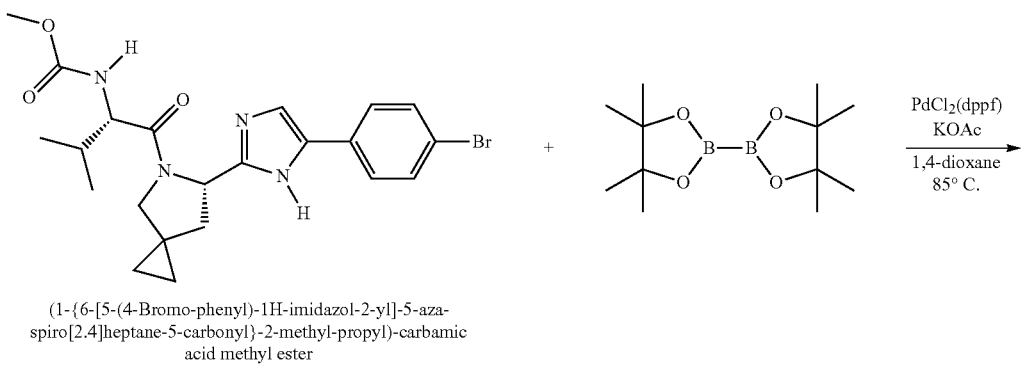

(1-{6-[5-(4-Bromo-phenyl)-1H-imidazol-2-yl]-5-aza-spiro[2.4]heptane-5-carbonyl}-2-methyl-propyl)-carbamic acid methyl ester

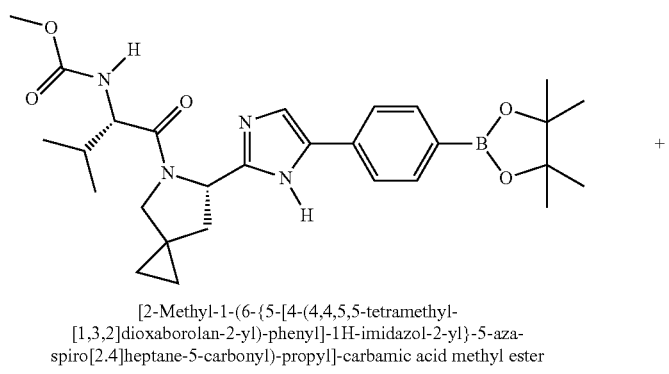

[2-Methyl-1-(6-{5-[4-(4,4,5,5-tetramethyl-[1,3,2]dioxaborolan-2-yl)-phenyl]-1H-imidazol-2-yl}-5-aza-spiro[2.4]heptane-5-carbonyl)-propyl]-carbamic acid methyl ester

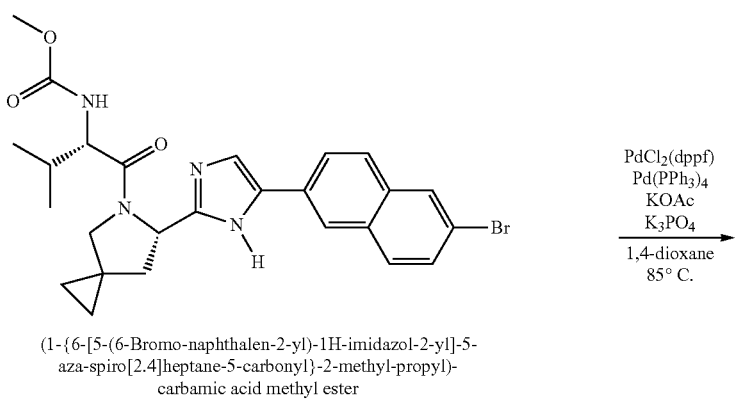

(1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester

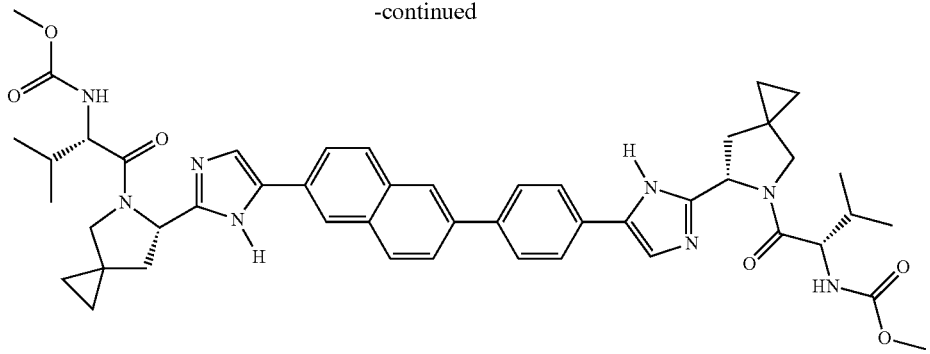

[1-(6-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester (1-{6-[5-(4-Bromo-phenyl)-1H-imidazol-2-yl]-5-aza-spiro[2.4]heptane-5-carbonyl}-2-methyl-propyl)-carbamic acid methyl ester (0.10 g, 0.24 mmol), bis(pinacolato)diboron (0.073 g, 0.29 mmol), Palladium dichloride (dppf) (0.018 g, 0.024 mmol), and potassium acetate (0.071 g, 0.72 mmol) were suspended in 1,4-dioxane (1.2 mL) and degassed with argon for 30 minutes. The suspension was heated at 85° C. for 2 hours. The mixture was cooled, (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester (0.182 g, 0.346 mmol) and aqueous potassium phosphate (2M, 0.84 mL, 0.84 mmol) was added. The mixture was returned to heat for 16 hours at which time, Palladium(tetrakis)triphenylphosphine (0.014 g, 0.012 mmol) was added. The reaction was heated for an additional 4 hours. Upon completion, the crude reaction mixture was concentrated in vacuo and filtered through a Pd scavenging cartridge (Polymer Labs, PL-Guanidine MP SPE). The resulting slurry was diluted in DMF and purified by reverse phase HPLC (15-40% acetonitrile: water; 0.1% formic acid modifier), and lyophilized giving [1-(6-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester (0.048 g, 24%) as a white solid.

$^1$H NMR (400 MHz, CDCl$_3$) δ 8.33-7.34 (m, 12H), 5.65-5.20 (m, 3H), 4.30 (s, 2H), 4.03-3.87 (m, 1H), 3.74 (d, 9H), 3.53 (s, 1H), 2.97 (s, 1H), 2.34-1.88 (m, 5H), 1.26 (s, 1H), 1.10 (m, 3H), 0.91 (m, 12H), 0.71 (s, 6H).

LCMS-ESI$^+$: calc'd for C$_{48}$H$_{56}$N$_8$O$_6$: 840.43 (M$^+$); Found: 841.9 (M+H$^+$).

Example IX

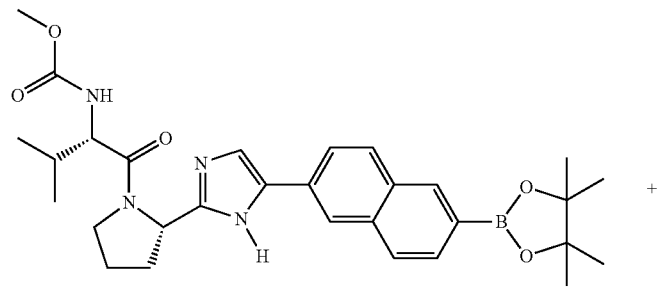

[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester

+

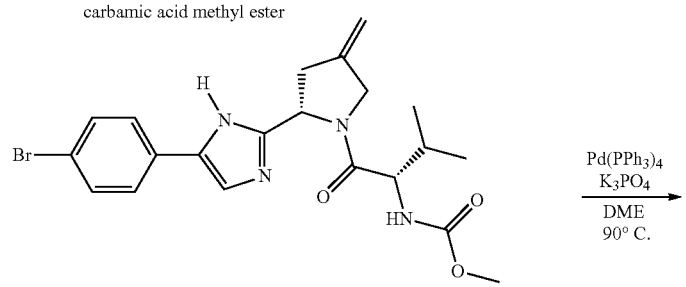

(1-{2-[5-(4-Bromo-phenyl)-1H-imidazol-2-yl]-4-methylene-pyrrolidine-1-carbonyl}-2-methyl-propyl)-carbamic acid methyl ester Pd(PPh$_3$)$_4$
K$_3$PO$_4$
$\xrightarrow{\text{DME}}$
90° C.

-continued

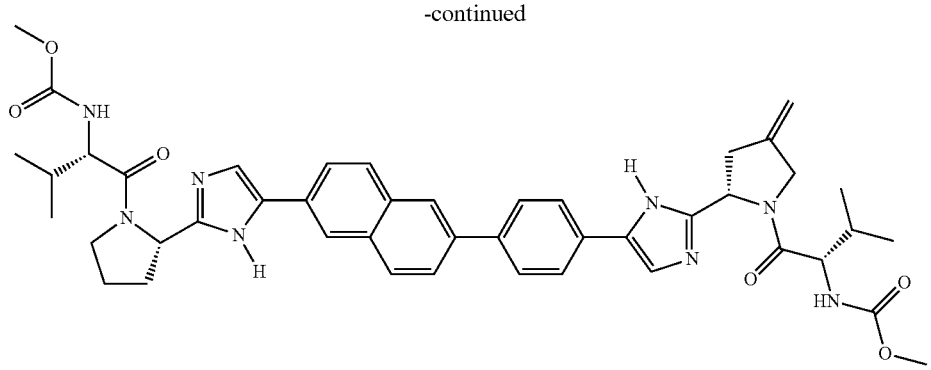

[1-(2-{5-[6-(4-{2-[1-(2-Methoxycarbonylamino-3-methyl-butyryl)-
4-methylene-pyrrolidin-2-yl]-3H-imidazol-4-yl}-phenyl)-
naphthalen-2-yl]-1H-imidazol-2-yl}-pyrrolidine-1-carbonyl)-2-methyl-propyl]-
carbamic acid methyl ester (1-{2-[5-(4-Bromo-phenyl)-1H-imidazol-2-yl]-4-methylene-pyrrolidine-1-carbonyl}-2-methyl-propyl)-carbamic acid methyl ester This compound was prepared using the procedure used to prepare (1-{2-[5-(4-Bromo-phenyl)-1H-imidazol-2-yl]-pyrrolidine-1-carbonyl}-2-methyl-propyl)-carbamic acid methyl ester using 4-Methylene-pyrrolidine-1,2-dicarboxylic acid 1-tert-butyl ester.

LCMS-ESI$^+$: calc'd for $C_{21}H_{25}BrN_4O_3$: 460.11 (M$^+$); Found: 463.61 (M+H$^+$).

[1-(2-{5-[6-(4-{2-[1-(2-Methoxycarbonylamino-3-methyl-butyryl)-4-methylene pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester This compound was prepared using the procedure used to prepare [1-(6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester using [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester (0.177 g, 0.324 mmol) and (1-{2-[5-(4-Bromo-phenyl)-1H-imidazol-2-yl]-4-methylene-pyrrolidine-1-carbonyl}-2-methyl-propyl)-carbamic acid methyl ester (0.100 g, 0.216 mmol). Potassium phosphate (aqueous, 0.32 mL, 0.648 mmol) was substituted for potassium carbonate and the reaction was performed under an argon atmosphere. The crude reaction was purified by reverse phase HPLC (10-45% acetonitrile: water; 0.1% formic acid modifier), and lyophilized giving [1-(2-{5-[6-(4-{2-[1-(2-Methoxycarbonylamino-3-methyl-butyryl)-4-methylene pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.009 g, 5%) as a white solid.

$^1$H NMR (400 MHz, CDCl$_3$) δ 8.12-7.96 (m, 1H), 7.93-7.79 (m, 5H), 7.77-7.67 (m, 5H), 6.32 (s, 1H), 5.73-5.54 (m, 1H), 5.50-5.22 (m, 6H), 4.49-4.28 (m, 3H), 3.96-3.82 (m, 2H), 3.72 (s, 9H), 3.06-2.86 (m, 2H), 2.50-2.34 (m, 1H), 2.31-2.21 (m, 1H), 2.18-2.09 (m, 2H), 2.05-1.95 (m, 3H), 1.90 (s, 4H), 1.26 (s, 3H), 1.13-1.04 (m, 3H).

LCMS-ESI$^+$: calc'd for $C_{45}H_{52}N_8O_6$: 800.4 (M$^+$); Found: 801.90 (M+H$^+$).

Example IY

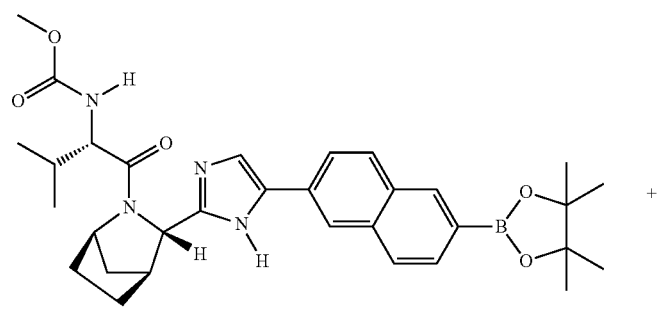

[2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-propyl]-carbamic acid methyl ester

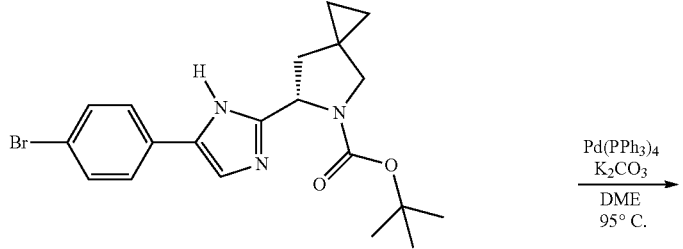

6-[5-(4-Bromo-phenyl)-1H-imidazol-
2-yl]-5-aza-spiro[2.4]heptane-5-
carboxylic acid tert-butyl ester

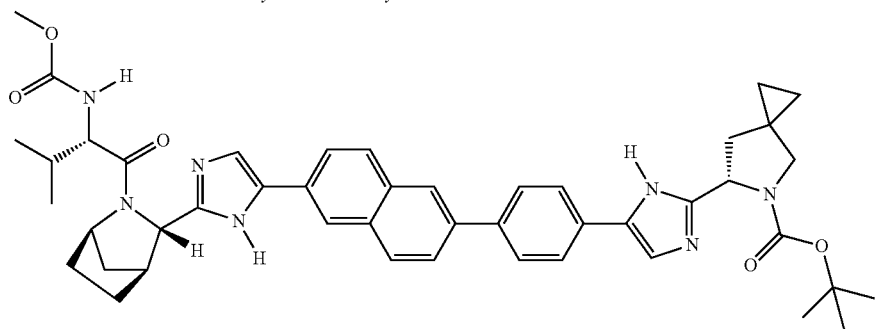

6-{5-[4-(6-{2-[2-(2-Methoxycarbonylamino-3-methyl-butyryl)-2-
aza-bicyclo[2.2.1]hept-3-yl]-3H-imidazol-4-yl}-naphthalen-
2-yl)-phenyl]-1H-imidazol-2-yl}-5-aza-spiro[2.4]heptane-
5-carboxylic acid tert-butyl ester

6-{5-[4-(6-{2-[2-(2-Methoxycarbonylamino-3-methyl-butyryl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carboxylic acid tert-butyl ester This compound was prepared using the procedure used to prepare [1-(6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester (example EZ) using [2-Methyl-1-(3-{5-[6-(4,4,5,5-tetramethyl-[1,3,2]dioxaborolan-2-yl)-naphthalen-2-yl]-1H-imidazol-2-yl}-2-aza-bicyclo[2.2.1]heptane-2-carbonyl)-propyl]-carbamic acid methyl ester (2.25 mmol), 6-[5-(4-Bromo-phenyl)-1H-imidazol-2-yl]-5-aza-spiro[2.4]heptane-5-carboxylic acid tert-butyl ester (2.39 mmol), and potassium carbonate (2M, 4.3 mL, 8.55 mmol). The reaction was performed under an argon atmosphere. The crude reaction was diluted in ethyl acetate, washed with water and purified by normal phase silica chromatography (50-100% Hexanes:EthylAcetate+10% Methanol). 6-{5-[4-(6-{2-[2-(2-Methoxycarbonylamino-3-methyl-butyryl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carboxylic acid tert-butyl ester (1.05 g, 60%) was obtained as a tan solid.

LCMS-ESI$^+$: calc'd for $C_{46}H_{53}N_7O_5$: 783.41 (M$^+$); Found: 784.35 (M+H$^+$).

Example IZ

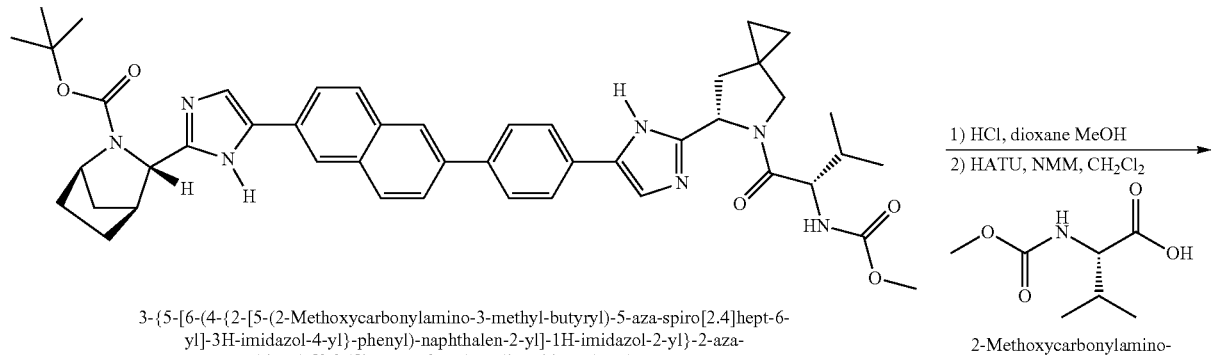

3-{5-[6-(4-{2-[5-(2-Methoxycarbonylamino-3-methyl-butyryl)-5-aza-spiro[2.4]hept-6-
yl]-3H-imidazol-4-yl}-phenyl)-naphthalen-2-yl]-1H-imidazol-2-yl}-2-aza-
bicyclo[2.2.1]heptane-2-carboxylic acid tert-butyl ester 2-Methoxycarbonylamino-
3-methyl-butyric acid

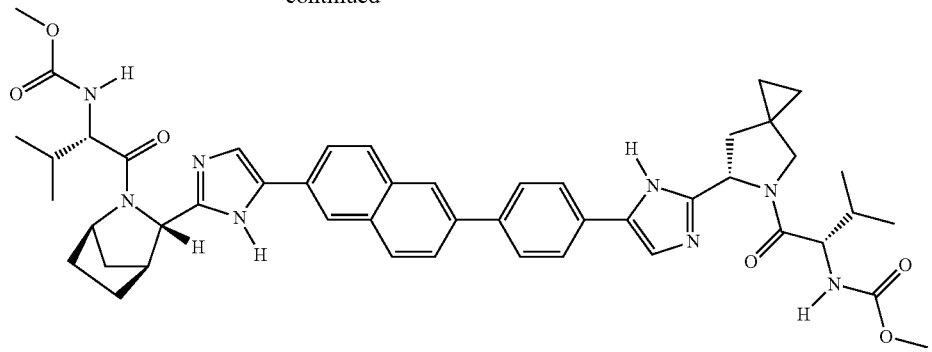

[1-(3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester

[1-(3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester using 2-Methoxycarbonylamino-3-methyl-butyric acid to provide [1-(3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (0.070 g, 65%) as a white powder.

$^1$H-NMR: 400 MHz, (DMSO-d$_6$) δ: 11.75 (s, 1H), 11.72 (s, 1H), 8.24 (s, 1H), 8.15 (d, 1H), 7.93-7.74 (m, 8H), 7.63 (s, 1H), 7.54 (s, 1H), 7.30 (d, 1H), 7.16 (d, 1H), 5.22 (t, 1H), 4.52-4.50 (m, 2H), 4.16 (t, 1H), 4.00 (t, 1H), 3.81 (d, 1H), 3.75 (d, 1H), 3.72 (s, 3H), 3.31 (s, 3H), 2.55 (m, 1H), 2.32-1.41 (m, 10H), 1.01-0.57 (m, 16H).

LCMS-ESI$^+$: calc'd for C$_{48}$H$_{56}$N$_8$O$_6$: 840.43 (M$^+$); Found: 841.99 (M+H$^+$).

Example JA

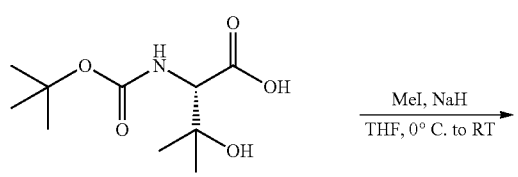

2-tert-Butoxycarbonylamino-3-hydroxy-3-methyl-butyric acid

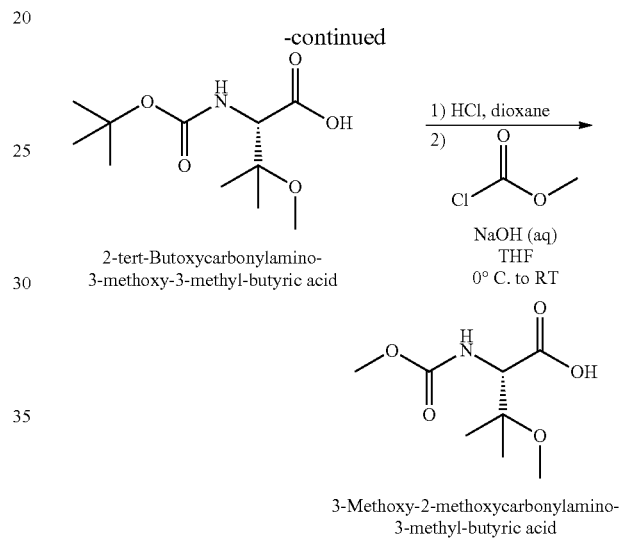

2-tert-Butoxycarbonylamino-3-methoxy-3-methyl-butyric acid

3-Methoxy-2-methoxycarbonylamino-3-methyl-butyric acid 2-tert-Butoxycarbonylamino-3-methoxy-3-methyl-butyric acid 2-tert-Butoxycarbonylamino-3-hydroxy-3-methyl-butyric acid (1.0 g, 4.29 mmol) was dissolved in THF (14 mL) and cooled to 0° C. in an external ice/brine bath. MeI (2.13 mL, 34.3 mmol) was added at 0° C. Solid NaH (60% dispersion in mineral oil, 0.514 g, 12.87 mmol) was added slowly at 0° C. Upon completion of the addition, the solution was removed from the ice bath and allowed to warm to room temperature, and stirred. After 18 hours, the crude reaction mixture was diluted in ethyl acetate and water was added slowly with stirring. The quenched mixture was concentrated in vacuo and partitioned between diethyl ether and water. The ether layer was extracted with sodium bicarbonate twice. The combined bicarbonate layers were acidified with aqueous citric acid to pH 3 and extracted three times with ethyl acetate. The combined ethyl acetate layers were washed with water, sodium thiosulfate, water, dried with sodium sulfate and concentrated to yield 2-tert-Butoxycarbonylamino-3-methoxy-3-methyl-butyric acid (0.99 g, 94%) as an oil.

$^1$H NMR (400 MHz, CDCl$_3$) δ 3.76-3.66 (m, 3H), 3.29 (s, 1H), 1.50 (s, 3H), 1.45 (s, 9H), 1.33 (s, 3H).

1125

3-Methoxy-2-methoxycarbonylamino-3-methyl-butyric acid 2-tert-Butoxycarbonylamino-3-methoxy-3-methyl-butyric acid was dissolved in dioxane (40 mL) and HCl (4N in dioxane, 5.4 mL, 21.6 mmol) was added at room temperature. The resulting solution was stirred at room temperature for 18 hours and the concentrated to dryness. The solid was dissolved in THF (14 mL) and cooled to 0° C. in an external ice/brine bath. Aqueous sodium hydroxide (6.25M, 1.9 mL, 11.76 mmol) and methyl chloroformate (0.5 mL, 5.88 mmol) were added at 0° C. Upon completion of the addition, the solution was removed from the ice bath and allowed to warm to room temperature, and stirred. After 18 hours, the crude reaction mixture was adjusted to pH 1 with 1N HCl and extracted twice with diethyl ether. The combined organic layers were washed with brine, dried with magnesium sulfate and concentrated to give 3-Methoxy-2-methoxycarbonylamino-3-methyl-butyric acid (0.653 g, 65%) as an off-white solid.

$^1$H NMR (400 MHz, acetone) δ 3.76 (s, 3H), 3.60 (s, 3H), 3.22 (s, 3H), 3.18 (s, 3H), 1.37-1.31 (m, 1H).

Example JB

1126

[2-Methoxy-1-(3-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using 3-Methoxy-2-methoxycarbonylamino-3-methyl-butyric acid (0.020 g, 0.096 mmol) to provide [2-Methoxy-1-(3-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester (0.019 g, 35%) as a white solid.

$^1$H NMR (400 MHz, CDCl$_3$) δ 8.37-7.88 (m, 4H), 7.84-7.35 (m, 8H), 5.81-5.33 (m, 2H), 4.88-4.57 (m, 2H), 4.34 (s, 1H), 3.91-3.54 (m, 9H), 3.46-3.16 (m, 4H), 3.09-2.82 (m,

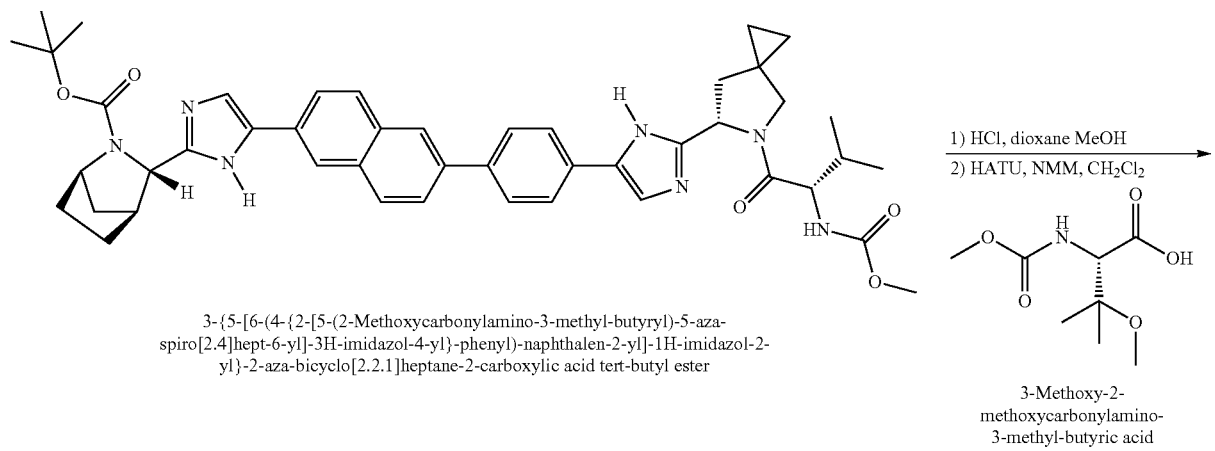

3-{5-[6-(4-{2-[5-(2-Methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carboxylic acid tert-butyl ester 1) HCl, dioxane MeOH
2) HATU, NMM, CH$_2$Cl$_2$ 3-Methoxy-2-methoxycarbonylamino-3-methyl-butyric acid

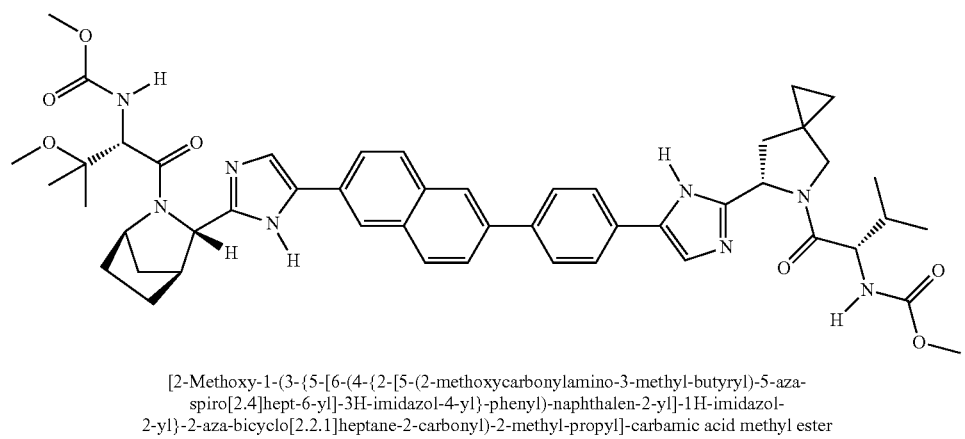

[2-Methoxy-1-(3-{5-[6-(4-{2-[5-(2-methoxycarbonylamino-3-methyl-butyryl)-5-aza-spiro[2.4]hept-6-yl]-3H-imidazol-4-yl}-phenyl)-naphthalen-2-yl]-1H-imidazol-2-yl}-2-aza-bicyclo[2.2.1]heptane-2-carbonyl)-2-methyl-propyl]-carbamic acid methyl ester 1H), 2.24 (dd, 2H), 1.93 (m, 6H), 1.61 (s, 1H), 1.47-1.17 (m, 7H), 1.11 (d, 1H), 1.02-0.83 (m, 7H), 0.72 (s, 3H).

LCMS-ESI$^+$: calc'd for $C_{49}H_{58}N_8O_7$: 870.44 (M$^+$); Found: 871.90 (M+H$^+$).

Example JC

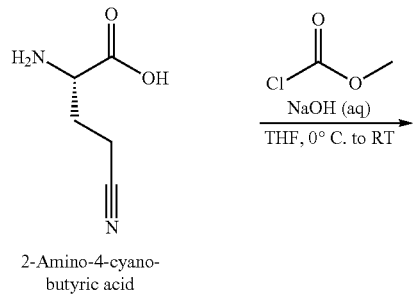

2-Amino-4-cyano-butyric acid

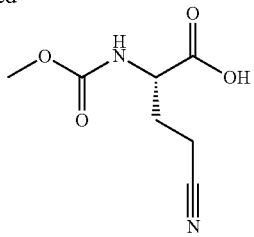

4-Cyano-2-methoxycarbonyl-amino-butyric acid

4-Cyano-2-methoxycarbonylamino-butyric acid

This compound was prepared using the procedure used to prepare 3-Methoxy-2-methoxycarbonylamino-3-methyl-butyric acid using 2-Amino-4-cyano-butyric acid. LCMS-ESI$^+$: calc'd for $C_7H_{10}N_2O_4$: 186.06 (M$^+$); Found: 187.09 (M+H$^+$).

Example JD

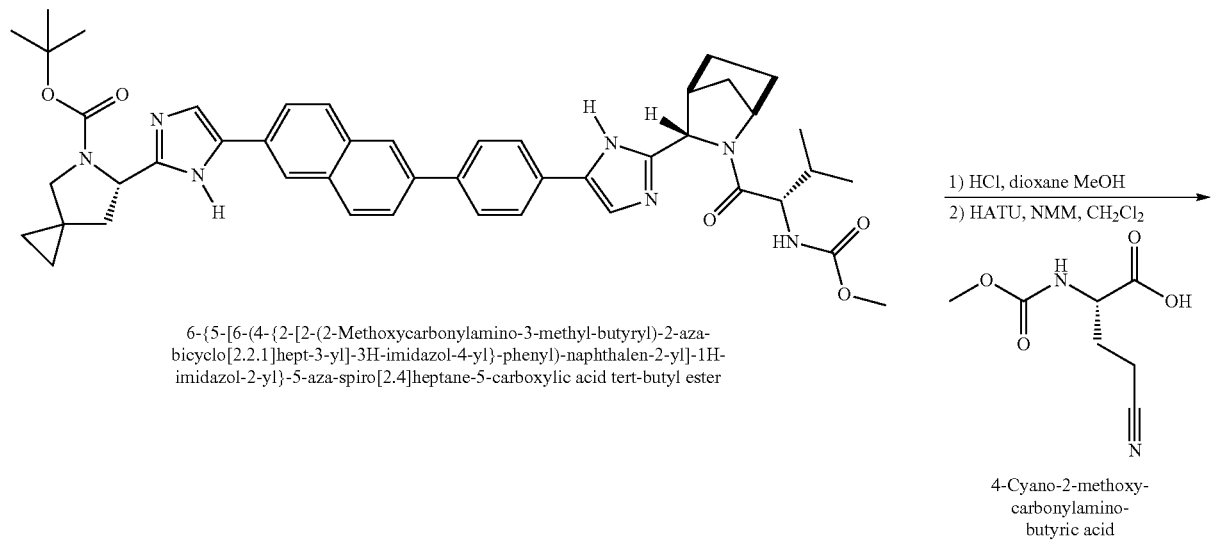

6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carboxylic acid tert-butyl ester 4-Cyano-2-methoxy-carbonylamino-butyric acid

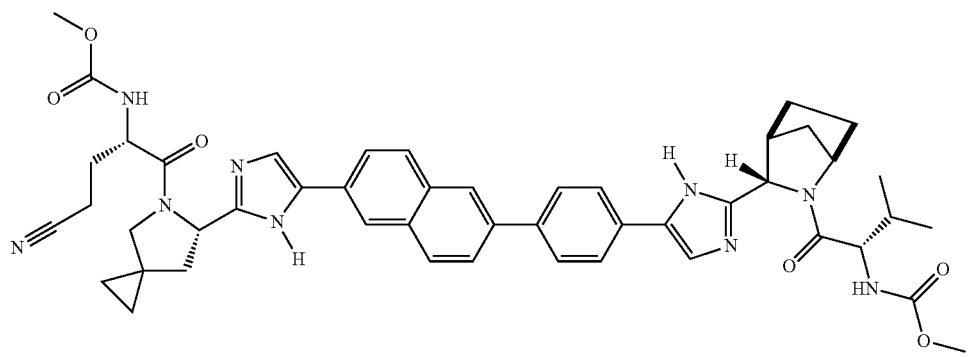

[3-Cyano-1-(6-{5-[6-(4-{2-[2-(2-methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-propyl]-carbamic acid methyl ester

[3-Cyano-1-(6-{5-[6-(4-{2-[2-(2-methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from BC) using 4-Cyano-2-methoxycarbonylamino-butyric acid to provide [3-Cyano-1-(6-{5-[6-(4-{2-[2-(2-methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-propyl]-carbamic acid methyl ester (0.015 g, 28%) as a white solid.

$^1$H NMR (400 MHz, CDCl$_3$) δ 8.34-8.10 (m, 1H), 8.05-7.84 (m, 1H), 7.80-7.62 (m, 8H), 7.53 (d, 2H), 5.47-5.22 (m, 1H), 4.92-4.61 (m, 1H), 4.49 (d, 2H), 4.25 (s, 2H), 4.10 (d, 2H), 3.79 (s, 2H), 3.70-3.42 (m, 6H), 3.32-3.23 (m, 2H), 3.00-2.85 (m, 1H), 2.59-2.06 (m, 4H), 2.02-1.79 (m, 3H), 1.75-1.60 (m, 2H), 1.50-1.38 (m, 1H), 1.18 (s, 3H), 1.06-0.77 (m, 6H), 0.72-0.50 (m, 3H).

LCMS-ESI$^+$: calc'd for C$_{48}$H$_{53}$N$_9$O$_6$: 851.41 (M$^+$); Found: 852.90 (M+H$^+$).

Example JE

[2-Methoxy-1-(3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using 3-Methoxy-2-methoxycarbonylamino-3-methyl-butyric acid (0.020 g, 0.096 mmol) to provide [2-Methoxy-1-(3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester (0.016 g, 29%) as a white solid.

$^1$H NMR (400 MHz, CDCl$_3$) δ 8.37-7.88 (m, 4H), 7.84-7.35 (m, 8H), 5.81-5.33 (m, 2H), 4.88-4.57 (m, 2H), 4.34 (s, 1H), 3.91-3.54 (m, 9H), 3.46-3.16 (m, 4H), 3.09-2.82 (m, 1H), 2.24 (dd, 2H), 1.93 (m, 6H), 1.61 (s, 1H), 1.47-1.17 (m, 7H), 1.11 (d, 1H), 1.02-0.83 (m, 7H), 0.72 (s, 3H).

LCMS-ESI$^+$: calc'd for C$_{49}$H$_{58}$N$_8$O$_7$: 870.44 (M$^+$); Found: 871.47 (M+H$^+$).

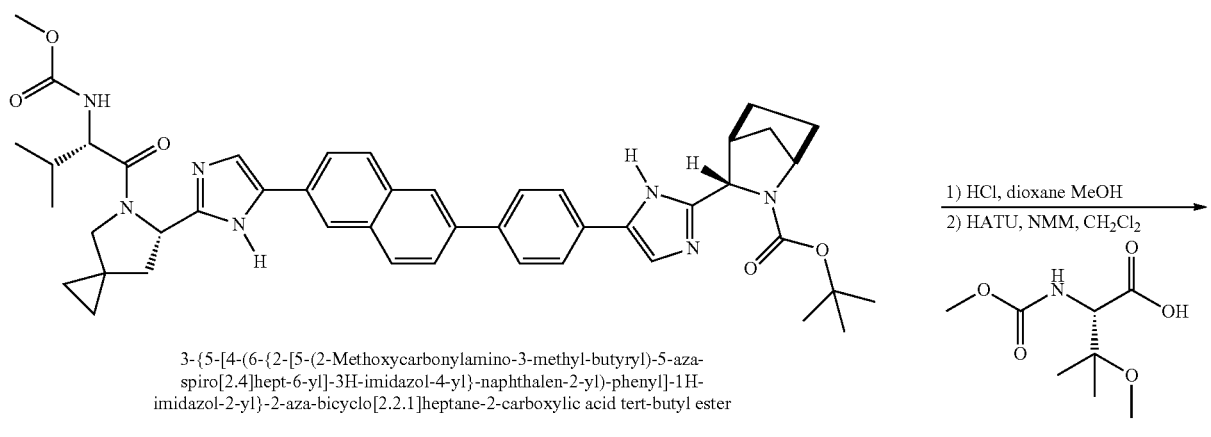

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 3-Methoxy-2-methoxycarbonylamino-3-methyl-butyric acid

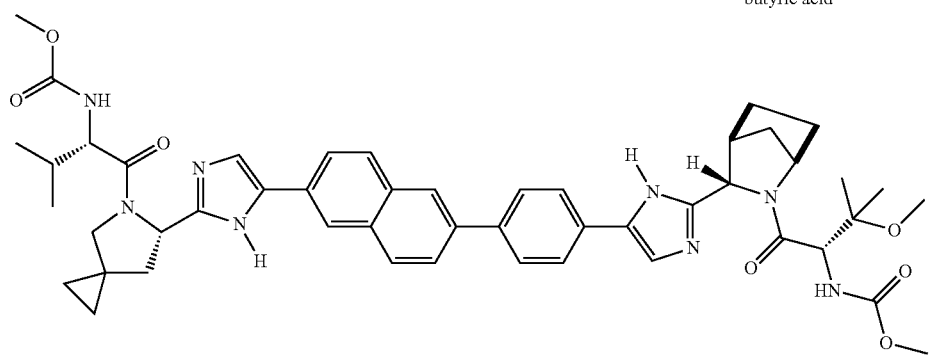

[2-Methoxy-1-(3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester

Example JF

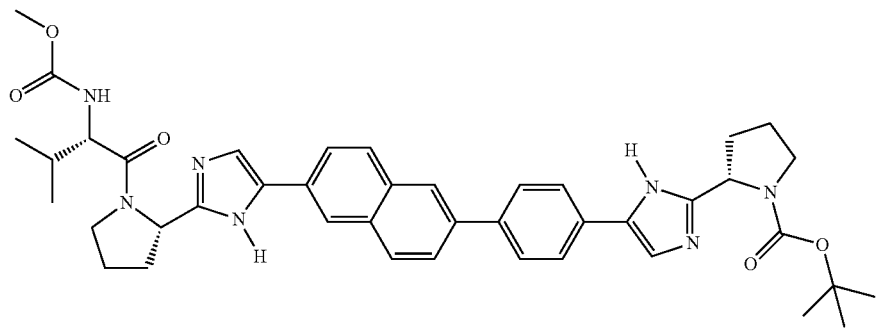

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) HATU, NMM, CH$_2$Cl$_2$

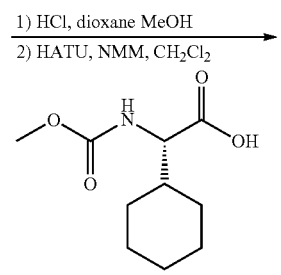

S-Cyclohexyl-methoxy-carbonylamino-acetic acid

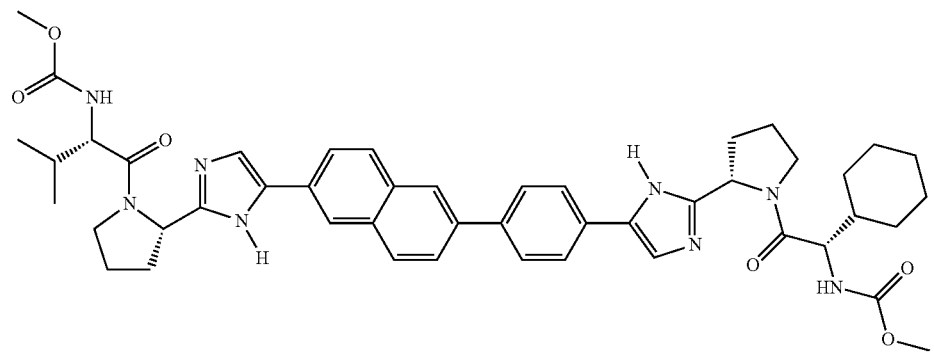

[1-(2-{5-[6-(4-{2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using S-Cyclohexyl-methoxycarbonylamino-acetic acid (0.022 g, 0.102 mmol) to provide [1-(2-{5-[6-(4-{(2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.036 g, 28%) as a white solid.

$^1$H NMR (400 MHz, CDCl$_3$) δ 7.90-7.62 (m, 10H), 7.30 (s, 1H), 7.25 (s, 1H), 5.60 (d, 1H), 5.53 (d, 1H), 5.41 (d, 1H), 5.31 (dd, 1H), 4.38 (t, 1H), 4.25 (t, 1H), 4.03-3.74 (m, 5H), 3.72-3.65 (m, 6H), 2.97-2.65 (m, 2H), 2.39 (m, 1H), 2.13 (m, 6H), 1.96-1.63 (m, 6H), 1.36-0.99 (m, 6H), 0.93 (dd, 6H).

LCMS-ESI$^+$: calc'd for C$_{47}$H$_{56}$N$_8$O$_6$: 828.43 (M$^+$); Found: 829.70 (M+H$^+$).

Example JG

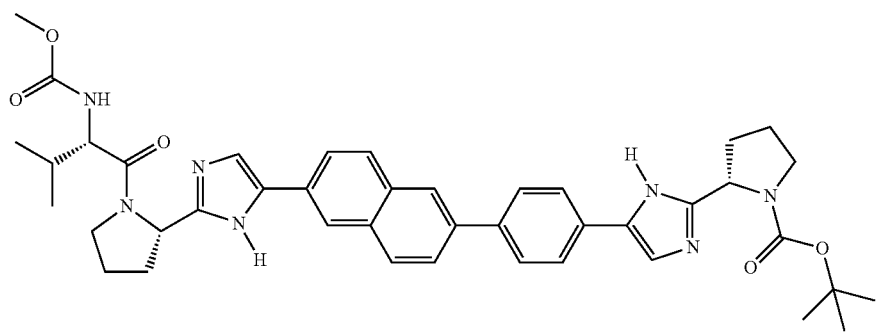

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) HATU, NMM, CH₂Cl₂

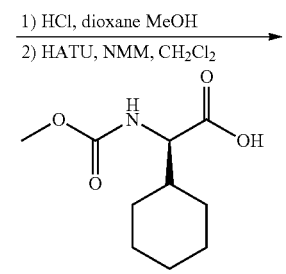

R-Cyclohexyl-methoxy-carbonylamino-acetic acid

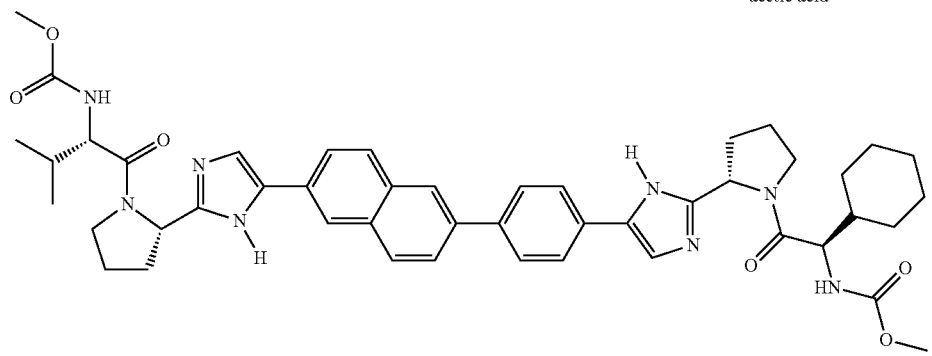

[1-(2-{5-[6-(4-{2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using R-Cyclohexyl-methoxycarbonylamino-acetic acid (0.041 g, 0.191 mmol) to provide [1-(2-{5-[6-(4-{2-[1-(2-Cyclohexyl-2-methoxycarbonylamino-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.047 g, 59%) as a white solid.

¹H NMR (400 MHz, CDCl₃) δ 7.90-7.62 (m, 10H), 7.30 (s, 1H), 7.25 (s, 1H), 5.60 (d, 1H), 5.53 (d, 1H), 5.41 (d, 1H), 5.31 (dd, 1H), 4.38 (t, 1H), 4.25 (t, 1H), 4.03-3.74 (m, 5H), 3.72-3.65 (m, 6H), 2.97-2.65 (m, 2H), 2.39 (m, 1H), 2.13 (m, 6H), 1.96-1.63 (m, 6H), 1.36-0.99 (m, 6H), 0.93 (dd, 6H).

LCMS-ESI⁺: calc'd for $C_{47}H_{56}N_8O_6$: 828.43 (M⁺); Found: 829.70 (M+H⁺).

Example JH

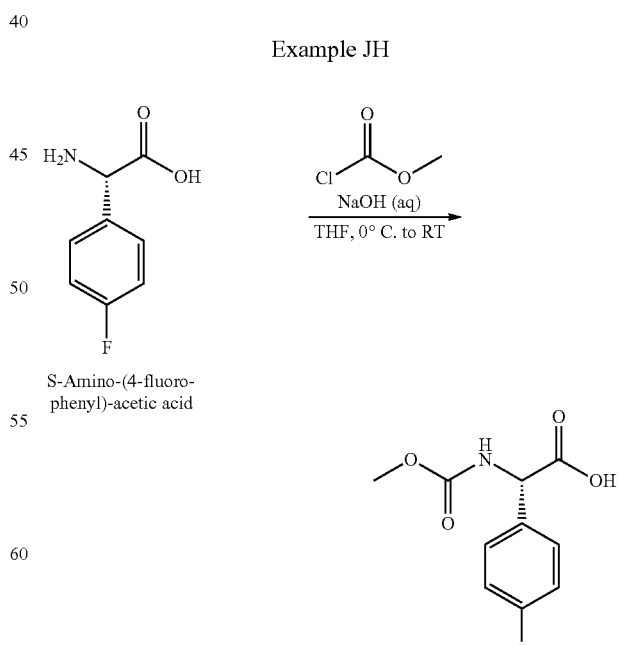

S-Amino-(4-fluoro-phenyl)-acetic acid

NaOH (aq)
THF, 0° C. to RT

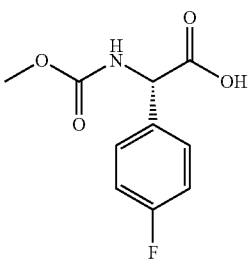

S-(4-Fluoro-phenyl)-methoxy-carbonylamino-acetic acid

1135

S-(4-Fluoro-phenyl)-methoxycarbonylamino-acetic acid

This compound was prepared using the procedure used to prepare 3-Methoxy-2-methoxycarbonylamino-3-methyl-butyric acid using S-Amino-(4-fluoro-phenyl)-acetic acid to give S-(4-Fluoro-phenyl)-methoxycarbonylamino-acetic acid (0.560 g, 82%).

LCMS-ESI$^+$: calc'd for $C_{10}H_{10}FNO_4$: 227.06 (M$^+$); Found: 227.84 (M+H$^+$).

Example JI

1136

{1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using S-(4-Fluoro-phenyl)-methoxycarbonylamino-acetic acid (0.023 g,

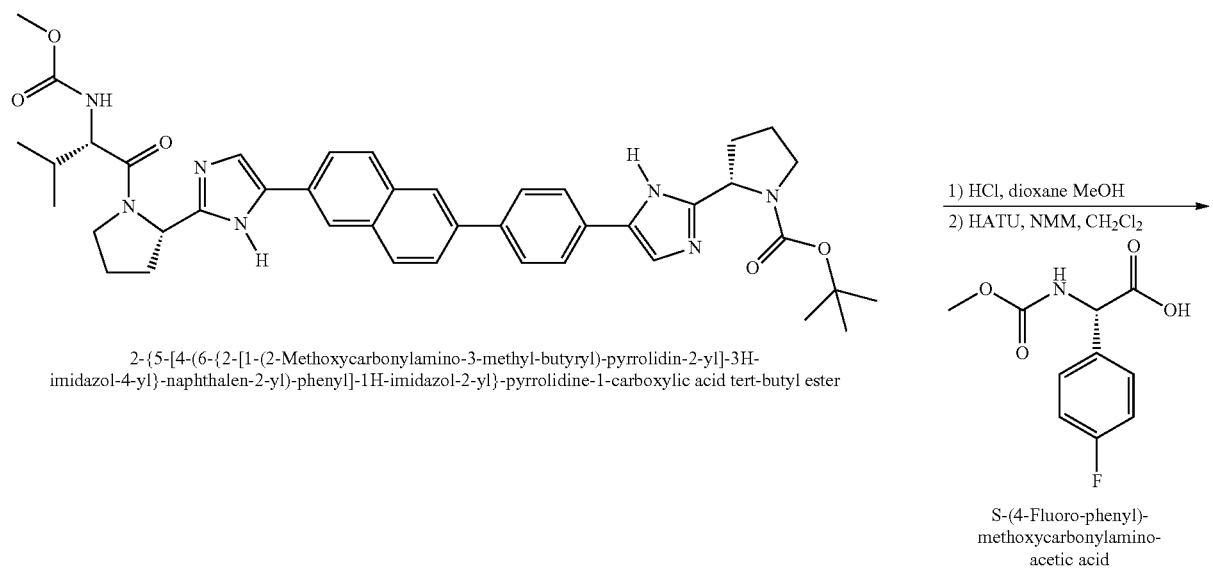

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester S-(4-Fluoro-phenyl)-methoxycarbonylamino-acetic acid

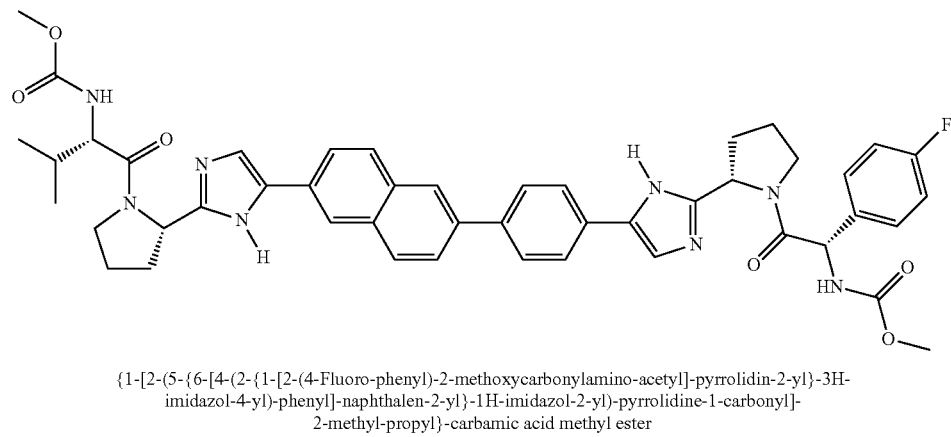

{1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester 0.100 mmol) to provide {1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.015 g, 27%) as a white solid.

$^1$H NMR (400 MHz, CDCl$_3$) δ 8.01-7.71 (m, 8H), 7.55-6.93 (m, 8H), 6.06 (d, 1H), 5.43 (dd, 1H), 5.30 (m, 3H), 4.34 (t, 1H), 3.85-3.77 (m, 2H), 3.74-3.47 (d, 6H), 3.25-2.92 (m, 4H), 2.36 (s, 1H), 2.23-1.98 (m, 7H), 1.05 (t, 1H), 0.88 (t, 6H).

LCMS-ESI$^+$: calc'd for C$_{47}$H$_{49}$FN$_8$O$_6$: 840.38 (M$^+$); Found: 841.42 (M+H$^+$).

Example JJ

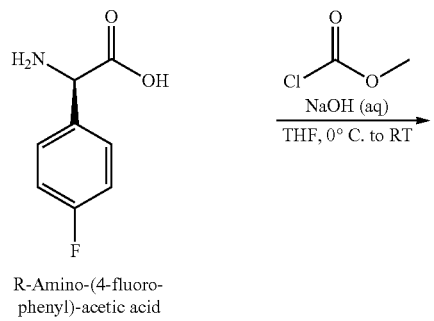

R-Amino-(4-fluoro-phenyl)-acetic acid

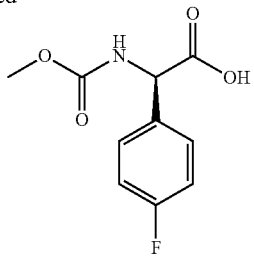

R-(4-Fluoro-phenyl)-methoxycarbonylamino-acetic acid

R-(4-Fluoro-phenyl)-methoxycarbonylamino-acetic acid

This compound was prepared using the procedure used to prepare 3-Methoxy-2-methoxycarbonylamino-3-methyl-butyric acid using R-Amino-(4-fluoro-phenyl)-acetic acid to give R-(4-Fluoro-phenyl)-methoxycarbonylamino-acetic acid (0.575 g, 84%)

LCMS-ESI$^+$: calc'd for C$_{10}$H$_{10}$FNO$_4$: 227.06 (M$^+$); Found: 227.84 (M+H$^+$).

Example JK

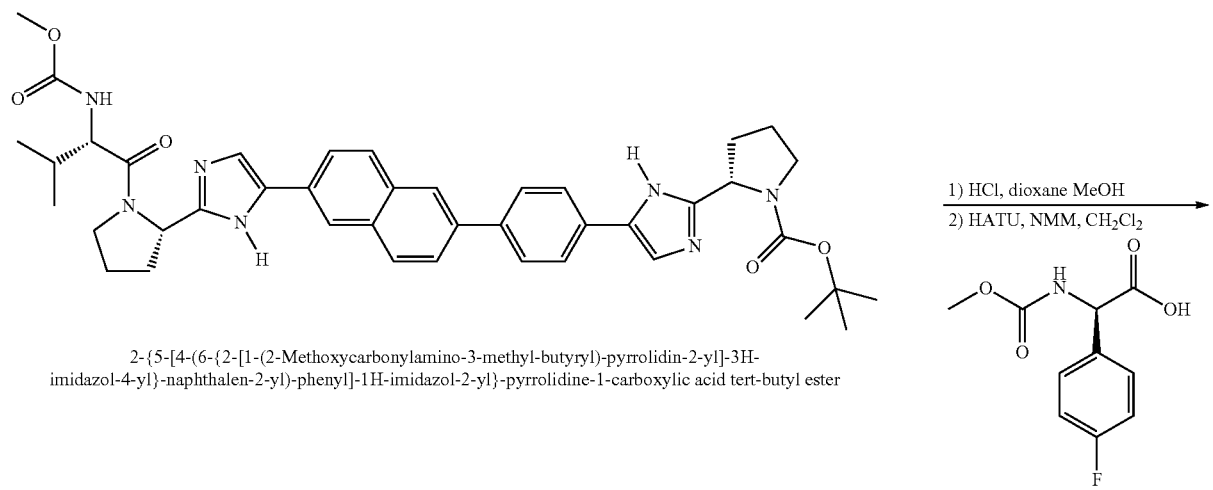

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

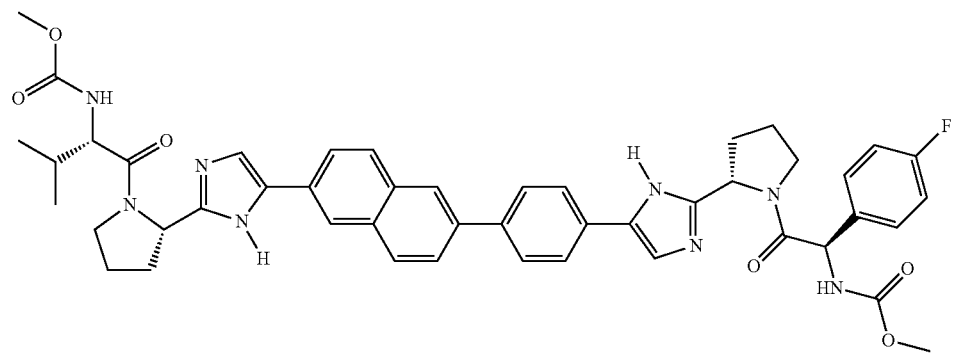

{1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester {1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester This compound was prepared using the procedure used to prepare [1-(6-{5-[4-(6-{2-[2-(2-Cyclopropyl-2-methoxycarbonylamino-acetyl)-2-aza-bicyclo[2.2.1]hept-3-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (example from JJC) using R-(4-Fluoro-phenyl)-methoxycarbonylamino-acetic acid (0.023 g, 0.100 mmol) to provide {1-[2-(5-{6-[4-(2-{1-[2-(4-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.008 g, 14%) as a white solid.

¹H NMR (400 MHz, CDCl₃) δ 8.01-7.71 (m, 8H), 7.55-6.93 (m, 8H), 6.06 (d, 1H), 5.43 (dd, 1H), 5.30 (m, 3H), 4.34 (t, 1H), 3.85-3.77 (m, 2H), 3.74-3.47 (d, 6H), 3.25-2.92 (m, 4H), 2.36 (s, 1H), 2.23-1.98 (m, 7H), 1.05 (t, 1H), 0.88 (t, 6H).

LCMS-ESI⁺: calc'd for $C_{47}H_{49}FN_8O_6$: 840.38 (M⁺); Found: 841.27 (M+H⁺).

Example JL

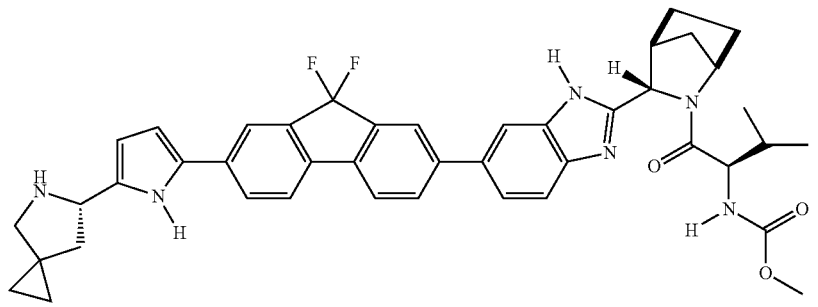

{1-[3-(6-{7-[5-(5-Aza-spiro[2.4]hept-6-yl)-1H-pyrrol-2-yl]-9,9-difluoro-9H-fluoren-2-yl}-1H-benzoimidazol-2-yl)-2-aza-bicyclo[2.2.1]heptane-2-carbonyl]-2-methyl-propyl}-carbamic acid methyl ester

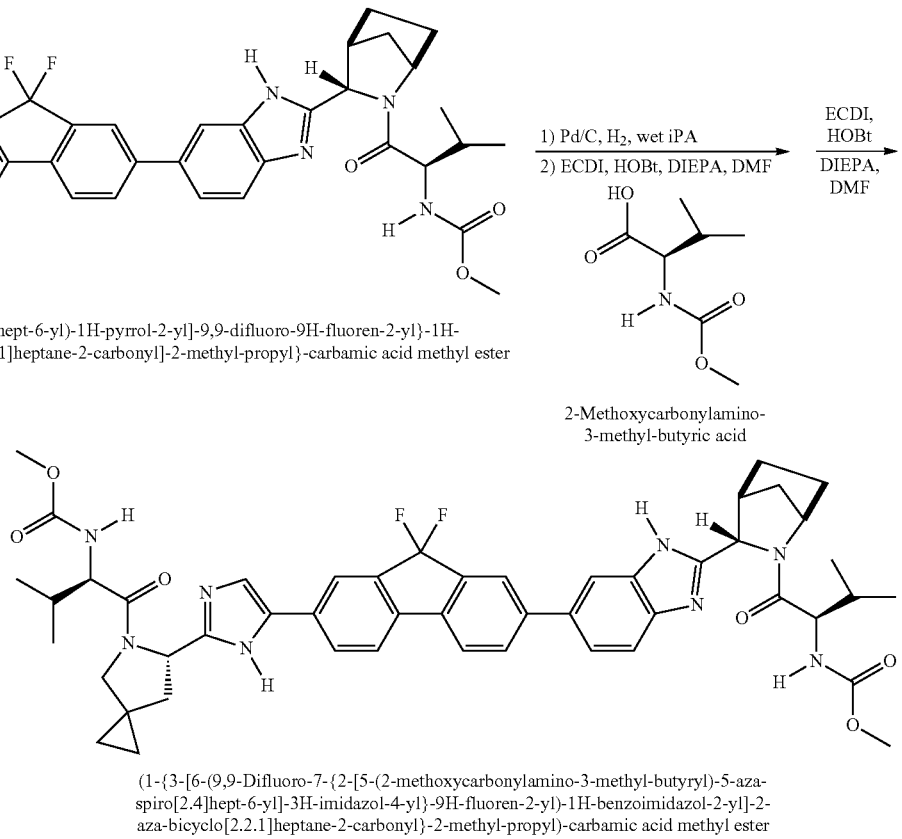

2-Methoxycarbonylamino-3-methyl-butyric acid (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (1-{3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester was prepared in a similar manner as Example C to give title compound as a white powder (68 mg).

¹H-NMR: 300 MHz, (DMSO-d₆) δ: 12.56 (d, J=13.5 Hz, 0.5H), 12.05 (dd, 1H), 11.84 (s, 0.5H), 8.1-7.1 (m, 12H), 5.71 (d, 0.5H), 5.27 (s, 0.5H), 5.19 (d, 0.5H), 4.70 (s, 0.5H), 4.64 (s, 0.5H), 4.49 (s, 0.5H), 4.2-3.9 (m, 2H), 3.6-3.2 (m, 20H), 2.8-1.1 (m, 12H), 0.9-0.4 (m, 16H).

LCMS-ESI⁺: calc'd for $C_{49}H_{54}F_2N_8O_6$: 890.0 (M+H⁺); Found: 889.4 (M+H⁺).

Example JM
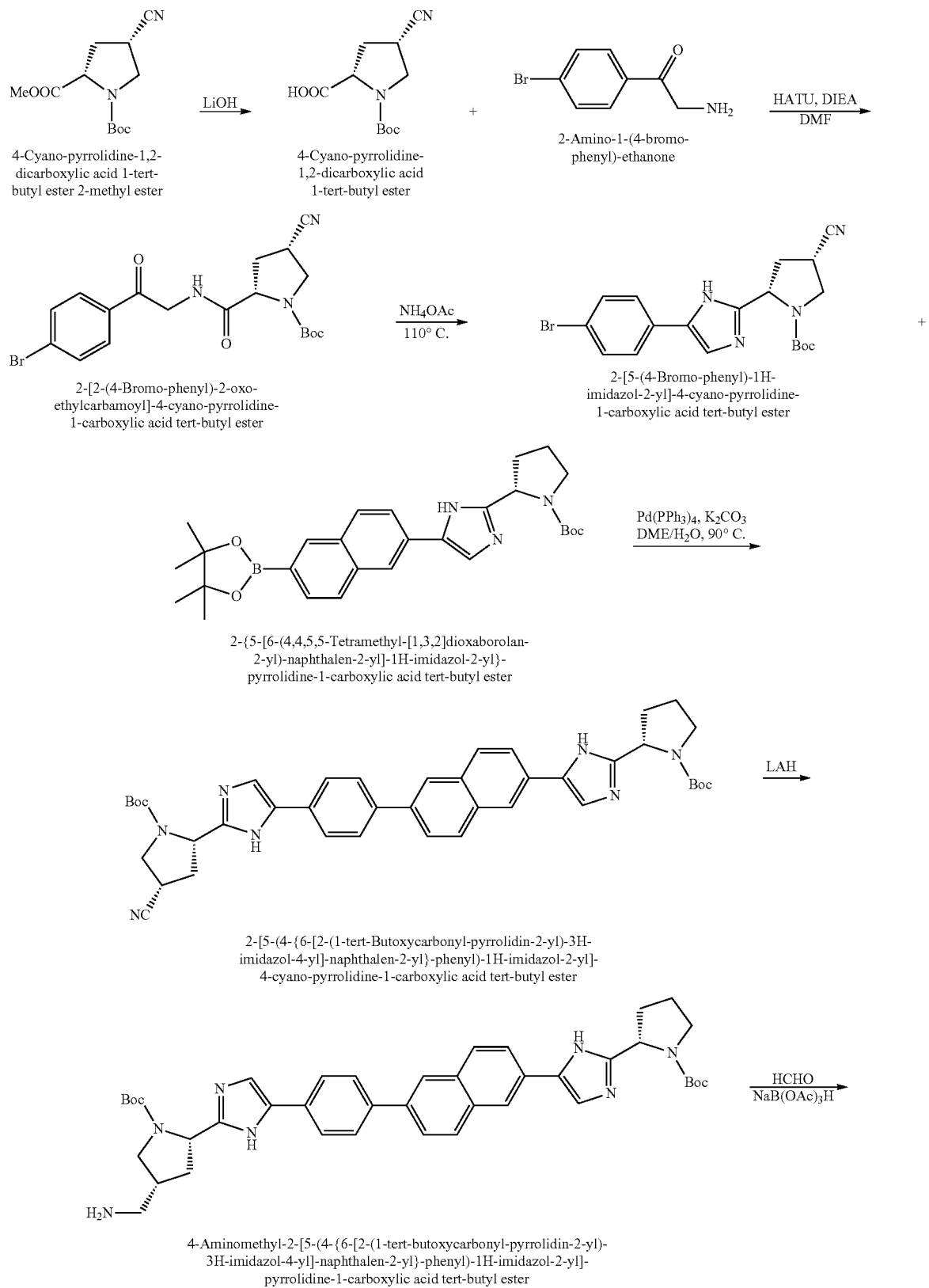

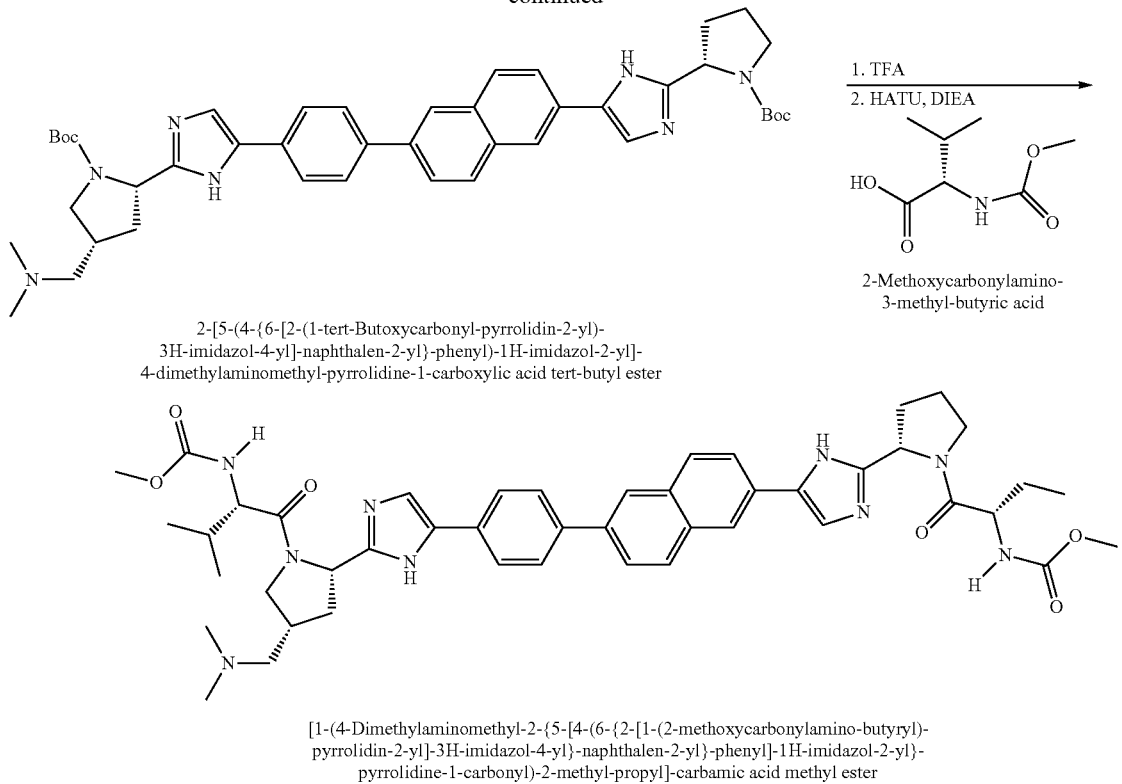

2-[5-(4-{6-[2-(1-tert-Butoxycarbonyl-pyrrolidin-2-yl)-
3H-imidazol-4-yl]-naphthalen-2-yl}-phenyl)-1H-imidazol-2-yl]-
4-dimethylaminomethyl-pyrrolidine-1-carboxylic acid tert-butyl ester 2-Methoxycarbonylamino-
3-methyl-butyric acid

[1-(4-Dimethylaminomethyl-2-{5-[4-(6-{2-[1-(2-methoxycarbonylamino-butyryl)-
pyrrolidin-2-yl]-3H-imidazol-4-yl}-naphthalen-2-yl)-phenyl]-1H-imidazol-2-yl}-
pyrrolidine-1-carbonyl)-2-methyl-propyl]-carbamic acid methyl ester LiOH.H$_2$O (167 mg, 3.98 mmol) was added to 4-cyano-pyrrolidine-1,2-dicarboxylic acid 1-tert-butyl ester 2-methyl ester (674 mg, 2.65 mmol) in methanol (5 mL) solution. The reaction was stirred at room temperature overnight. The reaction mixture was concentrated down. The crude is used in next step reaction.

2-Amino-1-(4-bromo-phenyl)-ethanone HCl salt (664 mg, 2.65 mmol) was dissolved in DMF (10 mL) and to this solution was added 4-Cyano-pyrrolidine-1,2-dicarboxylic acid 1-tert-butyl ester crude from the previous step, diisopropyl ethylamine (0.93 mL, 5.3 mmol), followed by HATU (1 g, 2.65 mmol). Reaction mixture was stirred at 0° C. for 30 minutes. The reaction mixture was dissolved in ethyl acetate and washed with dilute sodium bicarbonate solution. The organic layer was dried (MgSO4), concentrated and purified by flash column chromatography (silica gel, 20 to 80% ethyl acetate/hexane) to give 2-[2-(4-Bromo-phenyl)-2-oxo-ethylcarbamoyl]-4-cyano-pyrrolidine-1-carboxylic acid tert-butyl ester (1.05 g, yield 91%).

LCMS-ESI$^-$: calc'd for C$_{19}$H$_{22}$BrN$_3$O$_4$: 435.08; Found: 458.0 (M+Na$^+$).

A mixture of 2-[2-(4-Bromo-phenyl)-2-oxo-ethylcarbamoyl]-4-cyano-pyrrolidine-1-carboxylic acid tert-butyl ester (1.05 g, 2.4 mmol) and ammonia acetate (3.7 g, 20 eq.) in Xylene (2 mL) was heated in microwave at 110° C. for 2 hours. The mixture was concentrated and purified by flash column chromatography (silica gel, 20 to 80% ethyl acetate/hexane) to give 2-[5-(4-Bromo-phenyl)-1H-imidazol-2-yl]-4-cyano-pyrrolidine-1-carboxylic acid tert-butyl ester (356 mg, containing 15% starting material, yield 35%). LCMS-ESI$^-$: calc'd for C$_{19}$H$_{21}$BrN$_4$O$_2$: 417.30; Found: 418.9 (M+H$^+$).

The mixture of 2-[5-(4-Bromo-phenyl)-1H-imidazol-2-yl]-4-cyano-pyrrolidine-1-carboxylic acid tert-butyl ester (356 mg, 0.85 mmol), 2-{5-[6-(4,4,5,5-Tetramethyl-[1,3,2] dioxaborolan-2-yl)-naphthalen-2-yl]-1H-imidazol-2-yl}-pyrrolidine-1-carboxylic acid tert-butyl ester (501 mg, 1.02 mmol), tetrakis(triphenylphosphine)palladium (99 mg, 0.08 mmol) and potassium acetate (425 mg, 3.07 mmol) in 7 mL 1,2-dimethoxyethane and 2 mL water was heated to 90° C. for 2 hour. The reaction mixture was cooled and dissolved in ethyl acetate and washed with saturated sodium bicarbonate solution. The organic layer dried (MgSO4), concentrated and purified by flash column chromatography (silica gel, 20 to 80% ethyl acetate/hexane) to give 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-cyano-pyrrolidine-1-carboxylic acid tert-butyl ester (200 mg, yield 33%) and the amide product. LCMS-ESI$^-$: calc'd for C$_{41}$H$_{45}$N$_7$O$_4$: 699.84; Found: 700.2 (M+H$^+$).

LAH (45 mg, 6 eq.) was added to the solution of mixture of 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-cyano-pyrrolidine-1-carboxylic acid tert-butyl ester (146 mg, 0.066 mmol) in 3 ml THF at 0° C. The reaction was quenched after 30 minutes using water, 10% NaOH aqueous solution and water in 3 steps. The reaction mixture was filtered. The filtrate was concentrated down and purified by preparative reverse phase HPLC (Gemini, 5 to 100% ACN/H$_2$O+0.1% TFA). Product lyophilized to give 4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester TFA salt (150 mg, yield 95%). LCMS-ESI$^-$: calc'd for C$_{41}$H$_{49}$N$_7$O$_4$: 703.87; Found: 704.2 (M+H$^+$).

Sodium triacetyl boron hydride (54 mg, 3 eq.) was added to the mixture of 4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester (60 mg, 0.085 mmol) and 0.1 mL form-aldehyde (37% in water) in 3 ml THF, followed by 1 drop of acetic acid. The reaction was stirred at room temperature for 30 minutes. The reaction was complete by monitoring using LC-MS. The reaction mixture was filtered. The filtrate was concentrated down and purified by preparative reverse phase HPLC (Gemini, 5 to 100% ACN/H$_2$O+0.1% TFA). Product lyophilized to give 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-dimethylaminomethyl-pyrrolidine-1-carboxylic acid tert-butyl ester TFA salt (41.7 mg, yield 67%). LCMS-ESI$^-$: calc'd for $C_{43}H_{53}N_7O_4$: 731.93; Found: 732.3 (M+H$^+$).

Trifluoroacetic acid (0.5 mL) was added to 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-dimethylaminomethyl-pyrrolidine-1-carboxylic acid tert-butyl ester (41.7 mg, 0.057 mmol) in 1 ml DCM and the reaction mixture was stirred at room temperature for 2 hours. The reaction mixture was concentrated and dried overnight under vacuum. The residue was dissolved in DMF (1.5 mL) and to this solution was added 2-Methoxycarbonylamino-3-methyl-butyric acid (20 mg, 0.124 mmol), diisopropyl ethylamine (60 µl), followed by HATU (43 mg). Reaction mixture was stirred at 0° C. for 60 minutes. The reaction mixture was dissolved in ethyl acetate and washed with dilute sodium bicarbonate solution. The organic layer was dried (MgSO4), concentrated and purified by preparative reverse phase HPLC (Gemini, 5 to 100% ACN/H$_2$O+0.1% TFA). Product lyophilized to give [1-(4-Dimethylaminomethyl-2-{5-[4-(6-{2-[1-(2-methoxy-carbonylamino-butyryl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester the bis-TFA salt (Example A) (13.1 mg).

$^1$H-NMR: 300 MHz, (CD$_3$OD-d$_4$) δ: 8.28 (d, 2H), 8.02 (m, 2H), 7.83-7.92 (m, 8H), 5.38 (m, 2H), 4.58 (m, 1H), 4.22 (m, 2H), 4.18 (m, 2H), 3.92 (m, 2H), 3.62 (s, 6H), 3.42 (m, 2H), 3.02 (s, 6H), 3.00 (m, 1H), 2.81 (m, 1H), 2.62 (m, 1H), 2.40-2.00 (m, 5H), 0.95-1.05 (m, 12H).

LCMS-ESI$^+$: calc'd for $C_{47}H_{59}N_9O_6$: 846.03; Found: 848.4 (M+H$^+$).

Example JN

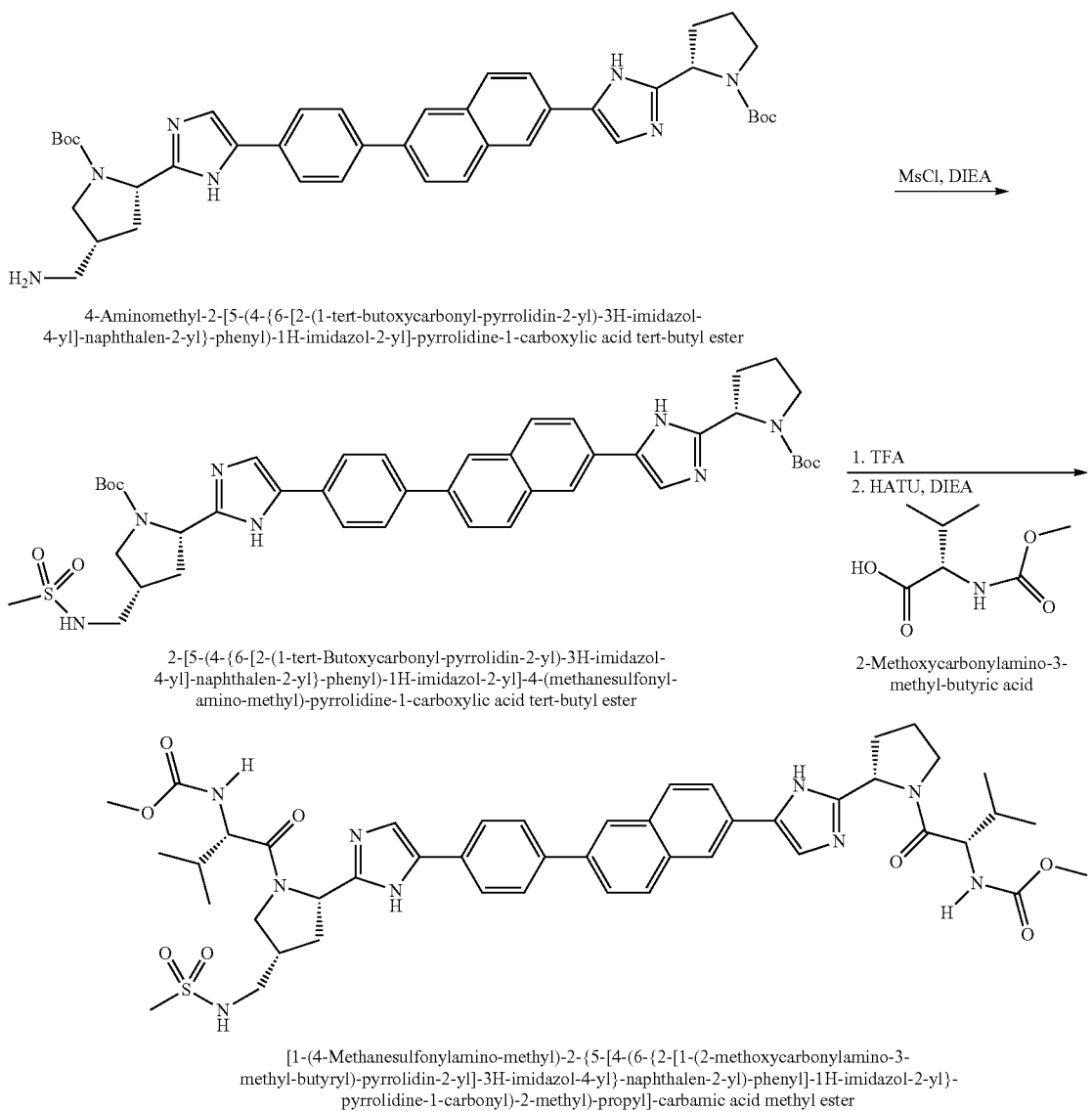

4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-(methanesulfonyl-amino-methyl)-pyrrolidine-1-carboxylic acid tert-butyl ester 2-Methoxycarbonylamino-3-methyl-butyric acid

[1-(4-Methanesulfonylamino-methyl)-2-{5-[4-(6-{2-[1-(2-methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-2-methyl)-propyl]-carbamic acid methyl ester MsCl (7.6 mg, 1 eq.) was added to the mixture of 4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester (69 mg, 0.098 mmol) and DIEA (51 μl, 3 eq) in 1 ml MeCN. The reaction was stirred at room temperature for 30 minutes. The reaction mixture was concentrated down and purified by preparative reverse phase HPLC (Gemini, 5 to 100% ACN/H$_2$O+ 0.1% TFA). Product lyophilized to give 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-(methanesulfonylamino-methyl)-pyrrolidine-1-carboxylic acid tert-butyl ester TFA salt (29 mg, yield 38%). LCMS-ESI$^-$: calc'd for $C_{42}H_{51}N_7O_6S$: 781.96; Found: 782.2 (M+H$^+$).

Trifluoroacetic acid (0.5 mL) was added to 2-[5-(4-{6-[2-(1-tert-Butoxycarbonyl-pyrrolidin-2-yl)-3H-imidazol-4-yl]-naphthalen-2-yl}-phenyl)-1H-imidazol-2-yl]-4-(methanesulfonylamino-methyl)-pyrrolidine-1-carboxylic acid tert-butyl ester (29 mg, 0.037 mmol) in 1 ml DCM and the reaction mixture was stirred at room temperature for 2 hours. The reaction mixture was concentrated and dried overnight under vacuum. The residue was dissolved in DMF (0.5 mL) and to this solution was added 2-Methoxycarbonylamino-3-methyl-butyric acid (13 mg, 2 eq.), diisopropyl ethylamine (39 μA 6 eq.), followed by HATU (28 mg, 2 eq.). Reaction mixture was stirred at 0° C. for 60 minutes. The reaction mixture was dissolved in ethyl acetate and washed with dilute sodium bicarbonate solution. The organic layer was dried (MgSO4), concentrated and purified by preparative reverse phase HPLC (Gemini, 5 to 100% ACN/H$_2$O+0.1% TFA). Product lyophilized to give [1-(4-(Methanesulfonylamino-methyl)-2-{5-[4-(6-{2-[1-(2-methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester the bis-TFA salt (Example B) (12.9 mg).

$^1$H-NMR: 300 MHz, (CD$_3$OD-d$_4$) δ: 8.28 (d, 2H), 8.08 (m, 2H), 7.95 (m, 4H), 7.82 (m, 4H), 5.28 (m, 2H), 4.38 (m, 1H), 4.22 (m, 2H), 4.12 (m, 2H), 3.92 (m, 2H), 3.62 (s, 6H), 3.61 (m, 2H), 3.02 (s, 3H), 2.72 (m, 2H), 2.60 (m, 1H), 2.40-1.98 (m, 5H), 0.95-1.05 (m, 12H).

LCMS-ESI$^+$: calc'd for $C_{46}H_{57}N_9O_8S$: 896.07; Found: 896.3 (M+H$^+$).

Example JO

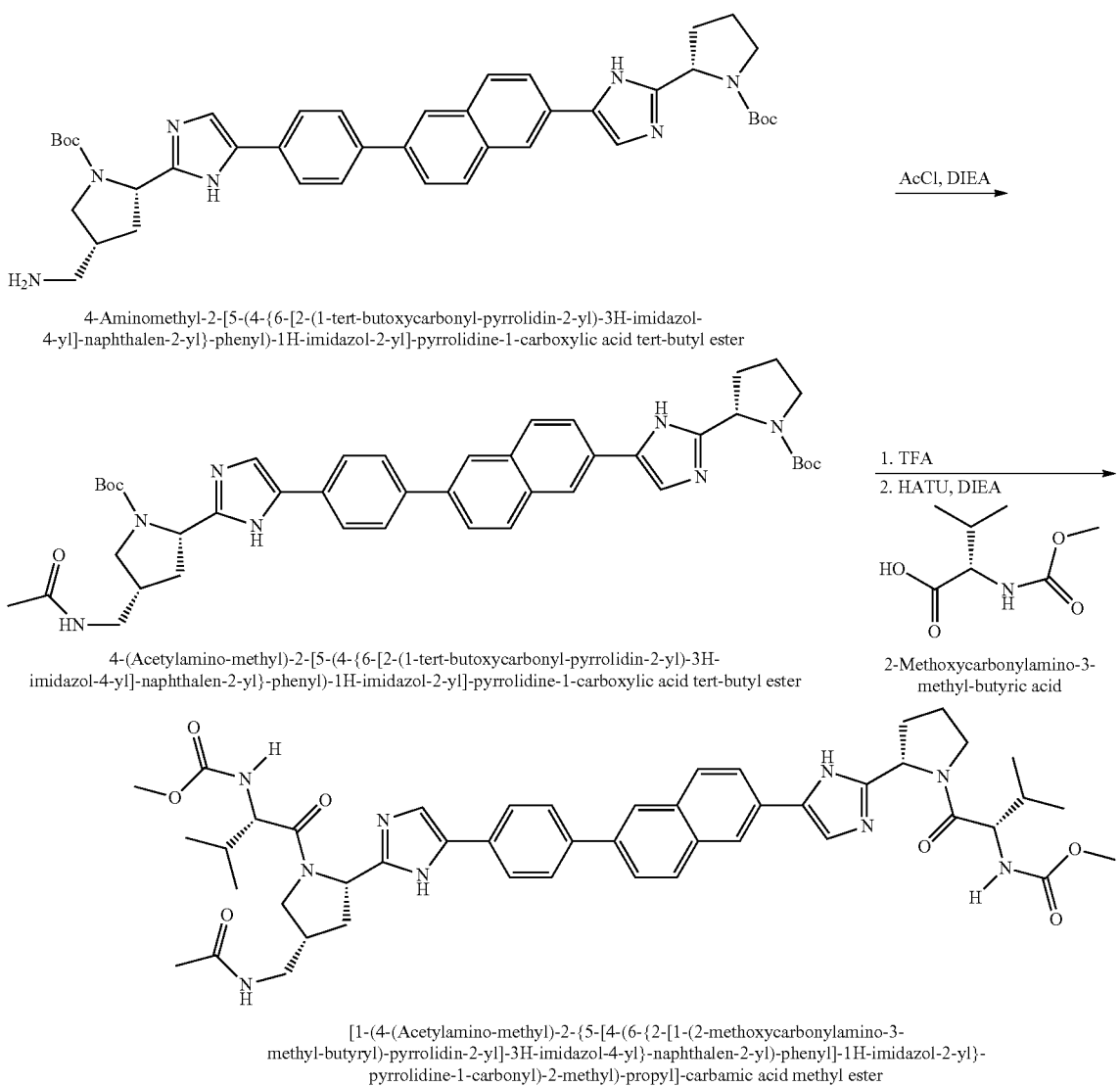

4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester 4-(Acetylamino-methyl)-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester 2-Methoxycarbonylamino-3-methyl-butyric acid

[1-(4-(Acetylamino-methyl)-2-{5-[4-(6-{2-[1-(2-methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-2-methyl)-propyl]-carbamic acid methyl ester AcCl (5 μL, 1 eq.) was added to the mixture of 4-Aminomethyl-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester (50 mg, 0.071 mmol) and DIEA (37 μl, 3 eq) in 1 ml DCM and 1 mL MeCN mixture. The reaction was stirred at room temperature for 1 hour. LC-MS shows desired and Bis-acetyl product. The reaction mixture was concentrated down and purified by preparative reverse phase HPLC (Gemini, 5 to 100% ACN/H$_2$O+0.1% TFA). Product lyophilized to give 4-(Acetylamino-methyl)-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester TFA salt (13 mg, yield 25%). LCMS-ESI$^-$: calc'd for C$_{43}$H$_{51}$N$_7$O$_5$: 745.91; Found: 746.2 (M+H$^+$).

Trifluoroacetic acid (0.5 mL) was added to 4-(Acetylamino-methyl)-2-[5-(4-{6-[2-(1-tert-butoxycarbonyl-pyrrolidin-2-yl)-3H-imidazol-4-yl]-naphthalen-2-yl}-phenyl)-1H-imidazol-2-yl]-pyrrolidine-1-carboxylic acid tert-butyl ester (13 mg, 0.017 mmol) in 1 ml DCM and the reaction mixture was stirred at room temperature for 2 hours. The reaction mixture was concentrated and dried overnight under vacuum. The residue was dissolved in DMF (0.5 mL) and to this solution was added 2-Methoxycarbonylamino-3-methyl-butyric acid (6 mg, 2 eq.), diisopropyl ethylamine (18 μl, 6 eq.), followed by HATU (13 mg, 2 eq.). Reaction mixture was stirred at 0° C. for 60 minutes. The reaction mixture was dissolved in ethyl acetate and washed with dilute sodium bicarbonate solution. The organic layer was dried (MgSO$_4$), concentrated and purified by preparative reverse phase HPLC (Gemini, 5 to 100% ACN/H$_2$O+0.1% TFA). Product lyophilized to give [1-(4-(Acetylamino-methyl)-2-{5-[4-(6-{2-[1-(2-methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester the bis-TFA salt (Example C) (6.6 mg).

$^1$H-NMR: 300 MHz, (CD$_3$OD-d$_4$) δ: 8.28 (d, 2H), 8.08 (m, 2H), 7.95 (m, 4H), 7.82 (m, 4H), 5.28 (m, 2H), 4.38 (m, 1H), 4.22 (m, 2H), 4.17 (m, 2H), 3.92 (m, 2H), 3.62 (s, 6H), 3.59 (m, 1H), 3.42 (m, 2H), 2.64 (m, 2H), 2.24 (m, 3H), 2.10 (m, 2H), 1.99 (s, 3H), 0.95-1.05 (m, 12H).

LCMS-ESI$^+$: calc'd for C$_{47}$H$_{57}$N$_9$O$_7$: 859.44; Found: 860.4 (M+H$^+$).

Example JP

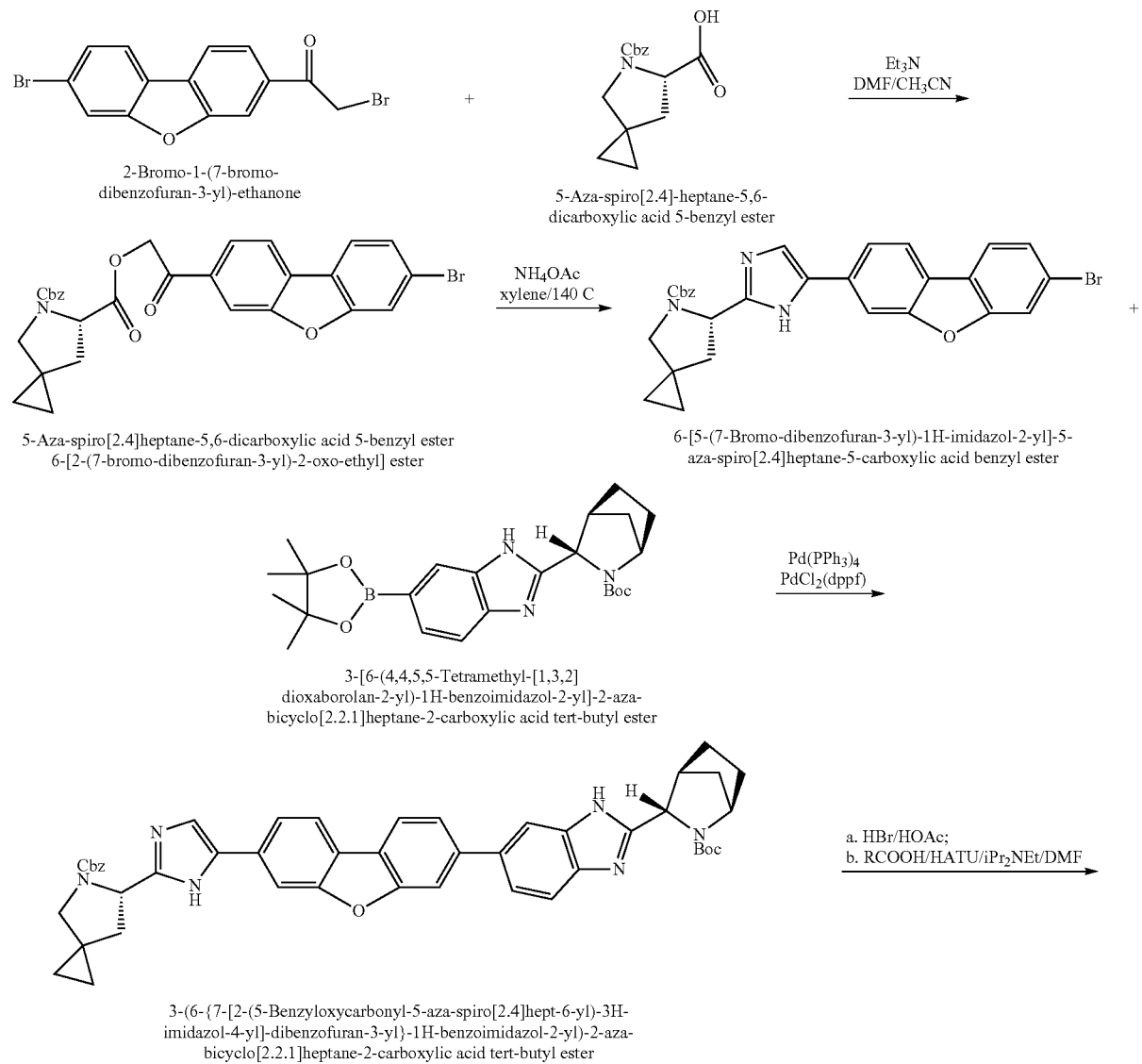

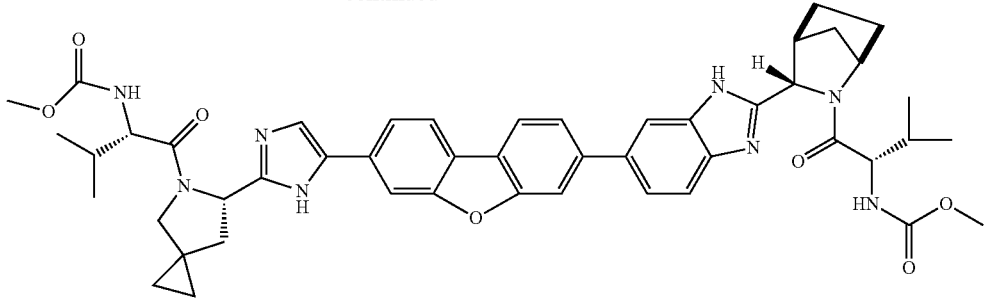

(1-{6-[5-(7-{2-[2-(2-Methoxycarbonylamino-3-methyl-butyryl)-2-aza-bicyclo[2.2.1]hept-3-yl]-3H-benzoimidazol-5-yl}-dibenzofuran-3-yl)-1H-imidazol-2-yl]-5-aza-spiro[2.4]heptane-5-carbonyl}-2-methyl-propyl)-carbamic acid methyl ester 5-Aza-spiro[2.4]heptane-5,6-dicarboxylic acid 5-benzyl ester 6-[2-(7-bromo-dibenzofuran-3-yl)-2-oxo-ethyl]ester To the solution of (s) 5-aza-spiro[2.4]heptane-5,6-dicarboxylic acid 5-benzyl ester (138 mg, 0.5 mmol) and triethylamine (65 μl, 0.47 mmol) in acetonitrile (3 ml) was added slowly a solution of 2-bromo-1-(7-bromo-dibenzofuran-3-yl)-ethanone (143 mg, 0.39 mmol) in DMF (4 ml). The mixture was stirred for 12 hours, and the solvent was evaporated. The mixture was diluted with EtOAc, and washed with 1.0 N NaOH solution, water and brine, and was dried with sodium sulfate. Concentration gave 5-Aza-spiro[2.4]heptane-5,6-dicarboxylic acid 5-benzyl ester 6-[2-(7-bromo-dibenzofuran-3-yl)-2-oxo-ethyl]ester (210 mg)

6-[5-(7-Bromo-dibenzofuran-3-yl)-1H-imidazol-2-yl]-5-aza-spiro[2.4]heptane-5-carboxylic acid benzyl ester The mixture of 5-aza-spiro[2.4]heptane-5,6-dicarboxylic acid 5-benzyl ester 6-[2-(7-bromo-dibenzofuran-3-yl)-2-oxo-ethyl]ester (210 mg, 0.39 mmol) and ammonium acetate (330 mg, 4.3 mmol) in xylene (3 ml) was heated at 140 C for 80 minutes under microwave. The mixture was quenched with water, and extracted with EtOAc. The organic phase was washed with water and brine, and was dried with sodium sulfate. Concentration and purification by flash column chromatography (EtOAc) gave 6-[5-(7-bromo-dibenzofuran-3-yl)-1H-imidazol-2-yl]-5-aza-spiro[2.4]heptane-5-carboxylic acid benzyl ester (150 mg). m/z: 542.1 (M+1), 540.1 (M−1).

3-(6-{7-[2-(5-Benzyloxycarbonyl-5-aza-spiro[2.4]hept-6-yl]-3H-imidazol-4-yl]-dibenzofuran-3-yl}-1H-benzoimidazol-2-yl)-2-aza-bicyclo[2.2.1]heptane-2-carboxylic acid tert-butyl ester To the solution of 6-[5-(7-bromo-dibenzofuran-3-yl)-1H-imidazol-2-yl]-5-aza-spiro[2.4]heptane-5-carboxylic acid benzyl ester (150 mg, 0.28 mmol) and 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester (160 mg, 0.36 mmol) in DME (2.25 ml) and water (0.75 ml) was added potassium carbonate (78 mg, 0.56 mmol), followed by Pd(PPh₃)₄ (15 mg) and PdCl₂(dppf)CH₂Cl₂ (15 mg). The mixture was heated at 90 C for 16 hours. The mixture was diluted with EtOAc, and was washed with water and brine, and was dried with sodium sulfate. Concentration and purification by flash column chromatography (hexanes/EtOAc) gave 3-(6-{7-[2-(5-benzyloxycarbonyl-5-aza-spiro[2.4]hept-6-yl)-3H-imidazol-4-yl]-dibenzofuran-3-yl}-1H-benzoimidazol-2-yl)-2-aza-bicyclo[2.2.1]heptane-2-carboxylic acid tert-butyl ester (190 mg). m/z: 775.2 (M+1), 773.3 (M−1), 338.2 (M+2)/2.

(1-{6-[5-(7-{2-[2-(2-Methoxycarbonylamino-3-methyl-butyryl)-2-aza-bicyclo[2.2.1]hept-3-yl]-3H-benzoimidazol-5-yl}-dibenzofuran-3-yl)-1H-imidazol-2-yl]-5-aza-spiro[2.4]heptane-5-carbonyl}-2-methyl-propyl)-carbamic acid methyl ester To the solution of 3-(6-{7-[2-(5-benzyloxycarbonyl-5-aza-spiro[2.4]hept-6-yl)-3H-imidazol-4-yl]-dibenzofuran-3-yl}-1H-benzoimidazol-2-yl)-2-aza-bicyclo[2.2.1]heptane-2-carboxylic acid tert-butyl ester (185 mg, 0.24 mmol) in DCM (3.6 ml) was added slowly 33% HBr/HOAc (1 ml). The mixture was stirred for two hours, and the solvent and reagent were removed under reduced pressure to give a brown solid. The solid was suspended in DCM/Et₂O (2.5 ml/25 ml) and was stirred. The solid was collected through filtration. To the solution of above solid (0.24 mmol) and MeOCO-Val-OH (84 mg, 0.48 mmol) in DMF (7.0 ml) was added HATU (192 mg, 0.50 mmol), followed by diisopropylethylamine (0.42 ml, 2.4 mmol). The mixture was stirred for ten hours and was evaporated and then diluted with EtOAc. The organic phase was washed with 1 N NaOH solution, water, and brine, and was dried with sodium sulfate. Concentration and purification by HPLC (0.1% TFA/CH₃CN/0.1% TFA/H₂O) gave (1-{6-[5-(7-{2-[2-(2-methoxycarbonylamino-3-methyl-butyryl)-2-aza-bicyclo[2.2.1]hept-3-yl]-3H-benzoimidazol-5-yl}-dibenzofuran-3-yl)-1H-imidazol-2-yl]-5-aza-spiro[2.4]heptane-5-carbonyl}-2-methyl-propyl)-carbamic acid methyl ester (151 mg). m/z: 855.3 (M+1), 853.2 (M−1), 428.4 (M+2)/2. ¹H NMR (CD₃OD, 300 MHz) δ 8.25-7.70 (10H, m), 5.4 (1H, m), 4.95-4.7 (1H, m), 4.38 (1H, m), 4.16 (1H, m), 3.95 (1H, m), 3.83 (1H, m), 3.69 (3H, s), 3.67 (3H, s), 3.5-3.2 (1H, m), 2.98 (1H, m), 2.5-1.7 (10H, m), 1.2-0.8 (16H, m).

Example JQ

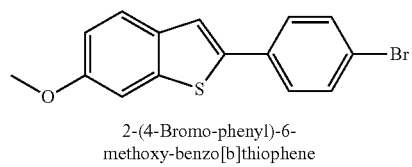

2-(4-Bromo-phenyl)-6-methoxy-benzo[b]thiophene

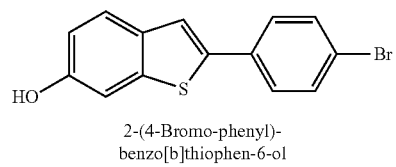

2-(4-Bromo-phenyl)-benzo[b]thiophen-6-ol

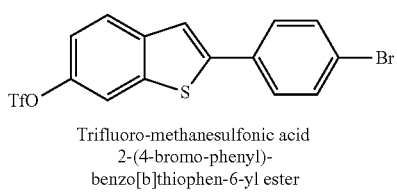

Trifluoro-methanesulfonic acid 2-(4-bromo-phenyl)-benzo[b]thiophen-6-yl ester

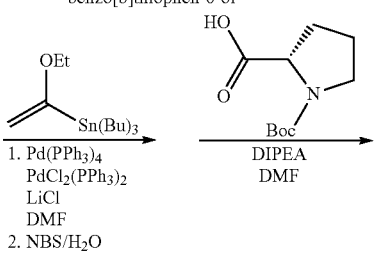

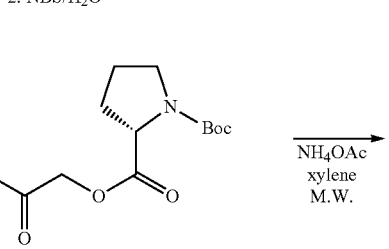

Pyrrolidine-1,2-dicarboxylic acid 1-tert-butyl ester 2-[2-(2-{4-[2-(1-Boc-pyrrolidine-2-carbonyloxy)-acetyl]-phenyl}-benzo[b]thiophen-6-yl)-2-oxo-ethyl] ester

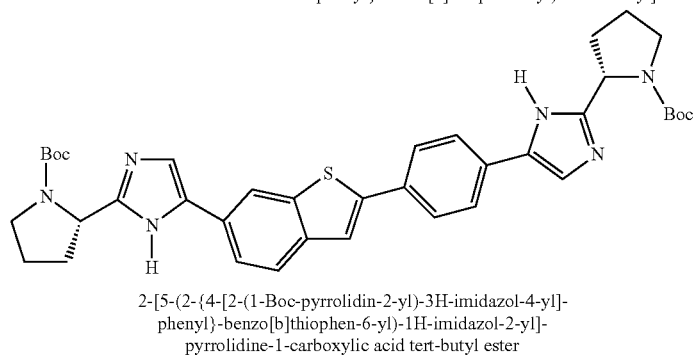

2-[5-(2-{4-[2-(1-Boc-pyrrolidin-2-yl)-3H-imidazol-4-yl]-phenyl}-benzo[b]thiophen-6-yl)-1H-imidazol-2-yl]-pyrrolidine-1-carboxylic acid tert-butyl ester

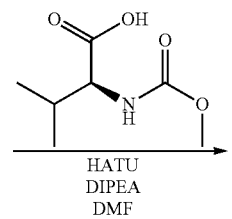

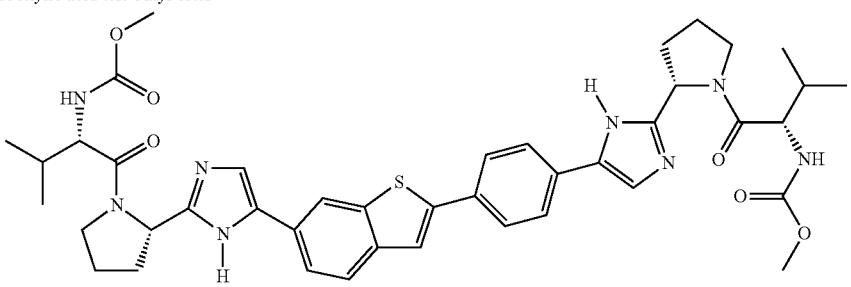

[1-(2-{5-[2-(4-{2-[1-(2-Methoxycarbonylamino-3-methyl-butyryl)-pyrrolidin-2-yl]-3H-imidazol-4-yl}-phenyl)-benzo[b]thiophen-6-yl]-1H-imidazol-2-yl}-pyrrolidine-1-carbonyl)-2-methyl-propyl]-carbamic acid methyl ester 2-(4-Bromo-phenyl)-6-methoxy-benzo[b]thiophene was reported in the literature (Journal of Medicinal Chemistry, 2007, 50, 2682-2692).

2-(4-Bromo-phenyl)-benzo[b]thiophen-6-ol

To a stirred solution of 2-(4-bromo-phenyl)-6-methoxy-benzo[b]thiophene (80 mg, 0.25 mmol) was added BBr$_3$ (0.5 mL of 1 M in DCM, 0.5 mmol) at 0° C. The mixture was stirred for 3 hours at ambient temperature. DCM was removed under vacuum, and the residue was dissolved in ethyl acetate (30 mL) The organic layer was washed with NaHCO$_3$ solution, water and brine, dried over Na$_2$SO$_4$, filtered and concentrated in vacuo. The obtained residue was treated with hexane to give the product (67 mg, 88%). m/z 303.0, 305.0 (M−H)⁻.

Trifluoro-methanesulfonic acid 2-(4-bromo-phenyl)-benzo[b]thiophen-6-yl ester Tf$_2$O was added slowly to a mixture of 2-(4-bromo-phenyl)-benzo[b]thiophen-6-ol (200 mg, 0.66 mol) in pyridine (3 mL) at 0° C. with stirring. The mixture was stirred at ambient temperature for 16 hours before quenched with NaHCO$_3$ solution. The mixture was extracted with ethyl acetate (50 mL). The organic layer was washed with water and brine, dried over Na$_2$SO$_4$, filtered and concentrated in vacuo. The obtained residue was used for next step reaction without further purification.

Pyrrolidine-1,2-dicarboxylic acid 1-tert-butyl ester 2-[2-(2-{4-[2-(1-Boc-pyrrolidine-2-carbonyloxy)-acetyl]-phenyl}-benzo[b]thiophen-6-yl)-2-oxo-ethyl] ester Pd(Ph$_3$)$_4$ (43 mg, 0.037 mmol), PdCl$_2$(Ph$_3$)$_2$ (26 mg, 0.037 mmol) and LiCl (78 mg, 1.8 mmol) were added to a mixture trifluoro-methanesulfonic acid 2-(4-bromo-phenyl)-benzo[b]thiophen-6-yl ester (200 mg, 0.46 mmol) and tributyl(1-ethoxyvinyl)tin (0.37 mL, 1.1 mmol) in 8 mL DMF. The reaction mixture was flushed with nitrogen, heated at 80° C. for 16 hours, then cooled to ambient temperature. Water (3 mL) and NBS (180 mg, 1.0 mmol) were added and the mixture was stirred at room temperature for 40 min, then diluted with ethyl acetate (300 mL). The ethyl acetate layer was washed with water and brine, dried over Na$_2$SO$_4$, filtered and concentrated in vacuo. The obtained residue was suspended in acetonitrile (30 mL). To it was added a solution of pyrrolidine-1,2-dicarboxylic acid 1-tert-butyl ester (792 mg, 3.7 mmol) and DIPEA (0.56 mL, 3.2 mmol) in 5 mL acetonitrile. The mixture was stirred at room temperature for 16 hours, diluted with ethyl acetate (100 mL). The organic layer was washed with NaHCO$_3$ solution and water, dried over Na$_2$SO$_4$, filtered and concentrated in vacuo. The obtained residue was purified by flash chromatography to provide the desired product (90 mg, 27% over two steps). m/z 743.2 (M+Na)$^+$.

2-[5-(2-{4-[2-(1-Boc-pyrrolidin-2-yl)-3H-imidazol-4-yl]-phenyl}-benzo[b]thiophen-6-yl)-1H-imidazol-2-yl]-pyrrolidine-1-carboxylic acid tert-butyl ester A mixture of pyrrolidine-1,2-dicarboxylic acid 1-tert-butyl ester 2-[2-(2-{4-[2-(1-Boc-pyrrolidine-2-carbonyloxy)-acetyl]-phenyl}-benzo[b]thiophen-6-yl)-2-oxo-ethyl]ester (90 mg, 0.12 mmol) and ammonium acetate (192 mg, 2.5 mmol) in xylene (10 mL) was heated in a sealed tube at 140° C. for 1.5 hours under microwave condition. The volatile component was removed in vacuo, and the residue was dissolved in ethyl acetate (100 mL), washed with NaHCO$_3$ solution, water and brine, dried over Na$_2$SO$_4$, filtered and concentrated in vacuo. The obtained residue was purified by flash chromatography to provide the desired product (60 mg, 70%). m/z 681.2 (M+H)$^+$.

[1-(2-{5-[2-(4-{2-[1-(2-Methoxycarbonylamino-3-methyl-butyryl)-pyrrolidin-2-yl]-3H-imidazol-4-yl}-phenyl)-benzo[b]thiophen-6-yl]-1H-imidazol-2-yl}-pyrrolidine-1-carbonyl)-2-methyl-propyl]-carbamic acid methyl ester To a solution of 2-[5-(2-{4-[2-(1-Boc-pyrrolidin-2-yl)-3H-imidazol-4-yl]-phenyl}-benzo[b]thiophen-6-yl)-1H-imidazol-2-yl]-pyrrolidine-1-carboxylic acid tert-butyl ester (60 mg, 0.09 mmol) in methanol (3 mL) was added 4N HCl in 1,4-dioxane (0.4 mL, excess). The mixture was stirred for 2 hours at 50° C. and concentrated under reduced pressure. The residue was dissolved in water and freezing-dried overnight. The obtained white solid was dissolved in DMF (3 mL), to the solution was added 2-methoxycarbonylamino-3-methyl-butyric acid (34 mg, 0.19 mmol), HATU (84 mg, 0.22 mmol) and N,N-diisopropylethylamine (0.12 mL, 0.70 mmol). The mixture was stirred at ambient for 2 hours, and then the volatile component was removed in vacuo. The residue was dissolved in ethyl acetate (100 mL), washed with 1 N NaOH solution, water and brine, dried over Na$_2$SO$_4$, filtered and concentrated in vacuo. The obtained residue was purified by HPLC to provide the desired product as a TFA salt (45 mg, 64%). $^1$H-NMR (300 MHz, CD$_3$OD) δ 8.26 (s, 1H), 8.00-7.70 (m, 9H), 5.30-5.20 (m, 2H), 4.23 (d, 2H), 4.18-4.10 (m, 2H), 3.95-3.80 (m, 2H), 3.75-3.60 (m, 6H), 2.65-2.50 (m, 2H), 2.35-2.00 (m, 8H), 1.00-0.80 (m, 12H); m/z 795.3 (M+H)$^+$.

Example JR

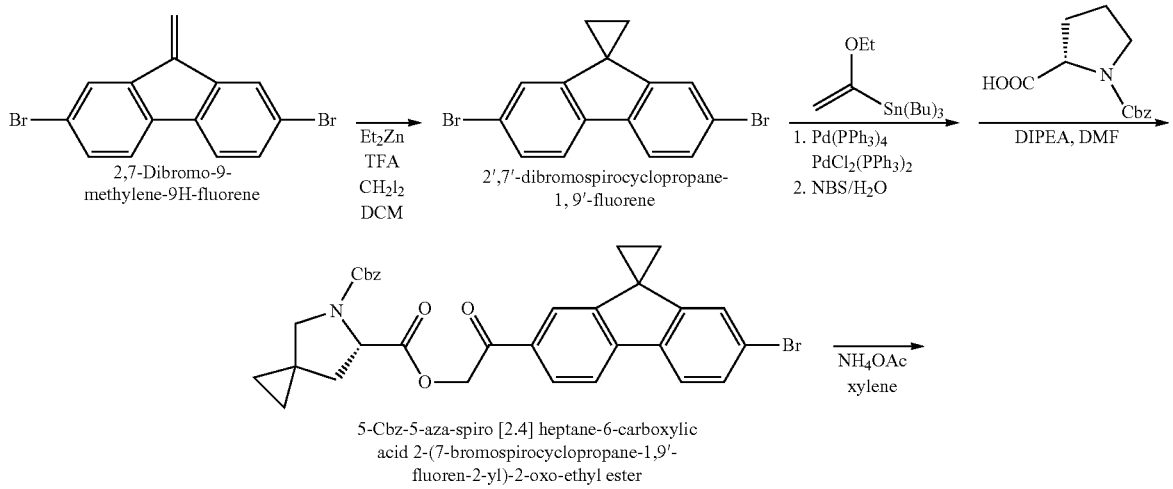

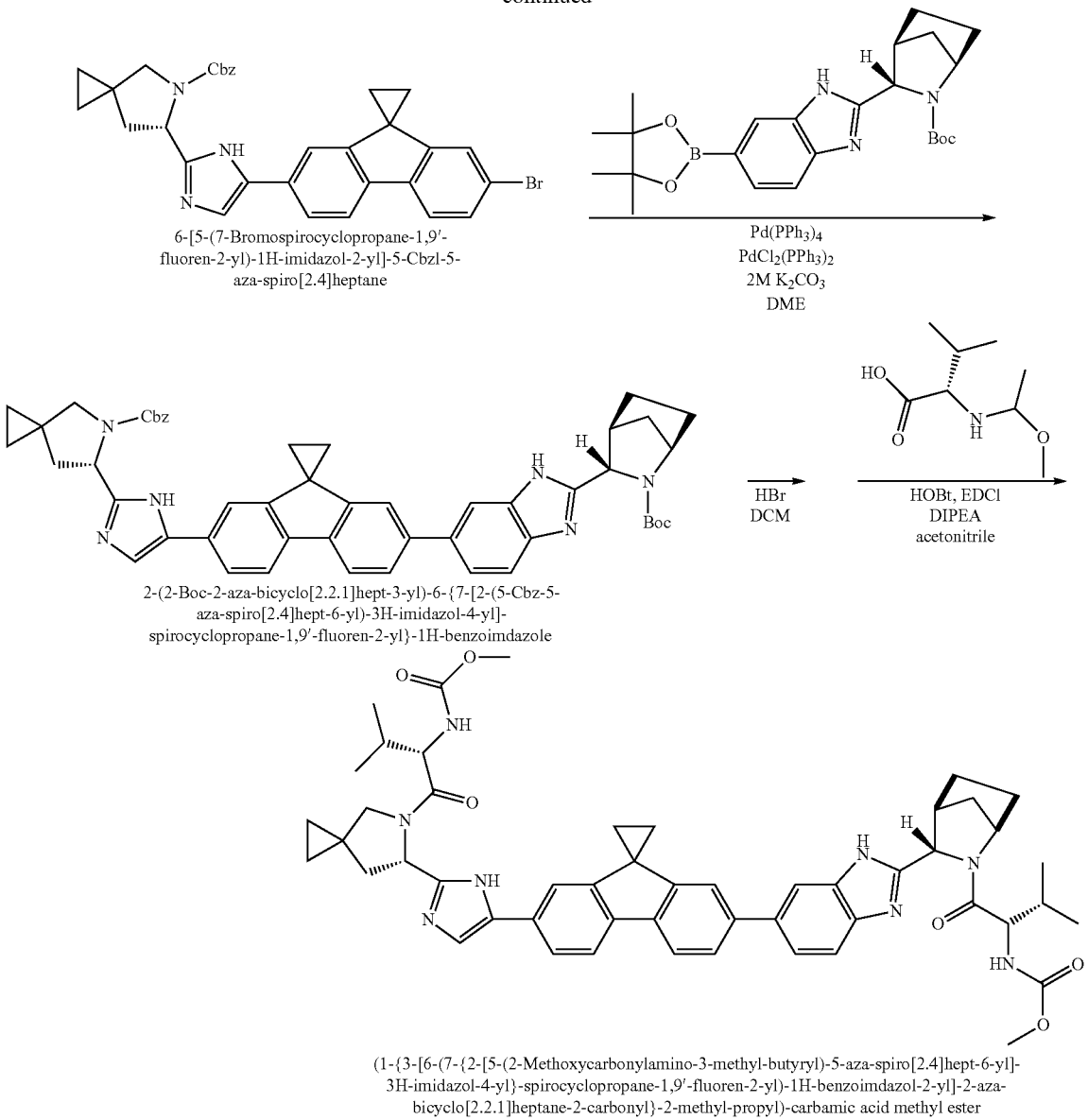

2,7-Dibromo-9-methylene-9H-fluorene was reported in the literature (Tetrahedron, 2006, 62, 3355-3361).

2',7'-Dibromospirocyclopropane-1,9'-fluorene

To a stirred solution of diethylzinc (9.0 mL of 1.0 M in hexane, 9.0 mmol) in DCM (10 mL) was added trifluoroacetic acid (0.69 mL, 9.0 mmol) in DCM (10 mL) slowly at 0° C. The mixture was stirred for 20 min at 0° C. before the addition of diiodomethane (0.72 mL, 9.0 mmol). The mixture was stirred for another 20 min at 0° C., then a solution of 2,7-dibromo-9-methylene-9H-fluorene (750 mg, 2.2 mmol) in DCM (5 mL) was added. The mixture was stirred at ambient temperature for 5 days, then quenched slowly with NH$_4$Cl solution. The mixture was extracted with ethyl acetate, washed with water and brine, dried over Na$_2$SO$_4$, filtered and concentrated in vacuo. The obtained residue was dissolved in a mixed solvent of THF/water/acetone (18 mL with ration 12/4/4), NMO (264 mg, 2.2 mmol) and OsO$_4$ was added. The mixture was stirred for 16 hs at ambient temperature, quenched with 1 M Na$_2$S$_2$O$_3$, then extracted with ethyl acetate. The organic layer was washed with water and brine, dried over Na$_2$SO$_4$, filtered and concentrated in vacuo. The obtained residue was purified by flash chromatography to provide the desired product (480 mg, 61%).

5-Cbz-5-aza-spiro[2.4]heptane-6-carboxylic acid 2-(7-bromospirocyclopropane-1,9'-fluoren-2-yl)-2-oxo-ethyl ester Pd(Ph$_3$)$_4$ (67 mg, 0.058 mmol) and PdCl$_2$(Ph$_3$)$_2$ (41 mg, 0.058 mmol) were added to a mixture 2',7'-dibromospirocyclopropane-1,9'-fluorene (670 mg, 1.93 mmol) and tributyl (1-ethoxyvinyl)tin (0.66 mL, 1.93 mmol) in 20 mL dioxane. The reaction mixture was flushed with nitrogen, heated at 80° C. for 16 hours, then cooled to ambient temperature. Water (7 mL) and NBS (344 mg, 1.93 mmol) were added and the mixture was stirred at room temperature for 40 min, then diluted with ethyl acetate (300 mL). The ethyl acetate layer was washed with water and brine, dried over $Na_2SO_4$, filtered and concentrated in vacuo. The obtained residue was suspended in acetonitrile (30 mL). To it was added a solution of pyrrolidine-1,2-dicarboxylic acid 1-benzyl ester (780 mg, 2.8 mmol) and DIPEA (0.44 mL, 2.5 mmol) in 5 mL acetonitrile. The mixture was stirred at room temperature for 16 hours, diluted with ethyl acetate (100 mL). The organic layer was washed with $NaHCO_3$ solution and water, dried over $Na_2SO_4$, filtered and concentrated in vacuo. The obtained residue was purified by flash chromatography to provide the desired product (825 mg, 73% over two steps). m/z 585.9, 587.9 $(M+H)^+$.

6-[5-(7-Bromospirocyclopropane-1,9'-fluoren-2-yl)-1H-imidazol-2-yl]-5-Cbzl-5-aza-spiro[2.4]heptane A mixture of 5-Cbz-5-aza-spiro[2.4]heptane-6-carboxylic acid 2-(7-bromospirocyclopropane-1,9'-fluoren-2-yl)-2-oxo-ethyl ester (825 mg, 1.4 mmol) and ammonium acetate (1.5 g, 19.5 mmol) in xylene (15 mL) was heated in a sealed tube at 140° C. for 1.5 hours under microwave condition. The volatile component was removed in vacuo, and the residue was dissolved in ethyl acetate (100 mL), washed with $NaHCO_3$ solution, water and brine, dried over $Na_2SO_4$, filtered and concentrated in vacuo. The obtained residue was purified by flash chromatography to provide the desired product (140 mg, 18%). m/z 566.1, 568.1 $(M+H)^+$.

2-(2-Boc-2-aza-bicyclo[2.2.1]hept-3-yl)-6-{7-[2-(5-Cbz-5-aza-spiro[2.4]hept-6-yl)-3H-imidazol-4-yl]-spirocyclopropane-1,9'-fluoren-2-yl}-1H-benzoimidazole $Pd(Ph_3)_4$ (14 mg, 0.012 mmol) and $PdCl_2(Ph_3)_2$ (9 mg, 0.012 mmol) were added to a mixture 6-[5-(7-bromospirocyclopropane-1,9'-fluoren-2-yl)-1H-imidazol-2-yl]-5-Cbzl-5-aza-spiro[2.4]heptane (140 mg, 0.25 mmol), 3-[6-(4,4,5,5-tetramethyl-[1,3,2]dioxaborolan-2-yl)-1H-benzoimidazol-2-yl]-2-aza-bicyclo[2.2.1]heptane-2-carboxylic acid tert-butyl ester (120 mg, 0.27 mmol), 2M $K_2CO_3$ (0.5 mL, 1.0 mmol) in 1,2-dimethoxyethane (5 mL). The reaction mixture was flushed with nitrogen, heated at 80° C. for 16 hours, and then the volatile component was removed in vacuo. The residue was dissolved in ethyl acetate (100 mL), washed with $NaHCO_3$ solution, water and brine, dried over $Na_2SO_4$, filtered and concentrated in vacuo. The obtained residue was purified by flash chromatography to provide the desired product (80 mg, 40%). m/z 799.3 $(M+H)^+$.

(1-{3-[6-(7-{2-[5-(2-Methoxycarbonylamino-3-methyl-butyryl)-5-aza-spiro[2.4]hept-6-yl]-3H-imidazol-4-yl}-spirocyclopropane-1,9'-fluoren-2-yl)-1H-benzoimidazol-2-yl]-2-aza-bicyclo[2.2.1]heptane-2-carbonyl}-2-methyl-propyl)-carbamic acid methyl ester To a solution of 2-(2-Boc-2-aza-bicyclo[2.2.1]hept-3-yl)-6-{7-[2-(5-Cbz-5-aza-spiro[2.4]hept-6-yl)-3H-imidazol-4-yl]-spirocyclopropane-1,9'-fluoren-2-yl}-1H-benzoimidazole (80 mg, 0.1 mmol) in DCM (3 mL) was added HBr (0.8 mL 5.7M in AcOH, excess). The mixture was stirred for 2 hours at ambient temperature and concentrated under reduced pressure. The residue was treated with ether/DCM to give an off-white solid. The obtained product was dissolved in DMF (3 mL), to the solution was added 2-methoxycarbonylamino-3-methyl-butyric acid (39 mg, 0.22 mmol), HATU (95 mg, 0.25 mmol) and N,N-diisopropylethylamine (0.14 mL, 0.80 mmol). The mixture was stirred at ambient for 2 hours, and then the volatile component was removed in vacuo. The residue was dissolved in ethyl acetate (100 mL), washed with 1 N NaOH solution, water and brine, dried over $Na_2SO_4$, filtered and concentrated in vacuo. The obtained residue was purified by HPLC to provide the desired product as a TFA salt (55 mg, 62%). m/z 879.4 $(M+H)^+$.

Example JS

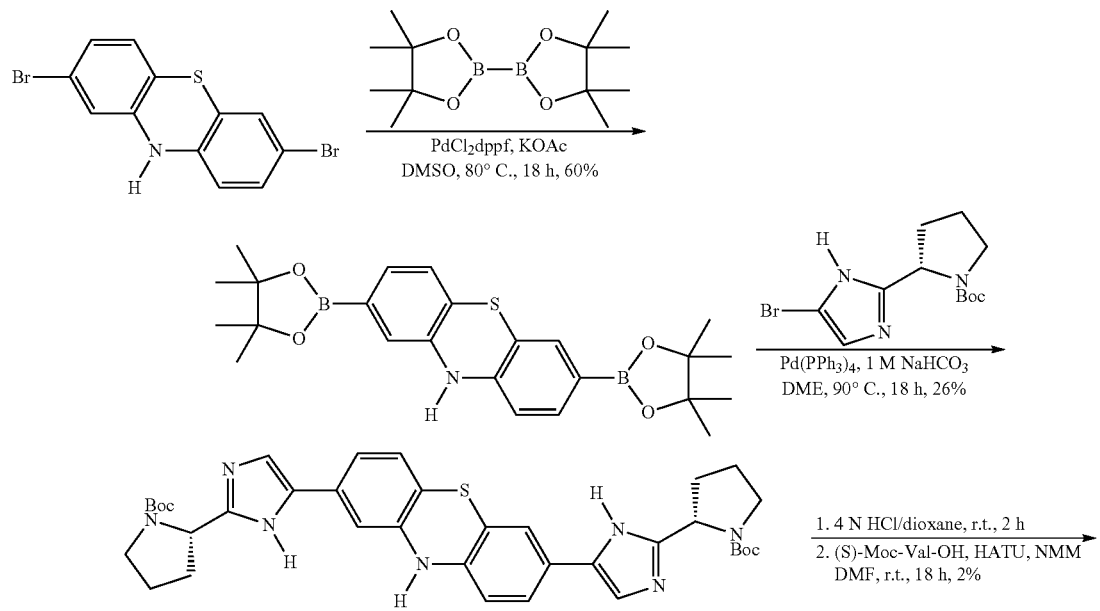

-continued

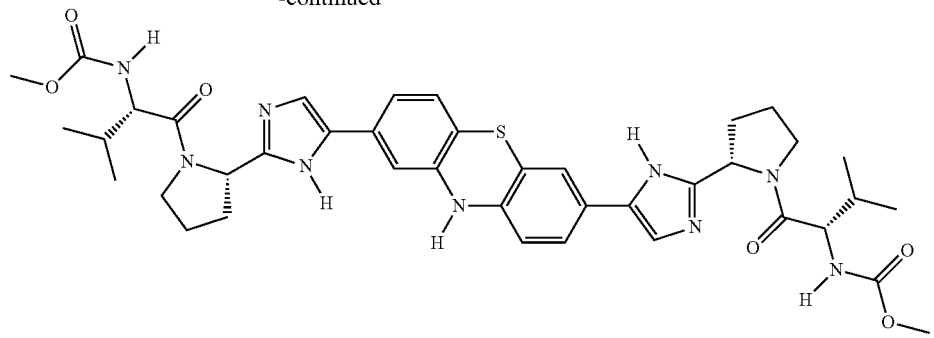

2,7-Bis(4,4,5,5-tetramethyl-1,3,2-dioxaborolan-2-yl)-10H-phenothiazine 2,7-Dibromo-10H-phenothiazine (590 mg, 1.65 mmol, WuXi AppTec) in DMSO (16 mL) was treated with bis(pinacolato)diboron (1.68 g, 6.60 mmol), KOAc (1.30 g, 13.2 mmol), and $PdCl_2dppf$ (135 mg, 0.165 mmol). The reaction mixture was stirred at 80° C. for 18 h and the mixture was cooled and filtered through a CELITE pad. The mixture was diluted with EtOAc (100 mL) and washed with $H_2O$ (2 50 mL) and saturated NaCl solution (1 50 mL). The solution was dried over $MgSO_4$ and treated to a 80 g $SiO_2$ COMBIFLASH column (0-25% EtOAc-hexanes gradient) to afford 2,7-bis(4,4,5,5-tetramethyl-1,3,2-dioxaborolan-2-yl)-10H-phenothiazine (450 mg, 60%): HPLC (RP: 6-98% MeCN—$H_2O$ gradient [non-polar], 0.05% TFA modifier) $t_R$=6.821 min (~80% purity @ 254 nM).

(2S,2'S)-tert-Butyl 2,2'-5,5'-(10H-phenothiazine-2,7-diyl)bis(1H-imidazole-5,2-diyl))dipyrrolidine-1-carboxylate 2,7-Bis(4,4,5,5-tetramethyl-1,3,2-dioxaborolan-2-yl)-10H-phenothiazine (450 mg, 1.00 mmol) in DME (10 mL) was treated with (S)-tert-butyl 2-(5-bromo-1H-imidazol-2-yl)pyrrolidine-1-carboxylate (662 mg, 2.09 mmol), 1 M $NaHCO_3$ (5 mL, 5.00 mmol), and $Pd(PPh_3)_4$ (69 mg, 0.06 mmol). The reaction mixture was stirred at 90° C. for 18 h and the mixture was cooled and filtered through a CELITE pad. The mixture was diluted with EtOAc (100 mL) and washed with $H_2O$ (2 50 mL) and saturated NaCl solution (1 50 mL) The solution was dried over $MgSO_4$ and treated to a 40 g $SiO_2$ COMBIFLASH column (0-100% EtOAc-hexanes gradient, followed by a 0-100% 20%-MeOH/EtOAc-hexanes gradient) to afford (2S,2'S)-tert-butyl 2,2'-(5,5'-(10H-phenothiazine-2,7-diyl)bis(1H-imidazole-5,2-diyl))dipyrrolidine-1-carboxylate (175 mg, 26%): MS (ESI) m/z 670 $[M+H]^+$.

Dimethyl (2S,2'S)-1,1'-((2S,2'S)-2,2'-(5,5'-(10H-phenothiazine-2,7-diyl)bis(1H-imidazole-5,2-diyl))bis(pyrrolidine-2,1-diyl))bis(3-methyl-1-oxobutane-2,1-diyl)dicarbamate (2S,2'S)-tert-butyl 2,2'-(5,5'-(10H-phenothiazine-2,7-diyl)bis(1H-imidazole-5,2-diyl))dipyrrolidine-1-carboxylate (175 mg, 0.26 mmol) was treated with 4 N HCl (5 mL) and stirred for 2 h. The reaction mixture was concentrated and the mixture was suspended in DMF (5.5 mL) and treated with (S)-Moc-Val-OH (96 mg, 0.55 mmol), HATU (219 mg, 0.57 mmol), and 4-methylmorpholine (143 μL, 1.31 mmol; or until basic). The stirred for 18 h then diluted with EtOAc (100 mL) and washed with saturated $NaHCO_3$ solution (2 50 mL), $H_2O$ (2 50 mL), and saturated NaCl solution (1 50 mL). The solution was dried over $MgSO_4$ and treated to a 40 g $SiO_2$ COMBIFLASH column (0-100% EtOAc-hexanes gradient, followed by a 0-100% 20%-MeOH/EtOAc-hexanes gradient) and RP HPLC (6-98% MeCN—$H_2O$ gradient, 0.1% TFA modifier). Finally, the material was subjected to a 20 20 preparative TLC (10% MeOH-EtOAc) to afford dimethyl (2S,2'S)-1,1'-((2S,2'S)-2,2'-(5,5'-(10H-phenothiazine-2,7-diyl)bis(1H-imidazole-5,2-diyl))bis(pyrrolidine-2,1-diyl))bis(3-methyl-1-oxobutane-2,1-diyl)dicarbamate (3.6 mg, 2%): MS (ESI) m/z 784 $[M+H]^+$.

Example JT

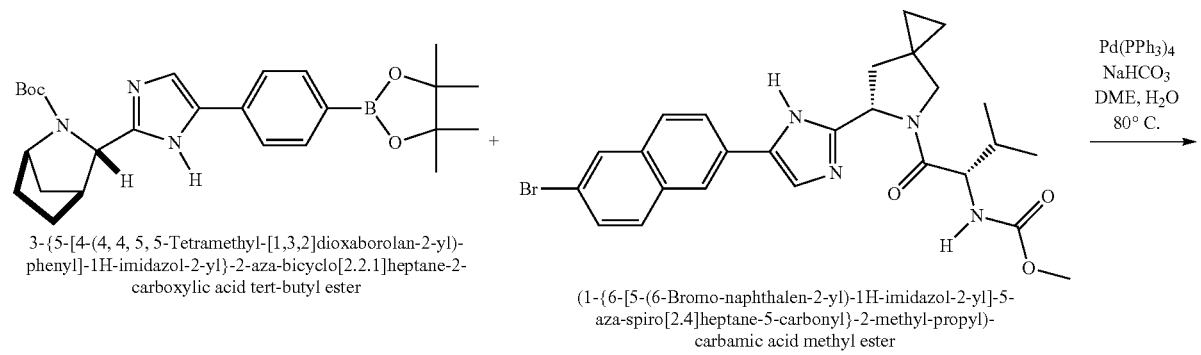

3-{5-[4-(4, 4, 5, 5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (1-{6-[5-(6-Bromo-naphthalen-2-yl)-1H-imidazol-2-yl]-5-aza-spiro[2.4]heptane-5-carbonyl}-2-methyl-propyl)-carbamic acid methyl ester

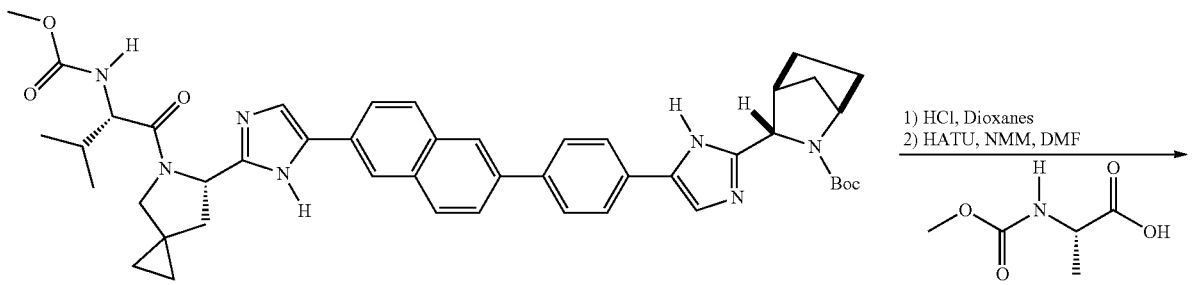

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 2-Methoxycarbonylamino-propionic acid

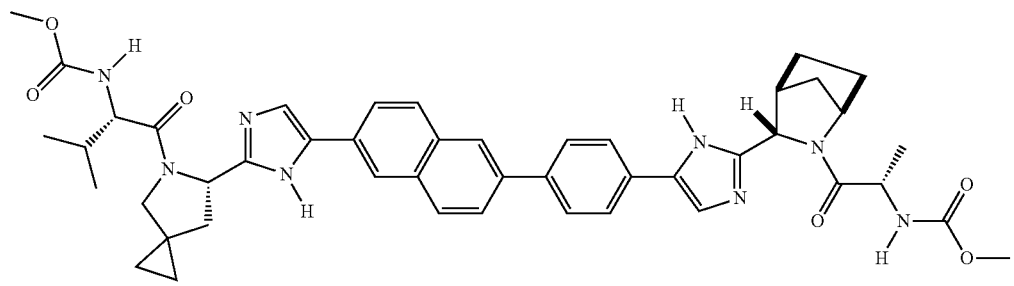

[1-(6-{5-[6-(4-{2-[2-(2-Methoxycarbonylamino-propionyl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{5-[6-(4-{2-[2-(2-Methoxycarbonylamino-propionyl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester A solution of (1-{6-[5-(6-bromo-naphthalen-2-yl)-1H-imidazol-2-yl]-5-aza-spiro[2.4]heptane-5-carbonyl}-2-methyl-propyl)-carbamic acid methyl ester (1.00 g, 1.9 mmol), 3-{5-[4-(4,4,5,5-tetramethyl-[1,3,2]dioxaborolan-2-yl)-phenyl]-1H-imidazol-2-yl}-2-aza-bicyclo[2.2.1]heptane-2-carboxylic acid tert-butyl ester (1.31 g, 2.8 mmol) and aq NaHCO$_3$ (7.6 mL of a 1M solution, 7.6 mmol) in DME (20 mL) was degassed with N$_2$ gas for 20 minutes. To the degassed solution was added Pd(PPh$_3$)$_4$ (110 mg, 0.095 mmol) and then the reaction was heated to 80° C. overnight. After cooling to room temperature, the solvent was removed under reduced pressure and the resulting residue was dissolved in ethyl acetate. The organic phase was washed with H$_2$O and then brine then dried over sodium sulfate. After filtration the solvent was removed from the filtrate under reduced pressure. The crude material was purified by silica gel chromatography (70-100% EtOAc/Hexanes) to afford 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (835 mg, 1.07 mmol, 56% yield).

LCMS-ESI$^+$: calc'd for C$_{46}$H$_{54}$N$_7$O$_5$: 784.4 (M+H$^+$); Found: 784.8 (M+H$^+$).

[1-(6-{5-[6-(4-{2-[2-(2-Methoxycarbonylamino-propionyl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester To 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (46 mg, 0.059 mmol) in dioxanes (2 mL) and MeOH (0.5 mL) was added 4N HCl in dioxanes (160 µL). The suspension was stirred for 2 h then concentrated to afford the HCl salt of the crude amine. To the crude amine in DMF (1 mL) was added N-methylmorpholine (19.5 pt, 0.18 mmol), 2-methoxycarbonylamino-propionic acid (13 mg, 0.089 mmol) and HATU (25 mg, 0.065 mmol). After stirring for overnight the reaction was quenched with formic acid then purified by reverse phase preparative HPLC (5-45% MeCN—H$_2$O; 0.1% formic acid modifier) to afford the title product (26 mg, 0.032 mmol, 54% yield). LCMS-ESI$^+$: calc'd for C$_{46}$H$_{53}$N$_8$O$_6$: 813.4 (M+H$^+$); Found: 813.4 (M+H$^+$).

Example JU

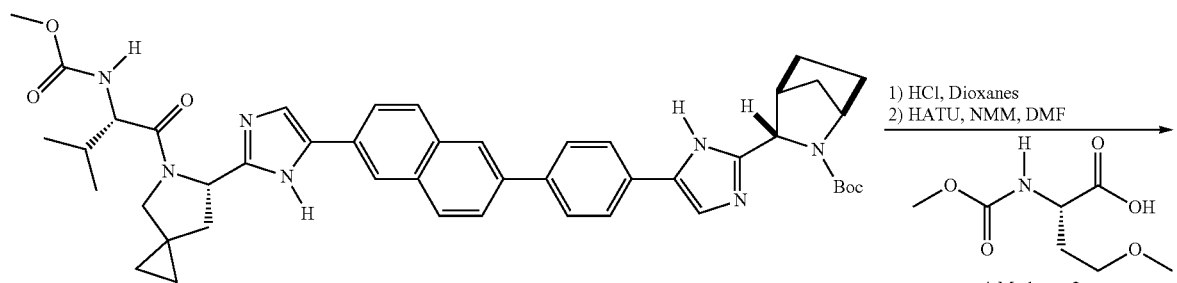

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 4-Methoxy-2-methoxycarbonylamino-butyric acid

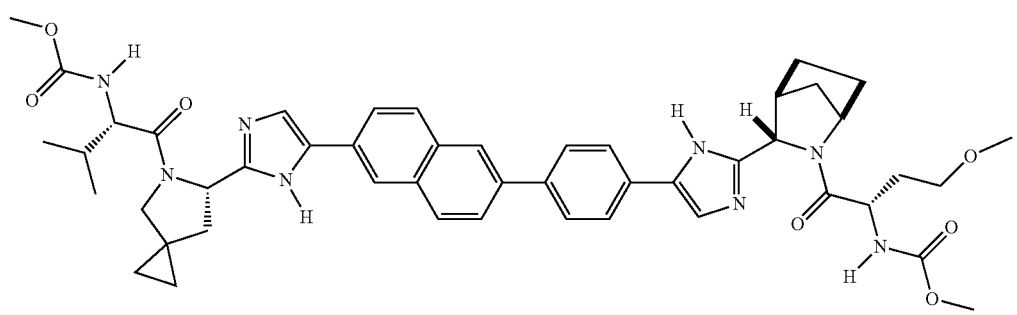

[1-(6-{5-[6-(4-{2-[2-(4-Methoxy-2-methoxycarbonylamino-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{5-[6-(4-{2-[2-(4-Methoxy-2-methoxycarbonylamino-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester To 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (46 mg, 0.059 mmol) in dioxanes (2 mL) and MeOH (0.5 mL) was added 4N HCl in dioxanes (160 µL). The suspension was stirred for 2 h then concentrated to afford the HCl salt of the crude amine. To the crude amine in DMF (1 mL) was added N-methylmorpholine (19.5 µL, 0.18 mmol), 4-methoxy-2-methoxycarbonylamino-butyric acid (17 mg, 0.089 mmol) and HATU (25 mg, 0.065 mmol). After stirring for overnight the reaction was quenched with formic acid then purified by reverse phase preparative HPLC (5-45% MeCN—H$_2$O; 0.1% formic acid modifier) to afford the title product (40 mg, 0.047 mmol, 79% yield).

LCMS-ESI$^+$: calc'd for $C_{48}H_{57}N_8O_7$: 857.4 (M+H$^+$); Found: 857.4 (M+H$^+$).

Example JV

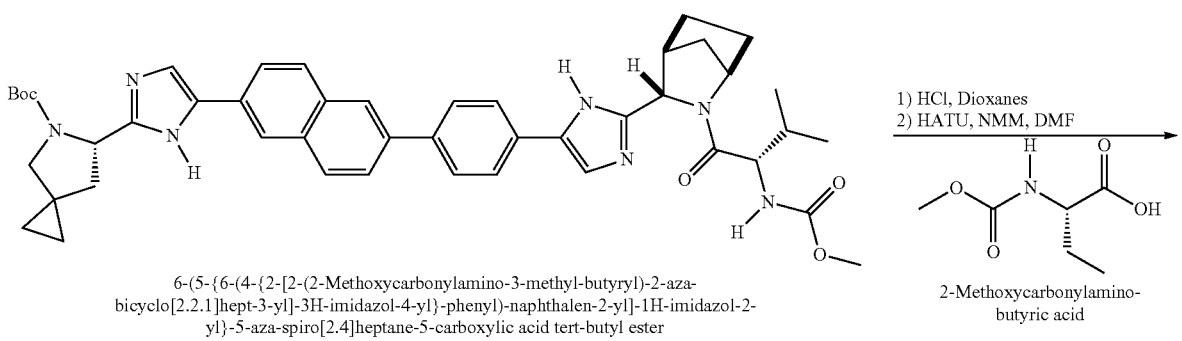

6-(5-{6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carboxylic acid tert-butyl ester 2-Methoxycarbonylamino-butyric acid -continued

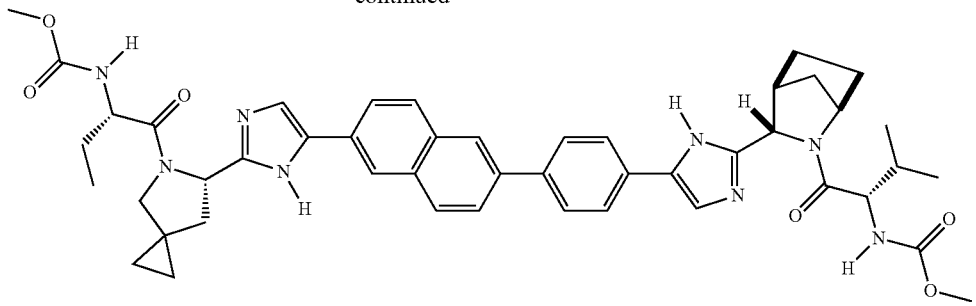

[1-(3-{5-[4-(6-{2-[5-(2-Methoxycarbonylamino-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester

[1-(3-{5-[4-(6-{2-[5-(2-Methoxycarbonylamino-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester To 6-{5-[6-(4-{2-[2-(2-methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carboxylic acid tert-butyl ester (50 mg, 0.064 mmol) in dioxanes (2 mL) and MeOH (0.5 mL) was added 4N HCl in dioxanes (160 μL). The suspension was stirred for 2 h then concentrated to afford the HCl salt of the crude amine. To the crude amine in DMF (1 mL) was added N-methylmorpholine (21 μL, 0.19 mmol), 2-methoxycarbonylamino-butyric acid (16 mg, 0.096 mmol) and HATU (27 mg, 0.070 mmol). After stirring for overnight the reaction was quenched with formic acid then purified by reverse phase preparative HPLC (5-45% MeCN—H$_2$O; 0.1% formic acid modifier) to afford the title product (30 mg, 0.036 mmol, 57% yield). LCMS-ESI$^+$: calc'd for C$_{47}$H$_{55}$N$_8$O$_6$: 827.4 (M+H$^+$); Found: 827.4 (M+H$^+$).

Example JW

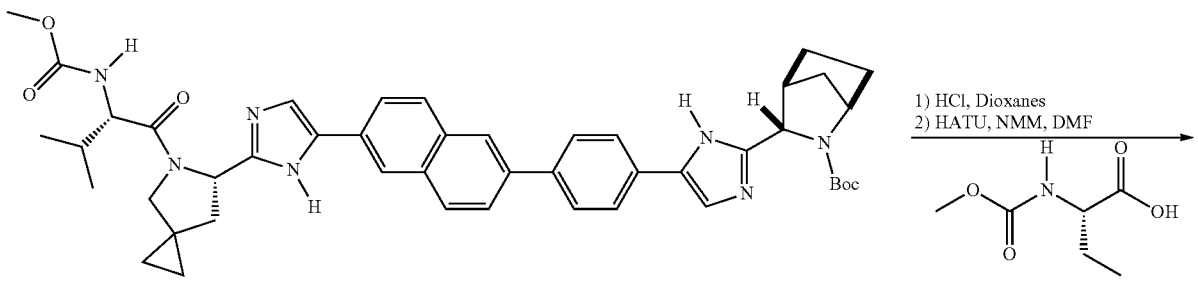

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 2-Methoxycarbonylamino-butyric acid

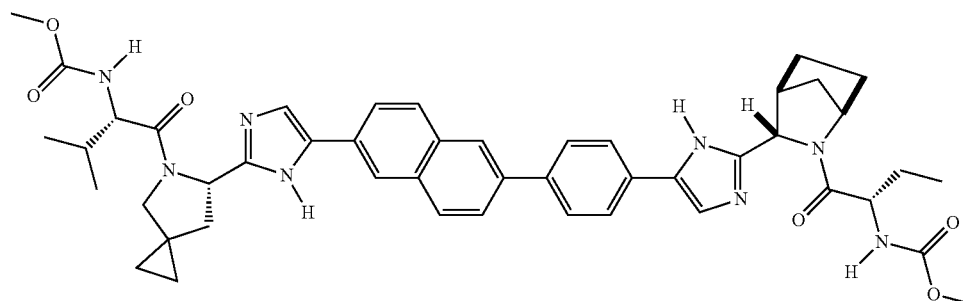

[1-(6-{5-[6-(4-{2-[2-(2-Methoxycarbonylamino-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

1169

[1-(6-{5-[6-(4-{2-[2-(2-Methoxycarbonylamino-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester To 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (60 mg, 0.077 mmol) in dioxanes (2 mL) and MeOH (0.5 mL) was added 4N HCl in dioxanes (160 µL). The suspension was stirred for 2 h then concentrated to afford the HCl salt of the crude amine. To the crude amine in DMF (1 mL) was added N-methylmorpholine (34 µL, 0.31 mmol), 2-methoxycarbonylamino-butyric acid (19 mg, 0.11 mmol) and HATU (35 mg, 0.09 mmol). After stirring for overnight the reaction was quenched with formic acid then purified by reverse phase preparative HPLC (5-45% MeCN—H$_2$O; 0.1% formic acid modifier) to afford the title product (51 mg, 0.062 mmol, 80% yield). LCMS-ESI$^+$: calc'd for C$_{47}$H$_{55}$H$_8$O$_6$: 827.4 (M+H$^+$); Found: 827.4 (M+H$^+$).

Example JX

1170

[1-(3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2,2-dimethyl-propyl]-carbamic acid methyl ester To 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (60 mg, 0.077 mmol) in dioxanes (2 mL) and MeOH (0.5 mL) was added 4N HCl in dioxanes (160 µL). The suspension was stirred overnight then concentrated to afford the HCl salt of the crude amine. To the crude amine in DMF (1 mL) was added N-methylmorpholine (25 µL, 0.23 mmol), 2-methoxycarbonylamino-3,3-dimethyl-butyric acid (22 mg, 0.12 mmol) and HATU (35 mg, 0.092 mmol). After stirring for overnight the reaction was quenched with formic acid then purified by reverse phase preparative HPLC (5-45% MeCN—H$_2$O; 0.1% formic acid modifier) to afford the title product (42 mg, 0.049 mmol, 57% yield). LCMS-ESI$^+$: calc'd for C$_{49}$H$_{59}$N$_8$O$_6$: 855.5 (M+H$^+$); Found: 855.5 (M+H$^+$).

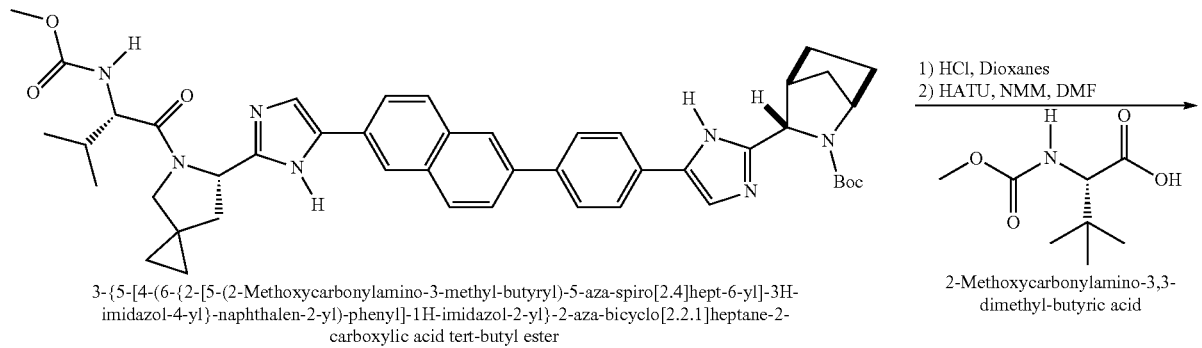

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 2-Methoxycarbonylamino-3,3-dimethyl-butyric acid

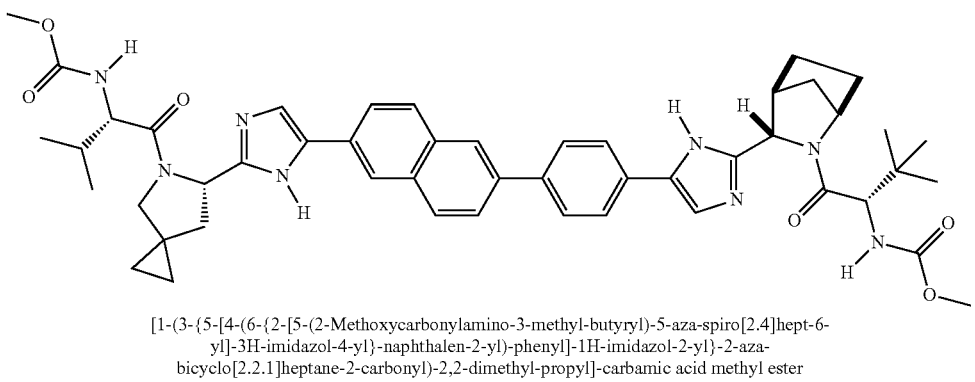

[1-(3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2,2-dimethyl-propyl]-carbamic acid methyl ester

Example JY

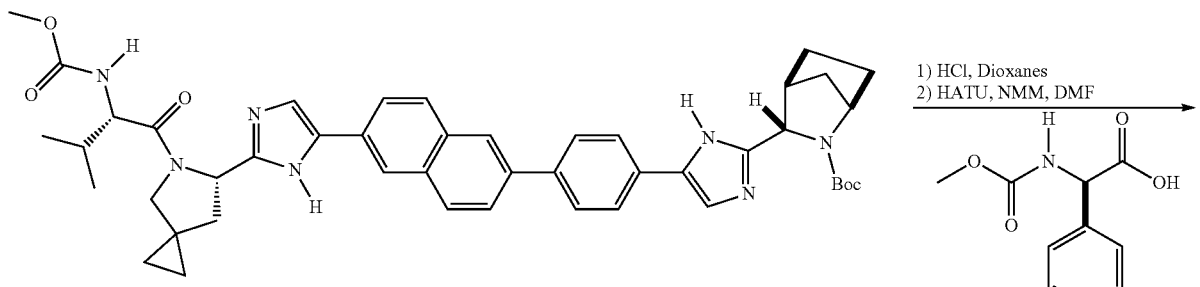

3-{5-[4-(6-{2-[5-(2-Methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester Methoxycarbonylamino-phenyl-acetic acid

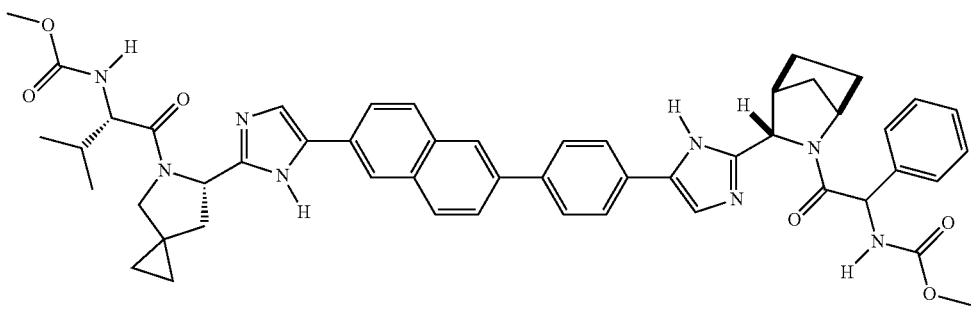

[1-(6-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester

[1-(6-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester To 3-{5-[4-(6-{2-[5-(2-methoxycarbonylamino-3-methyl-butyryl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (60 mg, 0.077 mmol) in dioxanes (2 mL) and MeOH (0.5 mL) was added 4N HCl in dioxanes (160 µL). The suspension was stirred for 6 h then concentrated to afford the HCl salt of the crude amine. To the crude amine in DMF (1 mL) was added N-methylmorpholine (25 µL, 0.23 mmol), methoxycarbonylamino-phenyl-acetic acid (22 mg, 0.12 mmol) and HATU (35 mg, 0.092 mmol). After stirring for overnight the reaction was quenched with formic acid then purified by reverse phase preparative HPLC (5-45% MeCN—H$_2$O; 0.1% formic acid modifier) to afford the different diastereomers of the title product (Diastereomer 1: 24 mg, 0.027 mmol, 36% yield; Diastereomer 2: 17 mg, 0.019 mmol, 22% yield). LCMS-ESI$^+$: calc'd for C$_{51}$H$_{55}$N$_8$O$_6$: 875.4 (M+H$^+$); Found: 875.5 (M+H$^+$).

Example JZ

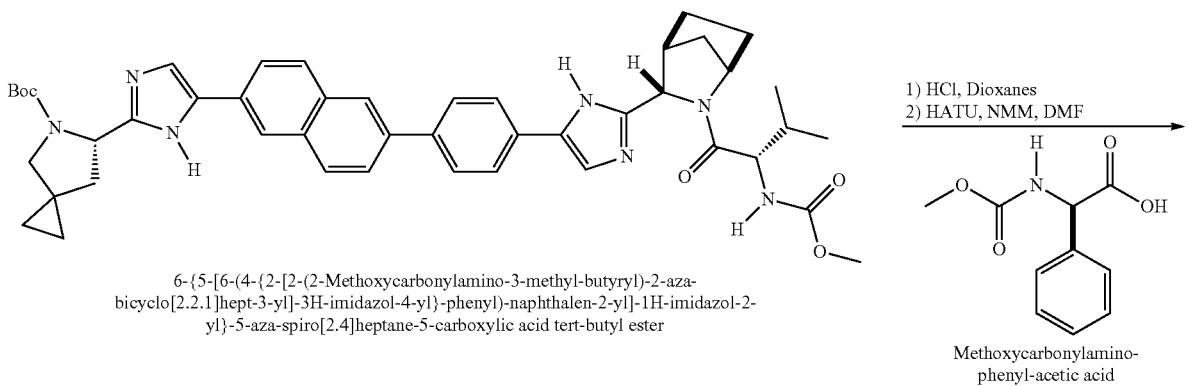

6-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carboxylic acid tert-butyl ester Methoxycarbonylamino-phenyl-acetic acid

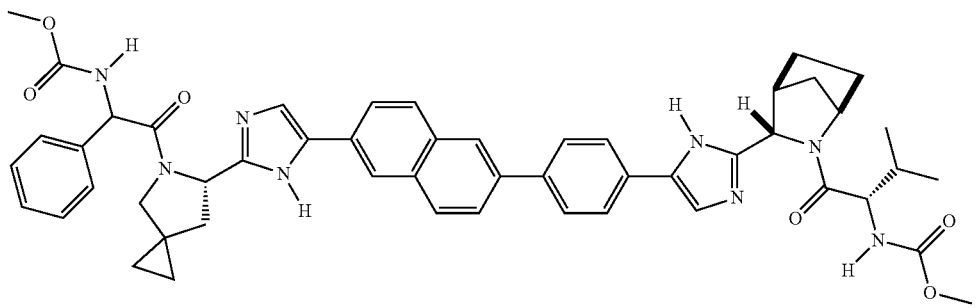

[1-(3-{5-[4-(6-{2-[5-(2-Methoxycarbonylamino-2-phenyl-acetyl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester

[1-(3-{5-[4-(6-{2-[5-(2-Methoxycarbonylamino-2-phenyl-acetyl)-5-aza-spiro[2.4]hept-6-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester To 6-{5-[6-(4-[2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-5-aza-spiro[2.4]heptane-5-carboxylic acid tert-butyl ester (60 mg, 0.077 mmol) in dioxanes (2 mL) and MeOH (0.5 mL) was added 4N HCl in dioxanes (160 µL). The suspension was stirred for 6 h then concentrated to afford the HCl salt of the crude amine. To the crude amine in DMF (1 mL) was added N-methylmorpholine (25 µL, 0.23 mmol), methoxycarbonylamino-phenyl-acetic acid (22 mg, 0.12 mmol) and HATU (35 mg, 0.092 mmol). After stirring for overnight the reaction was quenched with formic acid then purified by reverse phase preparative HPLC (5-45% MeCN—H$_2$O; 0.1% formic acid modifier) to afford the title product as a diastereometric mixture (30 mg, 0.035 mmol, 39% yield). LCMS-ESI$^+$: calc'd for C$_{51}$H$_{55}$N$_8$O$_6$: 875.4 (M+H); Found: 875.6 (M+H$^+$).

Example KA

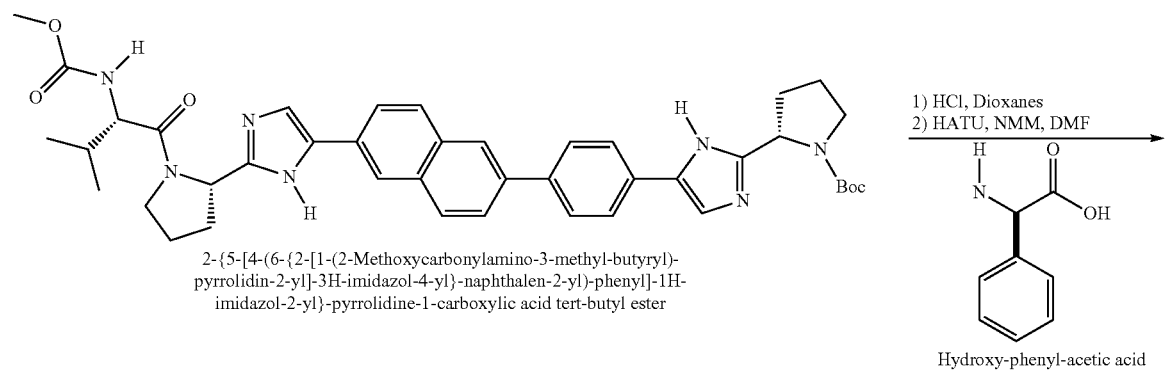

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester Hydroxy-phenyl-acetic acid

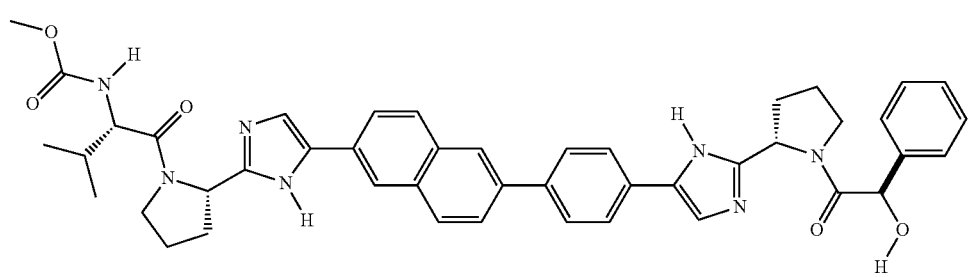

[1-(2-{5-[6-(4-{2-[1-(2-Hydroxy-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

1175

[1-(2-{5-[6-(4-{2-[1-(2-Hydroxy-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester To 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (40 mg, 0.055 mmol) in MeOH (1 mL) was added 4N HCl in dioxanes (160 µL). The reaction was stirred overnight then concentrated to afford the HCl salt of the crude amine. To the crude amine in DMF (1 mL) was added N-methylmorpholine (100 µL), hydroxy-phenyl-acetic acid (21 mg, 0.083 mmol) and HATU (35 mg, 0.092 mmol). After stirring overnight the reaction was quenched with formic acid then purified by reverse phase preparative HPLC (10-40% MeCN—$H_2O$; 0.1% formic acid modifier) to afford the title compound (32 mg, 0.042 mmol, 76% yield). LCMS-ESI$^+$: calc'd for $C_{45}H_{48}N_7O_5$: 766.4 (M+H$^+$); Found: 766.4 (M+H$^+$).

Example KB

1176

[1-(2-{5-[6-(4-{2-[1-(2-Methoxy-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester To 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (40 mg, 0.055 mmol) in MeOH (1 mL) was added 4N HCl in dioxanes (160 µL). The reaction was stirred overnight then concentrated to afford the HCl salt of the crude amine. To the crude amine in $CH_2Cl_2$ and DMF (1 ml of 4:1 solution) was added (R)-methoxy-phenyl-acetic acid (13.7 mg, 0.083 mmol) and 2-ethoxy-1-ethoxycarbonyl-1,2-dihydroquinoline (17 mg, 0.069 mmol). After stirring overnight the reaction was concentrated then purified by reverse phase preparative HPLC (10-40% MeCN—$H_2O$; 0.1% formic acid modifier) to afford the title compound (13.1 mg, 0.017 mmol, 31% yield). LCMS-ESI$^+$: calc'd for $C_{46}H_{50}N_7O_5$: 780.4 (M+H$^+$); Found: 780.4 (M+H$^+$).

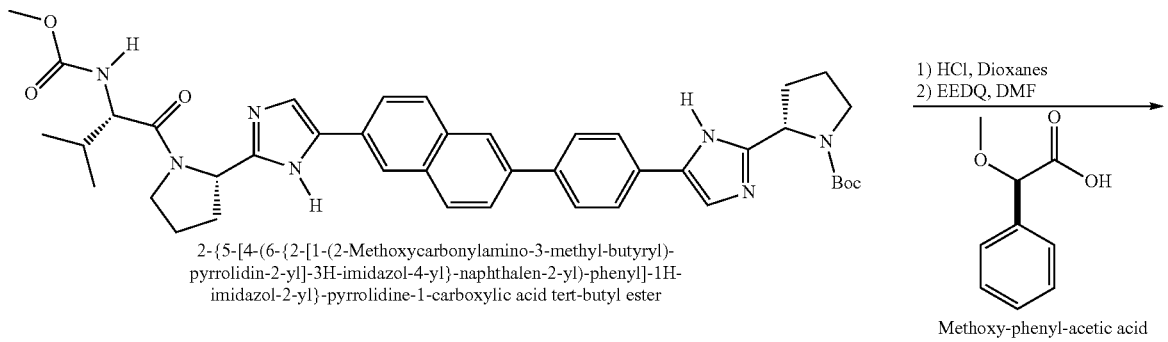

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester Methoxy-phenyl-acetic acid

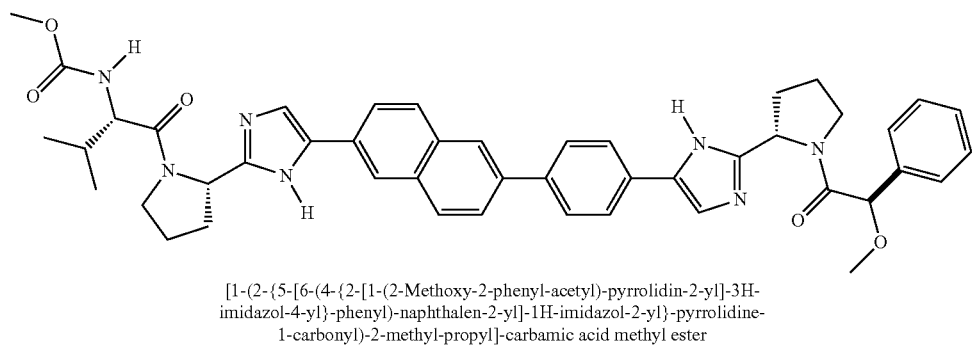

[1-(2-{5-[6-(4-{2-[1-(2-Methoxy-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

Example KC

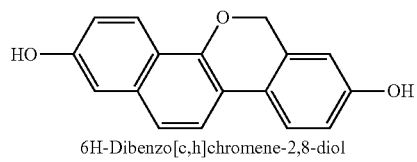 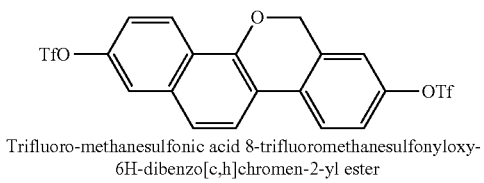

6H-Dibenzo[c,h]chromene-2,8-diol → Trifluoro-methanesulfonic acid 8-trifluoromethanesulfonyloxy-6H-dibenzo[c,h]chromen-2-yl ester Tf₂O, pyridine, CH₂Cl₂

Bis(pinacolato)diboron
PdCl₂dppf, Et₃N,
1,4-Dioxanes

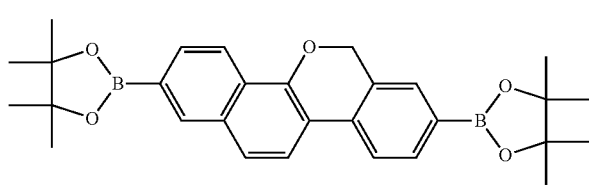

2,8-Bis-(4,4,5,5-tetramethyl-[1,3,2]dioxaborolan-2-yl)-6H-dibenzo[c,h]chromene

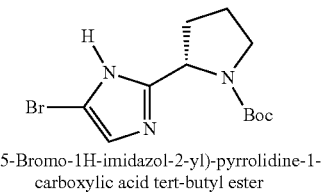

2-(5-Bromo-1H-imidazol-2-yl)-pyrrolidine-1-carboxylic acid tert-butyl ester

Pd(OAc)₂,
PPh₃,
NaHCO₃,
DME, H₂O
80° C.

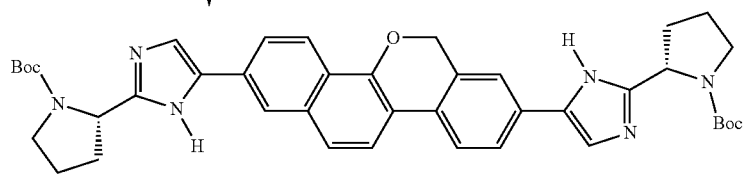

(1-{2-[5-(2-{2-[1-(carboxylic acid tert-butyl ester)-pyrrolidin-2-yl]-3H-imidazol-4-yl}-6H-dibenzo[c,h]chromen-8-yl)-1H-imidazol-2-yl]-pyrrolidine-1-carboxylic acid tert-butyl ester 1) HCl, Dioxanes
2) HATU, NMM, DMF 2-Methoxycarbonylamino-3-methyl-butyric acid

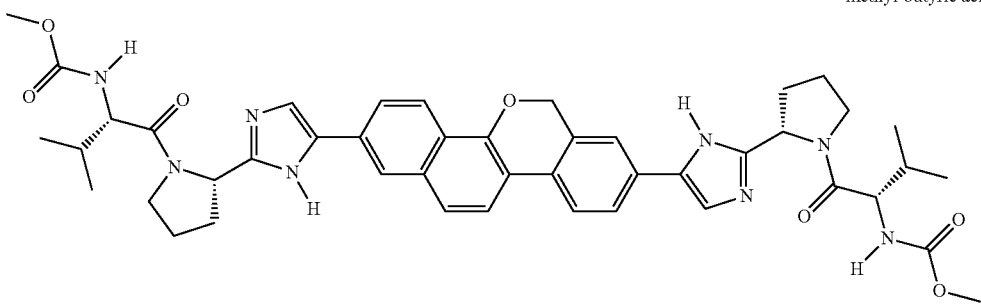

(1-{2-[5-(2-{2-[1-(2-Methoxycarbonylamino-3-methyl-butyryl)-pyrrolidin-2-yl]-3H-imidazol-4-yl}-6H-dibenzo[c,h]chromen-8-yl)-1H-imidazol-2-yl]-pyrrolidine-1-carbonyl}-2-methyl-propyl)-carbamic acid methyl ester

Trifluoro-methanesulfonic acid 8-trifluoromethanesulfonyloxy-6H-dibenzo[c,h]chromen-2-yl ester To a suspension of 6H-Dibenzo[c,h]chromene-2,8-diol (3.46 g, 13.1 mmol) in CH₂Cl₂ at 0° C. was added pyridine (2.65 mL, 32.8 mmol) followed by triflic anhydride (4.85 mL, 28.8 mmol). The reaction was allowed to warm to room temperature then poured into H₂O. The organic phase was collected then washed with 1N HCl and Brine. After concentration, the crude material was recrystallized from CH₂Cl₂/Hexanes to afford the title compound (4.07 g, 7.70 mmol, 59% yield). ¹H NMR (CDCl₃, 400 MHz): δ 8.35 (d, 1H), 7.88 (d, 1H), 7.79 (d, 1H), 7.71 (d, 1H), 7.57 (d, 1H), 7.40 (dd, 1H), 7.34 (dd, 1H), 7.18 (s, 1H), 5.34 (s, 2H).

2,8-Bis-(4,4,5,5-tetramethyl-[1,3,2]dioxaborolan-2-yl)-6H-dibenzo[c,h]chromene A solution of Trifluoro-methanesulfonic acid 8-trifluoromethanesulfonyloxy-6H-dibenzo[c,h]chromen-2-yl ester (1.00 g, 1.9 mmol), bis(pinacolato)diboron (1.44 g, 5.7 mmol) and triethylamine (1.32 mL, 9.5 mmol) in 1,4-Dioxanes (20 mL) was degassed with Argron gas for 20 minutes. To the degassed solution was added PdCl₂dppf (139 mg, 0.19 mmol) and then the reaction was heated to 90° C. overnight. Reaction stalled at approximately 60% conversion so additional PdCl₂dppf (139 mg, 0.19 mmol) and bis(pinacolato) diboron (0.500 g, 1.97 mmol) was added and reaction stirred for 3 h. After cooling to room temperature, the crude material was preabsorbed onto silica then purified by silica gel chromatography (25-50% CH$_2$Cl$_2$/Hexanes) to afford the title compound [1.106 g, >100% yield due to some bis(pinacolato) diboron impurity]. LCMS-ESI$^+$: calc'd for C$_{29}$H$_{35}$B$_2$O$_5$: 485.3 (M+H$^+$); Found: 485.3 (M+H$^+$). $^1$H NMR (CDCl$_3$, 400 MHz): δ 8.28 (s, 1H), 8.21 (d, 1H), 7.84-7.81 (m, 3H), 7.72 (d, 1H), 7.64 (s, 1H), 7.55 (d, 1H), 5.31 (s, 2H), 1.38 (s, 12H), 1.35 (s, 12H).

(1-{2-[5-(2-{2-[1-(carboxylic acid tert-butyl ester)-pyrrolidin-2-yl]-3H-imidazol-4-yl}-6H-dibenzo[c,h]chromen-8-yl)-1H-imidazol-2-yl]-pyrrolidine-1-carboxylic acid tert-butyl ester A solution of 2,8-bis-(4,4,5,5-tetramethyl-[1,3,2]dioxaborolan-2-yl)-6H-dibenzo[c,h]chromene (500 mg, 1.03 mmol), 2-(5-bromo-1H-imidazol-2-yl)-pyrrolidine-1-carboxylic acid tert-butyl ester (979 mg, 3.09 mmol) and NaHCO$_3$ (3.8 ml of 1N solution, 3.8 mmol) in DME (10 mL) and DMF (3 mL) was degassed with Argron gas for 20 minutes. To the degassed solution was added Pd(OAc)$_2$ (22 mg, 0.098 mmol) and PPh$_3$ (52 mg, 0.19 mmol) and then the reaction was heated to 90° C. overnight. After cooling to room temperature, the reaction was poured into H$_2$O then extracted with EtOAc. The organic phase was then washed with Brine. Purification of the crude material by silica gel chromatography (50-100% EtOAc/Hexanes) afforded the title compound [250 mg, 0.35 mmol, 35% yield]. LCMS-ESI$^+$: calc'd for C$_{41}$H$_{47}$N$_6$O$_5$: 703.4 (M+H$^+$); Found: 703.2 (M+H$^+$).

(1-{2-[5-(2-{2-[1-(2-Methoxycarbonylamino-3-methyl-butyryl)-pyrrolidin-2-yl]-3H-imidazol-4-yl}-6H-dibenzo[c,h]chromen-8-yl)-1H-imidazol-2-yl]-pyrrolidine-1-carbonyl}-2-methyl-propyl)-carbamic acid methyl ester To (1-{2-[5-(2-{2-[1-(carboxylic acid tert-butyl ester)-pyrrolidin-2-yl]-3H-imidazol-4-yl}-6H-dibenzo[c,h]chromen-8-yl)-1H-imidazol-2-yl]-pyrrolidine-1-carboxylic acid tert-butyl ester (70 mg, 0.10 mmol) in MeOH (0.5 mL) was added 4N HCl in dioxanes (1 mL). The reaction was stirred overnight then concentrated to afford the HCl salt of the crude amine. To the crude amine in DMF (1 mL) was added N-methylmorpholine (44 µL, 0.40 mmol), HATU (46 mg, 0.12 mmol) and 2-methoxycarbonylamino-3-methyl-butyric acid (26 mg, 0.15 mmol). After stirring for 3 h the reaction was quenched with formic acid then purified by reverse phase preparative HPLC (10-40% MeCN—H$_2$O; 0.1% formic acid modifier) to afford the title compound (27 mg, 0.033 mmol, 33% yield). LCMS-ESI$^+$: calc'd for C$_{45}$H$_{53}$N$_8$O$_7$: 817.4 (M+H$^+$); Found: 817.4 (M+H$^+$).

Example KD

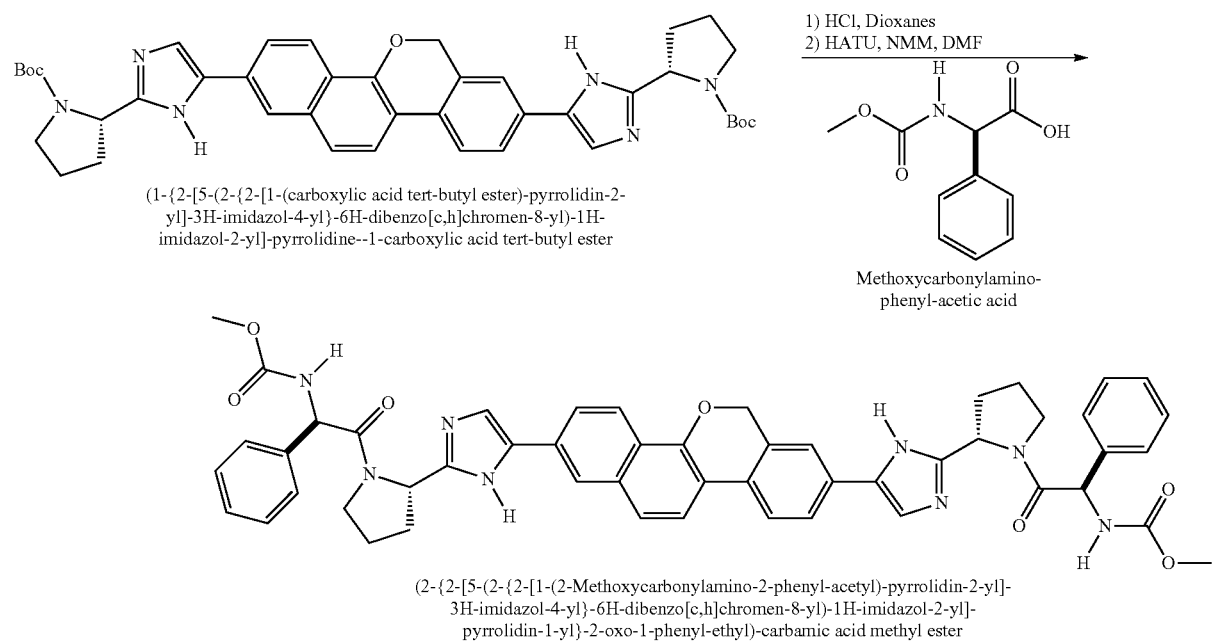

(2-{2-[5-(2-{2-[1-(2-Methoxycarbonylamino-2-phenyl-acetyl)-pyrrolidin-2-yl]-3H-imidazol-4-yl}-6H-dibenzo[c,h]chromen-8-yl)-1H-imidazol-2-yl]-pyrrolidin-1-yl}-2-oxo-1-phenyl-ethyl)-carbamic acid methyl ester To (1-{2-[5-(2-{2-[1-(carboxylic acid tert-butyl ester)-pyrrolidin-2-yl]-3H-imidazol-4-yl}-6H-dibenzo[c,h]chromen-8-yl)-1H-imidazol-2-yl]-pyrrolidine-1-carboxylic acid tert-butyl ester (60 mg, 0.85 mmol) in MeOH (0.5 mL) was added 4N HCl in dioxanes (0.5 mL). The reaction was stirred for 4 h then concentrated to afford the HCl salt of the crude amine. To the crude amine in CH$_2$Cl$_2$ (1 mL) was added K$_3$PO$_4$ (90 mg, 0.42 mmol), HATU (80 mg, 0.21 mmol) and methoxycarbonylamino-phenyl-acetic acid (45 mg, 0.21 mmol). After stirring for 3 h the reaction was filtered then concentrated. Purification by reverse phase preparative HPLC (10-40% MeCN—H$_2$O; 0.1% formic acid modifier) afforded the title compound (34 mg, 0.038 mmol, 45% yield). LCMS-ESI$^+$: calc'd for C$_{51}$H$_{49}$N$_8$O$_7$: 885.4 (M+H$^+$); Found: 885.9 (M+H$^+$).

Example KE

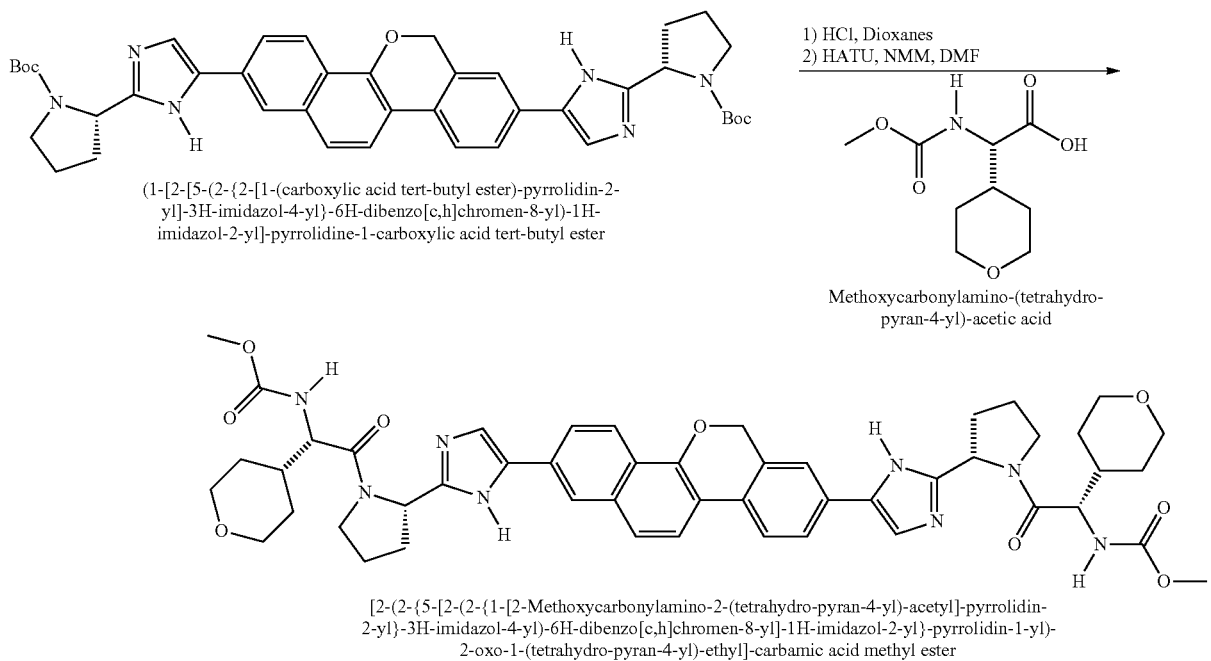

[2-(2-{5-[2-(2-{1-[2-Methoxycarbonylamino-2-(tetrahydro-pyran-4-yl)-acetyl]-pyrrolidin-2-yl}-3H-imidazol-4-yl)-6H-dibenzo[c,h]chromen-8-yl]-1H-imidazol-2-yl}-pyrrolidin-1-yl)-2-oxo-1-(tetrahydro-pyran-4-yl)-ethyl]-carbamic acid methyl ester To (1-{2-[5-(2-{2-[1-(carboxylic acid tert-butyl ester)-pyrrolidin-2-yl]-3H-imidazol-4-yl}-6H-dibenzo[c,h]chromen-8-yl)-1H-imidazol-2-yl]-pyrrolidine-1-carboxylic acid tert-butyl ester (20 mg, 0.028 mmol) in MeOH (0.5 mL) was added 4N HCl in dioxanes (0.5 mL). The reaction was stirred for 4 h then concentrated to afford the HCl salt of the crude amine. To the crude amine in DMF (1 mL) was added N-methylmorpholine (15 μL, 0.14 mmol), HATU (33 mg, 0.085 mmol) and methoxycarbonylamino-(tetrahydro-pyran-4-yl)-acetic acid (19 mg, 0.085 mmol). After stirring overnight the reaction was quenched with formic acid then purified by reverse phase preparative HPLC (10-40% MeCN—$H_2O$; 0.1% formic acid modifier) to afford the title compound (15 mg, 0.017 mmol, 59% yield). LCMS-ESI$^+$: calc'd for $C_{49}H_{57}N_8O_9$: 901.4 (M+H$^+$); Found: 901.4 (M+H$^+$).

Example KF

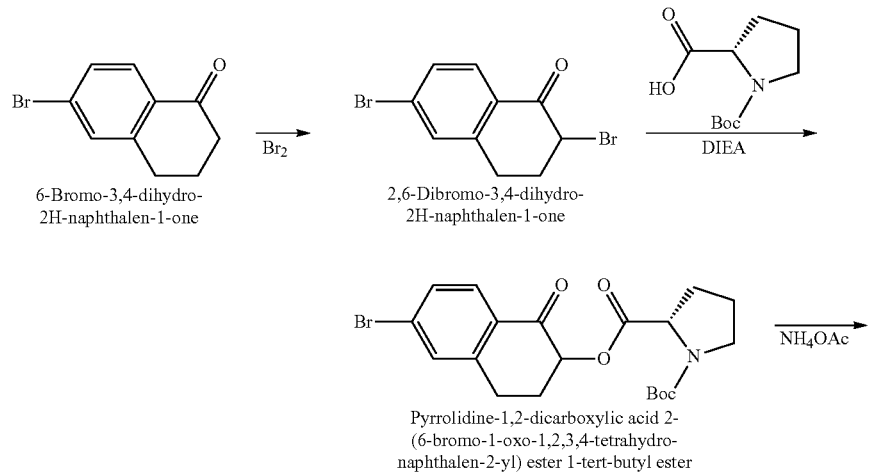

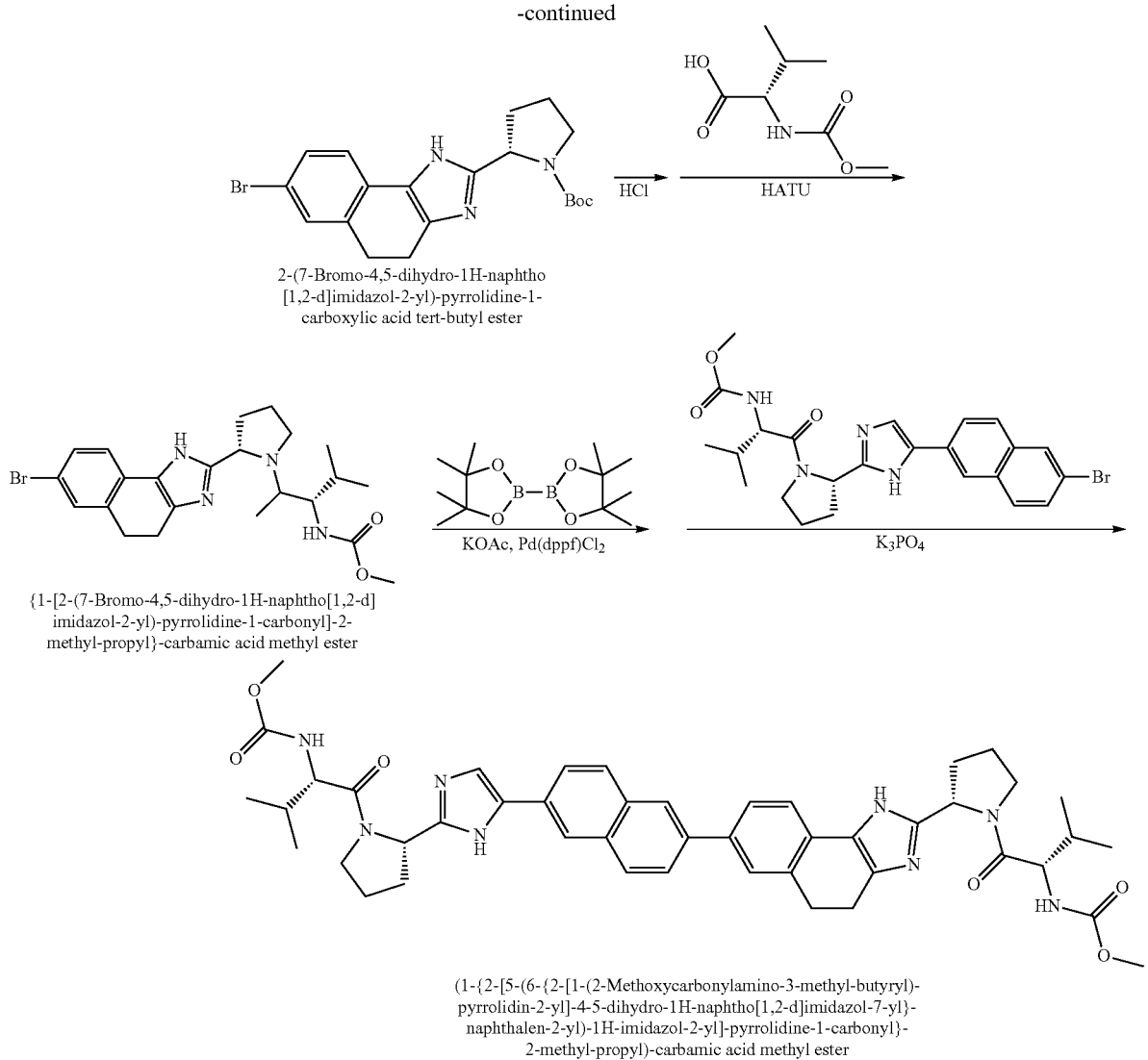

(1-{2-[5-(6-{2-[1-(2-Methoxycarbonylamino-3-methyl-butyryl)-
pyrrolidin-2-yl]-4-5-dihydro-1H-naphtho[1,2-d]imidazol-7-yl}-
naphthalen-2-yl)-1H-imidazol-2-yl]-pyrrolidine-1-carbonyl}-
2-methyl-propyl)-carbamic acid methyl ester

2-6-Dibromo-3,4-dihydro-2H-naphthalen-1-one

6-Bromo-3,4-dihydro-2H-naphthalen-1-one (2.0 g) was dissolved in ether (80 mL), and Br₂ (455 µl) was added at 0° C. over 30 min. After diluting with ether (80 mL), the reaction mixture was washed with 10% Na₂SO₃, sat. NaHCO₃ and brine. After the solvent was removed, the crude material was used for the next step without further purification.

Pyrrolidine-1,2-dicarboxylic acid 2-(6-bromo-1-oxo-1,2,3,4-tetrahydro-naphthalen-2-yl)ester 1-tert-butyl ester The crude 2-6-dibromo-3,4-dihydro-2H-naphthalen-1-one and pyrrolidine-1,2-dicarboxylic acid 1-tert-butyl ester (3.15 g) were dissolved in MeCN (80 mL), and DIEA (2.55 mL) was added. The mixture was stirred at 65° C. for overnight and diluted with ethyl acetate. The mixture was washed with 1 N HCl. NaHCO₃ and brine. After the solvent was removed, the resulting material was subjected to silica gel chromatography using effluent of 10-40% ethyl acetate and hexanes. The fractions containing product were combined and the solvent was removed under reduced pressure to provide pyrrolidine-1,2-dicarboxylic acid 2-(6-bromo-1-oxo-1,2,3,4-tetrahydro-naphthalen-2-yl) ester 1-tert-butyl ester (1.54 g, 40% over 2 steps).

2-(7-Bromo-4,5-dihydro-1H-naphtho[1,2-d]imidazol-2-yl)-pyrrolidine-1-carboxylic acid tert-butyl ester Pyrrolidine-1,2-dicarboxylic acid 2-(6-bromo-1-oxo-1,2,3,4-tetrahydro-naphthalen-2-yl) ester 1-tert-butyl ester (1.54 g) and ammonium acetate (2.71 g) were suspended in toluene (35 mL). The reaction mixture was stirred at 110° C. for overnight and evaporated under reduced pressure and resulting residue was taken up in ethyl acetate (100 mL). The organic phase was washed with saturated sodium bicarbonate (1×150 mL) and dried over sodium sulfate. After the solvent was removed, the resulting oil was subjected to silica gel chromatography using effluent of 60-90% ethyl acetate and hexanes. The fractions containing product were combined and the solvent was removed under reduced pressure to provide 2-(7-bromo-4,5-dihydro-1H-naphtho[1,2-d]imidazol-2-yl)-pyrrolidine-1-carboxylic acid tert-butyl ester (1.05 g, 71%) as a pale brown solid. MS (ESI) m/z 418.1 [M+H]⁺.

(1-{2-[5-(6-{2-[1-(2-Methoxycarbonylamino-3-me-
thyl-butyryl)-pyrrolidin-2-yl]-4,5-dihydro-1H-naph-
tho [1,2-d]imidazol-7-yl}-naphthalen-2-yl)-1H-imi-
dazol-2-yl]-pyrrolidine-1-carbonyl}-2-methyl-
propyl)-carbamic acid methyl ester Title compound was prepared according to the method employed to [1-(6-{5-[6-(4-{2-[1-(2-Methoxycarbony-lamino-3-methyl-butyryl)-4-(2-methoxy-ethoxy)-pyrroli-din-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester: MS (ESI) m/z 815.5 [M+H]$^+$.

BIOLOGICAL ASSAYS

Effect of Serum Proteins on Replicon Potency

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

Enyzmatic Selectivity:

The inhibition of mammalian proteases including Porcine Pancreatic Elastase, Human Leukocyte Elastase, Protease 3, and Cathepsin D are measured at $K_m$ for the respective substrates for each enzyme. $IC_{50}$ for each enzyme is compared to the $IC_{50}$ obtained with NS31b protease to calculate selectivity. Representative compounds of the invention have shown activity.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$:

Huh-luc cultures are incubated with compound at concentrations equal to $EC_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the invention have shown activity.

Solubility and Stability:

Solubility is determined by taking an aliquot of 10 mM DMSO stock solution and preparing the compound at a final concentration of 100 µM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes:

Each compound is incubated for up to 1 hour in hepatocyte suspensions (100 µl, 80,000° Cells per well) at 37° C. Cryopreserved hepatocytes are reconstituted in the serum-free incubation medium. The suspension is transferred into 96-well plates (50 µL/well). The compounds are diluted to 2 µM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat:

Each compound is incubated for up to 1 hour in S9 suspension (500 µl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar TRANSWELL® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-4 aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 µM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left( \frac{C_f}{C_b + C_f} \right)$$

Where $C_f$ and $C_b$ are free and bound concentrations determined as the post-dialysis buffer and plasma concentrations, respectively.

CYP450 Profiling:

Each compound is incubated with each of 5 recombinant human CYP450 enzymes, including CYP1A2, CYP2C9, CYP3A4, CYP2D6 and CYP2C19 in the presence and absence of NADPH.

Serial samples will be taken from the incubation mixture at the beginning of the incubation and at 5, 15, 30, 45 and 60 minutes after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hours in plasma (rat, dog, monkey, or human) at 37° C. Compounds are added to the plasma at final concentrations of 1 and 10 µg/mL. Aliquots are taken at 0, 5, 15, 30, 60, and 120 minutes after adding the compound. Concentration of compounds and major metabolites at each timepoint are measured by LC/MS/MS.

Evaluation of Cell-Based Anti-HCV Activity:

Antiviral potency ($EC_{50}$) was determined using a Renilla luciferase (RLuc)-based HCV replicon reporter assay. To perform the assay, HCV 1b RLuc cells (harboring a dicistronic genotype 1b Con1 replicon that encodes a RLuc reporter), or HCV 1a RLuc cells (harboring a dicistronic genotype 1a H77 replicon that encodes a RLuc reporter), were dispensed into 384-well plates. Compounds were re-suspended in DMSO at a concentration of 10 mM and serially diluted in DMSO using an automated pipeting instrument. Serially diluted compounds were mixed with cell culture media and added to the seeded cells. DMSO was used as a negative (solvent) control, and the protease inhibitor ITMN-191 was included at a concentration >100×$EC_{50}$ as a positive control. 72 hours later, cells were lysed and Renilla luciferase activity quantified as recommended by the manufacturer (Promega-Madison, Wis.). Non-linear regression was performed to calculate $EC_{50}$ values.

Typically the compounds of the invention can inhibit multiple genotypes of HCV. For example, compounds of the present invention are active against multiple HCV genotypes selected from 1a, 1b, 2a, 2b, 3a, 4a, and 5a.

Biological data (antiviral potency [$EC_{50}$] was determined using a Renilla luciferase (RLuc)-based HCV replicon reporter assay —HCV 1b RLuc) for representative compounds of the invention is provided in the following table. These compounds can be prepared using procedures similar to those described above.

| Representative Compound of the Invention | Activity (nM) |
|---|---|
| | 0.0100 |
| | 0.0240 |
| | 37.7670 |
| | 0.0852 |

-continued
| Representative Compound of the Invention | Activity (nM) |
|---|---|
| 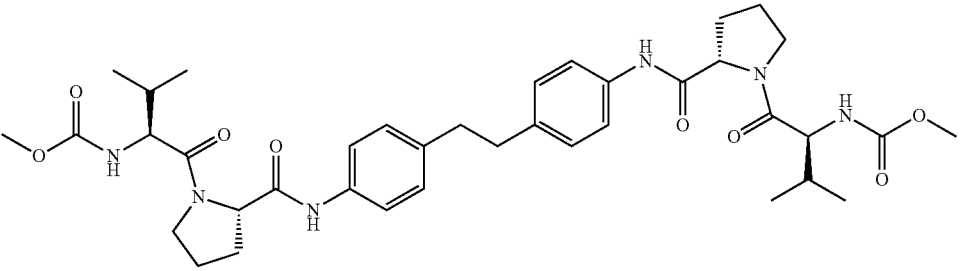 | 0.2639 |
| 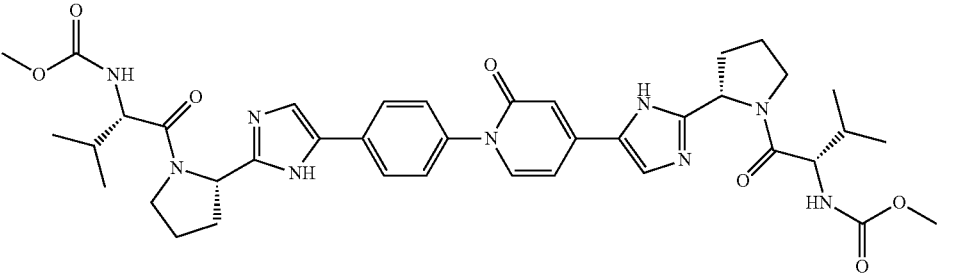 | 38.1323 |
| 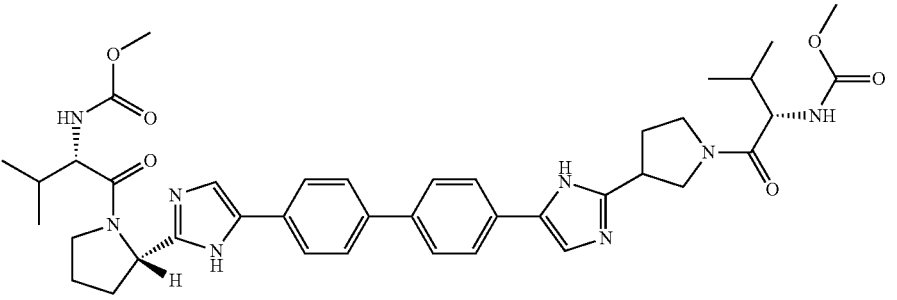 [SMILES: COC(=O)N[C@H](C(=O)N1CCC(c2ncc(-c3ccc(-c4ccc(-c5cnc([C@@H]6CCCN6C(=O)[C@@H](NC(=O)OC)C(C)C)[nH]5)cc4)cc3)[nH]2)C1)C(C)C] | 0.7747 |
| 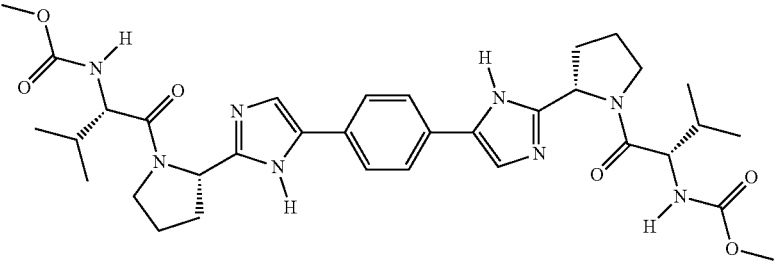 | 1.2200 |
| 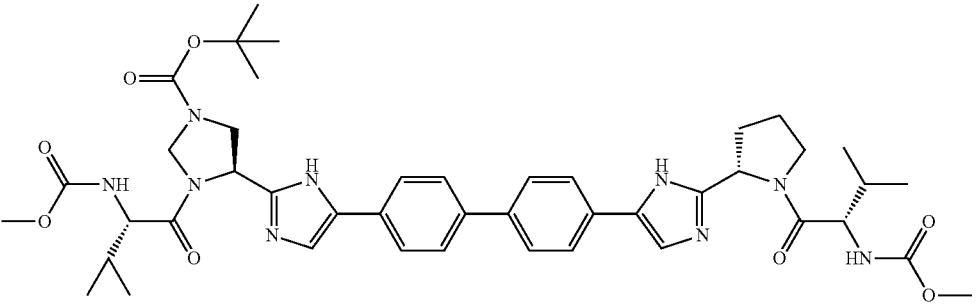 | 0.0050 |

| Representative Compound of the Invention | Activity (nM) |
|---|---|
| | 1.4010 |
| | 0.0073 |
| | 0.0383 |
| | 0.1181 |
| | 0.0372 |

| Representative Compound of the Invention | Activity (nM) |
|---|---|
| | 0.1238 |
| | 0.0664 |
| | 0.0535 |
| | 0.4556 |

| Representative Compound of the Invention | Activity (nM) |
|---|---|
| [chemical structure] | >21.2592 |
| [chemical structure] | 0.0385 |
| [chemical structure] | 0.0989 |
| [chemical structure] | 26.7302 |

-continued
| Representative Compound of the Invention | Activity (nM) |
|---|---|
| 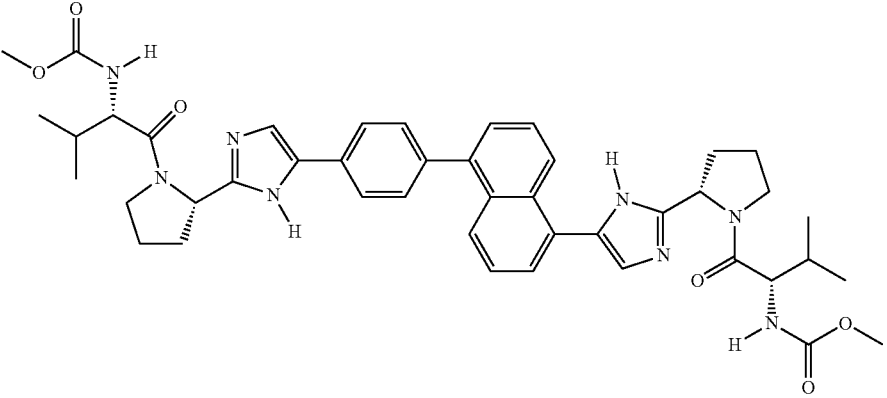 | 0.0032 |
| 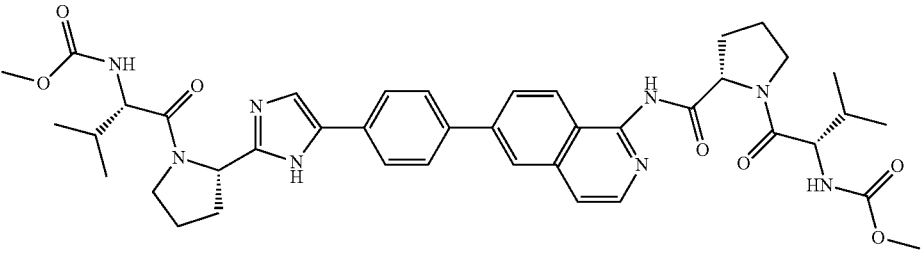 | 0.7293 |
| 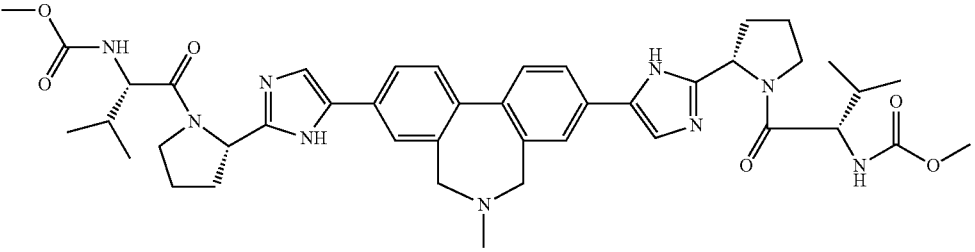 | 11.1196 |
| 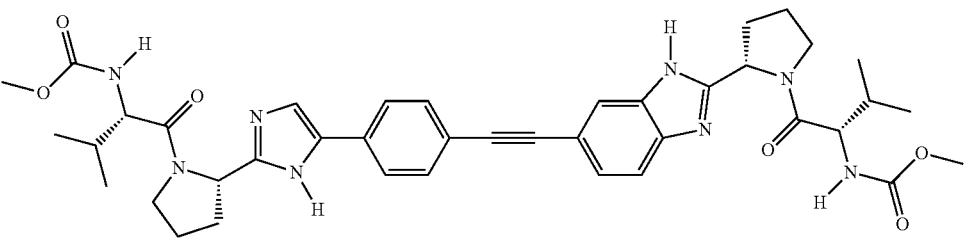 | 0.0111 |
| 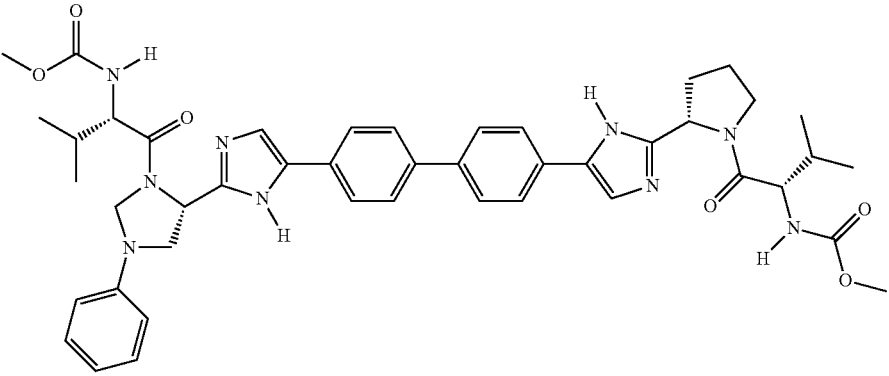 | 0.0074 |

| Representative Compound of the Invention | Activity (nM) |
|---|---|
| | 0.0136 |
| | 0.0074 |
| | 0.0081 |
| | 0.0539 |

|  | Activity (nM) |
|---|---|
| Representative Compound of the Invention | |
| (structure) | 0.0126 |
| (structure) | 0.1985 |
| (structure) | 0.0327 |
| (structure) | 0.1389 |
| (structure) | 0.0915 |

-continued
| Representative Compound of the Invention | Activity (nM) |
|---|---|
| 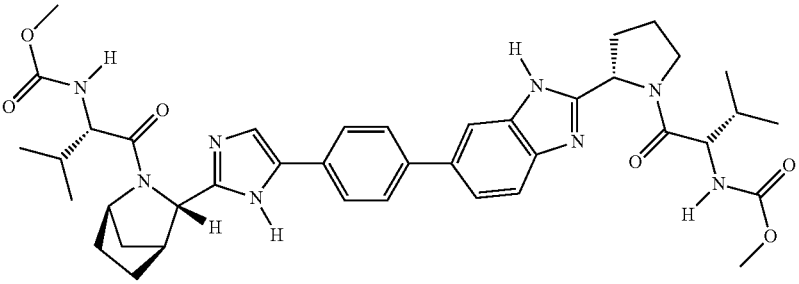 | 0.0553 |
| 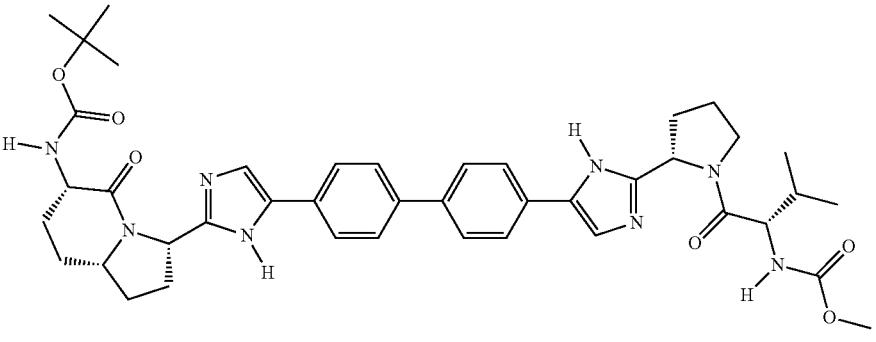 [SMILES: COC(=O)N[C@H](C(=O)N1CCC[C@H]1c1ncc(-c2ccc(-c3ccc(-c4cnc([C@@H]5CC[C@@H]6CC[C@H](NC(=O)OC(C)(C)C)C(=O)N65)[nH]4)cc3)cc2)[nH]1)C(C)C] | 0.3249 |
| 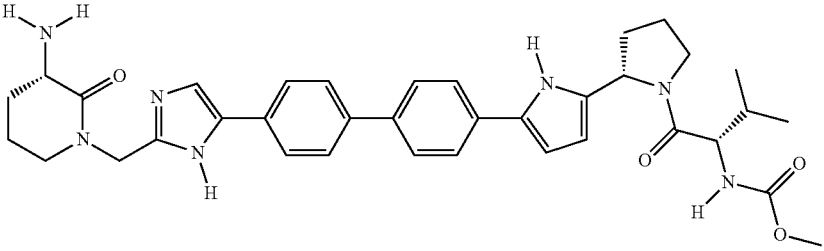 [SMILES: COC(=O)N[C@H](C(=O)N1CCC[C@H]1c1ccc(-c2ccc(-c3ccc(-c4cnc(CN5CCC[C@H](N)C5=O)[nH]4)cc3)cc2)[nH]1)C(C)C] | 4.8013 |
| 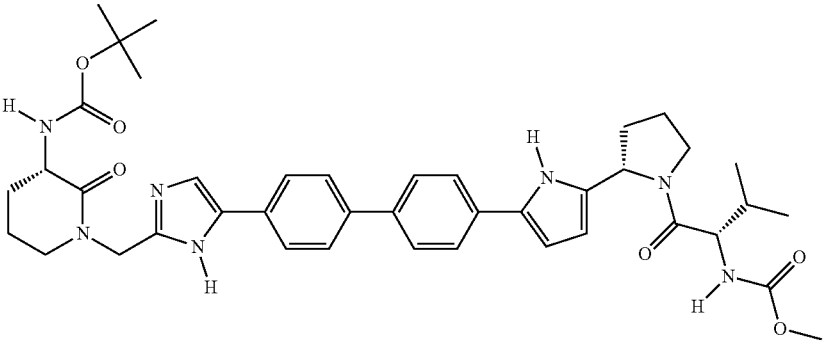 [SMILES: COC(=O)N[C@H](C(=O)N1CCC[C@H]1c1ccc(-c2ccc(-c3ccc(-c4cnc(CN5CCC[C@H](NC(=O)OC(C)(C)C)C5=O)[nH]4)cc3)cc2)[nH]1)C(C)C] | 0.0580 |
| 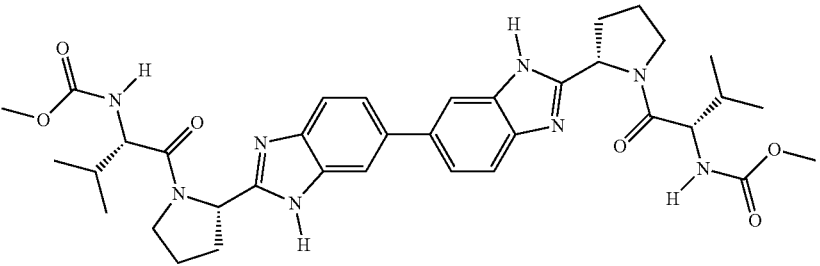 | 35.4673 |

| Representative Compound of the Invention | Activity (nM) |
|---|---|
| 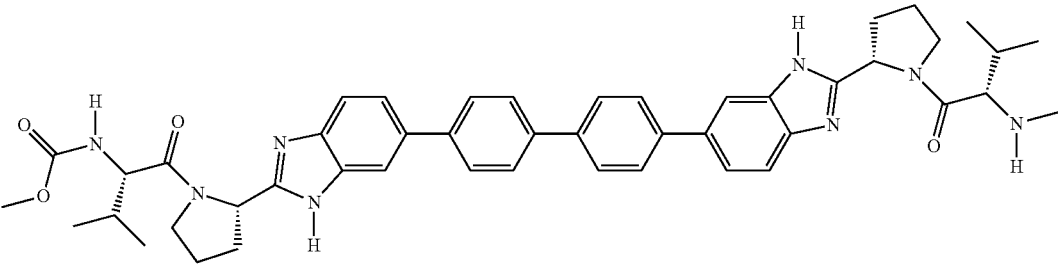 | 0.0441 |
| 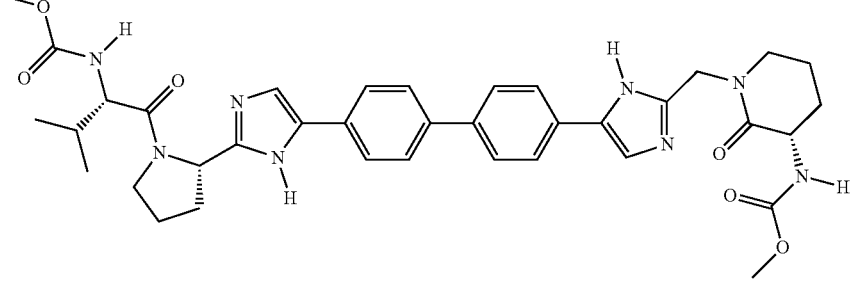 | 0.1468 |
| 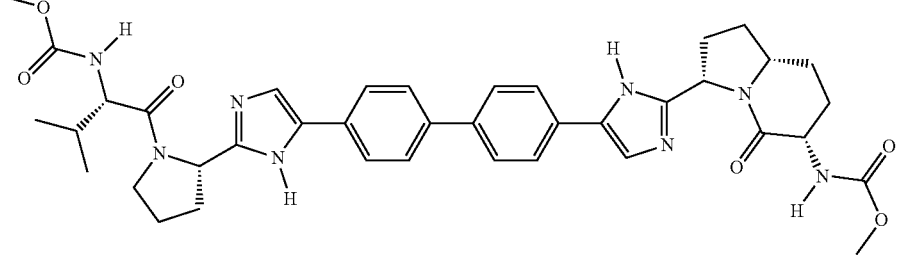 | 0.1559 |
| 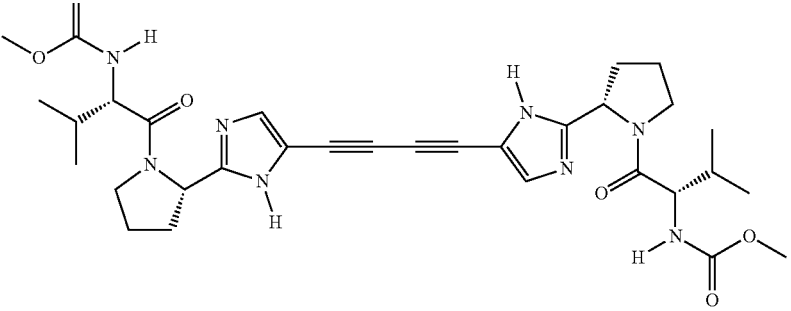 | 1.3319 |
| 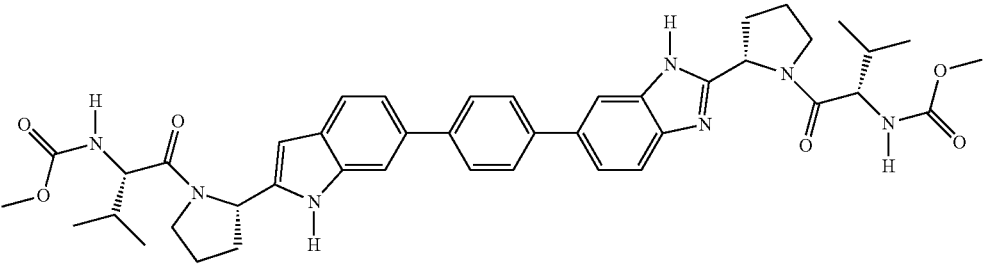 | 0.0099 |

-continued
| Representative Compound of the Invention | Activity (nM) |
|---|---|
| 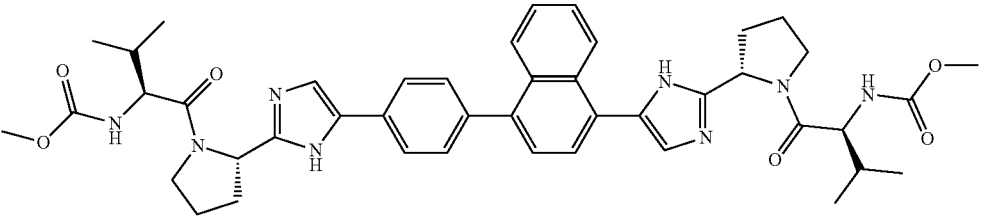 | 0.0067 |
| 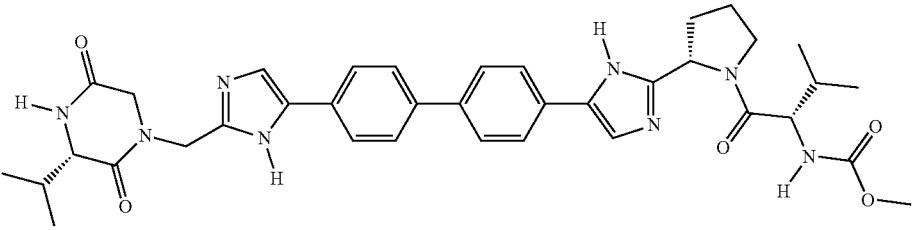 [SMILES: COC(=O)N[C@H](C(=O)N1CCC[C@H]1c1ncc(-c2ccc(-c3ccc(-c4cnc(CN5CC(=O)N[C@@H](C(C)C)C5=O)[nH]4)cc3)cc2)[nH]1)C(C)C] | 0.5135 |
| 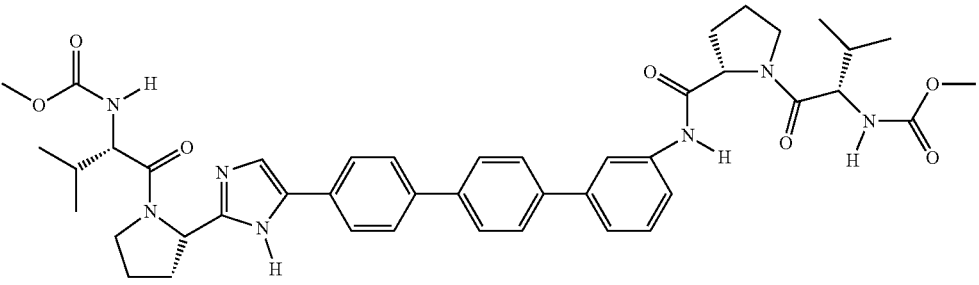 | 0.0111 |
| 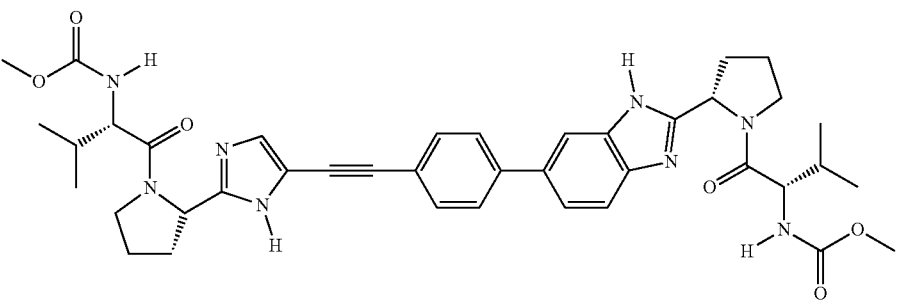 | 0.0168 |
| 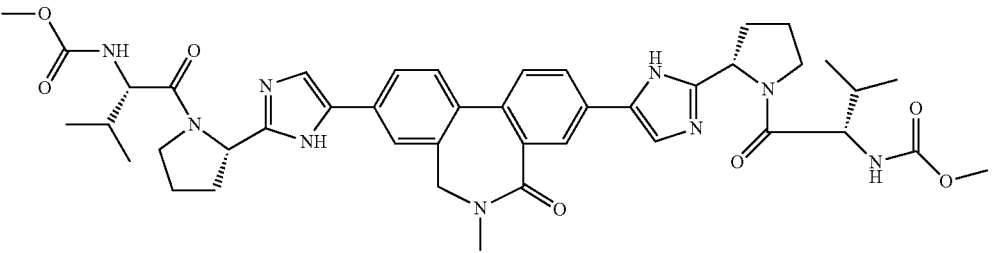 | 2.1380 |

| Representative Compound of the Invention | Activity (nM) |
|---|---|
| | 15.8915 |
| | 0.0511 |
| | 0.0788 |
| | 0.0054 |
| | 0.0030 |

| Representative Compound of the Invention | Activity (nM) |
|---|---|
| | 0.0474 |
| | 0.0345 |
| | 7.5453 |
| | 0.2395 |

| Representative Compound of the Invention | Activity (nM) |
|---|---|
| | 0.0142 |
| | 3.4144 |
| | 0.0115 |
| | >44.4000 |

| Representative Compound of the Invention | Activity (nM) |
|---|---|
| | >44.4000 |
| | 0.0184 |
| | >44.4000 |
| | 0.0103 |
| | 0.0865 |

| Representative Compound of the Invention | Activity (nM) |
|---|---|
| 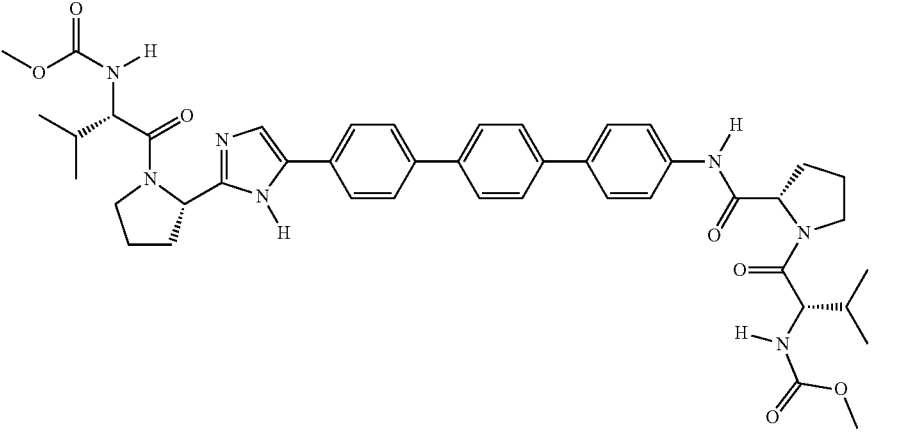 [SMILES: COC(=O)N[C@H](C(=O)N1CCC[C@H]1C(=O)Nc1ccc(-c2ccc(-c3ccc(-c4cnc([C@@H]5CCCN5C(=O)[C@@H](NC(=O)OC)C(C)C)[nH]4)cc3)cc2)cc1)C(C)C] | 0.0875 |
| 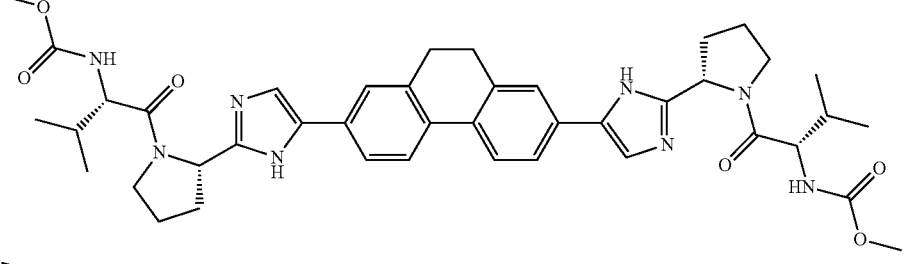 | 0.0099 |
| 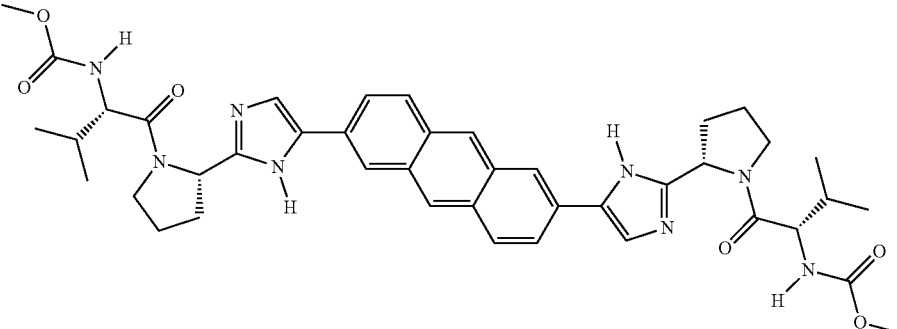 | 0.0070 |
| 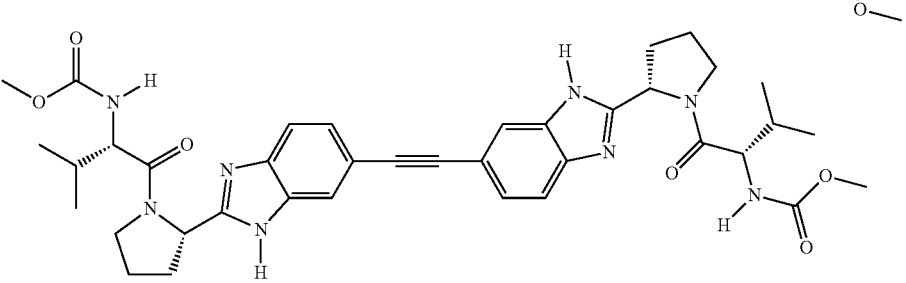 | 0.1386 |
| 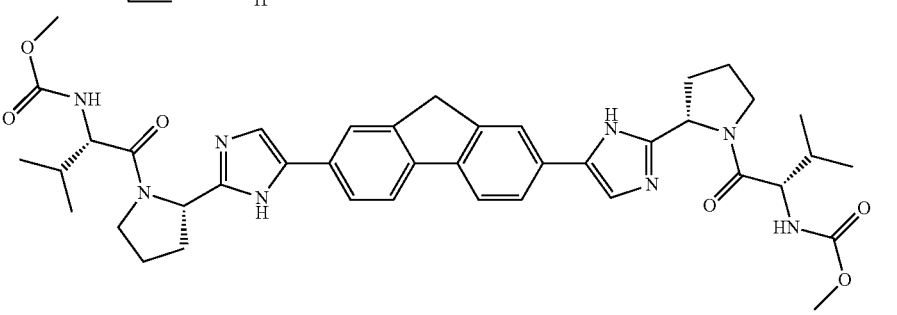 | 0.0137 |

-continued
| Representative Compound of the Invention | Activity (nM) |
|---|---|
| 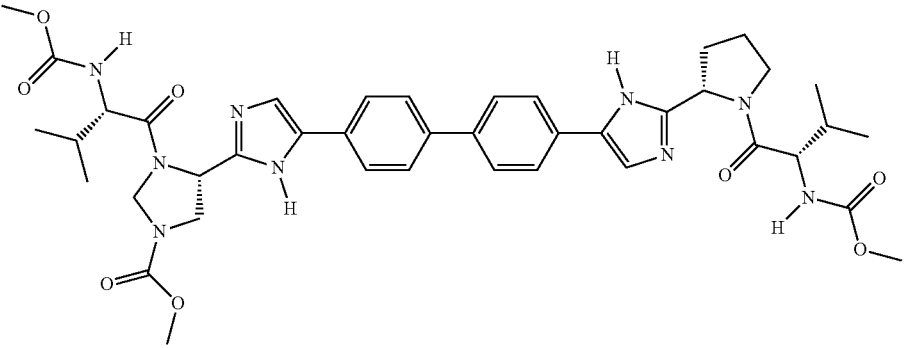 | 0.0300 |
| 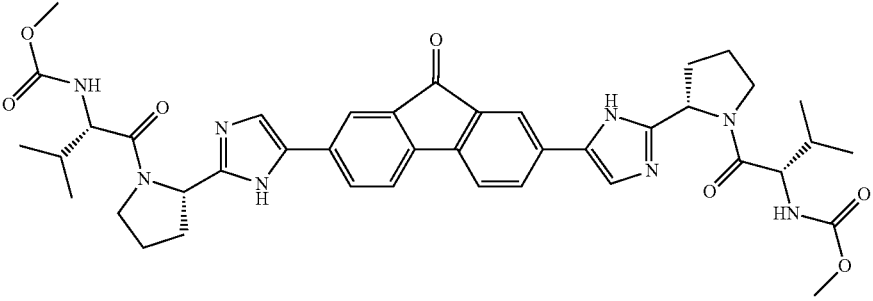 [SMILES: COC(=O)N[C@H](C(=O)N1CCC[C@H]1c1ncc(-c2ccc3c(c2)C(=O)c2cc(-c4cnc([C@@H]5CCCN5C(=O)[C@@H](NC(=O)OC)C(C)C)[nH]4)ccc2-3)[nH]1)C(C)C] | 0.0184 |
| 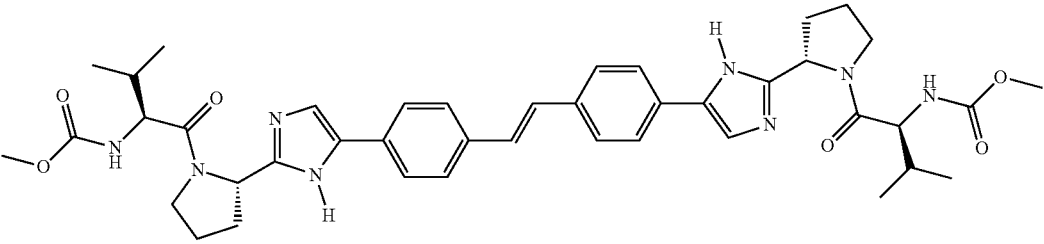 | 0.0264 |
| 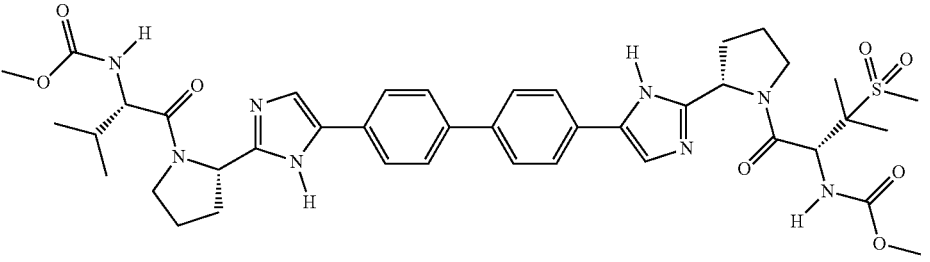 | 0.1613 |
| 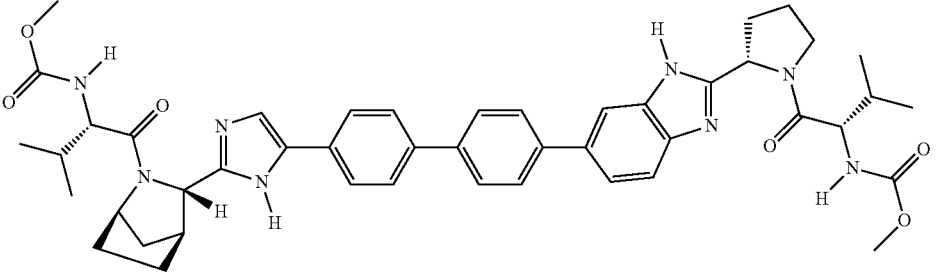 [SMILES: COC(=O)N[C@H](C(=O)N1CCC[C@H]1c1nc2ccc(-c3ccc(-c4ccc(-c5cnc([C@@H]6[C@H]7CC[C@H](C7)N6C(=O)[C@@H](NC(=O)OC)C(C)C)[nH]5)cc4)cc3)cc2[nH]1)C(C)C] | 0.0213 |

| Representative Compound of the Invention | Activity (nM) |
|---|---|
| 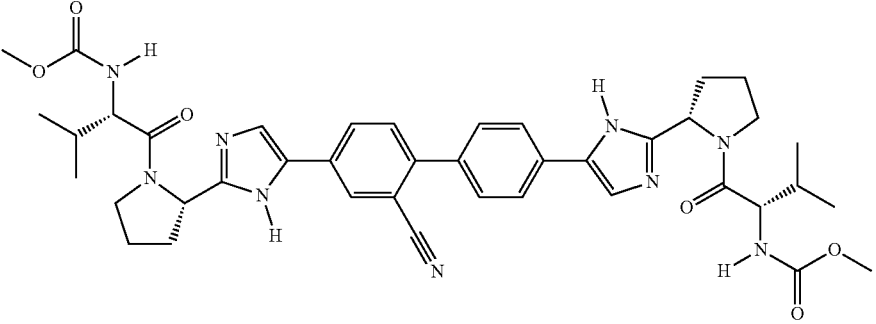 | 0.0158 |
| 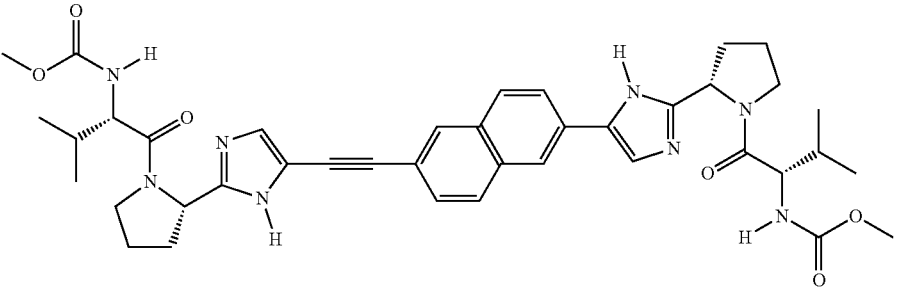 | 0.0106 |
| 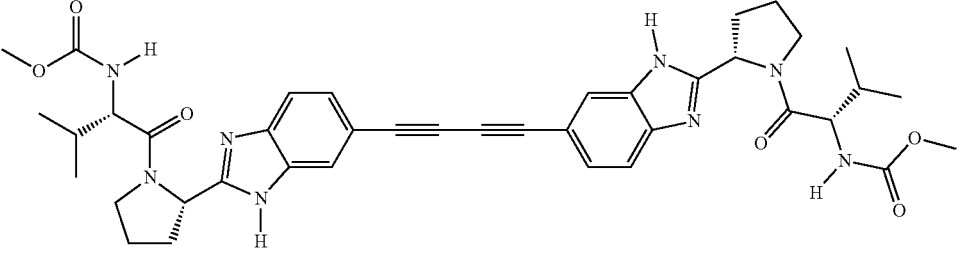 | 0.0261 |
| 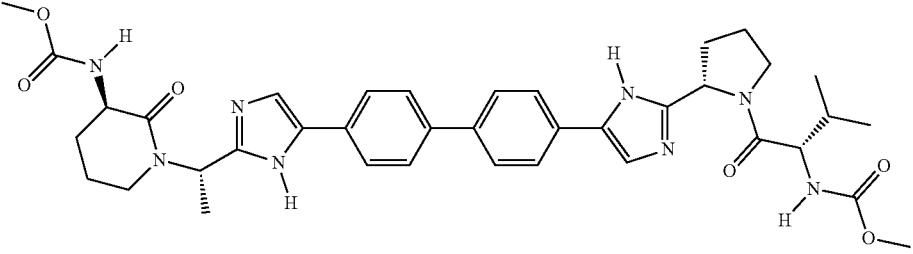 | 0.6607 |
| 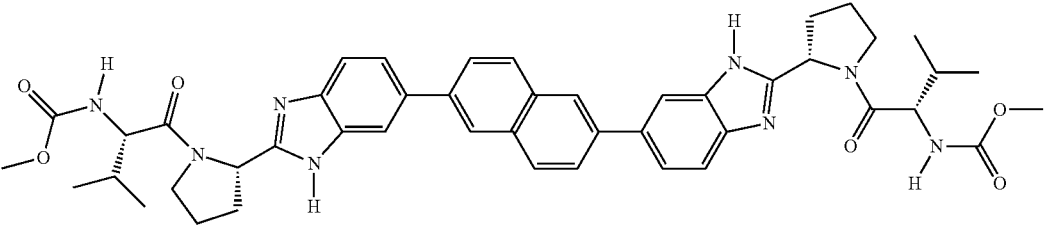 | <0.0041 |

| Representative Compound of the Invention | Activity (nM) |
|---|---|
| | 0.0221 |
| | 0.0239 |
| | 1.5060 |
| | 0.0304 |

| Representative Compound of the Invention | Activity (nM) |
| --- | --- |
| | 0.0047 |
| | 0.3490 |
| | 0.0058 |
| | 0.1270 |

| Representative Compound of the Invention | Activity (nM) |
|---|---|
| 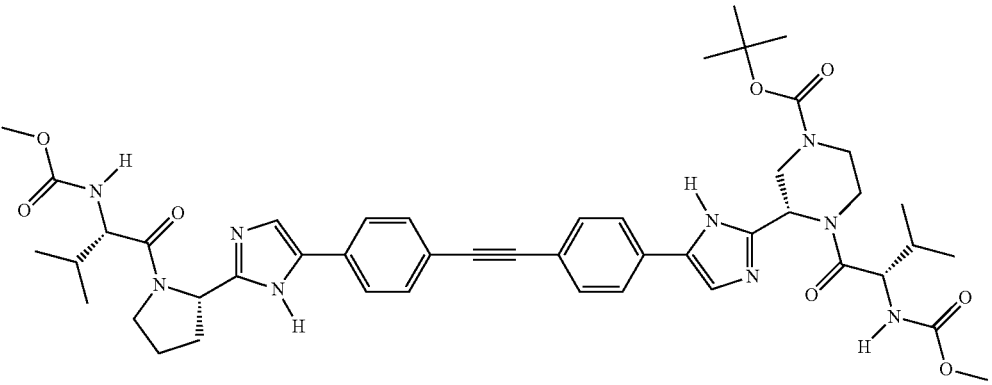 | 4.7270 |
| 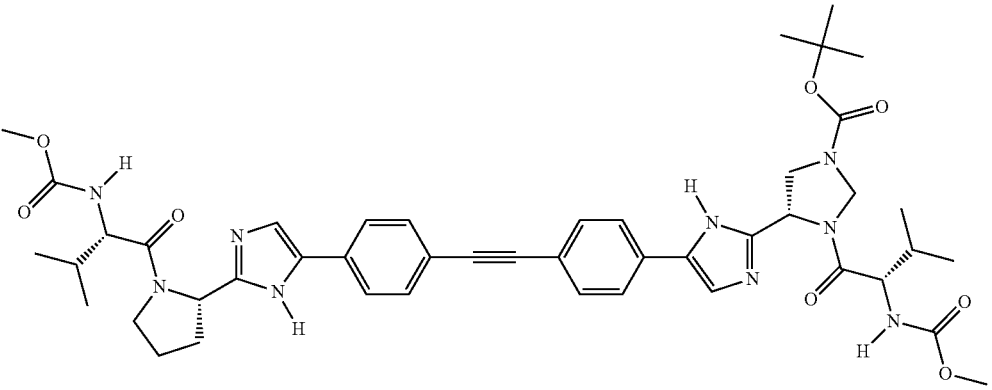 | 0.3180 |
| 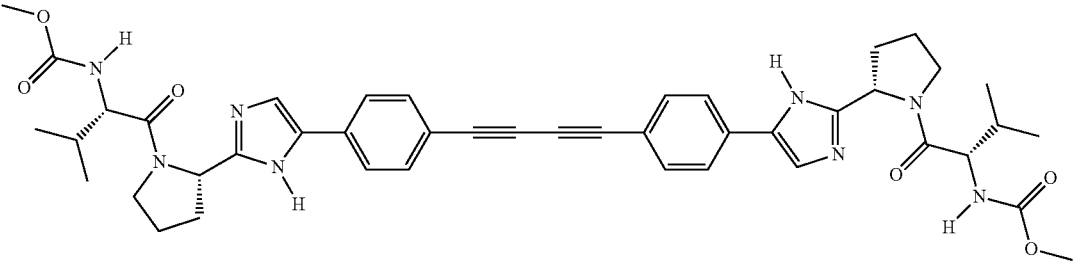 | 0.3841 |
| 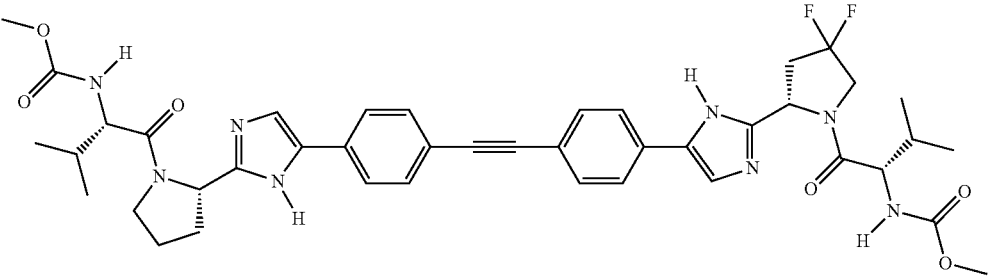 | 0.0091 |

| Representative Compound of the Invention | Activity (nM) |
|---|---|
| 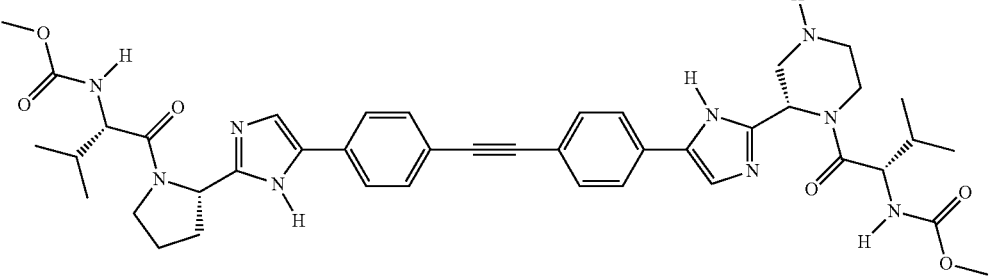 | 0.2012 |
| 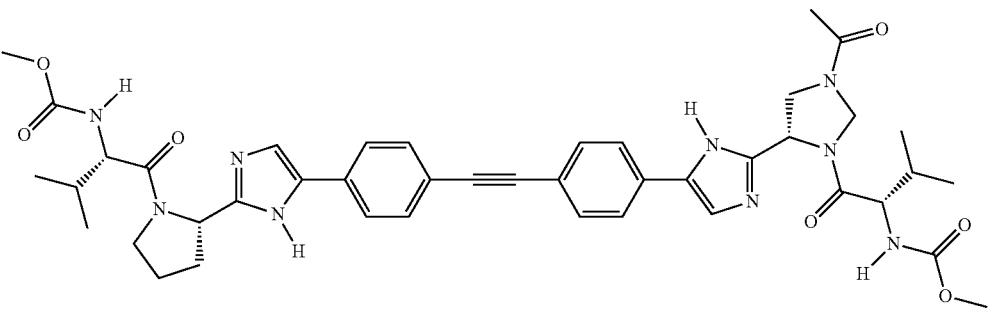 | 0.0403 |
| 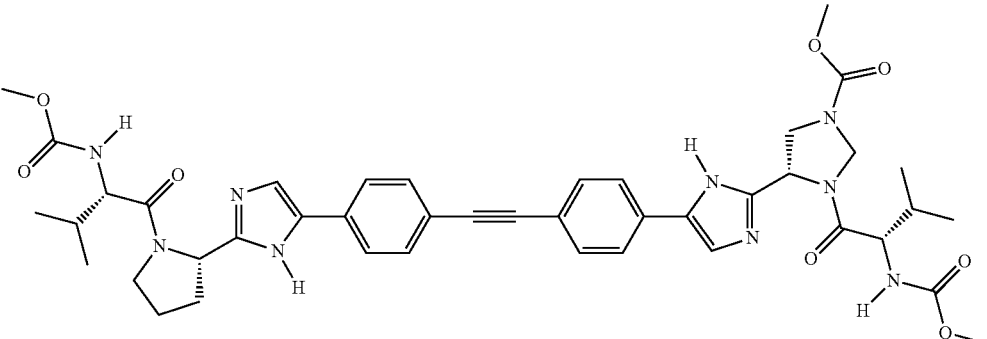 | 0.0187 |
| 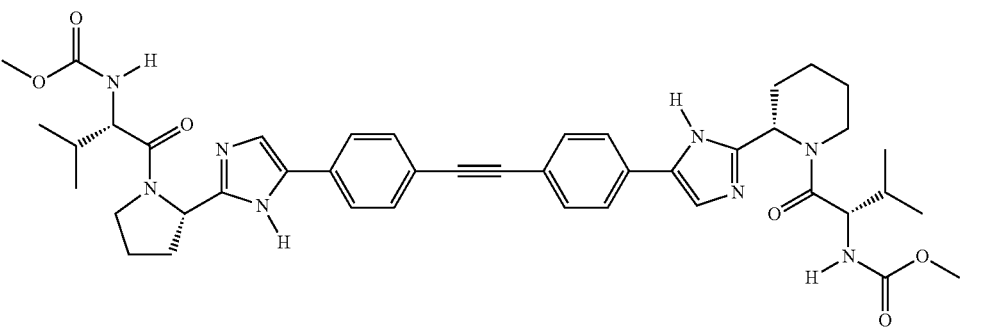 | 0.0224 |
| 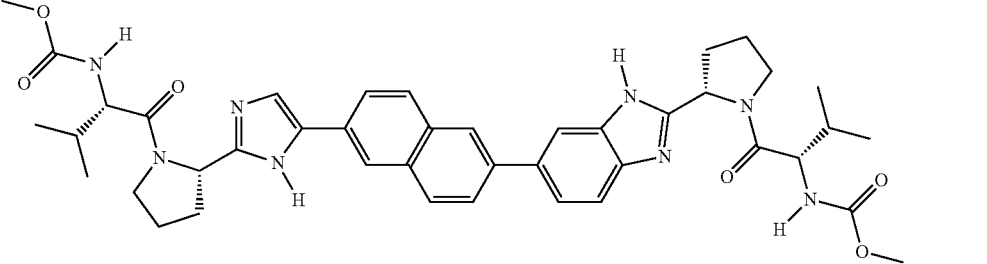 | 0.0067 |

-continued

| Representative Compound of the Invention | Activity (nM) |
|---|---|
| | 0.0102 |
| | 0.0088 |
| | 0.0060 |
| | 0.2835 |
| | 0.0198 |

| Representative Compound of the Invention | Activity (nM) |
|---|---|
| | 0.0074 |
| | >44.4000 |
| | 0.2042 |
| | 0.2564 |

| Representative Compound of the Invention | Activity (nM) |
|---|---|
| | 0.2448 |
| | 0.0530 |
| | 1.0487 |
| | 10.2665 |

| Representative Compound of the Invention | Activity (nM) |
|---|---|
| 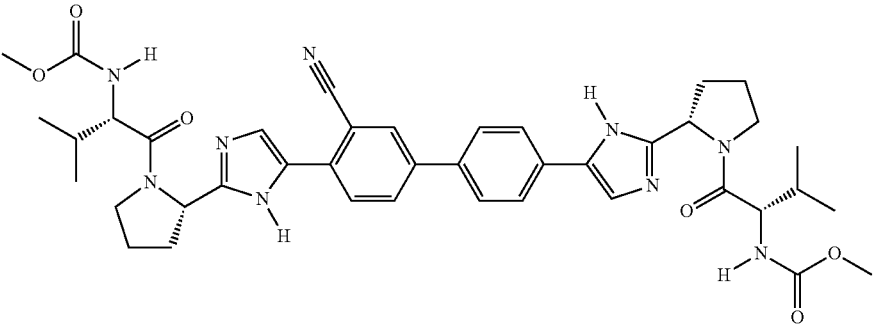 | 0.0192 |
| 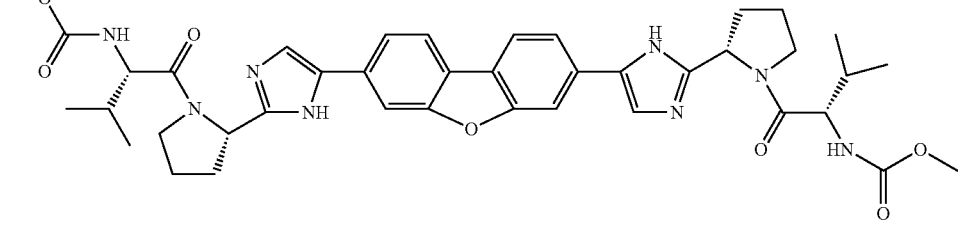 | 0.0052 |
| 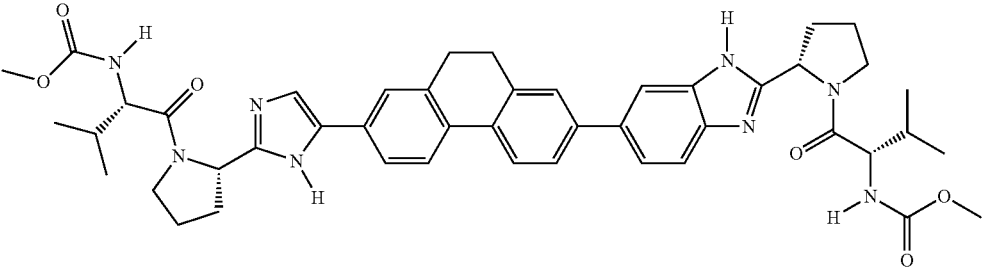 | 0.0037 |
| 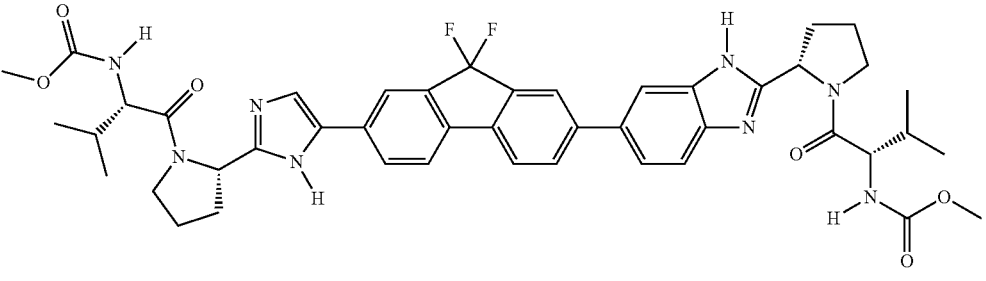 | <0.0023 |
| 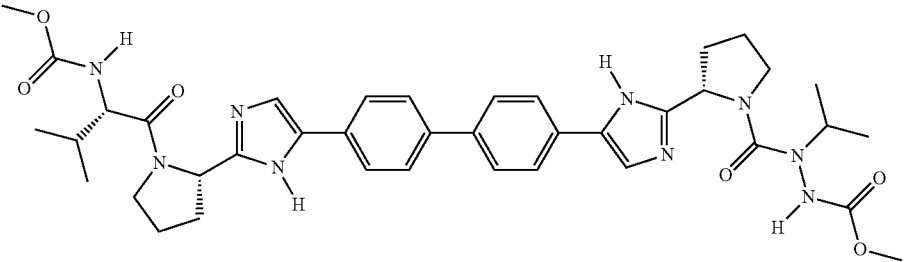 | 0.0719 |

-continued

| Representative Compound of the Invention | Activity (nM) |
|---|---|
| | 0.0214 |
| | 0.0082 |
| | 0.0171 |
| | 0.0322 |
| | 0.0424 |

-continued

| Representative Compound of the Invention | Activity (nM) |
|---|---|
| | 0.0131 |
| | 0.2239 |
| | 0.0075 |
| | 0.0775 |
| | 0.0048 |

-continued

| Representative Compound of the Invention | Activity (nM) |
|---|---|
| | 0.0037 |
| | 2.6102 |
| | 0.0195 |
| | 0.0067 |
| | 0.0898 |

| Representative Compound of the Invention | Activity (nM) |
| --- | --- |
| | 0.0029 |
| | 0.016 |
| | |
| | 0.0054 |
| | 0.0368 |

| Representative Compound of the Invention | Activity (nM) |
|---|---|
| 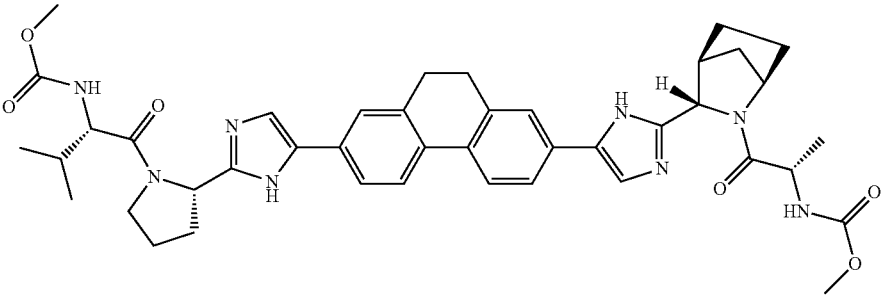 [SMILES: COC(=O)N[C@@H](C)C(=O)N1[C@@H]2CC[C@@H](C2)[C@H]1c1ncc(-c2ccc3c(c2)CCc2cc(-c4cnc([C@@H]5CCCN5C(=O)[C@@H](NC(=O)OC)C(C)C)[nH]4)ccc2-3)[nH]1] | 0.0126 |
| 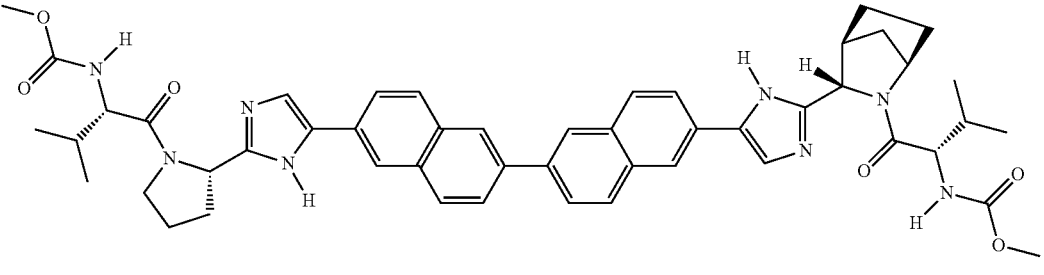 | 0.28 |
| 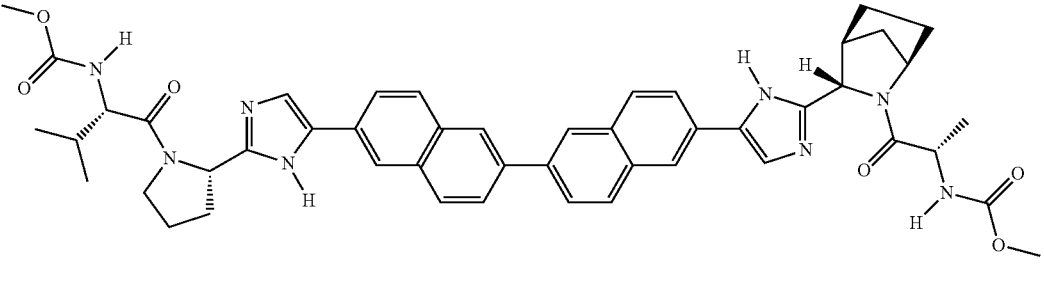 | 1.17 |
| 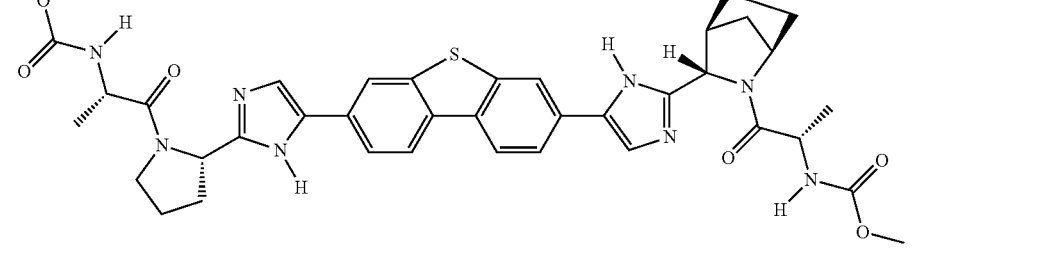 | 0.0185 |
| 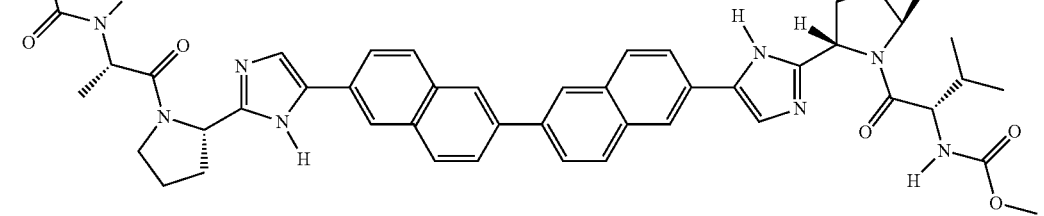 | 1.15 |

-continued
| Representative Compound of the Invention | Activity (nM) |
|---|---|
| 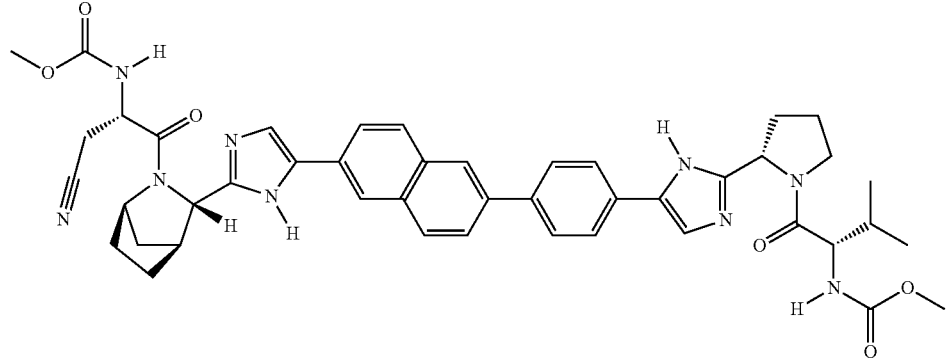 | 0.013 |
| 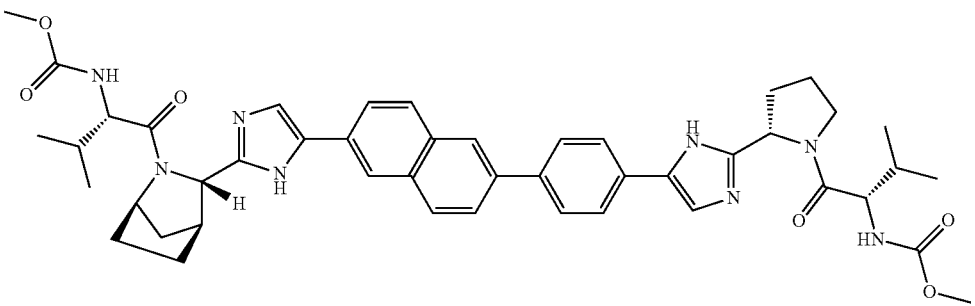 | 0.011 |
| 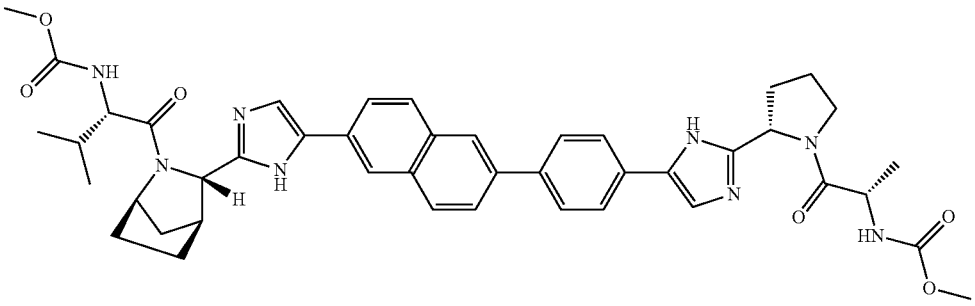 | 0.034 |
| 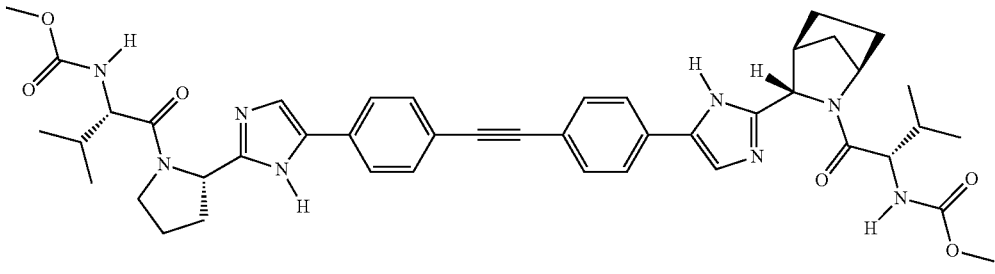 | 0.073 |
| 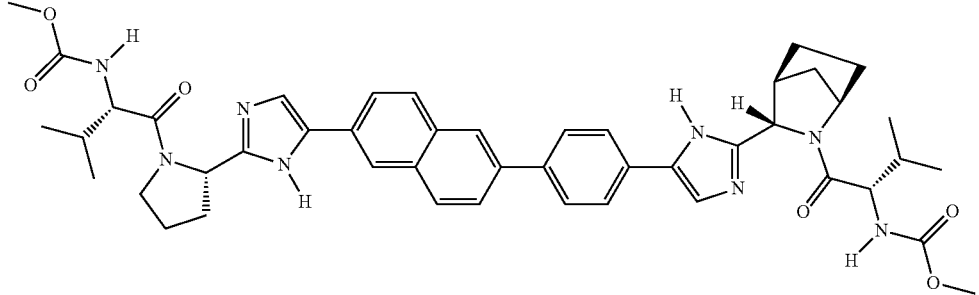 | 0.006 |

| Representative Compound of the Invention | Activity (nM) |
| --- | --- |
| | 0.077 |
| | 0.075 |
| | 0.013 |
| | 0.018 |
| | 0.014 |

| Representative Compound of the Invention | Activity (nM) |
|---|---|
| | 0.0149 |
| | 0.0058 |
| | 0.0069 |
| | 0.0059 |

| Representative Compound of the Invention | Activity (nM) |
|---|---|
| | 0.0036 |
| | 0.0045 |
| | 0.0067 |
| | 0.0218 |
| | 0.0064 |

| Representative Compound of the Invention | Activity (nM) |
|---|---|
| | 0.006 |
| | 0.2561 (Abs) |
| | 0.0405 (Abs) |
| | 0.0097 |

-continued
| Representative Compound of the Invention | Activity (nM) |
|---|---|
| 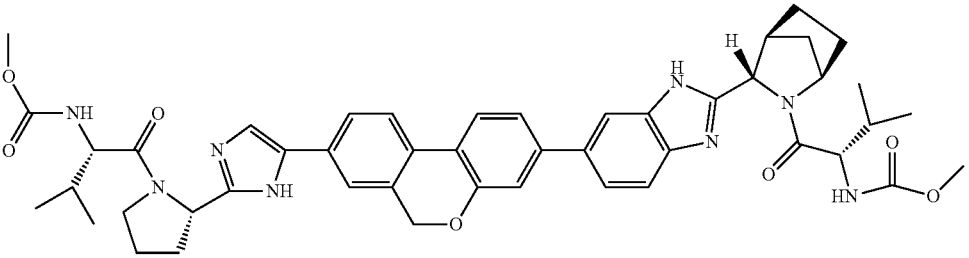 [SMILES: COC(=O)N[C@H](C(=O)N1CCC[C@H]1c1ncc(-c2ccc3c(c2)COc2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C] | 0.007 |
| 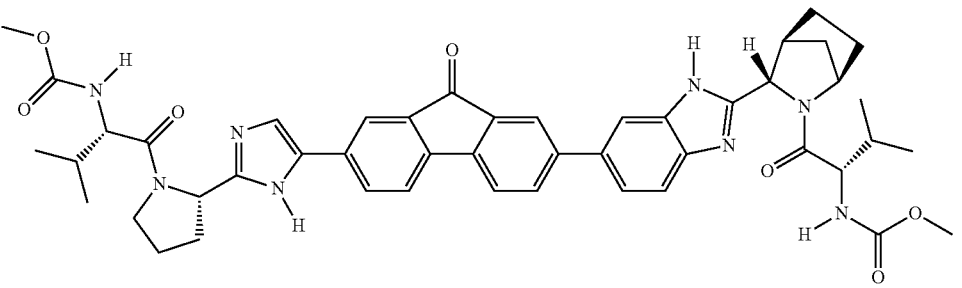 | 0.006 |
| 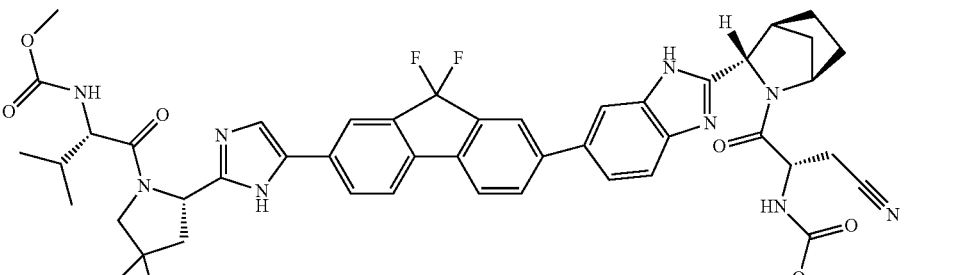 | 0.004 |
| 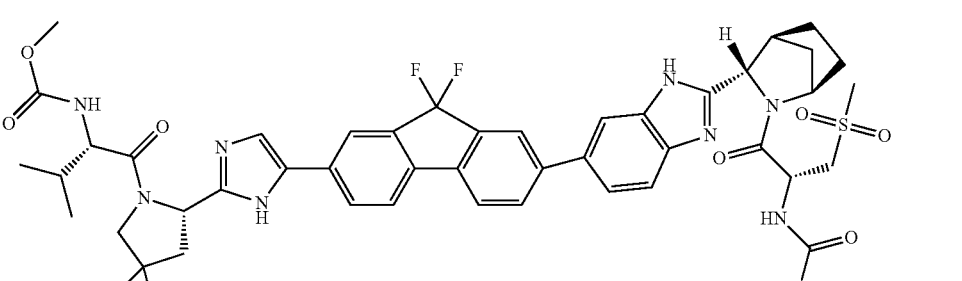 | 0.005 |
| 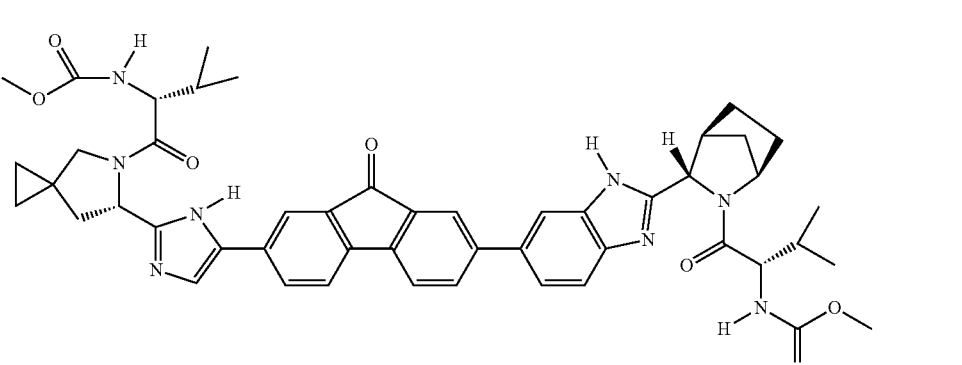 | 0.005 |

| Representative Compound of the Invention | Activity (nM) |
|---|---|
| 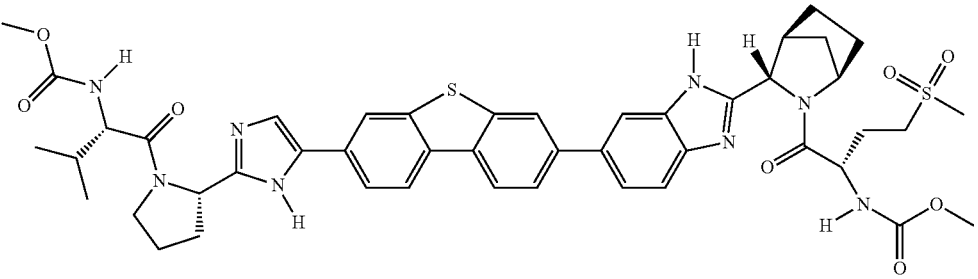 | |
| Additional Representative Compounds of the Invention | Activity (nM) |
|---|---|
| 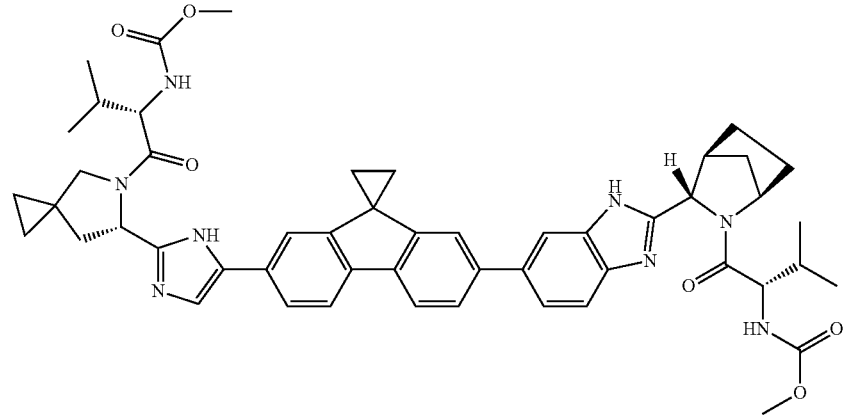 [SMILES: COC(=O)N[C@H](C(=O)N1CC2(CC2)C[C@H]1c1ncc(-c2ccc3c(c2)C2(CC2)c2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C] | 0.0073 |
| 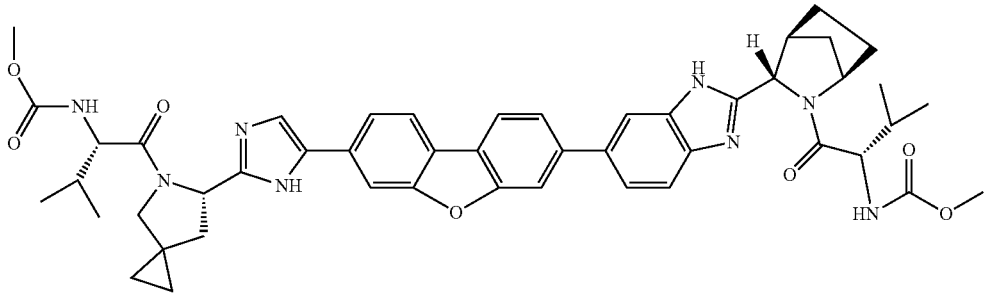 [SMILES: COC(=O)N[C@H](C(=O)N1CC2(CC2)C[C@H]1c1ncc(-c2ccc3c(c2)oc2cc(-c4ccc5nc([C@@H]6[C@H]7CC[C@H](C7)N6C(=O)[C@@H](NC(=O)OC)C(C)C)[nH]c5c4)ccc23)[nH]1)C(C)C] | 0.0041 |
| 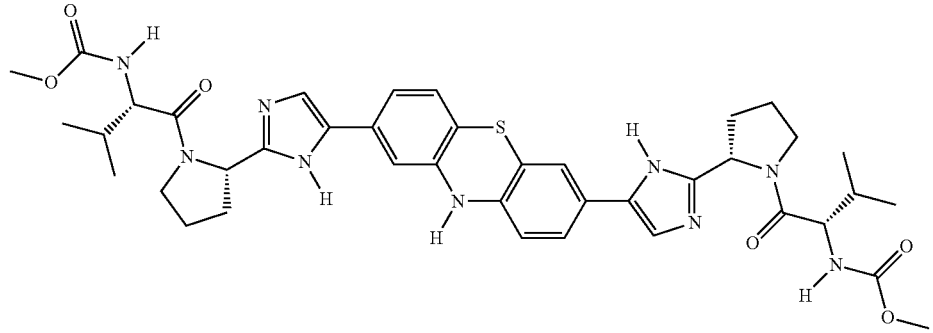 | 1.7224 |

-continued
| Additional Representative Compounds of the Invention | Activity (nM) |
|---|---|
| 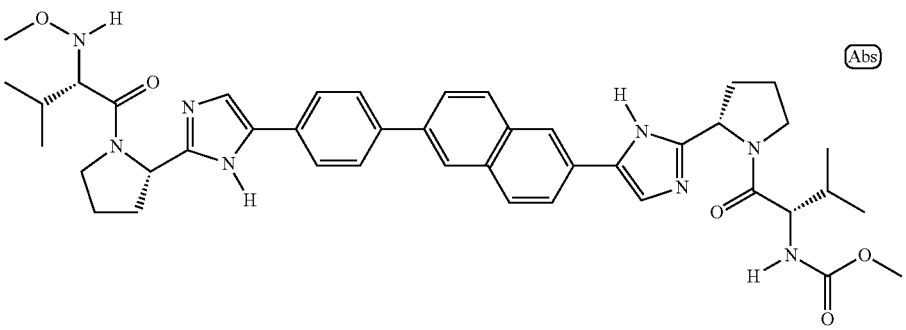 [SMILES: CON[C@H](C(=O)N1CCC[C@H]1c1ncc(-c2ccc(-c3ccc4cc(-c5cnc([C@@H]6CCCN6C(=O)[C@@H](NC(=O)OC)C(C)C)[nH]5)ccc4c3)cc2)[nH]1)C(C)C] | 0.525 |
| 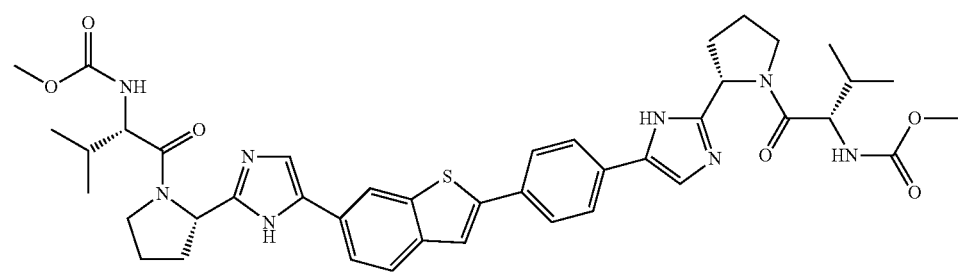 | 0.0093 |
| 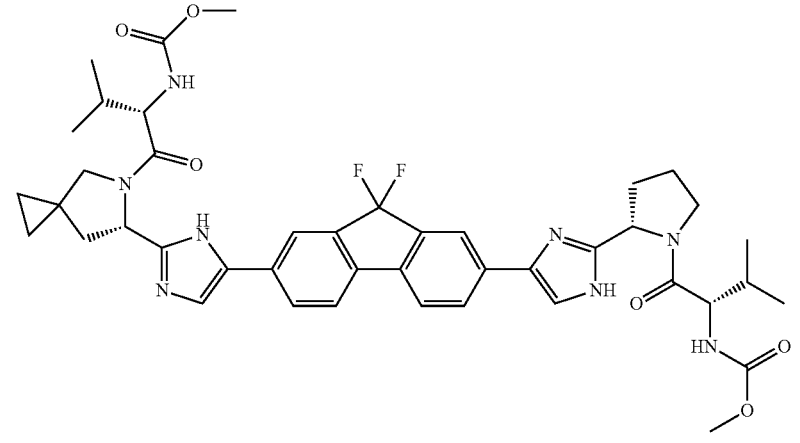 [SMILES: COC(=O)N[C@H](C(=O)N1CCC[C@H]1c1nc(-c2ccc3c(c2)C(F)(F)c2cc(-c4cnc([C@@H]5CC6(CC6)CN5C(=O)[C@@H](NC(=O)OC)C(C)C)[nH]4)ccc2-3)c[nH]1)C(C)C] | 0.0125 |
| 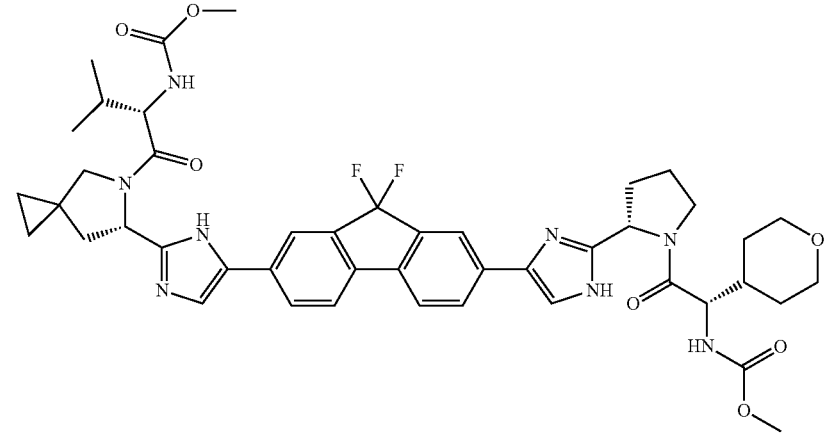 [SMILES: COC(=O)N[C@H](C(=O)N1CC2(CC2)C[C@H]1c1ncc(-c2ccc3c(c2)C(F)(F)c2cc(-c4c[nH]c([C@@H]5CCCN5C(=O)[C@@H](NC(=O)OC)C5CCOCC5)n4)ccc2-3)[nH]1)C(C)C] | 0.0614 |

| Additional Representative Compounds of the Invention | Activity (nM) |
|---|---|
| 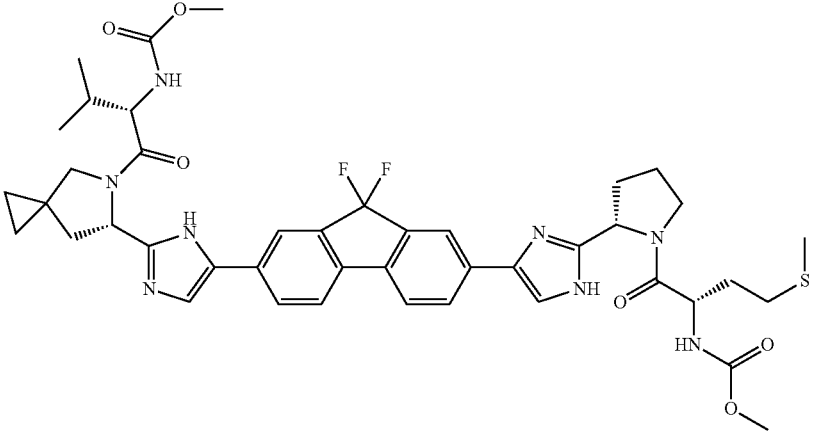 [SMILES: COC(=O)N[C@@H](CCSC)C(=O)N1CCC[C@H]1c1nc(-c2ccc3c(c2)C(F)(F)c2cc(-c4cnc([C@@H]5CC6(CC6)CN5C(=O)[C@@H](NC(=O)OC)C(C)C)[nH]4)ccc2-3)c[nH]1] | 0.0204 |
| 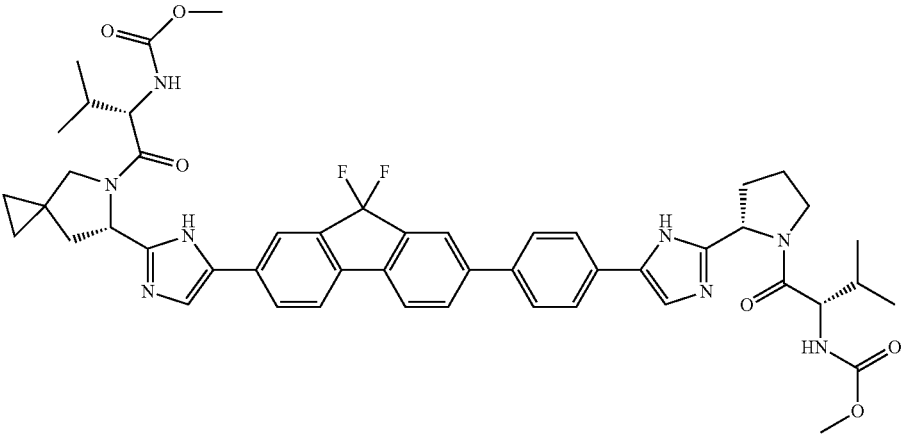 [SMILES: COC(=O)N[C@H](C(=O)N1CCC[C@H]1c1ncc(-c2ccc(-c3ccc4c(c3)C(F)(F)c3cc(-c5cnc([C@@H]6CC7(CC7)CN6C(=O)[C@@H](NC(=O)OC)C(C)C)[nH]5)ccc3-4)cc2)[nH]1)C(C)C] | 0.0208 |
| 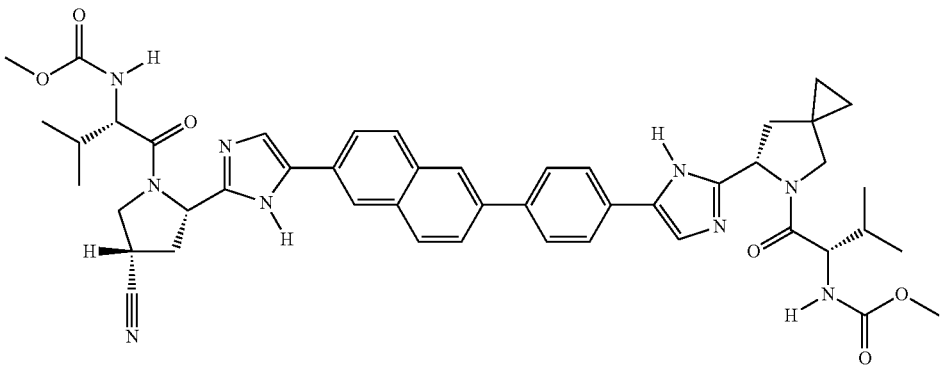 | 0.0169 |
| 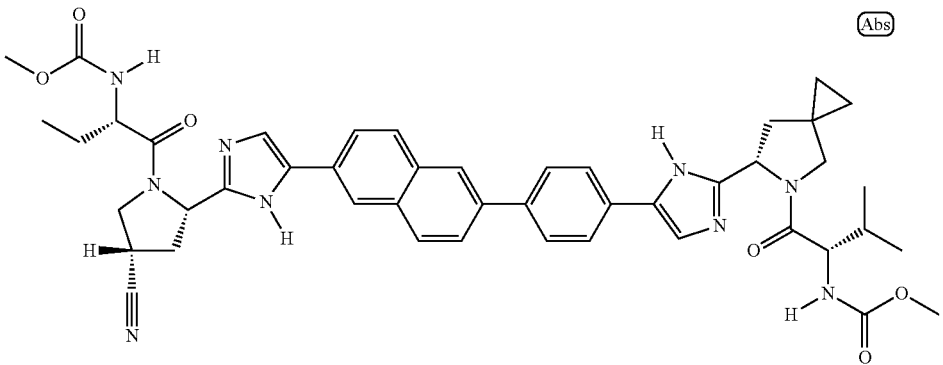 | 0.0155 |

| Additional Representative Compounds of the Invention | Activity (nM) |
|---|---|
| | 0.1249 |
| | 0.1196 |
| | 0.1383 |
| | 0.0165 |

-continued
| Additional Representative Compounds of the Invention | Activity (nM) |
|---|---|
| 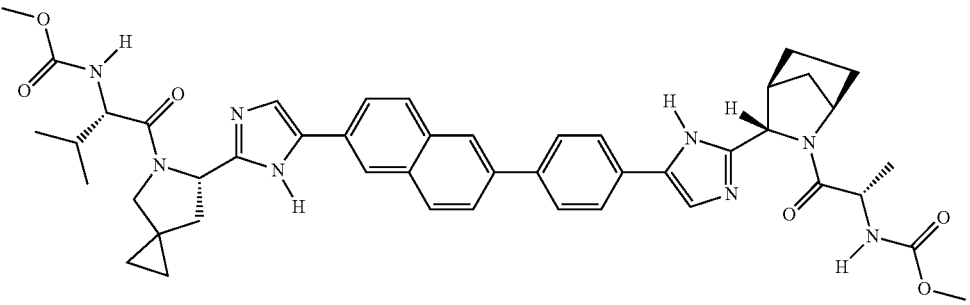 Abs | 0.0156 |
| 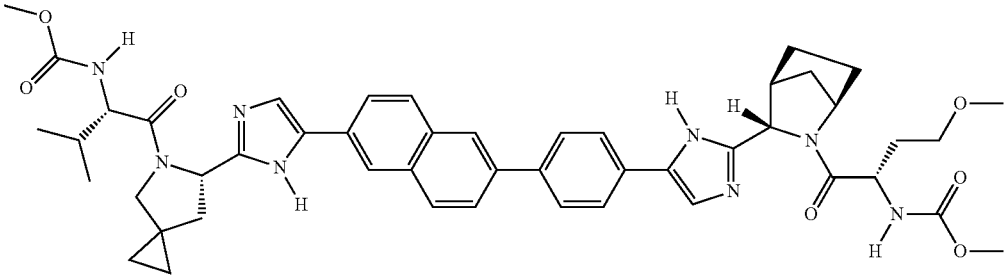 Abs | 0.0119 |
| 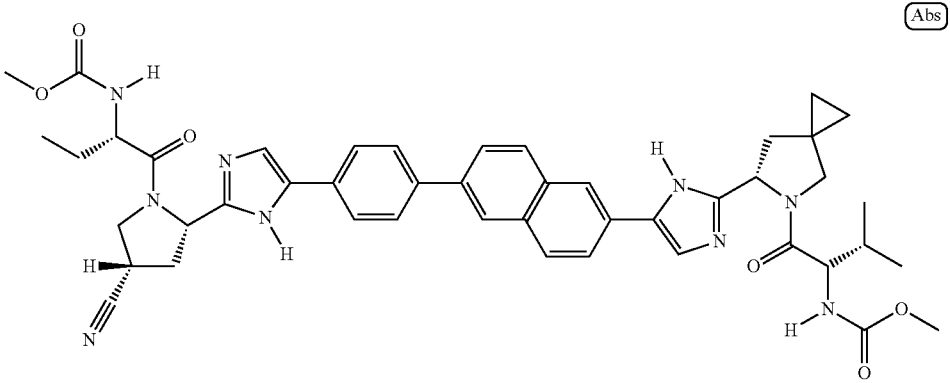 Abs | 0.0176 |
| 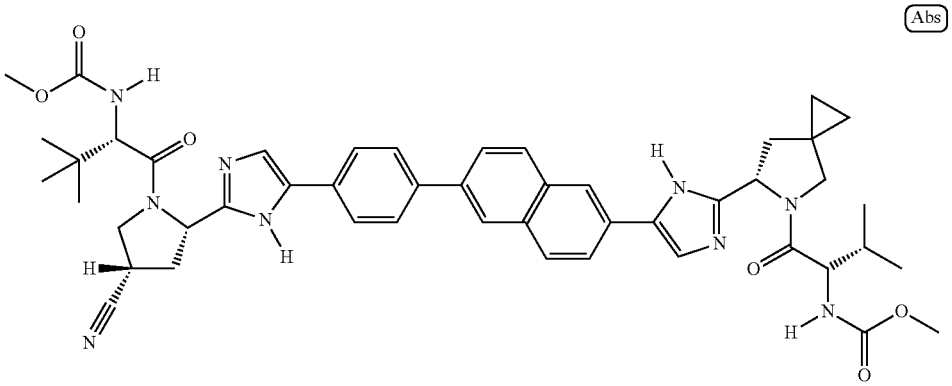 Abs | 0.0127 |

-continued
| Additional Representative Compounds of the Invention | Activity (nM) |
|---|---|
| 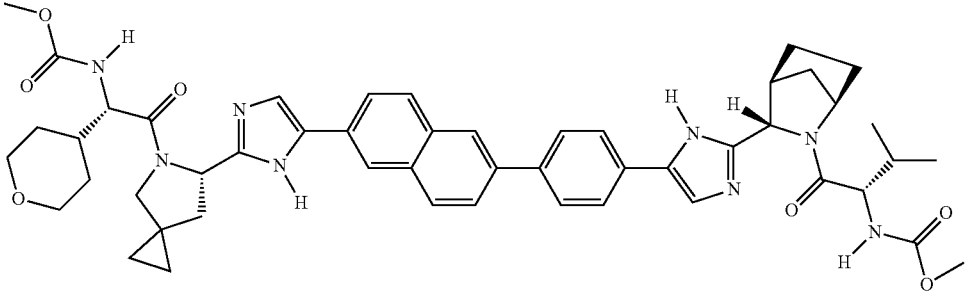 | 0.0136 |
| 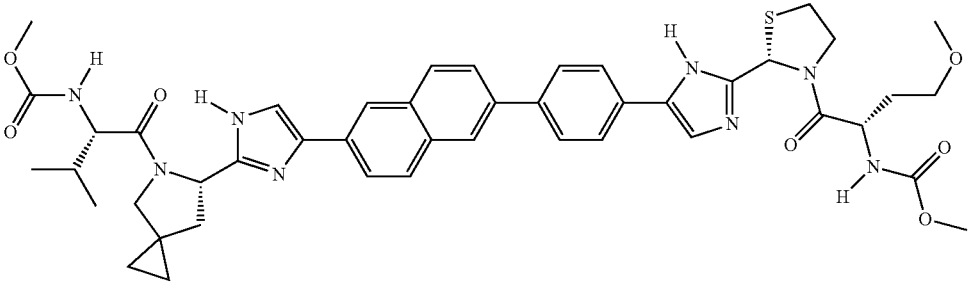 [SMILES: COCC[C@H](NC(=O)OC)C(=O)N1CCS[C@H]1c1ncc(-c2ccc(-c3ccc4cc(-c5c[nH]c([C@@H]6CC7(CC7)CN6C(=O)[C@@H](NC(=O)OC)C(C)C)n5)ccc4c3)cc2)[nH]1] | 0.0402 |
| 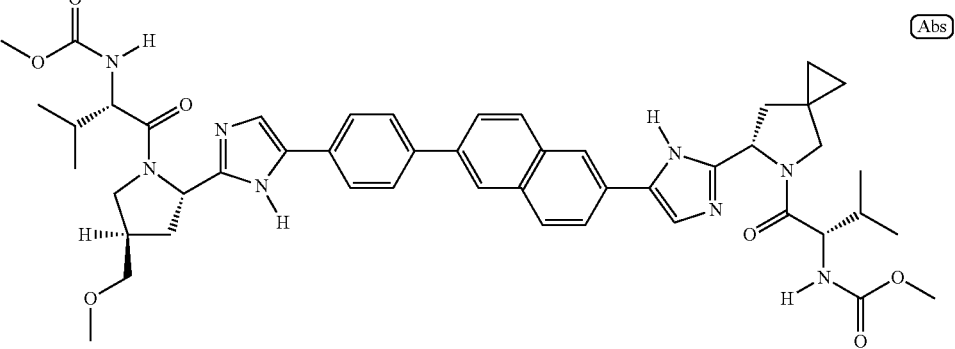 Abs | 0.0092 |
| 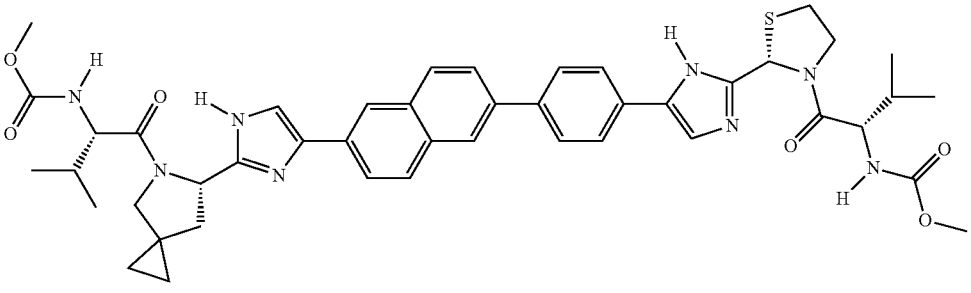 [SMILES: COC(=O)N[C@H](C(=O)N1CC2(CC2)C[C@H]1c1nc(-c2ccc3cc(-c4ccc(-c5cnc([C@@H]6SCCN6C(=O)[C@@H](NC(=O)OC)C(C)C)[nH]5)cc4)ccc3c2)c[nH]1)C(C)C] | 0.0192 |
| 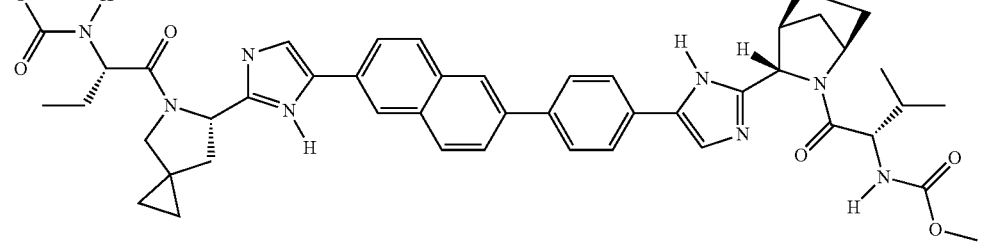 | 0.0181 |

-continued
| Additional Representative Compounds of the Invention | Activity (nM) |
|---|---|
| 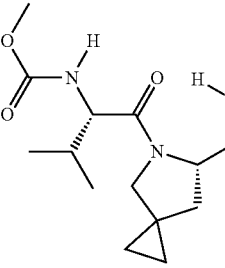 | 0.1324 |
| 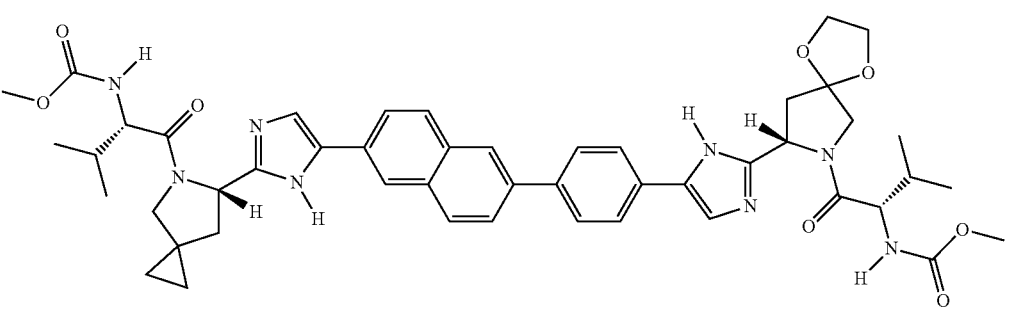 | 0.0063 |
| 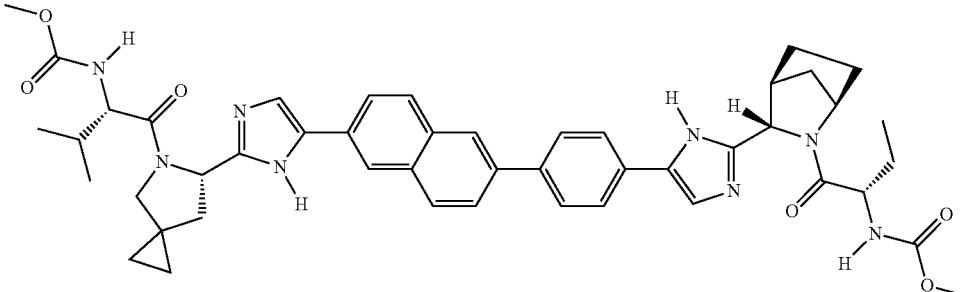 | 0.0086 |
| 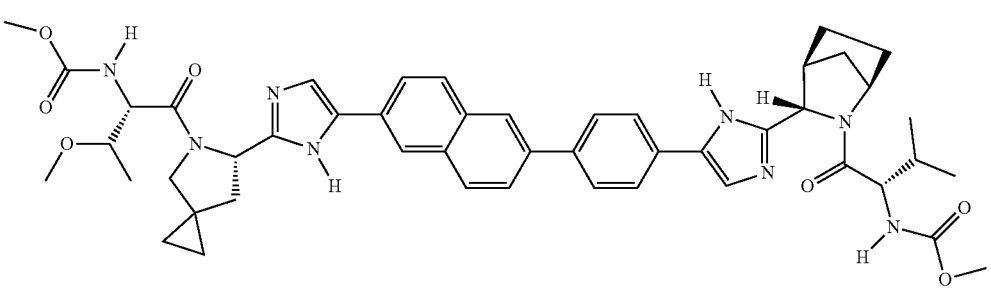 | 0.0077 |
| 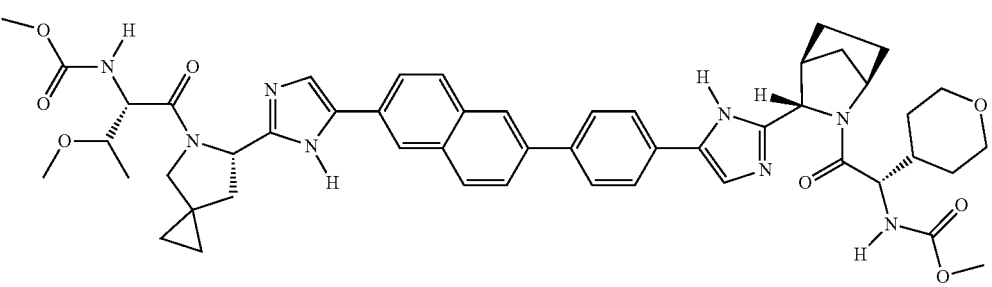 [SMILES: COC(=O)N[C@H](C(=O)N1[C@@H]2CC[C@@H](C2)[C@H]1c1ncc(-c2ccc(-c3ccc4cc(-c5cnc([C@@H]6CC7(CC7)CN6C(=O)[C@@H](NC(=O)OC)C(C)OC)[nH]5)ccc4c3)cc2)[nH]1)C1CCOCC1] | 0.0115 |

| Additional Representative Compounds of the Invention | Activity (nM) |
|---|---|
| 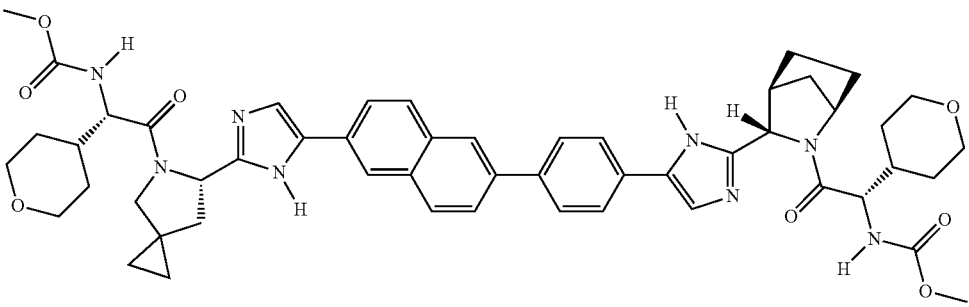 | 0.0255 |
| 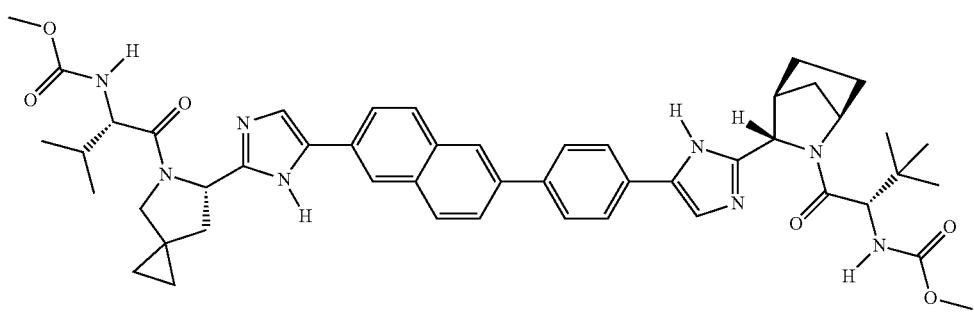 | 0.009 |
| 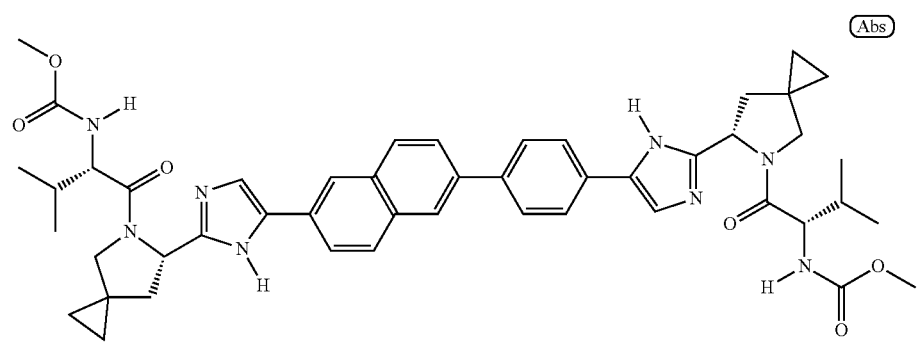 [SMILES: COC(=O)N[C@H](C(=O)N1CC2(CC2)C[C@H]1c1ncc(-c2ccc(-c3ccc4cc(-c5cnc([C@@H]6CC7(CC7)CN6C(=O)[C@@H](NC(=O)OC)C(C)C)[nH]5)ccc4c3)cc2)[nH]1)C(C)C] | 0.0048 |
| 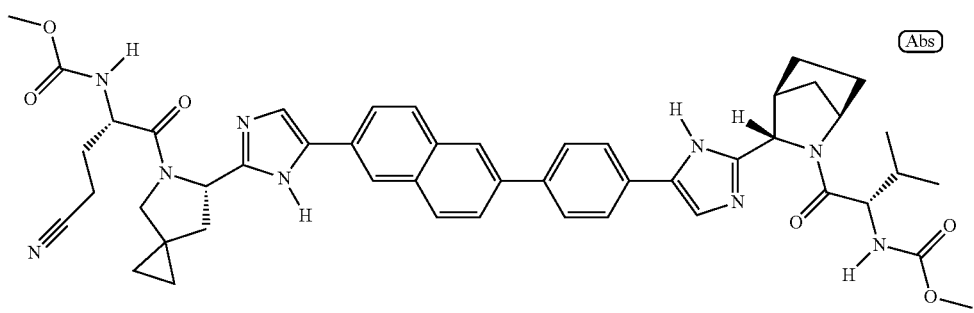 | 0.0159 |

-continued
| Additional Representative Compounds of the Invention | Activity (nM) |
|---|---|
| 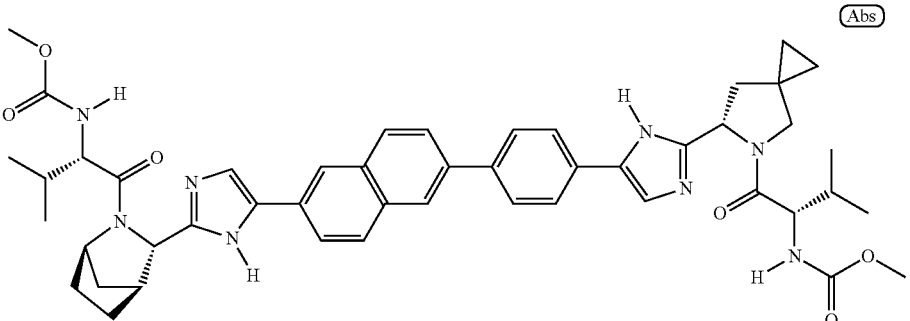 | 0.0076 |
| 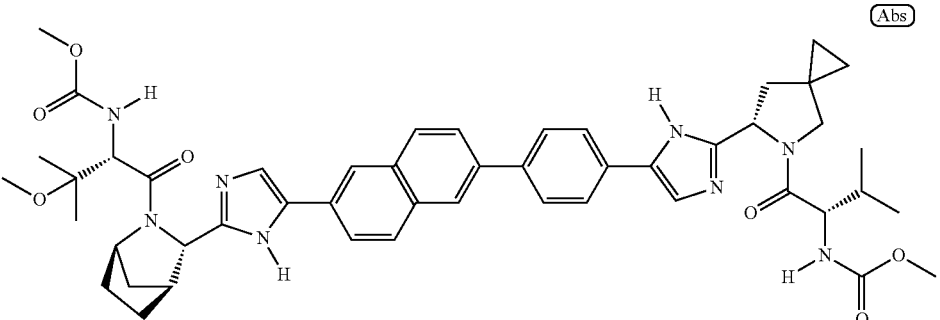 | 0.0155 |
| 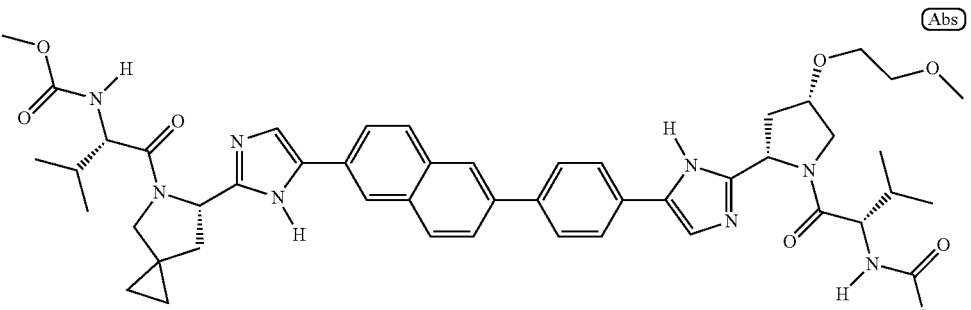 | 0.0146 |
| 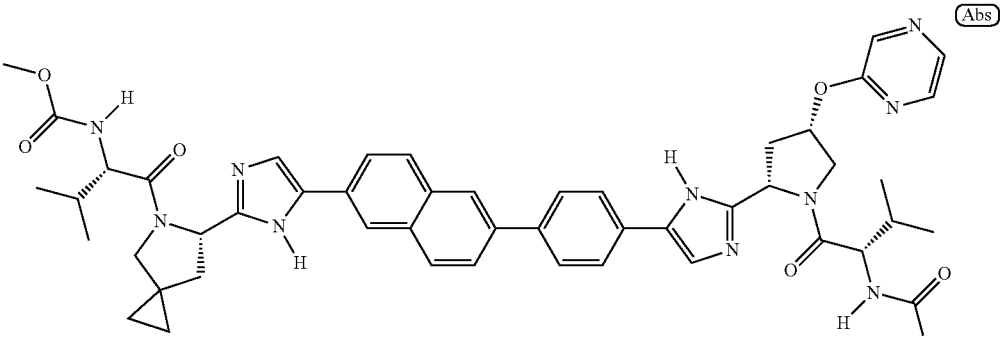 | 0.014 |

| Additional Representative Compounds of the Invention | Activity (nM) |
|---|---|
| | 0.0534 |
| | 0.2865 |
| | 0.008 |
| | 0.0201 |
| | 0.0071 |

| Additional Representative Compounds of the Invention | Activity (nM) |
|---|---|
| 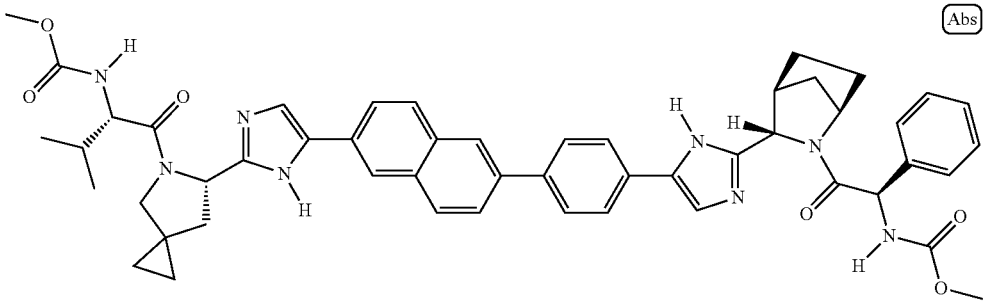 | 0.0261 |
| 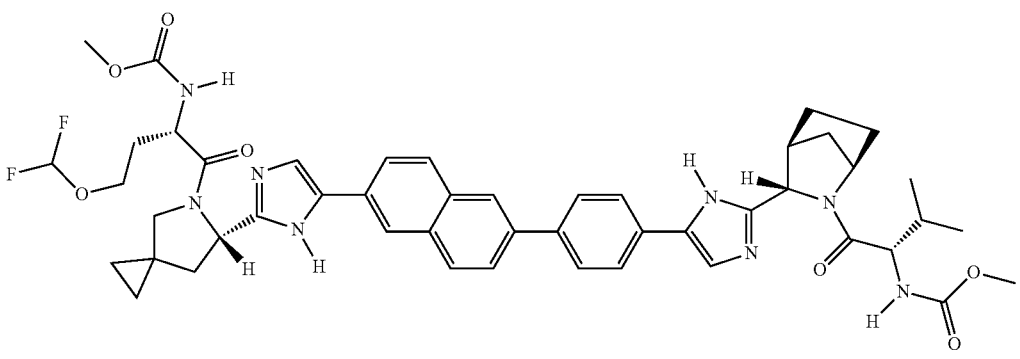 [SMILES: COC(=O)N[C@@H](CCOC(F)F)C(=O)N1CC2(CC2)C[C@H]1c1ncc(-c2ccc3cc(-c4ccc(-c5cnc([C@@H]6[C@H]7CC[C@H](C7)N6C(=O)[C@@H](NC(=O)OC)C(C)C)[nH]5)cc4)ccc3c2)[nH]1] | 0.0114 |
| 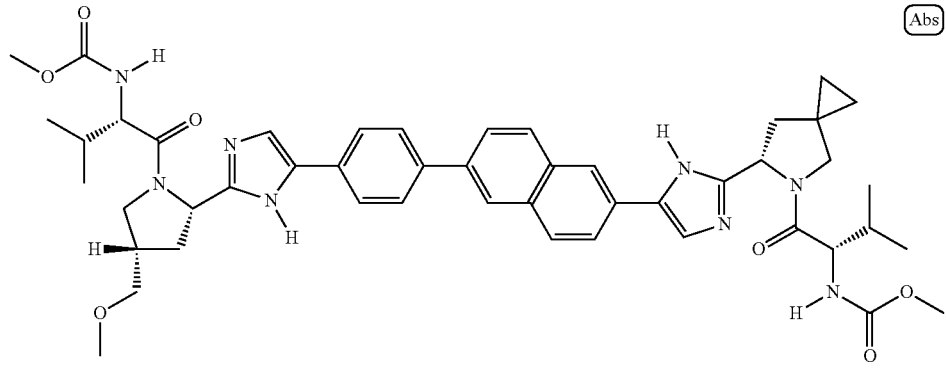 | 0.0073 |
| 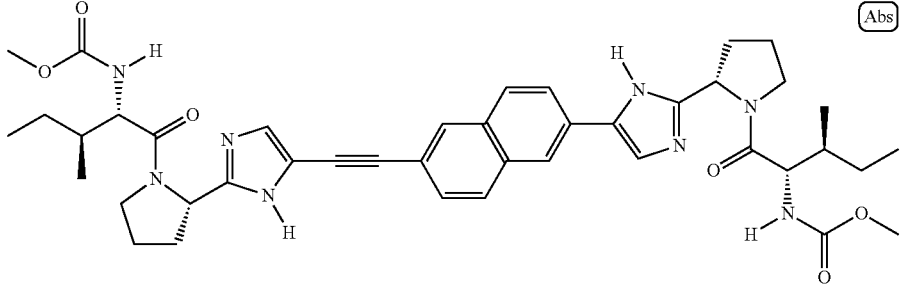 [SMILES: CC[C@H](C)[C@H](NC(=O)OC)C(=O)N1CCC[C@H]1c1ncc(C#Cc2ccc3cc(-c4cnc([C@@H]5CCCN5C(=O)[C@@H](NC(=O)OC)[C@@H](C)CC)[nH]4)ccc3c2)[nH]1] | 0.0147 |

-continued

| Additional Representative Compounds of the Invention | Activity (nM) |
|---|---|
| | 0.0097 |
| | 0.0145 |
| | 0.0394 |
| | 0.0145 |
| | 0.0074 |

-continued
| Additional Representative Compounds of the Invention | Activity (nM) |
|---|---|
| 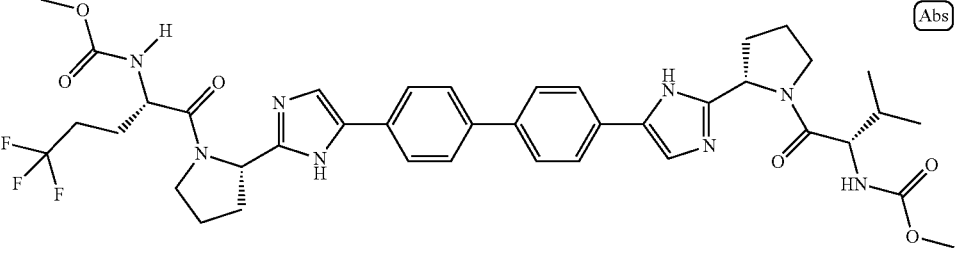 [SMILES: COC(=O)N[C@@H](CCC(F)(F)F)C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1] Abs | 0.04 |
| 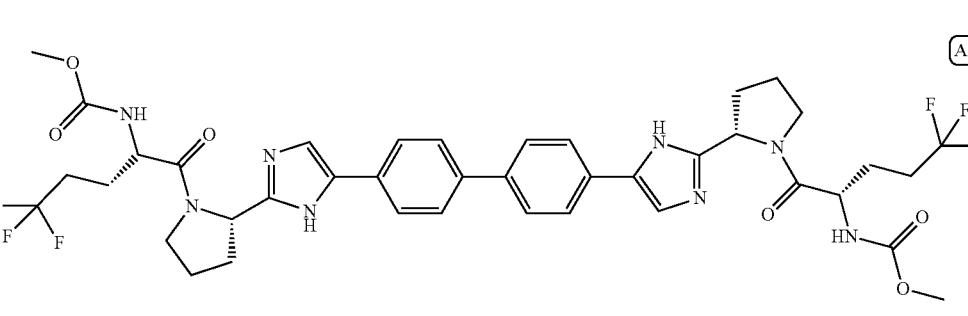 Abs | 0.0635 |
| 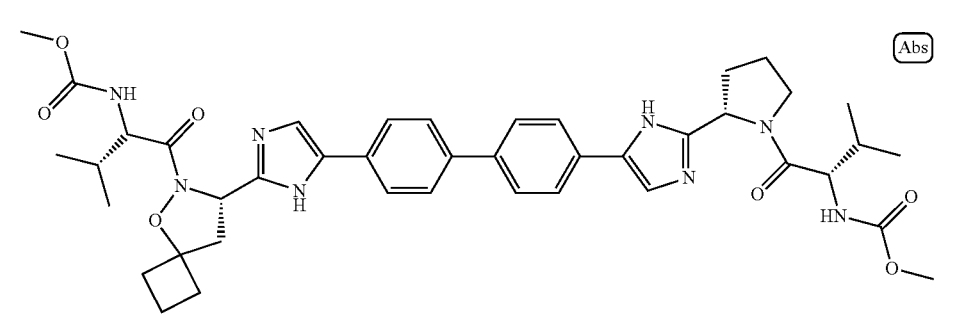 Abs | 0.0083 |
| 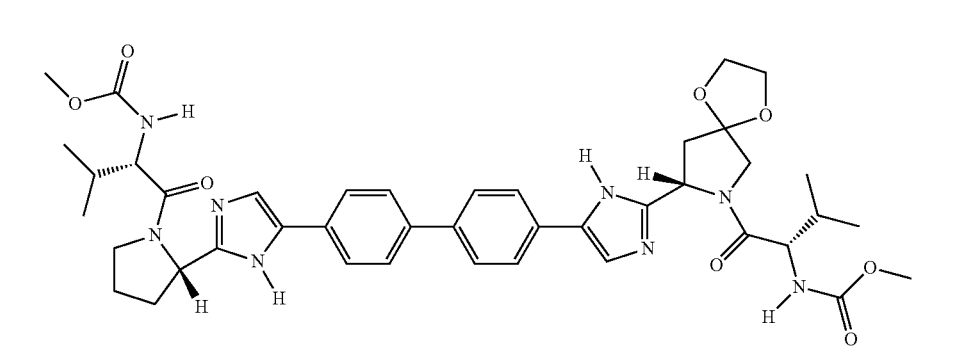 | 0.0555 |
| 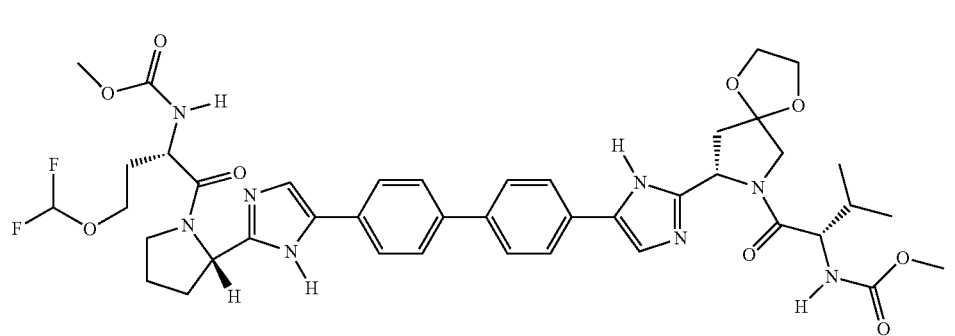 [SMILES: COC(=O)N[C@@H](CCOC(F)F)C(=O)N1CCC[C@H]1c1ncc(-c2ccc(-c3ccc(-c4cnc([C@@H]5CC6(CN5C(=O)[C@@H](NC(=O)OC)C(C)C)OCCO6)[nH]4)cc3)cc2)[nH]1] | 0.1282 |

| Additional Representative Compounds of the Invention | Activity (nM) |
|---|---|
| 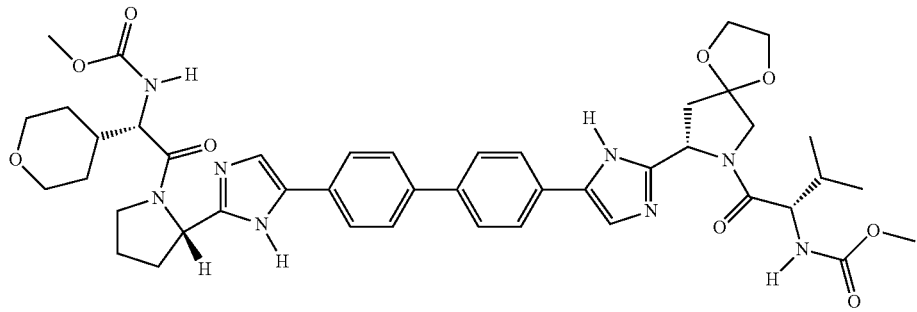 [SMILES: COC(=O)N[C@H](C(=O)N1CC2(C[C@H]1c1ncc(-c3ccc(-c4ccc(-c5cnc([C@@H]6CCCN6C(=O)[C@@H](NC(=O)OC)C6CCOCC6)[nH]5)cc4)cc3)[nH]1)OCCO2)C(C)C] | 0.5458 |
| 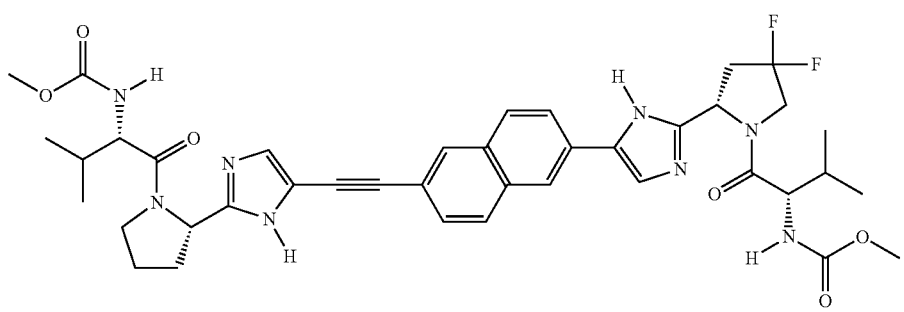 | 0.0147 |
| 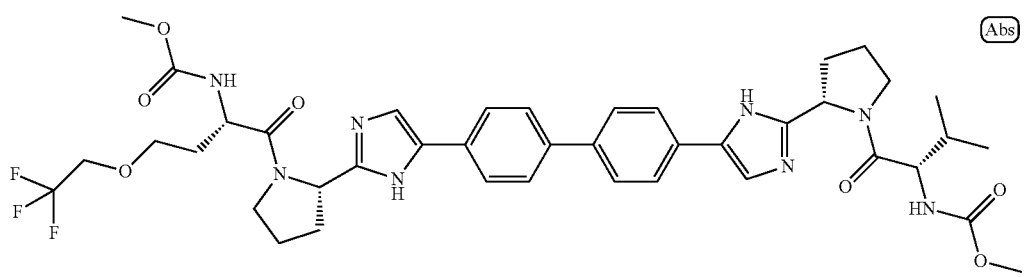 [SMILES: COC(=O)N[C@@H](CCOCC(F)(F)F)C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1] | 0.0273 |
| 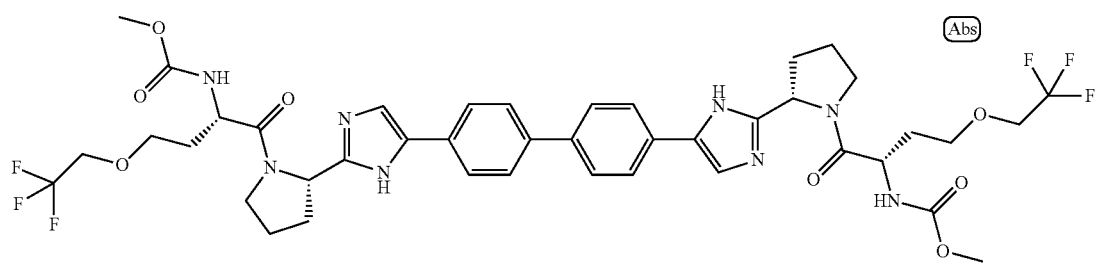 [SMILES: COC(=O)N[C@@H](CCOCC(F)(F)F)C(=O)N1CCC[C@H]1c1ncc(-c2ccc(-c3ccc(-c4cnc([C@@H]5CCCN5C(=O)[C@H](CCOCC(F)(F)F)NC(=O)OC)[nH]4)cc3)cc2)[nH]1] | 0.0244 |
| 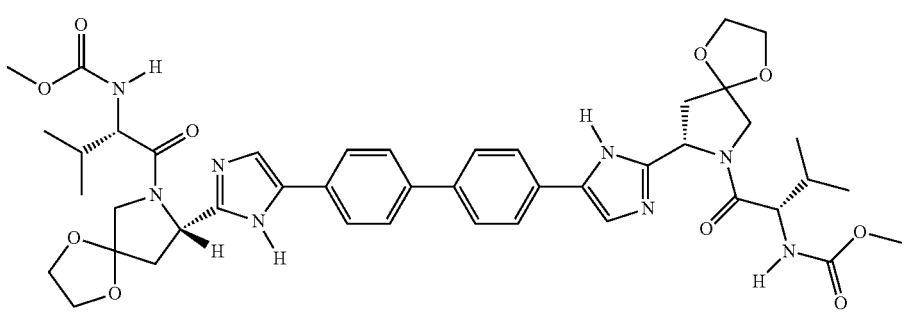 | 0.1049 |

| Additional Representative Compounds of the Invention | Activity (nM) |
|---|---|
| 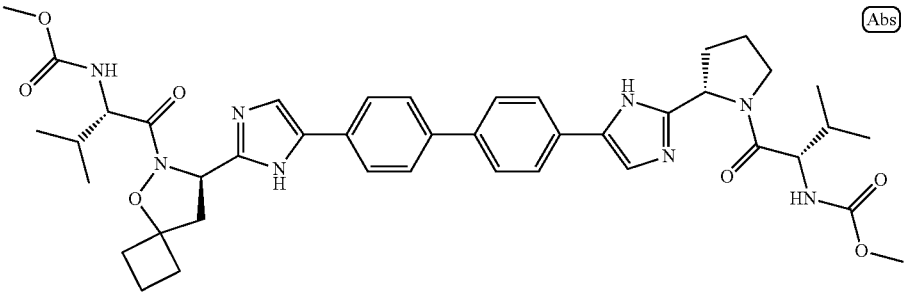 Abs | 0.1103 |
| 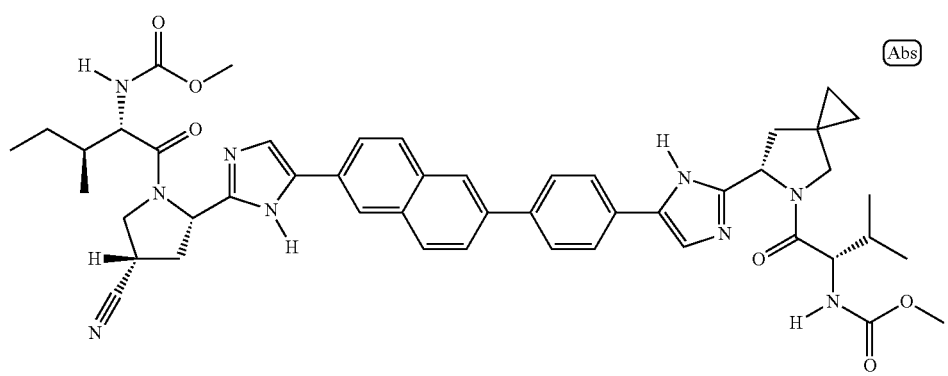 [SMILES: CC[C@H](C)[C@H](NC(=O)OC)C(=O)N1C[C@@H](C#N)C[C@H]1c1ncc(-c2ccc3cc(-c4ccc(-c5cnc([C@@H]6CC7(CC7)CN6C(=O)[C@@H](NC(=O)OC)C(C)C)[nH]5)cc4)ccc3c2)[nH]1] Abs | 0.01 |
| 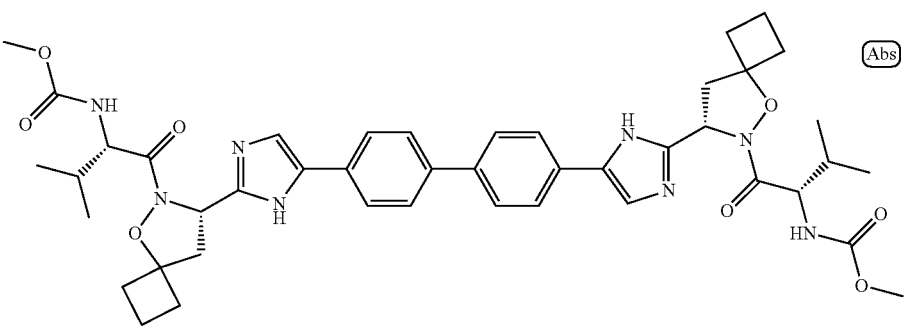 Abs | 0.0054 |
| 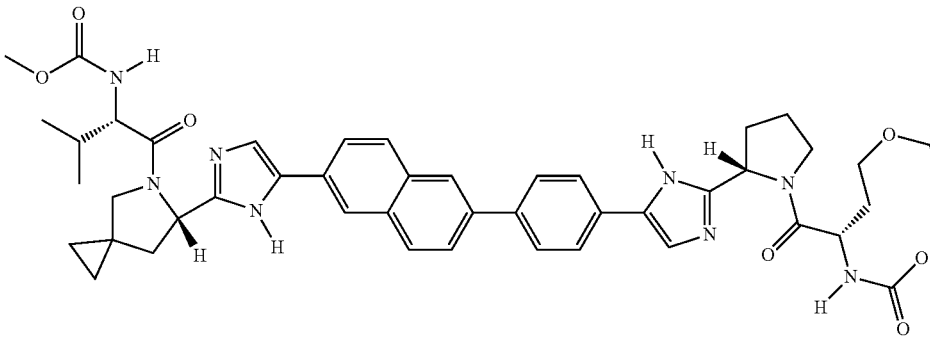 | 0.0052 |

| Additional Representative Compounds of the Invention | Activity (nM) |
|---|---|
| 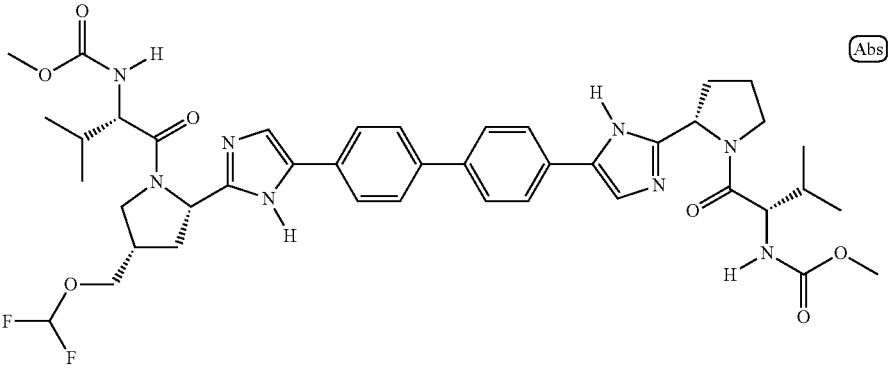 [SMILES: COC(=O)N[C@H](C(=O)N1CCC[C@H]1c1ncc(-c2ccc(-c3ccc(-c4cnc([C@@H]5C[C@H](COC(F)F)CN5C(=O)[C@@H](NC(=O)OC)C(C)C)[nH]4)cc3)cc2)[nH]1)C(C)C] | 0.015 |
| 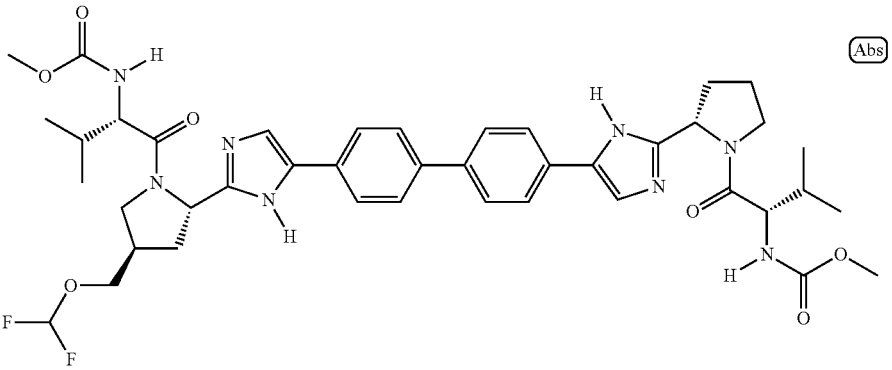 | 0.0129 |
| 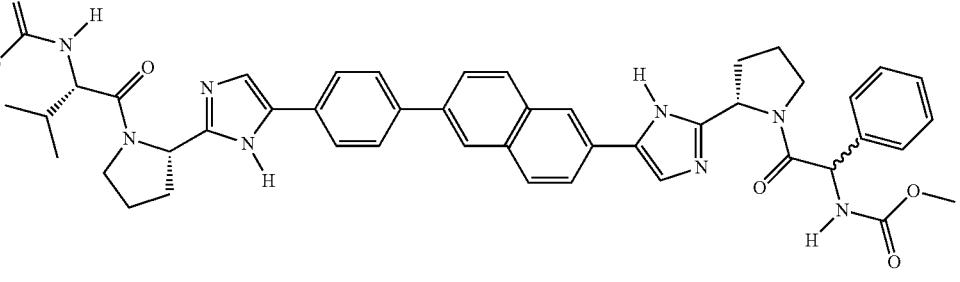 | 0.0092 |
| 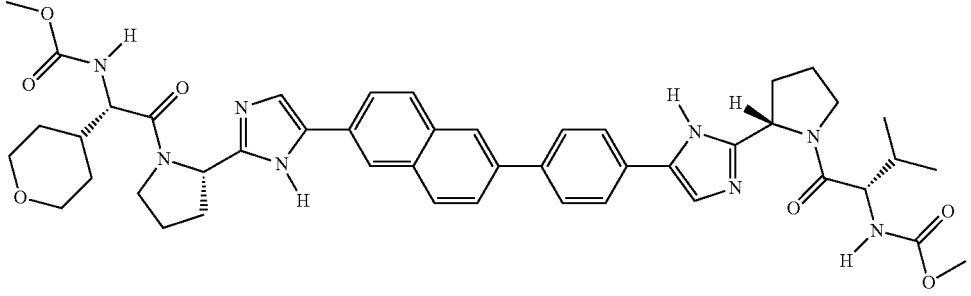 | 0.0193 |

| Additional Representative Compounds of the Invention | Activity (nM) |
|---|---|
| 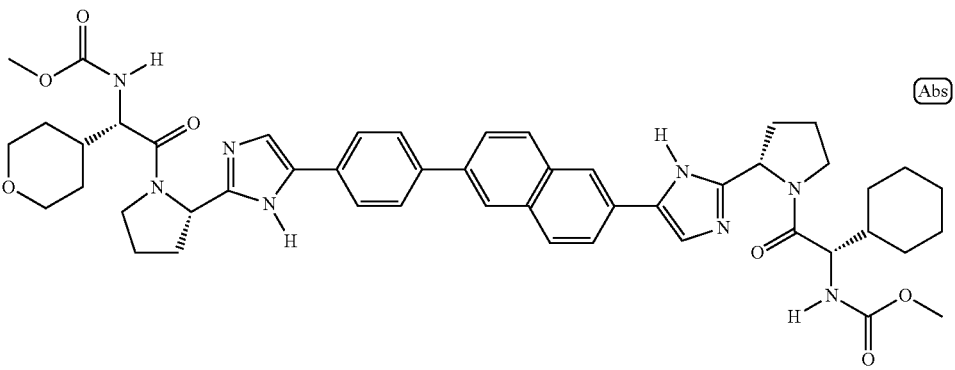 [SMILES: COC(=O)N[C@H](C(=O)N1CCC[C@H]1c1ncc(-c2ccc3cc(-c4ccc(-c5cnc([C@@H]6CCCN6C(=O)[C@@H](NC(=O)OC)C6CCOCC6)[nH]5)cc4)ccc3c2)[nH]1)C1CCCCC1] | 0.0116 |
| 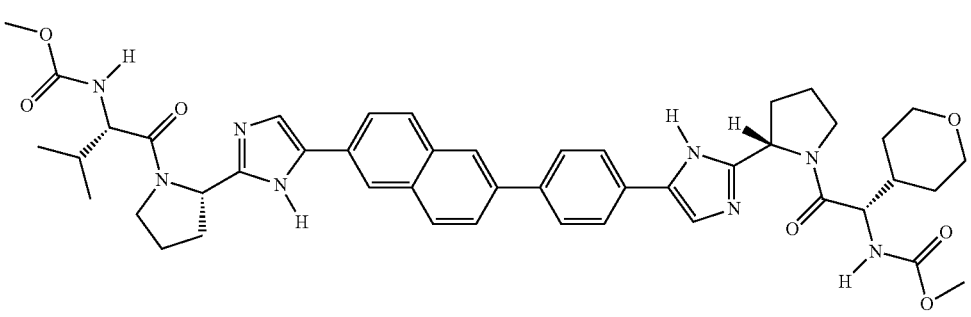 [SMILES: COC(=O)N[C@H](C(=O)N1CCC[C@H]1c1ncc(-c2ccc3cc(-c4ccc(-c5cnc([C@@H]6CCCN6C(=O)[C@@H](NC(=O)OC)C6CCOCC6)[nH]5)cc4)ccc3c2)[nH]1)C(C)C] | 0.0131 |
| 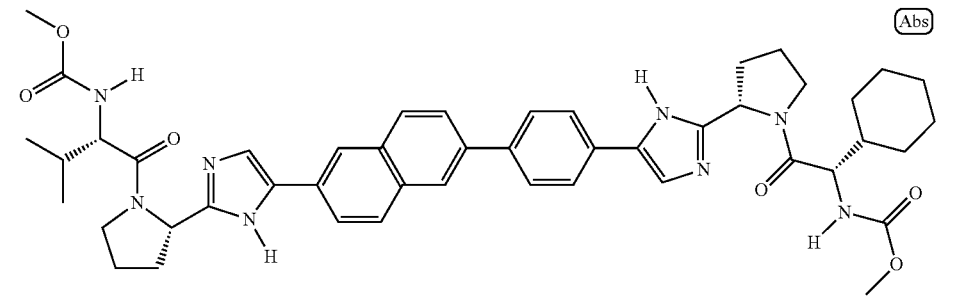 [SMILES: COC(=O)N[C@H](C(=O)N1CCC[C@H]1c1ncc(-c2ccc3cc(-c4ccc(-c5cnc([C@@H]6CCCN6C(=O)[C@@H](NC(=O)OC)C6CCCCC6)[nH]5)cc4)ccc3c2)[nH]1)C(C)C] | 0.0092 |
| 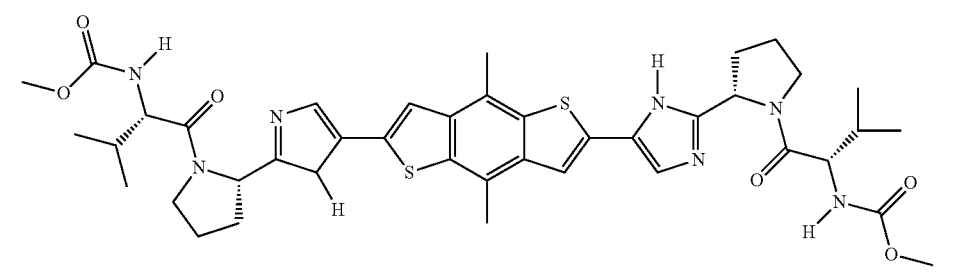 | 0.0166 |
| 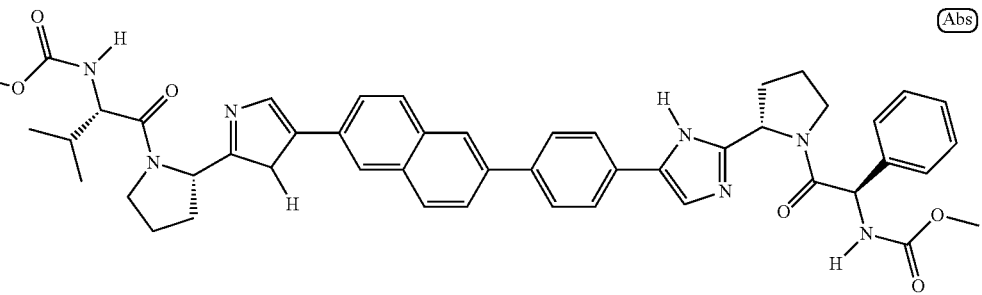 | 0.0081 |

| Additional Representative Compounds of the Invention | Activity (nM) |
|---|---|
| | 0.0272 |
| | 0.0228 |
| | 0.0077 |
| | 0.0483 |
| | 0.0104 |

| Additional Representative Compounds of the Invention | Activity (nM) |
|---|---|
| 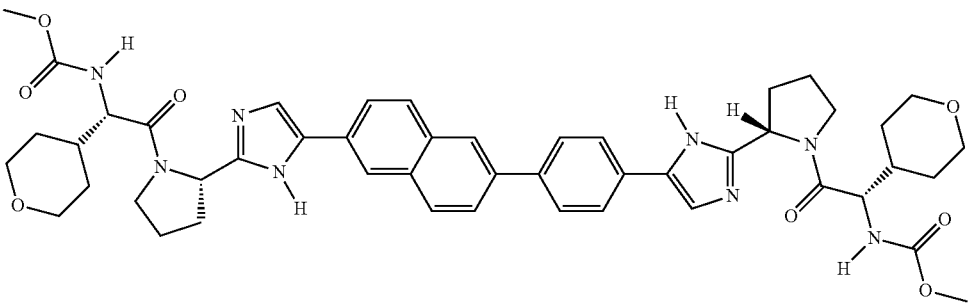 | 0.0686 |
| 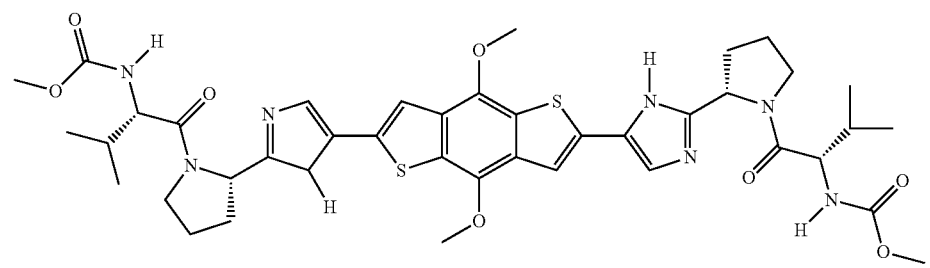 | 0.0161 |
| 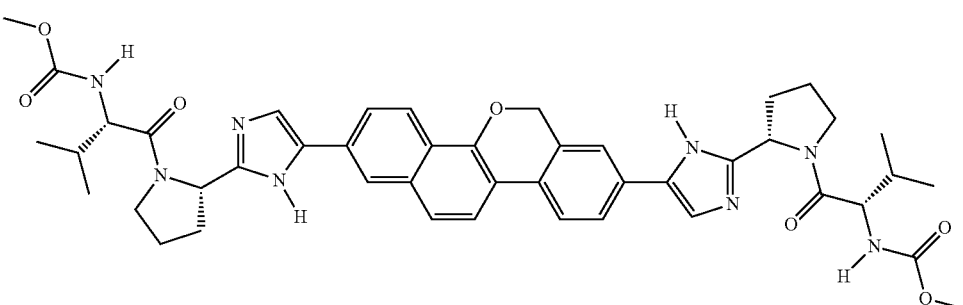 | 0.0044 |
| 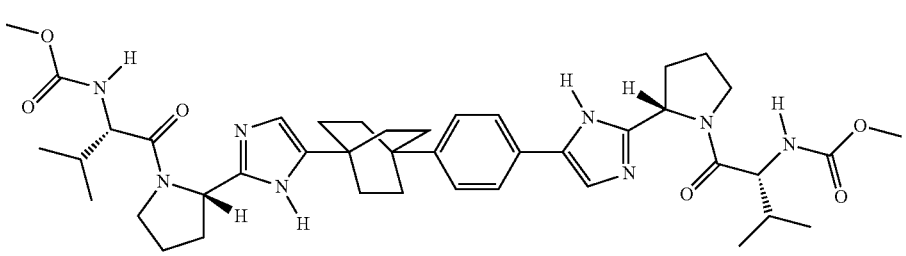 | 39.7293 |
| 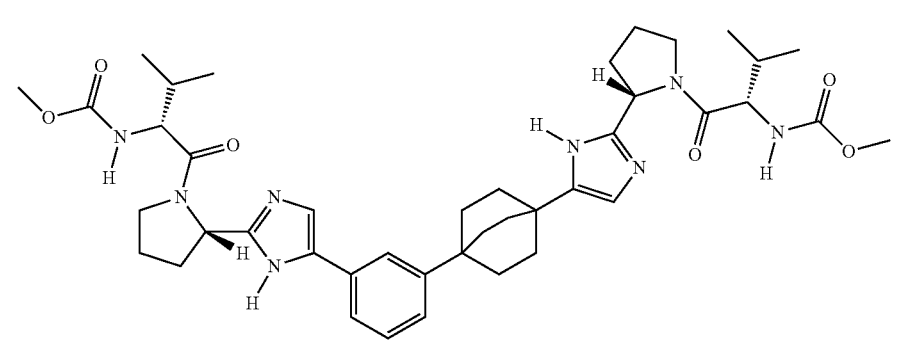 | 44.4 |

| Additional Representative Compounds of the Invention | Activity (nM) |
|---|---|
| 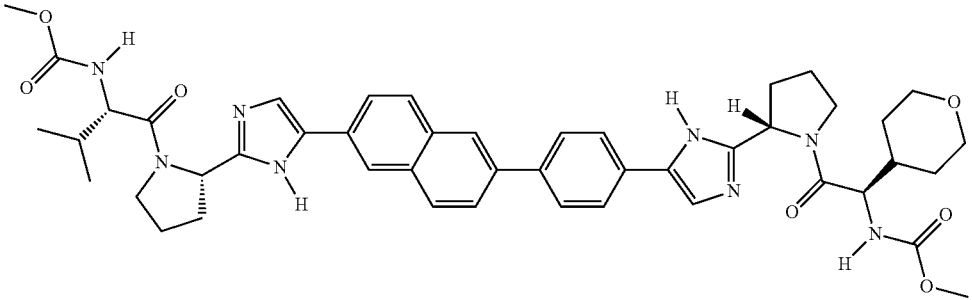 | 0.1709 |
| 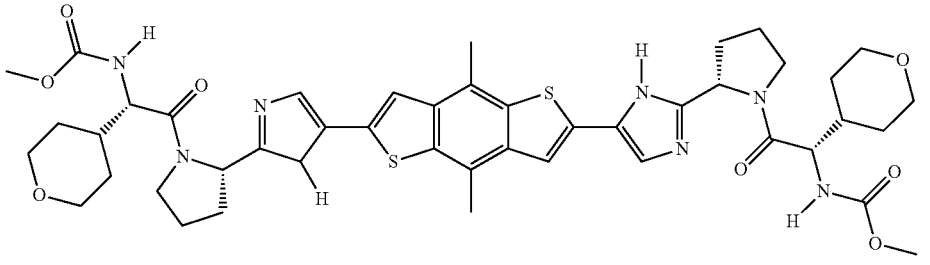 | 0.1062 |
| 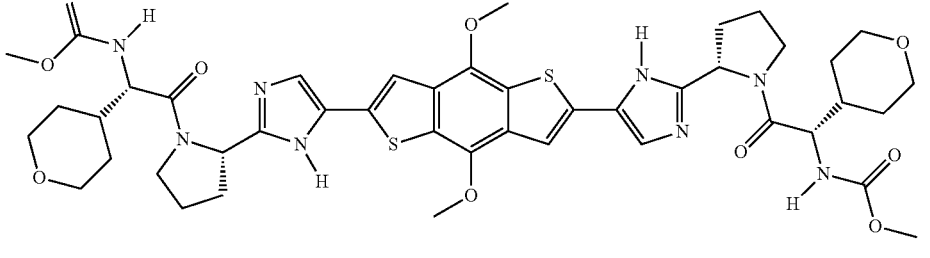 | 0.419 |
| 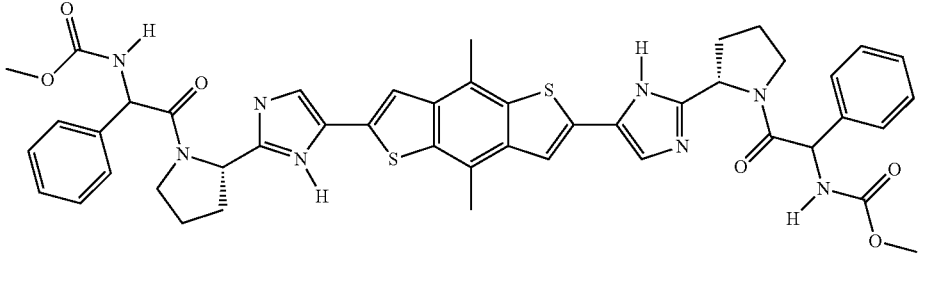 | 0.0214 |
| 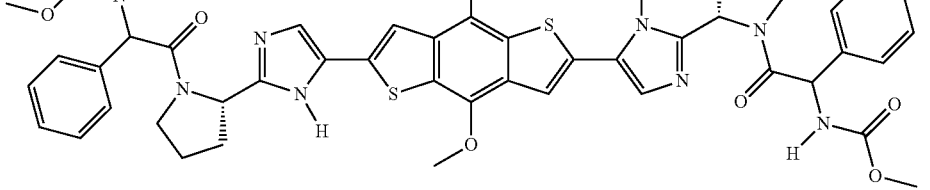 | 0.0262 |

| Additional Representative Compounds of the Invention | Activity (nM) |
|---|---|
| 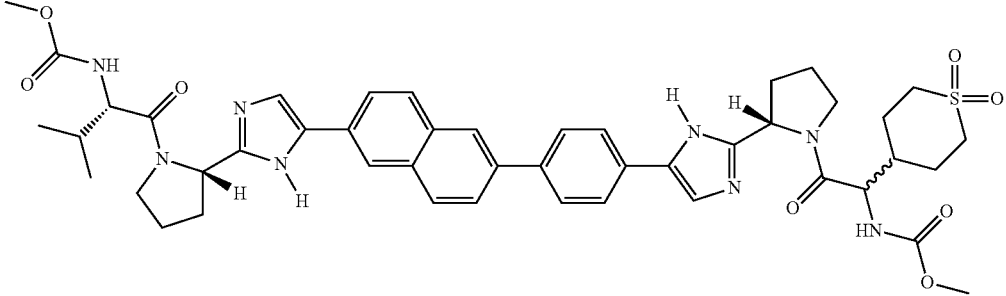 [SMILES: COC(=O)NC(C(=O)N1CCC[C@H]1c1ncc(-c2ccc(-c3ccc4cc(-c5cnc([C@@H]6CCCN6C(=O)[C@@H](NC(=O)OC)C(C)C)[nH]5)ccc4c3)cc2)[nH]1)C1CCS(=O)(=O)CC1] | 0.1354 |
| 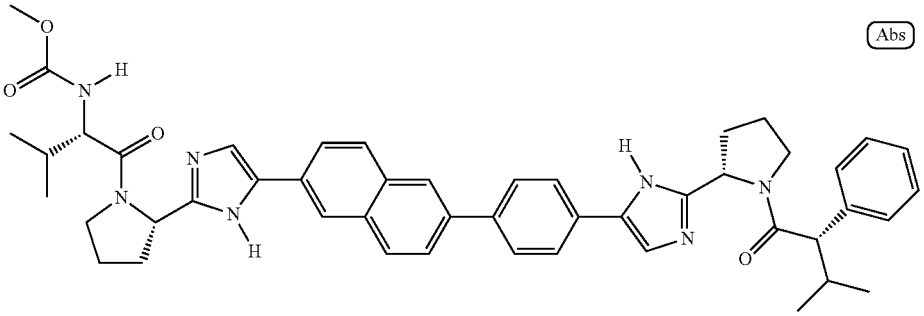 [SMILES: COC(=O)N[C@H](C(=O)N1CCC[C@H]1c1ncc(-c2ccc3cc(-c4ccc(-c5cnc([C@@H]6CCCN6C(=O)[C@H](c6ccccc6)C(C)C)[nH]5)cc4)ccc3c2)[nH]1)C(C)C] | 0.0112 |
| 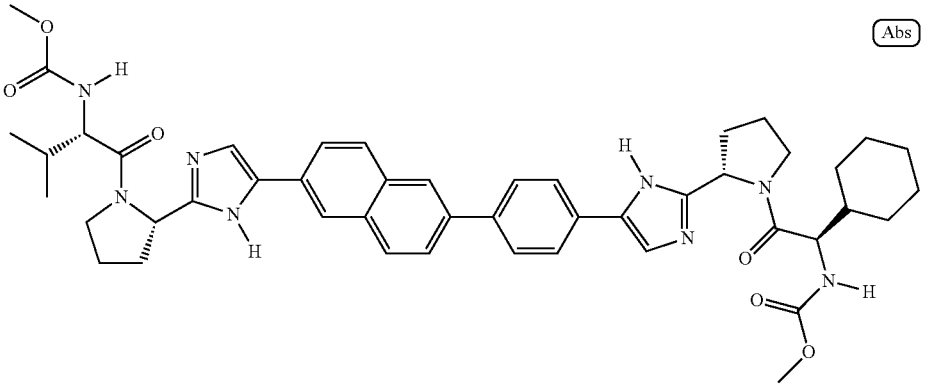 [SMILES: COC(=O)N[C@H](C(=O)N1CCC[C@H]1c1ncc(-c2ccc3cc(-c4ccc(-c5cnc([C@@H]6CCCN6C(=O)[C@H](NC(=O)OC)C6CCCCC6)[nH]5)cc4)ccc3c2)[nH]1)C(C)C] | 0.0972 |
| 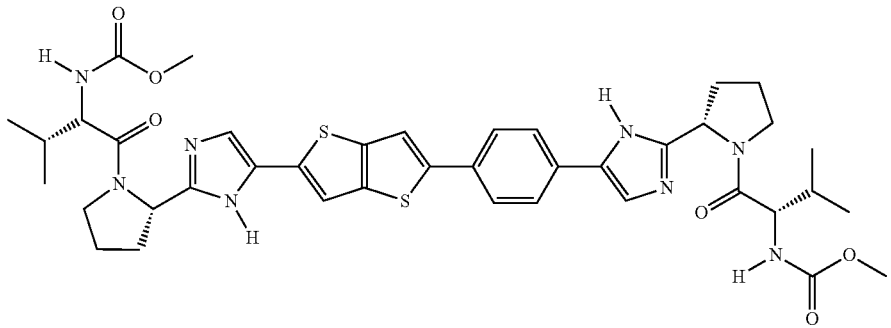 | 0.0129 |

-continued
| Additional Representative Compounds of the Invention | Activity (nM) |
|---|---|
| 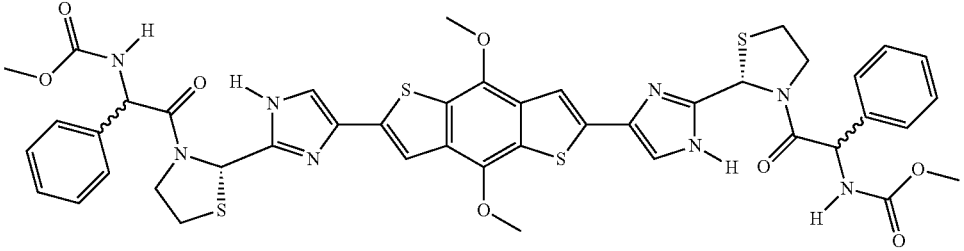 | 4.3733 |
| 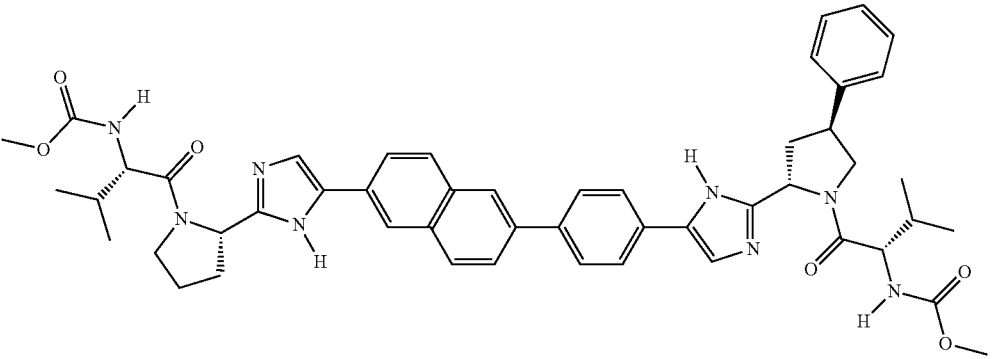 | 0.0724 |
| 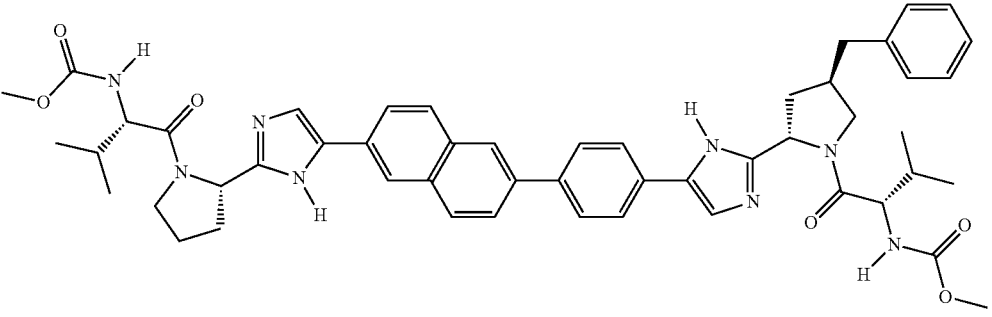 | 0.014 |
| 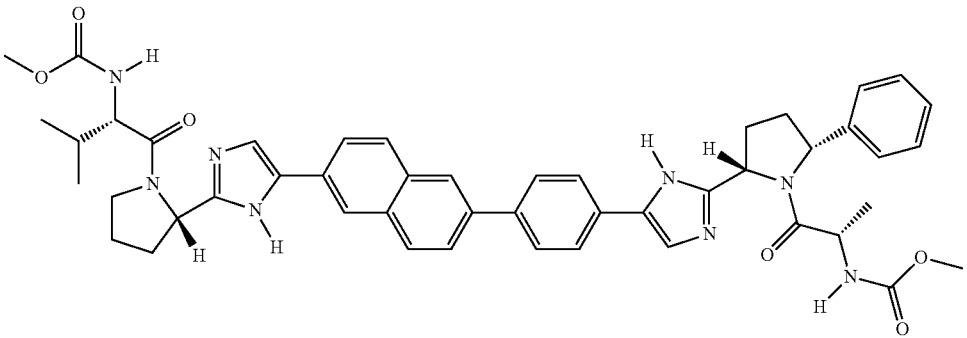 | 0.7879 |

| Additional Representative Compounds of the Invention | Activity (nM) |
|---|---|
| 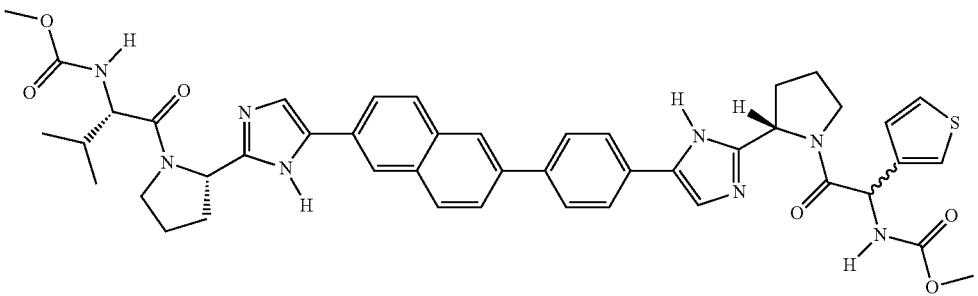 | 0.0197 |
| 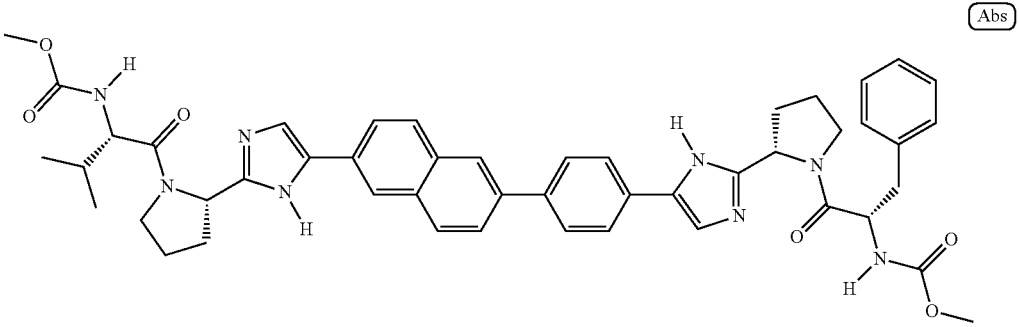 Abs | 0.0181 |
| 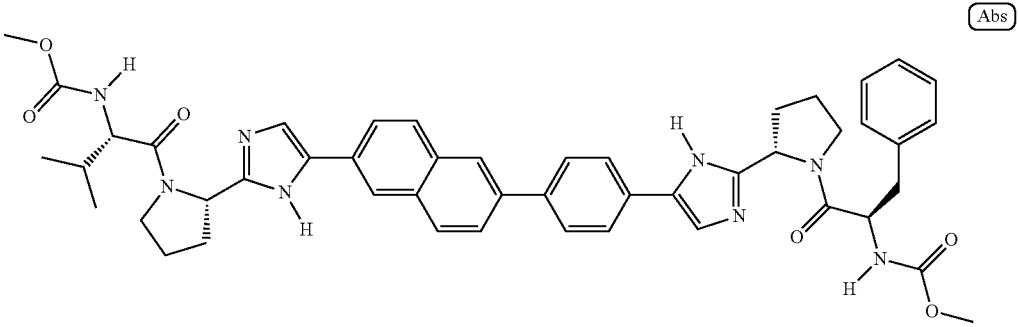 Abs | 0.858 |
| 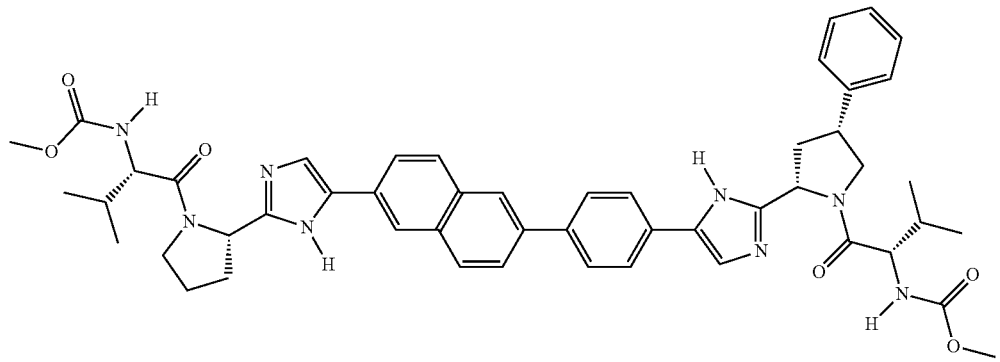 | 0.0189 |

-continued
| Additional Representative Compounds of the Invention | Activity (nM) |
|---|---|
| 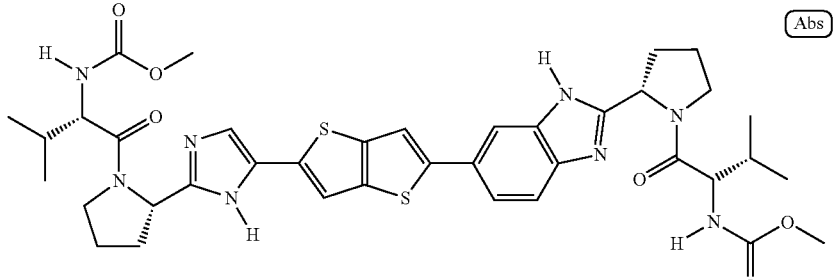 | 0.0229 |
| 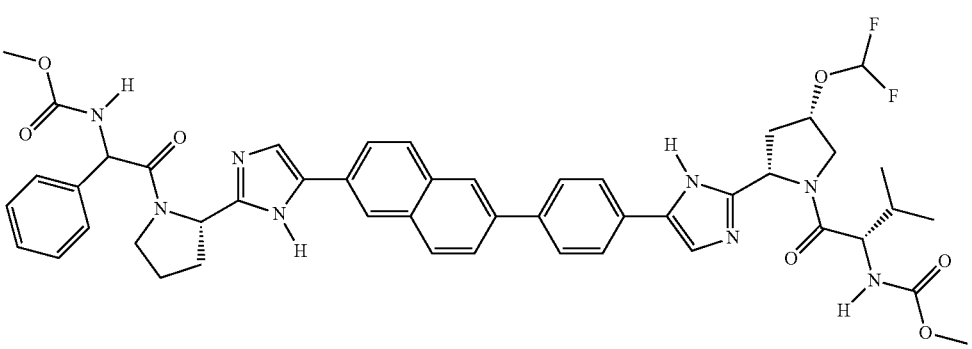 | 0.0171 |
| 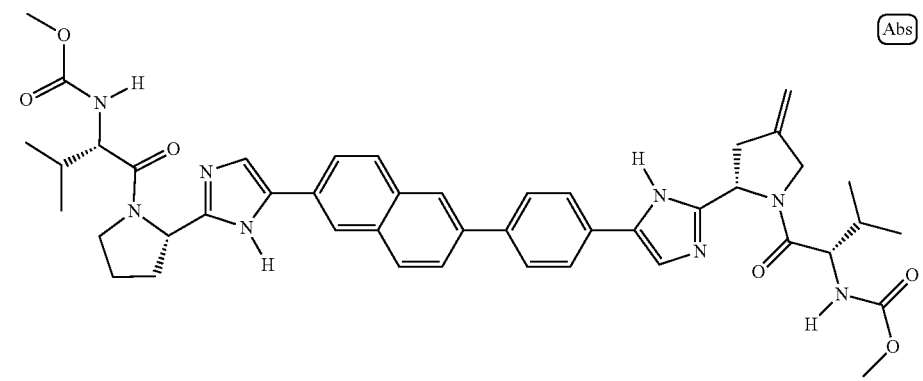 [SMILES: C=C1C[C@@H](c2ncc(-c3ccc(-c4ccc5cc(-c6cnc([C@@H]7CCCN7C(=O)[C@@H](NC(=O)OC)C(C)C)[nH]6)ccc5c4)cc3)[nH]2)N(C(=O)[C@@H](NC(=O)OC)C(C)C)C1] | 0.0113 |
| 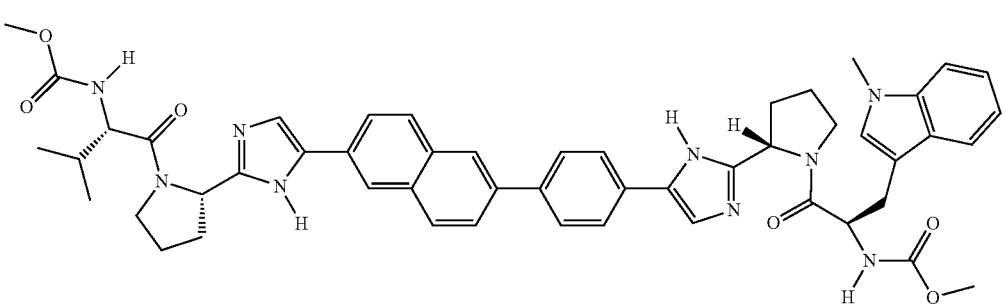 [SMILES: COC(=O)N[C@H](C(=O)N1CCC[C@H]1c1ncc(-c2ccc3cc(-c4ccc(-c5cnc([C@@H]6CCCN6C(=O)[C@@H](Cc6cn(C)c7ccccc67)NC(=O)OC)[nH]5)cc4)ccc3c2)[nH]1)C(C)C] | 6.1793 |

| Additional Representative Compounds of the Invention | Activity (nM) |
|---|---|
| 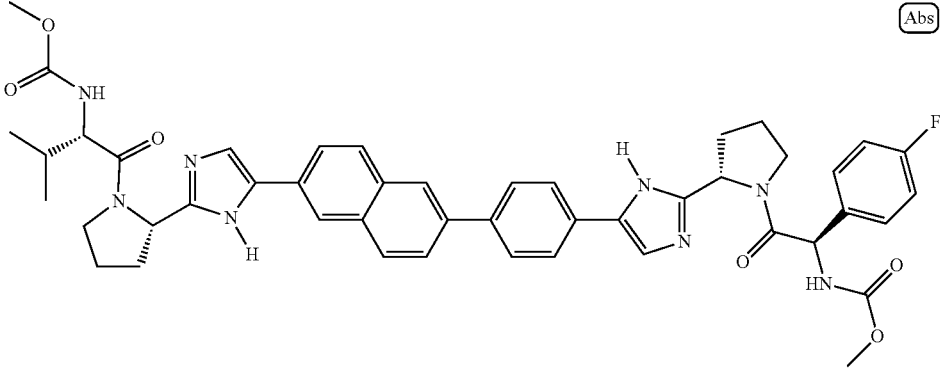 [SMILES: COC(=O)N[C@H](C(=O)N1CCC[C@H]1c1ncc(-c2ccc3cc(-c4ccc(-c5cnc([C@@H]6CCCN6C(=O)[C@H](NC(=O)OC)c6ccc(F)cc6)[nH]5)cc4)ccc3c2)[nH]1)C(C)C] Abs | 0.0142 |
| 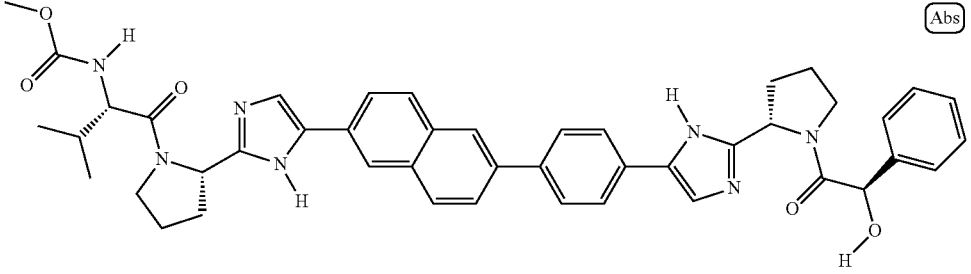 [SMILES: COC(=O)N[C@H](C(=O)N1CCC[C@H]1c1ncc(-c2ccc3cc(-c4ccc(-c5cnc([C@@H]6CCCN6C(=O)[C@H](O)c6ccccc6)[nH]5)cc4)ccc3c2)[nH]1)C(C)C] Abs | 0.0097 |
| 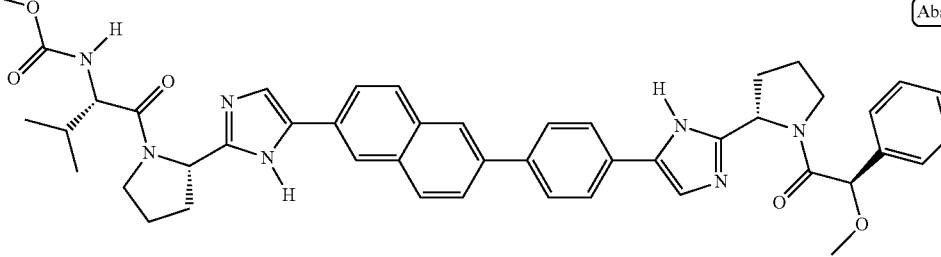 Abs | 0.0163 |
| 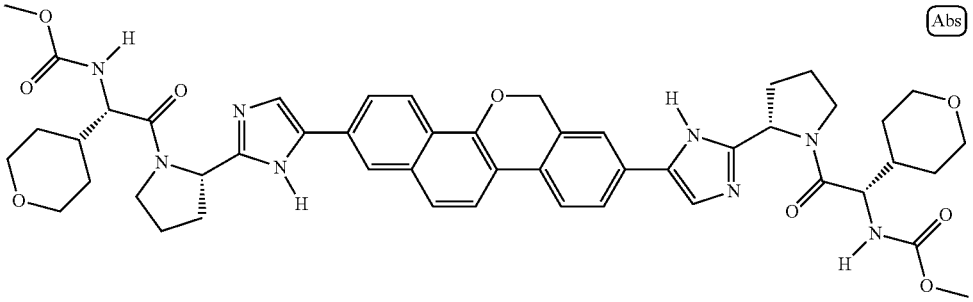 Abs | 0.0417 |
| 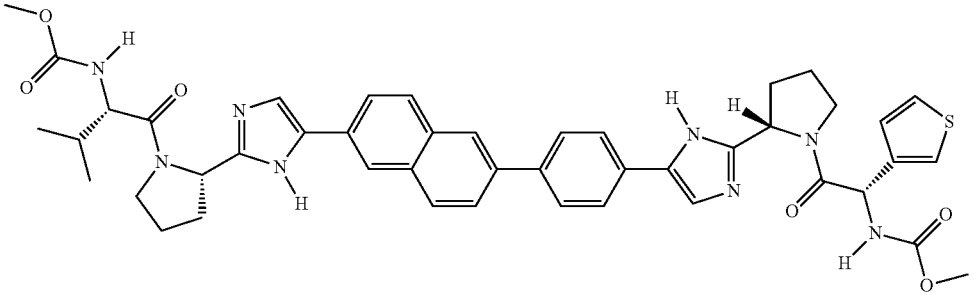 | 0.0906 |

| Additional Representative Compounds of the Invention | Activity (nM) |
|---|---|
| 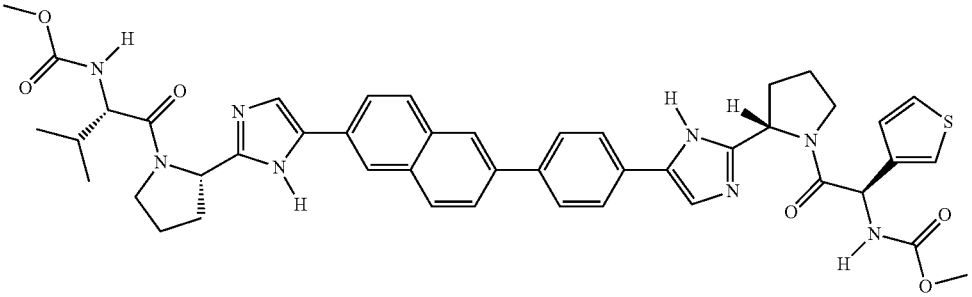 | 0.0157 |
| 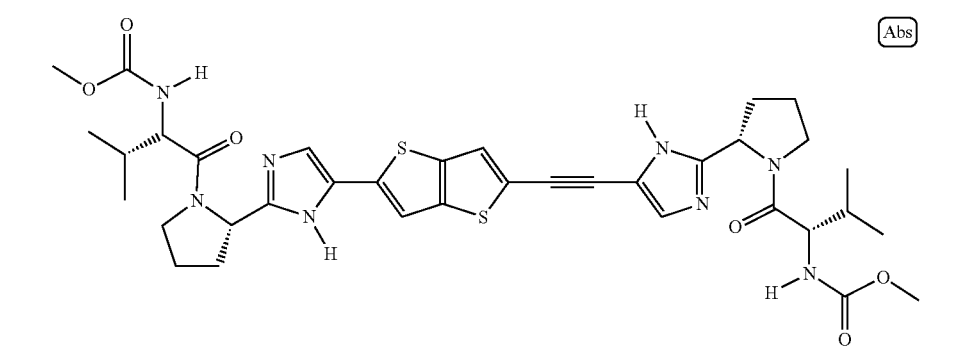 | 0.0503 |
| 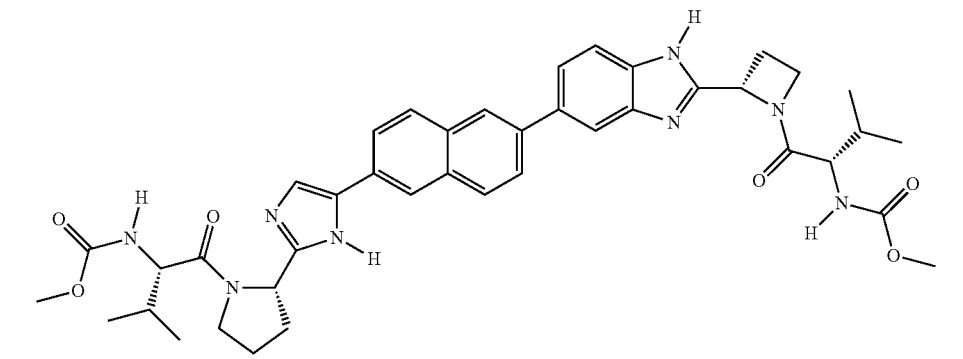 | 0.026 |
| 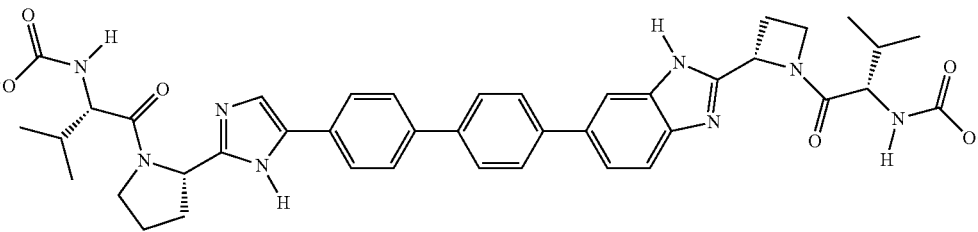 | 0.0282 |
| 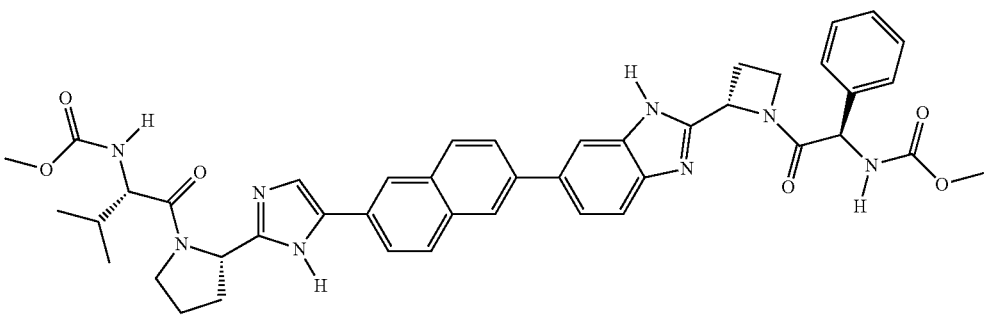 | 0.07 |

| Additional Representative Compounds of the Invention | Activity (nM) |
|---|---|
| 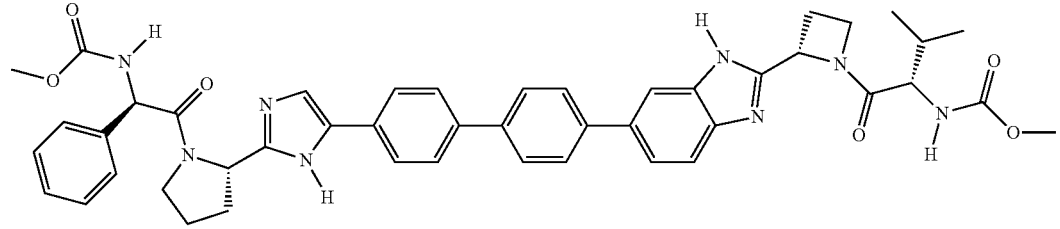 | 0.0195 |
| 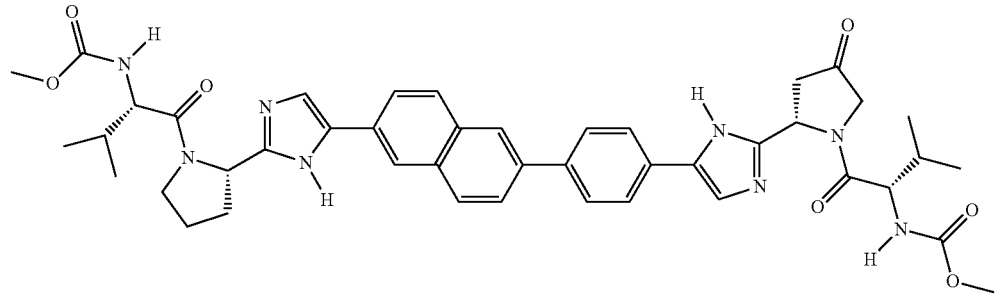 | 0.0103 |
| 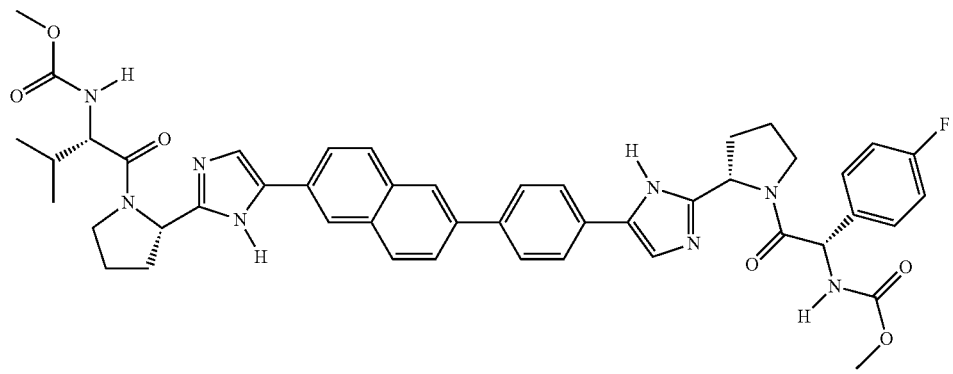 | 0.043 |
| 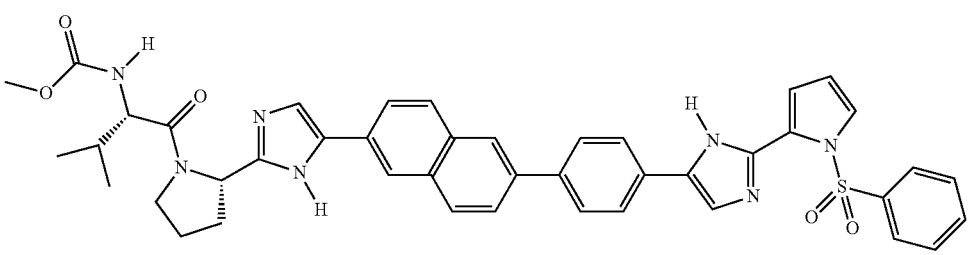 [SMILES: COC(=O)N[C@H](C(=O)N1CCC[C@H]1c1ncc(-c2ccc3cc(-c4ccc(-c5cnc(-c6cccn6S(=O)(=O)c6ccccc6)[nH]5)cc4)ccc3c2)[nH]1)C(C)C] | 24.0657 |

-continued
| Additional Representative Compounds of the Invention | Activity (nM) |
|---|---|
| 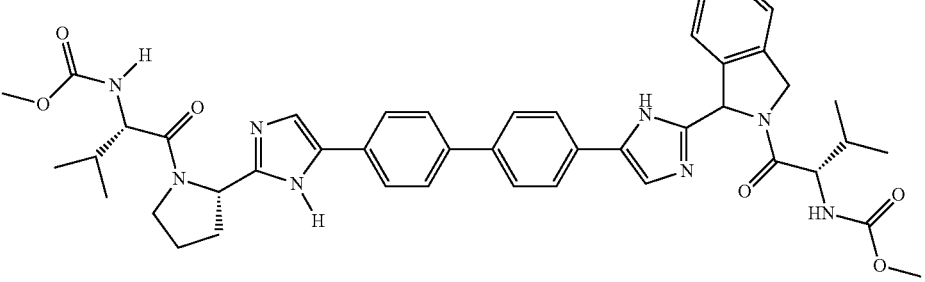 | 0.0414 |
| 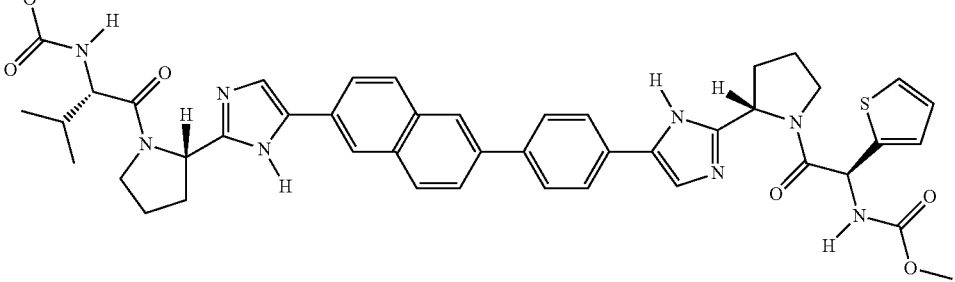 | 0.0262 |
| 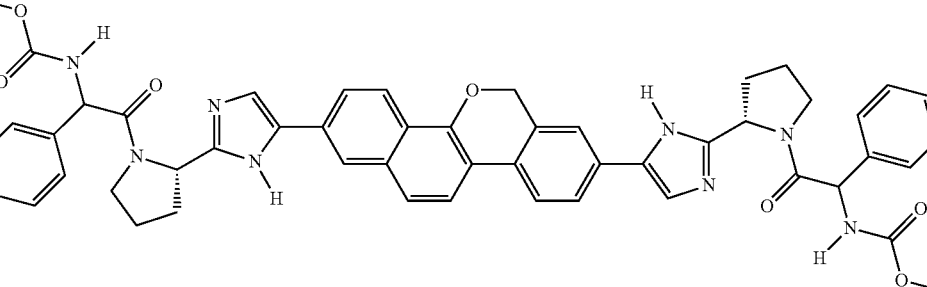 | 0.0275 |
| 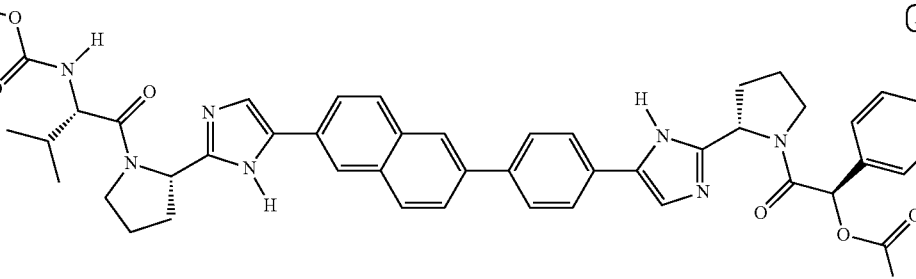 | 0.0083 |

-continued
| Additional Representative Compounds of the Invention | Activity (nM) |
|---|---|
| 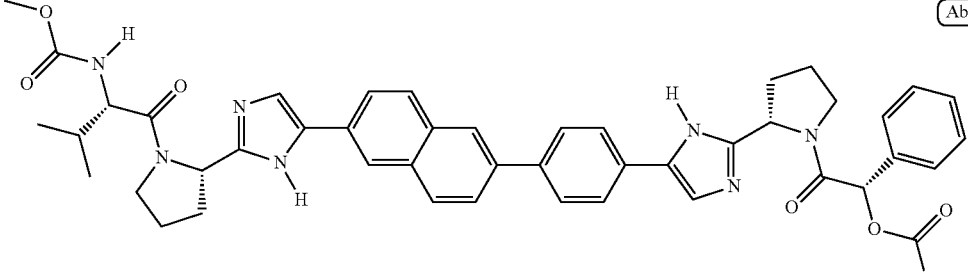 Abs | 0.0794 |
| 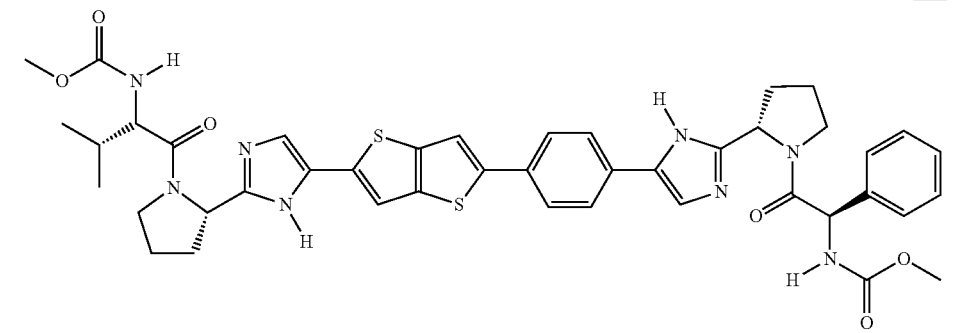 Abs | 0.0059 |
| 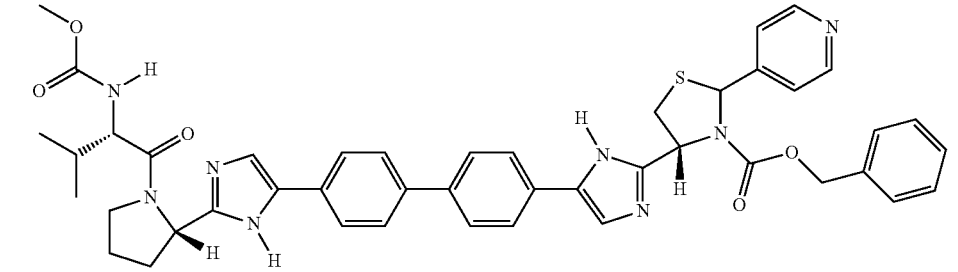<br>Diastereomer 1 | 0.0765 |
| 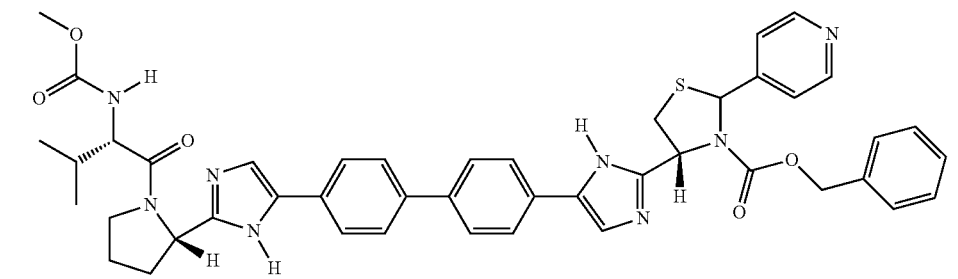<br>Diastereomer 2 | 0.0209 |

| Additional Representative Compounds of the Invention | Activity (nM) |
|---|---|
|  | 0.0305 |
|  | 0.0083 |
|  | 0.0117 |
|  | 0.0073 |

| Additional Representative Compounds of the Invention | Activity (nM) |
|---|---|
| 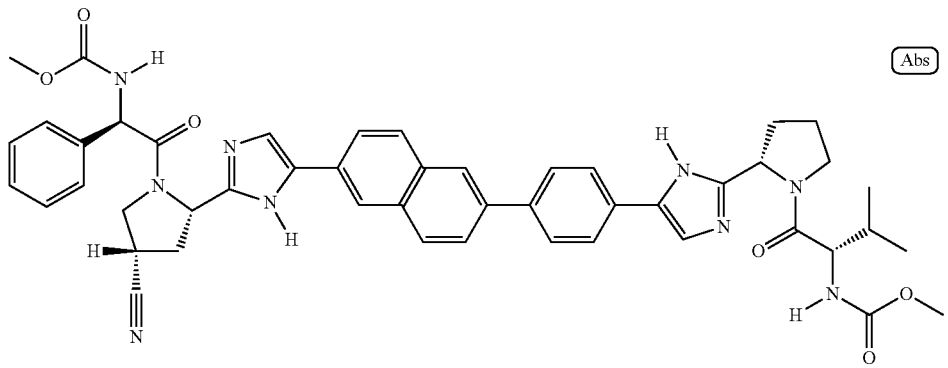 [SMILES: COC(=O)N[C@H](C(=O)N1CCC[C@H]1c1ncc(-c2ccc(-c3ccc4cc(-c5cnc([C@@H]6C[C@H](C#N)CN6C(=O)[C@H](NC(=O)OC)c6ccccc6)[nH]5)ccc4c3)cc2)[nH]1)C(C)C] Abs | 0.0097 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula:

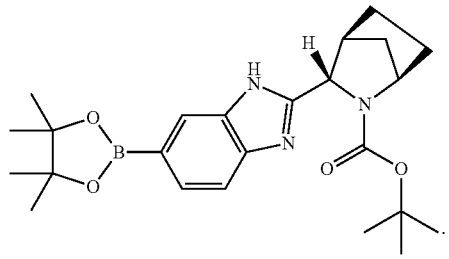 [SMILES: CC(C)(C)OC(=O)N1[C@@H]2CC[C@@H](C2)[C@H]1c1nc2ccc(B3OC(C)(C)C(C)(C)O3)cc2[nH]1]

2. A compound of formula:

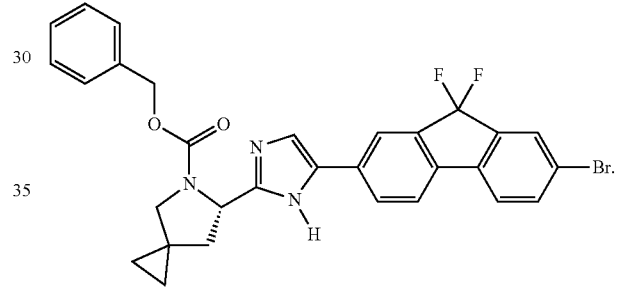

3. A compound of formula:

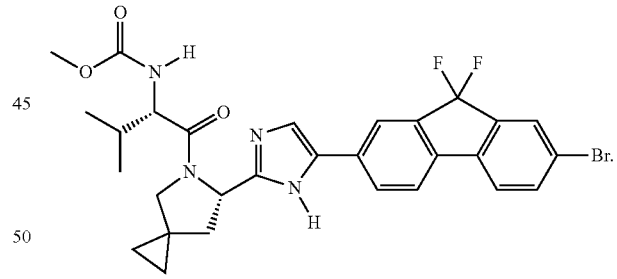

4. A compound of formula:

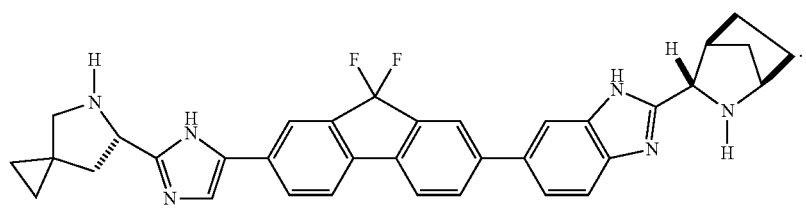

* * * * *